United States Patent
Andrews et al.

(10) Patent No.: US 10,174,028 B2
(45) Date of Patent: *Jan. 8, 2019

(54) SUBSTITUTED PYRAZOLO[1,5-A]PYRIDINE COMPOUNDS AS RET KINASE INHIBITORS

(71) Applicant: Array BioPharma, Inc., Boulder, CO (US)

(72) Inventors: Steven W. Andrews, Boulder, CO (US); James F. Blake, Boulder, CO (US); Mark J. Chicarelli, Boulder, CO (US); Adam Golos, Boulder, CO (US); Julia Haas, Boulder, CO (US); Yutong Jiang, Boulder, CO (US); Gabrielle R. Kolakowski, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/860,849

(22) Filed: Jan. 3, 2018

(65) Prior Publication Data

US 2018/0179203 A1   Jun. 28, 2018

Related U.S. Application Data

(63) Continuation of application No. 15/211,702, filed on Jul. 15, 2016.

(60) Provisional application No. 62/274,018, filed on Dec. 31, 2015, provisional application No. 62/193,448, filed on Jul. 16, 2015.

(51) Int. Cl.
| | |
|---|---|
| *C07D 471/04* | (2006.01) |
| *A61K 31/444* | (2006.01) |
| *A61K 31/4545* | (2006.01) |
| *A61K 31/496* | (2006.01) |
| *A61K 31/497* | (2006.01) |
| *A61K 31/499* | (2006.01) |
| *A61K 31/506* | (2006.01) |
| *A61K 31/5377* | (2006.01) |
| *A61K 31/55* | (2006.01) |
| *A61K 45/06* | (2006.01) |
| *C07D 519/00* | (2006.01) |

(52) U.S. Cl.
CPC .......... *C07D 471/04* (2013.01); *A61K 31/444* (2013.01); *A61K 31/4545* (2013.01); *A61K 31/496* (2013.01); *A61K 31/497* (2013.01); *A61K 31/499* (2013.01); *A61K 31/506* (2013.01); *A61K 31/5377* (2013.01); *A61K 31/55* (2013.01); *A61K 45/06* (2013.01); *C07D 519/00* (2013.01)

(58) Field of Classification Search
CPC .. C07D 471/04; C07D 519/00; A61K 31/444; A61K 31/4545; A61K 31/496; A61K 31/497; A61K 31/499; A61K 31/506; A61K 31/5377; A61K 31/55

USPC ...... 544/362; 546/16, 121; 514/253.04, 278, 514/300

See application file for complete search history.

(56) References Cited

U.S. PATENT DOCUMENTS

| | | |
|---|---|---|
| 5,844,092 A | 12/1998 | Presta et al. |
| 5,877,016 A | 3/1999 | Presta et al. |
| 5,910,574 A | 6/1999 | Presta et al. |
| 6,025,166 A | 2/2000 | Presta et al. |
| 6,027,927 A | 2/2000 | Presta et al. |
| 6,153,189 A | 11/2000 | Presta et al. |
| 6,531,152 B1 | 3/2003 | Lerner et al. |
| 6,861,509 B1 | 3/2005 | Sanicola-Nadel et al. |
| 7,384,632 B2 | 6/2008 | Devaux et al. |
| 7,465,726 B2 | 12/2008 | Ahmed et al. |
| 7,504,509 B2 | 3/2009 | Ibrahim et al. |
| 7,514,446 B2 | 4/2009 | Davis-Ward et al. |
| 7,615,383 B2 | 11/2009 | Devaux et al. |
| 7,795,273 B2 | 9/2010 | Imbach et al. |
| 7,863,288 B2 | 1/2011 | Ibrahim et al. |

(Continued)

FOREIGN PATENT DOCUMENTS

| | | |
|---|---|---|
| CN | 105255927 A | 1/2016 |
| EP | 3037547 A1 | 6/2016 |

(Continued)

OTHER PUBLICATIONS

U.S. Appl. No. 15/211,702, filed Jul. 15, 2016, Steven W. Andrews.

(Continued)

*Primary Examiner* — Deepak R Rao
(74) *Attorney, Agent, or Firm* — Fish & Richardson P.C.

(57) ABSTRACT

Provided herein are compounds of the General Formula I:

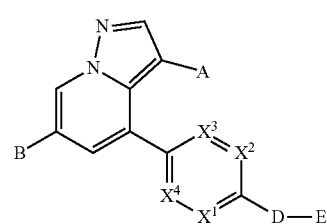

and stereoisomers and pharmaceutically acceptable salts or solvates thereof, in which A, B, D, E, $X^1$, $X^2$, $X^3$ and $X^4$ have the meanings given in the specification, which are inhibitors of RET kinase and are useful in the treatment and prevention of diseases which can be treated with a RET kinase inhibitor, including diseases or disorders mediated by a RET kinase.

29 Claims, No Drawings

Specification includes a Sequence Listing.

(56) References Cited

U.S. PATENT DOCUMENTS

| | | |
|---|---|---|
| 7,863,289 B2 | 1/2011 | Spevak et al. |
| 8,012,966 B2 | 9/2011 | Tang et al. |
| 8,026,247 B2 | 9/2011 | Bold et al. |
| 8,067,434 B2 | 11/2011 | Ibrahim et al. |
| 8,106,069 B2 | 1/2012 | Salom et al. |
| 8,114,989 B2 | 2/2012 | Wang et al. |
| 8,129,374 B2 | 3/2012 | Bhagwat et al. |
| 8,198,298 B2 | 6/2012 | Salom et al. |
| 8,299,057 B2 | 10/2012 | Lombardi Borgia et al. |
| 8,338,417 B2 | 12/2012 | Li et al. |
| 8,354,526 B2 | 1/2013 | Ding et al. |
| 8,399,442 B2 | 3/2013 | Berdini et al. |
| 8,450,322 B2 | 5/2013 | Andrews et al. |
| 8,461,161 B2 | 6/2013 | Burns et al. |
| 8,501,756 B2 | 8/2013 | Artman, III et al. |
| 8,513,263 B2 | 8/2013 | Haas et al. |
| 8,524,709 B2 | 9/2013 | Liang et al. |
| 8,552,002 B2 | 10/2013 | Ding et al. |
| 8,568,998 B2 | 10/2013 | Mani et al. |
| 8,629,135 B2 | 1/2014 | Gujral et al. |
| 8,637,256 B2 | 1/2014 | Ernst |
| 8,637,516 B2 | 1/2014 | Fan et al. |
| 8,642,035 B2 | 2/2014 | Luehrsen |
| 8,673,347 B2 | 3/2014 | Traversa et al. |
| 8,686,005 B2 | 4/2014 | Gregor |
| 8,691,221 B2 | 4/2014 | Pavone et al. |
| 8,741,849 B2 | 6/2014 | Panitch et al. |
| 8,754,209 B2 | 6/2014 | Sim et al. |
| 8,791,123 B2 | 7/2014 | Allen et al. |
| 8,815,901 B2 | 8/2014 | Furet et al. |
| 8,815,906 B2 | 8/2014 | Gregor et al. |
| 8,895,744 B2 | 11/2014 | Gambacorti Passerini et al. |
| 8,912,194 B2 | 12/2014 | Ciomei et al. |
| 8,912,204 B2 | 12/2014 | Ibrahim et al. |
| 8,933,084 B2 | 1/2015 | Andrews et al. |
| 8,933,230 B2 | 1/2015 | Yun et al. |
| 8,937,071 B2 | 1/2015 | Eidam et al. |
| 8,946,226 B2 | 2/2015 | Ciomei et al. |
| 9,006,256 B2 | 4/2015 | Matsui |
| 9,035,063 B2 | 5/2015 | Eidam et al. |
| 9,102,671 B2 | 8/2015 | Molteni et al. |
| 9,149,464 B2 | 10/2015 | Bakale et al. |
| 9,150,517 B2 | 10/2015 | Bakale et al. |
| 9,186,318 B2 | 11/2015 | Yun et al. |
| 9,216,172 B2 | 12/2015 | Kohno et al. |
| 9,242,977 B2 | 1/2016 | Takeuchi et al. |
| 9,260,437 B2 | 2/2016 | Ibrahim et al. |
| 9,273,051 B2 | 3/2016 | Chen et al. |
| 9,297,011 B2 | 3/2016 | Downing et al. |
| 9,321,772 B2 | 4/2016 | Dar et al. |
| 9,487,491 B2 | 11/2016 | Shimada et al. |
| 9,493,455 B2 | 11/2016 | Cheve et al. |
| 9,505,784 B2 | 11/2016 | Choi et al. |
| 9,522,910 B2 | 12/2016 | Chilov et al. |
| 9,550,772 B2 | 1/2017 | Cheve et al. |
| 9,604,980 B2 | 3/2017 | Menichincheri et al. |
| 9,669,028 B2 | 6/2017 | Vankayalapati et al. |
| 9,682,083 B2 | 6/2017 | Angiolini et al. |
| 9,738,660 B2 | 8/2017 | Yang et al. |
| 9,758,508 B2 | 9/2017 | Hong et al. |
| 9,789,100 B2 | 10/2017 | Eidam |
| 9,801,880 B2 | 10/2017 | Micklem |
| 2004/0185547 A1 | 9/2004 | Mohammadi et al. |
| 2005/0209195 A1 | 9/2005 | Menta et al. |
| 2005/0222171 A1 | 10/2005 | Bold et al. |
| 2006/0183900 A1 | 8/2006 | Huang et al. |
| 2007/0117800 A1 | 5/2007 | Arnold et al. |
| 2007/0149523 A1 | 6/2007 | Ehlert et al. |
| 2007/0265274 A1 | 11/2007 | Fagin et al. |
| 2008/0199426 A1 | 8/2008 | Sukhatme et al. |
| 2008/0234267 A1 | 9/2008 | Lackey |
| 2008/0234276 A1 | 9/2008 | Boyle et al. |
| 2008/0234284 A1 | 9/2008 | Imbach et al. |
| 2008/0262021 A1 | 10/2008 | Capraro et al. |
| 2008/0275054 A1 | 11/2008 | Holzer et al. |
| 2008/0287427 A1 | 11/2008 | Bold et al. |
| 2008/0312192 A1 | 12/2008 | Bold et al. |
| 2008/0319005 A1 | 12/2008 | Bold et al. |
| 2009/0012045 A1 | 1/2009 | Hitoshi et al. |
| 2009/0027556 A1 | 1/2009 | Bleau et al. |
| 2009/0048249 A1 | 2/2009 | Chiu et al. |
| 2009/0069360 A1 | 3/2009 | Batt et al. |
| 2009/0099167 A1 | 4/2009 | Bold et al. |
| 2009/0130229 A1 | 5/2009 | Lanzi et al. |
| 2009/0143399 A1 | 6/2009 | Hurley et al. |
| 2009/0152083 A1 | 6/2009 | Cheng et al. |
| 2009/0209496 A1 | 8/2009 | Chaplin et al. |
| 2009/0215761 A1 | 8/2009 | Whitten et al. |
| 2009/0227556 A1 | 9/2009 | Obaishi |
| 2009/0312321 A1 | 12/2009 | Ren et al. |
| 2010/0004239 A1 | 1/2010 | Tang et al. |
| 2010/0048540 A1 | 2/2010 | Boyle et al. |
| 2010/0069395 A1 | 3/2010 | Imbach et al. |
| 2010/0075916 A1 | 3/2010 | Gant et al. |
| 2010/0081675 A1 | 4/2010 | Hsieh et al. |
| 2010/0152219 A1 | 6/2010 | Block et al. |
| 2010/0173954 A1 | 7/2010 | Wilhelm et al. |
| 2010/0209488 A1 | 8/2010 | Wrasidlo et al. |
| 2010/0280012 A1 | 11/2010 | Lee |
| 2010/0297115 A1 | 11/2010 | Blaustein |
| 2010/0324065 A1 | 12/2010 | Ibrahim et al. |
| 2011/0046370 A1 | 2/2011 | Sim et al. |
| 2011/0053934 A1 | 3/2011 | Angell et al. |
| 2011/0133637 A1 | 6/2011 | Ota |
| 2011/0189167 A1 | 8/2011 | Flynn et al. |
| 2011/0195072 A1 | 8/2011 | Boulay et al. |
| 2011/0212053 A1 | 9/2011 | Qian et al. |
| 2011/0269739 A1 | 11/2011 | Kim et al. |
| 2011/0281841 A1 | 11/2011 | Lee et al. |
| 2011/0301157 A1 | 12/2011 | Bold et al. |
| 2012/0065233 A1 | 3/2012 | Gregor |
| 2012/0070410 A1 | 3/2012 | Apuy et al. |
| 2012/0225057 A1 | 9/2012 | Flynn et al. |
| 2012/0271048 A1 | 10/2012 | Sim et al. |
| 2012/0277247 A1 | 11/2012 | Menet et al. |
| 2012/0277424 A1 | 11/2012 | Sim et al. |
| 2012/0283261 A1 | 11/2012 | Bearss et al. |
| 2012/0302567 A1 | 11/2012 | Jung et al. |
| 2013/0012703 A1 | 1/2013 | Sim et al. |
| 2013/0029925 A1 | 1/2013 | Vandier et al. |
| 2013/0053370 A1 | 2/2013 | Son et al. |
| 2013/0079343 A1 | 3/2013 | Sim et al. |
| 2013/0303518 A1 | 11/2013 | Tang et al. |
| 2014/0121239 A1 | 5/2014 | Aftab |
| 2014/0137274 A1 | 5/2014 | Ishikawa |
| 2014/0272951 A1 | 9/2014 | Chakravarti et al. |
| 2014/0371219 A1 | 12/2014 | Bae et al. |
| 2015/0018336 A1 | 1/2015 | Chen et al. |
| 2015/0051222 A1 | 2/2015 | Barbugian et al. |
| 2015/0057335 A1 | 2/2015 | Kohno et al. |
| 2015/0065468 A1 | 3/2015 | Holladay et al. |
| 2015/0099721 A1 | 4/2015 | Acquaviva et al. |
| 2015/0099762 A1 | 4/2015 | Eidam et al. |
| 2015/0166564 A1 | 6/2015 | Allen et al. |
| 2015/0177246 A1 | 6/2015 | Shibata et al. |
| 2015/0238477 A1 | 8/2015 | Aftab |
| 2015/0272958 A1 | 10/2015 | Kodama et al. |
| 2015/0283132 A1 | 10/2015 | Lim et al. |
| 2015/0306086 A1 | 10/2015 | Wilcoxen |
| 2016/0000783 A1 | 1/2016 | Takeuchi et al. |
| 2016/0009709 A1 | 1/2016 | Cheve et al. |
| 2016/0046636 A1 | 2/2016 | Gray et al. |
| 2016/0137654 A1 | 5/2016 | Arrigo et al. |
| 2016/0176865 A1 | 6/2016 | Ibrahim et al. |
| 2017/0014413 A1 | 1/2017 | Downing et al. |
| 2017/0044106 A1 | 2/2017 | Aftab et al. |
| 2017/0096425 A1 | 4/2017 | Andrews et al. |
| 2017/0114032 A1 | 4/2017 | Cheng et al. |
| 2017/0121312 A1 | 5/2017 | Brubaker et al. |
| 2017/0226100 A1 | 8/2017 | Jiaang et al. |
| 2017/0267661 A1 | 9/2017 | Kim et al. |
| 2017/0281632 A1 | 10/2017 | Cox et al. |
| 2017/0283404 A1 | 10/2017 | Cheung et al. |
| 2017/0298074 A1 | 10/2017 | Cheung et al. |

(56) References Cited

U.S. PATENT DOCUMENTS

| | | |
|---|---|---|
| 2018/0009817 A1 | 1/2018 | Miyazaki et al. |
| 2018/0009818 A1 | 1/2018 | Miyazaki et al. |
| 2018/0133200 A1 | 5/2018 | Andrews et al. |
| 2018/0133207 A1 | 5/2018 | Andrews et al. |
| 2018/0133213 A1 | 5/2018 | Andrews et al. |
| 2018/0134702 A1 | 5/2018 | Andrews et al. |
| 2018/0134703 A1 | 5/2018 | Andrews et al. |
| 2018/0148445 A1 | 5/2018 | Andrews et al. |

FOREIGN PATENT DOCUMENTS

| | | |
|---|---|---|
| JP | 2015109806 A | 6/2015 |
| WO | WO8705297 | 9/1987 |
| WO | WO1997044356 | 11/1997 |
| WO | WO2001016169 | 3/2001 |
| WO | WO2001062273 | 8/2001 |
| WO | WO2003020698 | 3/2003 |
| WO | WO2005044835 | 5/2005 |
| WO | WO2005051366 | 6/2005 |
| WO | WO2005062795 | 7/2005 |
| WO | WO2005070431 | 8/2005 |
| WO | WO2006089298 | 8/2006 |
| WO | WO2006123113 | 11/2006 |
| WO | WO2006130613 | 12/2006 |
| WO | WO2006131952 | 12/2006 |
| WO | WO2007002325 | 1/2007 |
| WO | WO2007002433 | 1/2007 |
| WO | WO2007022999 | 3/2007 |
| WO | WO2007054357 | 5/2007 |
| WO | WO2007057397 | 5/2007 |
| WO | WO2007057399 | 5/2007 |
| WO | WO2007087245 | 8/2007 |
| WO | WO2007109045 | 9/2007 |
| WO | WO2007110344 | 10/2007 |
| WO | WO2007136103 | 11/2007 |
| WO | WO2008031551 | 3/2008 |
| WO | WO2008079903 | 7/2008 |
| WO | WO2008079906 | 7/2008 |
| WO | WO2008079909 | 7/2008 |
| WO | WO2008080001 | 7/2008 |
| WO | WO2008080015 | 7/2008 |
| WO | WO2009007748 | 1/2009 |
| WO | WO2009012283 | 1/2009 |
| WO | WO2009013126 | 1/2009 |
| WO | WO2009014637 | 1/2009 |
| WO | WO2009017838 | 2/2009 |
| WO | WO2009023978 | 2/2009 |
| WO | WO2009042646 | 4/2009 |
| WO | WO2009053442 | 4/2009 |
| WO | WO2009071480 | 6/2009 |
| WO | WO2009092049 | 7/2009 |
| WO | WO2009118411 | 10/2009 |
| WO | WO2009143018 | 11/2009 |
| WO | WO2009143024 | 11/2009 |
| WO | WO2009152083 | 12/2009 |
| WO | WO2010031816 | 3/2010 |
| WO | WO2010033941 | 3/2010 |
| WO | WO2010048314 | 4/2010 |
| WO | WO2010058006 | 5/2010 |
| WO | WO2010111527 | 9/2010 |
| WO | WO2010145998 | 12/2010 |
| WO | WO2011006074 | 1/2011 |
| WO | WO2011022439 | 2/2011 |
| WO | WO2011045344 | 4/2011 |
| WO | WO2011092120 | 8/2011 |
| WO | WO2011133637 | 10/2011 |
| WO | WO2011146336 | 11/2011 |
| WO | WO2012034091 | 3/2012 |
| WO | WO2012034095 | 3/2012 |
| WO | WO2012047017 | 4/2012 |
| WO | WO2012053606 | 4/2012 |
| WO | WO2012101029 | 8/2012 |
| WO | WO2012101032 | 8/2012 |
| WO | WO2012109075 | 8/2012 |
| WO | WO2012113774 | 8/2012 |
| WO | WO2012116217 | 8/2012 |
| WO | WO2012139930 | 10/2012 |
| WO | WO2012143248 | 10/2012 |
| WO | WO2012152763 | 11/2012 |
| WO | WO2012158413 | 11/2012 |
| WO | WO2012171337 | 12/2012 |
| WO | WO2013014039 | 1/2013 |
| WO | WO2013016720 | 1/2013 |
| WO | WO2013036232 | 3/2013 |
| WO | WO2013042137 | 3/2013 |
| WO | WO2013050446 | 4/2013 |
| WO | WO2013050448 | 4/2013 |
| WO | WO2013074518 | 5/2013 |
| WO | WO2013102059 | 7/2013 |
| WO | WO2013174876 | 11/2013 |
| WO | WO2013183578 | 12/2013 |
| WO | WO2014011900 | 1/2014 |
| WO | WO2014019908 | 2/2014 |
| WO | WO2014072220 | 5/2014 |
| WO | WO2014075035 | 5/2014 |
| WO | WO2014078322 | 5/2014 |
| WO | WO2014078323 | 5/2014 |
| WO | WO2014078325 | 5/2014 |
| WO | WO2014078328 | 5/2014 |
| WO | WO2014078331 | 5/2014 |
| WO | WO2014078372 | 5/2014 |
| WO | WO2014078378 | 5/2014 |
| WO | WO2014078408 | 5/2014 |
| WO | WO2014078417 | 5/2014 |
| WO | WO2014078454 | 5/2014 |
| WO | WO2014083567 | 6/2014 |
| WO | WO2014086284 | 6/2014 |
| WO | WO2014141187 | 9/2014 |
| WO | WO2014160521 | 10/2014 |
| WO | WO2014160524 | 10/2014 |
| WO | WO2014184069 | 11/2014 |
| WO | WO2014194127 | 12/2014 |
| WO | WO2015017528 | 2/2015 |
| WO | WO2015017533 | 2/2015 |
| WO | WO2015057873 | 4/2015 |
| WO | WO2015058129 | 4/2015 |
| WO | WO2015061572 | 4/2015 |
| WO | WO2015079251 | 6/2015 |
| WO | WO2015108992 | 7/2015 |
| WO | WO2015112806 | 7/2015 |
| WO | WO2015124697 | 8/2015 |
| WO | WO2015161274 | 10/2015 |
| WO | WO2015161277 | 10/2015 |
| WO | WO2015175788 | 11/2015 |
| WO | WO2015191666 | 12/2015 |
| WO | WO2015191667 | 12/2015 |
| WO | WO2016011141 | 1/2016 |
| WO | WO2016011144 | 1/2016 |
| WO | WO2016011147 | 1/2016 |
| WO | WO2016022569 | 2/2016 |
| WO | WO2016027754 | 2/2016 |
| WO | WO2016037578 | 3/2016 |
| WO | WO2016038519 | 3/2016 |
| WO | WO2016038552 | 3/2016 |
| WO | WO2016075224 | 5/2016 |
| WO | WO2016077841 | 5/2016 |
| WO | WO2016081450 | 5/2016 |
| WO | WO2016096709 | 6/2016 |
| WO | WO2016127074 | 8/2016 |
| WO | WO2016137060 | 9/2016 |
| WO | WO2016141169 | 9/2016 |
| WO | WO2016168992 | 10/2016 |
| WO | WO2017009644 | 1/2017 |
| WO | WO2017011776 | 1/2017 |
| WO | WO2017013160 | 1/2017 |
| WO | WO2017026718 | 2/2017 |
| WO | WO2017027883 | 2/2017 |
| WO | WO2017043550 | 3/2017 |
| WO | WO2017049462 | 3/2017 |
| WO | WO2017097697 | 6/2017 |
| WO | WO2017122815 | 7/2017 |
| WO | WO2017145050 | 8/2017 |

(56) References Cited

FOREIGN PATENT DOCUMENTS

| WO | WO2017146116 | 8/2017 |
|---|---|---|
| WO | WO2017178844 | 10/2017 |
| WO | WO2017178845 | 10/2017 |

OTHER PUBLICATIONS

U.S. Appl. No. 15/858,658, filed Dec. 29, 2017, Steven W. Andrews.
U.S. Appl. No. 15/860,781, filed Jan. 3, 2018, Steven W. Andrews.
U.S. Appl. No. 15/858,240, filed Dec. 29, 2017, Steven W. Andrews.
U.S. Appl. No. 15/860,808, filed Jan. 3, 2018, Steven W. Andrews.
U.S. Appl. No. 15/860,852, filed Jan. 3, 2018, Steven W. Andrews.
U.S. Appl. No. 15/858,929, filed Dec. 29, 2017, Steven W. Andrews.
U.S. Appl. No. 15/860,894, filed Jan. 3, 2018, Steven W. Andrews.
U.S. Appl. No. 15/861,244, filed Jan. 3, 2018, Steven W. Andrews.
Albaugh et al., "Discovery of GNF-5837, a Selective TRK Inhibitor with Efficacy in Rodent Cancer Tumor Models," ACS Med Chem. Lett., Jan. 1, 2012;3(2):140-145.
Amit M et al., "Upregulation of RET induces perineurial invasion of pancreatic adenocarcinoma." Oncogene Jun. 8, 2017; 36:3232-3239.
Andreucci et al., "Targeting the receptor tyrosine kinase RET in combination with aromatase inhibitors in ER positive breast cancer xenografts," Oncotarget, Dec. 6, 2016, 7(49):80543-80553.
Antonescu et al., "Molecular characterization of inflammatory myofibroblastic tumors with frequent ALK and ROS1 gene fusions and rare novel RET rearrangement," Am J Surg Pathol, Jul. 2015;39(7):957-967.
Arighi et al., "RET tyrosine kinase signaling in development and cancer," Cytokine Growth Factor Rev, Aug.-Oct. 2005; 16(4-5):441-467.
Ballerini et al., "RET fusion genes are associated with chronic myelomonocytic leukemia and enhance monocytic differentiation," Leukemia, Nov. 2012;26(11):2384-2389.
Bastien et al., Journal of Molecular Diagnostics, 18(6):1027, Abstract Number: S120, 2016 Annual Meeting of the Association for Molecular Pathology, Charlotte, NC, 2016.
Behrens et al., "Gö 6976 is a potent inhibitor of neurotrophin-receptor intrinsic tyrosine kinase," J Neurochem. Mar. 1999;72(3):919-924.
Bhinge et al., "EGFR mediates activation of RET in lung adenocarcinoma with neuroendocrine differentiation characterized by ASCL1 expression," Oncotarget, Apr. 18, 2017, 8(16):27155-27165.
Borecka et al., European Journal of Cancer, (Jul. 2016) vol. 61, No. 1, pp. S26, Abstract No. 162, Meeting Info: 24th Biennial Congress of the European Association for Cancer Research, EACR 2016. Manchester, United Kingdom.
Borrello et al., "RET inhibition: implications in cancer therapy," Expert Opin. Ther. Targets, Apr. 2013, 17(4):403-419.
Boulay et al., "The Ret receptor tyrosine kinase pathway functionally interacts with the ERalpha pathway in breast cancer," Cancer Res., May 15, 2008;68(10):3743-3751.
Brodeur, "Neuroblastoma: biological insights into a clinical enigma," Nat Rev Cancer., Mar. 2003, 3(3):203-216.
Butler Tjaden et al., "The developmental etiology and pathogenesis of Hirschsprung disease," Transl. Res., Jul. 2013;162(1):1-15.
Calero et al., "Sunitinib suppress neuroblastoma growth through degradation of MYCN and inhibition of angiogenesis," PLoS One. Apr. 23, 2014;9(4):e95628.
Camilleri, "Peripheral mechanisms in irritable bowel syndrome," N Engl J Med, Oct. 25, 2012, 367(17):1626-1635.
Camoratto et al., "CEP-751 inhibits TRK receptor tyrosine kinase activity in vitro exhibits anti-tumor activity," Int J Cancer. Aug. 7, 1997;72(4):673-679.
Camós et al., "Gene expression profiling of acute myeloid leukemia with translocation t(8;16)(p11;p13) and MYST3-CREBBP rearrangement reveals a distinctive signature with a specific pattern of HOX gene expression," Cancer Res., Jul. 15, 2006;66(14):6947-6954.
Cancer Genome Atlas Network, "Comprehensive molecular characterization of human colon and rectal cancer," Nature, Jul. 18, 2012;487(7407):330-337.
Carlomagno et al., "Identification of tyrosine 806 as a molecular determinant of RET kinase sensitivity to ZD6474," Endocr. Rel. Cancer, Mar. 2009;16(1):233-241.
Carpinelli et al., "PHA-739358, a potent inhibitor of Aurora kinases with a selective target inhibition profile relevant to cancer," Mol Cancer Ther., Dec. 2007;6(12 Pt 1):3158-68.
Cecchirini et al., "Somatic in frame deletions not involving juxtamembranous cysteine residues strongly activate the RET proto-oncogene," Oncogene, May 29, 1997;14(21):2609-2612.
Ceolin et al., "Effect of 3'UTR RET Variants on RET mRNA Secondary Structure and Disease Presentation in Medullary Thyroid Carcinoma," PLoS One, Feb. 1, 2016;11(2):e0147840. doi: 10.1371/journal.pone.0147840. eCollection 2016.
Chang et al., "EGF Induced RET Inhibitor Resistance in CCDC6-RET Lung Cancer Cells," Yonsei Med J, Jan. 2017, 58(1):9-18.
Choi et al., "(R)-2-Phenylpyrrolidine Substituted Imidazopyridazines: A New Class of Potent and Selective Pan-TRK Inhibitors," ACS Med Chem Lett., Mar. 16, 2015;6(5):562-567.
Corsello et al., Endocrine Reviews, (Jun. 2014) vol. 35, No. 3, Suppl. S, pp. SUN-0322, Meeting Info.: 96th Annual Meeting and Expo of the Endocrine-Society, Chicago, IL, USA, Jun. 21-24, 2014.
Cranston et al., "RET is constitutively activated by novel tandem mutations that alter the active site resulting in multiple endocrine neoplasia type 2B," Cancer Res., Oct. 15, 2006;66(20):10179-10187.
Croucher et al., "TrkB inhibition by GNF-4256 slows growth and enhances chemotherapeutic efficacy in neuroblastoma xenografts," Cancer Chemother Pharmacol., Jan. 2015;75(1):131-141.
Davila et al., "Comprehensive genomic profiling of a rare thyroid follicular dendritic cell sarcoma," Rare Tumors, 2017, 9(2):6834.
Dawson et al., "Altered expression of RET proto-oncogene product in prostatic intraepithelial neoplasia and prostate cancer," J Natl Cancer Inst, Apr. 1, 1998;90(7):519-523.
De Almeida et al., Endocrine Reviews, 2016, vol. 37, No. 2, Supp. Supplement 1. Abstract No. SUN-068; 93th Annual Meeting and Expo of the Endocrine Society, Endo 2016. Boston, MA, US. Apr. 1, 2016-Apr. 4, 2016.
De Groot et al., "RET as a diagnostic and therapeutic target in sporadic and hereditary endocrine tumors," Endocrine Rev, Aug. 2006;27(5):535-560.
Demeure et al., "Whole-genome Sequencing of an Aggressive BRAF Wild-type Papillary Thyroid Cancer Identified EML4-ALK Translocation as a Therapeutic Target," World J. Surg., Jun. 2014, 38(6):1296-305.
Dinér er al., "Preparation of 3-substituted-1-isopropyl-1H-pyrazolo[3,4-d]pyrimidin-4-amines as RET kinase inhibitors," J. Med. Chem., May 24, 2012, 55(10):4872-4876.
Ding et al., "Artemin, a member of the glial cell line-derived neurotrophic factor family of ligands, is HER2-regulated and mediates acquired trastuzumab resistance by promoting cancer stem cell-like behavior in mammary carcinoma cells," J Biol Chem, Jun. 6, 2014, 289(23):16057-71.
Dogan et al., Laboratory Investigation, (Feb. 2017) vol. 97, Supp. 1, pp. 323 A. Abstract No. 1298, Meeting Info: 106th Annual Meeting of the United States and Canadian Academy of Pathology, USCAP 2017. San Antonio, TX, United States.
Dogan et al., "Genomic Profiling of the Two Closely Related "cousins" Acinic Cell Carcinoma and Mammary Analog Secretory Carcinoma of Salivary Glands Reveals Novel NVOA4-RET Fusion in Mammary Analog Secretory Carcinoma," Modern Pathology, vol. 30, Supp. [2], pp. 323A-323A. MA 1298, 2017.
Drilon et al., "Phase II study of cabozantinib for patients with advanced RET-rearranged lung cancers," Journal of Clinical Oncology, May 20, 2015, 33(15S):8007-8007 [Abstract Only], 6 pages.
Esseghir et al., "A role for glial cell derived neurotrophic factor induced expression by inflammatory cytokines and RET/GFR alpha 1 receptor up-regulation in breast cancer," Cancer Res, Dec. 15, 2007;67(24):11732-11741.

(56) References Cited

OTHER PUBLICATIONS

Fang et al., "Detection of a novel RET gene fusion in a non-small cell lung cancer patient using AMP chemistry." Journal of Thoracic Oncology, Feb. 1, 2016, 11(2):S21-S22.
Flavin et al., "RET protein expression in papillary renal cell carcinoma," Urol. Oncol., Nov.-Dec, 2012;30(6):900-905.
Fugazzola et al., "Molecular and biochemical analysis of RET/PTC4, a novel oncogenic rearrangement between RET and ELE1 genes, in a post-Chernobyl papillary thyroid cancer," Oncogene, Sep. 1996, 13(5): 1093-7.
Futami et al., "A novel somatic point mutation of the RET Proto-oncogene in tumor tissues of small cell lung cancer patients," Jpn. J. Cancer Res., Dec. 1995, 86(12):1127-1130.
Gao et al., "Neurotrophic Factor Artemin Promotes Invasiveness and Neurotrophic Function of Pancreatic Adenocarcinoma In Vivo and In Vitro," Pancreas, Jan. 2015, 44(1):134-143.
Gattei et al., "Expression of the RET receptor tyrosine kinase and GDNFR-alpha in normal and leukemic human hematopoietic cells and stromal cells of the bone marrow microenvironment," Blood, Apr. 15, 1997;89(8):2925-2937.
Gattei, et al., "Differential expression of the RET gene in human acute myeloid leukemia," Ann. Hematol, Nov. 1998, 77(5):207-210.
Gattelli et al., "Ret inhibition decreases growth and metastatic potential of estrogen receptor positive breast cancer cells," EMBO Mol. Med., Sep. 2013;5(9):1335-1350.
Gazizova et al., Endocrine Reviews, (Jun. 2014) vol. 35, No. 3, Suppl. S, pp. SAT-0304, Meeting Info.: 96th Annual Meeting and Expo of the Endocrine-Society, Chicago, IL, USA, Jun. 21-24, 2014.
Gil et al., "Paracrine regulation of pancreatic cancer cell invasion by peripheral nerves," J. Natl. Cancer Inst., Jan. 20, 2010;102(2):107-118.
Gozgit et al., "RET fusions identified in colorectal cancer PDX models are sensitive to the potent RET inhibitor ponatinib," AACR Annual Meeting, Apr. 7, 2014, Presentation Abstract, [Abstract Only], 1 page.
Greco et al., "Molecular pathology of differentiated thyroid cancer," J. Nucl. Med. Mol. Imaging, Oct. 2009, 53:440-454.
Greene & Wuts, eds., "Protecting Groups in Organic Synthesis", 2nd ed. New York; John Wiley & Sons, Inc., 1991, Chapter One, 20 pages.
Grey et al., "The RET E616Q Variant is a Gain of Function Mutation Present in a Family with Features of Multiple Endocrine Neoplasia 2A," Endocrine Pathology, Mar. 2017, 28(1):41-48.
Grieco et al.., "PTC is a novel rearranged form of the ret proto-oncogene and is frequently detected in vivo in human thyroid papillary carcinomas," Cell, Feb. 23, 1990, 60(4):557-563.
Grubbs et al., "RET fusion as a novel driver of medullary thyroid carcinoma," J. Clin. Endocrinol. Metab., Mar. 2015;100(3):788-793.
Gura et al., "Systems for identifying new drugs are often faulty," Science, 1997, 278:1041-1042.
Halkova et al., "A novel RET/PTC variant detected in a pediatric patient with papillary thyroid cancer without ionization history," Human Pathology, Dec. 2015, 46(12):1962-1969.
Hezam et al., "Artemin promotes oncogenicity, metastasis and drug resistance in cancer cells," Rev Neurosci, Jan. 26, 2018, 29(1):93-98.
Hirshfield et al., Cancer Research, (Feb. 2017) vol. 77, No. 4, Supp. 1. Abstract No. P3-07-02. Meeting Info: 39th Annual CTRC-AACR San Antonio Breast Cancer Symposium. San Antonio, TX, United States. Dec. 6,2016-Dec. 10, 2016.
Hoffman et al., "Activation of colonic mucosal 5-HT(4) receptors accelerates propulsive motility and inhibits visceral hypersensitivity," Gastroenterology, Apr. 2012;142(4):844-854.
Hofstra et al., "No mutations found by RET mutation scanning in sporadic and hereditary neuroblastoma," Hum Genet., Mar. 1996, 97(3):362-364.

Huang et al., "Preclinical Modeling of KIF5B-RET Fusion Lung Adenocarcinoma," Mol. Cancer Ther., Oct. 2016, 15(10):2521-2529.
Ibrahimpasic et al., "Genomic Alterations in Fatal Forms of Non-Anaplastic Thyroid Cancer: Identification of MED12 and RBM10 as Novel Thyroid Cancer Genes Associated with Tumor Virulence," Clin. Cancer Res., Oct. 2017, 23(19):5970-5980.
International Preliminary Report on Patentability in International Application No. PCT/US2016/042576, dated Jan. 25, 2018, 8 pages.
International Search Report and Written Opinion in International Application No. PCT/US2016/042576, dated Sep. 27, 2016, 14 pages.
Ito et al., "Expression of glial cell line-derived neurotrophic factor family members and their receptors in pancreatic cancers," Surgery, Oct. 2005, 138(4):788-794.
Iwahashi et al., "Expression of glial cell line-derived neurotrophic factor correlates with perineural invasion of bile duct carcinoma," Cancer, Jan. 1, 2002, 94(1):167-174.
Iyama et al., "Identification of Three Novel Fusion Oncogenes, SQSTM1/NTRK3, AFAP1L2/RET, and PPFIBP2/RET, in Thyroid Cancers of Young Patients in Fukushima ," Thyroid, Jun. 2017, 27(6):811-818.
Iyer et al, "AZ64 inhibits TrkB and enhances the efficacy of chemotherapy and local radiation in neuroblastoma xenografts," Cancer Chemother Pharmacol., Sep. 2012;70(3):477-486.
Johnson et al., Relationships between drug activity in NCI preclinical in vitro and in vivo models and early clinical trials, British Journal of Cancer, 84(10):1424-1431, 2001.
Joung et al., "Diffuse sclerosing variant of papillary thyroid carcinoma: major genetic alterations and prognostic implications," Histopathology, Jul. 2016, 69(1):45-53.
Jovanovic et al., "Novel RET mutations in macedonian patients with medullary thyroid carcinoma: genotype-phenotype correlations," Pril (Makedon Akad Nauk Umet Odd Med Nauki), 2015;36(1):93-107.
Ju et al., "A transforming KIF5B and RET gene fusion in lung adenocarcinoma revealed from whole-genome and transcriptome sequencing," Genome Res., Mar. 2012;22(3):436-445.
Kaneta et al., Abstract B173: Preclinical characterization and anti-tumor efficacy of DS-5010, a highly potent and selective RET inhibitor, Mol Cancer Ther Jan. 1, 2018 (17) (1 Supplement) B173; DOI:10.1158/1535-7163.TARG-17-B173.
Karachialiou et al ., "Real-time liquid biopsies become a reality in cancer treatment," Ann. Transl. Med , Mar. 2015, 3(3):36.
Karrasch et al., "How to Assess the Clinical Relevance of Novel RET Missense Variants in the Absence of Functional Studies?" Eur. Thyroid J., Mar. 2016;5(1):73-77.
Kato et al., "Repair by Src kinase of function-impaired RET with multiple endocrine neoplasia type 2A mutation with substitutions of tyrosines in the COOH-terminal kinase domain for phenylalanine," Cancer Res., Apr. 15, 2002, 62(8):2414-2422.
Kato et al., "RET Aberrations in Diverse Cancers: Next-Generation Sequencing of 4,871 Patients," Clin. Cancer Res., Apr. 15, 2017, 23(8):1988-1997.
Keszthelyi et al., "Revisiting concepts of visceral nociception in irritable bowel syndrome," Eur. J. Pain, Nov. 2012;16(10):1444-1454.
Kheiroddin et al., "RET Gene Analysis in Patients with Medullary Thyroid Carcinoma," Clin. Lab., Jan. 2016, 62(5):871-876.
Kim et al., "A New Germline Ala641Thr Variant in the Transmembrane Domain of the RET Gene Associated With Medullary Thyroid Cancer," Acto Endocrinologica-Bucharest, Apr. 2015, 11(2):189-194.
Kim et al., "Mammaglobin-A is a target for breast cancer vaccination," Oncoimmunology. Feb. 26, 2016;5(2):e1069940. eCollection Feb. 2016.
Kloosterman et al., "A systematic analysis of oncogenic gene fusions in primary colon cancer," Cancer Res., Jul. 15, 2017, 77(14):3814-3822.
Klugbauer et al., "A novel type of RET rearrangement (PTC8) in childhood papillary thyroid carcinomas and characterization of the involved gene (RFG8)," Cancer Res., Dec. 15, 2000;60(24):7028-32.

(56) References Cited

OTHER PUBLICATIONS

Kohlmann, et al., "Next-Generation Sequencing Technology Reveals a Characteristic Pattern of Molecular Mutations in 72.8% of Chronic Myelomonocytic Leukemia by Detecting Frequent Alterations in TET2, CBL, RAS, and RUNX1," J. Clin. Oncol. Aug. 20, 2010, 28(24):3858-3865.

Kohno et al., "KIF5B-RET fusions in lung adenocarcinoma," Nature Med., Feb. 12, 2012;18(3):375-377.

Kooistra et al., "KLIFS: A structural kinaseligand interaction database," Nucleic Acids Res., Jan. 2016, 44(D1)D365-D371.

Kraft et al, Cancer Research, 2017, vol. 77, No. 13, Supp. Supplement 1. Abstract No. 4882; American Association for Cancer Research Annual Meeting 2017. Washington, DC, United States. Apr. 1, 2017-Apr. 5, 2017.

Krampitz et al., "RET gene mutations (genotype and phenotype) of multiple endocrine neoplasia type 2 and familial medullary thyroid carcinoma," Cancer, Jul. 1, 2014;120(13):1920-1931.

Kubler et al. "Self-adjuvanted mRNA vaccination in advanced prostate cancer patients: a first-in-man phase I/IIa study," J Immunother Cancer. Jun. 16, 2015, 3:26, 14 pages.

Latteyer et al., "A 6-Base Pair in Frame Germline Deletion in Exon 7 of RET Leads to Increased RET Phosphorylation, ERK Activation, and MEN2A," J. Clin Endocrinol. Metab., Mar. 2016;101(3):1016-1022.

Le Rolle et al., "Identification and characterization of RET fusions in advanced colorectal cancer," Oncotarget, Oct. 6, 2015;6(30):28929-28937.

Lecht et al., "Angiostatic effects of K252a, a Trk inhibitor, in murine brain capillary endothelial cells," Mol Cell Biochem. Jun. 2010;339(1-2):201-213.

Lee et al., "Identification of a novel partner gene, KIAA1217, fused to RET: Functional characterization and inhibitor sensitivity of two isoforms in lung adenocarcinoma," Oncotarget, May 2, 2016, 7(24):36101-36114.

Lee et al., "Whole-exome sequencing identified mutational profiles of high-grade colon adenomas," Oncotarget, Jan. 2017, 8(4): 6579-6588.

Li et al., "Trk inhibitor attenuates the BDNF/TrkB-induced protection of neuroblastoma cells from etoposide in vitro and in vivo," Cancer Biol Ther., 2015;16(3):477-483.

Lipson et al., "Identification of new ALK and RET gene fusions from colorectal and lung cancer biopsies," Nature Med., Feb. 12, 2012;18(3):382-384.

Liu et al., "Oncogenic RET receptors display different autophosphorylation sites and substrate binding specificities," J Biol. Chem., J Biol Chem. Mar. 8, 1996;271(10):5309-5312.

Lopez-Delisle et al., "Activated ALK signals through the ERK-ETV5-RET pathway to drive neuroblastoma oncogenesis," Oncogene, Jan. 11, 2018, doi: 10.1038/s41388-017-0039-5. [Epub ahead of print].

Louis et al., "The 2016 World Health Organization Classification of Tumors of the Central Nervous System: a summary," Acta Neuropathol, Jun. 2016, 131(6):803-820.

Lu et al., "Targeted next generation sequencing identifies somatic mutations and gene fusions in papillary thyroid carcinoma," Oncotarget, Jul. 2017, 8(28):45784-45792.

Luo et al., "RET is a potential tumor suppressor gene in colorectal cancer," Oncogene, Apr. 18, 2013;32(16):2037-2047.

Mamedova et al., "Abstract #6: Construction of Baculovirial Vectors for RET Kinase Domain Mutants," Summer Undergraduate Research Programs (SURP) Student Abstracts, University of Oklahoma Health Sciences Center, 2016, p. 28 [Abstract Only].

Matsubara et al., "Identification of CCDC6-RET fusion in the human lung adenocarcinoma cell line, LC-2/ad," Journal of Thoracic Oncology, Dec. 2012;7(12):1872-1876.

McCarthy et al., "Tropomyosin receptor kinase inhibitors: a patent update 2009-2013," Expert. Opin. Ther. Pat., Jul. 2014;24(7):731-744.

Mendiola et al., "Preparation, Use, and Safety of O-Mesitylenesulfonylhydroxylamine," Org. Process Res. Dev., Jan. 2009, 13(2):263-267.

Montagnoli et al., "Anti-proliferative effects of GW441756, a novel inhibitor of NGFreceptor tyrosine kinase a (TRKA), in human sarcoma," Italian Journal of Anatomy and Embryology, Nov. 11, 2010, 115(1/2):117.

Morandi et al., "GDNF-RET signaling in ER-positive breast cancers is a key determinant of response and resistance to aromatase inhibitors," Cancer Res., Jun. 15, 2013;73(12):3783-3795.

Morgensztern et al., Journal of Thoracic Oncology, (Jan. 2017) vol. 12, No. 1, Supp. 1, pp. S717-S718, Abstract No. P1.07-035, Meeting Info: 17th World Conference of the International Association for the Study of Lung Cancer, IASLC 2016. Vienna, Austria. Dec. 4, 2016.

Mulligan et al., "Investigation of the genes for RET and its ligand complex, GDNF/GFR alpha-I, in small cell lung carcinoma," Genes Chromosomes Cancer, Apr. 1998, 21(4):326-332.

Mulligan, "RET revisited: expanding the oncogenic portfolio," Nature Reviews Cancer, Mar. 2014, 14(3):173-186.

Narayanan et al., "Discovery and preclinical characterization of novel small molecule TRK and ROS1 tyrosine kinase inhibitors for the treatment of cancer and inflammation," PLoS One. Dec. 26, 2013;8(12):e83380.

Narita et al., "Functional RET G691S polymorphism in cutaneous malignant melanoma," Oncogene, Aug. 27, 2009;28(34):3058-3068.

Nelson-Taylor et al., "Resistance to RET-Inhibition in RET-Rearranged NSCLC Is Mediated by Reactivation of RAS/MAPK Signaling," Mol. Cancer Ther., Aug. 2017, 16(8):1623-1633.

Ott et al., "An immunogenic personal neoantigen vaccine for patients with melanoma," Nature. Jul. 13, 2017 547(7662):217-221.

Pearce et al., Failure modes in anticancer drug discovery and development, Cancer Drug Design and Discovery Edited by Stephen Neidle, Chapter 18, pp. 424-435 (2008).

Petersen and Bogenmann, "The RET and TRKA pathways collaborate to regulate neuroblastoma differentiation," Oncogene, Jan. 8, 2004;23(1):213-225.

Pirker et al., "Alectinib in RET-rearranged non-small cell lung cancer—Another progress in precision medicine?" Transl. Lung Cancer Res., Dec. 2015;4(6):797-800.

Plaza-Menacho et al., "Targeting the receptor tyrosine kinase RET sensitizes breast cancer cells to tamoxifen treatment and reveals a role for RET in endocrine resistance," Oncogene, Aug. 19, 2010;29(33):4648-4657.

Plenker et al., "Drugging the catalytically inactive state of RET kinase in RET-rearranged tumors," Sci Transl Med, Jun. 14, 2017, 9(394). pii: eaah6144. doi: 10.1126/scitranslmed.aah6144.

Plosker, "Sipuleucel-T: in metastatic castration-resistant prostate cancer," Drugs. Jan. 1, 2011;71(1):101-108.

Postow et al., "Immune Checkpoint Blockade in Cancer Therapy," Journal of Clinical Oncology, Jun. 10, 2015;33(17):1974-1982.

Qi, et al., "RET mutation p. S891A in a Chinese family with familial medullary thyroid carcinoma and associated cutaneous amyloidosis binding OSMR variant p. G513D," Oncotarget, Oct. 20, 2015;6(32):33993-4003.

Rausch et al., "mRNA vaccine CV9103 and CV9104 for the treatment of prostate cancer," Human Vaccin immunother, 2014;10(11):3146-3152.

Reeser et al., "Validation of a Targeted RNA Sequencing Assay for Kinase Fusion Detection in Solid Tumors," J Mol. Diagn., Sep. 2017, 19(5):682-696.

Reungwetwattana et al., "Targeted therapies in development for non-small cell lung cancer," J Carcinog., Dec. 31, 2013;12:22.

Roblin et al., "Topical TrkA Kinase Inhibitor CT327 is an Effective, Novel Therapy for the Treatment of Pruritus due to Psoriasis: Results from Experimental Studies, and Efficacy and Safety of CT327 in a Phase 2b Clinical Trial in Patients with Psoriasis," Acta Derm Venereol, May 2015;95(5):542-548.

Romei and Elisei, "RET/PTC Translocations and Clinico-Pathological Features in Human Papillary Thyroid Carcinoma," Front Endocrinol (Lausanne), Apr. 11, 2012, 3:54.

(56) References Cited

OTHER PUBLICATIONS

Romei et al., European Thyroid Journal (Aug. 2016) vol. 5, Supp. Supplement 1, pp. 75; 39th Annual Meeting of the European Thyroid Association, ETA 2016. Copenhagen, Denmark. Sep. 3, 2016-Sep. 6, 2016.
Rosenzweig et al., "A case of advanced infantile myofibromatosis harboring a novel MYH10-RET fusion," Pediatr Blood Cancer, Jul. 2017;64(7). doi: 10.1002/pbc.26377. Epub Dec. 28, 2016.
Sabari et al., "Targeting RET-rearranged lung cancers with multikinase inhibitors," Oncoscience, Mar. 2017, 4(3-4):23-24.
Sahin et al., "Personalized RNA mutanome vaccines mobilize poly-specific therapeutic immunity against cancer," Nature, Jul. 13, 2017, 547(7662):222-226.
Saito et al., "Gene aberrations for precision medicine against lung adenocarcinoma," Cancer Science, Jun. 2016;107(6):713-720.
Santoro et al., "Development of thyroid papillary carcinomas secondary to tissue-specific expression of the RET/PTC1 oncogene in transgenic mice," Oncogene, Apr. 18, 1996, 12(8):1821-1826.
Scollo et al., "A novel RET gene mutation in a patient with apparently sporadic pheochromocytoma," Endocr. J., 2016;63(1):87-91.
Silva et al., "Identification and characterization of two novel germline RET variants associated with medullary thyroid carcinoma," Endrocrine, Jun. 2015, 49(2):366-372.
Simone, Oncology: Introduction, Cecil Textbook of Medicine, 20th Edition, vol. 1, pp. 1004-1101 O, 1995.
Sjoblom et al., "The consensus coding sequences of human breast and colorectal cancers," Science, Oct. 13, 2006;314(5797):268-274.
Skalova et al., "Molecular Profiling of Mammary Analog Secretory Carcinoma Revealed a Subset of Tumors Harboring a Novel ETV6-RET Translocation: Report of 10 Cases," Am. J Surg. Pathol., Feb. 2018, 42(2):234-246.
Song et al., "Potent antitumor activity of cabozantinib, a c-MET and VEGFR2 inhibitor, in a colorectal cancer patient-derived tumor explant model," International Journal of Cancer, Apr. 15, 2015;136(8):1967-1975.
Sromek et al., "Analysis of Newly Identified and Rare Synonymous Genetic Variants in the RET Gene in Patients with Medullary Thyroid Carcinoma in Polish Population," Endocr Pathol., Sep. 2017, 28(3):198-206.
Su et al., "RET/PTC Rearrangements Are Associated with Elevated Postoperative TSH Levels and Multifocal Lesions in Papillary Thyroid Cancer without Concomitant Thyroid Benign Disease," PLoS One, Nov. 1, 2016, 11(11):e0165596.
Takeuchi et al., "RET, ROS1 and ALK fusions in lung cancer," Nature Med., Feb. 12, 2012;18(3):378-381.
Tang et al., "Coexistent genetic alterations involving ALK, RET, ROS1 or MET in 15 cases of lung adenocarcinoma," Mod Pathol., Sep. 15, 2017, doi: 10.1038/modpathol.2017.109. [Epub ahead of print].
Taraviras et al., "Signalling by the RET receptor tyrosine kinase and its role in the development of the mammalian enteric nervous system," Development, Jun. 1999;126(12):2785-2797.
Thress et al., "Identification and preclinical characterization of AZ-23, a novel, selective, and orally bioavailable inhibitor of the Trk kinase pathway," Mol. Cancer Ther., Jul. 2009;8(7):1818-1827.
Van Linden et al., "KLIFS: A knowledge based structural database to navigate kinase-ligand interaction space," J Med Chem., Jan. 23, 2014, 57(2):249-277.
Vanden et al., Annals of Oncology, 2016, vol. 27, Supp. Supplement 6. Abstract No. 427PD; 4pt European Society for Medical Oncology Congress, ESMP 2016. Copenhagen, Denmark. Oct. 7, 2016-Oct. 11, 2016.
Velcheti et al., "FRMD4A/RET: A Novel RET Oncogenic Fusion Variant in Non-Small Cell Lung Carcinoma," J Thorac Oncol., Feb. 2017, 12(2):e15-e16.
Wang et al., "Identification of 4-aminopyrazolylpyrimidines as potent inhibitors of Trk kinases," J Med Chem. Aug. 14, 2008;51(15):4672-4684.
Wang et al., "Trk kinase inhibitors as new treatments for cancer and pain," Expert Opin. Ther. Pat., Mar. 2009;19(3):305-319.
Wells and Santoro, "Targeting the RET pathway in thyroid cancer," Clin Cancer Res., Dec. 1, 2009;15(23):7119-7123.
Wells et al., "Revised American Thyroid Association guidelines for the management of medullary thyroid carcinoma," Thyroid, Jun. 2015;25(6):567-610.
Wood et al, "The genomic landscapes of human breast and colorectal cancers," Science, Nov. 16, 2007, 318(5853):1108-1113.
Yoon et al., "A Pyrazolo[3,4-d]pyrimidin-4-amine Derivative Containing an Isoxazole Moiety Is a Selective and Potent Inhibitor of RET Gatekeeper Mutants," J. Med. Chem., Jan. 14, 2016, 59(1):358-373.
Zage et al.,"The selective Trk inhibitor AZ623 inhibits brain-derived neurotrophic factor-mediated neuroblastoma cell proliferation and signaling and is synergistic with topotecan," Cancer, Mar. 15, 2011;117(6):1321-1391. doi: 10.1002/cncr.25674. Epub Oct. 19, 2010.
Zeng et al. "The relationship between overexpression of glial cell-derived neurotrophic factor and its RET receptor with progression and prognosis of human pancreatic cancer," J. Int. Med. Res., Jul.-Aug. 2008;36(4):656-664.
Zhang et al., Laboratory Investigation, (Feb. 2017) vol. 97, Supp. 1, pp. 209A. Abstract No. 840, Meeting Info: 106th Annual Meeting of the United States and Canadian Academy of Pathology, USCAP 2017. San Antonio, TX, United States.

SUBSTITUTED PYRAZOLO[1,5-A]PYRIDINE COMPOUNDS AS RET KINASE INHIBITORS

CROSS-REFERENCE TO RELATED APPLICATIONS

This application is a continuation of U.S. application Ser. No. 15/211,702, filed Jul. 15, 2016, which claims priority to U.S. Provisional Application Ser. No. 62/193,448, filed Jul. 16, 2015 and 62/274,018, filed Dec. 31, 2015, both of which are hereby incorporated by reference in their entireties.

BACKGROUND

The present disclosure relates to novel compounds which exhibit Rearranged during Transfection (RET) kinase inhibition, pharmaceutical compositions comprising the compounds, processes for making the compounds, and the use of the compounds in therapy. More particularly, it relates to substituted pyrazolo[1,5-a]pyridine compounds useful in the treatment and prevention of diseases which can be treated with a RET kinase inhibitor, including RET-associated diseases and disorders.

RET is a single-pass transmembrane receptor belonging to the tyrosine kinase superfamily that is required for normal development, maturation and maintenance of several tissues and cell types (Mulligan, L. M., *Nature Reviews Cancer*, 2014, 14, 173-186). The extracellular portion of the RET kinase contains four calcium-dependent cadherin-like repeats involved in ligand binding and a juxtamembrane cysteine-rich region necessary for the correct folding of the RET extracellular domain, while the cytoplasmic portion of the receptor includes two tyrosine kinase subdomains.

RET signaling is mediated by the binding of a group of soluble proteins of the glial cell line-derived neurotrophic factor (GDNF) family ligands (GFLs), which also includes neurturin (NTRN), artemin (ARTN) and persephin (PSPN) (Arighi et al., *Cytokine Growth Factor Rev.*, 2005, 16, 441-67). Unlike other receptor tyrosine kinases, RET does not directly bind to GFLs and requires an additional co-receptor: that is, one of four GDNF family receptor-α (GFRα) family members, which are tethered to the cell surface by a glycosylphosphatidylinositol linkage. GFLs and GFRα family members form binary complexes that in turn bind to RET and recruit it into cholesterol-rich membrane subdomains, which are known as lipid rafts, where RET signaling occurs.

Upon binding of the ligand-co-receptor complex, RET dimerization and autophosphorylation on intracellular tyrosine residues recruits adaptor and signaling proteins to stimulate multiple downstream pathways. Adaptor protein binding to these docking sites leads to activation of Ras-MAPK and PI3K-Akt/mTOR signaling pathways or to recruitment of the CBL family of ubiquitin ligases that functions in RET downregulation of the RET-mediated functions.

Aberrant RET expression and/or activity have been demonstrated in different cancers and in gastrointestinal disorders such as irritable bowel syndrome (IBS).

SUMMARY OF THE INVENTION

It has now been found that substituted pyrazolo[1,5-a]pyridine compounds are inhibitors of RET kinase, and are useful for treating diseases such as proliferative diseases including cancers.

Accordingly, provided herein is a compound of the General Formula I:

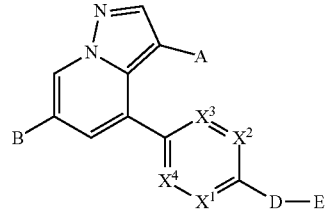

or a pharmaceutically acceptable salt or solvate thereof, wherein A, B, D, E, $X^1$, $X^2$, $X^3$ and $X^4$ are as defined herein.

Also provided herein is a pharmaceutical composition comprising a compound of General Formula I or a pharmaceutically acceptable salt or solvate thereof, in admixture with a pharmaceutically acceptable diluent or carrier.

Also provided herein is a method of inhibiting cell proliferation, in vitro or in vivo, the method comprising contacting a cell with an effective amount of a compound of General Formula I or a pharmaceutically acceptable salt or solvate thereof, or a pharmaceutical composition thereof as defined herein.

Also provided herein is a method of treating a RET-associated disease or disorder in a patient in need of such treatment, the method comprising administering to the patient a therapeutically effective amount of a compound of General Formula I or a pharmaceutically acceptable salt or solvate thereof, or a pharmaceutical composition thereof as defined herein.

Also provided herein is a method of treating cancer and/or inhibiting metastasis associated with a particular cancer in a patient in need of such treatment, the method comprising administering to the patient a therapeutically effective amount of a compound of General Formula I or a pharmaceutically acceptable salt or solvate thereof or a pharmaceutical composition thereof as defined herein.

Also provided herein is a method of treating irritable bowel syndrome (IBS) and/or pain associated with IBS in a patient in need of such treatment, the method comprising administering to the patient a therapeutically effective amount of a compound of General Formula I or a pharmaceutically acceptable salt or solvate thereof or a pharmaceutical composition thereof as defined herein.

Also provided is a method of providing supportive care to a cancer patient, including preventing or minimizing gastrointestinal disorders, such as diarrhea, associated with treatment, including chemotherapeutic treatment, the method comprising administering to the patient a therapeutically effective amount of a compound of General Formula I or a pharmaceutically acceptable salt or solvate thereof or a pharmaceutical composition thereof as defined herein.

Also provided herein is a compound of General Formula I or a pharmaceutically acceptable salt or solvate thereof, or a pharmaceutical composition thereof as defined herein for use in therapy.

Also provided herein is a compound of General Formula I or a pharmaceutically acceptable salt or solvate thereof or a pharmaceutical composition thereof as defined herein for use in the treatment of cancer and/or inhibiting metastasis associated with a particular cancer.

Also provided herein is a compound of General Formula I or a pharmaceutically acceptable salt or solvate thereof or a pharmaceutical composition thereof as defined herein for use in the treatment of irritable bowel syndrome (IBS) or pain associated with IBS.

Also provided is a compound of General Formula I or a pharmaceutically acceptable salt or solvate thereof or a pharmaceutical composition thereof as defined herein for use providing supportive care to a cancer patient, including preventing or minimizing gastrointestinal disorders, such as diarrhea, associated with treatment, including chemotherapeutic treatment.

Also provided herein is a compound of General Formula I or a pharmaceutically acceptable salt or solvate thereof for use in the inhibition of RET kinase activity.

Also provided herein is a compound of General Formula I or a pharmaceutically acceptable salt or solvate thereof or a pharmaceutical composition thereof as defined herein, for use in the treatment of a RET-associated disease or disorder.

Also provided herein is the use of a compound of General Formula I or a pharmaceutically acceptable salt or solvate thereof, as defined herein in the manufacture of a medicament for the treatment of cancer and/or inhibiting metastasis associated with a particular cancer.

Also provided herein is the use of a compound of General Formula I or a pharmaceutically acceptable salt or solvate thereof, as defined herein in the manufacture of a medicament for the treatment of irritable bowel syndrome (IBS) or pain associated with IBS.

Also provided herein is the use of a compound of General Formula I or a pharmaceutically acceptable salt or solvate thereof, as defined herein in the manufacture of a medicament for providing supportive care to a cancer patient, including preventing or minimizing gastrointestinal disorders, such as diarrhea, associated with treatment, including chemotherapeutic treatment.

Also provided herein is a use of a compound of General Formula I or a pharmaceutically acceptable salt or solvate thereof, as defined herein in the manufacture of a medicament for the inhibition of RET kinase activity.

Also provided herein is the use of a compound of General Formula I or a pharmaceutically acceptable salt or solvate thereof, as defined herein, in the manufacture of a medicament for the treatment of a RET-associated disease or disorder.

Also provided herein is a method for treating cancer in a patient in need thereof, the method comprising (a) determining if the cancer is associated with a dysregulation of a RET gene, a RET kinase, or expression or activity or level of any of the same (e.g., a RET-associated cancer); and (b) if the cancer is determined to be associated with a dysregulation of a RET gene, a RET kinase, or expression or activity or level of any of the same (e.g., a RET-associated cancer), administering to the patient a therapeutically effective amount of a compound of General Formula I or a pharmaceutically acceptable salt or solvate thereof, or a pharmaceutical composition thereof.

Also provided herein is a pharmaceutical combination for treating cancer (e.g., a RET-associated cancer, such as a RET-associated cancer having one or more RET inhibitor resistance mutations) in a patient in need thereof, which comprises (a) a compound of General Formula I or a pharmaceutically acceptable salt or solvate thereof, (b) an additional therapeutic agent, and (c) optionally at least one pharmaceutically acceptable carrier, wherein the compound of General Formula I or the pharmaceutically acceptable salt or solvate thereof and the additional therapeutic are formulated as separate compositions or dosages for simultaneous, separate or sequential use for the treatment of cancer, wherein the amounts of the compound of General Formula I or a pharmaceutically acceptable salt or solvate thereof and of the additional therapeutic agent are together effective in treating the cancer. Also provided herein is a pharmaceutical composition comprising such a combination. Also provided herein is the use of such a combination for the preparation of a medicament for the treatment of cancer. Also provided herein is a commercial package or product comprising such a combination as a combined preparation for simultaneous, separate or sequential use; and to a method of treatment of cancer a patient in need thereof.

Also provided herein is a method for reversing or preventing acquired resistance to an anticancer drug, comprising administering a therapeutically effective amount of a compound of General Formula I or a pharmaceutically acceptable salt or solvate thereof, to a patient at risk for developing or having acquired resistance to an anticancer drug. In some embodiments, the patient is administered a dose of the anticancer drug (e.g., at substantially the same time as a dose of a compound of Formula I or a pharmaceutically acceptable salt or solvate thereof is administered to the patient).

Also provided herein is a method of delaying and/or preventing development of cancer resistant to an anticancer drug in an individual, comprising administering to the individual an effective amount of a compound of General Formula I or a pharmaceutically acceptable salt or solvate thereof, before, during, or after administration of an effective amount of the anticancer drug.

Also provided herein is a method of treating an individual with cancer who has an increased likelihood of developing resistance to an anticancer drug, comprising concomitantly administering to the individual (a) an effective amount of a compound of General Formula I and (b) an effective amount of the anticancer drug.

Also provided are methods of treating an individual with a RET-associated cancer that has one or more RET inhibitor resistance mutations that increase resistance of the cancer to a RET inhibitor that is not a compound of General Formula I or a pharmaceutically acceptable salt or solvate thereof (e.g., a substitution at amino acid position 804, e.g., V804M, V804L, or V804E), that include administering a compound of General Formula I or a pharmaceutically acceptable salt or solvate thereof, before, during, or after administration of another anticancer drug (e.g., a RET kinase inhibitor that is not a compound of General Formula I or a pharmaceutically acceptable salt or solvate thereof).

Also provided are methods of treating an individual with a RET-associated cancer that include administering a compound of General Formula I or a pharmaceutically acceptable salt or solvate thereof, before, during, or after administration of another anticancer drug (e.g., a RET kinase inhibitor that is not a compound of General Formula I or a pharmaceutically acceptable salt or solvate thereof).

Also provided herein is a method for treating irritable bowel syndrome (IBS) in a patient in need thereof, the method comprising (a) determining if the IBS is associated with a dysregulation of a RET gene, a RET kinase, or expression or activity or level of any of the same; and (b) if the IBS is determined to be associated with a dysregulation of a RET gene, a RET kinase, or expression or activity or level of any of the same, administering to the patient a therapeutically effective amount of a compound of General Formula I or a pharmaceutically acceptable salt or solvate thereof, or a pharmaceutical composition thereof.

Also provided herein is a pharmaceutical combination for treating irritable bowel syndrome (IBS) in a patient in need thereof, which comprises administering (a) a compound of General Formula I or a pharmaceutically acceptable salt or solvate thereof, (b) an additional therapeutic agent, and (c) optionally at least one pharmaceutically acceptable carrier, for simultaneous, separate or sequential use for the treatment of IBS, wherein the amounts of the compound of General Formula I or a pharmaceutically acceptable salt or solvate thereof and of the additional therapeutic agent are together effective in treating the IBS. Also provided herein is a pharmaceutical composition comprising such a combination. Also provided herein is the use of such a combination for the preparation of a medicament for the treatment of the IBS. Also provided herein is a commercial package or product comprising such a combination as a combined preparation for simultaneous, separate or sequential use; and to a method of treatment of the IBS a patient in need thereof.

Also provided herein is a process for preparing a compound of General Formula I or a pharmaceutically acceptable salt or solvate thereof.

Also provided herein is a compound of General Formula I or a pharmaceutically acceptable salt or solvate thereof obtained by a process of preparing the compound as defined herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION OF THE INVENTION

Provided herein is a compound of the General Formula I:

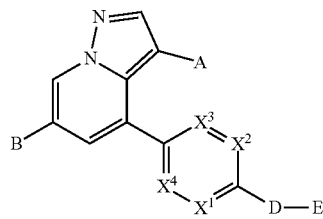

I or a pharmaceutically acceptable salt or solvate thereof, wherein:

$X^1$ is CH, CCH$_3$, CF, CCl or N;
$X^2$ is CH, CF or N;
$X^3$ is CH, CF or N;
$X^4$ is CH, CF or N;
wherein zero, one or two of $X^1$, $X^2$, $X^3$ and $X^4$ is N;
A is H, Cl, CN, Br, CH$_3$, CH$_2$CH$_3$ or cyclopropyl;
B is hetAr$^1$;
hetAr$^1$ is a 5-membered heteroaryl ring having 1-3 ring heteroatoms independently selected from N, S and O, wherein the heteroaryl ring is optionally substituted with one or more substituents independently selected from the group consisting of halogen, C1-C6 alkyl, hydroxyC1-C6 alkyl, fluoroC1-C6 alkyl, difluoroC1-C6 alkyl, trifluoroC1-C6 alkyl, cyanoC1-C6 alkyl, (C1-C6 alkoxy)C1-C6 alkyl, (C1-C4 alkoxy)CH$_2$C(=O)—, (C1-C4 alkoxy)C(=O)C1-C3 alkyl, C3-C6 cycloalkyl, (R$^a$R$^b$N)C1-C6 alkyl, (R$^a$R$^b$N)C(=O)C1-C6 alkyl, (C1-C6 alkyl SO$_2$)C1-C6 alkyl, hetCyc$^a$ and 4-methoxybenzyl;

R$^a$ and R$^b$ are independently H or C1-C6 alkyl;

hetCyc$^a$ is a 4-6 membered heterocyclic ring having a ring heteroatom selected from N and O, wherein the heterocyclic ring is optionally substituted with halogen, C1-C6 alkyl, fluoroC1-C6 alkyl, difluoroC1-C6 alkyl, trifluoroC1-C6 alkyl, (C1-C6 alkoxy)C1-C6 alkyl, di(C1-C3 alkyl)NCH$_2$C(=O), (C1-C6 alkoxy)C(=O) or (C1-C6 alkoxy)CH$_2$C(=O);

D is hetCyc$^a$, hetCyc$^2$, hetCyc$^3$ or hetCyc$^9$;

hetCyc$^a$ is a 4-6 membered heterocyclic ring having 1-2 ring atoms selected from N and O, wherein the heterocyclic ring is optionally substituted with one or more substituents independently selected from the group consisting of C1-C3 alkyl, fluoroC1-C3 alkyl, difluoroC1-C3 alkyl, trifluoroC1-C3 alkyl and OH, or said heterocyclic ring is substituted with a C3-C6 cycloalkylidene ring, or said heterocyclic ring is substituted with an oxo group;

hetCyc$^2$ is a 7-8 membered bridged heterocyclic ring having 1-3 ring heteroatoms independently selected from N and O, wherein the heterocyclic ring is optionally substituted with one or more substituents independently selected from the group consisting of C1-C3 alkyl;

hetCyc$^3$ is a 7-11 membered heterospirocyclic ring having 1-2 ring heteroatoms independently selected from N and O, wherein the ring is optionally substituted with C1-C3 alkyl;

hetCyc$^9$ is a fused 9-10 membered heterocyclic ring having 1-3 ring nitrogen atoms and optionally substituted with oxo;

E is
(a) hydrogen,
(b) OH,
(c) R$^a$R$^b$N—, wherein R$^a$ is H or C1-C6 alkyl and R$^b$ is H, C1-C6 alkyl or phenyl;
(d) C1-C6 alkyl optionally substituted with one to three fluoros,
(e) hydroxyC1-C6 alkyl- optionally substituted with one to three fluoros,
(f) C1-C6 alkoxy optionally substituted with one to three fluoros,
(g) hydroxy(C1-C6 alkoxy) optionally substituted with one to three fluoros,
(h) (C1-C6 alkoxy)hydroxy C1-C6 alkyl- optionally substituted with one to three fluoros,
(i) (C1-C6 alkyl)C(=O)— optionally substituted with one to three fluoros,
(j) (hydroxy C1-C6 alkyl)C(=O)— optionally substituted with one to three fluoros,
(k) (C1-C6 alkoxy)C(=O)—,
(l) (C1-C6 alkoxy)(C1-C6 alkyl)C(=O)—,
(m) HC(=O)—,
(n) Cyc$^1$,
(o) Cyc$^1$C(=O)—,
(p) Cyc$^1$(C1-C6 alkyl)C(=O)— wherein the alkyl portion is optionally substituted with one or more groups independently selected from the group consisting of OH, fluoro, C1-C3 alkoxy and R$^c$R$^d$N—, where R$^c$ and R$^d$ are independently H or C1-C6 alkyl, (q) hetCyc⁴,
(r) hetCyc⁴C(=O)—,
(s) hetCyc⁴(C1-C3 alkyl)C(=O)—,
(t) (hetCyc⁴)C(=O)C1-C2 alkyl-,
(u) hetCyc⁴C(=O)NH—,
(v) Ar²,
(w) Ar²C(=O)—,
(x) Ar²C1-C6 alkyl-,
(y) (Ar²)hydroxy C2-C6 alkyl-,
(z) Ar²(C1-C3 alkyl)C(=O)— wherein the alkyl portion is optionally substituted with one or two groups independently selected from the group consisting of OH, C1-C6 alkyl (optionally substituted with 1-3 fluoros), hydroxyC1-C6 alkyl, C1-C6 alkoxy and $R^eR^fN$—, where $R^e$ and $R^f$ are independently H or C1-C6 alkyl, or $R^e$ and $R^f$ together with the nitrogen to which they are attached form a 5-6 membered azacyclic ring optionally having an additional ring heteroatom selected from N and O,
(aa) hetAr²C(=O)—,
(bb) (hetAr²)hydroxyC2-C6 alkyl-,
(cc) hetAr²(C1-C3 alkyl)C(=O)— wherein the alkyl portion is optionally substituted with one or two groups independently selected from the group consisting of OH, C1-C6 alkyl, hydroxyC1-C6 alkyl, C1-C6 alkoxy and $R^eR^fN$—, where $R^e$ and $R^f$ are independently H or C1-C6 alkyl, or $R^e$ and $R^f$ together with the nitrogen to which they are attached form a 5-6 membered azacyclic ring optionally having an additional ring heteroatom selected from N and O,
(dd) $R^1R^2NC$(=O)—,
(ee) $R^1R^2N$(C1-C3 alkyl)C(=O)— wherein the alkyl portion is optionally substituted with phenyl,
(ff) $R^1R^2NC$(=O)C1-C2 alkyl-,
(gg) $R^1R^2NC$(=O)NH—,
(hh) $CH_3SO_2$(C1-C6 alkyl)C(=O)—,
(ii) (C1-C6 alkyl)$SO_2$—,
(jj) (C3-C6 cycloalkyl)$CH_2SO_2$—,
(kk) hetCyc⁵-$SO_2$—,
(ll) $R^4R^5NSO_2$—,
(mm) $R^6C$(=O)NH—,
(nn) hetCyc⁶;
(oo) hetAr²C1-C6 alkyl-,
(pp) (hetCyc⁴)C1-C6 alkyl-,
(qq) (C1-C6 alkoxy)C1-C6 alkyl- wherein said alkoxy portion is optionally substituted with 1-3 fluoros,
(rr) (C3-C6 cycloalkoxy)C1-C6 alkyl-,
(ss) (C3-C6 cycloalkyl)C1-C6 alkyl- wherein said cycloalkyl is optionally substituted with 1-2 fluoros,
(tt) ($R^gR^hN$)C1-C6 alkyl- wherein $R^g$ and $R^h$ are independently H or C1-C6 alkyl,
(uu) Ar²—O—,
(vv) (C1-C6 alkyl$SO_2$)C1-C6 alkyl-,
(ww) (C1-C6 alkoxy)C(=O)NHC1-C6 alkyl-,
(xx) (C3-C6 cycloalkoxy)C(=O)—,
(yy) (C3-C6 cycloalkyl)$SO_2$— wherein said cycloalkyl is optionally substituted with C1-C6 alkyl,
(zz) Ar⁴$CH_2OC$(=O)—,
(aaa) (N—(C1-C3 alkyl)pyridinonyl)C1-C3 alkyl-, and
(bbb) (Ar⁴$SO_2$)C1-C6 alkyl-;
Cyc¹ is a C3-C6 cycloalkyl, wherein (a) the cycloalkyl is optionally substituted with one or more substituents independently selected from the group consisting of OH, halogen, C1-C6 alkoxy, CN, hydroxyC1-C6 alkyl, (C1-C6 alkoxy)C1-C6 alkyl, and C1-C6 alkyl optionally substituted with 1-3 fluoros, or (b) the cycloalkyl is substituted with phenyl, wherein the phenyl is optionally substituted with one or more substituents independently selected from the group consisting of halogen, C1-C3 alkyl, C1-C3 alkoxy and $CF_3$, or (c) the cycloalkyl is substituted with a 5-6 membered heteroaryl ring having 1-3 ring heteroatoms independently selected from N and O, wherein the heteroaryl ring is optionally substituted with one or more substituents independently selected from the group consisting of halogen, C1-C3 alkyl, C1-C3 alkoxy and $CF_3$;

Ar² is phenyl optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, CN, a 5-6 membered heterocyclic ring having 1-2 ring heteroatoms independently selected from N and O, and $R^iR^jN$— where $R^i$ and $R^j$ are independently H and C1-C6 alkyl;

hetAr² is a 5-6 membered heteroaryl ring having 1-3 ring heteroatoms independently selected from N, O and S and optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, hydroxyC1-C6 alkyl, (C3-C6)cycloalkyl, (C1-C6 alkoxy)C1-C6 alkyl, CN and R'R"N— where R' and R" are independently H or C1-C3 alkyl;

hetCyc⁴ is (a) a 4-6 membered heterocyclic ring having 1-2 ring heteroatoms independently selected from N, O and S wherein said S is optionally oxidized to $SO_2$, (b) a 7-8 membered bridged heterocyclic ring having 1-2 ring heteroatoms independently selected from N and O, (c) a 6-12 membered fused bicyclic heterocyclic ring having 1-2 ring heteroatoms independently selected from N and O and optionally independently substituted with 1-2 C1-C6 alkyl substitutents, or (d) a 7-10 membered spirocyclic heterocyclic ring having 1-2 ring heteroatoms independently selected from N and O, wherein each of the heterocyclic rings is optionally substituted with one or more substituents independently selected from the group consisting of halogen, OH, CN, C1-C6 alkyl (optionally substituted with 1-3 fluoros), C1-C6 alkoxy, (C1-C6 alkoxy)C1-C6 alkyl, (C3-C6)cycloalkyl, (C1-C6 alkyl)C(=O)—, a 5-6 membered heterocyclic ring having 1-2 ring heteroatoms independently selected from N and O, and phenyl wherein said phenyl is optionally substituted with one or more substituents selected from halogen, C1-C6 alkyl and C1-C6 alkoxy;

hetCyc⁵ is a 5-6 membered heterocyclic ring having a ring heteroatom selected from O and N;

hetCyc⁶ is a 5 membered heterocyclic ring having one or two ring heteroatoms independently selected from N and O, wherein the ring substituted with oxo and wherein the ring is further optionally substituted with one or more substituents independently selected from the group consisting of OH and C1-C6 alkyl;

R¹ is H, C1-C6 alkyl or (C1-C6 alkoxy)C1-C6 alkyl;

R² is H, C1-C6 alkyl (optionally substituted with 1-3 fluoros), (C1-C6 alkoxy)C1-C6 alkyl (optionally substituted with 1-3 fluoros), Cyc³, hydroxyC1-C6 alkyl (optionally substituted with 1-3 fluoros), C1-C6 alkoxy (optionally substituted with 1-3 fluoros), (C1-C6 alkoxy)C(=O), hetCyc⁷, Ar³, Ar³C1-C3 alkyl-, hydroxyC1-C6 alkoxy or (C3-C6 cycloalkyl)$CH_2O$—;

Cyc³ is a 3-6 membered carbocyclic ring optionally substituted with 1-2 groups independently selected from the group consisting of C1-C6 alkoxy, OH and halogen;

hetCyc⁷ is a 5-6 membered heterocyclic ring having a ring heteroatom selected from O and N wherein the ring is optionally substituted with C1-C6 alkyl;

Ar³ is phenyl optionally substituted with one or more substituents independently selected from halogen, C1-C3 alkyl, C1-C3 alkoxy, fluoroC1-C3 alkyl, difluoroC1-C3 alkyl and trifluoroC1-C3 alkyl;

$R^4$ and $R^5$ are independently H or C1-C6 alkyl;

$R^6$ is C1-C6 alkyl, hydroxyC1-C6 alkyl, C1-C6 alkoxy, (C1-C6 alkoxy)C1-C6 alkyl, phenyl or hetCyc$^8$;

hetCyc$^8$ is a 5-6 membered heterocyclic ring having a ring heteroatom selected from O and N, wherein the heterocyclic ring is optionally substituted with C1-C6 alkyl; and $Ar^4$ is phenyl optionally substituted with one or more halogens.

As used herein, the word "a" before a noun represents one or more of the particular noun. For example, the phrase "a cell" represents "one or more cells."

For complex chemical names employed herein, a substituent group is typically named before the group to which it attaches. For example, methoxyethyl group comprises an ethyl backbone with a methoxy substituent.

The term "halogen" means —F (sometimes referred to herein as "fluoro" or "fluoros"), —Cl, —Br and —I.

The term "azacyclic ring" as used herein refers to a saturated heterocyclic ring having a ring nitrogen atom.

The terms "C1-C3 alkyl" and "C1-C6 alkyl" as used herein refer to saturated linear or branched-chain monovalent hydrocarbon radicals of one to three or one to six carbon atoms, respectively. Examples include, but are not limited to, methyl, ethyl, 1-propyl, isopropyl, 1-butyl, isobutyl, sec-butyl, tert-butyl, 2-methyl-2-propyl, pentyl, and hexyl.

The terms "C1-C3 alkoxy", "C1-C4 alkoxy" and "C1-C6 alkoxy", as used herein refer to saturated linear or branched-chain monovalent alkoxy radicals of one to three, one to four or one to six carbon atoms, respectively, wherein the radical is on the oxygen atom. Examples include methoxy, ethoxy, propoxy, isopropoxy, and butoxy.

The term "fluoroC1-C6 alkyl" as use herein refers to saturated linear or branched-chain monovalent radicals of one to six carbon atoms, wherein one of the hydrogen atoms is replaced by fluorine. Examples include fluoromethyl, 3-fluoropropyl and 2-fluoroethyl.

The term "difluoroC1-C6 alkyl" as use herein refers to saturated linear or branched-chain monovalent radicals of one to six carbon atoms, wherein two of the hydrogen atoms are replaced by fluorine. Examples include difluoromethyl, 2,2-difluoroethyl, and 1,3-difluoroprop-2-yl.

The term "trifluoroC1-C6 alkyl" as used herein refers to saturated linear or branched-chain monovalent radicals of one to six carbon atoms, wherein three of the hydrogen atoms are replaced by fluorine. Examples include trifluoromethyl, 2,2,2-trifluoroethyl, and 3,3,3-trifluoropropyl.

The term "(C1-C6 alkoxy)C1-C6 alkyl" as used herein refers to saturated linear or branched-chain monovalent radicals of one to six carbon atoms, wherein one of the carbon atoms is substituted with a (C1-C6 alkoxy) group as defined herein. Examples include methoxymethyl ($CH_3OCH_2$—) and methoxyethyl ($CH_3OCH_2CH_2$—).

The term "hydroxyC1-C6 alkyl" as used herein refers to saturated linear or branched-chain monovalent alkyl radicals of one to six carbon atoms, wherein one of the carbon atoms is substituted with a hydroxy group.

The term "hydroxyC1-C6 alkoxy" as used herein refers to saturated linear or branched-chain monovalent alkoxy radicals of one to six carbon atoms, wherein one of the carbon atoms is substituted with a hydroxy group.

The term "(C1-C6 alkoxy)hydroxyC1-C6 alkyl" as used herein refers to a hydroxy (C1-C6 alkyl) radical as defined herein, wherein one of the carbon atoms is substituted with a C1-C6 alkoxy group as defined herein.

The term "Cyc$^1$(C1-C6 alkyl)" as used herein refers to saturated linear or branched-chain monovalent alkyl radicals of one to six carbon atoms, wherein one of the carbon atoms is substituted with a 3-6 membered cycloalkyl ring.

The term "Cyc$^1$(C1-C6 alkyl)C(=O)—" as used herein refers to a (C1-C6 alkyl)C(=O)— group, wherein the C1-C6 alkyl is a saturated linear or branched-chain monovalent radical of one to six carbon atoms and wherein one of the carbon atoms of the C1-C6 alkyl portion is substituted with a C3-C6 cycloalkyl group.

The term "Ar$^2$C1-C6 alkyl" as used herein refers to C1-C6 alkyl radical as defined herein one of the carbon atoms of the alkyl portion is substituted with Ar$^2$.

The term "(Ar$^2$)hydroxy C2-C6 alkyl" as used herein refers to a hydroxyC1-C6 alkyl radical as defined herein wherein one of the carbon atoms of the alkyl portion is substituted with Ar$^2$.

The term "Ar$^2$(C1-C3 alkyl)C(=O)—" as used herein refers to a C1-C3 alkyl(C=O)— radical wherein the C1-C3 alkyl portion is a saturated linear or branched-chain monovalent alkyl radicals of one to three carbon atoms, wherein one of the carbon atoms is substituted with Ar$^2$.

The term "(hetAr$^2$)hydroxy C2-C6 alkyl" as used herein refers to a hydroxyC1-C6 alkyl radical as defined herein wherein one of the carbon atoms is substituted with hetAr$^2$.

The term "hetAr$^2$(C1-C3 alkyl)C(=O)—" as used herein refers to a C1-C3 alkyl(C=O)— radical wherein the C1-C3 alkyl portion is a saturated linear or branched-chain monovalent alkyl radical of one to three carbon atoms, wherein one of the carbon atoms is substituted with hetAr$^2$.

The term "$R^1R^2$NC(=O)C1-C2 alkyl" as used herein refers to a C1-C2 alkyl radical wherein one of the carbon atoms is substituted with a $R^1R^2$NC(=O)— group.

The term "$R^1R^2$N(C1-C3 alkyl)C(=O)—" as used herein refers to a C1-C3 alkyl(C=O)— radical wherein the C1-C3 alkyl portion is a saturated linear or branched-chain monovalent alkyl radicals of one to three carbon atoms, wherein one of the carbon atoms is substituted with a $R^1R^2$N— group, wherein $R^1$ and $R^2$ are as defined for General Formula I.

The term "(C1-C6 alkylSO$_2$)C1-C6 alkyl" as used herein as used herein refers to saturated linear or branched-chain monovalent radicals of one to six carbon atoms, wherein one of the carbon atoms is substituted with a (C1-C6 alkyl) SO$_2$— group (e.g., a $(CH_3)_2CH_2SO_2$— group).

The term "(Ar$^4$SO$_2$)C1-C6 alkyl" as used herein as used herein refers to saturated linear or branched-chain monovalent radicals of one to six carbon atoms, wherein one of the carbon atoms is substituted with a (Ar$^4$)SO$_2$— group.

The term "bridged heterocyclic ring" as used herein refers to a bicyclic heterocycle, wherein two common nonadjacent carbon atoms of the ring are linked by an alkylene bridge of 1, 2, 3, or 4 carbon atoms. Examples of bridged heterocyclic ring systems include 3,6-diazabicyclo[3.1.1]heptane, 2,5-diazabicyclo[2.2.1]heptane, 3,8-diazabicyclo[3.2.1]octane, 3,8-diazabicyclo[3.2.1]octane, 8-azabicyclo[3.2.1]octane and 7-azabicyclo[2.2.1]heptane.

The term "spirocyclic ring" as used herein refers to a group having two rings joined by a spirocyclic linkage through a common single carbon atom, wherein each ring is a 4-7-membered ring (including the common carbon atom).

The term "heterospirocyclic" as used herein refers to a group having two rings joined by a spirocyclic linkage through a carbon atom, wherein each ring has 4 to 6 ring atoms (with one ring atom being common to both rings), and wherein 1 or 2 of the ring atoms is a heteroatom selected from the group consisting of N and O, provided that the heteroatoms are not adjacent. Examples include 2,6-diazaspiro[3.3]heptane, 2,5-diazaspiro[3.4]octane, 2,6-diazaspiro[3.4]octane, 6-oxa-2-azaspiro[3.4]octane, 2-oxa-7-azaspiro[4.4]nonane, 7-oxa-2-azaspiro[4.5]decane, 7-oxa-2-azaspiro[3.5]nonane, 2,7-diazaspiro[3.5]nonane, 2,6-diazaspiro[3.5]nonane, 2,5-diazaspiro[3.5]nonane, 1,6-diazaspiro[3.4]octane, 1,7-diazaspiro[4.4]nonane, 2,7-diazaspiro[4.4]nonane, 2,8-diazaspiro[4.5]decane, 2,7-diazaspiro[4.5]decane, 2,6-diazaspiro[4.5]decane, 1,7-diazaspiro[3.5]nonane, 2,7-diazaspiro[3.5]nonane, 1,6-diazaspiro[3.5]nonane, 1,8-diazaspiro[4.5]decane, 2,8-diazaspiro[4.5]decane, 2,7-diazaspiro[4.5]decane, 1,7-diazaspiro[4.5]decane, 2,9-diazaspiro[5.5]undecane, and 7-azaspiro[3.5]nonane.

As used herein, the term "cycloalkylidine ring" refers to a divalent carbocyclic ring. The suffix "ylidine" refers to bivalent radical derived from a saturated hydrocarbon by removal of two hydrogen atoms from the same carbon atom.

The term "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified.

The term "tautomer" as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the invention, and the naming of the compounds does not exclude any tautomer.

The term "oxo" as used herein means an oxygen that is double bonded to a carbon atom. For example, a non-limiting example of a heterocyclic ring that is substituted with an oxo group is the structure:

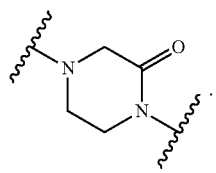 [SMILES: *N1CCN(*)C(=O)C1]

The term "(N—(C1-C3 alkyl)pyridinonyl)C1-C3 alkyl" as used herein refers to a C1-C3 alkyl radical as defined herein where one of the carbon atoms of the alkyl portion is substituted with a 2-oxo-1,2-dihydropyridine that is substituted on the pyridone nitrogen with 1-3 carbons. Examples include 1-methyl-1,2-dihydropyridin-2-one In certain embodiments of Formula I, $X^1$ is CH, CCH$_3$, CF, or CCl, $X^2$ is CH or CF, $X^3$ is CH or CF, and $X^4$ is CH or CF. In certain embodiments, each of $X^1$, $X^2$, $X^3$ and $X^4$ is CH.

In certain embodiments of Formula I, $X^1$ is CH, CCH$_3$, CF, CCl or N, $X^2$ is CH, CF or N, $X^3$ is CH, CF or N, and $X^4$ is CH, CF or N, wherein one of $X^1$, $X^2$, $X^3$ and $X^4$ is N.

In certain embodiments of Formula I, $X^1$ is N, $X^2$ is CH or CF, $X^3$ is CH or CF, and $X^4$ is CH or CF. In certain embodiments, $X^1$ is N, and $X^2$, $X^3$ and $X^4$ are CH.

In certain embodiments of Formula I, $X^1$ is CCH$_3$, $X^2$ is CH, CF or N; $X^3$ is CH, CF or N, and $X^4$ is CH, CF or N; wherein one of $X^2$, $X^3$ and $X^4$ is N. In certain embodiments, $X^1$ is CCH$_3$, $X^2$ is N; $X^3$ is CH or CF, and $X^4$ is CH or CF. In certain embodiments, $X^1$ is CCH$_3$, $X^2$ is N, and $X^3$ and $X^4$ are CH.

In certain embodiments of Formula I, $X^1$ is CH, CCH$_3$, CF, CCl or N; $X^2$ is CH, CF or N; $X^3$ is CH, CF or N; and $X^4$ is CH, CF or N, wherein two of $X^1$, $X^2$, $X^3$ and $X^4$ are N.

In certain embodiments of Formula I, $X^1$ and $X^2$ are N, and $X^3$ and $X^4$ are CH or CF. In certain embodiments, $X^1$ and $X^2$ are N, and $X^3$ and $X^4$ are CH.

In certain embodiments, $X^1$ and $X^3$ are N, and $X^2$ and $X^4$ are CH or CF. In certain embodiments, $X^1$ and $X^3$ are N, and $X^2$ and $X^4$ are CH.

In certain embodiments, A is H, Cl, CN, Br, CH$_3$, or CH$_2$CH$_3$.

In certain embodiments, A is H.
In certain embodiments, A is Cl.
In certain embodiments, A is CN.
In certain embodiments, A is Br.
In certain embodiments, A is CH$_3$.
In certain embodiments, A is CH$_3$CH$_2$—.
In certain embodiments, A is cyclopropyl.

In certain embodiments, B is hetAr$^1$ where hetAr$^1$ is a 5-membered heteroaryl ring having 1-3 ring heteroatoms independently selected from N, S and O, wherein the heteroaryl ring is optionally substituted with one or more substituents independently selected from the group consisting of halogen, C1-C6 alkyl, hydroxyC1-C6 alkyl, fluoroC1-C6 alkyl, difluoroC1-C6 alkyl, trifluoroC1-C6 alkyl, cyanoC1-C6 alkyl, (C1-C6 alkoxy)C1-C6 alkyl, (C1-C4 alkoxy)CH$_2$C(=O)—, (C1-C4 alkoxy)C(=O)C1-C3 alkyl, C3-C6 cycloalkyl, (R$^a$R$^b$N)C1-C6 alkyl, (R$^a$R$^b$N)C(=O)C1-C6 alkyl, (C1-C6 alkylSO$_2$)C1-C6 alkyl, hetCyc$^a$ and 4-methylbenzyl.

In certain embodiments, B is hetAr$^1$ where hetAr$^1$ is a 5-membered heteroaryl ring having 1-3 ring heteroatoms independently selected from N, S and O, wherein the heteroaryl ring is optionally substituted with one or more substituents independently selected from the group consisting of C1-C6 alkyl fluoroC1-C6 alkyl, difluoroC1-C6 alkyl, trifluoroC1-C6 alkyl and hydroxyC1-C6 alkyl.

In certain embodiments, hetAr$^1$ is pyrazolyl, imidazolyl, oxazolyl, isoxazolyl thiazolyl, thiadiazolyl, triazolyl or oxadiazolyl optionally substituted with one or more substituents independently selected from the group consisting of halogen, C1-C6 alkyl, hydroxyC1-C6 alkyl, fluoroC1-C6 alkyl, difluoroC1-C6 alkyl, trifluoroC1-C6 alkyl, cyanoC1-C6 alkyl, (C1-C6 alkoxy)C1-C6 alkyl, (C1-C4 alkoxy)CH$_2$C(=O)—, (C1-C4 alkoxy)C(=O)C1-C3 alkyl, C3-C6 cycloalkyl, (R$^a$R$^b$N)C1-C6 alkyl, (R$^a$R$^b$N)C(=O)C1-C6 alkyl, (C1-C6 alkylSO$_2$)C1-C6 alkyl, hetCyc$^a$ and 4-methoxybenzyl.

In certain embodiments, B is pyrazolyl, imidazolyl, oxazolyl or isoxazolyl optionally substituted with one or more substituents independently selected from C1-C6 alkyl, fluoroC1-C6 alkyl, difluoroC1-C6 alkyl, trifluoroC1-C6 alkyl, hydroxyC1-C6 alkyl, C3-C6 cycloalkyl, hetCyc$^a$ and 4-methoxybenzyl.

In certain embodiments, B is pyrazolyl or imidazolyl optionally substituted with one or more substituents independently selected from C1-C6 alkyl, fluoroC1-C6 alkyl, difluoroC1-C6 alkyl, trifluoroC1-C6 alkyl and hydroxyC1-C6 alkyl.

In certain embodiments, B is pyrazolyl optionally substituted with one or more substituents independently selected from C1-C6 alkyl.

Non-limiting examples of hetAr[1] include the structures:
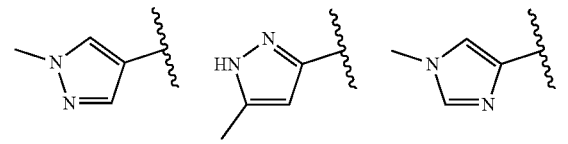
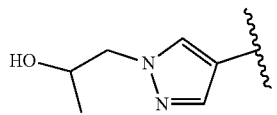
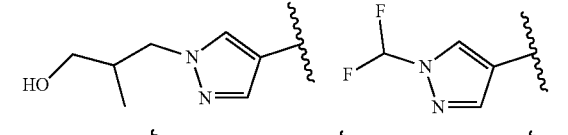
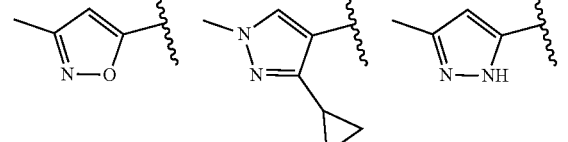
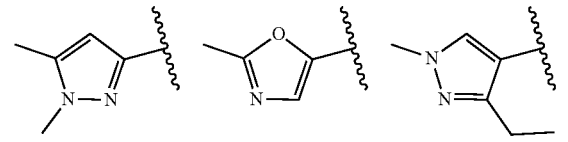
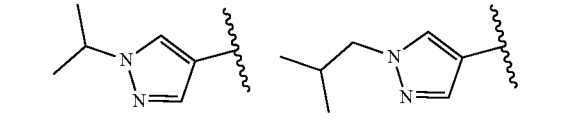
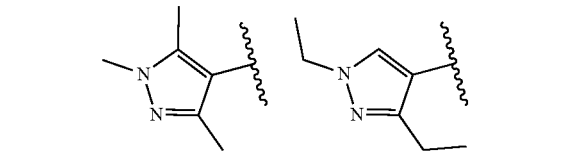
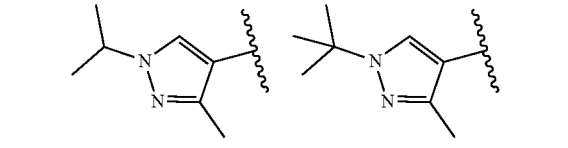
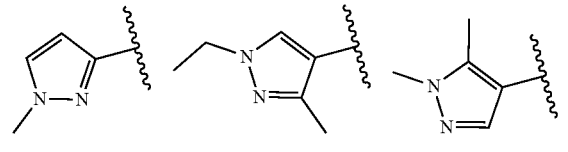
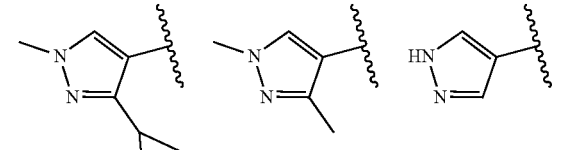
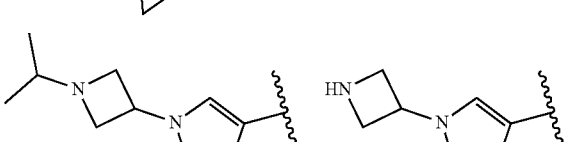
-continued
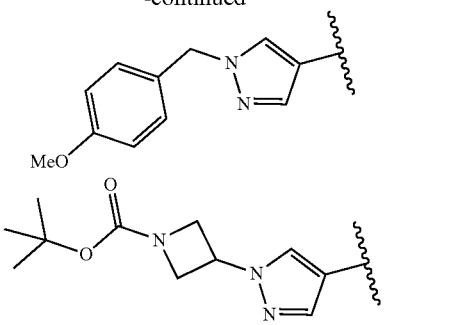
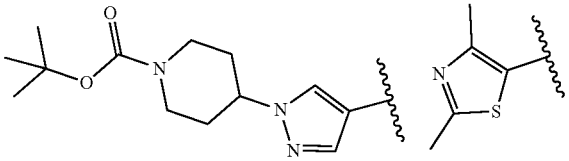
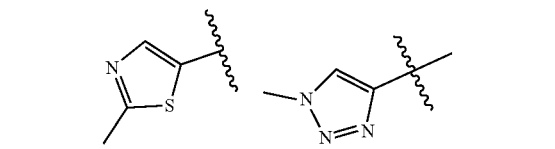
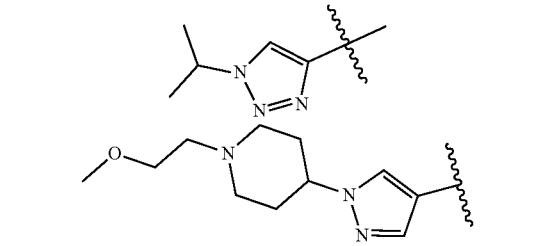
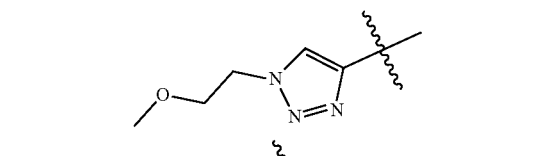
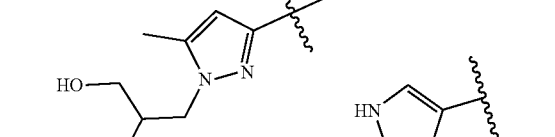
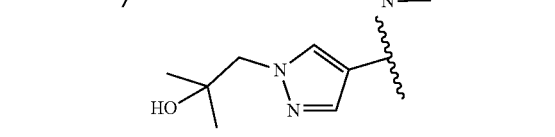
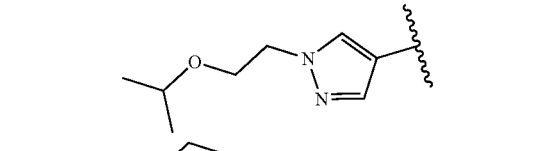
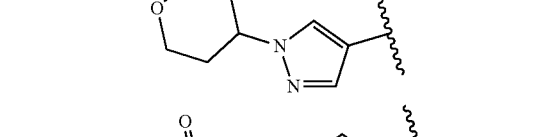
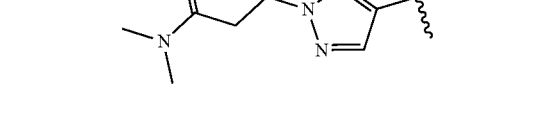

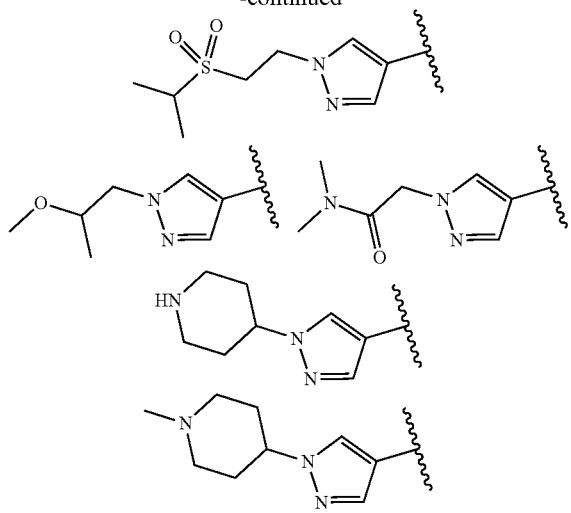

In certain embodiments, D is hetCyc¹ where hetCyc¹ is a 4-6 membered heterocyclic ring having 1-2 ring atoms selected from N and O, wherein the heterocyclic ring is optionally substituted with one or more substituents independently selected from the group consisting of C1-C3 alkyl, fluoroC1-C3 alkyl, difluoroC1-C3 alkyl, trifluoroC1-C3 alkyl and OH, or the heterocyclic ring is substituted with a C3-C6 cycloalkylidene ring, or said heterocyclic ring is substituted with an oxo group.

In certain embodiments, hetCyc¹ is a pyrrolidinyl, piperidinyl, piperazinyl, morpholinyl or azetidinyl ring optionally substituted with one or more substituents independently selected from the group consisting of C1-C3 alkyl, fluoroC1-C3 alkyl, difluoroC1-C3 alkyl, trifluoroC1-C3 alkyl and OH, or hetCyc¹ is a piperazinyl ring substituted with a C3-C6 cycloalkylidene ring, or hetCyc¹ is a piperazinyl ring substituted with an oxo group.

In certain embodiments, hetCyc¹ is a pyrrolidinyl, piperidinyl, piperazinyl, morpholinyl, or azetidinyl ring optionally substituted with a group selected from C1-C3 alkyl and trifluoroC1-C3 alkyl, or the hetCyc¹ is substituted with a C3-C6 cycloalkylidene ring, or hetCyc¹ is piperazin-2-onyl.

In certain embodiments, hetCyc¹ is a pyrrolidinyl, piperidinyl, piperazinyl or morpholinyl ring optionally substituted with a group selected from C1-C3 alkyl and trifluoroC1-C3 alkyl, or the hetCyc¹ is substituted with a C3-C6 cycloalkylidene ring.

In certain embodiments, hetCyc¹ is piperidinyl or piperazinyl.

In certain embodiments, hetCyc¹ is piperazinyl.

Non-limiting examples of D when represented by hetCyc¹ include the structures:

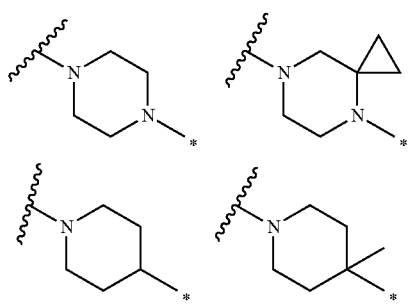

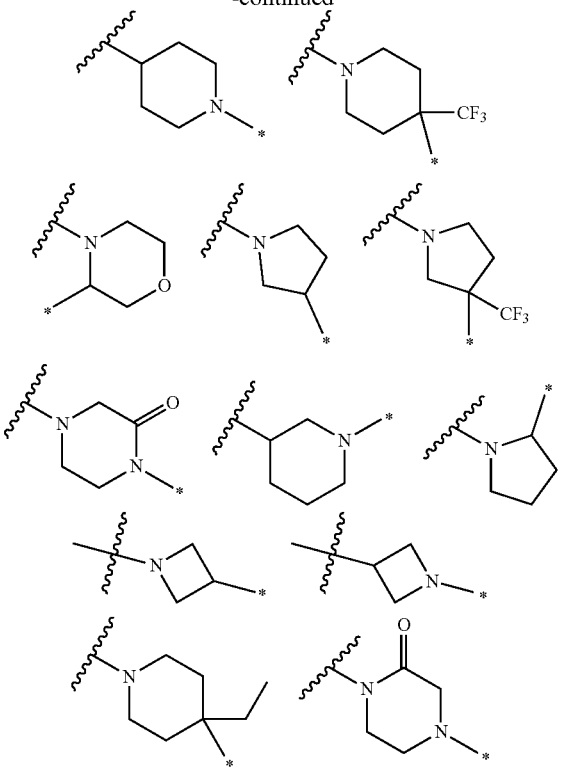

where the asterisk indicates the point of attachment to the E group.

In one embodiment of the D-E group, D is hetCyc¹ and E is hydrogen. Non-limiting examples include the structures:

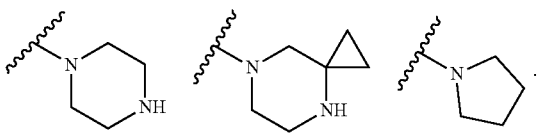

In one embodiment, D is hetCyc¹ and E is OH. In one embodiment, hetCyc¹ is a 5-6 membered heterocyclic ring having a ring nitrogen atom, wherein the ring is optionally substituted with trifluoro1-C3 alkyl. Non-limiting examples include the structures:

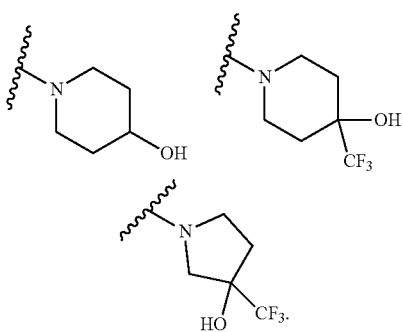

In one embodiment, D is hetCyc¹ and E is RᵃRᵇN— where Rᵃ is H or C1-C6 alkyl and Rᵇ is H, C1-C6 alkyl or phenyl. In one embodiment, hetCyc[1] is a 6 membered heterocyclic ring having a ring nitrogen atom, wherein the ring is optionally substituted with C1-C3 alkyl. Non-limiting examples include the structures:

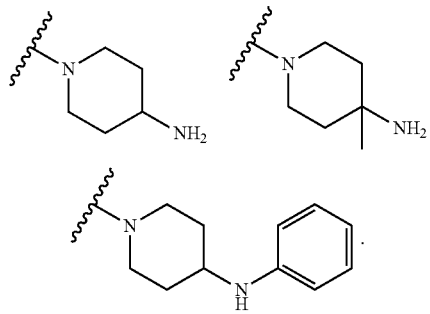

In one embodiment of the D-E group, D is hetCyc[1] and E is C1-C6 alkyl optionally substituted with one to three fluoros. Non-limiting examples include the structures:

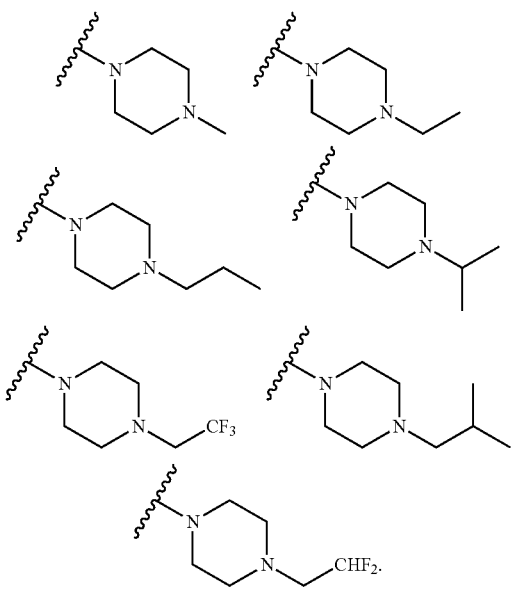

In one embodiment, D is hetCyc[1] and E is hydroxyC1-C6 alkyl optionally substituted with one to three fluoros. Non-limiting examples include the structures:

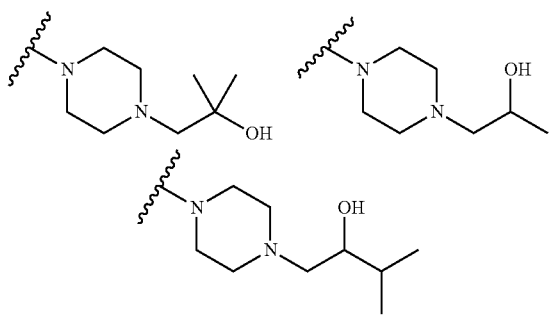

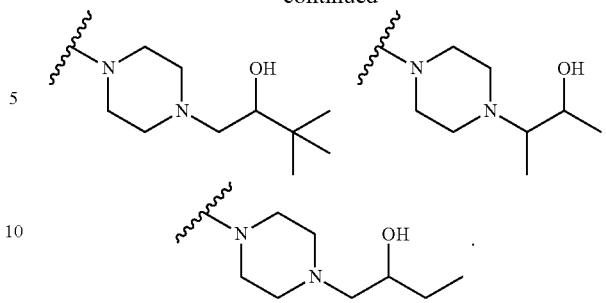

In one embodiment, D is hetCyc[1] and E is C1-C6 alkoxy optionally substituted with one to three fluoros. Non-limiting examples include the structures:

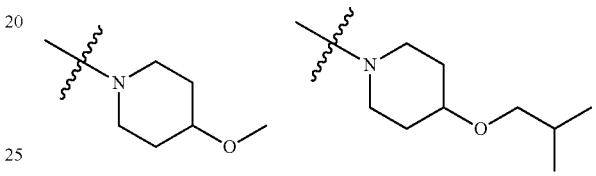

In one embodiment, D is hetCyc[1] and E is hydroxy(C1-C6 alkoxy) optionally substituted with one to three fluoros. A non-limiting examples include the structure:

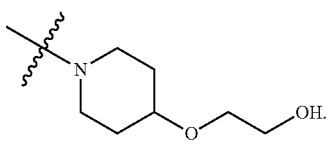 [SMILES: *N1CCC(OCCO)CC1]

In one embodiment, D is hetCyc[1] and E is (C1-C6 alkoxy)hydroxy C1-C6 alkyl optionally substituted with one to three fluoros. A non-limiting example includes the structure:

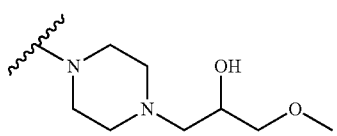

In one embodiment, D is hetCyc[1] and E is (C1-C6 alkyl)C(=O)— optionally substituted with one to three fluoros. In one embodiment, hetCyc[1] is a 6-membered heterocyclic ring having 1-2 ring nitrogen atoms, wherein the heterocyclic ring is optionally substituted with cyclopropyl. Non-limiting examples include the structures:

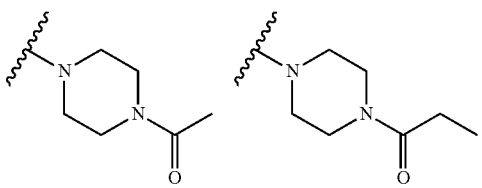

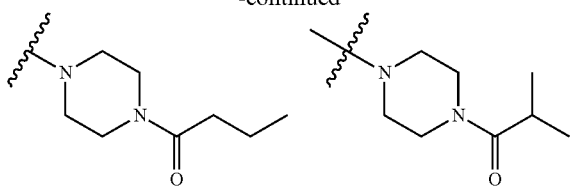
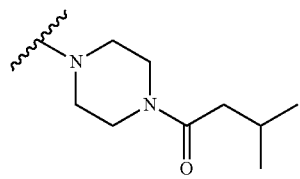
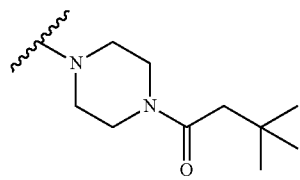
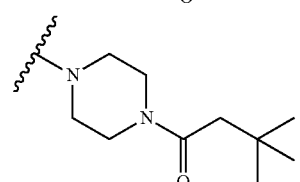
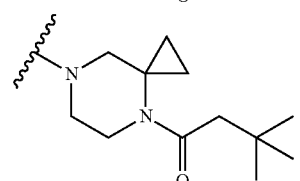
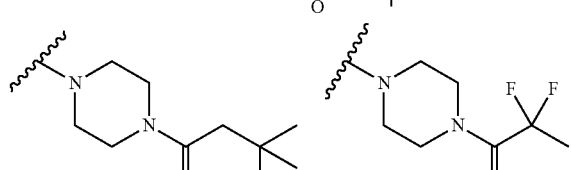
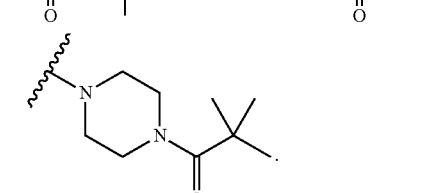

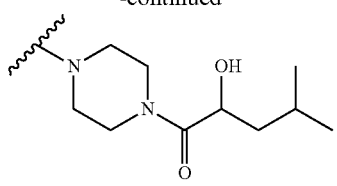
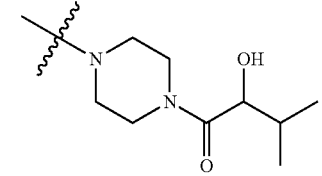
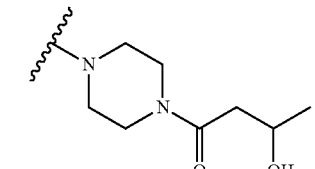
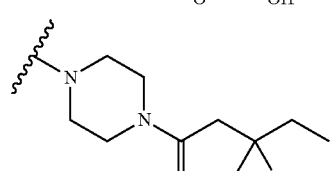
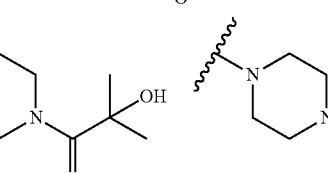
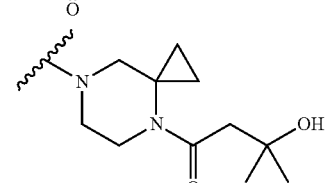
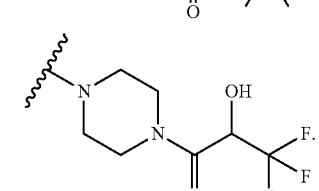

In one embodiment, D is hetCyc[1] and E is (hydroxy C1-C6 alkyl)C(=O)— optionally substituted with one to three fluoros. In one embodiment, hetCyc[1] is a 6-membered heterocyclic ring having a ring nitrogen atom, wherein the heterocyclic ring is optionally substituted with cyclopropyl. Non-limiting examples include the structures:

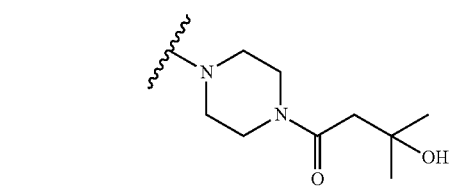

In one embodiment, D is hetCyc[1] and E is (C1-C6 alkoxy)C(=O)—. In one embodiment, hetCyc[1] is a 6-membered heterocyclic ring having 1-2 ring nitrogen atoms, wherein the heterocyclic ring is optionally substituted with cyclopropyl or C1-C3 alkyl. Non-limiting examples include the structures:

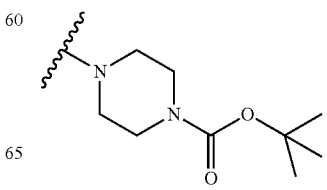
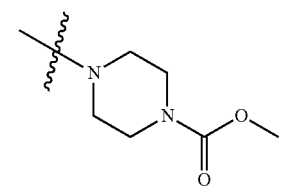

-continued

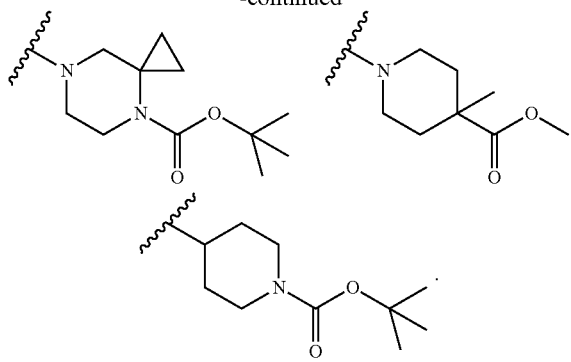

In one embodiment, D is hetCyc$^1$ and E is (C1-C6 alkoxy)(C1-C6 alkyl)C(=O)—. Non-limiting examples include the structures:

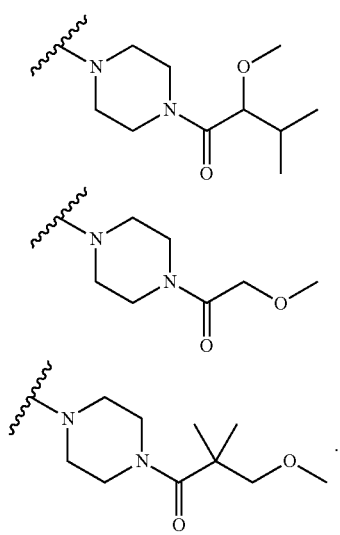

In one embodiment, D is hetCyc$^1$ and E is HC(=O)—. A non-limiting example is the structure:

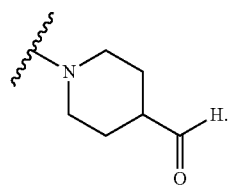

In one embodiment, D is hetCyc$^1$ and E is Cyc$^1$, Cyc$^1$C(=O)—, or Cyc$^1$(C1-C6 alkyl)C(=O)—, wherein in each instance, Cyc$^1$ is a C3-C6 cycloalkyl, wherein (a) Cyc$^1$ is optionally substituted with one or more substituents independently selected from the group consisting of OH, halogen, C1-C6 alkoxy, CN, hydroxyC1-C6 alkyl, (C1-C6 alkoxy)C1-C6 alkyl, and C1-C6 alkyl optionally substituted with 1-3 fluoros, or (b) Cyc$^1$ is substituted with phenyl, wherein the phenyl is optionally substituted with one or more substituents independently selected from the group consisting of halogen, C1-C3 alkyl, C1-C3 alkoxy and CF, or (c) Cyc$^1$ is substituted with a 5-6 membered heteroaryl ring having 1-3 ring heteroatoms independently selected from N and O, wherein the heteroaryl ring is optionally substituted with one or more substituents independently selected from the group consisting of halogen, C1-C3 alkyl, C1-C3 alkoxy and CF$_3$.

In one embodiment, D is hetCyc$^1$ and E is Cyc$^1$, where Cyc$^1$ is a C3-C6 cycloalkyl, wherein the cycloalkyl is optionally substituted with one or more substituents independently selected from the group consisting of OH, halogen, C1-C6 alkoxy, CN, hydroxyC1-C6 alkyl, (C1-C6 alkoxy)C1-C6 alkyl, and C1-C6 alkyl optionally substituted with 1-3 fluoros. In one embodiment, Cyc$^1$ is a C3-C6 cycloalkyl optionally substituted with OH. Non-limiting examples when D is hetCyc$^1$ and E is Cyc$^1$ include the structures:

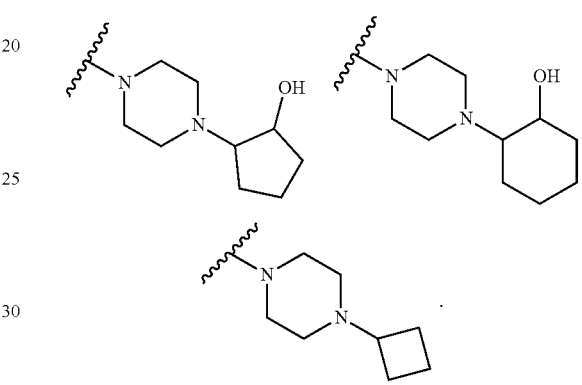

In one embodiment, D is hetCyc$^1$ and E is Cyc$^1$C(=O)— where Cyc$^1$ is as defined for General Formula I. In one embodiment, Cyc$^1$ is a C3-C6 cycloalkyl, wherein the cycloalkyl is optionally substituted with one or more substituents independently selected from the group consisting of OH or halogen. In one embodiment, the cycloalkyl is substituted with phenyl. Non-limiting examples when D is hetCyc$^1$ and E is Cyc$^1$C(=O)— include the structures:

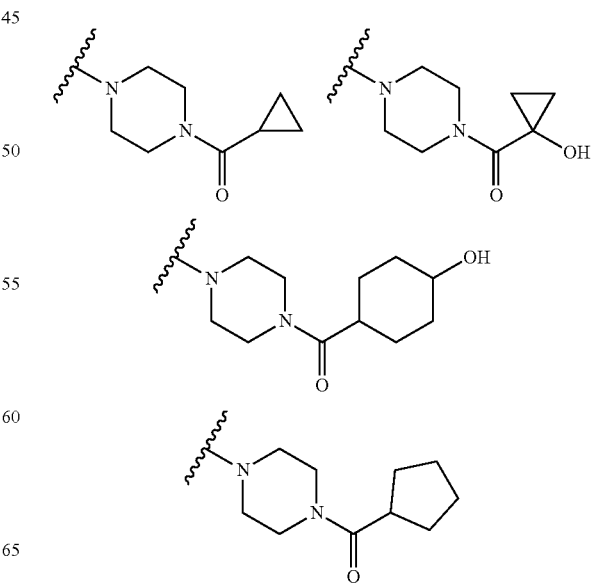

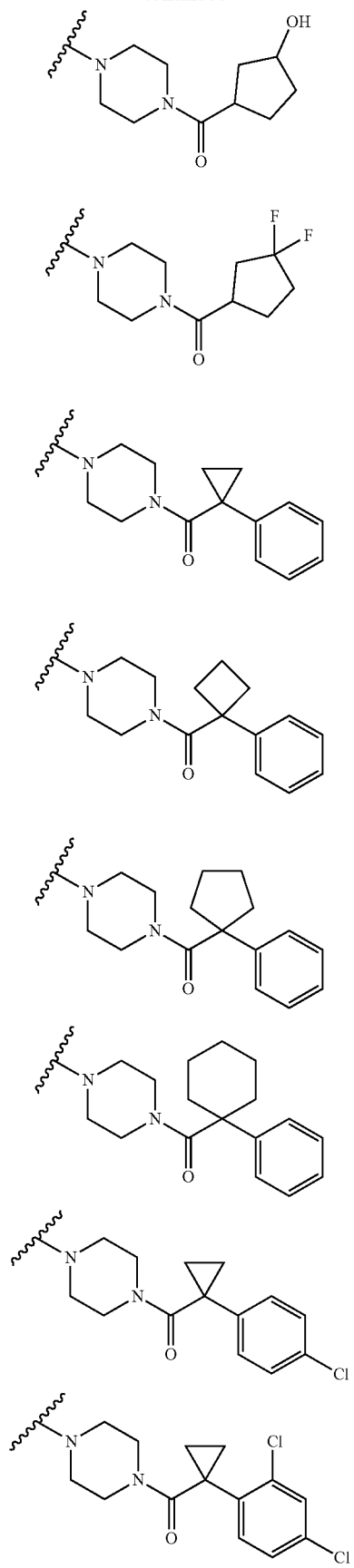
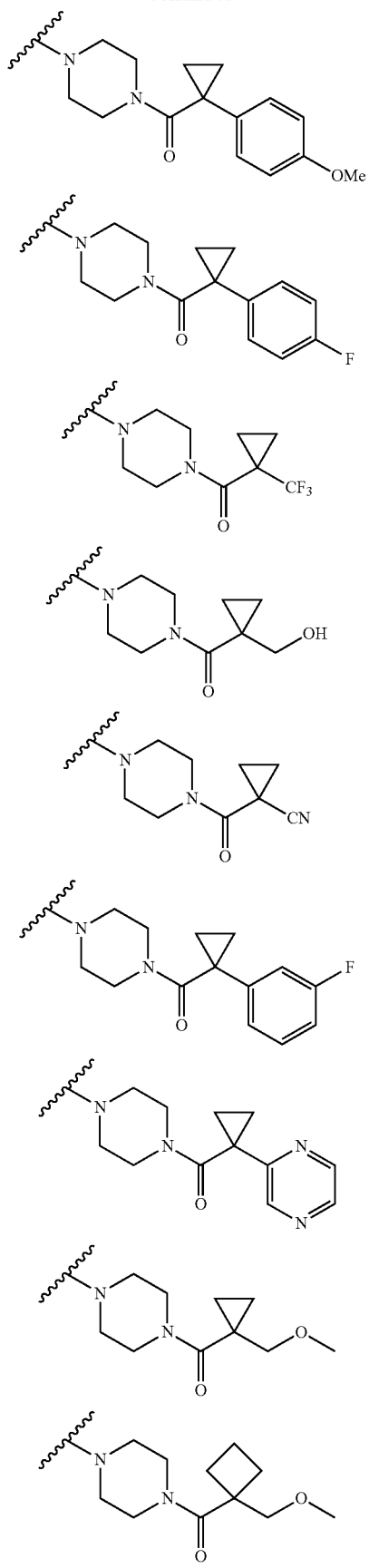

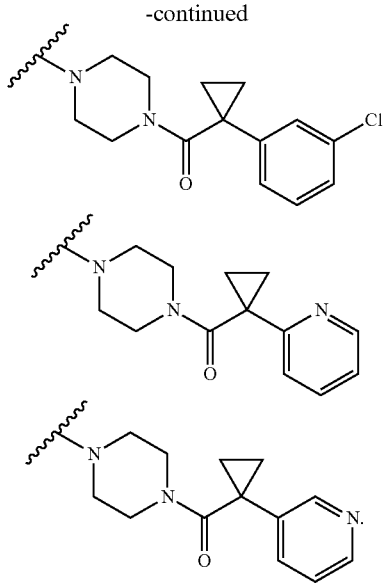

In one embodiment, D is hetCyc¹ and E is Cyc¹(C1-C6 alkyl)C(=O)— wherein the alkyl portion is optionally substituted with one or more groups independently selected from the group consisting of OH, fluoro, C1-C3 alkoxy and $R^cR^dN$— where $R^c$ and $R^d$ are independently H or C1-C6 alkyl. In one embodiment, Cyc¹ is a C3-C6 cycloalkyl optionally substituted with one or more substituents independently selected from the group consisting of OH, halogen, C1-C6 alkoxy, CN, hydroxyC1-C6 alkyl, (C1-C6 alkoxy)C1-C6 alkyl, and C1-C6 alkyl optionally substituted with 1-3 fluoros. In one embodiment, the alkyl portion of Cyc¹(C1-C6 alkyl)C(=O)— is unsubstituted. In one embodiment, Cyc¹ is unsubstituted. A non-limiting example when D is hetCyc¹ and E is Cyc¹(C1-C6 alkyl)C(=O)— is the structure:

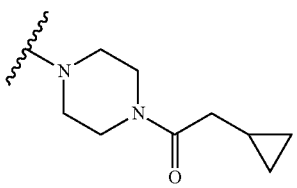

In one embodiment, D is hetCyc¹ and E is hetCyc⁴, hetCyc⁴C(=O)—, hetCyc⁴(C1-C3 alkyl)C(=O)—, (hetCyc⁴)C(=O)C1-C2 alkyl, or hetCyc⁴C(=O)NH—, wherein in each instance, hetCyc⁴ is as defined for General Formula I.

In one embodiment, D is hetCyc¹ and E is hetCyc⁴, hetCyc⁴C(=O)—, hetCyc⁴(C1-C3 alkyl)C(=O)—, (hetCyc⁴)C(=O)C1-C2 alkyl, or hetCyc⁴C(=O)NH—, wherein in each instance hetCyc⁴ is (a) a 5-6 membered heterocyclic ring, (b) a 7-8 membered bridged heterocyclic ring, (c) a 8-12 membered fused bicyclic heterocyclic ring, or (d) a 7-10 membered spirocyclic heterocyclic ring, wherein each of the heterocyclic rings has 1-2 ring heteroatoms independently selected from N and O, and wherein each of the heterocyclic rings is optionally substituted with one or more substituents independently selected from the group consisting of halogen, OH, CN, C1-C6 alkyl (optionally substituted with 1-3 fluoros), C1-C6 alkoxy and (C1-C6 alkoxy)C1-C6 alkyl.

In one embodiment, hetCyc⁴ is tetrahydrofuranyl, pyrrolidinyl, piperidinyl, morpholinyl or tetrahydro-2H-thiopyranyl 1,1-dioxide optionally substituted with one or more substituents independently selected from the group consisting of halogen, OH, CN, C1-C6 alkyl (optionally substituted with 1-3 fluoros), C1-C6 alkoxy and (C1-C6 alkoxy)C1-C6 alkyl.

In one embodiment, D is hetCyc¹ and E is hetCyc⁴, where hetCyc⁴ is as defined for General Formula I. In one embodiment, hetCyc⁴ is a 4-6 membered heterocyclic ring having 1-2 ring heteroatoms independently selected from N, O and S wherein the S is optionally oxidized to $SO_2$, and wherein the heterocyclic ring is optionally substituted with one or more substituents independently selected from the group consisting of halogen, OH, CN, C1-C6 alkyl (optionally substituted with 1-3 fluoros), C1-C6 alkoxy and (C1-C6 alkoxy)C1-C6 alkyl.

In one embodiment, D is hetCyc¹ and E is hetCyc⁴, wherein hetCyc⁴ is a 4-6 membered heterocyclic ring having 1-2 ring heteroatoms independently selected from N, O, and S wherein the S is optionally oxidized to $SO_2$ and wherein the heterocyclic ring is optionally substituted with OH or C1-C6 alkoxy.

In one embodiment, D is hetCyc¹ and E is hetCyc⁴, wherein hetCyc⁴ is a 4-6 membered heterocyclic ring having a ring heteroatom selected from O and S wherein the S is optionally oxidized to $SO_2$, and wherein the heterocyclic ring is optionally substituted with OH or C1-C6 alkoxy.

Non-limiting examples when D is hetCyc¹ and E is hetCyc⁴ include the structures:

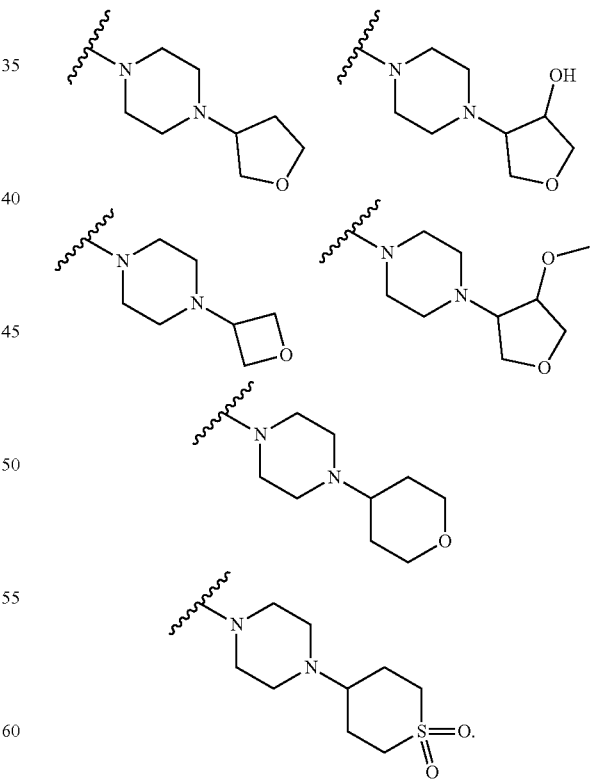

In one embodiment, D is hetCyc¹ and E is hetCyc⁴C (=O)—, where hetCyc⁴ is as defined for General Formula I. In one embodiment, hetCyc⁴ is (a) a 4-6 membered heterocyclic ring having 1-2 ring heteroatoms independently selected from N, O and S wherein said S is optionally oxidized to $SO_2$, (b) a 7-8 membered bridged heterocyclic ring having 1-2 ring heteroatoms independently selected from N and O, (c) a 6-12 membered fused bicyclic heterocyclic ring having 1-2 ring heteroatoms independently selected from N and O and optionally independently substituted with 1-2 C1-C6 alkyl substitutents, or (d) a 7-10 membered spirocyclic heterocyclic ring having 1-2 ring heteroatoms independently selected from N and O, wherein each of said heterocyclic rings is optionally substituted with one or more substituents independently selected from the group consisting of halogen, OH, CN, C1-C6 alkyl (optionally substituted with 1-3 fluoros), C1-C6 alkoxy, (C1-C6 alkoxy)C1-C6 alkyl, (C3-C6)cycloalkyl, (C1-C6 alkyl)C(=O)—, a 5-6 membered heterocyclic ring having 1-2 ring heteroatoms independently selected from N and O, and phenyl.

In one embodiment, D is hetCyc$^1$ and E is hetCyc$^4$C(=O)—, where hetCyc$^4$ is (a) a 5-6 membered heterocyclic ring, (b) a 7-8 membered bridged heterocyclic ring, (c) a 6-12 membered fused bicyclic heterocyclic ring, or (d) a 7-10 membered spirocyclic heterocyclic ring, wherein each of the heterocyclic rings has 1-2 ring heteroatoms independently selected from N and O, and wherein each of the heterocyclic rings is optionally substituted with one or more substituents independently selected from the group consisting of halogen, OH, CN, C1-C6 alkyl (optionally substituted with 1-3 fluoros), C1-C6 alkoxy and (C1-C6 alkoxy)C1-C6 alkyl.

In one embodiment, D is hetCyc$^1$ and E is hetCyc$^4$C(=O)—, where hetCyc$^4$ is (a) a 4-6 membered heterocyclic ring, (b) a 7-8 membered bridged heterocyclic ring, (c) a 6-12 membered fused bicyclic heterocyclic ring, or (d) a 7-10 membered spirocyclic heterocyclic ring, wherein each of the heterocyclic rings has 1-2 ring heteroatoms independently selected from N and O, and wherein each of the heterocyclic rings is optionally substituted with one or more substituents independently selected from the group consisting of halogen, OH, CN, C1-C6 alkyl (optionally substituted with 1-3 fluoros), C1-C6 alkoxy, (C1-C6 alkoxy)C1-C6 alkyl, (C3-C6)cycloalkyl, a 5-6 membered heterocyclic ring having 1-2 ring heteroatoms independently selected from N and O, and phenyl wherein said phenyl is optionally substituted with one or more substituents selected from halogen, C1-C6 alkyl and C1-C6 alkoxy.

In one embodiment, D is pyrrolidinyl, piperidinyl or piperazinyl, and E is hetCyc$^4$C(=O)—, where hetCyc$^4$ is (a) a 5-6 membered heterocyclic ring having 1-2 ring heteroatoms independently selected from N and O, wherein the ring is optionally substituted with one or more substituents independently selected from the group consisting of halogen, OH, CN, C1-C6 alkyl (optionally substituted with 1-3 fluoros), C1-C6 alkoxy, (C1-C6 alkoxy)C1-C6 alkyl, (C3-C6)cycloalkyl, a 5-6 membered heterocyclic ring having 1-2 ring heteroatoms independently selected from N and O, and phenyl (b) a 7-8 membered bridged heterocyclic ring having a ring nitrogen atom, (c) a 6-12 membered fused bicyclic heterocyclic ring having 1-2 ring heteroatoms independently selected from N and O and optionally substituted with 1-2 groups independently selected from C1-C6 alkyl, or (d) a 7-10 membered spirocyclic heterocyclic ring a ring nitrogen atom.

In one embodiment, D is pyrrolidinyl, piperidinyl or piperazinyl, and E is hetCyc$^4$C(=O)—, where hetCyc$^4$ is a 5-6 membered heterocyclic ring having 1-2 ring heteroatoms independently selected from N and O, wherein the ring is optionally substituted with one or more substituents independently selected from the group consisting of halogen, OH, CN, C1-C6 alkyl (optionally substituted with 1-3 fluoros), C1-C6 alkoxy, (C1-C6 alkoxy)C1-C6 alkyl, (C3-C6)cycloalkyl, a 5-6 membered heterocyclic ring having 1-2 ring heteroatoms independently selected from N and O, and phenyl. In one embodiment, the ring is optionally substituted with one or more substituents independently selected from the group consisting of halogen, OH, CN, C1-C6 alkyl (optionally substituted with 1-3 fluoros), C1-C6 alkoxy and (C1-C6 alkoxy)C1-C6 alkyl.

Non-limiting examples when D is hetCyc$^1$ and E is hetCyc$^4$C(=O)— include the structures:

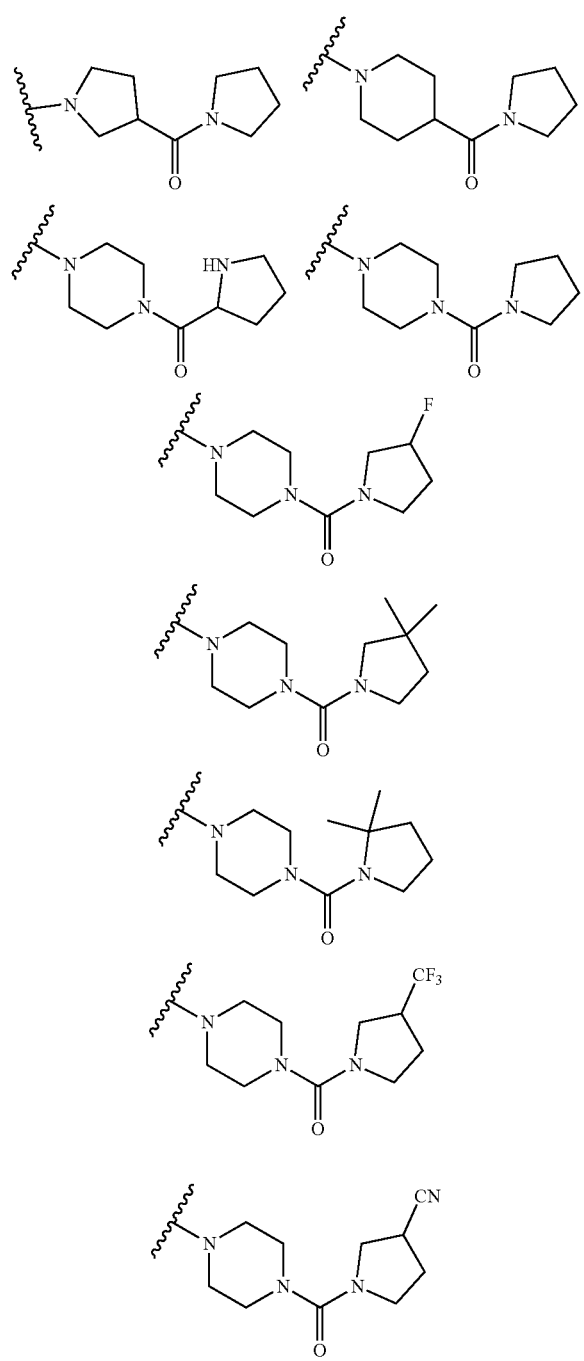

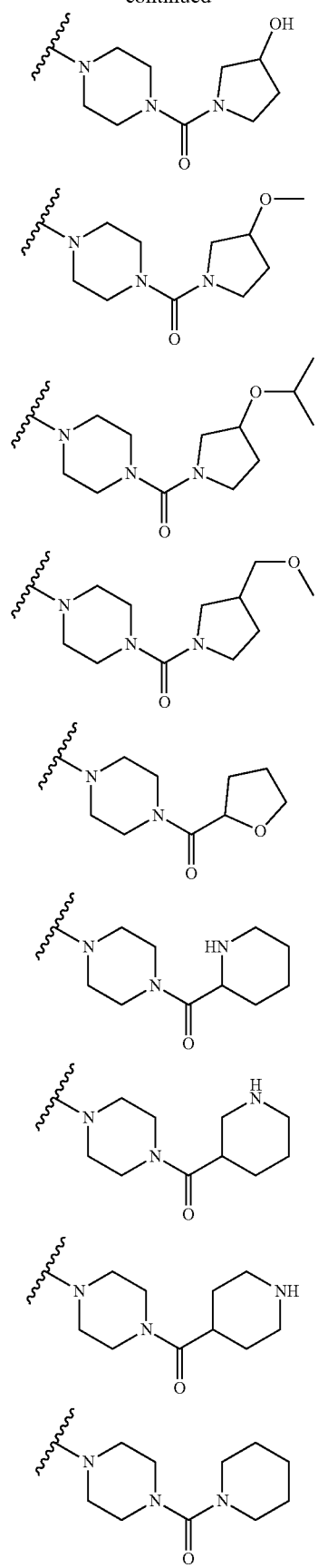
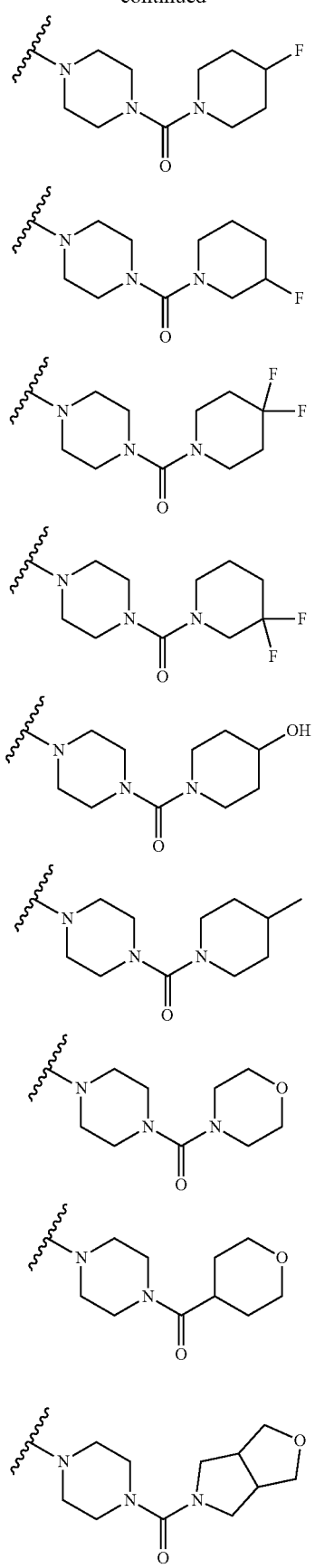

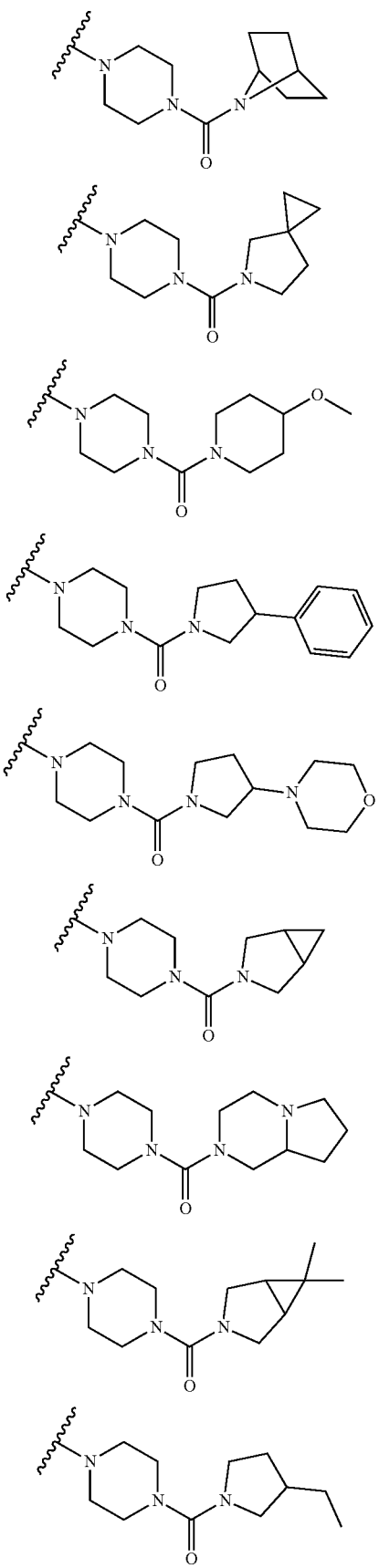

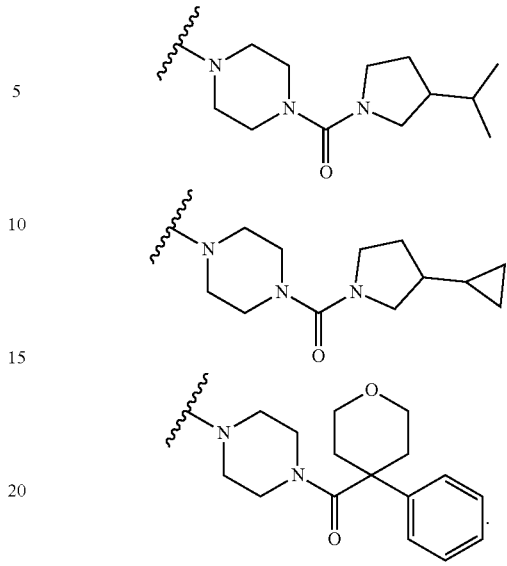

In one embodiment, D is hetCyc[1] and E is hetCyc[4](C1-C3 alkyl)C(=O)— where hetCyc[4] is as defined for General Formula I. In one embodiment, hetCyc[4] is a 4-6 membered heterocyclic ring having 1-2 ring heteroatoms independently selected from N and O, and wherein the heterocyclic ring is optionally substituted with one or more substituents independently selected from the group consisting of halogen, OH, CN, C1-C6 alkyl (optionally substituted with 1-3 fluoros), C1-C6 alkoxy, (C1-C6 alkoxy)C1-C6 alkyl, (C3-C6)cycloalkyl, a 5-6 membered heterocyclic ring having 1-2 ring heteroatoms independently selected from N and O, and phenyl wherein said phenyl is optionally substituted with one or more substituents selected from halogen, C1-C6 alkyl and C1-C6 alkoxy. In one embodiment, the heterocyclic ring is optionally substituted with one or more substituents independently selected from the group consisting of halogen, OH, CN, C1-C6 alkyl (optionally substituted with 1-3 fluoros), C1-C6 alkoxy, (C1-C6 alkoxy)C1-C6 alkyl, (C3-C6)cycloalkyl, a 5-6 membered heterocyclic ring having 1-2 ring heteroatoms independently selected from N and O, and phenyl.

In one embodiment, D is hetCyc[1] and E is hetCyc[4](C1-C3 alkyl)C(=O)—, where hetCyc[4] is a 4-6 membered heterocyclic ring having 1-2 ring heteroatoms independently selected from N and O, wherein the heterocyclic ring is unsubstituted or substituted with C1-C6 alkyl. In one embodiment, D is hetCyc[1] and E is hetCyc[4](C1-C3 alkyl)C(=O)—, where hetCyc[4] is a 5-6 membered heterocyclic ring having 1-2 ring heteroatoms independently selected from N and O, wherein the heterocyclic ring is unsubstituted.

In one embodiment, D is piperazinyl and E is hetCyc[4](C1-C3 alkyl)C(=O)—, where hetCyc[4] is a 5-6 membered heterocyclic ring having 1-2 ring heteroatoms independently selected from N and O, wherein the heterocyclic ring is unsubstituted or substituted with C1-C6 alkyl. In one embodiment, the ring is unsubstituted.

Non-limiting examples when D is hetCyc[1] and E is hetCyc[4](C1-C3 alkyl)C(=O)— include the structures:

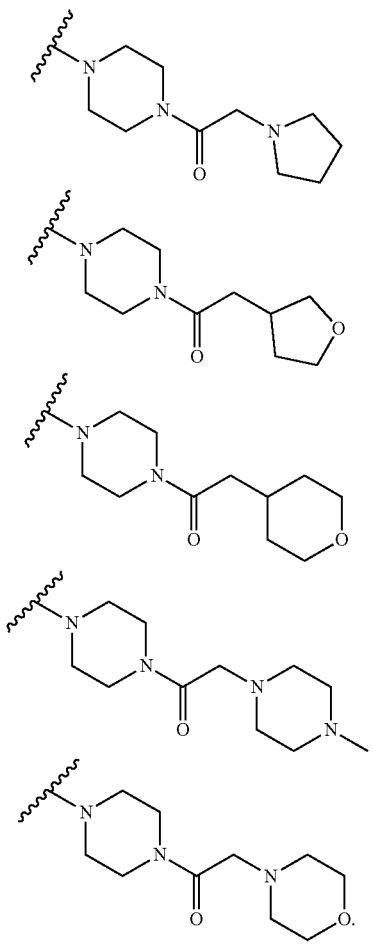

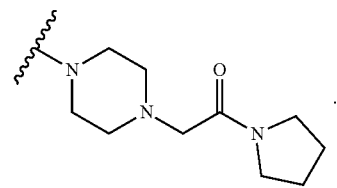 [SMILES: *N1CCN(CC(=O)N2CCCC2)CC1]

In one embodiment, D is hetCyc¹ and E is hetCyc⁴C(=O)NH—, where hetCyc⁴ is as defined for General Formula I. In one embodiment, hetCyc⁴ is (a) a 4-6 membered heterocyclic ring having 1-2 ring heteroatoms independently selected from N and O, wherein said ring is optionally substituted with one or more substituents independently selected from the group consisting of halogen, OH, CN, C1-C6 alkyl (optionally substituted with 1-3 fluoros), C1-C6 alkoxy, and (C1-C6 alkoxy)C1-C6 alkyl, (b) a 7-8 membered bridged heterocyclic ring having 1-2 ring heteroatoms independently selected from N and O, (c) a 8-12 membered fused bicyclic heterocyclic ring having 1-2 ring heteroatoms independently selected from N and O, or (d) a 7-10 membered spirocyclic heterocyclic ring having 1-2 ring heteroatoms independently selected from N and O.

Non-limiting examples when D is hetCyc¹ and E is hetCyc⁴C(=O)NH— include the structures:

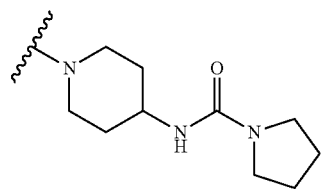

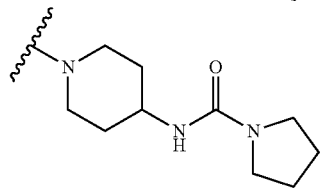

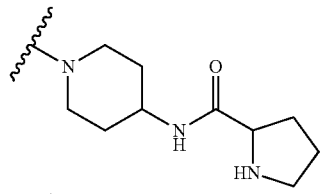

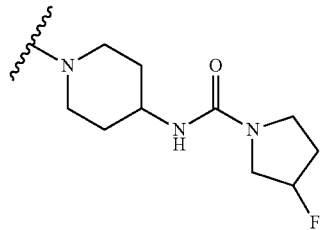

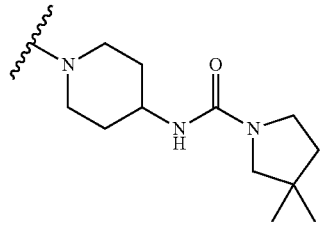

In one embodiment, D is hetCyc¹ and E is (hetCyc⁴)C(=O)C1-C2 alkyl, where hetCyc⁴ is as defined for General Formula I. In one embodiment, hetCyc⁴ is a 4-6 membered heterocyclic ring having 1-2 ring heteroatoms independently selected from N and O, and wherein the heterocyclic ring is optionally substituted with one or more substituents independently selected from the group consisting of halogen, OH, CN, C1-C6 alkyl (optionally substituted with 1-3 fluoros), C1-C6 alkoxy, (C1-C6 alkoxy)C1-C6 alkyl, (C3-C6)cycloalkyl, a 5-6 membered heterocyclic ring having 1-2 ring heteroatoms independently selected from N and O, and phenyl wherein said phenyl is optionally substituted with one or more substituents selected from halogen, C1-C6 alkyl and C1-C6 alkoxy. In one embodiment, the heterocyclic ring is optionally substituted with one or more substituents independently selected from the group consisting of halogen, OH, CN, C1-C6 alkyl (optionally substituted with 1-3 fluoros), C1-C6 alkoxy and (C1-C6 alkoxy)C1-C6 alkyl.

In one embodiment, D is hetCyc¹ and E is (hetCyc⁴)C(=O)C1-C2 alkyl, where hetCyc⁴ is a 4-6 membered heterocyclic ring having 1-2 ring heteroatoms independently selected from N and O, wherein the heterocyclic ring is unsubstituted. In one embodiment, D is piperazinyl and hetCyc⁴ is a 4-6 membered heterocyclic ring having a ring nitrogen atom. In one embodiment, hetCyc⁴ is 5-6 membered heterocyclic ring having a ring nitrogen atom.

A non-limiting example when D is hetCyc¹ and E is (hetCyc⁴)C(=O)C1-C2 alkyl is the structure:

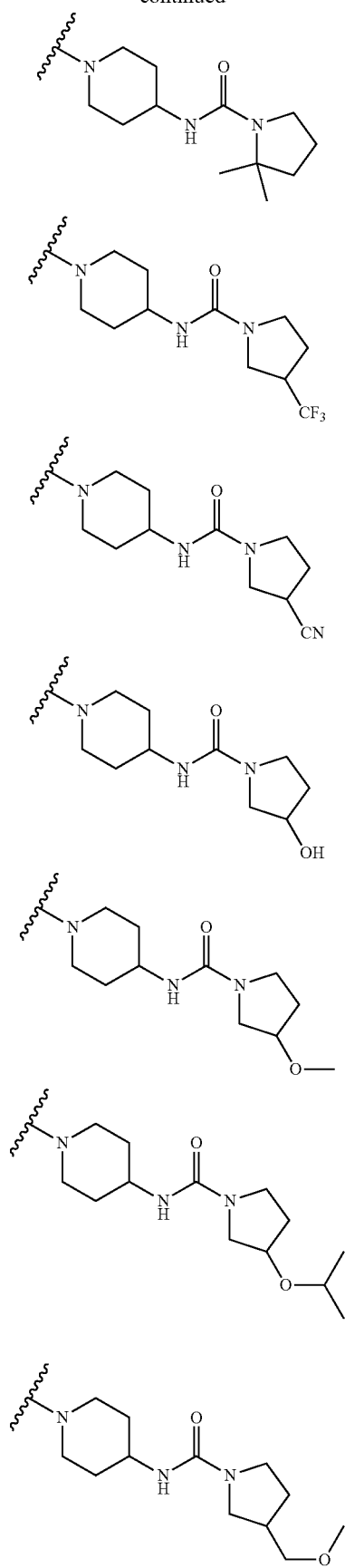
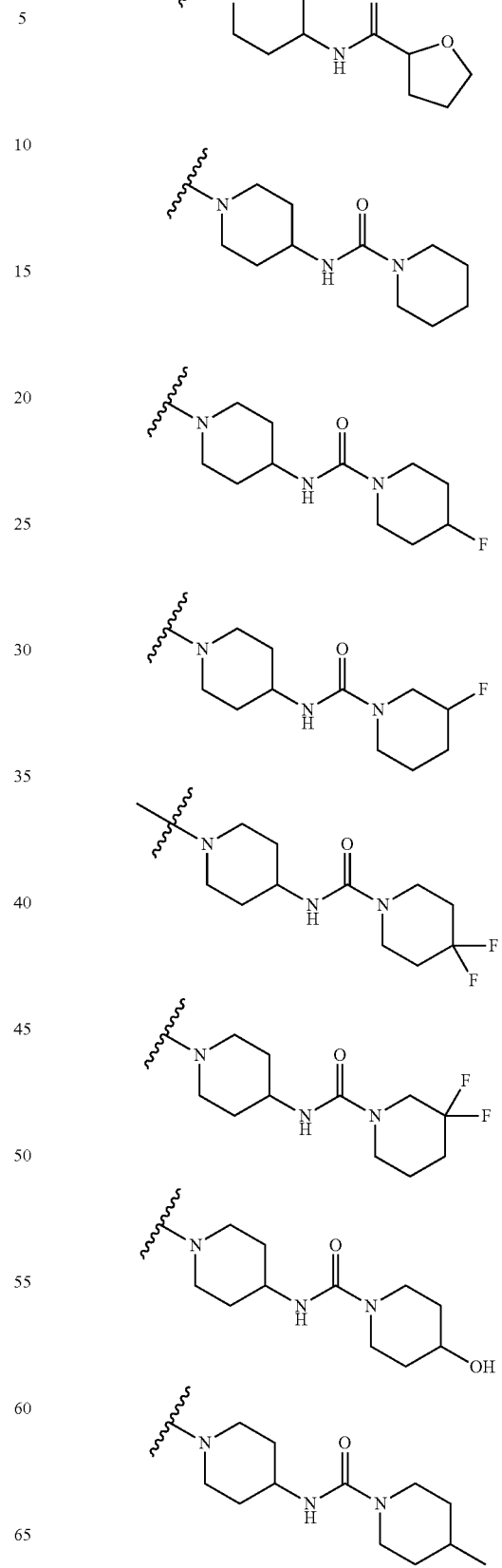

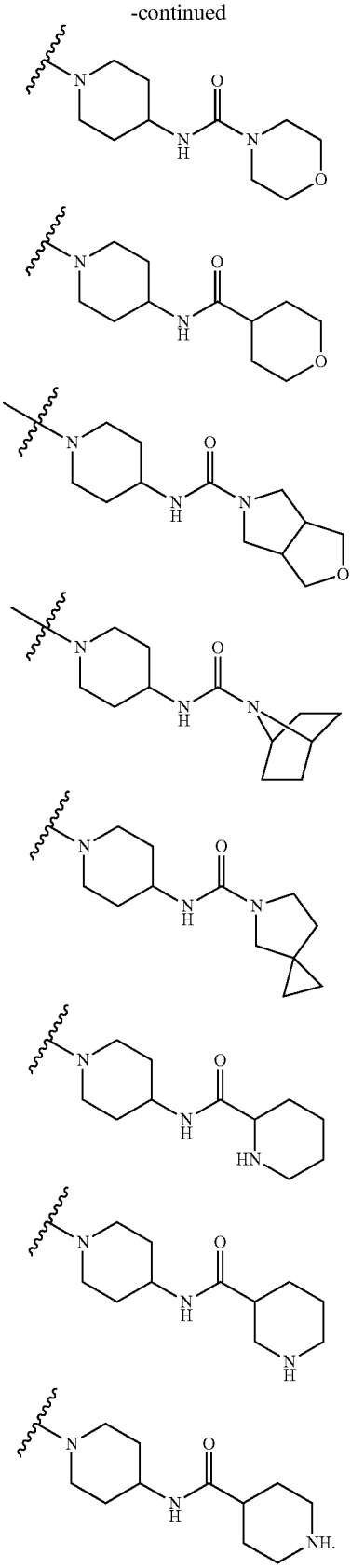

In one embodiment, D is hetCyc¹ and E is Ar²; Ar²C(=O)—; Ar²C1-C6 alkyl; (Ar²)hydroxy C2-C6 alkyl; or Ar²(C1-C3 alkyl)C(=O)— wherein the alkyl portion is optionally substituted with one or two groups independently selected from the group consisting of OH, C1-C6 alkyl (optionally substituted with 1-3 fluoros), hydroxyC1-C6 alkyl, C1-C6 alkoxy and $R^eR^fN$— where $R^e$ and $R^f$ are independently H or C1-C6 alkyl, or $R^e$ and $R^f$ together with the nitrogen to which they are attached form a 5-6 membered azacyclic ring optionally having an additional ring heteroatom selected from N and O; wherein for each instance of E, Ar² is phenyl optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, CN, a 5-6 membered heterocyclic ring having 1-2 ring heteroatoms independently selected from N and O, and $R^iR^jN$— where $R^i$ and $R^j$ are independently H and C1-C6 alkyl. In one embodiment, Ar² is phenyl optionally substituted with one or more substituents independently selected from the group consisting of halogen and C1-C3 alkyl.

In one embodiment, D is hetCyc¹ and E is Ar²; Ar²C(=O)—; Ar²C1-C6 alkyl; (Ar²)hydroxy C2-C6 alkyl; or Ar²(C1-C3 alkyl)C(=O)— wherein the alkyl portion is optionally substituted with one or two groups independently selected from the group consisting of OH, C1-C6 alkyl, hydroxyC1-C6 alkyl, C1-C6 alkoxy and $R^eR^fN$— where $R^e$ and $R^f$ are independently H or C1-C6 alkyl; wherein for each instance of E, Ar² is phenyl optionally substituted with one or more substituents independently selected from the group consisting of halogen, C1-C3 alkyl, C1-C3 alkoxy, fluoroC1-C3 alkyl, difluoroC1-C3 alkyl and trifluoroC1-C3 alkyl. In one embodiment, Ar² is phenyl optionally substituted with one or more substituents independently selected from the group consisting of halogen and C1-C3 alkyl.

In one embodiment, D is hetCyc¹ and E is Ar² wherein Ar² is as defined for General Formula I. In one embodiment, Ar² is phenyl optionally substituted with one or more substituents independently selected from the group consisting of halogen. In one embodiment, hetCyc¹ is pyrrolidinyl, piperidinyl or morpholinyl. Non-limiting examples when D is hetCyc¹ and E is Ar² include the structures:

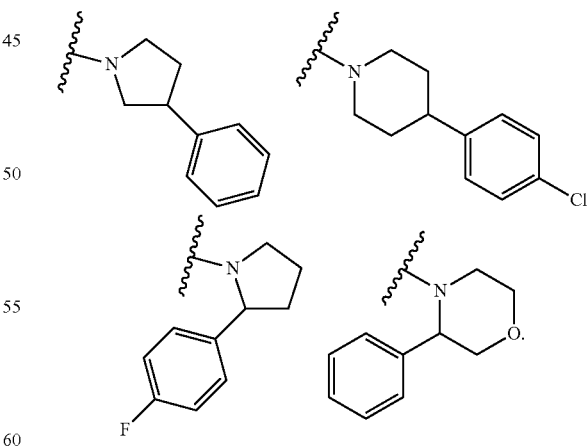

In one embodiment, D is hetCyc¹ and E is Ar²C(=O)— wherein Ar² is as defined for General Formula I. In one embodiment, Ar² is phenyl optionally substituted with one or more substituents independently selected from the group consisting of halogen or a 5-6 membered heterocyclic ring having 1-2 ring heteroatoms independently selected from N and O. In one embodiment, hetCyc[1] is piperazinyl. Non-limiting examples include the structures:

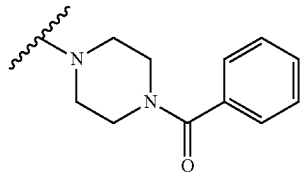

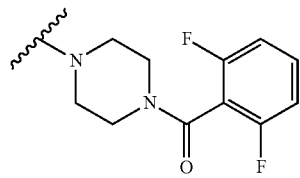

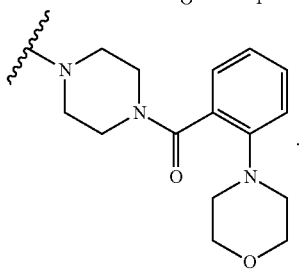

In one embodiment, D is hetCyc[1] and E is Ar[2]C1-C6 alkyl wherein Ar[2] is as defined for General Formula I. In one embodiment, Ar[2] is phenyl optionally substituted with one or more substituents independently selected from the group consisting of halogen, C1-C3 alkyl, C1-C3 alkoxy, CN, and R[i]R[j]N— where R[i] and R[j] are independently H and C1-C6 alkyl. In one embodiment, hetCyc[1] is piperazinyl, piperidinyl, azetidinyl, or piperazin-2-onyl. In one embodiment, E is Ar[2]C1-C2 alkyl where Ar[2] is phenyl optionally substituted with one or more substituents independently selected from the group consisting of halogen, C1-C6 alkyl, C1-C6 alkoxy, CN, and R[i]R[j]N— where R[i] and R[j] are independently H and C1-C6 alkyl.

Non-limiting examples when D is hetCyc[1] and E is Ar[2]C1-C6 alkyl include the structures:

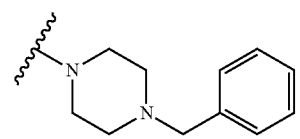

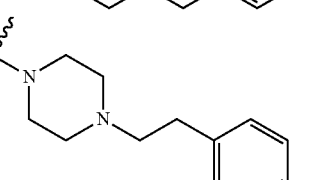

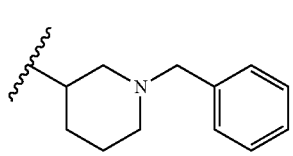   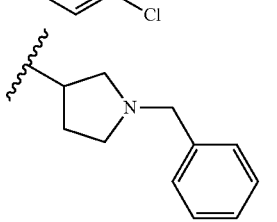

-continued

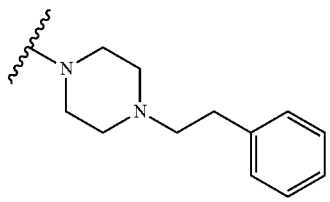

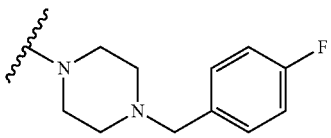

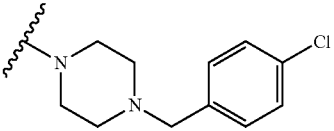

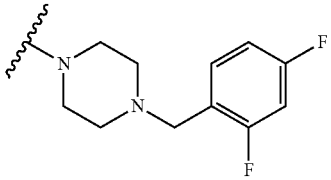

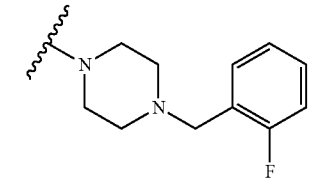

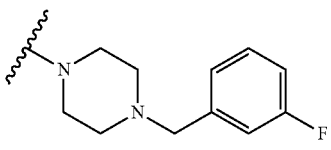

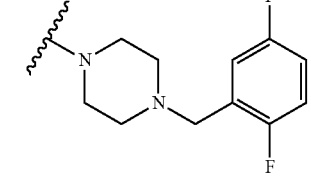

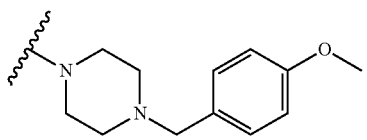

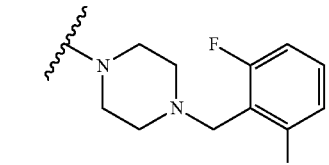

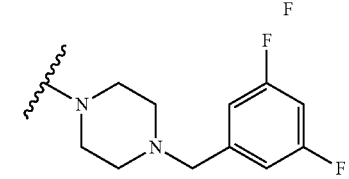

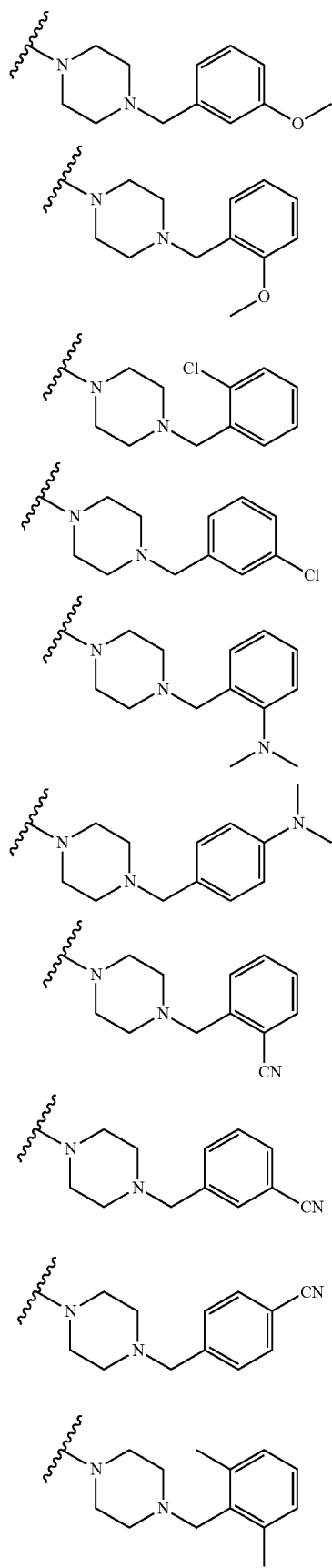

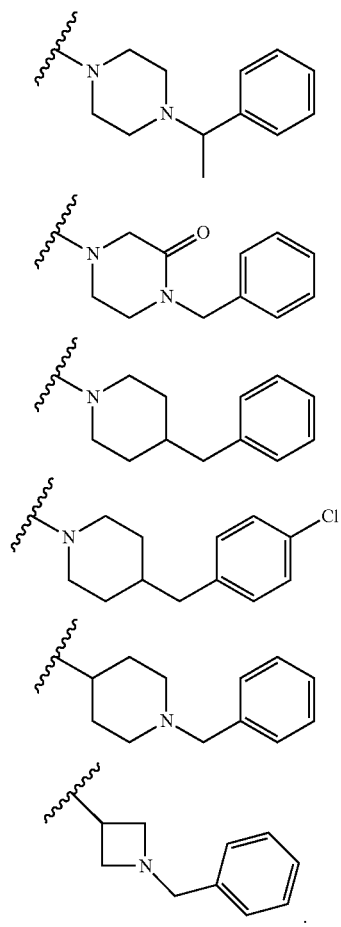

In one embodiment, D is hetCyc[1] and E is (Ar[2])hydroxy C2-C6 alkyl wherein Ar[2] is as defined for General Formula I. In one embodiment, Ar[2] is phenyl optionally substituted with one or more substituents independently selected from the group consisting of halogen. In one embodiment, hetCyc[1] is piperazinyl.

Non-limiting examples when D is hetCyc[1] and E is (Ar[2])hydroxy C2-C6 alkyl include the structures:

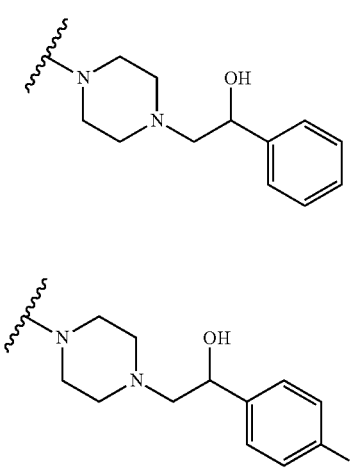

-continued

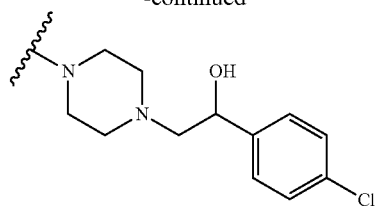

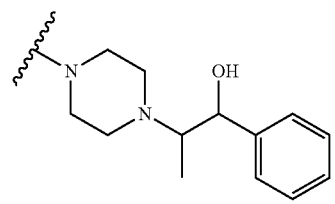

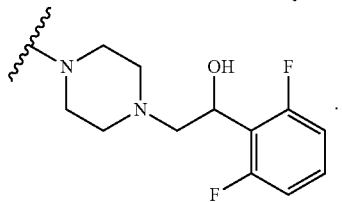

In one embodiment, D is hetCyc[1] and E is Ar[2](C1-C3 alkyl)C(=O)—, wherein Ar[2] is as defined for General Formula I and the alkyl portion is optionally substituted with one or two groups independently selected from the group consisting of OH, C1-C6 alkyl (optionally substituted with 1-3 fluoros), hydroxyC1-C6 alkyl, C1-C6 alkoxy and $R^eR^fN$—, where $R^e$ and $R^f$ are independently H and C1-C6 alkyl, or $R^e$ and $R^f$ together with the nitrogen to which they are attached form a 5-6 membered azacyclic ring optionally having an additional ring heteroatom selected from N and O. In one embodiment, hetCyc[1] is piperazinyl. In one embodiment, Ar[2] is phenyl optionally substituted with one or more substituents independently selected from halogen, CN, C1-C6 alkyl and C1-C6 alkoxy (optionally substituted with 1-3 fluoros).

In one embodiment, D is hetCyc[1] and E is Ar[2](C1-C3 alkyl)C(=O)—, wherein Ar[2] is as defined for General Formula I and the alkyl portion is optionally substituted with one or two groups independently selected from the group consisting of OH, C1-C6 alkyl, hydroxyC1-C6 alkyl, C1-C6 alkoxy and $R^eR^fN$—, where $R^e$ and $R^f$ are independently H and C1-C6 alkyl. In one embodiment, hetCyc[1] is piperazinyl.

Non-limiting examples when D is hetCyc[1] and E is Ar[2](C1-C3 alkyl)C(=O)— include the structures:

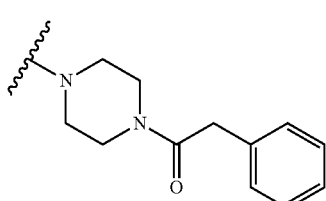

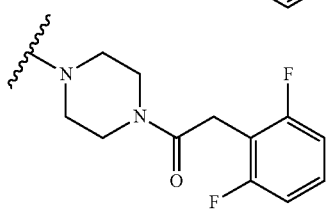

-continued

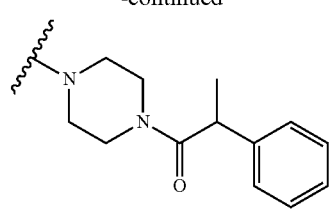

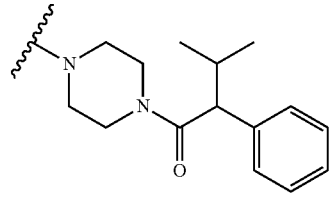

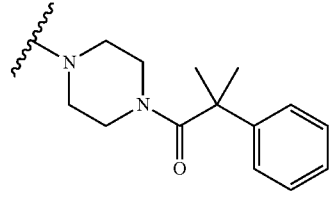

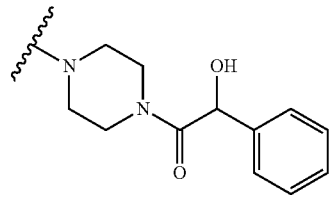

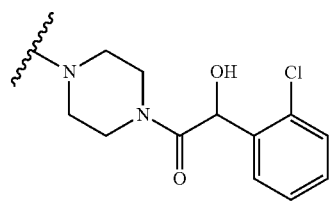

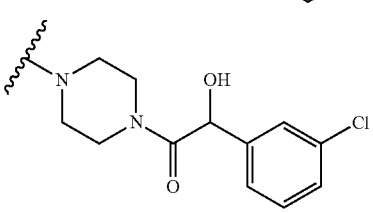

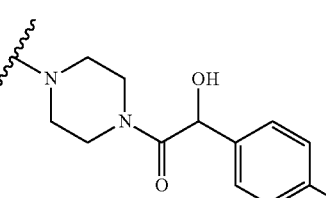

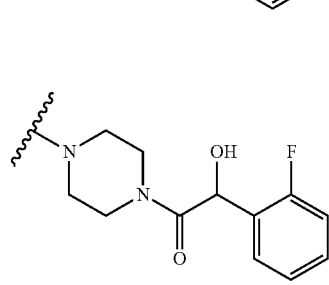

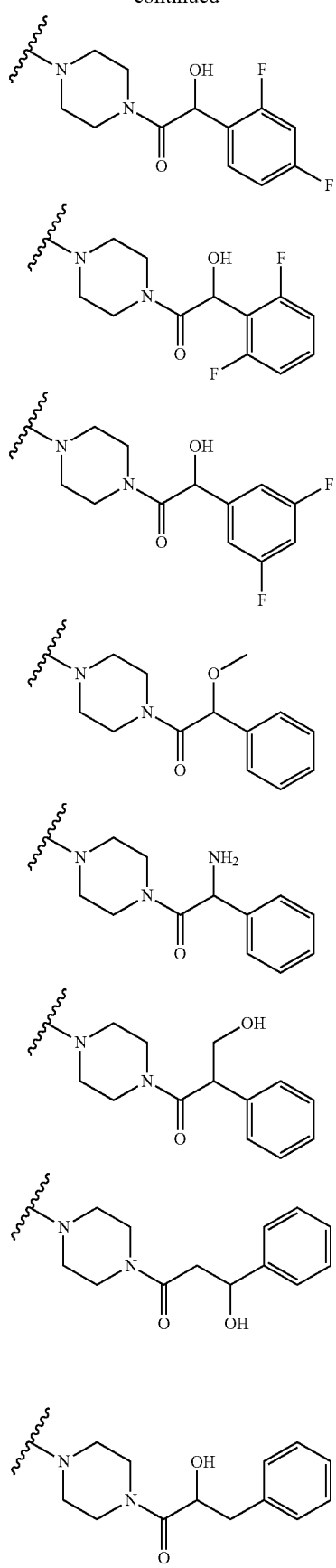
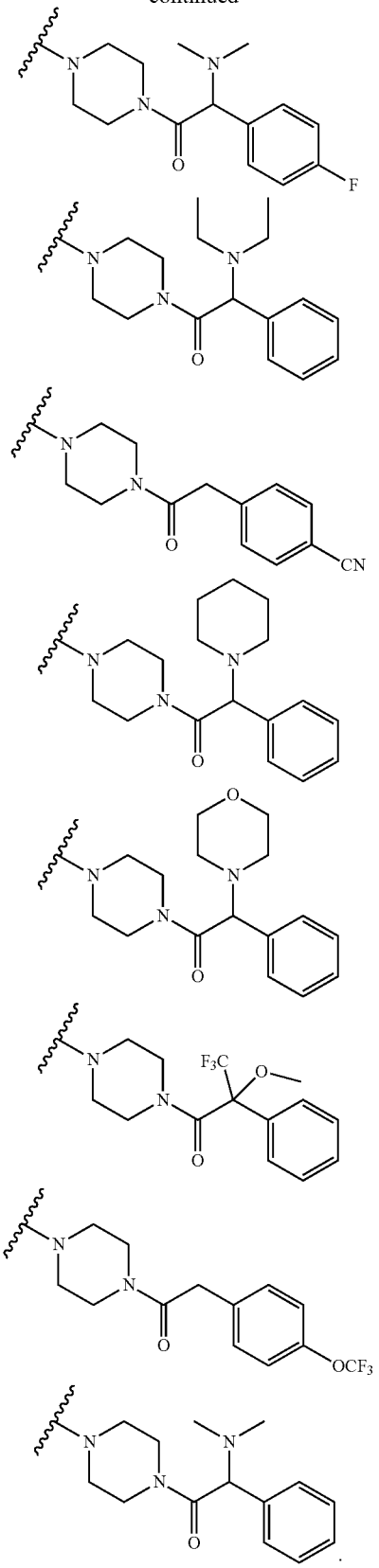
In one embodiment, D is hetCyc¹ and E is hetAr²C(=O)—; (hetAr²)hydroxyC2-C6 alkyl; or hetAr²(C1-C3 alkyl)C(=O)— wherein the alkyl portion is optionally substituted with one or two groups independently selected from the group consisting of OH, C1-C6 alkyl, hydroxyC1-C6 alkyl, C1-C6 alkoxy and R$^e$R$^f$N—, where R$^e$ and R$^f$ are independently H or C1-C6 alkyl, or R$^e$ and R$^f$ together with the nitrogen to which they are attached form a 5-6 membered azacyclic ring optionally having an additional ring heteroatom selected from N and O; wherein for each instance of E, hetAr$^2$ is a 5-6 membered heteroaryl ring having 1-3 ring heteroatoms independently selected from N, O and S and optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, hydroxyC1-C6 alkyl, (C3-C6)cycloalkyl, (C1-C6 alkoxy)C1-C6 alkyl, CN, and R'R''N— where R' and R'' are independently H or C1-C6 alkyl.

In one embodiment, D is hetCyc$^1$ and E is hetAr$^2$C(=O)—; (hetAr$^2$)hydroxyC2-C6 alkyl; hetAr$^2$(C1-C3 alkyl)C(=O)— wherein the alkyl portion is optionally substituted with one or two groups independently selected from the group consisting of OH, C1-C6 alkyl, hydroxyC1-C6 alkyl, C1-C6 alkoxy and R$^e$R$^f$N—, where R$^e$ and R$^f$ are independently H or C1-C6 alkyl; or hetAr$^2$C1-C6 alkyl; wherein for each instance of E, hetAr$^2$ is a 5-6 membered heteroaryl ring having 1-3 ring heteroatoms independently selected from N and O and optionally substituted with one or more substituents independently selected from the group consisting of halogen, C1-C3 alkyl, C1-C3 alkoxy (optionally substituted with 1-3 fluoros), fluoroC1-C3 alkyl, difluoroC1-C3 alkyl, trifluoroC1-C3 alkyl and hydroxyC1-C3 alkyl.

In one embodiment, hetAr$^2$ is pyridyl, pyridazinyl, imidazolyl, pyrazolyl or isoxazolyl optionally substituted with one or more substituents independently selected from the group consisting of halogen, C1-C3 alkyl, C1-C3 alkoxy (optionally substituted with 1-3 fluoros), fluoroC1-C3 alkyl, difluoroC1-C3 alkyl, trifluoroC1-C3 alkyl, hydroxyC1-C6 alkyl, (C3-C6)cycloalkyl and (C1-C6 alkoxy)C1-C6 alkyl. In one embodiment, hetAr$^2$ is optionally substituted with one or more substituents independently selected C1-C3 alkyl.

In one embodiment, D is hetCyc$^1$ and E is hetAr$^2$C(=O)—, where hetAr$^2$ is as defined for General Formula I. In one embodiment, hetAr$^2$ is a 5-6 membered heteroaryl ring having 1-2 ring heteroatoms independently selected from N and O and optionally substituted with one or more substituents independently selected from the group consisting of halogen, C1-C3 alkyl, (C3-C6)cycloalkyl and (C1-C6 alkoxy)C1-C6 alkyl. In one embodiment, hetCyc$^1$ is piperazinyl.

Non-limiting examples when D is hetCyc$^1$ and E is hetAr$^2$C(=O)— include the structures:

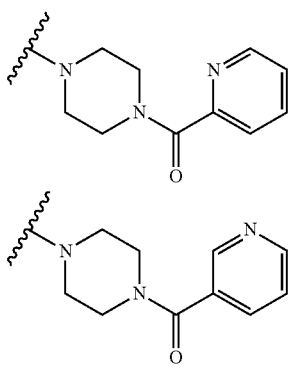

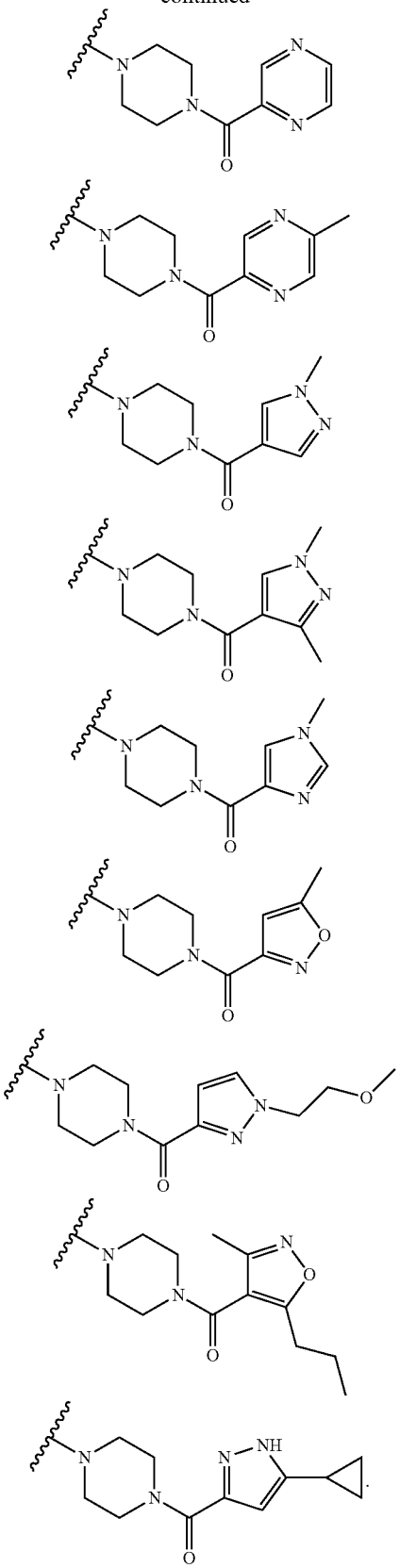

In one embodiment, D is hetCyc$^1$ and E is (hetAr$^2$)hydroxyC2-C6 alkyl where hetAr$^2$ is as defined for General Formula I. In one embodiment, hetAr² is a 5-6 membered heteroaryl ring having 1-2 ring heteroatoms independently selected from N and O wherein said ring is unsubstituted. In one embodiment, hetAr² is pyridinyl. Non-limiting examples includes the structures:

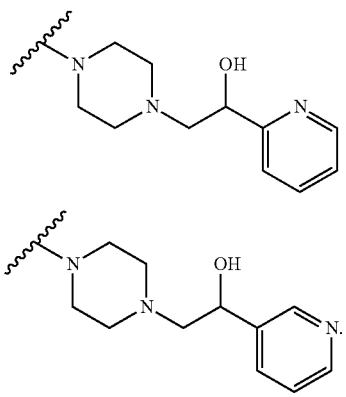

In one embodiment, D is hetCyc¹ and E is hetAr²(C1-C3 alkyl)C(=O)—, wherein hetAr² is as defined for General Formula I and the alkyl portion is optionally substituted with one or two groups independently selected from the group consisting of OH, C1-C6 alkyl, hydroxyC1-C6 alkyl, C1-C6 alkoxy (optionally substituted with 1-3 fluoros) and R$^e$R$^f$N—, where R$^e$ and R$^f$ are independently H or C1-C6 alkyl. In one embodiment, the alkyl portion of hetAr²(C1-C3 alkyl)C(=O)— is unsubstituted. In one embodiment, hetAr² is a 5-6 membered heteroaryl ring having 1-2 ring nitrogen atoms and optionally substituted with one or more substituents independently selected from the group consisting of halogen and C1-C6 alkyl. In one embodiment, hetCyc¹ is piperazinyl.

Non-limiting examples D is hetCyc¹ and E is hetAr²(C1-C3 alkyl)C(=O)— include the structures:

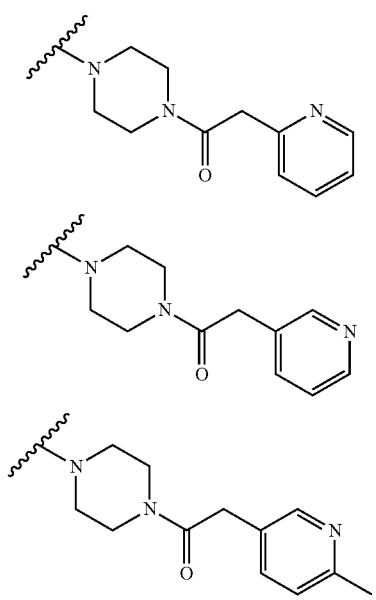

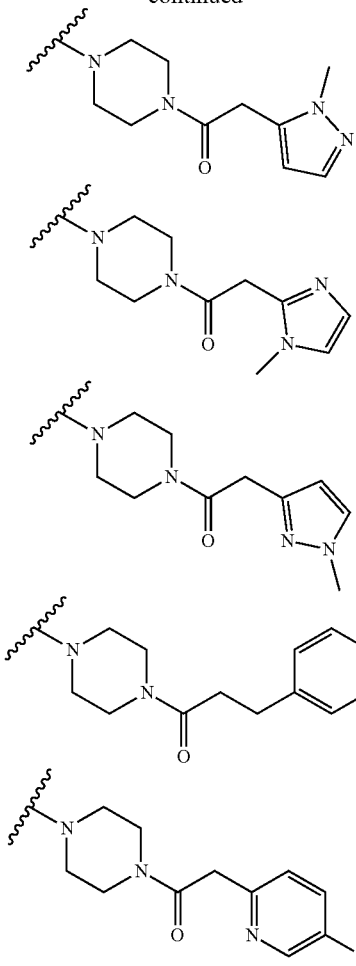

In one embodiment, D is hetCyc¹ and E is R¹R²NC(=O)—; R¹R²N(C1-C3 alkyl)C(=O)— wherein the alkyl portion is optionally substituted with phenyl; R¹R²NC(=O) C1-C2 alkyl; or R¹R²NC(=O)NH—; where in each instance, R¹ is H, C1-C6 alkyl or (C1-C6 alkoxy)C1-C6 alkyl, and R² is H, C1-C6 alkyl (optionally substituted with 1-3 fluoros), (C1-C6 alkoxy)C1-C6 alkyl (optionally substituted with 1-3 fluoros), Cyc³, hydroxyC1-C6 alkyl (optionally substituted with 1-3 fluoros), C1-C6 alkoxy (optionally substituted with 1-3 fluoros), (C1-C6 alkoxy)C(=O), hetCyc⁷, Ar³, Ar³C1-C3 alkyl-, hydroxyC1-C6 alkoxy or (3-6C cycloalkyl)CH₂O—.

In one embodiment, D is hetCyc¹ and E is R¹R²NC(=O)—; R¹R²N(C1-C3 alkyl)C(=O)— wherein the alkyl portion is optionally substituted with phenyl; R¹R²NC(=O) C1-C2 alkyl; or R¹R²NC(=O)NH—; where in each instance, R¹ is H or C1-C6 alkyl, and R² is H, C1-C6 alkyl (optionally substituted with 1-3 fluoros), (C1-C6 alkoxy)C1-C6 alkyl (optionally substituted with 1-3 fluoros), Cyc³, hydroxyC1-C6 alkyl (optionally substituted with 1-3 fluoros), C1-C6 alkoxy (optionally substituted with 1-3 fluoros), (C1-C6 alkoxy)C(=O), hetCyc⁷, Ar³ or Ar³C1-C3 alkyl-.

In one embodiment, D is hetCyc¹ and E is R¹R²NC(=O)—, where R¹ is H, C1-C6 alkyl or (C1-C6 alkoxy)C1-C6 alkyl, and R² is C1-C6 alkyl (optionally substituted with 1-3 fluoros), (C1-C6 alkoxy)C1-C6 alkyl (optionally substituted with 1-3 fluoros), Cyc³, hydroxyC1-C6 alkyl (optionally substituted with 1-3 fluoros), C1-C6 alkoxy (optionally substituted with 1-3 fluoros), (C1-C6 alkoxy)C(=O), hetCyc⁷, Ar³, Ar³C1-C3 alkyl-, hydroxyC1-C6 alkoxy or (3-6C cycloalkyl)CH₂O—. In one embodiment, hetCyc¹ is pyrrolidinyl, piperidinyl (optionally substituted with C1-C3 alkyl), piperazinyl, morpholinyl or azetidinyl. In one embodiment, hetCyc¹ is pyrrolidinyl, piperidinyl (optionally substituted with C1-C3 alkyl), piperazinyl, or morpholinyl.

Non-limiting examples when D is hetCyc¹ and E is R¹R²NC(=O)— include the structures:

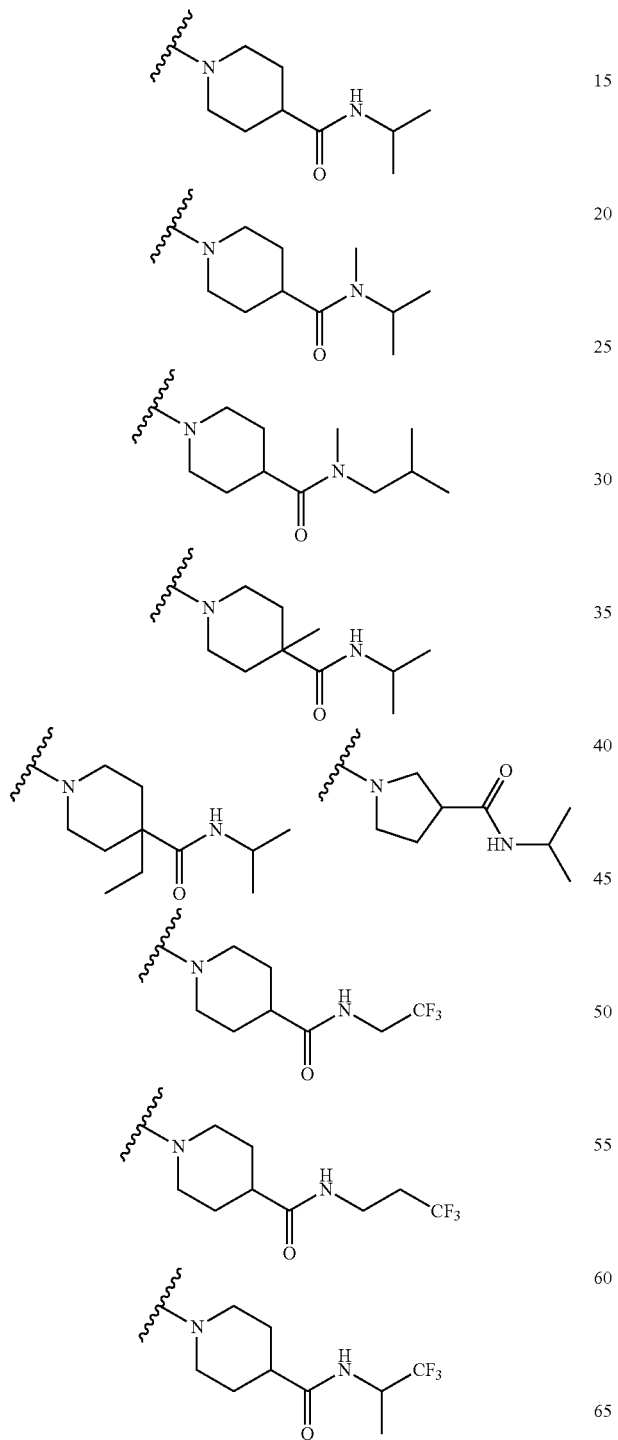

-continued

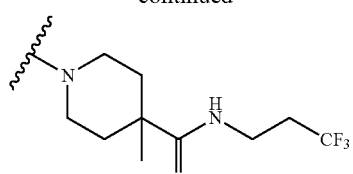

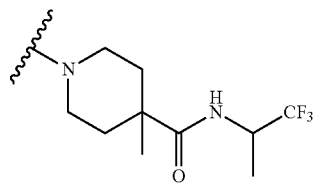

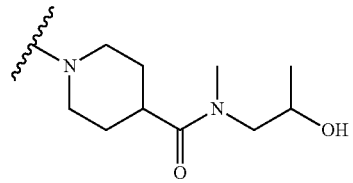

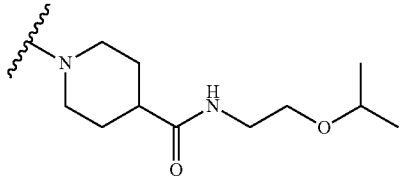

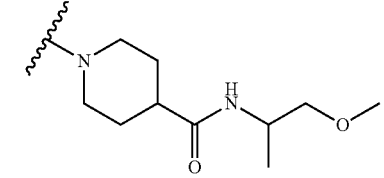

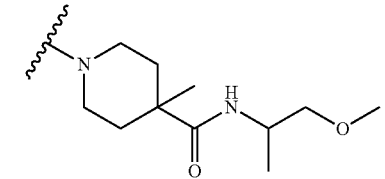

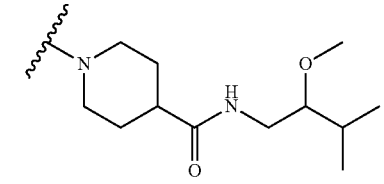

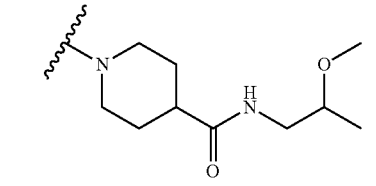

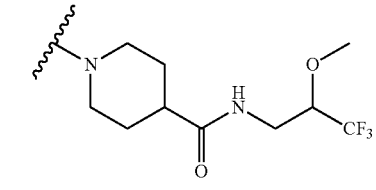

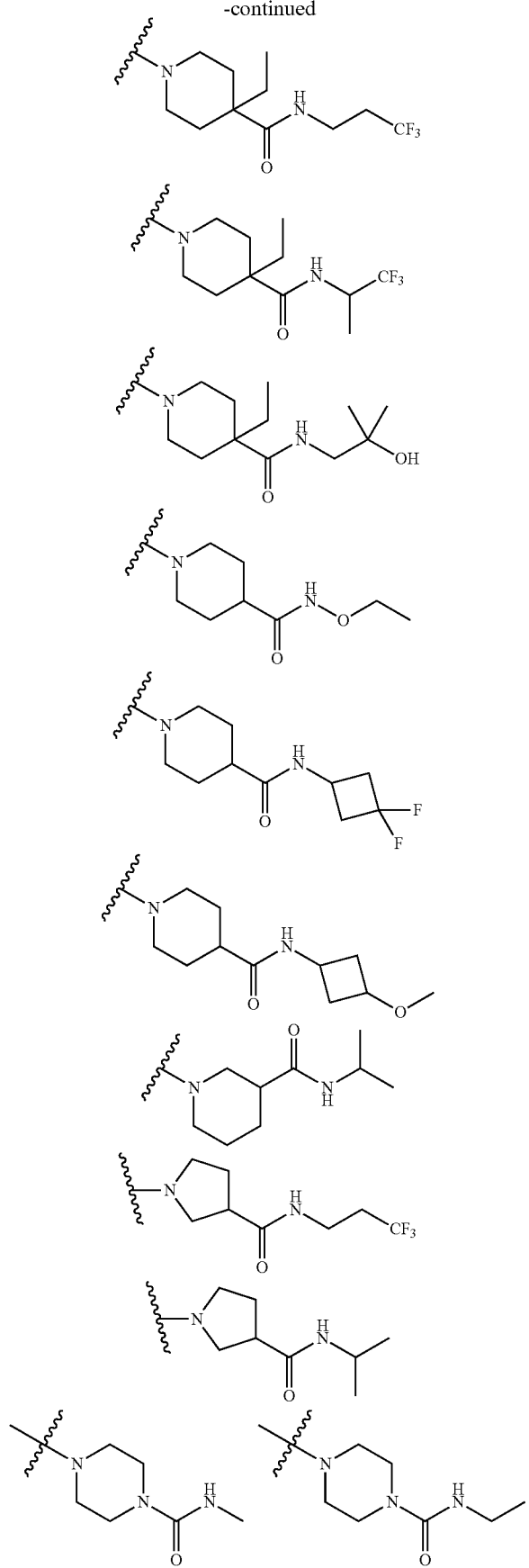
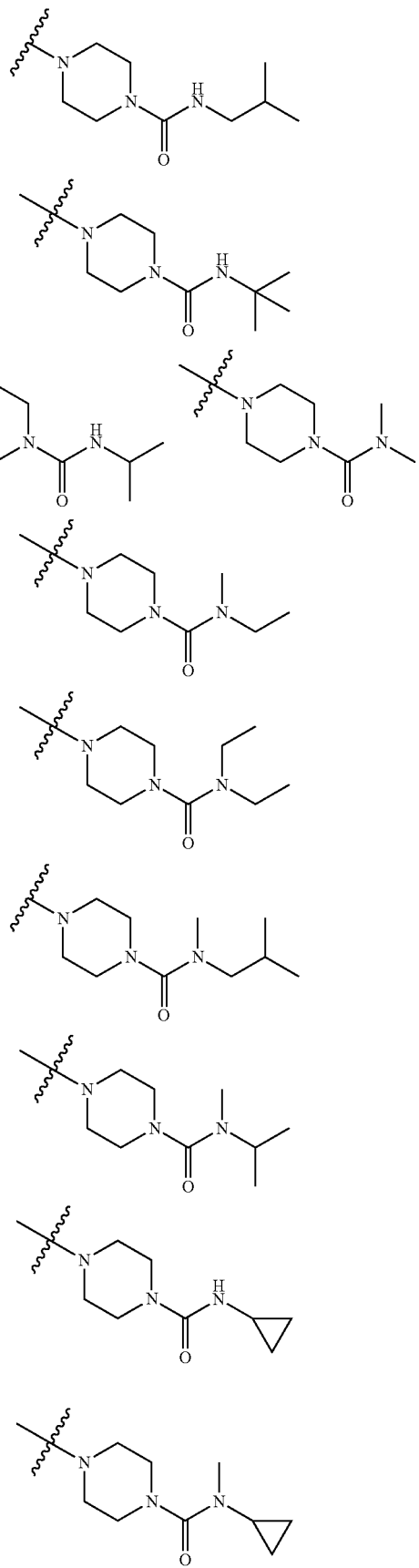

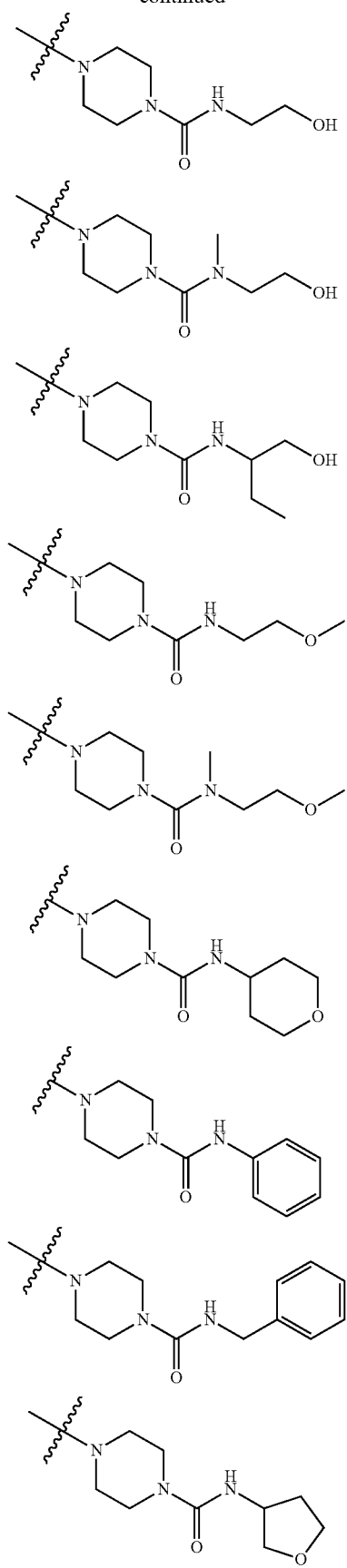
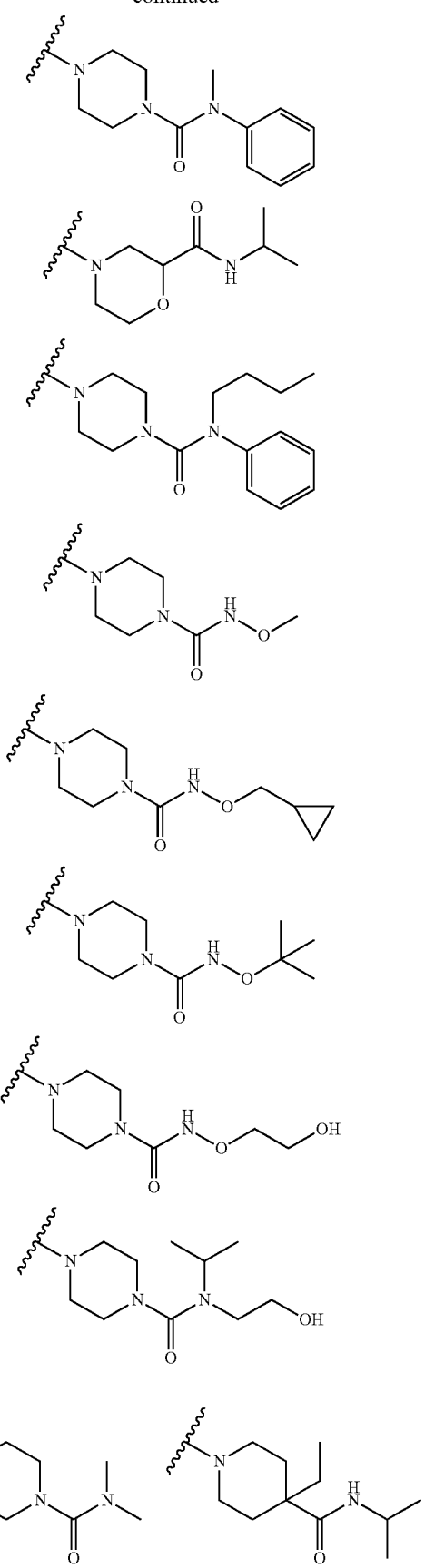

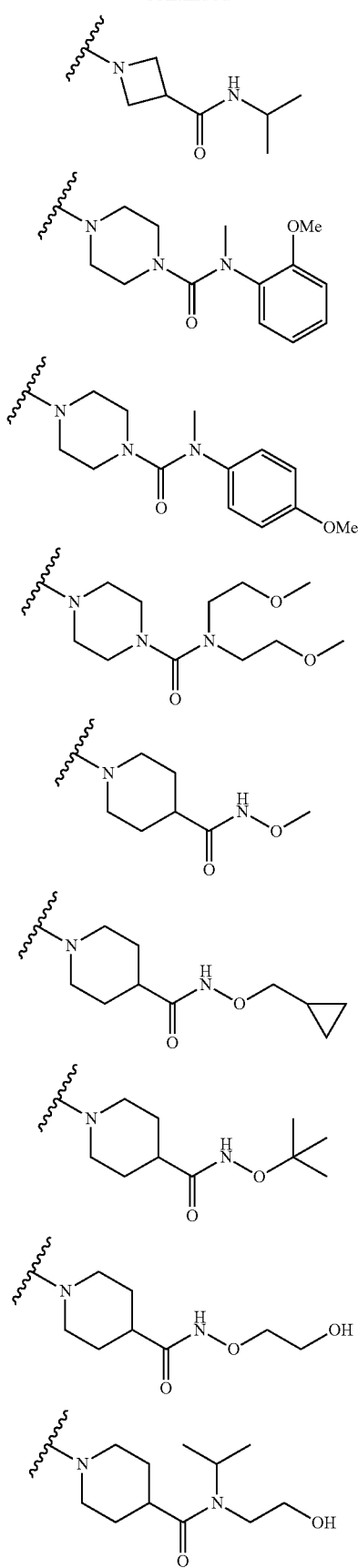
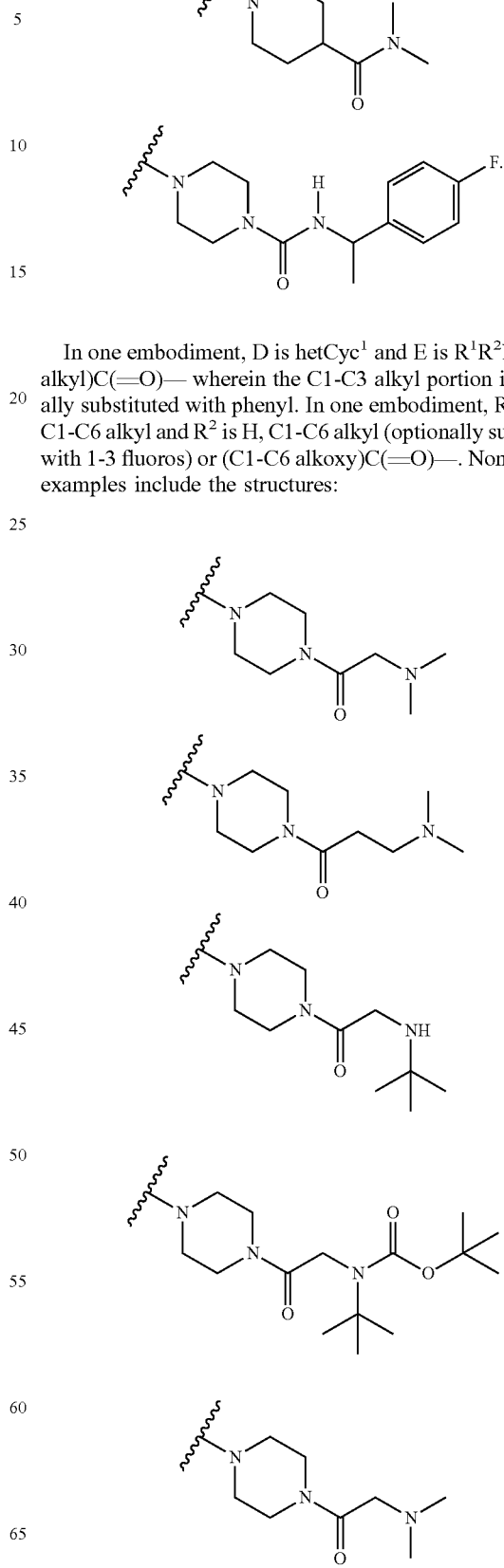
In one embodiment, D is hetCyc[1] and E is R[1]R[2]N(C1-C3 alkyl)C(=O)— wherein the C1-C3 alkyl portion is optionally substituted with phenyl. In one embodiment, R[1] is H or C1-C6 alkyl and R[2] is H, C1-C6 alkyl (optionally substituted with 1-3 fluoros) or (C1-C6 alkoxy)C(=O)—. Non-limiting examples include the structures:

-continued

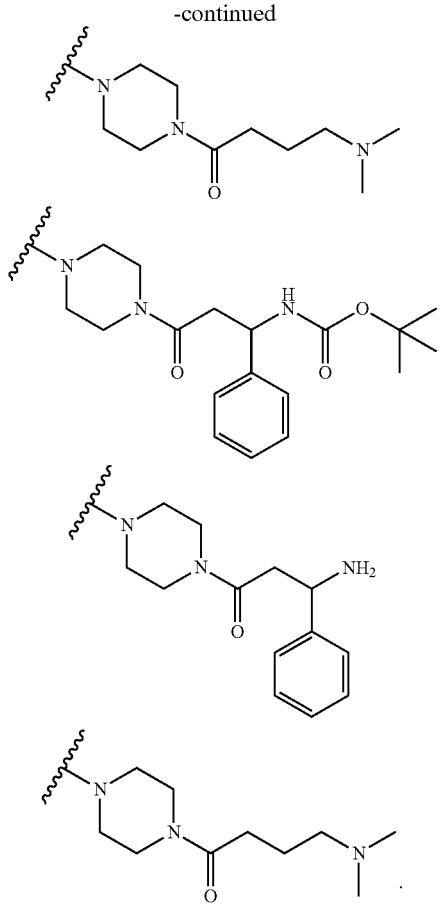

In one embodiment, D is hetCyc¹ and E is R¹R²NC(=O) C1-C2 alkyl. In one embodiment, R¹ is H or C1-C6 alkyl and R² is C1-C6 alkyl (optionally substituted with 1-3 fluoros). Non-limiting examples include the structures:

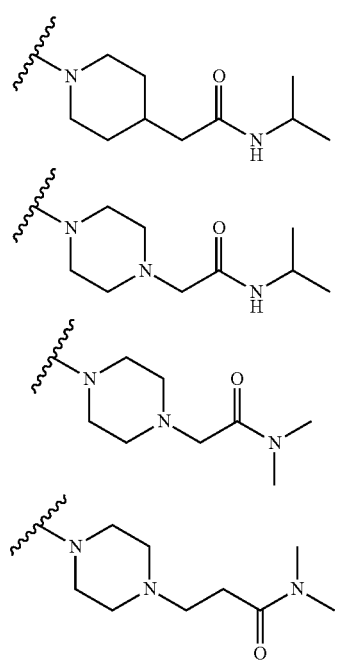

-continued

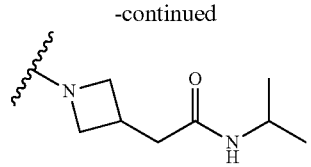

In one embodiment, D is hetCyc¹ and E is R¹R²NC(=O)NH—, where R¹ is H or C1-C6 alkyl, and R² is C1-C6 alkyl (optionally substituted with 1-3 fluoros). Non-limiting examples include the structures:

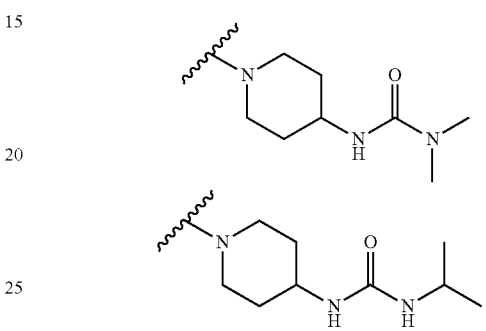

In one embodiment, D is hetCyc¹ and E is $CH_3SO_2$(C1-C6 alkyl)C(=O)—. A non-limiting example is the structure:

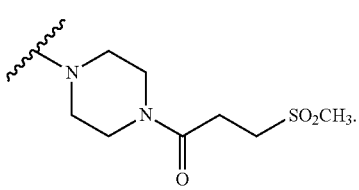 [SMILES: *N1CCN(C(=O)CCS(C)(=O)=O)CC1]

In one embodiment, D is hetCyc¹ and E is (C1-C6 alkyl)$SO_2$—. Non-limiting examples include the structures:

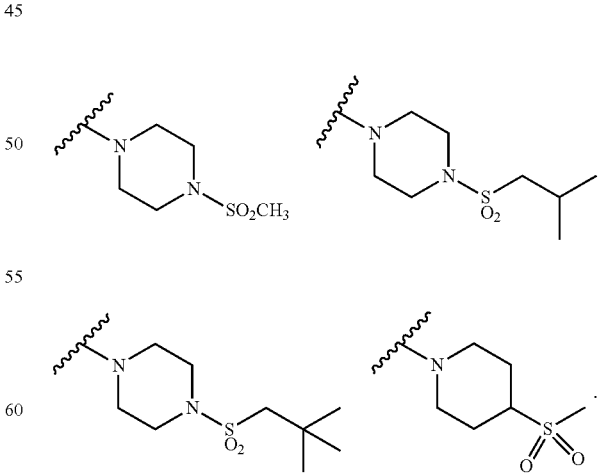

In one embodiment, D is hetCyc¹ and E is (C3-C6 cycloalkyl)$CH_2SO_2$—. A non-limiting example is the structure:

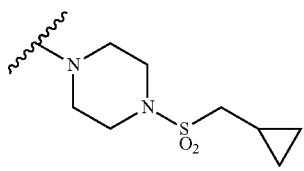

In one embodiment, D is hetCyc¹ and E is hetCyc¹-SO₂—, where hetCyc⁵ is a 5-6 membered heterocyclic ring having a ring heteroatom selected from O and N. Non-limiting examples include the structures:

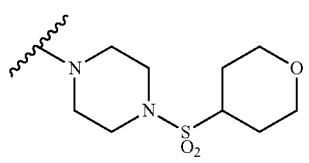

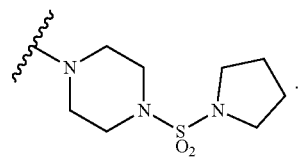

In one embodiment, D is hetCyc¹ and E is R⁴R⁵NSO₂—, where R⁴ and R⁵ are independently H or C1-C6 alkyl. Non-limiting examples include the structures:

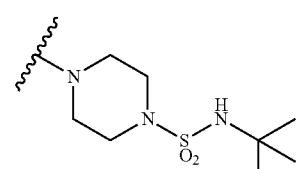

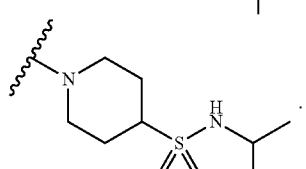

In one embodiment, D is hetCyc¹ and E is R⁶C(=O)NH—, where R⁶ is C1-C6 alkyl, hydroxyC1-C6 alkyl, C1-C6 alkoxy, (C1-C6 alkoxy)(C1-C6 alkyl), phenyl or hetCyc⁸. Non-limiting examples include the structures:

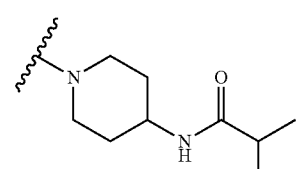

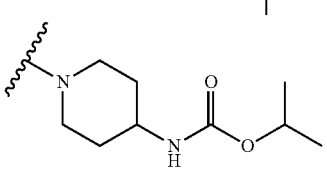

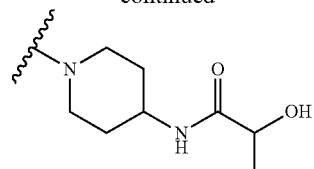

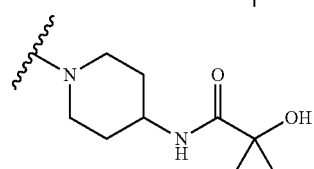

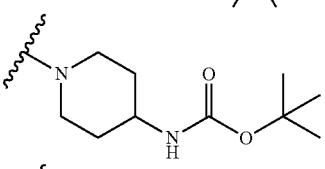

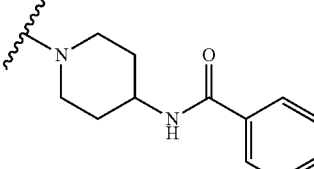

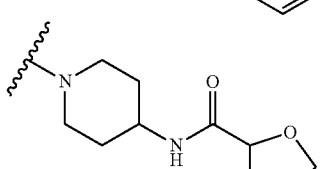

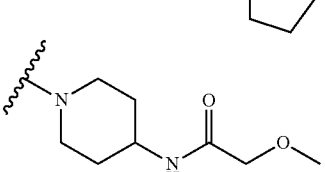

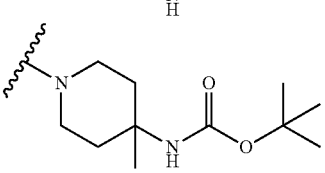

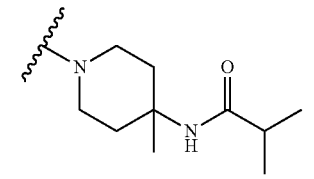

In one embodiment, D is hetCyc¹ and E is hetCyc⁶, where hetCyc⁶ is a 5 membered heterocyclic ring having one or two ring heteroatoms independently selected from N and O, wherein the ring substituted with oxo and wherein the ring is further optionally substituted with one or more substituents independently selected from the group consisting of OH and C1-6 alkyl. Non-limiting examples include the structures:

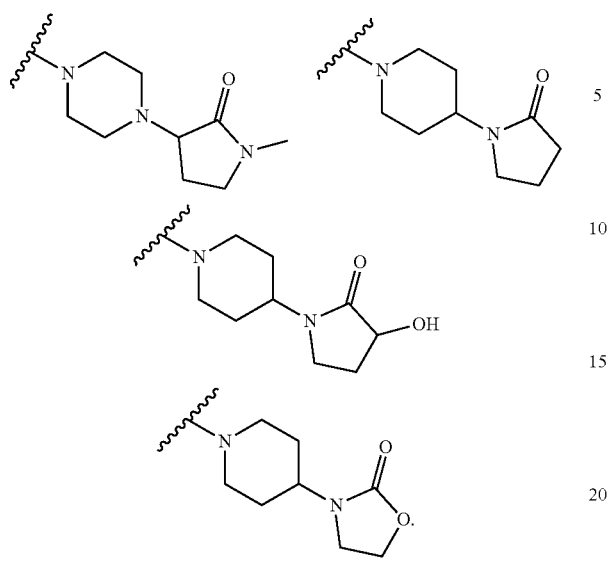

In one embodiment, D is hetCyc$^1$ and E is hetAr$^2$C1-C6 alkyl, where hetAr$^2$ is as defined for General Formula I. In one embodiment, D is hetCyc$^1$ and E is hetAr$^2$C1-C6 alkyl, where hetAr$^2$ is a 5-6 membered heteroaryl ring having 1-3 ring heteroatoms independently selected from N and O, and optionally substituted with one or more substituents independently selected from the group consisting of halogen, C1-C6 alkyl, trifluoroC1-C6 alkyl, C1-C6 alkoxy (optionally substituted with 1-3 fluoros), hydroxyC1-C6 alkyl, CN and (R$^a$R$^b$N)C1-C6 alkyl; and hetCyc$^1$ is piperazinyl (optionally substituted with oxo), piperidinyl or pyrrolidinyl. In one embodiment, hetAr$^2$ is a 5-6-membered heteroaryl ring having 1-2 ring nitrogen atoms optionally substituted with one or more substituents independently selected from the group consisting of halogen, C1-C6 alkyl, trifluoroC1-C6 alkyl, C1-C6 alkoxy (optionally substituted with 1-3 fluoros), hydroxyC1-C6 alkyl, CN and (R$^a$R$^b$N)C1-C6 alkyl. In one embodiment, hetAr$^2$ is pyridyl optionally substituted with one or more substituents independently selected from the group consisting of halogen, C1-C6 alkyl, trifluoroC1-C6 alkyl, C1-C6 alkoxy (optionally substituted with 1-3 fluoros), hydroxyC1-C6 alkyl, CN and (R$^a$R$^b$N)C1-C6 alkyl. In one embodiment, hetAr$^2$ is pyridyl optionally substituted with C1-C6 alkoxy (optionally substituted with 1-3 fluoros). In one embodiment, hetAr$^2$ is a 5-membered heteroaryl ring having 1-2 ring nitrogen atoms optionally substituted with one or more substituents independently selected from the group consisting of halogen, C1-C6 alkyl, trifluoroC1-C6 alkyl, C1-C6 alkoxy (optionally substituted with 1-3 fluoros), hydroxyC1-C6 alkyl, CN and (R$^a$R$^b$N) C1-C6 alkyl.

Non-limiting examples when D is hetCyc$^1$ and E is hetAr$^2$C1-C6 alkyl include the structures:

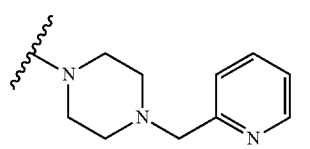

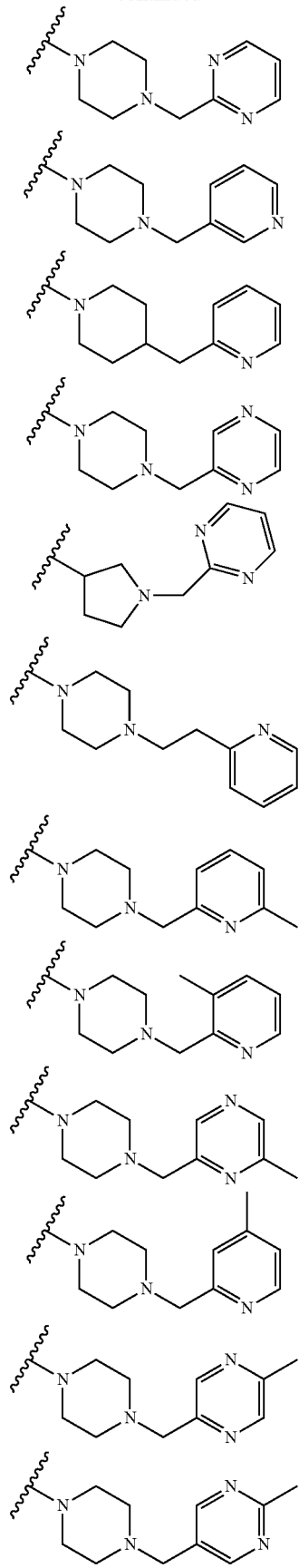

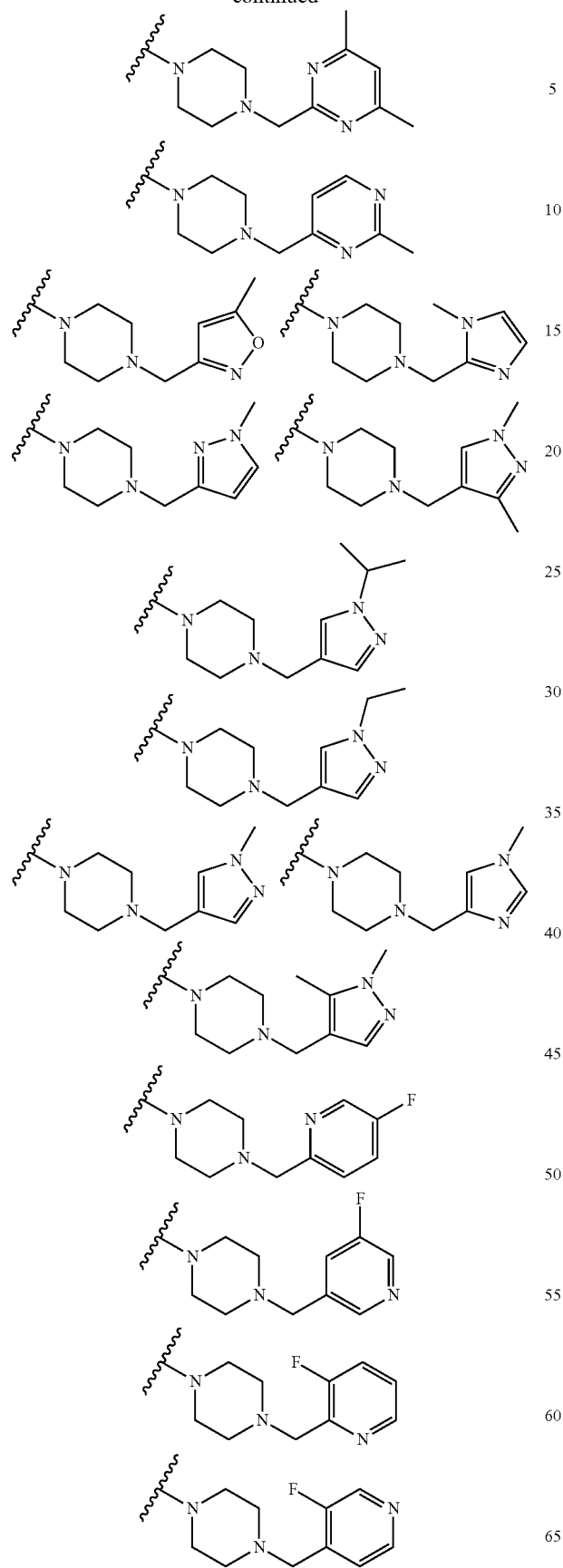
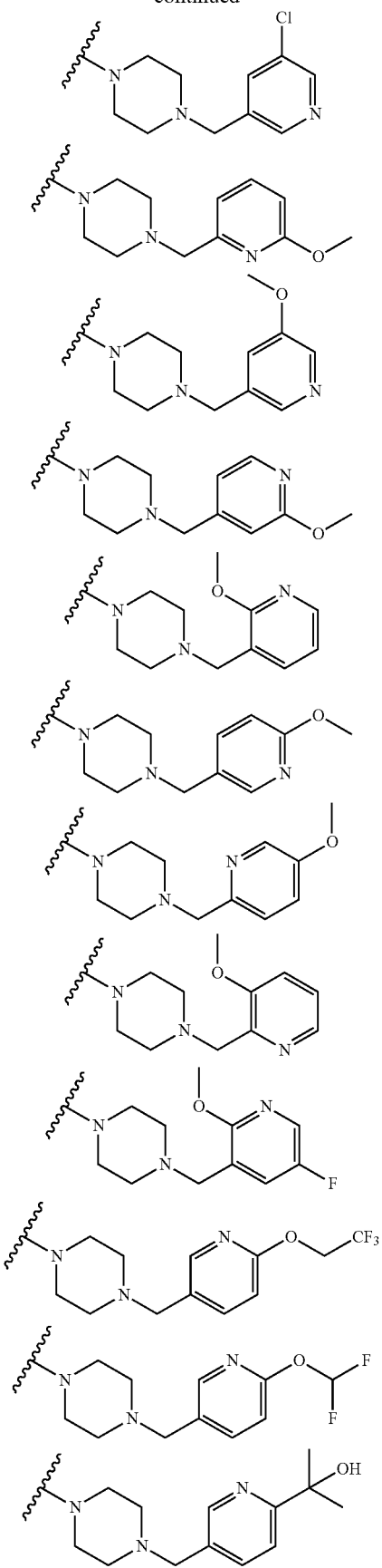

-continued

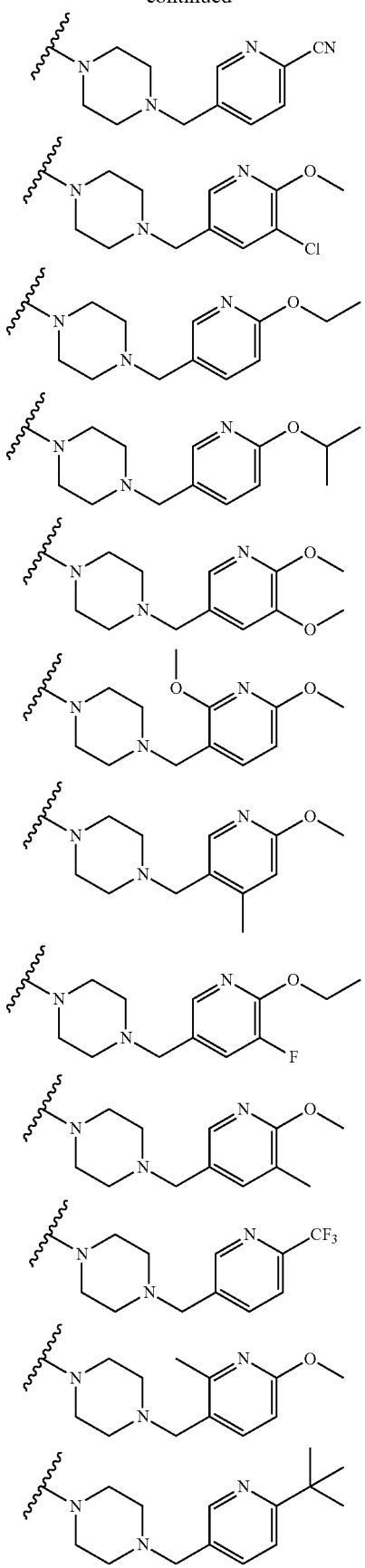

-continued

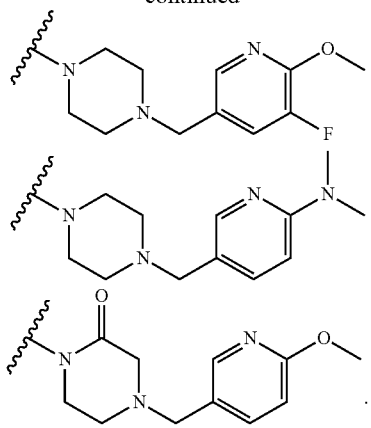

In one embodiment, D is hetCyc[1] and E is (hetCyc[4])C1-C6 alkyl, where hetCyc[4] is as defined for General Formula I. In one embodiment, E is (hetCyc[4])C1-C6 alkyl, where hetCyc[4] is a 4-6 membered heterocyclic ring having 1-2 ring heteroatoms independently selected from N and O, wherein said heterocyclic ring is optionally substituted with (C1-C6 alkyl)C(=O)—. In one embodiment, D is hetCyc[1] and E is hetCyc[4](C1-C2 alkyl), where hetCyc[4] is a 4-6 membered heterocyclic ring having 1-2 ring heteroatoms independently selected from N and O, wherein said heterocyclic ring is optionally substituted with (C1-C6 alkyl)C(=O)—.

Non-limiting embodiments when D is hetCyc[1] and E is (hetCyc[4])C1-C6 alkyl include the structures:

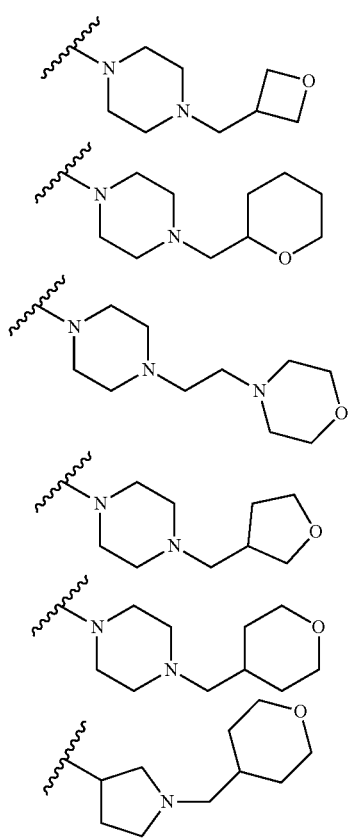

-continued

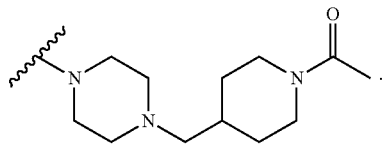

In one embodiment, D is hetCyc¹ and E is (C1-C6 alkoxy)C1-C6 alkyl wherein said alkoxy portion is optionally substituted with 1-3 fluoros. Non-limiting examples include the structures:

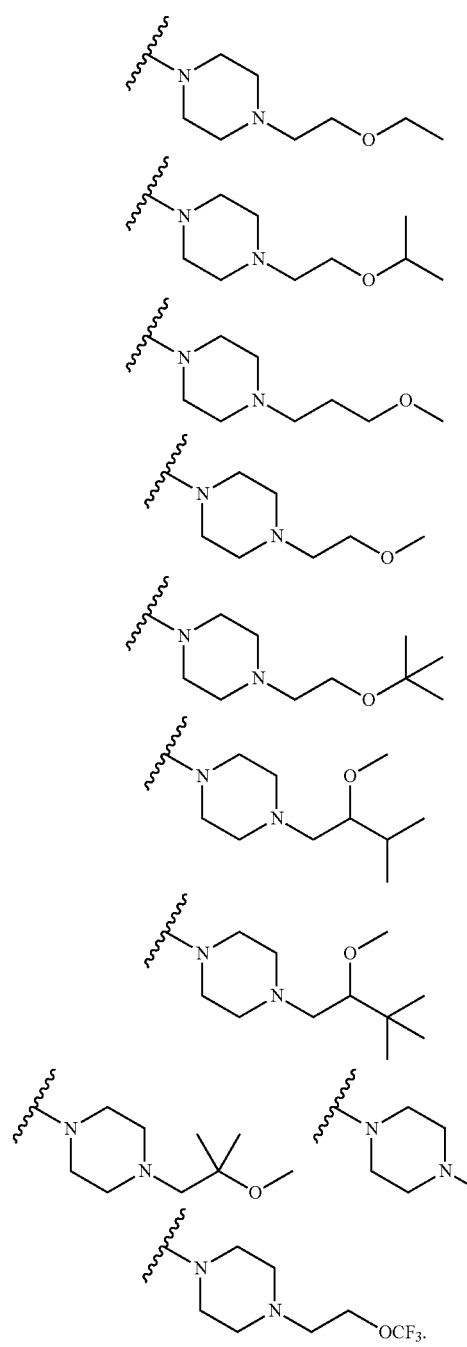

In one embodiment, D is hetCyc¹ and E is (C3-C6 cycloalkoxy)C1-C6 alkyl. A non-limiting example is the structure:

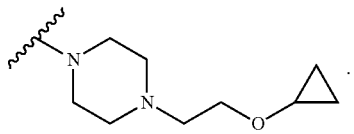 [SMILES: *N1CCN(CCOC2CC2)CC1]

In one embodiment, D is hetCyc¹ and E is (C3-C6 cycloalkyl)C1-C6 alkyl wherein said cycloalkyl is optionally substituted with 1-2 fluoros. Non-limiting examples include the structures:

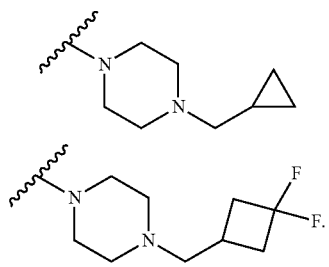

In one embodiment, D is hetCyc¹ and E is (R$^g$R$^h$N)C1-C6 alkyl wherein R$^g$ and R$^h$ are independently H or C1-C6 alkyl. Non-limiting examples include the structures:

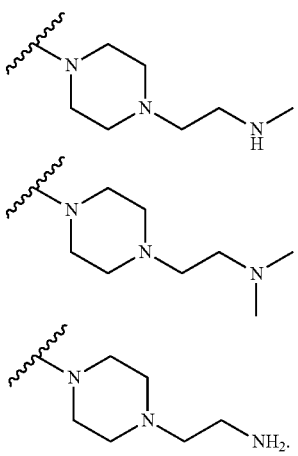

In one embodiment, D is hetCyc¹ and E is Ar²—O—, where Ar² is as defined for General Formula I. In one embodiment, Ar² is phenyl optionally substituted with one or more halogens. Non-limiting examples include the structures:

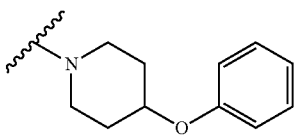

-continued

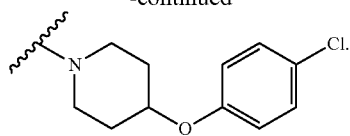

In one embodiment, D is hetCyc¹ and E is (C1-C6 alkylSO₂)C1-C6 alkyl. A non-limiting example is the structure:

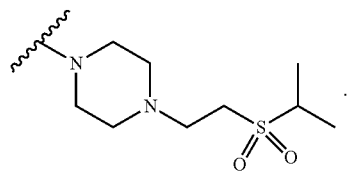 [SMILES: *N1CCN(CCS(=O)(=O)C(C)C)CC1]

In one embodiment, D is hetCyc¹ and E is (C1-C6 alkoxy)C(=O)NHC1-C6 alkyl. A non-limiting example is the structure:

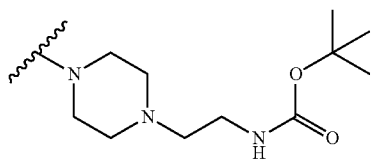

In one embodiment, D is hetCyc¹ and E is (C3-C6 cycloalkyl)SO₂— wherein said cycloalkyl is optionally substituted with C1-C6 alkyl. A non-limiting example includes the structure:

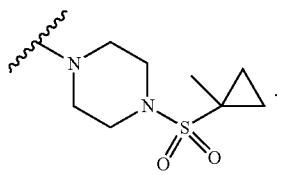 [SMILES: *N1CCN(S(=O)(=O)C2(C)CC2)CC1]

In one embodiment, D is hetCyc¹ and E is (N—(C1-C3 alkyl)pyridinonyl)C1-C3 alkyl. Non-limiting examples include the structures:

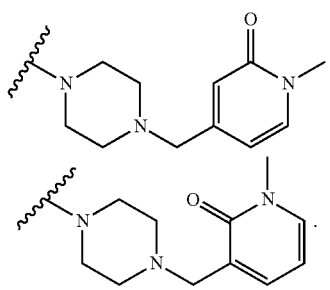

In one embodiment, D is hetCyc¹ and E is (Ar⁴SO₂)C1-C6 alkyl where Ar⁴ is as defined for Formula I. In one embodiment, Ar⁴ is unsubstituted phenyl. A non-limiting example when D is hetCyc¹ and E is (Ar⁴SO₂)C1-C6 alkyl includes the structure:

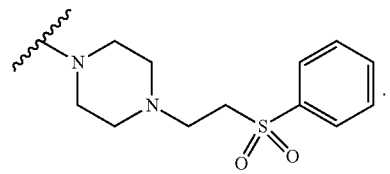 [SMILES: *N1CCN(CCS(=O)(=O)c2ccccc2)CC1]

In one embodiment, D is hetCyc¹ and E is (N—(C1-C3 alkyl)pyridinonyl)C1-C3 alkyl. Non-limiting examples include the structures:

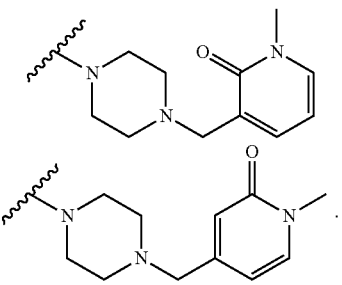

In one embodiment of the D-E group, D is hetCyc¹ (wherein hetCyc¹ is a 4-6 membered heterocyclic ring having 2 ring atoms and is optionally substituted with a C3-C6 cycloalkylidene ring, or an oxo group) and the E group is on a ring nitrogen atom of the D ring, wherein E is selected from (a) hydrogen, (d) C1-C6 alkyl optionally substituted with one to three fluoros, (e) hydroxyC1-C6 alkyl optionally substituted with one to three fluoros, (h) (C1-C6 alkoxy) hydroxy C1-C6 alkyl optionally substituted with one to three fluoros, (i) (C1-C6 alkyl)C(=O)— optionally substituted with one to three fluoros, (j) (hydroxy C1-C6 alkyl)C(=O)— optionally substituted with one to three fluoros, (k) (C1-C6 alkoxy)C(=O)—, (l) (C1-C6 alkoxy)(C1-C6 alkyl)C(=O)—, (n) Cyc¹, (o) Cyc¹C(=O)—, (p) Cyc¹(C1-C6 alkyl)C(=O)— wherein the alkyl portion is optionally substituted with one or more groups independently selected from the group consisting of OH, fluoro, C1-C3 alkoxy and R$^c$R$^d$N—, where R$^c$ and R$^d$ are independently H or C1-C6 alkyl, (q) hetCyc⁴, (r) hetCyc⁴C(=O)—, (s) hetCyc⁴(C1-C3 alkyl)C(=O)—, (t) (hetCyc⁴)C(=O)C1-C2 alkyl, (w) Ar²C(=O)—, (x) Ar²C1-C6 alkyl, (y) (Ar²)hydroxy C2-C6 alkyl, (z) Ar²(C1-C3 alkyl)C(=O)— wherein the alkyl portion is optionally substituted with one or two groups independently selected from the group consisting of OH, C1-C6 alkyl, hydroxyC1-C6 alkyl, C1-C6 alkoxy and R$^e$R$^f$N—, where R$^e$ and R$^f$ are independently H or C1-C6 alkyl, (aa) hetAr²C(=O)—, (bb) (hetAr²)hydroxyC2-C6 alkyl, (cc) hetAr²(C1-C3 alkyl)C(=O)— wherein the alkyl portion is optionally substituted with one or two groups independently selected from the group consisting of OH, C1-C6 alkyl, hydroxyC1-C6 alkyl, C1-C6 alkoxy and R$^e$R$^f$N—, where R$^e$ and R$^f$ are independently H or C1-C6 alkyl, (dd) R¹R²NC(=O)—, (ee) R¹R²N(C1-C3 alkyl)C(=O)— wherein the alkyl portion is optionally substituted with phenyl, (ff) R¹R²NC(=O)C1-C2 alkyl, (hh) CH₃SO₂(C1-C6 alkyl)C(=O)—, (ii) (C1-C6 alkyl)SO₂—, (jj) (C3-C6 cycloalkyl)CH₂SO₂—, (kk) hetCyc⁵-SO₂—, (ll)

$R^4R^5NSO_2$—, (nn) hetCyc$^6$, (oo) hetAr$^2$C1-C6 alkyl, (pp) (hetCyc$^4$)C1-C6 alkyl, (qq) (C1-C6 alkoxy)C1-C6 alkyl wherein said alkoxy portion is optionally substituted with 1-3 fluoros, (rr) (C3-C6 cycloalkoxy)C1-C6 alkyl, (ss) (C3-C6 cycloalkyl)C1-C6 alkyl wherein said cycloalkyl is optionally substituted with 1-2 fluoros, (tt) ($R^gR^hN$)C1-C6 alkyl wherein $R^g$ and $R^h$ are independently H or C1-C6 alkyl, (vv) (C1-C6 alkylSO$_2$)C1-C6 alkyl, (ww) (C1-C6 alkoxy)C(=O)NHC1-C6 alkyl, (C3-C6 cycloalkyl)SO$_2$— wherein said cycloalkyl is optionally substituted with C1-C6 alkyl, (yy) (C3-C6 cycloalkyl)SO$_2$— wherein said cycloalkyl is optionally substituted with C1-C6 alkyl, (aaa) (N—(C1-C3 alkyl)pyridinonyl)C1-C3 alkyl, or (bbb) (Ar$^4$SO$_2$)C1-C6 alkyl. In one embodiment, D is a piperazinyl ring.

In one embodiment of the D-E group, D is piperidinyl, pyrrolidinyl, azetidinyl or morphylinyl, each of which is optionally substituted with C1-C3 alkyl, fluoroC1-C3 alkyl, difluoroC1-C3 alkyl, or trifluoroC1-C3 alkyl, wherein E is selected from (a) hydrogen, (b) OH, (c) $R^aR^bN$—, (f) C1-C6 alkoxy optionally substituted with one to three fluoros, (g) hydroxy(C1-C6 alkoxy) optionally substituted with one to three fluoros, (i) (C1-C6 alkyl)C(=O)— optionally substituted with one to three fluoros, (k) (C1-C6 alkoxy)C(=O)—, (m) HC(=O)—, (r) hetCyc$^4$C(=O)—, (u) hetCyc$^4$C(=O)NH—, (v) Ar$^2$, (dd) $R^1R^2NC$(=O)—, (x) Ar$^2$C1-C6 alkyl, (ff) $R^1R^2NC$(=O)C1-C2 alkyl, (gg) $R^1R^2NC$(=O)NH—, (ii) (C1-C6 alkyl)SO$_2$—, (ll) $R^4R^5NSO_2$—, (mm) $R^6$C(=O)NH—, (nn) hetCyc$^6$, or (uu) Ar$^2$—O—. In one embodiment, D is a piperidinyl ring.

In one embodiment of Formula I, D is hetCyc$^2$, where hetCyc$^2$ is a 7-8 membered bridged heterocyclic ring having 1-3 ring heteroatoms independently selected from N and O, wherein the heterocyclic ring is optionally substituted with one or more substituents independently selected from the group consisting of C1-C3 alkyl. In one embodiment, hetCyc$^2$ is a 7-8 membered bridged heterocyclic ring having 1-2 ring nitrogen atoms, wherein the ring is optionally substituted with one or more substituents independently selected from the group consisting of C1-C3 alkyl. In one embodiment, hetCyc$^2$ is unsubstituted. Non-limiting examples of D when represented by hetCyc$^2$ include the structures:

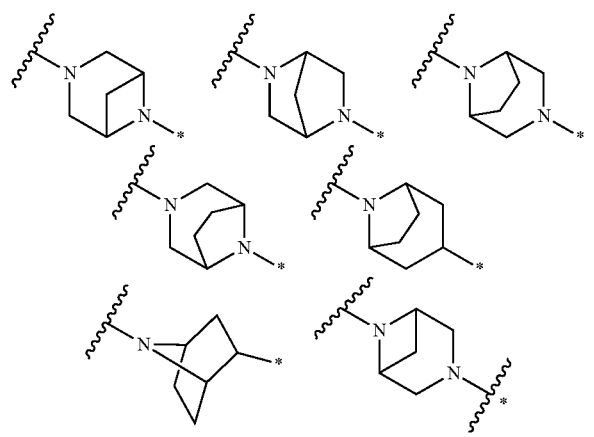

where the asterisk indicates the point of attachment to the E group.

In one embodiment of Formula I, D is hetCyc$^2$ and E is (a) hydrogen, (b) OH, (c) $R^aR^bN$— where $R^a$ is H or C1-C6 alkyl and $R^b$ is H, C1-C6 alkyl or phenyl, (d) C1-C6 alkyl optionally substituted with one to three fluoros, (e) hydroxyC1-C6 alkyl optionally substituted with one to three fluoros, (f) C1-C6 alkoxy optionally substituted with one to three fluoros, (i) (C1-C6 alkyl)C(=O)— optionally substituted with one to three fluoros, (k) (C1-C6 alkoxy)C(=O)—(O) Cyc$^1$C(=O)—, (w) Ar$^2$C(=O)—, (x) Ar$^2$C1-C6 alkyl, (y) (Ar$^2$)hydroxy C2-C6 alkyl, (aa) hetAr$^2$C(=O)—, (cc) hetAr$^2$(C1-C3 alkyl)C(=O)— wherein the alkyl portion is optionally substituted with one or two groups independently selected from the group consisting of OH, C1-C6 alkyl, hydroxyC1-C6 alkyl, C1-C6 alkoxy and $R^eR^fN$—, where $R^e$ and $R^f$ are independently H or C1-C6 alkyl, or $R^e$ and $R^f$ together with the nitrogen to which they are attached form a 5-6 membered azacyclic ring optionally having an additional ring heteroatom selected from N and O, (ee) $R^1R^2N$ (C1-C3 alkyl)C(=O)— wherein said alkyl portion is optionally substituted with phenyl, (oo) hetAr$^2$C1-C6 alkyl or (qq) (C1-C6 alkoxy)C1-C6 alkyl wherein said alkoxy portion is optionally substituted with 1-3 fluoros.

In one embodiment, D is hetCyc$^2$ and E is hydrogen. Non-limiting examples include the structures:

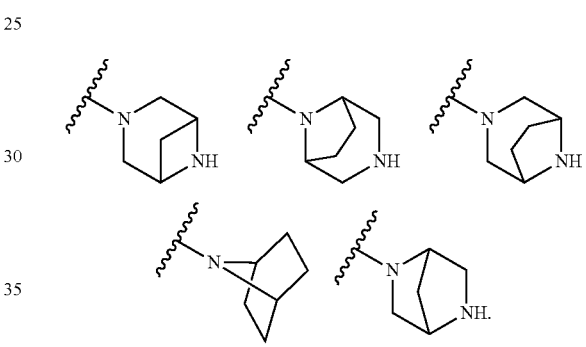

In one embodiment, D is hetCyc$^2$ and E is OH. A non-limiting example is the structure:

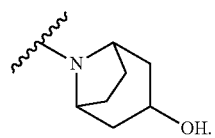 [SMILES: *N1C2CCC1CC(O)C2]

In one embodiment, D is hetCyc$^2$ and E is $R^aR^bN$— where $R^a$ is H or C1-C6 alkyl and $R^b$ is H, C1-C6 alkyl or phenyl. In one embodiment, D is hetCyc$^2$ and E is $R^aR^bN$— where $R^a$ and $R^b$ are H. A non-limiting example is the structure:

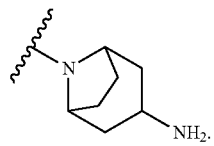 [SMILES: *N1C2CCC1CC(N)C2]

In one embodiment, D is hetCyc$^2$ and E is C1-C6 alkyl optionally substituted with one to three fluoros. A non-limiting example includes the structure:

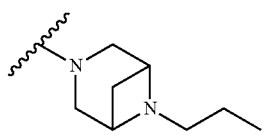

In one embodiment, D is hetCyc² and E is C1-C6 alkoxy optionally substituted with one to three fluoros. A non-limiting example is the structure:

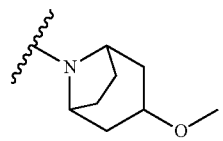

In one embodiment, D is hetCyc² and E is (C1-C6 alkyl)C(=O)— optionally substituted with one to three fluoros. Non-limiting examples include the structures:

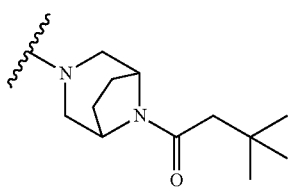

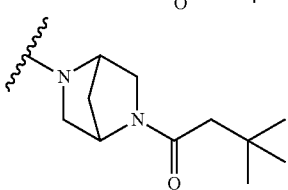

In one embodiment, D is hetCyc² and E is (C1-C6 alkoxy)C(=O)—. Non-limiting examples include the structures:

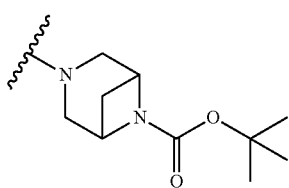

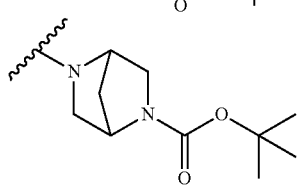

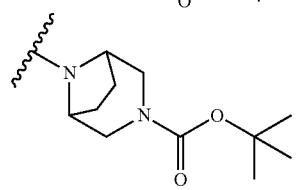

-continued

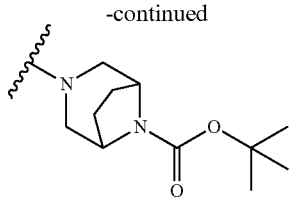

In one embodiment, D is hetCyc² and E is Ar²C(=O)—, where Ar² is as defined for General Formula I. In one embodiment, Ar² is phenyl optionally substituted with one or more substituents independently selected from halogen and C1-C6 alkoxy (optionally substituted with 1-3 fluoros). Non-limiting examples when D is hetCyc² and E is Ar²C(=O) include the structures:

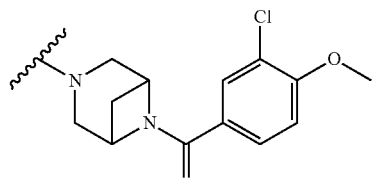

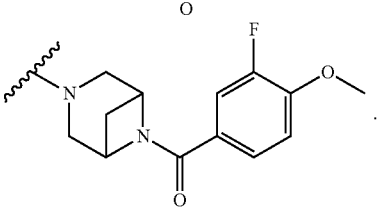

In one embodiment, D is hetCyc² and E is Ar²C1-C6 alkyl where Ar² is as defined for General Formula I. In one embodiment, Ar² is an unsubstituted phenyl. Non-limiting examples when D is hetCyc² and E is Ar²C1-C6 alkyl include the structures:

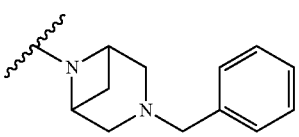

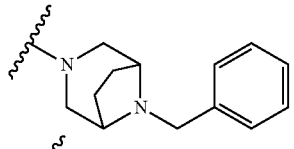

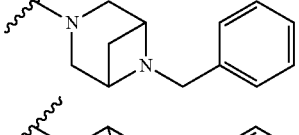

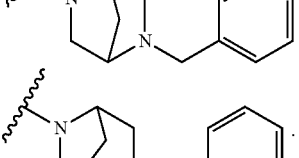

In one embodiment, D is hetCyc² and E is hetAr²C(=O)— where hetAr² is as defined for Formula I. In one embodiment hetAr² is a 6-membered heteroaryl ring having 1-2 ring nitrogen atoms and optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, hydroxyC1-C6 alkyl, (C3-C6)cycloalkyl, (C1-C6 alkoxy)C1-C6 alkyl, CN and R'R"N— where R' and R" are independently H or C1-C3 alkyl. In one embodiment hetAr² is pyridyl optionally substituted with one or more substituents independently selected from halogen and C1-C6 alkoxy (optionally substituted with 1-3 fluoros). Non-limiting examples when D is hetCyc² and E is hetAr²C(=O)— include the structures:

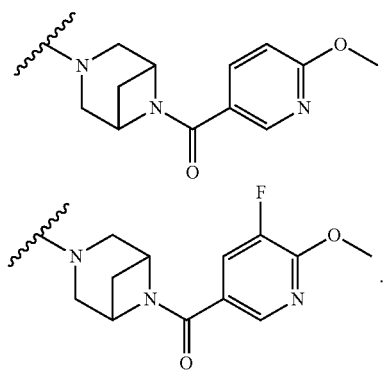

In one embodiment, D is hetCyc² and E is hetAr²(C1-C3 alkyl)C(=O)— wherein the alkyl portion is optionally substituted with one or two groups independently selected from the group consisting of OH, C1-C6 alkyl, hydroxyC1-C6 alkyl, C1-C6 alkoxy and R^eR^fN—, where R^e and R^f are independently H or C1-C6 alkyl, or R^e and R^f together with the nitrogen to which they are attached form a 5-6 membered azacyclic ring optionally having an additional ring heteroatom selected from N and O, and hetAr² is as defined for Formula I. In one embodiment, E is hetAr²(C1-C3 alkyl)C(=O)— wherein the alkyl portion is unsubstituted. In one embodiment, hetAr² is is a 6-membered heteroaryl ring having 1-2 ring nitrogen atoms and optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, hydroxyC1-C6 alkyl, (C3-C6)cycloalkyl, (C1-C6 alkoxy)C1-C6 alkyl, CN and R'R"N— where R' and R" are independently H or C1-C3 alkyl. In one embodiment hetAr² is pyridyl optionally substituted with one or more substituents independently selected from halogen. A non-limiting example D is hetCyc² and E is hetAr²(C1-C3 alkyl)C(=O)— includes the structure:

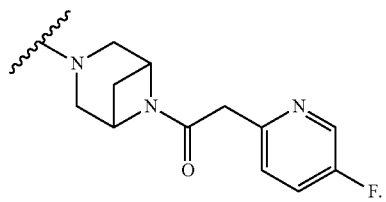 [SMILES: *N1CC2CC(C1)N2C(=O)Cc1ccc(F)cn1]

In one embodiment, D is hetCyc² and E is R¹R²N(C1-C3 alkyl)C(=O)—. A non-limiting example is the structure:

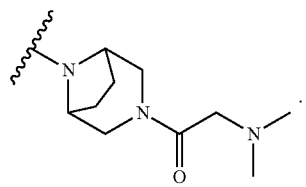 [SMILES: *N1C2CCC1CN(C(=O)CN(C)C)C2]

In one embodiment, D is hetCyc² and E is hetAr²C1-C6 alkyl, where hetAr² is as defined for Formula I. In one embodiment, E is hetAr²C1-C6 alkyl wherein the alkyl portion is unsubstituted. In one embodiment, hetAr² is a 6-membered heteroaryl ring having 1-2 ring nitrogen atoms and optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, hydroxyC1-C6 alkyl, (C3-C6)cycloalkyl, (C1-C6 alkoxy)C1-C6 alkyl, CN and R'R"N— where R' and R" are independently H or C1-C3 alkyl. In one embodiment hetAr² is pyridyl optionally substituted with C1-C6 alkoxy (optionally substituted with 1-3 fluoros). Non-limiting examples when D is hetCyc² and E is hetAr²C1-C6 alkyl include the structures:

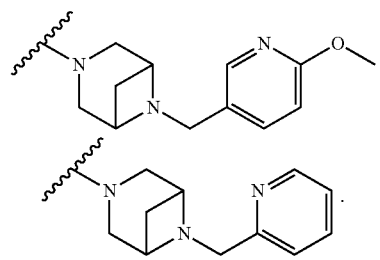

In one embodiment, D is hetCyc² and E is (C1-C6 alkoxy)C1-C6 alkyl wherein said alkoxy portion is optionally substituted with 1-3 fluoros. A non-limiting example includes the structure:

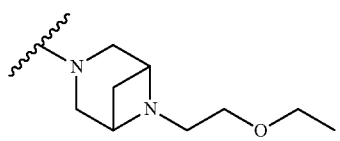

In one embodiment, D is hetCyc² (where hetCyc² is a 7-8 membered bridged heterocyclic ring having two ring nitrogen atoms, wherein the heterocyclic ring is optionally substituted with one or more substituents independently selected from the group consisting of C1-C3 alkyl), and E is on a ring nitrogen atom of hetCyc² wherein E is (a) hydrogen, (d) C1-C6 alkyl optionally substituted with one to three fluoros, (i) (C1-C6 alkyl)C(=O)— optionally substituted with one to three fluoros, (w) Ar²C(=O)—, (x) Ar²C1-C6 alkyl, (aa) hetAr²C(=O)—, (oo) hetAr²C1-C6 alkyl, or (qq) (C1-C6 alkoxy)C1-C6 alkyl wherein said alkoxy portion is optionally substituted with 1-3 fluoros.

In one embodiment, D is hetCyc² (where hetCyc² is a 7-8 membered bridged heterocyclic ring having one ring nitrogen atom, wherein the heterocyclic ring is optionally substituted with one or more substituents independently selected from the group consisting of C1-C3 alkyl), and E is on a ring carbon atom of hetCyc² wherein E is (b) OH, (c) R$^a$R$^b$N— where R$^a$ is H or C1-C6 alkyl and R$^b$ is H, C1-C6 alkyl or phenyl, or (f) C1-C6 alkoxy optionally substituted with one to three fluoros.

In one embodiment of Formula I, D is hetCyc³, where hetCyc³ is a 7-11 membered heterospirocyclic ring having 1-2 ring heteroatoms independently selected from N and O and wherein the ring is optionally substituted with C1-C3 alkyl. In one embodiment, hetCyc³ is unsubstituted. Non-limiting examples when D is represented by hetCyc³ include the structures:

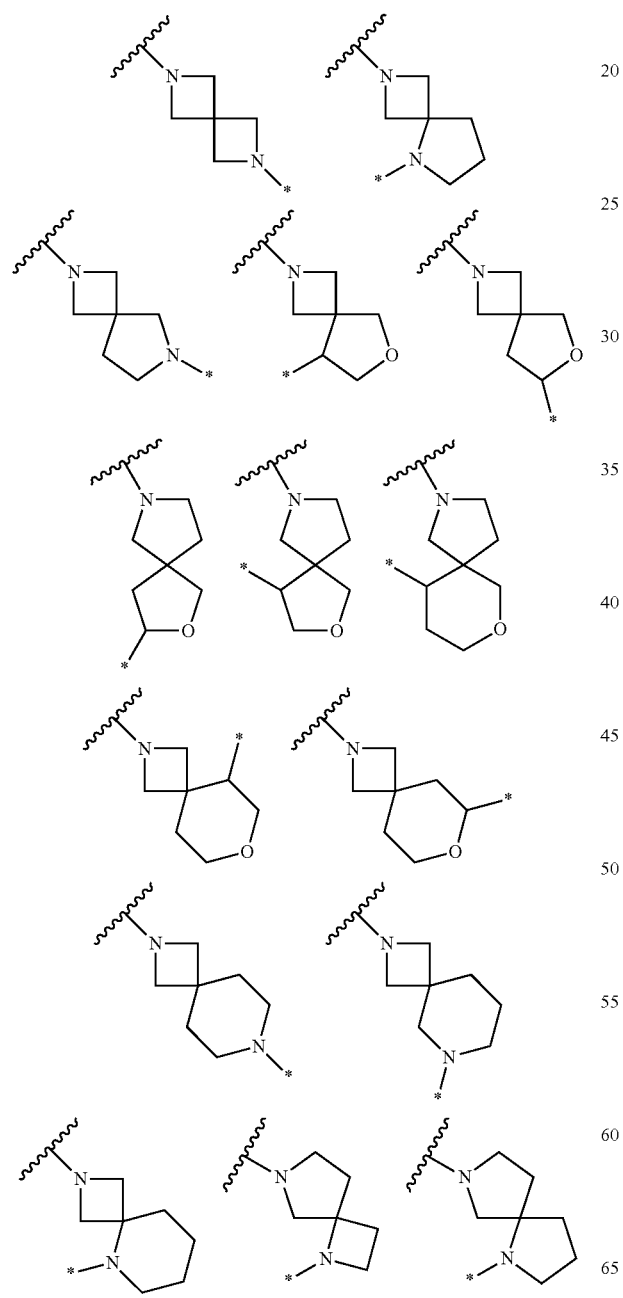
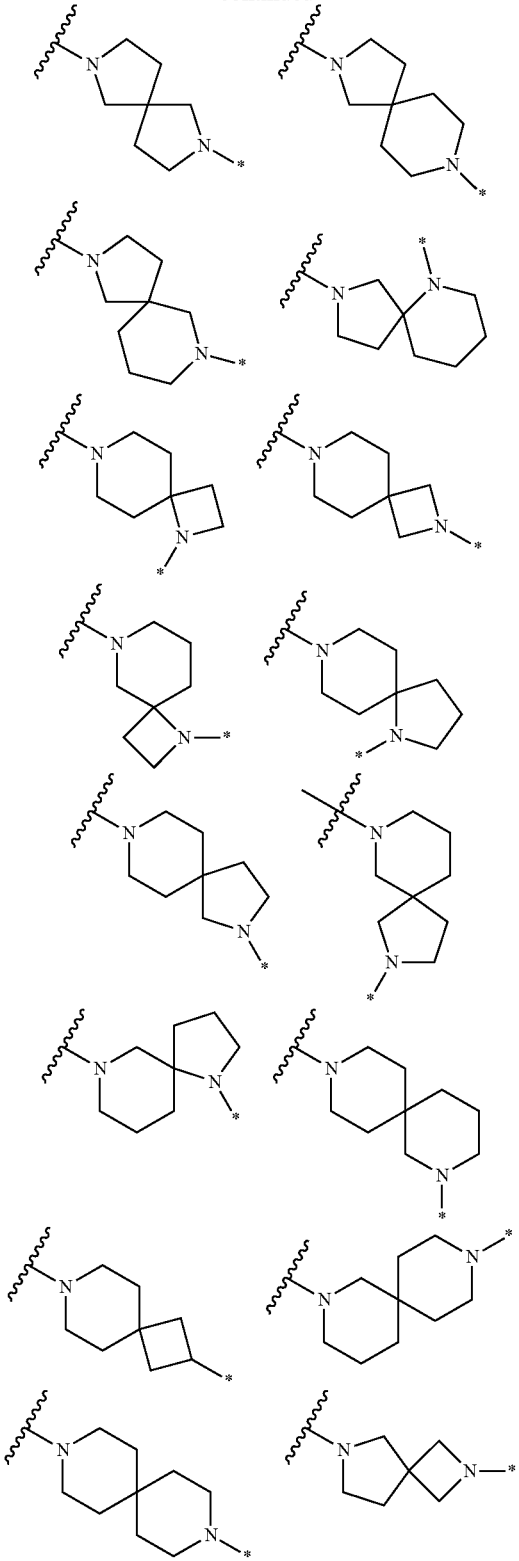

where the asterisk indicates the point of attachment to the E group.

In one embodiment, D is hetCyc³ and E is selected from (a) hydrogen, (c) R$^a$R$^b$N— where R$^a$ is H or C1-C6 alkyl and R$^b$ is H, C1-C6 alkyl or phenyl, (d) C1-C6 alkyl optionally substituted with one to three fluoros, (e)

hydroxyC1-C6 alkyl optionally substituted with one to three fluoros, (i) (C1-C6 alkyl)C(=O)— optionally substituted with one to three fluoros, (j) (hydroxy C1-C6 alkyl)C(=O)— optionally substituted with one to three fluoros, (k) (C1-C6 alkoxy)C(=O)—, (o) Cyc¹C(=O)—, (p) Cyc¹(C1-C6 alkyl)C(=O), (r) hetCyc⁴C(=O)—, (w) Ar²C(=O)—, (x) Ar²C1-C6 alkyl, (y) (Ar²)hydroxy C2-C6 alkyl, (z) Ar²(C1-C3 alkyl)C(=O)— wherein said alkyl portion is optionally substituted with one or two groups independently selected from the group consisting of OH, C1-C6 alkyl (optionally substituted with 1-3 fluoros), hydroxyC1-C6 alkyl, C1-C6 alkoxy and R$^e$R$^f$N—, where R$^e$ and R$^f$ are independently H or C1-C6 alkyl, or R$^e$ and R$^f$ together with the nitrogen to which they are attached form a 5-6 membered azacyclic ring optionally having an additional ring heteroatom selected from N and O, (dd) R¹R²NC(=O), (ee) R¹R²N(C1-C3 alkyl)C(=O)—, (mm) R⁶C(=O)NH—, (xx) (C3-C6 cycloalkoxy)C(=O)— and (zz) Ar⁴CH₂OC(=O)—.

In one embodiment, D is hetCyc³ (wherein a 7-11 membered heterospirocyclic ring having two ring nitrogen atoms), wherein the ring is optionally substituted with C1-C3 alkyl, and E is on a ring nitrogen atom of ring D, and E is selected from (a) hydrogen, (d) C1-C6 alkyl optionally substituted with one to three fluoros, (e) hydroxyC1-C6 alkyl optionally substituted with one to three fluoros, (i) (C1-C6 alkyl)C(=O)— optionally substituted with one to three fluoros, (j) (hydroxy C1-C6 alkyl)C(=O)— optionally substituted with one to three fluoros, (k) (C1-C6 alkoxy)C(=O)—, (o) Cyc¹C(=O)—, (p) Cyc¹(C1-C6 alkyl)C(=O), (r) hetCyc⁴C(=O)—, (w) Ar²C(=O)—, (x) Ar²C1-C6 alkyl, (y) (Ar²)hydroxy C2-C6 alkyl, (z) Ar²(C1-C3 alkyl)C(=O)— wherein said alkyl portion is optionally substituted with one or two groups independently selected from the group consisting of OH, C1-C6 alkyl (optionally substituted with 1-3 fluoros), hydroxyC1-C6 alkyl, C1-C6 alkoxy and R$^e$R$^f$N—, where R$^e$ and R$^f$ are independently H or C1-C6 alkyl, or R$^e$ and R$^f$ together with the nitrogen to which they are attached form a 5-6 membered azacyclic ring optionally having an additional ring heteroatom selected from N and O, (dd) R¹R²NC(=O), (ee) R¹R²N(C1-C3 alkyl)C(=O)—, (xx) (C3-C6 cycloalkoxy)C(=O)— and (zz) Ar⁴CH₂OC(=O)—.

In one embodiment, D is hetCyc³ (wherein hetCyc³ is a 7-11 membered heterospirocyclic ring having one ring nitrogen atom, wherein the ring is optionally substituted with C1-C3 alkyl), and E is on a ring carbon atom of ring D, and E is selected from (a) hydrogen, (c) R$^a$R$^b$N— where R$^a$ is H or C1-C6 alkyl and R$^b$ is H, C1-C6 alkyl or phenyl, and (mm) R⁶C(=O)NH—.

In one embodiment, D is hetCyc³ and E is hydrogen. Non-limiting examples include the structures:

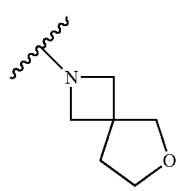 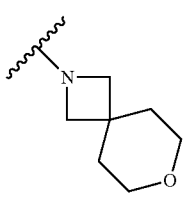

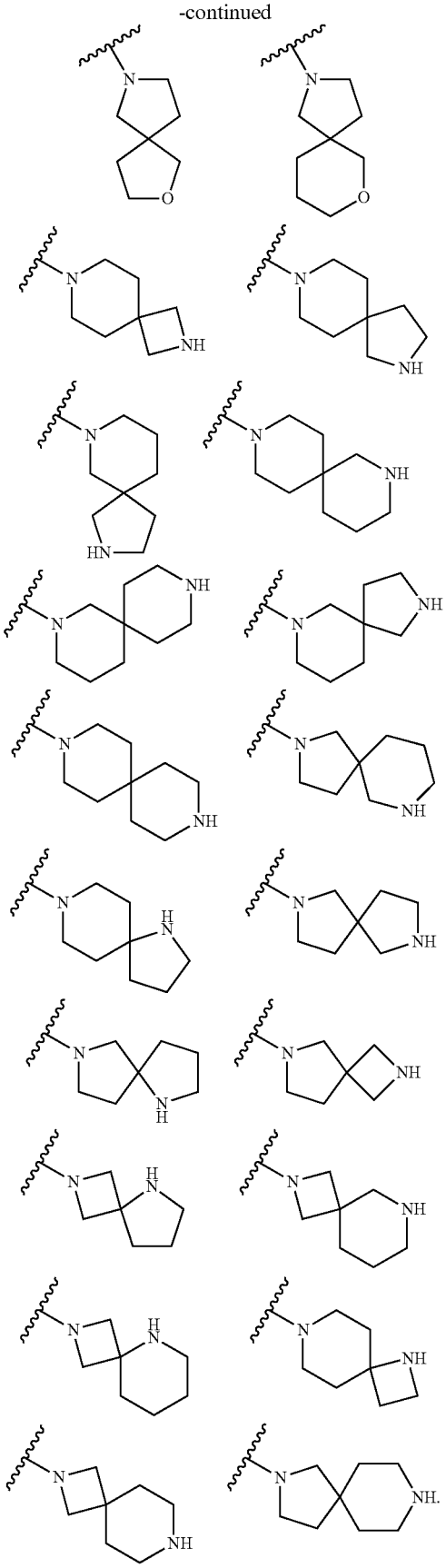

In one embodiment, D is hetCyc³ and E is RᵃRᵇN— where Rᵃ is H or C1-C6 alkyl and Rᵇ is H, C1-C6 alkyl or phenyl. In one embodiment, Rᵃ and Rᵇ are H. A non-limiting example is the structure:

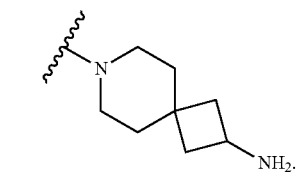 [SMILES: *N1CCC2(CC1)CC(N)C2]

In one embodiment, D is hetCyc³ and E is C1-C6 alkyl optionally substituted with one to three fluoros. Non-limiting examples include the structures:

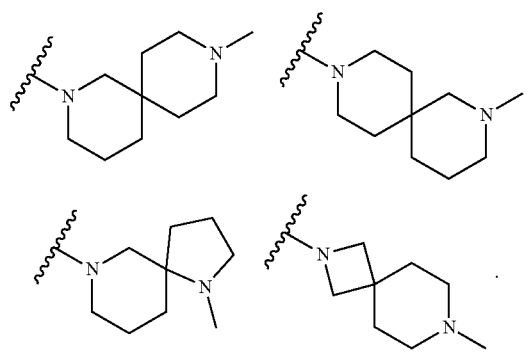

In one embodiment, D is hetCyc³ and E is hydroxyC1-C6 alkyl optionally substituted with one to three fluoros. Non-limiting examples include the structures:

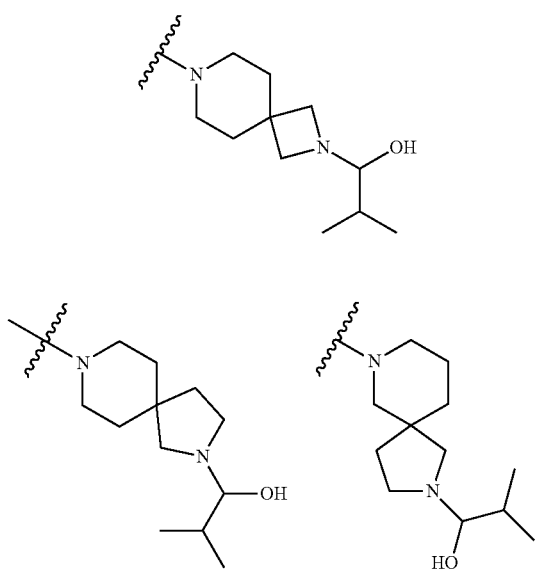

In one embodiment, D is hetCyc³ and E is (C1-C6 alkyl)C(=O)— optionally substituted with one to three fluoros. Non-limiting examples include the structures:

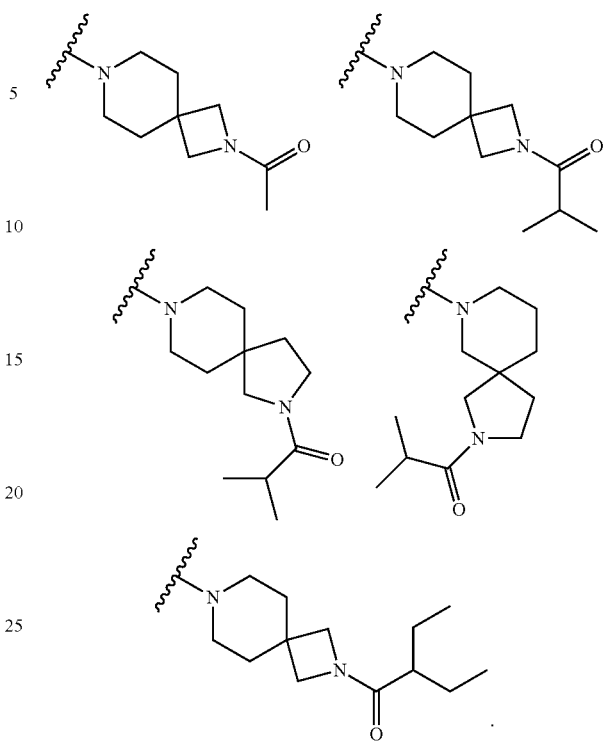

In one embodiment, D is hetCyc³ and E is (hydroxy C1-C6 alkyl)C(=O)— optionally substituted with one to three fluoros. Non-limiting examples include the structures:

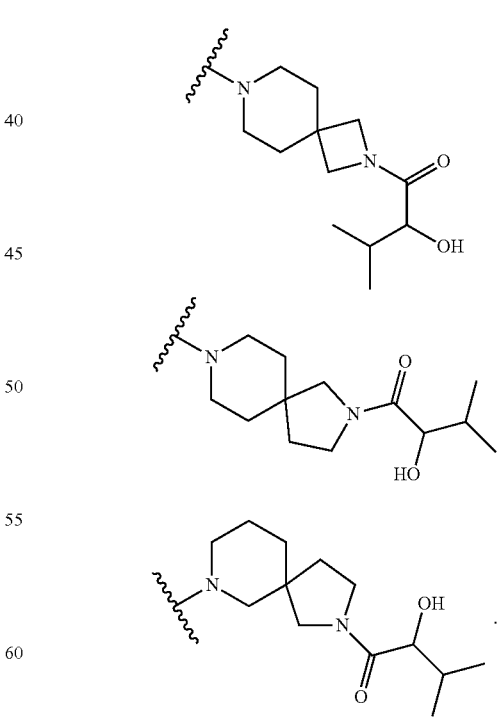

In one embodiment, D is hetCyc³ and E is (C1-C6 alkoxy)C(=O)—. Non-limiting examples include the structures:

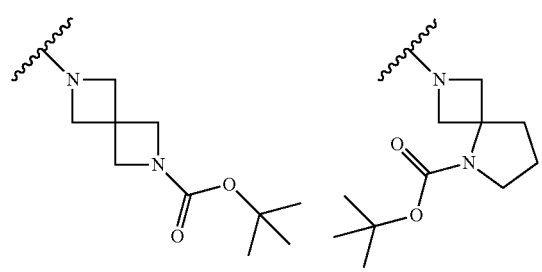
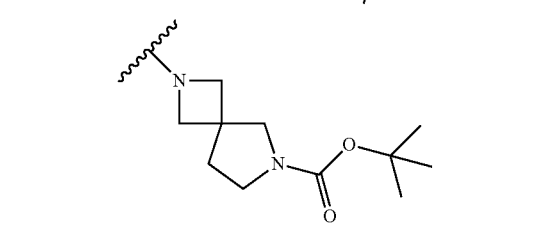
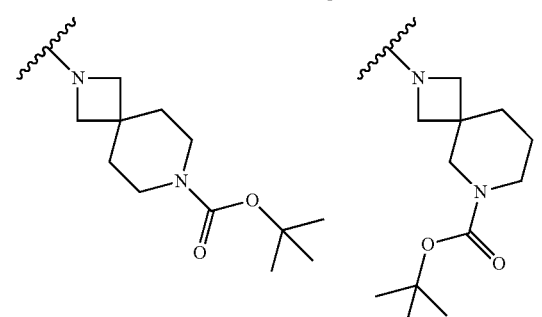
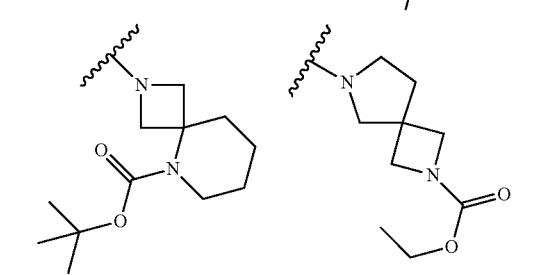
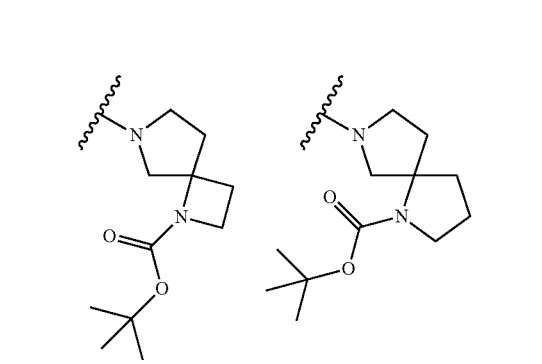
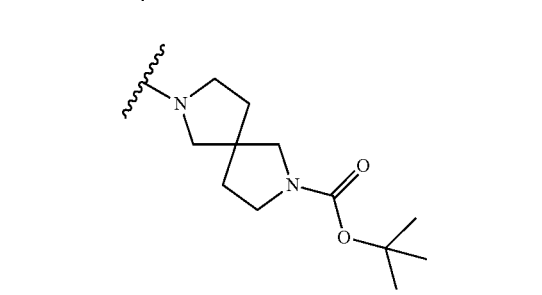
-continued
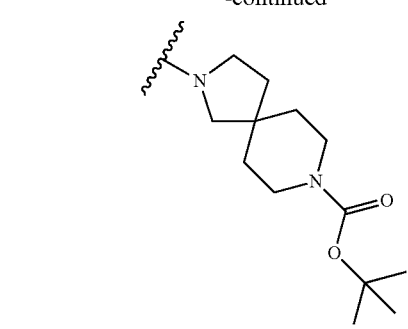
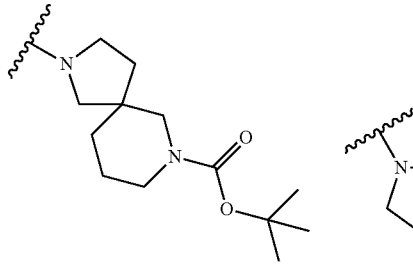
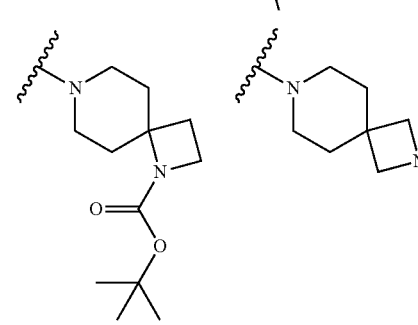
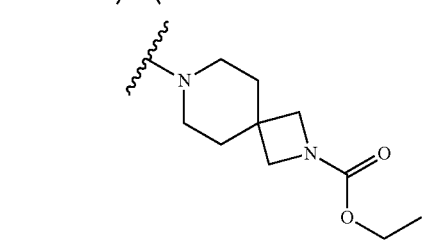
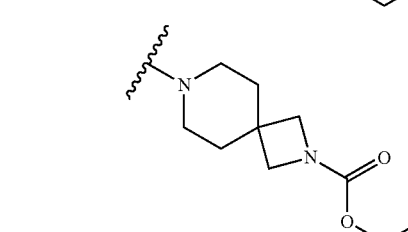
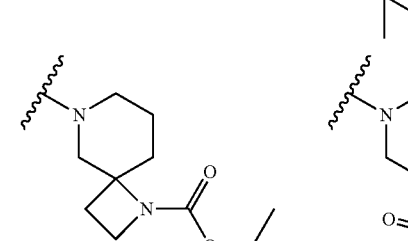

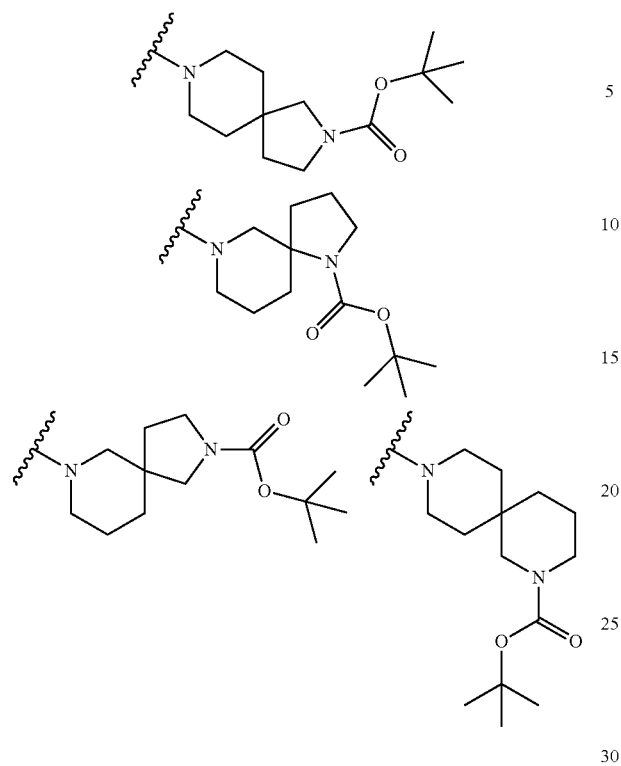

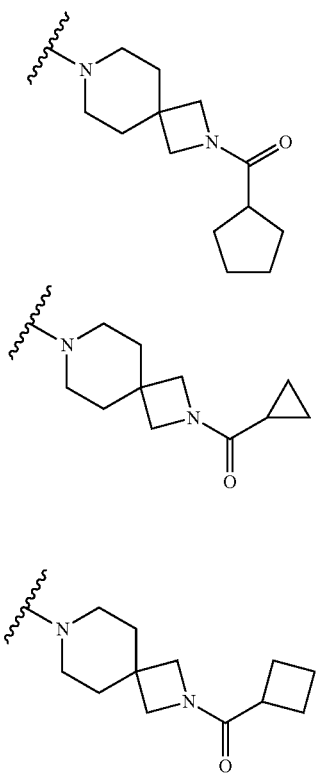

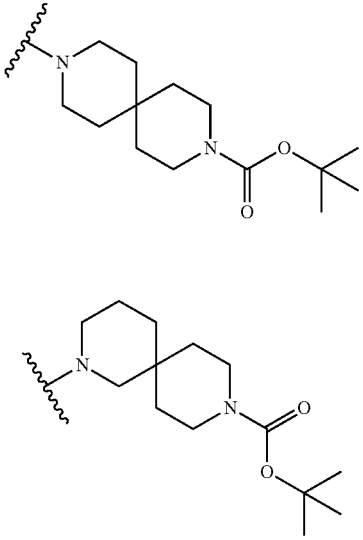

In one embodiment, D is hetCyc³ and E is Cyc¹C(=O)—, where Cyc¹ is as defined for General Formula I. In one embodiment, Cyc¹ is unsubstituted. Non-limiting examples include the structures:

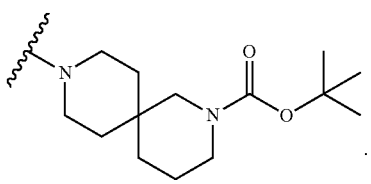

In one embodiment, D is hetCyc³ and E is Cyc¹(C1-C6 alkyl)C(=O)— wherein said alkyl portion is optionally substituted with one or more groups independently selected from the group consisting of OH, fluoro, C1-C3 alkoxy and R^c R^d N—, where R^c and R^d are independently H or C1-C6 alkyl, and Cyc¹ is as defined for General Formula I.

In one embodiment, D is hetCyc³ and E is Cyc¹(C1-C6 alkyl)C(=O)— wherein said alkyl portion is unsubstituted, and Cyc¹ is as defined for General Formula I. In one embodiment, Cyc¹ is an unsubstituted C3-C6 cycloalkyl.

Non-limiting examples when D is hetCyc³ and E is Cyc¹(C1-C6 alkyl)C(=O)— include the structures:

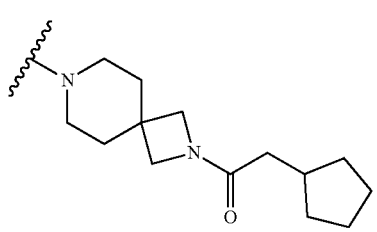

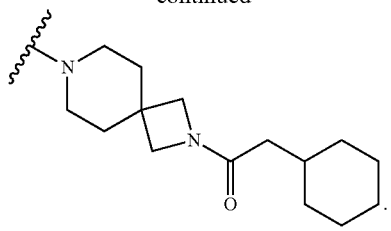

In one embodiment, D is hetCyc³ and E is hetCyc⁴C(=O)—, where hetCyc⁴ is as defined for General Formula I. In one embodiment, hetCyc⁴ is a 4-6 membered heterocyclic ring having 1-2 ring heteroatoms independently selected from N and O, wherein said ring is unsubstituted. A non-limiting example when D is hetCyc³ and E is hetCyc⁴C(=O)— is the structure:

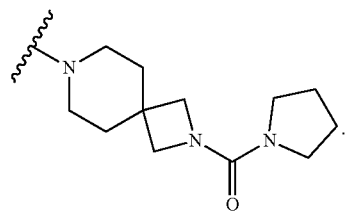

In one embodiment, D is hetCyc³ and E is Ar²C(=O)— where Ar² is as defined for General Formula I. In one embodiment, Ar² is unsubstituted. A non-limiting example is the structure:

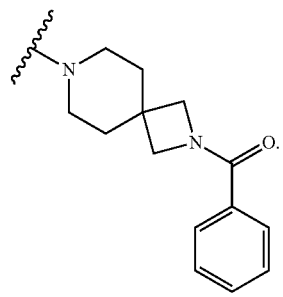

In one embodiment, D is hetCyc³ and E is Ar²C1-C6 alkyl. In one embodiment, Ar² is phenyl which is unsubstituted. Non-limiting examples include the structures:

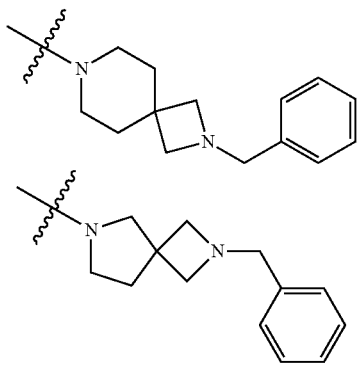

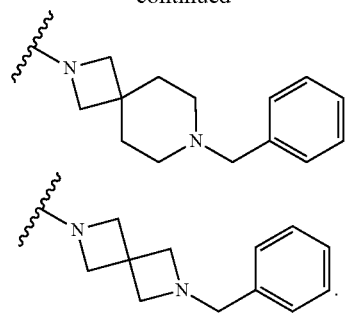

In one embodiment, D is hetCyc³ and E is Ar²(C1-C3 alkyl)C(=O)— wherein the alkyl portion is optionally substituted with one or two groups independently selected from the group consisting of OH, C1-C6 alkyl, hydroxyC1-C6 alkyl, C1-C6 alkoxy and R$^e$R$^f$N—, where R$^e$ and R$^f$ are independently H or C1-C6 alkyl or R$^e$ and R$^f$ together with the nitrogen to which they are attached form a 5-6 membered azacyclic ring optionally having an additional ring heteroatom selected from N and O, and Ar² is as defined for General Formula I. In one embodiment, D is hetCyc³ and E is Ar²(C1-C3 alkyl)C(=O)— wherein the alkyl portion is unsubstituted. In one embodiment, Ar² is phenyl which is unsubstituted. A non-limiting example is the structure:

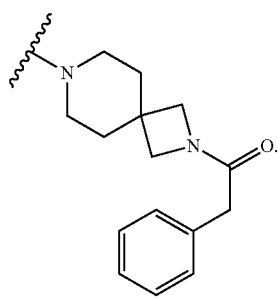

In one embodiment, D is hetCyc³ and E is R¹R²NC(=O)— where R¹ and R² are as defined for General Formula I. In one embodiment, R¹ is H or C1-C6 alkyl and R² is H or C1-C6 alkyl optionally substituted with 1-3 fluoros. Non-limiting examples include the structures:

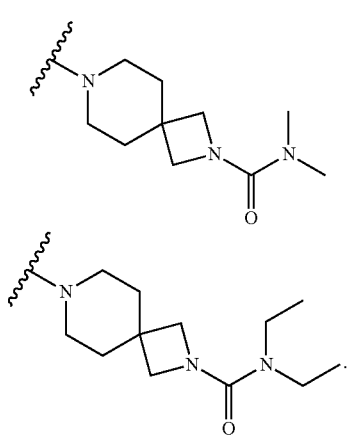

In one embodiment, D is hetCyc³ and E is R¹R²N(C1-C3 alkyl)C(=O)— wherein the C1-C3 alkyl portion is optionally substituted with phenyl, and R¹ and R² are as defined for General Formula I. In one embodiment, R¹ is H or C1-C6 alkyl and R² is H or C1-C6 alkyl optionally substituted with 1-3 fluoros. A non-limiting example is the structure:

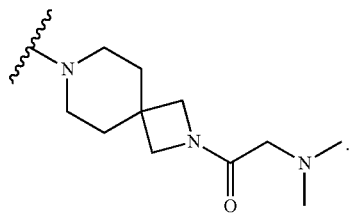

In one embodiment, D is hetCyc³ and E is R⁶C(=O)NH—, where R⁶ is C1-C6 alkyl, hydroxyC1-C6 alkyl, C1-C6 alkoxy, (C1-C6 alkoxy)C1-C6 alkyl, phenyl or hetCyc⁸. In one embodiment, R⁶ is C1-C6 alkoxy. A non-limiting example is the structure:

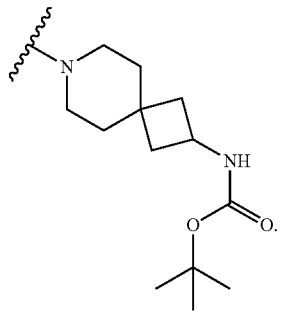 [SMILES: *N1CCC2(CC1)CC(NC(=O)OC(C)(C)C)C2]

In one embodiment, D is hetCyc³ and E is (C3-C6 cycloalkoxy)C(=O)—. A non-limiting example is the structure:

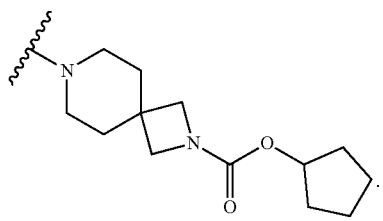 [SMILES: *N1CCC2(CC1)CN(C(=O)OC1CCCC1)C2]

In one embodiment, D is hetCyc³ and E is Ar⁴CH₂OC(=O)—. A non-limiting example is the structure:

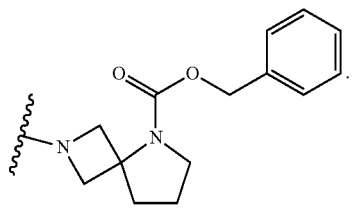 [SMILES: *N1CC2(CCCN2C(=O)OCc2ccccc2)C1]

In one embodiment of Formula I, D is hetCyc⁹, where hetCyc⁹ is a fused 9-10 membered heterocyclic ring having 1-3 ring nitrogen atoms and optionally substituted with oxo

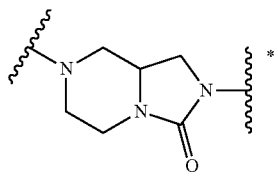 [SMILES: *N1CCN2C(=O)N(*)CC2C1]

where the asterisk indicates the point of attachment to the E group.

In one embodiment, General Formula I includes compounds of Formula I-A, wherein X¹ is CH or CH₃, X² is CH, X³ is CH, and X³ is CH; and A, B, D and E are as defined for General Formula I.

In one embodiment, General Formula I includes compounds of Formula I-B, wherein X¹ is N, CH or CH₃, X² is CH or N, X³ is CH or N, and X³ is CH or N, wherein one of X¹, X², X³ and X⁴ is N; and A, B, D and E are as defined for General Formula I.

In one embodiment, General Formula I includes compounds of Formula I-C, wherein B is hetAr¹, wherein hetAr¹ is a 5-membered heteroaryl ring having 1-2 ring nitrogen atoms, wherein the heteroaryl ring is optionally substituted with one or more substituents independently selected from the group consisting of C1-C6 alkyl, fluoroC1-C6 alkyl, difluoroC1-C6 alkyl, trifluoroC1-C6 alkyl, and hydroxyC1-C6 alkyl; and X¹, X², X³, X⁴, A, D and E are as defined for General Formula I.

In one embodiment, General Formula I includes compounds of Formula I-D, wherein D is hetCyc¹ or hetCyc³, where hetCyc¹ is a 4-6 membered heterocyclic ring having 1-2 ring atoms selected from N and O, wherein the heterocyclic ring is optionally substituted with one or more substituents independently selected from the group consisting of C1-C3 alkyl, fluoroC1-C3 alkyl, difluoroC1-C3 alkyl, trifluoroC1-C3 alkyl, OH, or the heterocyclic ring is substituted with a C3-C6 cycloalkylidene ring, or said heterocyclic ring is substituted with an oxo group; hetCyc³ is a 7-11 membered heterospirocyclic ring having 1-2 ring heteroatoms independently selected from N and O, wherein the ring is optionally substituted with C1-C3 alkyl; and X¹, X², X³, X⁴, A, B and E are as defined for General Formula I. In one embodiment of Formula I-D, D is hetCyc¹.

In one embodiment of Formula I-D, D is hetCyc¹ where hetCyc¹ is a 5-6 membered heterocyclic ring having 1-2 ring nitrogen atoms, wherein the heterocyclic ring is optionally substituted with one or more substituents independently selected from the group consisting of C1-C3 alkyl; and X¹, X², X³, X⁴, A, B and E are as defined for General Formula I. In one embodiment of Formula I-D, D is hetCyc¹ where hetCyc¹ is piperazinyl or piperidinyl, wherein the piperidinyl ring is optionally substituted with C1-C3 alkyl, and X¹, X², X³, X⁴, A, B and E are as defined for General Formula I. In one embodiment of Formula I-D, D is hetCyc¹ where hetCyc¹ is piperazinyl, and X¹, X², X³, X⁴, A, B and E are as defined for General Formula I.

In one embodiment of Formula I-D, D is hetCyc³ wherein the hetCyc³ is optionally substituted with C1-C3 alkyl, and X¹, X², X³, X⁴, A, B and E are as defined for General Formula I. In one embodiment of Formula I-D, D is hetCyc³ wherein hetCyc³ is unsubstituted.

In one embodiment, Formula I includes compounds of Formula I-E, wherein:
X¹ is CH or N;
X² is CH or N;

X³ is CH;
X⁴ is CH;
wherein zero, one or two of X¹ and X² is N;
A is H, Cl or CN;
B is hetAr¹;
hetAr¹ is a 5-membered heteroaryl ring having 1-3 ring heteroatoms independently selected from N, S and O, wherein the heteroaryl ring is optionally substituted with one or more substituents independently selected from the group consisting of halogen, C1-C6 alkyl, hydroxyC1-C6 alkyl, fluoroC1-C6 alkyl, difluoroC1-C6 alkyl, trifluoroC1-C6 alkyl, cyanoC1-C6 alkyl, (C1-C6 alkoxy)C1-C6 alkyl, (C1-C4 alkoxy)CH$_2$C(=O)—, (C1-C4 alkoxy)C(=O)C1-C3 alkyl, C3-C6 cycloalkyl, (R$^a$R$^b$N)C1-C6 alkyl and hetCyc$^a$;
D is hetCyc¹ or hetCyc³;
hetCyc¹ is a 4-6 membered heterocyclic ring having 1-2 ring nitrogen atoms, wherein the heterocyclic ring is optionally substituted with one or more substituents independently selected from the group consisting of C1-C3 alkyl, or said heterocyclic ring is substituted with an oxo group;
hetCyc³ is a 7-11 membered heterospirocyclic ring having 2 ring nitrogen atoms, wherein the ring is optionally substituted with C1-C3 alkyl;
E is
(a) hydrogen,
(d) C1-C6 alkyl optionally substituted with one to three fluoros,
(e) hydroxyC1-C6 alkyl optionally substituted with one to three fluoros,
(i) (C1-C6 alkyl)C(=O)— optionally substituted with one to three fluoros,
(j) (hydroxy C1-C6 alkyl)C(=O)— optionally substituted with one to three fluoros,
(k) (C1-C6 alkoxy)C(=O)—,
(o) Cyc¹C(=O)—,
(r) hetCyc⁴C(=O)—,
(x) Ar²C1-C6 alkyl,
(y) (Ar²)hydroxy C2-C6 alkyl,
(z) Ar²(C1-C3 alkyl)C(=O)— wherein the alkyl portion is optionally substituted with one or two groups independently selected from the group consisting of OH, C1-C6 alkyl (optionally substituted with 1-3 fluoros), hydroxyC1-C6 alkyl, C1-C6 alkoxy and R$^e$R$^f$N—, where R$^e$ and R$^f$ are independently H and C1-C6 alkyl, or R$^e$ and R$^f$ together with the nitrogen to which they are attached form a 5-6 membered azacyclic ring optionally having an additional ring heteroatom selected from N and O,
(cc) hetAr²(C1-C3 alkyl)C(=O)— wherein the alkyl portion is optionally substituted with one or two groups independently selected from the group consisting of OH, C1-C6 alkyl, hydroxyC1-C6 alkyl, C1-C6 alkoxy and R$^e$R$^f$N—, where R$^e$ and R$^f$ are independently H or C1-C6 alkyl, R$^e$ and R$^f$ together with the nitrogen to which they are attached form a 5-6 membered azacyclic ring optionally having an additional ring heteroatom selected from N and O,
(dd) R¹R²NC(=O)—,
(ee) R¹R²N(C1-C3 alkyl)C(=O)— wherein the alkyl portion is optionally substituted with phenyl,
(ii) (C1-C6 alkyl)SO$_2$—, or
(mm) R⁶C(=O)NH—;
Cyc¹ is a C3-C6 cycloalkyl, wherein (a) the cycloalkyl is optionally substituted with one or more substituents independently selected from the group consisting of OH, halogen, C1-C6 alkoxy, CN, hydroxyC1-C6 alkyl, (C1-C6 alkoxy)C1-C6 alkyl, and C1-C6 alkyl optionally substituted with 1-3 fluoros, or (b) the cycloalkyl is substituted with phenyl, wherein the phenyl is optionally substituted with one or more substituents independently selected from the group consisting of halogen, C1-C3 alkyl, C1-C3 alkoxy and CF$_3$, or (c) the cycloalkyl is substituted with a 5-6 membered heteroaryl ring having 1-3 ring heteroatoms independently selected from N and O, wherein the heteroaryl ring is optionally substituted with one or more substituents independently selected from the group consisting of halogen, C1-C3 alkyl, C1-C3 alkoxy and CF$_3$;
hetCyc⁴ is a 4-6 membered heterocyclic ring having 1-2 ring heteroatoms independently selected from N, O and S wherein said S is optionally oxidized to SO$_2$ and is optionally substituted with one or more substituents independently selected from the group consisting of halogen, OH, CN, C1-C6 alkyl (optionally substituted with 1-3 fluoros), C1-C6 alkoxy, (C1-C6 alkoxy)C1-C6 alkyl, (C3-C6)cycloalkyl, (C1-C6 alkyl)C(=O)—, a 5-6 membered heterocyclic ring having 1-2 ring heteroatoms independently selected from N and O, and phenyl wherein said phenyl is optionally substituted with one or more substituents selected from halogen, C1-C6 alkyl and C1-C6 alkoxy;
Ar² is phenyl optionally substituted with one or more substituents independently selected from the group consisting of halogen, C1-C6 alkyl, C1-C6 alkoxy, fluoroC1-C6 alkyl, difluoroC1-C6 alkyl, trifluoroC1-C6 alkyl, CN, a 5-6 membered heterocyclic ring having 1-2 ring heteroatoms independently selected from N and O, and R$^i$R$^j$N— where R$^i$ and R$^j$ are independently H and C1-C6 alkyl;
hetAr² is a 5-6 membered heteroaryl ring having 1-3 ring heteroatoms independently selected from N, O and S, and optionally substituted with one or more substituents independently selected from the group consisting of halogen, C1-C6 alkyl, C1-C6 alkoxy, fluoroC1-C6 alkyl, difluoroC1-C6 alkyl, trifluoroC1-C6 alkyl, (C3-C6)cycloalkyl, (C1-C6 alkoxy)C1-C6 alkyl, CN and R'R"N— where R' and R" are independently H or C1-C3 alkyl;
R¹ is H, C1-C6 alkyl or (C1-C6 alkoxy)C1-C6 alkyl;
R² is H, C1-C6 alkyl (optionally substituted with 1-3 fluoros), (C1-C6 alkoxy)C1-C6 alkyl (optionally substituted with 1-3 fluoros), Cyc³, hydroxyC1-C6 alkyl (optionally substituted with 1-3 fluoros), C1-C6 alkoxy (optionally substituted with 1-3 fluoros), (C1-C6 alkoxy(C(=O), hetCyc⁷, Ar³, Ar³C1-C3 alkyl-, hydroxyC1-C6 alkoxy or (C3-C6 cycloalkyl)CH$_2$O—;
Cyc³ is a 3-6 membered carbocyclic ring optionally substituted with 1-2 groups independently selected from the group consisting of C1-C6 alkoxy, OH and halogen;
Ar³ is phenyl optionally substituted with one or more substituents independently selected from halogen, C1-C3 alkyl, C1-C3 alkoxy, fluoroC1-C3 alkyl, difluoroC1-C3 alkyl and trifluoroC1-C3 alkyl;
hetCyc⁷ is a 5-6 membered heterocyclic ring having a ring heteroatom selected from O and N wherein the ring is optionally substituted with C1-C6 alkyl;
R⁶ is C1-C6 alkyl, hydroxyC1-C6 alkyl, C1-C6 alkoxy, (C1-C6 alkoxy)C1-C6 alkyl, phenyl or hetCyc⁸; and
hetCyc⁸ is a 5-6 membered heterocyclic ring having a ring heteroatom selected from O and N, wherein the heterocyclic ring is optionally substituted with C1-C6 alkyl.
In one embodiment of Formula I-E, hetAr¹ is a 5-membered heteroaryl ring having 1-2 ring nitrogen atoms, wherein the heteroaryl ring is optionally substituted with one or more substituents independently selected from the group consisting of C1-C6 alkyl, fluoroC1-C6 alkyl, difluoroC1-C6 alkyl, trifluoroC1-C6 alkyl and hydroxyC1-C6 alkyl. In one embodiment, B is pyrazolyl or imidazolyl optionally substituted with C1-C6 alkyl, fluoroC1-C6 alkyl, difluoroC1-C6 alkyl, trifluoroC1-C6 alkyl or hydroxyC1-C6 alkyl. In one embodiment, B is pyrazolyl optionally substituted with C1-C6 alkyl.

In one embodiment of Formula I-E, hetCyc$^1$ is piperazinyl and E is (a) hydrogen, (d) C1-C6 alkyl optionally substituted with one to three fluoros, (e) hydroxyC1-C6 alkyl optionally substituted with one to three fluoros, (i) (C1-C6 alkyl)C(=O)— optionally substituted with one to three fluoros, (j) (hydroxy C1-C6 alkyl)C(=O)— optionally substituted with one to three fluoros, (k) (C1-C6 alkoxy)C(=O)—, (o) Cyc$^1$C(=O)—, (r) hetCyc$^4$C(=O)—, (x) Ar$^2$C1-C6 alkyl, (y) (Ar$^2$)hydroxy C2-C6 alkyl, (z) Ar$^2$(C1-C3 alkyl)C(=O)— wherein the alkyl portion is optionally substituted with one or two groups independently selected from the group consisting of OH, C1-C6 alkyl, hydroxyC1-C6 alkyl, C1-C6 alkoxy and R$^e$R$^f$N—, where R$^e$ and R$^f$ are independently H or C1-C6 alkyl, (cc) hetAr$^2$(C1-C3 alkyl)C(=O)— wherein the alkyl portion is optionally substituted with one or two groups independently selected from the group consisting of OH, C1-C6 alkyl, hydroxyC1-C6 alkyl, C1-C6 alkoxy and R$^e$R$^f$N—, where R$^e$ and R$^f$ are independently H or C1-C6 alkyl, (dd) R$^1$R$^2$NC(=O)—, (ee) R$^1$R$^2$N(C1-C3 alkyl)C(=O)— wherein the alkyl portion is optionally substituted with phenyl, (ii) (C1-C6 alkyl)SO$_2$—, or (mm) R$^6$C(=O)NH—. In some such embodiments, E is (d) C1-C6 alkyl optionally substituted with one to three fluoros, (e) hydroxyC1-C6 alkyl optionally substituted with one to three fluoros, (i) (C1-C6 alkyl)C(=O)— optionally substituted with one to three fluoros, (j) (hydroxy C1-C6 alkyl)C(=O)— optionally substituted with one to three fluoros, (o) Cyc$^1$C(=O)—, (r) hetCyc$^4$C(=O)—, (x) Ar$^2$C1-C6 alkyl, or (y) (Ar$^2$)hydroxy C2-C6 alkyl.

In one embodiment of Formula I-E, hetCyc$^1$ is piperazinyl and E is (i) (C1-C6 alkyl)C(=O)— optionally substituted with one to three fluoros, (j) (hydroxy C1-C6 alkyl)C(=O)— optionally substituted with one to three fluoros, or (r) hetCyc$^4$C(=O)—.

In one embodiment of Formula I-E, hetCyc$^1$ is piperazinyl and E is (hydroxy C1-C6 alkyl)C(=O)— optionally substituted with one to three fluoros.

In one embodiment of Formula I-E, hetCyc$^1$ is piperazinyl and E is hetCyc$^4$C(=O)—. In one embodiment of Formula I-E, hetCyc$^1$ is piperazinyl and E is hetCyc$^4$C(=O)— where hetCyc$^4$ is pyrrolidinyl optionally substituted with one or more substituents independently selected from the group consisting of halogen, OH, CN, C1-C6 alkyl (optionally substituted with 1-3 fluoros), C1-C6 alkoxy and (C1-C6 alkoxy)C1-C6 alkyl.

In one embodiment of Formula I-E, hetCyc$^1$ is piperazinyl and E is hetCyc$^4$C(=O)—, where hetCyc$^4$ is pyrrolidinyl optionally substituted with C1-C6 alkoxy.

In one embodiment of Formula I-E, hetCyc$^1$ is piperazinyl and E is (C1-C6 alkyl)C(=O)— optionally substituted with one to three fluoros.

In one embodiment of Formula I-E, X$^1$ is N and each of X$^2$, X$^3$ and X$^4$ is CH.

In one embodiment of Formula I-E, A is CN.

In one embodiment of Formula I-E, A is Cl.

In one embodiment, Formula I includes compounds of Formula I-F, wherein:
X$^1$ is N and each of X$^2$, X$^3$ and X$^4$ is CH;
A is CN or Cl;
B is hetAr$^1$;
hetAr$^1$ is a 5-membered heteroaryl ring having 1-2 ring nitrogen atoms, wherein the heteroaryl ring is optionally substituted with one or more substituents independently selected from the group consisting of C1-C6 alkyl, fluoroC1-C6 alkyl, difluoroC1-C6 alkyl, trifluoroC1-C6 alkyl and hydroxyC1-C6 alkyl;
D is hetCyc$^1$;
hetCyc$^1$ is piperazinyl;
E is (i) (C1-C6 alkyl)C(=O)— optionally substituted with one to three fluoros, (j) (hydroxy C1-C6 alkyl)C(=O)— optionally substituted with one to three fluoros, or (r) hetCyc$^4$C(=O)—; and
hetCyc$^4$ is as defined for General Formula I.

In one embodiment of Formula I-F, hetAr$^1$ is pyrazolyl optionally substituted one or more substituents independently selected from the group consisting of C1-C6 alkyl, fluoroC1-C6 alkyl, difluoroC1-C6 alkyl, trifluoroC1-C6 alkyl and hydroxyC1-C6 alkyl. In one embodiment, B is pyrazolyl or imidazolyl optionally substituted with C1-C6 alkyl, fluoroC1-C6 alkyl, difluoroC1-C6 alkyl, trifluoroC1-C6 alkyl or hydroxyC1-C6 alkyl. In one embodiment of Formula I-F, hetAr$^1$ is pyrazolyl optionally substituted one or more substituents independently selected from the group consisting of C1-C6 alkyl. In one embodiment, B is pyrazolyl or imidazolyl optionally substituted with C1-C6 alkyl, fluoroC1-C6 alkyl, difluoroC1-C6 alkyl, trifluoroC1-C6 alkyl or hydroxyC1-C6 alkyl.

In one embodiment of Formula I-F, hetCyc$^4$ is a 5-membered heterocyclic ring having a ring nitrogen atom, wherein the heterocyclic ring is optionally substituted with C1-C6 alkoxy.

In one embodiment of Formula I-F, A is CN.

In one embodiment, Formula I includes compounds of Formula I-G, wherein:
X$^1$ is N and each of X$^2$, X$^3$ and X$^4$ is CH;
A is CN;
B is hetAr$^1$;
hetAr$^1$ is a 5-membered heteroaryl ring having 2 ring nitrogen atoms, wherein the heteroaryl ring is optionally substituted with one or more substituents independently selected from the group consisting of C1-C6 alkyl, fluoroC1-C6 alkyl, difluoroC1-C6 alkyl, trifluoroC1-C6 alkyl and hydroxyC1-C6 alkyl;
D is hetCyc$^1$;
hetCyc$^1$ is piperazinyl;
E is (i) (C1-C6 alkyl)C(=O)— optionally substituted with one to three fluoros, (j) (hydroxy C1-C6 alkyl)C(=O)— optionally substituted with one to three fluoros, or (r) hetCyc$^4$C(=O)—; and
hetCyc$^4$ is a 5-membered heterocyclic ring having a ring nitrogen atom, wherein the heterocyclic ring is optionally substituted with C1-C6 alkoxy.

In one embodiment of Formula I-G, B is pyrazolyl optionally substituted one or more substituents independently selected from the group consisting of C1-C6 alkyl, fluoroC1-C6 alkyl, difluoroC1-C6 alkyl, trifluoroC1-C6 alkyl and hydroxyC1-C6 alkyl. In one embodiment of Formula I-G, B is pyrazolyl optionally substituted one or more substituents independently selected from the group consisting of C1-C6 alkyl.

In one embodiment of Formula I-G, E is (i) (C1-C6 alkyl)C(=O)— optionally substituted with one to three fluoros.

In one embodiment of Formula I-G, E is (j) (hydroxy C1-C6 alkyl)C(=O)— optionally substituted with one to three fluoros.

In one embodiment of Formula I-G, E is (r) hetCyc$^4$C(=O)—.

In one embodiment, Formula I includes compounds of Formula I-H wherein:

$X^1$ is N and each of $X^2$, $X^3$ and $X^4$ is CH;

A is CN;

B is hetAr$^1$;

hetAr$^1$ is a 5-membered heteroaryl ring having 1-2 ring nitrogen atoms, wherein the heteroaryl ring is optionally substituted with one or more substituents independently selected from the group consisting of C1-C6 alkyl, fluoroC1-C6 alkyl, difluoroC1-C6 alkyl, trifluoroC1-C6 alkyl and hydroxyC1-C6 alkyl;

D is hetCyc$^3$;

hetCyc$^3$ is a 7-11 membered heterospirocyclic ring having 1-2 ring heteroatoms independently selected from N and O, wherein the ring is optionally substituted with C1-C3 alkyl; and E is as defined for General Formula I.

In one embodiment of Formula I-H, E is (a) hydrogen; (e) hydroxyC1-C6 alkyl optionally substituted with one to three fluoros; (i) (C1-C6 alkyl)C(=O)— optionally substituted with one to three fluoros; (j) (hydroxy C1-C6 alkyl)C(=O)— optionally substituted with one to three fluoros; (k) (C1-C6 alkoxy)C(=O)—; (o) Cyc$^1$C(=O)—; (w) Ar$^2$C(=O)—; or (z) Ar$^2$(C1-C3 alkyl)C(=O)— wherein the alkyl portion is optionally substituted with one or two groups independently selected from the group consisting of OH, C1-C6 alkyl, hydroxyC1-C6 alkyl, C1-C6 alkoxy and R$^e$R$^f$N—, where R$^e$ and R$^f$ are independently H or C1-C6 alkyl; or (mm) R$^6$C(=O)NH—.

In one embodiment of Formula I-H, E is (k) (C1-C6 alkoxy)C(=O)— or (o) Cyc$^1$C(=O)—.

In one embodiment, Formula I includes compounds of Formula I-I, wherein:

$X^1$, $X^2$, $X^3$ and $X^4$ are CH;

A is H, Cl or CN;

B is hetAr$^1$;

hetAr$^1$ is a 5-membered heteroaryl ring having 1-3 ring heteroatoms independently selected from N, S and O, wherein the heteroaryl ring is optionally substituted with one or more substituents independently selected from the group consisting of halogen, C1-C6 alkyl, hydroxyC1-C6 alkyl, fluoroC1-C6 alkyl, difluoroC1-C6 alkyl, trifluoroC1-C6 alkyl, cyanoC1-C6 alkyl, (C1-C6 alkoxy)C1-C6 alkyl, (C1-C4 alkoxy)CH$_2$C(=O)—, (C1-C4 alkoxy)C(=O)C1-C3 alkyl, C3-C6 cycloalkyl, (R$^a$R$^b$N)C1-C6 alkyl and hetCyc$^a$;

D is hetCyc$^1$;

hetCyc$^1$ is a 5-6 membered heterocyclic ring having 1-2 ring nitrogen atoms, wherein the heterocyclic ring is optionally substituted with one or more substituents independently selected from the group consisting of C1-C3 alkyl;

E is (a) hydrogen, (i) (C1-C6 alkyl)C(=O)— optionally substituted with one to three fluoros, (j) (hydroxy C1-C6 alkyl)C(=O)— optionally substituted with one to three fluoros, (k) (C1-C6 alkoxy)C(=O)—, (ee) R$^1$R$^2$N(C1-C3 alkyl)C(=O)— wherein the alkyl portion is optionally substituted with phenyl, or (ii) (C1-C6 alkyl)SO$_2$;

R$^1$ is H or C1-C6 alkyl;

R$^2$ is H, C1-C6 alkyl (optionally substituted with 1-3 fluoros), (C1-C6 alkoxy)C1-C6 alkyl (optionally substituted with 1-3 fluoros), Cyc$^3$, hydroxyC1-C6 alkyl (optionally substituted with 1-3 fluoros), C1-C6 alkoxy (optionally substituted with 1-3 fluoros), (C1-C6 alkoxy(C(=O), hetCyc$^7$, Ar$^3$ or Ar$^3$C1-C3 alkyl-;

Cyc$^3$ is a 3-6 membered carbocyclic ring optionally substituted with 1-2 groups independently selected from the group consisting of C1-C6 alkoxy, OH and halogen;

Ar$^3$ is phenyl optionally substituted with one or more substituents independently selected from halogen, C1-C3 alkyl, C1-C3 alkoxy, fluoroC1-C3 alkyl, difluoroC1-C3 alkyl and trifluoroC1-C3 alkyl; and hetCyc$^7$ is a 5-6 membered heterocyclic ring having a ring heteroatom selected from O and N wherein the ring is optionally substituted with C1-C6 alkyl.

In one embodiment of Formula I-I, hetAr$^1$ is a 5-membered heteroaryl ring having 2 ring nitrogen atoms, wherein the heteroaryl ring is optionally substituted with one or more substituents independently selected from the group consisting of C1-C6 alkyl, fluoroC1-C6 alkyl, difluoroC1-C6 alkyl, trifluoroC1-C6 alkyl and hydroxyC1-C6 alkyl.

In one embodiment, Formula I includes compounds of Formula I-I wherein $X^1$ is N and each of $X^2$, $X^3$ and $X^4$ is CH;

A is CN or Cl;

B is hetAr$^1$;

hetAr$^1$ is a 5-membered heteroaryl ring having 1-2 ring nitrogen atoms, wherein said heteroaryl ring is optionally substituted with one or more substituents independently selected from the group consisting of C1-C6 alkyl, fluoroC1-C6 alkyl, difluoroC1-C6 alkyl, trifluoroC1-C6 alkyl and hydroxyC1-C6 alkyl;

D is hetCyc$^1$;

hetCyc$^1$ is piperazinyl;

E is (d) C1-C6 alkyl optionally substituted with one to three fluoros, (e) hydroxyC1-C6 alkyl optionally substituted with one to three fluoros, (o) Cyc$^1$C(=O)—, (x) Ar$^2$C1-C6 alkyl, (y) (Ar$^2$)hydroxy C2-C6 alkyl, or (bb) (hetAr$^2$)hydroxyC2-C6 alkyl; and Ar$^2$ and hetAr$^2$ are as defined for General Formula I.

In one embodiment, Formula I includes compounds of Formula I-J, wherein:

$X^1$ is N and each of $X^2$, $X^3$ and $X^4$ is CH;

A is CN;

B is hetAr$^1$;

hetAr$^1$ is a 5-membered heteroaryl ring having 1-3 ring heteroatoms independently selected from N, S and O, wherein the heteroaryl ring is optionally substituted with one or more substituents independently selected from the group consisting of halogen, C1-C6 alkyl, hydroxyC1-C6 alkyl, fluoroC1-C6 alkyl, difluoroC1-C6 alkyl, trifluoroC1-C6 alkyl, cyanoC1-C6 alkyl, (C1-C6 alkoxy)C1-C6 alkyl, (C1-C4 alkoxy)CH$_2$C(=O)—, (C1-C4 alkoxy)C(=O)C1-C3 alkyl, C3-C6 cycloalkyl, (R$^a$R$^b$N)C1-C6 alkyl, and hetCyc$^a$;

D is hetCyc$^1$;

hetCyc$^1$ is piperazinyl;

E is (x) Ar$^2$C1-C6 alkyl or (oo) hetAr$^2$C1-C6 alkyl;

Ar$^2$ is phenyl optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, CN, a 5-6 membered heterocyclic ring having 1-2 ring heteroatoms independently selected from N and O, and R$^i$R$^j$N— where R$^i$ and R$^j$ are independently H and C1-C6 alkyl; and hetAr$^2$ is a 5-6 membered heteroaryl ring having 1-3 ring heteroatoms independently selected from N, O and S and optionally substituted with one or more substituents independently selected from the group consisting of halogen, C1-C6 alkyl, C1-C6 alkoxy, fluoroC1-C6 alkyl, difluoroC1-C6 alkyl, trifluoroC1-C6 alkyl, (C3-C6)cycloalkyl, (C1-C6 alkoxy)C1-C6 alkyl, CN and R'R"N— where R' and R" are independently H or C1-C3 alkyl.

In one embodiment of Formula I-J, hetAr$^1$ is a 5-membered heteroaryl ring having 1-2 ring nitrogen atoms, wherein the heteroaryl ring is optionally substituted with one or more substituents independently selected from the group consisting of C1-C6 alkyl, fluoroC1-C6 alkyl, difluoroC1-C6 alkyl, trifluoroC1-C6 alkyl and hydroxyC1-C6 alkyl. In one embodiment, B is pyrazolyl or imidazolyl optionally substituted with C1-C6 alkyl, fluoroC1-C6 alkyl, difluoroC1-C6 alkyl, trifluoroC1-C6 alkyl or hydroxyC1-C6 alkyl. In one embodiment, B is pyrazolyl optionally substituted with C1-C6 alkyl.

In one embodiment of Formula I-J, E is (x) Ar$^2$C1-C6 alkyl or (oo) hetAr$^2$C1-C6 alkyl. In one embodiment of Formula I-J, E is hetAr$^2$C1-C6 alkyl.

In one embodiment of Formula I-J, B is pyrazolyl optionally substituted one or more substituents independently selected from the group consisting of C1-C6 alkyl, fluoroC1-C6 alkyl, difluoroC1-C6 alkyl, trifluoroC1-C6 alkyl and hydroxyC1-C6 alkyl. In one embodiment of Formula I-J, B is pyrazolyl optionally substituted one or more substituents independently selected from the group consisting of C1-C6 alkyl.

It will be appreciated that certain compounds provided herein may contain one or more centers of asymmetry and may therefore be prepared and isolated in a mixture of isomers such as a racemic mixture, or in an enantiomerically pure form.

It will further be appreciated that the compounds of General Formula I or their salts may be isolated in the form of solvates, and accordingly that any such solvate is included within the scope of the present invention. For example, compounds of General Formula I and salts thereof can exist in unsolvated as well as solvated forms with pharmaceutically acceptable solvents such as water, ethanol, and the like.

The compounds of General Formula I include pharmaceutically acceptable salts thereof. In addition, the compounds of General Formula I also include other salts of such compounds which are not necessarily pharmaceutically acceptable salts, and which may be useful as intermediates for preparing and/or purifying compounds of General Formula I and/or for separating enantiomers of compounds of Formula I. Non-limiting examples of salts include monochloride, dichloride, trifluoroacetic acid, and di-trifluoroacetic acid salts of compounds of Formula I.

In one embodiment, the compounds of General Formula I include the compounds of Examples 1-567, 569-570, 572, 574-654, and 656-744 and stereoisomers and pharmaceutically acceptable salts and solvates thereof. In one embodiment, the compounds of Examples 1-567, 569-570, 572, 574-654, and 656-744 are in the free base form. In one embodiment, the compounds of Examples 1-567, 569-570, 572, 574-654, and 656-744 are monochloride, dichloride, trifluoroacetic acid, or di-trifluoroacetic acid salts.

In some embodiments, the compounds provided herein exhibit potent and selective RET inhibition. For example, the compounds provided herein exhibit nanomolar potency against wild type RET and select RET mutants, including the KIF5B-RET fusion and V804M gatekeeper mutation, with minimal activity against related kinases.

In some embodiments, the compounds of General Formula I or a pharmaceutically acceptable salt or solvate thereof, selectively target a RET kinase. For example, a compound of General Formula I or a pharmaceutically acceptable salt or solvate thereof, can selectively target a RET kinase over another kinase or non-kinase target.

In some embodiments, a compound of General Formula I or a pharmaceutically acceptable salt or solvate thereof, exhibits at least a 30-fold selectivity for a RET kinase over another kinase. For example, a compound of General Formula I or a pharmaceutically acceptable salt or solvate thereof, exhibits at least a 40-fold selectivity; at least a 50-fold selectivity; at least a 60-fold selectivity; at least a 70-fold selectivity; at least a 80-fold selectivity; at least a 90-fold selectivity; or at least 100-fold selectivity for a RET kinase over another kinase. In some embodiments, selectivity for a RET kinase over another kinase is measured in a cellular assay (e.g., a cellular assay as provided herein).

In some embodiments, the compounds provided herein can exhibit selectivity for a RET kinase over a KDR kinase (e.g., VEGFR$^2$). In some embodiments, the selectivity for a RET kinase over a KDR kinase is observed without loss of gatekeeper mutant potency. In some embodiments, the selectivity over a KDR kinase is at least 10-fold (e.g., at least a 40-fold selectivity; at least a 50-fold selectivity; at least a 60-fold selectivity; at least a 70-fold selectivity; at least a 80-fold selectivity; at least a 90-fold selectivity; or at least 100-fold) as compared to the inhibition of KIF5B-RET (i.e. the compounds were more potent against KIF5B-RET than KDR). In some embodiments, the selectivity for a RET kinase over a KDR kinase is about 30-fold. Without being bound by any theory, potent KDR kinase inhibition is believed to be a common feature among multikinase inhibitors (MKIs) that target RET and may be the source of the dose-limiting toxicities observed with such compounds.

In some embodiments, inhibition of V804M was similar to that observed for wild-type RET. For example, inhibition of V804M was within about 2-fold (e.g., about 5-fold, about 7-fold, about 10-fold) of inhibition of wild-type RET (i.e. the compounds were similarly potent against wild-type RET and V804M). In some embodiments, the compounds provided herein exhibit selective cytotoxicity to RET-mutant cells.

In some embodiments, the compounds of General Formula I or a pharmaceutically acceptable salt or solvate thereof, exhibit one or more of high GI absorption, low clearance, and low potential for drug-drug interactions.

The term "pharmaceutically acceptable" indicates that the substance or composition is compatible chemically and/or toxicologically, with the other ingredients comprising a formulation, and/or the patient being treated therewith.

Compounds provided herein may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^1$H, $^2$H, $^3$H or mixtures thereof; when carbon is mentioned, it is understood to refer to $^{11}$C, $^{12}$C, $^{13}$C, $^{14}$C or mixtures thereof; when nitrogen is mentioned, it is understood to refer to $^{13}$N, $^{14}$N, $^{15}$N or mixtures thereof; when oxygen is mentioned, it is understood to refer to $^{14}$O, $^{15}$O, $^{16}$O, $^{17}$O, $^{18}$O or mixtures thereof; and when fluoro is mentioned, it is understood to refer to $^{18}$F, $^{19}$F or mixtures thereof. The compounds provided herein therefore also comprise compounds with one or more isotopes of one or more atom, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present invention.

For illustrative purposes, Schemes 1-4 show general methods for preparing the compounds provided herein as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

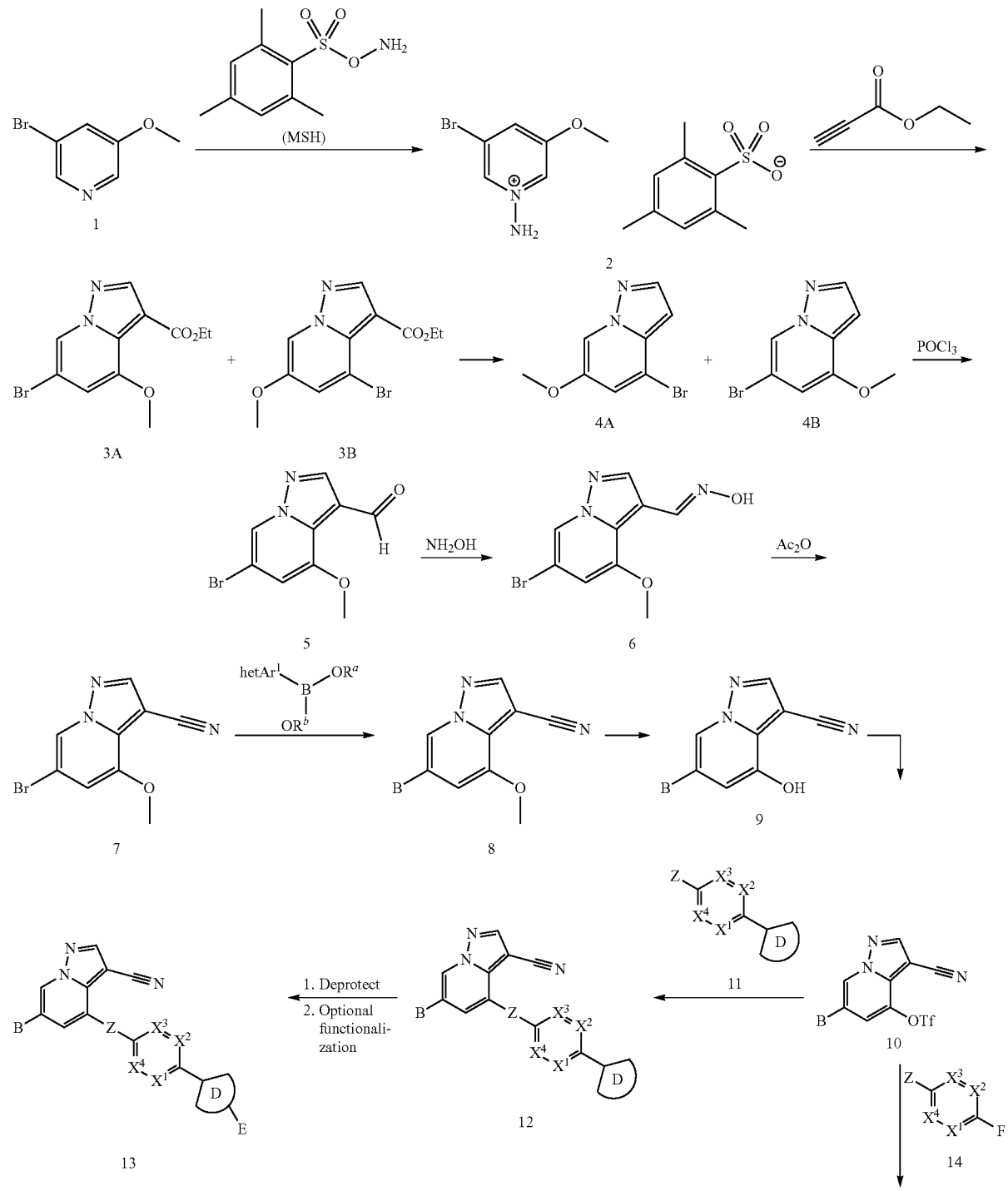

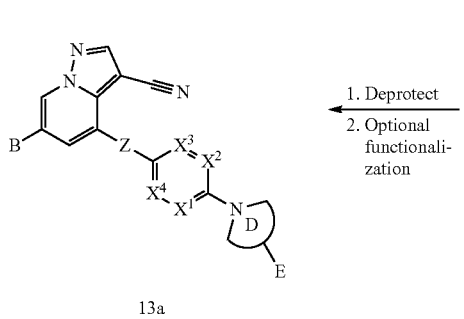

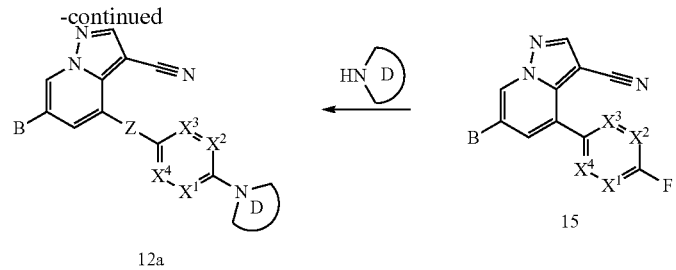

Scheme 1 shows a general scheme for the synthesis of compound 13 where A is CN, and B, $X^1$, $X^2$, $X^3$, $X^4$, D and E are as defined for General Formula I, and the synthesis of compound 13a where A is CN, D is as defined for General Formula I provided that the D ring is coupled to the ring defined by $X^1$, $X^2$, $X^3$ and $X^4$ through a ring nitrogen atom in the D ring, $X^1$, $X^2$, $X^3$, $X^4$ are as defined for Formula I provided that at least one of $X^1$ and $X^2$ is nitrogen, and B, $X^3$, $X^4$, and E is as defined for General Formula I.

Compound 2 is obtained by treating MSH reagent with 3-bromo-5-methoxypyridine, which is commercially available. The aminating reagent O-mesitylsulfonylhydroxylamine (MSH) may be prepared as described in Mendiola, J., et al., Org. Process Res. Dev. 2009, 13(2), 263-267. Compound 2 may be reacted with ethyl propiolate to provide the pyrazolo[1,5-a]pyridine a mixture of compounds 3A and 3B, which typically are obtained in a ratio of approximately 2:1 to 9:1. The mixture of compounds 3A and 3B may be treated with 48% HBr at elevated temperatures, followed by recrystallization or chromatography purifications to isolate compound 4A as the minor isomer and compound 4B as the major isomer.

The isolated compound 4B may be functionalized with a formyl group using $POCl_3$ followed by purification to provide compound 5. The formyl group of compound 5 may be converted to an oxime group using $NH_2OH$ to provide compound 6. The oxime group of compound 6 may be converted to a nitrile group using acetic anhydride to provide compound 7. The B group may be installed by treating compound 7 with a corresponding boronic ester having the formula hetAr$^1$—B(OR$^a$)(OR$^b$) where hetAr$^1$ is as defined for General Formula I and R$^a$ and R$^b$ are H or C1-C6 alkyl, or R$^a$ and R$^b$ together with the atoms to which they are connected form a 5-6 membered ring optionally substituted with one to four C1-C3 alkyl groups, using appropriate palladium-catalyzed cross-coupling reaction conditions, e.g., Suzuki coupling reaction conditions (for example, a palladium catalyst and optionally a ligand in the presence of an inorganic base, for example, $Pd_2(dba)_3$, X-Phos and $Na_2CO_3$ in dioxane at elevated temperatures) to provide compound 8 where B is hetAr$^1$ as defined for General Formula I. The methoxy group of compound 8 may be converted to a hydroxy group by treating compound 8 with aluminum trichloride to provide compound 9. The free hydroxy group of compound 9 may be converted to a triflate group by treating compound 9 with a triflating reagent, for example 1,1,1-trifluoro-N-phenyl-N—((trifluoromethyl)sulfonyl)methanesulfonamide to provide compound 10. Compound 12 may be prepared by coupling compound 10 with the corresponding boronic ester compound 11 where Z is —B(OR$^a$)(OR$^b$) and R$^a$ and R$^b$ are H or C1-C6 alkyl, or R$^a$ and R$^b$ together with the atoms to which they are connected form a 5-6 membered ring optionally substituted with one to four C1-C3 alkyl groups, using appropriate palladium-catalyzed cross-coupling reaction conditions, e.g., Suzuki coupling reaction conditions (for example, a palladium catalyst and optionally a ligand in the presence of an inorganic base, for example, $Pd_2(dba)_3$, X-Phos and $Na_2CO_3$ in dioxane at elevated temperatures), wherein if the D ring of compound 11 comprises an unsubstituted ring nitrogen atom, the nitrogen atom is protected with an appropriate amine protecting group prior to coupling. The protecting group if present on the D ring of compound 12 may be removed under standard conditions (for example, a Boc protecting group may be removed by treating compound 12 under acidic conditions, e.g., using HCl) to provide compound 13 where E is H. Alternatively, the deprotected D ring may be functionalized (i.e., reacted or treated with an appropriate reagent) to introduce the E group under standard conditions such as described below to provide compound 13 where E is as defined for General Formula I except that E is not H.

Alternatively, compound 10 may be coupled with compound 14 using appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and $Na_2CO_3$) to provide compound 15. Compound 15 may be reacted with compound 16 under appropriate $S_NAr$ conditions (for example, optionally in the presence of a base such as $K_2CO_3$ and at elevated temperature) to provide compound 12a, wherein if the D ring of compound 16 comprises a second unsubstituted ring nitrogen atom, the second nitrogen atom is protected with an appropriate amine protecting group prior to coupling. The protecting group if present on the D ring of compound 12a may be removed under standard conditions (for example, a Boc group may be removed by treating compound 12a to acidic conditions, e.g., HCl) to provide compound 13a where E is H. Alternatively, the deprotected D ring may be functionalized (i.e., reacted or treated with an appropriate reagent) to introduce the E group under standard conditions such as described below to provide compound 13a where E is as defined for General Formula I except that E is not H.

Scheme 2

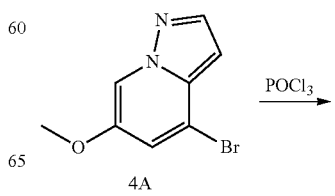

4A

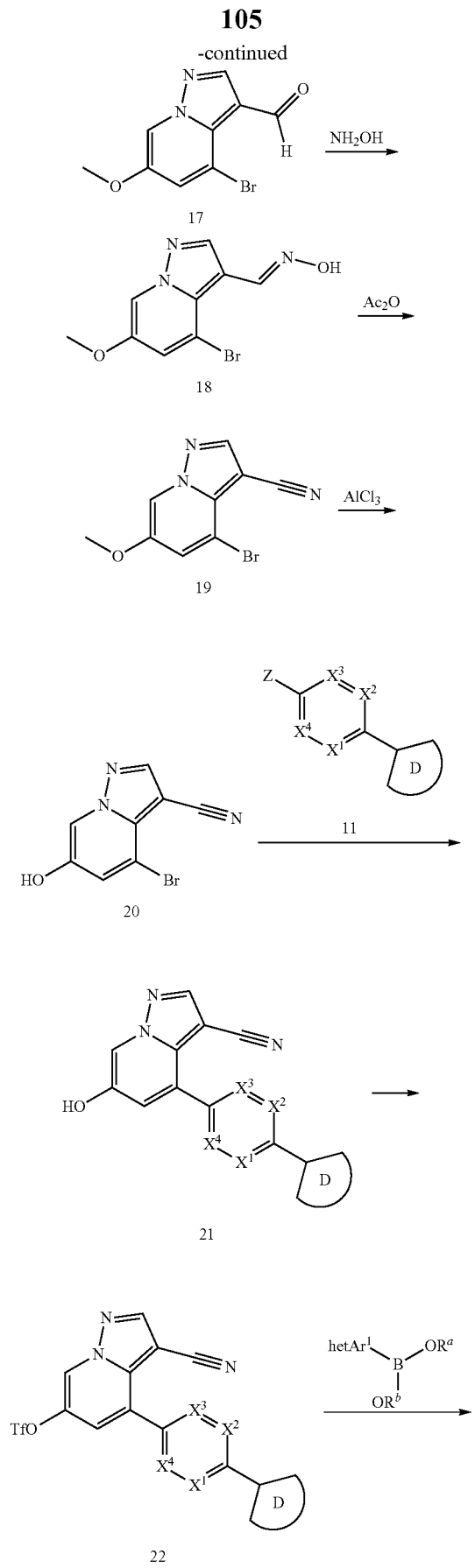

Scheme 2 shows an alternative route for the synthesis of compound 13, wherein A is CN, and B, $X^1$, $X^2$, $X^3$, $X^4$, D and E are as defined for General Formula I. Compound 4A (prepared as in Scheme 1) may be functionalized with a formyl group using $POCl_3$ to provide compound 17. The formyl group may be converted to an oxime group using $NH_2OH$ to provide compound 18. The oxime group may be converted to a nitrile group using acetic anhydride to provide compound 19. The methoxy group of compound 19 may be converted to a hydroxy group by treating compound 19 with aluminum trichloride to provide compound 20. Compound 21 may be prepared by coupling compound 20 with the corresponding boronic ester compound 11 where Z is —$B(OR^a)(OR^b)$ and $R^a$ and $R^b$ are H or C1-C6 alkyl, or $R^a$ and $R^b$ together with the atoms to which they are connected form a 5-6 membered ring optionally substituted with one to four C1-C3 alkyl groups, using appropriate palladium-catalyzed cross-coupling reaction conditions, e.g., Suzuki coupling reaction conditions (for example, a palladium catalyst and optionally a ligand in the presence of an inorganic base, for example, $Pd(PPh_3)_4$ and $Na_2CO_3$ in dioxane at elevated temperatures), wherein if the D ring of compound 11 comprises an unsubstituted ring nitrogen atom, the nitrogen atom is protected with an appropriate amine protecting group prior to coupling. The free hydroxy group of compound 21 may be converted to a triflate group by treating compound 21 with a triflating reagent, for example 1,1,1-trifluoro-N-phenyl-N— ((trifluoromethyl)sulfonyl)methanesulfonamide to provide compound 22. The B group may be installed by treating compound 22 with the corresponding boronic ester having the formula $hetAr^1$—$B(OR^a)(OR^b)$ where $hetAr^1$ is as defined for General Formula I and $R^a$ and $R^b$ are H or C1-C6 alkyl, or $R^a$ and $R^b$ together with the atoms to which they are connected form a 5-6 membered ring optionally substituted with one to four C1-C3 alkyl groups, using appropriate palladium-catalyzed cross-coupling reaction conditions, e.g., Suzuki coupling reaction conditions (for example, a palladium catalyst and optionally a ligand in the presence of an inorganic base, for example, $Pd_2(dba)_3$, X-Phos and $Na_2CO_3$ in dioxane at elevated temperatures) to provide compound 12 where B is hetAr¹ as defined for General Formula I. The protecting group if present on the D ring of compound 12 may be removed under standard conditions (for example, a Boc group may be removed by treating compound 12 to acidic conditions, e.g., HCl in propan-2-ol) to provide compound 13 where E is H. Alternatively, the deprotected D ring may be functionalized (i.e., reacted or treated with an appropriate reagent) to introduce the E group under standard conditions such as described below to provide compound 13 where E is as defined for General Formula I except that E is not H.

Scheme 3

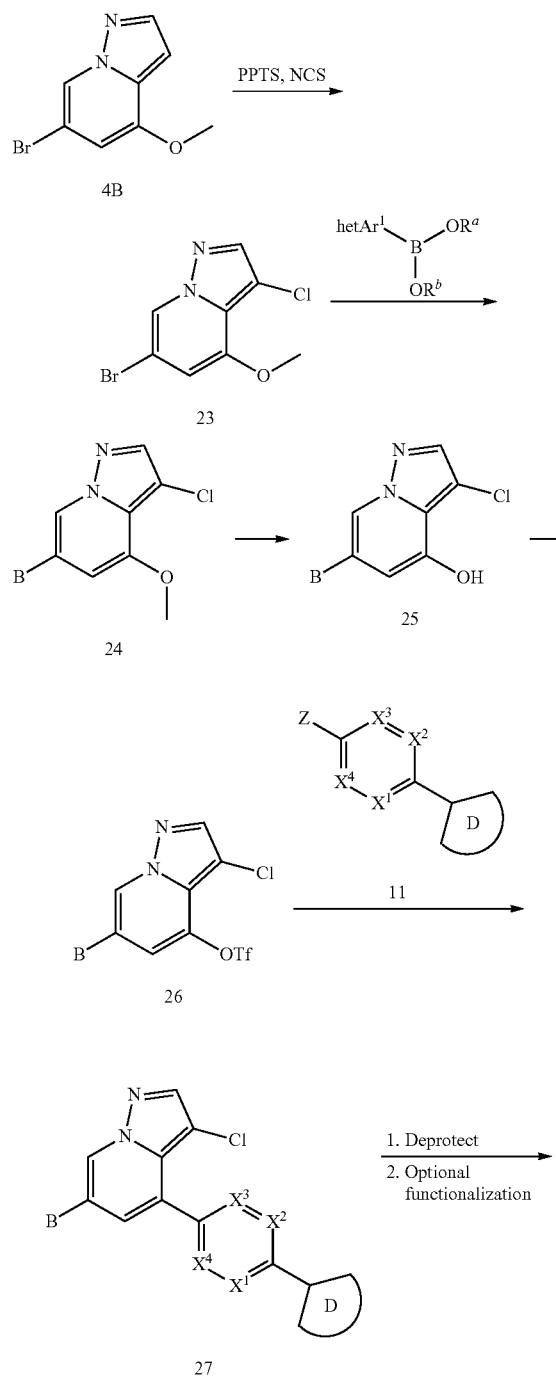

-continued

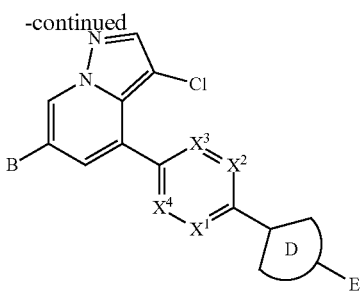

28

Scheme 3 shows a general scheme for the synthesis of compound 28 where A is Cl, and B, X¹, X², X³, X⁴, D and E are as defined for General Formula I. Compound 4B (prepared as in Scheme 1) may be chlorinated using N-chlorosuccinimide to provide compound 23. The B group may be installed by coupling compound 23 with an appropriate boronic ester having the formula hetAr¹—B(OR$^a$)(OR$^b$) where hetAr¹ is as defined for General Formula I and R$^a$ and R$^b$ are H or C1-C6 alkyl, or R$^a$ and R$^b$ together with the atoms to which they are connected form a 5-6 membered ring optionally substituted with one to four C1-C3 alkyl groups, under appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures) to provide compound 24 where B is hetAr¹ as defined for General Formula I. The methoxy group of compound 24 may be converted to a hydroxy group under standard conditions, for example by treating compound 24 with BBr$_3$, to yield compound 25. The free hydroxy group of compound 25 may be converted to a triflate group by treating compound 25 with an appropriate triflating reagent in the presence of a base, e.g., 1,1,1-trifluoro-N-phenyl-N-((trifluoromethyl)sulfonyl)methanesulfonamide and DIEA to provide compound 26. Compound 27 may be prepared by coupling compound 26 with the corresponding boronic ester compound 11 where Z is —B(OR$^a$)(OR$^b$) and R$^a$ and R$^b$ are H or C1-C6 alkyl, or R$^a$ and R$^b$ together with the atoms to which they are connected form a 5-6 membered ring optionally substituted with one to four C1-C3 alkyl groups, using under standard coupling conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures), wherein if the D ring of compound 11 comprises an unsubstituted ring nitrogen atom, the nitrogen atom is protected with an appropriate amine protecting group prior to coupling. The protecting group if present on the D ring of compound 27 may be removed under standard conditions (for example, a Boc group may be removed by treating compound 27 with acid (e.g., 5-6 N HCl in propan-2-ol) to provide compound 28 where E is H. Alternatively, the deprotected D ring may be functionalized (i.e., reacted or treated with an appropriate reagent) to introduce the E group under standard conditions such as described below to provide compound 28 where E is as defined for General Formula I except that E is not H.

Scheme 4

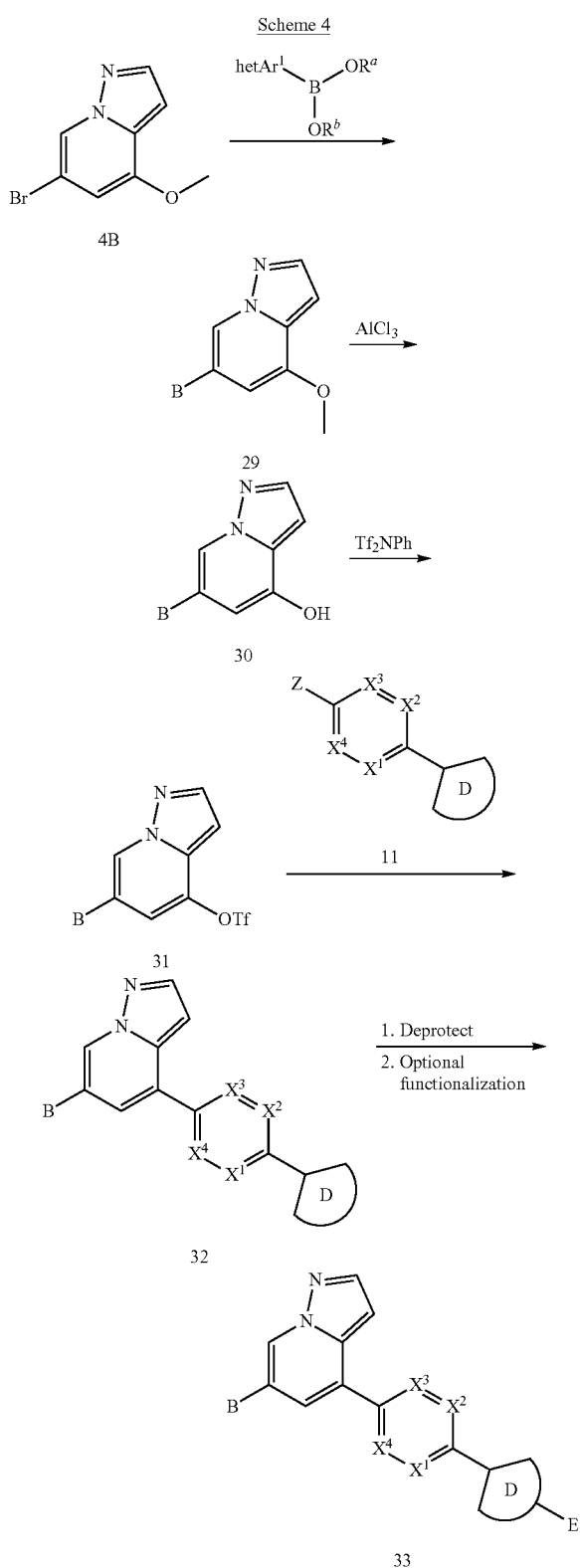

Scheme 4 shows a general scheme for the synthesis of compound 33, wherein A is H, and B, $X^1$, $X^2$, $X^3$, $X^4$, D and E are as defined for General Formula I. Compound 4B (prepared as in Scheme 1) may be coupled with an appropriate boronic ester having the formula hetAr$^1$—B(OR$^a$)(OR$^b$) where hetAr$^1$ is as defined for General Formula I and R$^a$ and R$^b$ are H or C1-C6 alkyl, or R$^a$ and R$^b$ together with the atoms to which they are connected form a 5-6 membered ring optionally substituted with one to four C1-C3 alkyl groups, under appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures) to install the B group to provide compound 29 where B is hetAr$^1$ as defined for General Formula I. The methoxy group of compound 29 may be converted to a hydroxy group by treating compound 29 with aluminum trichloride to provide compound 30. The free hydroxy group of compound 30 may be converted to a triflate group by treating compound 33 with a triflating reagent in the presence of a base, e.g., 1,1,1-trifluoro-N-phenyl-N-((trifluoromethyl)sulfonyl)methanesulfonamide and DIEA in an appropriate solvent such as THF to provide compound 31. Compound 32 may be prepared by coupling compound 31 with compound 11 under appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures), wherein if the D ring of compound 11 comprises an unsubstituted ring nitrogen atom, the nitrogen atom is protected with an appropriate amine protecting group prior to coupling. The protecting group if present on the D ring of compound 32 may be removed under standard conditions (for example, a Boc group may be removed by treating compound 32 under acidic conditions, e.g., HCl in propan-2-ol) to provide compound 33 where E is H. Alternatively, the deprotected D ring may be functionalized (i.e., reacted or treated with an appropriate reagent) to introduce the E group under standard conditions such as described below to provide compound 33 where E is as defined for General Formula I except that E is not H.

The D ring of any one of compounds 13, 13a, 28, and 33 described in Schemes 1-4 may be functionalized (i.e., reacted or treated with an appropriate reagent) to introduce an E group, where E is any of the E groups defined for General Formula I with the exception of hydrogen, using standard chemistry well known to persons skilled in the art. As used herein, the term "functionalized" refers to a process step in which a compound of Formula I where E is hydrogen is reacted or treated with an appropriate reagent to provide a compound of Formula I where E is other than hydrogen.

For example, an amide derivative (e.g., where D is hetCyc$^1$ where hetCyc$^1$ is piperazinyl and E is (C1-C6 alkyl)C(=O)— optionally substituted with one to three fluoros; (hydroxy C1-C6 alkyl)C(=O)— optionally substituted with one to three fluoros; (C1-C6 alkoxy)(C1-C6 alkyl)C(=O)—; Cyc$^1$C(=O)—; Cyc$^1$(C1-C6 alkyl)C (=O)—; hetCyc$^4$(C1-C3 alkyl)C(=O)—; Ar$^2$C(=O)—; Ar$^2$(C1-C3 alkyl)C(=O)— wherein the alkyl portion is optionally substituted with one or two groups independently selected from the group consisting of OH, C1-C6 alkyl, hydroxyC1-C6 alkyl, C1-C6 alkoxy and R$^e$R$^f$N—, where R$^e$ and R$^f$ are independently H and C1-C6 alkyl or R$^e$ and R$^f$ together with the nitrogen to which they are attached form a 5-6 membered azacyclic ring optionally having an additional ring heteroatom selected from N and O; hetAr$^2$C (=O)—; or hetAr$^2$(C1-C3 alkyl)C(=O)— wherein the alkyl portion is optionally substituted with one or two groups independently selected from the group consisting of OH, C1-C6 alkyl, hydroxyC1-C6 alkyl, C1-C6 alkoxy and R$^e$R$^f$N—, where R$^e$ and R$^f$ are independently H or C1-C6 alkyl) or R$^e$ and R$^f$ together with the nitrogen to which they are attached form a 5-6 membered azacyclic ring optionally having an additional ring heteroatom selected from N and O, may be obtained by treating compound 13 having a deprotected amino D ring with an carboxylic acid (e.g., with an acid having the formula (C1-C6 alkyl)C(=O)OH optionally substituted with one to three fluoros; (hydroxy C1-C6 alkyl) C(=O)OH optionally substituted with one to three fluoros; (C1-C6 alkoxy)(C1-C6 alkyl)C(=O)OH; Cyc$^1$C(=O)OH; Cyc$^1$(C1-C6 alkyl)C(=O)OH; hetCyc$^4$(C1-C3 alkyl)C (=O)OH; Ar$^2$C(=O)OH; Ar$^2$(C1-C3 alkyl)C(=O)OH wherein the alkyl portion is optionally substituted with one or two groups independently selected from the group consisting of OH, C1-C6 alkyl, hydroxyC1-C6 alkyl, C1-C6 alkoxy and R$^e$R$^f$N—, where R$^e$ and R$^f$ are independently H and C1-C6 alkyl or R$^e$ and R$^f$ together with the nitrogen to which they are attached form a 5-6 membered azacyclic ring optionally having an additional ring heteroatom selected from N and O; hetAr$^2$C(=O)OH; or hetAr$^2$(C1-C3 alkyl) C(=O)OH wherein the alkyl portion is optionally substituted with one or two groups independently selected from the group consisting of OH, C1-C6 alkyl, hydroxyC1-C6 alkyl, C1-C6 alkoxy and R$^e$R$^f$N—, where R$^e$ and R$^f$ are independently H or C1-C6 alkyl) or R$^e$ and R$^f$ together with the nitrogen to which they are attached form a 5-6 membered azacyclic ring optionally having an additional ring heteroatom selected from N and O) using conventional amide bond formation conditions, for example by treating the carboxylic acid with an activating agent (e.g., HATU), followed by addition of the compound 13 having a deprotected amino D ring in the presence of a base (e.g., an amine base such as DIEA) in an appropriate solvent (such as DMA) to provide a functionalized compound 13. The same chemistry may be utilized with compounds 13a, 28 and 33 to prepare functionalized compounds 13a, 28 and 33, respectively.

As another example, a urea derivative (e.g., where D is hetCyc$^1$ where hetCyc$^1$ is piperazinyl and E is hetCyc$^4$C (=O)— or R$^1$R$^2$NC(=O)—) may be prepared by first activating a ring nitrogen in the D ring of compound 13 with triphosgene in the presence of DIEA and in a solvent such as DCM, followed by addition of a primary or secondary amine reagent (e.g., a reagent having the formula hetCyc$^4$NH$_2$ or R$^1$R$^2$NH) to provide a functionalized compound 13. The same chemistry may be utilized with compounds 13a, 28 and 33 to prepare functionalized compounds 13a, 28 and 33, respectively.

As another example, an N-alkyl derivative (e.g., where D is hetCyc$^1$ where hetCyc$^1$ is piperazinyl and E is hydroxyC1-C6 alkyl optionally substituted with one to three fluoros; (C1-C6 alkoxy)hydroxy C1-C6 alkyl; Ar$^2$C1-C6 alkyl; (Ar$^2$) hydroxy C2-C6 alkyl; or (hetAr$^2$)hydroxyC2-C6 alkyl, may be prepared by treating compound 13 where E is H with an alkyl bromide or alkyl chloride (e.g., hydroxyC1-C6 alkyl-X optionally substituted with one to three fluoros; (C1-C6 alkoxy)hydroxy C1-C6 alkyl-X; Ar$^2$C1-C6 alkyl-X; (Ar$^2$) hydroxy C2-C6 alkyl-X; or (hetAr$^2$)hydroxyC2-C6 alkyl-X where X is Br or Cl) or an epoxide in the presence of a base such as DIEA in a solvent at ambient or elevated temperatures) to provide a functionalized compound 13. The same chemistry may be utilized with compounds 13a, 28 and 33 to prepare functionalized compounds 13a, 28 and 33, respectively.

As another example, a compound of Formula I wherein D is hetCyc$^1$ (where hetCyc$^1$ is a 4-6 membered heterocyclic ring having 2 ring nitrogen atoms, wherein the heterocyclic ring is optionally substituted with one or more substituents independently selected from the group consisting of C1-C3 alkyl, fluoroC1-C3 alkyl, difluoroC1-C3 alkyl, trifluoroC1-C3 alkyl and OH, or said heterocyclic ring is substituted with a C3-C6 cycloalkylidene ring, or said heterocyclic ring is substituted with an oxo group) and E is Ar$^2$C1-C6 alkyl, hetAr$^2$C1-C6 alkyl, (hetCyc$^4$)C1-C6 alkyl, or (C3-C6 cycloalkoxy)C1-C6 alkyl, may be prepared by treating compound 13 where E is H (wherein E is on a ring nitrogen atom of hetCyc$^1$) with an appropriate aldehyde having the formula Ar$^2$(C1-C5 alkyl)C(=O)H, hetAr$^2$(C1-C5 alkyl)C(=O)H, (hetCyc$^4$)(C1-C5 alkyl)C(=O)H, or (C3-C6 cycloalkoxy) (C1-C5 alkyl)C(=O)H under standard reductive amination reaction conditions, for example in the presence of a base and a reducing agent, for example in the presence of a reducing agent such as sodium triacetoxyborohydride or sodium cyanoborohydride.

As another example, a sulfonamide derivative may be prepared by treating compound 13 where E is H with an appropriate sulfonyl chloride in the presence of a base, such as an amine base (such as triethylamine) in an appropriate solvent to provide a functionalized compound 13. The same chemistry may be utilized with compounds 13a, 28 and 33 to prepare functionalized compounds 13a, 28 and 33, respectively.

Further provided herein is a process for preparing of a compound of General Formula I or a pharmaceutically acceptable salt thereof as defined herein which comprises:

(a) for a compound of General Formula I where E is H and A, B, X$^1$, X$^2$, X$^3$, X$^4$, and D are as defined for General Formula I, coupling a corresponding compound having the formula

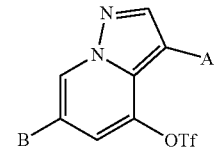

where A and B are as defined for General Formula I, with a corresponding compound having the formula 11

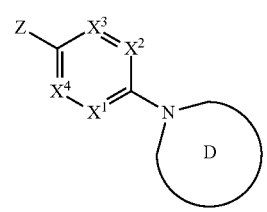

11 in the presence of a palladium catalyst and optionally a ligand and in the presence of a base, where Z is —B(OR$^a$) (OR$^b$) and R$^a$ and R$^b$ are H or (1-6C)alkyl, or R$^a$ and R$^b$ together with the atoms to which they are connected form a 5-6 membered ring optionally substituted with 1-4 substituents selected from (C1-C3 alkyl), the

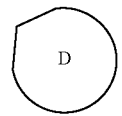

ring is as defined for hetCyc¹, hetCyc² and hetCyc³ of Formula I, and X¹, X², X³ and X⁴ are as defined for General Formula I, followed by removal of a protecting group on the D ring if present; or (b) for a compound of General Formula I where A, B, X¹, X², X³, X⁴, D and E are as defined for General Formula I with the exception that E is not hydrogen, functionalizing a corresponding compound having the formula

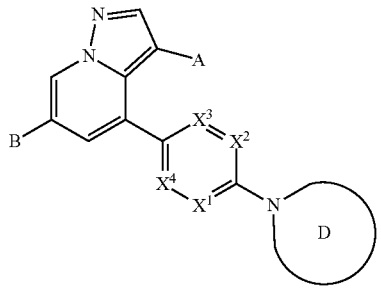

wherein the

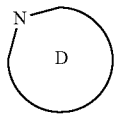

moiety is as defined for hetCyc¹, hetCyc² and hetCyc³ of Formula I, and A, B, X¹, X², X³ and X⁴ are as defined for General Formula I; or (c) for a compound of General Formula I where A is CN, D is as defined for General Formula I provided that the D ring is coupled to the ring defined by X¹, X², X³ and X⁴ through a ring nitrogen atom in the D ring, X¹, X², X³, X⁴ are as defined for Formula I provided that at least one of X¹ and X² is nitrogen, and E is as defined for General Formula I, reacting a corresponding compound having the formula 15

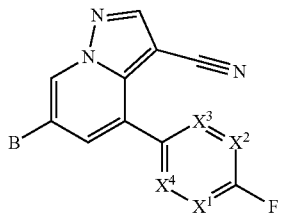

where B, X¹, X², X³ and X⁴ are as defined for General Formula I provided that at least one of X¹ and X² is nitrogen, with a corresponding compound having the formula 17

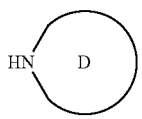

in the presence of a base, wherein the

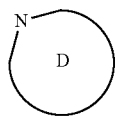

ring is as defined for hetCyc¹, hetCyc² and hetCyc³ of Formula I; or (d) for a compound of General Formula I where A is CN, E is H, and B, X¹, X², X³, X⁴, and D are as defined for General Formula I, reacting a compound having the formula 22

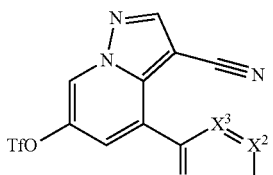

where X¹, X², X³, X⁴ and D are as defined for General Formula I, with a corresponding boronic ester having the formula

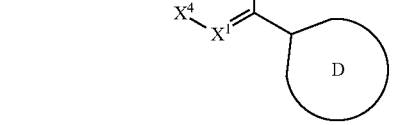

where hetAr¹ is as defined for General Formula I and $R^a$ and $R^b$ are H or CC6 alkyl, or $R^a$ and $R^b$ together with the atoms to which they are connected form a 5-6 membered ring optionally substituted with one to four C1-C3 alkyl substituents, in the presence of a palladium catalyst and optionally a ligand and in the presence of a base; and removing any protecting groups and optionally forming a pharmaceutically acceptable salt thereof.

Referring to processes (a) and (d), suitable palladium catalysts include $Pd(PPh_3)_4$, $Pd_2(dba)_3$, $Pd(OAc)_2$, and $Pd(PPh_3)_2Cl2$. Suitable ligands include X-PHOS (2-dicyclohexylphosphino-2',4',6'-triisopropylbiphenyl), DIPHOS (1,2-Bis(diphenylphosphino)ethane) or rac-BINAP (racemic-2,2'-Bis(diphenylphosphino)-1,1'-binaphthyl). The base may be, for example, an alkali metal carbonate, hydroxide, alkoxide or acetate, such as for example cesium carbonate, sodium carbonate, potassium carbonate, sodium hydroxide, sodium tert-butoxide or potassium acetate. Convenient solvents include aprotic solvents such as ethers (for example tetrahydrofuran or p-dioxane), toluene, DMF or DME. The reaction can be conveniently performed at a temperature ranging from ambient temperature to 120° C., for example from 80 to 110° C.

The ability of test compounds to act as RET inhibitors may be demonstrated by the assay described in Example A. $IC_{50}$'s are shown in Table 5.

Compounds of General Formula I have been found to be inhibitors of a RET kinase, and are useful for treating diseases and disorders which can be treated with a RET kinase inhibitor, such as RET-associated diseases and disorders, e.g., proliferative disorders such as cancers, including hematological cancers and solid tumors, and gastrointestinal disorders such as IBS.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer with dysregulation of a RET gene, a RET protein, or expression or activity, or level of any of the same (a RET-associated cancer) (e.g., as determined using a regulatory agency-approved, e.g., FDA-approved, assay or kit). In some embodiments, the subject has a tumor that is positive for dysregulation of a RET gene, a RET protein, or expression or activity, or level of any of the same (e.g., as determined using a regulatory agency-approved assay or kit). The subject can be a subject with a tumor(s) that is positive for dysregulation of a RET gene, a RET protein, or expression or activity, or level of any of the same (e.g., identified as positive using a regulatory agency-approved, e.g., FDA-approved, assay or kit). The subject can be a subject whose tumors have dysregulation of a RET gene, a RET protein, or expression or activity, or a level of the same (e.g., where the tumor is identified as such using a regulatory agency-approved, e.g., FDA-approved, kit or assay). In some embodiments, the subject is suspected of having a RET-associated cancer. In some embodiments, the subject has a clinical record indicating that the subject has a tumor that has dysregulation of a RET gene, a RET protein, or expression or activity, or level of any of the same (and optionally the clinical record indicates that the subject should be treated with any of the compositions provided herein). In some embodiments, the patient is a pediatric patient.

The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson Textbook of Pediatrics, 15th Ed. Philadelphia: W.B. Saunders Company, 1996; Rudolph A M, et al. Rudolph's Pediatrics, 21st Ed. New York: McGraw-Hill, 2002; and Avery M D, First L R. Pediatric Medicine, 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

In certain embodiments, compounds of General Formula I are useful for preventing diseases and disorders as defined herein (for example, autoimmune diseases, inflammatory diseases, and cancer). The term "preventing" as used herein means the prevention of the onset, recurrence or spread, in whole or in part, of the disease or condition as described herein, or a symptom thereof.

The term "RET-associated disease or disorder" as used herein refers to diseases or disorders associated with or having a dysregulation of a RET gene, a RET kinase (also called herein RET kinase protein or RET kinase), or the expression or activity or level of any (e.g., one or more) of the same (e.g., any of the types of dysregulation of a RET gene, a RET kinase, a RET kinase domain, or the expression or activity or level of any of the same described herein). Non-limiting examples of a RET-associated disease or disorder include, for example, cancer and gastrointestinal disorders such as irritable bowel syndrome (IBS).

The term "RET-associated cancer" as used herein refers to cancers associated with or having a dysregulation of a RET gene, a RET kinase (also called herein RET kinase protein or RET kinase), or expression or activity, or level of any of the same. Non-limiting examples of a RET-associated cancer are described herein.

The phrase "dysregulation of a RET gene, a RET kinase, or the expression or activity or level of any of the same" refers to a genetic mutation (e.g., a RET gene translocation that results in the expression of a fusion protein, a deletion in a RET gene that results in the expression of a RET protein that includes a deletion of at least one amino acid as compared to the wild-type RET protein, or a mutation in a RET gene that results in the expression of a RET protein with one or more point mutations, or an alternative spliced version of a RET mRNA that results in a RET protein that results in the deletion of at least one amino acid in the RET protein as compared to the wild-type RET protein), or a RET gene amplification that results in overexpression of a RET protein or an autocrine activity resulting from the overexpression of a RET gene a cell, that results in a pathogenic increase in the activity of a kinase domain of a RET protein (e.g., a constitutively active kinase domain of a RET protein) in a cell. As another example, a dysregulation of a RET gene, a RET protein, or expression or activity, or level of any of the same, can be a mutation in a RET gene that encodes a RET protein that is constitutively active or has increased activity as compared to a protein encoded by a RET gene that does not include the mutation. For example, a dysregulation of a RET gene, a RET protein, or expression or activity, or level of any of the same, can be the result of a gene or chromosome translocation which results in the expression of a fusion protein that contains a first portion of RET that includes a functional kinase domain, and a second portion of a partner protein (i.e., that is not RET). In some examples, dysregulation of a RET gene, a RET protein, or expression or activity, can be a result of a gene translation of one RET gene with another RET gene. Non-limiting examples of fusion proteins are described in Table 1. Non-limiting examples of RET kinase protein point mutations/insertions are described in Table 2. Additional examples of RET kinase protein point mutations are RET inhibitor resistance mutations. Non-limiting examples of RET inhibitor resistance mutations are described in Tables 3 and 4.

The term "wildtype" or "wild-type" describes a nucleic acid (e.g., a RET gene or a RET mRNA) or protein (e.g., a RET protein) that is found in a subject that does not have a RET-associated disease, e.g., a RET-associated cancer (and optionally also does not have an increased risk of developing a RET-associated disease and/or is not suspected of having a RET-associated disease), or is found in a cell or tissue from a subject that does not have a RET-associated disease, e.g., a RET-associated cancer (and optionally also does not have an increased risk of developing a RET-associated disease and/or is not suspected of having a RET-associated disease).

The term "regulatory agency" refers to a country's agency for the approval of the medical use of pharmaceutical agents with the country. For example, a non-limiting example of a regulatory agency is the U.S. Food and Drug Administration (FDA).

Provided herein is a method of treating cancer (e.g., a RET-associated cancer) in a patient in need of such treatment, the method comprising administering to the patient a therapeutically effective amount of a compound of General Formula I or a pharmaceutically acceptable salt or solvate thereof or a pharmaceutical composition thereof.

In some embodiments of any of the methods or uses described herein, the cancer (e.g., RET-associated cancer) is a hematological cancer. In some embodiments of any of the methods or uses described herein, the cancer (e.g., RET-associated cancer) is a solid tumor. In some embodiments of any of the methods or uses described herein, the cancer (e.g., RET-associated cancer) is lung cancer (e.g., small cell lung carcinoma or non-small cell lung carcinoma), papillary thyroid cancer, medullary thyroid cancer, differentiated thyroid cancer, recurrent thyroid cancer, refractory differentiated thyroid cancer, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, colorectal cancer (e.g., metastatic colorectal cancer), papillary renal cell carcinoma, ganglioneuromatosis of the gastroenteric mucosa, inflammatory myofibroblastic tumor, or cervical cancer. In some embodiments of any of the methods or uses described herein, the cancer (e.g., RET-associated cancer) is selected from the group of: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, colon cancer, colorectal cancer, craniopharyngioma, cutaneous T-cell lymphoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy and breast cancer, primary central nervous system lymphoma, primary peritoneal cancer, prostate cancer, rectal cancer, renal cell cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor.

In some embodiments, a hematological cancer (e.g., hematological cancers that are RET-associated cancers) is selected from the group consisting of leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). In one embodiment, the hematological cancer (e.g., the hematological cancer that is a RET-associated cancer) is AML or CMML.

In some embodiments, the cancer (e.g., the RET-associated cancer) is a solid tumor. Examples of solid tumors (e.g., solid tumors that are RET-associated cancers) include, for example, thyroid cancer (e.g., papillary thyroid carcinoma, medullary thyroid carcinoma), lung cancer (e.g., lung adenocarcinoma, small-cell lung carcinoma), pancreatic cancer, pancreatic ductal carcinoma, breast cancer, colon cancer, colorectal cancer, prostate cancer, renal cell carcinoma, head and neck tumors, neuroblastoma, and melanoma. See, for example, Nature Reviews Cancer, 2014, 14, 173-186.

In some embodiments, the cancer is selected from the group consisting of lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

In some embodiments, the patient is a human.

Compounds of General Formula I and pharmaceutically acceptable salts and solvates thereof are also useful for treating a RET-associated cancer.

Accordingly, also provided herein is a method for treating a patient diagnosed with or identified as having a RET-associated cancer, e.g., any of the exemplary RET-associated cancers disclosed herein, comprising administering to the patient a therapeutically effective amount of a compound of General Formula I or a pharmaceutically acceptable salt or solvate thereof, or a pharmaceutical composition thereof as defined herein.

Dysregulation of a RET kinase, a RET gene, or the expression or activity or level of any (e.g., one or more) of the same can contribute to tumorigenesis. For example, a dysregulation of a RET kinase, a RET gene, or expression or activity or level of any of the same can be a translocation, overexpression, activation, amplification, or mutation of a RET kinase, a RET gene, or a RET kinase domain. Translocation can include translocations involving the RET kinase domain, mutations can include mutations involving the RET ligand-binding site, and amplification can be of a RET gene. Other dysregulations can include RET mRNA splice variants and RET autocrine/paracrine signaling, which can also contribute to tumorigenesis.

In some embodiments, the dysregulation in a RET gene, a RET kinase, or expression or activity or level of any of the same, includes overexpression of wild-type RET kinase (e.g., leading to autocrine activation). In some embodiments, the dysregulation in a RET gene, a RET kinase protein, or expression or activity or level of any of the same, includes overexpression, activation, amplification, or mutation in a chromosomal segment comprising the RET gene or a portion thereof, including for example the kinase domain portion, or a portion capable of exhibiting kinase activity.

In some embodiments, the dysregulation of a RET gene, a RET kinase protein, or expression or activity or level of any of the same, includes one or more chromosome translocations or inversions resulting in a RET gene fusions. In some embodiments, the dysregulation of a RET gene, a RET kinase protein, or expression or activity or level of any of the same, is a result of genetic translocations in which the expressed protein is a fusion protein containing residues from a non-RET partner protein, and includes a minimum of a functional RET kinase domain.

Non-limiting examples of RET fusion proteins are shown in Table 1.

TABLE 1

Exemplary RET Fusion Partners and Cancers

| Fusion Partner | Non-limiting Exemplary RET-Associated Cancer(s) |
|---|---|
| BCR | Chronic Myelomonocytic Leukemia (CMML) |
| CLIP1 | Adenocarcinoma |
| KIF5B | NSCLC, Ovarian Cancer, Spitzoid Neoplasms; Lung Adenocarcinoma[3,4,14]; Adenosquamous Carcinomas[15] |
| CCDC6 (also called PTC1, D10S170, or H4) | NSCLC, Colon Cancer, Papillary Thyroid Cancer; Adenocarcinomas; Lung Adenocarcinoma; Metastatic Colorectal Cancer[5]; Adenosquamous Carcinomas[15] |
| PTC1ex9 | Metastatic papillary thyroid cancer[2] |
| NCOA4 (also called PTC3, ELE1, and RFG) | Papillary Thyroid Cancer, NSCLC, Colon Cancer, Salivary Gland Cancer, Metastatic Colorectal Cancer[5]; Lung Adenocarcinoma[15]; Adenosquamous Carcinomas[15] Diffuse Sclerosing Variant of Papillary Thyroid Cancer[16] |
| TRIM33 (also called PTC7 and RFG7) | NSCLC, Papillary Thyroid Cancer |
| ERC1 (also called ELKS) | Papillary Thyroid Cancer, Breast Cancer |
| FGFR1OP | CMML, Primary Myelofibrosis with secondary Acute Myeloid Leukemia |
| MBD1(also known as PCM1) | Papillary Thyroid Cancer |
| RAB6IP2 | Papillary Thyroid Cancer |
| PRKAR1A (also called PTC2) | Papillary Thyroid Cancer |
| TRIM24 (also called PTC6) | Papillary Thyroid Cancer |
| KTN1 (also called PTC8) | Papillary Thyroid Cancer |
| GOLGA5 (also called PTC5) | Papillary Thyroid Cancer, Spitzoid Neoplasms |
| HOOK3 | Papillary Thyroid Cancer |
| KIAA1468 (also called PTC9 and RFG9) | Papillary Thyroid Cancer, Lung Adenocarcinoma[8] |
| TRIM27 (also called RFP) | Papillary Thyroid Cancer |
| AKAP13 | Papillary Thyroid Cancer |
| FKBP15 | Papillary Thyroid Cancer |
| SPECC1L | Papillary Thyroid Cancer; Thyroid Gland Carcinoma |
| TBL1XR1 | Papillary Thyroid Cancer; Thyroid Gland Carcinoma |
| CEP55 | Diffuse Gastric Cancer[7] |
| CUX1 | Lung Adenocarcinoma |
| KIAA1468 | Lung Adenocarcinoma[12] |
| ACBD5 | Papillary Thyroid Carcinoma |

TABLE 1-continued

Exemplary RET Fusion Partners and Cancers

| Fusion Partner | Non-limiting Exemplary RET-Associated Cancer(s) |
|---|---|
| MYH13 | Medullary Thyroid Carcinoma[1] |
| Uncharacterized | Inflammatory Myofibroblastic Tumor[6] |
| PIBF1 | Bronchiolus Lung Cell Carcinoma[9] |
| KIAA1217 | Papillary Thyroid Cancer[10,13] Lung Adenocarcinoma[14] NSCLC[14] |
| MPRIP | NSCLC[11] |

[1]Grubbs et al., *J. Clin. Endocrinol. Metab.* 100: 788-793, 2015.
[2]Halkova et al., *Human Pathology* 46: 1962-1969, 2015.
[3]U.S. Pat. No. 9,297,011
[4]U.S. Pat. No. 9,2161,72
[5]Le Rolle et al., *Oncotarget.* 6(30): 28929-37, 2015.
[6]Antonescu et al., *Am J Surg Pathol.* 39(7): 957-67, 2015.
[7]U.S. Patent Application Publication No. 2015/0177246.
[8]U.S. Patent Application Publication No. 2015/0057335.
[9]Japanese Patent Application Publication No. 2015/109806A.
[10]Chinese Patent Application Publication No. 105255927A.
[11]Fang, et al. *Journal of Thoracic Oncology* 11.2 (2016): S21-S22.
[12]European Patent Application Publication No. EP3037547A1.
[13]Lee et al., *Oncotarget.* DOI: 10.18632/oncotarget.9137, e-published ahed of printing, 2016.
[14]Saito et al., *Cancer Science* 107: 713-720, 2016.
[15]Pirker et al., *Transl. Lung Cancer* Res. 4(6): 797-800, 2015
[16]Joung et al., *Histopathology* 69(1): 45-53, 2016

In some embodiments, the dysregulation of a RET gene, a RET kinase, or expression or activity or level of any of the same, includes one or more deletions (e.g., deletion of an amino acid at position 4), insertions, or point mutation(s) in a RET kinase. In some embodiments, the dysregulation of a RET gene, a RET kinase, or expression or activity or level of any of the same, includes a deletion of one or more residues from the RET kinase, resulting in constitutive activity of the RET kinase domain.

In some embodiments, the dysregulation of a RET gene, a RET kinase, or expression or activity or level of any of the same, includes at least one point mutation in a RET gene that results in the production of a RET kinase that has one or more amino acid substitutions as compared to the wild-type RET kinase (see, for example, the missense point mutations listed in Table 2).

TABLE 2

Activating RET Kinase Protein Point Mutations/Insertions/Deletions Exemplary RET Point Mutations Amino acid position 2
Amino acid position 3
Amino acid position 4
Amino acid position 5
Amino acid position 6
Amino acid position 7
Amino acid position 8
Amino acid position 11
Amino acid position 12
Amino acid position 13
Amino acid position 20
Amino acid position 32 (e.g., S32L)
Amino acid position 34 (e.g., D34S)
Amino acid position 40 (e.g., L40P)
Amino acid position 64 (e.g., P64L)
Amino acid position 67 (e.g., R67H)
Amino acid position 114 (e.g., R114H)
Amino acid position 136 (e.g., glutamic acid to stop codon)

TABLE 2-continued

Activating RET Kinase Protein Point Mutations/Insertions/Deletions Exemplary RET Point Mutations Amino acid position 145 (e.g., V145G)
Amino acid position 180 (e.g., arginine to stop codon)
Amino acid position 200
Amino acid position 292 (e.g., V292M)
Amino acid position 294
Amino acid position 321 (e.g., G321R)
Amino acid position 330 (e.g., R330Q)
Amino acid position 338 (e.g., T338I)
Amino acid position 360 (e.g., R360W)
Amino acid position 373 (e.g., alanine to frameshift)
Amino acid position 393 (e.g., F393L)
Amino acid position 432
Δ Amino acid residues 505-506 (6-Base Pair In-Frame Germline Deletion in Exon 7)[3]
Amino acid position 510 (e.g., A510V)
Amino acid position 511 (e.g., E511K)
Amino acid position 513 (e.g., A513D)[7]*
Amino acid position 515 (e.g., C515S, C515W[4])
Amino acid position 525 (e.g., R525W)[7]*
Amino acid position 531 (e.g., C531R, or 9 base pair duplication[2])
Amino acid position 532 (e.g., duplication)[2]
Amino acid position 533 (e.g., G533C[12], G533S)
Amino acid position 550 (e.g., G550E)
Amino acid position 591 (e.g., V591I)
Amino acid position 593 (e.g., G593E)
Amino acid position 600 (e.g., R600Q)
Amino acid position 602 (e.g., I602V)[6]
Amino acid position 603 (e.g., K603Q, K603E[2])
Amino acid position 606 (e.g., Y606C)
Amino acid position 609 (e.g., C609Y, C609S, C609G, C609R, C609F, C609W)
Amino acid position 611 (e.g., C611R, C611S, C611G, C611Y, C611F, C611W)
Amino acid position 618 (e.g., C618S, C618Y, C618R, C618Y, C618G, C618F, C618W)
Amino acid position 619 (e.g., F619F)
Amino acid position 620 (e.g., C620S, C620W, C620R, C620G, C620L, C620Y, C620F)
Amino acid position 623 (e.g., E623K)
Amino acid position 624 (e.g., D624N)
Amino acid position 630 (e.g., C630A, C630R, C630S, C630Y, C630F)
Amino acid position 631 (e.g., D631N, D631Y, D631A, D631G, D631V, D631E, )
Amino acid position 632 (e.g., E632K, E632G[5, 11])
Δ Amino acid residues 632-633 (6-Base Pair In-Frame Germline Deletion in Exon 11)[9]
Amino acid position 633 (e.g., 9 base pair duplication[2])
Amino acid position 634 (e.g., C634W, C634Y, C634S, C634R, C634F, C634G, C634L, C634A, or C634T, or an insertion ELCR[2], or a 12 base pair duplication[2]) (e.g., causing MTC)
Amino acid position 635 (e.g., R635G)
Amino acid position 636 (e.g., T636P[2], T636M[4])
Amino acid position 640 (e.g., A640G)
Amino acid position 641 (e.g., A641S, A641T[8])
Amino acid position 648 (e.g., V648I)
Amino acid position 649 (e.g., S649L)
Amin acid position 664 (e.g., A664D)
Amino acid position 665 (e.g., H665Q)
Amino acid position 666 (e.g., K666E, K666M, K666N)
Amino acid position 686 (e.g., S686N)
Amino acid position 691 (e.g., G691S)
Amino acid position 694 (e.g., R694Q)
Amino acid position 700 (e.g., M700L)
Amino acid position 706 (e.g., V706M, V706A)
Amino acid position 713 splice variant (e.g., E713K)[6]
Amino acid position 736 (e.g., G736R)[6]
Amino acid position 748 (e.g., G748C)
Amino acid position 750 (e.g., A750P)
Amino acid position 765 (e.g., S765P)
Amino acid position 766 (e.g., P766S, P766M[6])
Amino acid position 768 (e.g., E768Q, E768D)
Amino acid position 769 (e.g., L769L)
Amino acid position 770 (e.g., R770Q)

TABLE 2-continued

Activating RET Kinase Protein Point Mutations/Insertions/Deletions
Exemplary RET Point Mutations Amino acid position 771 (e.g., D771N)
Amino acid position 777 (e.g., N777S)
Amino acid position 778 (e.g., V778I)
Amino acid position 781 (e.g., Q781R)
Amino acid position 790 (e.g., L790F)
Amino acid position 791 (e.g., Y791F)
Amino acid position 802
Amino acid position 804 (e.g., V804L, V804M, or V804E) (e.g., causing MTC)
Amino acid position 805 (e.g., E805K)
Amino acid position 806 (e.g., E806C; Y806E, Y806F, Y806S, Y806G, Y806C[2])
Amino acid position 818 (e.g., E818K)
Amino acid position 819 (e.g., S819I)
Amino acid position 823 (e.g., G823E)
Amino acid position 826 (e.g., Y826M)[10]
Amino acid position 833 (e.g., R833C)
Amino acid position 841 (e.g., P841L, P841P)
Amino acid position 843 (e.g., E843D)
Amino acid position 844 (e.g., R844W, R844Q, R844L)
Amino acid position 848 (e.g., M848T)
Amino acid position 852 (e.g., I852M)
Amino acid position 866 (e.g., A866W[2])
Amino acid position 873 (e.g., R873W)
Amino acid position 876 (e.g., A876V)
Amino acid position 881 (e.g., L881V)
Amino acid position 882
Amino acid position 883 (e.g., A883F, A883S, A883T)
Amino acid position 884 (e.g., E884K)
Amino acid position 886 (e.g., R886W)
Amino acid position 891 (e.g., S891A)
Amino acid position 897 (e.g., R897Q)
Amino acid position 898 (e.g., D898V)
Amino acid position 901 (e.g., E901K)
Amino acid position 904 (e.g., S904F, S904C[2])
Amino acid position 907 (e.g., K907E, K907M)
Amino acid position 908 (e.g., R908K)
Amino acid position 911 (e.g., G911D)
Amino acid position 912 (e.g., R912P, R912Q)
Amino acid position 918 (e.g., M918T, M918V, M918L[6]) (e.g., causing MTC)
Amino acid position 919 (e.g., A919V)
Amino acid position 921 (e.g., E921K)
Amino acid position 922 (e.g., S922P, S922Y)
Amino acid position 930 (e.g., T930M)
Amino acid position 961 (e.g., F961L)
Amino acid position 972 (e.g., R972G)
Amino acid position 982 (e.g., R982C)
Amino acid position 1009 (e.g., M1009V)
Amino acid position 1017 (e.g., D1017N)
Amino acid position 1041 (e.g., V1041G)
Amino acid position 1064 (e.g., M1064T)
RET + 3[1]

[1]U.S. Patent Application Publication No. 2014/0272951.
[2]Krampitz et al., Cancer 120: 1920-1931, 2014.
[3]Latteyer, et al., J. Clin. Endocrinol. Metab. 101(3): 1016-22, 2016.
[4]Silva, et al. Endocrine 49.2: 366-372, 2015.
[5]Scollo, et al., Endocr. J. 63(1): 87-91, 2016.
[6]Jovanovic, et al., Prilozi 36(1): 93-107, 2015.
[7]Qi, et al., Oncotarget. 6(32): 33993-4003, 2015. *R525W and A513D appear to act in combination with S891A to enchance oncogenic activity.
[8]Kim, et al. ACTA ENDOCRINOLOGICA-BUCHAREST 11.2, 189-194, 2015.
[9]Cecchirini, et al. Oncogene, 14, 2609-2612, 1997.
[10]Karrasch, et al. Eur. Thyroid J., 5(1): 73-7, 2016.
[11]Scollo et al., Endocr. J. 63: 87-91, 2016.
[12]Wells et al., Thyroid 25: 567-610, 2015.

In some embodiments, the dysregulation of a RET gene, a RET kinase, or expression or activity or level of any of the same, includes a splice variation in a RET mRNA which results in an expressed protein that is an alternatively spliced variant of RET having at least one residue deleted (as compared to the wild-type RET kinase) resulting in a constitutive activity of a RET kinase domain.

In some embodiments, the dysregulation of a RET gene, a RET kinase, or expression or activity or level of any of the same, includes at least one point mutation in a RET gene that results in the production of a RET kinase that has one or more amino acid substitutions or insertions or deletions in a RET gene that results in the production of a RET kinase that has one or more amino acids inserted or removed, as compared to the wild-type RET kinase, which is more resistant to inhibition of its phosphotransferase activity by one or more RET kinase inhibitor(s) that is not a compound of General Formula I or a pharmaceutically acceptable salt or solvate thereof, as compared to a wildtype RET kinase or a RET kinase not including the same mutation. Such mutations can, optionally, not cause a cancer cell or a tumor to decrease its sensitivity to treatment with a compound of General Formula I or a pharmaceutically acceptable salt or solvate thereof (e.g., as compared to a cancer cell or a tumor that does not include the particular RET inhibitor resistance mutation). In such embodiments, a RET inhibitor resistance mutation can result in a RET kinase that has one or more of an increased $V_{max}$, a decreased $K_m$ for ATP, and an increased $K_D$ for a RET kinase inhibitor that is not a compound of General Formula I or a pharmaceutically acceptable salt or solvate thereof, when in the presence of a RET kinase inhibitor that is not a compound of General Formula I or a pharmaceutically acceptable salt or solvate thereof, as compared to a wildtype RET kinase or a RET kinase not having the same mutation in the presence of the same RET kinase inhibitor.

In other embodiments, the dysregulation of a RET gene, a RET kinase, or expression or activity or level of any of the same, includes at least one point mutation in a RET gene that results in the production of a RET kinase that has one or more amino acid substitutions as compared to the wild-type RET kinase, and which has increased resistance to a compound of General Formula I or a pharmaceutically acceptable salt or solvate thereof, as compared to a wildtype RET kinase or a RET kinase not including the same mutation. In such embodiments, a RET inhibitor resistance mutation can result in a RET kinase that has one or more of an increased $V_{max}$, a decreased $K_m$, and a decreased $K_D$ in the presence of a compound of General Formula I or a pharmaceutically acceptable salt or solvate thereof, as compared to a wildtype RET kinase or a RET kinase not having the same mutation in the presence of the same compound of General Formula I or a pharmaceutically acceptable salt or solvate thereof.

Examples of RET inhibitor resistance mutations can, e.g., include point mutations, insertions, or deletions in and near the ATP binding site in the tertiary structure of RET kinase, including but not limited to the gatekeeper residue, P-loop residues, residues in or near the DFG motif, and ATP cleft solvent front amino acid residues. Additional examples of these types of mutations include changes in residues that may affect enzyme activity and/or drug binding including but are not limited to residues in the activation loop, residues near or interacting with the activation loop, residues contributing to active or inactive enzyme conformations, changes including mutations, deletions, and insertions in the loop proceeding the C-helix and in the C-helix. Specific residues or residue regions that may be changed (and are RET inhibitor resistance mutations) include but are not limited to those listed in Table 3 based on the human wildtype RET protein sequence (e.g., SEQ ID NO: 1). Additional examples of RET inhibitor resistance mutation positions are shown in Table 4. Changes to these residues may include single or multiple amino acid changes, insertions within or flanking the sequences, and deletions within or flanking the sequences.

In some embodiments, compounds of General Formula I and pharmaceutically acceptable salts and solvates are useful in treating patients that develop cancers with RET inhibitor resistance mutations (that result in an increased resistance to a RET inhibitor that is not a compound of General Formula I or a pharmaceutically acceptable salt or solvate thereof, e.g., a substitution at amino acid position 804, e.g., V804M, V804L, or V804E) by either dosing in combination or as a follow-up therapy to existing drug treatments (e.g., other RET kinase inhibitors that are not a compound of General Formula I or a pharmaceutically acceptable salt or solvate thereof). Exemplary RET kinase inhibitors (e.g., other RET kinase inhibitors that are not a compound of General Formula I or a pharmaceutically acceptable salt or solvate thereof) are described herein. In some embodiments, a RET kinase inhibitor can be selected from the group consisting of cabozantinib, vandetanib, alectinib, sorafenib, levatinib, ponatinib, dovitinib, sunitinib, foretinib, BLU667, and BLU6864.

In some embodiments, compounds of the General Formula I and pharmaceutically acceptable salts and solvates would be useful for treating a cancer that has been identified as having one or more RET inhibitor resistance mutations (that result in an increased resistance to a RET inhibitor that is not a compound of General Formula I or a pharmaceutically acceptable salt or solvate thereof, e.g., a substitution at amino acid position 804, e.g., V804M, V804L, or V804E).

TABLE 3

RET Inhibitor Resistance Mutations
Exemplary RET Inhibitor Resistance Mutations

Amino acid position 804 (V804M, V804L, V804E)[1,2]
Amino acid position 804/805 (V804M/E805K)[3]
Amino acid position 806 (Y806C, Y806E)[4]

[1]Yoon et al., *J. Med. Chem.* 59(1): 358-73, 2016.
[2]U.S. Pat. No. 8,629,135.
[3]Cranston, et al., *Cancer Res.* 66(20): 10179-87, 2006.
[4]Carlomagno, et al., *Endocr. Rel. Cancer* 16(1): 233-41, 2009.

TABLE 4

Additional Exemplary Amino Acid Positions of RET Inhibitor Resistance Mutations

| RET Residue # | Kinase Location |
|---|---|
| 788 | CONTRIBUTES TO INACTIVE/ACTIVE CONFORMATION EQUILIBRIUM |
| 804 | GATEKEEPER |
| 806 | ATP CLEFT SOLVENT FRONT |
| 810 | SOLVENT FRONT |
| 891 | NEAR DFG MOTIF |
| 729-739 | P-LOOP RESIDUES |
| 759-768 | LOOP PROCEEDING C-HELIX |
| 769-781 | C-HELIX |
| 868-874 | NEAR OR INTERACTING WITH THE ACTIVATION LOOP |
| 891-914 | ACTIVATION LOOP |

The oncogenic role of RET was firstly described in papillary thyroid carcinoma (PTC) (Grieco et al., *Cell*, 1990, 60, 557-63), which arises from follicular thyroid cells and is the most common thyroid malignancy. Approximately 20-30% of PTC harbor somatic chromosomal rearrangements (translocations or inversions) linking the promoter and the 5' portions of constitutively expressed, unrelated genes to the RET tyrosine kinase domain (Greco et al., *Q. J. Nucl. Med. Mol. Imaging,* 2009, 53, 440-54), therefore driving its ectopic expression in thyroid cells. To date, a variety of fusion partners have been identified, all providing a protein/protein interaction domain that induces ligand-independent RET dimerization and constitutive kinase activity (see, e.g., Table 1). The role of RET-PTC rearrangements in the pathogenesis of PTC has been confirmed in transgenic mice (Santoro et al., *Oncogene*, 1996, 12, 1821-6). Recently, a 10.6 Mb pericentric inversion in chromosome 10, where RET gene maps, has been identified in about 2% of lung adenocarcinoma patients, generating different variants of the chimeric gene KIF5B-RET (Ju et al., *Genome Res.,* 2012, 22, 436-45; Kohno et al., 2012, *Nature Med.,* 18, 375-7; Takeuchi et al., *Nature Med.,* 2012, 18, 378-81; Lipson et al., 2012, *Nature Med.,* 18, 382-4). The fusion transcripts are highly expressed and all the resulting chimeric proteins contain the N— terminal portion of the coiled-coil region of KIF5B, which mediates homodimerization, and the entire RET kinase domain. None of RET positive patients harbor other known oncogenic alterations (such as EGFR or K-Ras mutation, ALK translocation), supporting the possibility that KIF5B-RET fusion could be a driver mutation of lung adenocarcinoma. The oncogenic potential of KIF5B-RET has been confirmed by transfecting the fusion gene into cultured cell lines: similarly to what has been observed with RET-PTC fusion proteins, KIF5B-RET is constitutively phosphorylated and induces NIH-3T3 transformation and IL-3 independent growth of BA-F3 cells. However, other RET fusion proteins have been identified in lung adenocarcinoma patients, such as the CCDC6-RET fusion protein, which has been found to play a key role in the proliferation of the human lung adenocarcinoma cell line LC-2/ad (*Journal of Thoracic Oncology,* 2012, 7(12): 1872-1876). RET inhibitors have been shown to be useful in treating lung cancers involving RET rearrangements (Drilon, A. E. et al. *J Clin Oncol* 33, 2015 (suppl; abstr 8007)). RET fusion proteins have also been identified in patients having colorectal cancer (Song Eun-Kee, et al. *International Journal of Cancer,* 2015, 136: 1967-1975).

Besides rearrangements of the RET sequence, gain of function point mutations of RET proto-oncogene are also driving oncogenic events, as shown in medullary thyroid carcinoma (MTC), which arises from parafollicular calcitonin-producing cells (de Groot, et al., *Endocrine Rev.,* 2006, 27, 535-60; Wells and Santoro, *Clin. Cancer Res.,* 2009, 15, 7119-7122). Around 25% of MTC are associated with multiple endocrine neoplasia type 2 (MEN2), a group of inherited cancer syndromes affecting neuroendocrine organs caused by germline activating point mutations of RET. In MEN2 subtypes (MEN2A, MEN2B and Familial MTC/FMTC) RET gene mutations have a strong phenotype-genotype correlation defining different MTC aggressiveness and clinical manifestations of the disease. In MEN2A syndrome mutations involve one of the six cysteine residues (mainly C634) located in the cysteine-rich extracellular region, leading to ligand-independent homodimerization and constitutive RET activation. Patients develop MTC at a young age (onset at 5-25 years) and may also develop pheochromocytoma (50%) and hyperparathyroidism. MEN2B is mainly caused by M918T mutation, which is located in the kinase domain. This mutation constitutively activates RET in its monomeric state and alters substrate recognition by the kinase. MEN2B syndrome is characterized by an early onset (<1 year) and very aggressive form of MTC, pheochromocytoma (50% of patients) and ganglioneuromas. In FMTC the only disease manifestation is MTC, usually occurring at an adult age. Many different mutations have been detected, spanning the entire RET gene. The remaining 75% of MTC cases are sporadic and about 50% of them harbor RET somatic mutations: the most frequent mutation is M918T that, as in MEN2B, is associated with the most aggressive phenotype. Somatic point mutations of RET have also been described in other tumors such as colorectal cancer (Wood et al., *Science*, 2007, 318, 1108-13) and small cell lung carcinoma (*Jpn. J. Cancer Res.*, 1995, 86, 1127-30).

RET signaling components have been found to be expressed in primary breast tumors and to functionally interact with estrogen receptor-α pathway in breast tumor cell lines (Boulay et al., *Cancer Res.* 2008, 68, 3743-51; Plaza-Menacho et al., *Oncogene*, 2010, 29, 4648-57), while RET expression and activation by GDNF family ligands could play an important role in perineural invasion by different types of cancer cells (Ito et al., *Surgery*, 2005, 138, 788-94; Gil et al., J. Natl. Cancer Inst., 2010, 102, 107-18; Iwahashi et al., Cancer, 2002, 94, 167-74).

RET is also expressed in 30-70% of invasive breast cancers, with expression being relatively more frequent in estrogen receptor-positive tumors (Plaza-Menacho, I., et al., *Oncogene*, 2010, 29, 4648-4657; Esseghir, S., et al., *Cancer Res.*, 2007, 67, 11732-11741; Morandi, A., et al., *Cancer Res.*, 2013, 73, 3783-3795; Gattelli, A., *EMBO Mol. Med.*, 2013, 5, 1335-1350).

The identification of RET rearrangements has been reported in a subset of (patient-derived xenograft) PDX established from colorectal cancer. Although the frequency of such event in colorectal cancer patients remains to be defined, these data suggest a role of RET as a target in this indication (Gozgit et al., AACR Annual Meeting 2014). Studies have shown that the RET promoter is frequently methylated in colorectal cancers, and heterozygous missense mutations, which are predicted to reduce RET expression, are identified in 5-10% of cases, which suggests that RET might have some features of a tumor suppressor in sporadic colon cancers (Luo, Y., et al., *Oncogene*, 2013, 32, 2037-2047; Sjoblom, T., et al., *Science*, 2006, 268-274; Cancer Genome Atlas Network, *Nature*, 2012, 487, 330-337).

An increasing number of tumor types are now being shown to express substantial levels of wild-type RET kinase that could have implications for tumor progression and spread. RET is expressed in 50-65% of pancreatic ductal carcinomas, and expression is more frequent in metastatic and higher grade tumors (Ito, Y, et al., *Surgery*, 2005, 138, 788-794; Zeng, Q., et al., *J. Int. Med. Res.* 2008, 36, 656-664).

In neoplasms of hematopoietic lineages, RET is expressed in acute myeloid leukemia (AML) with monocytic differentiation, as well as in CMML (Gattei, V. et al., *Blood*, 1997, 89, 2925-2937; Gattei, V., et al., *Ann. Hematol.* 1998, 77, 207-210; Camos, M., *Cancer Res.* 2006, 66, 6947-6954). Recent studies have identified rare chromosomal rearrangements that involve RET in patients with chronic myelomonocytic leukemia (CMML). CMML is frequently associated with rearrangements of several tyrosine kinases, which result in the expression of chimeric cytosolic oncoproteins that lead to activation of RAS pathways (Kohlmann, A., et al., *J. Clin. Oncol.* 2010, 28, 2858-2865). In the case of RET, gene fusions that link RET with BCR (BCR-RET) or with fibroblast growth factor receptor 1 oncogene partner (FGFR1OP-RET) were transforming in early hematopoietic progenitor cells and could shift maturation of these cells towards monocytic paths, probably through the initiation of RET-mediated RAS signaling (Ballerini, P., et al., *Leukemia*, 2012, 26, 2384-2389).

RET expression has also been shown to occur in several other tumor types, including prostate cancer, small-cell lung carcinoma, melanoma, renal cell carcinoma, and head and neck tumors (Narita, N., et al., *Oncogene*, 2009, 28, 3058-3068; Mulligan, L. M., et al., *Genes Chromosomes Cancer*, 1998, 21, 326-332; Flavin, R., et al., *Urol. Oncol.*, 2012, 30, 900-905; Dawson, D. M., *J Natl Cancer Inst*, 1998, 90, 519-523).

In neuroblastoma, RET expression and activation by GFLs has roles in tumor cell differentiation, potentially collaborating with other neurotrophic factor receptors to down regulate N-Myc, the expression of which is a marker of poor prognosis (Hofstra, R. M., W., et al., *Hum. Genet.* 1996, 97, 362-364; Petersen, S. and Bogenmann, E., *Oncogene*, 2004, 23, 213-225; Brodeur, G. M., *Nature Ref. Cancer*, 2003, 3, 203-216).

Multitargeted inhibitors which cross react with RET are known (Borrello, M. G., et al., *Expert Opin. Ther. Targets*, 2013, 17(4), 403-419; International Patent Application Nos. WO 2014/141187, WO 2014/184069, and WO 2015/079251).

Accordingly, provided herein are methods for treating a patient diagnosed with (or identified as having) a cancer (e.g., a RET-associated cancer) (e.g., a RET-associated cancer that includes one or more RET inhibitor resistance mutations) that include administering to the patient a therapeutically effective amount of a compound of General Formula I or a pharmaceutically acceptable salt or solvate thereof. Also provided herein are methods for treating a patient identified or diagnosed as having a RET-associated cancer (e.g., a patient that has been identified or diagnosed as having a RET-associated cancer through the use of a regulatory agency-approved, e.g., FDA-approved test or assay for identifying dysregulation of a RET gene, a RET kinase, or expression or activity or level of any of the same, in a patient or a biopsy sample from the patient) (e.g., any of the RET-associated cancers described herein or known in the art) (e.g., a RET-associated cancer that includes one or more RET inhibitor resistance mutations) that include administering to the patient a therapeutically effective amount of a compound of General Formula I or a pharmaceutically acceptable salt or solvate thereof or a pharmaceutical composition thereof. In some embodiments, the test or assay is provided as a kit.

Also provided are methods for treating cancer in a patient in need thereof, the method comprising: (a) determining if the cancer in the patient is a RET-associated cancer (e.g., a RET-associated cancer including RET-associated cancers having one or more RET inhibitor resistance mutations) (e.g., using a regulatory-agency approved, e.g., FDA-approved, kit for identifying dysregulation of a RET gene, a RET kinase, or expression or activity or level of any of the same, in a patient or a biopsy sample from the patient, or by performing any of the non-limiting examples of assays described herein); and (b) if the cancer is determined to be a RET-associated cancer, administering to the patient a therapeutically effective amount of a compound of General Formula I or a pharmaceutically acceptable salt or solvate thereof or a pharmaceutical composition thereof. Some embodiments of these methods further include administering to the subject another anticancer agent (e.g., another RET inhibitor, e.g., a RET inhibitor that is not a compound of General Formula I or a pharmaceutically acceptable salt or solvate thereof, or a different RET inhibitor that is a compound of General Formula I or a pharmaceutically acceptable salt or solvate thereof). In some embodiments, the subject was previously treated with a RET inhibitor that is not a compound of General Formula I or a pharmaceutically acceptable salt or solvate thereof or previously treated with another anticancer treatment, e.g., after resection of a tumor or radiation therapy.

Also provided are methods of treating a patient (e.g., a patient suspected of having a RET-associated cancer, a patient presenting with one or more symptoms of a RET-associated cancer, or a patient having an elevated risk of developing a RET-associated cancer) that include performing an assay (e.g., an assay that utilizes next generation sequencing, pyrosequencing, immunohistochemistry, or break apart FISH analysis) (e.g., using a regulatory agency-approved, e.g., FDA-approved kit) on a sample obtained from the patient to determine whether the patient has dysregulation of a RET gene, a RET kinase, or expression or activity or level of any of the same (e.g., one or more RET inhibitor resistance mutations), and administering (e.g., specifically or selectively administering) a therapeutically effective amount of a compound of General Formula I or a pharmaceutically acceptable salt or solvate thereof or a pharmaceutical composition thereof to the patient determined to have dysregulation of a RET gene, a RET kinase, or expression or activity or level of any of the same. Additional, non-limiting assays that may be used in these methods are described herein. Additional assays are also known in the art. Some embodiments of these methods further include administering to the subject another anticancer agent (e.g., another RET inhibitor, e.g., a RET inhibitor that is not a compound of General Formula I or a pharmaceutically acceptable salt or solvate thereof, or a different RET inhibitor that is a compound of General Formula I or a pharmaceutically acceptable salt or solvate thereof). In some embodiments of these methods, the subject was previously treated with a RET inhibitor that is not a compound of General Formula I or a pharmaceutically acceptable salt or solvate thereof or previously treated with another anticancer treatment, e.g., after resection of a tumor or radiation therapy.

Also provided is a compound of General Formula I or a pharmaceutically acceptable salt or solvate thereof or a pharmaceutical composition thereof for use in treating a RET-associated cancer (e.g., a RET-associated cancer including RET-associated cancers having one or more RET inhibitor resistance mutations) in a patient identified or diagnosed as having a RET-associated cancer through a step of performing an assay (e.g., an in vitro assay) (e.g., an assay that utilizes next generation sequencing, immunohistochemistry, or break apart FISH analysis) (e.g., using a regulatory agency-approved, e.g., FDA-approved kit) on a sample obtained from the patient to determine whether the patient has dysregulation of a RET gene, a RET kinase, or expression or activity or level of any of the same (e.g., one or more RET inhibitor resistance mutations), where the presence of dysregulation of a RET gene, a RET kinase, or expression or activity or level of any of the same, identifies that the patient has a RET-associated cancer. Also provided is the use of a compound of General Formula I or a pharmaceutically acceptable salt or solvate thereof for the manufacture of a medicament for treating a RET-associated cancer (e.g., a RET-associated cancer having one or more RET inhibitor resistance mutations) in a patient identified or diagnosed as having a RET-associated cancer through a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the patient to determine whether the patient has a dysregulation of a RET gene, a RET kinase, or expression or activity or level of any of the same where the presence of dysregulation of a RET gene, a RET kinase, or expression or activity or level of any of the same, identifies that the patient has a RET-associated cancer. Some embodiments of any of the methods or uses described herein further include recording in the patient's clinical record (e.g., a computer readable medium) that the patient determined to have dysregulation of a RET gene, a RET kinase, or expression or activity or level of any of the same (e.g., determined to have one or more RET inhibitor resistance mutations), through the performance of the assay, should be administered a compound of General Formula I or a pharmaceutically acceptable salt or solvate thereof or a pharmaceutical composition thereof.

Also provided is a compound of General Formula I or a pharmaceutically acceptable salt or solvate thereof, for use in the treatment of a cancer (e.g., a RET-associated cancer, e.g., a RET-associated cancer having one or more RET inhibitor resistance mutations) in a patient in need thereof or a patient identified or diagnosed as having a RET-associated cancer (e.g., a patient that has been identified or diagnosed as having a RET-associated cancer through the use of a regulatory agency-approved, e.g., FDA-approved, kit for identifying dysregulation of a RET gene, a RET kinase, or expression or activity or level of any of the same, in a patient or a biopsy sample from the sample) (e.g., any of the RET-associated cancers described herein or known in the art). Also provided is the use of a compound of General Formula I or a pharmaceutically acceptable salt or solvate thereof for the manufacture of a medicament for treating a cancer (e.g., a RET-associated cancer, e.g., a RET-associated cancer having one or more RET inhibitor resistance mutations) in a patient identified or diagnosed as having a RET-associated cancer (e.g., a patient that has been identified or diagnosed as having a RET-associated cancer through the use of a regulatory agency-approved, e.g., FDA-approved, kit for identifying dysregulation of a RET gene, a RET kinase, or expression or activity or level of any of the same, in a patient or a biopsy sample from the patient) (e.g., any of the RET-associated cancers described herein or known in the art).

In some embodiments of any of the methods or uses described herein, the patient has been identified or diagnosed as having a cancer with dysregulation of a RET gene, a RET kinase, or expression or activity or level of any of the same (e.g., a cancer having one or more RET inhibitor resistance mutations) (e.g., as determined using a regulatory agency-approved, e.g., FDA-approved, assay or kit). In some embodiments of any of the methods or uses described herein, the patient has a tumor that is positive for dysregulation of a RET gene, a RET kinase, or expression or activity or level of any of the same (e.g., a tumor positive for one or more RET inhibitor resistance mutations) (e.g., as determined using a regulatory-agency-approved assay or kit). In some embodiments of any of the methods or uses described herein, the patient can be a patient with a tumor(s) that is positive for dysregulation of a RET gene, a RET kinase, or expression or activity or level of any of the same (e.g., a tumor that is positive for one or more RET inhibitor resistance mutations) (e.g., identified as positive using a regulatory agency-approved, e.g., FDA-approved, assay or kit). In some embodiments of any of the methods or uses described herein, the patient can be a patient whose tumors have dysregulation of a RET gene, a RET kinase, or expression or activity or level of any of the same (e.g., a patient whose tumors have one or more RET inhibitor resistance mutations) (e.g., where the tumor is identified as such using a regulatory agency-approved, e.g., FDA-approved, kit or assay). In some embodiments of any of the methods or uses described herein, the patient is suspected of having a RET-associated cancer. In some embodiments of any of the methods or uses described herein, the patient has a clinical record indicating that the patient has a tumor that has dysregulation of a RET gene, a RET kinase, or expression or activity or level of any of the same (e.g., a tumor having one or more RET inhibitor resistance mutations) (and optionally the clinical record indicates that the patient should be treated with any of the compounds of General Formula I or a pharmaceutically acceptable salts or solvates thereof or compositions provided herein).

Also provided are methods of treating a patient that include administering a therapeutically effective amount of a compound of General Formula I or a pharmaceutically acceptable salt or solvate thereof to a patient having a clinical record that indicates that the patient has dysregulation of a RET gene, a RET kinase, or expression or activity or level of any of the same (e.g., one or more RET inhibitor resistance mutations). Also provided is the use of a compound of General Formula I or a pharmaceutically acceptable salt or solvate thereof for the manufacture of a medicament for treating a RET-associated cancer in a patient having a clinical record that indicates that the patient has dysregulation of a RET gene, a RET kinase, or expression or activity or level of any of the same (e.g., one or more RET inhibitor resistance mutations). Also provided is the use of a compound of General Formula I or a pharmaceutically acceptable salt or solvate thereof for treating a RET-associated cancer in a patient having a clinical record that indicates that the patient has dysregulation of a RET gene, a RET kinase, or expression or activity or level of any of the same (e.g., one or more RET inhibitor resistance mutations). Some embodiments of these methods and uses can further include: a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the patient to determine whether the patient has dysregulation of a RET gene, a RET kinase, or expression or activity or level of any of the same, and recording the information in a patient's clinical file (e.g., a computer readable medium) that the patient has been identified to have dysregulation of a RET gene, a RET kinase, or expression or activity or level of any of the same (e.g., one or more RET inhibitor resistance mutations).

Also provided herein is a method of treating a subject. The method includes performing an assay on a sample obtained from the subject to determine whether the subject has dysregulation of a RET gene, a RET protein, or expression or level of any of the same (e.g., one or more RET inhibitor resistance mutations). The method also includes administering to a subject determined to have dysregulation of a RET gene, a RET protein, or expression or activity, or level of any of the same (e.g., one or more RET inhibitor resistance mutations) a therapeutically effective amount of a compound of General Formula I or a pharmaceutically acceptable salt or solvate thereof. In some embodiments, the RET fusion can be selected from a KIF5B-RET fusion and a CCDC6-RET fusion. In some embodiments, the dysregulation in a RET gene, a RET kinase protein, or expression or activity of the same is a gene or chromosome translocation that results in the expression of a RET fusion protein (e.g., any of the RET fusion proteins described herein). In some embodiments, the dysregulation in a RET gene, a RET kinase protein, or expression or activity or level of any of the same is one or more point mutation in the RET gene (e.g., any of the one or more of the RET point mutations described herein). The one or more point mutations in a RET gene can result, e.g., in the translation of a RET protein having one or more of the following amino acid substitutions: M918T, M918V, C634W, V804L, and V804M. In some embodiments, the dysregulation in a RET gene, a RET kinase protein, or expression or activity or level of any of the same is one or more RET inhibitor resistance mutations (e.g., any combination of the one or more RET inhibitor resistance mutations described herein). Some embodiments of these methods further include administering to the subject another anticancer agent (e.g., another RET inhibitor, e.g., a RET inhibitor that is not a compound of General Formula I or a pharmaceutically acceptable salt or solvate thereof, or a different RET inhibitor that is a compound of General Formula I or a pharmaceutically acceptable salt or solvate thereof).

Also provided are methods (e.g., in vitro methods) of selecting a treatment for a patient that includes administration of a therapeutically effective amount of a compound of General Formula I or a pharmaceutically acceptable salt or solvate thereof for a patient identified or diagnosed as having a RET-associated cancer (e.g., a RET-associated cancer having one or more RET inhibitor resistance mutations) (e.g., a patient that has been identified or diagnosed as having a RET-associated cancer through the use of a regulatory agency-approved, e.g., FDA-approved, kit for identifying dysregulation of a RET gene, a RET kinase, or expression or activity or level of any of the same, in a patient or a biopsy sample from the patient) (e.g., any of the RET-associated cancers described herein or known in the art). Some embodiments can further include administering the selected treatment to the patient identified or diagnosed as having a RET-associated cancer (e.g., a RET-associated cancer having one or more RET inhibitor resistance mutations). Some embodiments can further include administering the selected treatment to the patient identified or diagnosed as having a RET-associated cancer (e.g., a RET-associated cancer having one or more RET inhibitor resistance mutations). Some embodiments can further include a step of performing an assay (e.g., an in vitro assay) (e.g., an assay that utilizes the next generation sequencing, immunohistochemistry, or break apart FISH analysis) (e.g., using a regulatory agency-approved, e.g., FDA-approved, kit) on a sample obtained from the patient to determine whether the patient has dysregulation of a RET gene, a RET kinase, or expression or activity or level of any of the same (e.g., one or more RET inhibitor resistance mutations), and identifying and diagnosing a patient determined to have dysregulation of a RET gene, a RET kinase, or expression or activity or level of any of the same (e.g., one or more RET inhibitor resistance mutations), as having a RET-associated cancer.

Also provided herein are methods of selecting a treatment for a patient that include administration of a therapeutically effective amount of a compound of General Formula I or a pharmaceutically acceptable salt or solvate thereof, wherein the methods include a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the patient to determine whether the patient has dysregulation of a RET gene, a RET kinase, or expression or activity or level of any of the same (e.g., one or more RET inhibitor resistance mutations), and identifying or diagnosing a patient determined to have dysregulation of a RET gene, a RET kinase, or expression or activity or level of any of the same (e.g., one or more RET inhibitor resistance mutations), as having a RET-associated cancer, and selecting a therapeutic treatment including administration of a therapeutically effective amount of a compound of General Formula I or a pharmaceutically acceptable salt or solvate thereof to the patient identified or diagnosed as having a RET-associated cancer. Some embodiments further include administering the selected treatment to the patient identified or diagnosed as having a RET-associated cancer.

Also provided are methods of selecting a patient for treatment including administration of a therapeutically effective amount of a compound of General Formula I or a pharmaceutically acceptable salt or solvate thereof or a pharmaceutical composition thereof, wherein the methods include selecting, identifying, or diagnosing a patient having a RET-associated cancer (e.g., a RET-associated cancer having one or more RET inhibitor resistance mutations), and selecting the patient for treatment including administration of a therapeutically-effective amount of a compound of General Formula I or a pharmaceutically acceptable salt or solvate thereof. In some embodiments, identifying or diagnosing a patient as having a RET-associated cancer can include a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the patient to determine whether the patient has dysregulation of a RET gene, a RET kinase, or expression or activity or level of any of the same (e.g., one or more RET inhibitor resistance mutations), and identifying or diagnosing a patient determined to have dysregulation of a RET gene, a RET kinase, or expression or activity or level of any of the same, as having a RET-associated cancer. In some embodiments, the method of selecting a treatment can be used as a part of a clinical study that includes administration of various treatments of a RET-associated cancer.

In some embodiments of any of the methods or uses described herein, an assay used to determine whether the patient has dysregulation of a RET gene, or a RET kinase, or expression or activity or level of any of the same (e.g., one or more RET inhibitor resistance mutations), using a sample (e.g., a biological sample or a biopsy sample (e.g., a paraffin-embedded biopsy sample) from a patient (e.g., a patient suspected of having a RET-associated cancer, a patient having one or more symptoms of a RET-associated cancer, and/or a patient that has an increased risk of developing a RET-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a RET gene, a RET kinase, or expression or activity or levels of any of the same (see, e.g., the references cited herein).

In the field of medical oncology it is normal practice to use a combination of different forms of treatment to treat each patient with cancer. In medical oncology the other component(s) of such conjoint treatment or therapy in addition to compositions provided herein may be, for example, surgery, radiotherapy, and chemotherapeutic agents, such as kinase inhibitors, signal transduction inhibitors and/or monoclonal antibodies. Compounds of General Formula I therefore may also be useful as adjuvants to cancer treatment, that is, they can be used in combination with one or more additional therapies or therapeutic agents, for example a chemotherapeutic agent that works by the same or by a different mechanism of action.

In some embodiments of any the methods described herein, the compound of General Formula I (or a pharmaceutically acceptable salt or solvate thereof) is administered in combination with a therapeutically effective amount of at least one additional therapeutic agent selected from one or more additional therapies or therapeutic (e.g., chemotherapeutic) agents.

Non-limiting examples of additional therapeutic agents include: other RET-targeted therapeutic agents (i.e. other RET kinase inhibitors; RET inhibitors that are not a compound of General Formula I or a pharmaceutically acceptable salt or solvate thereof), receptor tyrosine kinase-targeted therapeutic agents, signal transduction pathway inhibitors, checkpoint inhibitors, modulators of the apoptosis pathway (e.g. obataclax); cytotoxic chemotherapeutics, angiogenesis-targeted therapies, immune-targeted agents, and radiotherapy.

In some embodiments, the other RET-targeted therapeutic is a multikinase inhibitor exhibiting RET inhibition activity. In some embodiments, the other RET-targeted therapeutic inhibitor is selective for a RET kinase. Exemplary RET-targeted therapeutics can exhibit inhibition activity ($IC_{50}$) against a RET kinase of less than about 1000 nM, less than about 500 nM, less than about 200 nM, less than about 100 nM, less than about 50 nM, less than about 25 nM, less than about 10 nM, or less than about 1 nM.

Non-limiting examples of RET-targeted therapeutic agents include alectinib, apatinib, cabozantinib (XL-184), dovitinib, lenvatinib, motesanib, nintedanib, ponatinib, regorafenib, sitravatinib (MGCD516), sunitinib, sorafenib, vatalanib, vandetanib, AUY-922 (5-(2,4-Dihydroxy-5-isopropyl-phenyl)-N-ethyl-4-[4-(morpholinomethyl)phenyl] isoxazole-3-carboxamide), BLU6864, BLU-667, DCC-2157, NVP-AST487 (1-[4-[(4-ethylpiperazin-1-yl)methyl]-3-(trifluoromethyl)phenyl]-3-[4-[6-(methylamino) pyrimidin-4-yl]oxyphenyl]urea), PZ-1, RPI-1 (1,3-dihydro-5,6-dimethoxy-3-[(4-hydroxyphenyl)methylene]-H-indol-2-one), RXDX-105 (1-(3-((6,7-dimethoxyquinazolin-4-yl) oxy)phenyl)-3-(5-(1,1,1-trifluoro-2-methylpropan-2-yl) isoxazol-3-yl)urea), SPP86 (1-Isopropyl-3-(phenylethynyl)-1H-pyrazolo[3,4-d]pyrimidin-4-amine), and TG101209 (N-(1,1-dimethylethyl)-3-[[5-methyl-2-[[4-(4-methyl-1-piperazinyl)phenyl]amino]-4-pyrimidinyl]amino]-benzenesulfonamide).

Additional examples of other RET kinase inhibitors include those described in U.S. Pat. Nos. 9,150,517 and 9,149,464, and International Publication No. WO 2014075035, all of which are hereby incorporated by reference. For example, in some embodiments the other RET inhibitor is a compound of formula I:

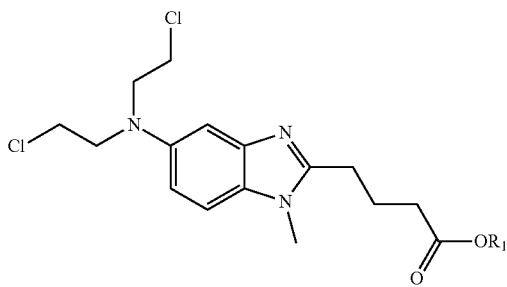

I wherein $R_1$ is $C_6$-$C_{24}$alkyl or polyethylene glycol; or a pharmaceutically acceptable alt form thereof. In some embodiments, the other RET inhibitor is 4-{5-[bis-(chloroethyl)-amino]-1-methyl-1H-benzimidazol-2-yl}butyric acid dodecyl ester.

Yet other therapeutic agents include RET inhibitors such as those described, for example, in U.S. Pat. Nos. 7,504,509; 8,299,057; 8,399,442; 8,067,434; 8,937,071; 9,006,256; and 9,035,063; U.S. Publication Nos. 2014/0121239; 20160176865; 2011/0053934; 2011/0301157; 2010/0324065; 2009/0227556; 2009/0130229; 2009/0099167; 2005/0209195; International Publication Nos. WO 2014/184069; WO 2014/072220; WO 2012/053606; WO 2009/017838; WO 2008/031551; WO 2007/136103; WO 2007/087245; WO 2007/057399; WO 2005/051366; WO 2005/062795; and WO 2005/044835; and J. Med. Chem. 2012, 55 (10), 4872-4876, all of which are hereby incorporated by reference in their entireties.

Non-limiting examples of receptor tyrosine kinase (Trk) targeted therapeutic agents, include afatinib, cabozantinib, cetuximab, crizotinib, dabrafenib, entrectinib, erlotinib, gefitinib, imatinib, lapatinib, lestaurtinib, nilotinib, pazopanib, panitumumab, pertuzumab, sunitinib, trastuzumab, 1-((3 S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea, AG 879, AR-772, AR-786, AR-256, AR-618, AZ-23, AZ623, DS-6051, Gö 6976, GNF-5837, GTx-186, GW 441756, LOXO-101, MGCD516, PLX7486, RXDX101, TPX-0005, and TSR-011. Additional Trk targeted thereapeutic agents include those described in U.S. Pat. Nos. 8,450,322; 8,513,263; 8,933,084; 8,791,123; 8,946,226; 8,450,322; 8,299,057; and 8,912,194; U.S. Publication No. 2016/0137654; 2015/0166564; 2015/0051222; 2015/0283132; and 2015/0306086; International Publication No. WO 2010/033941; WO 2010/048314; WO 2016/077841; WO 2011/146336; WO 2011/006074; WO 2010/033941; WO 2012/158413; WO 2014078454; WO 2014078417; WO 2014078408; WO 2014078378; WO 2014078372; WO 2014078331; WO 2014078328; WO 2014078325; WO 2014078323; WO 2014078322; WO 2015175788; WO 2009/013126; WO 2013/174876; WO 2015/124697; WO 2010/058006; WO 2015/017533; WO 2015/112806; WO 2013/183578; and WO 2013/074518, all of which are hereby incorporated by reference in their entireties.

Further examples of Trk inhibitors can be found in U.S. Pat. No. 8,637,516, International Publication No. WO 2012/034091, U.S. Pat. No. 9,102,671, International Publication No. WO 2012/116217, U.S. Publication No. 2010/0297115, International Publication No. WO 2009/053442, U.S. Pat. No. 8,642,035, International Publication No. WO 2009092049, U.S. Pat. No. 8,691,221, International Publication No. WO2006131952, all of which are incorporated by reference in their entireties herein. Exemplary Trk inhibitors include GNF-4256, described in Cancer Chemother. Pharmacol. 75(1):131-141, 2015; and GNF-5837 (N-[3-[[2,3-dihydro-2-oxo-3-(1H-pyrrol-2-ylmethylene)-1H-indol-6-yl]amino]-4-methylphenyl]-N'-[2-fluoro-5-(trifluoromethyl)phenyl]-urea), described in ACS Med. Chem. Lett. 3(2):140-145, 2012, each of which is incorporated by reference in its entirety herein.

Additional examples of Trk inhibitors include those disclosed in U.S. Publication No. 2010/0152219, U.S. Pat. No. 8,114,989, and International Publication No. WO 2006/123113, all of which are incorporated by reference in their entireties herein. Exemplary Trk inhibitors include AZ623, described in Cancer 117(6):1321-1391, 2011; AZD6918, described in Cancer Biol. Ther. 16(3):477-483, 2015; AZ64, described in Cancer Chemother. Pharmacol. 70:477-486, 2012; AZ-23 ((S)-5-Chloro-N2-(1-(5-fluoropyridin-2-yl)ethyl)-N4-(5-isopropoxy-1H-pyrazol-3-yl)pyrimidine-2,4-diamine), described in Mol. Cancer Ther. 8:1818-1827, 2009; and AZD7451; each of which is incorporated by reference in its entirety.

A Trk inhibitor can include those described in U.S. Pat. Nos. 7,615,383; 7,384,632; 6,153,189; 6,027,927; 6,025,166; 5,910,574; 5,877,016; and 5,844,092, each of which is incorporated by reference in its entirety.

Further examples of Trk inhibitors include CEP-751, described in Int. J. Cancer 72:672-679, 1997; CT327, described in Acta Derm. Venereol. 95:542-548, 2015; compounds described in International Publication No. WO 2012/034095; compounds described in U.S. Pat. No. 8,673,347 and International Publication No. WO 2007/022999; compounds described in U.S. Pat. No. 8,338,417; compounds described in International Publication No. WO 2016/027754; compounds described in U.S. Pat. No. 9,242,977; compounds described in U.S. Publication No. 2016/0000783; sunitinib (N-(2-diethylaminoethyl)-5-[(Z)-(5-fluoro-2-oxo-1H-indol-3-ylidene)methyl]-2,4-dimethyl-1H-pyrrole-3-carboxamide), as described in PLoS One 9:e95628, 2014; compounds described in International Publication No. WO 2011/133637; compounds described in U.S. Pat. No. 8,637,256; compounds described in Expert. Opin. Ther. Pat. 24(7):731-744, 2014; compounds described in Expert Opin. Ther. Pat. 19(3):305-319, 2009; (R)-2-phenylpyrrolidine substituted imadizopyridazines, e.g., (4-((5-chloro-4-(methylamino)-7H-pyrrolo[2,3-d]pyrimidin-2-yl)amino)-3-methoxyphenyl)(morpholino)methanone as described in ACS Med. Chem. Lett. 6(5):562-567, 2015; GTx-186 and others, as described in PLoS One 8(12): e83380, 2013; $K_{252}$a ((9S-(9α,10β,12α))-2,3,9,10,11,12-hexahydro-10-hydroxy-10-(methoxycarbonyl)-9-methyl-9,12-epoxy-1H-diindolo[1,2,3-fg:3',2',1'-kl]pyrrolo[3,4-i][1,6]benzodiazocin-1-one), as described in Mol. Cell Biochem. 339(1-2):201-213, 2010; 4-aminopyrazolylpyrimidines, e.g., AZ-23 (((S)-5-chloro-N2-(1-(5-fluoropyridin-2-yl)ethyl)-N4-(5-isopropoxy-1H-pyrazol-3-yl)pyrimidine-2,4-diamine)), as described in J. Med. Chem. 51(15):4672-4684, 2008; PHA-739358 (danusertib), as described in Mol. Cancer Ther. 6:3158, 2007; Gö 6976 (5,6,7,13-tetrahydro-13-methyl-5-oxo-12H-indolo[2,3-a]pyrrolo[3,4-c]carbazole-12-propanenitrile), as described in J. Neurochem. 72:919-924, 1999; GW441756 ((3Z)-3-[(1-methylindol-3-yl)methylidene]-1H-pyrrolo[3,2-b]pyridin-2-one), as described in IJAE 115:117, 2010; milciclib (PHA-848125AC), described in J. Carcinog. 12:22, 2013; AG-879 ((2E)-3-[3, 5-Bis(1,1-dimethylethyl)-4-hydroxyphenyl]-2-cyano-2-propenethioamide); altiratinib (N-(4-((2-(cyclopropanecarboxamido)pyridin-4-yl)oxy)-2,5-difluorophenyl)-N-(4- fluorophenyl)cyclopropane-1,1-dicarboxamide); cabozantinib (N-(4-((6,7-Dimethoxyquinolin-4-yl)oxy)phenyl)-N'-(4-fluorophenyl)cyclopropane-1,1-dicarboxamide); lestaurtinib ((5S,6S,8R)-6-Hydroxy-6-(hydroxymethyl)-5-methyl-7,8,14,15-tetrahydro-5H-16-oxa-4b,8a, 14-triaza-5, 8-methanodibenzo[b,h]cycloocta[jkl]cyclopenta[e]-as-indacen-13(6H)-one); dovatinib (4-amino-5-fluoro-3-[6-(4-methylpiperazin-1-yl)-1H-benzimidazol-2-yl]quinolin-2 (1H)-one mono 2-hydroxypropanoate hydrate); sitravatinib (N-(3-fluoro-4-((2-(5-(((2-methoxyethyl)amino)methyl) pyridin-2-yl)thieno[3,2-b]pyridin-7-yl)oxy)phenyl)-N-(4-fluorophenyl)cyclopropane-1,1-dicarboxamide); ONO-5390556; regorafenib (4-[4-({[4-Chloro-3-(trifluoromethyl) phenyl]carbamoyl}amino)-3-fluorophenoxy]-N-methylpyridine-2-carboxamide hydrate); VSR-902A; all of the references above are incorporated by reference in their entireties herein.

The ability of a Trk inhibitor to act as a TrkA, TrkB, and/or Trk C inhibitor may be tested using the assays described in Examples A and B in U.S. Pat. No. 8,513,263, which is incorporated herein by reference.

In some embodiments, signal transduction pathway inhibitors include Ras-Raf-MEK-ERK pathway inhibitors (e.g., binimetinib, selumetinib, encorafinib, sorafenib, trametinib, and vemurafenib), PI3K-Akt-mTOR-S6K pathway inhibitors (e.g. everolimus, rapamycin, perifosine, temsirolimus), and other kinase inhibitors, such as baricitinib, brigatinib, capmatinib, danusertib, ibrutinib, milciclib, quercetin, regorafenib, ruxolitinib, semaxanib, AP32788, BLU285, BLU554, INCB39110, INCB40093, INCB50465, INCB52793, INCB54828, MGCD265, NMS-088, NMS-1286937, PF 477736 ((R)-amino-N-[5,6-dihydro-2-(1-methyl-1H-pyrazol-4-yl)-6-oxo-1Hpyrrolo[4,3,2-ef][2,3] benzodiazepin-8-yl]-cyclohexaneacetamide), PLX3397, PLX7486, PLX8394, PLX9486, PRN1008, PRN1371, RXDX103, RXDX106, RXDX108, and TG101209 (N-tert-butyl-3-(5-methyl-2-(4-(4-methylpiperazin-1-yl)phenylamino)pyrimidin-4-ylamino)benzenesulfonamide).

Non-limiting examples of checkpoint inhibitors include ipilimumab, tremelimumab, nivolumab, pidilizumab, MPDL3208A, MEDI4736, MSB0010718C, BMS-936559, BMS-956559, BMS-935559 (MDX-1105), AMP-224, and pembrolizumab.

In some embodiments, cytotoxic chemotherapeutics are selected from arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

Non-limiting examples of angiogenesis-targeted therapies include aflibercept and bevacizumab.

In some embodiments, immune-targeted agents are selected from aldesleukin, interferon alfa-2b, ipilimumab, lambrolizumab, nivolumab, prednisone, and sipuleucel-T.

Non-limiting examples of radiotherapy include radioiodide therapy, external-beam radiation, and radium 223 therapy.

Additional kinase inhibitors include those described in, for example, U.S. Pat. Nos. 7,514,446; 7,863,289; 8,026, 247; 8,501,756; 8,552,002; 8,815,901; 8,912,204; 9,260, 437; 9,273,051; U.S. Publication No. US 2015/0018336; International Publication No. WO 2007/002325; WO 2007/002433; WO 2008/080001; WO 2008/079906; WO 2008/079903; WO 2008/079909; WO 2008/080015; WO 2009/012283; WO 2009/143018; WO 2009/143024; WO 2009/152083; WO 2010/111527; WO 2012/109075; WO 2014/194127; WO 2015/112806; WO 2007/110344; WO 2009/071480; WO 2009/118411; WO 2010/031816; WO 2010/145998; WO 2011/092120; WO 2012/101032; WO 2012/139930; WO 2012/143248; WO 2012/152763; WO 2013/014039; WO 2013/102059; WO 2013/050448; WO 2013/050446; WO 2014/019908; WO 2014/072220; WO 2014/184069; and WO 2016/075224 all of which are hereby incorporated by reference in their entireties.

Further examples of kinase inhibitors include those described in, for example, WO 2016/081450; WO 2016/022569; WO 2016/011141; WO 2016/011144; WO 2016/011147; WO 2015/191667; WO 2012/101029; WO 2012/113774; WO 2015/191666; WO 2015/161277; WO 2015/161274; WO 2015/108992; WO 2015/061572; WO 2015/058129; WO 2015/057873; WO 2015/017528; WO/2015/017533; WO 2014/160521; and WO 2014/011900, each of which is hereby incorporated by reference in its entirety.

Accordingly, also provided herein is a method of treating cancer, comprising administering to a patient in need thereof a pharmaceutical combination for treating cancer which comprises (a) a compound of General Formula I or a pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of General Formula I or a pharmaceutically acceptable salt or solvate thereof and the additional therapeutic agent are together effective in treating the cancer.

In some embodiments, the additional therapeutic agent(s) includes any one of the above listed therapies or therapeutic agents which are standards of care in cancers wherein the cancer has a dysregulation of a RET gene, a RET protein, or expression or activity, or level of any of the same.

These additional therapeutic agents may be administered with one or more doses of the compound of General Formula I, or a pharmaceutically acceptable salt or solvate thereof, or pharmaceutical composition thereof, as part of the same or separate dosage forms, via the same or different routes of administration, and/or on the same or different administration schedules according to standard pharmaceutical practice known to one skilled in the art.

Also provided herein is (i) a pharmaceutical combination for treating a cancer (e.g., a RET-associated cancer (e.g., a RET-associated cancer having one or more RET inhibitor resistance mutations)) in a patient in need thereof, which comprises (a) a compound of General Formula I or a pharmaceutically acceptable salt or solvate thereof, (b) at least one additional therapeutic agent (e.g., any of the exemplary additional therapeutic agents described herein or known in the art), and (c) optionally at least one pharmaceutically acceptable carrier for simultaneous, separate or sequential use for the treatment of cancer, wherein the amounts of the compound of General Formula I or pharmaceutically acceptable salt or solvate thereof and of the additional therapeutic agent are together effective in treating the cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer a patient in need thereof. In one embodiment the patient is a human.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of General Formula I or a pharmaceutically acceptable salt or solvate thereof and at least one additional therapeutic agent (e.g., a chemotherapeutic agent), are both administered to a patient simultaneously in the form of a single composition or dosage. The term "non-fixed combination" means that a compound of General Formula I or a pharmaceutically acceptable salt or solvate thereof and at least one additional therapeutic agent (e.g., chemotherapeutic agent) are formulated as separate compositions or dosages such that they may be administered to a patient in need thereof simultaneously, concurrently or sequentially with variable intervening time limits, wherein such administration provides effective levels of the two or more compounds in the body of the patient. These also apply to cocktail therapies, e.g. the administration of three or more active ingredients Accordingly, also provided herein is a method of treating a cancer (e.g., a RET-associated cancer (e.g., a RET-associated cancer having one or more RET inhibitor resistance mutations)), comprising administering to a patient in need thereof a pharmaceutical combination for treating cancer which comprises (a) a compound of General Formula I or pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of General Formula I or pharmaceutically acceptable salt or solvate thereof and the additional therapeutic agent are together effective in treating the cancer. In one embodiment, the compound of General Formula I or pharmaceutically acceptable salt or solvate thereof, and the additional therapeutic agent are administered simultaneously as separate dosages. In one embodiment, the compound of General Formula I or pharmaceutically acceptable salt or solvate thereof, and the additional therapeutic agent are administered as separate dosages sequentially in any order, in jointly therapeutically effective amounts, e.g. in daily or intermittently dosages. In one embodiment, compound of General Formula I or pharmaceutically acceptable salt or solvate thereof, and the additional therapeutic agent are administered simultaneously as a combined dosage.

Also provided herein is a method of treating a disease or disorder mediated by RET (e.g., dysregulation of RET gene, a RET kinase, or expression or activity or level of any of the same, e.g., one or more RET inhibitor resistance mutations) in a patient in need of such treatment, the method comprising administering to the patient a therapeutically effective amount of a compound of General Formula I or a pharmaceutically acceptable salt or solvate thereof or a pharmaceutical composition thereof. A disease or disorder mediated by RET (e.g., dysregulation of RET gene, a RET kinase, or expression or activity or level of any of the same, e.g., one or more RET inhibitor resistance mutations) can include any disease, disorder or condition that is directly or indirectly linked to expression or activity of RET, including overexpression and/or abnormal activity levels. In one embodiment, the disease is cancer (e.g., a RET-associated cancer). In one embodiment, the cancer is any of the cancers or RET-associated cancers described herein.

Although the genetic basis of tumorigenesis may vary between different cancer types, the cellular and molecular mechanisms required for metastasis appear to be similar for all solid tumor types. During a metastatic cascade, the cancer cells lose growth inhibitory response, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies. A number of genes have been identified as being promoters or suppressors of metastasis. For example, overexpression of glial cell-derived neurotrophic factor (GDNF) and its RET receptor tyrosine kinase have been correlated with cancer proliferation and metastasis. See, e.g., Zeng, Q. et al. *J. Int. Med. Res.* (2008) 36(4): 656-64.

Accordingly, also provided herein are methods for inhibiting, preventing, aiding in the prevention, or decreasing the symptoms of metastasis of a cancer in a patient in need thereof, the method comprising administering to the patient a therapeutically effective amount of a compound of General Formula I or a pharmaceutically acceptable salt or solvate thereof or a pharmaceutical composition thereof. Such methods can be used in the treatment of one or more of the cancers described herein. See, e.g., US Publication No. 2013/0029925; International Publication No. WO 2014/083567; and U.S. Pat. No. 8,568,998. In some embodiments, the cancer is a RET-associated cancer. In some embodiments, the compound of General Formula I or a pharmaceutically acceptable salt or solvate thereof is used in combination with an additional therapy or another therapeutic agent, including a chemotherapeutic agent, such as a kinase inhibitor.

The term "metastasis" is an art known term and means the formation of an additional tumor (e.g., a solid tumor) at a site distant from a primary tumor in a subject or patient, where the additional tumor includes the same or similar cancer cells as the primary tumor.

Also provided are methods of decreasing the risk of developing a metastasis or an additional metastasis in a patient having a RET-associated cancer (e.g., a RET-associated cancer having one or more RET inhibitor resistance mutations) that include: selecting, identifying, or diagnosing a patient as having a RET-associated cancer (e.g., a RET-associated cancer having one or more RET inhibitor resistance mutations), and administering a therapeutically effective amount of a compound of General Formula I or a pharmaceutically acceptable salt or solvate thereof to the patient selected, identified, or diagnosed as having a RET-associated cancer. Also provided are methods of decreasing the risk of developing a metastasis or an additional metastasis in a patient having a RET-associated cancer (e.g., a RET-associated cancer having one or more RET inhibitor resistance mutations) that includes administering a therapeutically effective amount of a compound of General Formula I or a pharmaceutically acceptable salt or solvent thereof to a patient having a RET-associated cancer. The decrease in the risk of developing a metastasis or an additional metastasis in a patient having a RET-associated cancer can be compared to the risk of developing a metastasis or an additional metastasis in the patient prior to treatment, or as compared to a patient or a population of patients having a similar or the same RET-associated cancer that has received no treatment or a different treatment.

The phrase "risk of developing a metastasis" means the risk that a subject or patient having a primary tumor will develop an additional tumor (e.g., a solid tumor) at a site distant from a primary tumor in a subject or patient over a set period of time, where the additional tumor includes the same or similar cancer cells as the primary tumor. Methods for reducing the risk of developing a metastasis in a subject or patient having a cancer are described herein.

The phrase "risk of developing additional metastases" means the risk that a subject or patient having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

In some embodiments, the presence of one or more RET inhibitor resistance mutations in a tumor causes the tumor to be more resistant to treatment with a RET inhibitor that is not a compound of General Formula I or a pharmaceutically acceptable salt or solvate thereof (e.g., a substitution at amino acid position 804, e.g., V804M, V804L, or V804E). Methods useful when a RET inhibitor resistance mutation causes the tumor to be more resistant to treatment with a RET inhibitor that is not a compound of General Formula I or a pharmaceutically acceptable salt or solvate thereof are described below. For example, provided herein are methods of treating a subject having a cancer that include: identifying a subject having a cancer cell that has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E); and administering to the identified subject a treatment that does not include a RET inhibitor that is not a compound of General Formula I or a pharmaceutically acceptable salt or solvate thereof as a monotherapy (e.g., a treatment that includes a compound of General Formula I or a pharmaceutically acceptable salt or solvate thereof). Also provided are methods of treating a subject identified as having a cancer cell that has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E) that include administering to the subject a treatment that does not include a RET inhibitor that is not a compound of General Formula I or a pharmaceutically acceptable salt or solvate thereof as a monotherapy (e.g., a treatment that includes a compound of General Formula I or a pharmaceutically acceptable salt or solvate thereof). Also provided are methods of selecting a treatment for a subject having a cancer that include: identifying a subject having a cancer cell that has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E); and selecting a treatment that does not include a RET inhibitors that is not a compound of General Formula I or a pharmaceutically acceptable salt or solvate thereof as a monotherapy for the identified subject (e.g., a treatment that includes a compound of General Formula I or a pharmaceutically acceptable salt or solvate thereof). Also provided are methods of selecting a treatment for a subject having a cancer that include: selecting a treatment that does not include a RET inhibitor that is not a compound of General Formula I or a pharmaceutically acceptable salt or solvate thereof as a monotherapy (e.g., a treatment that includes a compound of General Formula I or a pharmaceutically acceptable salt or solvate thereof) for a subject identified as having a cancer cell that has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E). Also provided are methods of selecting a subject having a cancer for a treatment that does not include a RET inhibitor that is not a compound of General Formula I or a pharmaceutically acceptable salt or solvate thereof as a monotherapy that include: identifying a subject having a cancer cell that has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E); and selecting the identified subject for a treatment that does not include a RET inhibitor that is not a compound of General Formula I or a pharmaceutically acceptable salt or solvate thereof as a monotherapy (e.g., a treatment that includes a compound of General Formula I or a pharmaceutically acceptable salt or solvate thereof). Also provided are methods of selecting a subject having a cancer for a treatment that does not include a RET inhibitor that is not a compound of General Formula I or a pharmaceutically acceptable salt or solvate thereof as a monotherapy that include: selecting a subject identified as having a cancer cell that has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E), for a treatment that does not include a RET inhibitor that is not a compound of General Formula I or a pharmaceutically acceptable salt or solvate thereof as a monotherapy (e.g., a treatment that includes a compound of General Formula I or a pharmaceutically acceptable salt or solvate thereof). Also provided are methods of determining the likelihood that a subject having a cancer will have a positive response to treatment with a RET inhibitor that is not a compound of General Formula I or a pharmaceutically acceptable salt or solvate thereof as a monotherapy that include: determining whether a cancer cell in a sample obtained from the subject has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E); and determining that a subject having a cancer cell that has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E), has a decreased likelihood of having a positive response to treatment with a RET inhibitor that is not a compound of General Formula I or a pharmaceutically acceptable salt or solvate thereof as a monotherapy. Also provided are methods of determining the likelihood that a subject having cancer will have a positive response to treatment with a RET inhibitor that is not a compound of General Formula I or a pharmaceutically acceptable salt or solvate thereof as a monotherapy that include: determining that a subject having a cancer cell that has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E), has a decreased likelihood of having a positive response to treatment with a RET inhibitor that is not a compound of General Formula I or a pharmaceutically acceptable salt or solvate thereof as a monotherapy. Also provided are methods of predicting the efficacy of treatment with a RET inhibitor that is not a compound of General Formula I or a pharmaceutically acceptable salt or solvate thereof as a monotherapy in a subject having cancer that include: determining whether a cancer cell in a sample obtained from the subject has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E); and determining that treatment with a RET inhibitor that is not a compound of General Formula I or a pharmaceutically acceptable salt or solvate thereof as a monotherapy is less likely to be effective in a subject having a cancer cell in a sample obtained from the subject that has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E). Also provided are methods of predicting the efficacy of treatment with a RET inhibitor that is not a compound of General Formula I or a pharmaceutically acceptable salt or solvate thereof as a monotherapy in a subject having cancer that include: determining that treatment with a RET inhibitor that is not a compound of General Formula I or a pharmaceutically acceptable salt or solvate thereof as a monotherapy is less likely to be effective in a subject having a cancer cell in a sample obtained from the subject that has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E).

Also provided are methods of treating a subject having a cancer that include: (a) administering one or more doses of a RET inhibitor that is not a compound of General Formula I or a pharmaceutically acceptable salt or solvate thereof, to the subject for a period of time; (b) after (a), determining whether a cancer cell in a sample obtained from the subject has at least one RET inhibitor resistance mutation (that confers increased resistance to a cancer cell or tumor to treatment with a RET inhibitor that is not a compound of General Formula I or a pharmaceutically acceptable salt or solvate thereof of (a), e.g., a substitution at amino acid position 804, e.g., V804M, V804L, or V804E); and (c) administering a compound of General Formula I or a pharmaceutically acceptable salt or solvate thereof as a monotherapy or in conjunction with another anticancer agent (e.g., any anticancer agent known in the art, e.g., another RET inhibitor, e.g., the same RET inhibitor administered in step (a)) to the subject if the subject has a cancer cell that has at least one RET inhibitor resistance mutation (that confers increased resistance to a cancer cell or tumor to treatment with a RET inhibitor that is not a compound of General Formula I or a pharmaceutically acceptable salt or solvate thereof of (a), e.g., a substitution at amino acid position 804, e.g., V804M, V804L, or V804E); or (d) administering additional doses of the RET inhibitor that is not a compound of General Formula I or a pharmaceutically acceptable salt or solvate thereof of step (a) to the subject if the subject has a cancer cell that does not have a RET inhibitor resistance mutation (that confers increased resistance to a cancer cell or tumor to treatment with a RET inhibitor that is not a compound of General Formula I or a pharmaceutically acceptable salt or solvate thereof of (a), e.g., a substitution at amino acid position 804, e.g., V804M, V804L, or V804E). In some embodiments, where the subject is administered additional doses of the RET inhibitor that is not a compound of General Formula I or a pharmaceutically acceptable salt or solvate thereof of step (a), the subject can also be administered another anticancer agent (e.g., another RET inhibitor, e.g., a compound of General Formula I or a pharmaceutically acceptable salt or solvate thereof).

Also provided are methods of treating a subject having a cancer that include: (a) administering one or more doses of a RET inhibitor that is not a compound of General Formula I or a pharmaceutically acceptable salt or solvate thereof, to the subject for a period of time; (b) after (a), determining whether a cancer cell in a sample obtained from the subject has at least one RET inhibitor resistance mutation (that confers increased resistance to a cancer cell or tumor to treatment with a RET inhibitor that is not a compound of General Formula I or a pharmaceutically acceptable salt or solvate thereof of (a), e.g., a substitution at amino acid position 804, e.g., V804M, V804L, or V804E); and (c) administering a different RET inhibitor that is not a compound of General Formula I or a pharmaceutically acceptable salt or solvate thereof (different from the RET inhibitor administered in (a)) as a monotherapy or in conjunction with another anticancer agent (e.g., any anticancer agent known in the art, e.g., another RET inhibitor, e.g., the same RET inhibitor administered in (a)) to the subject if the subject has a cancer cell that has at least one RET inhibitor resistance mutation (that confers increased resistance to a cancer cell or tumor to treatment with a RET inhibitor that is not a compound of General Formula I or a pharmaceutically acceptable salt or solvate thereof of (a), e.g., a substitution at amino acid position 804, e.g., V804M, V804L, or V804E); or (d) administering additional doses of the RET inhibitor that is not a compound of General Formula I or a pharmaceutically acceptable salt or solvate thereof of step (a) to the subject if the subject has a cancer cell that does not have a RET inhibitor resistance mutation (that confers increased resistance to a cancer cell or tumor to treatment with a RET inhibitor that is not a compound of General Formula I or a pharmaceutically acceptable salt or solvate thereof of (a), e.g., a substitution at amino acid position 804, e.g., V804M, V804L, or V804E). In some embodiments, where the subject is administered additional doses of the RET inhibitor that is not a compound of General Formula I or a pharmaceutically acceptable salt or solvate thereof of step (a), the subject can also be administered another anticancer agent (e.g., another RET inhibitor, e.g., a compound of General Formula I or a pharmaceutically acceptable salt or solvate thereof).

Also provided are methods of treating a subject having a cancer that include: (a) determining whether a cancer cell in a sample obtained from a subject having a cancer and previously administered one or more doses of a RET inhibitor that is not a compound of General Formula I or a pharmaceutically acceptable salt or solvate thereof, has one or more RET inhibitor resistance mutations (that confer increased resistance to a cancer cell or tumor to treatment with a RET inhibitor that is not a compound of General Formula I or a pharmaceutically acceptable salt or solvate thereof that was previously administered to the subject, e.g., a substitution at amino acid position 804, e.g., V804M, V804L, or V804E); and (c) administering a compound of General Formula I or a pharmaceutically acceptable salt or solvate thereof as a monotherapy or in conjunction with another anticancer agent (e.g., any anticancer agent known in the art, e.g., another RET inhibitor, e.g., the same RET inhibitor previously administered to the subject) to the subject if the subject has a cancer cell that has at least one RET inhibitor resistance mutation (that confers increased resistance to a cancer cell or tumor to treatment with a RET inhibitor that is not a compound of General Formula I or a pharmaceutically acceptable salt or solvate thereof that was previously administered to the subject, e.g., a substitution at amino acid position 804, e.g., V804M, V804L, or V804E); or (d) administering additional doses of the RET inhibitor that is not a compound of General Formula I or a pharmaceutically acceptable salt or solvate thereof previously administered to the subject if the subject has cancer cell that does not have a RET inhibitor resistance mutation (that confers increased resistance to a cancer cell or tumor to treatment with a RET inhibitor that is not a compound of General Formula I or a pharmaceutically acceptable salt or solvate thereof previously administered to the subject, e.g., a substitution at amino acid position 804, e.g., V804M, V804L, or V804E). In some embodiments, where the subject is administered additional doses of the RET inhibitor that is not a compound of General Formula I or a pharmaceutically acceptable salt or solvate thereof previously administered to the subject, the subject can also be administered another anticancer agent (e.g., another RET inhibitor, e.g., a compound of General Formula I or a pharmaceutically acceptable salt or solvate thereof).

Also provided are methods of treating a subject having a cancer that include: (a) determining whether a cancer cell in a sample obtained from a subject having a cancer and previously administered one or more doses of a RET inhibitor that is not a compound of General Formula I or a pharmaceutically acceptable salt or solvate thereof, has one or more RET inhibitor resistance mutations (that confer increased resistance to a cancer cell or tumor to treatment with a RET inhibitor that is not a compound of General Formula I or a pharmaceutically acceptable salt or solvate thereof that was previously administered to the subject, e.g., a substitution at amino acid position 804, e.g., V804M, V804L, or V804E); and (b) administering a different RET inhibitor that is not a compound of General Formula I or a pharmaceutically acceptable salt or solvate thereof (different from the RET inhibitor previously administered to the subject) as a monotherapy or in conjunction with another anticancer agent (e.g., any anticancer agent known in the art, e.g., another RET inhibitor, e.g., the same RET inhibitor previously administered to the subject) to the subject if the subject has a cancer cell that has at least one RET inhibitor resistance mutation (that confers increased resistance to a cancer cell or tumor to treatment with a RET inhibitor that is not a compound of General Formula I or a pharmaceutically acceptable salt or solvate thereof that was previously administered to the subject, e.g., a substitution at amino acid position 804, e.g., V804M, V804L, or V804E); or (d) administering additional doses of the RET inhibitor that is not a compound of General Formula I or a pharmaceutically acceptable salt or solvate thereof previously administered to the subject if the subject has cancer cell that does not have a RET inhibitor resistance mutation (that confers increased resistance to a cancer cell or tumor to treatment with a RET inhibitor that is not a compound of General Formula I or a pharmaceutically acceptable salt or solvate thereof that was previously administered to the subject, e.g., a substitution at amino acid position 804, e.g., V804M, V804L, or V804E). In some embodiments, where the subject is administered additional doses of the RET inhibitor that is not a compound of General Formula I or a pharmaceutically acceptable salt or solvate thereof previously administered to the subject, the subject can also be administered another anticancer agent (e.g., another RET inhibitor, e.g., a compound of General Formula I or a pharmaceutically acceptable salt or solvate thereof).

Also provided are methods of selecting a treatment for a subject having a cancer that include (a) administering one or more doses of a RET inhibitor that is not a compound of General Formula I or a pharmaceutically acceptable salt or solvate thereof to the subject for a period of time; (b) after (a), determining whether a cancer cell in a sample obtained from the subject has at least one RET inhibitor resistance mutation (that confers increased resistance to a cancer cell or tumor to treatment with a RET inhibitor that is not a compound of General Formula I or a pharmaceutically acceptable salt or solvate thereof of (a), e.g., a substitution at amino acid position 804, e.g., V804M, V804L, or V804E); and (c) selecting a compound of General Formula I or a pharmaceutically acceptable salt or solvate thereof as a monotherapy or in conjunction with another anticancer agent (e.g., any anticancer agent known in the art, e.g., another RET inhibitor, e.g., the same RET inhibitor administered in step (a)) for the subject if the subject has a cancer cell that has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E); or (d) selecting additional doses of the RET inhibitor that is not a compound of General Formula I or a pharmaceutically acceptable salt or solvate thereof of step (a) for the subject if the subject has a cancer cell that does not have a RET inhibitor resistance mutation (that confers increased resistance to a cancer cell or tumor to treatment with a RET inhibitor that is not a compound of General Formula I or a pharmaceutically acceptable salt or solvate thereof of (a), e.g., a substitution at amino acid position 804, e.g., V804M, V804L, or V804E). In some embodiments, when additional doses of the RET inhibitor that is not a compound of General Formula I or a pharmaceutically acceptable salt or solvate thereof of step (a) are selected for the subject, the method can further include selecting doses of another anticancer agent (e.g., another RET inhibitor, e.g., a compound of General Formula I or a pharmaceutically acceptable salt or solvate thereof) for the subject.

Also provided are methods of selecting a treatment for a subject having a cancer that include (a) administering one or more doses of a RET inhibitor that is not a compound of General Formula I or a pharmaceutically acceptable salt or solvate thereof to the subject for a period of time; (b) after (a), determining whether a cancer cell in a sample obtained from the subject has at least one RET inhibitor resistance mutation (that confers increased resistance to a cancer cell or tumor to treatment with a RET inhibitor that is not a compound of General Formula I or a pharmaceutically acceptable salt or solvate thereof of (a), e.g., a substitution at amino acid position 804, e.g., V804M, V804L, or V804E); and (c) selecting a different RET inhibitor that is not a compound of General Formula I or a pharmaceutically acceptable salt or solvate thereof (different from the RET inhibitor administered to the subject in (a)) as a monotherapy or in conjunction with another anticancer agent (e.g., any anticancer agent known in the art, e.g., another RET inhibitor, e.g., the same RET inhibitor administered to the subject in (a)) for the subject if the subject has a cancer cell that has one or more RET inhibitor resistance mutations (that confer increased resistance to a cancer cell or tumor to treatment with a RET inhibitor that is not a compound of General Formula I or a pharmaceutically acceptable salt or solvate thereof of (a), e.g., a substitution at amino acid position 804, e.g., V804M, V804L, or V804E); or (d) selecting additional doses of the RET inhibitor that is not a compound of General Formula I or a pharmaceutically acceptable salt or solvate thereof of step (a) for the subject if the subject has a cancer cell that does not have a RET inhibitor resistance mutation (that confers increased resistance to a cancer cell or tumor to treatment with a RET inhibitor that is not a compound of General Formula I or a pharmaceutically acceptable salt or solvate thereof of (a), e.g., a substitution at amino acid position 804, e.g., V804M, V804L, or V804E). In some embodiments, when additional doses of the RET inhibitor that is not a compound of General Formula I or a pharmaceutically acceptable salt or solvate thereof of step (a) are selected for the subject, the method can further include selecting doses of another anticancer agent (e.g., another RET inhibitor, e.g., a compound of General Formula I or a pharmaceutically acceptable salt or solvate thereof) for the subject.

Also provided are methods of method of selecting a treatment for a subject having a cancer that include (a) determining whether a cancer cell in a sample obtained from a subject having a cancer and previously administered one or more doses of a RET inhibitor that is not a compound of General Formula I or a pharmaceutically acceptable salt or solvate thereof, has one or more RET inhibitor resistance mutations (that confer increased resistance to a cancer cell or tumor to treatment with a RET inhibitor that is not a compound of General Formula I or a pharmaceutically acceptable salt or solvate thereof that was previously administered to the subject, e.g., a substitution at amino acid position 804, e.g., V804M, V804L, or V804E); (b) selecting a compound of General Formula I or a pharmaceutically acceptable salt or solvate thereof as a monotherapy or in conjunction with another anticancer agent (e.g., any anticancer agent known in the art, e.g., another RET inhibitor, e.g., the same RET inhibitor previously administered to the subject) for the subject if the subject has a cancer cell that has at least one RET inhibitor resistance mutation (that confers increased resistance to a cancer cell or tumor to treatment with a RET inhibitor that is not a compound of General Formula I or a pharmaceutically acceptable salt or solvate thereof that was previously administered to the subject, e.g., a substitution at amino acid position 804, e.g., V804M, V804L, or V804E); or (c) selecting additional doses of the RET inhibitor that is not a compound of General Formula I or a pharmaceutically acceptable salt or solvate thereof previously administered to the subject if the subject has a cancer cell that does not have a RET inhibitor resistance mutation (that confers increased resistance to a cancer cell or tumor to treatment with a RET inhibitor that is not a compound of General Formula I or a pharmaceutically acceptable salt or solvate thereof that was previously administered to the subject, e.g., a substitution at amino acid position 804, e.g., V804M, V804L, or V804E). In some embodiments, when additional doses of the RET inhibitor that is not a compound of General Formula I or a pharmaceutically acceptable salt or solvate previously administered to the subject are selected for the subject, the method can further include selecting doses of another anticancer agent (e.g., another RET inhibitor, e.g., a compound of General Formula I or a pharmaceutically acceptable salt or solvate thereof) for the subject.

Also provided are methods of method of selecting a treatment for a subject having a cancer that include (a) determining whether a cancer cell in a sample obtained from a subject having a cancer and previously administered one or more doses of a RET inhibitor that is not a compound of General Formula I or a pharmaceutically acceptable salt or solvate thereof, has one or more RET inhibitor resistance mutations (that confer increased resistance to a cancer cell or tumor to treatment with a RET inhibitor that is not a compound of General Formula I or a pharmaceutically acceptable salt or solvate thereof that was previously administered to the subject, e.g., a substitution at amino acid position 804, e.g., V804M, V804L, or V804E); (b) selecting a different RET inhibitor that is not a compound of General Formula I or a pharmaceutically acceptable salt or solvate thereof (different from the RET inhibitor previously administered to the subject) as a monotherapy or in conjunction with another anticancer agent (e.g., any anticancer agent known in the art, e.g., another RET inhibitor, e.g., the same RET inhibitor previously administered to the subject) for the subject if the subject has a cancer cell that has at least one RET inhibitor resistance mutation (that confers increased resistance to a cancer cell or tumor to treatment with a RET inhibitor that is not a compound of General Formula I or a pharmaceutically acceptable salt or solvate thereof that was previously administered to the subject, e.g., a substitution at amino acid position 804, e.g., V804M, V804L, or V804E); or (c) selecting additional doses of the RET inhibitor that is not a compound of General Formula I or a pharmaceutically acceptable salt or solvate thereof previously administered to the subject if the subject has a cancer cell that does not have a RET inhibitor resistance mutation (that confers increased resistance to a cancer cell or tumor to treatment with a RET inhibitor that is not a compound of General Formula I or a pharmaceutically acceptable salt or solvate thereof that was previously administered to the subject, e.g., a substitution at amino acid position 804, e.g., V804M, V804L, or V804E). In some embodiments, when additional doses of the RET inhibitor that is not a compound of General Formula I or a pharmaceutically acceptable salt or solvate previously administered to the subject are selected for the subject, the method can further include selecting doses of another anticancer agent (e.g., another RET inhibitor, e.g., a compound of General Formula I or a pharmaceutically acceptable salt or solvate thereof) for the subject.

Also provided are methods of determining a subject's risk for developing a cancer that has some resistance to a RET inhibitor that is not a compound of General Formula I or a pharmaceutically acceptable salt or solvate thereof that include: determining whether a cell in a sample obtained from the subject has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E); and identifying a subject having a cell that has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E), as having an increased likelihood of developing a cancer that has some resistance to a RET inhibitor that is not a compound of General Formula I or a pharmaceutically acceptable salt or solvate thereof. Also provided are methods of determining a subject's risk for developing a cancer that has some resistance to a RET inhibitor that is not a compound of General Formula I or a pharmaceutically acceptable salt or solvate thereof that include: identifying a subject having a cell that has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E), as having an increased likelihood of developing a cancer that has some resistance to a RET inhibitor that is not a compound of General Formula I or a pharmaceutically acceptable salt or solvate thereof. Also provided are methods of determining the presence of a cancer that has some resistance to a RET inhibitor that is not a compound of General Formula I or a pharmaceutically acceptable salt or solvate thereof that includes: determining whether a cancer cell in a sample obtained from the subject has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E); and determining that a subject having a cancer cell that has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E), has a cancer that has some resistance to a RET inhibitor that is not a compound of General Formula I or a pharmaceutically acceptable salt or solvate thereof. Also provided are methods of determining the presence of a cancer that has some resistance to a RET inhibitor that is not a compound of General Formula I or a pharmaceutically acceptable salt or solvate thereof in a subject that include: determining that a subject having a cancer cell that has one or more RET inhibitor resistance mutations (that confer increased resistance to a cancer cell or tumor to treatment with a RET inhibitor that is not a compound of General Formula I or a pharmaceutically acceptable salt or solvate thereof, e.g., a substitution at amino acid position 804, e.g., V804M, V804L, or V804E), has a cancer that has some resistance to a RET inhibitor that is not a compound of General Formula I or a pharmaceutically acceptable salt or solvate thereof.

In some embodiments of any of the methods described herein, a RET inhibitor resistance mutation that confers increased resistance to a cancer cell or tumor to treatment with a RET inhibitor that is not a compound of General Formula I or a pharmaceutically acceptable salt or solvate thereof, can be any of the RET inhibitor resistance mutations listed in Table 3 or 4 (e.g., a substitution at amino acid position 804, e.g., V804M, V804L, or V804E).

In some embodiments, the presence of one or more RET inhibitor resistance mutations in a tumor causes the tumor to be more resistant to treatment with a compound of General Formula I or a pharmaceutically acceptable salt or solvate thereof. Methods useful when a RET inhibitor resistance mutation causes the tumor to be more resistant to treatment with a compound of General Formula I or a pharmaceutically acceptable salt or solvate thereof are described below. For example, provided herein are methods of treating a subject having a cancer that include: identifying a subject having a cancer cell that has one or more RET inhibitor resistance mutations (that confer increased resistance to a cancer cell or tumor to treatment with a compound of General Formula I or a pharmaceutically acceptable salt or solvate thereof); and administering to the identified subject a treatment that does not include a compound of General Formula I or a pharmaceutically acceptable salt or solvate thereof as a monotherapy. Also provided are methods of treating a subject identified as having a cancer cell that has one or more RET inhibitor resistance mutations (that confer increased resistance to a cancer cell or tumor to treatment with a compound of General Formula I or a pharmaceutically acceptable salt or solvate thereof) that include administering to the subject a treatment that does not include a compound of General Formula I or a pharmaceutically acceptable salt or solvate thereof as a monotherapy. Also provided are methods of selecting a treatment for a subject having a cancer that include: identifying a subject having a cancer cell that has one or more RET inhibitor resistance mutations (that confer increased resistance to a cancer cell or tumor to treatment with a compound of General Formula I or a pharmaceutically acceptable salt or solvate thereof); and selecting a treatment that does not include a compound of General Formula I or a pharmaceutically acceptable salt or solvate thereof as a monotherapy for the identified subject. Also provided are methods of selecting a treatment for a subject having a cancer that include: selecting a treatment that does not include a compound of General Formula I or a pharmaceutically acceptable salt or solvate thereof as a monotherapy for a subject identified as having a cancer cell that has one or more RET inhibitor resistance mutations (that confer increased resistance to a cancer cell or tumor to treatment with a compound of General Formula I or a pharmaceutically acceptable salt or solvate thereof). Also provided are methods of selecting a subject having a cancer for a treatment that does not include a compound of General Formula I or a pharmaceutically acceptable salt or solvate thereof as a monotherapy that include: identifying a subject having a cancer cell that has one or more RET inhibitor resistance mutations (that confer increased resistance to a cancer cell or tumor to treatment with a compound of General Formula I or a pharmaceutically acceptable salt or solvate thereof); and selecting the identified subject for a treatment that does not include a compound of General Formula I or a pharmaceutically acceptable salt or solvate thereof as a monotherapy. Also provided are methods of selecting a subject having a cancer for a treatment that does not include a compound of General Formula I or a pharmaceutically acceptable salt or solvate thereof as a monotherapy that include: selecting a subject identified as having a cancer cell that has one or more RET inhibitor resistance mutations (that confer increased resistance to a cancer cell or tumor to treatment with a compound of General Formula I or a pharmaceutically acceptable salt or solvate thereof), for a treatment that does not include a compound of General Formula I or a pharmaceutically acceptable salt or solvate thereof as a monotherapy. Also provided are methods of determining the likelihood that a subject having a cancer will have a positive response to treatment with a compound of General Formula I or a pharmaceutically acceptable salt or solvate thereof as a monotherapy that include: determining whether a cancer cell in a sample obtained from the subject has one or more RET inhibitor resistance mutations (that confer increased resistance to a cancer cell or tumor to treatment with a compound of General Formula I or a pharmaceutically acceptable salt or solvate thereof); and determining that a subject having a cancer cell that has one or more RET inhibitor resistance mutations (that confer increased resistance to a cancer cell or tumor to treatment with a compound of General Formula I or a pharmaceutically acceptable salt or solvate thereof), has a decreased likelihood of having a positive response to treatment with a compound of General Formula I or a pharmaceutically acceptable salt or solvate thereof as a monotherapy. Also provided are methods of determining the likelihood that a subject having cancer will have a positive response to treatment with a compound of General Formula I or a pharmaceutically acceptable salt or solvate thereof as a monotherapy that include: determining that a subject having a cancer cell that has one or more RET inhibitor resistance mutations (that confer increased resistance to a cancer cell or tumor to treatment with a compound of General Formula I or a pharmaceutically acceptable salt or solvate thereof), has a decreased likelihood of having a positive response to treatment with a compound of General Formula I or a pharmaceutically acceptable salt or solvate thereof as a monotherapy. Also provided are methods of predicting the efficacy of treatment with a compound of General Formula I or a pharmaceutically acceptable salt or solvate thereof as a monotherapy in a subject having cancer that include: determining whether a cancer cell in a sample obtained from the subject has one or more RET inhibitor resistance mutations (that confer increased resistance to a cancer cell or tumor to treatment with a compound of General Formula I or a pharmaceutically acceptable salt or solvate thereof); and determining that treatment with a compound of General Formula I or a pharmaceutically acceptable salt or solvate thereof as a monotherapy is less likely to be effective in a subject having a cancer cell in a sample obtained from the subject that has one or more RET inhibitor resistance mutations (that confer increased resistance to a cancer cell or tumor to treatment with a compound of General Formula I or a pharmaceutically acceptable salt or solvate thereof). Also provided are methods of predicting the efficacy of treatment with a compound of General Formula I or a pharmaceutically acceptable salt or solvate thereof as a monotherapy in a subject having cancer that include: determining that treatment with a compound of General Formula I or a pharmaceutically acceptable salt or solvate thereof as a monotherapy is less likely to be effective in a subject having a cancer cell in a sample obtained from the subject that has one or more RET inhibitor resistance mutations (that confer increased resistance to a cancer cell or tumor to treatment with a compound of General Formula I or a pharmaceutically acceptable salt or solvate thereof).

Also provided are methods of treating a subject having a cancer that include: (a) administering one or more doses of a compound of General Formula I or a pharmaceutically acceptable salt or solvate thereof for a period of time; (b) after (a), determining whether a cancer cell in a sample obtained from the subject has one or more RET inhibitor resistance mutations (that confer increased resistance to a cancer cell or tumor to treatment with a compound of General Formula I or a pharmaceutically acceptable salt or solvate thereof of (a)); and (c) administering a different RET inhibitor (e.g., a compound that is not a compound of General Formula I or a pharmaceutically acceptable salt or solvate thereof, or a compound of General Formula I or a pharmaceutically acceptable salt or solvate thereof that is different from that administered in step (a)) as a monotherapy or in conjunction with another anticancer agent (e.g., any of the RET inhibitors described herein, e.g., a compound of General Formula I or a pharmaceutically acceptable salt or solvate thereof, e.g., the same compound of General Formula I or a pharmaceutically acceptable salt or solvate thereof administered in (a)) to a subject having a cancer cell that has one or more RET inhibitor resistance mutations (that confer increased resistance to a cancer cell or tumor to treatment with a compound of General Formula I or a pharmaceutically acceptable salt or solvate thereof of (a)); or (d) administering additional doses of a compound of General Formula I or a pharmaceutically acceptable salt or solvate thereof of step (a) to a subject having a cancer cell that does not have a RET inhibitor resistance mutation (that confers increased resistance to a cancer cell or tumor to treatment with a compound of General Formula I or a pharmaceutically acceptable salt or solvate thereof of (a)). In some embodiments, where the subject is administered additional doses of the compound of General Formula I or a pharmaceutically acceptable salt or solvate thereof of step (a), the subject can also be administered another anticancer agent (e.g., another RET inhibitor, e.g., a RET inhibitor that is not a compound of General Formula I or a pharmaceutically acceptable salt or solvate thereof, or a compound of General Formula I or a pharmaceutically acceptable salt or solvate thereof that is different from the compound of step (a)).

Also provided are methods of treating a subject having a cancer that include: (a) determining whether a cancer cell in a sample obtained from a subject having a cancer and previously administered one or more doses of a compound of General Formula I or a pharmaceutically acceptable salt or solvate thereof, has one or more RET inhibitor resistance mutations (that confer increased resistance to a cancer cell or tumor to treatment with a compound of General Formula I or a pharmaceutically acceptable salt or solvate thereof that was previously administered to the subject); (b) administering a different RET inhibitor (e.g., a compound that is not a compound of General Formula I or a pharmaceutically acceptable salt or solvate thereof, or a compound of General Formula I or a pharmaceutically acceptable salt or solvate thereof that is different from the compound of General Formula I or a pharmaceutically acceptable salt or solvate thereof previously administered to the subject) as a monotherapy or in conjunction with another anticancer agent (e.g., any of the RET inhibitors described herein, e.g., a compound of General Formula I or a pharmaceutically acceptable salt or solvate thereof, e.g., the same compound of General Formula I or a pharmaceutically acceptable salt or solvate thereof previously administered to the subject) to a subject having a cancer cell that has one or more RET inhibitor resistance mutations (that confer increased resistance to a cancer cell or tumor to treatment with a compound of General Formula I or a pharmaceutically acceptable salt or solvate thereof that was previously administered to the subject); or (c) administering additional doses of a compound of General Formula I or a pharmaceutically acceptable salt or solvate thereof previously administered to a subject having a cancer cell that does not have a RET inhibitor resistance mutation (that confers increased resistance to a cancer cell or tumor to treatment with a compound of General Formula I or a pharmaceutically acceptable salt or solvate thereof that was previously administered to the subject). In some embodiments, where the subject is administered additional doses of the compound of General Formula I or a pharmaceutically acceptable salt or solvate thereof of step (a), the subject can also be administered another anticancer agent (e.g., another RET inhibitor, e.g., a RET inhibitor that is not a compound of General Formula I or a pharmaceutically acceptable salt or solvate thereof, or a compound of General Formula I or a pharmaceutically acceptable salt or solvate thereof that is different from the compound of step (a)).

Also provided are methods of selecting a treatment for a subject having a cancer that include: (a) administering one or more doses of a compound of General Formula I or a pharmaceutically acceptable salt or solvate thereof to the subject for a period of time; (b) after (a), determining whether a cancer cell in a sample obtained from the subject has one or more RET inhibitor resistance mutations (that confer increased resistance to a cancer cell or tumor to treatment with a compound of General Formula I or a pharmaceutically acceptable salt or solvate thereof of (a)); and (c) selecting a different RET inhibitor (e.g., a compound that is not a compound of General Formula I or a pharmaceutically acceptable salt or solvate thereof, or a compound of General Formula I or a pharmaceutically acceptable salt or solvate thereof that is different from that administered in step (a)) as a monotherapy or in conjunction with another anticancer agent (e.g., any of the RET inhibitors described herein, e.g., a compound of General Formula I or a pharmaceutically acceptable salt or solvate thereof, e.g., the same compound of General Formula I or a pharmaceutically acceptable salt or solvate thereof administered in (a)) for the subject if the subject has a cancer cell that has a RET inhibitor resistance mutation (that confer increased resistance to a cancer cell or tumor to treatment with a compound of General Formula I or a pharmaceutically acceptable salt or solvate thereof of (a)); or (d) selecting additional doses of a compound of General Formula I or a pharmaceutically acceptable salt or solvate thereof of step (a) for the subject if the subject has a cancer cell that does not have a RET inhibitor resistance mutation (that confers increased resistance to a cancer cell or tumor to treatment with a compound of General Formula I or a pharmaceutically acceptable salt or solvate thereof of (a)). In some embodiments, where additional doses of a compound of General Formula I or a pharmaceutically acceptable salt or solvate thereof of step (a) are selected for the subject, the method can also include further selecting another anticancer agent (e.g., another RET inhibitor, e.g., a RET inhibitor that is not a compound of General Formula I or a pharmaceutically acceptable salt or solvate thereof, or a compound of General Formula I or a pharmaceutically acceptable salt or solvate thereof that is different from the compound of step (a)).

Also provided are methods of selecting a treatment for a subject having a cancer that include: (a) determining whether a cancer cell in a sample obtained from a subject having a cancer and previously administered one or more doses of a compound of General Formula I or a pharmaceutically acceptable salt or solvate thereof, has one or more RET inhibitor resistance mutations (that confer increased resistance to a cancer cell or tumor to treatment with a compound of General Formula I or a pharmaceutically acceptable salt or solvate thereof that was previously administered to the subject); (b) selecting a different RET inhibitor (e.g., a compound that is not a compound of General Formula I or a pharmaceutically acceptable salt or solvate thereof, or a compound of General Formula I or a pharmaceutically acceptable salt or solvate thereof that is different from the compound of General Formula I or a pharmaceutically acceptable salt or solvate thereof previously administered to the subject) as a monotherapy or in conjunction with another anticancer agent (e.g., any of the RET inhibitors described herein, e.g., a compound of General Formula I or a pharmaceutically acceptable salt or solvate thereof, e.g., the same compound of General Formula I or a pharmaceutically acceptable salt or solvate thereof previously administered to the subject) for the subject if the subject has a cancer cell that has a RET inhibitor resistance mutation (that confers increased resistance to a cancer cell or tumor to treatment with a compound of General Formula I or a pharmaceutically acceptable salt or solvate thereof that was previously administered to the subject); or (c) selecting additional doses of the compound of General Formula I or a pharmaceutically acceptable salt or solvate thereof previously administered to the subject if the subject has a cancer cell that does not have a RET inhibitor resistance mutation (that confers increased resistance to a cancer cell or tumor to treatment with a compound of General Formula I or a pharmaceutically acceptable salt or solvate thereof that was previously administered to the subject). In some embodiments, where additional doses of a compound of General Formula I or a pharmaceutically acceptable salt or solvate thereof of step (a) are selected for the subject, the method can also include further selecting another anticancer agent (e.g., another RET inhibitor, e.g., a RET inhibitor that is not a compound of General Formula I or a pharmaceutically acceptable salt or solvate thereof, or a compound of General Formula I or a pharmaceutically acceptable salt or solvate thereof that is different from the compound of step (a)).

Also provided are methods of determining a subject's risk for developing a cancer that has some resistance to a compound of General Formula I or a pharmaceutically acceptable salt or solvate thereof that include: determining whether a cell in a sample obtained from the subject has one or more RET inhibitor resistance mutations (that confer increased resistance to a cancer cell or tumor to treatment with a compound of General Formula I or a pharmaceutically acceptable salt or solvate thereof); and identifying the subject if the subject has a cell that has one or more RET inhibitor resistance mutations (that confer increased resistance to a cancer cell or tumor to treatment with a compound of General Formula I or a pharmaceutically acceptable salt or solvate thereof), as having an increased likelihood of developing a cancer that has some resistance to a compound of General Formula I or a pharmaceutically acceptable salt or solvate thereof. Also provided are methods of determining a subject's risk for developing a cancer that has some resistance to a compound of General Formula I or a pharmaceutically acceptable salt or solvate thereof that include: identifying a subject having a cell that has one or more RET inhibitor resistance mutations (that confer increased resistance to a cancer cell or tumor to treatment with a compound of General Formula I or a pharmaceutically acceptable salt or solvate thereof), as having an increased likelihood of developing a cancer that has some resistance to a compound of General Formula I or a pharmaceutically acceptable salt or solvate thereof. Also provided are methods of determining the presence of a cancer that has some resistance to a compound of General Formula I or a pharmaceutically acceptable salt or solvate thereof that includes: determining whether a cancer cell in a sample obtained from the subject has one or more RET inhibitor resistance mutations (that confer increased resistance to a cancer cell or tumor to treatment with a compound of General Formula I or a pharmaceutically acceptable salt or solvate thereof); and determining that a subject having a cancer cell that has one or more RET inhibitor resistance mutations (that confer increased resistance to a cancer cell or tumor to treatment with a compound of General Formula I or a pharmaceutically acceptable salt or solvate thereof), has a cancer that has some resistance to a compound of General Formula I or a pharmaceutically acceptable salt or solvate thereof. Also provided are methods of determining the presence of a cancer that has some resistance to a compound of General Formula I or a pharmaceutically acceptable salt or solvate thereof in a subject that include: determining that a subject having a cancer cell that has one or more RET inhibitor resistance mutations (that confer increased resistance to a cancer cell or tumor to treatment with a compound of General Formula I or a pharmaceutically acceptable salt or solvate thereof), has a cancer that has some resistance to a compound of General Formula I or a pharmaceutically acceptable salt or solvate thereof.

In some embodiments of any of the methods described herein, a RET inhibitor resistance mutation that confers increased resistance to a cancer cell or tumor to treatment with a compound of General Formula I or a pharmaceutically acceptable salt or solvate thereof, can be any of the RET inhibitor resistance mutations listed in Table 3 or 4.

Methods of determining the level of resistance of a cancer cell or a tumor to a RET inhibitor (e.g., any of the RET inhibitors described herein or known in the art) can be determined using methods known in the art. For example, the level of resistance of a cancer cell to a RET inhibitor can be assessed by determining the $IC_{50}$ of a RET inhibitor (e.g., any of the RET inhibitors described herein or known in the art) on the viability of a cancer cell. In other examples, the level of resistance of a cancer cell to a RET inhibitor can be assessed by determining the growth rate of the cancer cell in the presence of a RET inhibitor (e.g., any of the RET inhibitors described herein). In other examples, the level of resistance of a tumor to a RET inhibitor can be assessed by determining the mass or size of one or more tumors in a subject over time during treatment with a RET inhibitor (e.g., any of the RET inhibitors described herein). In other examples, the level of resistance of a cancer cell or a tumor to a RET inhibitor can be indirectly assessed by determining the activity of a RET kinase including one or more of the RET inhibitor resistance mutations (i.e., the same RET kinase expressed in a cancer cell or a tumor in a subject). The level of resistance of a cancer cell or tumor having one or more RET inhibitor resistance mutations to a RET inhibitor is relative to the level of resistance in a cancer cell or tumor that does not have a RET inhibitor resistance mutation (e.g., a cancer cell or tumor that does not have the same RET inhibitor resistance mutations, a cancer cell or a tumor that does not have any RET inhibitor resistance mutations, or a cancer cell or a tumor that expresses a wildtype RET protein). For example, the determined level of resistance of a cancer cell or a tumor having one or more RET inhibitor resistance mutations can be greater than about 1%, greater than about 2%, greater than about 3%, greater than about 4%, greater than about 5%, greater than about 6%, greater than about 7%, greater than about 8%, greater than about 9%, greater than about 10%, greater than about 11%, greater than about 12%, greater than about 13%, greater than about 14%, greater than about 15%, greater than about 20%, greater than about 25%, greater than about 30%, greater than about 35%, greater than about 40%, greater than about 45%, greater than about 50%, greater than about 60%, greater than about 70%, greater than about 80%, greater than about 90%, greater than about 100%, greater than about 110%, greater than about 120%, greater than about 130%, greater than about 140%, greater than about 150%, greater than about 160%, greater than about 170%, greater than about 180%, greater than about 190%, greater than about 200%, greater than about 210%, greater than about 220%, greater than about 230%, greater than about 240%, greater than about 250%, greater than about 260%, greater than about 270%, greater than about 280%, greater than about 290%, or greater than about 300% of the level of resistance in a cancer cell or tumor that does not have a RET inhibitor resistance mutation (e.g., a cancer cell or tumor that does not have the same RET inhibitor resistance mutations, a cancer cell or a tumor that does not have any RET inhibitor resistance mutations, or a cancer cell or a tumor that expresses a wildtype RET protein).

RET is thought to play an important role in the development and survival of afferent nociceptors in the skin and gut. RET kinase knock-out mice lack enteric neurons and have other nervous system anomalies suggesting that a functional RET kinase protein product is necessary during development (Taraviras, S. et al., *Development*, 1999, 126:2785-2797). Moreover population studies of patients with Hirschsprung's disease characterized by colonic obstruction due to lack of normal colonic enervation have a higher proportion of both familial and sporadic loss of function RET mutations (Butler Tjaden N., et al., *Transl. Res.*, 2013, 162: 1-15). Irritable bowel syndrome (IBS) is a common illness affecting 10-20% of individuals in developed countries and is characterized by abnormal bowel habits, bloating and visceral hypersensitivity (Camilleri, M., *N. Engl. J. Med.*, 2012, 367: 1626-1635). While the etiology of IBS is unknown it is thought to result from either a disorder between the brain and gastrointestinal tract, a disturbance in the gut microbiome or increased inflammation. The resulting gastrointestinal changes affect normal bowel transit resulting in either diarrhea or constipation. Furthermore in many IBS patients the sensitization of the peripheral nervous system results in visceral hypersensitivity or allodynia (Keszthelyi, D., *Eur. J. Pain*, 2012, 16: 1444-1454). See, e.g., U.S. Publication No. 2015/0099762.

Accordingly, provided herein are methods for treating a patient diagnosed with (or identified as having) an irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, and inflammatory bowel disease that include administering to the patient a therapeutically effective amount of a compound of General Formula I or a pharmaceutically acceptable salt or solvate thereof.

Also provided herein are methods for treating a patient identified or diagnosed as having a RET-associated irritable bowel syndrome (IBS) (e.g., a patient that has been identified or diagnosed as having a RET-associated irritable bowel syndrome (IBS) through the use of a regulatory agency-approved, e.g., FDA-approved, kit for identifying dysregulation of a RET gene, a RET kinase, or expression or activity or level of any of the same, in a patient or a biopsy sample from the patient) that include administering to the patient a therapeutically effective amount of a compound of General Formula I or a pharmaceutically acceptable salt or solvate thereof.

Also provided herein are methods for treating pain associated with IBS that include administering to the patient a therapeutically effective amount of a compound of General Formula I or a pharmaceutically acceptable salt or solvate thereof. In some embodiments, a compound of General Formula I or a pharmaceutically acceptable salt or solvate thereof is administered in combination with another therapeutic agent useful for treating one or more symptoms of IBS.

Also provided are methods for treating an irritable bowel syndrome (IBS) in a patient in need thereof, the method comprising: (a) determining if the irritable bowel syndrome (IBS) in the patient is a RET-associated IBS (e.g., using a regulatory-agency approved, e.g., FDA-approved, kit for identifying dysregulation of a RET gene, a RET kinase, or expression or activity or level of any of the same, in a patient or a biopsy sample from the patient, or by performing any of the non-limiting examples of assays described herein); and (b) if the IBS is determined to be a RET-associated IBS, administering to the patient a therapeutically effective amount of a compound of General Formula I or a pharmaceutically acceptable salt or solvate thereof.

In some embodiments, the compounds of the present invention are useful for treating irritable bowel syndrome (IBS) in combination with one or more additional therapeutic agents or therapies effective in treating the irritable bowel syndrome that work by the same or a different mechanism of action. The at least one additional therapeutic agent may be administered with a compound of General Formula I or a pharmaceutically acceptable salt or solvate thereof as part of the same or separate dosage forms, via the same or different routes of administration, and on the same or different administration schedules according to standard pharmaceutical practice known to one skilled in the art.

Non-limiting examples of additional therapeutics for the treatment of irritable bowel syndrome (IBS) include probiotics, fiber supplements (e.g., *psyllium*, methylcellulose), anti-diarrheal medications (e.g., loperamide), bile acid binders (e.g., cholestyramine, colestipol, colesevelam), anticholinergic and antispasmodic medications (e.g., hyoscyamine, dicyclomine), antidepressant medications (e.g., tricyclic antidepressant such as imipramine or notriptyline or a selective serotonin reuptake inhibitor (SSRI) such as fluoxetine or paroxetine), antibiotics (e.g., rifaximin), alosetron, and lubiprostone.

Accordingly, also provided herein are methods of treating irritable bowel syndrome (IBS), comprising administering to a patient in need thereof a pharmaceutical combination for treating IBS which comprises (a) a compound of General Formula I or pharmaceutically acceptable salt or solvate thereof, (b) an additional therapeutic agent, and (c) optionally at least one pharmaceutically acceptable carrier for simultaneous, separate or sequential use for the treatment of IBS, wherein the amounts of the compound of General Formula I or pharmaceutically acceptable salt or solvate thereof and the additional therapeutic agent are together effective in treating the IBS. In one embodiment, the compound of General Formula I or pharmaceutically acceptable salt or solvate thereof, and the additional therapeutic agent are administered simultaneously as separate dosages. In one embodiment, the compound of General Formula I or pharmaceutically acceptable salt or solvate thereof, and the additional therapeutic agent are administered as separate dosages sequentially in any order, in jointly therapeutically effective amounts, e.g. in daily or intermittently dosages. In one embodiment, compound of General Formula I or pharmaceutically acceptable salt or solvate thereof, and the additional therapeutic agent are administered simultaneously as a combined dosage.

Also provided herein is (i) a pharmaceutical combination for treating irritable bowel syndrome in a patient in need thereof, which comprises (a) a compound of General Formula I or a pharmaceutically acceptable salt or solvate thereof, (b) at least one additional therapeutic agent (e.g., any of the exemplary additional therapeutic agents described herein for treating irritable bowel syndrome or known in the art), and (c) optionally at least one pharmaceutically acceptable carrier for simultaneous, separate or sequential use for the treatment of irritable bowel syndrome, wherein the amounts of the compound of General Formula I or pharmaceutically acceptable salt or solvate thereof and of the additional therapeutic agent are together effective in treating the irritable bowel syndrome; (ii) a pharmaceutical composition comprising such a combination; (iii) the use of such a combination for the preparation of a medicament for the treatment of irritable bowel syndrome; and (iv) a commercial package or product comprising such a combination as a combined preparation for simultaneous, separate or sequential use; and to a method of treatment of irritable bowel syndrome in a patient in need thereof. In one embodiment the patient is a human.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of General Formula I or a pharmaceutically acceptable salt or solvate thereof and at least one additional therapeutic agent (e.g., an agent effective in treating irritable bowel syndrome), are both administered to a patient simultaneously in the form of a single composition or dosage. The term "non-fixed combination" means that a compound of General Formula I or a pharmaceutically acceptable salt or solvate thereof and at least one additional therapeutic agent (e.g., an agent effective in treating irritable bowel syndrome) are formulated as separate compositions or dosages, such that they may be administered to a patient in need thereof simultaneously, concurrently or sequentially with variable intervening time limits, wherein such administration provides effective levels of the two or more compounds in the body of the patient. In one embodiment, the compound of Formula I and the additional therapeutic agent are formulated as separate unit dosage forms, wherein the separate dosages forms are suitable for either sequential or simultaneous administration. These also apply to cocktail therapies, e.g. the administration of three or more active ingredients.

In some embodiments, a compound provided herein can be used as an agent for supportive care for a patient undergoing cancer treatment. For example, a compound of General Formula I or a pharmaceutically acceptable salt or solvate thereof, can be useful to reduce one or more symptoms associated with treatment with one or more cancer therapies such as diarrheal or constipations complications and/or abdominal pain. See, for example, U.S. Publication No. 2015/0099762 and Hoffman, J. M. et al. *Gastroenterology* (2012) 142:844-854. Accordingly, a compound, or a pharmaceutically acceptable salt thereof, or composition provided herein can be administered to a patient to address one or more complications associated with cancer treatment (e.g., gastrointestinal complications such as diarrhea, constipation, or abdominal pain).

In some embodiments, a therapeutically effective amount of a compound of General Formula I or a pharmaceutically acceptable salt or solvate thereof, can be administered to a patient undergoing cancer treatment (e.g., a patient experiencing an adverse event associated with cancer treatment such as an immune-related adverse event or a gastrointestinal complication including diarrhea, constipation, and abdominal pain). For example, a compound provided herein, or a pharmaceutically acceptable salt thereof, can be used in the treatment of colitis or IBS associated with administration of a checkpoint inhibitor; see, e.g., Postow, M. A. et al. *Journal of Clinical Oncology* (2015) 33: 1974-1982. In some such embodiments, a compound provided herein, or a pharmaceutically acceptable salt thereof, can be formulated to exhibit low bioavailability and/or be targeted for delivery in the gastrointestinal tract. See, for example, U.S. Pat. No. 6,531,152.

Also provided is a method for inhibiting RET kinase activity in a cell, comprising contacting the cell with a compound of General Formula I. In one embodiment, the contacting is in vitro. In one embodiment, the contacting is in vivo. In one embodiment, the contacting is in vivo, wherein the method comprises administering an effective amount of a compound of General Formula I or a pharmaceutically acceptable salt or solvate thereof to a subject having a cell having RET kinase activity. In some embodiments, the cell is a cancer cell. In one embodiment, the cancer cell is any cancer as described herein. In some embodiments, the cancer cell is a RET-associated cancer cell. In some embodiments, the cell is a gastrointestinal cell.

Also provided is a method for inhibiting RET kinase activity in a mammalian cell, comprising contacting the cell with a compound of General Formula I. In one embodiment, the contacting is in vitro. In one embodiment, the contacting is in vivo. In one embodiment, the contacting is in vivo, wherein the method comprises administering an effective amount of a compound of General Formula I or a pharmaceutically acceptable salt or solvate thereof to a mammal having a cell having RET kinase activity. In some embodiments, the mammalian cell is a mammalian cancer cell. In one embodiment, the mammalian cancer cell is any cancer as described herein. In some embodiments, the mammalian cancer cell is a RET-associated cancer cell. In some embodiments, the mammalian cell is a gastrointestinal cell.

As used herein, the term "contacting" refers to the bringing together of indicated moieties in an in vitro system or an in vivo system. For example, "contacting" a RET kinase with a compound provided herein includes the administration of a compound provided herein to an individual or patient, such as a human, having a RET kinase, as well as, for example, introducing a compound provided herein into a sample containing a cellular or purified preparation containing the RET kinase.

Also provided herein is a method of inhibiting cell proliferation, in vitro or in vivo, the method comprising contacting a cell with an effective amount of a compound of General Formula I or a pharmaceutically acceptable salt or solvate thereof, or a pharmaceutical composition thereof as defined herein The phrase "effective amount" means an amount of compound that, when administered to a patient in need of such treatment, is sufficient to (i) treat a RET kinase-associated disease or disorder, (ii) attenuate, ameliorate, or eliminate one or more symptoms of the particular disease, condition, or disorder, or (iii) delay the onset of one or more symptoms of the particular disease, condition, or disorder described herein. The amount of a compound of General Formula I that will correspond to such an amount will vary depending upon factors such as the particular compound, disease condition and its severity, the identity (e.g., weight) of the patient in need of treatment, but can nevertheless be routinely determined by one skilled in the art.

When employed as pharmaceuticals, the compounds of General Formula I can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable Also provided herein are pharmaceutical compositions which contain, as the active ingredient, a compound of General Formula I or a pharmaceutically acceptable salt or solvate thereof, in combination with one or more pharmaceutically acceptable carriers (excipients). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In one embodiment, the composition is formulated for oral administration. In one embodiment, the composition is formulated as a tablet or capsule.

The compositions comprising a compound of General Formula I or a pharmaceutically acceptable salt or solvate thereof can be formulated in a unit dosage form, each dosage containing from about 5 to about 1,000 mg (1 g), more usually about 100 mg to about 500 mg, of the active ingredient. The term "unit dosage form" refers to physically discrete units suitable as unitary dosages for human subjects and other patients, each unit containing a predetermined quantity of active material (i.e., a compound for General Formula I as provided herein) calculated to produce the desired therapeutic effect, in association with a suitable pharmaceutical excipient.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

Provided herein are pharmaceutical kits useful, for example, in the treatment of RET-associated diseases or disorders, such as cancer or irritable bowel syndrome (IBS), which include one or more containers containing a pharmaceutical composition comprising a therapeutically effective amount of a compound provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

EXAMPLES

The following examples illustrate the invention.

Biological Examples

Example A

RET Enzyme Assay

Compounds of General Formula I were screened for their ability to inhibit wild type and V804M mutant RET kinase using CisBio's HTRF® KinEASE™-TK assay technology. Briefly, N-terminal GST tagged recombinant human RET cytoplasmic domain (aa 658-end) from Eurofins (0.25 nM RET; Cat. No. 14-570M) or N-terminal GST tagged recombinant human V804M mutant RET cytoplasmic domain (aa 658-end) from Millipore (0.25 nM enzyme; Cat. No. 14-760) was incubated with 250 nM TK-substrate biotin (CisBio, part of Cat. No. 62TK0PEC) and 1 mM ATP along with test compound in a buffer consisting of 25 mM HEPES pH 7.4, 10 mM $MgCl_2$, 0.01% Triton X-100, and 2% DMSO in a volume of 8 µL. Compounds were typically prepared in a threefold serial dilution in DMSO and added to the assay to give the appropriate final concentration. After a 30-minute incubation at 22° C., the reaction was quenched by adding 8 µL of quench solution containing 31.25 nM Sa-XL665 and 1× TK-ab-Cryptate in HTRF detection buffer (all from CisBio, part of Cat. No. 62TK0PEC). After a 1 hour incubation at 22° C., the extent of reaction was determined using a PerkinElmer EnVision multimode plate reader via HTRF dual wavelength detection, and the percent of control (POC) was calculated using a ratiometric emission factor. 100 POC was determined using no test compounds and 0 POC was determined using pre-quenched control reactions. The POC values were fit to a 4 parameter logistic curve, and the $IC_{50}$ is defined as the concentration of inhibitor at which the POC equals 50 for the fitted curve. The $IC_{50}$ values for the compounds tested in this assay are provided in Table 5.

Example B

RET Cell Assay

The cellular potency of a compound inhibiting RET kinase was determined in HEK-293 cells expressing a Kif5b-RET fusion protein. Briefly, HEK-293 cells expressing a Kif5b-RET fusion protein were plated at 50K cells/well in 96 well poly-D-Lysine coated plates the day prior to the assay. The cells were incubated for 1 hour with test compound in DMEM (Dulbecco's Modified Eagle Medium) at a final DMSO concentration of 0.5%. Compounds were typically prepared in a three fold serial dilution in DMSO and added to the assay to give the appropriate final concentration. After 1 hour the media was removed, the cells were fixed with 3.8% formaldehyde for 20 min, washed with PBS, and permeabilized for 10 min with 100% methanol. The plates were then washed with PBS-0.05% Tween20, and blocked with LI-COR Blocking solution (LI-COR catalog #927-40000) for 1 hour. Plates were washed with PBS-0.05% Tween20, then incubated with anti-phospho-RET (Tyr1062) (Santa Cruz catalog #sc-20252-R) antibody and anti-GAPDH (Millipore catalog # MAB374) antibody for 2 hours. The plates were washed with PBS-0.05% Tween20, and incubated with anti-rabbit 680 (Molecular Probes cat# A21109) and anti-mouse 800 (LI-COR catalog #926-32210) secondary antibodies for 1 hour. All antibodies were diluted in LI-COR Block containing 0.05% Tween. The plates were washed with PBS-0.05% Tween20, 100 µL PBS was added to each well, and the plates were read on a LI-COR Aerius fluorescent plate reader. The phospho-RET signal was normalized to the GAPDH signal. 100 POC (percent of control) was determined using no test compounds and 0 POC was determined using 1 µM of a control inhibitor. The POC values were fit to a 4 parameter logistic curve. The $IC_{50}$ value is the point where the curve crosses 50 POC. The $IC_{50}$ values for the compounds tested in this assay are provided in Table 5.

Example C

KDR Cell Assay

The cellular potency of a compound inhibiting KDR kinase was determined in HEK-293 cells expressing an inducible human KDR protein. Briefly, HEK-293 cells expressing KDR protein were plated at 40K cells/well in 96-well collagen (compounds of Example Nos. 2, 88, 290, 291, 295, 297, 298, 299, 332, 333, and 339) or poly-D-lysine (all other tested compounds) coated plates the day prior to the assay. Cells were incubated for 4 to 6 hours to allow them to adhere to the plate and then protein expression is induced by the addition of 1 μg/mL Doxycycline overnight. The cells were incubated for 1 hour with test compound in DMEM at a final DMSO concentration of 0.25%. Compounds were typically prepared in a three-fold serial dilution in DMSO and added to the assay to give the appropriate final concentration. After 1 hour, wells were stimulated with VEGF (75 ng/ml final; compounds of Example Nos. #2, 88, 290, 291, 295, 297, 298, 299, 332, 333, 339) or VEGF (56 ng/ml final; all other tested compounds) for 5 minutes at 37 C. The media was aspirated and 35 μL of a 1× lysis buffer was added. Plates were shaken for 1-2 mins to finalize cell lysis. The lysate was stored at −80° C. until ready for assay. Phospho-KDR was measured using a phospho-KDR kit (Catalog #K151BOC) purchased from Meso Scale Diagnostics (Rockville, Md.) according to the manufacturer's instructions. All values are expressed as percent of percent of control (POC). The POC values were fitted to a 4 parameter logistic curve fit and the $IC_{50}$ value is point where the curve crosses 50 POC. The $IC_{50}$ values for the compounds tested in this assay are provided in Table 5.

TABLE 5

$IC_{50}$ values of compounds tested in the assay of Examples A, B and/or C.

| Ex# | RET Enzyme $IC_{50}$ (nM) | RET FRET_ATP_V804M $IC_{50}$ (nM) | KIF5B-RET pTYR1062 Cell $IC_{50}$ (nM) | pKDR Cell HEK 10% FBS $IC_{50}$ (nM) |
|---|---|---|---|---|
| 1 | 35.8 | 302.2 | 47.5 | N/A |
| 2 | 19.6 | N/A | 110.8 | 1081.9 |
| 3 | 11.9 | N/A | 119.0 | N/A |
| 4 | 3.1 | N/A | 15.9 | 327.6 |
| 5 | 4.6 | 32.0 | 4.3 | 242.9 |
| 6 | 4.9 | 38.3 | 4.2 | 114.9 |
| 7 | 3.9 | 20.8 | 2.9 | 115.1 |
| 8 | 3.6 | N/A | 4.3 | 98.9 |
| 9 | 5.3 | 23.3 | 4.2 | 32.7 |
| 10 | 4.5 | N/A | 2.5 | 47.4 |
| 11 | 28.9 | N/A | 123.5 | N/A |
| 12 | 15.4 | N/A | 47.6 | 1190.0 |
| 13 | 154.5 | N/A | 3768.9 | N/A |
| 14 | 4.4 | N/A | 3.7 | 1781.0 |
| 15 | 12.5 | N/A | 21.2 | 642.9 |
| 16 | 5.7 | 20.9 | 2.1 | 435.0 |
| 17 | 19.9 | N/A | 29.2 | 83.4 |
| 18 | 30.6 | N/A | 19.8 | 229.4 |
| 19 | 12.6 | N/A | 54.1 | 546.5 |
| 20 | 9.8 | 76.8 | 36.8 | 1647.2 |
| 21 | 9.4 | N/A | 21.3 | 539.8 |
| 22 | 14.8 | 162.7 | 22.5 | 630.1 |
| 23 | 3.8 | 26.6 | 4.8 | 45.4 |
| 24 | 34.0 | N/A | 18.9 | 960.5 |
| 25 | 5.0 | 14.9 | 1.6 | 269.9 |
| 26 | 13.0 | N/A | 9.6 | 476.1 |
| 27 | 14.2 | N/A | 20.0 | 651.4 |
| 28 | 89.0 | N/A | 240.8 | N/A |
| 29 | 16.4 | N/A | 16.4 | 607.5 |
| 30 | 22.1 | N/A | 123.8 | 920.7 |
| 31 | 36.7 | N/A | 76.1 | 2550.8 |
| 32 | 23.9 | N/A | 108.0 | 749.0 |
| 33 | 42.9 | N/A | 309.5 | N/A |
| 34 | 34.8 | N/A | 61.2 | 3038.9 |
| 35 | 18.9 | N/A | 54.6 | 437.1 |
| 36 | 24.0 | N/A | 25.5 | 211.8 |
| 37 | 6.8 | 54.9 | 6.6 | 91.2 |
| 38 | 15.5 | N/A | 16.6 | 396.2 |
| 39 | 6.3 | N/A | 2.7 | 83.9 |
| 40 | 13.7 | N/A | 11.2 | 221.5 |
| 41 | 22.9 | N/A | 29.3 | 871.0 |
| 42 | 15.8 | N/A | 23.4 | 502.2 |
| 43 | 22.4 | N/A | 31.6 | 653.1 |
| 44 | 18.3 | N/A | 378.9 | N/A |
| 45 | 27.0 | N/A | 603.9 | N/A |
| 46 | 9.8 | N/A | 2244.2 | N/A |
| 47 | 12.6 | N/A | 2076.0 | N/A |
| 48 | 9.7 | 76.2 | 21.9 | 611.9 |
| 49 | 7.0 | N/A | 5.8 | 236.7 |
| 50 | 7.9 | 47.1 | 22.1 | 1192.6 |
| 51 | 4.1 | N/A | 3.5 | 267.2 |
| 52 | 17.7 | N/A | 340.4 | N/A |
| 53 | 4.4 | 74.6 | 9.9 | 305.2 |
| 54 | 12.4 | N/A | 66.6 | 1484.9 |
| 55 | 10.4 | N/A | 54.9 | 922.5 |
| 56 | 16.0 | N/A | 35.5 | 895.8 |
| 57 | 12.7 | N/A | 48.6 | 1036.2 |
| 58 | 8.3 | N/A | 16.6 | 438.9 |
| 59 | 16.3 | N/A | 26.6 | 554.3 |
| 60 | 14.8 | N/A | 16.9 | 376.4 |
| 61 | 5.5 | N/A | 5.5 | 148.5 |
| 62 | 17.3 | N/A | 27.7 | 1298.8 |
| 63 | 11.5 | N/A | 8.2 | 527.2 |
| 64 | 31.9 | N/A | 138.9 | N/A |
| 65 | 8.2 | N/A | 39.3 | 901.7 |
| 66 | 14.1 | N/A | 25.4 | 911.1 |
| 67 | 19.4 | N/A | 60.7 | 521.5 |
| 68 | 10.2 | N/A | 32.2 | 788.5 |
| 69 | 4.4 | N/A | 2.7 | 117.4 |
| 70 | 8.4 | N/A | 18.5 | 510.1 |
| 71 | 6.4 | N/A | 19.6 | 503.3 |
| 72 | 6.1 | 57.2 | 12.5 | 99.9 |
| 73 | 9.8 | N/A | 32.7 | 296.5 |
| 74 | 28.8 | N/A | 45.9 | 1346.1 |
| 75 | 6.3 | 40.1 | 7.0 | 392.1 |
| 76 | 8.0 | N/A | 13.3 | 1009.9 |
| 77 | 8.0 | N/A | 19.2 | 605.2 |
| 78 | 4.4 | N/A | 5.3 | 80.6 |
| 79 | 14.5 | N/A | 31.3 | 1263.1 |
| 80 | 33.6 | N/A | 542.2 | N/A |
| 81 | 12.6 | N/A | 66.1 | 761.9 |
| 82 | 4.8 | 13.2 | 3.1 | 91.2 |
| 83 | 7.6 | 20.5 | 3.7 | 135.2 |
| 84 | 13.0 | 75.0 | 8.3 | 1264.1 |
| 85 | 7.6 | 52.6 | 6.5 | 770.7 |
| 86 | 10.6 | N/A | 5.6 | 427.8 |
| 87 | 5.3 | N/A | 3.5 | 5.8 |
| 88 | 9.8 | N/A | 43.3 | 194.8 |
| 89 | 10.6 | 59.7 | 6.4 | 189.1 |
| 90 | 5.2 | 39.9 | 4.3 | 24.1 |
| 91 | 5.6 | N/A | 7.5 | 60.1 |
| 92 | 41.2 | N/A | 535.8 | N/A |
| 93 | 10.1 | N/A | 11.2 | 1699.2 |
| 94 | 8.5 | N/A | 8.5 | 1703.6 |
| 95 | 15.4 | N/A | 26.2 | 1307.1 |
| 96 | 6.3 | N/A | 51.9 | 1555.3 |
| 97 | 12.1 | 78.8 | 12.5 | 751.5 |
| 98 | 3.6 | N/A | 13.0 | 1596.5 |
| 99 | 13.9 | N/A | 406.3 | N/A |
| 100 | 15.3 | N/A | 455.5 | N/A |
| 101 | 11.7 | N/A | 13.6 | 868.4 |
| 102 | 11.7 | N/A | 8.3 | 551.3 |
| 103 | 23.5 | N/A | 23.5 | 847.6 |
| 104 | 23.1 | N/A | 33.2 | 637.4 |
| 105 | 13.9 | N/A | 63.0 | 1142.5 |
| 106 | 12.0 | N/A | 63.4 | 1370.3 |
| 107 | 22.9 | N/A | 42.8 | 893.0 |
| 108 | 11.1 | N/A | 15.6 | 531.0 |
| 109 | 8.8 | 36.3 | 2.1 | 359.6 |
| 110 | 12.0 | 100.5 | 11.7 | 1310.3 |
| 111 | 33.1 | N/A | 58.1 | 1957.3 |

TABLE 5-continued

IC$_{50}$ values of compounds tested in the assay of Examples A, B and/or C.

| Ex# | RET Enzyme IC$_{50}$ (nM) | RET FRET_ATP_V804M IC$_{50}$ (nM) | KIF5B-RET pTYR1062 Cell IC$_{50}$ (nM) | pKDR Cell HEK 10% FBS IC$_{50}$ (nM) |
|---|---|---|---|---|
| 112 | 10.3 | N/A | 22.7 | 868.9 |
| 113 | 11.5 | 105.6 | 11.4 | 653.8 |
| 114 | 25.9 | N/A | 36.0 | 2245.3 |
| 115 | 32.1 | N/A | 59.3 | 3180.2 |
| 116 | 11.7 | N/A | 12.7 | 2274.6 |
| 117 | 6.5 | N/A | 10.9 | 353.9 |
| 118 | 8.0 | N/A | 10.7 | 606.0 |
| 119 | 29.1 | N/A | 74.7 | 2268.8 |
| 120 | 17.9 | N/A | 54.8 | 2242.9 |
| 121 | 12.6 | N/A | 56.6 | 1340.9 |
| 122 | 11.3 | N/A | 266.7 | N/A |
| 123 | 19.1 | N/A | 67.9 | 1610.8 |
| 124 | 18.9 | N/A | 36.5 | 1859.6 |
| 125 | 5.6 | 60.5 | 6.1 | 615.8 |
| 126 | 11.7 | N/A | 10.8 | 347.2 |
| 127 | 2.7 | 13.4 | 2.7 | 13.5 |
| 128 | 11.6 | 127.7 | 11.1 | 554.5 |
| 129 | 2.9 | 17.3 | 5.0 | 93.5 |
| 130 | 20.8 | 152.6 | 33.0 | 2254.3 |
| 131 | 8.1 | N/A | 24.7 | 447.0 |
| 132 | 11.2 | 65.6 | 16.1 | 1151.0 |
| 133 | 4.3 | 10.9 | 1.7 | 147.1 |
| 134 | 5.5 | 34.2 | 11.5 | 319.9 |
| 135 | 12.8 | 93.6 | 35.4 | 1033.2 |
| 136 | 9.1 | 50.2 | 11.9 | 1580.0 |
| 137 | 8.3 | 32.1 | 5.2 | 71.3 |
| 138 | 5.4 | N/A | 5.2 | 16.1 |
| 139 | 4.5 | 11.3 | 5.4 | 288.9 |
| 140 | 25.5 | N/A | 59.1 | 711.9 |
| 141 | 7.4 | N/A | 13.2 | 203.1 |
| 142 | 50.2 | N/A | 332.7 | N/A |
| 143 | 34.1 | 361.4 | 69.8 | 1795.5 |
| 144 | 25.2 | N/A | 58.9 | 1683.1 |
| 145 | 13.8 | N/A | 29.6 | 682.0 |
| 146 | 12.3 | N/A | 29.0 | 736.5 |
| 147 | 19.2 | N/A | 25.7 | 1288.2 |
| 148 | 19.8 | N/A | 46.7 | 1062.5 |
| 149 | 16.5 | N/A | 21.9 | 563.5 |
| 150 | 28.3 | N/A | 49.3 | 728.4 |
| 151 | 44.0 | N/A | 70.4 | 1432.3 |
| 152 | 13.6 | N/A | 18.5 | 207.3 |
| 153 | 9.9 | N/A | 12.2 | 164.1 |
| 154 | 10.1 | N/A | 8.7 | 155.5 |
| 155 | 19.9 | N/A | 23.7 | 979.0 |
| 156 | 37.4 | N/A | 74.5 | 1757.6 |
| 157 | 29.3 | N/A | 56.6 | 893.7 |
| 158 | 18.0 | N/A | 30.2 | 1366.2 |
| 159 | 23.9 | N/A | 89.0 | 1301.4 |
| 160 | 13.6 | N/A | 11.0 | 191.5 |
| 161 | 6.6 | N/A | 3.7 | 48.5 |
| 162 | 6.1 | 35.7 | 5.4 | 42.0 |
| 163 | 23.1 | N/A | 42.8 | 991.4 |
| 164 | 6.9 | N/A | 8.8 | 73.6 |
| 165 | 24.8 | N/A | 28.9 | 2019.4 |
| 166 | 42.8 | N/A | 43.1 | 1988.9 |
| 167 | 34.2 | N/A | 48.5 | 779.5 |
| 168 | 12.1 | N/A | 43.3 | 1091.5 |
| 169 | 10.8 | N/A | 31.1 | 1437.8 |
| 170 | 54.0 | N/A | 200.9 | N/A |
| 171 | 52.6 | N/A | 734.6 | N/A |
| 172 | 68.2 | N/A | 264.7 | N/A |
| 173 | 17.2 | N/A | 32.8 | 1265.6 |
| 174 | 14.9 | N/A | 70.9 | 1218.5 |
| 175 | 21.6 | N/A | 221.6 | N/A |
| 176 | 7.6 | N/A | 15.3 | 928.4 |
| 177 | 47.0 | N/A | 69.9 | 1181.4 |
| 178 | 9.0 | N/A | 10.8 | 426.2 |
| 179 | 18.0 | N/A | 30.8 | 546.6 |
| 180 | 13.6 | N/A | 135.2 | N/A |
| 181 | 10.5 | N/A | 108.7 | 1195.3 |
| 182 | 11.6 | N/A | 27.0 | 563.5 |
| 183 | 11.9 | N/A | 15.8 | 443.7 |
| 184 | 4.0 | N/A | 2.8 | 75.2 |
| 185 | 11.5 | 77.8 | 14.3 | 627.7 |
| 186 | 14.3 | N/A | 22.5 | 451.2 |
| 187 | 15.9 | N/A | 20.4 | 871.4 |
| 188 | 16.8 | N/A | 9.7 | 613.7 |
| 189 | 7.7 | N/A | 9.5 | 254.6 |
| 190 | 14.0 | N/A | 20.4 | 277.3 |
| 191 | 8.3 | N/A | 6.3 | 21.8 |
| 192 | 12.2 | N/A | 30.1 | 932.1 |
| 193 | 10.1 | N/A | 198.7 | N/A |
| 194 | 6.7 | N/A | 11.0 | 242.0 |
| 195 | 9.4 | N/A | 28.1 | 246.5 |
| 196 | 10.9 | 102.7 | 45.5 | 629.7 |
| 197 | 14.0 | N/A | 39.6 | 1295.9 |
| 198 | 14.3 | N/A | 25.3 | 659.1 |
| 199 | 5.1 | 34.8 | 21.7 | 565.4 |
| 200 | 8.5 | 50.7 | 9.2 | 463.2 |
| 201 | 10.7 | N/A | 7.1 | 1152.3 |
| 202 | 41.7 | N/A | 110.4 | 992.3 |
| 203 | 5.8 | 16.7 | 5.2 | 559.7 |
| 204 | 27.3 | N/A | 12.2 | 429.4 |
| 205 | 14.4 | N/A | 309.2 | N/A |
| 206 | 14.1 | N/A | 23.3 | 1195.0 |
| 207 | 16.2 | N/A | 39.1 | 1958.3 |
| 208 | 98.2 | N/A | 221.6 | 4675.2 |
| 209 | 5.8 | N/A | 164.9 | N/A |
| 210 | 116.1 | N/A | 274.8 | N/A |
| 211 | 107.9 | N/A | 322.7 | N/A |
| 212 | 90.3 | N/A | 300.6 | N/A |
| 213 | 72.9 | N/A | 185.3 | N/A |
| 214 | 14.9 | 36.3 | 4.6 | 597.2 |
| 215 | 13.7 | 229.9 | 112.7 | N/A |
| 216 | 12.2 | N/A | 20.4 | 573.7 |
| 217 | 6.4 | N/A | 7.4 | 1672.4 |
| 218 | 7.2 | N/A | 10.7 | 4793.0 |
| 219 | 7.8 | N/A | 9.0 | N/A |
| 220 | 9.4 | N/A | 10.9 | 616.8 |
| 221 | 22.1 | N/A | 42.8 | 1659.8 |
| 222 | 6.2 | N/A | 1.5 | 257.4 |
| 223 | 8.7 | 24.2 | 5.8 | 1552.5 |
| 224 | 13.5 | N/A | 34.2 | 555.2 |
| 225 | 103.6 | N/A | 461.7 | N/A |
| 226 | 31.8 | N/A | 57.1 | 1174.2 |
| 227 | 201.9 | N/A | 277.5 | N/A |
| 228 | 54.4 | N/A | 80.7 | 4528.8 |
| 229 | 333.6 | N/A | N/A | N/A |
| 230 | 242.0 | N/A | N/A | N/A |
| 231 | 6.9 | N/A | 5.6 | 279.4 |
| 232 | 12.1 | N/A | 24.4 | 812.0 |
| 233 | 13.6 | N/A | 27.3 | 510.5 |
| 234 | 25.6 | N/A | 31.9 | 1209.8 |
| 235 | 7.4 | N/A | 5.1 | 1510.6 |
| 236 | 4.0 | N/A | 3.2 | 476.6 |
| 237 | 6.1 | 43.9 | 15.8 | 840.2 |
| 238 | 5.8 | N/A | 5.5 | 420.2 |
| 239 | 8.7 | N/A | 5.8 | 916.4 |
| 240 | 15.0 | N/A | 18.6 | 897.3 |
| 241 | 11.6 | N/A | 14.7 | 1835.1 |
| 242 | 4.5 | N/A | 6.3 | 223.2 |
| 243 | 5.6 | N/A | 5.4 | 103.2 |
| 244 | 20.9 | N/A | 69.2 | 659.7 |
| 245 | 30.2 | N/A | 190.7 | N/A |
| 246 | 12.0 | 115.0 | 13.6 | 949.5 |
| 247 | 48.1 | N/A | 167.5 | N/A |
| 248 | 33.2 | N/A | 75.3 | 1236.9 |
| 249 | 26.6 | N/A | 33.5 | 997.5 |
| 250 | 7.0 | N/A | 6.1 | 467.7 |
| 251 | 7.8 | 29.2 | 5.6 | 495.3 |
| 252 | 11.6 | N/A | 4.8 | 655.8 |
| 253 | 16.1 | N/A | 8.4 | 596.3 |
| 254 | 9.2 | N/A | 12.3 | 446.0 |
| 255 | 9.1 | N/A | 7.3 | 1086.2 |
| 256 | 12.9 | N/A | 4.5 | 735.4 |
| 257 | 14.9 | N/A | 9.3 | 1354.7 |

TABLE 5-continued

IC$_{50}$ values of compounds tested in the assay of Examples A, B and/or C.

| Ex# | RET Enzyme IC$_{50}$ (nM) | RET FRET_ATP_V804M IC$_{50}$ (nM) | KIF5B-RET pTYR1062 Cell IC$_{50}$ (nM) | pKDR Cell HEK 10% FBS IC$_{50}$ (nM) |
|---|---|---|---|---|
| 258 | 12.5 | N/A | 10.0 | 504.8 |
| 259 | 40.1 | N/A | 104.2 | 2770.3 |
| 260 | 83.3 | N/A | 261.0 | 5000.0 |
| 261 | 209.2 | N/A | 499.4 | N/A |
| 262 | 19.2 | N/A | 41.8 | 617.1 |
| 263 | 161.9 | N/A | 536.5 | N/A |
| 264 | 58.4 | N/A | 134.2 | N/A |
| 265 | 153.4 | N/A | 288.6 | N/A |
| 266 | 47.7 | N/A | 161.5 | N/A |
| 267 | 11.0 | N/A | 13.6 | 2762.2 |
| 268 | 6.3 | 30.7 | 4.1 | 496.5 |
| 269 | 13.2 | N/A | 17.6 | 1703.7 |
| 270 | 68.1 | N/A | 295.3 | N/A |
| 271 | 62.7 | N/A | 235.9 | N/A |
| 272 | 7.2 | 39.0 | 4.7 | 574.7 |
| 273 | 20.5 | N/A | 33.0 | 2138.7 |
| 274 | 51.2 | N/A | 65.6 | 5000.0 |
| 275 | 1504.1 | N/A | N/A | N/A |
| 276 | 395.1 | N/A | N/A | N/A |
| 277 | 299.5 | N/A | N/A | N/A |
| 278 | 14.7 | N/A | 22.7 | 137.6 |
| 279 | 317.5 | N/A | N/A | N/A |
| 280 | 176.5 | N/A | 376.4 | N/A |
| 281 | 179.9 | N/A | 193.0 | N/A |
| 282 | 8.2 | N/A | 8.1 | 662.3 |
| 283 | 18.1 | 144.4 | 21.4 | N/A |
| 284 | 12.5 | N/A | 5.1 | 663.1 |
| 285 | 25.8 | N/A | 23.8 | 1710.4 |
| 286 | 25.2 | N/A | 91.7 | 4833.8 |
| 287 | 137.9 | N/A | 259.3 | N/A |
| 288 | 6.1 | 32.2 | 3.7 | 1937.1 |
| 289 | 29.4 | N/A | 38.2 | 229.0 |
| 290 | 27.7 | N/A | 105.1 | 3442.2 |
| 291 | 38.2 | N/A | 137.7 | 917.6 |
| 292 | 20.8 | N/A | 69.4 | 1081.5 |
| 293 | 23.4 | N/A | 73.3 | 531.8 |
| 294 | 10.7 | N/A | 37.0 | 2102.4 |
| 295 | 14.1 | N/A | 56.6 | 720.2 |
| 296 | 37.4 | 629.4 | 90.6 | 2353.6 |
| 297 | 7.6 | N/A | 44.8 | 189.5 |
| 298 | 20.9 | N/A | 101.5 | 1831.2 |
| 299 | 9.6 | N/A | 36.8 | 150.7 |
| 300 | 235.7 | N/A | N/A | N/A |
| 301 | 20.5 | N/A | 129.1 | 158.0 |
| 302 | 49.6 | N/A | 168.9 | 2986.4 |
| 303 | 96.1 | N/A | 228.3 | N/A |
| 304 | 30.0 | N/A | 62.1 | 1614.6 |
| 305 | 24.3 | N/A | 52.2 | 1487.5 |
| 306 | 19.6 | N/A | 18.3 | 879.9 |
| 307 | 16.7 | N/A | 14.2 | 864.3 |
| 308 | 68.0 | N/A | 194.7 | N/A |
| 309 | 27.6 | N/A | 100.8 | 4777.6 |
| 310 | 15.7 | N/A | 71.0 | 1756.4 |
| 311 | 3046.3 | N/A | N/A | N/A |
| 312 | 606.7 | N/A | N/A | N/A |
| 313 | 39.3 | 87.4 | 79.2 | 5000.0 |
| 314 | 75.9 | N/A | 231.5 | N/A |
| 315 | 53.5 | N/A | 154.8 | N/A |
| 316 | 106.9 | N/A | 169.0 | N/A |
| 317 | 33.0 | N/A | 98.3 | 5000.0 |
| 318 | 197.1 | N/A | 768.2 | N/A |
| 319 | 104.8 | N/A | 464.5 | N/A |
| 320 | 36.4 | N/A | 97.9 | 5000.0 |
| 321 | 46.0 | N/A | 123.5 | N/A |
| 322 | 41.4 | 57.7 | 80.8 | 4860.5 |
| 323 | 76.4 | N/A | 314.3 | N/A |
| 324 | 144.2 | N/A | 673.2 | N/A |
| 325 | 371.8 | N/A | 742.0 | N/A |
| 326 | 75.0 | N/A | 70.4 | 579.0 |
| 327 | 7.4 | 28.0 | 7.1 | 605.7 |
| 328 | 62.1 | 239.4 | 60.4 | 1366.5 |
| 329 | 23.2 | N/A | 45.6 | 381.3 |
| 330 | 38.3 | N/A | 84.0 | 565.9 |
| 331 | 31.1 | N/A | 147.7 | 2352.9 |
| 332 | 16.2 | N/A | 47.0 | 206.6 |
| 333 | 63.7 | 251.2 | 155.8 | 2394.0 |
| 334 | 184.4 | N/A | 182.1 | N/A |
| 335 | 30.8 | N/A | 147.5 | N/A |
| 336 | 26.5 | N/A | 64.3 | 613.7 |
| 337 | 445.8 | N/A | N/A | N/A |
| 338 | 118.4 | N/A | 403.9 | N/A |
| 339 | 129.2 | 454.8 | 470.4 | 3697.1 |
| 340 | 91.8 | N/A | 411.6 | N/A |
| 341 | 23.5 | 66.1 | 4.1 | 237.2 |
| 342 | 28.6 | 337.2 | 30.8 | 4752.2 |
| 343 | 67.9 | 662.9 | 34.7 | 1663.9 |
| 344 | 15.1 | 111.5 | 10.8 | 385.4 |
| 345 | 6.1 | 13.9 | 4.5 | 305.1 |
| 346 | 10.1 | 73.8 | 15.5 | 1772.6 |
| 347 | 14.7 | 88.4 | 166.0 | N/A |
| 348 | 8.1 | 102.5 | 12.2 | 1407.4 |
| 349 | 10.5 | 31.4 | 5.3 | 403.5 |
| 350 | 15.9 | 91.1 | 20.8 | 1855.4 |
| 351 | 10.9 | 61.9 | 6.9 | 1756.0 |
| 352 | 13.9 | 184.9 | 13.7 | 2203.8 |
| 353 | 15.3 | 86.1 | 11.4 | 1708.0 |
| 354 | 22.1 | 194.7 | 16.2 | 1293.3 |
| 355 | 22.4 | 171.3 | 257.1 | N/A |
| 356 | 12.1 | 40.8 | 2.5 | 125.9 |
| 357 | 30.9 | 1540.1 | 36.8 | 2042.9 |
| 358 | 5.1 | 57.0 | 3.7 | 160.8 |
| 359 | 6.7 | 32.8 | 3.6 | 910.2 |
| 360 | 3.9 | 8.9 | 1.1 | 384.8 |
| 361 | 24.6 | 129.6 | 54.8 | N/A |
| 362 | 19.9 | 168.7 | 20.7 | 1857.7 |
| 363 | 11.2 | 48.3 | 6.7 | 2640.1 |
| 364 | 21.3 | 128.8 | 13.6 | 4360.4 |
| 365 | 4.0 | 31.7 | 9.9 | 597.3 |
| 366 | 7.8 | 42.5 | 9.1 | 422.4 |
| 367 | 7.7 | 56.2 | 4.9 | 355.4 |
| 368 | 18.8 | 161.6 | 11.9 | 1847.0 |
| 369 | 11.7 | 77.7 | 10.7 | 1268.3 |
| 370 | 2.5 | 9.4 | 3.8 | 29.8 |
| 371 | 61.7 | 382.9 | 19.7 | 1907.8 |
| 372 | 492.7 | 5686.8 | N/A | N/A |
| 373 | 8.9 | 75.3 | 18.7 | 1820.4 |
| 374 | 11.8 | 93.9 | 12.6 | N/A |
| 375 | 12.3 | 56.7 | 6.9 | 841.0 |
| 376 | 24.4 | 150.8 | 32.1 | 1826.2 |
| 377 | 48.1 | 348.1 | 18.0 | 2027.1 |
| 378 | 24.8 | 108.9 | 32.7 | 466.8 |
| 379 | 41.8 | 331.1 | 126.5 | N/A |
| 380 | 9.8 | 40.9 | 7.3 | 554.6 |
| 381 | 22.1 | 198.6 | 21.1 | 811.3 |
| 382 | 14.4 | 194.2 | 17.3 | 1712.9 |
| 383 | 17.0 | 220.5 | 19.7 | 639.2 |
| 384 | 5.5 | 25.2 | 8.9 | 1042.1 |
| 385 | 27.1 | 159.0 | 47.3 | 1968.9 |
| 386 | 5.6 | 55.0 | 9.4 | 1408.0 |
| 387 | 25.1 | 171.2 | 53.2 | N/A |
| 388 | 5.7 | 24.6 | 10.0 | 346.5 |
| 389 | 5.4 | 29.6 | 11.4 | 856.6 |
| 390 | 9.0 | 32.5 | 13.0 | 951.2 |
| 391 | 8.3 | 49.8 | 14.7 | 985.7 |
| 392 | 8.5 | 31.3 | 3.6 | 764.5 |
| 393 | 22.9 | 151.9 | 65.0 | N/A |
| 394 | 9.0 | 64.5 | 19.7 | 453.2 |
| 395 | 6.5 | 20.4 | 13.5 | 489.9 |
| 396 | 10.6 | 75.0 | 34.7 | 1464.5 |
| 397 | 10.8 | 53.6 | 17.7 | 1498.9 |
| 398 | 11.1 | 108.4 | 18.6 | 1299.1 |
| 399 | 10.8 | 34.9 | 7.7 | N/A |
| 400 | 65.5 | 430.0 | 249.9 | N/A |
| 401 | 21.6 | 138.9 | 36.1 | 692.4 |
| 402 | 41.1 | 314.5 | 76.4 | N/A |
| 403 | 10.8 | 25.6 | 4.6 | N/A |

TABLE 5-continued

IC₅₀ values of compounds tested in the assay of Examples A, B and/or C.

| Ex# | RET Enzyme IC$_{50}$ (nM) | RET FRET_ATP_V804M IC$_{50}$ (nM) | KIF5B-RET pTYR1062 Cell IC$_{50}$ (nM) | pKDR Cell HEK 10% FBS IC$_{50}$ (nM) |
|---|---|---|---|---|
| 404 | 13.2 | 66.6 | 7.0 | N/A |
| 405 | 30.8 | 114.2 | 32.5 | N/A |
| 406 | 42.6 | 223.2 | 39.9 | N/A |
| 407 | 9.0 | 39.4 | 7.7 | 827.6 |
| 408 | 29.0 | 184.2 | 16.9 | 1298.2 |
| 409 | 49.2 | 283.7 | 36.0 | 1666.7 |
| 410 | 38.4 | 240.6 | 103.7 | 1633.0 |
| 411 | 7.9 | 54.3 | 30.1 | 263.3 |
| 412 | 21.6 | 146.2 | 18.2 | 2133.2 |
| 413 | 15.6 | 105.9 | 29.1 | 549.1 |
| 414 | 41.3 | 200.3 | 41.5 | 2280.9 |
| 415 | 25.2 | 157.6 | 25.4 | 2028.6 |
| 416 | 46.1 | 344.8 | 70.8 | N/A |
| 417 | 37.1 | 283.3 | 48.5 | N/A |
| 418 | 14.7 | 105.3 | 28.1 | 1510.9 |
| 419 | 29.2 | 127.9 | 31.1 | 1901.3 |
| 420 | 10.9 | 28.1 | 5.6 | 791.7 |
| 421 | 18.0 | 111.7 | 11.0 | 1620.8 |
| 422 | 12.9 | 79.3 | 13.1 | 941.5 |
| 423 | 7.6 | 29.7 | 5.5 | 1368.4 |
| 424 | 6.6 | 19.1 | 7.3 | 629.8 |
| 425 | 25.6 | 71.4 | 10.2 | 916.1 |
| 426 | 14.3 | 52.8 | 12.6 | 1252.0 |
| 427 | 8.2 | 26.1 | 5.3 | 936.7 |
| 428 | 10.5 | 22.7 | 7.0 | 879.9 |
| 429 | 9.1 | 23.9 | 4.6 | 1563.9 |
| 430 | 7.5 | 31.8 | 5.4 | 791.0 |
| 431 | 24.5 | 145.2 | 11.6 | 1498.2 |
| 432 | 6.1 | 14.2 | 3.6 | 263.0 |
| 433 | 9.7 | 52.2 | 6.0 | 1075.2 |
| 434 | 6.5 | 65.6 | 10.8 | 1695.5 |
| 435 | 14.0 | 109.6 | 12.7 | 1327.2 |
| 436 | 14.9 | 110.2 | 9.5 | 536.5 |
| 437 | 15.1 | 118.8 | 25.7 | 1971.4 |
| 438 | 6.1 | 47.3 | 4.8 | 1988.4 |
| 439 | 11.8 | 46.1 | 5.0 | 1239.7 |
| 440 | 13.6 | 127.4 | 17.3 | 1694.5 |
| 441 | 4.7 | 12.5 | 4.2 | 576.5 |
| 442 | 12.0 | 85.8 | 24.8 | 1672.7 |
| 443 | 6.6 | 23.0 | 5.3 | 652.8 |
| 444 | 12.2 | 76.6 | 15.0 | 1286.9 |
| 445 | 12.2 | 79.0 | 10.6 | 1659.3 |
| 446 | 10.4 | 120.4 | 20.8 | 1473.3 |
| 447 | 9.0 | 43.7 | 3.6 | 667.6 |
| 448 | 24.2 | 157.4 | 37.4 | 1721.4 |
| 449 | 12.2 | 68.1 | 12.0 | 1344.7 |
| 450 | 5.5 | 16.9 | 1.6 | 466.8 |
| 451 | 4.9 | 23.7 | 4.9 | 593.4 |
| 452 | 10.0 | 74.7 | 12.1 | 844.4 |
| 453 | 17.3 | 122.0 | 17.5 | 1684.5 |
| 454 | 12.9 | 34.0 | 3.3 | 697.8 |
| 455 | 14.7 | 48.2 | 4.2 | 464.3 |
| 456 | 44.6 | 357.7 | 65.4 | N/A |
| 457 | 13.1 | 105.9 | 19.5 | 876.9 |
| 458 | 6.9 | 17.0 | 2.4 | 323.5 |
| 459 | 21.4 | 179.2 | 25.0 | 5000.0 |
| 460 | 21.0 | 169.4 | 14.6 | 1778.9 |
| 461 | 7.5 | 14.0 | 1.8 | 129.1 |
| 462 | 5.7 | 13.9 | 9.6 | 804.1 |
| 463 | 9.7 | 47.3 | 17.7 | 677.8 |
| 464 | 11.6 | 67.8 | 8.0 | N/A |
| 465 | 26.7 | 187.6 | 87.1 | N/A |
| 466 | 24.8 | 191.1 | 43.9 | 2156.1 |
| 467 | 33.3 | 157.8 | 28.1 | 1543.6 |
| 468 | 11.1 | 45.9 | 10.8 | N/A |
| 469 | 19.9 | 87.2 | 20.0 | N/A |
| 470 | 99.2 | 397.0 | 38.7 | N/A |
| 471 | 11.5 | 71.2 | 9.6 | 1580.2 |
| 472 | 9.4 | 92.0 | 17.6 | 1765.0 |
| 473 | 6.6 | 28.7 | 4.6 | 968.4 |
| 474 | 4.5 | 18.9 | 4.0 | 304.7 |
| 475 | 44.3 | 356.6 | 81.8 | N/A |
| 476 | 48.2 | 396.6 | 90.7 | N/A |
| 477 | 33.5 | 197.0 | 59.9 | N/A |
| 478 | 45.1 | 292.5 | 93.1 | N/A |
| 479 | 49.3 | 373.9 | 81.9 | N/A |
| 480 | 33.6 | 154.9 | 239.3 | N/A |
| 481 | 49.8 | 248.7 | 118.6 | N/A |
| 482 | 4.4 | 9.3 | 2.4 | N/A |
| 483 | 8.4 | 50.7 | 4.1 | 77.1 |
| 484 | 10.2 | 18.2 | 2.0 | 208.7 |
| 485 | 6.7 | 41.9 | 13.3 | 4796.9 |
| 486 | N/A | N/A | N/A | N/A |
| 487 | N/A | N/A | N/A | N/A |
| 488 | N/A | N/A | N/A | N/A |
| 489 | 4.5 | 5.7 | 3.8 | 19.5 |
| 490 | 13.9 | 44.7 | 9.6 | 619.4 |
| 491 | 31.9 | 63.4 | 3.4 | 119.6 |
| 492 | 9.0 | 45.9 | 16.6 | 563.2 |
| 493 | 6.9 | 38.3 | 10.4 | 927.5 |
| 494 | 28.1 | 202.0 | 96.9 | 1834.3 |
| 495 | 13.6 | 73.0 | 17.3 | 771.3 |
| 496 | 22.8 | 161.7 | 69.7 | 2119.5 |
| 497 | 14.6 | 46.1 | 22.5 | N/A |
| 498 | 17.4 | 70.2 | 34.1 | N/A |
| 499 | 20.1 | 35.3 | 9.0 | 462.0 |
| 500 | 9.3 | 29.6 | 12.4 | 457.9 |
| 501 | 7.7 | 29.7 | 7.2 | 554.3 |
| 502 | 8.2 | 35.9 | 8.3 | 436.9 |
| 503 | 18.5 | 203.3 | 55.5 | N/A |
| 504 | 47.9 | 409.2 | 42.4 | 2068.1 |
| 505 | 26.5 | 304.6 | 62.8 | 1304.3 |
| 506 | 31.3 | 69.4 | 6.5 | 212.5 |
| 507 | 6.2 | 10.8 | 1.3 | 24.9 |
| 508 | 6.6 | 26.2 | 2.1 | 2.9 |
| 509 | 13.8 | 55.0 | 2.9 | 9.2 |
| 510 | 6.7 | 31.1 | 9.6 | 322.9 |
| 511 | 27.3 | 62.3 | 11.3 | 1054.6 |
| 512 | 154.0 | 1006.9 | 213.3 | N/A |
| 513 | 17.1 | 85.7 | 61.4 | 2940.0 |
| 514 | 528.8 | 3433.0 | N/A | N/A |
| 515 | 15.3 | 53.5 | 10.3 | 284.0 |
| 516 | 15.3 | 39.4 | 4.4 | 172.6 |
| 517 | 19.1 | 39.6 | 23.1 | 1785.7 |
| 518 | 36.7 | 154.1 | 46.4 | 4630.9 |
| 519 | 13.1 | 77.6 | 10.5 | 1247.6 |
| 520 | 69.5 | 572.6 | 164.9 | N/A |
| 521 | 8.8 | 21.0 | 5.8 | 674.6 |
| 522 | 50.4 | 489.7 | 103.3 | N/A |
| 523 | 326.5 | 3336.8 | N/A | N/A |
| 524 | 109.5 | 693.3 | 230.6 | N/A |
| 525 | 20.4 | 173.9 | 59.7 | 1580.1 |
| 526 | 11.5 | 21.2 | 5.6 | 5000.0 |
| 527 | 14.9 | 110.5 | 29.2 | 917.9 |
| 528 | 20.2 | 138.9 | 57.0 | 1666.7 |
| 529 | 28.5 | 148.0 | 79.2 | 5000.0 |
| 530 | 18.0 | 109.4 | 40.0 | 1535.8 |
| 531 | 17.0 | 89.8 | 34.3 | 689.7 |
| 532 | 148.9 | 1578.6 | 811.5 | N/A |
| 533 | 10.9 | 43.7 | 22.2 | 4855.8 |
| 534 | 33.9 | 173.0 | 15.8 | 12.5 |
| 535 | 34.9 | 125.9 | 6.2 | 374.4 |
| 536 | 69.8 | 91.0 | 32.8 | 787.0 |
| 536 | 9.9 | 86.2 | 17.7 | 655.5 |
| 538 | 43.4 | 438.2 | 224.3 | N/A |
| 539 | 13.9 | 177.7 | 73.1 | 1638.5 |
| 540 | 5.1 | 52.3 | 98.2 | 1217.5 |
| 541 | 5.2 | 135.2 | 95.3 | 534.4 |
| 542 | 20.7 | 238.6 | 34.8 | 221.7 |
| 543 | 15.2 | 113.1 | 101.0 | N/A |
| 544 | 9.9 | 57.0 | 4.7 | 234.0 |
| 545 | 18.9 | 255.6 | 302.0 | N/A |
| 546 | 16.6 | 128.2 | 35.8 | 810.8 |
| 547 | 20.4 | 137.9 | 213.3 | N/A |
| 548 | 72.1 | 545.2 | 99.9 | N/A |
| 549 | 15.6 | 81.8 | 89.1 | 986.4 |

TABLE 5-continued

IC$_{50}$ values of compounds tested in the assay of Examples A, B and/or C.

| Ex# | RET Enzyme IC$_{50}$ (nM) | RET FRET_ATP_V804M IC$_{50}$ (nM) | KIF5B-RET pTYR1062 Cell IC$_{50}$ (nM) | pKDR Cell HEK 10% FBS IC$_{50}$ (nM) |
|---|---|---|---|---|
| 550 | 47.2 | 464.7 | 348.4 | N/A |
| 551 | 56.6 | 450.1 | 107.1 | N/A |
| 552 | 172.0 | 1242.2 | 330.4 | N/A |
| 553 | 173.7 | 1167.2 | 197.6 | N/A |
| 554 | 267.5 | 1695.3 | N/A | N/A |
| 555 | 19.6 | 122.8 | 26.6 | 1027.6 |
| 556 | 50.4 | 397.3 | 38.9 | 1897.3 |
| 557 | 49.2 | 430.6 | 38.3 | 802.0 |
| 558 | 12.0 | 122.2 | 9.1 | 548.2 |
| 559 | N/A | N/A | N/A | N/A |
| 560 | 82.7 | 504.6 | 94.6 | N/A |
| 561 | 23.8 | 144.9 | 37.5 | 1725.1 |
| 562 | 56.0 | 358.8 | 58.6 | N/A |
| 563 | 4.4 | 11.7 | 3.8 | 195.3 |
| 564 | 6.4 | 30.3 | 26.2 | 740.0 |
| 565 | 6.4 | 28.7 | 10.3 | 540.3 |
| 566 | 9.0 | 35.9 | 145.7 | N/A |
| 567 | 3.1 | 14.4 | 4.9 | 198.3 |
| 568 | 6.1 | 30.4 | 5000.0 | N/A |
| 569 | 6.2 | 20.6 | 2.8 | 2.2 |
| 570 | 4.2 | 7.3 | 2.2 | N/A |
| 571 | 92.0 | 720.5 | 5000.0 | N/A |
| 572 | 58.2 | 779.0 | 293.2 | N/A |
| 573 | 497.8 | 3063.1 | N/A | N/A |
| 574 | 258.0 | 2925.4 | N/A | N/A |
| 575 | N/A | N/A | N/A | N/A |
| 576 | 63.2 | 477.9 | 89.6 | N/A |
| 577 | N/A | N/A | N/A | N/A |
| 578 | N/A | N/A | N/A | N/A |
| 579 | N/A | N/A | N/A | N/A |
| 580 | 11.5 | 61.3 | 23.5 | 1243.5 |
| 581 | 13.8 | 96.5 | 21.5 | 670.7 |
| 582 | 11.6 | 52.5 | 19.3 | 561.0 |
| 583 | 865.3 | 6194.3 | N/A | N/A |
| 584 | 136.5 | 601.4 | N/A | N/A |
| 585 | 13.6 | 58.4 | 13.2 | N/A |
| 586 | 5.2 | 40.0 | 15.6 | 5000.0 |
| 587 | 22.2 | 109.0 | 28.0 | N/A |
| 588 | 14.4 | 124.7 | 144.8 | 5000.0 |
| 589 | N/A | N/A | N/A | N/A |
| 590 | 14.6 | 146.6 | 51.5 | 1486.1 |
| 591 | 5.7 | 19.5 | 4.1 | 1486.1 |
| 592 | 16.1 | 58.9 | 17.4 | 283.3 |
| 593 | 13.3 | 29.1 | 12.4 | 153.7 |
| 594 | 78.9 | 233.5 | 9.1 | 761.8 |
| 595 | 12.7 | 25.8 | 5.3 | 217.4 |
| 596 | 18.5 | 41.9 | 8.7 | 304.9 |
| 597 | 34.0 | 172.7 | 39.7 | 830.2 |
| 598 | 73.6 | 581.0 | 137.7 | N/A |
| 599 | 27.6 | 189.2 | 16.5 | 4859.0 |
| 600 | 53.0 | 526.5 | 96.3 | N/A |
| 601 | N/A | N/A | N/A | N/A |
| 602 | N/A | N/A | N/A | N/A |
| 603 | N/A | N/A | N/A | N/A |
| 604 | N/A | N/A | N/A | N/A |
| 605 | N/A | N/A | N/A | N/A |
| 606 | N/A | N/A | N/A | N/A |
| 607 | N/A | N/A | N/A | N/A |
| 608 | N/A | N/A | N/A | N/A |
| 609 | 16.5 | 93.8 | 31.5 | 1982.5 |
| 610 | 48.1 | 319.3 | 109.4 | 4442.3 |
| 611 | 11.9 | 26.8 | 2.5 | 298.5 |
| 612 | 38.2 | 91.8 | 5.2 | 430.6 |
| 613 | 121.8 | 642.0 | 360.9 | N/A |
| 614 | 22.2 | 121.3 | 17.0 | 2303.6 |
| 615 | 60.0 | 303.3 | 117.3 | N/A |
| 616 | 60.8 | 269.4 | 85.2 | N/A |
| 617 | N/A | N/A | N/A | N/A |
| 618 | N/A | N/A | N/A | N/A |
| 619 | 62.7 | 414.9 | 128.8 | 5000.0 |
| 620 | 116.4 | 723.7 | N/A | N/A |
| 621 | 883.3 | 10000.0 | N/A | N/A |
| 622 | 83.0 | 657.6 | 98.8 | N/A |
| 623 | 63.7 | 486.5 | 101.9 | N/A |
| 624 | 397.4 | 1865.8 | N/A | N/A |
| 625 | 304.7 | 2918.5 | N/A | N/A |
| 626 | 35.7 | 291.9 | 141.2 | N/A |
| 627 | 66.6 | 513.3 | 69.4 | N/A |
| 628 | 11.4 | 67.5 | 16.7 | 5000.0 |
| 629 | 15.3 | 76.9 | 34.4 | 5000.0 |
| 630 | 10.2 | 26.4 | 11.7 | N/A |
| 631 | 98.1 | 412.1 | 130.2 | N/A |
| 632 | 147.7 | 417.6 | N/A | N/A |
| 633 | 136.6 | 1154.3 | N/A | N/A |
| 634 | 98.9 | 498.9 | 140.2 | N/A |
| 635 | 48.8 | 295.7 | 90.2 | N/A |
| 636 | 9.4 | 28.0 | 4.5 | N/A |
| 637 | 6.2 | 15.2 | 3.9 | N/A |
| 638 | 16.9 | 76.5 | 15.8 | N/A |
| 639 | 9.2 | 48.8 | 24.6 | 4684.4 |
| 640 | N/A | N/A | N/A | N/A |
| 641 | N/A | N/A | N/A | N/A |
| 642 | 20.5 | 156.5 | 41.0 | N/A |
| 643 | 377.4 | 841.2 | N/A | N/A |
| 644 | N/A | N/A | N/A | N/A |
| 645 | 26.7 | 81.9 | 40.3 | 1683.7 |
| 646 | 15.6 | 43.1 | 45.7 | 1958.1 |
| 647 | 34.4 | 101.3 | 63.0 | N/A |
| 648 | 34.1 | 98.4 | 182.9 | N/A |
| 649 | 656.2 | 1329.7 | N/A | N/A |
| 650 | 345.4 | 1708.5 | N/A | N/A |
| 651 | 208.1 | 382.2 | N/A | N/A |
| 652 | 23.1 | 57.8 | 17.8 | 1695.6 |
| 653 | 86.9 | 169.4 | 69.4 | N/A |
| 654 | 70.6 | 81.8 | 163.7 | N/A |
| 655 | N/A | N/A | N/A | N/A |
| 656 | N/A | N/A | N/A | N/A |
| 657 | 139.7 | 174.8 | 215.5 | N/A |
| 658 | 15.0 | 32.3 | 25.1 | 1844.2 |
| 659 | 74.3 | 92.0 | 173.0 | N/A |
| 660 | 83.2 | 79.7 | 283.4 | N/A |
| 661 | 112.2 | 413.9 | N/A | N/A |
| 662 | 10.4 | 58.3 | 13.9 | N/A |
| 663 | 7.5 | 51.3 | 14.7 | N/A |
| 664 | 4.9 | 11.8 | 6.6 | N/A |
| 665 | 5.9 | 20.7 | 2.2 | N/A |
| 666 | 10.4 | 19.1 | 5.9 | 190.7 |
| 667 | 8.2 | 32.6 | 12.4 | N/A |
| 668 | 9.5 | 31.0 | 10.8 | N/A |
| 669 | 20.6 | 67.8 | 21.1 | N/A |
| 670 | 32.4 | 183.3 | 36.4 | N/A |
| 671 | 13.3 | 44.5 | 13.3 | N/A |
| 672 | 19.3 | 156.9 | 17.3 | N/A |
| 673 | 12.0 | 30.9 | 11.4 | N/A |
| 674 | 42.5 | 178.1 | 74.7 | N/A |
| 675 | 13.6 | 59.3 | 24.1 | N/A |
| 676 | 9.0 | 41.9 | 15.6 | N/A |
| 677 | 15.4 | 72.2 | 36.0 | N/A |
| 678 | 15.0 | 81.6 | 16.3 | N/A |
| 679 | 15.8 | 38.8 | 15.2 | N/A |
| 680 | 13.3 | 52.1 | 10.8 | N/A |
| 681 | 33.3 | 281.4 | 81.0 | N/A |
| 682 | 12.6 | 53.1 | 17.5 | N/A |
| 683 | 36.9 | 147.8 | 67.2 | N/A |
| 684 | 36.6 | 307.4 | 77.3 | N/A |
| 685 | 31.4 | 125.7 | 31.4 | N/A |
| 686 | 8.1 | 26.1 | 10.1 | N/A |
| 687 | 6.5 | 13.3 | 3.7 | N/A |
| 688 | 7.6 | 15.1 | 3.7 | 50.9 |
| 689 | 6.3 | 11.9 | 3.8 | N/A |
| 690 | 12.3 | 25.7 | 6.0 | N/A |
| 691 | 11.2 | 51.2 | 19.7 | N/A |
| 692 | 8.2 | 10.2 | 4.7 | N/A |
| 693 | 8.6 | 15.4 | 4.4 | 1015.3 |
| 694 | 13.1 | 36.7 | 16.3 | N/A |
| 695 | 14.1 | 148.5 | 27.1 | N/A |

TABLE 5-continued

IC$_{50}$ values of compounds tested in the assay of Examples A, B and/or C.

| Ex# | RET Enzyme IC$_{50}$ (nM) | RET FRET_ATP_V804M IC$_{50}$ (nM) | KIF5B-RET pTYR1062 Cell IC$_{50}$ (nM) | pKDR Cell HEK 10% FBS IC$_{50}$ (nM) |
|---|---|---|---|---|
| 696 | 9.6 | 47.3 | 16.1 | N/A |
| 697 | 28.1 | 60.0 | 13.8 | N/A |
| 698 | 6.7 | 30.3 | 12.4 | N/A |
| 699 | 19.4 | 115.6 | 24.3 | N/A |
| 700 | 16.8 | 40.1 | 5.3 | 346.7 |
| 701 | 16.5 | 37.0 | 8.0 | N/A |
| 702 | 15.3 | 41.0 | 5.6 | N/A |
| 703 | 16.4 | 48.1 | 9.8 | N/A |
| 704 | 30.1 | 99.3 | 8.3 | N/A |
| 705 | 16.7 | 41.3 | 5.1 | N/A |
| 706 | 18.3 | 44.9 | 6.4 | N/A |
| 707 | 20.1 | 49.0 | 6.5 | N/A |
| 708 | 19.4 | 32.0 | 7.0 | N/A |
| 709 | 26.2 | 70.5 | 9.3 | N/A |
| 710 | 20.0 | 51.6 | 12.6 | N/A |
| 711 | 15.5 | 31.7 | 26.9 | N/A |
| 712 | 136.8 | 365.1 | N/A | N/A |
| 713 | 10.8 | 20.1 | 17.0 | N/A |
| 714 | 18.1 | 29.1 | 7.8 | N/A |
| 715 | 34.2 | 68.9 | 13.5 | N/A |
| 716 | 23.7 | 36.4 | 8.0 | N/A |
| 717 | 92.1 | 1003.8 | 185.5 | N/A |
| 718 | 45.4 | 331.9 | 59.5 | N/A |
| 719 | 87.6 | 356.8 | 121.4 | N/A |
| 720 | 38.4 | 278.6 | 34.2 | N/A |
| 721 | 36.9 | 174.2 | 76.4 | N/A |
| 722 | 89.4 | 530.4 | 108.6 | N/A |
| 723 | 17.7 | 62.6 | 18.8 | N/A |
| 724 | 11.8 | 59.7 | 32.8 | N/A |
| 725 | 116.6 | 520.3 | N/A | N/A |
| 726 | 389.3 | 3899.9 | N/A | N/A |
| 727 | 61.7 | 450.2 | 128.2 | N/A |
| 728 | 176.9 | 1497.8 | N/A | N/A |
| 729 | 28.4 | 185.3 | 35.1 | N/A |
| 730 | 25.8 | 113.4 | 30.5 | N/A |
| 731 | 19.1 | 98.9 | 37.4 | N/A |
| 732 | 40.7 | 235.0 | 81.5 | N/A |
| 733 | 23.4 | 181.9 | 21.6 | N/A |
| 734 | 61.4 | 430.6 | 117.0 | N/A |
| 735 | 26.3 | 152.4 | 91.2 | N/A |
| 736 | 35.1 | 189.1 | 67.4 | N/A |
| 737 | 24.7 | 203.3 | 24.4 | N/A |
| 738 | 31.6 | 109.5 | 69.3 | N/A |
| 739 | 36.1 | 245.2 | 92.5 | N/A |
| 740 | 4.0 | 38.6 | 8.7 | N/A |
| 741 | 42.4 | 77.4 | 45.5 | N/A |
| 742 | 37.3 | 90.0 | 38.5 | N/A |
| 743 | 184.7 | 282.9 | N/A | N/A |
| 744 | 46.2 | 103.6 | 66.3 | N/A |

N/A = Not available

Synthetic Examples

Synthesis of Synthetic Intermediates

Examples P1 and P2

6-bromo-4-methoxypyrazolo[1,5-a]pyridine (P1) and 4-bromo-6-methoxypyrazolo[1,5-a]pyridine (P2)

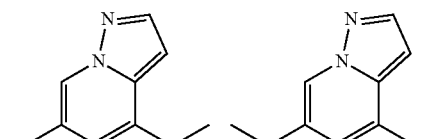

Step 1: Preparation of 1-amino-3-bromo-5-methoxypyridin-1-ium 2,4,6-trimethylbenzenesulfonate To a solution of O-(mesitylsulfonyl)hydroxylamine (Intermediate R1, 26.6 g, 117 mmol) in DCM (570 mL) cooled to 0° C. was added 3-bromo-5-methoxypyridine (22.1 g, 117 mmol) in portions. The reaction mixture was stirred for 1 h at 0° C. then treated with additional 3-bromo-5-methoxypyridine (250 mg, 1.39 mmol) and stirred for an additional 2 h at 0° C. The reaction mixture was diluted with Et$_2$O (600 mL), stirred at 0° C. for 10 min and then vacuum filtered, rinsed with Et$_2$O (3×250 mL). Upon reduction in volume by about ⅓, the filtrate yielded additional precipitate which was collected by filtration. Both filter cakes were dried in vacuo to provide the title compound (39.3 g, 83% yield). $^1$H NMR (CDCl$_3$) δ 9.25 (br s, 1H), 8.99 (m, 1H), 8.74 (m, 1H), 7.46 (m, 1H), 6.83 (s, 2H), 3.92 (s, 3H), 2.65 (s, 6H), 2.22 (s, 3H).

Step 2: Preparation of Ethyl 6-bromo-4-methoxypyrazolo[1,5-a]pyridine-3-carboxylate and Ethyl 4-bromo-6-methoxypyrazolo[1,5-a]pyridine-3-carboxylate To a magnetically stirred white suspension of 1-amino-3-bromo-5-methoxypyridin-1-ium 2,4,6-trimethylbenzenesulfonate (33.24 g, 82.42 mmol) in DMF (82 mL) at ambient temperature was added TEA (22.98 mL, 164.8 mmol), followed by drop-wise addition of ethyl propiolate (16.71 mL, 164.8 mmol). After vigorous stirring for 2 d, the reaction was slowly quenched via portion-wise addition to rapidly stirring ice water (820 mL). The mixture was stirred at ambient temperature for 10 min and then vacuum filtered. Solids collected were rinsed with water and air-dried, yielding the title compounds as an orange solid in an isomeric ratio of about 4:1 (by $^1$H NMR) with the 6-Br isomer as the major isomer (21 g). The wet solid isomeric mixture (about 75% w/w) was directly used in Step 3 without further purification. MS (apci) m/z=298.9, 300.9 (M+H). Regioisomeric ratio was determined by MeO chemical shift in $^1$H NMR (CDCl$_3$) δ 3.98 (6-Br isomer) vs. 3.83 (4-Br isomer).

Step 3: Preparation of 6-bromo-4-methoxypyrazolo[1,5-a]pyridine (P1) and 4-bromo-6-methoxypyrazolo[1,5-a]pyridine (P2)

The isomeric mixture of ethyl 6-bromo-4-methoxypyrazolo[1,5-a]pyridine-3-carboxylate and ethyl 4-bromo-4- methoxypyrazolo[1,5-a]pyridine-3-carboxylate from Step 2 (15 g, 50.1 mmol) was added to 48% HBr (114 mL) while stirring, then heated at 80° C. for 90 min followed by stirring at ambient temperature overnight. The resulting suspension was vacuum filtered and rinsed with water. The aqueous filtrate and the filter cake were treated independently. The filter cake was taken up in MTBE and vacuum filtered to remove insoluble impurities. The MTBE filtrate was dried over anhydrous Na$_2$SO$_4$, filtered and concentrated in vacuo to yield 6-bromo-4-methoxypyrazolo[1,5-a]pyridine (Intermediate P1) as a beige solid (about 98:2 6-/4-Br; 5.08 g). MS (apci) m/z=226.9, 228.9 (M+H). $^1$H NMR (CDCl$_3$) δ 8.26 (m, 1H), 7.82 (d, 1H), 6.61 (m, 1H), 6.43 (m, 1H), 3.94 (s, 3H).

Independently the original aqueous reaction mixture filtrate was extracted with EtOAc (2×500 mL). The combined organic extracts were dried (Na$_2$SO$_4$), filtered and concentrated in vacuo. The crude residue was taken up in DCM (50 mL) and then filtered to remove insoluble solids. Concentration of the DCM filtrate under vacuum followed by silica chromatography (0 to 50% EtOAc/hexanes) yielded a second batch of 6-bromo-4-methoxypyrazolo[1,5-a]pyridine (Intermediate P1) as white solid (upper R$_f$ spot, 2.06 g), as well as the minor isomer title compound 4-bromo-6-methoxypyrazolo[1,5-a]pyridine (Intermediate P2) also as white solid (lower R$_f$ spot, 1.32 g). MS (apci) m/z=226.9, 228.9 (M+H). $^1$H NMR (CDCl$_3$) δ 8.02 (m, 1H), 7.85 (d, 1H), 7.17 (d, 1H), 6.55 (m, 1H), 3.80 (s, 3H).

Intermediate P3

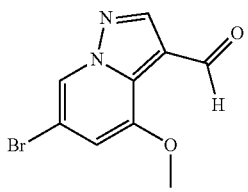

6-bromo-4-methoxypyrazolo[1,5-a]pyridine-3-carbaldehyde

To a 0° C. solution of 6-bromo-4-methoxypyrazolo[1,5-a]pyridine (Intermediate P1, 0.75 g, 3.303 mmol) in DMF (33 mL) was slowly added POCl$_3$ (0.92 mL, 9.909 mmol). The reaction was warmed to ambient temperature and stirred for 4 h and then diluted with H$_2$O (30 mL). The resulting suspension was basified to pH 9-10 with 1 M NaOH$_{(aq)}$, then stirred for 1 h and vacuum filtered, then rinsed sequentially with H$_2$O (25 mL) and MTBE (50 mL) to yield the title compound (0.76 g, 90% yield). MS (apci) m/z=256.9 (M+H).

Intermediate P4

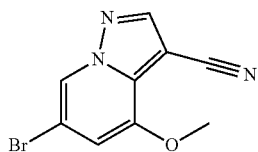

6-bromo-4-methoxypyrazolo[1,5-a]pyridine-3-carbonitrile

Step 1: Preparation of (E)-6-bromo-4-methoxypyrazolo[1,5-a]pyridine-3-carbaldehyde Oxime To a suspension of 6-Bromo-4-methoxypyrazolo[1,5-a]pyridine-3-carbaldehyde (Intermediate P3, 0.76 g, 3.0 mmol) and hydroxylamine hydrochloride (0.31 g, 4.5 mmol) in EtOH (40 mL) was added water (20 mL), and the reaction was stirred at 50° C. for 4 h. After cooling to ambient temperature the reaction mixture was concentrated in vacuo. The residue was suspended in water, then treated with saturated NaHCO$_{3(aq)}$ and vacuum filtered. The solids were rinsed sequentially with H$_2$O (25 mL) and MTBE (50 mL) to yield the title compound (0.68 g, 84% yield). MS (apci) m/z=271.9 (M+H).

Step 2: Preparation of 6-bromo-4-methoxypyrazolo[1,5-a]pyridine-3-carbonitrile

A solution of (E)-6-bromo-4-methoxypyrazolo[1,5-a]pyridine-3-carbaldehyde oxime (17.15 g, 63.50 mmol) in acetic anhydride (707 mL, 7.49 mol) was heated at 120° C. overnight. Following subsequent distillation to remove the acetic anhydride, the remaining residue was dried in vacuo to yield the title compound (15.92 g, 99.4% yield). $^1$H NMR (CDCl$_3$) δ 8.32 (m, 1H), 8.12 (s, 1H), 6.74 (m, 1H), 4.03 (s, 3H).

Intermediate P5

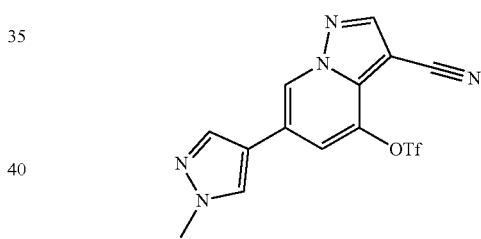

3-cyano-6-(1-methyl-1H-pyrazol-4-yl)pyrazolo[1,5-a]pyridin-4-yl trifluoromethanesulfonate Step 1: Preparation of 4-methoxy-6-(1-methyl-1H-pyrazol-4-yl)pyrazolo[1,5-a]pyridine-3-carbonitrile To a solution of 6-bromo-4-methoxypyrazolo[1,5-a]pyridine-3-carbonitrile (Intermediate P4, 50 g, 198.4 mmol) and 1-methyl-4-(4,4,5,5-tetramethyl-1,3,2-dioxaborolan-2-yl)-1H-pyrazole (49.53 g, 238.0 mmol) in dioxane (660 mL) was added 2 M Na$_2$CO$_{3(aq)}$ (297.5 mL, 595.1 mmol). The reaction mixture was sparged with nitrogen for 20 min before Pd(PPh$_3$)$_4$ (4.584 g, 3.967 mmol) was introduced, followed by additional 5 min of sparging with nitrogen. The reaction was heated at 80° C. for 18 h, then cooled to ambient temperature and vigorously stirred for 2 h. The suspension was vacuum filtered, rinsed sequentially with H$_2$O (2×300 mL) and MTBE (3×300 mL), then dried in vacuo overnight to yield the title compound, which was used in the next step without further purification (52.62 g). MS (apci), m/z=254.1 (M+H).

Step 2: Preparation of 4-hydroxy-6-(1-methyl-1H-pyrazol-4-yl)pyrazolo[1,5-a]pyridine-3-carbonitrile To a suspension of 4-methoxy-6-(1-methyl-1H-pyrazol-4-yl)pyrazolo[1,5-a]pyridine-3-carbonitrile (52.62 g, 207.8 mmol) in DCE (2 L) was added AlCl₃ (92.86 g, 696.42 mmol), and the reaction mixture was stirred at 80° C. for 3 h. Additional AlCl₃ (2.5 g, 18.75 mmol) was introduced and the reaction was refluxed overnight. After cooling to ambient temperature the reaction mixture was diluted with DCE (1 L) and then quenched with portions of H₂O (5×500 mL). The mixture was stirred at ambient temperature for 3 h before the resulting suspension was vacuum filtered and the filter cake dried in a vacuum oven (40° C.) to afford the title compound, which was used in the next step without further purification (43.69 g). MS (apci) m/z=239.9 (M+H). ¹H NMR (d⁶-DMSO) δ 11.38 (s, 1H), 8.74 (d, 1H), 8.50 (s, 1H), 8.21 (s, 1H), 7.94 (s, 1H), 6.96 (d, 1H), 3.88 (s, 3H).

Step 3: Preparation of 3-cyano-6-(1-methyl-1H-pyrazol-4-yl)pyrazolo[1,5-a]pyridin-4-yl trifluoromethanesulfonate To a suspension of 4-hydroxy-6-(1-methyl-1H-pyrazol-4-yl)pyrazolo[1,5-a]pyridine-3-carbonitrile (43.69 g, 182.6 mmol) in DMA (365 mL) was added DIEA (63.6 mL, 365.3 mmol) followed by 1,1,1-trifluoro-N-phenyl-N—((trifluoromethyl)sulfonyl)methanesulfonamide (71.77 g, 200.9 mmol). The resulting solution was stirred at ambient temperature for 2 h and then slowly poured into H₂O (4 L). The resulting suspension was stirred for 2 h then vacuum filtered. The filter cake was rinsed with H₂O (3×500 mL) and air dried overnight. The filter cake was then dissolved in DCM (1.6 L) and the resulting biphasic mixture was phase-separated. The organic layer was dried over anhydrous MgSO₄, filtered through Celite® and rinsed with DCM. The combined organic layers were concentrated to yield the title compound as a 90% pure tan solid (64.3 g, 95% yield). The purity of the title compound can be further improved to >95% via silica chromatography (0-90% acetone/hexanes). ¹⁹F NMR (CDCl₃) δ −72.0. ¹H NMR (CDCl₃) δ 8.66 (d, 1H), 8.29 (s, 1H), 7.77 (d, 1H), 7.70 (s, 1H), 7.55 (d, 1H), 4.01 (s, 3H).

Intermediate P6

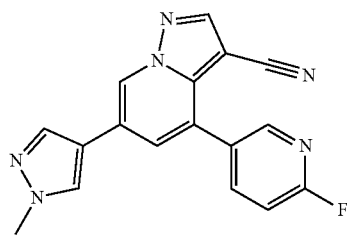 [SMILES: Cn1cc(-c2cc(-c3ccc(F)nc3)c3c(C#N)cnn3c2)cn1]

4-(6-Fluoropyridin-3-yl)-6-(1-methyl-1H-pyrazol-4-yl)pyrazolo[1,5-a]pyridine-3-carbonitrile In a pressure tube a solution of 3-cyano-6-(1-methyl-1H-pyrazol-4-yl)pyrazolo[1,5-a]pyridin-4-yl trifluoromethanesulfonate (Intermediate P5, 500 mg, 1.35 mmol) in dioxane (13 mL) was treated sequentially with 2-fluoro-5-(4,4,5,5-tetramethyl-1,3,2-dioxaborolan-2-yl)pyridine (451 mg, 2.02 mmol), Pd(PPh₃)₄ (77.8 mg, 0.0673 mmol), then 2 M Na₂CO₃₍aq₎ (3367 μL, 6.73 mmol). The resulting reaction mixture was sparged with nitrogen, sealed, and heated at 90° C. overnight. After cooling to ambient temperature the reaction mixture was diluted with water (10 mL) and vigorously stirred. The suspension was vacuum filtered and the filter cake was rinsed with water (3×5 mL), and subsequently dried in vacuo overnight to yield the title compound (285 mg, 67% yield). MS (apci), m/z=319.0 (M+H).

Intermediate P7

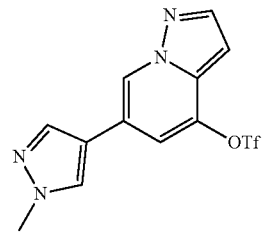 [SMILES: Cn1cc(-c2cc(OS(=O)(=O)C(F)(F)F)c3ccnn3c2)cn1]

6-(1-Methyl-1H-pyrazol-4-yl)pyrazolo[1,5-a]pyridin-4-yl trifluoromethanesulfonate Step 1: Preparation of 4-methoxy-6-(1-methyl-1H-pyrazol-4-yl)pyrazolo[1,5-a]pyridine To a solution of 6-bromo-4-methoxypyrazolo[1,5-a]pyridine (Intermediate P1; 2.00 g, 227.1 mmol) and 1-methyl-4-(4,4,5,5-tetramethyl-1,3,2-dioxaborolan-2-yl)-1H-pyrazole (2.02 g, 208.1 mmol) in dioxane (10 mL) was added 2 M Na₂CO₃₍aq₎ (8.1 mL, 17.6 mmol) and Pd(PPh₃)₄ (4.584 g, 3.967 mmol). The reaction mixture was purged with nitrogen for 2 min, sealed and heated at 90° C. for 4 h. After cooling to ambient temperature, the reaction mixture was diluted with water (50 mL) and stirred for 30 min. The resulting suspension was vacuum filtered, rinsed sequentially with water (2×20 mL) and Et₂O (2×10 mL) to yield the crude title compound, which was used in the next step without further purification. MS (apci), m/z=229.1 (M+H).

Step 2: Preparation of 6-(1-methyl-1H-pyrazol-4-yl)pyrazolo[1,5-a]pyridin-4-ol

4-Methoxy-6-(1-methyl-1H-pyrazol-4-yl)pyrazolo[1,5-a]pyridine (2.1 g, 9.2 mmol) was suspended in DCE (50 mL) and treated with AlCl₃ (6.134 g, 46.00 mmol). The resulting reaction mixture was heated at 90° C. overnight. Upon cooling to ambient temperature, the reaction mixture was quenched with Na₂SO₄*10H₂O in THF (50 mL) and stirred for 2 h before filtering and concentrating in vacuo. The crude residue was taken up in saturated NH₄Cl₍aq₎ (50 mL) and extracted with EtOAc (2×100 mL). The combined organic extracts were filtered through PS paper and concentrated in vacuo to afford the crude title compound, which was used in the next step without further purification. MS (apci) m/z=215.1 (M+H).

Step 3: Preparation of 6-(1-Methyl-1H-pyrazol-4-yl)pyrazolo[1,5-a]pyridin-4-yl Trifluoromethanesulfonate A suspension of 6-(1-methyl-1H-pyrazol-4-yl)pyrazolo[1,5-a]pyridin-4-ol (1.0 g, 4.67 mmol), DIEA (4.1 mL, 23.3 mmol) and 1,1,1-trifluoro-N-phenyl-N—((trifluoromethyl)sulfonyl)methanesulfonamide (2.2 g, 6.07 mmol) in THF (20 mL) was stirred at ambient temperature overnight, then concentrated in vacuo and purified by silica chromatography (0-20% MeOH/EtOAc) to afford the title compound (757 mg, 47% yield). MS (apci) m/z=346.9 (M+H).

Intermediate P8

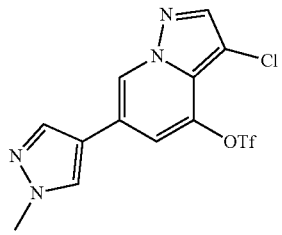 [SMILES: Cn1cc(-c2cc(OS(=O)(=O)C(F)(F)F)c3c(Cl)cnn3c2)cn1]

3-Chloro-6-(1-methyl-1H-pyrazol-4-yl)pyrazolo[1,5-a]pyridin-4-yl Trifluoromethanesulfonate Step 1: Preparation of 6-bromo-3-chloro-4-methoxypyrazolo[1,5-a]pyridine To a solution of 6-bromo-4-methoxypyrazolo[1,5-a]pyridine (Intermediate P1 as a partial HBr salt; 1000 mg, 4.40 mmol) in DCM (16 mL) was added NCS (433.59 mg, 3.247 mmol) at ambient temperature. After stirring overnight, additional NCS (125 mg, 0.936 mmol) was introduced and the reaction was stirred for another 2 h. The mixture was then diluted with water (25 mL) and extracted with DCM (2×25 mL). The combined organic extracts were washed with water, dried over anhydrous MgSO₄, filtered and concentrated to yield an 85:15 mixture of two components (1106 mg), with the major component being the title compound. $^1$H NMR (CDCl₃): Major component δ 8.18 (d, 1H), 7.75 (s, 1H), 6.45 (d, 1H), 3.96 (s, 3H). Minor component δ 8.22 (d, 1H), 7.78 (s, 1H), 6.48 (d, 1H), 2.78 (s, 3H). Major component: MS (apci) m/z=260.1, 262.9 (M+H). This crude mixture was used in the next without further purification.

Step 2: Preparation of 3-chloro-4-methoxy-6-(1-methyl-1H-pyrazol-4-yl)pyrazolo[1,5-a]pyridine In a pressure tube a suspension of 6-bromo-3-chloro-4-methoxypyrazolo[1,5-a]pyridine (550 mg, 2.10 mmol) in dioxane (7 mL) was treated with 1-methyl-4-(4,4,5,5-tetramethyl-1,3,2-dioxaborolan-2-yl)-1H-pyrazole (656 mg, 3.15 mmol), 2 M Na₂CO₃$_{(aq)}$ (3155 μL, 6.31 mmol) and Pd(PPh₃)₄ (122 mg, 0.105 mmol). The resulting mixture was sparged with nitrogen and then heated at 90° C. overnight. After cooling to ambient temperature the reaction mixture was diluted with water (50 mL) and extracted with DCM (2×50 mL). The combined organic extracts were dried over anhydrous MgSO₄ and filtered, and the filtrate was concentrated. The crude residue was purified by silica chromatography (25-100% EtOAc/hexanes) to provide the title compound (393 mg, 71% yield). MS (apci) m/z=263.0 (M+H). $^1$H NMR (CDCl₃) δ 8.16 (d, 1H), 7.76 (s, 1H), 7.75 (s, 1H), 7.62 (s, 1H), 6.46 (s, 1H), 4.01 (s, 3H), 3.99 (s, 1H).

Step 3: Preparation of 3-chloro-6-(1-methyl-1H-pyrazol-4-yl)pyrazolo[1,5-a]pyridin-4-ol A suspension of 3-chloro-4-methoxy-6-(1-methyl-1H-pyrazol-4-yl)pyrazolo[1,5-a]pyridine (1.0 g, 3.807 mmol) in 1 M BBr₃ in DCM (19.03 mL, 19.03 mmol) was stirred overnight at ambient temperature followed by another 22 h at 40° C. Upon cooling to ambient temperature, the reaction mixture was quenched with water (100 mL) and MeOH (10 mL). The resulting mixture was extracted with DCM (100 mL) and 10% MeOH in DCM (2×100 mL). The combined organic extracts were concentrated in vacuo to provide the crude title compound, which was used directly in the next step without further purification (1959 mg). MS (apci) m/z=249.0 (M+H).

Step 4: Preparation of 3-chloro-6-(1-methyl-1H-pyrazol-4-yl)pyrazolo[1,5-a]pyridin-4-yl Trifluoromethanesulfonate To a suspension of 3-chloro-6-(1-methyl-1H-pyrazol-4-yl)pyrazolo[1,5-a]pyridin-4-ol (0.95 g, 3.82 mmol) in DCM (20 mL) was added DIEA (1.33 mL, 7.64 mmol) followed by 1,1,1-trifluoro-N-phenyl-N—((trifluoromethyl)sulfonyl)methanesulfonamide (1.50 g, 4.20 mmol). The resulting suspension was stirred at ambient temperature overnight and subsequently diluted with DCM (20 mL) and quenched with water (50 mL). The aqueous phase was extracted with DCM (3×50 mL) and the combined organic extracts were dried (MgSO₄), filtered, and concentrated. The crude residue was purified by silica chromatography (25-100% EtOAc/hexanes) to yield the title compound (860 mg, 59% yield). $^1$H NMR (CDCl₃) δ 8.49 (d, 1H), 7.92 (s, 1H), 7.73 (s, 1H), 7.63 (s, 1H), 7.23 (d, 1H), 3.99 (s, 3H). $^{19}$F NMR (CDCl₃) δ −72.5. $^{19}$F NMR (CDCl₃) δ −72.5.

Intermediate P9

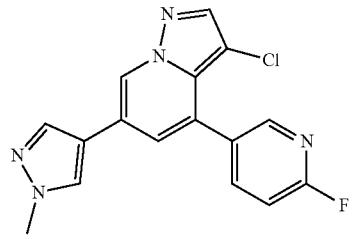 [SMILES: Cn1cc(-c2cc(-c3ccc(F)nc3)c3c(Cl)cnn3c2)cn1]

3-chloro-4-(6-fluoropyridin-3-yl)-6-(1-methyl-1H-pyrazol-4-yl)pyrazolo[1,5-a]pyridine In a pressure tube a solution of 3-chloro-6-(1-methyl-1H-pyrazol-4-yl)pyrazolo[1,5-a]pyridin-4-yl trifluoromethanesulfonate (Intermediate P8; 150 mg, 0.394 mmol) in dioxane (3 mL) was treated sequentially with 2-fluoro-5-(4,4,5,5-tetramethyl-1,3,2-dioxaborolan-2-yl)pyridine (132 mg, 0.591 mmol), 2 M Na₂CO₃$_{(aq)}$ (985 μL, 1.97 mmol) and Pd(PPh₃)₄ (22.8 mg, 0.0197 mmol). The reaction mixture was sparged with nitrogen and then heated at 90° C. overnight. After cooling to ambient temperature the reaction mixture was diluted with water (10 mL) and vigorously stirred. The suspension was vacuum filtered and the filter cake was rinsed sequentially with water (10 mL) and MTBE (3×5 mL), and subsequently dried in vacuo to yield the title compound (79 mg, 61% yield). MS (apci), m/z=327.9 (M+H).

Intermediate P10

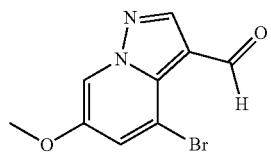

4-Bromo-6-methoxypyrazolo[1,5-a]pyridine-3-carbaldehyde

A solution of 4-bromo-6-methoxypyrazolo[1,5-a]pyridine (Intermediate P2; 5.0 g, 22 mmol) in DMF (220 mL) was cooled to 0° C. and then slowly treated with POCl₃ (6.2 mL, 66 mmol). The reaction was warmed to ambient temperature and stirred overnight. The reaction mixture was cooled to 0° C., quenched with water (220 mL), and basified with 6 M NaOH(aq) to pH 9-10. The reaction mixture was stirred for 1 h and then vacuum filtered. The solids were rinsed sequentially with water (3×50 mL) and MTBE (3×50 mL). The collected solid was suspended in DCM (500 mL) and stirred in a sonicating bath for 30 min and then vacuum filtered. The filtrate was retained, while the filter cake was taken up in water (300 mL) and extracted with DCM (2×300 mL). The organic extracts, along with the retained DCM filtrate, were combined and dried over anhydrous Na₂SO₄, then filtered and concentrated in vacuo to provide the title compound (4.84 g, 86% yield). MS (apci), m/z=256.9 (M+H).

Intermediate P11

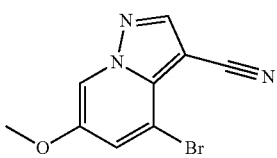

4-Bromo-6-methoxypyrazolo[1,5-a]pyridine-3-carbonitrile

Step 1: Preparation of 4-bromo-6-methoxypyrazolo[1,5-a]pyridine-3-carbaldehyde Oxime To a suspension of 4-bromo-6-methoxypyrazolo[1,5-a]pyridine-3-carbaldehyde (Intermediate P10; 4.84 g, 19.0 mmol) in EtOH (253 mL) at ambient temperature was added water (127 mL) and hydroxylamine hydrochloride (1.98 g, 28.5 mmol). After stirring at 50° C. overnight, the reaction mixture was cooled to ambient temperature and concentrated in vacuo. The residue was suspended in water (150 mL) and then quenched slowly with saturated NaHCO₃(aq) (30 mL). After stirring for 1 hour at ambient temperature the suspension was vacuum filtered and the filter cake rinsed sequentially with H₂O (500 mL) and MTBE (100 mL) to yield the title compound as a 2:1 E/Z mixture (5.13 g, quantitative yield), which was used in the next step without further purification. MS (apci) m/z=271.9 (M+H).

Step 2: Preparation of 4-bromo-6-methoxypyrazolo[1,5-a]pyridine-3-carbonitrile The E/Z mixture from Step 1 (4.95 g, 18.33 mmol) in acetic anhydride (172.9 mL, 1833 mmol) was stirred at 140° C. for 25 h, then cooled to ambient temperature. The resulting suspension was further cooled in an ice bath for 15 min and then vacuum filtered and rinsed sequentially with water (200 mL) and MTBE (300 mL) to provide the title compound (3.74 g, 81% yield). ¹H NMR (d⁶-DMSO) δ 8.70 (s, 1H), 8.60 (s, 1H), 7.78 (s, 1H), 3.83 (s, 3H).

Intermediate P12

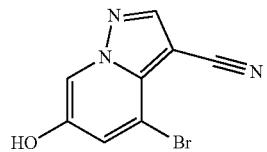 [SMILES: N#Cc1cnn2cc(O)cc(Br)c12]

4-bromo-6-hydroxypyrazolo[1,5-a]pyridine-3-carbonitrile

To a suspension of 4-Bromo-6-methoxypyrazolo[1,5-a]pyridine-3-carbonitrile (Intermediate P11; 1500 mg, 5.951 mmol) in DCE (10 mL) was added AlCl₃ (2380 mg, 17.85 mmol), and the reaction mixture was stirred at 80° C. for 4 h. Upon cooling to ambient temperature, the reaction mixture was quenched with Na₂SO₄*10H₂O in THF (100 mL), then stirred overnight and then filtered and concentrated in vacuo to afford the title compound (963 mg, 68% yield). MS (apci) m/z=238.0 (M–H).

Intermediate P13

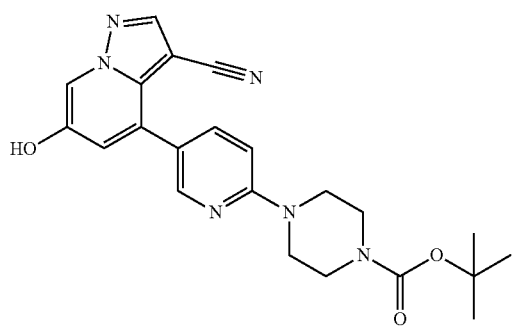 [SMILES: CC(C)(C)OC(=O)N1CCN(c2ccc(-c3cc(O)cn4ncc(C#N)c34)cn2)CC1]

Tert-Butyl 4-(5-(3-cyano-6-hydroxypyrazolo[1,5-a]pyridin-4-yl)pyridin-2-yl)piperazine-1-carboxylate In a pressure tube a solution of 4-bromo-6-hydroxypyrazolo[1,5-a]pyridine-3-carbonitrile (Intermediate P12; 419 mg, 1.76 mmol) in dioxane (30 mL) was treated with tert-butyl 4-(5-(4,4,5,5-tetramethyl-1,3,2-dioxaborolan-2-yl)pyridin-2-yl)piperazine-1-carboxylate (824 mg, 2.12 mmol), 2 M Na₂CO₃(aq) (1764 µL, 3.53 mmol) and Pd(PPh₃)₄ (20.4 mg, 0.0176 mmol). The resulting reaction mixture was sparged with nitrogen for 5 min and then stirred at 100° C. for 4 h. After cooling to ambient temperature, the reaction mixture was diluted with saturated NH₄Cl(aq) (20 mL) and brine (2 mL), and then extracted with EtOAc (3×50 mL). The combined organic extracts were filtered through PS paper and then concentrated in vacuo to afford the crude title compound, which was used without further purification. MS (apci) m/z=421.1 (M+H).

Intermediate P14

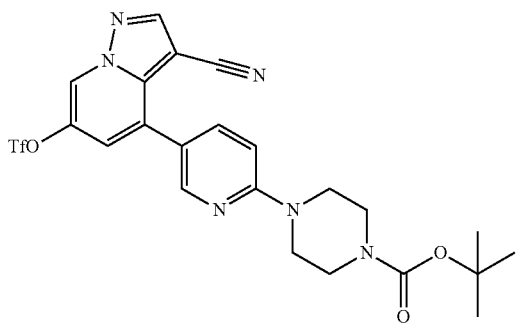 [SMILES: CC(C)(C)OC(=O)N1CCN(c2ccc(-c3cc(OS(=O)(=O)C(F)(F)F)cn4ncc(C#N)c34)cn2)CC1]

Tert-Butyl 4-(5-(3-cyano-6-(((trifluoromethyl)sulfonyl)oxy)pyrazolo[1,5-a]pyridin-4-yl)pyridin-2-yl)piperazine-1-carboxylate Tert-butyl 4-(5-(3-cyano-6-hydroxypyrazolo[1,5-a]pyridin-4-yl)pyridin-2-yl)piperazine-1-carboxylate (Intermediate P13; 750 mg, 1.78 mmol), DIEA (1553 μL, 8.92 mmol) and 1,1,1-trifluoro-N-phenyl-N-((trifluoromethyl)sulfonyl)methanesulfonamide (828 mg, 2.32 mmol) were combined in THF (20 mL) and stirred at ambient temperature overnight. The reaction was subsequently concentrated in vacuo and directly purified by silica chromatography (20-100% EtOAc/hexanes) to yield the title compound (723 mg, 73% yield). MS (apci) m/z=553.1 (M+H).

Intermediate P15

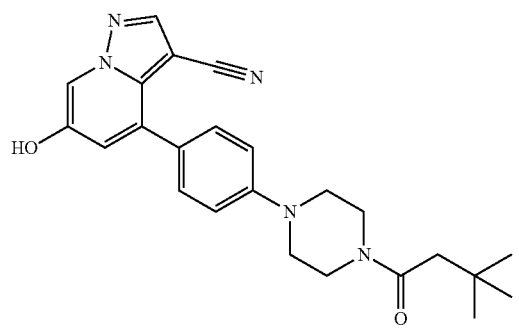 [SMILES: CC(C)(C)CC(=O)N1CCN(c2ccc(-c3cc(O)cn4ncc(C#N)c34)cc2)CC1]

4-(4-(4-(3,3-Dimethylbutanoyl)piperazin-1-yl)phenyl)-6-hydroxypyrazolo[1,5-a]pyridine-3-carbonitrile In a pressure tube a solution of 4-bromo-6-hydroxypyrazolo[1,5-a]pyridine-3-carbonitrile, (Intermediate P12; 500 mg, 2.10 mmol) in dioxane (10 mL) was treated with 3,3-dimethyl-1-(4-(4-(4,4,5,5-tetramethyl-1,3,2-dioxaborolan-2-yl)phenyl)piperazin-1-yl)butan-1-one (Intermediate R11; 974 mg, 2.52 mmol), 2 M $Na_2CO_{3(aq)}$ (2100 μL, 4.20 mmol) and $Pd(PPh_3)_4$ (24.3 mg, 0.0210 mmol). The resulting reaction mixture was sparged with nitrogen for 5 min then heated at 100° C. overnight. After cooling to ambient temperature, the reaction mixture was diluted with water and brine (2 mL each) and then extracted with EtOAc (2×50 mL). The combined organic extracts were filtered through PS paper then concentrated in vacuo to afford the crude title compound, which was used without further purifications (510 mg, 58% yield). MS (apci), m/z=419.1 (M+H).

Intermediate P16

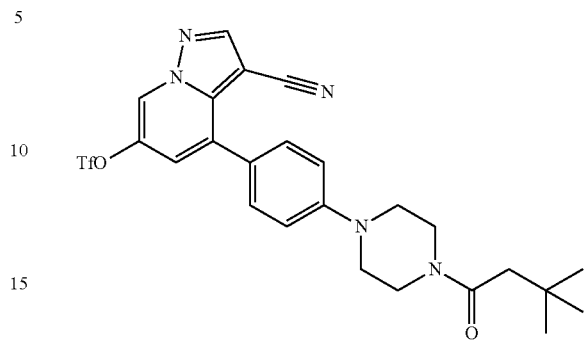

3-cyano-4-(4-(4-(3,3-dimethylbutanoyl)piperazin-1-yl)phenyl)pyrazolo[1,5-a]pyridin-6-yl Trifluoromethanesulfonate To a suspension of 4-(4-(4-(3,3-dimethylbutanoyl)piperazin-1-yl)phenyl)-6-hydroxypyrazolo[1,5-a]pyridine-3-carbonitrile (Intermediate P15; 510 mg, 1.22 mmol) in THF (20 mL) was added DIEA (439 μL, 2.44 mmol) and 1,1,1-trifluoro-N-phenyl-N— ((trifluoromethyl)sulfonyl)methanesulfonamide (480 mg, 1.34 mmol). This reaction mixture was stirred at ambient temperature overnight then directly purified by silica chromatography (0-100% EtOAc/hexanes) to yield the title compound (611 mg, 91% yield).

Intermediate R1

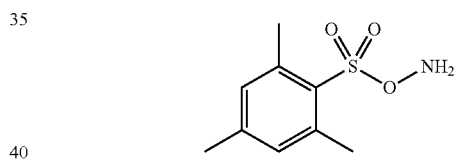

O-(mesitylsulfonyl)hydroxylamine

Step 1: Preparation of Tert-Butyl (Mesitylsulfonyl)Oxycarbamate

To a 0° C. solution of 2,4,6-trimethylbenzene-1-sulfonyl chloride (10.0 g, 45.72 mmol) and tert-butyl hydroxycarbamate (6.088 g, 45.72 mmol) in MTBE (100 mL) was added TEA (14.46 mL, 48.01 mmol) drop-wise while stirring. The resulting suspension was stirred at 0° C. for an additional 30 min and then warmed to ambient temperature. The reaction was then diluted with water (100 mL), adjusted to pH 4 with 1 N $HCl_{(aq)}$. The organic layer was dried ($Na_2SO_4$), filtered and concentrated to yield the title compound initially as a yellowish oil, which upon drying overnight under high vacuum became a white solid (12.89 g, 89% yield). $^1H$ NMR ($CDCl_3$) δ 7.66 (br s, 1H), 6.98 (s, 2H), 2.67 (s, 6H), 2.32 (s, 3H), 1.31 (s, 9H).

Step 2: Preparation of O-(mesitylsulfonyl)hydroxylamine (Intermediate R1, MSH)

To TFA (117 mL, 1521 mmol) at 0° C. was slowly added tert-butyl (mesitylsulfonyl)oxycarbamate (39.0 g, 124 mmol) over 25 min. The reaction mixture was stirred at 0° C. for 1.5 h and then quenched with the sequential addition of crushed ice (5×ca. 200 mL) and water (2×125 mL). The resulting thick suspension was vigorously stirred at ambient temperature for 5 min. Without allowing the filter cake to run dry, the solids were collected by careful vacuum filtration followed by subsequent rinsing with water (4 L) until the filtrate reached pH 6 (Caution: explosion risk exists with dry compound at ambient temperature). The wet filter cake was taken up in DCM (150 mL) and the resulting biphasic solution was separated. The DCM layer was dried over MgSO$_4$ for 30 min and then filtered and rinsed with DCM (420 mL) to provide the title compound as a 0.22 M solution in DCM.

Intermediate R2

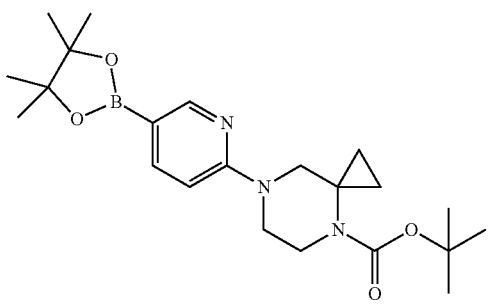 [SMILES: CC(C)(C)OC(=O)N1CCN(c2ccc(B3OC(C)(C)C(C)(C)O3)cn2)CC12CC2]

Tert-Butyl 7-(5-(4,4,5,5-tetramethyl-1,3,2-dioxaborolan-2-yl)pyridin-2-yl)-4,7-diazaspiro[2.5]octane-4-carboxylate A solution of tert-butyl 4,7-diazaspiro[2.5]octane-4-carboxylate (177 mg, 0.835 mmol) and 2-chloro-5-(4,4,5,5-tetramethyl-1,3,2-dioxaborolan-2-yl)pyridine (100 mg, 0.418 mmol) in DMSO (1.4 mL) was heated to 150° C. in a pressure tube overnight. After cooling to ambient temperature the reaction mixture was diluted with EtOAc (30 mL) and washed with brine (3×25 mL). The combined organic extracts were dried over MgSO$_4$, filtered and concentrated. The crude residue was purified by silica chromatography (0-100% EtOAc/hexanes) to provide the title compound (91 mg, 53% yield). $^1$H NMR (CDCl$_3$) δ 8.51 (d, 1H), 7.80 (dd, 1H), 6.53 (d, 1H), 3.65 (m, 2H), 3.59 (m, 2H), 3.45 (s, 2H), 1.47 (s, 9H), 1.32 (s, 12H), 1.00 (m, 2H), 0.88 (m, 2H).

The borolane intermediates shown in Table A were prepared according the method used for the synthesis of Intermediate R2, using the appropriate starting materials.

TABLE A

| Intermediate | Structure | Name | Spectral Data |
| --- | --- | --- | --- |
| R3 | 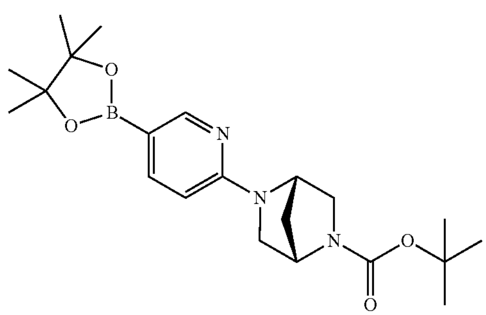 | tert-butyl (1S,4S)-5-(5-(4,4,5,5-tetramethyl-1,3,2-dioxaborolan-2-yl)pyridin-2-yl)-2,5-diazabicyclo[2.2.1]heptane-2-carboxylate | $^1$H NMR (CDCl$_3$) δ 8.50 (s, 1H), 7.79 (d, 1H), 6.29 (d, 1H), 4.98 (br s, 0.6H), 4.88 (br s, 0.4H), 4.67 (s, 0.6H), 4.52 (s, 0.4H), 3.35-3.55 (m, 4H), 1.93 (d, 2H), 1.46 (s, 4H), 1.41 (s, 5H), 1.32 (s, 12H). |
| R4 | 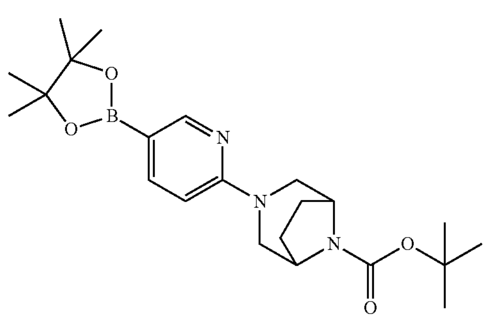 | tert-butyl 3-(5-(4,4,5,5-tetramethyl-1,3,2-dioxaborolan-2-yl)pyridin-2-yl)-3,8-diazabicyclo[3.2.1]octane-8-carboxylate | $^1$H NMR (CDCl$_3$) δ 8.53 (s, 1H), 7.81 (d, 1H), 6.52 (d, 1H), 4.35 (br m, 2H), 3.99 (br m, 2H), 3.11 (br m, 2H), 1.93 (m, 2H), 1.74 (m, 2H), 1.48 (s, 9H), 1.32 (s, 12H). |

TABLE A-continued

| Intermediate | Structure | Name | Spectral Data |
|---|---|---|---|
| R5 | 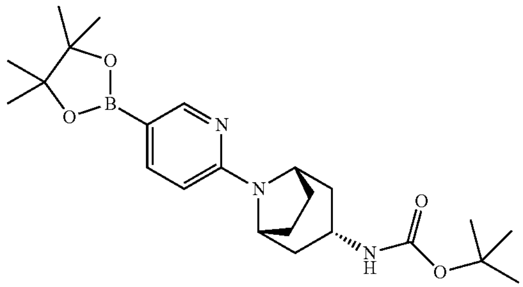 | tert-butyl ((1R,3s,5S)-8-(5-(4,4,5,5-tetramethyl-1,3,2-dioxaborolan-2-yl)pyridin-2-yl)-8-azabicyclo[3.2.1]octan-3-yl)carbamate | ¹H NMR (CDCl₃) δ 8.53 (s, 1H), 7.80 (d, 1H), 6.59 (d, 1H), 4.57 (m, 2H), 4.07-4.20 (m, 2H), 2.07 (m, 2H), 1.89 (m, 4H), 1.50 (m, 2H), 1.40 (s, 9H), 1.32 (s, 12H). |
| R6 | 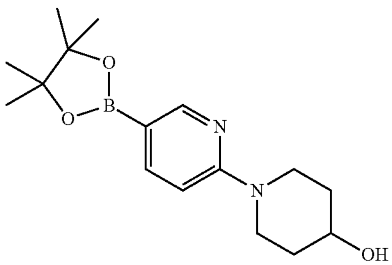 | 1-(5-(4,4,5,5-tetramethyl-1,3,2-dioxaborolan-2-yl)pyridin-2-yl)piperidin-4-ol | ¹H NMR (CDCl₃) δ 8.53 (s, 1H), 7.80 (d, 1H), 6.59 (d, 1H), 4.57 (m, 2H), 4.07-4.20 (m, 2H), 2.07 (m, 2H), 1.89 (m, 4H), 1.50 (m, 2H), 1.40 (s, 9H), 1.32 (s, 12H). |
| R7 | 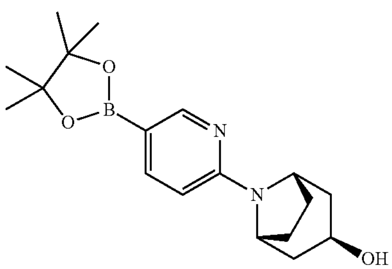 | (1R,3r,5S)-8-(5-(4,4,5,5-tetramethyl-1,3,2-dioxaborolan-2-yl)pyridin-2-yl)-8-azabicyclo[3.2.1]octan-3-ol | ¹H NMR (CDCl₃) δ 8.53 (d, 1H), 7.78 (dd, 1H), 6.48 (d, 1H), 4.52 (s, 2H), 4.04 (s, 1H), 2.31 (m, 2H), 2.18 (dt, 2H), 2.06 (m, 1H), 1.69 (d, 2H), 1.31 (s, 12H). |
| R8 | 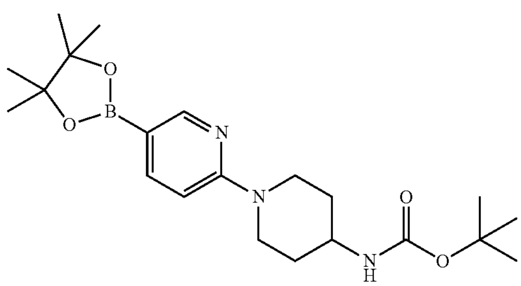 | tert-butyl (1-(5-(4,4,5,5-tetramethyl-1,3,2-dioxaborolan-2-yl)pyridin-2-yl)piperidin-4-yl)carbamate | ¹H NMR (CDCl₃) δ 8.52 (s, 1H), 7.79 (d, 1H), 6.60 (d, 1H), 4.46 (br s, 1H), 4.30 (m, 2H), 3.71 (br s, 1H), 3.01 (t, 2H), 2.01 (m, 2H, 1.45 (s, 9H), 1.38 (m, 2H), 1.32 (s, 12H). |

Intermediate R9

Tert-Butyl ((1R,3r,5S)-8-(5-(4,4,5,5-tetramethyl-1,3,2-dioxaborolan-2-yl)pyridin-2-yl)-8-azabicyclo[3.2.1]octan-3-yl)carbamate

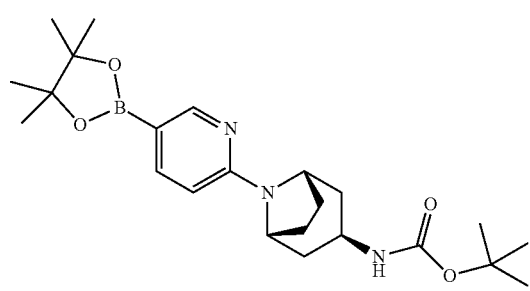 [SMILES: CC(C)(C)OC(=O)N[C@H]1C[C@H]2CC[C@@H](C1)N2c1ccc(B2OC(C)(C)C(C)(C)O2)cn1]

A solution of tert-butyl (1R,3r,5S)-8-azabicyclo[3.2.1]octan-3-ylcarbamate (378 mg, 1.67 mmol) and 2-chloro-5-(4,4,5,5-tetramethyl-1,3,2-dioxaborolan-2-yl)pyridine (200 mg, 0.835 mmol) in DMSO (3 mL) was stirred at 150° C. in a pressure tube for 3 d. After cooling to ambient temperature the reaction mixture was diluted with water (10 mL) and the resulting suspension was filtered, rinsed with water and dried in vacuo to provide the title compound (228 mg, 64% yield). ¹H NMR (CDCl₃) δ 8.53 (dd, 1H), 7.79 (dd, 1H), 6.48 (d, 1H), 4.96 (br s, 1H), 4.55 (br s, 2H), 3.75 (br s, 1H), 2.14-2.27 (m, 4H), 2.01 (m, 2H), 1.67 (d, 2H), 1.44 (s, 9H), 1.32 (s, 12H).

Intermediate R10

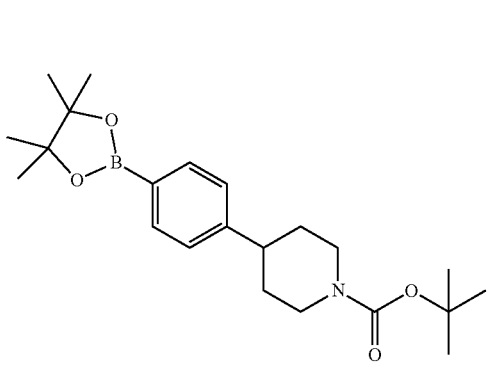 [SMILES: CC(C)(C)OC(=O)N1CCC(c2ccc(B3OC(C)(C)C(C)(C)O3)cc2)CC1]

Tert-Butyl 4-(4-(4,4,5,5-tetramethyl-1,3,2-dioxaborolan-2-yl)phenyl)piperidine-1-carboxylate

Step 1: Preparation of Tert-Butyl 4-(4-bromophenyl)piperidine-1-carboxylate

At ambient temperature, a suspension of 4-(4-bromophenyl)piperidine (1000 mg, 4.164 mmol) in DCM (20 mL) was treated with DIEA (1451 μL, 8.328 mmol) followed by Boc-anhydride (1064 μL, 4.581 mmol), and then stirred overnight. The reaction mixture was subsequently diluted with water (50 mL) and then extracted with DCM (3×50 mL). The combined organic extracts were dried (MgSO$_4$), filtered and concentrated in vacuo to afford the title compound (1363 mg, 96% yield). $^1$H NMR (CDCl$_3$) δ 7.42 (m, 2H), 7.07 (m, 2H), 4.24 (m, 2H), 2.79 (dt, 2H), 2.61 (tt, 1H), 1.79 (m, 2H), 1.58 (qd, 2H), 1.48 (s, 9H).

Step 2: Preparation of Tert-Butyl 4-(4-(4,4,5,5-tetramethyl-1,3,2-dioxaborolan-2-yl)phenyl)piperidine-1-carboxylate In a pressure tube a solution of tert-butyl 4-(4-bromophenyl)piperidine-1-carboxylate (1363 mg, 4.006 mmol) in dioxane was treated with bis(pinacolato)diboron (1526 mg, 6.009 mmol), KOAc (1179 mg, 12.02 mmol), and PdCl$_2$(dppf).DCM (327.1 mg, 0.4006 mmol). The mixture was sparged with nitrogen for 1 min and then sealed and heated at 100° C. overnight. After cooling to ambient temperature, the reaction mixture was diluted with a mixture of EtOAc (75 mL)/water (50 mL)/brine (25 mL), and the resulting emulsion was filtered through Celite® and rinsed with EtOAc. The biphasic filtrate was separated and the organic phase was washed with brine and then dried (MgSO$_4$), filtered and concentrated in vacuo. The crude residue was purified by silica chromatography (0-50% EtOAc/hexanes) to afford the title compound (1437 mg, 93% yield). $^1$H NMR (CDCl$_3$) δ 7.76 (d, 2H), 7.22 (m, 2H), 4.24 (d, 2H), 2.79 (dt, 2H), 2.65 (tt, 1H), 1.81 (m, 2H), 1.63 (dq, 2H), 1.48 (s, 9H), 1.33 (s, 12H).

Intermediate R11

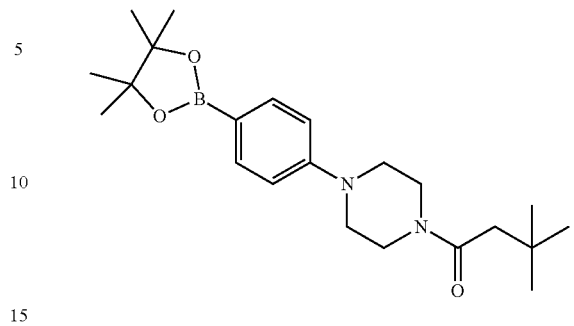

3,3-dimethyl-1-(4-(4-(4,4,5,5-tetramethyl-1,3,2-dioxaborolan-2-yl)phenyl)piperazin-1-yl)butan-1-one To a mixture of 1-(4-(4,4,5,5-tetramethyl-1,3,2-dioxaborolan-2-yl)phenyl)piperazine (850 mg, 2.95 mmol) and TEA (1233 μL, 8.85 mmol) in DCM (10 mL) was added 3,3-dimethylbutanoyl chloride (486 μL, 3.54 mmol). The reaction was stirred overnight at ambient temperature and subsequently quenched with MeOH (1 mL), concentrated in vacuo, taken up in water (5 mL) and sonicated. The solid was collected by filtration, washed with water (2 mL) and hexanes (3×5 mL) to afford the title compound (938 mg, 82% yield).

Intermediate P17

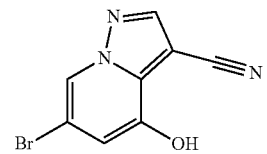 [SMILES: N#Cc1cnn2cc(Br)cc(O)c12]

6-bromo-4-hydroxypyrazolo[1,5-a]pyridine-3-carbonitrile

A room temperature solution of 6-bromo-4-methoxypyrazolo[1,5-a]pyridine-3-carbonitrile (Intermediate P4; 0.200 g, 0.793 mmol) in DCE (7.93 mL) was treated with AlCl$_3$ (0.529 g, 3.97 mmol), then stirred at 80° C. for 2 h. After cooling to room temperature, the reaction mixture was quenched with water (100 mL), and extracted with DCM. The combined organic extracts were dried over anhydrous Na$_2$SO$_4$, filtered and concentrated in vacuo. The residue was purified by silica chromatography (0-75% EtOAc/Hexanes as the gradient eluent) to cleanly afford the title compound (78.6 mg, 42% yield). MS (apci) m/z=237.9 (M+H).

Intermediate P18

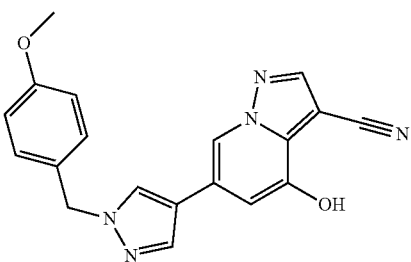 [SMILES: COc1ccc(Cn2cc(-c3cc(O)c4c(C#N)cnn4c3)cn2)cc1]

4-hydroxy-6-(1-(4-methoxybenzyl)-1H-pyrazol-4-yl)pyrazolo[1,5-a]pyridine-3-carbonitrile A room temperature solution of 6-bromo-4-hydroxypyrazolo[1,5-a]pyridine-3-carbonitrile (Intermediate P17; 1.00 g, 4.20 mmol) in dioxane (42.0 mL) was treated with 1-(4-methoxybenzyl)-4-(4,4,5,5-tetramethyl-1,3,2-dioxaborolan-2-yl)-1H-pyrazole (1.98 g, 6.30 mmol) and 2 M aqueous K$_2$CO$_3$ (4.20 mL, 8.402 mmol), then sparged with N$_2$ for 5 min. The reaction mixture was treated with XPhos (0.401 g, 0.842 mmol) and Pd$_2$(dba)$_3$ (0.192 g, 0.210 mmol), then sparged with N$_2$ for 5 min, sealed and stirred overnight at 80° C. After cooling to room temperature, the reaction mixture was diluted with water, and extracted with EtOAc. The combined organic extracts were dried over anhydrous Na$_2$SO$_4$, filtered and concentrated in vacuo. The residue was purified by silica gel (Biotage Isolera, 80 g, Isco RediSep, 0-10% MeOH in DCM as the gradient eluent) to afford the title compound (1.06 g, 73% yield).

Intermediate P19

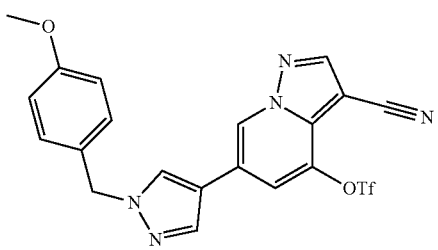 [SMILES: COc1ccc(Cn2cc(-c3cc(OS(=O)(=O)C(F)(F)F)c4c(C#N)cnn4c3)cn2)cc1]

3-cyano-6-(1-(4-methoxybenzyl)-1H-pyrazol-4-yl)pyrazolo[1,5-a]pyridin-4-yl Trifluoromethanesulfonate A room temperature solution of 4-hydroxy-6-(1-(4-methoxybenzyl)-1H-pyrazol-4-yl)pyrazolo[1,5-a]pyridine-3-carbonitrile (Intermediate P18; 1.057 g, 3.061 mmol) in DCM (15.3 mL) was treated with 1,1,1-trifluoro-N-phenyl-N-((trifluoromethyl)sulfonyl)methanesulfonamide (2.187 g, 6.121 mmol) and DIEA (1.6 mL, 9.2 mmol). The reaction mixture was stirred overnight at room temperature, and then quenched with water. The resulting biphasic mixture was extracted with DCM. The combined organic extracts were dried over anhydrous Na$_2$SO$_4$, filtered, and concentrated in vacuo. The residue was purified by silica chromatography (0-50% DCM/EtOAc as the gradient eluent) to afford the title compound (958 mg, 66% yield).

Intermediate P20

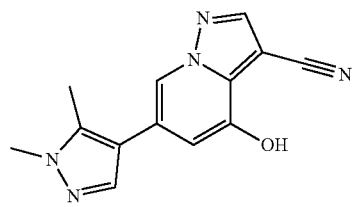 [SMILES: Cc1c(-c2cc(OS(=O)(=O)C(F)(F)F)c3c(C#N)cnn3c2)cnn1C]

6-(1,5-dimethyl-1H-pyrazol-4-yl)-4-hydroxypyrazolo[1,5-a]pyridine-3-carbonitrile A room temperature solution of 6-bromo-4-hydroxypyrazolo[1,5-a]pyridine-3-carbonitrile (Intermediate P17; 0.250 g, 1.05 mmol) in dioxane (10.5 mL) was treated with 1,5-dimethyl-1H-pyrazole-4-boronic acid pinacol ester (0.350 g, 1.58 mmol) and 2M aqueous K$_2$CO$_3$ (1.10 mL, 2.10 mmol), then sparged with N$_2$ for 5 min. The reaction mixture was treated with XPhos (0.100 g, 0.210 mmol) and Pd$_2$(dba)$_3$ (0.0481 g, 0.0525 mmol), then sparged with N$_2$ for 5 min, sealed, and stirred overnight at 80° C. After cooling to room temperature, the reaction mixture was diluted with water, and extracted with EtOAc. The combined organic extracts were dried over anhydrous Na$_2$SO$_4$, filtered, and concentrated in vacuo. 1:1 DCM and hexanes were added to the crude material and the solids were filtered to afford the title compound (0.135 g, 51% yield). MS (apci) m/z=254.1 (M+H).

Intermediate P21

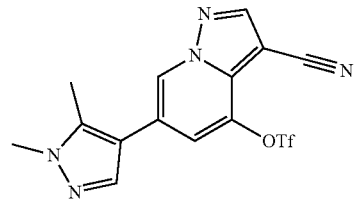

3-cyano-6-(1,5-dimethyl-1H-pyrazol-4-yl)pyrazolo[1,5-a]pyridin-4-yl Trifluoromethanesulfonate A room temperature solution of 6-(1,5-dimethyl-1H-pyrazol-4-yl)-4-hydroxypyrazolo[1,5-a]pyridine-3-carbonitrile (Intermediate P20; 0.135 g, 0.533 mmol) in DCM (2.67 mL) was treated with 1,1,1-trifluoro-N-phenyl-N-((trifluoromethyl)sulfonyl)methanesulfonamide (0.209 g, 0.586 mmol) and DIEA (0.186 mL, 1.07 mmol). The reaction mixture was stirred overnight at room temperature, and then quenched with water. The resulting biphasic mixture was extracted with DCM. The combined organic extracts were dried over anhydrous Na$_2$SO$_4$, filtered, and concentrated in vacuo. The residue was purified by silica chromatography (0-50% DCM/EtOAc as the gradient eluent) to afford the title compound (125 mg, 61% yield). MS (apci) m/z=386.0 (M+H).

Intermediate P22

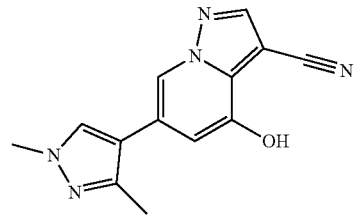

6-(1,3-dimethyl-1H-pyrazol-4-yl)-4-hydroxypyrazolo[1,5-a]pyridine-3-carbonitrile A room temperature solution of 6-bromo-4-hydroxypyrazolo[1,5-a]pyridine-3-carbonitrile (Intermediate P17; 0.250 g, 1.05 mmol) in dioxane (10.5 mL) was treated with 1,3-dimethyl-1H-pyrazole-4-boronic acid pinacol ester (0.350 g, 1.58 mmol) and 2 M aqueous K$_2$CO$_3$ (1.10 mL, 2.10 mmol), then sparged with N$_2$ for 5 min. The reaction mixture was treated with XPhos (0.100 g, 0.210 mmol) and Pd$_2$(dba)$_3$ (0.0481 g, 0.0525 mmol), then sparged with N$_2$ for 5 min, sealed and stirred overnight at 80° C. After cooling to room temperature, the reaction mixture was diluted with water, and extracted with EtOAc. The combined organic extracts were dried over anhydrous Na$_2$SO$_4$, filtered, and concentrated in vacuo. 1:1 DCM and hexanes were added to the crude material and the solids were filtered to afford the title compound (0.192 g, 72% yield). MS (apci) m/z=254.1 (M+H).

Intermediate P23

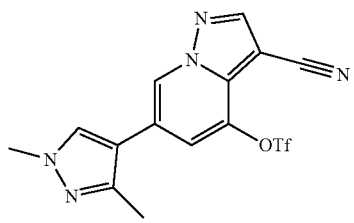 [SMILES: Cc1nn(C)cc1-c1cc(OS(=O)(=O)C(F)(F)F)c2c(C#N)cnn2c1]

3-cyano-6-(1,3-dimethyl-1H-pyrazol-4-yl)pyrazolo[1,5-a]pyridin-4-yl Trifluoromethanesulfonate A room temperature solution of 6-(1,3-dimethyl-1H-pyrazol-4-yl)-4-hydroxypyrazolo[1,5-a]pyridine-3-carbonitrile (Intermediate P22; 0.192 g, 0.757 mmol) in DCM (3.79 mL) was treated with 1,1,1-trifluoro-N-phenyl-N—((trifluoromethyl)sulfonyl)methanesulfonamide (0.298 g, 0.833 mmol) and DIEA (0.264 mL, 1.51 mmol). The reaction mixture was stirred overnight at room temperature, and then quenched with water. The resulting biphasic mixture was extracted with DCM. The combined organic extracts were dried over anhydrous Na$_2$SO$_4$, filtered, and concentrated in vacuo. The residue was purified by silica chromatography (0-50% DCM/EtOAc as the gradient eluent) to afford the title compound (189 mg, 65% yield). MS (apci) m/z=386.0 (M+H).

Intermediate P24

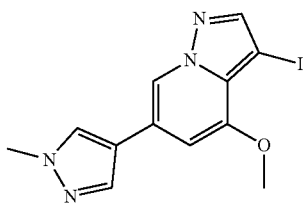 [SMILES: COc1cc(-c2cnn(C)c2)cn2ncc(I)c12]

3-iodo-4-methoxy-6-(1-methyl-1H-pyrazol-4-yl)pyrazolo[1,5-a]pyridine

A room temperature solution of 4-methoxy-6-(1-methyl-1H-pyrazol-4-yl)pyrazolo[1,5-a]pyridine (Intermediate P7, step 1; 1.90 g, 8.32 mmol) and PPTS (0.209 g, 0.832 mmol) in DCM (20 mL) was treated with NIS (1.97 g, 8.74 mmol) then stirred overnight at room temperature. The reaction mixture was diluted with DCM, and washed with 2 N aqueous NaOH. The combined organic extracts were dried over anhydrous Na$_2$SO$_4$, filtered, and concentrated in vacuo. The residue was purified by silica chromatography (0-50% EtOAc in Hexanes as the gradient eluent) to afford the title compound (2.4 g, 81% yield). MS (apci) m/z=355.0 (M+H).

Intermediate P25

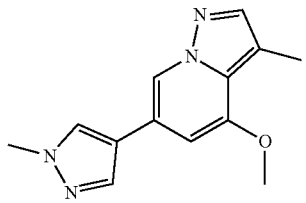

4-methoxy-3-methyl-6-(1-methyl-1H-pyrazol-4-yl)pyrazolo[1,5-a]pyridine

A mixture of 3-iodo-4-methoxy-6-(1-methyl-1H-pyrazol-4-yl)pyrazolo[1,5-a]pyridine (Intermediate P24; 2.4 g, 6.78 mmol), 2,4,6-trimethyl-1,3,5,2,4,6-trioxatriborinane (2.84 mL, 20.3 mmol), PdCl$_2$(dppf).CH$_2$Cl2 (0.553 g, 0.678 mmol), and K$_2$CO$_3$ (4.68 g, 33.9 mmol) in DMF (67.8 mL) was sparged with Argon, then sealed and stirred for 18 h at 100° C. The reaction mixture was diluted with water (60 mL) and extracted with EtOAc (3×100 mL). The combined organic extracts were dried over anhydrous Na$_2$SO$_4$, filtered, and concentrated in vacuo. The residue was purified by silica chromatography (using 50-100% EtOAc in Hexanes as the gradient eluent) and then by reverse phase HPLC (5-95% water/ACN with 0.1% TFA as the gradient eluent) to afford the title compound (500 mg, 31% yield). MS (apci) m/z=243.1 (M+H).

Intermediate P26

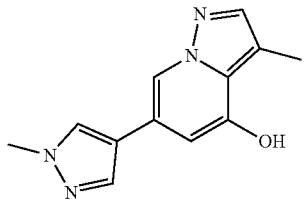

3-methyl-6-(1-methyl-1H-pyrazol-4-yl)pyrazolo[1,5-a]pyridin-4-ol

A room temperature solution of 4-methoxy-3-methyl-6-(1-methyl-1H-pyrazol-4-yl)pyrazolo[1,5-a]pyridine (Intermediate P25; 500 mg, 2.06 mmol) in DCE (20.6 mL) was treated with AlCl$_3$ (1.38 g, 10.3 mmol), then stirred for 2 h at 80° C. After cooling to room temperature, the reaction mixture was quenched with water (100 mL), and extracted with 20% iPrOH in DCM. The combined organic extracts were dried over anhydrous Na$_2$SO$_4$, filtered, and concentrated in vacuo to cleanly afford the title compound (390 mg, 83% yield). MS (apci) m/z=229.1 (M+H).

Intermediate P27

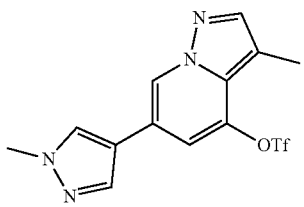

3-methyl-6-(1-methyl-1H-pyrazol-4-yl)pyrazolo[1,5-a]pyridin-4-yl Trifluoromethanesulfonate A room temperature solution of 3-methyl-6-(1-methyl-1H-pyrazol-4-yl)pyrazolo[1,5-a]pyridine-4-ol (Intermediate P26; 0.390 g, 1.71 mmol) in DCM (17.1 mL) was treated with DIEA (0.613 mL, 3.42 mmol) and 1,1,1-trifluoro-N-phenyl-N—((trifluoromethyl)sulfonyl)methanesulfonamide (0.671 g, 1.88 mmol). The reaction mixture was stirred for 5 d at room temperature. The reaction mixture was purified directly by silica chromatography (25-75% EtOAc/Hexanes as the gradient eluent) to afford the title compound (400 mg, 65% yield). MS (apci) m/z=361.0 (M+H).

Intermediate R12

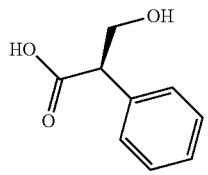 [SMILES: O=C(O)[C@@H](CO)c1ccccc1]

(R)-3-hydroxy-2-phenylpropanoic Acid

Step 1: Preparation of (S)-4-benzyl-3-(2-phenylacetyl)oxazolidin-2-one

A solution of (S)-(−)-4-benzyl-2-oxazolidinone (1.34 g, 7.57 mmol) in THF (100 mL) was cooled to −78° C. then treated with 1.0 M lithium bis(trimethylsilyl)amide in THF (7.95 mL, 7.95 mmol). The reaction mixture was stirred for 30 min at −78° C., then stirred 16 h at room temperature, before quenching with water. The resulting biphasic mixture was extracted with EtOAc. The combined organic extracts were washed with water and brine, then dried over anhydrous $Na_2SO_4$, filtered, and concentrated in vacuo. The residue was purified by silica chromatography (5-60% Hexanes-EtOAc as the gradient eluent) to cleanly afford the title compound (1.55 g, 69% yield). MS (apci) m/z=252 [(M-$CO_2$)+1].

Step 2: Preparation of (S)-4-benzyl-3-((R)-3-hydroxy-2-phenylpropanoyl)oxazolidin-2-one A room temperature solution of (S)-4-benzyl-3-(2-phenylacetyl)oxazolidin-2-one (step 1; 1.55 g, 5.25 mmol) in DCM (50 mL) was sparged with $N_2$, then cooled to 0° C. The resulting degassed solution was treated with titanium (IV) chloride (0.604 mL, 5.51 mmol), and stirred for 5 min at 0° C., before treating with DIEA (1.01 mL, 5.77 mmol). The resulting mixture was stirred for 1 h at 0° C., then treated sequentially with 0.60 M 1,3,5-trioxane in DCM (10 mL, 6.04 mmol) and additional titanium (IV) chloride (0.604 mL, 5.51 mmol). The reaction mixture was stirred for an additional 4 h at 0° C., before quenching with saturated $NH_4Cl$. The resulting biphasic mixture was extracted with DCM. The combined organic extracts were washed with water, then dried over anhydrous $Na_2SO_4$, filtered, and concentrated in vacuo. The residue was purified by silica chromatography (5-50% DCM-Acetone as the gradient eluent) to cleanly afford the title compound (1.22 g, 71% yield). $^1$H NMR (400 MHz, DMSO-$d_6$) δ 7.34-7.23 (m, 10H), 5.20-5.14 (m, 2H), 4.74-4.70 (m, 1H), 4.28-4.24 (t, 1H), 4.16-4.08 (m, 2H), 3.61-3.56 (m, 1H), 3.06-2.96 (m, 2H).

Step 3: Preparation of (R)-3-hydroxy-2-phenylpropanoic Acid

A cold (0° C.) solution of (S)-4-benzyl-3-((R)-3-hydroxy-2-phenylpropanoyl)oxazolidin-2-one (step 2; 1.22 g, 3.75 mmol) in THF (40 mL) was treated sequentially with 30% (w/w) aqueous $H_2O_2$ (3.60 mL, 37.5 mmol) and 2 M aqueous LiOH in (3.75 mL, 7.50 mmol). The resulting reaction mixture was stirred for 2 h at room temperature. The reaction mixture was treated with 2 M aqueous KOH (3.75 mL, 7.50 mmol), and refluxed for 2 h. After cooling to room temperature, the reaction mixture was treated with 1 M aqueous $Na_2SO_3$ (5 mL), before concentrating in vacuo to remove the volatile organics. The resulting aqueous residue was diluted with $Et_2O$, and washed with 1 M aqueous NaOH. The aqueous extracts were acidified to pH 2 using 4 M aqueous HCl, and extracted with 4:1 DCM/iPrOH. The combined DCM/iPrOH extracts were dried over anhydrous $Na_2SO_4$, filtered, and concentrated in vacuo. The residue was purified by C18 reverse phase chromatography (5-95% water/ACN with 0.1% TFA as the gradient eluent) to cleanly afford the title compound (355.6 mg, 57% yield). $^1$H NMR (400 MHz, DMSO-$d_6$) δ 12.34 (s, 1H), 7.34-7.23 (m, 5H), 3.93-3.89 (t, 1H), 3.65-3.54 (m, 2H).

Intermediate R13

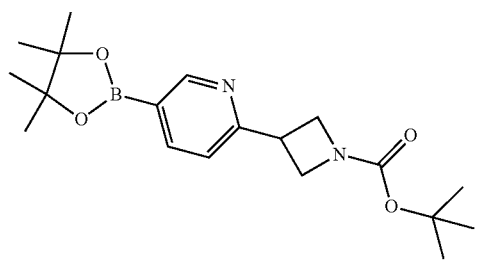 [SMILES: CC(C)(C)OC(=O)N1CC(c2ccc(B3OC(C)(C)C(C)(C)O3)cn2)C1]

Tert-Butyl 3-(5-(4,4,5,5-tetramethyl-1,3,2-dioxaborolan-2-yl)pyridine-2-yl)azetidine-1-carboxylate Step 1: Preparation of Tert-Butyl 3-(5-bromopyridin-2-yl)azetidine-1-carboxylate A room temperature suspension of zinc dust (<10 um, 98+%; 0.353 g, 5.40 mmol) in THF (10 mL) was treated with 1,2-dibromoethane (0.0310 mL, 0.360 mmol) and chlorotrimethylsilane (0.0457 mL, 0.360 mmol) then stirred for 15 min at 60° C. The resulting mixture was treated with a solution of tert-butyl 3-iodoazetidine-1-carboxylate (1.02 g, 3.60 mmol) in DMA (10 mL), and stirred an additional 15 min at 60° C. before cooling to room temperature. The reaction mixture was treated with 2,5-dibromopyridine (0.896 g, 3.78 mmol), PdCl$_2$(dppf).CH$_2$Cl2 (0.147 g, 0.180 mmol), and CuI (0.0343 g, 0.180 mmol), sparged with Argon, sealed, and stirred 16 h at 80° C. The reaction mixture was cooled to room temperature, diluted with EtOAc and water, and then filtered. The filtrate was diluted with additional EtOAc, and washed with water and brine. The combined organic extracts were dried over anhydrous Na$_2$SO$_4$, filtered, and concentrated in vacuo. The residue was purified by silica chromatography (5-70% Hexanes-EtOAc as the gradient eluent) to cleanly afford the title compound (357.6 mg, 32% yield). $^1$H NMR (400 MHz, DMSO-d$_6$) δ 8.72-8.71 (m, 1H), 8.01-7.98 (m, 1H), 7.34-7.31 (m, 1H), 4.19-4.15 (m, 2H), 3.96-3.87 (m, 3H), 1.39 (s, 9H).

Step 2: Preparation of Tert-Butyl 3-(5-(4,4,5,5-tetramethyl-1,3,2-dioxaborolan-2-yl)pyridine-2-yl)azetidine-1-carboxylate A room temperature solution of tert-butyl 3-(5-bromopyridin-2-yl)azetidine-1-carboxylate (step 1; 153.5 mg, 0.4901 mmol) in dioxane (4.9 mL) was treated with bis(pinacolato)diboron (136.9 mg, 0.5391 mmol), PdCl$_2$(dppf).CH$_2$Cl2 (40.02 mg, 0.04901 mmol), and CH$_3$CO$_2$K (144.3 mg, 1.470 mmol). The resulting mixture was sparged with Argon, sealed, and stirred 16 h at 100° C. before cooling to room temperature. The reaction mixture was diluted with EtOAc, and washed with water and brine. The combined organic extracts were dried over anhydrous Na$_2$SO$_4$, filtered, and concentrated in vacuo to afford the title compound (176.0 mg, 99.7% yield). MS (apci) m/z=279.1; (M(BOH)+1).

The compounds in Table DD were prepared according to the method described for Intermediate R13, replacing tert-butyl 3-iodoazetidine-1-carboxylate with the appropriate alkyl iodide in Step 1. Reactions were monitored by LCMS, and reaction times were adjusted accordingly. Products were purified as in Intermediate R13 utilizing the appropriate gradient eluent in chromatography to cleanly afford the title compounds.

Intermediate R16

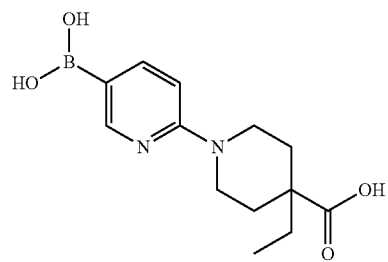

1-(5-boronopyridin-2-yl)-4-ethylpiperidine-4-carboxylic Acid

A room temperature solution of 2-fluoro-5-(4,4,5,5-tetramethyl-1,3,2-dioxaborolan-2-yl)pyridine (2.0 g, 9.0 mmol) in DMSO (18 mL) was treated with 4-ethylpiperidine-4-carboxylic acid (4.7 g, 30 mmol) and K$_2$CO$_3$ (5.0 g, 36 mmol), then stirred overnight at 80° C. After cooling to room temperature, the reaction mixture was diluted with water, and the resulting mixture was extracted with 20% MeOH/DCM. The combined organic extracts were dried over anhydrous Na$_2$SO$_4$, filtered, and concentrated in vacuo to afford the title compound containing impurities (4.2 g, quantitative yield). The material was used without further purification. MS (apci) m/z=279.1 (M+H).

TABLE DD

| Intermediate | Structure | Chemical Name | MS (apci) m/z |
|---|---|---|---|
| R14 | 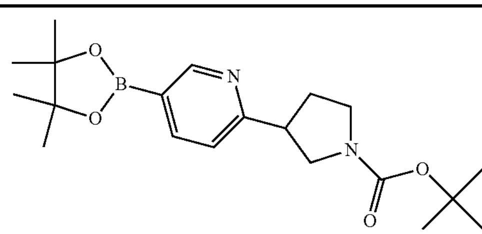 | tert-butyl 3-(5-(4,4,5,5-tetramethyl-1,3,2-dioxaborolan-2-yl)pyridin-2-yl)pyrrolidine-1-carboxylate | 293.1 |
| R15 | 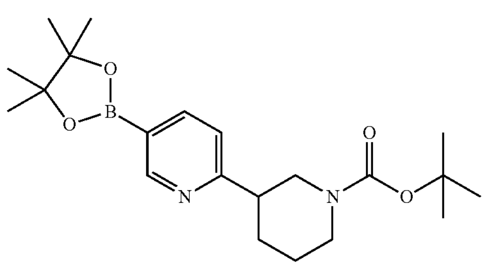 | tert-butyl 3-(5-(4,4,5,5-tetramethyl-1,3,2-dioxaborolan-2-yl)pyridin-2-yl)piperidine-1-carboxylate | 388.1 |

Intermediate R17

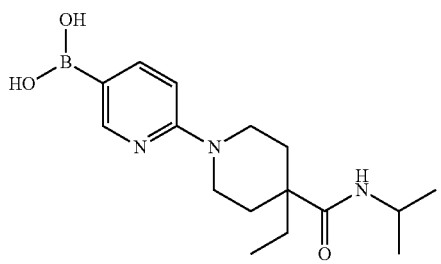 [SMILES: CCC1(C(=O)NC(C)C)CCN(c2ccc(B(O)O)cn2)CC1]

(6-(4-ethyl-4-(isopropylcarbamoyl)piperidin-1-yl)pyridin-3-yl)boronic Acid

A room temperature solution of 1-(5-boronopyridin-2-yl)-4-ethylpiperidine-4-carboxylic acid (Intermediate R16; 2.45 g, 8.81 mmol) in DMA (35.2 mL) was treated with DIEA (8.44 mL, 48.5 mmol), propan-2-amine (2.25 mL, 26.4 mmol), and HATU (8.37 g, 22.0 mmol), then allowed to stir overnight at room temperature. The reaction mixture was diluted with water and extracted with 20% MeOH/DCM. The combined organic extracts were dried over anhydrous $Na_2SO_4$, filtered, and concentrated in vacuo. The crude material was purified by C18 reverse phase chromatography (0-80% ACN/water as the gradient eluent) to afford the title compound (1.0 g, 36% yield). MS (apci) m/z=320.2 (M+H).

Intermediate R18

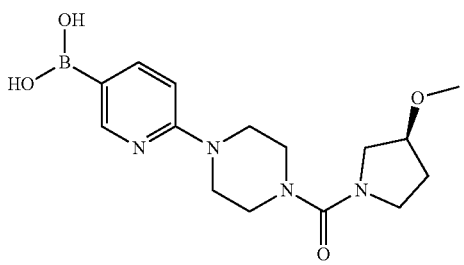 [SMILES: CO[C@H]1CCN(C(=O)N2CCN(c3ccc(B(O)O)cn3)CC2)C1]

(S)-(6-(4-(3-methoxypyrrolidine-1-carbonyl)piperazin-1-yl)pyridin-3-yl)boronic Acid A room temperature solution of (6-(piperazin-1-yl)pyridin-3-yl)boronic acid (1.5 g, 7.25 mmol) in DMA (36.2 mL) was treated with DIEA (5.05 mL, 29.0 mmol) and stirred for 20 min at room temperature and then treated with 4-nitrophenyl carbonochloridate (2.92 g, 14.5 mmol). The resulting mixture was stirred overnight at room temperature. DIEA (5 mL, 29.0 mmol) and (S)-3-methoxypyrrolidine (3.66 g, 36.2 mmol) were added, and the reaction mixture was stirred for 48 h at room temperature. The reaction mixture was diluted with water and extracted with 20% MeOH/DCM. The combined organic extracts were dried over anhydrous $Na_2SO_4$, filtered, and concentrated in vacuo. The residue was purified by C18 reverse phase chromatography (0-40% ACN/water as the gradient eluent) to afford the title compound (1.0 g, 41% yield). MS (apci) m/z=335.1 (M+H).

Intermediate R19

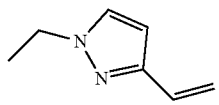

1-ethyl-3-vinyl-1H-pyrazole

A room temperature solution of 1-ethyl-3-iodopyrazole (2.52 g, 11.4 mmol) in 4:1 dioxane/water (100 mL) was treated with potassium vinyltrifluoroborate (1.67 g, 12.5 mmol), XPhos (0.107 g, 0.225 mmol) and $Pd_2(dba)_3$ (0.0516 g, 0.0563 mmol), then sparged with Argon, sealed, and stirred 16 h at 100° C. After cooling to room temperature, the reaction mixture was diluted with water, extracted with DCM, and filtered. The filtrate was diluted with additional DCM, and washed with water. The combined organic extracts were dried over anhydrous $Na_2SO_4$, filtered, and concentrated in vacuo. The residue was purified by silica chromatography (5-70% Hexanes-EtOAc as the gradient eluent) to afford the title compound (689.1 mg, 50% yield). MS (apci) m/z=123.1 (M+H).

Intermediate R20

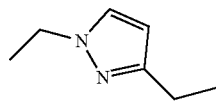

1,3-diethyl-1H-pyrazole

A room temperature solution of 1-ethyl-3-vinyl-1H-pyrazole (Intermediate R19; 689.1 mg, 5.641 mmol) in MeOH (28 mL) was treated with 10% Pd/C (600.3 mg, 0.2820 mmol). The resulting mixture was sparged with $N_2$ and then with $H_2$ for several minutes, then stirred under an atmosphere of $H_2$ for 16 h at ambient temperature and pressure. The resulting mixture was filtered through GF/F paper and the filtrate was concentrated in vacuo to afford the title compound (453.3 mg, 65% yield). MS (apci) m/z=125.2 (M+H).

Intermediate R21

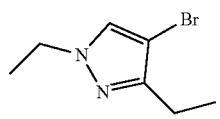

4-bromo-1,3-diethyl-1H-pyrazole

A room temperature solution of 1,3-diethyl-1H-pyrazole (Intermediate R20; 390.2 mg, 3.142 mmol) in ACN (30 mL) was treated with NBS (559.2 mg, 3.142 mmol), then stirred for 16 h at room temperature. The reaction mixture was concentrated in vacuo. The residue was purified by silica chromatography (5-50% Hexanes-EtOAc as the gradient eluent) to afford the title compound (418.2 mg, 66% yield). MS (apci) m/z=203.0 (M+H). $^1$H NMR (400 MHz, DMSO-$d_6$) δ 7.86 (s, 1H), 4.07-4.01 (q, 2H), 2.52-2.47 (q, 2H), 1.34-1.30 (t, 3H), 1.16-1.12 (t, 3H).

Intermediate R22

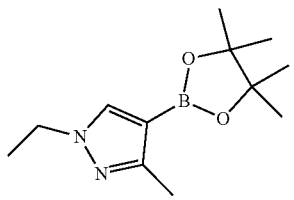 [SMILES: CCn1cc(B2OC(C)(C)C(C)(C)O2)c(C)n1]

1-ethyl-3-methyl-4-(4,4,5,5-tetramethyl-1,3,2-dioxaborolan-2-yl)-1H-pyrazole

A −78° C. solution of 4-bromo-1-ethyl-3-methyl-1H-pyrazole (404.4 mg, 2.139 mmol) in THF (21 mL) was treated dropwise with 2.5 M n-BuLi in hexanes (1198 μL, 2.995 mmol). The resulting mixture was stirred for 30 min at −78° C., then treated with 2-isopropoxy-4,4,5,5-tetramethyl-1,3,2-dioxaborolane (916.4 μL, 4.492 mmol). The reaction mixture was stirred for 30 min at room temperature, and then treated with saturated NH$_4$Cl. The biphasic mixture was extracted with EtOAc, and the combined organic extracts were washed with brine. The combined organic extracts were dried over anhydrous Na$_2$SO$_4$, filtered, and concentrated in vacuo. The residue was purified by silica chromatography (5-70% Hexanes-EtOAc as the gradient eluent) to afford the title compound (324.5 mg, 64% yield). $^1$H NMR (400 MHz, DMSO-d$_6$) δ 7.77 (s, 1H), 4.05-3.99 (q, 2H), 2.21 (s, 3H), 1.33-1.29 (t, 3H), 1.23 (s, 12H).

The compounds in Table EE were prepared according to the method described for Intermediate R22, replacing 4-bromo-1-ethyl-3-methyl-1H-pyrazole with the appropriate commercially available bromopyrazole (except where noted). Reactions were monitored by LCMS, and reaction times were adjusted accordingly. Products were purified as in Intermediate R22 utilizing the appropriate gradient eluent in chromatography to cleanly afford the title compounds.

TABLE EE

| Intermediate # | Structure | Chemical Name | Spectral data |
|---|---|---|---|
| R23 | 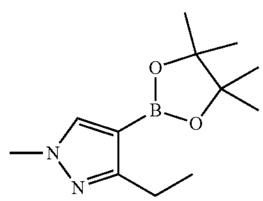 | 3-ethyl-1-methyl-4-(4,4,5,5-tetramethyl-1,3,2-dioxaborolan-2-yl)-1H-pyrazole | $^1$H NMR (400 MHz, CDCl$_3$) δ = 7.53 (s, 1 H), 3.80 (s, 3 H), 2.76 (q, 2 H), 1.28 (s, 12 H), 1.22 (t, 3 H) |
| R24 | 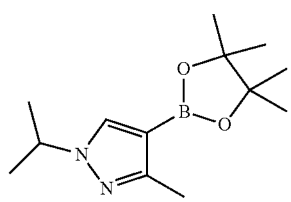 | 1-isopropyl-3-methyl-4-(4,4,5,5-tetramethyl-1,3,2-dioxaborolan-2-yl)-1H-pyrazole | MS (apci) m/z = 251.2 (M + H) |
| R25 | 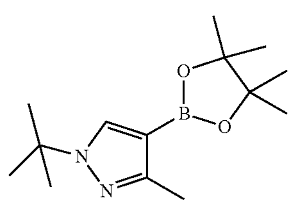 | 1-(tert-butyl)-3-methyl-4-(4,4,5,5-tetramethyl-1,3,2-dioxaborolan-2-yl)-1H-pyrazole | MS (apci) m/z = 265.2 (M + H) |
| R26* | 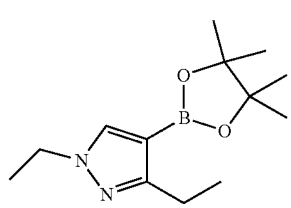 | 1,3-diethyl-4-(4,4,5,5-tetramethyl-1,3,2-dioxaborolan-2-yl)-1H-pyrazole | MS (apci) m/z = 251.2 (M + H) |

*prepared from Intermediate R21

Intermediate R27

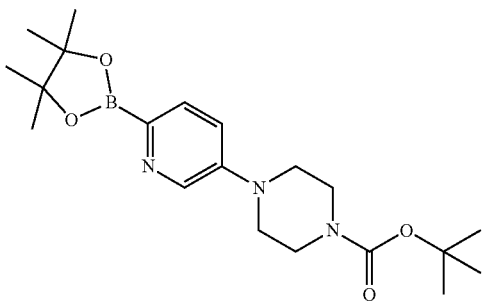 [SMILES: CC(C)(C)OC(=O)N1CCN(c2ccc(B3OC(C)(C)C(C)(C)O3)nc2)CC1]

Tert-Butyl 4-(6-(4,4,5,5-tetramethyl-1,3,2-dioxaborolan-2-yl)pyridin-3-yl)piperazine-1-carboxylate A room temperature solution of tert-butyl 4-(6-chloropyridin-3-yl)piperazine-1-carboxylate (100 mg, 0.336 mmol) in dioxane (4 mL) was treated with bis(pinacolato)diboron (93.8 mg, 0.369 mmol), Pd(OAc)$_2$ (9.05 mg, 0.0403 mmol), X-Phos (28.8 mg, 0.0604 mmol), and KOAc (98.9 mg, 1.01 mmol). The resulting mixture was sparged with Argon, sealed, and stirred overnight at 90° C. before cooling to room temperature. The reaction mixture was concentrated in vacuo and the crude product was used in the next step without purification, assuming quantitative yield. MS (apci) m/z=208 (M(B(OH)$_2$-BOC).

Preparation of Synthetic Examples

Example 1

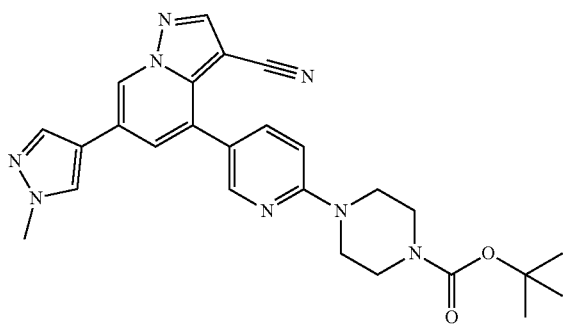

Tert-Butyl 4-(5-(3-cyano-6-(1-methyl-1H-pyrazol-4-yl)pyrazolo[1,5-a]pyridin-4-yl)pyridin-2-yl)piperazine-1-carboxylate To a mixture of 3-cyano-6-(1-methyl-1H-pyrazol-4-yl)pyrazolo[1,5-a]pyridin-4-yl trifluoromethanesulfonate (Intermediate P5; 10.0 g, 26.9 mmol) and tert-butyl 4-(5-(4,4,5,5-tetramethyl-1,3,2-dioxaborolan-2-yl)pyridin-2-yl)piperazine-1-carboxylate (12.6 g, 32.3 mmol) in dioxane (250 mL) was added 2 M Na$_2$CO$_{3(aq)}$ (14.3 g, 135 mmol), and the reaction mixture was sparged with nitrogen for 15 min before introducing Pd$_2$(dba)$_3$ (1.23 g, 1.35 mmol) and X-Phos (2.57 g, 5.39 mmol). The mixture was sparged with nitrogen for an additional 5 min and then heated at 80° C. overnight. After cooling to ambient temperature, the reaction mixture was poured into H$_2$O (1.5 L) and stirred for 2 h. The resulting suspension was filtered and rinsed sequentially with H$_2$O (3×200 mL), MTBE (4×100 mL) and hexanes (4×100 mL), yielding the title compound as a solid after drying in vacuo overnight (12 g, 92% yield). MS (apci) m/z=485.2 (M+H).

Example 2

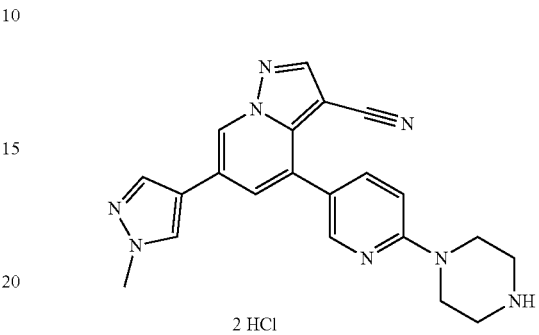

2 HCl 6-(1-methyl-1H-pyrazol-4-yl)-4-(6-(piperazin-1-yl)pyridin-3-yl)pyrazolo[1,5-a]pyridine-3-carbonitrile Dihydrochloride To a solution of tert-butyl 4-(5-(3-cyano-6-(1-methyl-1H-pyrazol-4-yl)pyrazolo[1,5-a]pyridin-4-yl)pyridin-2-yl)piperazine-1-carboxylate (Example 1, 12.0 g, 24.77 mmol) in MeOH (12 mL) and DCM (50 mL) was added HCl (5-6M in iPrOH, 49.53 mL, 247.7 mmol). After stirring at ambient temperature for 21 h the reaction was diluted with MeOH (50 mL) and DCM (50 mL). The suspension was stirred at ambient temperature until LCMS indicated the reaction was complete. The reaction mixture was filtered, rinsed with Et$_2$O (5×50 mL) and then dried for 19 h in a 45° C. vacuum oven to yield the title compound (9.97 g, 88% yield). MS (apci) m/z=385.1 (M+H).

Example 2a

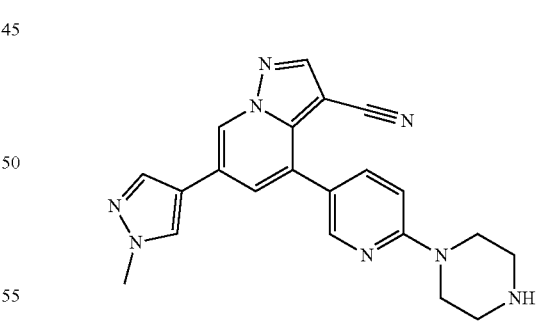

6-(1-methyl-1H-pyrazol-4-yl)-4-(6-(piperazin-1-yl)pyridin-3-yl)pyrazolo[1,5-a]pyridine-3-carbonitrile To a solution of tert-Butyl 4-(5-(3-cyano-6-(1-methyl-1H-pyrazol-4-yl)pyrazolo[1,5-a]pyridin-4-yl)pyridin-2-yl)piperazine-1-carboxylate (Example 1, 1.26 g, 2.60 mmol) in 20% MeOH/DCM (50 mL) was added 4 N HCl in dioxane (10 mL). The resulting mixture was stirred overnight and then treated with water and extracted with 20% MeOH/

DCM (3×50 mL). After phase-separation, the combined organic extracts and the aqueous layer were further treated independently. The aqueous layer was treated with saturated NaHCO$_{3(aq)}$, and the resulting suspension was vacuum filtered and rinsed with water and hexanes to provide the title compound (600 mg). The combined organic extracts from the reaction were washed with saturated NaHCO$_{3(aq)}$, then dried (Na$_2$SO$_4$), filtered and concentrated in vacuo to provide a second batch of the title compound (243 mg). The two batches of product were combined to provide the title compound (843 mg, 84% yield). MS (apci) m/z=385.1 (M+H).

Example 3

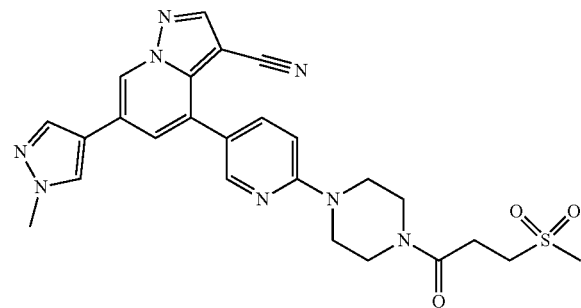 [SMILES: Cn1cc(-c2cc(-c3ccc(N4CCN(C(=O)CCS(C)(=O)=O)CC4)nc3)c3c(C#N)cnn3c2)cn1]

6-(1-methyl-1H-pyrazol-4-yl)-4-(6-(4-(3-(methylsulfonyl)propanoyl)piperazin-1-yl)pyridin-3-yl)pyrazolo[1,5-a]pyridine-3-carbonitrile 3-(Methylsulfonyl)propanoic acid (12 mg, 0.078 mmol) and HATU (30 mg, 0.078 mmol) were dissolved in DMA (325 μL) at ambient temperature. After 25 min, 6-(1-methyl-1H-pyrazol-4-yl)-4-(6-(piperazin-1-yl)pyridin-3-yl)pyrazolo[1,5-a]pyridine-3-carbonitrile (Example 2a, 25 mg, 0.065 mmol) was added in one portion followed by addition of DIEA (34 μL, 0.20 mmol). After stirring overnight at ambient temperature the resulting suspension was vacuum filtered and the solids were rinsed successively with ice-cold MeOH (1 mL) and Et$_2$O (3 mL) to provide the title compound (18 mg, 52% yield). MS (apci) m/z=519.0 (M+H).

Example 4

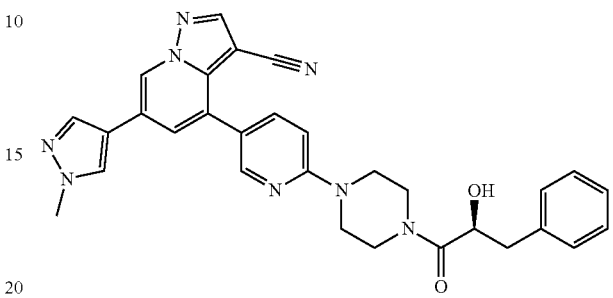

((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile (S)-2-Hydroxy-3-phenylpropanoic acid (8.18 mg, 0.0492 mmol) and HATU (18.7 mg, 0.0492 mmol) were dissolved in DMA (164 μL) at ambient temperature. After 25 min, 6-(1-methyl-1H-pyrazol-4-yl)-4-(6-(piperazin-1-yl)pyridin-3-yl)pyrazolo[1,5-a]pyridine-3-carbonitrile dihydrochloride (Example 2, 15 mg, 0.033 mmol) was added in one portion followed by DIEA (29 μL, 0.16 mmol). The reaction was stirred overnight at ambient temperature and then directly purified by reverse phase chromatography (5-50% ACN/water) to provide the title compound (16.8 mg, 94% yield). MS (apci) m/z=533.1 (M+H).

The compounds in the Table B were prepared in a similar fashion as described for the syntheses of Examples 3 and 4, replacing 3-(methylsulfonyl)propanoic acid or (S)-2-hydroxy-3-phenylpropanoic acid with the appropriate acid starting material.

TABLE B

| Ex # | Structure | Chemical Name | MS (apci) m/z |
|---|---|---|---|
| 5 | 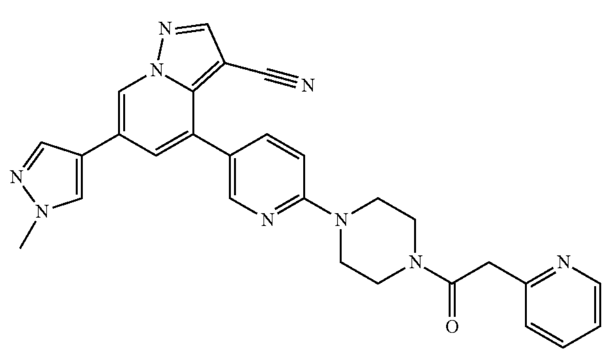 [SMILES: Cn1cc(-c2cc(-c3ccc(N4CCN(C(=O)Cc5ccccn5)CC4)nc3)c3c(C#N)cnn3c2)cn1] | 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile | 504.1 (M + H) |

TABLE B-continued

| Ex # | Structure | Chemical Name | MS (apci) m/z |
|---|---|---|---|
| 6 | 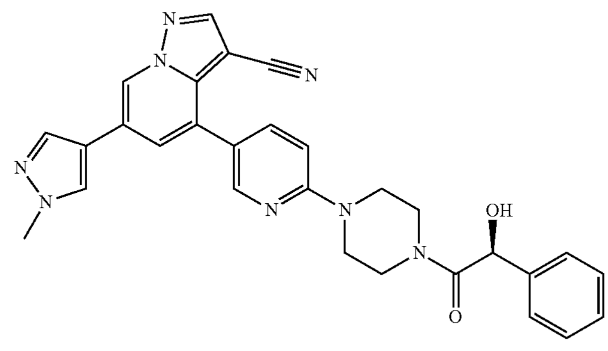 [SMILES: Cn1cc(-c2cc(-c3ccc(N4CCN(C(=O)[C@@H](O)c5ccccc5)CC4)nc3)c3c(C#N)cnn3c2)cn1] | (S)-4-(6-(4-(2-hydroxy-2-phenylacetyl)piperazin-1-yl)pyridin-3-yl)-6-(1-methyl-1H-pyrazol-4-yl)pyrazolo[1,5-a]pyridine-3-carbonitrile | 519.1 (M + H) |
| 7 | 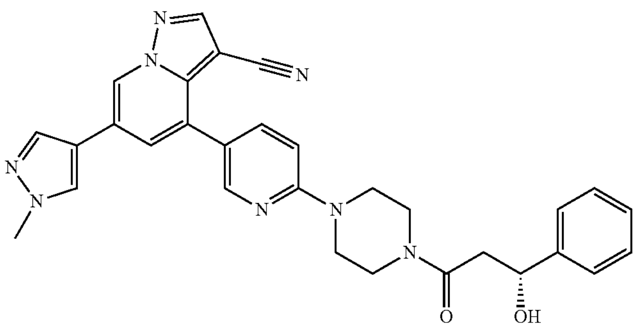 [SMILES: Cn1cc(-c2cc(-c3ccc(N4CCN(C(=O)C[C@@H](O)c5ccccc5)CC4)nc3)c3c(C#N)cnn3c2)cn1] | (R)-4-(6-(4-(3-hydroxy-3-phenylpropanoyl)piperazin-1-yl)pyridin-3-yl)-6-(1-methyl-1H-pyrazol-4-yl)pyrazolo[1,5-a]pyridine-3-carbonitrile | 533.1 (M + H) |
| 8 | 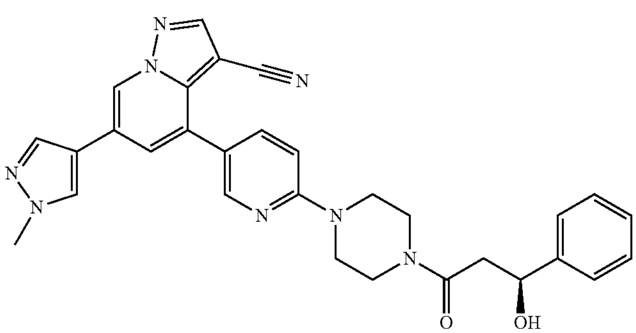 [SMILES: Cn1cc(-c2cc(-c3ccc(N4CCN(C(=O)C[C@H](O)c5ccccc5)CC4)nc3)c3c(C#N)cnn3c2)cn1] | (S)-4-(6-(4-(3-hydroxy-3-phenylpropanoyl)piperazin-1-yl)pyridin-3-yl)-6-(1-methyl-1H-pyrazol-4-yl)pyrazolo[1,5-a]pyridine-3-carbonitrile | 533.1 (M + H) |
| 9 | 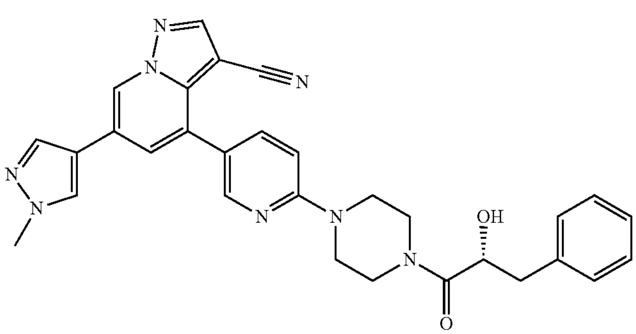 [SMILES: Cn1cc(-c2cc(-c3ccc(N4CCN(C(=O)[C@H](O)Cc5ccccc5)CC4)nc3)c3c(C#N)cnn3c2)cn1] | (R)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile | 533.1 (M + H) |

TABLE B-continued

| Ex # | Structure | Chemical Name | MS (apci) m/z |
|---|---|---|---|
| 10 | 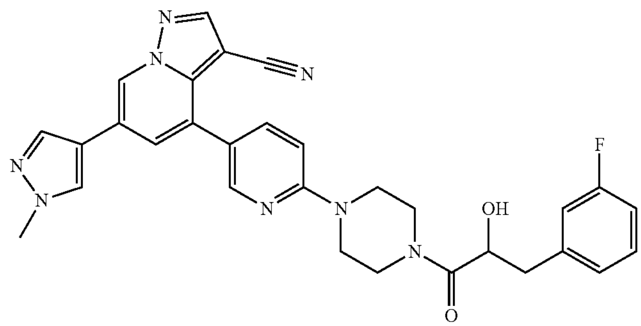 | 4-(6-(4-(2-(2-fluorophenyl)-2-hydroxyacetyl)piperazin-1-yl)pyridin-3-yl)-6-(1-methyl-1H-pyrazol-4-yl)pyrazolo[1,5-a]pyridine-3-carbonitrile | 537.2 (M + H) |
| 11 | 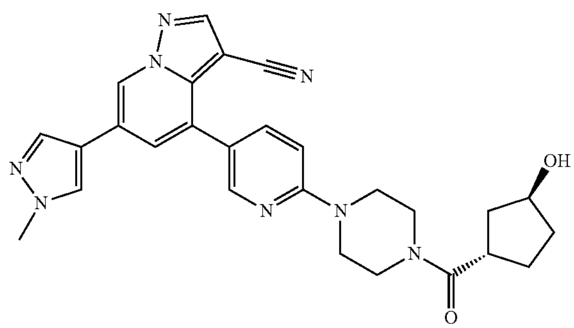 [SMILES: Cn1cc(-c2cc(-c3ccc(N4CCN(C(=O)[C@H]5CC[C@H](O)C5)CC4)nc3)c3c(C#N)cnn3c2)cn1] | 4-(6-(4-((1S,3S)-3-hydroxycyclopentane-1-carbonyl)piperazin-1-yl)pyridin-3-yl)-6-(1-methyl-1H-pyrazol-4-yl)pyrazolo[1,5-a]pyridine-3-carbonitrile | 497.1 (M + H) |
| 12 | 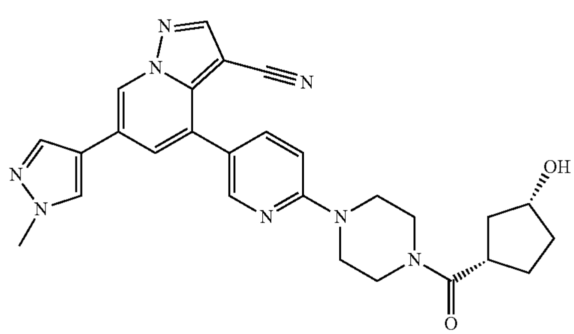 [SMILES: Cn1cc(-c2cc(-c3ccc(N4CCN(C(=O)[C@H]5CC[C@@H](O)C5)CC4)nc3)c3c(C#N)cnn3c2)cn1] | 4-(6-(4-((1S,3R)-3-hydroxycyclopentane-1-carbonyl)piperazin-1-yl)pyridin-3-yl)-6-(1-methyl-1H-pyrazol-4-yl)pyrazolo[1,5-a]pyridine-3-carbonitrile | 497.1 (M + H) |
| 13 | 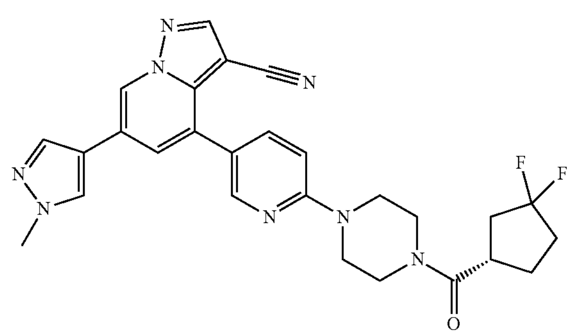 [SMILES: Cn1cc(-c2cc(-c3ccc(N4CCN(C(=O)[C@H]5CCC(F)(F)C5)CC4)nc3)c3c(C#N)cnn3c2)cn1] | (S)-4-(6-(4-(3,3-difluorocyclopentane-1-carbonyl)piperazin-1-yl)pyridin-3-yl)-6-(1-methyl-1H-pyrazol-4-yl)pyrazolo[1,5-a]pyridine-3-carbonitrile | 517.1 (M + H) |

TABLE B-continued

| Ex # | Structure | Chemical Name | MS (apci) m/z |
|---|---|---|---|
| 14 | 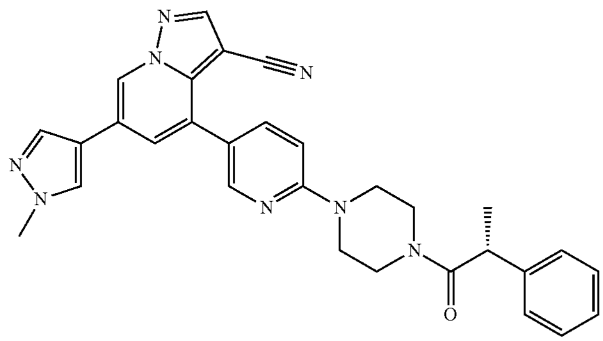 [SMILES: C[C@@H](C(=O)N1CCN(c2ccc(-c3cc(-c4cnn(C)c4)cn4ncc(C#N)c34)cn2)CC1)c1ccccc1] | (R)-6-(1-methyl-1H-pyrazol-4-yl)-4-(6-(4-(2-phenylpropanoyl)piperazin-1-yl)pyridin-3-yl)pyrazolo[1,5-a]pyridine-3-carbonitrile | 517.1 (M + H) |
| 15 | 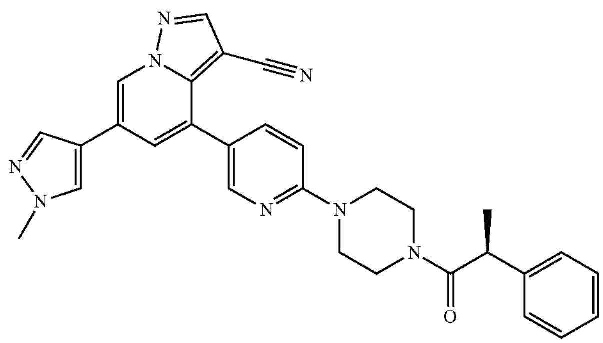 [SMILES: C[C@H](C(=O)N1CCN(c2ccc(-c3cc(-c4cnn(C)c4)cn4ncc(C#N)c34)cn2)CC1)c1ccccc1] | (S)-6-(1-methyl-1H-pyrazol-4-yl)-4-(6-(4-(2-phenylpropanoyl)piperazin-1-yl)pyridin-3-yl)pyrazolo[1,5-a]pyridine-3-carbonitrile | 517.2 (M + H) |
| 16 | 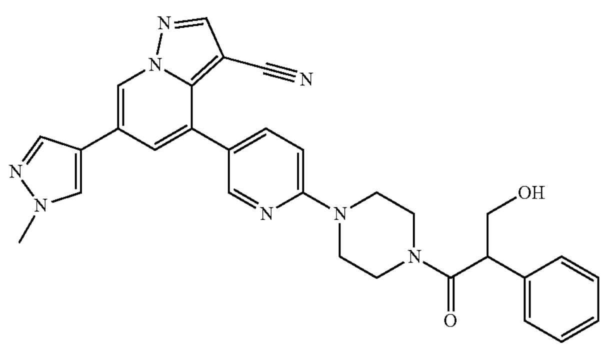 [SMILES: Cn1cc(-c2cc(-c3ccc(N4CCN(C(=O)C(CO)c5ccccc5)CC4)nc3)c3c(C#N)cnn3c2)cn1] | 4-(6-(4-(3-hydroxy-2-phenylpropanoyl)piperazin-1-yl)pyridin-3-yl)-6-(1-methyl-1H-pyrazol-4-yl)pyrazolo[1,5-a]pyridine-3-carbonitrile | 533.1 (M + H) |
| 17 | 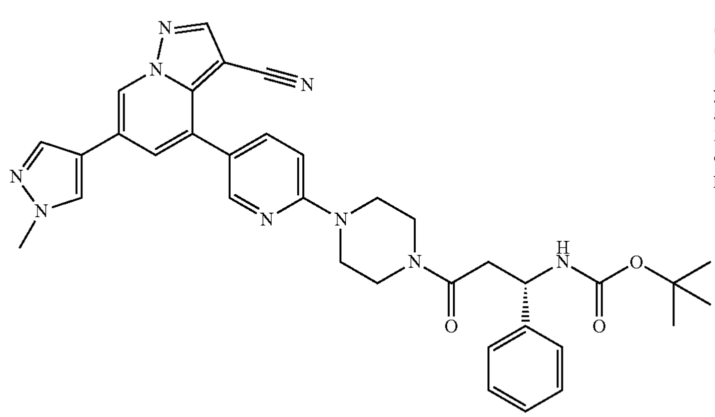 [SMILES: Cn1cc(-c2cc(-c3ccc(N4CCN(C(=O)C[C@H](NC(=O)OC(C)(C)C)c5ccccc5)CC4)nc3)c3c(C#N)cnn3c2)cn1] | (S)-tert-butyl (3-(4-(5-(3-cyano-6-(1-methyl-1H-pyrazol-4-yl)pyrazolo[1,5-a]pyridin-4-yl)pyridin-2-yl)piperazin-1-yl)-3-oxo-1-phenylpropyl)carbamate | 632.1 (M + H) |

TABLE B-continued

| Ex # | Structure | Chemical Name | MS (apci) m/z |
|---|---|---|---|
| 18 | 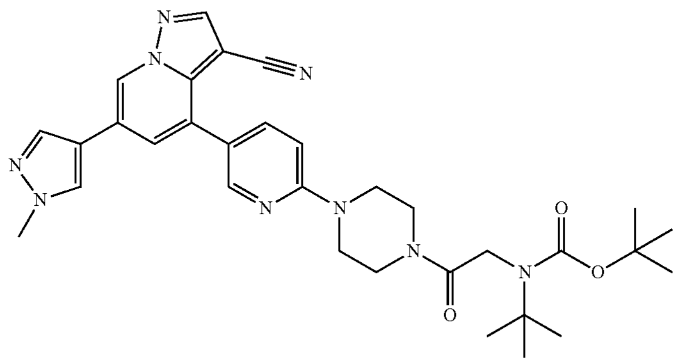 [SMILES: Cn1cc(-c2cc(-c3ccc(N4CCN(C(=O)CN(C(=O)OC(C)(C)C)C(C)(C)C)CC4)nc3)c3c(C#N)cnn3c2)cn1] | tert-butyl tert-butyl(2-(4-(5-(3-cyano-6-(1-methyl-1H-pyrazol-4-yl)pyrazolo[1,5-a]pyridin-4-yl)pyridin-2-yl)piperazin-1-yl)-2-oxoethyl)carbamate | 598.2 (M + H) |
| 19 | 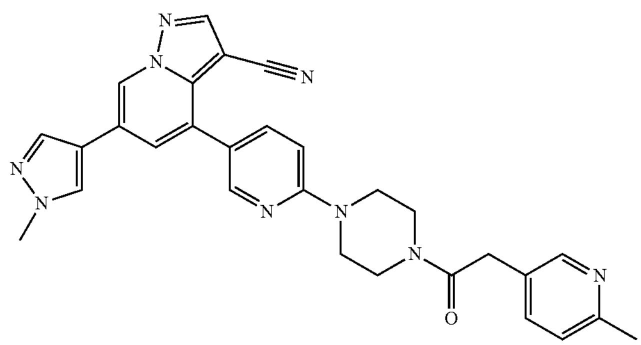 [SMILES: Cc1ccc(CC(=O)N2CCN(c3ccc(-c4cc(-c5cnn(C)c5)cn5ncc(C#N)c45)cn3)CC2)cn1] | 6-(1-methyl-1H-pyrazol-4-yl)-4-(6-(4-(2-(6-methypyridin-3-yl)acetyl)piperazin-1-yl)pyridin-3-yl)pyrazolo[1,5-a]pyridine-3-carbonitrile | 518.1 (M + H) |
| 20 | 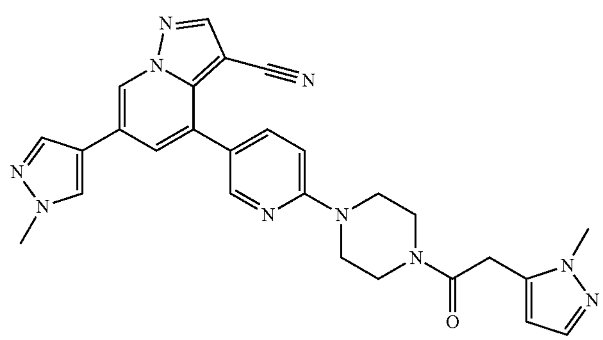 [SMILES: Cn1cc(-c2cc(-c3ccc(N4CCN(C(=O)Cc5ccnn5C)CC4)nc3)c3c(C#N)cnn3c2)cn1] | 6-(1-methyl-1H-pyrazol-4-yl)-4-(6-(4-(2-(1-methyl-1H-pyrazol-5-yl)acetyl)piperazin-1-yl)pyridin-3-yl)pyrazolo[1,5-a]pyridine-3-carbonitrile | 507.1 (M + H) |
| 21 | 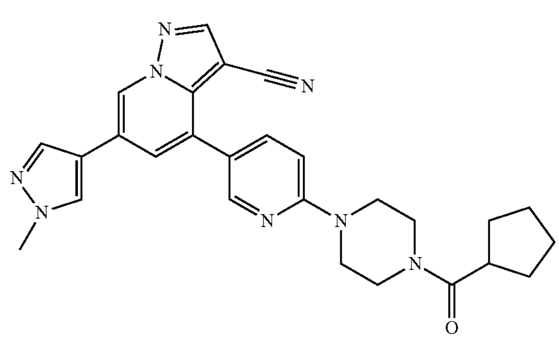 [SMILES: Cn1cc(-c2cc(-c3ccc(N4CCN(C(=O)C5CCCC5)CC4)nc3)c3c(C#N)cnn3c2)cn1] | 4-(6-(4-(cyclopentanecarbonyl)piperazin-1-yl)pyridin-3-yl)-6-(1-methyl-1H-pyrazol-4-yl)pyrazolo[1,5-a]pyridine-3-carbonitrile | 481.2 (M + H) |

Example 22

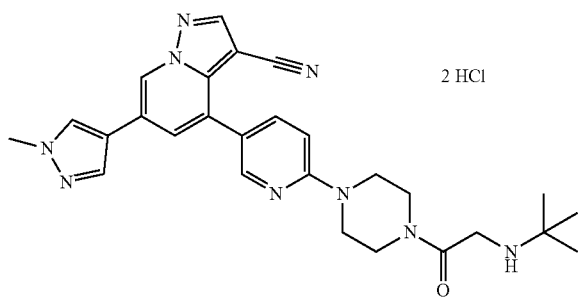 [SMILES: Cn1cc(-c2cc(-c3ccc(N4CCN(C(=O)CNC(C)(C)C)CC4)nc3)c3c(C#N)cnn3c2)cn1]

4-(6-(4-(2-(tert-butylamino)acetyl)piperazin-1-yl)pyridin-3-yl)-6-(1-methyl-1H-pyrazol-4-yl)pyrazolo[1,5-a]pyridine-3-carbonitrile Dihydrochloride To a solution of tert-butyl(2-(4-(5-(3-cyano-6-(1-methyl-1H-pyrazol-4-yl)pyrazolo[1,5-a]pyridin-4-yl)pyridin-2-yl)piperazin-1-yl)-2-oxoethyl)carbamate (Example 18, 10 mg, 0.017 mmol) in DCM (0.1 mL) was added 5 M HCl in iPrOH (167 µL, 0.84 mmol) and the reaction mixture was stirred at ambient temperature for 1 h. The reaction mixture was then concentrated in vacuo to afford the title compound (9 mg, 93% yield). MS (apci) m/z=498.2 (M+H).

Example 23

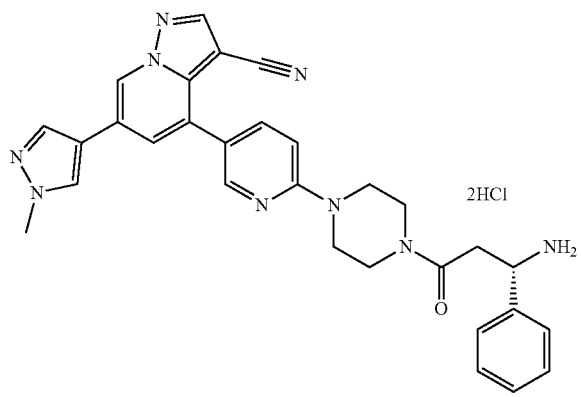 [SMILES: Cn1cc(-c2cc(-c3ccc(N4CCN(C(=O)C[C@H](N)c5ccccc5)CC4)nc3)c3c(C#N)cnn3c2)cn1]

(S)-4-(6-(4-(3-amino-3-phenylpropanoyl)piperazin-1-yl)pyridin-3-yl)-6-(1-methyl-1H-pyrazol-4-yl)pyrazolo[1,5-a]pyridine-3-carbonitrile Dihydrochloride To a solution of (S)-tert-butyl (3-(4-(5-(3-cyano-6-(1-methyl-1H-pyrazol-4-yl)pyrazolo[1,5-a]pyridin-4-yl)pyridin-2-yl)piperazin-1-yl)-3-oxo-1-phenylpropyl)carbamate (Example 17, 18 mg, 0.028 mmol) in DCM (0.1 mL) was added 5 M HCl in iPrOH (285 µL, 1.4 mmol) and the reaction mixture was stirred at ambient temperature for 1 h. The reaction mixture was then concentrated in vacuo to afford the title compound (17 mg, 98% yield). MS (apci) m/z=532.2 (M+H).

Example 24

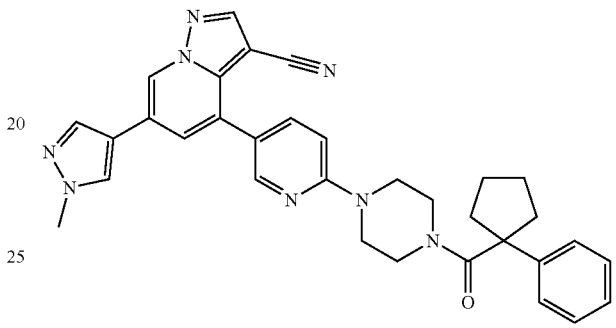

6-(1-methyl-1H-pyrazol-4-yl)-4-(6-(4-(1-phenylcyclopentanecarbonyl)piperazin-1-yl)pyridin-3-yl)pyrazolo[1,5-a]pyridine-3-carbonitrile 1-Phenylcyclopentanecarboxylic acid (12.5 mg, 0.0656 mmol) and HATU (24.9 mg, 0.0656 mmol) were dissolved in DMA (273 µL) at ambient temperature and the reaction mixture was stirred for 25 min, followed by addition of 6-(1-methyl-1H-pyrazol-4-yl)-4-(6-(piperazin-1-yl)pyridin-3-yl)pyrazolo[1,5-a]pyridine-3-carbonitrile dihydrochloride (25 mg, 0.0547 mmol) and DIEA (47.6 µL, 0.273 mmol), each in one portion. After overnight stirring the resulting suspension was diluted with EtOAc (0.5 mL) and vacuum filtered and rinsed successively with EtOAc (3×0.5 mL) and Et₂O (1 mL) to provide the title compound as a white solid (21 mg, 68% yield). MS (apci) m/z=557.2 (M+H).

The compounds in Table C were prepared according the method used for the synthesis of Example 24, replacing 1-phenylcyclopentanecarboxylic acid with the appropriate acid starting material.

TABLE C

| Ex # | Structure | Chemical Name | MS (apci) m/z |
|---|---|---|---|
| 25 | 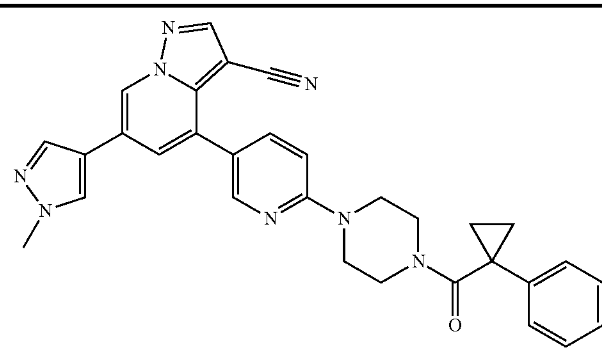 | 6-(1-methyl-1H-pyrazol-4-yl)-4-(6-(4-(1-phenylcyclopropane-1-carbonyl)piperazin-1-yl)pyridin-3-yl)pyrazolo[1,5-a]pyridine-3-carbonitrile | 529.1 (M + H) |

TABLE C-continued

| Ex # | Structure | Chemical Name | MS (apci) m/z |
|---|---|---|---|
| 26 | 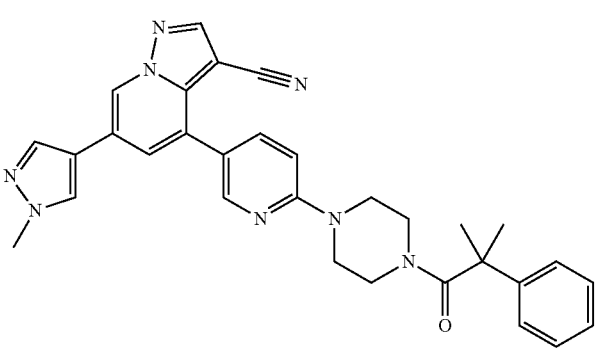 [SMILES: Cn1cc(-c2cc(-c3ccc(N4CCN(C(=O)C(C)(C)c5ccccc5)CC4)nc3)c3c(C#N)cnn3c2)cn1] | 6-(1-methyl-1H-pyrazol-4-yl)-4-(6-(4-(2-methyl-2-phenylpropanoyl)piperazin-1-yl)pyridin-3-yl)pyrazolo[1,5-a]pyridine-3-carbonitrile | 531.2 (M + H) |
| 27 | 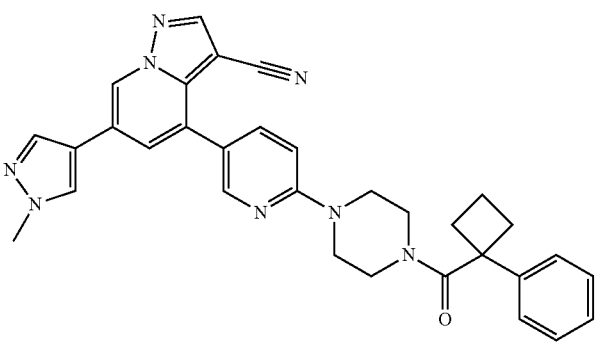 [SMILES: Cn1cc(-c2cc(-c3ccc(N4CCN(C(=O)C5(c6ccccc6)CCC5)CC4)nc3)c3c(C#N)cnn3c2)cn1] | 6-(1-methyl-1H-pyrazol-4-yl)-4-(6-(4-(1-phenylcyclobutane-1-carbonyl)piperazin-1-yl)pyridin-3-yl)pyrazolo[1,5-a]pyridine-3-carbonitrile | 543.2 (M + H) |
| 28 | 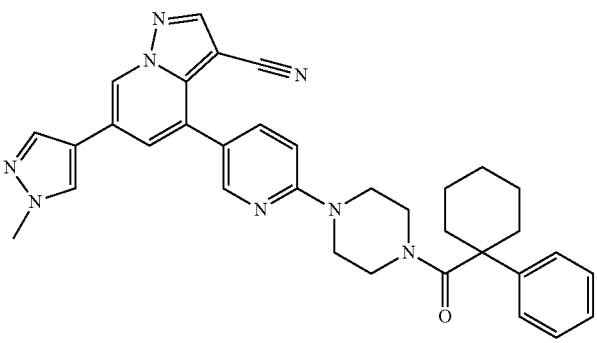 [SMILES: Cn1cc(-c2cc(-c3ccc(N4CCN(C(=O)C5(c6ccccc6)CCCCC5)CC4)nc3)c3c(C#N)cnn3c2)cn1] | 6-(1-methyl-1H-pyrazol-4-yl)-4-(6-(4-(1-phenylcyclohexane-1-carbonyl)piperazin-1-yl)pyridin-3-yl)pyrazolo[1,5-a]pyridine-3-carbonitrile | 571.2 (M + H) |
| 29 | 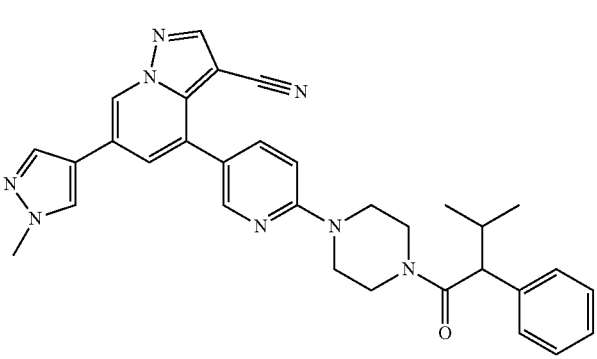 [SMILES: CC(C)C(C(=O)N1CCN(c2ccc(-c3cc(-c4cnn(C)c4)cn4ncc(C#N)c34)cn2)CC1)c1ccccc1] | 6-(1-methyl-1H-pyrazol-4-yl)-4-(6-(4-(3-methyl-2-phenylbutanoyl)piperazin-1-yl)pyridin-3-yl)pyrazolo[1,5-a]pyridine-3-carbonitrile | 545.2 (M + H) |

Example 30

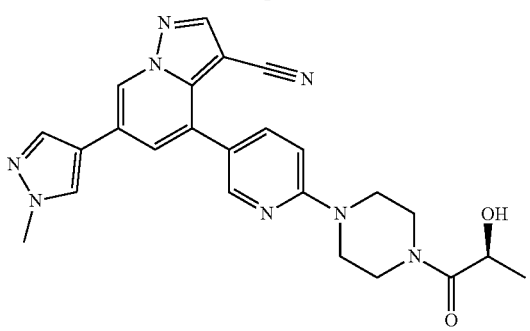 [SMILES: C[C@H](O)C(=O)N1CCN(c2ccc(-c3cc(-c4cnn(C)c4)cn4ncc(C#N)c34)cn2)CC1]

(S)-4-(6-(4-(2-hydroxypropanoyl)piperazin-1-yl)
pyridin-3-yl)-6-(1-methyl-1H-pyrazol-4-yl)pyrazolo
[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile (0.030 g, 0.0780 mmol) and L-(+)-Lactic acid (0.00729 mL, 0.0975 mmol) in DMF (2.60 mL) was added HATU (0.0386 g, 0.101 mmol). The reaction mixture was stirred for 24 h at ambient temperature and then quenched with water (10 mL). The reaction mixture was then extracted with EtOAc (3×15 mL) and the combined organic layers were dried over anhydrous Na$_2$SO$_4$, filtered and concentrated in vacuo. The crude residue was purified by silica chromatography (0-7% of a 5% NH$_4$OH in MeOH/DCM) to provide the title compound (0.010 g, 28% yield). MS (apci) m/z=457.2 (M+H).

The compounds in Table D were prepared and purified according the method used for the synthesis of Example 30, replacing L-(+)-Lactic acid with the appropriate acid starting material.

TABLE D

| Ex # | Structure | Chemical Name | MS (apci) m/z |
|---|---|---|---|
| 31 | 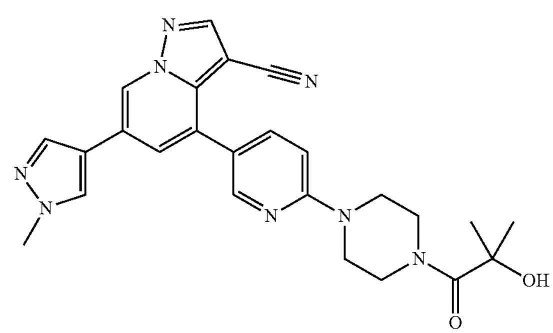 [SMILES: Cn1cc(-c2cc(-c3ccc(N4CCN(C(=O)C(C)(C)O)CC4)nc3)c3c(C#N)cnn3c2)cn1] | 4-(6-(4-(2-hydroxy-2-methylpropanoyl)piperazin-1-yl)pyridin-3-yl)-6-(1-methyl-1H-pyrazol-4-yl)pyrazolo[1,5-a]pyridine-3-carbonitrile | 471.2 (M + H) |
| 32 | 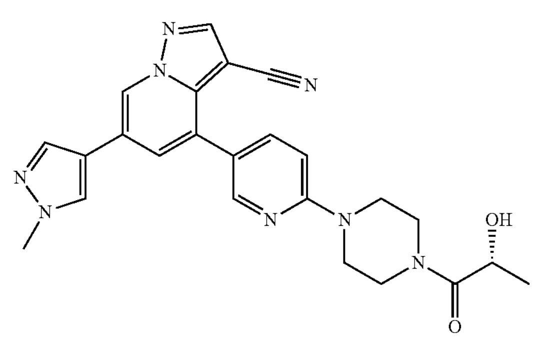 [SMILES: C[C@@H](O)C(=O)N1CCN(c2ccc(-c3cc(-c4cnn(C)c4)cn4ncc(C#N)c34)cn2)CC1] | (R)-4-(6-(4-(2-hydroxypropanoyl)piperazin-1-yl)pyridin-3-yl)-6-(1-methyl-1H-pyrazol-4-yl)pyrazolo[1,5-a]pyridine-3-carbonitrile | 457.2 (M + H) |

Example 33

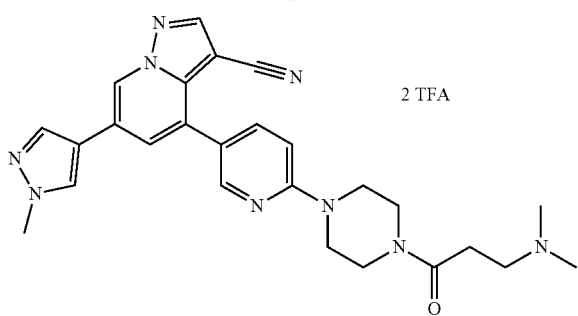 [SMILES: CN(C)CCC(=O)N1CCN(c2ccc(-c3cc(-c4cnn(C)c4)cn4ncc(C#N)c34)cn2)CC1]

4-(6-(4-(3-(dimethylamino)propanoyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate)

To a mixture of 6-(1-methyl-1H-pyrazol-4-yl)-4-(6-(piperazin-1-yl)pyridin-3-yl)pyrazolo[1,5-a]pyridine-3-carbonitrile dihydrochloride (30 mg 0.066 mmol) in DCM (1 mL) at ambient temperature was sequentially added N-methylmorpholine (14 μL, 0.13 mmol), 3-(dimethylamino)propanoic acid (9.2 mg, 0.079 mmol), and HATU (25 mg, 0.066 mmol). The reaction mixture was stirred at ambient temperature for 12 h, and then concentrated and purified by reverse-phase preparative HPLC (10 to 80% acetonitrile/water with 0.1 v/v % TFA) to yield the title compound (17 mg, 36% yield). MS (apci) m/z=484.2 (M+H).

The compounds in Table E were prepared according the method described for the synthesis of Example 33, replacing 3-(dimethylamino)propanoic acid with the appropriate acid starting material, and utilizing reverse-phase preparative HPLC (10 to 80% acetonitrile/water with 0.1 v/v % TFA or 0.04 v/v % NH$_4$OH) to yield purified title compounds as TFA salts unless otherwise stated.

TABLE E

| Ex # | Structure | Chemical Name | MS (apci) m/z |
|---|---|---|---|
| 34 | 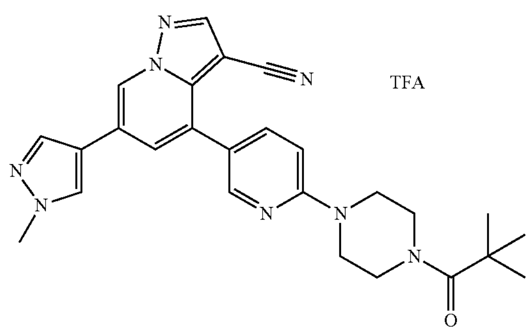 [SMILES: Cn1cc(-c2cc(-c3ccc(N4CCN(C(=O)C(C)(C)C)CC4)nc3)c3c(C#N)cnn3c2)cn1] | 6-(1-methyl-1H-pyrazol-4-yl)-4-(6-(4-pivaloylpiperazin-1-yl)pyridin-3-yl)pyrazolo[1,5-a]pyridine-3-carbonitrile 2,2,2-trifluoroacetate | 469.2 (M + H) |
| 35 | 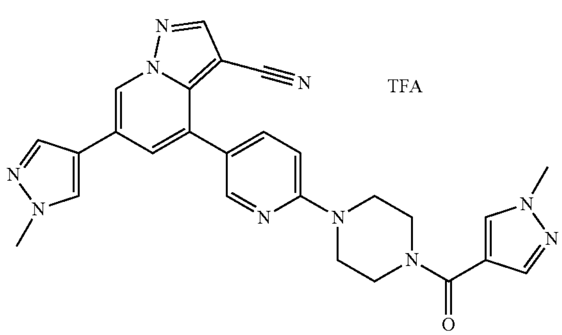 [SMILES: Cn1cc(C(=O)N2CCN(c3ccc(-c4cc(-c5cnn(C)c5)cn5ncc(C#N)c45)cn3)CC2)cn1] | 6-(1-methyl-1H-pyrazol-4-yl)-4-(6-(4-(1-methyl-1H-pyrazole-4-carbonyl)piperazin-1-yl)pyridin-3-yl)pyrazolo[1,5-a]pyridine-3-carbonitrile 2,2,2-trifluoroacetate | 493.1 (M + H) |

TABLE E-continued

| Ex # | Structure | Chemical Name | MS (apci) m/z |
|---|---|---|---|
| 36 | 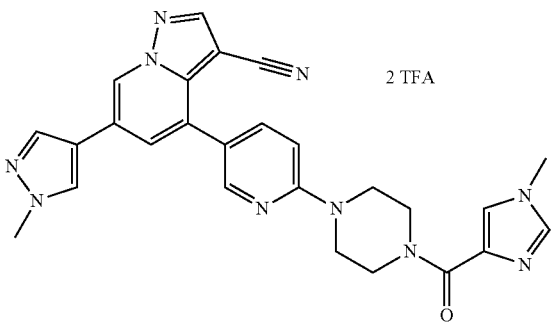 [SMILES: Cn1cnc(C(=O)N2CCN(c3ccc(-c4cc(-c5cnn(C)c5)cn5ncc(C#N)c45)cn3)CC2)c1] 2 TFA | 4-(6-(4-(1-methyl-1H-imidazole-4-carbonyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate) | 493.2 (M + H) |
| 37 | 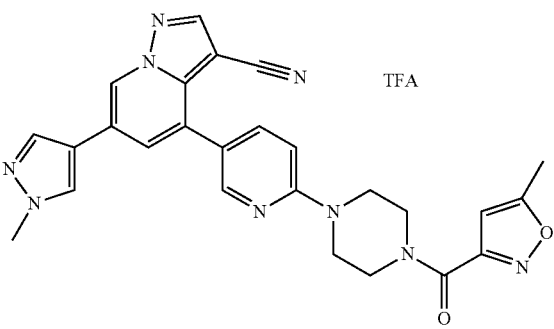 [SMILES: Cc1cc(C(=O)N2CCN(c3ccc(-c4cc(-c5cnn(C)c5)cn5ncc(C#N)c45)cn3)CC2)no1] TFA | 6-(1-methyl-1H-pyrazol-4-yl)-4-(6-(4-(5-methylisoxazole-3-carbonyl)piperazin-1-yl)pyridin-3-yl)pyrazolo[1,5-a]pyridine-3-carbonitrile 2,2,2-trifluoroacetate | 494.2 (M + H) |
| 38 | 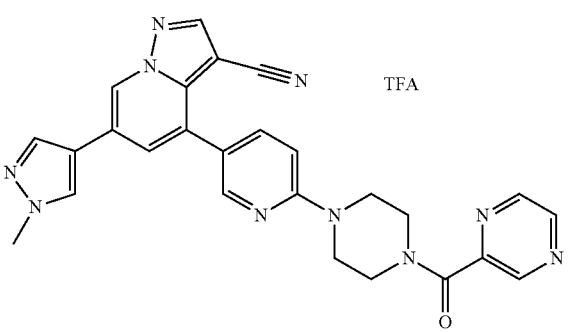 [SMILES: Cn1cc(-c2cc(-c3ccc(N4CCN(C(=O)c5cnccn5)CC4)nc3)c3c(C#N)cnn3c2)cn1] TFA | 6-(1-methyl-1H-pyrazol-4-yl)-4-(6-(4-(pyrazine-2-carbonyl)piperazin-1-yl)pyridin-3-yl)pyrazolo[1,5-a]pyridine-3-carbonitrile 2,2,2-trifluoroacetate | 491.2 (M + H) |
| 39 | 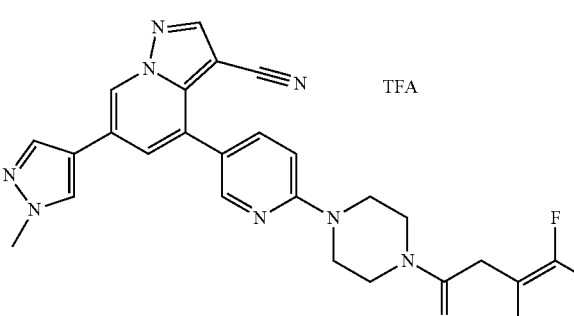 TFA | 4-(6-(4-(2-(2,6-difluorophenyl)acetyl)piperazin-1-yl)pyridin-3-yl)-6-(1-methyl-1H-pyrazol-4-yl)pyrazolo[1,5-a]pyridine-3-carbonitrile 2,2,2-trifluoroacetate | 539.2 (M + H) |

TABLE E-continued

| Ex # | Structure | Chemical Name | MS (apci) m/z |
|---|---|---|---|
| 40 | 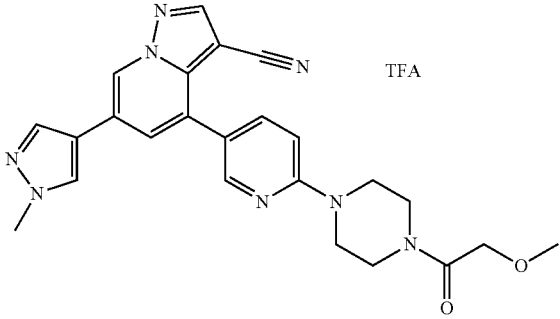 TFA | 4-(6-(4-(2-methoxyacetyl)piperazin-1-yl)pyridin-3-yl)-6-(1-methyl-1H-pyrazol-4-yl)pyrazolo[1,5-a]pyridine-3-carbonitrile 2,2,2-trifluoroacetate | 457.2 (M + H) |
| 41 | 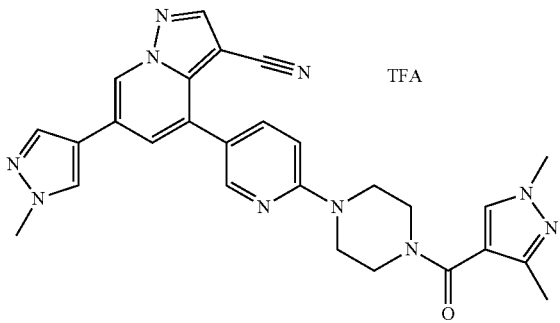 TFA | 4-(6-(4-(1,3-dimethyl-1H-pyrazole-4-carbonyl)piperazin-1-yl)pyridin-3-yl)-6-(1-methyl-1H-pyrazol-4-yl)pyrazolo[1,5-a]pyridine-3-carbonitrile 2,2,2-trifluoroacetate | 507.2 (M + H) |
| 42 | 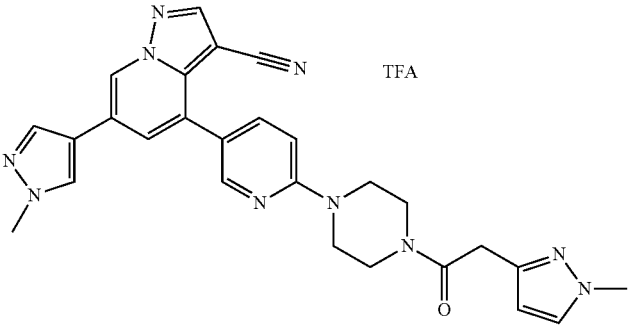 TFA | 4-(6-(4-(2-(1-methyl-1H-pyrazol-3-yl)acetyl)piperazin-1-yl)pyridin-3-yl)-6-(1-methyl-1H-pyrazol-4-yl)pyrazolo[1,5-a]pyridine-3-carbonitrile 2,2,2-trifluoroacetate | 507.2 (M + H) |
| 43 | 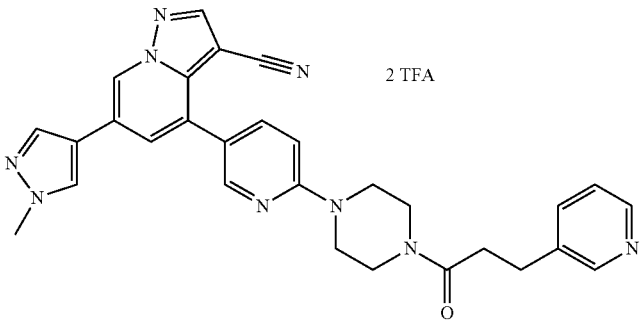 2 TFA | 6-(1-methyl-1H-pyrazol-4-yl)-4-(6-(4-(3-(pyridin-3-yl)propanoyl)piperazin-1-yl)pyridin-3-yl)pyraozlo[1,5-a]pyridine-3-carbontirile bis(2,2,2-trifluoroacetate) | 518.2 (M + H) |

TABLE E-continued

| Ex # | Structure | Chemical Name | MS (apci) m/z |
|---|---|---|---|
| 44 | 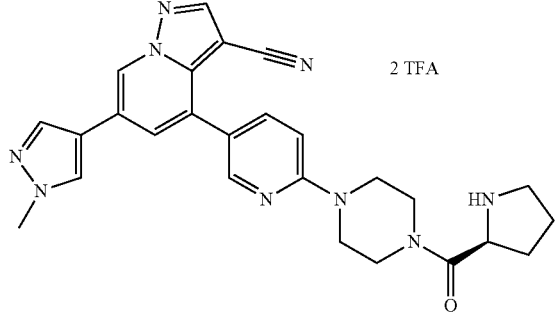 [SMILES: Cn1cc(-c2cc(-c3ccc(N4CCN(C(=O)[C@@H]5CCCN5)CC4)nc3)c3c(C#N)cnn3c2)cn1] 2 TFA | (S)-6-(1-methyl-1H-pyrazol-4-yl)-4-(6-(4-prolylpiperazin-1-yl)pyridin-3-yl)pyrazolo[1,5-a]pyridine-3-carbonitrile bis(2,2,2-trifluoroacetate) | 482.1 (M + H) |
| 45 | 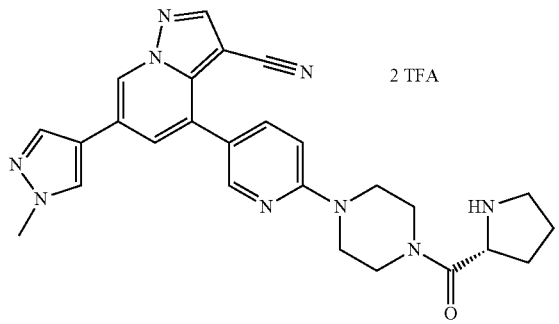 [SMILES: Cn1cc(-c2cc(-c3ccc(N4CCN(C(=O)[C@H]5CCCN5)CC4)nc3)c3c(C#N)cnn3c2)cn1] 2 TFA | (R)-6-(1-methyl-1H-pyrazol-4-yl)-4-(6-(4-prolylpiperazin-1-yl)pyridin-3-yl)pyrazolo[1,5-a]pyridine-3-carbonitrile bis(2,2,2-trifluoroacetate) | 482.2 (M + H) |
| 46 | 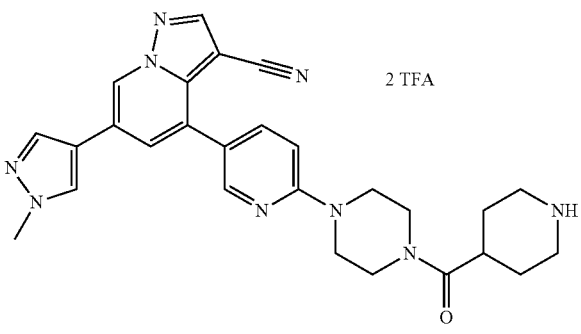 [SMILES: Cn1cc(-c2cc(-c3ccc(N4CCN(C(=O)C5CCNCC5)CC4)nc3)c3c(C#N)cnn3c2)cn1] 2 TFA | 6-(1-methyl-1H-pyrazol-4-yl)-4-(6-(4-(piperidine-4-carbonyl)piperazin-1-yl)pyridin-3-yl)pyrazolo[1,5-a]pyridine-3-carbonitrile bis(2,2,2-trifluoroacetate) | 496.2 (M + H) |
| 47 | 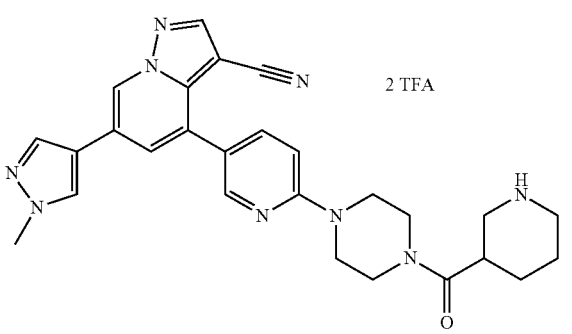 [SMILES: Cn1cc(-c2cc(-c3ccc(N4CCN(C(=O)C5CCCNC5)CC4)nc3)c3c(C#N)cnn3c2)cn1] 2 TFA | 6-(1-methyl-1H-pyrazol-4-yl)-4-(6-(4-(piperidine-3-carbonyl)piperazin-1-yl)pyridin-3-yl)pyrazolo[1,5-a]pyridine-3-carbonitrile bis(2,2,2-trifluoroacetate | 496.2 (M + H) |

TABLE E-continued

| Ex # | Structure | Chemical Name | MS (apci) m/z |
|---|---|---|---|
| 48 | 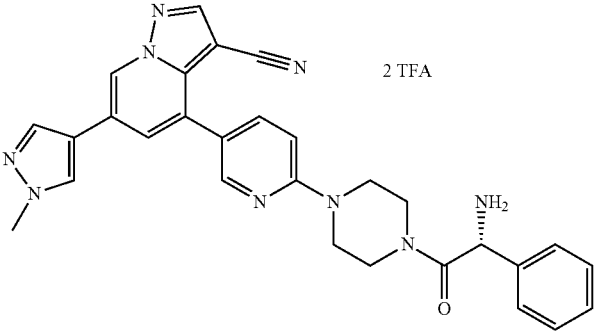 [SMILES: Cn1cc(-c2cc(-c3ccc(N4CCN(C(=O)[C@H](N)c5ccccc5)CC4)nc3)c3c(C#N)cnn3c2)cn1] 2 TFA | (R)-4-(6-(4-(2-amino-2-phenylacetyl)piperazin-1-yl)pyridin-3-yl)-6-(1-methyl-1H-pyrazol-4-yl)pyrazolo[1,5-a]pyridine-3-carbontirile bis(2,2,2-trifluoroacetate) | 518.2 (M + H) |
| 49 | 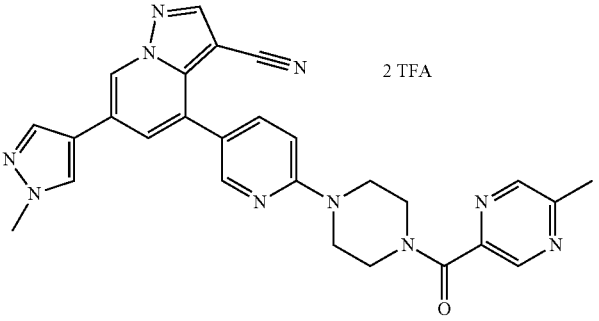 [SMILES: Cc1cnc(C(=O)N2CCN(c3ccc(-c4cc(-c5cnn(C)c5)cn5ncc(C#N)c45)cn3)CC2)cn1] 2 TFA | 6-(1-methyl-1H-pyrazol-4-yl)-4-(6-(4-(5-methylpyrazine-2-carbonyl)piperazin-1-yl)pyridin-3-yl)pyrazolo[1,5-a]pyridine-3-carbonitrile bis(2,2,2-trifluoroacetate) | 505.1 (M + H) |
| 50 | 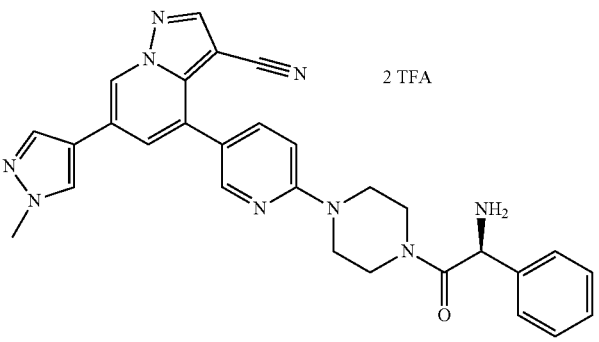 [SMILES: Cn1cc(-c2cc(-c3ccc(N4CCN(C(=O)[C@@H](N)c5ccccc5)CC4)nc3)c3c(C#N)cnn3c2)cn1] 2 TFA | (S)-4-(6-(4-(2-amino-2-phenylacetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate) | 518.2 (M + H) |
| 51 | 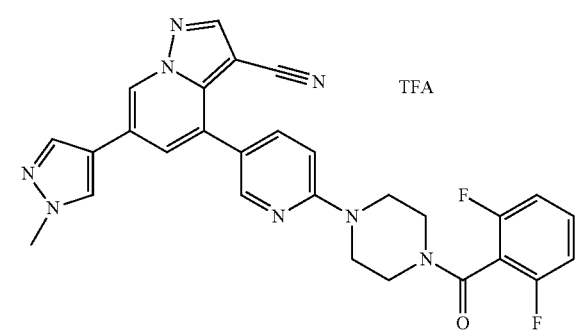 [SMILES: Cn1cc(-c2cc(-c3ccc(N4CCN(C(=O)c5c(F)cccc5F)CC4)nc3)c3c(C#N)cnn3c2)cn1] TFA | 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate | 525.1 (M + H) |

TABLE E-continued

| Ex # | Structure | Chemical Name | MS (apci) m/z |
|---|---|---|---|
| 52 | 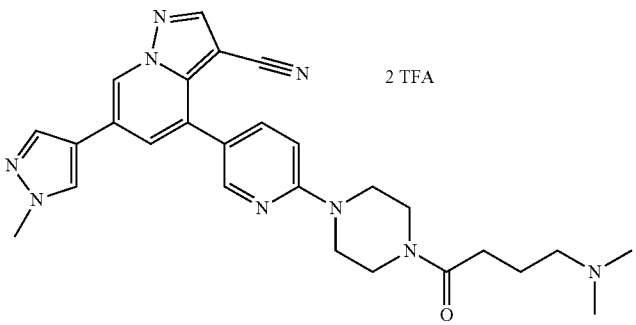 [SMILES: CN(C)CCCC(=O)N1CCN(c2ccc(-c3cc(-c4cnn(C)c4)cn4ncc(C#N)c34)cn2)CC1] | 4-(6-(4-(4-(dimethylamino)butanoyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate) | 498.2 (M + H) |

Example 53

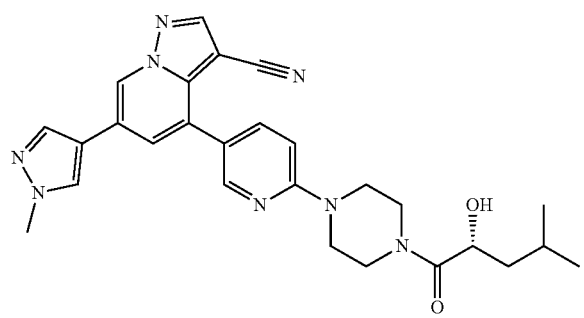 [SMILES: CC(C)C[C@@H](O)C(=O)N1CCN(c2ccc(-c3cc(-c4cnn(C)c4)cn4ncc(C#N)c34)cn2)CC1]

(R)-4-(6-(4-(2-hydroxy-4-methylpentanoyl)piperazin-1-yl)pyridin-3-yl)-6-(1-methyl-1H-pyrazol-4-yl)pyrazolo[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile (25 mg, 0.065 mmol) in DMF (2.17 mL) was added DIEA (0.0114 mL, 0.065 mmol), (R)-2-hydroxy-4-methylpentanoic acid (8.6 mg, 0.065 mmol), and HBTU (27.1 mg, 0.0715 mmol). The reaction mixture was heated to 40° C., stirred overnight, and then quenched with water. The reaction mixture was extracted with EtOAc (3×10 mL) and the combined organic layers were dried over anhydrous $Na_2SO_4$, filtered and concentrated in vacuo. The crude residue was purified by silica chromatography (0-50% of a 20% MeOH/DCM in EtOAc) to provide the title compound (0.0128 g, 40% yield). MS (apci) m/z=499.3 (M+H).

The compounds in Table F were prepared and purified according the method used for the synthesis of Example 53, replacing (R)-2-hydroxy-4-methylpentanoic acid with the appropriate acid starting material.

TABLE F

| Ex # | Structure | Chemical Name | MS (apci) m/z |
|---|---|---|---|
| 54 | 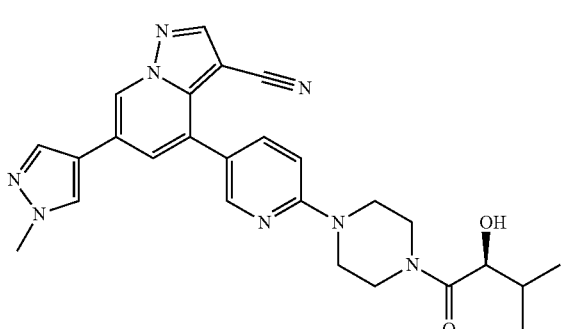 | (S)-4-(6-(4-(2-hydroxy-3-methylbutanoyl)piperazin-1-yl)pyridin-3-yl)-6-(1-methyl-1H-pyrazol-4-yl)pyrazolo[1,5-a]pyridine-3-carbonitrile | 485.2 (M + H) |

TABLE F-continued

| Ex # | Structure | Chemical Name | MS (apci) m/z |
|---|---|---|---|
| 55 | 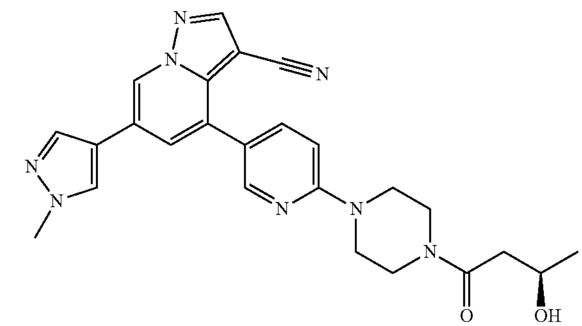 [SMILES: C[C@@H](O)CC(=O)N1CCN(c2ccc(-c3cc(-c4cnn(C)c4)cn4ncc(C#N)c34)cn2)CC1] | (R)-4-(6-(4-(3-hydroxybutanoyl)piperazin-1-yl)pyridin-3-yl)-6-(1-methyl-1H-pyrazol-4-yl)pyrazolo[1,5-a]pyridine-3-carbonitrile | 471.2 (M + H) |
| 56 | 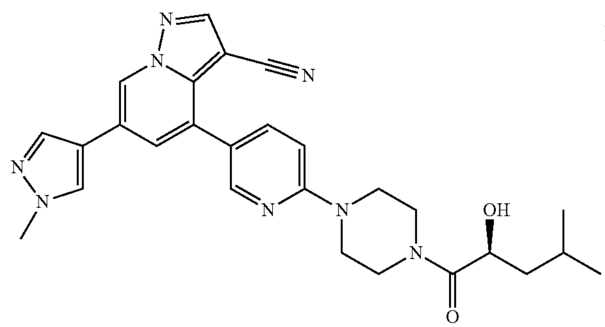 [SMILES: CC(C)C[C@H](O)C(=O)N1CCN(c2ccc(-c3cc(-c4cnn(C)c4)cn4ncc(C#N)c34)cn2)CC1] | (S)-4-(6-(4-(2-hydroxy-4-methylpentanoyl)piperazin-1-yl)pyridin-3-yl)-6-(1-methyl-1H-pyrazol-4-yl)pyrazolo[1,5-a]pyridine-3-carbonitrile | 499.1 (M + H) |
| 57 | 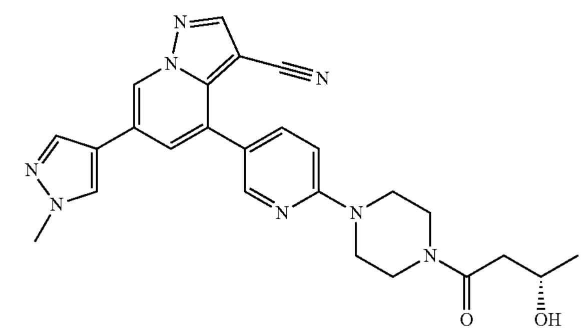 [SMILES: C[C@H](O)CC(=O)N1CCN(c2ccc(-c3cc(-c4cnn(C)c4)cn4ncc(C#N)c34)cn2)CC1] | (S)-4-(6-(4-(3-hydroxybutanoyl)piperazin-1-yl)pyridin-3-yl)-6-(1-methyl-1H-pyrazol-4-yl)pyrazolo[1,5-a]pyridine-3-carbonitrile | 471.1 (M + H) |
| 58 | 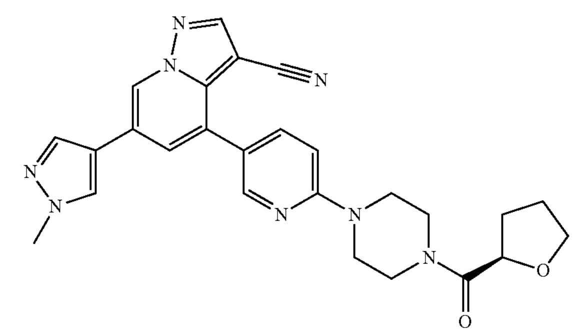 [SMILES: Cn1cc(-c2cc(-c3ccc(N4CCN(C(=O)[C@H]5CCCO5)CC4)nc3)c3c(C#N)cnn3c2)cn1] | (R)-6-(1-methyl-1H-pyrazol-4-yl)-4-(6-(4-(tetrahydrofuran-2-carbonyl)piperazin-1-yl)pyridin-3-yl)pyrazolo[1,5-a]pyridine-3-carbonitrile | 483.1 (M + H) |

TABLE F-continued

| Ex # | Structure | Chemical Name | MS (apci) m/z |
|---|---|---|---|
| 59 | 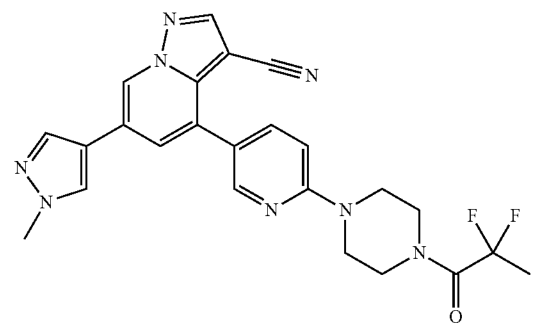 [SMILES: Cn1cc(-c2cc(-c3ccc(N4CCN(C(=O)C(C)(F)F)CC4)nc3)c3c(C#N)cnn3c2)cn1] | 4-(6-(4-(2,2-difluoropropanoyl)piperazin-1-yl)pyridin-3-yl)-6-(1-methyl-1H-pyrazol-4-yl)pyrazolo[1,5-a]pyridine-3-carbonitrile | 477.1 (M + H) |
| 60 | 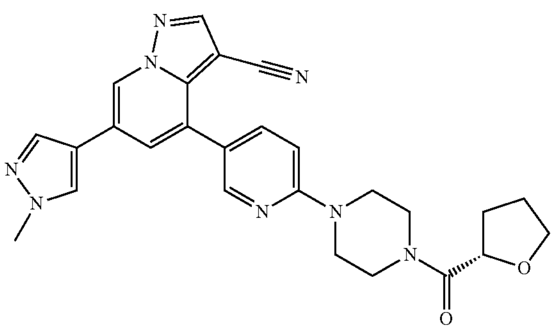 | (S)-6-(1-methyl-1H-pyrazol-4-yl)-4-(6-(4-(tetrahydrofuran-2-carbonyl)piperazin-1-yl)pyridin-3-yl)pyrazolo[1,5-a]pyridine-3-carbonitrile | 483.1 (M + H) |
| 61 | 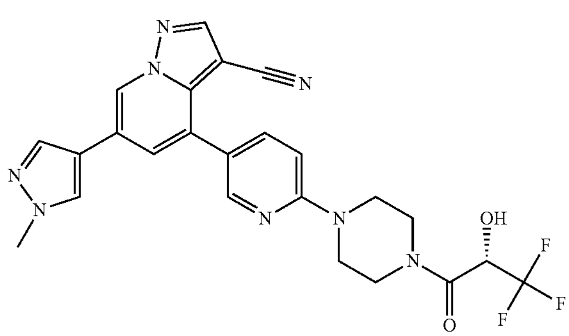 [SMILES: Cn1cc(-c2cc(-c3ccc(N4CCN(C(=O)[C@H](O)C(F)(F)F)CC4)nc3)c3c(C#N)cnn3c2)cn1] | (S)-6-(1-methyl-1H-pyrazol-4-yl)-4-(6-(4-(3,3,3-trifluoro-2-hydroxypropanoyl)piperazin-1-yl)pyridin-3-yl)pyrazolo[1,5-a]pyridine-3-carbonitrile | 511.2 (M + H) |
| 62 | 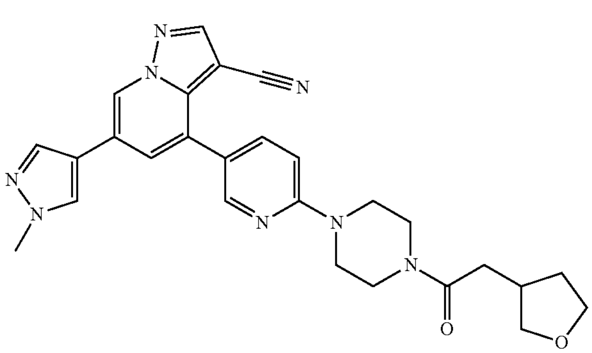 [SMILES: Cn1cc(-c2cc(-c3ccc(N4CCN(C(=O)CC5CCOC5)CC4)nc3)c3c(C#N)cnn3c2)cn1] | 6-(1-methyl-1H-pyrazol-4-yl)-4-(6-(4-(2-(tetrahydrofuran-3-yl)acetyl)piperazin-1-yl)pyridin-3-yl)pyrazolo[1,5-a]pyridine-3-carbonitrile | 497.1 (M + H) |

TABLE F-continued

| Ex # | Structure | Chemical Name | MS (apci) m/z |
|---|---|---|---|
| 63 | 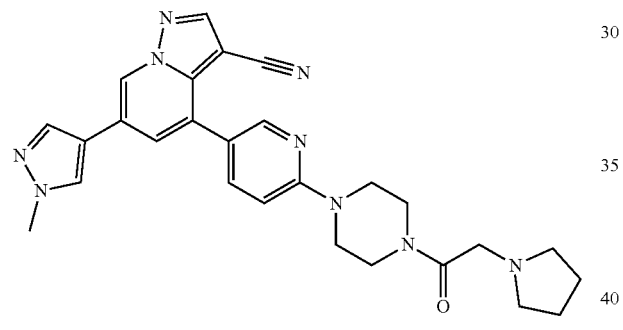 | 4-(6-(4-(3-hydroxy-3-methylpentanoyl)piperazin-1-yl)pyridin-3-yl)-6-(1-methyl-1H-pyrazol-4-yl)pyrazolo[1,5-a]pyridine-3-carbonitrile | 499.1 (M + H) |

Example 64

6-(1-methyl-1H-pyrazol-4-yl)-4-(6-(4-(2-(pyrrolidin-1-yl)acetyl)piperazin-1-yl)pyridin-3-yl)pyrazolo[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile (30 mg, 0.078 mmol) and TEA (54 µL, 0.39 mmol) in DMF (3 mL) was added 2-chloroacetyl chloride (9.3 µL, 0.117 mmol). The reaction was stirred at ambient temperature for 1 h then pyrrolidine (51.6 µL, 0.62 mmol) was added and the reaction was stirred for an additional 2 h. The reaction mixture was quenched with water (15 mL) and extracted with EtOAc (3×20 mL). The combined organic layers were dried over anhydrous $Na_2SO_4$, filtered, concentrated and purified by silica chromatography (0-50% of 20% MeOH/DCM in EtOAc) to provide the title compound (0.0244 g, 63% yield). MS (apci) m/z=496.2 (M+H). $^1$H NMR (DMSO) δ 9.20 (d, 1H), 8.61 (s, 1H), 8.37 (d, 1H), 8.36 (s, 1H), 8.09 (s, 1H), 7.82 (dd, 1H), 7.75 (d, 1H), 6.97 (d, 1H), 3.85 (s, 3H), 3.60 (m, 8H), 3.37 (s, 2H), 2.53 (s, 4H), 1.68 (s, 4H).

Example 65

4-(6-(4-(3,3-dimethylbutanoyl)piperazin-1-yl)pyridin-3-yl)-6-(1-methyl-1H-pyrazol-4-yl)pyrazolo[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile (40 mg, 0.10 mmol) and pyridine (33.7 µL, 0.42 mmol) in DCM (4 mL) was added 3,3-Dimethylbutyryl chloride (0.97 mL, 0.21 mmol). The reaction was stirred at ambient temperature for 2 h and then quenched with water (10 mL) and extracted with EtOAc (3×15 mL). The combined organic layers were dried over anhydrous $Na_2SO_4$, filtered, concentrated and purified by silica chromatography (0-20% MeOH with $NH_4OH$ in DCM) to provide the title compound (0.0327 g, 65% yield). MS (apci) m/z=483.2 (M+H).

Example 66

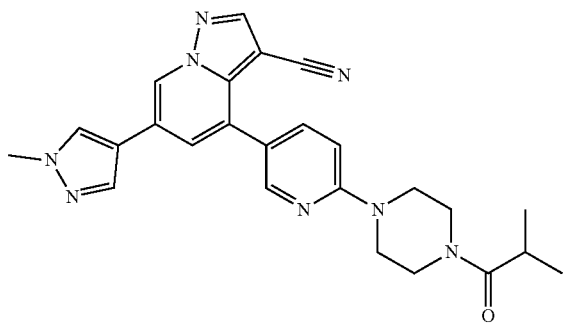 [SMILES: CC(C)C(=O)N1CCN(c2ccc(-c3cc(-c4cnn(C)c4)cn4ncc(C#N)c34)cn2)CC1]

4-(6-(4-isobutyrylpiperazin-1-yl)pyridin-3-yl)-6-(1-methyl-1H-pyrazol-4-yl)pyrazolo[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile dihydrochloride (10 mg, 0.022 mmol) in DCM (2 mL) was added isobutyryl chloride (3.5 mg, 0.033 mmol) and TEA (30 μL, 0.22 mmol). The reaction was stirred at ambient temperature for 1 h and then purified by reverse phase chromatography (0-75% ACN/water) to afford the title compound (9 mg, 91% yield). MS (apci) m/z=455.1 (M+H).

Example 67

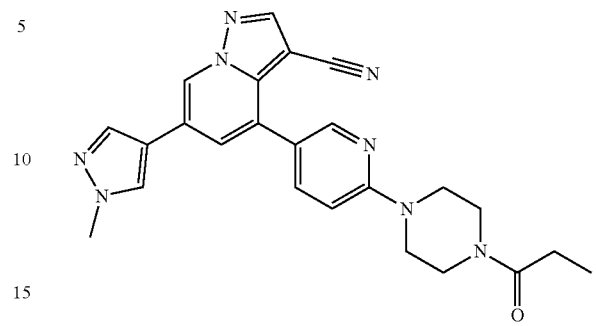

6-(1-methyl-1H-pyrazol-4-yl)-4-(6-(4-propionylpiperazin-1-yl)pyridin-3-yl)pyrazolo[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile dihydrochloride (10 mg, 0.022 mmol) in DCM (2 mL) was added propionyl chloride (3.0 mg, 0.033 mmol) and TEA (30 μL, 0.22 mmol). The reaction mixture was stirred at ambient temperature for 1 h, then concentrated in vacuo and purified by reverse phase chromatography (0-75% ACN/water) to afford the title compound (5 mg, 52% yield). MS (apci) m/z=441.1 (M+H).

The compounds in Table G were prepared and purified according the method used for the synthesis of Example 67, replacing propionyl chloride with the appropriate acid halide starting material.

TABLE G

| Ex # | Structure | Chemical Name | MS (apci) m/z |
|---|---|---|---|
| 68 | 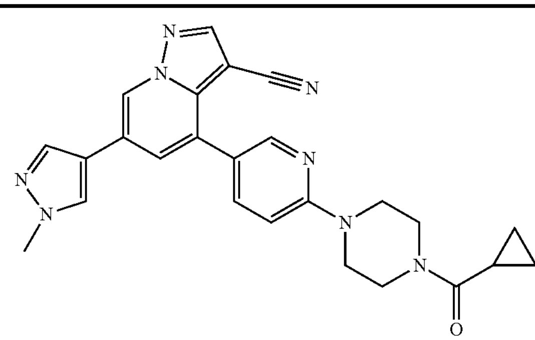 | 4-(6-(4-(cyclopropanecarbonyl)piperazin-1-yl)pyridin-3-yl)-6-(1-methyl-1H-pyrazol-4-yl)pyrazolo[1,5-a]pyridine-3-carbonitrile | 453.2 (M + H) |
| 69 | 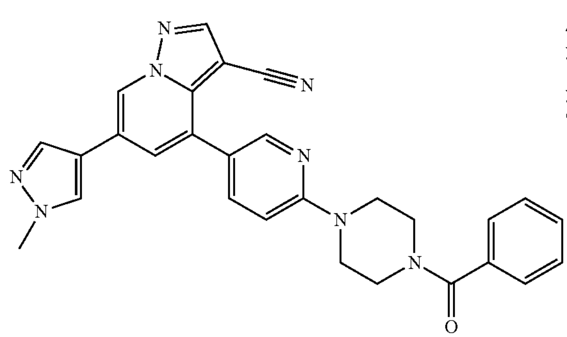 | 4-(6-(4-benzoylpiperazin-1-yl)pyridin-3-yl)-6-(1-methyl-1H-pyrazol-4-yl)pyrazolo[1,5-a]pyridine-3-carbonitrile | 489.1 (M + H) |

Example 70

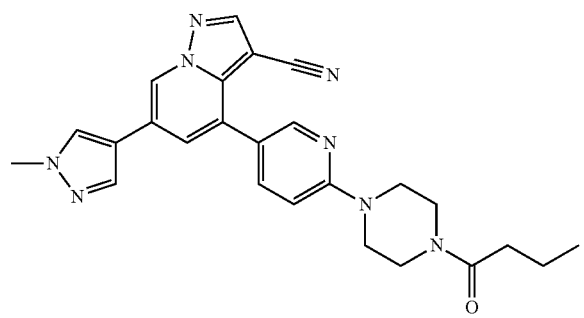 [SMILES: CCCC(=O)N1CCN(c2ccc(-c3cc(-c4cnn(C)c4)cn4ncc(C#N)c34)cn2)CC1]

4-(6-(4-butyrylpiperazin-1-yl)pyridin-3-yl)-6-(1-methyl-H-pyrazol-4-yl)pyrazolo[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile dihydrochloride (13 mg, 0.028 mmol) in DCM (2 mL) was added butyryl chloride (4.5 mg, 0.043 mmol) and TEA (40 μL, 0.28 mmol). The reaction mixture was stirred overnight at ambient temperature and then quenched with water (5 mL) and extracted with DCM (3×10 mL). The combined organic extracts were concentrated and purified by reverse phase chromatography (0-75% ACN/water) to afford the title compound (9 mg, 65% yield). MS (apci) m/z=455.2 (M+H).

The compounds in Table H were prepared and purified in a similar fashion as described for the synthesis of Example 70, replacing butyryl chloride with the appropriate acid halide starting material and utilizing the appropriate ACN/water gradient eluent for reverse phase chromatography.

TABLE H

| Ex # | Structure | Chemical Name | MS (apci) m/z |
|---|---|---|---|
| 71 | 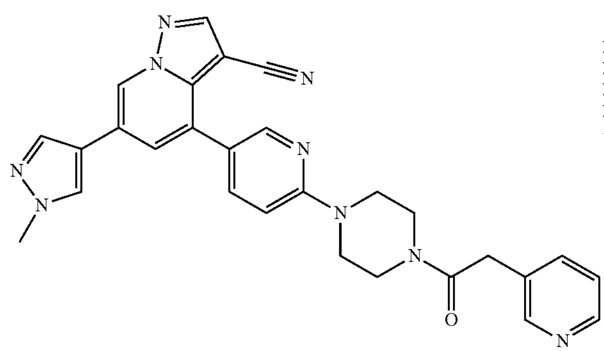 [SMILES: Cn1cc(-c2cc(-c3ccc(N4CCN(C(=O)Cc5cccnc5)CC4)nc3)c3c(C#N)cnn3c2)cn1] | 6-(1-methyl-1H-pyrazol-4-yl)-4-(6-(4-(2-(pyridin-3-yl)acetyl)piperazin-1-yl)pyridin-3-yl)pyrazolo[1,5-a]pyridine-3-carbonitrile | 504.1 (M + H) |
| 72 | 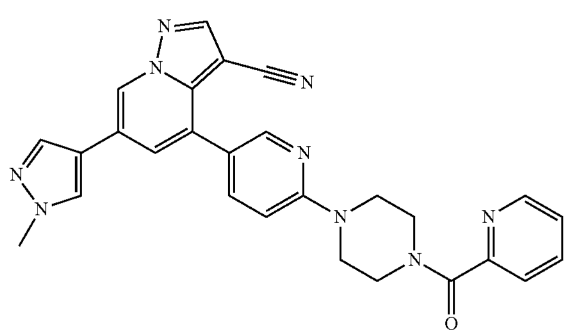 [SMILES: Cn1cc(-c2cc(-c3ccc(N4CCN(C(=O)c5ccccn5)CC4)nc3)c3c(C#N)cnn3c2)cn1] | 6-(1-methyl-1H-pyrazol-4-yl)-4-(6-(4-picolinoylpiperazin-1-yl)pyridin-3-yl)pyrazolo[1,5-a]pyridine-3-carbonitrile | 490.1 (M + H) |
| 73 | 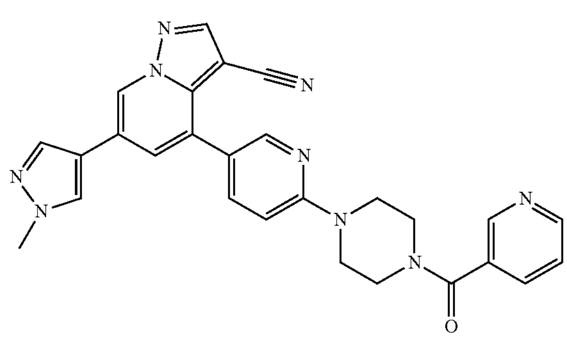 [SMILES: Cn1cc(-c2cc(-c3ccc(N4CCN(C(=O)c5cccnc5)CC4)nc3)c3c(C#N)cnn3c2)cn1] | 6-(1-methyl-1H-pyrazol-4-yl)-4-(6-(4-nicotinoylpiperazin-1-yl)pyridin-3-yl)pyrazolo[1,5-a]pyridine-3-carbonitrile | 490.0 (M + H) |

TABLE H-continued

| Ex # | Structure | Chemical Name | MS (apci) m/z |
|---|---|---|---|
| 74 | 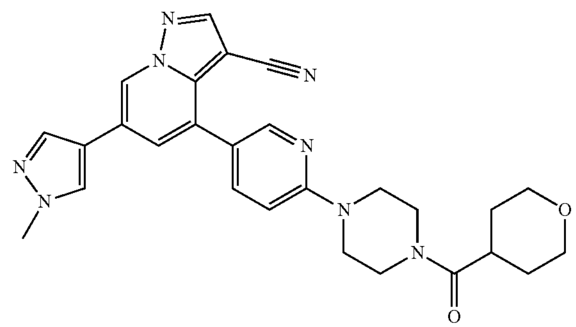 [SMILES: Cn1cc(-c2cc(-c3ccc(N4CCN(C(=O)C5CCOCC5)CC4)nc3)c3c(C#N)cnn3c2)cn1] | 6-(1-methyl-1H-pyrazol-4-yl)-4-(6-(4-(tetrahydro-2H-pyran-4-carbonyl)piperazin-1-yl)pyridin-3-yl)pyrazolo[1,5-a]pyridine-3-carbontirile | 497.1 (M + H) |

Example 75

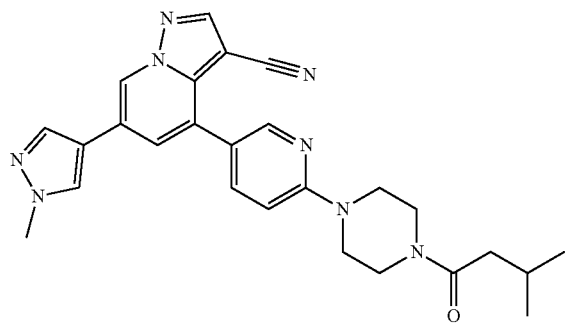 [SMILES: CC(C)CC(=O)N1CCN(c2ccc(-c3cc(-c4cnn(C)c4)cn4ncc(C#N)c34)cn2)CC1]

6-(1-methyl-1H-pyrazol-4-yl)-4-(6-(4-(3-methylbutanoyl)piperazin-1-yl)pyridin-3-yl)pyrazolo[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile dihydrochloride (15 mg, 0.033 mmol) in DCM (2 mL) was added 3-methylbutanoyl chloride (5.9 mg, 0.049 mmol) and TEA (46 μL, 0.33 mmol). The reaction was stirred overnight at ambient temperature and then quenched with water (5 mL) and extracted with DCM in a PS frit. The combined organic extracts were concentrated in vacuo, and the resulting crude residue was taken up in MeOH (0.3 mL) and sonicated. The resulting solid was collected by vacuum filtration, washed with Et$_2$O (3×2 mL) and air dried to afford the title compound (12 mg, 78% yield). MS (apci) m/z=469.2 (M+H).

The compounds in Table I were prepared and purified according the method used for the synthesis of Example 75, replacing 3-methylbutanoyl chloride with the appropriate acid halide starting material.

TABLE I

| Ex # | Structure | Chemical Name | MS (apci) m/z |
|---|---|---|---|
| 76 | 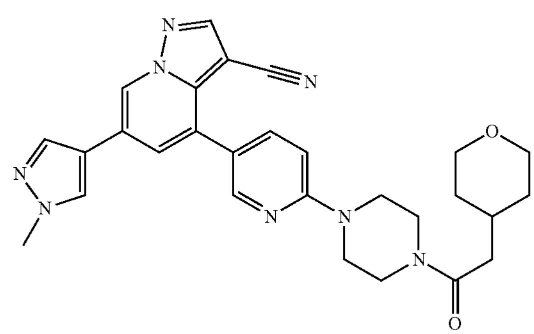 [SMILES: Cn1cc(-c2cc(-c3ccc(N4CCN(C(=O)CC5CCOCC5)CC4)nc3)c3c(C#N)cnn3c2)cn1] | 6-(1-methyl-1H-pyrazol-4-yl)-4-(6-(4-(2-(tetrahydro-2H-pyran-4-yl)acetyl)piperazin-1-yl)pyridin-3-yl)pyrazolo[1,5-a]pyridine-3-carbonitrile | 511.2 (M + H) |

TABLE I-continued

| Ex # | Structure | Chemical Name | MS (apci) m/z |
|---|---|---|---|
| 77 | 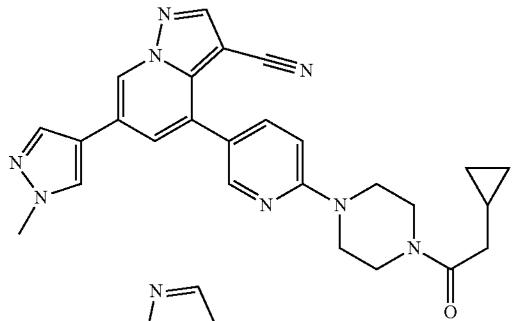 [SMILES: Cn1cc(-c2cc(-c3ccc(N4CCN(C(=O)CC5CC5)CC4)nc3)c3c(C#N)cnn3c2)cn1] | 4-(6-(4-(2-cyclopropylacetyl)piperazin-1-yl)pyridin-3-yl)-6-(1-methyl-1H-pyrazol-4-yl)pyrazolo[1,5-a]pyridine-3-carbonitrile | 467.1 (M + H) |
| 78 | 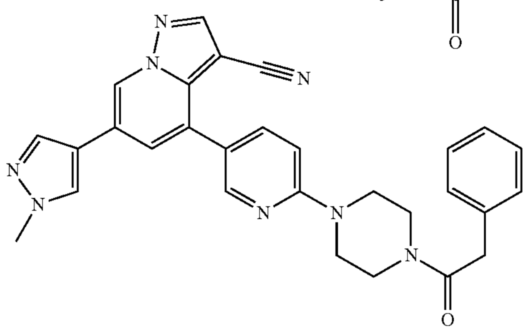 | 6-(1-methyl-1H-pyrazol-4-yl)-4-(6-(4-(2-phenylacetyl)piperazin-1-yl)pyridin-3-yl)pyrazolo[1,5-a]pyridine-3-carbonitrile | 503.2 (M + H) |

Example 79

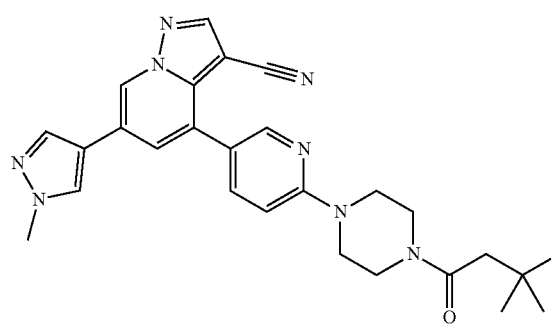

4-(6-(4-(3-hydroxy-3-methylbutanoyl)piperazin-1-yl)pyridin-3-yl)-6-(1-methyl-1H-pyrazol-4-yl)pyrazolo[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile (50 mg, 0.130 mmol) in DMF (4.34 mL) were added 3-hydroxy-3-methylbutanoic acid (210 μL, 0.195 mmol), DMAP (55.6 mg, 0.455 mmol), and EDC-HCl (31.2 mg, 0.163 mmol). After stirring overnight at ambient temperature, the reaction mixture was diluted with water (20 mL) and extracted with EtOAc (3×20 mL). The combined organic layers were dried over anhydrous $Na_2SO_4$, filtered and concentrated in vacuo. The resulting crude residue was purified by silica chromatography (0-50%, 20% MeOH/DCM in EtOAc) to provide the title compound (51.1 mg, 80% yield). MS (apci) m/z=485.1 (M+H). $^1$H NMR ($CDCl_3$) δ 8.63 (d, 1H), 8.37 (d, 1H), 8.25 (s, 1H), 7.77 (d, 1H), 7.75 (d, 1H), 7.67 (s, 1H), 7.38 (s, 1H), 6.78 (d, 1H), 3.98 (s, 3H), 3.80 (m, 2H), 3.75 (m, 2H), 3.63 (m, 4H), 2.50 (s, 2H), 1.31 (s, 6H).

The compounds in Table J were prepared and purified according the method used for the synthesis of Example 79, replacing 3-hydroxy-3-methylbutanoic acid with the appropriate acid starting material.

TABLE J

| Ex # | Structure | Chemical Name | MS (apci) m/z |
|---|---|---|---|
| 80 | 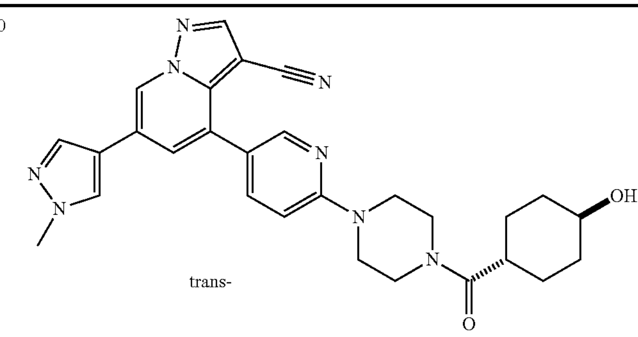 | 4-(6-(4-((1r,4r)-4-hydroxycyclohexanecarbonyl)piperazin-1-yl)pyridin-3-yl)-6-(1-methyl-1H-pyrazol-4-yl)pyrazolo[1,5-a]pyridine-3-carbonitrile | 511.2 (M + H) |

TABLE J-continued

| Ex # | Structure | Chemical Name | MS (apci) m/z |
|---|---|---|---|
| 81 | 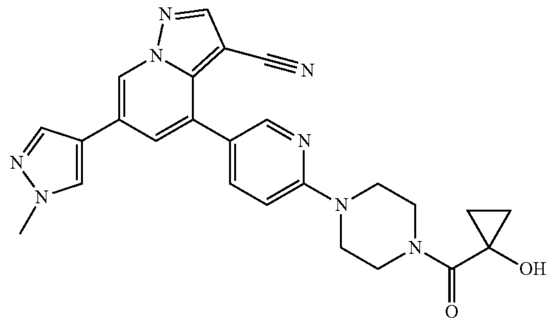 [SMILES: Cn1cc(-c2cc(-c3ccc(N4CCN(C(=O)C5(O)CC5)CC4)nc3)c3c(C#N)cnn3c2)cn1] | 4-(6-(4-(1-hydroxycyclopropane-1-carbonyl)piperazin-1-yl)pyridin-3-yl)-6-(1-methyl-1H-pyrazol-4-yl)pyrazolo[1,5-a]pyridine-3-carbonnitrile | 469.2 (M + H) |

Example 82

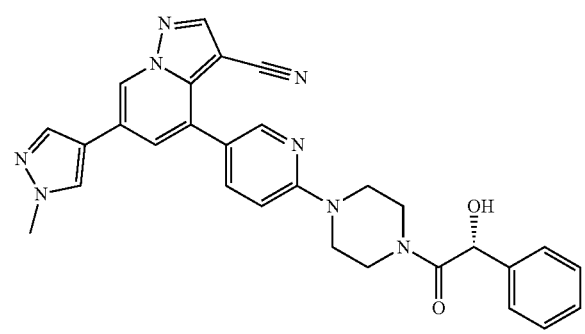 [SMILES: Cn1cc(-c2cc(-c3ccc(N4CCN(C(=O)[C@H](O)c5ccccc5)CC4)nc3)c3c(C#N)cnn3c2)cn1]

(R)-4-(6-(4-(2-hydroxy-2-phenylacetyl)piperazin-1-yl)pyridin-3-yl)-6-(1-methyl-1H-pyrazol-4-yl)pyrazolo[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile (35 mg, 0.0910 mmol) in DMF (910 μL) was added (R)-2-hydroxy-2-phenylacetic acid (13.9 mg, 0.0.0912 mmol), DMAP (33.4 mg, 0.273 mmol), and EDC-HCl (21.8 mg, 0.114 mmol). After stirring overnight at ambient temperature, the reaction mixture was diluted with water (5 mL) and then extracted with EtOAc (3×5 mL). The combined organic layers were dried over anhydrous Na$_2$SO$_4$, filtered and concentrated in vacuo. The crude residue was purified by reverse phase chromatography (0-60%, ACN/water) to provide the title compound (32.8 mg, 67% yield). MS (apci) m/z=519.1 (M+H). $^1$H NMR (CDCl$_3$) δ 8.61 (d, 1H), 8.31 (d, 1H), 8.22 (s, 1H), 7.76 (m, 1H), 7.71 (m, 1H), 7.65 (m, 1H), 7.35 (m, 6H), 6.68 (d, 1H), 5.25 (s, 1H), 4.00 (m, 1H), 3.88 (s, 3H), 3.80 (m, 1H), 3.62 (m, 2H), 3.37 (m, 3H), 3.00 (s, 1H), 2.86 (m, 1H).

Example 82a

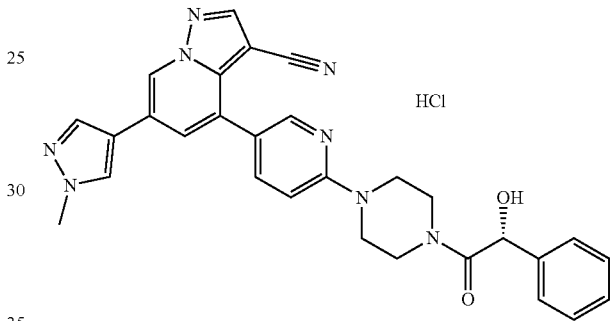

(R)-4-(6-(4-(2-hydroxy-2-phenylacetyl)piperazin-1-yl)pyridin-3-yl)-6-(1-methyl-1H-pyrazol-4-yl)pyrazolo[1,5-a]pyridine-3-carbonitrile Hydrochloride To a solution of (R)-4-(6-(4-(2-hydroxy-2-phenylacetyl)piperazin-1-yl)pyridin-3-yl)-6-(1-methyl-1H-pyrazol-4-yl)pyrazolo[1,5-a]pyridine-3-carbonitrile (19 mg, 0.037 mmol) in DCM (5 mL) was added 5 M HCl in iPrOH (29 μL, 0.15 mmol). The mixture was concentrated in vacuo to afford the title compound (22 mg, quantitative yield). MS (apci) m/z=519.1 (M+H).

Example 83

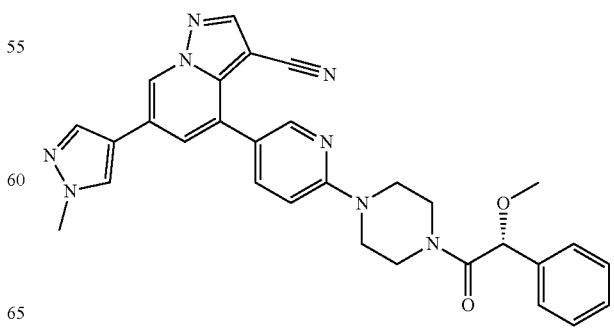

249

(R)-4-(6-(4-(2-hydroxy-2-phenylacetyl)piperazin-1-yl)pyridin-3-yl)-6-(1-methyl-1H-pyrazol-4-yl)pyrazolo[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile (15 mg, 0.0390 mmol) in DMF (390 μL) was added (R)-2-methoxy-2-phenylacetic acid (9.73 mg, 0.0585 mmol), DMAP (14.3 mg, 0.117 mmol), and EDC-HCl (11.6 mg, 0.0605 mmol). After stirring overnight at ambient temperature, the reaction mixture was diluted with MeOH and purified directly using reverse phase chromatography (0-70% ACN/water) to provide the title compound (9.2 mg, 44% yield). MS (apci) m/z=533.2 (M+H).

Example 84

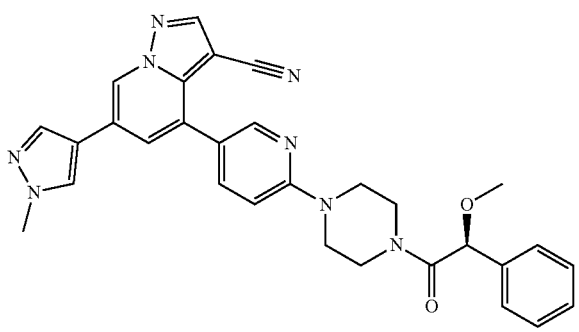 [SMILES: CO[C@H](C(=O)N1CCN(c2ccc(-c3cc(-c4cnn(C)c4)cn4ncc(C#N)c34)cn2)CC1)c1ccccc1]

(S)-4-(6-(4-(2-hydroxy-2-phenylacetyl)piperazin-1-yl)pyridin-3-yl)-6-(1-methyl-1H-pyrazol-4-yl)pyrazolo[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile (15 mg, 0.0390 mmol) in DMF (390 μL) was added (S)-2-methoxy-2-phenylacetic acid (9.73 mg, 0.0585 mmol), DMAP (14.3 mg, 0.117 mmol), and EDC-HCl (11.6 mg, 0.0605 mmol). After stirring overnight at ambient temperature, the reaction mixture was diluted with MeOH and then purified directly using reverse phase chromatography (0-70% ACN/water) to provide the title compound (4.0 mg, 19.2% yield). MS (apci) m/z=533.0 (M+H).

Example 85

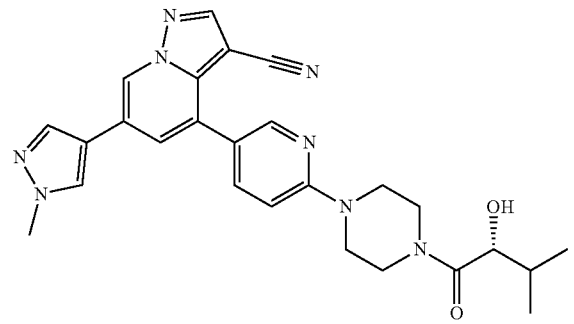 [SMILES: CC(C)[C@@H](O)C(=O)N1CCN(c2ccc(-c3cc(-c4cnn(C)c4)cn4ncc(C#N)c34)cn2)CC1]

250

(R)-4-(6-(4-(2-hydroxy-3-methylbutanoyl)piperazin-1-yl)pyridin-3-yl)-6-(1-methyl-1H-pyrazol-4-yl)pyrazolo[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile (25 mg, 0.065 mmol) in DMF (2.2 mL) was added (R)-2-hydroxy-3-methylbutanoic acid (11.5 mg, 0.098 mmol), DMAP (28 mg, 0.23 mmol), and, finally, EDC-HCl (15.6 mg, 0.081 mmol). After stirring overnight at ambient temperature, the reaction mixture was diluted with water (15 mL) and then extracted with EtOAc (3×20 mL). The combined organic layers was dried over anhydrous $Na_2SO_4$, filtered, concentrated and purified by silica chromatography (0-50%, 20% MeOH/DCM in EtOAc) to provide the title compound (7.7 mg, 24.2% yield). MS (apci) m/z=485.2 (M+H).

Example 85a

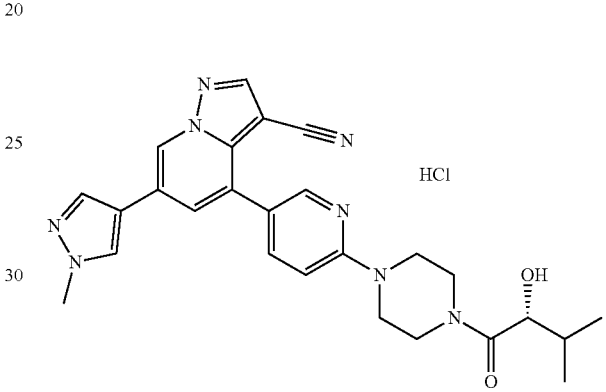

(R)-4-(6-(4-(2-hydroxy-3-methylbutanoyl)piperazin-1-yl)pyridin-3-yl)-6-(1-methyl-1H-pyrazol-4-yl)pyrazolo[1,5-a]pyridine-3-carbonitrile Hydrochloride To a solution of (R)-4-(6-(4-(2-hydroxy-3-methylbutanoyl)piperazin-1-yl)pyridin-3-yl)-6-(1-methyl-1H-pyrazol-4-yl)pyrazolo[1,5-a]pyridine-3-carbonitrile (17 mg, 0.035 mmol) in DCM (2 mL) was added 5 M HCl in iPrOH (21 μL, 0.11 mmol). The mixture was concentrated in vacuo and dried on high vacuum to afford the title compound (18 mg, 98% yield). MS (apci) m/z=485.2 (M+H).

Example 86

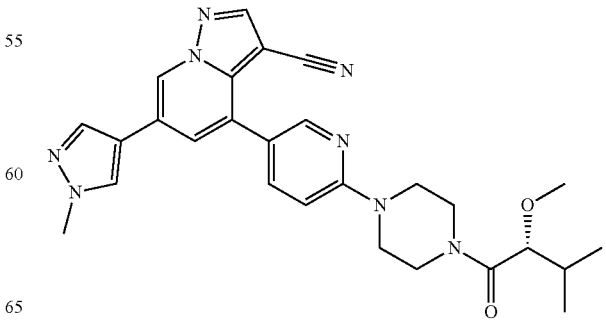

(R)-4-(6-(4-(2-methoxy-3-methylbutanoyl)piperazin-1-yl)pyridin-3-yl)-6-(1-methyl-1H-pyrazol-4-yl)pyrazolo[1,5-a]pyridine-3-carbonitrile NaH (1.7 mg, 0.041 mmol) was added to a solution of (R)-4-(6-(4-(2-hydroxy-3-methylbutanoyl)piperazin-1-yl)pyridin-3-yl)-6-(1-methyl-1H-pyrazol-4-yl)pyrazolo[1,5-a]pyridine-3-carbonitrile (10 mg, 0.021 mmol) in THF (1 mL) and the reaction mixture was stirred at ambient temperature for 20 min. MeI (41 µL, 0.041 mmol) was added and the reaction was stirred at ambient temperature for 1 h and then quenched with water (1 mL). The resulting mixture was extracted with DCM (3×5 mL). The combined organic extracts were concentrated and purified by reverse phase chromatography (0-70% ACN/water) to provide the title compound (5.5 mg, 53% yield). MS (apci) m/z=499.1 (M+H).

Example 87

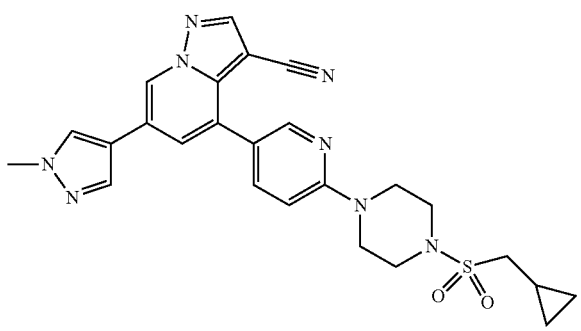 [SMILES: Cn1cc(-c2cc(-c3ccc(N4CCN(S(=O)(=O)CC5CC5)CC4)nc3)c3c(C#N)cnn3c2)cn1]

4-(6-(4-((cyclopropylmethyl)sulfonyl)piperazin-1-yl)pyridin-3-yl)-6-(1-methyl-1H-pyrazol-4-yl)pyrazolo[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile dihydrochloride (10 mg, 0.0219 mmol) in DCM (2 mL) was added cyclopropylmethanesulfonyl chloride (4.4 mg, 0.028 mmol) followed by TEA (30 µL, 0.22 mmol). The reaction mixture was stirred overnight at ambient temperature and then quenched with water (1 mL) and extracted with DCM (3×5 mL) in a PS frit. The combined DCM extracts were concentrated and purified by reverse phase chromatography (0-70% ACN/water) to provide the title compound (10.1 mg, 87% yield). MS (apci) m/z=503.1 (M+H).

The compounds in Table K were prepared according the method used for the synthesis of Example 87, replacing cyclopropylmethanesulfonyl chloride with the appropriate sulfonyl chloride starting material, and utilizing the appropriate ACN/water gradient eluent for reverse phase chromatography purifications.

TABLE K

| Ex # | Structure | Chemical Name | MS (apci) m/z |
|---|---|---|---|
| 88 | 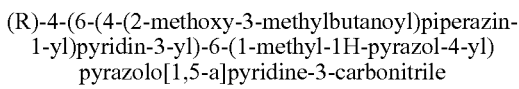 | 6-(1-methyl-1H-pyrazol-4-yl)-4-(6-(4-(methylsulfonyl)piperazin-1-yl)pyridin-3-yl)pyrazolo[1,5-a]pyridine-3-carbonitrile | 463.1 (M + H) |
| 89 | 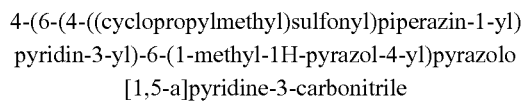 | 6-(1-methyl-1H-pyrazol-4-yl)-4-(6-(4-(neopentylsulfonyl)piperazin-1-yl)pyridin-3-yl)pyrazolo[1,5-a]pyridine-3-carbonitrile | 519.1 (M + H) |

TABLE K-continued

| Ex # | Structure | Chemical Name | MS (apci) m/z |
|---|---|---|---|
| 90 | 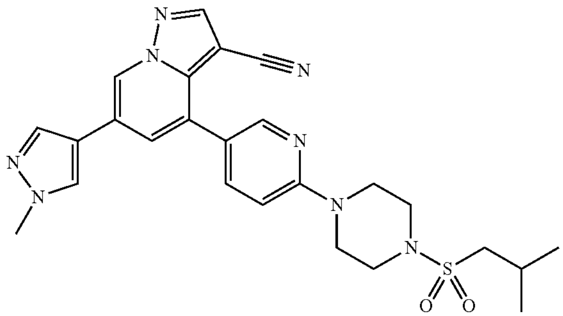 [SMILES: CC(C)CS(=O)(=O)N1CCN(c2ccc(-c3cc(-c4cnn(C)c4)cn4ncc(C#N)c34)cn2)CC1] | 4-(6-(4-(isobutylsulfonyl)piperazin-1-yl)pyridin-3-yl)-6-(1-methyl-1H-pyrazol-4-yl)pyrazolo[1,5-a]pyridine-3-carbonitrile | 505.1 (M + H) |
| 91 | 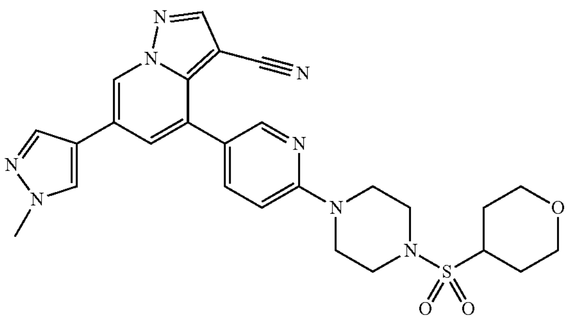 [SMILES: Cn1cc(-c2cc(-c3ccc(N4CCN(S(=O)(=O)C5CCOCC5)CC4)nc3)c3c(C#N)cnn3c2)cn1] | 6-(1-methyl-1H-pyrazol-4-yl)-4-(6-(4-((tetrahydro-2H-pyran-4-yl)sulfonyl)piperazin-1-yl)pyridin-3-yl)pyrazolo[1,5-a]pyridine-3-carbonitrile | 533.1 (M + H) |

Example 92

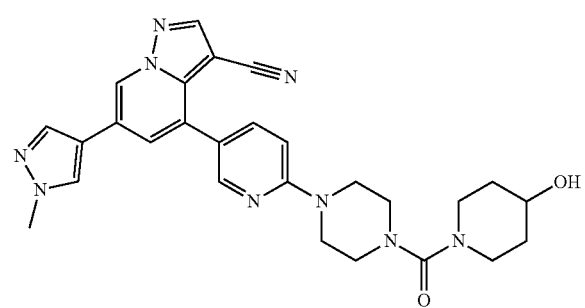 [SMILES: Cn1cc(-c2cc(-c3ccc(N4CCN(C(=O)N5CCC(O)CC5)CC4)nc3)c3c(C#N)cnn3c2)cn1]

4-(6-(4-(4-hydroxypiperidine-1-carbonyl)piperazin-1-yl)pyridin-3-yl)-6-(1-methyl-1H-pyrazol-4-yl)pyrazolo[1,5-a]pyridine-3-carbonitrile A suspension of 6-(1-methyl-1H-pyrazol-4-yl)-4-(6-(piperazin-1-yl)pyridin-3-yl)pyrazolo[1,5-a]pyridine-3-carbonitrile dihydrochloride (15 mg, 0.033 mmol) and DIEA (34 µL, 0.20 mmol) in DriSolv® DCM (164 µL) was added dropwise to a 0° C. solution of triphosgene (4.9 mg, 0.016 mmol) in DriSolv® DCM (164 µL). After stirring the reaction mixture for 1 hour at 0° C., piperidin-4-ol (3.3 mg, 0.033 mmol) was added, and the reaction was stirred at ambient temperature overnight. The reaction mixture was diluted with EtOAc (0.5 mL), vacuum filtered, and the solids were rinsed with EtOAc (3×0.5 mL) to provide the title compound as a white solid (16 mg, 93% yield). MS (apci) m/z=512.2 (M+H).

Example 93

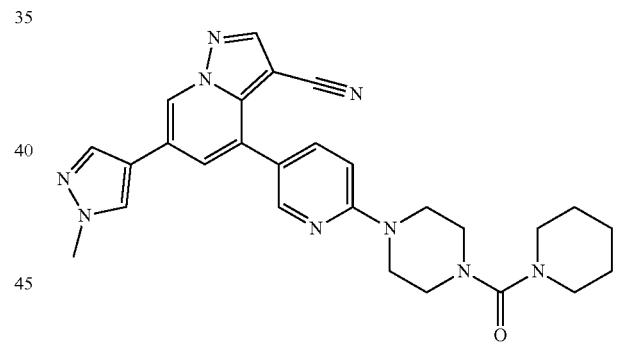

6-(1-methyl-1H-pyrazol-4-yl)-4-(6-(4-(piperidine-1-carbonyl)piperazin-1-yl)pyridin-3-yl)pyrazolo[1,5-a]pyridine-3-carbonitrile A suspension of 6-(1-methyl-1H-pyrazol-4-yl)-4-(6-(piperazin-1-yl)pyridin-3-yl)pyrazolo[1,5-a]pyridine-3-carbonitrile dihydrochloride (15 mg, 0.033 mmol) and DIEA (34 µL, 0.20 mmol) in DriSolv® DCM (328 µL+100 µL rinse) was added dropwise to a 0° C. solution of triphosgene (4.9 mg, 0.016 mmol) in DriSolv® DCM (328 µL). After stirring for 1 hour at 0° C., piperidine (4.9 µL, 0.049 mmol) was added and the reaction mixture was stirred at ambient temperature for 3 h. The reaction mixture was directly purified by reverse phase chromatography (5-80% ACN/water) to yield a solid that contained mostly desired product, which was triturated with MTBE (2 mL) to provide the title compound (7.0 mg, 43% yield). MS (apci) m/z=496.1 (M+H).

Example 94

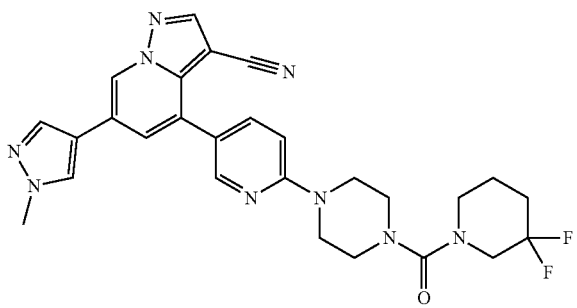 [SMILES: Cn1cc(-c2cc(-c3ccc(N4CCN(C(=O)N5CCCC(F)(F)C5)CC4)nc3)c3c(C#N)cnn3c2)cn1]

4-(6-(4-(3,3-difluoropiperidine-1-carbonyl)piperazin-1-yl)pyridin-3-yl)-6-(1-methyl-1H-pyrazol-4-yl)pyrazolo[1,5-a]pyridine-3-carbonitrile A suspension of 6-(1-methyl-1H-pyrazol-4-yl)-4-(6-(piperazin-1-yl)pyridin-3-yl)pyrazolo[1,5-a]pyridine-3-carbonitrile dihydrochloride (15 mg, 0.033 mmol) and DIEA (34 μL, 0.20 mmol) in DriSolv® DCM (428 μL) was added dropwise to a 0° C. solution of triphosgene (4.9 mg, 0.016 mmol) in DriSolv® DCM (328 μL). After the mixture was stirred for 1 h at 0° C., 3,3-difluoropiperidine hydrochloride (7.8 mg, 0.049 mmol) was added and the reaction mixture was stirred at ambient temperature for 3 h. The reaction mixture was then directly purified by reverse phase chromatography (5-80% ACN/water) to yield a solid that contained mostly desired product, which was triturated with MTBE (2 mL) to provide the title compound (2.2 mg, 13% yield). MS (apci) m/z=532.1 (M+H). $^{19}$F NMR (CDCl$_3$) δ −102.6.

Example 95

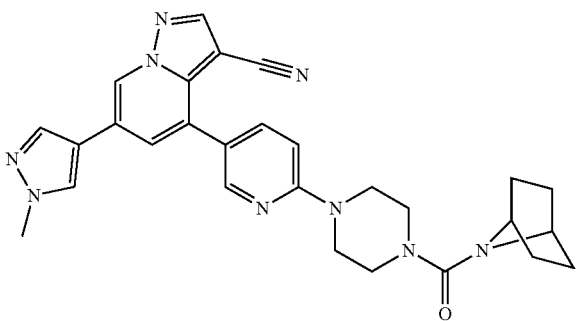 [SMILES: Cn1cc(-c2cc(-c3ccc(N4CCN(C(=O)N5C6CCC5CC6)CC4)nc3)c3c(C#N)cnn3c2)cn1]

4-(6-(4-(7-azabicyclo[2.2.1]heptane-7-carbonyl)piperazin-1-yl)pyridin-3-yl)-6-(1-methyl-1H-pyrazol-4-yl)pyrazolo[1,5-a]pyridine-3-carbonitrile A suspension of 6-(1-methyl-1H-pyrazol-4-yl)-4-(6-(piperazin-1-yl)pyridin-3-yl)pyrazolo[1,5-a]pyridine-3-carbonitrile dihydrochloride (15 mg, 0.033 mmol) and DIEA (46 μL, 0.26 mmol) in DriSolv® DCM (164 μL) was added dropwise to a 0° C. solution of triphosgene (4.9 mg, 0.016 mmol) in DriSolv® DCM (164 μL) and stirred for 4 h, followed by addition of 7-azabicyclo[2.2.1]heptane hydrochloride (4.4 mg, 0.033 mmol) in one portion. The reaction mixture was warmed to ambient temperature and stirred for 3 h. Additional 7-azabicyclo[2.2.1]heptane hydrochloride (4.4 mg, 0.033 mmol) was added and the reaction mixture was stirred for an additional 2 h to reach completion as shown by LCMS. The reaction mixture was then dissolved in minimal amount of warm DMSO and directly purified by reverse-phase chromatography (C18, 5-60% ACN/water) to provide the title compound (4.5 mg, 26% yield). MS (apci) m/z=508.1 (M+H).

Example 96

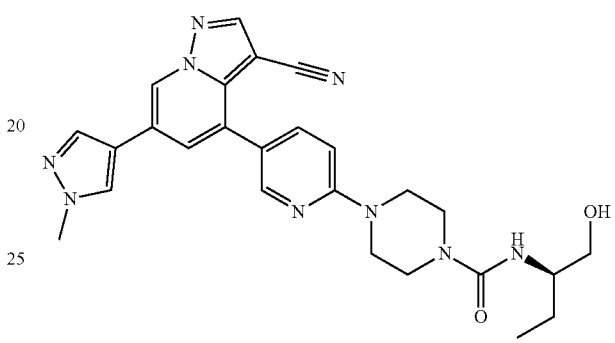

(R)-4-(5-(3-cyano-6-(1-methyl-1H-pyrazol-4-yl)pyrazolo[1,5-a]pyridin-4-yl)pyridin-2-yl)-N-(1-hydroxybutan-2-yl)piperazine-1-carboxamide A suspension of 6-(1-methyl-1H-pyrazol-4-yl)-4-(6-(piperazin-1-yl)pyridin-3-yl)pyrazolo[1,5-a]pyridine-3-carbonitrile (25 mg, 0.0650 mmol) and DIEA (68.0 μL, 0.390 mmol) in DriSolv® DCM (325 μL) was added dropwise to a 0° C. solution of triphosgene (9.65 mg, 0.0325 mmol) in DriSolv® DCM (325 μL). After stirring this reaction mixture for 1.5 h at 0° C., (R)-2-aminobutan-1-ol (6.96 mg, 0.0780 mmol) was added and the reaction was stirred at ambient temperature overnight. The reaction mixture was then diluted with DMSO (0.5 mL), warmed (to solubilize particulate matter), concentrated in vacuo to ½ the original volume and purified by reverse phase chromatography (5-50% ACN/water) to provide the title compound (11.3 mg, 34% yield). MS (apci) m/z=500.1 (M+H).

Example 97

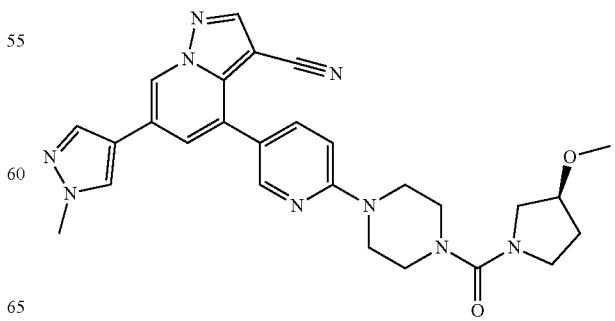

(S)-4-(6-(4-(3-methoxypyrrolidine-1-carbonyl)piperazin-1-yl)pyridin-3-yl)-6-(1-methyl-1H-pyrazol-4-yl)pyrazolo[1,5-a]pyridine-3-carbonitrile A suspension of 6-(1-methyl-1H-pyrazol-4-yl)-4-(6-(piperazin-1-yl)pyridin-3-yl)pyrazolo[1,5-a]pyridine-3-carbonitrile dihydrochloride (15 mg, 0.033 mmol) and DIEA (34 µL, 0.20) mmol) in DriSolv DCM (164 µL) was added dropwise to a 0° C. solution of triphosgene (4.9 mg, 0.016 mmol) in DriSolv DCM (164 µL). After stirring for 30 min at 0° C., (S)-3-methoxypyrrolidine hydrochloride (4.5 mg, 0.033 mmol) was added and the reaction mixture was stirred at ambient temperature for 48 h. The reaction mixture was then directly purified by reverse-phase chromatography (C18, 5-50% ACN/water) to provide the title compound as a white solid (11.7 mg, 68% yield). MS (apci) m/z=512.2 (M+H). $^1$H NMR (CDCl$_3$) δ 8.61 (d, 1H), 8.36 (d, 1H), 8.24 (s, 1H), 7.77 (d, 1H), 7.74 (dd, 1H), 7.66 (s, 1H), 7.37 (d, 1H), 6.77 (d, 1H), 3.97 (s, 3H), 3.95 (m, 1H), 3.37-3.72 (m, 12H), 3.33 (s, 3H), 1.98-2.04 (m, 1H), 1.88-1.94 (m, 1H).

The compounds in Table L were prepared in a similar fashion as described for the syntheses of Examples 96 and 97, replacing (R)-2-aminobutan-1-ol or (S)-3-methoxypyrrolidine hydrochloride with the appropriate amine starting material.

TABLE L

| Ex # | Structure | Chemical Name | MS (apci) m/z |
|---|---|---|---|
| 98 | 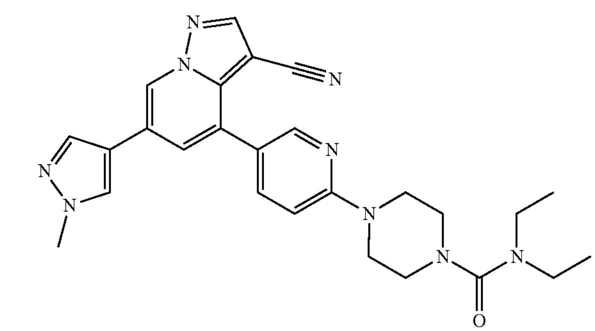 [SMILES: CCN(CC)C(=O)N1CCN(c2ccc(-c3cc(-c4cnn(C)c4)cn4ncc(C#N)c34)cn2)CC1] | 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide | 484.1 (M + H) |
| 99 | 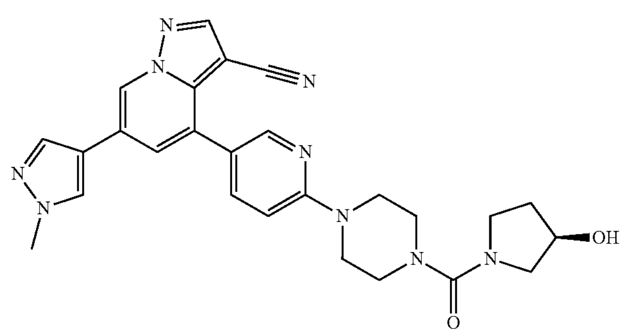 [SMILES: Cn1cc(-c2cc(-c3ccc(N4CCN(C(=O)N5CC[C@@H](O)C5)CC4)nc3)c3c(C#N)cnn3c2)cn1] | (R)-4-(6-(4-(3-hydroxypyrrolidine-1-carbonyl)piperazin-1-yl)pyridin-3-yl)-6-(1-methyl-1H-pyrazol-4-yl)pyrazolo[1,5-a]pyridine-3-carbonitrile | 498.2 (M + H) |
| 100 | 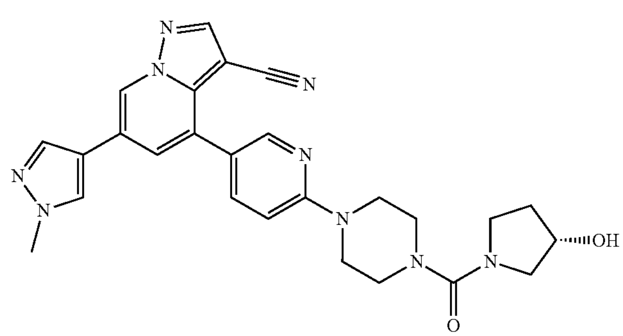 [SMILES: Cn1cc(-c2cc(-c3ccc(N4CCN(C(=O)N5CC[C@H](O)C5)CC4)nc3)c3c(C#N)cnn3c2)cn1] | (S)-4-(6-(4-(3-hydroxypyrrolidine-1-carbonyl)piperazin-1-yl)pyridin-3-yl)-6-(1-methyl-1H-pyrazol-4-yl)pyrazolo[1,5-a]pyridine-3-carbonitrile | 498.2 (M + H) |

TABLE L-continued

| Ex # | Structure | Chemical Name | MS (apci) m/z |
|---|---|---|---|
| 101 | 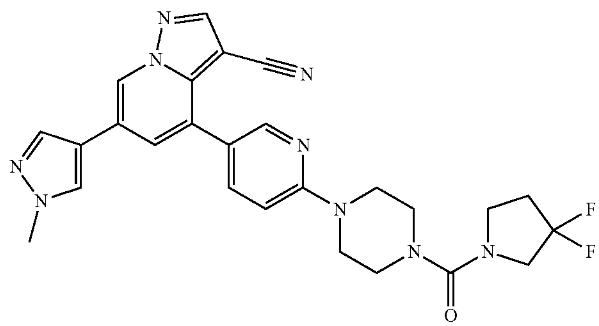 [SMILES: Cn1cc(-c2cc(-c3ccc(N4CCN(C(=O)N5CCC(F)(F)C5)CC4)nc3)c3c(C#N)cnn3c2)cn1] | 4-(6-(4-(3,3-difluoropyrrolidine-1-carbonyl)piperazin-1-yl)pyridin-3-yl)-6-(1-methyl-1H-pyrazol-4-yl)pyrazolo[1,5-a]pyridine-3-carbonitrile | 518.1 (M + H) |
| 102 | 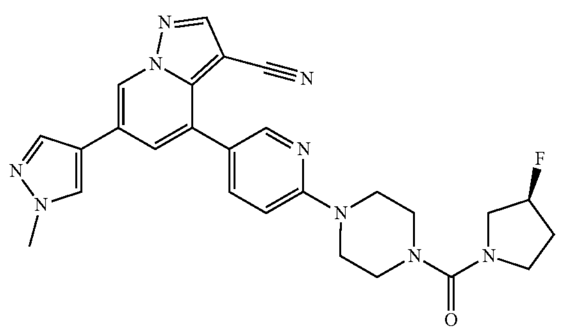 [SMILES: Cn1cc(-c2cc(-c3ccc(N4CCN(C(=O)N5CC[C@H](F)C5)CC4)nc3)c3c(C#N)cnn3c2)cn1] | (S)-4-(6-(4-(3-fluoropyrrolidine-1-carbonyl)piperazin-1-yl)pyridin-3-yl)-6-(1-methyl-1H-pyrazol-4-yl)pyrazolo[1,5-a]pyridine-3-carbonitrile | 500.1 (M + H) |
| 103 | 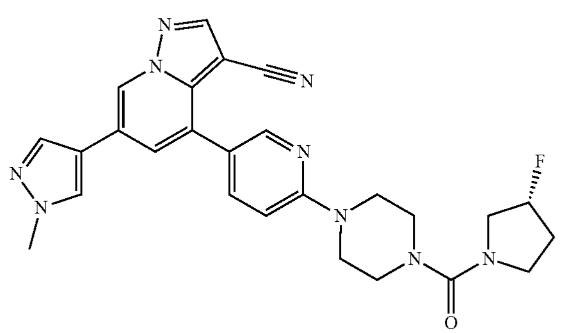 [SMILES: Cn1cc(-c2cc(-c3ccc(N4CCN(C(=O)N5CC[C@@H](F)C5)CC4)nc3)c3c(C#N)cnn3c2)cn1] | (R)-4-(6-(4-(3-fluoropyrrolidine-1-carbonyl)piperazin-1-yl)pyridin-3-yl)-6-(1-methyl-1H-pyrazol-4-yl)pyrazolo[1,5-a]pyridine-3-carbonitrile | 500.1 (M + H) |
| 104 | 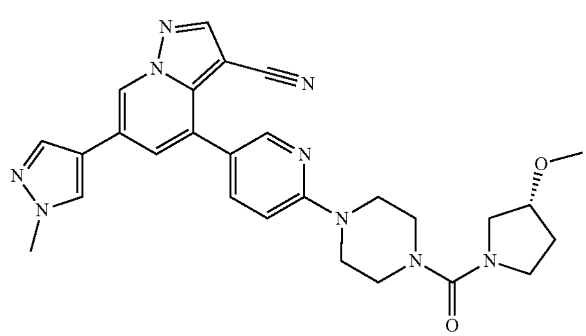 [SMILES: CO[C@@H]1CCN(C(=O)N2CCN(c3ccc(-c4cc(-c5cnn(C)c5)cn5ncc(C#N)c45)cn3)CC2)C1] | (R)-4-(6-(4-(3-methoxypyrrolidine-1-carbonyl)piperazin-1-yl)pyridin-3-yl)-6-(1-methyl-1H-pyrazol-4-yl)pyrazolo[1,5-a]pyridine-3-carbonitrile | 512.1 (M + H) |

TABLE L-continued

| Ex # | Structure | Chemical Name | MS (apci) m/z |
|---|---|---|---|
| 105 | 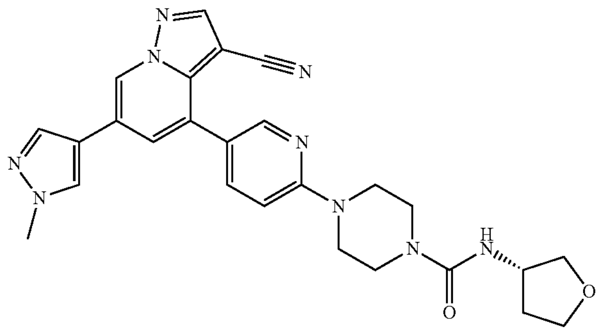 [SMILES: Cn1cc(-c2cc(-c3ccc(N4CCN(C(=O)N[C@H]5CCOC5)CC4)nc3)c3c(C#N)cnn3c2)cn1] | (S)-4-(5-(3-cyano-6-(1-methyl-1H-pyrazol-4-yl)pyrazolo[1,5-a]pyridin-4-yl)pyridin-2-yl)-N-(tetrahydrofuran-3-yl)piperazine-1-carboxamide | 498.1 (M + H) |
| 106 | 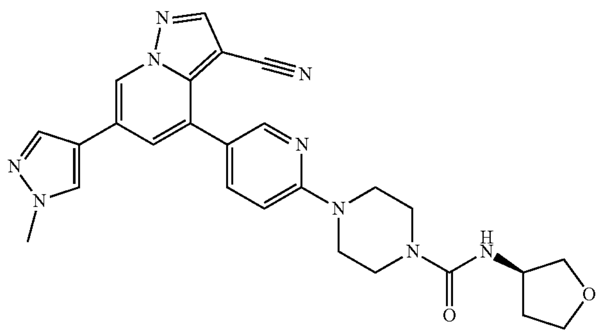 [SMILES: Cn1cc(-c2cc(-c3ccc(N4CCN(C(=O)N[C@@H]5CCOC5)CC4)nc3)c3c(C#N)cnn3c2)cn1] | (R)-4-(5-(3-cyano-6-(1-methyl-1H-pyrazol-4-yl)pyrazolo[1,5-a]pyridin-4-yl)pyridin-2-yl)-N-(tetrahydrofuran-3-yl)piperazine-1-carboxamide | 498.2 (M + H) |
| 107 | 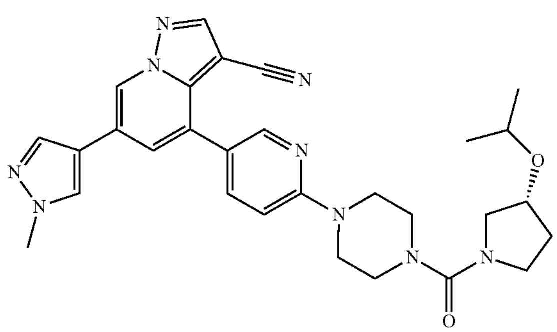 [SMILES: CC(C)O[C@@H]1CCN(C(=O)N2CCN(c3ccc(-c4cc(-c5cnn(C)c5)cn5ncc(C#N)c45)cn3)CC2)C1] | (R)-4-(6-(4-(3-isopropoxypyrrolidine-1-carbonyl)piperazin-1-yl)pyridin-3-yl)-6-(1-methyl-1H-pyrazol-4-yl)pyrazolo[1,5-a]pyridine-3-carbonitrile | 540.2 (M + H) |
| 108 | 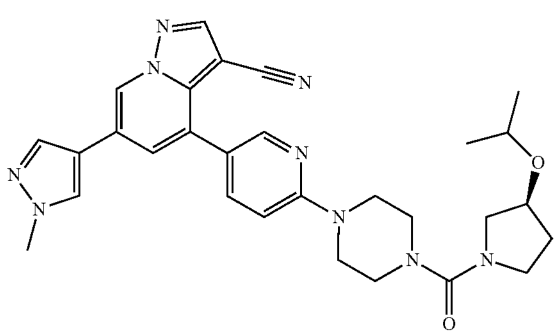 [SMILES: CC(C)O[C@H]1CCN(C(=O)N2CCN(c3ccc(-c4cc(-c5cnn(C)c5)cn5ncc(C#N)c45)cn3)CC2)C1] | (S)-4-(6-(4-(3-isopropoxypyrrolidine-1-carbonyl)piperazin-1-yl)pyridin-3-yl)-6-(1-methyl-1H-pyrazol-4-yl)pyrazolo[1,5-a]pyridine-3-carbonitrile | 540.2 (M + H) |

TABLE L-continued

| Ex # | Structure | Chemical Name | MS (apci) m/z |
|---|---|---|---|
| 109 | 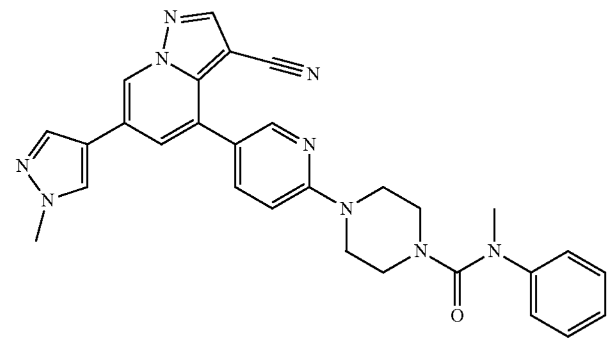 [SMILES: CN(C(=O)N1CCN(c2ccc(-c3cc(-c4cnn(C)c4)cn4ncc(C#N)c34)cn2)CC1)c1ccccc1] | 4-(5-(3-cyano-6-(1-methyl-1H-pyrazol-4-yl)pyrazolo[1,5-a]pyridin-4-yl)pyridin-2-yl)-N-methyl-N-phenylpiperazine-1-carboxamide | 518.2 (M + H) |
| 110 | 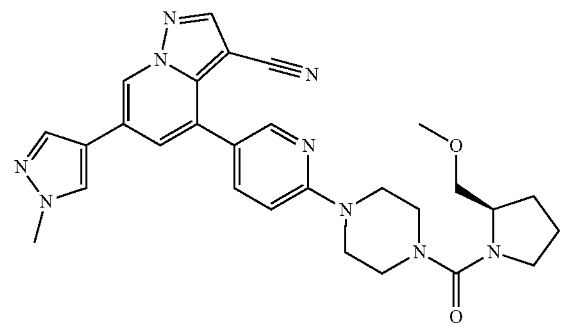 [SMILES: COC[C@H]1CCCN1C(=O)N1CCN(c2ccc(-c3cc(-c4cnn(C)c4)cn4ncc(C#N)c34)cn2)CC1] | (R)-4-(6-(4-(2-(methoxymethyl)pyrrolidine-1-carbonyl)piperazin-1-yl)pyridin-3-yl)-6-(1-methyl-1H-pyrazol-4-yl)pyrazolo[1,5-a]pyridine-3-carbonitrile | 526.2 (M + H) |
| 111 | 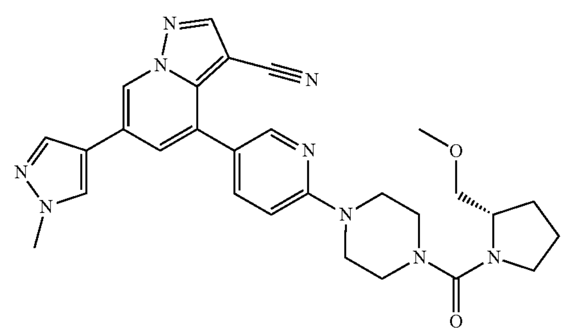 [SMILES: COC[C@@H]1CCCN1C(=O)N1CCN(c2ccc(-c3cc(-c4cnn(C)c4)cn4ncc(C#N)c34)cn2)CC1] | (S)-4-(6-(4-(2-(methoxymethyl)pyrrolidine-1-carbonyl)piperazin-1-yl)pyridin-3-yl)-6-(1-methyl-1H-pyrazol-4-yl)pyrazolo[1,5-a]pyridine-3-carbonitrile | 526.2 (M + H) |
| 112 | 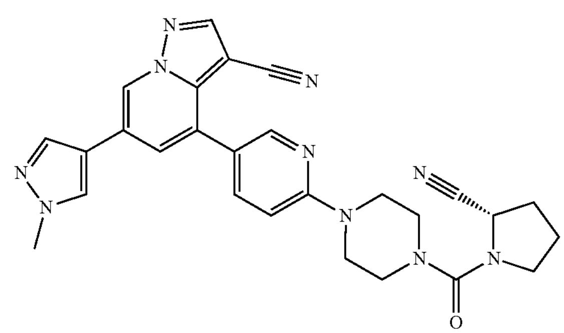 [SMILES: Cn1cc(-c2cc(-c3ccc(N4CCN(C(=O)N5CCC[C@H]5C#N)CC4)nc3)c3c(C#N)cnn3c2)cn1] | (S)-4-(6-(4-(2-cyanopyrrolidine-1-carbonyl)piperazin-1-yl)pyridin-3-yl)-6-(1-methyl-1H-pyrazol-4-yl)pyrazolo[1,5-a]pyridine-3-carbonitrile | 507.1 (M + H) |

TABLE L-continued

| Ex # | Structure | Chemical Name | MS (apci) m/z |
|---|---|---|---|
| 113 | 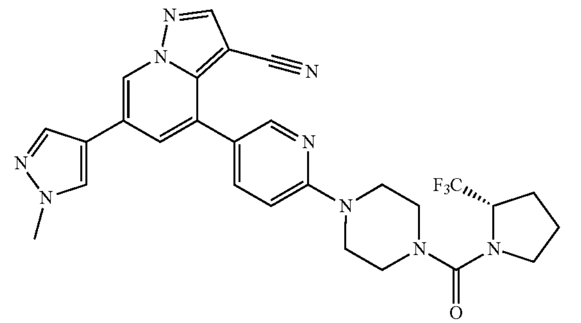 [SMILES: Cn1cc(-c2cc(-c3ccc(N4CCN(C(=O)N5CCC[C@H]5C(F)(F)F)CC4)nc3)c3c(C#N)cnn3c2)cn1] | (S)-6-(1-methyl-1H-pyrazol-4-yl)-4-(6-(4-(2-(trifluoromethyl)pyrrolidine-1-carbonyl)piperazin-1-yl)pyridin-3-yl)pyrazolo[1,5-a]pyridine-3-carbonitrile | 550.1 (M + H) |
| 114 | 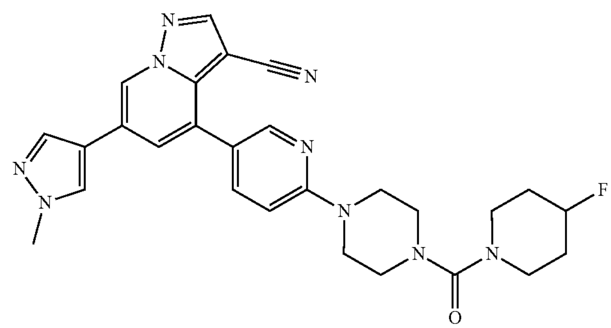 [SMILES: Cn1cc(-c2cc(-c3ccc(N4CCN(C(=O)N5CCC(F)CC5)CC4)nc3)c3c(C#N)cnn3c2)cn1] | 4-(6-(4-(4-fluoropiperidine-1-carbonyl)piperazin-1-yl)pyridin-3-yl)-6-(1-methyl-1H-pyrazol-4-yl)pyrazolo[1,5-a]pyridine-3-carbonitrile | 514.1 (M + H) |
| 115 | 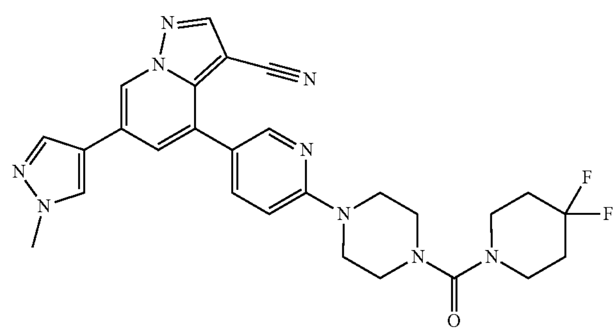 [SMILES: Cn1cc(-c2cc(-c3ccc(N4CCN(C(=O)N5CCC(F)(F)CC5)CC4)nc3)c3c(C#N)cnn3c2)cn1] | 4-(6-(4-(4,4-difluoropiperidine-1-carbonyl)piperazin-1-yl)pyridin-3-yl)-6-(1-methyl-1H-pyrazol-4-yl)pyrazolo[1,5-a]pyridine-3-carbonitrile | 532.2 (M + H) |
| 116 | 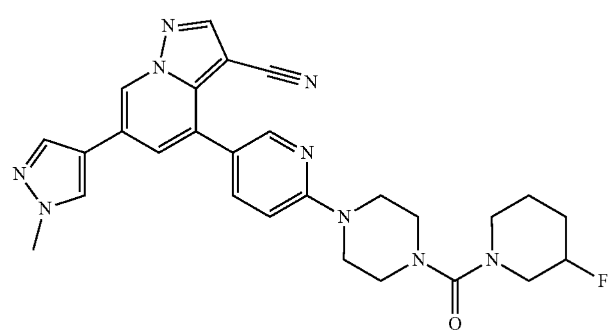 [SMILES: Cn1cc(-c2cc(-c3ccc(N4CCN(C(=O)N5CCCC(F)C5)CC4)nc3)c3c(C#N)cnn3c2)cn1] | 4-(6-(4-(3-fluoropiperidine-1-carbonyl)piperazin-1-yl)pyridin-3-yl)-6-(1-methyl-1H-pyrazol-4-yl)pyrazolo[1,5-a]pyridine-3-carbonitrile | 514.1 (M + H) |

TABLE L-continued

| Ex # | Structure | Chemical Name | MS (apci) m/z |
|---|---|---|---|
| 117 | 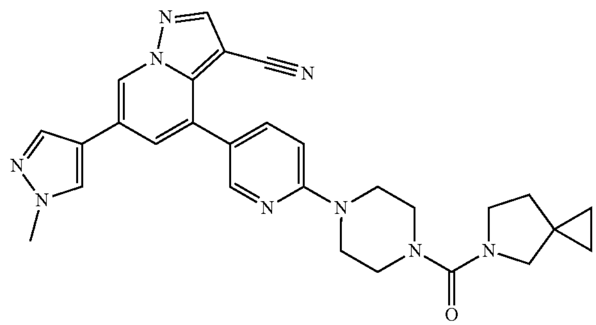 [SMILES: Cn1cc(-c2cc(-c3ccc(N4CCN(C(=O)N5CCC6(CC6)C5)CC4)nc3)c3c(C#N)cnn3c2)cn1] | 4-(6-(4-(5-azaspiro[2.4]heptane-5-carbonyl)piperazin-1-yl)pyridin-3-yl)-6-(1-methyl-1H-pyrazol-4-yl)pyrazolo[1,5-a]pyridine-3-carbonitrile | 508.1 (M + H) |
| 118 | 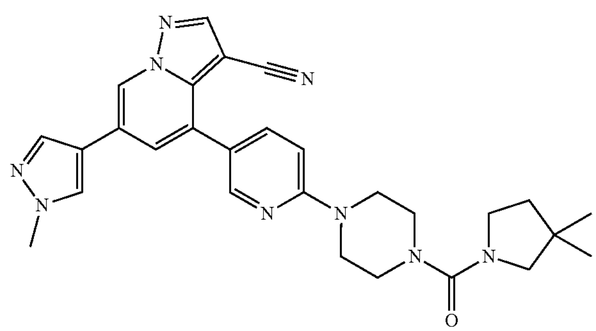 [SMILES: Cn1cc(-c2cc(-c3ccc(N4CCN(C(=O)N5CCC(C)(C)C5)CC4)nc3)c3c(C#N)cnn3c2)cn1] | 4-(6-(4-(3,3-dimethylpyrrolidine-1-carbonyl)piperazin-1-yl)pyridin-3-yl)-6-(1-methyl-1H-pyrazol-4-yl)pyrazolo[1,5-a]pyridine-3-carbonitrile | 510.2 (M + H) |
| 119 | 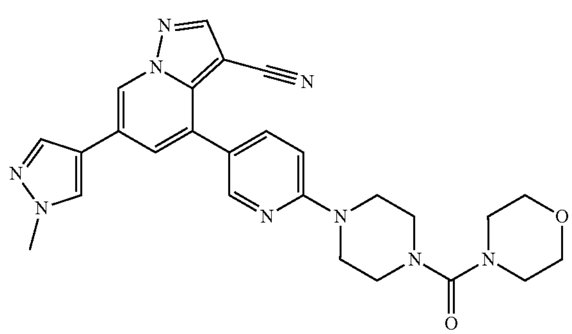 [SMILES: Cn1cc(-c2cc(-c3ccc(N4CCN(C(=O)N5CCOCC5)CC4)nc3)c3c(C#N)cnn3c2)cn1] | 6-(1-methyl-1H-pyrazol-4-yl)-4-(6-(4-(morpholine-4-carbonyl)piperazin-1-yl)pyridin-3-yl)pyrazolo[1,5-a]pyridine-3-carbonitrile | 498.1 (M + H) |
| 120 | 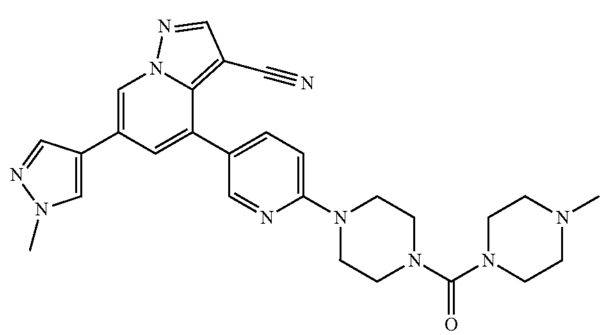 [SMILES: CN1CCN(C(=O)N2CCN(c3ccc(-c4cc(-c5cnn(C)c5)cn5ncc(C#N)c45)cn3)CC2)CC1] | 6-(1-methyl-1H-pyrazol-4-yl)-4-(6-(4-(4-methylpiperazine-1-carbonyl)piperazin-1-yl)pyridin-3-yl)pyrazolo[1,5-a]pyridine-3-carbonitrile | 511.2 (M + H) |

TABLE L-continued

| Ex # | Structure | Chemical Name | MS (apci) m/z |
|---|---|---|---|
| 121 | 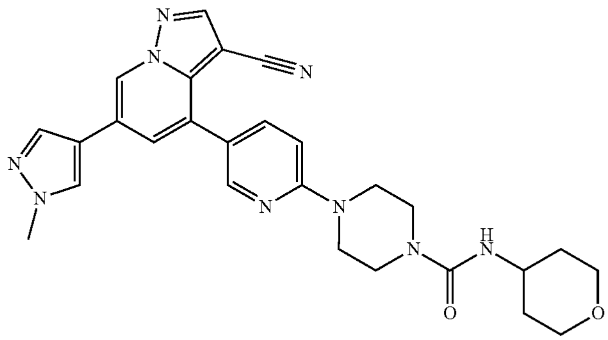 [SMILES: Cn1cc(-c2cc(-c3ccc(N4CCN(C(=O)NC5CCOCC5)CC4)nc3)c3c(C#N)cnn3c2)cn1] | 4-(5-(3-cyano-6-(1-methyl-1H-pyrazol-4-yl)pyrazolo[1,5-a]pyridin-4-yl)pyridin-2-yl)-N-(tetrahydro-2H-pyran-4-yl)piperazine-1-carboxamide | 512.2 (M + H) |
| 122 | 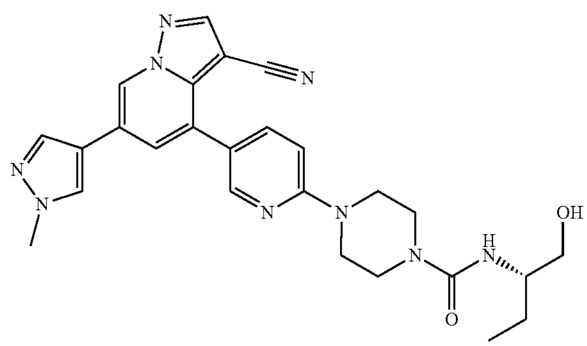 [SMILES: CC[C@@H](CO)NC(=O)N1CCN(c2ccc(-c3cc(-c4cnn(C)c4)cn4ncc(C#N)c34)cn2)CC1] | (S)-4-(5-(3-cyano-6-(1-methyl-1H-pyrazol-4-yl)pyrazolo[1,5-a]pyridin-4-yl)pyridin-2-yl)-N-(1-hydroxybutan-2-yl)piperazine-1-carboxamide | 500.1 (M + H) |
| 123 | 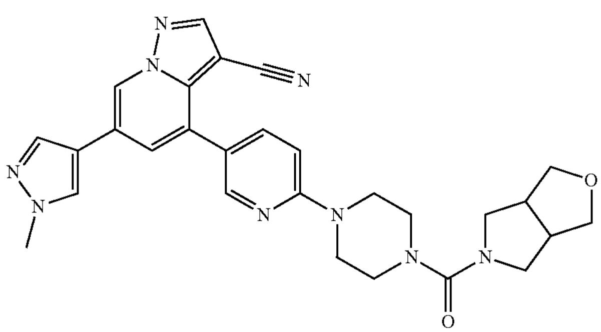 [SMILES: Cn1cc(-c2cc(-c3ccc(N4CCN(C(=O)N5CC6COCC6C5)CC4)nc3)c3c(C#N)cnn3c2)cn1] | 4-(6-(4-(hexahydro-1H-furo[3,4-c]pyrrole-5-carbonyl)piperazin-1-yl)pyridin-3-yl)-6-(1-methyl-1H-pyrazol-4-yl)pyrazolo[1,5-a]pyridine-3-carbonitrile | 524.2 (M + H) |
| 124 | 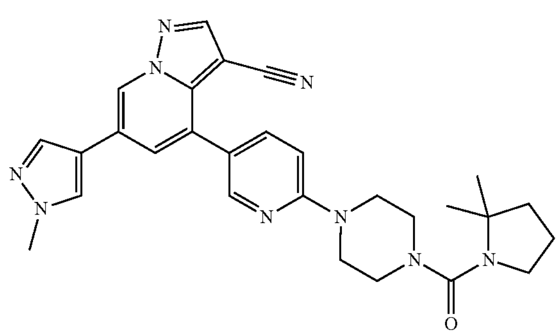 [SMILES: Cn1cc(-c2cc(-c3ccc(N4CCN(C(=O)N5CCCC5(C)C)CC4)nc3)c3c(C#N)cnn3c2)cn1] | 4-(6-(4-(2,2-dimethylpyrrolidine-1-carbonyl)piperazin-1-yl)pyridin-3-yl)-6-(1-methyl-1H-pyrazol-4-yl)pyrazolo[1,5-a]pyridine-3-carbonitrile | 510.1 (M + H) |

Example 125

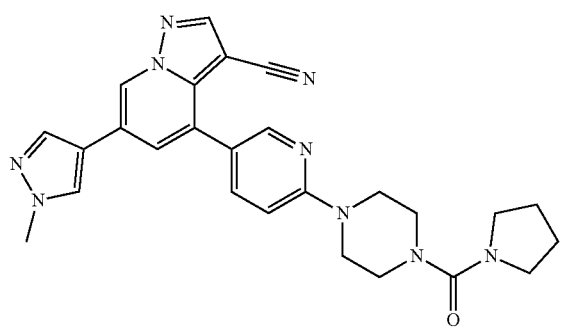 [SMILES: Cn1cc(-c2cc(-c3ccc(N4CCN(C(=O)N5CCCC5)CC4)nc3)c3c(C#N)cnn3c2)cn1]

6-(1-methyl-1H-pyrazol-4-yl)-4-(6-(4-(pyrrolidine-1-carbonyl)piperazin-1-yl)pyridin-3-yl)pyrazolo[1,5-a]pyridine-3-carbonitrile A suspension of 6-(1-methyl-1H-pyrazol-4-yl)-4-(6-(piperazin-1-yl)pyridin-3-yl)pyrazolo[1,5-a]pyridine-3-carbonitrile (100 mg, 0.260 mmol) and DIEA (136 µL, 0.780 mmol) in DCM (1.30 mL) at ambient temperature was treated with pyrrolidine-1-carbonyl chloride (52 mg, 0.39 mmol). The suspension was stirred overnight at ambient temperature and concentrated in vacuo to remove the bulk of the DCM and then diluted with hot DMSO (1 mL). The resulting solution was directly purified by reverse phase chromatography (5-60% ACN/water) to provide the title compound (66.4 mg, 53% yield). MS (apci) m/z=482.1 (M+H). $^1$H NMR (CDCl$_3$) δ 8.61 (d, 1H), 8.35 (d, 1H), 8.24 (s, 1H), 7.77 (s, 1H), 7.74 (dd, 1H), 7.66 (s, 1H), 7.37 (d, 1H), 6.76 (d, 1H), 3.97 (s, 3H), 3.65-3.68 (m, 4H), 3.38-3.44 (m, 8H), 1.82-1.86 (m, 4H).

Example 125a

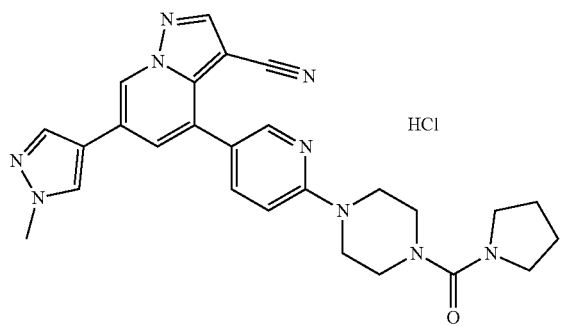 [SMILES: Cn1cc(-c2cc(-c3ccc(N4CCN(C(=O)N5CCCC5)CC4)nc3)c3c(C#N)cnn3c2)cn1 ; Cl]

6-(1-methyl-1H-pyrazol-4-yl)-4-(6-(4-(pyrrolidine-1-carbonyl)piperazin-1-yl)pyridin-3-yl)pyrazolo[1,5-a]pyridine-3-carbonitrile Hydrochloride To a solution of 6-(1-methyl-1H-pyrazol-4-yl)-4-(6-(4-(pyrrolidine-1-carbonyl)piperazin-1-yl)pyridin-3-yl)pyrazolo[1,5-a]pyridine-3-carbonitrile (Example 125, 50 mg, 0.10 mmol) in DCM (5 mL) was added 5 M HCl in iPrOH (29 µL, 0.15 mmol). After 30 min, the mixture was concentrated in vacuo to afford the title compound as a white solid (55 mg, quantitative yield). MS (apci) m/z=482.0 (M+H).

Example 126

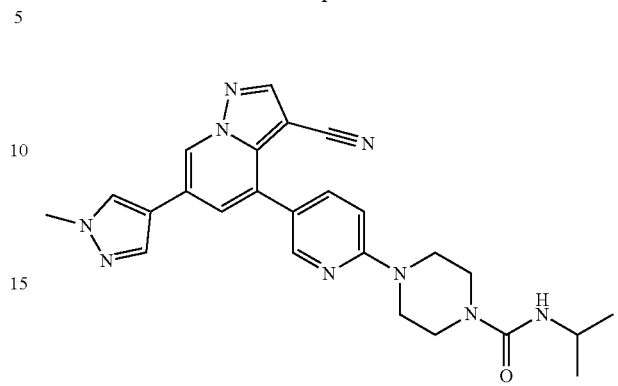

4-(5-(3-cyano-6-(1-methyl-1H-pyrazol-4-yl)pyrazolo[1,5-a]pyridin-4-yl)pyridin-2-yl)-N-isopropylpiperazine-1-carboxamide To a mixture of 6-(1-methyl-1H-pyrazol-4-yl)-4-(6-(piperazin-1-yl)pyridin-3-yl)pyrazolo[1,5-a]pyridine-3-carbonitrile (15 mg, 0.039 mmol) and DIEA (34 µL, 0.20 mmol) in DCM (195 µL) was added 2-isocyanatopropane (3.3 mg, 0.039 mmol) in one portion at ambient temperature. The resulting mixture was stirred overnight and then diluted with EtOAc (0.5 mL). The resulting suspension was vacuum filtered and successively rinsed with EtOAc (2 mL) and MTBE (1 mL). The isolated solids were taken up in DMSO and purified by reverse phase chromatography (5-60% ACN/water) to afford the title compound (7.9 mg, 43% yield). MS (apci) m/z=470.2. $^1$H NMR (CDCl$_3$) δ 8.62 (d, 1H), 8.36 (d, 1H), 8.24 (s, 1H), 7.77 (s, 1H), 7.74 (dd, 1H), 7.66 (s, 1H), 7.37 (d, 1H), 6.75 (d, 1H), 4.21 (d, 1H), 4.00 (m, 1H), 3.97 (s, 3H), 3.68-3.71 (m, 4H), 3.50-3.53 (m, 4H), 1.18 (m, 6H).

Example 127

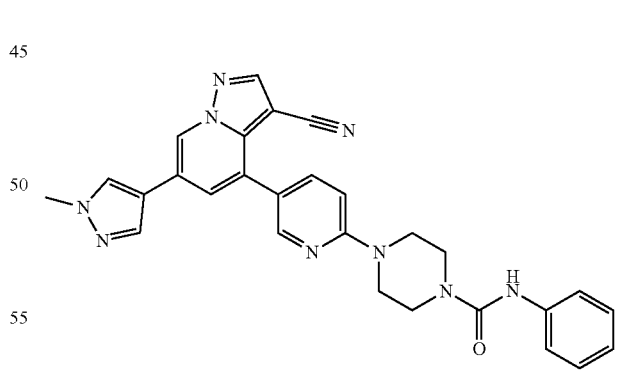

4-(5-(3-cyano-6-(1-methyl-1H-pyrazol-4-yl)pyrazolo[1,5-a]pyridin-4-yl)pyridin-2-yl)-N-phenylpiperazine-1-carboxamide To a suspension of 6-(1-methyl-1H-pyrazol-4-yl)-4-(6-(piperazin-1-yl)pyridin-3-yl)pyrazolo[1,5-a]pyridine-3-carbonitrile dihydrochloride (16 mg, 0.035 mmol) and DIEA (30 µL, 0.17 mmol) in DCM (175 µL) was added isocyanatobenzene (4.6 mg, 0.038 mmol). The resulting mixture was stirred at ambient temperature for 4 h and then diluted with EtOAc (0.5 mL), vacuum filtered and rinsed with EtOAc (2 mL) to afford the title compound (18 mg, 100% yield). MS (apci) m/z=504.1 (M+H).

The compounds in Table M were prepared according the method used for the synthesis of Example 127, replacing isocyanatobenzene with the appropriate isocyanate starting material.

4-(5-(3-cyano-6-(1-methyl-1H-pyrazol-4-yl)pyrazolo[1,5-a]pyridin-4-yl)pyridin-2-yl)-N-(2-methoxyethyl)-N-methylpiperazine-1-carboxamide 2,2,2-trifluoroacetate To a solution of 6-(1-methyl-1H-pyrazol-4-yl)-4-(6-(piperazin-1-yl)pyridin-3-yl)pyrazolo[1,5-a]pyridine-3-carbonitrile dihydrochloride (30 mg 0.066 mmol) in DMF (1.0 mL) was added (4-nitrophenyl) carbonochloridate (18.88 mg,

TABLE M

| Ex # | Structure | Chemical Name | MS (apci) m/z |
|------|-----------|---------------|---------------|
| 128 | 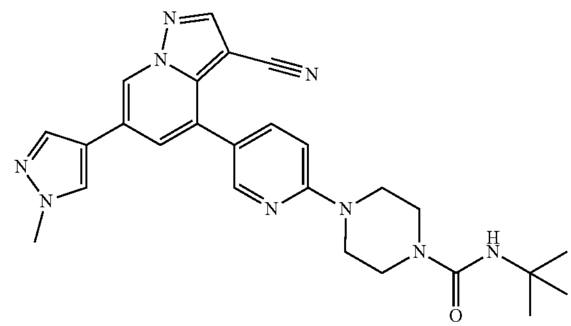 [SMILES: Cn1cc(-c2cc(-c3ccc(N4CCN(C(=O)NC(C)(C)C)CC4)nc3)c3c(C#N)cnn3c2)cn1] | N-(tert-butyl)-4-(5-(3-cyano-6-(1-methyl-1H-pyrazol-4-yl)pyrazolo[1,5-a]pyridin-4-yl)pyridin-2-yl)piperazine-1-carboxamide | 484.1 (M + H) |
| 129 | 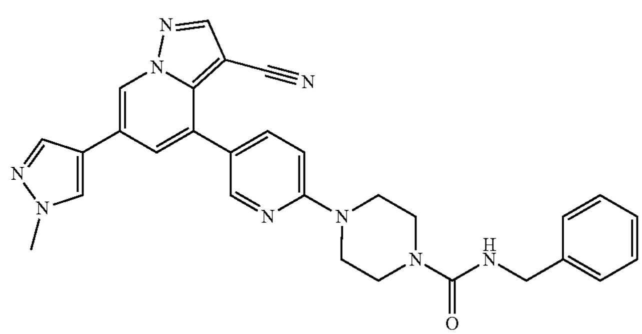 [SMILES: Cn1cc(-c2cc(-c3ccc(N4CCN(C(=O)NCc5ccccc5)CC4)nc3)c3c(C#N)cnn3c2)cn1] | N-benzyl-4-(5-(3-cyano-6-(1-methyl-1H-pyrazol-4-yl)pyrazolo[1,5-a]pyridin-4-yl)pyridin-2-yl)piperazine-1-carboxamide | 518.1 (M + H) |

Example 130

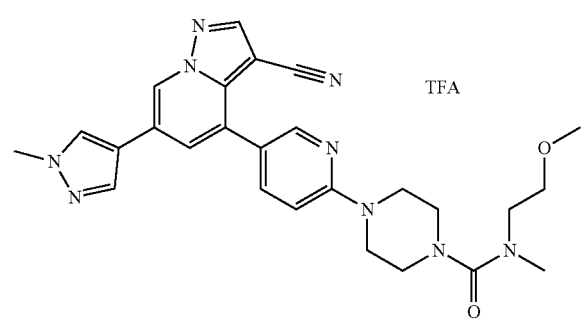

0.094 mmol), DMAP (1.91 mg, 0.016 mmol) and DIEA (83 µL, 0.47 mmol). The mixture was stirred at ambient temperature for 12 h, and then 2-methoxy-N-methyl-ethanamine (7.65 mg, 0.086 mmol) was added in one portion. The reaction mixture was stirred at 45° C. for 12 h and then directly purified by reverse-phase preparative HPLC (10 to 80% acetonitrile/water with 0.1 v/v % TFA) to give the title compound (10 mg, 25% yield). MS (ES-API Pos) m/z=500.4 (M+H), 522.3 (M+Na).

The compounds in Table N were prepared according the method described for the synthesis of Example 130, replacing 2-methoxy-N-methyl-ethanamine with the appropriate amine starting material. All compounds were purified similarly by reverse-phase preparative HPLC (10 to 80% acetonitrile/water with 0.1 v/v % TFA or 0.04 v/v % NH$_4$OH) to yield the title compound as TFA salt unless otherwise stated.

TABLE N

| Ex # | Structure | Chemical Name | MS (apci) m/z |
|---|---|---|---|
| 131 | 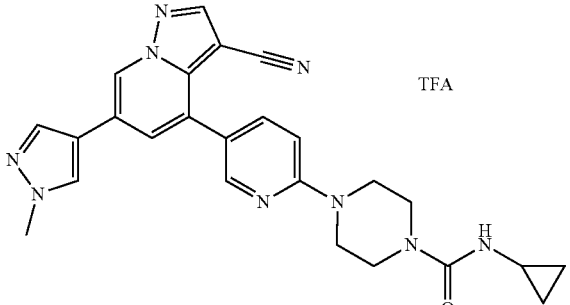 TFA | 4-(5-(3-cyano-6-(1-methyl-1H-pyrazol-4-yl)pyrazolo[1,5-a]pyridin-4-yl)pyridin-2-yl)-N-cyclopropylpiperazine-1-carboxamide 2,2,2-trifluoroacetate | 468.2 (M + H) |
| 132 | 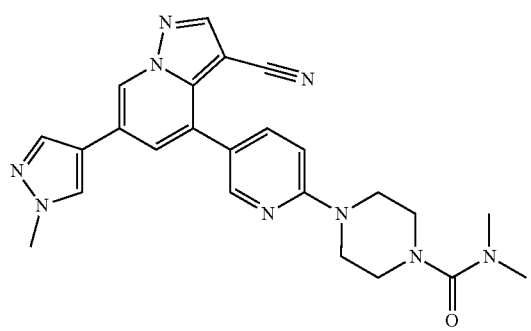 | 4-(5-(3-cyano-6-(1-methyl-1H-pyrazol-4-yl)pyrazolo[1,5-a]pyridin-4-yl)pyridin-2-yl)-N,N-dimethylpiperazine-1-carboxamide | 456.2 (M + H) |
| 133 | 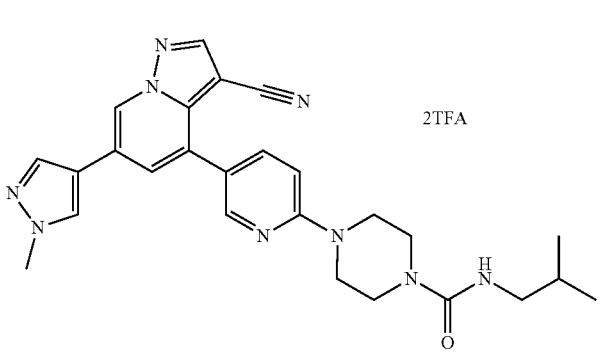 2TFA | 4-(5-(3-cyano-6-(1-methyl-1H-pyrazol-4-yl)pyrazolo[1,5-a]pyridin-4-yl)pyridin-2-yl)-N-isobutylpiperazine-1-carboxamide | 484.2 (M + H) |
| 134 | 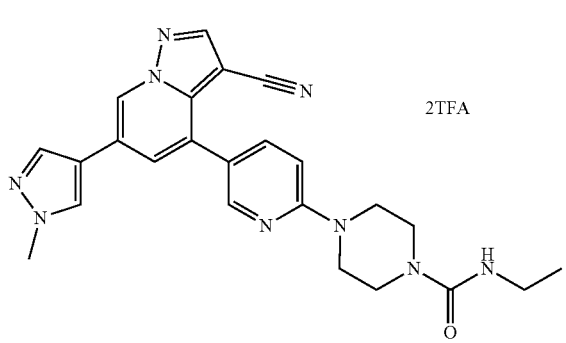 2TFA | 4-(5-(3-cyano-6-(1-methyl-1H-pyrazol-4-yl)pyrazolo[1,5-a]pyridin-4-yl)pyridin-2-yl)-N-ethylpiperazine-1-carboxamide | 456.2 (M + H) |

TABLE N-continued

| Ex # | Structure | Chemical Name | MS (apci) m/z |
|---|---|---|---|
| 135 | 2TFA | 4-(5-(3-cyano-6-(1-methyl-1H-pyrazol-4-yl)pyrazolo[1,5-a]pyridin-4-yl)pyridin-2-yl)-N-(2-methoxyethyl)piperazine-1-carboxamide | 486.2 (M + H) |
| 136 | 2TFA | 4-(5-(3-cyano-6-(1-methyl-1H-pyrazol-4-yl)pyrazolo[1,5-a]pyridin-4-yl)pyridin-2-yl)-N-ethyl-N-methylpiperazine-1-carboxamide | 470.2 (M + H) |

Example 137

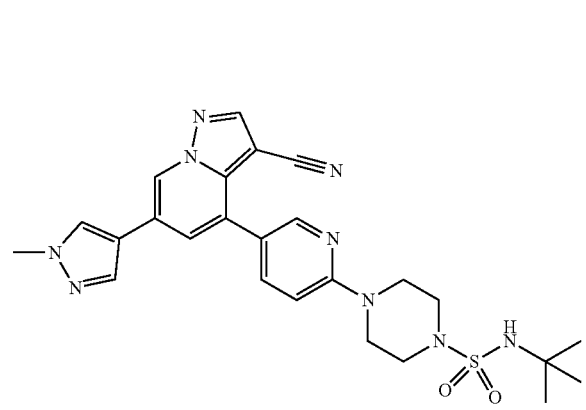 [SMILES: Cn1cc(-c2cc(-c3ccc(N4CCN(S(=O)(=O)NC(C)(C)C)CC4)nc3)c3c(C#N)cnn3c2)cn1]

N-(tert-butyl)-4-(5-(3-cyano-6-(1-methyl-1H-pyrazol-4-yl)pyrazolo[1,5-a]pyridin-4-yl)pyridin-2-yl)piperazine-1-sulfonamide To a solution of 6-(1-methyl-1H-pyrazol-4-yl)-4-(6-(piperazin-1-yl)pyridin-3-yl)pyrazolo[1,5-a]pyridine-3-carbonitrile dihydrochloride (10 mg, 0.022 mmol) in DCM (2 mL) was added tert-butylsulfamoyl chloride (4.5 mg, 0.026 mmol) followed by TEA (30 µL, 0.22 mmol). The mixture was stirred overnight at ambient temperature and then quenched with water and extracted with DCM in a PS frit. The combined DCM extracts were concentrated and purified by reverse phase chromatography (0-80% ACN/water) to provide the title compound (2.6 mg, 23% yield). MS (apci) m/z=520.2 (M+H).

Example 138

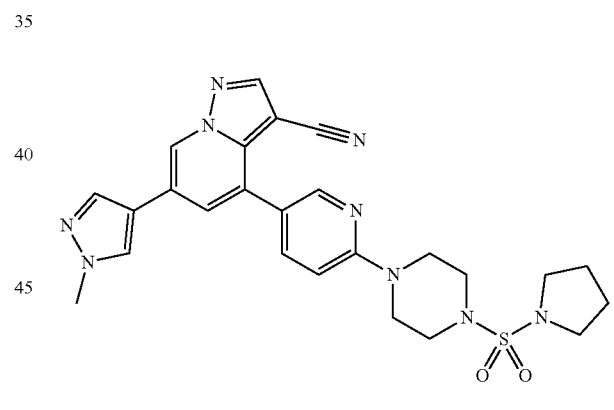

6-(1-methyl-1H-pyrazol-4-yl)-4-(6-(4-(pyrrolidin-1-ylsulfonyl)piperazin-1-yl)pyridin-3-yl)pyrazolo[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile dihydrochloride (15 mg, 0.033 mmol) in DCM (2 mL) was added pyrrolidine-1-sulfonyl chloride (5.6 mg, 0.033 mmol) followed by TEA (46 µL, 0.33 mmol). The mixture was stirred overnight at ambient temperature and then quenched with water and extracted with DCM in a PS frit. The combined DCM extracts were concentrated and purified by reverse phase chromatography (0-80% ACN/water) to provide the title compound (13 mg, 77% yield). MS (apci) m/z=518.1 (M+H).

Example 139

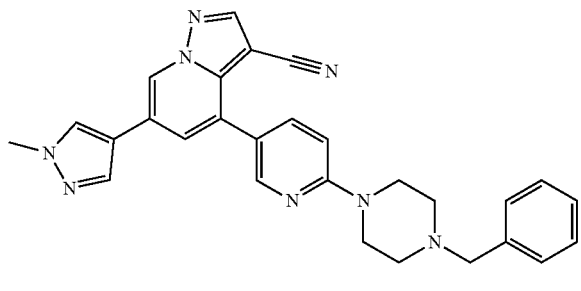 [SMILES: Cn1cc(-c2cc(-c3ccc(N4CCN(Cc5ccccc5)CC4)nc3)c3c(C#N)cnn3c2)cn1]

4-(6-(4-benzylpiperazin-1-yl)pyridin-3-yl)-6-(1-methyl-1H-pyrazol-4-yl)pyrazolo[1,5-a]pyridine-3-carbonitrile A solution of 6-(1-methyl-1H-pyrazol-4-yl)-4-(6-(piperazin-1-yl)pyridin-3-yl)pyrazolo[1,5-a]pyridine-3-carbonitrile dihydrochloride (15 mg, 0.0328 mmol) in DMF (0.2 mL) and TEA (22.9 µL, 0.164 mmol) was treated with (bromomethyl)benzene (11.2 mg, 0.0656 mmol). The reaction mixture was stirred at ambient temperature for 1 h and then directly purified by reverse phase chromatography (0-70% ACN/water) to afford the title compound (12.3 mg, 79% yield). MS (apci) m/z=475.1 (M+H).

Example 140

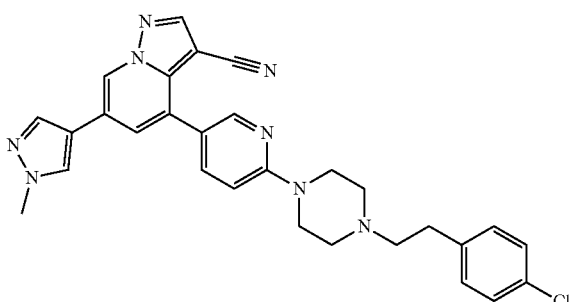

4-(6-(4-(4-chlorophenethyl)piperazin-1-yl)pyridin-3-yl)-6-(1-methyl-1H-pyrazol-4-yl)pyrazolo[1,5-a]pyridine-3-carbonitrile A mixture of 6-(1-methyl-1H-pyrazol-4-yl)-4-(6-(piperazin-1-yl)pyridin-3-yl)pyrazolo[1,5-a]pyridine-3-carbonitrile dihydrochloride (20 mg, 0.044 mmol), 1-(2-bromoethyl)-4-chlorobenzene (12 mg, 0.052 mmol) and N-ethyl-N-isopropylpropan-2-amine (39 µL, 0.22 mmol) in DMA (219 µL) was heated at 65° C. overnight, then at 100° C. for additional 2 d to reach completion as indicated by LCMS. The reaction mixture was directly purified by reverse phase chromatography (0-75% ACN/water) to yield the title compound (4.5 mg, 19% yield). MS (apci) m/z=523.0 (M+H).

Example 141

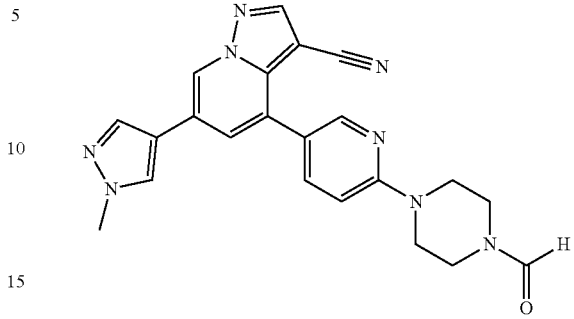

4-(6-(4-formylpiperazin-1-yl)pyridin-3-yl)-6-(1-methyl-1H-pyrazol-4-yl)pyrazolo[1,5-a]pyridine-3-carbonitrile The title compound was isolated as a side product from the chromatographic purification process in Example 140 as a white solid (1.8 mg, 9.7% yield). MS (apci) m/z=413.1 (M+H).

Example 142

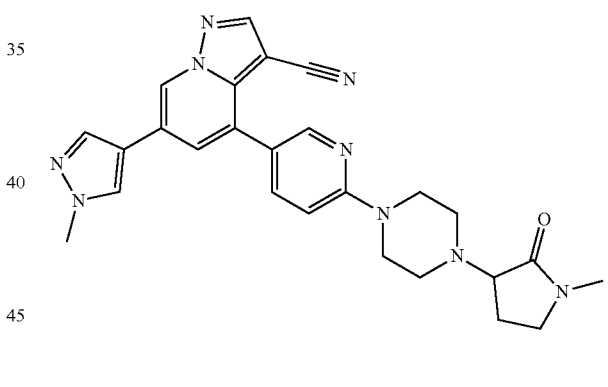

6-(1-methyl-1H-pyrazol-4-yl)-4-(6-(4-(1-methyl-2-oxopyrrolidin-3-yl)piperazin-1-yl)pyridin-3-yl)pyrazolo[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile (25 mg, 0.065 mmol) and 3-bromo-1-methylpyrrolidin-2-one (23 mg, 0.13 mmol) in DMF (1.3 mL) was added $Cs_2CO_3$ (42 mg, 0.13 mmol). The reaction mixture was heated to 80° C. and stirred overnight. After cooling to ambient temperature and diluting with water (10 mL), the reaction pH was adjusted to 8 with 1 M $HCl_{(aq)}$ and subsequently extracted with EtOAc (3×15 mL). The combined organic extracts were washed with brine (15 mL), dried ($Na_2SO_4$), filtered, concentrated and purified by silica chromatography (0-10% MeOH/DCM) to afford the title compound (2.8 mg, 8.8% yield). MS (apci) m/z=482.1 (M+H).

Example 143

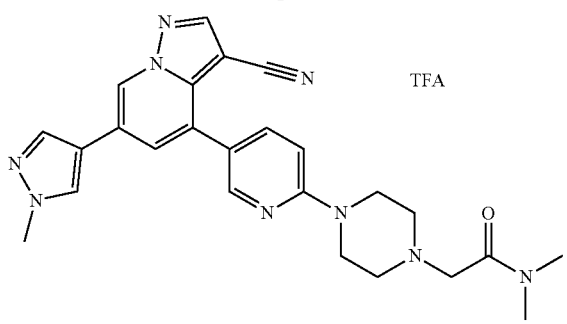 [SMILES: CN(C)C(=O)CN1CCN(c2ccc(-c3cc(-c4cnn(C)c4)cn4ncc(C#N)c34)cn2)CC1]

2-(4-(5-(3-cyano-6-(1-methyl-1H-pyrazol-4-yl)pyrazolo[1,5-a]pyridin-4-yl)pyridin-2-yl)piperazin-1-yl)-N,N-dimethylacetamide 2,2,2-trifluoroacetate To a mixture of 6-(1-methyl-1H-pyrazol-4-yl)-4-(6-(piperazin-1-yl)pyridin-3-yl)pyrazolo[1,5-a]pyridine-3-carbonitrile dihydrochloride (30 mg, 0.066 mmol) in ACN (1 mL) as ambient temperature were added K₂CO₃ (18 mg, 0.13 mmol) and 2-chloro-N,N-dimethylacetamide (9.6 mg, 0.079 mmol). The reaction mixture was stirred at ambient temperature for 12 h and purified by reverse-phase preparative HPLC (10 to 80% acetonitrile/water with 0.1 v/v % TFA) to give the title compound (23 mg, 60% yield). MS (ES-API Pos) m/z=470.3 (M+H).

The compounds in Table O were prepared according the method described for the synthesis of Example 143, replacing 2-chloro-N,N-dimethylacetamide with the appropriate alkyl halide. All compounds were purified similarly by reverse-phase preparative HPLC (10 to 80% acetonitrile/water with 0.1 v/v % TFA or 0.04 v/v % NH₄OH) to yield the title compound as TFA salt unless otherwise stated.

TABLE O

| Ex # | Structure | Chemical Name | MS (apci) m/z |
|---|---|---|---|
| 144 | 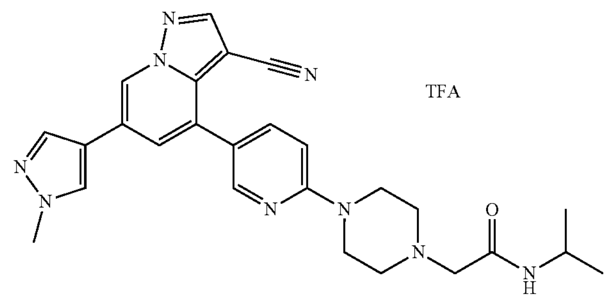 [SMILES: CC(C)NC(=O)CN1CCN(c2ccc(-c3cc(-c4cnn(C)c4)cn4ncc(C#N)c34)cn2)CC1 ; "TFA"] | 2-(4-(5-(3-cyano-6-(1-methyl-1H-pyrazol-4-yl)pyrazolo[1,5-a]pyridin-4-yl)pyridin-2-yl)piperazin-1-yl)-N-isopropylacetamide 2,2,2-trifluoroacetate | 484.2 (M + H) |
| 145 | 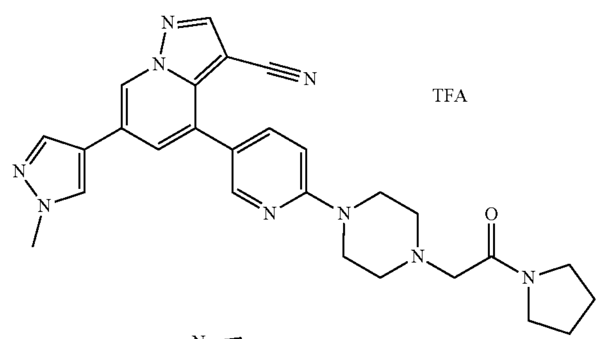 | 6-(1-methyl-1H-pyrazol-4-yl)-4-(6-(4-(2-oxo-2-(pyrrolidin-1-yl)ethyl)piperazin-1-yl)pyridin-3-yl)pyrazolo[1,5-a]pyridine-3-carbonitrile 2,2,2-trifluoroacetate | 496.2 (M + H) |
| 146 | 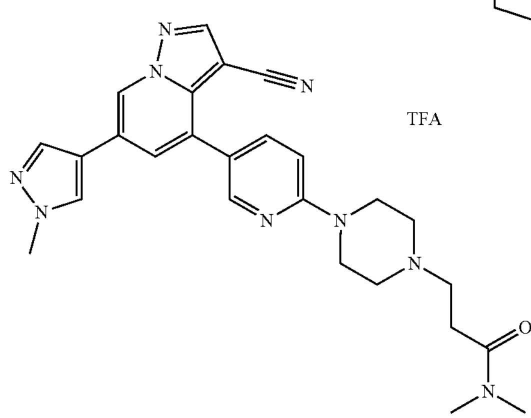 | 3-(4-(5-(3-cyano-6-(1-methyl-1H-pyrazol-4-yl)pyrazolo[1,5-a]pyridin-4-yl)pyridin-2-yl)piperazin-1-yl)-N,N-dimethylpropanamide 2,2,2-trifluoroacetate | 484.2 (M + H) |

Example 147

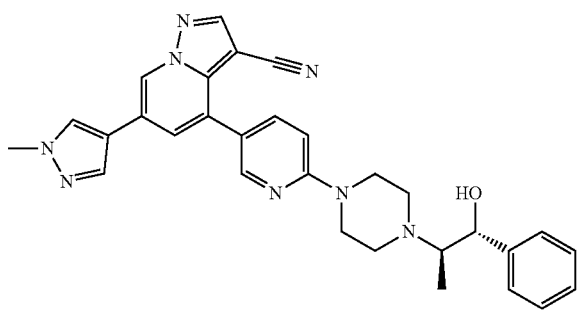 [SMILES: C[C@H]([C@H](O)c1ccccc1)N1CCN(c2ccc(-c3cc(-c4cnn(C)c4)cn4ncc(C#N)c34)cn2)CC1]

4-(6-(4-((1R,2R)-1-hydroxy-1-phenylpropan-2-yl)piperazin-1-yl)pyridin-3-yl)-6-(1-methyl-1H-pyrazol-4-yl)pyrazolo[1,5-a]pyridine-3-carbonitrile A mixture of 6-(1-methyl-1H-pyrazol-4-yl)-4-(6-(piperazin-1-yl)pyridin-3-yl)pyrazolo[1,5-a]pyridine-3-carbonitrile (25 mg, 0.0650 mmol) and (2R,3R)-2-methyl-3-phenyloxirane (8.73 mg, 0.0650 mmol) in methanol (325 µL) was stirred in a sealed vial and heated at 75° C. for 40 h. After cooling to ambient temperature, the reaction mixture was directly purified by reverse phase chromatography (C18, 5-50% ACN/water) to afford the title compound (17.0 mg, 50% yield). MS (apci) m/z=519.2 (M+H).

The compounds in Table P were prepared by a similar fashion as describe for the synthesis of Example 147, replacing (2R,3R)-2-methyl-3-phenyloxirane with the appropriate oxirane starting material.

TABLE P

| Ex # | Structure | Chemical Name | MS (apci) m/z |
|---|---|---|---|
| 148 | 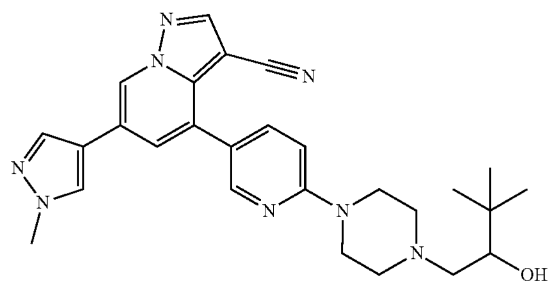 [SMILES: Cn1cc(-c2cc(-c3ccc(N4CCN(CC(O)C(C)(C)C)CC4)nc3)c3c(C#N)cnn3c2)cn1] | 4-(6-(4-(2-hydroxy-3,3-dimethylbutyl)piperazin-1-yl)pyridin-3-yl)-6-(1-methyl-1H-pyrazol-4-yl)pyrazolo[1,5-a]pyridine-3-carbonitrile | 485.1 (M + H) |
| 149 | 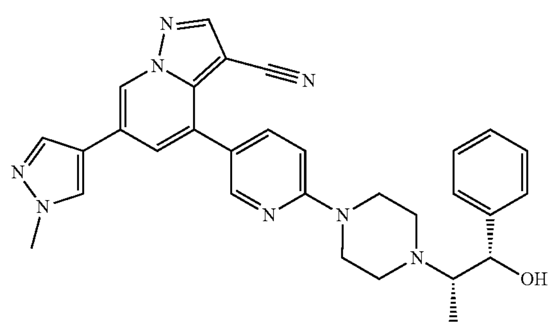 [SMILES: C[C@@H]([C@@H](O)c1ccccc1)N1CCN(c2ccc(-c3cc(-c4cnn(C)c4)cn4ncc(C#N)c34)cn2)CC1] | 4-(6-(4-((1S,2S)-1-hydroxy-1-phenylpropan-2-yl)piperazin-1-yl)pyridin-3-yl)-6-(1-methyl-1H-pyrazol-4-yl)pyrazolo[1,5-a]pyridine-3-carbonitrile | 519.2 (M + H) |
| 150 | 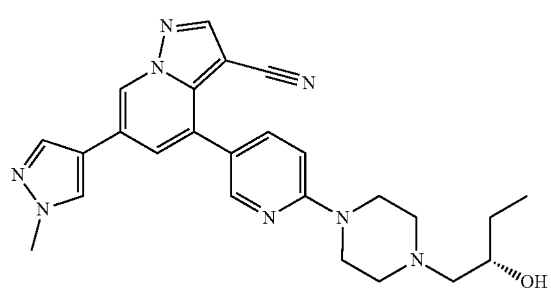 [SMILES: CC[C@H](O)CN1CCN(c2ccc(-c3cc(-c4cnn(C)c4)cn4ncc(C#N)c34)cn2)CC1] | (S)-4-(6-(4-(2-hydroxybutyl)piperazin-1-yl)pyridin-3-yl)-6-(1-methyl-1H-pyrazol-4-yl)pyrazolo[1,5-a]pyridine-3-carbonitrile | 457.2 (M + H) |

TABLE P-continued

| Ex # | Structure | Chemical Name | MS (apci) m/z |
|---|---|---|---|
| 151 | 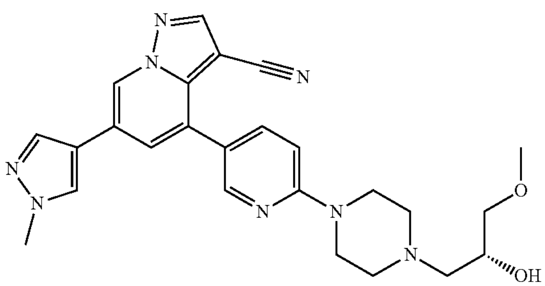 [SMILES: COC[C@H](O)CN1CCN(c2ccc(-c3cc(-c4cnn(C)c4)cn4ncc(C#N)c34)cn2)CC1] | (R)-4-(6-(4-(2-hydroxy-3-methoxypropyl)piperazin-1-yl)pyridin-3-yl)-6-(1-methyl-1H-pyrazol-4-yl)pyrazolo[1,5-a]pyridine-3-carbonitrile | 473.1 (M + H) |
| 152 | 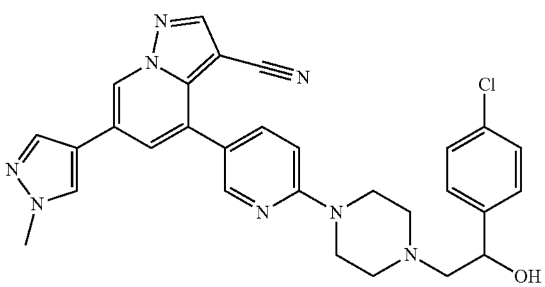 | 4-(6-(4-(2-(4-chlorophenyl)-2-hydroxyethyl)piperazin-1-yl)pyridin-3-yl)-6-(1-methyl-1H-pyrazol-4-yl)pyrazolo[1,5-a]pyridine-3-carbonitrile | 539.1 (M + H) |
| 153 | 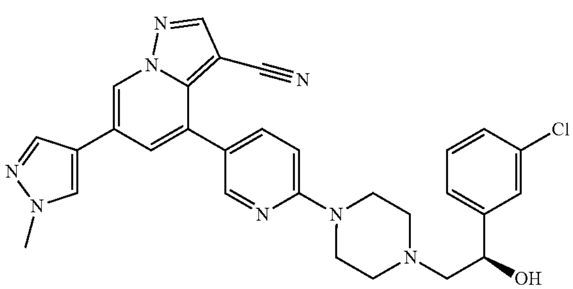 [SMILES: Cn1cc(-c2cc(-c3ccc(N4CCN(C[C@H](O)c5cccc(Cl)c5)CC4)nc3)c3c(C#N)cnn3c2)cn1] | (R)-4-(6-(4-(2-(3-chlorophenyl)-2-hydroxyethyl)piperazin-1-yl)pyridin-3-yl)-6-(1-methyl-1H-pyrazol-4-yl)pyrazolo[1,5-a]pyridine-3-carbonitrile | 539.1 (M + H) |
| 154 | 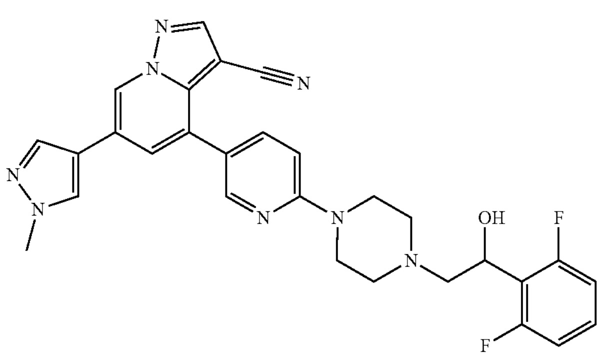 [SMILES: Cn1cc(-c2cc(-c3ccc(N4CCN(CC(O)c5c(F)cccc5F)CC4)nc3)c3c(C#N)cnn3c2)cn1] | 4-(6-(4-(2-(2,6-difluorophenyl)-2-hydroxyethyl)piperazin-1-yl)pyridin-3-yl)-6-(1-methyl-1H-pyrazol-4-yl)pyrazolo[1,5-a]pyridine-3-carbonitrile | 541.1 (M + H) |

Example 155

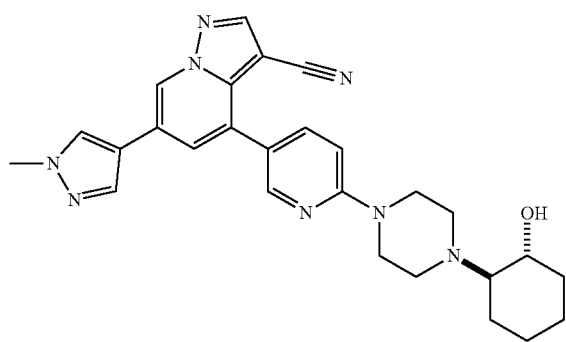

4-(6-(4-((1r,2r)-2-hydroxycyclohexyl)piperazin-1-yl)pyridin-3-yl)-6-(1-methyl-1H-pyrazol-4-yl)pyrazolo[1,5-a]pyridine-3-carbonitrile A mixture of 6-(1-methyl-1H-pyrazol-4-yl)-4-(6-(piperazin-1-yl)pyridin-3-yl)pyrazolo[1,5-a]pyridine-3-carbonitrile (25 mg, 0.065 mmol) and 7-oxabicyclo[4.1.0]heptane (6.4 mg, 0.065 mmol) in methanol (325 μL) was stirred in a sealed vial at 75° C. for 40 h. After cooling to ambient temperature, the reaction mixture was diluted with cold MeOH (325 μL), vacuum filtered, and rinsed sequentially with cold MeOH and Et₂O (1 mL each) to afford the title compound (19.9 mg, 62% yield). MS (apci) m/z=483.2 (M+H).

The compounds in Table Q were prepared according the method used for the synthesis of Example 155, replacing 7-oxabicyclo[4.1.0]heptane with the appropriate oxirane starting material. All compounds were purified similarly to the method described therein, utilizing either cold MeOH alone as the solvent for rinsing the solid product or cold MeOH and Et₂O.

TABLE Q

| Ex # | Structure | Chemical Name | MS (apci) m/z |
|---|---|---|---|
| 156 | 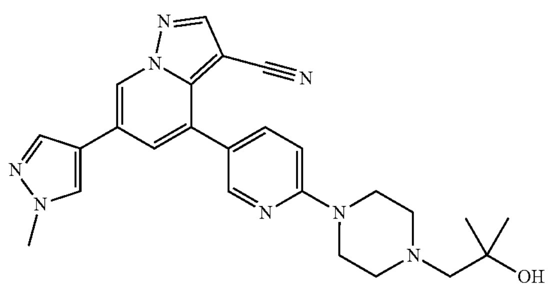 [SMILES: Cn1cc(-c2cc(-c3ccc(N4CCN(CC(C)(C)O)CC4)nc3)c3c(C#N)cnn3c2)cn1] | 4-(6-(4-(2-hydroxy-2-methylpropyl)piperazin-1-yl)pyridin-3-yl)-6-(1-methyl-1H-pyrazol-4-yl)pyrazolo[1,5-a]pyridine-3-carbonitrile | 457.2 (M + H) |
| 157 | 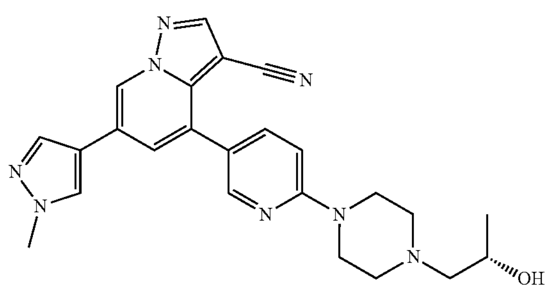 [SMILES: C[C@H](O)CN1CCN(c2ccc(-c3cc(-c4cnn(C)c4)cn4ncc(C#N)c34)cn2)CC1] | (S)-4-(6-(4-(2-hydroxypropyl)piperazin-1-yl)pyridin-3-yl)-6-(1-methyl-1H-pyrazol-4-yl)pyrazolo[1,5-a]pyridine-3-carbonitrile | 443.1 (M + H) |
| 158 | 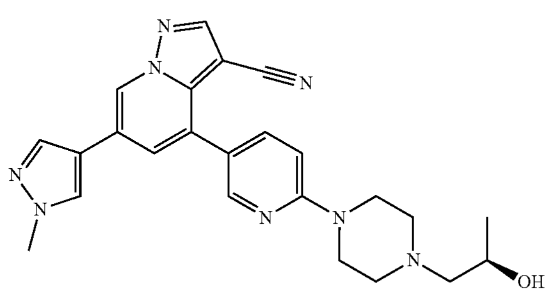 [SMILES: C[C@@H](O)CN1CCN(c2ccc(-c3cc(-c4cnn(C)c4)cn4ncc(C#N)c34)cn2)CC1] | (R)-4-(6-(4-(2-hydroxypropyl)piperazin-1-yl)pyridin-3-yl)-6-(1-methyl-1H-pyrazol-4-yl)pyrazolo[1,5-a]pyridine-3-carbonitrile | 443.1 (M + H) |

TABLE Q-continued

| Ex # | Structure | Chemical Name | MS (apci) m/z |
|---|---|---|---|
| 159 | 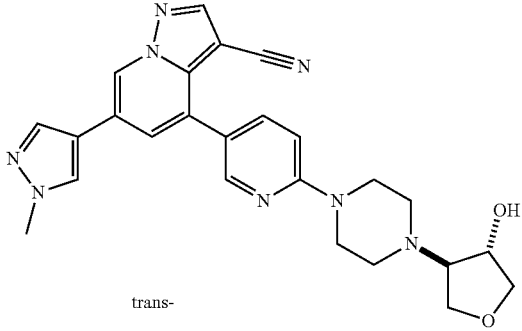 trans- | 4-(6-(4-((3r,4s)-4-hydroxytetrahydrofuran-3-yl)piperazin-1-yl)pyridin-3-yl)-6-(1-methyl-1H-pyrazol-4-yl)pyrazolo[1,5-a]pyridine-3-carbonitrile | 471.1 (M + H) |
| 160 | 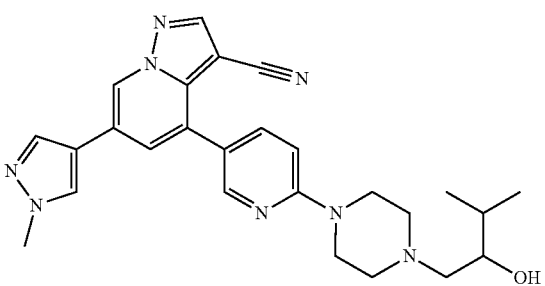 [SMILES: CC(C)C(O)CN1CCN(c2ccc(-c3cc(-c4cnn(C)c4)cn4ncc(C#N)c34)cn2)CC1] | 4-(6-(4-(2-hydroxy-3-methylbutyl)piperazin-1-yl)pyridin-3-yl)-6-(1-methyl-1H-pyrazol-4-yl)pyrazolo[1,5-a]pyridine-3-carbonitrile | 471.2 (M + H) |
| 161 | 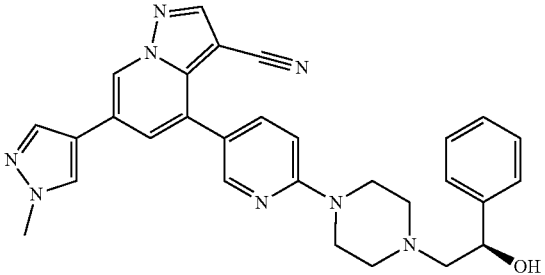 [SMILES: Cn1cc(-c2cc(-c3ccc(N4CCN(C[C@H](O)c5ccccc5)CC4)nc3)c3c(C#N)cnn3c2)cn1] | (R)-4-(6-(4-(2-hydroxy-2-phenylethyl)piperazin-1-yl)pyridin-3-yl)-6-(1-methyl-1H-pyrazol-4-yl)pyrazolo[1,5-a]pyridine-3-carbonitrile | 505.1 (M + H) |
| 162 | 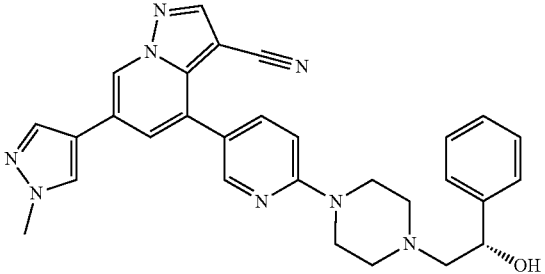 [SMILES: Cn1cc(-c2cc(-c3ccc(N4CCN(C[C@@H](O)c5ccccc5)CC4)nc3)c3c(C#N)cnn3c2)cn1] | (S)-4-(6-(4-(2-hydroxy-2-phenylethyl)piperazin-1-yl)pyridin-3-yl)-6-(1-methyl-1H-pyrazol-4-yl)pyrazolo[1,5-a]pyridine-3-carbonitrile | 505.1 (M + H) |
| 163 | 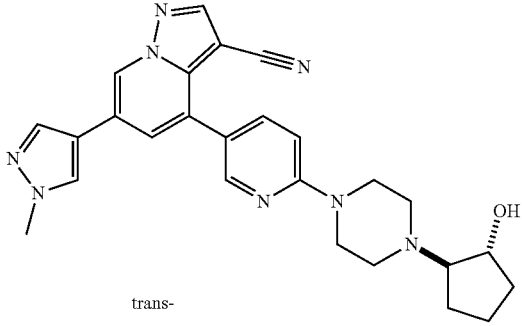 trans- | 4-(6-(4-((1r,2r)-2-hydroxycyclopentyl)piperazin-1-yl)pyridin-3-yl)-6-(1-methyl-1H-pyrazol-4-yl)pyrazolo[1,5-a]pyridine-3-carbonitrile | 469.1 (M + H) |

TABLE Q-continued

| Ex # | Structure | Chemical Name | MS (apci) m/z |
|---|---|---|---|
| 164 | 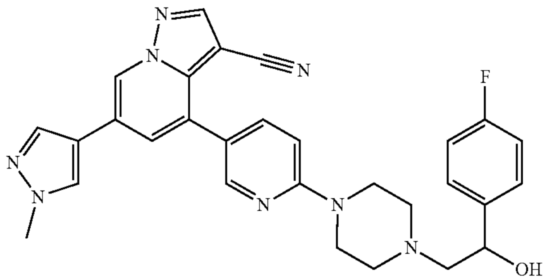 [SMILES: Cn1cc(-c2cc(-c3ccc(N4CCN(CC(O)c5ccc(F)cc5)CC4)nc3)c3c(C#N)cnn3c2)cn1] | 4-(6-(4-(2-(4-fluorophenyl)-2-hydroxyethyl)piperazin-1-yl)pyridin-3-yl)-6-(1-methyl-1H-pyrazol-4-yl)pyrazolo[1,5-a]pyridine-3-carbonitrile | 523.1 (M + H) |
| 165 | 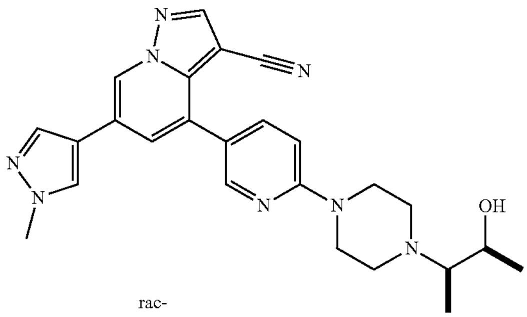 [SMILES: C[C@H](O)[C@@H](C)N1CCN(c2ccc(-c3cc(-c4cnn(C)c4)cn4ncc(C#N)c34)cn2)CC1] | rac-4-(6-(4-((2R*,3S*)-3-hydroxybutan-2-yl)piperazin-1-yl)pyridin-3-yl)-6-(1-methyl-1H-pyrazol-4-yl)pyrazolo[1,5-a]pyridine-3-carbonitrile | 457.1 (M + H) |

Example 166

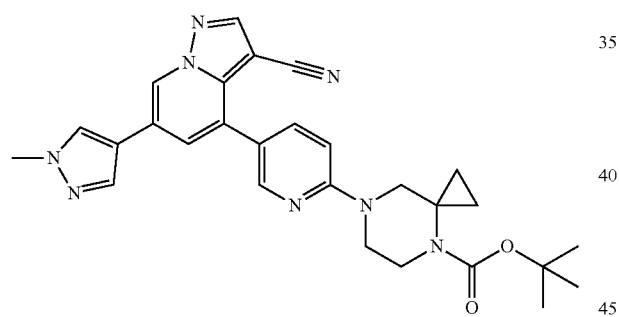

Tert-Butyl 7-(5-(3-cyano-6-(1-methyl-1H-pyrazol-4-yl)pyrazolo[1,5-a]pyridin-4-yl)pyridin-2-yl)-4,7-diazaspiro[2.5]octane-4-carboxylate A solution of tert-butyl 7-(5-(4,4,5,5-tetramethyl-1,3,2-dioxaborolan-2-yl)pyridin-2-yl)-4,7-diazaspiro[2.5]octane-4-carboxylate (Intermediate R2; 91 mg, 0.219 mmol) in dioxane (1.5 mL) was added to 3-cyano-6-(1-methyl-1H-pyrazol-4-yl)pyrazolo[1,5-a]pyridin-4-yl trifluoromethanesulfonate (Intermediate P5; 62.6 mg, 0.169 mmol). The resulting mixture was treated with 2 M $Na_2CO_{3(aq)}$ (421 µL, 0.843 mmol) and $Pd(PPh_3)_4$ (9.74 mg, 0.00843 mmol). The resulting reaction mixture was purged with nitrogen, then sealed and stirred at 90° C. overnight. After cooling to ambient temperature, the reaction mixture was partitioned between $H_2O$ (10 mL) and DCM (10 mL). After phase-separation and extracting the aqueous layer with DCM (2×10 mL), the organic layers were combined and concentrated and the residue was purified by silica chromatography (0-100% EtOAc/hexanes followed by 0-10% MeOH/EtOAc) to afford the title compound contaminated with $Ph_3PO$, which was removed by trituration with MTBE to yield the title product (19.4 mg, 23% yield). MS (apci) m/z=511.2 (M+H).

Example 167

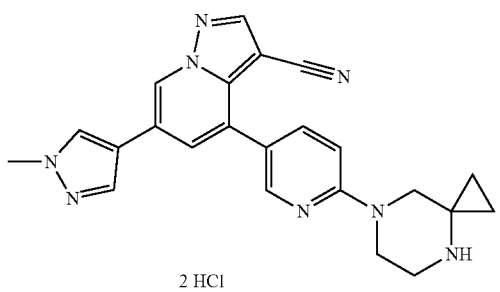 [SMILES: Cn1cc(-c2cc(-c3ccc(N4CCNC5(CC5)C4)nc3)c3c(C#N)cnn3c2)cn1]

4-(6-(4,7-diazaspiro[2.5]octan-7-yl)pyridin-3-yl)-6-(1-methyl-1H-pyrazol-4-yl)pyrazolo[1,5-a]pyridine-3-carbonitrile Dihydrochloride To a suspension of tert-butyl 7-(5-(3-cyano-6-(1-methyl-1H-pyrazol-4-yl)pyrazolo[1,5-a]pyridin-4-yl)pyridin-2-yl)-4,7-diazaspiro[2.5]octane-4-carboxylate (18.7 mg, 0.0366 mmol) in EtOH (0.2 mL) was added 5 M HCl in iPrOH (293 µL, 1.46 mmol). The resulting suspension was stirred at ambient temperature overnight and then filtered. The isolated solids were rinsed with $Et_2O$ (3 mL) and then dried in vacuo to afford the title compound (15.5 mg, 88% yield). MS (apci) m/z=411.1 (M+H).

Example 168

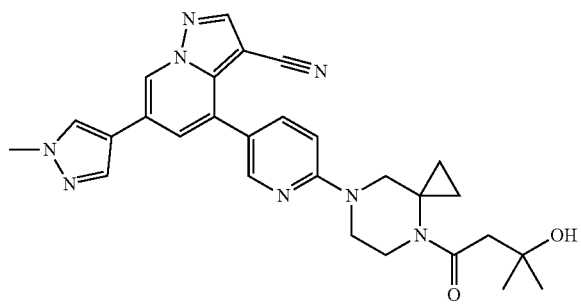 [SMILES: Cn1cc(-c2cc(-c3ccc(N4CCN(C(=O)CC(C)(C)O)C5(CC5)C4)nc3)c3c(C#N)cnn3c2)cn1]

4-(6-(4-(3-hydroxy-3-methylbutanoyl)-4,7-diaz-aspiro[2.5]octan-7-yl)pyridin-3-yl)-6-(1-methyl-1H-pyrazol-4-yl)pyrazolo[1,5-a]pyridine-3-carbonitrile DIEA (22 µL, 0.12 mmol), 3-hydroxy-3-methylbutanoic acid (4.9 mg, 0.041 mmol), and HATU (12 mg, 0.031 mmol) were added sequentially to a solution of 4-(6-(4,7-diazaspiro[2.5]octan-7-yl)pyridin-3-yl)-6-(1-methyl-1H-pyrazol-4-yl)pyrazolo[1,5-a]pyridine-3-carbonitrile dihydrochloride (10 mg, 0.021 mmol) in ACN (0.4 mL). The reaction mixture was stirred for 2 d at ambient temperature and then directly purified by reverse phase chromatography (5-75% ACN/water) to afford the title compound (10.8 mg, 98% yield). MS (apci) m/z=511.1 (M+H).

Example 169

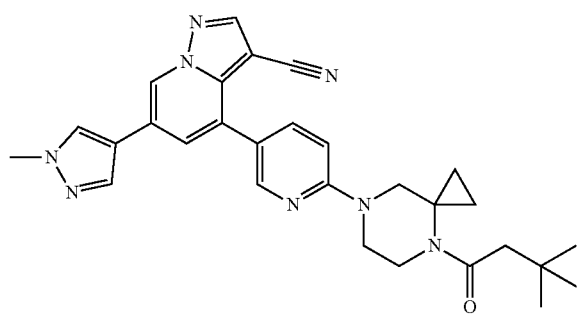 [SMILES: Cn1cc(-c2cc(-c3ccc(N4CCN(C(=O)CC(C)(C)C)C5(CC5)C4)nc3)c3c(C#N)cnn3c2)cn1]

4-(6-(4-(3,3-dimethylbutanoyl)-4,7-diazaspiro[2.5]octan-7-yl)pyridin-3-yl)-6-(1-methyl-1H-pyrazol-4-yl)pyrazolo[1,5-a]pyridine-3-carbonitrile To a solution of 4-(6-(4,7-diazaspiro[2.5]octan-7-yl)pyridin-3-yl)-6-(1-methyl-1H-pyrazol-4-yl)pyrazolo[1,5-a]pyridine-3-carbonitrile dihydrochloride (5 mg, 0.0103 mmol) in DCM (0.4 mL) was added DIEA (10.8 µL, 0.0621 mmol) and 3,3-dimethylbutanoyl chloride (2.17 µL, 0.0155 mmol) and the reaction mixture was stirred at ambient temperature 2 d. The resulting suspension was vacuum filtered and the filter cake was rinsed successively with water (1 mL) and Et$_2$O (2×1 mL), then dried in vacuo to afford the title compound (3.2 mg, 61% yield). MS (apci) m/z=509.2 (M+H).

Example 170

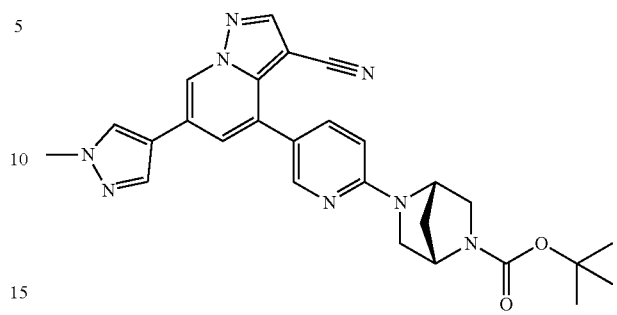

(1S,4S)-tert-butyl 5-(5-(3-cyano-6-(1-methyl-1H-pyrazol-4-yl)pyrazolo[1,5-a]pyridin-4-yl)pyridin-2-yl)-2,5-diazabicyclo[2.2.1]heptane-2-carboxylate (1S,4S)-tert-butyl5-(5-(4,4,5,5-tetramethyl-1,3,2-dioxaborolan-2-yl)pyridin-2-yl)-2,5-diazabicyclo[2.2.1]heptane-2-carboxylate (Intermediate R3; 48 mg, 0.12 mmol), 2 M Na$_2$CO$_{3(aq)}$ (236 µL, 0.47 mmol), and Pd(PPh$_3$)$_4$ (5.5 mg, 0.0047 mmol) were added sequentially to a solution of 3-cyano-6-(1-methyl-1H-pyrazol-4-yl)pyrazolo[1,5-a]pyridin-4-yl trifluoromethanesulfonate (Intermediate P5; 35 mg, 0.0943 mmol) in dioxane (0.4 mL). The resulting reaction mixture was purged with nitrogen, then sealed and stirred at 90° C. overnight. The reaction mixture was cooled to ambient temperature and then diluted with H$_2$O (5 mL). After vigorous stirring the resulting suspension was extracted with DCM (2×15 mL). The combined organic extracts were concentrated and purified by silica chromatography (25-100% EtOAc/hexanes then 0-10% MeOH/EtOAc) to afford the title compound (12.1 mg, 26% yield). MS (apci) m/z=497.1 (M+H).

Example 171

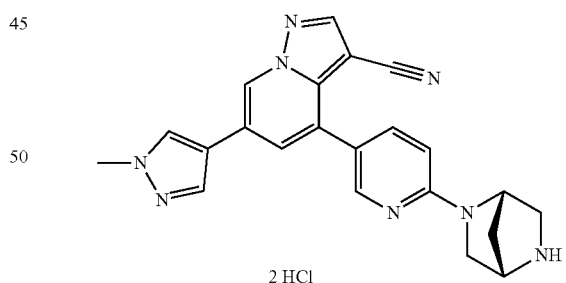

2 HCl 4-(6-((1S,4S)-2,5-diazabicyclo[2.2.1]heptan-2-yl)pyridin-3-yl)-6-(1-methyl-1H-pyrazol-4-yl)pyrazolo[1,5-a]pyridine-3-carbonitrile Dihydrochloride To a suspension of (1S,4S)-tert-butyl 5-(5-(3-cyano-6-(1-methyl-1H-pyrazol-4-yl)pyrazolo[1,5-a]pyridin-4-yl)pyridin-2-yl)-2,5-diazabicyclo[2.2.1]heptane-2-carboxylate (11 mg, 0.022 mmol) in EtOH (0.2 mL) was added 5 M HCl in iPrOH (301 µL, 1.5 mmol). The resulting suspension was stirred at ambient temperature for 4 h. LCMS indicated continued presence of starting material. Additional 5 M HCl in iPrOH (0.2 mL) was added. The reaction was stirred overnight and then filtered. The filter cake was rinsed with Et₂O (3 mL) and dried in vacuo to afford the title compound (7.6 mg, 73% yield). MS (apci) m/z=397.1 (M+H).

Example 172

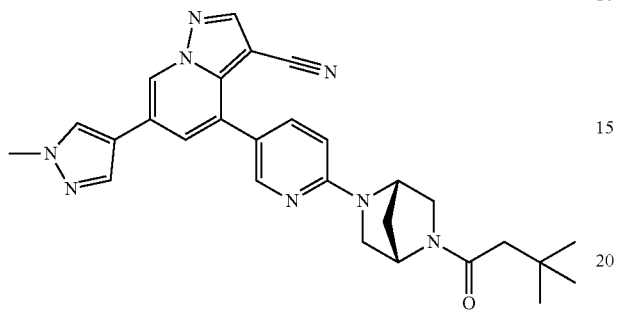

4-(6-((1S,4S)-5-(3,3-dimethylbutanoyl)-2,5-diazabi-cyclo[2.2.1]heptan-2-yl)pyridin-3-yl)-6-(1-methyl-1H-pyrazol-4-yl)pyrazolo[1,5-a]pyridine-3-carbonitrile DIEA (13.4 µL, 0.0767 mmol) and 3,3-dimethylbutanoyl chloride (2.7 µL, 0.019 mmol) were added sequentially to a suspension of 4-(6-((1S,4S)-2,5-diazabicyclo[2.2.1]heptan-2-yl)pyridin-3-yl)-6-(1-methyl-1H-pyrazol-4-yl)pyrazolo[1,5-a]pyridine-3-carbonitrile dihydrochloride (6 mg, 0.0128 mmol) in DCM (0.4 mL). The resulting solution was stirred overnight at ambient temperature and then quenched with MeOH (0.1 mL). The solution was partially concentrated in vacuo and then purified directly by silica chromatography (0-10% MeOH/EtOAc) to afford the title compound (5.0 mg, 79% yield). MS (apci) m/z=495.2 (M+H).

Example 173

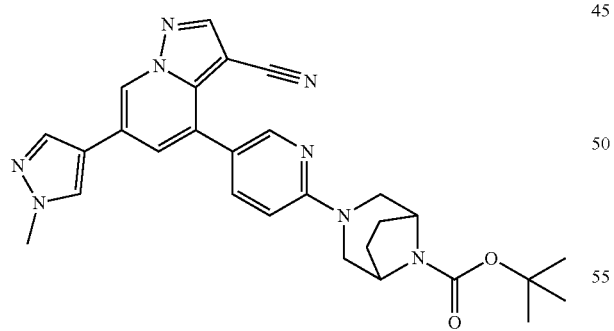

Tert-Butyl 3-(5-(3-cyano-6-(1-methyl-1H-pyrazol-4-yl)pyrazolo[1,5-a]pyridin-4-yl)pyridin-2-yl)-3,8-diazabicyclo[3.2.1]octane-8-carboxylate To a solution of 3-cyano-6-(1-methyl-1H-pyrazol-4-yl)pyrazolo[1,5-a]pyridin-4-yl trifluoromethanesulfonate, (Intermediate P5; 41.3 mg, 0.111 mmol) in dioxane (1 mL) was added tert-butyl 3-(5-(4,4,5,5-tetramethyl-1,3,2-dioxaborolan-2-yl)pyridin-2-yl)-3,8-diazabicyclo[3.2.1]octane-8-carboxylate (Intermediate R4; 60 mg, 0.144 mmol). The resulting mixture was treated with 2 M Na₂CO₃(aq) (278 µL, 0.56 mmol), and Pd(PPh₃)₄ (6.42 mg, 0.0056 mmol) and then sparged with nitrogen, sealed and heated at 90° C. overnight. The reaction mixture was cooled to ambient temperature and then diluted with H₂O (10 mL) and filtered. The isolated solids were dissolved in MTBE. The aqueous phase was washed with DCM (10 mL) and the combined organic extracts were concentrated in vacuo. The resulting residue was purified by silica chromatography (25-100% EtOAc/hexanes) to afford the title compound contaminated with Ph₃PO, which was removed via trituration with MTBE (3 mL) to yield the title compound (15.8 mg, 28% yield). MS (apci) m/z=511.1 (M+H).

Example 174

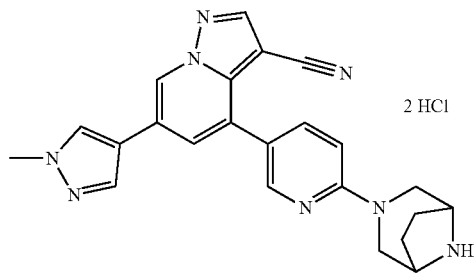 [SMILES: Cn1cc(-c2cc(-c3ccc(N4CC5CCC(C4)N5)nc3)c3c(C#N)cnn3c2)cn1]

4-(6-(3,8-diazabicyclo[3.2.1]octan-3-yl)pyridin-3-yl)-6-(1-methyl-1H-pyrazol-4-yl)pyrazolo[1,5-a]pyridine-3-carbonitrile Dihydrochloride To a suspension of tert-butyl 3-(5-(3-cyano-6-(1-methyl-1H-pyrazol-4-yl)pyrazolo[1,5-a]pyridin-4-yl)pyridin-2-yl)-3,8-diazabicyclo[3.2.1]octane-8-carboxylate (14.7 mg, 0.0288 mmol) in EtOH (0.2 mL) was added 5 M HCl in iPrOH (305 µL, 1.53 mmol). After stirring the suspension at ambient temperature for 2 h, additional 5 M HCl in iPrOH (0.3 mL, 1.50 mmol) was added and stirring continued overnight. The solids were collected by filtration, rinsed with Et₂O (3 mL) and then dried in vacuo to afford the title compound (10 mg, 72% yield). MS (apci) m/z=411.1 (M+H).

Example 175

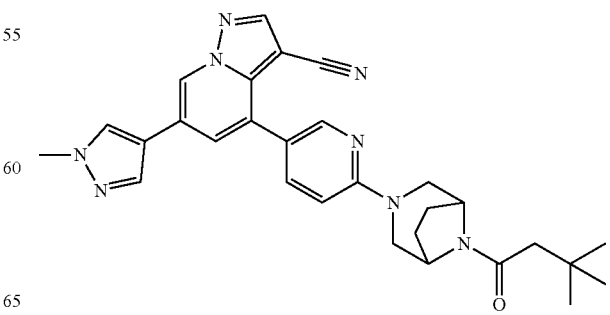

4-(6-(8-(3,3-dimethylbutanoyl)-3,8-diazabicyclo[3.2.1]octan-3-yl)pyridin-3-yl)-6-(1-methyl-1H-pyrazol-4-yl)pyrazolo[1,5-a]pyridine-3-carbonitrile To a solution of 4-(6-(3,8-diazabicyclo[3.2.1]octan-3-yl)pyridin-3-yl)-6-(1-methyl-1H-pyrazol-4-yl)pyrazolo[1,5-a]pyridine-3-carbonitrile dihydrochloride (4.5 mg, 0.00931 mmol) in DCM (0.4 mL) was added DIEA (9.7 µL, 0.056 mmol) and 3,3-dimethylbutanoyl chloride (2.0 µL, 0.014 mmol). The reaction mixture was stirred at ambient temperature overnight. The resulting suspension was vacuum filtered and the filter cake was rinsed with Et₂O (3×1 mL) and then dried in vacuo to afford the title compound (4.7 mg, 99% yield). MS (apci) m/z=509.2 (M+H).

Example 176

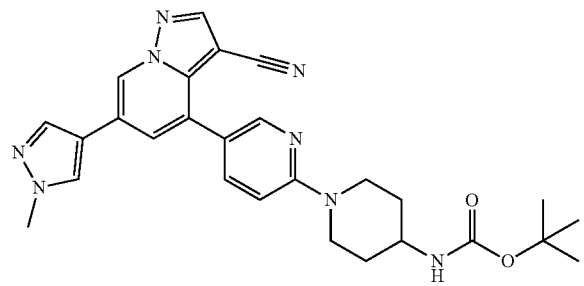 [SMILES: Cn1cc(-c2cc(-c3ccc(N4CCC(NC(=O)OC(C)(C)C)CC4)nc3)c3c(C#N)cnn3c2)cn1]

Tert-Butyl (1-(5-(3-cyano-6-(1-methyl-1H-pyrazol-4-yl)pyrazolo[1,5-a]pyridin-4-yl)pyridin-2-yl)piperidin-4-yl)carbamate In a pressure tube a solution of 3-cyano-6-(1-methyl-1H-pyrazol-4-yl)pyrazolo[1,5-a]pyridin-4-yl trifluoromethanesulfonate (Intermediate P5; 53.7 mg, 0.145 mmol), tert-butyl (1-(5-(4,4,5,5-tetramethyl-1,3,2-dioxaborolan-2-yl)pyridin-2-yl)piperidin-4-yl)carbamate (Intermediate R8; 70 mg, 0.174 mmol) and Pd(PPh₃)₄ (8.4 mg, 0.0072 mmol) in dioxane (1.2 mL) was treated with 2 M Na₂CO₃$_{(aq)}$ (362 µL, 0.72 mmol). The resulting reaction mixture was purged with nitrogen, sealed and then heated at 90° C. overnight. The reaction mixture was cooled to ambient temperature and diluted with water (3 mL). The resulting suspension was vacuum filtered, and the solids were rinsed with additional water to afford the title compound (57.9 mg, 83% yield). MS (apci) m/z=499.1 (M+H).

Example 177

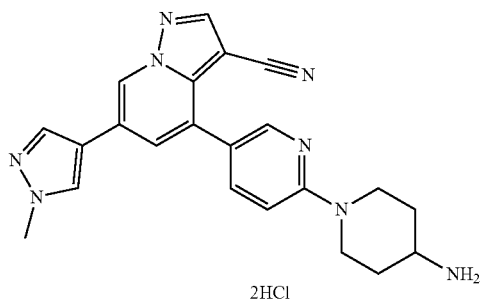 [SMILES: Cn1cc(-c2cc(-c3ccc(N4CCC(N)CC4)nc3)c3c(C#N)cnn3c2)cn1]

4-(6-(4-aminopiperidin-1-yl)pyridin-3-yl)-6-(1-methyl-1H-pyrazol-4-yl)pyrazolo[1,5-a]pyridine-3-carbonitrile Dihydrochloride To a suspension of to tert-butyl (1-(5-(3-cyano-6-(1-methyl-1H-pyrazol-4-yl)pyrazolo[1,5-a]pyridin-4-yl)pyridin-2-yl)piperidin-4-yl)carbamate (56 mg, 0.112 mmol) in EtOH (0.2 mL) was added 5 M HCl in iPrOH (449 µL, 2.25 mmol). After stirring at ambient temperature 3 d the resulting suspension was vacuum filtered, and the solids were rinsed with Et₂O (3 mL) and then dried in vacuo to afford the title compound (44.7 mg, 84% yield). MS (apci) m/z=399.1 (M+H).

Example 178

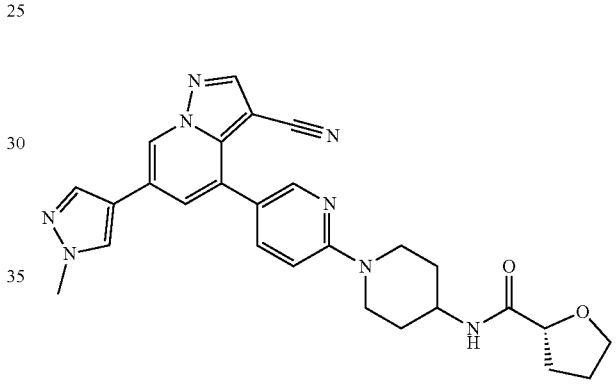

(R)—N-(1-(5-(3-cyano-6-(1-methyl-1H-pyrazol-4-yl)pyrazolo[1,5-a]pyridin-4-yl)pyridin-2-yl)piperidin-4-yl)tetrahydrofuran-2-carboxamide 4-(6-(4-Aminopiperidin-1-yl)pyridin-3-yl)-6-(1-methyl-1H-pyrazol-4-yl)pyrazolo[1,5-a]pyridine-3-carbonitrile dihydrochloride (10 mg, 0.0212 mmol) was treated sequentially with a solution of (R)-tetrahydrofuran-2-carboxylic acid (4.9 mg, 0.042 mmol) in DMA (0.4 mL), DIEA (22 µL, 0.13 mmol) and HATU (12.1 mg, 0.032 mmol). The resulting reaction mixture was stirred overnight at ambient temperature and then directly purified by chromatography (5-75% ACN/water) to afford the title compound (10.6 mg, quantitative yield). MS (apci) m/z=497.0 (M+H).

The compounds in Table R were prepared according the method used for the synthesis of Example 178, replacing (R)-tetrahydrofuran-2-carboxylic acid with the appropriate acid starting material and using either DMA (or DMF) as solvent.

TABLE R

| Ex # | Structure | Chemical Name | MS (apci) m/z |
|---|---|---|---|
| 179 | 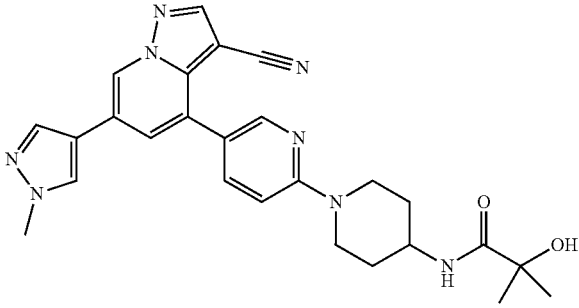 [SMILES: Cn1cc(-c2cc(-c3ccc(N4CCC(NC(=O)C(C)(C)O)CC4)nc3)c3c(C#N)cnn3c2)cn1] | N-(1-(5-(3-cyano-6-(1-methyl-1H-pyrazol-4-yl)pyrazolo[1,5-a]pyridin-4-yl)pyridin-2-yl)piperidin-4-yl)-2-hydroxy-2-methylpropanamide | 485.1 (M + H) |
| 180 | 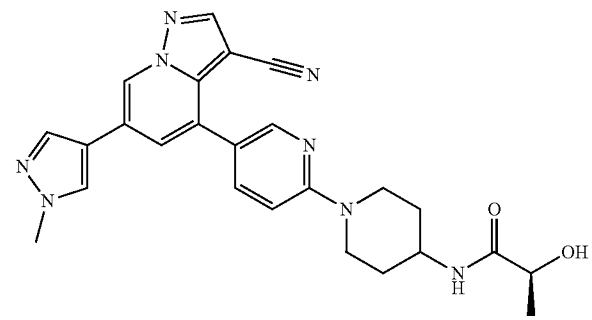 [SMILES: C[C@H](O)C(=O)NC1CCN(c2ccc(-c3cc(-c4cnn(C)c4)cn4ncc(C#N)c34)cn2)CC1] | (S)-N-(1-(5-(3-cyano-6-(1-methyl-1H-pyrazol-4-yl)pyrazolo[1,5-a]pyridin-4-yl)pyridin-2-yl)piperidin-4-yl)-2-hydroxypropanamide | 471.1 (M + H) |
| 181 | 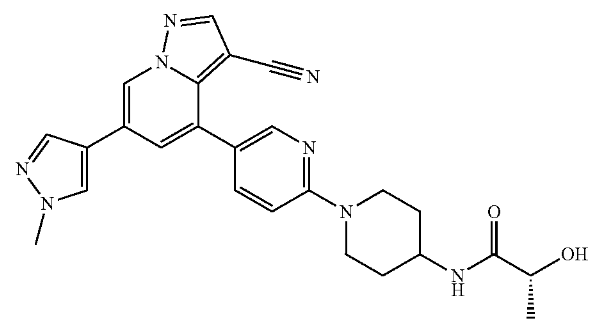 [SMILES: C[C@@H](O)C(=O)NC1CCN(c2ccc(-c3cc(-c4cnn(C)c4)cn4ncc(C#N)c34)cn2)CC1] | (R)-N-(1-(5-(3-cyano-6-(1-methyl-1H-pyrazol-4-yl)pyrazolo[1,5-a]pyridin-4-yl)pyridin-2-yl)piperidin-4-yl)-2-hydroxypropanamide | 471.0 (M + H) |
| 182 | 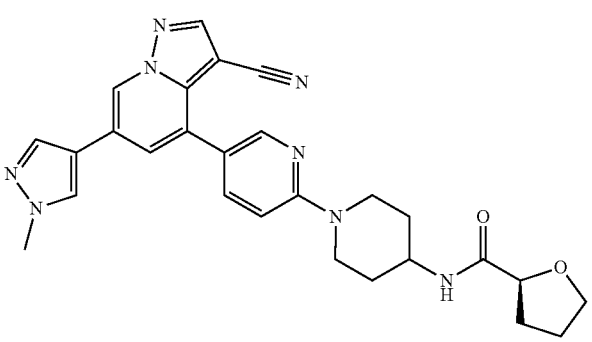 [SMILES: Cn1cc(-c2cc(-c3ccc(N4CCC(NC(=O)[C@@H]5CCCO5)CC4)nc3)c3c(C#N)cnn3c2)cn1] | (S)-N-(1-(5-(3-cyano-6-(1-methyl-1H-pyrazol-4-yl)pyrazolo[1,5-a]pyridin-4-yl)pyridin-2-yl)piperidin-4-yl)tetrahydrofuran-2-carboxamide | 497.1 (M + H) |

Example 183

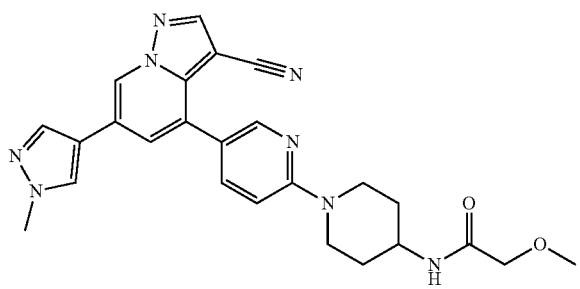 [SMILES: COCC(=O)NC1CCN(c2ccc(-c3cc(-c4cnn(C)c4)cn4ncc(C#N)c34)cn2)CC1]

N-(1-(5-(3-cyano-6-(1-methyl-1H-pyrazol-4-yl)pyrazolo[1,5-a]pyridin-4-yl)pyridin-2-yl)piperidin-4-yl)-2-methoxyacetamide A solution of 4-(6-(4-aminopiperidin-1-yl)pyridin-3-yl)-6-(1-methyl-1H-pyrazol-4-yl)pyrazolo[1,5-a]pyridine-3-carbonitrile dihydrochloride (10 mg, 0.021 mmol) in DMA (0.4 mL) was treated with DIEA (15 µL, 0.085 mmol) and 2-methoxyacetyl chloride (3.5 mg, 0.032 mmol). The resulting clear solution was stirred overnight at ambient temperature. LCMS indicated no reaction progress and acid halide degradation to acid was suspected. The reaction mixture was therefore treated with HATU (20 mg, 0.0526 mmol). After stirring the reaction mixture for an additional 2 h at ambient temperature, LCMS indicated complete consumption of the carbonitrile starting material. The reaction mixture was directly purified by chromatography (5-75% ACN/water) to afford the title compound (8.5 mg, 85% yield). MS (apci) m/z=471.1 (M+H).

Example 184

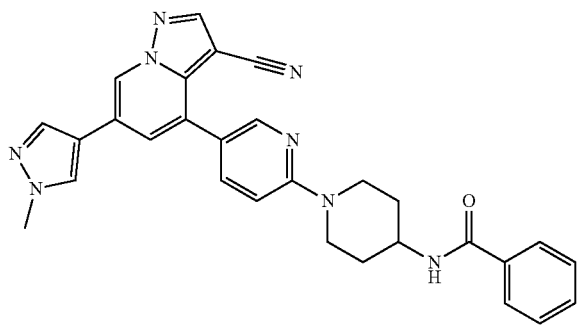 [SMILES: Cn1cc(-c2cc(-c3ccc(N4CCC(NC(=O)c5ccccc5)CC4)nc3)c3c(C#N)cnn3c2)cn1]

N-(1-(5-(3-cyano-6-(1-methyl-1H-pyrazol-4-yl)pyrazolo[1,5-a]pyridin-4-yl)pyridin-2-yl)piperidin-4-yl)benzamide A solution of 4-(6-(4-aminopiperidin-1-yl)pyridin-3-yl)-6-(1-methyl-1H-pyrazol-4-yl)pyrazolo[1,5-a]pyridine-3-carbonitrile dihydrochloride (8 mg, 0.017 mmol) in DCM (0.3 mL) was treated with DIEA (11.82 µL, 0.068 mmol) and benzoyl chloride (3.9 µL, 0.034 mmol). The resulting clear solution was stirred 2 d at ambient temperature. The reaction mixture was vacuum filtered, and the solids were rinse with Et₂O (3×1 mL) and dried in vacuo to afford the title compound (4.8 mg, 56% yield). MS (apci) m/z=503.1 (M+H).

Example 185

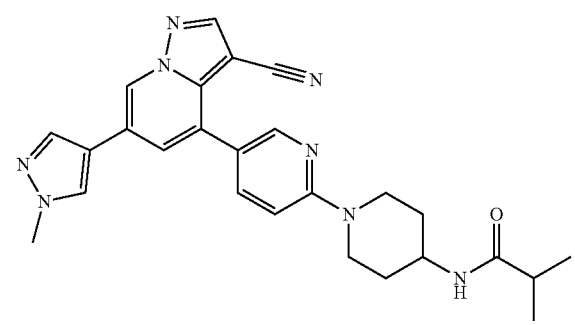 [SMILES: CC(C)C(=O)NC1CCN(c2ccc(-c3cc(-c4cnn(C)c4)cn4ncc(C#N)c34)cn2)CC1]

N-(1-(5-(3-cyano-6-(1-methyl-1H-pyrazol-4-yl)pyrazolo[1,5-a]pyridin-4-yl)pyridin-2-yl)piperidin-4-yl)isobutyramide A solution of 4-(6-(4-aminopiperidin-1-yl)pyridin-3-yl)-6-(1-methyl-1H-pyrazol-4-yl)pyrazolo[1,5-a]pyridine-3-carbonitrile dihydrochloride (40 mg, 0.085 mmol) in DMA (0.5 mL) was treated with DIEA (59 µL, 0.34 mmol) and isobutyryl chloride (13.4 µL, 0.13 mmol). The resulting clear solution was stirred overnight at ambient temperature. The reaction mixture was directly purified by chromatography (5-80%, ACN/water) to afford the title compound (26.4 mg, 66% yield). MS (apci) m/z=469.2 (M+H).

Example 185a

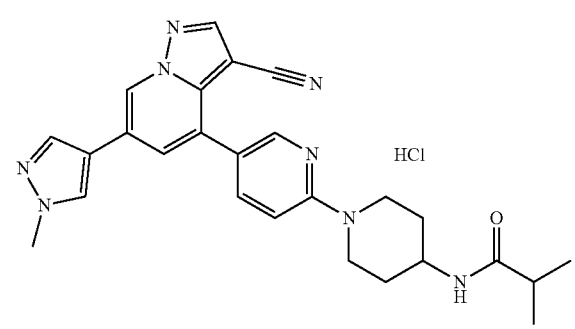 [SMILES: CC(C)C(=O)NC1CCN(c2ccc(-c3cc(-c4cnn(C)c4)cn4ncc(C#N)c34)cn2)CC1 ; Cl]

N-(1-(5-(3-cyano-6-(1-methyl-1H-pyrazol-4-yl)pyrazolo[1,5-a]pyridin-4-yl)pyridin-2-yl)piperidin-4-yl)isobutyramide Hydrochloride A solution of N-(1-(5-(3-cyano-6-(1-methyl-1H-pyrazol-4-yl)pyrazolo[1,5-a]pyridin-4-yl)pyridin-2-yl)piperidin-4-yl)isobutyramide (26.4 mg, 0.056 mmol) in a 4:1 solvent mixture of DCM/MeOH (3 mL) was treated with 5 M HCl in iPrOH (113 µL, 0.56 mmol). The resulting clear solution was stirred 10 min at ambient temperature and then concentrated in vacuo. The residue was diluted with Et₂O (5 mL) and concentrated in vacuo to afford the title compound (30.3 mg, quantitative yield). MS (apci) m/z=469.2 (M+H).

Example 186

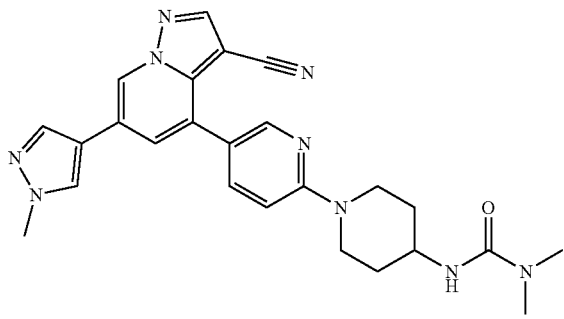 [SMILES: CN(C)C(=O)NC1CCN(c2ccc(-c3cc(-c4cnn(C)c4)cn4ncc(C#N)c34)cn2)CC1]

3-(1-(5-(3-cyano-6-(1-methyl-1H-pyrazol-4-yl)pyrazolo[1,5-a]pyridin-4-yl)pyridin-2-yl)piperidin-4-yl)-1,1-dimethylurea To a suspension of 4-(6-(4-aminopiperidin-1-yl)pyridin-3-yl)-6-(1-methyl-1H-pyrazol-4-yl)pyrazolo[1,5-a]pyridine-3-carbonitrile dihydrochloride (10 mg, 0.02121 mmol) in DCM (0.2 mL) and DIEA (18 µL, 0.11 mmol) at ambient temperature was added dimethylcarbamic chloride (4.9 µL, 0.053 mmol). The suspension was stirred overnight at ambient temperature before treated with additional DIEA (20 µL, 0.1148 mmol) and dimethylcarbamic chloride (10 µL, 0.1090 mmol). The reaction mixture was stirred at ambient temperature for another 4 d, then diluted with ACN and directly purified by reverse phase chromatography (5-75% ACN/water) to provide the title compound (6.4 mg, 64% yield). MS (apci) m/z=470.2 (M+H).

Example 187

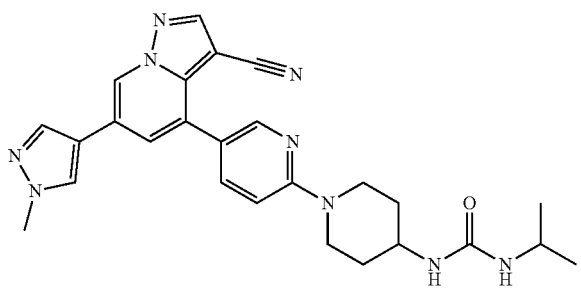 [SMILES: CC(C)NC(=O)NC1CCN(c2ccc(-c3cc(-c4cnn(C)c4)cn4ncc(C#N)c34)cn2)CC1]

1-(1-(5-(3-cyano-6-(1-methyl-1H-pyrazol-4-yl)pyrazolo[1,5-a]pyridin-4-yl)pyridin-2-yl)piperidin-4-yl)-3-isopropylurea To a suspension of 4-(6-(4-aminopiperidin-1-yl)pyridin-3-yl)-6-(1-methyl-1H-pyrazol-4-yl)pyrazolo[1,5-a]pyridine-3-carbonitrile dihydrochloride (10 mg, 0.021 mmol) in DCM (0.2 mL) and DIEA (18 µL, 0.11 mmol) was added 2-isocyanatopropane (2.7 mg, 0.032 mmol). The suspension was stirred at ambient temperature overnight and then vacuum filtered. The isolated solids were rinsed with Et₂O and dried in vacuo to afford the title compound (7.3 mg, 71% yield). MS (apci) m/z=484.2 (M+H).

Example 188

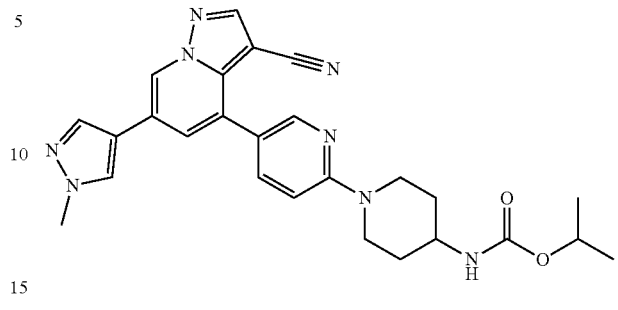

Isopropyl (1-(5-(3-cyano-6-(1-methyl-1H-pyrazol-4-yl)pyrazolo[1,5-a]pyridin-4-yl)pyridin-2-yl)piperidin-4-yl)carbamate To a suspension of 4-(6-(4-aminopiperidin-1-yl)pyridin-3-yl)-6-(1-methyl-1H-pyrazol-4-yl)pyrazolo[1,5-a]pyridine-3-carbonitrile dihydrochloride (10 mg, 0.021 mmol) in DCM (0.2 mL) and DIEA (18 µL, 0.11 mmol) was added isopropyl carbonochloridate (3.9 mg, 0.032 mmol). The suspension was stirred at ambient temperature overnight and then vacuum filtered. The isolated solids were rinsed with Et₂O and dried in vacuo to afford the title compound (5.7 mg, 55% yield). MS (apci) m/z=485.2 (M+H).

Example 189

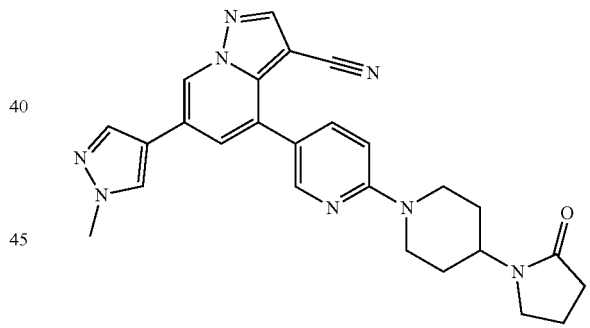

6-(1-methyl-1H-pyrazol-4-yl)-4-(6-(4-(2-oxopyrrolidin-1-yl)piperidin-1-yl)pyridin-3-yl)pyrazolo[1,5-a]pyridine-3-carbonitrile 4-(6-fluoropyridin-3-yl)-6-(1-methyl-1H-pyrazol-4-yl)pyrazolo[1,5-a]pyridine-3-carbonitrile (Intermediate P6; 13.6 mg, 0.043 mmol) and 1-(piperidin-4-yl)pyrrolidin-2-one (21.6 mg, 0.13 mmol) in DMSO (0.3 mL) were combined in a microwave vessel. The resulting thick suspension was subjected to microwave irradiation at 125° C. for 1 h. The reaction mixture was directly purified by reverse phase chromatography (5-90% ACN/water). The chromatographic fractions containing the title compound were combined, concentrated in vacuo and then triturated with MTBE to provide the title compound (6.3 mg, 32% yield). MS (apci) m/z=467.1 (M+H).

Example 190

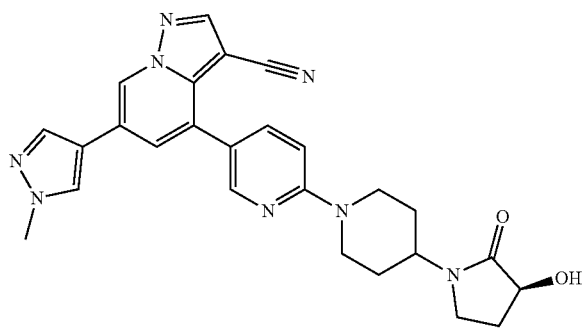 [SMILES: Cn1cc(-c2cc(-c3ccc(N4CCC(N5CC[C@H](O)C5=O)CC4)nc3)c3c(C#N)cnn3c2)cn1]

(S)-4-(6-(4-(3-hydroxy-2-oxopyrrolidin-1-yl)piperidin-1-yl)pyridin-3-yl)-6-(1-methyl-1H-pyrazol-4-yl)pyrazolo[1,5-a]pyridine-3-carbonitrile 4-(6-fluoropyridin-3-yl)-6-(1-methyl-1H-pyrazol-4-yl)pyrazolo[1,5-a]pyridine-3-carbonitrile (Intermediate P6; 15 mg, 0.047 mmol) and (S)-3-hydroxy-1-(piperidin-4-yl)pyrrolidin-2-one (26.0 mg, 0.14 mmol) was added DMSO (0.3 mL) were combined in a microwave vessel. The resulting thick suspension was subjected to microwave irradiation at 125° C. for 1 h. The reaction mixture was directly purified by reverse phase chromatography (5-75% ACN/water) to afford the title compound (12.4 mg, 55% yield). MS (apci) m/z=483.0 (M+H).

Example 191

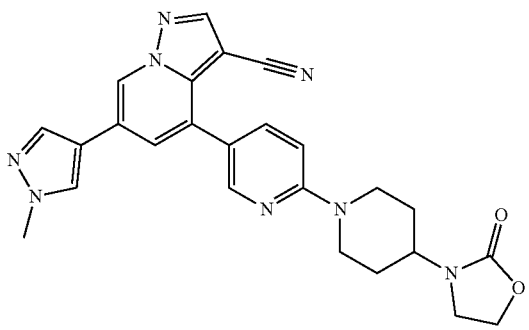 [SMILES: Cn1cc(-c2cc(-c3ccc(N4CCC(N5CCOC5=O)CC4)nc3)c3c(C#N)cnn3c2)cn1]

6-(1-methyl-1H-pyrazol-4-yl)-4-(6-(4-(2-oxooxazolidin-3-yl)piperidin-1-yl)pyridin-3-yl)pyrazolo[1,5-a]pyridine-3-carbonitrile A solution of 3-(piperidin-4-yl)oxazolidin-2-one hydrochloride (29 mg, 0.14 mmol) in MeOH (0.5 mL) was filtered through a basic resin (Stratospheres MP-HCO3, 100 mg, 0.18 mmol/g) and concentrated in vacuo. The resulting residue was taken up in DMSO (0.3 mL) and added to a microwave vessel containing 4-(6-fluoropyridin-3-yl)-6-(1-methyl-1H-pyrazol-4-yl)pyrazolo[1,5-a]pyridine-3-carbonitrile (Intermediate P6; 15 mg, 0.047 mmol). The resulting thick suspension was subjected to microwave irradiation at 125° C. for 1 h. The reaction mixture was directly purified by reverse phase chromatography (5-75% ACN/water) to afford the title compound (9.7 mg, 44% yield). MS (apci) m/z=469.1 (M+H).

Example 192

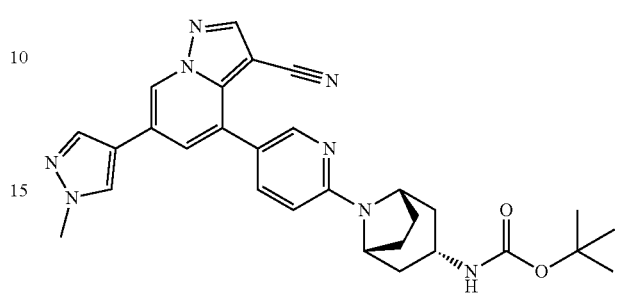

Tert-Butyl ((1R,3s,5S)-8-(5-(3-cyano-6-(1-methyl-1H-pyrazol-4-yl)pyrazolo[1,5-a]pyridin-4-yl)pyridin-2-yl)-8-azabicyclo[3.2.1]octan-3-yl)carbamate In a pressure tube a solution of 3-cyano-6-(1-methyl-1H-pyrazol-4-yl)pyrazolo[1,5-a]pyridin-4-yl trifluoromethanesulfonate (Intermediate P5; 45.4 mg, 0.12 mmol), tert-butyl ((1R,3s, 5S)-8-(5-(4,4,5,5-tetramethyl-1,3,2-dioxaborolan-2-yl)pyridin-2-yl)-8-azabicyclo[3.2.1]octan-3-yl)carbamate (Intermediate R5; 63 mg, 0.15 mmol) and Pd(PPh$_3$)$_4$ (7.1 mg, 0.0061 mmol) in dioxane (1.2 mL) was treated with 2 M Na$_2$CO$_{3(aq)}$ (306 µL, 0.61 mmol). The resulting reaction mixture was sparged with nitrogen, sealed and heated at 90° C. overnight. The reaction mixture was cooled to ambient temperature and then diluted with water (13 mL) and extracted with EtOAc (2×17 mL). The combined organic extracts were dried (MgSO$_4$), filtered, concentrated in vacuo and purified by reverse phase chromatography (5-95% ACN/water) to afford the title compound (32.7 mg, 51% yield). MS (apci) m/z=525.2 (M+H).

Example 193

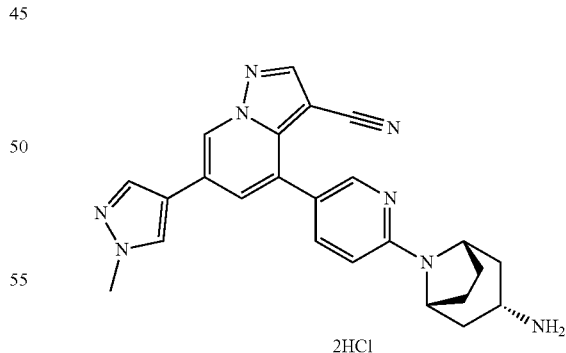

4-(6-((1R,3s,5S)-3-amino-8-azabicyclo[3.2.1]octan-8-yl)pyridin-3-yl)-6-(1-methyl-1H-pyrazol-4-yl)pyrazolo[1,5-a]pyridine-3-carbonitrile Dihydrochloride To a suspension of tert-butyl ((1R,3s,5S)-8-(5-(3-cyano-6-(1-methyl-1H-pyrazol-4-yl)pyrazolo[1,5-a]pyridin-4-yl)

pyridin-2-yl)-8-azabicyclo[3.2.1]octan-3-yl)carbamate (31 mg, 0.0591 mmol) in EtOH (0.2 mL) was added 5 M HCl in iPrOH (414 µL, 2.07 mmol). After stirring at ambient temperature for 4 h the reaction appeared complete by LCMS. The suspension was filtered, and the solids were rinsed with Et₂O (3 mL) and dried in vacuo to afford the title compound (23.5 mg, 80% yield). MS (apci) m/z=425.1 (M+H).

Example 194

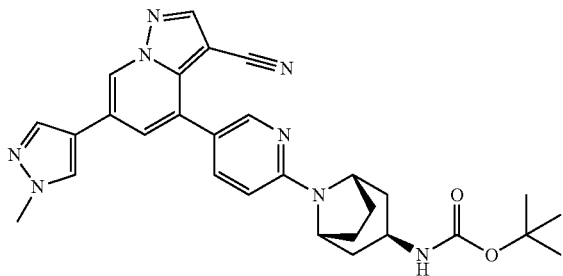 [SMILES: Cn1cc(-c2cc(-c3ccc(N4[C@@H]5CC[C@H]4C[C@@H](NC(=O)OC(C)(C)C)C5)nc3)c3c(C#N)cnn3c2)cn1]

Tert-Butyl ((1R,3r,5S)-8-(5-(3-cyano-6-(1-methyl-1H-pyrazol-4-yl)pyrazolo[1,5-a]pyridin-4-yl)pyridin-2-yl)-8-azabicyclo[3.2.1]octan-3-yl)carbamate In a pressure tube, a solution of 3-cyano-6-(1-methyl-1H-pyrazol-4-yl)pyrazolo[1,5-a]pyridin-4-yl trifluoromethanesulfonate (Intermediate P5; 75 mg, 0.202 mmol), tert-butyl ((1R,3r, 5S)-8-(5-(4,4,5,5-tetramethyl-1,3,2-dioxaborolan-2-yl)pyridin-2-yl)-8-azabicyclo[3.2.1]octan-3-yl)carbamate (Intermediate R9; 104 mg, 0.242 mmol) and Pd(PPh₃)₄ (11.7 mg, 0.0101 mmol) in dioxane (2 mL) was treated with 2 M Na₂CO₃(aq) (505 µL, 1.01 mmol). The resulting reaction mixture was sparged with N₂, sealed and heated at 90° C. overnight. The reaction mixture was cooled to ambient temperature and then diluted with water (3 mL) and EtOAc (5 mL) and stirred. The resulting emulsion was filtered and the filtrate was diluted with additional water (10 mL) and extracted with EtOAc (2×15 mL). The combined organic extracts were dried (MgSO₄), filtered, concentrated in vacuo and purified by reverse phase chromatography (5-95% ACN/water) to afford the title compound (25.9 mg, 24% yield). MS (apci) m/z=525.1 (M+H).

Example 195

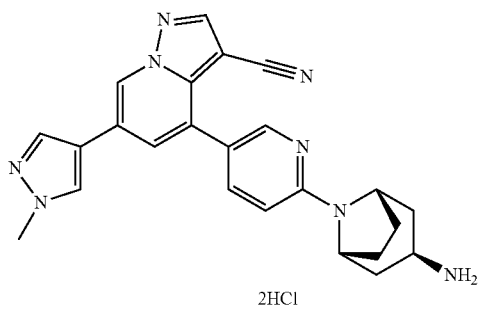 [SMILES: Cn1cc(-c2cc(-c3ccc(N4[C@@H]5CC[C@H]4C[C@@H](N)C5)nc3)c3c(C#N)cnn3c2)cn1]

2HCl 4-(6-((1R,3r,5S)-3-amino-8-azabicyclo[3.2.1]octan-8-yl)pyridin-3-yl)-6-(1-methyl-1H-pyrazol-4-yl)pyrazolo[1,5-a]pyridine-3-carbonitrile Dihydrochloride To a suspension of tert-butyl ((1R,3r,5S)-8-(5-(3-cyano-6-(1-methyl-1H-pyrazol-4-yl)pyrazolo[1,5-a]pyridin-4-yl)pyridin-2-yl)-8-azabicyclo[3.2.1]octan-3-yl)carbamate (24.8 mg, 0.0473 mmol) in EtOH (0.2 mL) was added 5 M HCl in iPrOH (407 µL, 2.03 mmol). After stirring at ambient temperature overnight the resulting suspension was filtered, and the solids were rinsed with Et₂O (3 mL) and dried in vacuo to afford the title compound (16.8 mg, 71% yield). MS (apci) m/z=425.1 (M+H).

Example 196

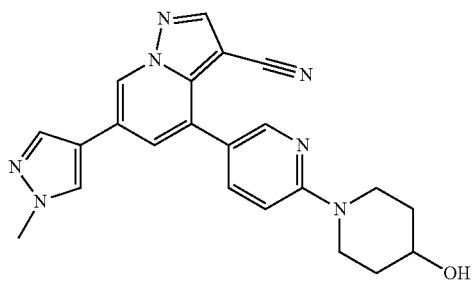 [SMILES: Cn1cc(-c2cc(-c3ccc(N4CCC(O)CC4)nc3)c3c(C#N)cnn3c2)cn1]

4-(6-(4-hydroxypiperidin-1-yl)pyridin-3-yl)-6-(1-methyl-1H-pyrazol-4-yl)pyrazolo[1,5-a]pyridine-3-carbonitrile In a pressure tube a solution of 3-cyano-6-(1-methyl-1H-pyrazol-4-yl)pyrazolo[1,5-a]pyridin-4-yl trifluoromethanesulfonate (Intermediate P5; 44.9 mg, 0.121 mmol), 1-(5-(4,4,5,5-tetramethyl-1,3,2-dioxaborolan-2-yl)pyridin-2-yl)piperidin-4-ol (Intermediate R6; 81 mg, 0.133 mmol) and Pd(PPh₃)₄ (7.0 mg, 0.0061 mmol) in dioxane (1.2 mL) was treated with 2 M Na₂CO₃(aq) (303 µL, 0.61 mmol). The resulting reaction mixture was sparged with nitrogen, sealed and heated at 90° C. overnight. After cooling to ambient temperature the reaction mixture was diluted with H₂O (3 mL) and EtOAc (5 mL), stirred for 30 min and vacuum filtered, rinsing the collected solids successively with water (20 mL) and EtOAc (20 mL). The isolated solids were purified by reverse phase chromatography (5-75% ACN/water) to afford the title compound (14.0 mg, 29% yield). MS (apci) m/z=400.1 (M+H).

Example 197

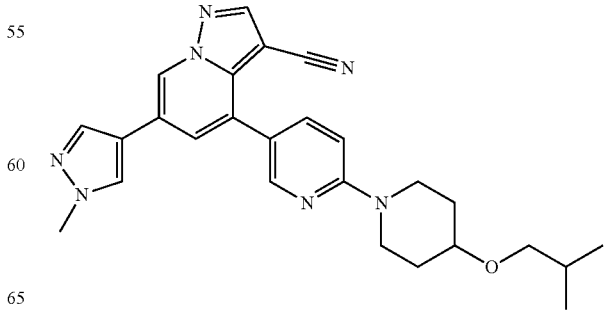

4-(6-(4-isobutoxypiperidin-1-yl)pyridin-3-yl)-6-(1-methyl-1H-pyrazol-4-yl)pyrazolo[1,5-a]pyridine-3-carbonitrile 4-(6-fluoropyridin-3-yl)-6-(1-methyl-1H-pyrazol-4-yl)pyrazolo[1,5-a]pyridine-3-carbonitrile (Intermediate P6; 15 mg, 0.0471 mmol) and 4-isobutoxypiperidine (22.2 mg, 0.141 mmol) in DMSO (0.2 mL) were combined in a microwave vessel and subjected to microwave irradiation at 125° C. for 1 h. The reaction mixture was directly purified by reverse phase chromatography (5-75% ACN/water) to provide the title compound (17.1 mg, 80% yield). MS (apci) m/z=456.1 (M+H).

Example 198

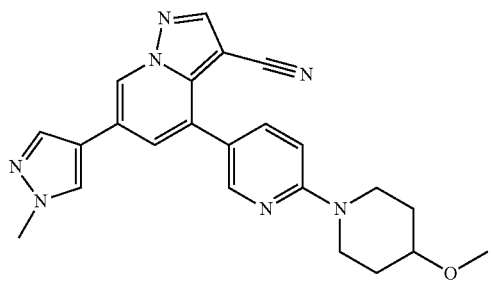 [SMILES: COC1CCN(c2ccc(-c3cc(-c4cnn(C)c4)cn4ncc(C#N)c34)cn2)CC1]

4-(6-(4-methoxypiperidin-1-yl)pyridin-3-yl)-6-(1-methyl-1H-pyrazol-4-yl)pyrazolo[1,5-a]pyridine-3-carbonitrile 4-(6-fluoropyridin-3-yl)-6-(1-methyl-1H-pyrazol-4-yl)pyrazolo[1,5-a]pyridine-3-carbonitrile (Intermediate P6; 17 mg, 0.0534 mmol) and 4-methoxypiperidine (18.5 mg, 0.160 mmol) in DMSO (0.2 mL) were combined in a microwave vessel and subjected to microwave irradiation at 125° C. for 30 min. The reaction mixture was directly purified by reverse phase chromatography (5-80% ACN/water). The chromatographic fractions containing the title compound were combined, concentrated in vacuo, and triturated with MTBE (1 mL) to yield the title product (12.4 mg, 56% yield). MS (apci) m/z=414.1 (M+H).

Example 199

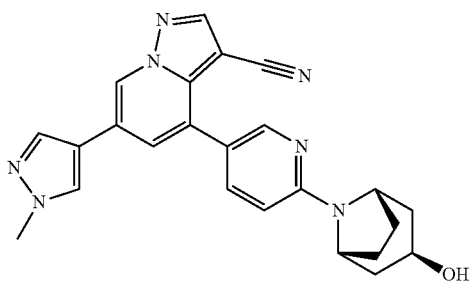 [SMILES: Cn1cc(-c2cc(-c3ccc(N4[C@@H]5CC[C@H]4C[C@@H](O)C5)nc3)c3c(C#N)cnn3c2)cn1]

4-(6-((1R,3r,5S)-3-hydroxy-8-azabicyclo[3.2.1]octan-8-yl)pyridin-3-yl)-6-(1-methyl-1H-pyrazol-4-yl)pyrazolo[1,5-a]pyridine-3-carbonitrile In a pressure tube, a solution of 3-cyano-6-(1-methyl-1H-pyrazol-4-yl)pyrazolo[1,5-a]pyridine-4-yl trifluoromethanesulfonate (Intermediate P5; 35 mg, 0.094 mmol), (1R,3r,5S)-8-(5-(4,4,5,5-tetramethyl-1,3,2-dioxaborolan-2-yl)pyridin-2-yl)-8-azabicyclo[3.2.1]octan-3-ol (Intermediate R7; 33 mg, 0.100 mmol) and Pd(PPh$_3$)$_4$ (5.4 mg, 0.0047 mmol) in dioxane (0.7 mL) was treated with 2 M Na$_2$CO$_{3(aq)}$ (236 μL, 0.47 mmol). The resulting reaction mixture was sparged with nitrogen, sealed and heated at 90° C. overnight. The reaction mixture was cooled to ambient temperature, diluted with H$_2$O (7 mL) and extracted with DCM (2×15 mL). The combined organic extracts were concentrated and purified by silica chromatography (0-10% MeOH/EtOAc) to afford the title compound (3.5 mg, 9% yield). MS (apci) m/z=426.1 (M+H).

Example 200

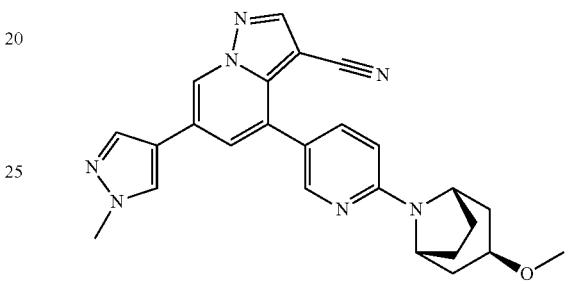

4-(6-((1R,3r,5S)-3-methoxy-8-azabicyclo[3.2.1]octan-8-yl)pyridin-3-yl)-6-(1-methyl-1H-pyrazol-4-yl)pyrazolo[1,5-a]pyridine-3-carbonitrile A solution of (1R,3r,5S)-3-methoxy-8-azabicyclo[3.2.1]octane hydrochloride (25 mg, 0.141 mmol) in MeOH (0.5 mL) was filtered through a basic resin (Stratospheres MP-HCO3, 100 mg, 1.8 mmol/g) and the filtrate was concentrated in vacuo. The residue was taken up in DMSO (0.3 mL) and added to a microwave vessel containing 4-(6-fluoropyridin-3-yl)-6-(1-methyl-1H-pyrazol-4-yl)pyrazolo[1,5-a]pyridine-3-carbonitrile (Intermediate P6; 15 mg, 0.047 mmol). The resulting thick suspension was subjected to microwave irradiation at 125° C. for 2 h. The reaction mixture was directly purified by reverse phase chromatography (5-90% ACN/water) to provide the title compound (10.7 mg, 52% yield). MS (apci) m/z=440.1 (M+H).

Example 201

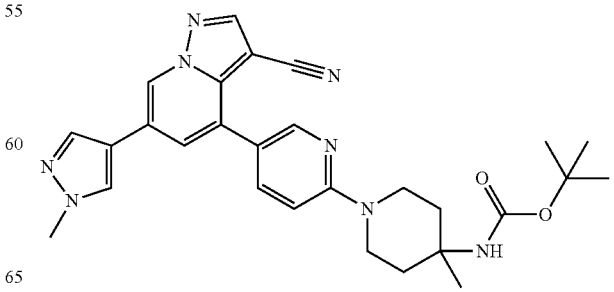

311

Tert-Butyl (1-(5-(3-cyano-6-(1-methyl-1H-pyrazol-4-yl)pyrazolo[1,5-a]pyridin-4-yl)pyridin-2-yl)-4-methylpiperidin-4-yl)carbamate In a microwave vessel, 4-(6-fluoropyridin-3-yl)-6-(1-methyl-H-pyrazol-4-yl)pyrazolo[1,5-a]pyridine-3-carbonitrile (Intermediate P6; 30 mg, 0.094 mmol) was treated with a solution of tert-butyl (4-methylpiperidin-4-yl)carbamate (61 mg, 0.28 mmol) in DMSO (0.4 mL). The resulting thick suspension was subjected to microwave irradiation at 125° C. for 1 h. The reaction mixture was directly purified by reverse phase chromatography (5-90% ACN/water) to afford the title compound (41 mg, 85% yield). MS (apci) m/z=513.1 (M+H).

Example 202

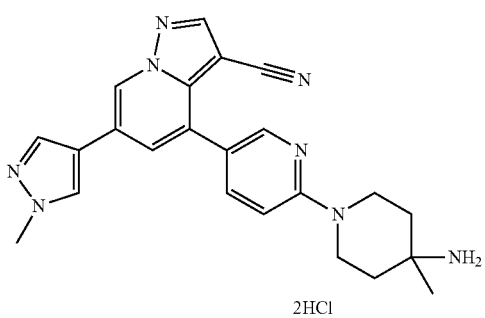 [SMILES: Cn1cc(-c2cc(-c3ccc(N4CCC(C)(N)CC4)nc3)c3c(C#N)cnn3c2)cn1]

4-(6-(4-amino-4-methylpiperidin-1-yl)pyridin-3-yl)-6-(1-methyl-1H-pyrazol-4-yl)pyrazolo[1,5-a]pyridine-3-carbonitrile Dihydrochloride To a suspension of tert-butyl (1-(5-(3-cyano-6-(1-methyl-1H-pyrazol-4-yl)pyrazolo[1,5-a]pyridin-4-yl)pyridin-2-yl)-4-methylpiperidin-4-yl)carbamate (40 mg, 0.0780 mmol) in EtOH (1 mL) was added 5 M HCl in iPrOH (2 mL, 10 mmol). After stirring at ambient temperature overnight the resulting suspension was filtered, and the solids were rinsed with Et₂O (3 mL) and dried in vacuo to afford the title compound (29.8 mg, 79% yield). MS (apci) m/z=413.1 (M+H).

Example 203

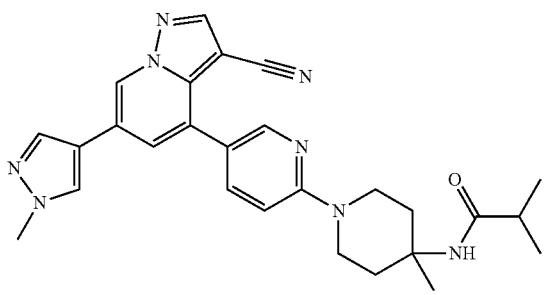 [SMILES: CC(C)C(=O)NC1(C)CCN(c2ccc(-c3cc(-c4cnn(C)c4)cn4ncc(C#N)c34)cn2)CC1]

312

N-(1-(5-(3-cyano-6-(1-methyl-1H-pyrazol-4-yl)pyrazolo[1,5-a]pyridin-4-yl)pyridin-2-yl)piperidin-4-yl)isobutyramide A solution of 4-(6-(4-amino-4-methylpiperidin-1-yl)pyridin-3-yl)-6-(1-methyl-1H-pyrazol-4-yl)pyrazolo[1,5-a]pyridine-3-carbonitrile dihydrochloride (8 mg, 0.016 mmol) in DMA (0.2 mL) was treated with DIEA (11.48 µL, 0.066 mmol) and isobutyryl chloride (2.6 µL, 0.025 mmol). The resulting clear solution was stirred at ambient temperature overnight. The reaction mixture was diluted with water and the resulting mixture was directly purified by chromatography (5-80% ACN/water) to afford the title compound (7.0 mg, 88% yield). MS (apci) m/z=483.1 (M+H).

Example 204

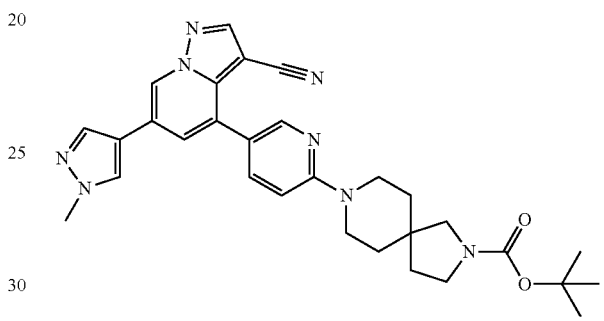

Tert-Butyl 8-(5-(3-cyano-6-(1-methyl-1H-pyrazol-4-yl)pyrazolo[1,5-a]pyridin-4-yl)pyridin-2-yl)-2,8-diazaspiro[4.5]decane-2-carboxylate In a microwave vessel, 4-(6-fluoropyridin-3-yl)-6-(1-methyl-H-pyrazol-4-yl)pyrazolo[1,5-a]pyridine-3-carbonitrile (Intermediate P6; 15 mg, 0.047 mmol) and tert-butyl 2,8-diazaspiro[4.5]decane-2-carboxylate (34.0 mg, 0.14 mmol) were suspended in DMSO (0.4 mL). The resulting thick suspension was subjected to microwave irradiation at 125° C. for 1 h. The reaction mixture was directly purified by reverse phase chromatography (5-75% ACN/water) to afford the title compound (17.0 mg, 67% yield). MS (apci) m/z=539.2 (M+H).

Example 205

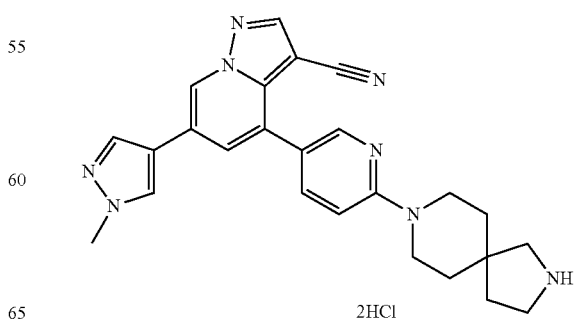

313

4-(6-(2,8-diazaspiro[4.5]decan-8-yl)pyridin-3-yl)-6-(1-methyl-1H-pyrazol-4-yl)pyrazolo[1,5-a]pyridine-3-carbonitrile Dihydrochloride To a suspension of tert-butyl 8-(5-(3-cyano-6-(1-methyl-1H-pyrazol-4-yl)pyrazolo[1,5-a]pyridin-4-yl)pyridin-2-yl)-2,8-diazaspiro[4.5]decane-2-carboxylate (16 mg, 0.030 mmol) in EtOH (0.1 mL) and DCM (0.1 mL) was added 5 M HCl in iPrOH (208 µL, 1.04 mmol). After stirring at ambient temperature for 2 h, the resulting suspension was concentrated in vacuo to afford the title compound (14.9 mg, 98% yield). MS (apci) m/z=439.1 (M+H).

Example 206

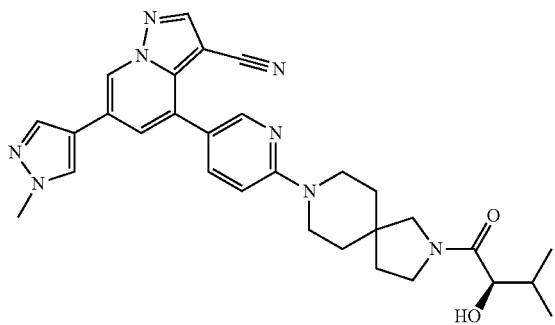 [SMILES: CC(C)[C@@H](O)C(=O)N1CCC2(CCN(c3ccc(-c4cc(-c5cnn(C)c5)cn5ncc(C#N)c45)cn3)CC2)C1]

(R)-4-(6-(2-(2-hydroxy-3-methylbutanoyl)-2,8-diazaspiro[4.5]decan-8-yl)pyridin-3-yl)-6-(1-methyl-1H-pyrazol-4-yl)pyrazolo[1,5-a]pyridine-3-carbonitrile (R)-2-hydroxy-3-methylbutanoic acid (1.7 mg, 0.015 mmol) and HATU (4.5 mg, 0.012 mmol) were added sequentially to a solution of 4-(6-(2,8-diazaspiro[4.5]decan-8-yl)pyridin-3-yl)-6-(1-methyl-1H-pyrazol-4-yl)pyrazolo[1,5-a]pyridine-3-carbonitrile dihydrochloride (5 mg, 0.0098 mmol) and DIEA (22 µL, 0.12 mmol) in DMA (0.2 mL). After stirring at ambient temperature for 45 min, the reaction mixture was quenched with water (0.2 mL) and directly purified by reverse phase chromatography (5-80% ACN/water) to afford the title compound (3.1 mg, 59% yield). MS (apci) m/z=539.2 (M+H).

Example 207

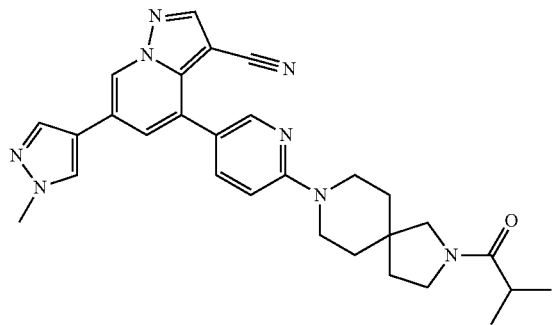 [SMILES: CC(C)C(=O)N1CCC2(CCN(c3ccc(-c4cc(-c5cnn(C)c5)cn5ncc(C#N)c45)cn3)CC2)C1]

314

4-(6-(2-isobutyryl-2,8-diazaspiro[4.5]decan-8-yl)pyridin-3-yl)-6-(1-methyl-1H-pyrazol-4-yl)pyrazolo[1,5-a]pyridine-3-carbonitrile To a solution of 4-(6-(2,8-diazaspiro[4.5]decan-8-yl)pyridin-3-yl)-6-(1-methyl-1H-pyrazol-4-yl)pyrazolo[1,5-a]pyridine-3-carbonitrile dihydrochloride (5 mg, 0.01 mmol) and DIEA (10.2 µL, 0.058 mmol) in DMA (0.2 mL) was added isobutyryl chloride (1.5 µL, 0.015 mmol). The reaction mixture was stirred at ambient temperature for 20 h and then diluted with water (3 mL) and stirred for another 1 h. The resulting suspension was vacuum filtered and the filter cake was rinsed with water and dried in vacuo to afford the title compound (1.9 mg, 38% yield). MS (apci) m/z=509.2 (M+H).

Example 208

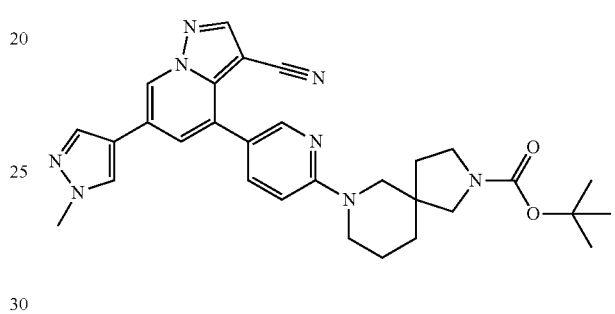

Tert-Butyl 7-(5-(3-cyano-6-(1-methyl-1H-pyrazol-4-yl)pyrazolo[1,5-a]pyridin-4-yl)pyridin-2-yl)-2,7-diazaspiro[4.5]decane-2-carboxylate In a microwave vessel, 4-(6-fluoropyridin-3-yl)-6-(1-methyl-H-pyrazol-4-yl)pyrazolo[1,5-a]pyridine-3-carbonitrile (Intermediate P6; 15 mg, 0.0471 mmol) and tert-butyl 2,7-diazaspiro[4.5]decane-2-carboxylate (34.0 mg, 0.141 mmol) were suspended in DMSO (0.2 mL). The resulting thick suspension was subjected to microwave irradiation at 125° C. for 1 h. The reaction mixture was directly purified by reverse phase chromatography (5-90% ACN/water) to afford the title compound (16.0 mg, 63% yield). MS (apci) m/z=539.2 (M+H).

Example 209

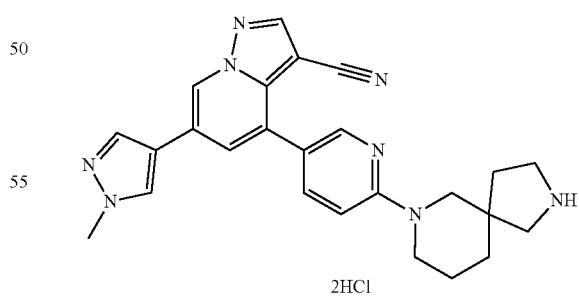

4-(6-(2,7-diazaspiro[4.5]decan-7-yl)pyridin-3-yl)-6-(1-methyl-1H-pyrazol-4-yl)pyrazolo[1,5-a]pyridine-3-carbonitrile Dihydrochloride To a solution of tert-butyl 7-(5-(3-cyano-6-(1-methyl-1H-pyrazol-4-yl)pyrazolo[1,5-a]pyridin-4-yl)pyridin-2-yl)-2,7- diazaspiro[4.5]decane-2-carboxylate (15 mg, 0.028 mmol) in EtOH (0.1 mL) and DCM (0.1 mL) was added 5 M HCl in iPrOH (195 μL, 0.98 mmol). After stirring at ambient temperature for 2 h the reaction mixture was concentrated in vacuo to afford the title compound (13.9 mg, 98% yield). MS (apci) m/z=439.1 (M+H).

Example 210

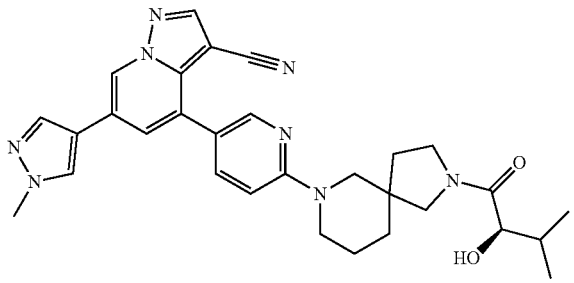

4-(6-(2-((R)-2-hydroxy-3-methylbutanoyl)-2,7-diazaspiro[4.5]decan-7-yl)pyridin-3-yl)-6-(1-methyl-1H-pyrazol-4-yl)pyrazolo[1,5-a]pyridine-3-carbonitrile (R)-2-hydroxy-3-methylbutanoic acid (1.7 mg, 0.015 mmol) and HATU (4.5 mg, 0.012 mmol) were added sequentially to a solution of 4-(6-(2,7-diazaspiro[4.5]decan-7-yl)pyridin-3-yl)-6-(1-methyl-1H-pyrazol-4-yl)pyrazolo[1,5-a]pyridine-3-carbonitrile dihydrochloride (5 mg, 0.0098 mmol) and DIEA (10 μL, 0.059 mmol) in DMA (0.2 mL). After stirring at ambient temperature for 1 h, additional HATU (4 mg, 0.011 mmol) and (R)-2-hydroxy-3-methylbutanoic acid (2 mg, 0.018 mmol) were added, and the reaction mixture was stirred for an additional 90 min. The reaction mixture was directly purified by reverse phase chromatography (5-80% ACN/water) to afford the title compound (1:1 diastereomeric mixture, 1.11 mg, 21% yield. MS (apci) m/z=539.2 (M+H)) plus the individual diastereoisomers as listed in Examples 211 and 212 below.

Example 211

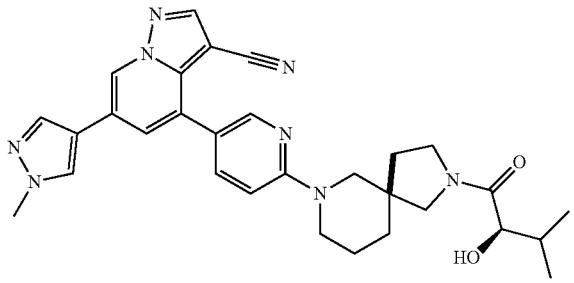

4-(6-((S)-2-((R)-2-hydroxy-3-methylbutanoyl)-2,7-diazaspiro[4.5]decan-7-yl)pyridin-3-yl)-6-(1-methyl-1H-pyrazol-4-yl)pyrazolo[1,5-a]pyridine-3-carbonitrile The diastereomeric mixture prepared in Example 210 was purified by reverse phase chromatographic separation using 5-80% ACN/water as the gradient eluent. The higher $R_f$ single diastereomeric isomer was isolated to afford the title compound (0.25 mg, 4.7% yield). The absolute chiral sense for the spirocycle was arbitrarily assigned. MS (apci) m/z=539.2 (M+H).

Example 212

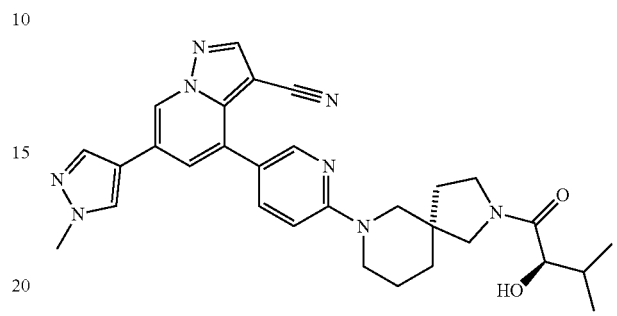

4-(6-((R)-2-((R)-2-hydroxy-3-methylbutanoyl)-2,7-diazaspiro[4.5]decan-7-yl)pyridin-3-yl)-6-(1-methyl-1H-pyrazol-4-yl)pyrazolo[1,5-a]pyridine-3-carbonitrile The diastereomeric mixture prepared in Example 210 was purified by reverse phase chromatographic separation using 5-80% ACN/water as the gradient eluent. The lower $R_f$ single diastereomeric isomer was isolated to afford the title compound (0.52 mg, 9.8% yield). The absolute chiral sense for the spirocycle was arbitrarily assigned. MS (apci) m/z=539.2 (M+H).

Example 213

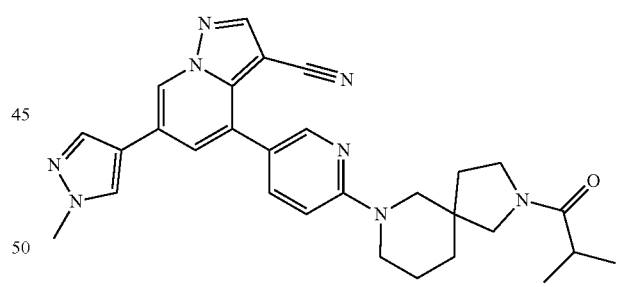

4-(6-(2-isobutyryl-2,7-diazaspiro[4.5]decan-7-yl)pyridin-3-yl)-6-(1-methyl-1H-pyrazol-4-yl)pyrazolo[1,5-a]pyridine-3-carbonitrile To a solution of 4-(6-(2,7-diazaspiro[4.5]decan-7-yl)pyridin-3-yl)-6-(1-methyl-1H-pyrazol-4-yl)pyrazolo[1,5-a]pyridine-3-carbonitrile dihydrochloride (5 mg, 0.01 mmol) and DIEA (10.2 μL, 0.058 mmol) in DMA (0.2 mL) was added isobutyryl chloride (1.55 μL, 0.015 mmol). The reaction mixture was stirred at ambient temperature for 20, then diluted with water (3 mL) and stirred for 3 h. The reaction mixture was extracted with DCM, and the combined organic extracts were concentrated in vacuo then purified by reverse phase chromatography (5-80% ACN/water) to afford the title compound (4.3 mg, 86% yield). MS (apci) m/z=509.1 (M+H).

Example 214

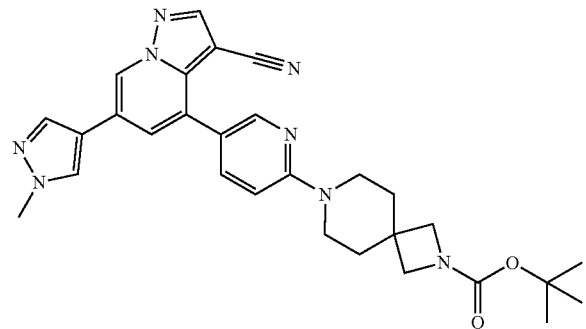 [SMILES: Cn1cc(-c2cc(-c3ccc(N4CCC5(CC4)CN(C(=O)OC(C)(C)C)C5)nc3)c3c(C#N)cnn3c2)cn1]

Tert-Butyl 7-(5-(3-cyano-6-(1-methyl-1H-pyrazol-4-yl)pyrazolo[1,5-a]pyridin-4-yl)pyridin-2-yl)-2,7-diazaspiro[3.5]nonane-2-carboxylate 4-(6-fluoropyridin-3-yl)-6-(1-methyl-1H-pyrazol-4-yl)pyrazolo[1,5-a]pyridine-3-carbonitrile (Intermediate P6; 15 mg, 0.047 mmol) and tert-butyl 2,7-diazaspiro[3.5]nonane-2-carboxylate (32.0 mg, 0.14 mmol) were suspended in DMSO (0.2 mL) in a microwave vessel. The resulting thick suspension was subjected to microwave irradiation at 125° C. for 1 h. The reaction mixture was then directly purified by reverse phase chromatography (5-75% ACN/water) to afford the title compound (14.0 mg, 57% yield). MS (apci) m/z=525.2 (M+H). $^1$H NMR (CDCl$_3$) δ 8.63 (d, 1H), 8.35 (d, 1H), 8.26 (s, 1H), 7.78 (s, 1H), 7.73 (dd, 1H), 7.68 (s, 1H), 7.39 (d, 1H), 6.81 (s, 1H), 3.99 (s, 3H), 3.72 (s, 4H), 3.62 (m, 4H), 1.85 (m, 4H), 1.46 (s, 9H).

Example 215

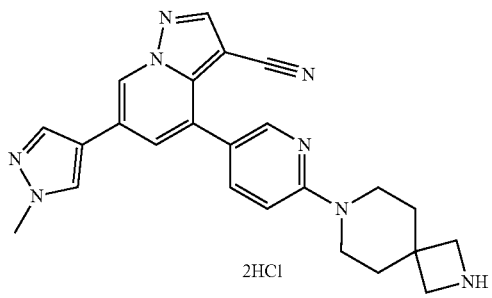 [SMILES: Cn1cc(-c2cc(-c3ccc(N4CCC5(CC4)CNC5)nc3)c3c(C#N)cnn3c2)cn1]

4-(6-(2,7-diazaspiro[3.5]nonan-7-yl)pyridin-3-yl)-6-(1-methyl-1H-pyrazol-4-yl)pyrazolo[1,5-a]pyridine-3-carbonitrile Dihydrochloride To a solution of tert-butyl 7-(5-(3-cyano-6-(1-methyl-1H-pyrazol-4-yl)pyrazolo[1,5-a]pyridin-4-yl)pyridin-2-yl)-2,7-diazaspiro[3.5]nonane-2-carboxylate (13 mg, 0.025 mmol) in EtOH (0.1 mL) and DCM (0.1 mL) was added 5 M HCl in iPrOH (198 µL, 0.99 mmol). After stirring at ambient temperature for 2 h the resulting suspension was diluted with DCM and stirred for an additional 2 d, then concentrated in vacuo to afford the title compound (11.0 mg, 89% yield). MS (apci) m/z=425.1 (M+H).

Example 216

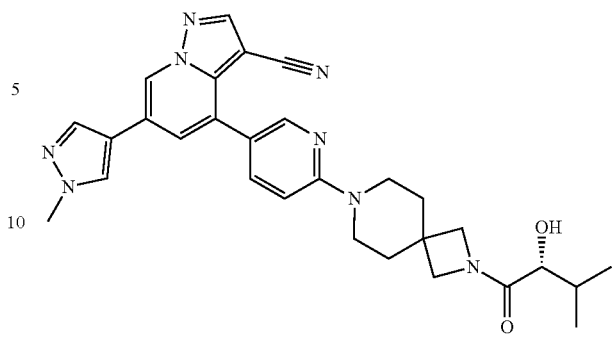

(R)-4-(6-(2-(2-hydroxy-3-methylbutanoyl)-2,7-diazaspiro[3.5]nonan-7-yl)pyridin-3-yl)-6-(1-methyl-1H-pyrazol-4-yl)pyrazolo[1,5-a]pyridine-3-carbonitrile (R)-2-hydroxy-3-methylbutanoic acid (1.8 mg, 0.015 mmol), then HATU (4.6 mg, 0.012 mmol) were added sequentially to a solution of 4-(6-(2,7-diazaspiro[3.5]nonan-7-yl)pyridin-3-yl)-6-(1-methyl-1H-pyrazol-4-yl)pyrazolo[1,5-a]pyridine-3-carbonitrile dihydrochloride (5 mg, 0.010 mmol) and DIEA (11 µL, 0.060 mmol) in DMA (0.2 mL). After stirring at ambient temperature for 45 min the reaction mixture was quenched with water (0.2 mL) and directly purified by reverse phase chromatography (5-80% ACN/water) to afford the title compound (3.7 mg, 70% yield). MS (apci) m/z=525.1 (M+H). $^1$H NMR (CDCl$_3$) δ 8.64 (d, 1H), 8.36 (d, 1H), 8.26 (s, 1H), 7.79 (s, 1H), 7.75 (dd, 1H), 7.68 (s, 1H), 7.39 (d, 1H), 6.83 (s, 1H), 3.99 (s, 3H), 3.91-3.98 (m, 4H), 3.81 (d, 1H), 3.65 (m, 4H), 3.19 (d, 1H), 1.86-1.93 (m, 5H), 1.05 (d, 3H), 0.88 (d, 3H).

Example 217

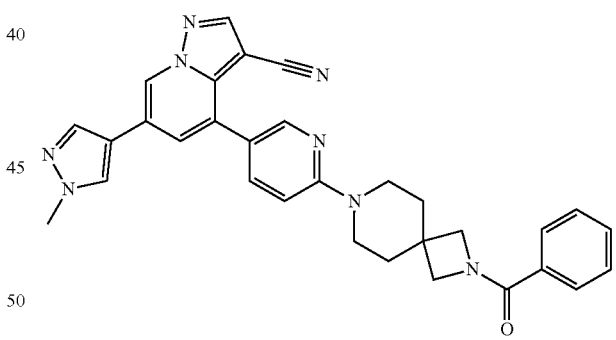

4-(6-(2-benzoyl-2,7-diazaspiro[3.5]nonan-7-yl)pyridin-3-yl)-6-(1-methyl-1H-pyrazol-4-yl)pyrazolo[1,5-a]pyridine-3-carbonitrile A solution of 4-(6-(2,7-diazaspiro[3.5]nonan-7-yl)pyridin-3-yl)-6-(1-methyl-1H-pyrazol-4-yl)pyrazolo[1,5-a]pyridine-3-carbonitrile dihydrochloride (5.4 mg, 0.011 mmol) in DMA (0.2 mL) was treated with DIEA (11.4 µL, 0.065 mmol) and benzoyl chloride (2.5 µL, 0.022 mmol). The reaction mixture was stirred at ambient temperature for 1 h and then quenched with water (0.1 mL) and stirred for 2 d. The reaction mixture was diluted with water (2 mL) and vacuum filtered. The isolated solids were rinsed with water and dried in vacuo to afford the title compound (3.8 mg, 66% yield). MS (apci) m/z=529.2 (M+H).

The compounds in Table S were prepared according the method used for the synthesis of Example 217, replacing benzoyl chloride with the appropriate acid chloride starting material.

dine-3-carbonitrile dihydrochloride (6.0 mg, 0.012 mmol) in DMA (0.2 mL) was treated with DIEA (13 µL, 0.072 mmol) and 1 M acetyl chloride in DCM (24 µL, 0.024 mmol). After stirring at ambient temperature for 1 h the reaction was quenched with water (0.1 mL) and directly purified by reverse phase chromatography (5-80% ACN/water) to afford

TABLE S

| Ex # | Structure | Chemical Name | MS (apci) m/z |
|---|---|---|---|
| 218 | 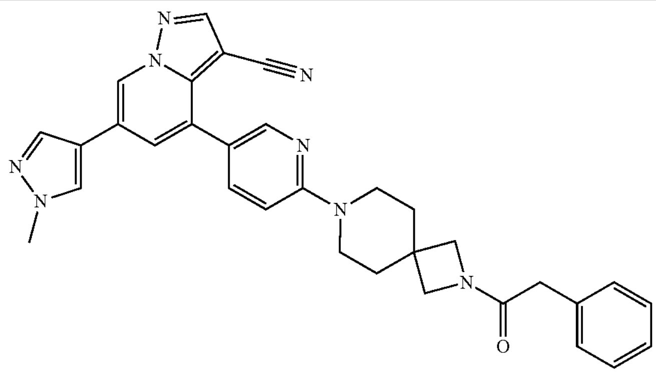 [SMILES: Cn1cc(-c2cc(-c3ccc(N4CCC5(CC4)CN(C(=O)Cc4ccccc4)C5)nc3)c3c(C#N)cnn3c2)cn1] | 6-(1-methyl-1H-pyrazol-4-yl)-4-(6-(2-(2-phenylacetyl)-2,7-diazaspiro[3.5]nonan-7-yl)pyridin-3-yl)pyrazolo[1,5-a]pyridine-3-carbonitrile | 543.2 (M + H) |
| 219 | 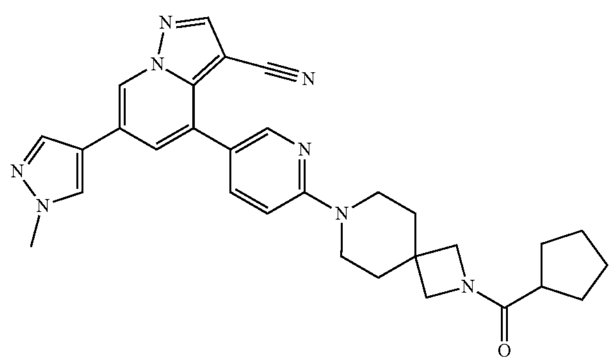 [SMILES: Cn1cc(-c2cc(-c3ccc(N4CCC5(CC4)CN(C(=O)C4CCCC4)C5)nc3)c3c(C#N)cnn3c2)cn1] | 4-(6-(2-(cyclopentanecarbonyl)-2,7-diazaspiro[3.5]nonan-7-yl)pyridin-3-yl)-6-(1-methyl-1H-pyrazol-4-yl)pyrazolo[1,5-a]pyridine-3-carbonitrile | 521.2 (M + H) |

Example 220

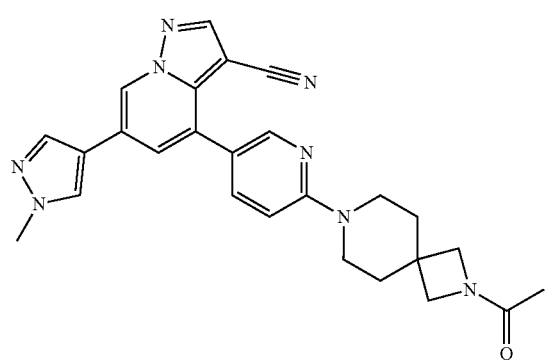 [SMILES: CC(=O)N1CC2(CCN(c3ccc(-c4cc(-c5cnn(C)c5)cn5ncc(C#N)c45)cn3)CC2)C1]

4-(6-(2-acetyl-2,7-diazaspiro[3.5]nonan-7-yl)pyridin-3-yl)-6-(1-methyl-1H-pyrazol-4-yl)pyrazolo[1,5-a]pyridine-3-carbonitrile A solution of 4-(6-(2,7-diazaspiro[3.5]nonan-7-yl)pyridin-3-yl)-6-(1-methyl-1H-pyrazol-4-yl)pyrazolo[1,5-a]pyrithe title compound (4.8 mg, 85% yield). MS (apci) m/z=467.1 (M+H).

Example 221

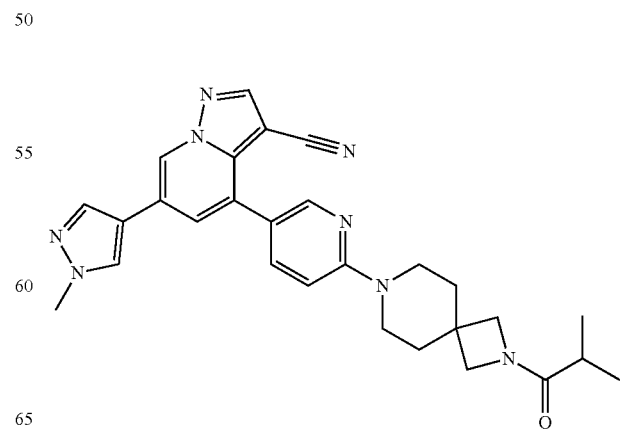

321

4-(6-(2-isobutyryl-2,7-diazaspiro[3.5]nonan-7-yl)pyridin-3-yl)-6-(1-methyl-1H-pyrazol-4-yl)pyrazolo[1,5-a]pyridine-3-carbonitrile A solution of 4-(6-(2,7-diazaspiro[3.5]nonan-7-yl)pyridin-3-yl)-6-(1-methyl-1H-pyrazol-4-yl)pyrazolo[1,5-a]pyridine-3-carbonitrile dihydrochloride (5 mg, 0.010 mmol) in DMA (0.2 mL) was treated with DIEA (10.5 µL, 0.060 mmol) and isobutyryl chloride (1.6 µL, 0.015 mmol). After stirring at ambient temperature overnight the reaction was quenched with water (3 mL) and stirred for an additional 3 h. The reaction mixture was extracted with DCM and the combined organic extracts were concentrated in vacuo and directly purified by reverse phase chromatography (5-80% ACN/water) to afford the title compound (4.4 mg, 85% yield). MS (apci) m/z=495.1 (M+H).

Example 222

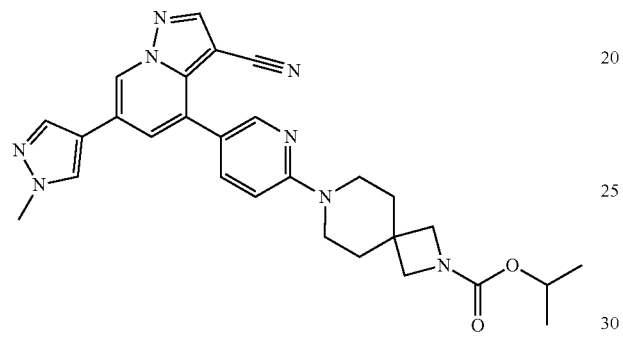

isopropyl 7-(5-(3-cyano-6-(1-methyl-1H-pyrazol-4-yl)pyrazolo[1,5-a]pyridin-4-yl)pyridin-2-yl)-2,7-diazaspiro[3.5]nonane-2-carboxylate A solution of 4-(6-(2,7-diazaspiro[3.5]nonan-7-yl)pyridin-3-yl)-6-(1-methyl-1H-pyrazol-4-yl)pyrazolo[1,5-a]pyridine-3-carbonitrile dihydrochloride (5.0 mg, 0.010 mmol) in DMA (0.2 mL) was treated with DIEA (11 µL, 0.060 mmol) and 1 M isopropyl carbonochloridate in toluene (20 µL, 0.020 mmol). After stirring at ambient temperature for 4 h the reaction was quenched with water (0.1 mL), diluted with additional water (2 mL) and vacuum filtered, rinsing the solids with water. The solids were dried in vacuo to afford the title compound (2.9 mg, 57% yield). MS (apci) m/z=511.2 (M+H). $^1$H NMR (CDCl$_3$) δ 8.63 (d, 1H), 8.36 (d, 1H), 8.26 (s, 1H), 7.79 (s, 1H), 7.74 (dd, 1H), 7.68 (s, 1H), 7.39 (d, 1H), 6.81 (s, 1H), 4.91 (m, 1H), 3.99 (s, 3H), 3.75 (s, 4H), 3.63 (m, 4H), 1.86 (m, 4H), 1.26 (d, 6H).

Example 223

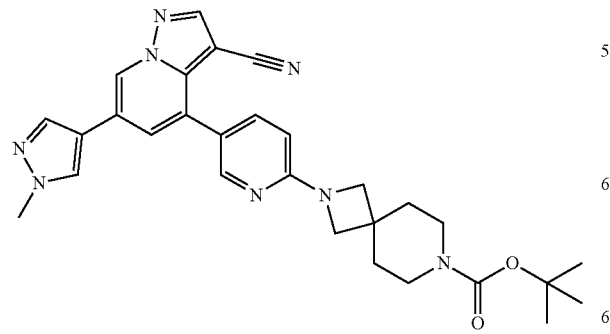

322

Tert-Butyl 2-(5-(3-cyano-6-(1-methyl-1H-pyrazol-4-yl)pyrazolo[1,5-a]pyridin-4-yl)pyridin-2-yl)-2,7-diazaspiro[3.5]nonane-7-carboxylate In a microwave vessel, a mixture of tert-butyl 2,7-diazaspiro[3.5]nonane-7-carboxylate (85 mg, 0.38 mmol), DIEA (44 µL, 0.25 mmol), and 4-(6-fluoropyridin-3-yl)-6-(1-methyl-1H-pyrazol-4-yl)pyrazolo[1,5-a]pyridine-3-carbonitrile (Intermediate P6; 40 mg, 0.13 mmol) in DMSO (1 mL) was subjected to microwave irradiation at 125° C. for 2 h. After cooling to ambient temperature, the reaction mixture was directly purified by reverse-phase preparative HPLC (10 to 80% acetonitrile/water) to give the title compound (12 mg, 18% yield). MS (apci) m/z=525.2 (M+H).

Example 224

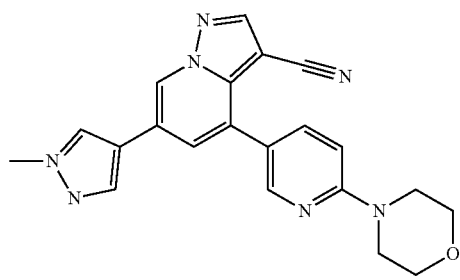

6-(1-methyl-1H-pyrazol-4-yl)-4-(6-morpholinopyridin-3-yl)pyrazolo[1,5-a]pyridine-3-carbonitrile In a microwave vessel, a mixture of 4-(6-fluoropyridin-3-yl)-6-(1-methyl-1H-pyrazol-4-yl)pyrazolo[1,5-a]pyridine-3-carbonitrile (Intermediate P6; 15 mg, 0.0471 mmol) and morpholine (12.3 µL, 0.128 mmol) in DMSO (0.2 mL) was subjected to microwave irradiation at 125° C. for 1 h. The reaction mixture was directly purified by reverse phase chromatography (5-90% ACN/water). The chromatographic fractions containing title compound were combined, concentrated and triturated with MTBE (2 mL) to yield the title compound (4.0 mg, 22% yield). MS (apci) m/z=386.1 (M+H).

Example 225

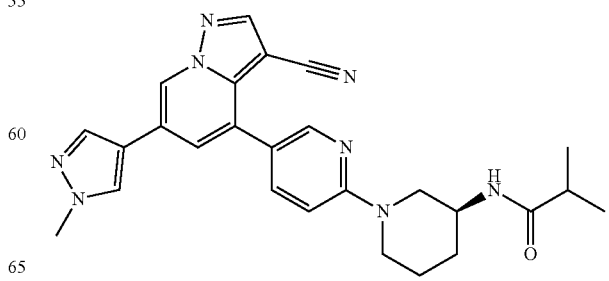

(S)—N-(1-(5-(3-cyano-6-(1-methyl-1H-pyrazol-4-yl)pyrazolo[1,5-a]pyridin-4-yl)pyridin-2-yl)piperidin-3-yl)isobutyramide Step 1: Preparation of (S)-4-(6-(3-aminopiperidin-1-yl)pyridin-3-yl)-6-(1-methyl-1H-pyrazol-4-yl)pyrazolo[1,5-a]pyridine-3-carbonitrile A mixture of 4-(6-fluoropyridin-3-yl)-6-(1-methyl-1H-pyrazol-4-yl)pyrazolo[1,5-a]pyridine-3-carbonitrile (Intermediate P6; 0.100 g, 0.314 mmol), (S)-tert-butyl piperidin-3-ylcarbamate (0.252 g, 1.26 mmol) and potassium carbonate (0.174 g, 1.26 mmol) in DMSO (6.28 mL) was stirred at 110° C. overnight. The reaction mixture was then acidified to pH 7 with 1 M HCl$_{(aq)}$ and the resulting suspension was vacuum filtered and rinsed with water. The isolated solids were dissolved in 20% MeOH/DCM (5 mL), treated with 4M HCl in dioxane (1 mL) and concentrated in vacuo to afford the crude title compound as a solid, which was used directly in the next step without further purification (0.106 g, 85% yield). MS (apci) m/z=399.2 (M+H).

Step 2: Preparation of (S)—N-(1-(5-(3-cyano-6-(1-methyl-1H-pyrazol-4-yl)pyrazolo[1,5-a]pyridin-4-yl)pyridin-2-yl)piperidin-3-yl)isobutyramide To a solution of (S)-4-(6-(3-aminopiperidin-1-yl)pyridin-3-yl)-6-(1-methyl-1H-pyrazol-4-yl)pyrazolo[1,5-a]pyridine-3-carbonitrile (30 mg, 0.075 mmol) and DIEA (0.079 mL, 0.45 mmol) in DMA (2.5 mL) was added isobutyric acid (13.3 mg, 0.15 mmol) and HATU (57.3 mg, 0.15 mmol). After stirring at ambient temperature overnight the reaction mixture was quenched with water and extracted with EtOAc (3×10 mL). The combined organic extracts were dried over anhydrous Na$_2$SO$_4$, filtered and concentrated in vacuo. The crude residue was purified by silica chromatography (0-50% of 20% MeOH/DCM in EtOAc) to afford the title compound (14.4 mg, 39% yield). MS (apci) m/z=469.2 (M+H).

Example 226

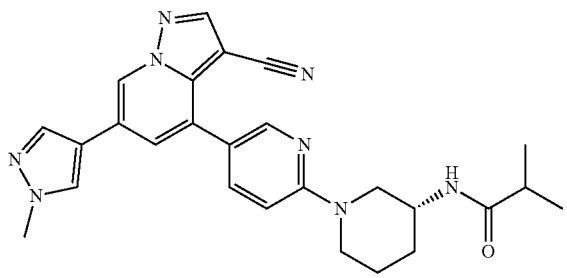 [SMILES: CC(C)C(=O)N[C@@H]1CCCN(c2ccc(-c3cc(-c4cnn(C)c4)cn4ncc(C#N)c34)cn2)C1]

(R)—N-(1-(5-(3-cyano-6-(1-methyl-1H-pyrazol-4-yl)pyrazolo[1,5-a]pyridin-4-yl)pyridin-2-yl)piperidin-3-yl)isobutyramide Step 1: Preparation of (R)-4-(6-(3-aminopiperidin-1-yl)pyridin-3-yl)-6-(1-methyl-1H-pyrazol-4-yl)pyrazolo[1,5-a]pyridine-3-carbonitrile A mixture of 4-(6-fluoropyridin-3-yl)-6-(1-methyl-1H-pyrazol-4-yl)pyrazolo[1,5-a]pyridine-3-carbonitrile (Intermediate P6; 0.100 g, 0.314 mmol), tert-butyl (R)-tert-butyl piperidin-3-yl-carbamate (0.252 g, 1.26 mmol) and potassium carbonate (0.174 g, 1.26 mmol) in DMSO (6.28 mL) was stirred at 110° C. overnight. The reaction mixture was acidified to pH 7 with 1 M HCl$_{(aq)}$ and the resulting suspension was vacuum filtered and rinsed with water. The isolated solids were dissolved in 20% MeOH/DCM (5 mL), treated with 4 M HCl in dioxane (1 mL) and concentrated to afford the crude title compound as a solid, which was used directly in the next step without further purification. MS (apci) m/z=399.2 (M+H).

Step 2: Preparation of (R)—N-(1-(5-(3-cyano-6-(1-methyl-1H-pyrazol-4-yl)pyrazolo[1,5-a]pyridin-4-yl)pyridin-2-yl)piperidin-3-yl)isobutyramide To a solution of (R)-4-(6-(3-aminopiperidin-1-yl)pyridin-3-yl)-6-(1-methyl-1H-pyrazol-4-yl)pyrazolo[1,5-a]pyridine-3-carbonitrile (30 mg, 0.075 mmol) and DIEA (0.066 mL, 0.38 mmol) in DMA (2.5 mL) was added isobutyric acid (13.3 mg, 0.15 mmol) and HATU (57.3 mg, 0.15 mmol). After stirring at ambient temperature overnight the reaction mixture was quenched with water and extracted with EtOAc (3×10 mL). The combined organic extracts were dried (Na$_2$SO$_4$), filtered, concentrated and purified by silica chromatography (0-50% of 20% MeOH/DCM in EtOAc) to afford the title compound (0.0131 g, 37% yield). MS (apci) m/z=469.2 (M+H).

Example 227

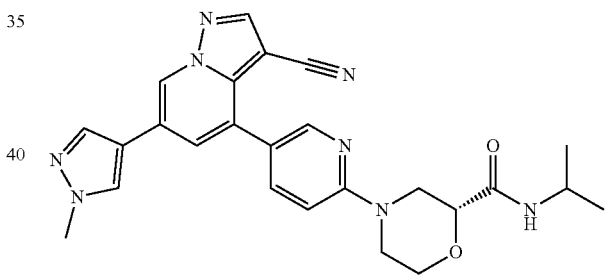

(R)-4-(5-(3-cyano-6-(1-methyl-1H-pyrazol-4-yl)pyrazolo[1,5-a]pyridin-4-yl)pyridin-2-yl)-N-isopropylmorpholine-2-carboxamide Step 1: Preparation of (R)-4-(5-(3-cyano-6-(1-methyl-1H-pyrazol-4-yl)pyrazolo[1,5-a]pyridin-4-yl)pyridin-2-yl)morpholine-2-carboxylic Acid A solution of 4-(6-fluoropyridin-3-yl)-6-(1-methyl-1H-pyrazol-4-yl)pyrazolo[1,5-a]pyridine-3-carbonitrile (Intermediate P6; 0.100 g, 0.314 mmol) in DMSO (3.14 mL) was treated with (R)-morpholine-2-carboxylic acid hydrochloride (0.211 g, 1.26 mmol) and potassium carbonate (0.347 g, 2.51 mmol). The resulting thick suspension was stirred and heated at 110° C. overnight. The reaction mixture was then acidified to pH 7 with the addition of 1 M HCl$_{(aq)}$. The resulting suspension was vacuum filtered rinsing solids with water to afford the title compound (0.091 g, 68% yield). MS (apci) m/z=430.0 (M+H).

Step 2: Preparation of (R)-4-(5-(3-cyano-6-(1-methyl-1H-pyrazol-4-yl)pyrazolo[1,5-a]pyridin-4-yl)pyridin-2-yl)-N-isopropylmorpholine-2-carboxamide DIEA (0.051 mL, 0.29 mmol), propan-2-amine (6.9 mg, 0.12 mmol) and HATU (56 mg, 0.15 mmol) were added sequentially to a solution of (R)-4-(5-(3-cyano-6-(1-methyl-1H-pyrazol-4-yl)pyrazolo[1,5-a]pyridin-4-yl)pyridin-2-yl)morpholine-2-carboxylic acid (25 mg, 0.058 mmol) in DMA (1.9 mL). After stirring at ambient temperature overnight the reaction mixture was quenched with water and extracted with EtOAc (3×20 mL). The combined organic extracts were dried ($Na_2SO_4$), filtered, concentrated in vacuo and purified by silica chromatography (4 stepwise separations using from 0-50% of 20% MeOH/DCM in EtOAc to 0-10% MeOH/DCM) to afford the title compound (0.0069 g, 25% yield). MS (apci) m/z=471.2 (M+H).

Example 228

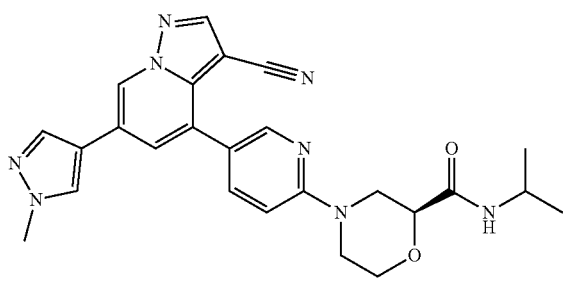 [SMILES: CC(C)NC(=O)[C@@H]1CN(c2ccc(-c3cc(-c4cnn(C)c4)cn4ncc(C#N)c34)cn2)CCO1]

(S)-4-(5-(3-cyano-6-(1-methyl-1H-pyrazol-4-yl)pyrazolo[1,5-a]pyridin-4-yl)pyridin-2-yl)-N-isopropylmorpholine-2-carboxamide Step 1: Preparation of (S)-4-(5-(3-cyano-6-(1-methyl-1H-pyrazol-4-yl)pyrazolo[1,5-a]pyridin-4-yl)pyridin-2-yl)morpholine-2-carboxylic Acid A solution of 4-(6-fluoropyridin-3-yl)-6-(1-methyl-1H-pyrazol-4-yl)pyrazolo[1,5-a]pyridine-3-carbonitrile (Intermediate P6; 0.100 g, 0.31 mmol) in DMSO (3.14 mL) was treated with (S)-Morpholine-2-carboxylic acid hydrochloride (0.211 g, 1.26 mmol) and potassium carbonate (0.347 g, 2.51 mmol). The resulting thick suspension was stirred and heated at 110° C. overnight. The reaction mixture was acidified to pH 7 with 1 M $HCl_{(aq)}$. The resulting suspension was vacuum filtered, rinsing solids with water to afford the title compound (0.100 g g, 74% yield). MS (apci) m/z=430.0 (M+H).

Step 2: Preparation of (S)-4-(5-(3-cyano-6-(1-methyl-1H-pyrazol-4-yl)pyrazolo[1,5-a]pyridin-4-yl)pyridin-2-yl)-N-isopropylmorpholine-2-carboxamide DIEA (0.051 mL, 0.29 mmol), propan-2-amine (6.9 mg, 0.12 mmol) and HATU (55.3 mg, 0.146 mmol) were added sequentially to a solution (S)-4-(5-(3-cyano-6-(1-methyl-1H-pyrazol-4-yl)pyrazolo[1,5-a]pyridin-4-yl)pyridin-2-yl)morpholine-2-carboxylic acid (25 mg, 0.058 mmol) in DMA (1.9 mL). After stirring at ambient temperature overnight, the reaction mixture was quenched with water and extracted with EtOAc (3×20 mL). The combined organic extracts were dried ($Na_2SO_4$), filtered, concentrated and purified by silica chromatography (4 stepwise separations using from 0-50% of 20% MeOH/DCM in EtOAc to 0-10% MeOH/DCM) to afford the title compound (5.6 mg, 20.0% yield). MS (apci) m/z=471.2 (M+H).

Example 229

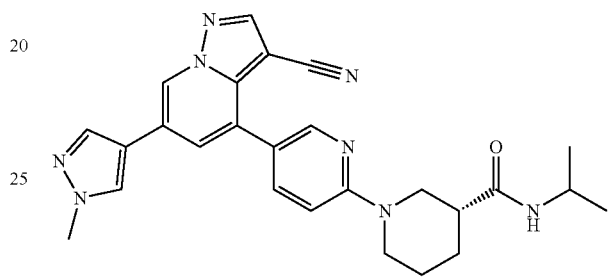

(R)-1-(5-(3-cyano-6-(1-methyl-1H-pyrazol-4-yl)pyrazolo[1,5-a]pyridin-4-yl)pyridin-2-yl)-N-isopropylpiperidine-3-carboxamide Step 1: Preparation of (R)-1-(5-(3-cyano-6-(1-methyl-1H-pyrazol-4-yl)pyrazolo[1,5-a]pyridin-4-yl)pyridin-2-yl)piperidine-3-carboxylic Acid A solution of 4-(6-fluoropyridin-3-yl)-6-(1-methyl-1H-pyrazol-4-yl)pyrazolo[1,5-a]pyridine-3-carbonitrile (Intermediate P6; 300 mg, 0.942 mmol) in DMSO (9.42 mL) was treated with (R)-piperidine-3-carboxylic acid (487 mg, 3.77 mmol) and potassium carbonate (521 mg, 3.77 mmol). The resulting thick suspension was stirred and heated at 110° C. overnight. The reaction mixture was then adjusted to pH 7 with saturated $NaHCO_{3(aq)}$. The resulting suspension was vacuum filtered, rinsing solids with water to afford the title compound (0.272 g, 68% yield). MS (apci) m/z=428.2 (M+H).

Step 2: Preparation of (R)-1-(5-(3-cyano-6-(1-methyl-1H-pyrazol-4-yl)pyrazolo[1,5-a]pyridin-4-yl)pyridin-2-yl)-N-isopropylpiperidine-3-carboxamide Propan-2-amine (6.9 mg, 0.12 mmol), DIEA (0.051 mL, 0.29 mmol), and HATU (55.3 mg, 0.15 mmol) were added sequentially to a solution (R)-1-(5-(3-cyano-6-(1-methyl-1H-pyrazol-4-yl)pyrazolo[1,5-a]pyridin-4-yl)pyridin-2-yl)piperidine-3-carboxylic acid (25 mg, 0.058 mmol) in DMA (2 mL). After stirring at ambient temperature overnight, the reaction mixture was quenched with water and brine and then extracted with EtOAc (3×20 mL). The combined organic extracts were dried ($Na_2SO_4$), filtered, concentrated and purified by silica chromatography (0-50% of 20%

MeOH/DCM in EtOAc) to afford the title compound (0.0147 g, 54% yield). MS (apci) m/z=469.2 (M+H).

Example 230

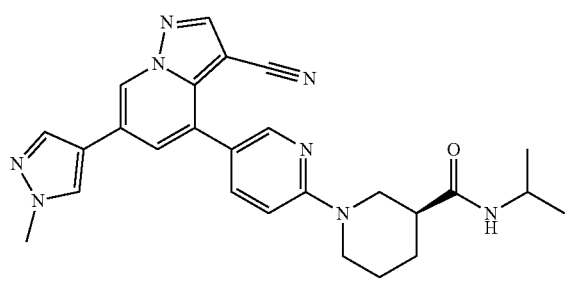 [SMILES: CC(C)NC(=O)[C@H]1CCCN(c2ccc(-c3cc(-c4cnn(C)c4)cn4ncc(C#N)c34)cn2)C1]

(S)-1-(5-(3-cyano-6-(1-methyl-1H-pyrazol-4-yl)pyrazolo[1,5-a]pyridin-4-yl)pyridin-2-yl)-N-isopropylpiperidine-3-carboxamide Step 1: Preparation of (S)-1-(5-(3-cyano-6-(1-methyl-1H-pyrazol-4-yl)pyrazolo[1,5-a]pyridin-4-yl)pyridin-2-yl)piperidine-3-carboxylic Acid A solution of 4-(6-fluoropyridin-3-yl)-6-(1-methyl-1H-pyrazol-4-yl)pyrazolo[1,5-a]pyridine-3-carbonitrile (Intermediate P6; 100 mg, 0.31 mmol) in DMSO (3 mL) was treated with (S)-piperidine-3-carboxylic acid (162 mg, 1.26 mmol) and potassium carbonate (174 mg, 1.26 mmol). The resulting suspension was stirred and heated at 110° C. overnight. The reaction mixture was then adjusted to pH 7 with the addition of saturated NaHCO$_{3(aq)}$. The resulting suspension was vacuum filtered, rinsing solids with water to afford the title compound (32.9 mg, 26% yield). MS (apci) m/z=428.2 (M+H).

Step 2: Preparation of (S)-1-(5-(3-cyano-6-(1-methyl-1H-pyrazol-4-yl)pyrazolo[1,5-a]pyridin-4-yl)pyridin-2-yl)-N-isopropylpiperidine-3-carboxamide Propan-2-amine (8.3 mg, 0.14 mmol), DIEA (0.061 mL, 0.35 mmol), and HATU (53.4 mg, 0.14 mmol) were added sequentially to a solution (S)-1-(5-(3-cyano-6-(1-methyl-1H-pyrazol-4-yl)pyrazolo[1,5-a]pyridin-4-yl)pyridin-2-yl)piperidine-3-carboxylic acid (30 mg, 0.070 mmol) in DMA (2.3 mL). After stirring at ambient temperature overnight, the reaction mixture was quenched with water and brine, and then extracted with EtOAc (3×20 mL). The combined organic extracts were dried (Na$_2$SO$_4$), filtered, concentrated and purified by silica chromatography (0-50% of 20% MeOH/DCM in EtOAc) to afford the title compound (0.0204 g, 62% yield). MS (apci) m/z=469.2 (M+H).

Example 231

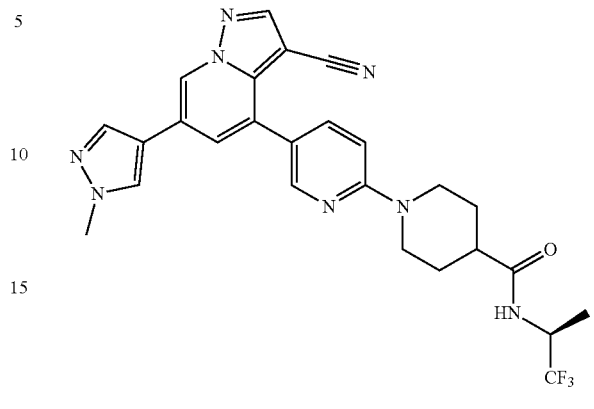

(S)-1-(5-(3-cyano-6-(1-methyl-1H-pyrazol-4-yl)pyrazolo[1,5-a]pyridin-4-yl)pyridin-2-yl)-N-(1,1,1-trifluoropropan-2-yl)piperidine-4-carboxamide Step 1: Preparation of 1-(5-(3-cyano-6-(1-methyl-1H-pyrazol-4-yl)pyrazolo[1,5-a]pyridin-4-yl)pyridin-2-yl)piperidine-4-carboxylic Acid A solution of 4-(6-fluoropyridin-3-yl)-6-(1-methyl-1H-pyrazol-4-yl)pyrazolo[1,5-a]pyridine-3-carbonitrile (Intermediate P6; 1.00 g, 3.14 mmol) in DMSO (31.4 mL) was treated with piperidine-4-carboxylic acid (1.623 g, 12.57 mmol) and potassium carbonate (1.737 g, 12.57 mmol). The resulting thick suspension was stirred and heated at 110° C. overnight. The reaction mixture was then adjusted to pH 7 with saturated NaHCO$_{3(aq)}$. The resulting suspension was vacuum filtered, rinsing solids with water to afford the title compound (1.077 g, 80% yield). MS (apci) m/z=428.2 (M+H).

Step 2: Preparation of (S)-1-(5-(3-cyano-6-(1-methyl-1H-pyrazol-4-yl)pyrazolo[1,5-a]pyridin-4-yl)pyridin-2-yl)-N-(1,1,1-trifluoropropan-2-yl)piperidine-4-carboxamide (S)-1,1,1-trifluoropropan-2-amine (13.2 mg, 0.12 mmol), DIEA (0.051 mL, 0.29 mmol), and HATU (44.5 mg, 0.12 mmol) were added sequentially to a solution 1-(5-(3-cyano-6-(1-methyl-1H-pyrazol-4-yl)pyrazolo[1,5-a]pyridin-4-yl)pyridin-2-yl)piperidine-4-carboxylic acid (25 mg, 0.058 mmol) in DMA (2 mL). After stirring at ambient temperature overnight, the reaction mixture was quenched with water and brine, and then extracted with EtOAc (3×10 mL). The combined organic extracts were dried over anhydrous Na$_2$SO$_4$, filtered, concentrated and purified by silica chromatography (0-50% of 20% MeOH/DCM in EtOAc) to afford the title compound (0.0151 g, 49% yield). MS (apci) m/z=523.2 (M+H).

The compounds in Table T were prepared and purified according the method described for the synthesis of Example 231, replacing (S)-1,1,1-trifluoropropan-2-amine with the appropriate amine starting materials.

TABLE T

| Ex # | Structure | Chemical Name | MS (apci) m/z |
|---|---|---|---|
| 232 | 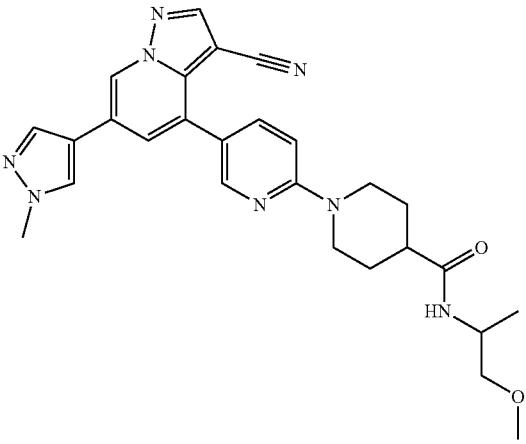 [SMILES: COCC(C)NC(=O)C1CCN(c2ccc(-c3cc(-c4cnn(C)c4)cn4ncc(C#N)c34)cn2)CC1] | 1-(5-(3-cyano-6-(1-methyl-1H-pyrazol-4-yl)pyrazolo[1,5-a]pyridin-4-yl)pyridin-2-yl)-N-(1-methoxypropan-2-yl)piperidine-4-carboxamide | 499.3 (M + H) |
| 233 | 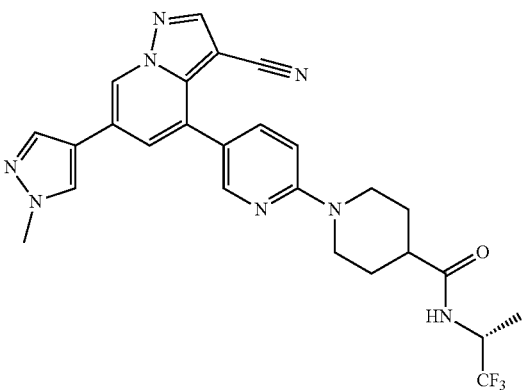 [SMILES: C[C@@H](NC(=O)C1CCN(c2ccc(-c3cc(-c4cnn(C)c4)cn4ncc(C#N)c34)cn2)CC1)C(F)(F)F] | (R)-1-(5-(3-cyano-6-(1-methyl-1H-pyrazol-4-yl)pyrazolo[1,5-a]pyridin-4-yl)pyridin-2-yl)-N-(1,1,1-trifluoropropan-2-yl)piperidine-4-carboxamide | 523.2 (M + H) |
| 234 | 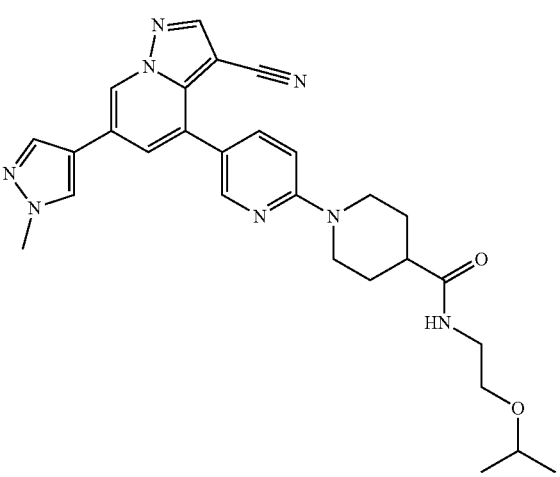 [SMILES: CC(C)OCCNC(=O)C1CCN(c2ccc(-c3cc(-c4cnn(C)c4)cn4ncc(C#N)c34)cn2)CC1] | 1-(5-(3-cyano-6-(1-methyl-1H-pyrazol-4-yl)pyrazolo[1,5-a]pyridin-4-yl)pyridin-2-yl)-N-(2-isopropoxyethyl)piperidine-4-carboxamide | 513.3 (M + H) |

TABLE T-continued

| Ex # | Structure | Chemical Name | MS (apci) m/z |
|---|---|---|---|
| 235 | 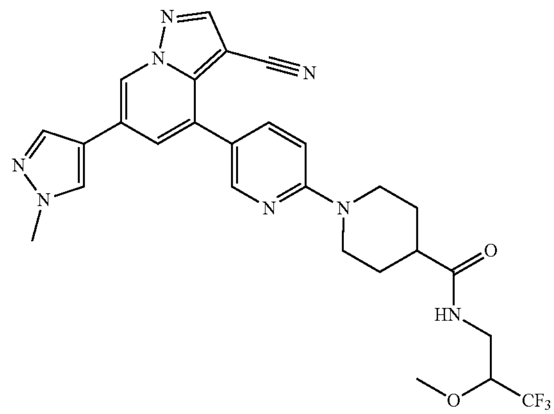 [SMILES: COC(CNC(=O)C1CCN(c2ccc(-c3cc(-c4cnn(C)c4)cn4ncc(C#N)c34)cn2)CC1)C(F)(F)F] | 1-(5-(3-cyano-6-(1-methyl-1H-pyrazol-4-yl)pyrazolo[1,5-a]pyridin-4-yl)pyridin-2-yl)-N-(3,3,3-trifluoro-2-methoxypropyl)piperidine-4-carboxamide | 553.2 (M + H) |
| 236 | 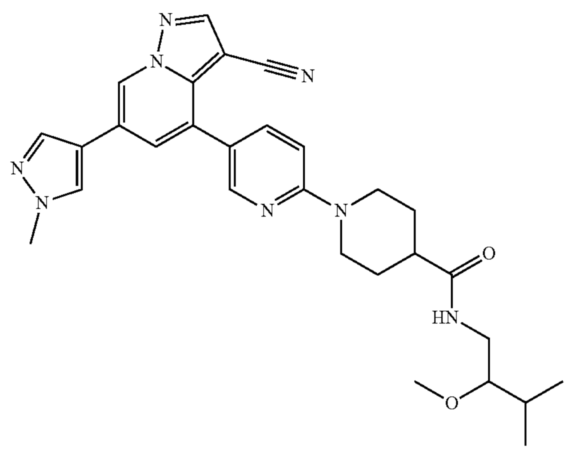 [SMILES: COC(CNC(=O)C1CCN(c2ccc(-c3cc(-c4cnn(C)c4)cn4ncc(C#N)c34)cn2)CC1)C(C)C] | 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide | 527.3 (M + H) |
| 237 | 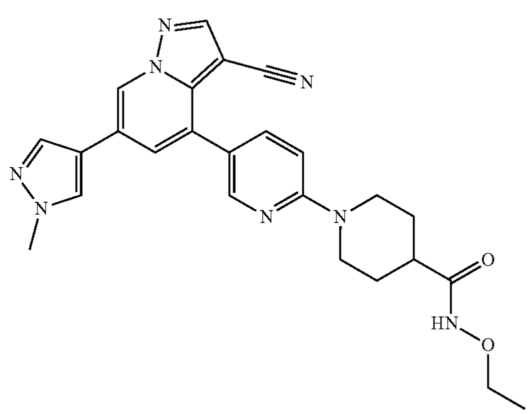 [SMILES: CCONC(=O)C1CCN(c2ccc(-c3cc(-c4cnn(C)c4)cn4ncc(C#N)c34)cn2)CC1] | 1-(5-(3-cyano-6-(1-methyl-1H-pyrazol-4-yl)pyrazolo[1,5-a]pyridin-4-yl)pyridin-2-yl)-N-ethoxypiperidine-4-carboxamide | 471.2 (M + H) |

TABLE T-continued

| Ex # | Structure | Chemical Name | MS (apci) m/z |
|---|---|---|---|
| 238 | 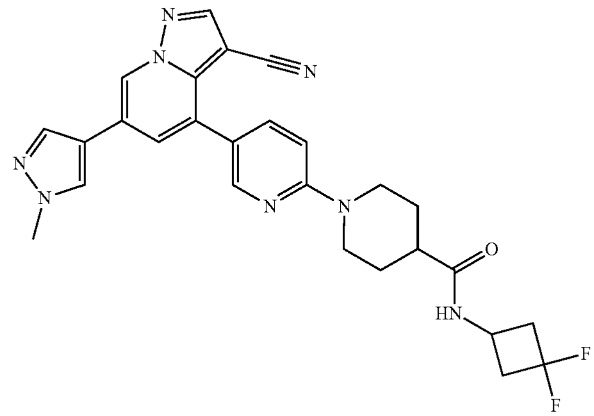 [SMILES: Cn1cc(-c2cc(-c3ccc(N4CCC(C(=O)NC5CC(F)(F)C5)CC4)nc3)c3c(C#N)cnn3c2)cn1] | 1-(5-(3-cyano-6-(1-methyl-1H-pyrazol-4-yl)pyrazolo[1,5-a]pyridin-4-yl)pyridin-2-yl)-N-(3,3-difluorocyclobutyl)piperidine-4-carboxamide | 517.1 (M + H) |
| 239 | 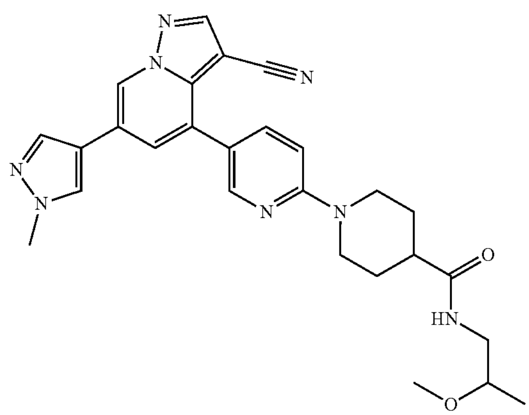 [SMILES: COC(C)CNC(=O)C1CCN(c2ccc(-c3cc(-c4cnn(C)c4)cn4ncc(C#N)c34)cn2)CC1] | 1-(5-(3-cyano-6-(1-methyl-1H-pyrazol-4-yl)pyrazolo[1,5-a]pyridin-4-yl)pyridin-2-yl)-N-(2-methoxypropyl)piperidine-4-carboxamide | 499.1 (M + H) |
| 240 | 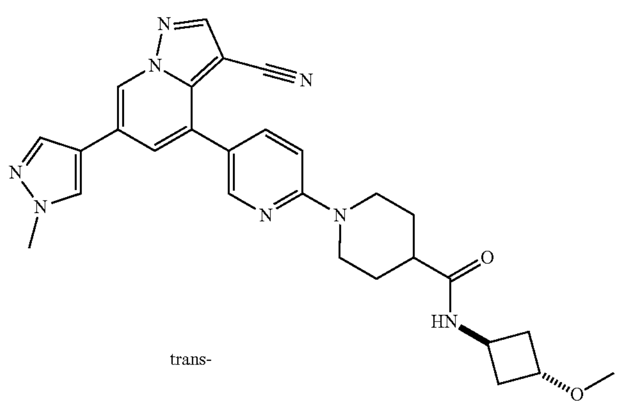 | 1-(5-(3-cyano-6-(1-methyl-1H-pyrazol-4-yl)pyrazolo[1,5-a]pyridin-4-yl)pyridin-2-yl)-N-((1r,3r)-3-methoxycyclobutyl)piperidine-4-carboxamide | 511.2 (M + H) |

| Ex # | Structure | Chemical Name | MS (apci) m/z |
|---|---|---|---|
| 241 | 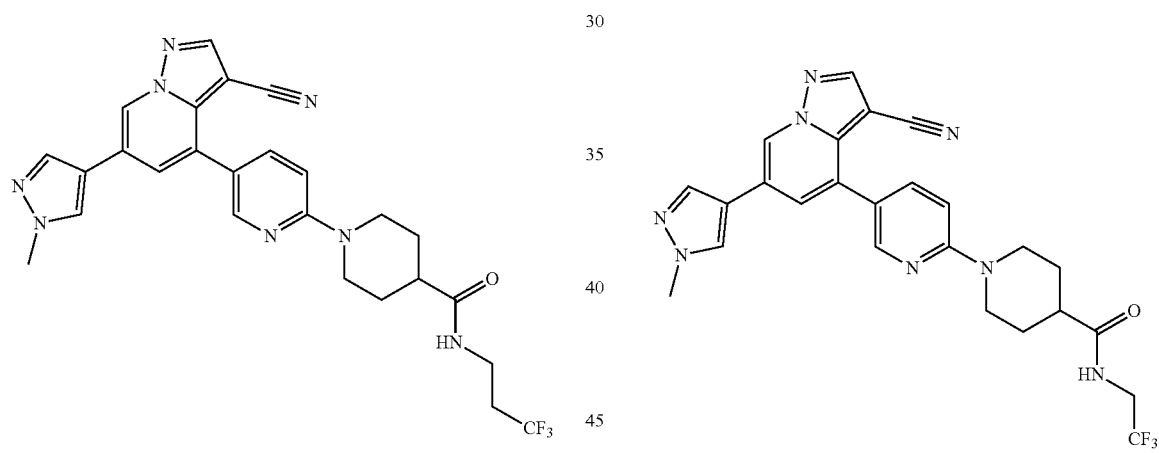 cis- | 1-(5-(3-cyano-6-(1-methyl-1H-pyrazol-4-yl)pyrazolo[1,5-a]pyridin-4-yl)pyridin-2-yl)-N-((1s,3s)-3-methoxycyclobutyl)piperidine-4-carboxamide | 511.2 (M + H) |

Example 242

1-(5-(3-cyano-6-(1-methyl-1H-pyrazol-4-yl)pyrazolo[1,5-a]pyridin-4-yl)pyridin-2-yl)-N-(3,3,3-trifluoropropyl)piperidine-4-carboxamide To a solution of 1-(5-(3-cyano-6-(1-methyl-1H-pyrazol-4-yl)pyrazolo[1,5-a]pyridin-4-yl)pyridin-2-yl)piperidine-4-carboxylic acid (25 mg, 0.058 mmol) in DMF (2 mL) was added DIEA (0.0102 mL, 0.058 mmol), 3,3,3-trifluoropropylamine (6.6 mg, 0.058 mmol), and HBTU (24.4 mg, 0.064 mmol). After stirring at 40° C. overnight, the reaction mixture was quenched with water and brine and then extracted with EtOAc (3×10 mL). The combined organic extracts were dried (Na₂SO₄), filtered, concentrated and purified by silica chromatography (0-50% of 20% MeOH/DCM in EtOAc) to afford the title compound (0.017 g, 55% yield). MS (apci) m/z=523.1 (M+H).

Example 243

1-(5-(3-cyano-6-(1-methyl-1H-pyrazol-4-yl)pyrazolo[1,5-a]pyridin-4-yl)pyridin-2-yl)-N-(2,2,2-trifluoroethyl)piperidine-4-carboxamide To a solution 1-(5-(3-cyano-6-(1-methyl-1H-pyrazol-4-yl)pyrazolo[1,5-a]pyridin-4-yl)pyridin-2-yl)piperidine-4-carboxylic acid (0.025 g, 0.05849 mmol) in DMF (2 mL) was added DIEA (0.0102 mL, 0.0585 mmol), 2,2,2-trifluoroethanamine (5.8 mg, 0.058 mmol), and HBTU (0.0244 g, 0.0643 mmol). After stirring at 40° C. overnight, the reaction mixture was quenched with water and brine and then extracted with EtOAc (3×10 mL). The combined organic extracts were dried (Na₂SO₄), filtered, concentrated and purified by reverse phase chromatography (0-80% ACN/water) to afford the title compound (8.8 mg, 28% yield). MS (apci) m/z=509.1 (M+H).

Example 244

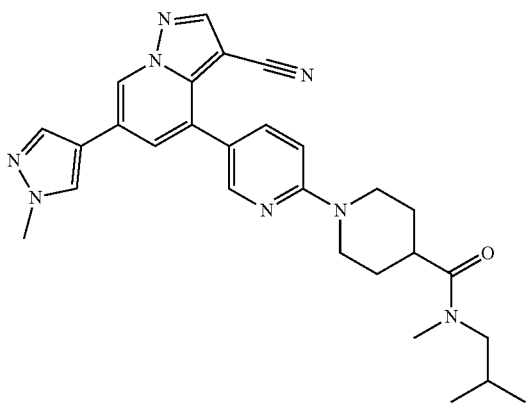 [SMILES: CC(C)CN(C)C(=O)C1CCN(c2ccc(-c3cc(-c4cnn(C)c4)cn4ncc(C#N)c34)cn2)CC1]

1-(5-(3-cyano-6-(1-methyl-1H-pyrazol-4-yl)pyrazolo[1,5-a]pyridin-4-yl)pyridin-2-yl)-N-isobutyl-N-methylpiperidine-4-carboxamide N-methylisobutylamine (5.1 mg, 0.058 mmol), DIEA (0.010 mL, 0.058 mmol), and HBTU (24.4 mg, 0.064 mmol) were added sequentially to a solution 1-(5-(3-cyano-6-(1-methyl-1H-pyrazol-4-yl)pyrazolo[1,5-a]pyridin-4-yl)pyridin-2-yl)piperidine-4-carboxylic acid (25 mg, 0.058 mmol) in DMF (2 mL). After stirring at 30° C. overnight, the reaction mixture was quenched with water then extracted with EtOAc (3×10 mL). The combined organic extracts were dried over anhydrous $Na_2SO_4$, filtered, concentrated in vacuo, and purified by silica chromatography (0-50% of 20% MeOH/DCM in EtOAc) to afford the title compound (0.019 g, 64% yield). MS (apci) m/z=497.2 (M+H).

The compounds in Table U were prepared and purified according to the method described for the synthesis of Example 244, replacing N-methylisobutylamine with the appropriate amine starting material.

TABLE U

| Ex # | Structure | Chemical Name | MS (apci) m/z |
|---|---|---|---|
| 245 | 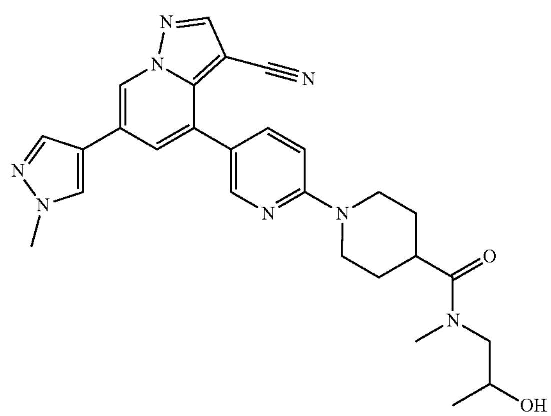 [SMILES: CC(O)CN(C)C(=O)C1CCN(c2ccc(-c3cc(-c4cnn(C)c4)cn4ncc(C#N)c34)cn2)CC1] | 1-(5-(3-cyano-6-(1-methyl-1H-pyrazol-4-yl)pyrazolo[1,5-a]pyridin-4-yl)pyridin-2-yl)-N-(2-hydroxypropyl)-N-methylpiperidine-4-carboxamide | 499.2 (M + H) |
| 246 | 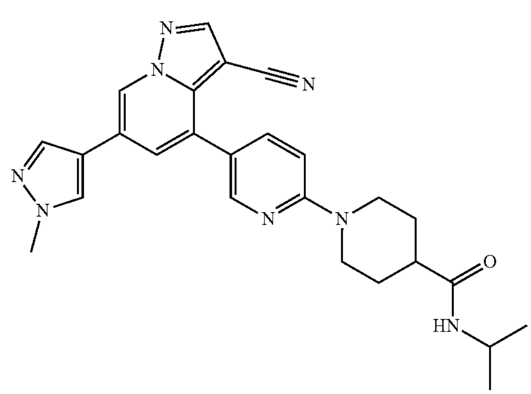 [SMILES: CC(C)NC(=O)C1CCN(c2ccc(-c3cc(-c4cnn(C)c4)cn4ncc(C#N)c34)cn2)CC1] | 1-(5-(3-cyano-6-(1-methyl-1H-pyrazol-4-yl)pyrazolo[1,5-a]pyridin-4-yl)pyridin-2-yl)-N-isopropylpiperidine-4-carboxamide | 469.2 (M + H) |

TABLE U-continued

| Ex # | Structure | Chemical Name | MS (apci) m/z |
|------|-----------|---------------|---------------|
| 247 | 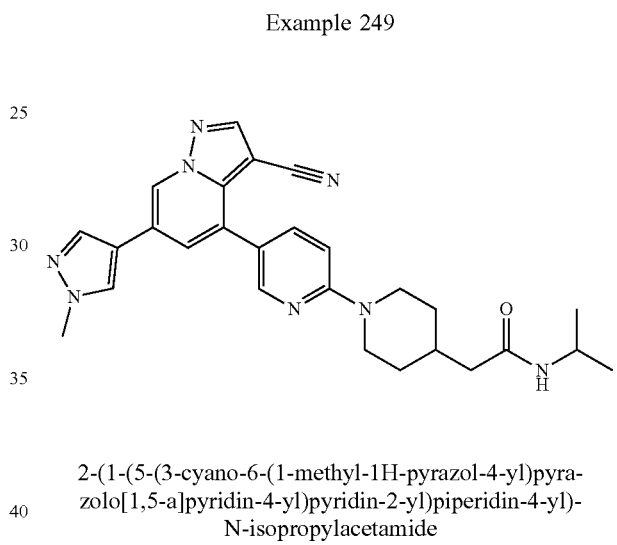 | 1-(5-(3-cyano-6-(1-methyl-1H-pyrazol-4-yl)pyrazolo[1,5-a]pyridin-4-yl)pyridin-2-yl)-N-isopropyl-N-methylpiperidine-4-carboxamide | 483.3 (M + H) |

Example 248

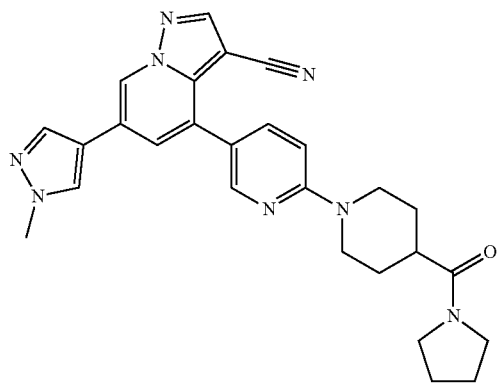 [SMILES: Cn1cc(-c2cc(-c3ccc(N4CCC(C(=O)N5CCCC5)CC4)nc3)c3c(C#N)cnn3c2)cn1]

6-(1-methyl-1H-pyrazol-4-yl)-4-(6-(4-(pyrrolidine-1-carbonyl)piperidin-1-yl)pyridin-3-yl)pyrazolo[1,5-a]pyridine-3-carbonitrile A solution of 1-(5-(3-cyano-6-(1-methyl-1H-pyrazol-4-yl)pyrazolo[1,5-a]pyridin-4-yl)pyridin-2-yl)piperidine-4-carboxylic acid (0.100 g, 0.23 mmol) in THF (4 mL) was cooled to −5° C. and then treated with TEA (0.098 mL, 0.70 mmol) and ethyl carbonochloridate (0.11 mL, 1.170 mmol). The resulting reaction mixture was stirred for 30 min, and then pyrrolidine (0.097 mL, 1.17 mmol) was then added. After stirring at −5° C. for 30 min the reaction mixture was stirred at ambient temperature for 4 h, and then several more drops of TEA and pyrrolidine were added. The resulting reaction mixture was stirred at ambient temperature for an additional 1 h, then quenched with water and extracted with EtOAc (3×10 mL). The combined organic extracts were dried over anhydrous $Na_2SO_4$, filtered, concentrated and purified by silica chromatography (0-50% of 20% MeOH/DCM in EtOAc) to afford the title compound (0.0045 g, 4% yield). MS (apci) m/z=481.1 (M+H).

Example 249

2-(1-(5-(3-cyano-6-(1-methyl-1H-pyrazol-4-yl)pyrazolo[1,5-a]pyridin-4-yl)pyridin-2-yl)piperidin-4-yl)-N-isopropylacetamide Step 1: Preparation of 2-(1-(5-(3-cyano-6-(1-methyl-1H-pyrazol-4-yl)pyrazolo[1,5-a]pyridin-4-yl)pyridin-2-yl)piperidin-4-yl)acetic Acid A solution of 4-(6-fluoropyridin-3-yl)-6-(1-methyl-1H-pyrazol-4-yl)pyrazolo[1,5-a]pyridine-3-carbonitrile (Intermediate P6; 0.309 g, 0.97 mmol) in DMSO (9.7 mL) was treated with 2-(piperidin-4-yl)acetic acid (0.556 g, 3.88 mmol) and potassium carbonate (0.537 g, 3.88 mmol). The resulting suspension was stirred and heated at 110° C. overnight. The reaction mixture was then adjusted to pH 7 with saturated $NaHCO_{3(aq)}$. The resulting suspension was vacuum filtered, rinsing solids with water to afford the title compound (0.1924 g, 45% yield). MS (apci) m/z=442.2 (M+H).

Step 2: Preparation of 2-(1-(5-(3-cyano-6-(1-methyl-1H-pyrazol-4-yl)pyrazolo[1,5-a]pyridin-4-yl)pyridin-2-yl)piperidin-4-yl)-N-isopropylacetamide Propan-2-amine (0.00669 g, 0.113 mmol), DIEA (0.049 mL, 0.283 mmol), and HATU (0.0431 g, 0.113 mmol) were added sequentially to a solution 2-(1-(5-(3-cyano-6-(1-methyl-1H-pyrazol-4-yl)pyrazolo[1,5-a]pyridin-4-yl)pyridin-2-yl)piperidin-4-yl)acetic acid (0.025 g, 0.0566 mmol)

in DMA (1.89 mL). After stirring at ambient temperature for 30 min, the reaction mixture was quenched with water and brine and then extracted with EtOAc (3×10 mL). The combined organic extracts were dried over anhydrous Na$_2$SO$_4$, filtered, concentrated and purified by silica chromatography (0-50% of 20% MeOH/DCM in EtOAc) to afford the title compound (0.014 g, 51% yield). MS (apci) m/z=483.3 (M+H).

Example 250

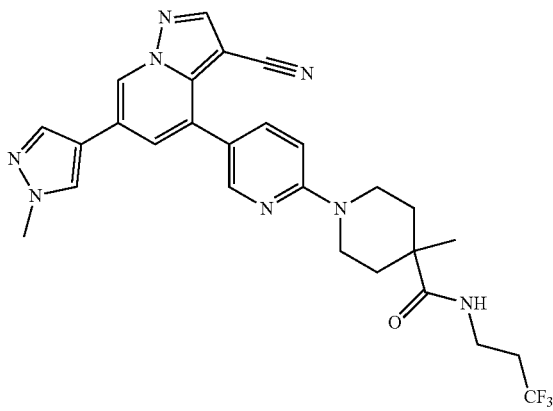 [SMILES: Cn1cc(-c2cc(-c3ccc(N4CCC(C)(C(=O)NCCC(F)(F)F)CC4)nc3)c3c(C#N)cnn3c2)cn1]

1-(5-(3-cyano-6-(1-methyl-1H-pyrazol-4-yl)pyrazolo[1,5-a]pyridin-4-yl)pyridin-2-yl)-4-methyl-N-(3,3,3-trifluoropropyl)piperidine-4-carboxamide Step 1: Preparation of 1-(5-(3-cyano-6-(1-methyl-1H-pyrazol-4-yl)pyrazolo[1,5-a]pyridin-4-yl)pyridin-2-yl)-4-methylpiperidine-4-carboxylic Acid A mixture of 4-(6-fluoropyridin-3-yl)-6-(1-methyl-1H-pyrazol-4-yl)pyrazolo[1,5-a]pyridine-3-carbonitrile (Intermediate P6; 0.45 g, 1.41 mmol), 4-methylpiperidine-4-carboxylic acid (0.81 g, 5.66 mmol) and potassium carbonate (0.78 g, 5.66 mmol) in DMSO (14 mL) was stirred at 110° C. overnight. The reaction mixture was then adjusted to pH 7 with saturated NaHCO$_{3(aq)}$. The resulting suspension was vacuum filtered and the solids were rinsed with water to afford the crude title product as a solid, which was directly used in the next step without further purification. MS (apci) m/z=442.2 (M+H).

Step 2: Preparation of 1-(5-(3-cyano-6-(1-methyl-1H-pyrazol-4-yl)pyrazolo[1,5-a]pyridin-4-yl)pyridin-2-yl)-4-methyl-N-(3,3,3-trifluoropropyl)piperidine-4-carboxamide To a solution of 1-(5-(3-cyano-6-(1-methyl-1H-pyrazol-4-yl)pyrazolo[1,5-a]pyridin-4-yl)pyridin-2-yl)-4-methylpiperidine-4-carboxylic acid (25 mg, 0.056 mmol) in DMA (1.9 mL) was added 3,3,3-trifluoropropylamine (12.8 mg, 0.11 mmol), DIEA (0.050 mL, 0.28 mmol) and HATU (43.1 mg, 0.11 mmol). After stirring at ambient temperature for 30 min, the reaction mixture was quenched with water and brine and then extracted with EtOAc (3×10 mL). The combined organic extracts were dried over anhydrous Na$_2$SO$_4$, filtered, concentrated and purified by silica chromatography (0-50% of 20% MeOH/DCM in EtOAc) to afford the title compound (0.0234 g, 73% yield). MS (apci) m/z=537.2 (M+H).

The compounds in Table V were prepared and purified according the method described for the synthesis of Example 250, replacing 3,3,3-trifluoropropylamine with the appropriate amine starting material.

TABLE V

| Ex # | Structure | Chemical Name | MS (apci) m/z |
|---|---|---|---|
| 251 | 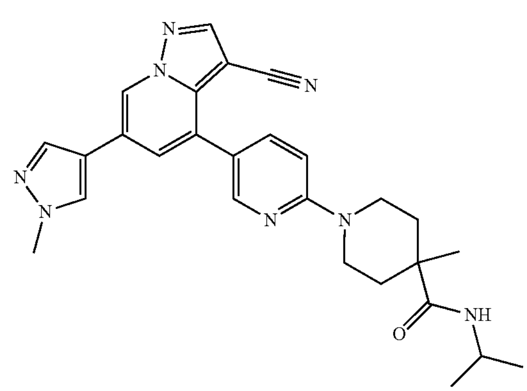 [SMILES: CC(C)NC(=O)C1(C)CCN(c2ccc(-c3cc(-c4cnn(C)c4)cn4ncc(C#N)c34)cn2)CC1] | 1-(5-(3-cyano-6-(1-methyl-1H-pyrazol-4-yl)pyrazolo[1,5-a]pyridin-4-yl)pyridin-2-yl)-N-isopropyl-4-methylpiperidine-4-carboxamide | 483.3 (M + H) |

TABLE V-continued

| Ex # | Structure | Chemical Name | MS (apci) m/z |
|---|---|---|---|
| 252 | 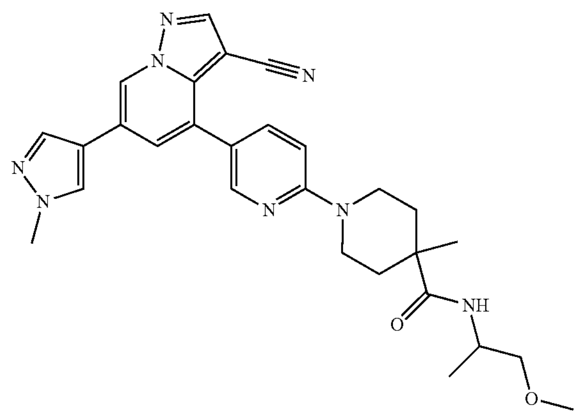 [SMILES: COCC(C)NC(=O)C1(C)CCN(c2ccc(-c3cc(-c4cnn(C)c4)cn4ncc(C#N)c34)cn2)CC1] | 1-(5-(3-cyano-6-(1-methyl-1H-pyrazol-4-yl)pyrazolo[1,5-a]pyridin-4-yl)pyridin-2-yl)-N-(1-methoxypropan-2-yl)-4-methylpiperidine-4-carboxamide | 513.3 (M + H) |
| 253 | 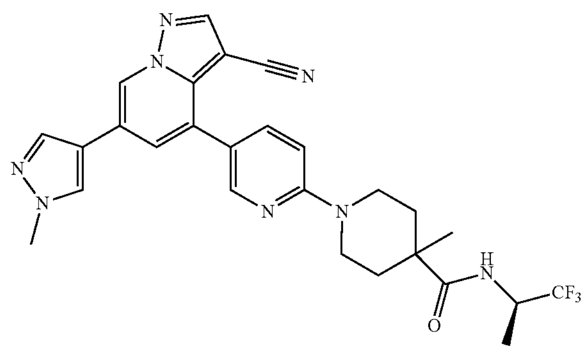 [SMILES: C[C@@H](NC(=O)C1(C)CCN(c2ccc(-c3cc(-c4cnn(C)c4)cn4ncc(C#N)c34)cn2)CC1)C(F)(F)F] | (R)-1-(5-(3-cyano-6-(1-methyl-1H-pyrazol-4-yl)pyrazolo[1,5-a]pyridin-4-yl)pyridin-2-yl)-4-methyl-N-(1,1,1-trifluoropropan-2-yl)piperidine-4-carboxamide | 537.3 (M + H) |

Example 254

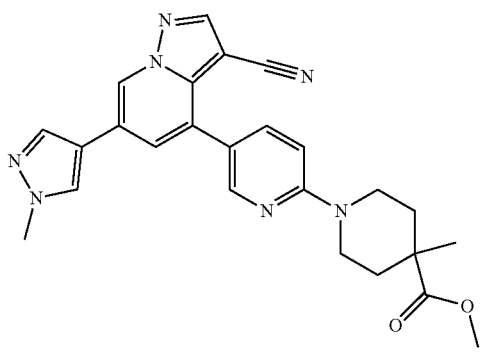 [SMILES: COC(=O)C1(C)CCN(c2ccc(-c3cc(-c4cnn(C)c4)cn4ncc(C#N)c34)cn2)CC1]

Methyl 1-(5-(3-cyano-6-(1-methyl-1H-pyrazol-4-yl)pyrazolo[1,5-a]pyridin-4-yl)pyridin-2-yl)-4-methyl-piperidine-4-carboxylate A mixture of 4-(6-fluoropyridin-3-yl)-6-(1-methyl-1H-pyrazol-4-yl)pyrazolo[1,5-a]pyridine-3-carbonitrile (Intermediate P6; 0.060 g, 0.188 mmol), methyl 4-methyl-4-piperidinecarboxylate (0.119 g, 0.754 mmol) and potassium carbonate (0.104 g, 0.754 mmol) in DMSO (1.88 mL) was heated overnight at 110° C. The pH of the reaction mixture was then adjusted to 7 with saturated NaHCO$_{3(aq)}$. The resulting suspension was vacuum filtered and rinsed with water and hexanes to afford the title compound (0.0451 g, 50% yield). MS (apci) m/z=456.2 (M+H).

Example 255

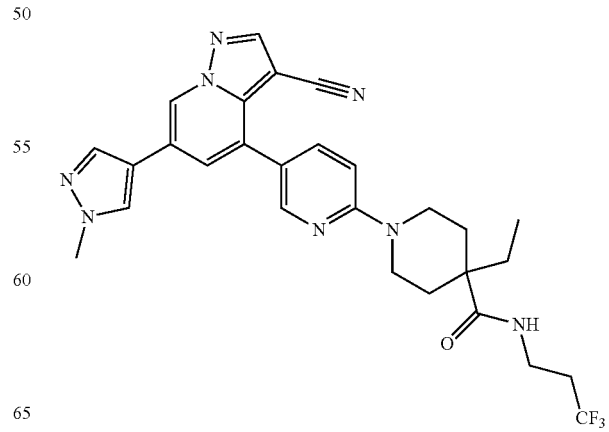

1-(5-(3-cyano-6-(1-methyl-1H-pyrazol-4-yl)pyrazolo[1,5-a]pyridin-4-yl)pyridin-2-yl)-4-ethyl-N-(3,3,3-trifluoropropyl)piperidine-4-carboxamide Step 1: Preparation of 1-(5-(3-cyano-1H-pyrazol-4-yl)pyrazolo[1,5-a]pyridin-4-yl)pyridin-2-yl)-4-ethylpiperidine-4-carboxylic Acid A mixture of 4-(6-fluoropyridin-3-yl)-6-(1-methyl-1H-pyrazol-4-yl)pyrazolo[1,5-a]pyridine-3-carbonitrile (Intermediate P6; 0.300 g, 0.942 mmol), 4-ethylpiperidine-4-carboxylic acid (0.593 g, 3.77 mmol) and potassium carbonate (0.521 g, 3.77 mmol) in DMSO (9.4 mL) was heated overnight at 110° C. The reaction mixture pH was then adjusted to 7 with saturated NaHCO$_{3(aq)}$. The resulting suspension was vacuum filtered and rinsed with water to afford the title compound (0.176 g, 41% yield). MS (apci) m/z=456.2 (M+H).

Step 2: Preparation of 1-(5-(3-cyano-6-(1-methyl-1H-pyrazol-4-yl)pyrazolo[1,5-a]pyridin-4-yl)pyridin-2-yl)-4-ethyl-N-(3,3,3-trifluoropropyl)piperidine-4-carboxamide 3,3,3-trifluoropropan-1-amine (12.4 mg, 0.11 mmol), DIEA (0.0478 mL, 0.274 mmol), and HATU (41.7 mg, 0.110 mmol) were added sequentially to a solution 1-(5-(3-cyano-6-(1-methyl-1H-pyrazol-4-yl)pyrazolo[1,5-a]pyridin-4-yl)pyridin-2-yl)-4-ethylpiperidine-4-carboxylic acid (25 mg, 0.055 mmol) in DMA (1.83 mL). After stirring at ambient temperature for 1.5 h, the reaction mixture was quenched with water and brine and then extracted with EtOAc (3×10 mL). The combined organic extracts were dried over anhydrous Na$_2$SO$_4$, filtered, concentrated and purified by silica chromatography (0-50% of 20% MeOH/DCM in EtOAc) to afford the title compound (0.0072 g, 24% yield). MS (apci) m/z=551.2 (M+H).

The compounds in the following Table W were prepared and purified according the method described for the synthesis of Example 255, replacing 3,3,3-trifluoropropylamine with the appropriate amine starting material.

TABLE W

| Ex # | Structure | Chemical Name | MS (apci) m/z |
|---|---|---|---|
| 256 | 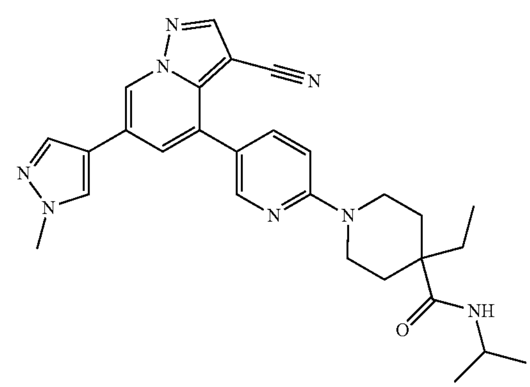 [SMILES: CCC1(C(=O)NC(C)C)CCN(c2ccc(-c3cc(-c4cnn(C)c4)cn4ncc(C#N)c34)cn2)CC1] | 1-(5-(3-cyano-6-(1-methyl-1H-pyrazol-4-yl)pyrazolo[1,5-a]pyridin-4-yl)pyridin-2-yl)-4-ethyl-N-isopropylpiperidine-4-carboxamide | 497.2 (M + H) |
| 257 | 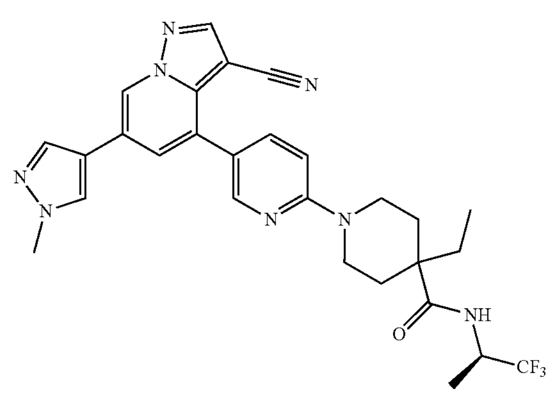 [SMILES: CCC1(C(=O)N[C@H](C)C(F)(F)F)CCN(c2ccc(-c3cc(-c4cnn(C)c4)cn4ncc(C#N)c34)cn2)CC1] | (R)-1-(5-(3-cyano-6-(1-methyl-1H-pyrazol-4-yl)pyrazolo[1,5-a]pyridin-4-yl)pyridin-2-yl)-4-ethyl-N-(1,1,1-trifluoropropan-2-yl)piperidine-4-carboxamide | 551.1 (M + H) |

TABLE W-continued

| Ex # | Structure | Chemical Name | MS (apci) m/z |
|---|---|---|---|
| 258 | 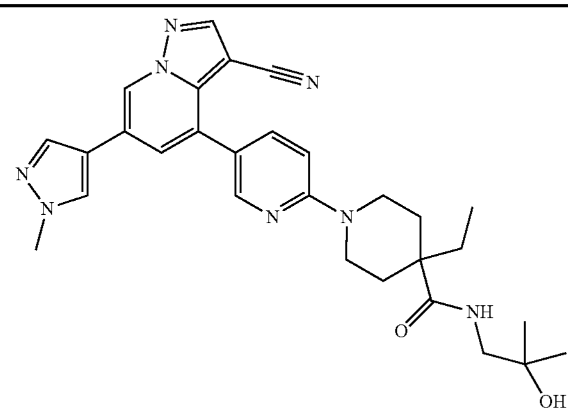 | 1-(5-(3-cyano-6-(1-methyl-1H-pyrazol-4-yl)pyrazolo[1,5-a]pyridin-4-yl)pyridin-2-yl)-4-ethyl-N-(2-hydroxy-2-methylpropyl)piperidine-4-carboxamide | 527.3 (M + H) 549.3 (M + Na) |

Example 259

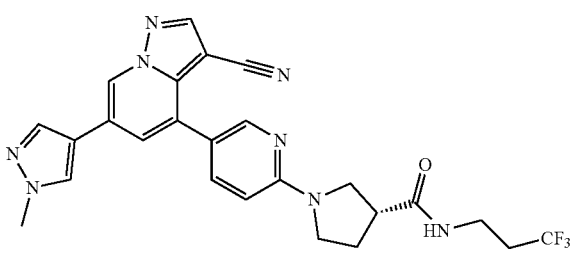 [SMILES: Cn1cc(-c2cc(-c3ccc(N4CC[C@@H](C(=O)NCCC(F)(F)F)C4)nc3)c3c(C#N)cnn3c2)cn1]

(R)-1-(5-(3-cyano-6-(1-methyl-1H-pyrazol-4-yl)pyrazolo[1,5-a]pyridin-4-yl)pyridin-2-yl)-N-(3,3,3-trifluoropropyl)pyrrolidine-3-carboxamide Step 1: Preparation of (R)-1-(5-(3-cyano-6-(1-methyl-1H-pyrazol-4-yl)pyrazolo[1,5-a]pyridin-4-yl)pyridin-2-yl)pyrrolidine-3-carboxylic Acid A solution of 4-(6-fluoropyridin-3-yl)-6-(1-methyl-1H-pyrazol-4-yl)pyrazolo[1,5-a]pyridine-3-carbonitrile (Intermediate P6; 0.300 g, 0.9425 mmol) in DMSO (9.425 mL) was treated with (R)-pyrrolidine-3-carboxylic acid (0.4340 g, 3.770 mmol) and potassium carbonate (0.5210 g, 3.770 mmol). The resulting thick suspension was stirred and heated overnight at 110° C. The reaction mixture was acidified to pH 7 with saturated NaHCO$_{3(aq)}$. The resulting suspension was diluted with water and brine and then vacuum filtered, rinsing solids with water and hexanes to afford the title compound (0.31 g, 79% yield). MS (apci) m/z=414.1 (M+H).

Step 2: Preparation of (R)-1-(5-(3-cyano-6-(1-methyl-1H-pyrazol-4-yl)pyrazolo[1,5-a]pyridin-4-yl)pyridin-2-yl)-N-(3,3,3-trifluoropropyl)pyrrolidine-3-carboxamide 3,3,3-trifluoropropan-1-amine (13.7 mg, 0.121 mmol), DIEA (0.0527 mL, 0.30 mmol), and HATU (46.0 mg, 0.12 mmol) were added sequentially to a solution (R)-1-(5-(3-cyano-6-(1-methyl-1H-pyrazol-4-yl)pyrazolo[1,5-a]pyridin-4-yl)pyridin-2-yl)pyrrolidine-3-carboxylic acid (25 mg, 0.060 mmol) in DMA (2.0 mL). After stirring at ambient temperature overnight, the reaction mixture was quenched with water and brine and then extracted with EtOAc (3×20 mL). The combined organic extracts were dried over anhydrous Na$_2$SO$_4$, filtered, concentrated and purified by silica chromatography (0-50% of 20% MeOH/DCM in EtOAc) to afford the title compound (18.5 mg, 59% yield). MS (apci) m/z=509.1 (M+H).

The compounds in Table X were prepared and purified according the method described for the synthesis of Example 259, replacing 3,3,3-trifluoropropan-1-amine with the appropriate amine starting material.

TABLE X

| Ex # | Structure | Chemical Name | MS (apci) m/z |
|---|---|---|---|
| 260 | 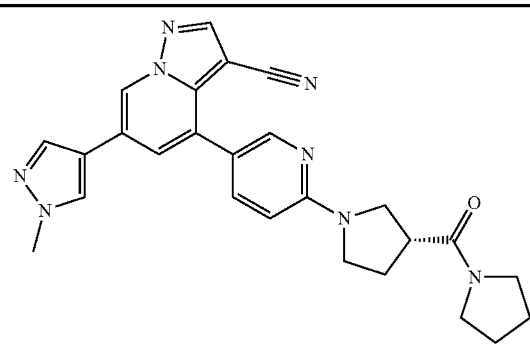 | (R)-6-(1-methyl-1H-pyrazol-4-yl)-4-(6-(3-(pyrrolidine-1-carbonyl)pyrrolidin-1-yl)pyridin-3-yl)pyrazolo[1,5-a]pyridine-3-carbonitrile | 467.2 (M + H) |

TABLE X-continued

| Ex # | Structure | Chemical Name | MS (apci) m/z |
|------|-----------|---------------|---------------|
| 261 | 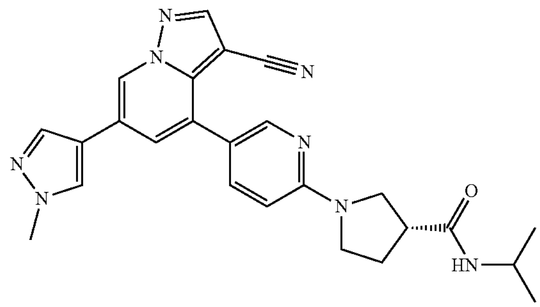 [SMILES: CC(C)NC(=O)[C@@H]1CCN(c2ccc(-c3cc(-c4cnn(C)c4)cn4ncc(C#N)c34)cn2)C1] | (R)-1-(5-(3-cyano-6-(1-methyl-1H-pyrazol-4-yl)pyrazolo[1,5-a]pyridin-4-yl)pyridin-2-yl)-N-isopropylpyrrolidine-3-carboxamide | 455.2 (M + H) |

Example 262

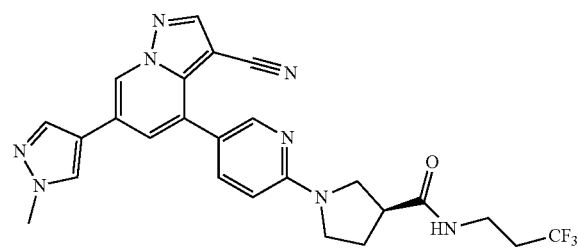 [SMILES: Cn1cc(-c2cc(-c3ccc(N4CC[C@H](C(=O)NCCC(F)(F)F)C4)nc3)c3c(C#N)cnn3c2)cn1]

(S)-1-(5-(3-cyano-6-(1-methyl-1H-pyrazol-4-yl)
pyrazolo[1,5-a]pyridin-4-yl)pyridin-2-yl)-N-(3,3,3-
trifluoropropyl)pyrrolidine-3-carboxamide

Step 1: Preparation of (S)-1-(5-(3-cyano-6-(1-methyl-1H-pyrazol-4-yl)pyrazolo[1,5-a]pyridin-4-yl)pyridin-2-yl)pyrrolidine-3-carboxylic Acid A solution of 4-(6-fluoropyridin-3-yl)-6-(1-methyl-1H-pyrazol-4-yl)pyrazolo[1,5-a]pyridine-3-carbonitrile (Intermediate P6; 0.300 g, 0.9425 mmol) in DMSO (9.425 mL) was treated with (S)-pyrrolidine-3-carboxylic acid (0.434 g, 3.77 mmol) and potassium carbonate (0.521 g, 3.77 mmol). The resulting thick suspension was stirred and heated at 110° C. overnight. The reaction mixture was then acidified to pH 7 with saturated NaHCO$_{3(aq)}$. The resulting suspension was diluted with water and brine and then vacuum filtered, rinsing the solids with water and hexanes to afford the title compound (0.523 g, quantitative yield). MS (apci) m/z=414.2 (M+H).

Step 2: Preparation of (S)-1-(5-(3-cyano-6-(1-methyl-1H-pyrazol-4-yl)pyrazolo[1,5-a]pyridin-4-yl)pyridin-2-yl)-N-(3,3,3-trifluoropropyl)pyrrolidine-3-carboxamide 3,3,3-trifluoropropan-1-amine (0.0137 g, 0.121 mmol), DIEA (0.0527 mL, 0.302 mmol), and HATU (0.0460 g, 0.121 mmol) were added sequentially to a solution (S)-1-(5-(3-cyano-6-(1-methyl-1H-pyrazol-4-yl)pyrazolo[1,5-a]pyridin-4-yl)pyridin-2-yl)pyrrolidine-3-carboxylic acid (0.025 g, 0.0605 mmol) in DMA (2.02 mL). After stirring at ambient temperature overnight, the reaction mixture was quenched with water and brine and then extracted with EtOAc (3×10 mL). The combined organic extracts were dried over anhydrous Na$_2$SO$_4$, filtered, concentrated and purified by silica chromatography (0-50% of 20% MeOH/DCM in EtOAc) to afford the title compound (0.0141 g, 45% yield). MS (apci) m/z=509.2 (M+H).

The compounds in Table Y were prepared and purified according the method described for the synthesis of Example 262, replacing 3,3,3-trifluoropropan-1-amine with the appropriate amine starting materials.

TABLE Y

| Ex # | Structure | Chemical Name | MS (apci) m/z |
|------|-----------|---------------|---------------|
| 263 | 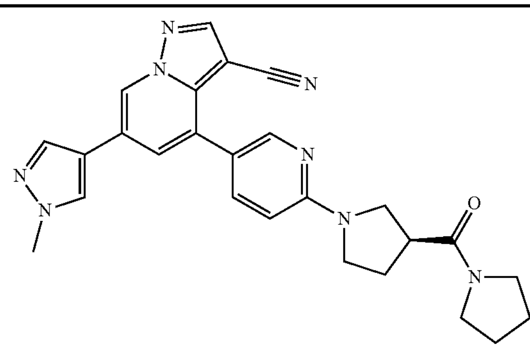 | (S)-6-(1-methyl-1H-pyrazol-4-yl)-4-(6-(3-(pyrrolidine-1-carbonyl)pyrrolidin-1-yl)pyridin-3-yl)pyrazolo[1,5-a]pyridine-3-carbonitrile | 467.2 (M + H) |

TABLE Y-continued

| Ex # | Structure | Chemical Name | MS (apci) m/z |
|---|---|---|---|
| 264 | 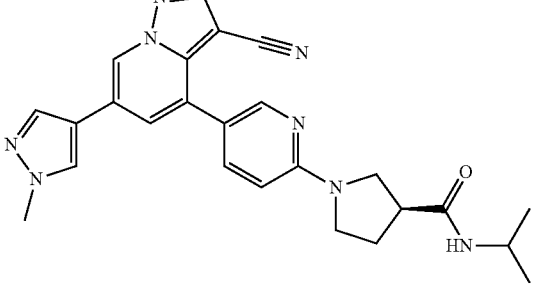 | (S)-1-(5-(3-cyano-6-(1-methyl-1H-pyrazol-4-yl)pyrazolo[1,5-a]pyridin-4-yl)pyridin-2-yl)-N-isopropylpyrrolidine-3-carboxamide | 455.2 (M + H) |

Example 265

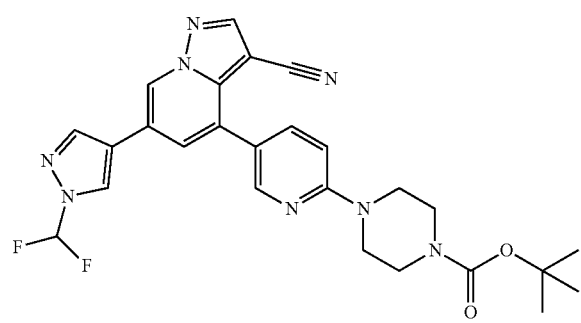 [SMILES: CC(C)(C)OC(=O)N1CCN(c2ccc(-c3cc(-c4cnn(C(F)F)c4)cn4ncc(C#N)c34)cn2)CC1]

Tert-Butyl 4-(5-(3-cyano-6-(1-(difluoromethyl)-1H-pyrazol-4-yl)pyrazolo[1,5-a]pyridin-4-yl)pyridin-2-yl)piperazine-1-carboxylate In a pressure tube tert-butyl 4-(5-(3-cyano-6-(((trifluoromethyl)sulfonyl)oxy)pyrazolo[1,5-a]pyridin-4-yl)pyridin-2-yl)piperazine-1-carboxylate (Intermediate P14; 150 mg, 0.271 mmol), 1-(difluoromethyl)-4-(4,4,5,5-tetramethyl-1,3,2-dioxaborolan-2-yl)-1H-pyrazole (133 mg, 0.543 mmol), Pd(PPh₃)₄ (31.4 mg, 0.0271 mmol) and 2 M Na₂CO₃(aq) (679 µL, 1.36 mmol) in dioxane (20 mL) was sparged with nitrogen, then sealed and heated at 100° C. overnight with stirring. After cooling to ambient temperature, the reaction mixture was diluted with water (10 mL) and filtered, and the solids were rinsed with water and Et₂O and then air dried to afford the title compound (124 mg, 88% yield). MS (apci) m/z=521.2 (M+H).

Example 266

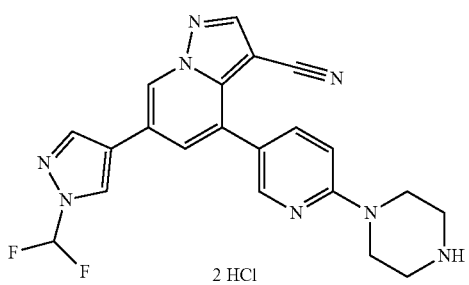 [SMILES: N#Cc1cnn2cc(-c3cnn(C(F)F)c3)cc(-c3ccc(N4CCNCC4)nc3)c12]

6-(1-(difluoromethyl)-1H-pyrazol-4-yl)-4-(6-(piperazin-1-yl)pyridin-3-yl)pyrazolo[1,5-a]pyridine-3-carbonitrile Dihydrochloride To a solution of tert-butyl 4-(5-(3-cyano-6-(1-(difluoromethyl)-1H-pyrazol-4-yl)pyrazolo[1,5-a]pyridin-4-yl)pyridin-2-yl)piperazine-1-carboxylate (120 mg, 0.231 mmol) in DCM (5 mL) was added 5 M HCl in iPrOH (231 µL, 1.15 mmol). After stirring the resulting suspension at ambient temperature overnight the reaction mixture was concentrated in vacuo to afford the title compound (111 mg, 98% yield). MS (apci) m/z=421.1 (M+H).

Example 267

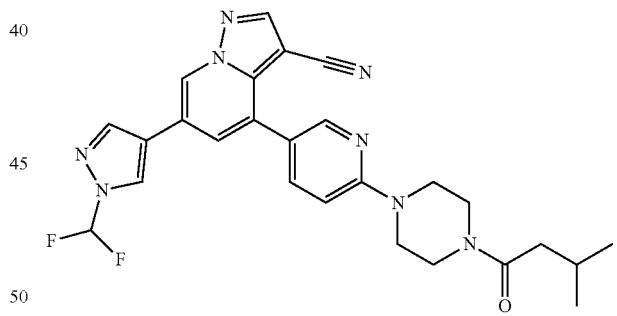

6-(1-(difluoromethyl)-1H-pyrazol-4-yl)-4-(6-(4-(3-methylbutanoyl)piperazin-1-yl)pyridin-3-yl)pyrazolo[1,5-a]pyridine-3-carbonitrile To a solution of 6-(1-(difluoromethyl)-1H-pyrazol-4-yl)-4-(6-(piperazin-1-yl)pyridin-3-yl)pyrazolo[1,5-a]pyridine-3-carbonitrile dihydrochloride (10 mg, 0.020 mmol) in DMF (0.2 mL) was added 3-methylbutanoyl chloride (3.7 mg, 0.030 mmol) and TEA (8.5 µL, 0.061 mmol). The reaction mixture stirred at ambient temperature for 1 h and then directly purified by reverse phase chromatography (0-60% ACN/water) to afford the title compound (3.4 mg, 33% yield). MS (apci) m/z=505.1 (M+H).

Example 268

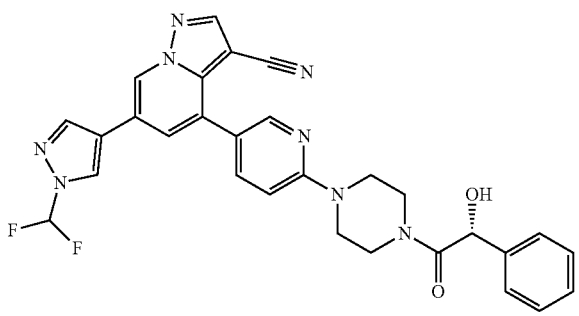 [SMILES: N#Cc1cnn2cc(-c3cnn(C(F)F)c3)cc(-c3ccc(N4CCN(C(=O)[C@H](O)c5ccccc5)CC4)nc3)c12]

(R)-6-(1-(difluoromethyl)-1H-pyrazol-4-yl)-4-(6-(4-(2-hydroxy-2-phenylacetyl)piperazin-1-yl)pyridin-3-yl)pyrazolo[1,5-a]pyridine-3-carbonitrile To a solution of 6-(1-(difluoromethyl)-1H-pyrazol-4-yl)-4-(6-(piperazin-1-yl)pyridin-3-yl)pyrazolo[1,5-a]pyridine-3-carbonitrile dihydrochloride (10 mg, 0.020 mmol) in DMF (0.2 mL) was added 3-methylbutanoyl chloride (3.7 mg, 0.030 mmol) and TEA (8.5 µL, 0.061 mmol). The reaction mixture was stirred at ambient temperature for 1 h and then directly purified by reverse phase chromatography (0-60% ACN/water) to afford the title compound (3.4 mg, 33% yield). MS (apci) m/z=555.1 (M+H).

Example 269

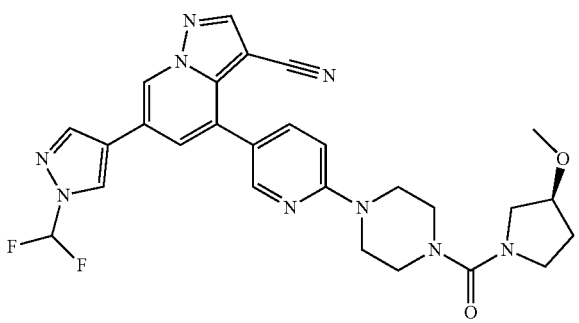 [SMILES: CO[C@H]1CCN(C(=O)N2CCN(c3ccc(-c4cc(-c5cnn(C(F)F)c5)cn5ncc(C#N)c45)cn3)CC2)C1]

(S)-6-(1-(difluoromethyl)-1H-pyrazol-4-yl)-4-(6-(4-(3-methoxypyrrolidine-1-carbonyl)piperazin-1-yl)pyridin-3-yl)pyrazolo[1,5-a]pyridine-3-carbonitrile

Step 1: Preparation of (S)-3-methoxypyrrolidine-1-carbonyl Chloride

Triphosgene (129 mg, 0.436 mmol) was added in small portions over a 30 min period to a suspension of (S)-3-methoxypyrrolidine hydrochloride (200 mg, 1.45 mmol) and DIEA (1.52 mL, 8.72 mmol) in DCM (3.48 mL). The resulting mixture was stirred at ambient temperature for 3 h to provide the title compound as a fine suspension in DCM (0.25 M) which was used in the next step without further purification.

Step 2: Preparation of (S)-6-(1-(difluoromethyl)-1H-pyrazol-4-yl)-4-(6-(4-(3-methoxypyrrolidine-1-carbonyl)piperazin-1-yl)pyridin-3-yl)pyrazolo[1,5-a]pyridine-3-carbonitrile To a mixture of 6-(1-(difluoromethyl)-1H-pyrazol-4-yl)-4-(6-(piperazin-1-yl)pyridin-3-yl)pyrazolo[1,5-a]pyridine-3-carbonitrile dihydrochloride (20 mg, 0.0405 mmol) and DIEA (42.4 µL, 0.243 mmol) in DCM (405 µL) was added (S)-3-methoxypyrrolidine-1-carbonyl chloride in DCM (0.25 M, 195 µL, 0.0486 mmol). The reaction was stirred at ambient temperature for 3 d and then directly purified by reverse phase chromatography (0-75% ACN/water) to afford the title compound (1.8 mg, 8% yield). MS (apci) m/z=548.1 (M+H).

Example 270

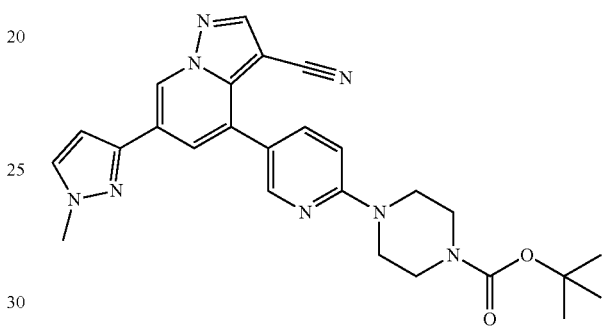

Tert-Butyl 4-(5-(3-cyano-6-(1-methyl-1H-pyrazol-3-yl)pyrazolo[1,5-a]pyridin-4-yl)pyridin-2-yl)piperazine-1-carboxylate tert-Butyl 4-(5-(3-cyano-6-(((trifluoromethyl)sulfonyl)oxy)pyrazolo[1,5-a]pyridin-4-yl)pyridin-2-yl)piperazine-1-carboxylate (Intermediate P14; 150 mg, 0.271 mmol),1-methyl-3-(4,4,5,5-tetramethyl-1,3,2-dioxaborolan-2-yl)-1H-pyrazole (113 mg, 0.543 mmol), Pd(PPh$_3$)$_4$ (31.4 mg, 0.0271 mmol) and 2 M Na$_2$CO$_{3(aq)}$ (679 µL, 1.36 mmol) in dioxane (2 mL) were combined in a pressure tube. The resulting reaction mixture was sparged with nitrogen and then sealed and heated at 100° C. overnight. The reaction mixture was cooled to ambient temperature, then diluted with water (10 mL) and filtered. The solids were washed with water (2×5 mL) and Et$_2$O (2×5 mL) and air dried to afford the title compound (108 mg, 82% yield). MS (apci) m/z=485.2 (M+H).

Example 271

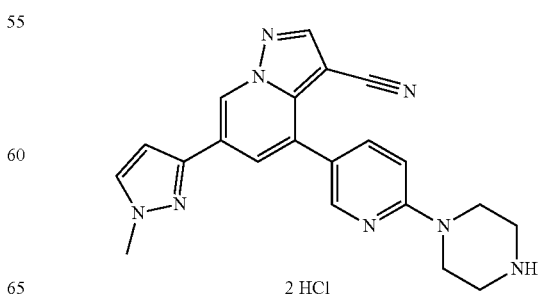

2 HCl

6-(1-methyl-1H-pyrazol-3-yl)-4-(6-(piperazin-1-yl)pyridin-3-yl)pyrazolo[1,5-a]pyridine-3-carbonitrile Dihydrochloride To a solution of tert-butyl 4-(5-(3-cyano-6-(1-methyl-1H-pyrazol-3-yl)pyrazolo[1,5-a]pyridin-4-yl)pyridin-2-yl)piperazine-1-carboxylate (100 mg, 0.206 mmol) in DCM (5 mL) was added 5 M HCl in iPrOH (206 µL, 1.03 mmol). After stirring at ambient temperature overnight the resulting suspension was filtered. The isolated solids were washed with Et$_2$O (2×5 mL) and then air dried to afford the title compound (95 mg, quantitative yield). MS (apci) m/z=385.1 (M+H).

Example 272

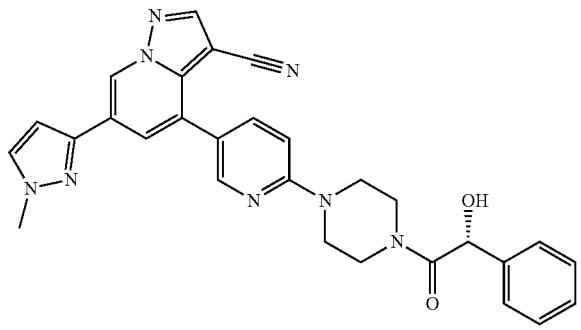 [SMILES: Cn1ccc(-c2cc(-c3ccc(N4CCN(C(=O)[C@H](O)c5ccccc5)CC4)nc3)c3c(C#N)cnn3c2)n1]

(R)-4-(6-(4-(2-hydroxy-2-phenylacetyl)piperazin-1-yl)pyridin-3-yl)-6-(1-methyl-1H-pyrazol-3-yl)pyrazolo[1,5-a]pyridine-3-carbonitrile (R)-2-hydroxy-2-phenylacetic acid (7.5 mg, 0.049 mmol), HATU (25 mg, 0.066 mmol), and TEA (23 µL, 0.16 mmol) were added sequentially to a solution of 6-(1-methyl-1H-pyrazol-3-yl)-4-(6-(piperazin-1-yl)pyridin-3-yl)pyrazolo[1,5-a]pyridine-3-carbonitrile dihydrochloride (15 mg, 0.033 mmol) in DMF (328 µL). After stirring at ambient temperature for 1 h, the reaction mixture was purified by reverse phase chromatography (0-60% ACN/water) to afford the title compound (4.3 mg, 25% yield). MS (apci) m/z=519.2 (M+H).

Example 273

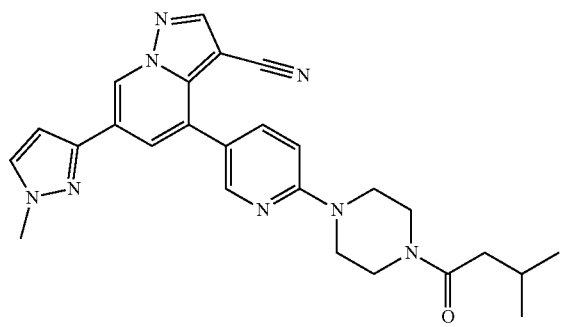 [SMILES: CC(C)CC(=O)N1CCN(c2ccc(-c3cc(-c4ccn(C)n4)cn4ncc(C#N)c34)cn2)CC1]

6-(1-methyl-1H-pyrazol-3-yl)-4-(6-(4-(3-methylbutanoyl)piperazin-1-yl)pyridin-3-yl)pyrazolo[1,5-a]pyridine-3-carbonitrile A solution of 6-(1-methyl-1H-pyrazol-3-yl)-4-(6-(piperazin-1-yl)pyridin-3-yl)pyrazolo[1,5-a]pyridine-3-carbonitrile dihydrochloride (10 mg, 0.22 mmol) in DMF (0.2 mL) was treated with 3-methylbutanoyl chloride (4.0 mg, 0.033 mmol) and TEA (9.1 µL, 0.066 mmol). After stirring at ambient temperature for 1 h, the reaction mixture was purified by reverse phase chromatography (0-60% ACN/water) to afford the title compound (5.7 mg, 56% yield). MS (apci) m/z=469.1 (M+H).

Example 274

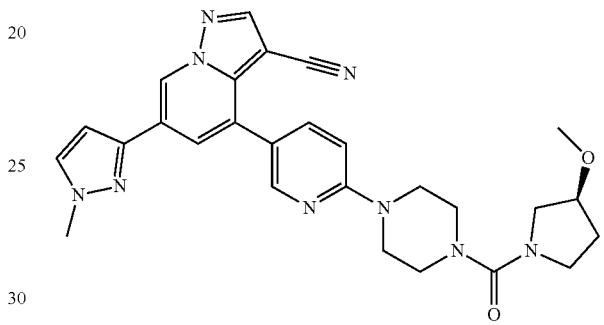

(S)-4-(6-(4-(3-methoxypyrrolidine-1-carbonyl)piperazin-1-yl)pyridin-3-yl)-6-(1-methyl-1H-pyrazol-3-yl)pyrazolo[1,5-a]pyridine-3-carbonitrile A solution of 6-(1-methyl-1H-pyrazol-3-yl)-4-(6-(piperazin-1-yl)pyridin-3-yl)pyrazolo[1,5-a]pyridine-3-carbonitrile dihydrochloride (20 mg, 0.0437 mmol) and DIEA (45.7 µL, 0.262 mmol) in DCM (437 µL) was treated with (S)-3-methoxypyrrolidine-1-carbonyl chloride (Example 269, Step 1, 0.25 M, 210 µL, 0.0525 mmol) and TEA (9.1 µL, 0.066 mmol). After stirring at ambient temperature for 3 d, the reaction mixture was purified by reverse phase chromatography (0-75% ACN/water) to afford the title compound (2.9 mg, 13% yield). MS (apci) m/z=512.2 (M+H).

Example 275

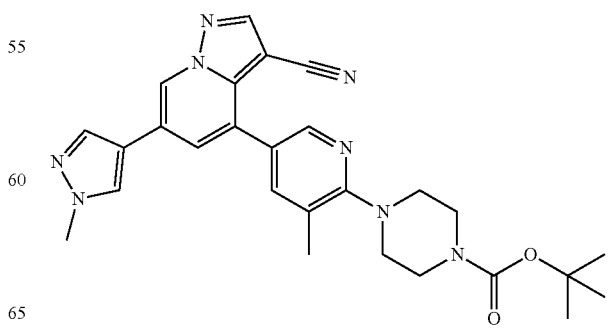

Tert-Butyl 4-(5-(3-cyano-6-(1-methyl-1H-pyrazol-4-yl)pyrazolo[1,5-a]pyridin-4-yl)-3-methylpyridin-2-yl)piperazine-1-carboxylate A mixture of 3-cyano-6-(1-methyl-1H-pyrazol-4-yl)pyrazolo[1,5-a]pyridin-4-yl trifluoromethanesulfonate (Intermediate P5; 250 mg, 0.673 mmol), tert-butyl 4-(3-methyl-5-(4,4,5,5-tetramethyl-1,3,2-dioxaborolan-2-yl)pyridin-2-yl)piperazine-1-carboxylate (299 mg, 0.741 mmol), Pd(PPh$_3$)$_4$ (19.5 mg, 0.0168 mmol), and 2 M K$_2$CO$_{3(aq)}$ (2020 μL, 4.04 mmol) in dioxane (2693 μL) was sparged with nitrogen, then sealed and heated at 85° C. for 12 h. After cooling to ambient temperature, the reaction mixture was partitioned between EtOAc (10 mL) and 2 M K$_2$CO$_{3(aq)}$ (10 mL) and the phases were separated. The emulsified organic phase was filtered through a PVDF (0.45 μm) disc and the filtrate was washed with brine. The combined organic extracts were concentrated in vacuo and the residue was purified directly by reverse phase chromatography (5-75% ACN/water) to afford the title compound (0.11 g, 32% yield). MS (apci) m/z=499.2 (M+H).

Example 276

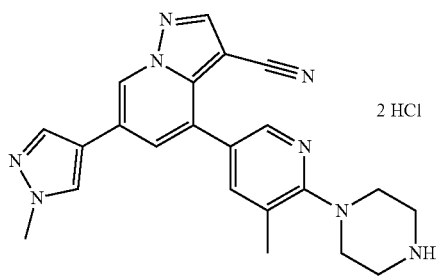 [SMILES: Cc1cc(-c2cc(-c3cnn(C)c3)cn3ncc(C#N)c23)cnc1N1CCNCC1]

6-(1-methyl-1H-pyrazol-4-yl)-4-(5-methyl-6-(piperazin-1-yl)pyridin-3-yl)pyrazolo[1,5-a]pyridine-3-carbonitrile Dihydrochloride To a solution of tert-butyl 4-(5-(3-cyano-6-(1-methyl-1H-pyrazol-4-yl)pyrazolo[1,5-a]pyridin-4-yl)-3-methylpyridin-2-yl)piperazine-1-carboxylate (Example 275, 110 mg, 0.221 mmol) in DCM (4 mL) was added 5 M HCl in iPrOH (2206 μL, 11.0 mmol). The resulting suspension was stirred at ambient temperature 1 h and then concentrated to near dryness in vacuo. The residue was treated with Et$_2$O, concentrated, and dried in vacuo to afford the title compound (104 mg, 98% yield). MS (apci) m/z=399.1 (M+H).

Example 277

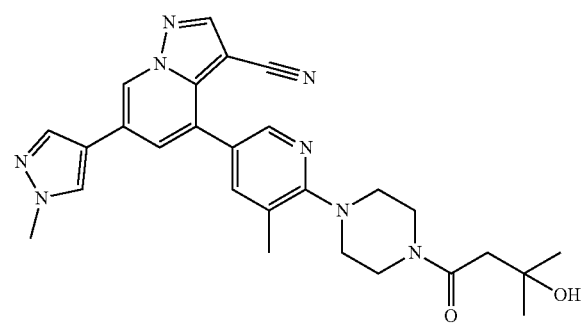 [SMILES: Cc1cc(-c2cc(-c3cnn(C)c3)cn3ncc(C#N)c23)cnc1N1CCN(C(=O)CC(C)(C)O)CC1]

4-(6-(4-(3-hydroxy-3-methylbutanoyl)piperazin-1-yl)-5-methylpyridin-3-yl)-6-(1-methyl-1H-pyrazol-4-yl)pyrazolo[1,5-a]pyridine-3-carbonitrile 3-hydroxy-3-methylbutanoic acid (4.51 mg, 0.0382 mmol) and HATU (14.5 mg, 0.0382 mmol) were dissolved in DMA (159 μL) and the mixture was stirred at ambient temperature for 10 min. 6-(1-methyl-1H-pyrazol-4-yl)-4-(5-methyl-6-(piperazin-1-yl)pyridin-3-yl)pyrazolo[1,5-a]pyridine-3-carbonitrile dihydrochloride (Example 276, 15 mg, 0.0318 mmol) was added in one portion followed by DIEA (27.7 μL, 0.159 mmol). After stirring for 45 min, the reaction mixture was directly purified by reverse-phase chromatography (5-60% ACN/water) to afford the title compound (10.2 mg, 62% yield). MS (apci) m/z=499.2 (M+H).

Example 278

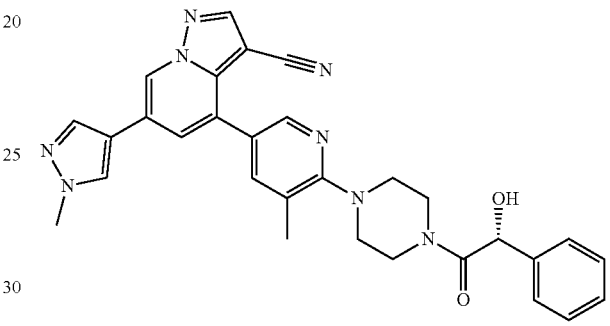

(R)-4-(6-(4-(2-hydroxy-2-phenylacetyl)piperazin-1-yl)-5-methylpyridin-3-yl)-6-(1-methyl-1H-pyrazol-4-yl)pyrazolo[1,5-a]pyridine-3-carbonitrile (R)-2-hydroxy-2-phenylacetic acid (5.8 mg, 0.038 mmol) and HATU (15 mg, 0.038 mmol) were dissolved in DMA (159 μL) and stirred at ambient temperature for 10 min. 6-(1-methyl-1H-pyrazol-4-yl)-4-(5-methyl-6-(piperazin-1-yl)pyridin-3-yl)pyrazolo[1,5-a]pyridine-3-carbonitrile dihydrochloride (Example 276, 15 mg, 0.032 mmol) was added in one portion followed by DIEA (28 μL, 0.16 mmol). After stirring for 90 min, the reaction was directly purified by reverse-phase chromatography (5-60% ACN/water) to afford the title compound (9.3 mg, 53% yield). MS (apci) m/z=533.1 (M+H).

Example 279

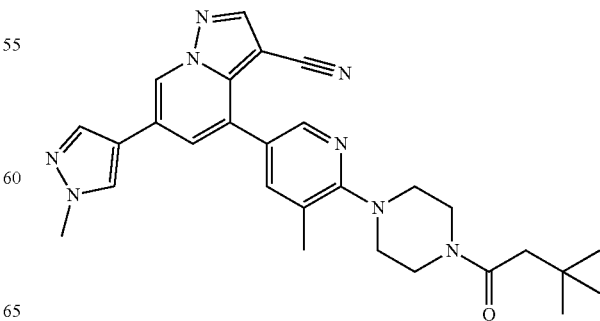

4-(6-(4-(3,3-dimethylbutanoyl)piperazin-1-yl)-5-methylpyridin-3-yl)-6-(1-methyl-1H-pyrazol-4-yl)pyrazolo[1,5-a]pyridine-3-carbonitrile To a mixture of 6-(1-methyl-1H-pyrazol-4-yl)-4-(5-methyl-6-(piperazin-1-yl)pyridin-3-yl)pyrazolo[1,5-a]pyridine-3-carbonitrile dihydrochloride (Example 276, 15 mg, 0.0318 mmol) in DCM (159 µL) was added DIEA (27.7 µL, 0.159 mmol) followed by 3,3-dimethylbutanoyl chloride (5.14 mg, 0.0382 mmol). After stirring for 45 min at ambient temperature, the reaction mixture was directly purified by reverse-phase chromatography (C18, 5-75% ACN/water) to afford the title compound (12.7 mg, 78% yield). MS (apci) m/z=497.1 (M+H).

Example 280

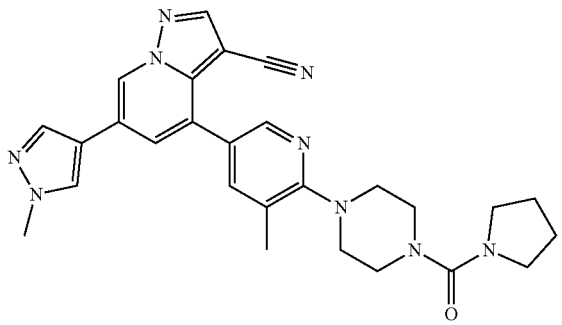 [SMILES: Cc1cc(-c2cc(-c3cnn(C)c3)cn3ncc(C#N)c23)cnc1N1CCN(C(=O)N2CCCC2)CC1]

6-(1-methyl-1H-pyrazol-4-yl)-4-(5-methyl-6-(4-(pyrrolidine-1-carbonyl)piperazin-1-yl)pyridin-3-yl)pyrazolo[1,5-a]pyridine-3-carbonitrile A suspension of 6-(1-methyl-1H-pyrazol-4-yl)-4-(5-methyl-6-(piperazin-1-yl)pyridin-3-yl)pyrazolo[1,5-a]pyridine-3-carbonitrile dihydrochloride (Example 276, 20 mg, 0.0424 mmol) and DIEA (44.3 µL, 0.255 mmol) in Dri-Solv® DCM (212 µL) was added dropwise to a 0° C. solution of triphosgene (6.30 mg, 0.0212 mmol) in Dri-Solv® DCM (212 µL) and the reaction mixture was stirred for 2 h, followed by the addition of pyrrolidine (3.02 mg, 0.0424 mmol) in one portion. The reaction mixture was stirred at ambient temperature for 2 d and then directly purified by reverse-phase chromatography (C18, 5-60% ACN/water) to provide the title compound (16.2 mg, 76% yield). MS (apci) m/z=496.2 (M+H).

Example 281

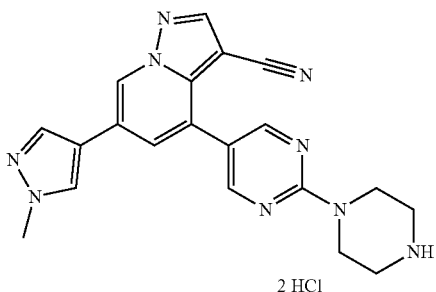 [SMILES: Cn1cc(-c2cc(-c3cnc(N4CCNCC4)nc3)c3c(C#N)cnn3c2)cn1]

6-(1-methyl-1H-pyrazol-4-yl)-4-(2-(piperazin-1-yl)pyrimidin-5-yl)pyrazolo[1,5-a]pyridine-3-carbonitrile Dihydrochloride Step 1: Preparation of Tert-Butyl 4-(5-(3-cyano-6-(1-methyl-1H-pyrazol-4-yl)pyrazolo[1,5-a]pyridin-4-yl)pyrimidin-2-yl)piperazine-1-carboxylate 3-cyano-6-(1-methyl-1H-pyrazol-4-yl)pyrazolo[1,5-a]pyridin-4-yl trifluoromethanesulfonate (Intermediate P5; 2.00 g, 5.39 mmol), (2-(4-(tert-butoxycarbonyl)piperazin-1-yl)pyrimidin-5-yl)boronic acid (2.49 g, 8.08 mmol), Pd(PPh$_3$)$_4$ (0.124 g, 0.108 mmol) and K$_3$PO$_4$ (3.43 g, 16.2 mmol) were combined in dioxane (20 mL) in a pressure tube. The resulting reaction mixture was sparged with nitrogen, sealed, and heated at 100° C. overnight and then cooled to ambient temperature. The reaction mixture was diluted with water (10 mL) and extracted with several portions of DCM in a PS frit. The combined DCM extracts were concentrated in vacuo and purified by silica chromatography (10-100% EtOAc/hexanes) to afford the title compound (0.148 g, 6% yield). MS (apci) m/z=386.1 (M+H-Boc).

Step 2: Preparation of 6-(1-methyl-1H-pyrazol-4-yl)-4-(2-(piperazin-1-yl)pyrimidin-5-yl)pyrazolo[1,5-a]pyridine-3-carbonitrile Dihydrochloride To a solution tert-butyl 4-(5-(3-cyano-6-(1-methyl-1H-pyrazol-4-yl)pyrazolo[1,5-a]pyridin-4-yl)pyridin-2-yl)piperazine-1-carboxylate (140 mg, 0.289 mmol) in DCM (10 mL) was added 5 M HCl in iPrOH (173 µL, 0.867 mmol). The reaction mixture was stirred at ambient temperature for 6 h and then diluted with Et$_2$O (10 mL). The resulting suspension was vacuum filtered and the solids were washed with Et$_2$O and air dried to afford the title compound (92 mg, 70% yield). MS (apci) m/z=386.0 (M+H).

Example 282

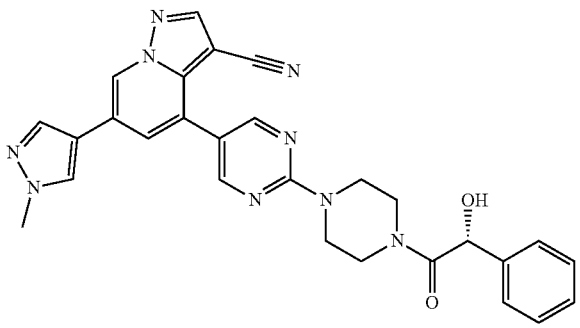

(R)-4-(2-(4-(2-hydroxy-2-phenylacetyl)piperazin-1-yl)pyrimidin-5-yl)-6-(1-methyl-1H-pyrazol-4-yl)pyrazolo[1,5-a]pyridine-3-carbonitrile A solution of 6-(1-methyl-1H-pyrazol-4-yl)-4-(2-(piperazin-1-yl)pyrimidin-5-yl)pyrazolo[1,5-a]pyridine-3-carbonitrile dihydrochloride (12 mg, 0.262 mmol) in DMF (105 µL) was treated sequentially with (R)-2-hydroxy-2-phenylacetic acid (0.0133 g, 0.151 mmol), HATU (19.9 mg, 0.0524 mmol), and TEA (18.2 µL, 0.131 mmol). The resulting reaction mixture was stirred at ambient temperature

Example 283

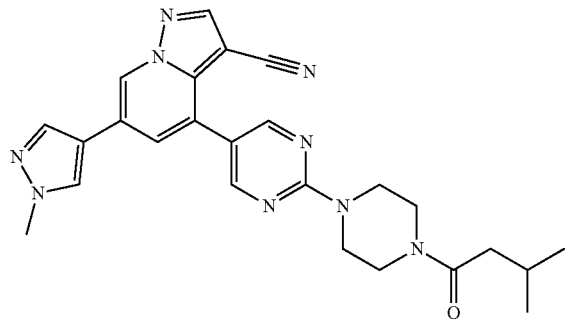 [SMILES: CC(C)CC(=O)N1CCN(c2ncc(-c3cc(-c4cnn(C)c4)cn4ncc(C#N)c34)cn2)CC1]

6-(1-methyl-1H-pyrazol-4-yl)-4-(2-(4-(3-methylbutanoyl)piperazin-1-yl)pyrimidin-5-yl)pyrazolo[1,5-a]pyridine-3-carbonitrile A solution of 6-(1-methyl-1H-pyrazol-4-yl)-4-(2-(piperazin-1-yl)pyrimidin-5-yl)pyrazolo[1,5-a]pyridine-3-carbonitrile dihydrochloride (10 mg, 0.22 mmol) in DMF (0.2 mL) was treated with TEA (9.1 µL, 0.065 mmol) and 3-methylbutanoyl chloride (3.9 mg, 0.033 mmol). The resulting reaction mixture was stirred at ambient temperature overnight and then directly purified by reverse phase chromatography (0-60% ACN/water) to afford the title compound (3.1 mg, 30% yield). MS (apci) m/z=470.1 (M+H).

Example 284

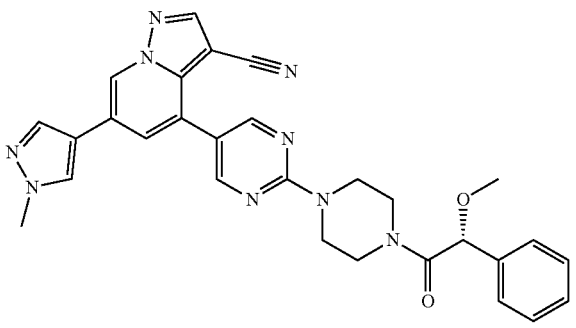

(R)-4-(2-(4-(2-methoxy-2-phenylacetyl)piperazin-1-yl)pyrimidin-5-yl)-6-(1-methyl-1H-pyrazol-4-yl)pyrazolo[1,5-a]pyridine-3-carbonitrile To a solution of 6-(1-methyl-1H-pyrazol-4-yl)-4-(2-(piperazin-1-yl)pyrimidin-5-yl)pyrazolo[1,5-a]pyridine-3-carbonitrile dihydrochloride (10 mg, 0.22 mmol) in DMF (87 µL) was added (R)-2-methoxy-2-phenylacetic acid (11 mg, 0.065 mmol), DMAP (2.7 mg, 0.022 mmol), DIEA (11 µL, 0.065 mmol) and EDC-HCl (17 mg, 0.087 mmol). The resulting reaction mixture was stirred at ambient temperature overnight and then directly purified by reverse phase chromatography (0-65% ACN/water) to afford the title compound (10.8 mg, 79.4% yield). MS (apci) m/z=520.1 (M+H).

Example 285

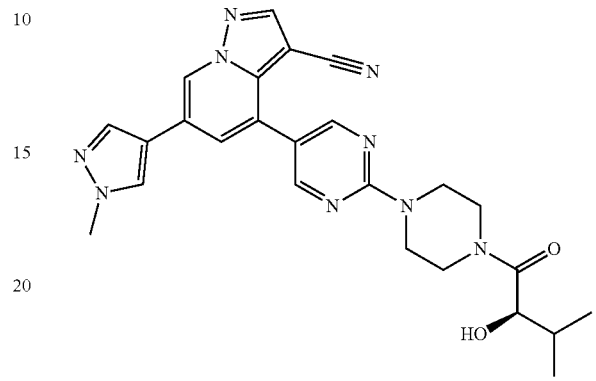

(R)-4-(2-(4-(2-hydroxy-3-methylbutanoyl)piperazin-1-yl)pyrimidin-5-yl)-6-(1-methyl-1H-pyrazol-4-yl)pyrazolo[1,5-a]pyridine-3-carbonitrile A solution of 6-(1-methyl-1H-pyrazol-4-yl)-4-(2-(piperazin-1-yl)pyrimidin-5-yl)pyrazolo[1,5-a]pyridine-3-carbonitrile dihydrochloride (10 mg, 0.022 mmol) and EDC-HCl (17 mg, 0.087 mmol) in DMF (0.2 mL) was treated with (R)-2-hydroxy-3-methylbutanoic acid (7.7 mg, 0.065 mmol), DMAP (2.7 mg, 0.022 mmol) and TEA (15 µL, 0.11 mmol). The resulting reaction mixture was stirred at ambient temperature overnight and then purified directly using reverse phase chromatography (0-55% ACN/water) to provide the title compound (6.2 mg, 59% yield). MS (apci) m/z=486.1 (M+H).

Example 286

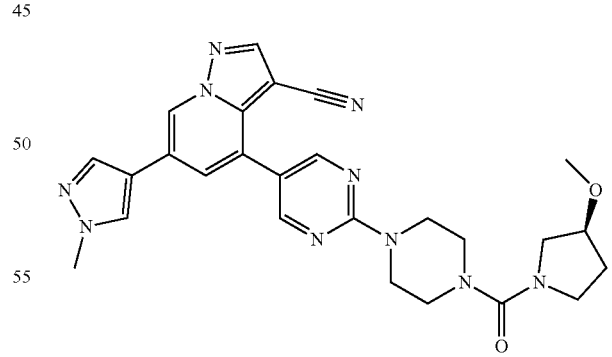

(S)-4-(2-(4-(3-methoxypyrrolidine-1-carbonyl)piperazin-1-yl)pyrimidin-5-yl)-6-(1-methyl-1H-pyrazol-4-yl)pyrazolo[1,5-a]pyridine-3-carbonitrile A mixture of 6-(1-methyl-1H-pyrazol-4-yl)-4-(2-(piperazin-1-yl)pyrimidin-5-yl)pyrazolo[1,5-a]pyridine-3-carbonitrile dihydrochloride (20 mg, 0.044 mmol) and DIEA (46

µL, 0.26 mmol) in DCM (436 µL) was treated with (S)-3-methoxypyrrolidine-1-carbonyl chloride (Example 269, Step 1, 0.25 M, 209 µL, 0.052 mmol). The reaction was stirred for 3 d at ambient temperature and directly purified by reverse phase chromatography (0-75% ACN/water) to provide the title compound (4.5 mg, 20% yield). MS (apci) m/z=513.1 (M+H).

Example 287

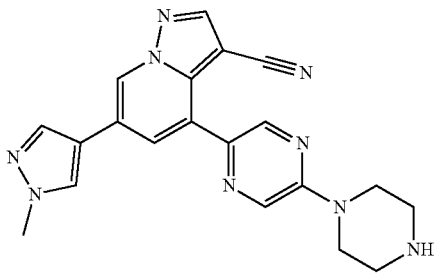

6-(1-methyl-1H-pyrazol-4-yl)-4-(5-(piperazin-1-yl)pyrazin-2-yl)pyrazolo[1,5-a]pyridine-3-carbonitrile Step 1: Preparation of Tert-Butyl 4-(5-(3-cyano-6-(1-methyl-1H-pyrazol-4-yl)pyrazolo[1,5-a]pyridin-4-yl)pyrazin-2-yl)piperazine-1-carboxylate 3-Cyano-6-(1-methyl-1H-pyrazol-4-yl)pyrazolo[1,5-a]pyridin-4-yl trifluoromethanesulfonate (Intermediate P5; 100 mg, 0.269 mmol), tert-butyl 4-(5-(4,4,5,5-tetramethyl-1,3,2-dioxaborolan-2-yl)pyrazin-2-yl)piperazine-1-carboxylate (105 mg, 0.269 mmol), Na$_2$CO$_3$ (143 mg, 1.35 mmol) and Pd(PPh$_3$)$_4$ (15.6 mg, 0.0135 mmol) were combined in 4:1 dioxane/water (4 mL). The resulting reaction mixture was purged with Argon for 10 min and then heated at 90° C. under continued atmosphere of Argon overnight. The reaction mixture was cooled to ambient temperature and then concentrated in vacuo. The crude residue was partitioned between DCM (50 mL) and water (50 mL) and the combined organic extracts were dried over MgSO$_4$, filtered and concentrated in vacuo to afford the title compound. MS (apci) m/z=486.2 (M+H). The crude product was used directly in the next step without further purification.

Step 2: Preparation of 6-(1-methyl-1H-pyrazol-4-yl)-4-(5-(piperazin-1-yl)pyrazin-2-yl)pyrazolo[1,5-a]pyridine-3-carbonitrile Dihydrochloride A solution of tert-butyl 4-(5-(3-cyano-6-(1-methyl-1H-pyrazol-4-yl)pyrazolo[1,5-a]pyridin-4-yl)pyrazin-2-yl)piperazine-1-carboxylate (131 mg, 0.270 mmol) in DCM (4 mL) was treated with TFA (2 mL) at ambient temperature. The resulting mixture was stirred overnight at ambient temperature and then concentrated in vacuo. The crude residue was dissolved in a solution of 20% iPrOH in DCM (50 mL) and extracted with 10% NaHCO$_{3(aq)}$ (50 mL). The aqueous layer was separated and then extracted with a solution of 20% iPrOH in DCM (50 mL). The combined organic extracts were dried over MgSO$_4$, filtered and concentrated in vacuo. The resulting crude residue was purified twice, first by silica chromatography (eluting with 10% MeOH in DCM and then with 5% MeOH in DCM containing 2% TEA), then by reverse phase chromatography (5-95% ACN/water) to afford the title compound (0.051 g, 49% yield). MS (apci) m/z=386.0 (M+H).

Example 288

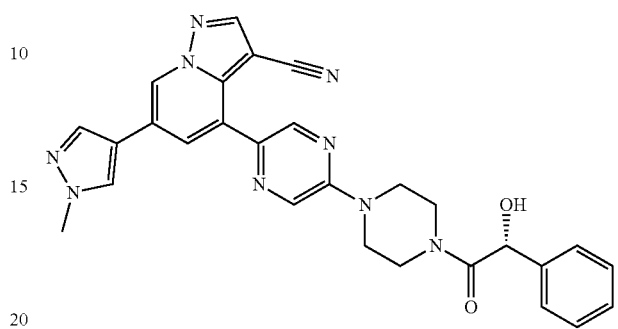

(R)-4-(5-(4-(2-hydroxy-2-phenylacetyl)piperazin-1-yl)pyrazin-2-yl)-6-(1-methyl-1H-pyrazol-4-yl)pyrazolo[1,5-a]pyridine-3-carbonitrile A solution of 6-(1-methyl-1H-pyrazol-4-yl)-4-(5-(piperazin-1-yl)pyrazin-2-yl)pyrazolo[1,5-a]pyridine-3-carbonitrile (20 mg, 0.052 mmol) in DMF (4 mL) was treated sequentially with D-(−)-Mandelic acid (11.84 mg, 0.07784 mmol), HATU (19.9 mg, 0.0524 mmol), and DIEA (90.38 µL, 0.5189 mmol). The resulting reaction mixture was stirred at ambient temperature overnight and then partitioned between water (50 mL) and EtOAc (50 mL). The combined organic extracts were dried over MgSO$_4$, filtered and concentrated in vacuo. The crude residue was purified by silica chromatography (1:4 hexanes/EtOAc) to afford the title compound (0.016 g, 60% yield). MS (apci) m/z=520.2 (M+H).

Example 289

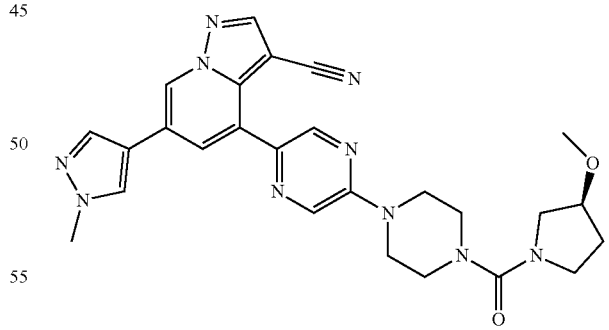

(S)-4-(5-(4-(3-methoxypyrrolidine-1-carbonyl)piperazin-1-yl)pyrazin-2-yl)-6-(1-methyl-1H-pyrazol-4-yl)pyrazolo[1,5-a]pyridine-3-carbonitrile A suspension of 6-(1-methyl-1H-pyrazol-4-yl)-4-(5-(piperazin-1-yl)pyrazin-2-yl)pyrazolo[1,5-a]pyridine-3-carbonitrile (32 mg, 0.083 mmol) and DIEA (87 µL, 0.50 mmol) in DriSolv® DCM (415 µL) was cooled to 0° C. and then added dropwise to a 0° C. solution of triphosgene (11 mg, 0.037 mmol) in DriSolv® DCM (415 µL). After stirring the reaction mixture for 0.5 h at 0° C., (S)-3-methoxypyrrolidine hydrochloride (11 mg, 0.083 mmol) was added in one portion, and the reaction was stirred at ambient temperature overnight. The reaction mixture was directly purified by silica chromatography (5% MeOH in EtOAc as eluent) to afford the title compound (0.023 g, 54% yield). MS (apci) m/z=513.3 (M+H).

Example 290

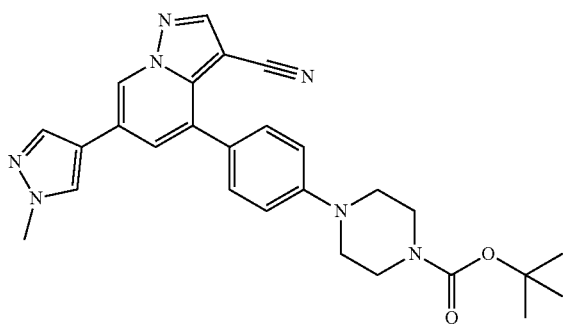 [SMILES: Cn1cc(-c2cc(-c3ccc(N4CCN(C(=O)OC(C)(C)C)CC4)cc3)c3c(C#N)cnn3c2)cn1]

Tert-Butyl 4-(4-(3-cyano-6-(1-methyl-1H-pyrazol-4-yl)pyrazolo[1,5-a]pyridin-4-yl)phenyl)piperazine-1-carboxylate 3-cyano-6-(1-methyl-1H-pyrazol-4-yl)pyrazolo[1,5-a]pyridin-4-yl trifluoromethanesulfonate (Intermediate P5; 25 mg, 0.0673 mmol), tert-butyl 4-(4-(4,4,5,5-tetramethyl-1,3,2-dioxaborolan-2-yl)phenyl)piperazine-1-carboxylate (34.0 mg, 0.0875 mmol), Pd(PPh$_3$)$_4$ (7.78 mg, 0.00673 mmol) and 2 M Na$_2$CO$_{3(aq)}$ (362 µL, 0.723 mmol) were combined in dioxane (0.3 mL) in a pressure tube. The resulting reaction mixture was sparged with nitrogen and then sealed and heated at 100° C. for 2 h. The reaction mixture was cooled to ambient temperature, then diluted with brine (1 mL) and extracted with several portions of DCM. The combined DCM extracts were concentrated in vacuo and purified directly by reverse phase chromatography (0-70% ACN/water) to afford the title compound (28 mg, 72% yield). MS (apci) m/z=215.1 (M+H-Boc).

Example 291

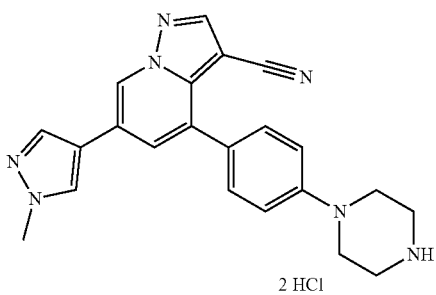 [SMILES: Cn1cc(-c2cc(-c3ccc(N4CCNCC4)cc3)c3c(C#N)cnn3c2)cn1]

6-(1-methyl-1H-pyrazol-4-yl)-4-(4-(piperazin-1-yl)phenyl)pyrazolo[1,5-a]pyridine-3-carbonitrile Dihydrochloride To a solution tert-butyl 4-(4-(3-cyano-6-(1-methyl-1H-pyrazol-4-yl)pyrazolo[1,5-a]pyridin-4-yl)phenyl)piperazine-1-carboxylate (28 mg, 0.049 mmol) in DCM (1 mL) was added 5 M HCl in iPrOH (49 µL, 0.24 mmol). The reaction was stirred at ambient temperature overnight and then vacuum filtered. The isolated solids were washed with DCM and Et$_2$O and air dried to afford the title compound (19 mg, 86% yield). MS (apci) m/z=384.1 (M+H).

Example 292

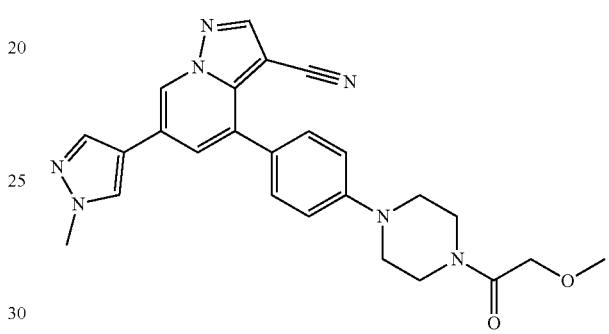

4-(4-(4-(2-methoxyacetyl)piperazin-1-yl)phenyl)-6-(1-methyl-1H-pyrazol-4-yl)pyrazolo[1,5-a]pyridine-3-carbonitrile A solution of 6-(1-methyl-1H-pyrazol-4-yl)-4-(4-(piperazin-1-yl)phenyl)pyrazolo[1,5-a]pyridine-3-carbonitrile dihydrochloride (10 mg, 0.0219 mmol) in DCM (0.1 mL) was treated with TEA (30.5 µL, 0.219 mmol) and 2-methoxyacetyl chloride (4.76 mg, 0.0438 mmol). The resulting reaction mixture was stirred at ambient temperature for 30 min, then concentrated in vacuo and directly purified by reverse phase chromatography (0-70% ACN/water) to afford the title compound (5.2 mg, 52.1% yield). MS (apci) m/z=456.1 (M+H).

Example 293

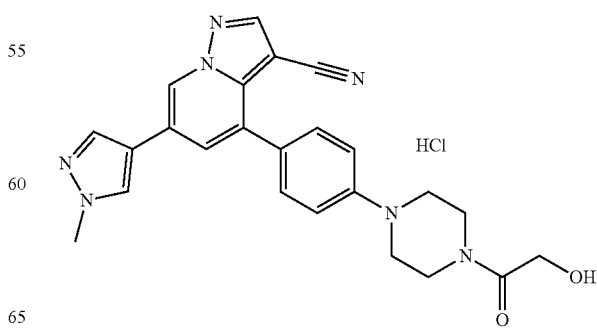

367

4-(4-(4-(2-hydroxyacetyl)piperazin-1-yl)phenyl)-6-(1-methyl-1H-pyrazol-4-yl)pyrazolo[1,5-a]pyridine-3-carbonitrile Hydrochloride A solution of 6-(1-methyl-1H-pyrazol-4-yl)-4-(4-(piperazin-1-yl)phenyl)pyrazolo[1,5-a]pyridine-3-carbonitrile dihydrochloride (35 mg, 0.077 mmol) in DCM (0.5 mL) was treated with 2-chloro-2-oxoethyl acetate (31.41 mg, 0.23 mmol) and TEA (30.5 µL, 0.219 mmol. The resulting reaction mixture was stirred at ambient temperature for 30 min, then MeOH (0.2 mL) and NaOH (383.46 µL, 0.383 mmol) were added and the reaction was stirred at ambient temperature overnight. The reaction was quenched with water (1 mL) and extracted with several portions of DCM in a PS frit. The DCM extracts were concentrated in vacuo and the crude residue was dissolved in 1:1 DCM/MeOH (1 mL) and treated with 5 M HCl in iPrOH (46 µL, 0.23 mmol). The resulting mixture was concentrated in vacuo and the residue was taken up in DCM (2 mL) and sonicated. The suspension was vacuum filtered and the solids were successively rinsed with DCM (2 mL) and Et$_2$O (3×2 mL) and then dried in vacuo to afford the title compound (27 mg, 80% yield). MS (apci) m/z=442.0 (M+H).

368

4-(4-(4-(3,3-dimethylbutanoyl)piperazin-1-yl)phenyl)-6-(1-methyl-1H-pyrazol-4-yl)pyrazolo[1,5-a]pyridine-3-carbonitrile A solution of 6-(1-methyl-1H-pyrazol-4-yl)-4-(4-(piperazin-1-yl)phenyl)pyrazolo[1,5-a]pyridine-3-carbonitrile dihydrochloride (12 mg, 0.026 mmol) in DCM (1 mL) was treated with 3,3-dimethylbutanoyl chloride (11 mg, 0.079 mmol) and TEA (18 µL, 0.13 mmol). The resulting reaction mixture was stirred at ambient temperature for 1 h and then quenched with water (1 mL) and extracted with several portions of DCM (3×5 mL) in a PS frit. The combined DCM extracts were concentrated in vacuo and then taken up in MeOH (0.5 mL) and sonicated. The resulting suspension was vacuum filtered and the solids were rinsed with Et$_2$O (3×2 mL) to afford the title compound (10 mg, 79% yield). MS (apci) m/z=482.2 (M+H).

The compounds in Table Z were prepared and purified according to the method described for the synthesis of Example 294, replacing 3,3-dimethylbutanoyl chloride for the appropriate acid chloride starting material.

Example 294

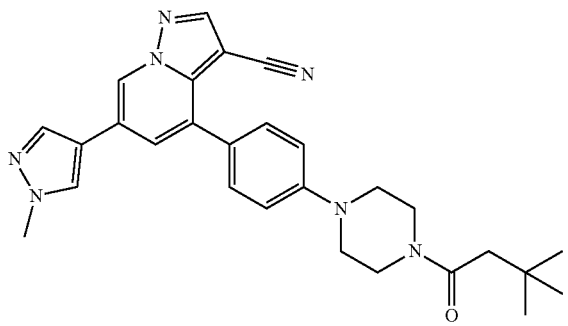 [SMILES: Cn1cc(-c2cc(-c3ccc(N4CCN(C(=O)CC(C)(C)C)CC4)cc3)c3c(C#N)cnn3c2)cn1]

TABLE Z

| Ex # | Structure | Chemical Name | MS (apci) m/z |
|---|---|---|---|
| 295 | 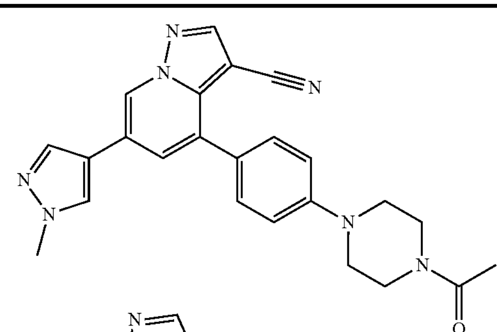 | 4-(4-(4-acetylpiperazin-1-yl)phenyl)-6-(1-methyl-1H-pyrazol-4-yl)pyrazolo[1,5-a]pyridine-3-carbonitrile | 426.1 (M + H) |
| 296 | 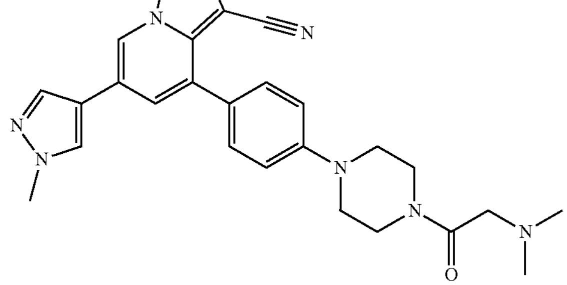 | 4-(4-(4-(2-(dimethylamino)acetyl)piperazin-1-yl)phenyl)-6-(1-methyl-1H-pyrazol-4-yl)pyrazolo[1,5-a]pyridine-3-carbonitrile | 469.1 (M + H) |

Example 297

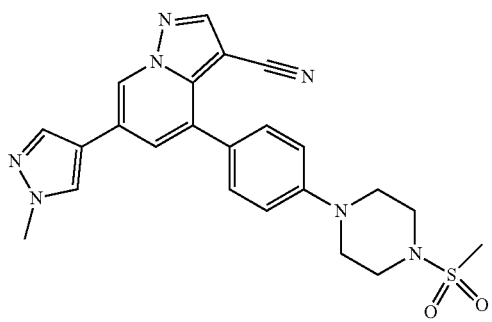 [SMILES: Cn1cc(-c2cc(-c3ccc(N4CCN(S(C)(=O)=O)CC4)cc3)c3c(C#N)cnn3c2)cn1]

6-(1-methyl-1H-pyrazol-4-yl)-4-(4-(4-(methyl sulfonyl)piperazin-1-yl)phenyl)pyrazolo[1,5-a]pyridine-3-carbonitrile To a solution of 6-(1-methyl-1H-pyrazol-4-yl)-4-(6-(piperazin-1-yl)pyridin-3-yl)pyrazolo[1,5-a]pyridine-3-carbonitrile hydrochloride (6 mg, 0.014 mmol) in DCM (0.2 mL) was added TEA (10 μL, 0.071 mmol) followed by methanesulfonyl chloride (29 μL, 0.029 mmol). The mixture was stirred at ambient temperature for 1 h, then concentrated in vacuo and purified by reverse phase chromatography (0-70% ACN/water) to provide the title compound (6.2 mg, 94% yield). MS (apci) m/z=462.1 (M+H).

Example 298

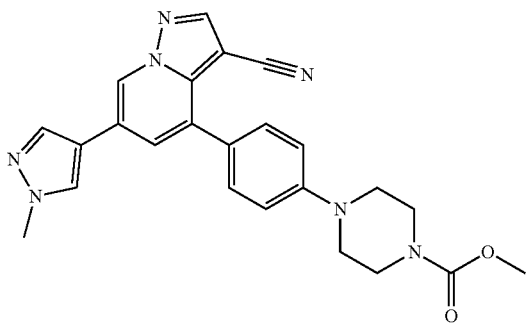

Methyl 4-(4-(3-cyano-6-(1-methyl-1H-pyrazol-4-yl)pyrazolo[1,5-a]pyridin-4-yl)phenyl)piperazine-1-carboxylate 6-(1-methyl-1H-pyrazol-4-yl)-4-(4-(piperazin-1-yl)phenyl)pyrazolo[1,5-a]pyridine-3-carbonitrile dihydrochloride (10 mg, 0.022 mmol), methyl carbonochloridate (6.2 mg, 0.066 mmol) and TEA (18 μL, 0.13 mmol) were combined in DCM (0.1 mL) and stirred at ambient temperature for 30 min. The reaction mixture was concentrated in vacuo and purified by reverse phase chromatography (0-60% ACN/water) to afford the title compound (5.1 mg, 53% yield). MS (apci) m/z=442.2 (M+H).

Example 299

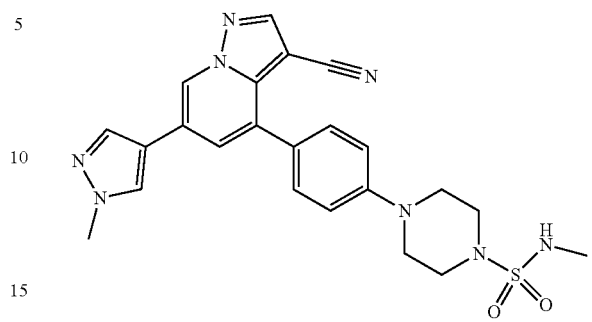

4-(4-(3-cyano-6-(1-methyl-1H-pyrazol-4-yl)pyrazolo[1,5-a]pyridin-4-yl)phenyl)-N-methylpiperazine-1-sulfonamide A solution of 6-(1-methyl-1H-pyrazol-4-yl)-4-(4-(piperazin-1-yl)phenyl)pyrazolo[1,5-a]pyridine-3-carbonitrile dihydrochloride (10 mg, 0.0219 mmol) in DCM (0.2 mL) was treated with TEA (30.5 μL, 0.219 mmol) and methylsulfamoyl chloride (110 μL, 0.110 mmol) and stirred at ambient temperature overnight. The resulting mixture was concentrated in vacuo and purified by reverse phase chromatography (0-70% ACN/water) to afford the title compound (1.2 mg, 12% yield). MS (apci) m/z=477.2 (M+H).

Example 300

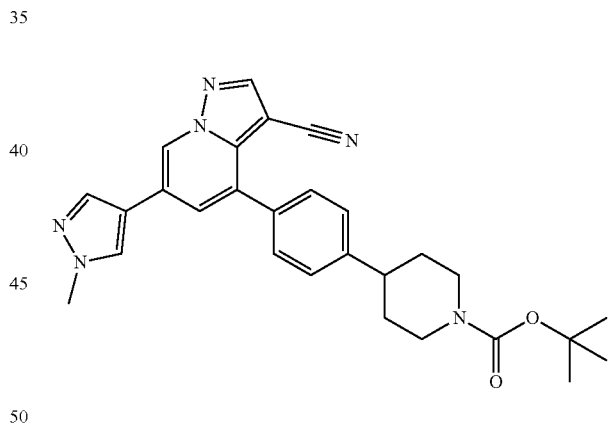

Tert-Butyl 4-(4-(3-cyano-6-(1-methyl-1H-pyrazol-4-yl)pyrazolo[1,5-a]pyridin-4-yl)phenyl)piperidine-1-carboxylate A solution of 3-cyano-6-(1-methyl-1H-pyrazol-4-yl)pyrazolo[1,5-a]pyridin-4-yl trifluoromethanesulfonate (Intermediate P5; 30 mg, 0.0808 mmol) in dioxane (0.8 mL) was treated with tert-butyl 4-(4-(4,4,5,5-tetramethyl-1,3,2-dioxaborolan-2-yl)phenyl)piperidine-1-carboxylate (Intermediate R10; 46.9 mg, 0.121 mmol), 2 M Na$_2$CO$_{3(aq)}$ (202 μL, 0.404 mmol) and Pd(PPh$_3$)$_4$ (4.67 mg, 0.00404 mmol) in a pressure tube. The resulting reaction mixture was sparged with nitrogen, sealed and heated at 90° C. overnight. The reaction mixture was cooled to ambient temperature and then diluted with water (5 mL) and stirred well. The resulting suspension was diluted with additional water (3 mL) and the aqueous suspension was extracted with DCM (2×10 mL). The combined organic extracts were concentrated in vacuo and purified by silica chromatography (25-100% EtOAc/hexanes) to afford the title compound (23.4 mg, 60% yield). MS (apci) m/z=383.1 (M+H-Boc). $^1$H NMR (CDCl$_3$) δ 8.65 (d, 1H), 8.26 (s, 1H), 7.80 (s, 1H), 7.69 (s, 1H), 7.53 (m, 2H), 7.45 (d, 1H), 7.38 (m, 2H), 4.28 (m, 2H), 4.00 (s, 3H), 2.83 (m, 2H), 2.76 (m, 1H), 1.91 (m, 2H), 1.69 (m, 2H), 1.49 (s, 9H).

Example 301

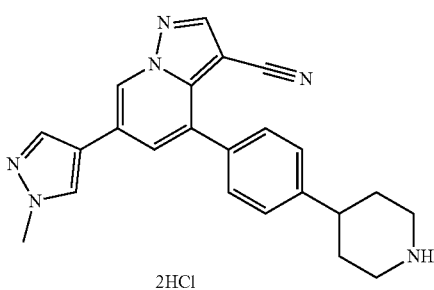 [SMILES: Cn1cc(-c2cc(-c3ccc(C4CCNCC4)cc3)c3c(C#N)cnn3c2)cn1]

2HCl 6-(1-methyl-1H-pyrazol-4-yl)-4-(4-(piperidin-4-yl)phenyl)pyrazolo[1,5-a]pyridine-3-carbonitrile Dihydrochloride To a suspension of tert-butyl 4-(4-(3-cyano-6-(1-methyl-1H-pyrazol-4-yl)pyrazolo[1,5-a]pyridin-4-yl)phenyl)piperidine-1-carboxylate (22.3 mg, 0.0462 mmol) in EtOH (0.2 mL) was added 5 M HCl in iPrOH (305 µL, 1.52 mmol). After stirring at ambient temperature 2 h, the resulting suspension was vacuum filtered, and the solids were rinsed with Et$_2$O (2 mL) and dried in vacuo to afford the title compound (17.0 mg, 81% yield). MS (apci) m/z=383.1 (M+H).

Example 302

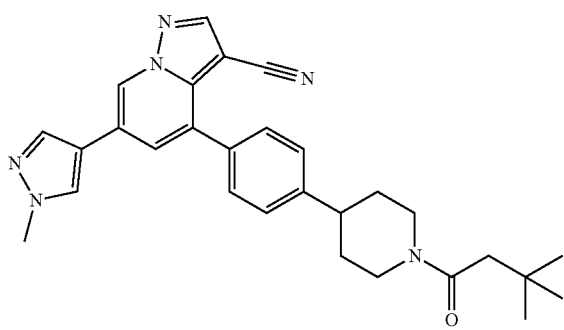

4-(4-(1-(3,3-dimethylbutanoyl)piperidin-4-yl)phenyl)-6-(1-methyl-1H-pyrazol-4-yl)pyrazolo[1,5-a]pyridine-3-carbonitrile A solution of 6-(1-methyl-1H-pyrazol-4-yl)-4-(4-(piperidin-4-yl)phenyl)pyrazolo[1,5-a]pyridine-3-carbonitrile dihydrochloride (8 mg, 0.0176 mmol) in DCM (0.4 mL) was treated with 3,3-dimethylbutanoyl chloride (3.68 µL, 0.0264 mmol) and DIEA (12.2 µL, 0.0703 mmol), and the resulting solution was stirred at ambient temperature for overnight. The reaction was quenched with MeOH (0.2 mL), then partially concentrated in vacuo and purified by silica chromatography (0-100% EtOAc/hexanes) to afford the title compound (6.5 mg, 77% yield). MS (apci) m/z=481.2 (M+H).

Example 303

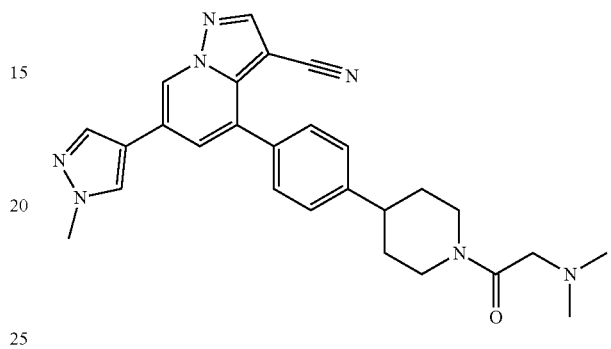

4-(4-(1-(2-(dimethylamino)acetyl)piperidin-4-yl)phenyl)-6-(1-methyl-1H-pyrazol-4-yl)pyrazolo[1,5-a]pyridine-3-carbonitrile A solution of 6-(1-methyl-1H-pyrazol-4-yl)-4-(4-(piperidin-4-yl)phenyl)pyrazolo[1,5-a]pyridine-3-carbonitrile dihydrochloride (8 mg, 0.018 mmol) in DCM (0.4 mL) was treated with 2-(dimethylamino)acetyl chloride hydrochloride (4.2 mg, 0.026 mmol) and DIEA (18 µL, 0.11 mmol), and the resulting solution was stirred at ambient temperature overnight. The reaction was quenched with MeOH (0.2 mL), partially concentrated in vacuo, and then purified by reverse phase chromatography (5-75% MeCN/water) to afford the title compound (2.4 mg, 29% yield). MS (apci) m/z=468.1 (M+H).

Example 304

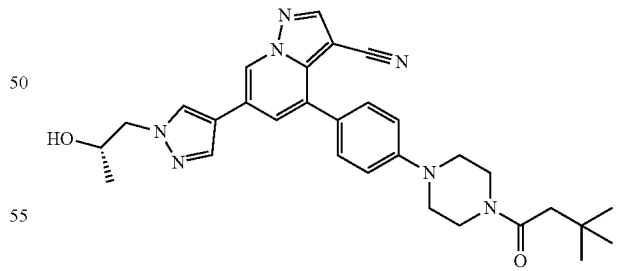

(S)-4-(4-(4-(3,3-dimethylbutanoyl)piperazin-1-yl)phenyl)-6-(1-(2-hydroxypropyl)-1H-pyrazol-4-yl)pyrazolo[1,5-a]pyridine-3-carbonitrile A solution of 3-cyano-4-(4-(4-(3,3-dimethylbutanoyl)piperazin-1-yl)phenyl)pyrazolo[1,5-a]pyridin-6-yl trifluoromethanesulfonate (Intermediate P16; 0.030 g, 0.055 mmol) in dioxane (4 mL) was treated with (S)-1-(4-(4,4,5, 5-tetramethyl-1,3,2-dioxaborolan-2-yl)-1H-pyrazol-1-yl) propan-2-ol (0.021 g, 0.082 mmol) and 2 M K$_2$CO$_{3(aq)}$ (0.055 mL, 0.11 mmol). The resulting reaction mixture was purged with N$_2$ for 5 min, and then X-Phos (0.0052 g, 0.011 mmol) and Pd$_2$(dba)$_3$ (0.0025 g, 0.0027 mmol) were added to the reaction mixture. The mixture was purged with nitrogen for an additional 5 min then heated at 80° C. under a nitrogen atmosphere overnight. The reaction mixture was cooled to ambient temperature, then diluted with water (5 mL) and extracted with EtOAc (3×5 mL). The combined organic extracts were dried over anhydrous Na$_2$SO$_4$, filtered, concentrated in vacuo and purified by silica chromatography (0-50% 20% MeOH/DCM in EtOAc) to afford the title compound (5.4 mg, 18% yield). MS (apci) m/z=526.2 (M+H).

Example 305

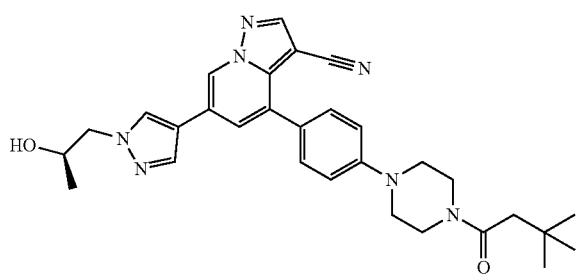 [SMILES: C[C@@H](O)Cn1cc(-c2cc(-c3ccc(N4CCN(C(=O)CC(C)(C)C)CC4)cc3)c3c(C#N)cnn3c2)cn1]

(R)-4-(4-(4-(3,3-dimethylbutanoyl)piperazin-1-yl) phenyl)-6-(1-(2-hydroxypropyl)-1H-pyrazol-4-yl) pyrazolo[1,5-a]pyridine-3-carbonitrile A solution of 3-cyano-4-(4-(4-(3,3-dimethylbutanoyl)piperazin-1-yl)phenyl)pyrazolo[1,5-a]pyridin-6-yl trifluoromethanesulfonate (0.030 g, 0.0546 mmol) in dioxane (4 mL) was treated with (R)-1-(4-(4,4,5,5-tetramethyl-1,3,2-dioxaborolan-2-yl)-1H-pyrazol-1-yl)propan-2-ol (0.0206 g, 0.0819 mmol) and 2 M K$_2$CO$_{3(aq)}$ (0.0546 mL, 0.109 mmol). The resulting reaction mixture was purged with nitrogen for 5 min, and then X-Phos (0.00520 g, 0.0109 mmol) and Pd$_2$(dba)$_3$ (0.00250 g, 0.00273 mmol) were added. The reaction mixture was purged with nitrogen for an additional 5 min and then heated overnight at 80° C. under a nitrogen atmosphere. The reaction mixture was cooled to ambient temperature, then diluted with water (5 mL) and extracted with EtOAc (3×5 mL). The combined organic extracts were dried (Na$_2$SO$_4$), filtered, concentrated and purified by silica chromatography (0-50% of 20% MeOH/ DCM in EtOAc) to afford the title compound (0.0161 g, 54% yield). MS (apci) m/z=526.2 (M+H).

Example 306

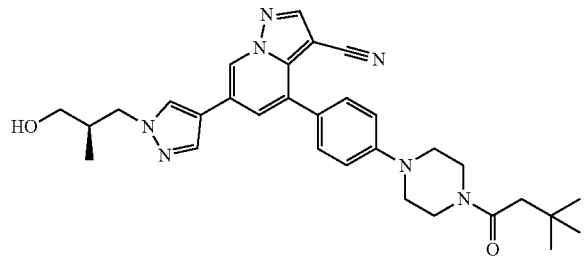 [SMILES: C[C@@H](CO)Cn1cc(-c2cc(-c3ccc(N4CCN(C(=O)CC(C)(C)C)CC4)cc3)c3c(C#N)cnn3c2)cn1]

(R)-4-(4-(4-(3,3-dimethylbutanoyl)piperazin-1-yl) phenyl)-6-(1-(3-hydroxy-2-methylpropyl)-1H-pyrazol-4-yl)pyrazolo[1,5-a]pyridine-3-carbonitrile Step 1: Preparation of 4-(4-(4-(3,3-dimethylbutanoyl)piperazin-1-yl)phenyl)-6-(1H-pyrazol-4-yl) pyrazolo[1,5-a]pyridine-3-carbonitrile A solution of 3-cyano-4-(4-(4-(3,3-dimethylbutanoyl)piperazin-1-yl)phenyl)pyrazolo[1,5-a]pyridin-6-yl trifluoromethanesulfonate (Intermediate P16; 0.200 g, 0.3639 mmol) in dioxane (15 mL) was treated with tert-butyl 4-(4,4,5,5-tetramethyl-1,3,2-dioxaborolan-2-yl)-1H-pyrazole-1-carboxylate (0.1606 g, 0.5459 mmol) and 2 M K$_2$CO$_{3(aq)}$ (0.3639 mL, 0.7278 mmol). The resulting reaction mixture was purged with nitrogen for 5 min, and then X-Phos (0.03470 g, 0.07278 mmol) and Pd$_2$(dba)$_3$ (0.01666 g, 0.01820 mmol) were added. The reaction mixture was purged with nitrogen for an additional 5 min and then heated overnight at 80° C. under a nitrogen atmosphere. The reaction mixture was cooled to ambient temperature and then diluted with water (20 mL) and extracted with EtOAc (3×50 mL). The combined organic extracts were dried over anhydrous Na$_2$SO$_4$, filtered and concentrated in vacuo. The crude residue was purified by silica chromatography (0-50% of 20% MeOH/DCM in EtOAc). The fractions containing the desired mass for tert-butyl 4-(3-cyano-4-(4-(4-(3,3-dimethylbutanoyl)piperazin-1-yl)phenyl)pyrazolo[1,5-a]pyridin-6-yl)-1H-pyrazole-1-carboxylate (by LCMS) were combined, concentrated in vacuo, dissolved in 20% MeOH/ DCM (25 mL), treated with 4 N HCl in dioxane (5 mL) and stirred overnight. The reaction mixture was quenched with saturated NaHCO$_{3(aq)}$ and extracted with 10% MeOH/DCM (3×50 mL). The organic and aqueous extracts were treated separately. The organic extracts were combined, dried over anhydrous Na$_2$SO$_4$, filtered and reserved. The aqueous layer was filtered and the insoluble solid collected was separately washed with MeOH (50 mL) and DCM (50 mL). The organic filtrates from both the original extraction and the solid wash were combined and concentrated in vacuo to afford the title compound (0.1663 g, 98% yield). MS (apci) m/z=468.1 (M+H).

Step 2: Preparation of (R)-4-(4-(4-(3,3-dimethylbutanoyl)piperazin-1-yl)phenyl)-6-(1-(3-hydroxy-2-methylpropyl)-1H-pyrazol-4-yl)pyrazolo[1,5-a]pyridine-3-carbonitrile A solution of 4-(4-(4-(3,3-dimethylbutanoyl)piperazin-1-yl)phenyl)-6-(1H-pyrazol-4-yl)pyrazolo[1,5-a]pyridine-3-carbonitrile (0.030 g, 0.06416 mmol) and (S)-3-bromo-2- methylpropan-1-ol (0.0134 mL, 0.1283 mmol) in DMF (1.283 mL, 0.0645 mmol) was treated with Cs₂CO₃ (0.04181 g, 0.128 mmol). The resulting mixture was heated at 80° C. and stirred overnight. After cooling to ambient temperature, the reaction mixture was diluted with water (10 mL), pH adjusted to 8 with 1 N HCl$_{(aq)}$, then extracted with EtOAc (3×15 mL). The combined organic extracts were washed with brine, dried (Na₂SO₄), filtered, concentrated and purified by silica chromatography (0-50% of 20% MeOH/DCM in EtOAc) to afford the title compound (0.0131 g, 38% yield). MS (apci) m/z=540.2 (M+H).

Example 307

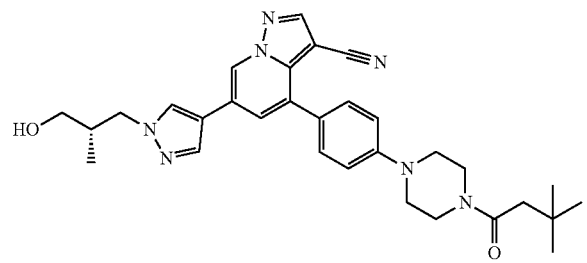 [SMILES: C[C@H](CO)Cn1cc(-c2cc(-c3ccc(N4CCN(C(=O)CC(C)(C)C)CC4)cc3)c3c(C#N)cnn3c2)cn1]

(S)-4-(4-(4-(3,3-dimethylbutanoyl)piperazin-1-yl) phenyl)-6-(1-(3-hydroxy-2-methylpropyl)-1H-pyrazol-4-yl)pyrazolo[1,5-a]pyridine-3-carbonitrile A solution of 4-(4-(4-(3,3-dimethylbutanoyl)piperazin-1-yl)phenyl)-6-(1H-pyrazol-4-yl)pyrazolo[1,5-a]pyridine-3-carbonitrile (0.030 g, 0.0645 mmol) and (R)-3-bromo-2-methylpropan-1-ol (0.01344 mL, 0.1283 mmol) in DMF (1.283 mL, 0.0645 mmol) was treated with Cs₂CO₃ (0.04181 g, 0.128 mmol). The resulting mixture was heated at 80° C. and stirred overnight. After cooling to ambient temperature, the reaction mixture was diluted with water (10 mL), the pH adjusted to 8 with 1 N HCl$_{(aq)}$, and extracted with EtOAc (3×15 mL). The combined organic extracts were washed with brine, dried (Na₂SO₄), filtered, concentrated and purified by silica chromatography (0-50% of 20% MeOH/DCM in EtOAc) to afford the title compound (0.0133 g, 38% yield). MS (apci) m/z=540.2 (M+H).

Example 308

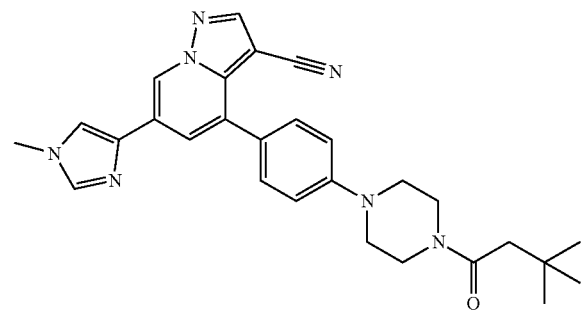 [SMILES: Cn1cnc(-c2cc(-c3ccc(N4CCN(C(=O)CC(C)(C)C)CC4)cc3)c3c(C#N)cnn3c2)c1]

4-(4-(4-(3,3-dimethylbutanoyl)piperazin-1-yl)phenyl)-6-(1-methyl-1H-imidazol-4-yl)pyrazolo[1,5-a]pyridine-3-carbonitrile In a pressure tube, 3-cyano-4-(4-(4-(3,3-dimethylbutanoyl)piperazin-1-yl)phenyl)pyrazolo[1,5-a]pyridin-6-yl trifluoromethanesulfonate (20 mg, 0.036 mmol), 1-methyl-4-(4,4,5,5-tetramethyl-1,3,2-dioxaborolan-2-yl)-1H-imidazole (15 mg, 0.073 mmol), PdCl₂(dppf).CH₂Cl2 (3.0 mg, 0.0036 mmol) and Cs₂CO₃ (59 mg, 0.18 mmol) were combined in dioxane (0.2 mL), sparged with N₂, sealed and heated at 100° C. for 3 h. After cooling to ambient temperature, the reaction mixture was diluted with water (1 mL) and extracted with DCM (3×5 mL). The combined organic extracts were concentrated in vacuo and purified by reverse phase chromatography (0-75% ACN/water with 0.1% HCl) to afford the title compound (2 mg, 11% yield). MS (apci) m/z=482.3 (M+H).

Example 309

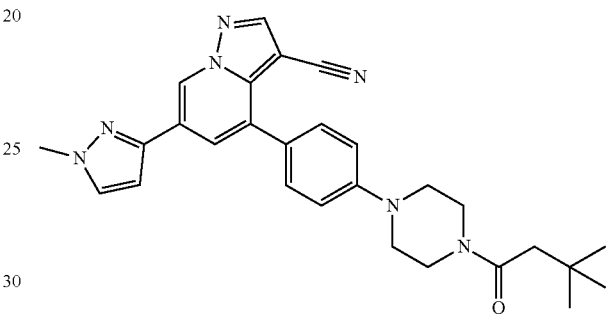

4-(4-(4-(3,3-dimethylbutanoyl)piperazin-1-yl)phenyl)-6-(1-methyl-1H-pyrazol-3-yl)pyrazolo[1,5-a]pyridine-3-carbonitrile In a pressure tube, 3-cyano-4-(4-(4-(3,3-dimethylbutanoyl)piperazin-1-yl)phenyl)pyrazolo[1,5-a]pyridin-6-yl trifluoromethanesulfonate (Intermediate P16; 20 mg, 0.036 mmol), 1-methyl-3-(4,4,5,5-tetramethyl-1,3,2-dioxaborolan-2-yl)-1H-pyrazole (15 mg, 0.073 mmol), Pd(PPh₃)₄ (4.2 mg, 0.0036 mmol) and 2 M Na₂CO₃$_{(aq)}$ (91 μL, 0.18 mmol) were combined in dioxane (0.2 mL), sparged with N₂, sealed and heated at 100° C. for 3 h. After cooling to ambient temperature and stirring overnight, the reaction mixture was diluted with water (1 mL) and extracted with DCM (3×5 mL). The combined organic extracts were concentrated in vacuo and purified by reverse phase chromatography (0-95% ACN/water) to afford the title compound (4.6 mg, 26% yield). MS (apci) m/z=482.1 (M+H).

Example 310

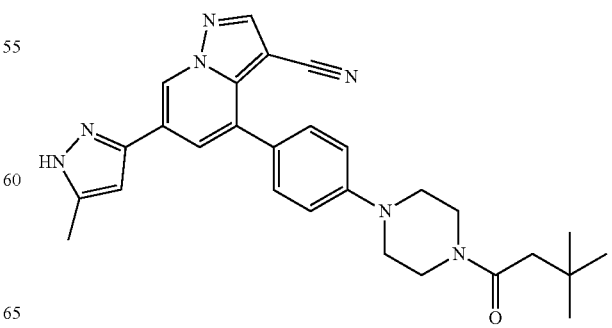

4-(4-(4-(3,3-dimethylbutanoyl)piperazin-1-yl)phenyl)-6-(5-methyl-1H-pyrazol-3-yl)pyrazolo[1,5-a]pyridine-3-carbonitrile In a pressure tube, 3-cyano-4-(4-(4-(3,3-dimethylbutanoyl)piperazin-1-yl)phenyl)pyrazolo[1,5-a]pyridin-6-yl trifluoromethanesulfonate (Intermediate P16; 20 mg, 0.036 mmol), 5-methyl-3-(4,4,5,5-tetramethyl-1,3,2-dioxaborolan-2-yl)-1H-pyrazole (15 mg, 0.073 mmol), Pd(PPh$_3$)$_4$ (4.2 mg, 0.0036 mmol) and 2 M Na$_2$CO$_{3(aq)}$ (91 µL, 0.18 mmol) were combined in dioxane (0.2 mL). The reaction mixture was sparged with N$_2$, sealed and heated at 100° C. for 3 h and then stirred at ambient temperature overnight. The reaction mixture was diluted with water (1 mL) and extracted with DCM (3×5 mL). The combined organic extracts were concentrated in vacuo then triturated with MeOH (0.2 mL). The resulting suspension was vacuum filtered, and the isolated solids were rinsed with Et$_2$O and air dried to afford the title compound (7 mg, 40% yield). MS (apci) m/z=482.1 (M+H).

Example 311

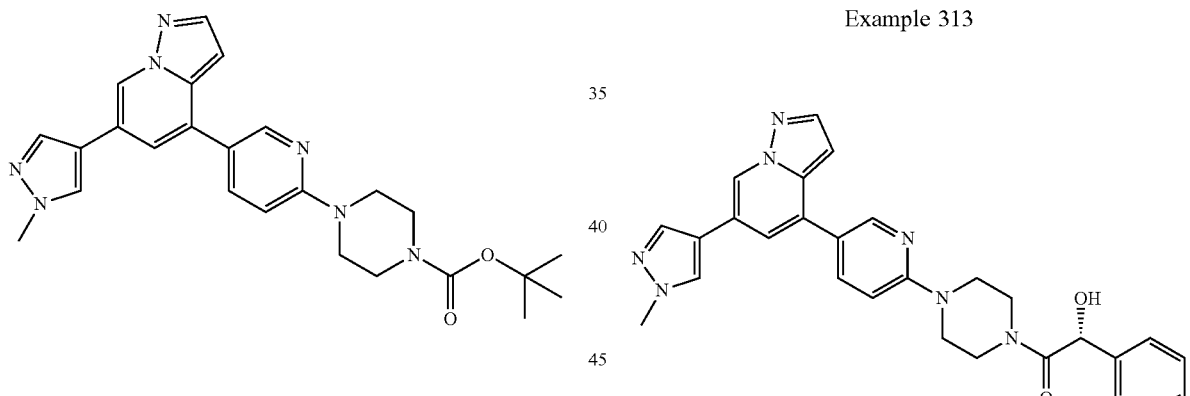

Tert-Butyl 4-(5-(6-(1-methyl-1H-pyrazol-4-yl)pyrazolo[1,5-a]pyridin-4-yl)pyridin-2-yl)piperazine-1-carboxylate In a pressure tube, 6-(1-methyl-1H-pyrazol-4-yl)pyrazolo[1,5-a]pyridin-4-yl trifluoromethanesulfonate (Intermediate P7; 750 mg, 2.17 mmol), (6-(4-(tert-butoxycarbonyl)piperazin-1-yl)pyridin-3-yl)boronic acid (998 mg, 3.25 mmol), Pd(PPh$_3$)$_4$ (250 mg, 0.217 mmol) and 2 M Na$_2$CO$_{3(aq)}$ (5.42 mL, 10.8 mmol) were combined in dioxane (20 mL). The resulting reaction mixture was sparged with nitrogen, then sealed and heated at 100° C. overnight. After cooling to ambient temperature the reaction mixture was diluted with water (10 mL) and extracted with several portions of DCM in a PS frit. The combined organic extracts were concentrated in vacuo and purified by silica chromatography (10-100% EtOAc/hexanes) to afford the title compound (826 mg, 83% yield). MS (apci) m/z=460.1 (M+H).

Example 312

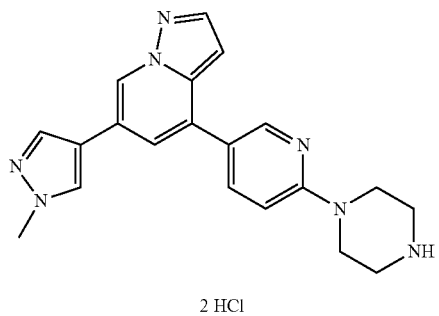 [SMILES: Cn1cc(-c2cc(-c3ccc(N4CCNCC4)nc3)c3ccnn3c2)cn1]

2 HCl 6-(1-methyl-1H-pyrazol-4-yl)-4-(6-(piperazin-1-yl)pyridin-3-yl)pyrazolo[1,5-a]pyridine Dihydrochloride To a solution of tert-butyl 4-(5-(6-(1-methyl-1H-pyrazol-4-yl)pyrazolo[1,5-a]pyridin-4-yl)pyridin-2-yl)piperazine-1-carboxylate (820 mg, 1.78 mmol) in DCM (5 mL) was added 5 M HCl in iPrOH (1784 µL, 8.92 mmol). The reaction was stirred at ambient temperature overnight. The resulting suspension was vacuum filtered and the solids were washed with Et$_2$O (2×5 mL) then air dried to afford the title compound (640 mg, 99% yield). MS (apci) m/z=360.1 (M+H).

Example 313

(R)-2-hydroxy-1-(4-(5-(6-(1-methyl-1H-pyrazol-4-yl)pyrazolo[1,5-a]pyridin-4-yl)pyridin-2-yl)piperazin-1-yl)-2-phenylethanone A solution of 6-(1-methyl-1H-pyrazol-4-yl)-4-(6-(piperazin-1-yl)pyridin-3-yl)pyrazolo[1,5-a]pyridine dihydrochloride (24.6 mg, 0.0568984 mmol) in DCM (1.2 mL) was treated with D-(−)-Mandelic acid (12.99 mg, 0.08535 mmol), HATU (21.63 mg, 0.05690 mmol) and DIEA (99.11 µL, 0.5690 mmol). The resulting reaction mixture was stirred at ambient temperature overnight, then concentrated in vacuo and purified by silica chromatography (10-80% DCM/acetone) to afford the title compound (13.2 mg, 47% yield). MS (apci) m/z=494.1 (M+H).

The compounds in Table AA were prepared in a similar fashion as described for the synthesis of Example 313, replacing D-(−)-Mandelic acid with the appropriate acid starting material.

TABLE AA

| Ex # | Structure | Chemical Name | MS (apci) m/z |
|---|---|---|---|
| 314 | 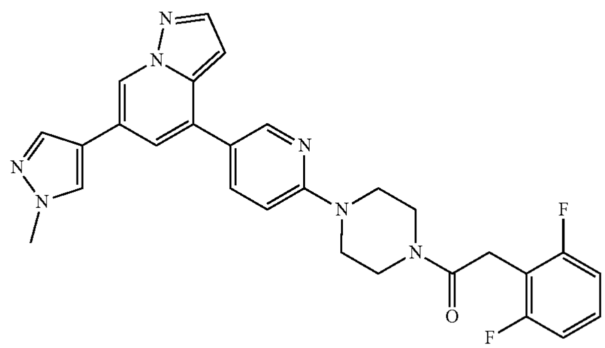 [SMILES: Cn1cc(-c2cc(-c3ccc(N4CCN(C(=O)Cc5c(F)cccc5F)CC4)nc3)c3ccnn3c2)cn1] | 2-(2,6-difluorophenyl)-1-(4-(5-(6-(1-methyl-1H-pyrazol-4-yl)pyrazolo[1,5-a]pyridin-4-yl)pyridin-2-yl)piperazin-1-yl)ethanone | 514.1 (M + H) |
| 315 | 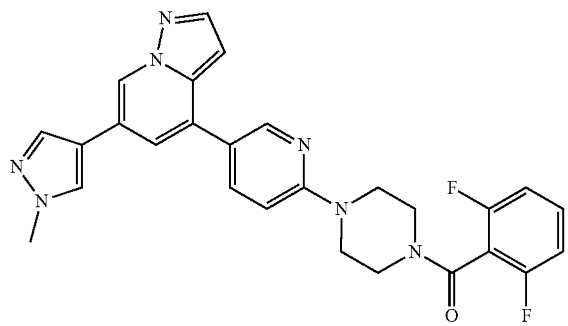 [SMILES: Cn1cc(-c2cc(-c3ccc(N4CCN(C(=O)c5c(F)cccc5F)CC4)nc3)c3ccnn3c2)cn1] | (2,6-difluorophenyl)(4-(5-(6-(1-methyl-1H-pyrazol-4-yl)pyrazolo[1,5-a]pyridin-4-yl)pyridin-2-yl)piperazin-1-yl)methanone | 500.1 (M + H) |
| 316 | 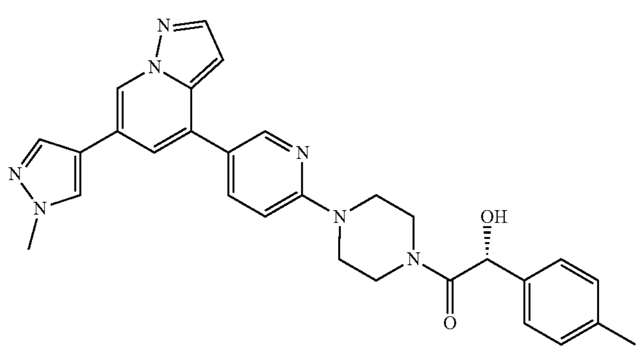 [SMILES: Cc1ccc([C@@H](O)C(=O)N2CCN(c3ccc(-c4cc(-c5cnn(C)c5)cn5nccc45)cn3)CC2)cc1] | (R)-2-hydroxy-1-(4-(5-(6-(1-methyl-1H-pyrazol-4-yl)pyrazolo[1,5-a]pyridin-4-yl)pyridin-2-yl)piperazin-1-yl)-2-(p-tolyl)ethanone | 508.1 (M + H) |
| 317 | 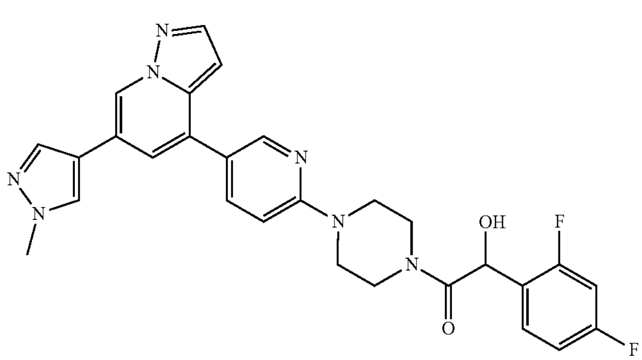 [SMILES: Cn1cc(-c2cc(-c3ccc(N4CCN(C(=O)C(O)c5ccc(F)cc5F)CC4)nc3)c3ccnn3c2)cn1] | 2-(2,4-difluorophenyl)-2-hydroxy-1-(4-(5-(6-(1-methyl-1H-pyrazol-4-yl)pyrazolo[1,5-a]pyridin-4-yl)pyridin-2-yl)piperazin-1-yl)ethanone | 530.1 (M + H) |

TABLE AA-continued

| Ex # | Structure | Chemical Name | MS (apci) m/z |
|---|---|---|---|
| 318 | 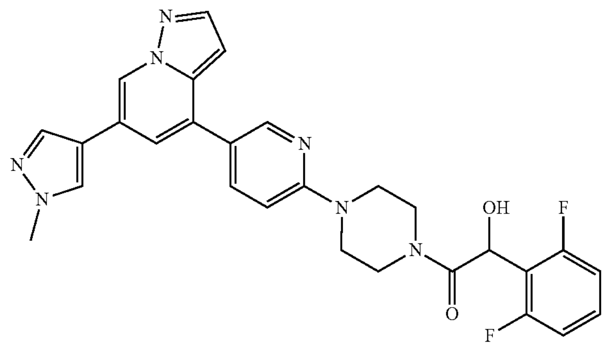 [SMILES: Cn1cc(-c2cc(-c3ccc(N4CCN(C(=O)C(O)c5c(F)cccc5F)CC4)nc3)c3ccnn3c2)cn1] | 2-(2,6-difluorophenyl)-2-hydroxy-1-(4-(5-(6-(1-methyl-1H-pyrazol-4-yl)pyrazolo[1,5-a]pyridin-4-yl)pyridin-2-yl)piperazin-1-yl)ethanone | 530.1 (M + H) |
| 319 | 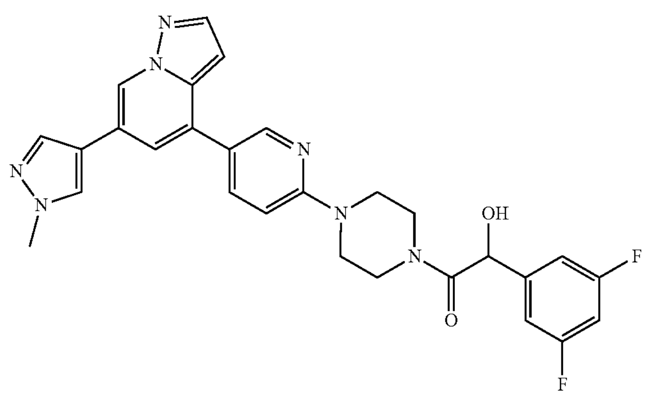 [SMILES: Cn1cc(-c2cc(-c3ccc(N4CCN(C(=O)C(O)c5cc(F)cc(F)c5)CC4)nc3)c3ccnn3c2)cn1] | 2-(3,5-difluorophenyl)-2-hydroxy-1-(4-(5-(6-(1-methyl-1H-pyrazol-4-yl)pyrazolo[1,5-a]pyridin-4-yl)pyridin-2-yl)piperazin-1-yl)ethanone | 530.1 (M + H) |

Example 320

(R)-2-(2-chlorophenyl)-2-hydroxy-1-(4-(5-(6-(1-methyl-1H-pyrazol-4-yl)pyrazolo[1,5-a]pyridin-4-yl)pyridin-2-yl)piperazin-1-yl)ethanone

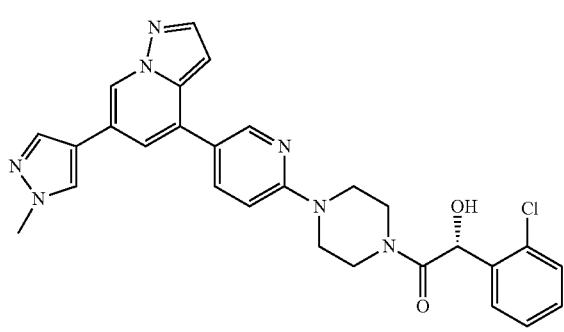 [SMILES: Cn1cc(-c2cc(-c3ccc(N4CCN(C(=O)[C@H](O)c5ccccc5Cl)CC4)nc3)c3ccnn3c2)cn1]

A solution of 6-(1-methyl-1H-pyrazol-4-yl)-4-(6-(piperazin-1-yl)pyridin-3-yl)pyrazolo[1,5-a]pyridine dihydrochloride (17.4 mg, 0.040 mmol) in DMF (1.2 mL) was treated with (R)-(−)-2-chloromandelic acid (9.0 mg, 0.048 mmol), HATU (18.4 mg, 0.048 mmol) and DIEA (70 μL, 0.40 mmol). The resulting reaction mixture was stirred at ambient temperature overnight and then diluted with EtOAc (10 mL). The reaction mixture was washed with water (2×10 mL) and brine (10 mL), and the combined organic extracts were dried over anhydrous $Na_2SO_4$, filtered, concentrated in vacuo and purified by silica chromatography (10-80% DCM/acetone) to afford the title compound (8.6 mg, 40% yield). MS (apci) m/z=528.1 (M+H).

The compounds in Table BB were prepared according the method described for the synthesis of Example 320, replacing D-(−)-Mandelic acid with the appropriate acid starting material.

TABLE BB

| Ex # | Structure | Chemical Name | MS (apci) m/z |
|---|---|---|---|
| 321 | 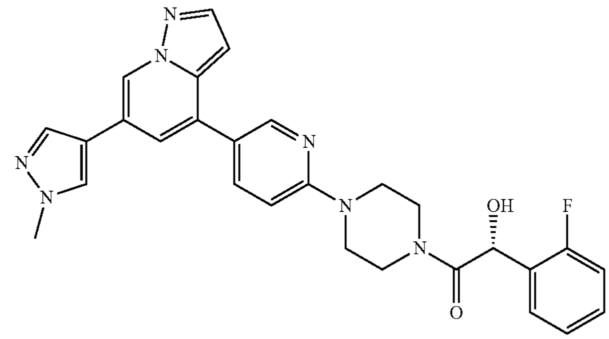 [SMILES: Cn1cc(-c2cc(-c3ccc(N4CCN(C(=O)[C@H](O)c5ccccc5F)CC4)nc3)c3ccnn3c2)cn1] | (R)-2-(2-fluorophenyl)-2-hydroxy-1-(4-(5-(6-(1-methyl-1H-pyrazol-4-yl)pyrazolo[1,5-a]pyridin-4-yl)pyridin-2-yl)piperazin-1-yl)ethanone | 512.2 (M + H) |
| 322 | 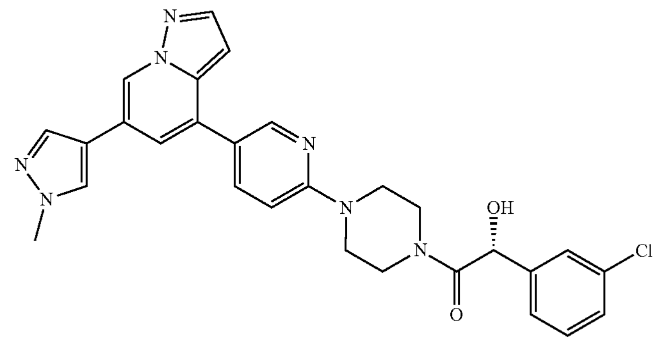 [SMILES: Cn1cc(-c2cc(-c3ccc(N4CCN(C(=O)[C@H](O)c5cccc(Cl)c5)CC4)nc3)c3ccnn3c2)cn1] | (R)-2-(3-chlorophenyl)-2-hydroxy-1-(4-(5-(6-(1-methyl-1H-pyrazol-4-yl)pyrazolo[1,5-a]pyridin-4-yl)pyridin-2-yl)piperazin-1-yl)ethanone | 528.1 (M + H) |

Example 323

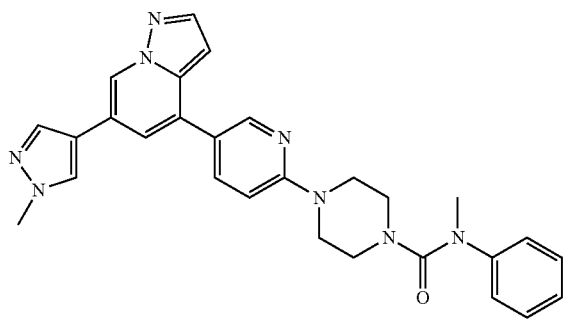 [SMILES: CN(C(=O)N1CCN(c2ccc(-c3cc(-c4cnn(C)c4)cn4nccc34)cn2)CC1)c1ccccc1]

N-methyl-4-(5-(6-(1-methyl-1H-pyrazol-4-yl)pyrazolo[1,5-a]pyridin-4-yl)pyridin-2-yl)-N-phenylpiperazine-1-carboxamide A suspension of 6-(1-methyl-1H-pyrazol-4-yl)-4-(6-(piperazin-1-yl)pyridin-3-yl)pyrazolo[1,5-a]pyridine dihydrochloride (50.4 mg, 0.117 mmol) and DIEA (122 µL, 0.699 mmol) in DriSolv® DCM (0.5 mL) was cooled to 0° C. and then added dropwise to a 0° C. solution of triphosgene (13.8 mg, 0.0466 mmol) in DriSolv® DCM (1.1 mL). After stirring the reaction mixture for 1 h at 0° C., N-methylaniline (13.9 µL, 0.128 mmol) was added in one portion, and the reaction was stirred at ambient temperature overnight. The reaction mixture was diluted with DCM and washed with saturated NaHCO$_{3(aq)}$. The combined organic extracts were dried (Na$_2$SO$_4$), filtered, concentrated and purified by silica chromatography (10-80% DCM/acetone) to afford the title compound (13.1 mg, 23% yield). MS (apci) m/z=493.1 (M+H).

Example 324

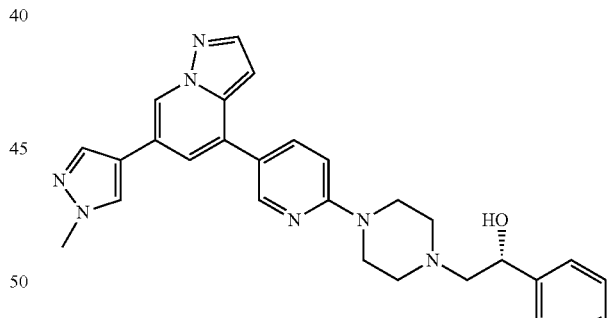

(R)-2-(4-(5-(6-(1-methyl-1H-pyrazol-4-yl)pyrazolo[1,5-a]pyridin-4-yl)pyridin-2-yl)piperazin-1-yl)-1-phenylethanol A mixture of 6-(1-methyl-1H-pyrazol-4-yl)-4-(6-(piperazin-1-yl)pyridin-3-yl)pyrazolo[1,5-a]pyridine (22.1 mg, 0.0615 mmol) and (R)-(+)-Styrene oxide (8.43 µL, 0.0738 mmol) in methanol (1.2 mL) was heated at 75° C. in a sealed tube overnight. The reaction mixture was subsequently cooled to ambient temperature and directly purified by silica chromatography (10-90% DCM/acetone) to afford the title compound (7.8 mg, 27% yield). MS (apci) m/z=480.1 (M+H).

Example 325

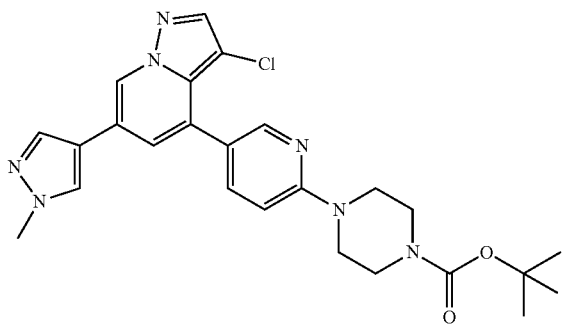 [SMILES: Cn1cc(-c2cc(-c3ccc(N4CCN(C(=O)OC(C)(C)C)CC4)nc3)c3c(Cl)cnn3c2)cn1]

Tert-Butyl 4-(5-(3-chloro-6-(1-methyl-1H-pyrazol-4-yl)pyrazolo[1,5-a]pyridin-4-yl)pyridin-2-yl)piperazine-1-carboxylate In a pressure tube, a solution of 3-chloro-6-(1-methyl-1H-pyrazol-4-yl)pyrazolo[1,5-a]pyridin-4-yl trifluoromethanesulfonate (Intermediate P8; 150 mg, 0.394 mmol) in dioxane (3 mL) was treated with tert-butyl 4-(5-(4,4,5,5-tetramethyl-1,3,2-dioxaborolan-2-yl)pyridin-2-yl)piperazine-1-carboxylate (230 mg, 0.591 mmol), 2 M $Na_2CO_{3(aq)}$ (985 µL, 1.97 mmol) and $Pd(PPh_3)_4$ (22.8 mg, 0.0197 mmol). The reaction mixture was purged with nitrogen, sealed and heated at 90° C. overnight. After cooling to ambient temperature, the reaction mixture was diluted with $H_2O$ (10 mL) and extracted with DCM (3×15 mL). The combined organic extracts were dried over anhydrous $MgSO_4$, vacuum filtered, and concentrated in vacuo. The crude residue was purified by silica chromatography (25-100% EtOAc/hexanes) to afford the title compound as a solid contaminated with triphenylphosphine oxide (131 mg). That solid mixture was suspended in MTBE (3 mL), sonicated then vacuum filtered to cleanly provide the title compound (75.7 mg, 39% yield). MS (apci) m/z=494.0 (M+H).

Example 326

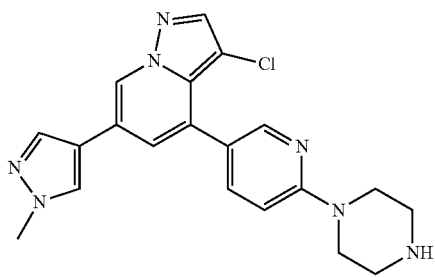

3-chloro-6-(1-methyl-1H-pyrazol-4-yl)-4-(6-(piperazin-1-yl)pyridin-3-yl)pyrazolo[1,5-a]pyridine Dihydrochloride Tert-butyl 4-(5-(3-chloro-6-(1-methyl-1H-pyrazol-4-yl)pyrazolo[1,5-a]pyridin-4-yl)pyridin-2-yl)piperazine-1-carboxylate (70 mg, 0.14 mmol) was suspended in EtOH (0.5 mL) and DCM (0.5 mL) and then treated with 5 M HCl in iPrOH (0.5 mL, 2.8 mmol). The reaction mixture was stirred at ambient temperature overnight. The resulting suspension was concentrated in vacuo. The solids were sonicated in $Et_2O$ and then dried in vacuo to cleanly afford the title compound (75 mg, quantitative yield). MS (apci) m/z=394.0 (M+H).

Example 327

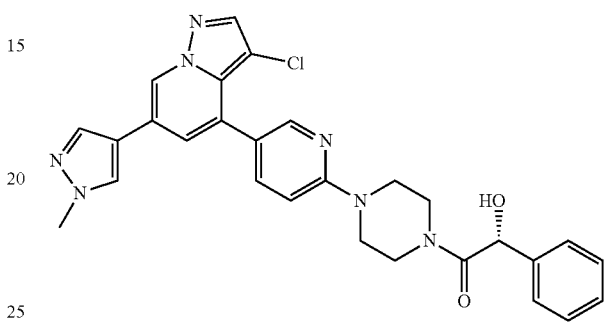

(R)-1-(4-(5-(3-chloro-6-(1-methyl-1H-pyrazol-4-yl)pyrazolo[1,5-a]pyridin-4-yl)pyridin-2-yl)piperazin-1-yl)-2-hydroxy-2-phenylethanone A solution of 3-chloro-6-(1-methyl-1H-pyrazol-4-yl)-4-(6-(piperazin-1-yl)pyridin-3-yl)pyrazolo[1,5-a]pyridine dihydrochloride (8.0 mg, 0.017 mmol) in DCM (0.5 mL) was treated with D-(-)-Mandelic acid (3.13 mg, 0.0206 mmol), HATU (7.82 mg, 0.0206 mmol) and DIEA (29.85 µL, 0.1714 mmol). The resulting reaction mixture was stirred at ambient temperature overnight and then directly purified by silica chromatography (5-60% DCM/acetone) to afford the title compound (3.9 mg, 43% yield). MS (apci) m/z=528.1 (M+H).

Example 328

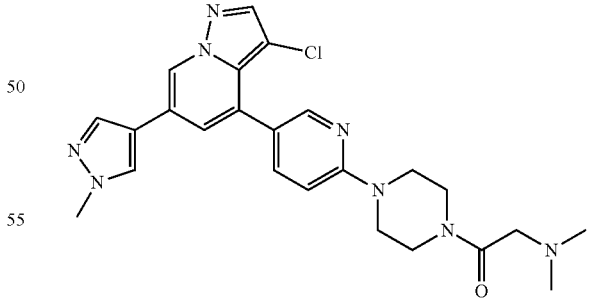

1-(4-(5-(3-chloro-6-(1-methyl-1H-pyrazol-4-yl)pyrazolo[1,5-a]pyridin-4-yl)pyridin-2-yl)piperazin-1-yl)-2-(dimethylamino)ethanone A solution of 3-chloro-6-(1-methyl-1H-pyrazol-4-yl)-4-(6-(piperazin-1-yl)pyridin-3-yl)pyrazolo[1,5-a]pyridine dihydrochloride (10 mg, 0.021 mmol) and 2-(dimethylamino)acetyl chloride hydrochloride (5.1 mg, 0.032 mmol) in DCM (0.4 mL) was treated with DIEA (22 µL, 0.13 mmol) and the reaction mixture was stirred at ambient temperature overnight. The reaction was quenched with the addition of MeOH (0.2 mL), partially concentrated in vacuo and then purified by reverse phase chromatography (5-75% ACN/water) to afford the title compound (6.2 mg, 60% yield). MS (apci) m/z=479.0 (M+H).

Example 329

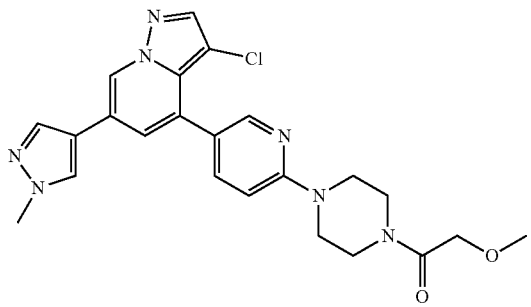 [SMILES: COCC(=O)N1CCN(c2ccc(-c3cc(-c4cnn(C)c4)cn4ncc(Cl)c34)cn2)CC1]

1-(4-(5-(3-chloro-6-(1-methyl-1H-pyrazol-4-yl)pyrazolo[1,5-a]pyridin-4-yl)pyridin-2-yl)piperazin-1-yl)-2-methoxyethanone A solution of 3-chloro-6-(1-methyl-1H-pyrazol-4-yl)-4-(6-(piperazin-1-yl)pyridin-3-yl)pyrazolo[1,5-a]pyridine dihydrochloride (10 mg, 0.021 mmol) in DCM (0.4 mL) was treated with a 10 M solution of 2-methoxyacetyl chloride in DCM (2.9 µL, 0.032 mmol) and DIEA (19 µL, 0.11 mmol) and the reaction mixture was stirred at ambient temperature overnight. The reaction was quenched with the addition of MeOH (0.2 mL). The resulting suspension was sonicated and vacuum filtered, rinsing the solids collected with $Et_2O$ (2×1 mL), to afford the title compound (7.2 mg, 72% yield). MS (apci) m/z=466.0 (M+H).

The compounds in Table CC were prepared and purified according the method described for the synthesis of Example 329, replacing 2-methoxyacetyl chloride for the appropriate acid chloride starting material. Sonication was performed using either MeOH or $Et_2O$.

TABLE CC

| Ex # | Structure | Chemical Name | MS (apci) m/z |
|---|---|---|---|
| 330 | 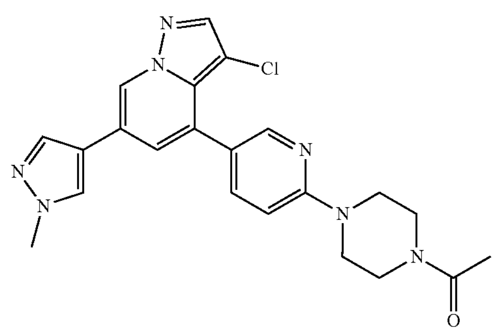 [SMILES: CC(=O)N1CCN(c2ccc(-c3cc(-c4cnn(C)c4)cn4ncc(Cl)c34)cn2)CC1] | 1-(4-(5-(3-chloro-6-(1-methyl-1H-pyrazol-4-yl)pyrazolo[1,5-a]pyridin-4-yl)pyridin-2-yl)piperazin-1-yl)ethanone | 436.1 (M + H) |
| 331 | 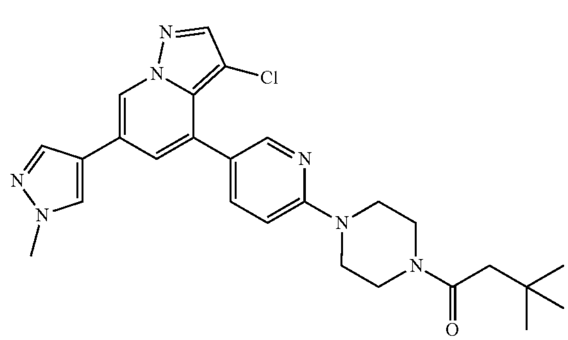 [SMILES: Cn1cc(-c2cc(-c3ccc(N4CCN(C(=O)CC(C)(C)C)CC4)nc3)c3c(Cl)cnn3c2)cn1] | 1-(4-(5-(3-chloro-6-(1-methyl-1H-pyrazol-4-yl)pyrazolo[1,5-a]pyridin-4-yl)pyridin-2-yl)piperazin-1-yl)-3,3-dimethylbutan-1-one | 492.1 (M + H) |

Example 332

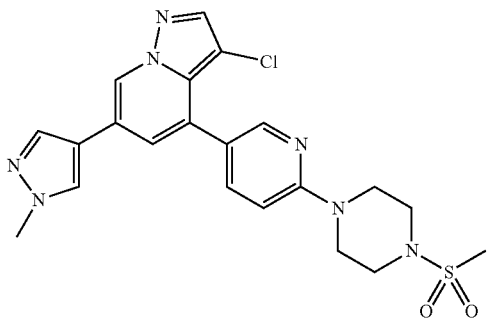 [SMILES: Cn1cc(-c2cc(-c3ccc(N4CCN(S(C)(=O)=O)CC4)nc3)c3c(Cl)cnn3c2)cn1]

3-chloro-6-(1-methyl-1H-pyrazol-4-yl)-4-(6-(4-(methylsulfonyl)piperazin-1-yl)pyridin-3-yl)pyrazolo[1,5-a]pyridine A solution of 3-chloro-6-(1-methyl-1H-pyrazol-4-yl)-4-(6-(piperazin-1-yl)pyridin-3-yl)pyrazolo[1,5-a]pyridine hydrochloride (8.9 mg, 0.021 mmol) in DCM (1 mL) was treated pyridine (8.4 µL, 0.10 mmol) and methanesulfonic anhydride (4.3 mg, 0.025 mmol) and the reaction mixture was stirred at ambient temperature for 6 d. Additional pyridine (0.1 mL, 1.19 mmol) and methanesulfonic anhydride (20 mg, 0.115 mmol) were added and the reaction mixture was stirred for an additional 18 h. The crude reaction mixture was purified by silica chromatography (25-100% EtOAc/hexanes) to cleanly provide the title compound (1.5 mg, 15% yield). MS (apci) m/z=472.0 (M+H).

Example 333

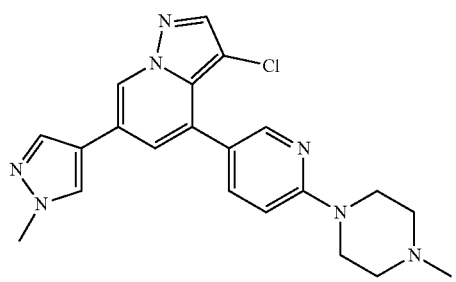

3-chloro-6-(1-methyl-1H-pyrazol-4-yl)-4-(6-(4-methylpiperazin-1-yl)pyridin-3-yl)pyrazolo[1,5-a]pyridine In a pressure tube, a solution of 3-chloro-6-(1-methyl-1H-pyrazol-4-yl)pyrazolo[1,5-a]pyridin-4-yl trifluoromethanesulfonate (Intermediate P8; 15 mg, 0.039 mmol) in dioxane (0.5 mL) was treated with (6-(4-methylpiperazin-1-yl)pyridin-3-yl)boronic acid (13 mg, 0.059 mmol), 2 M Na$_2$CO$_{3(aq)}$ (98 µL, 0.20 mmol) and Pd(PPh$_3$)$_4$ (2.3 mg, 0.0020 mmol). The reaction mixture was purged with nitrogen, sealed and then heated at 90° C. overnight. After cooling to ambient temperature, the reaction mixture was diluted with water (25 mL) and extracted with DCM (25 mL) and then with a 5:95 solution of MeOH/DCM (2×25 mL). The combined organic extracts were dried over anhydrous MgSO$_4$, vacuum filtered, and concentrated in vacuo. The crude residue was purified directly by reverse phase chromatography (5-60% ACN/water) to afford the title compound as a solid contaminated with triphenylphosphine oxide (9.0 mg). That material was purified by preparative thin layer silica chromatography (10:90 0.2 M NH$_3$ in MeOH:DCM). The lower band was isolated, suspended in 10:90 MeOH/DCM with NH$_4$OH, and then filtered. The filtrate was concentrated in vacuo to cleanly provide the title compound (7.1 mg, 44% yield). MS (apci) m/z=408.1 (M+H).

Example 333a

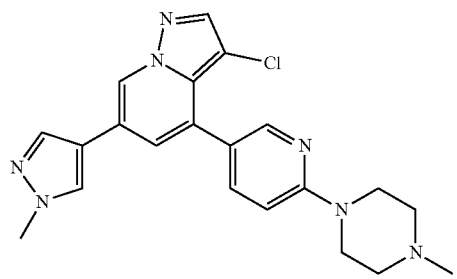 [SMILES: CN1CCN(c2ccc(-c3cc(-c4cnn(C)c4)cn4ncc(Cl)c34)cn2)CC1]

2 HCl 3-chloro-6-(1-methyl-1H-pyrazol-4-yl)-4-(6-(4-methylpiperazin-1-yl)pyridin-3-yl)pyrazolo[1,5-a]pyridine Dihydrochloride In a pressure tube a solution of 3-chloro-6-(1-methyl-1H-pyrazol-4-yl)pyrazolo[1,5-a]pyridin-4-yl trifluoromethanesulfonate (Intermediate P8; 95 mg, 0.250 mmol) in dioxane (3 mL) was treated with (6-(4-methylpiperazin-1-yl)pyridin-3-yl)boronic acid (82.7 mg, 0.374 mmol), 2 M Na$_2$CO$_{3(aq)}$ (624 µL, 1.25 mmol) and Pd(PPh$_3$)$_4$ (14.4 mg, 0.0125 mmol). The reaction mixture was purged with nitrogen, sealed and then heated at 90° C. overnight. After cooling to ambient temperature, the reaction mixture was diluted with water (25 mL) and extracted with a 10:90 solution of MeOH/DCM (3×25 mL). The combined organic extracts were dried over anhydrous MgSO$_4$, filtered and concentrated in vacuo. The crude residue was purified by reverse phase chromatography (5-60% ACN/water with 0.1 N HCl). The product was triturated in Et$_2$O (5 mL) and then filtered. The isolated solids were rinsed with Et$_2$O (3 mL) and dried in vacuo to afford the title compound (69.3 mg, 58% yield). MS (apci) m/z=408.0 (M+H).

Example 334

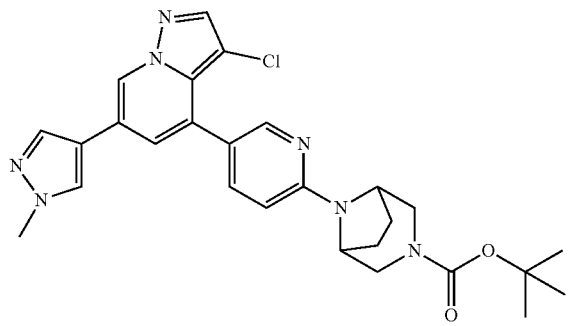 [SMILES: Cn1cc(-c2cc(-c3ccc(N4C5CCC4CN(C(=O)OC(C)(C)C)C5)nc3)c3c(Cl)cnn3c2)cn1]

Tert-Butyl 8-(5-(3-chloro-6-(1-methyl-1H-pyrazol-4-yl)pyrazolo[1,5-a]pyridin-4-yl)pyridin-2-yl)-3,8-diazabicyclo[3.2.1]octane-3-carboxylate In a pressure tube a solution of 3-chloro-4-(6-fluoropyridin-3-yl)-6-(1-methyl-1H-pyrazol-4-yl)pyrazolo[1,5-a]pyridine (Intermediate P9; 8 mg, 0.024 mmol) and tert-butyl 3,8-diazabicyclo[3.2.1]octane-8-carboxylate hydrochloride (52 mg, 0.24 mmol) in DMSO (3 mL) was heated at 150° C. for 2 d. The reaction mixture was cooled to ambient temperature and then directly purified by reverse phase chromatography (5-95% ACN/water) to afford the title compound (8.0 mg, 63% yield). MS (apci) m/z=520.2 (M+H).

Example 335

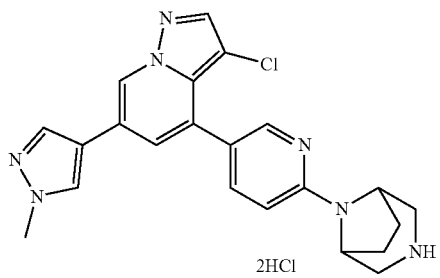 [SMILES: Cn1cc(-c2cc(-c3ccc(N4C5CCC4CNC5)nc3)c3c(Cl)cnn3c2)cn1]

4-(6-(3,8-diazabicyclo[3.2.1]octan-8-yl)pyridin-3-yl)-3-chloro-6-(1-methyl-1H-pyrazol-4-yl)pyrazolo[1,5-a]pyridine Dihydrochloride A mixture of t-Butyl 8-(5-(3-chloro-6-(1-methyl-1H-pyrazol-4-yl)pyrazolo[1,5-a]pyridin-4-yl)pyridin-2-yl)-3,8-diazabicyclo[3.2.1]octane-3-carboxylate (Example 334, 7.3 mg, 0.0140 mmol) in 5 M HCl in iPrOH (562 µL, 2.81 mmol) was stirred at ambient temperature for 1 h and then concentrated in vacuo to afford the title compound (6.2 mg, 90% yield). MS (apci) m/z=420.1 (M+H).

Example 336

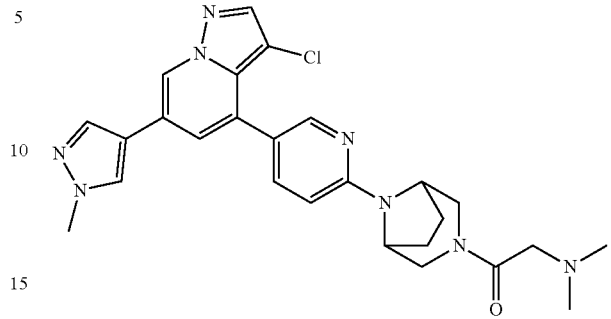

1-(8-(5-(3-chloro-6-(1-methyl-1H-pyrazol-4-yl)pyrazolo[1,5-a]pyridin-4-yl)pyridin-2-yl)-3,8-diazabicyclo[3.2.1]octan-3-yl)-2-(dimethylamino)ethanone A solution of 4-(6-(3,8-diazabicyclo[3.2.1]octan-8-yl)pyridin-3-yl)-3-chloro-6-(1-methyl-1H-pyrazol-4-yl)pyrazolo[1,5-a]pyridine dihydrochloride (5 mg, 0.010 mmol) and 2-(dimethylamino)acetyl chloride hydrochloride (2.4 mg, 0.015 mmol) in DCM (0.4 mL) was treated with DIEA (11 µL, 0.061 mmol) and the resulting solution was stirred at ambient temperature overnight. The reaction was quenched with the addition of MeOH (0.2 mL), concentrated in vacuo and purified by reverse phase chromatography (5-75% ACN/water) to afford the title compound (2.1 mg, 12% yield). MS (apci) m/z=505.1 (M+H).

Example 337

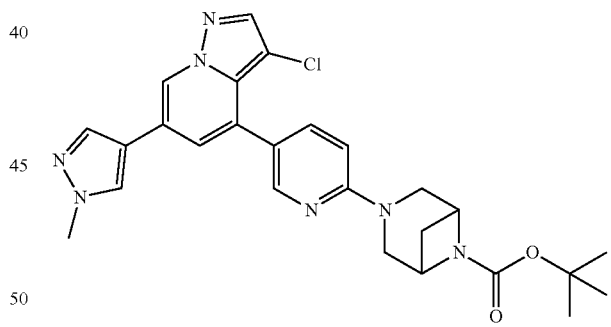

Tert-Butyl 3-(5-(3-chloro-6-(1-methyl-1H-pyrazol-4-yl)pyrazolo[1,5-a]pyridin-4-yl)pyridin-2-yl)-3,6-diazabicyclo[3.1.1]heptane-6-carboxylate In a microwave vial a solution of 3-chloro-4-(6-fluoropyridin-3-yl)-6-(1-methyl-1H-pyrazol-4-yl)pyrazolo[1,5-a]pyridine (Intermediate P9; 5 mg, 0.015 mmol) and tert-butyl 3,6-diazabicyclo[3.1.1]heptane-6-carboxylate (9.1 mg, 0.046 mmol) in DMSO (0.2 mL) was subjected to microwave irradiation at 130° C. for 5 h and then at 150° C. for 6 h. The reaction mixture was cooled to ambient temperature and then directly purified by reverse phase chromatography (5-95% ACN/water) to afford the title compound (2.6 mg, 34% yield). $^1$H NMR (CDCl$_3$) δ 8.51 (d, 1H), 8.34 (d, 1H), 7.88 (s, 1H), 7.76 (s, 1H), 7.65 (m, 2H), 7.12 (d, 1H), 6.62 (d, 1H), 4.33 (m, 2H), 4.20 (m, 2H), 3.98 (s, 3H), 3.55 (m, 2H), 1.45 (d, 2H), 1.38 (s, 9H).

Example 338

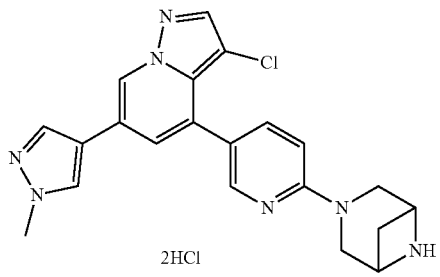 [SMILES: Cn1cc(-c2cc(-c3ccc(N4CC5CC(C4)N5)nc3)c3c(Cl)cnn3c2)cn1]

3-(5-(3-chloro-6-(1-methyl-1H-pyrazol-4-yl)pyrazolo[1,5-a]pyridin-4-yl)pyridin-2-yl)-3,6-diazabicyclo[3.1.1]heptane Dihydrochloride A mixture of t-Butyl 3-(5-(3-chloro-6-(1-methyl-1H-pyrazol-4-yl)pyrazolo[1,5-a]pyridin-4-yl)pyridin-2-yl)-3,6-diazabicyclo[3.1.1]heptane-6-carboxylate (Example 337, 1.24 mg, 0.00245 mmol) in 5 M HCl in iPrOH (98.0 µL, 0.490 mmol) was stirred at ambient temperature for 1 h and then concentrated in vacuo to afford the title compound (0.98 mg, 84% yield). MS (apci) m/z=406.0 (M+H).

Example 339

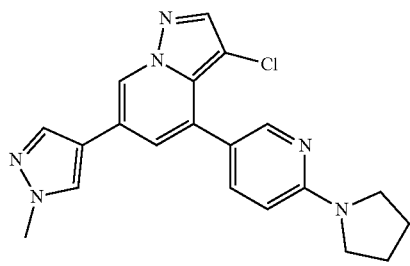 [SMILES: Cn1cc(-c2cc(-c3ccc(N4CCCC4)nc3)c3c(Cl)cnn3c2)cn1]

3-chloro-6-(1-methyl-1H-pyrazol-4-yl)-4-(6-(pyrrolidin-1-yl)pyridin-3-yl)pyrazolo[1,5-a]pyridine In a pressure tube a solution of 3-chloro-4-(6-fluoropyridin-3-yl)-6-(1-methyl-1H-pyrazol-4-yl)pyrazolo[1,5-a]pyridine (Intermediate P9; 16 mg, 0.0488 mmol) and pyrrolidine (40.8 µL, 0.488 mmol) in DMA (0.5 mL) was heated at 110° C. overnight. The reaction mixture was cooled to ambient temperature and then directly purified by reverse phase chromatography (5-95% ACN/water containing 0.1% TFA) to afford the title compound as a TFA salt (27 mg) which was subsequently dissolved in MeOH and filtered through a basic resin (Stratospheres SPE HCO3-MP resin, 100 mg, 0.18 mmol/g). The filtrate was concentrated in vacuo to afford the title compound (13.3 mg, 72% yield). MS (apci) m/z=379.0 (M+H).

Example 340

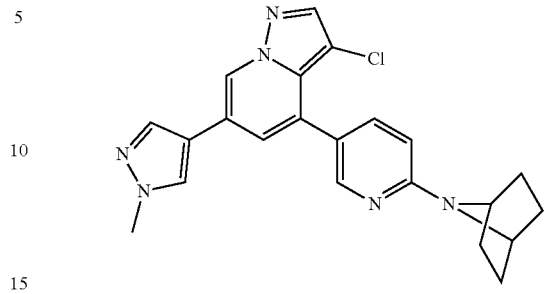

4-(6-(7-azabicyclo[2.2.1]heptan-7-yl)pyridin-3-yl)-3-chloro-6-(1-methyl-1H-pyrazol-4-yl)pyrazolo[1,5-a]pyridine In a pressure tube a solution of 3-chloro-4-(6-fluoropyridin-3-yl)-6-(1-methyl-1H-pyrazol-4-yl)pyrazolo[1,5-a]pyridine (Intermediate P9; 10 mg, 0.031 mmol) and 7-azabicyclo[2.2.1]heptane hydrochloride (12 mg, 0.092 mmol) in DMA (0.3 mL) was heated at 110° C. overnight. Additional 7-azabicyclo[2.2.1]heptane hydrochloride (12 mg, 0.092 mmol) was added along with DIEA (18 µL, 0.15 mmol). The reaction mixture was heated at 110° C. for 7 d and then cooled to ambient temperature. The reaction mixture was diluted with EtOAc (25 mL) and washed with brine (2×25 mL). The combined organic extracts were dried over anhydrous MgSO4, filtered, concentrated and purified by reverse phase chromatography (5-95% ACN/water) to afford the title compound (10 mg, 37% yield). MS (apci) m/z=405.0 (M+H).

Example 341

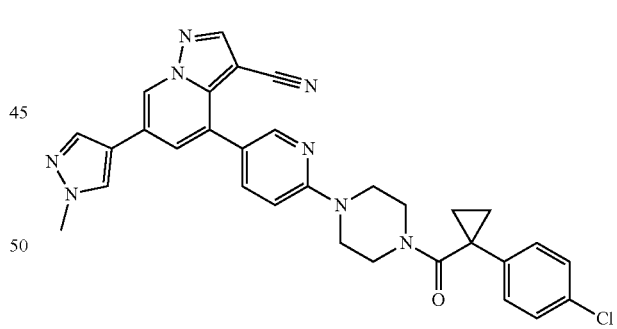

4-(6-(4-(1-(4-chlorophenyl)cyclopropanecarbonyl)piperazin-1-yl)pyridin-3-yl)-6-(1-methyl-1H-pyrazol-4-yl)pyrazolo[1,5-a]pyridine-3-carbonitrile 1-(4-chlorophenyl)cyclopropanecarboxylic acid (12.9 mg, 0.0656 mmol) and HATU (24.9 mg, 0.0656 mmol) were dissolved in DMA (273 µL) at room temperature. After 25 min, 6-(1-methyl-1H-pyrazol-4-yl)-4-(6-(piperazin-1-yl)pyridine-3-yl)pyrazolo[1,5-a]pyridine-3-carbonitrile dihydrochloride (Example 2; 25 mg, 0.0547 mmol) and DIEA (47.6 µL, 0.273 mmol) were added sequentially. The reaction mixture was stirred 18 h at room temperature and then directly purified by C18 reverse phase chromatography (5-85% ACN/water as the gradient eluent) to provide the title compound (22.6 mg, 71% yield). MS (apci) m/z=563.3 (M+H).

The compounds in the Table FF were prepared according to the method described for Example 341, replacing 1-(4-chlorophenyl)cyclopropanecarboxylic acid with the appropriate carboxylic acid starting material. Reaction progression in each was followed by LCMS, and reaction times were adjusted as necessary. Products were purified as in Example 341 (except where noted), utilizing the appropriate gradient eluent in chromatography to cleanly afford the title compounds.

TABLE FF

| Ex # | Structure | Chemical Name | MS (apci) m/z |
|---|---|---|---|
| 342* | 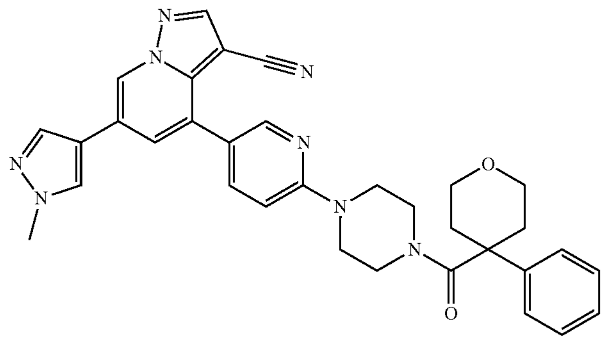 [SMILES: Cn1cc(-c2cc(-c3ccc(N4CCN(C(=O)C5(c6ccccc6)CCOCC5)CC4)nc3)c3c(C#N)cnn3c2)cn1] | 6-(1-methyl-1H-pyrazol-4-yl)-4-(6-(4-(4-phenyltetrahydro-2H-pyran-4-carbonyl)piperazin-1-yl)pyridin-3-yl)pyrazolo[1,5-a]pyridine-3-carbonitrile | 573.3 (M + H) |
| 343 | 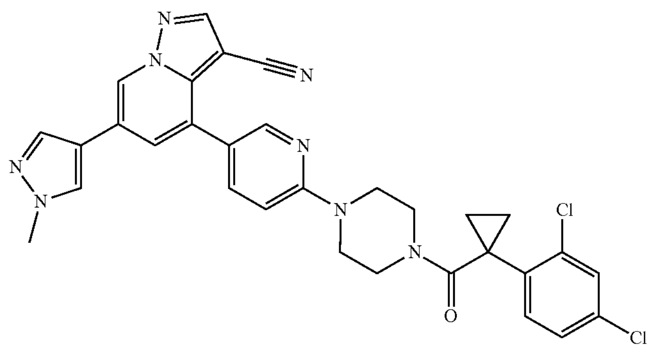 [SMILES: Cn1cc(-c2cc(-c3ccc(N4CCN(C(=O)C5(c6ccc(Cl)cc6Cl)CC5)CC4)nc3)c3c(C#N)cnn3c2)cn1] | 4-(6-(4-(1-(2,4-dichlorophenyl)cyclopropanecarbonyl)piperazin-1-yl)pyridin-3-yl)-6-(1-methyl-1H-pyrazol-4-yl)pyrazolo[1,5-a]pyridine-3-carbonitrile | 597.1 (M + H) |
| 344 | 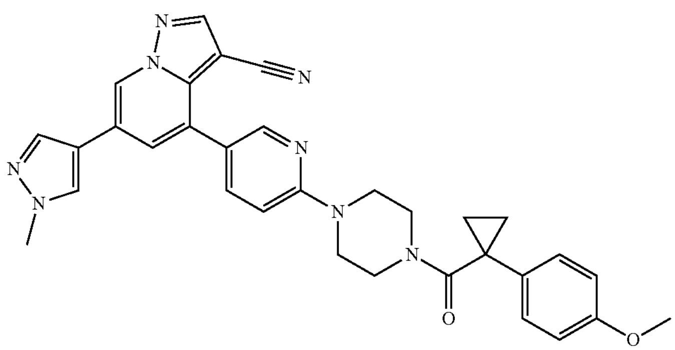 [SMILES: COc1ccc(C2(C(=O)N3CCN(c4ccc(-c5cc(-c6cnn(C)c6)cn6ncc(C#N)c56)cn4)CC3)CC2)cc1] | 4-(6-(4-(1-(4-methoxyphenyl)cyclopropanecarbonyl)piperazin-1-yl)pyridin-3-yl)-6-(1-methyl-1H-pyrazol-4-yl)pyrazolo[1,5-a]pyridine-3-carbonitrile | 559.2 (M + H) |
| 345 | 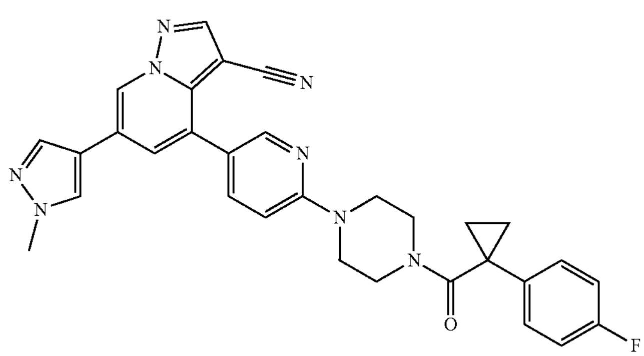 [SMILES: Cn1cc(-c2cc(-c3ccc(N4CCN(C(=O)C5(c6ccc(F)cc6)CC5)CC4)nc3)c3c(C#N)cnn3c2)cn1] | 4-(6-(4-(1-(4-fluorophenyl)cyclopropanecarbonyl)piperazin-1-yl)pyridin-3-yl)-6-(1-methyl-1H-pyrazol-4-yl)pyrazolo[1,5-a]pyridine-3-carbonitrile | 547.2 (M + H) |

TABLE FF-continued

| Ex # | Structure | Chemical Name | MS (apci) m/z |
|---|---|---|---|
| 346 | 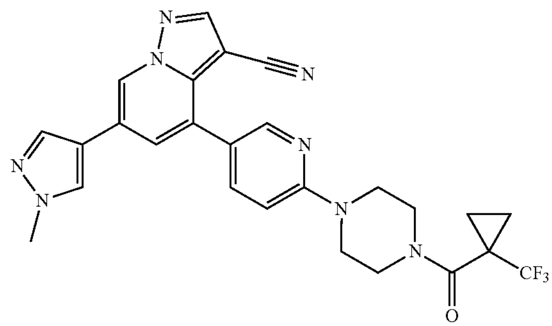 [SMILES: Cn1cc(-c2cc(-c3ccc(N4CCN(C(=O)C5(C(F)(F)F)CC5)CC4)nc3)c3c(C#N)cnn3c2)cn1] | 6-(1-methyl-1H-pyrazol-4-yl)-4-(6-(4-(1-(trifluoromethyl)cyclopropanecarbonyl)piperazin-1-yl)pyridin-3-yl)pyrazolo[1,5-a]pyridine-3-carbonitrile | 521.3 (M + H) |
| 347 | 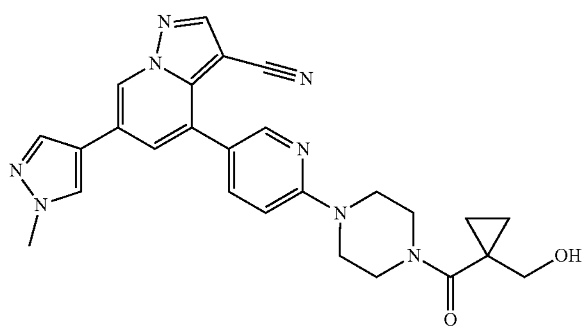 [SMILES: Cn1cc(-c2cc(-c3ccc(N4CCN(C(=O)C5(CO)CC5)CC4)nc3)c3c(C#N)cnn3c2)cn1] | 4-(6-(4-(1-(hydroxymethyl)cyclopropanecarbonyl)piperazin-1-yl)pyridin-3-yl)-6-(1-methyl-1H-pyrazol-4-yl)pyrazolo[1,5-a]pyridine-3-carbonitrile | 483.3 (M + H) |
| 348 | 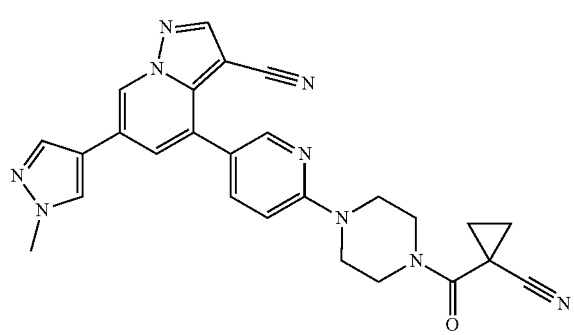 [SMILES: Cn1cc(-c2cc(-c3ccc(N4CCN(C(=O)C5(C#N)CC5)CC4)nc3)c3c(C#N)cnn3c2)cn1] | 4-(6-(4-(1-cyanocyclopropanecarbonyl)piperazin-1-yl)pyridin-3-yl)-6-(1-methyl-1H-pyrazol-4-yl)pyrazolo[1,5-a]pyridine-3-carbonitrile | 478.3 (M + H) |
| 349 | 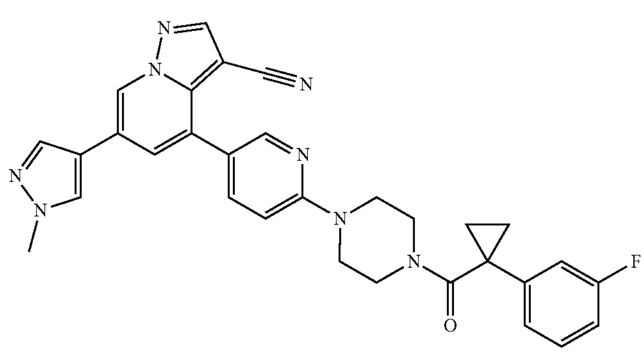 [SMILES: Cn1cc(-c2cc(-c3ccc(N4CCN(C(=O)C5(c6cccc(F)c6)CC5)CC4)nc3)c3c(C#N)cnn3c2)cn1] | 4-(6-(4-(1-(3-fluorophenyl)cyclopropanecarbonyl)piperazin-1-yl)pyridin-3-yl)-6-(1-methyl-1H-pyrazol-4-yl)pyrazolo[1,5-a]pyridine-3-carbonitrile | 547.2 (M + H) |

TABLE FF-continued

| Ex # | Structure | Chemical Name | MS (apci) m/z |
|---|---|---|---|
| 350 | 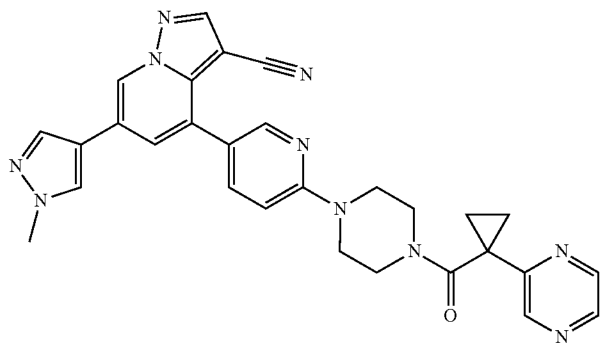 [SMILES: Cn1cc(-c2cc(-c3ccc(N4CCN(C(=O)C5(c6cnccn6)CC5)CC4)nc3)c3c(C#N)cnn3c2)cn1] | 6-(1-methyl-1H-pyrazol-4-yl)-4-(6-(4-(1-(pyrazin-2-yl)cyclopropanecarbonyl)piperazin-1-yl)pyridin-3-yl)pyrazolo[1,5-a]pyridine-3-carbonitrile | 531.2 (M + H) |
| 351 | 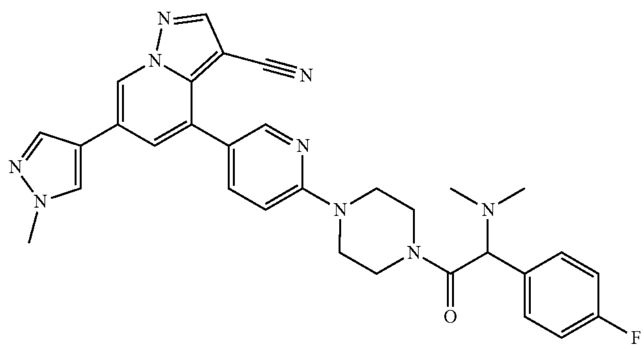 [SMILES: CN(C)C(C(=O)N1CCN(c2ccc(-c3cc(-c4cnn(C)c4)cn4ncc(C#N)c34)cn2)CC1)c1ccc(F)cc1] | 4-(6-(4-(2-(dimethylamino)-2-(4-fluorophenyl)acetyl)piperazin-1-yl)pyridin-3-yl)-6-(1-methyl-1H-pyrazol-4-yl)pyrazolo[1,5-a]pyridine-3-carbonitrile | 564.2 (M + H) |
| 352 | 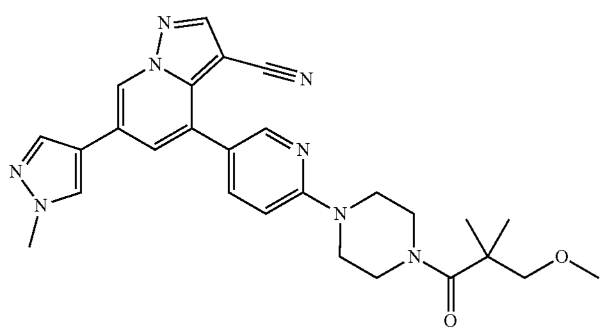 [SMILES: COCC(C)(C)C(=O)N1CCN(c2ccc(-c3cc(-c4cnn(C)c4)cn4ncc(C#N)c34)cn2)CC1] | 4-(6-(4-(3-methoxy-2,2-dimethylpropanoyl)piperazin-1-yl)pyridin-3-yl)-6-(1-methyl-1H-pyrazol-4-yl)pyrazolo[1,5-a]pyridine-3-carbonitrile | 499.2 (M + H) |
| 353 | 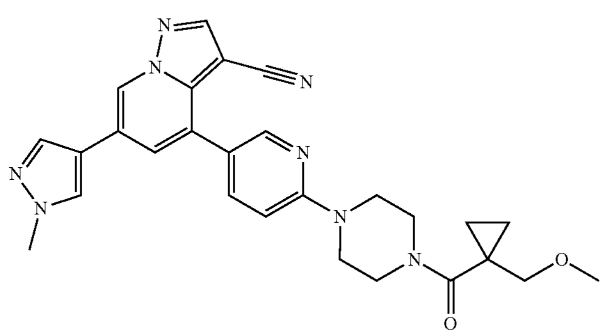 [SMILES: COCC1(C(=O)N2CCN(c3ccc(-c4cc(-c5cnn(C)c5)cn5ncc(C#N)c45)cn3)CC2)CC1] | 4-(6-(4-(1-(methoxymethyl)cyclopropanecarbonyl)piperazin-1-yl)pyridin-3-yl)-6-(1-methyl-1H-pyrazol-4-yl)pyrazolo[1,5-a]pyridine-3-carbonitrile | 497.2 (M + H) |

TABLE FF-continued

| Ex # | Structure | Chemical Name | MS (apci) m/z |
|---|---|---|---|
| 354 | 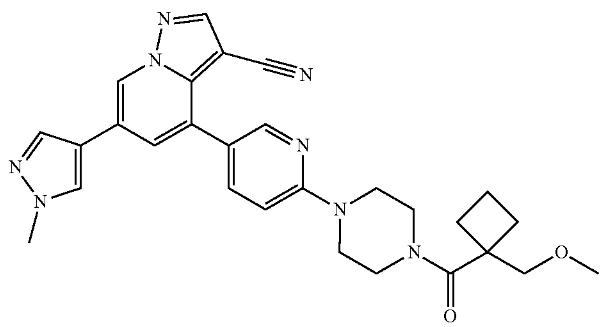 [SMILES: COCC1(C(=O)N2CCN(c3ccc(-c4cc(-c5cnn(C)c5)cn5ncc(C#N)c45)cn3)CC2)CCC1] | 4-(6-(4-(1-(methoxymethyl)cyclobutanecarbonyl)piperazin-1-yl)pyridin-3-yl)-6-(1-methyl-1H-pyrazol-4-yl)pyrazolo[1,5-a]pyridine-3-carbonitrile | 511.2 (M + H) |

*Example 342: Instead of directly chromatographing the reaction mixture, it was triturated with EtOAc and the title compound was isolated by filtration, rinsing solids with EtOAc and Et₂O and drying in vacuo.

The compounds in Table GG were prepared according the method described for the synthesis of Example 33, replacing 3-(dimethylamino)propanoic acid with the appropriate carboxylic acid starting material. Reactions were monitored by LCMS, and reaction times were adjusted as necessary. Products were purified by reverse-phase preparative HPLC utilizing an appropriate gradient eluent with 0.1 v/v % TFA to cleanly afford the title compounds as TFA salts.

TABLE GG

| Ex # | Structure | Chemical Name | MS (apci) m/z |
|---|---|---|---|
| 355 | 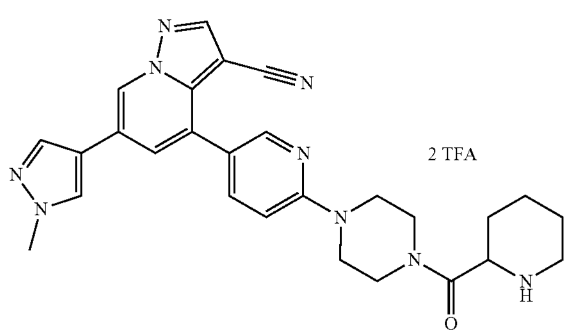 [SMILES: Cn1cc(-c2cc(-c3ccc(N4CCN(C(=O)C5CCCCN5)CC4)nc3)c3c(C#N)cnn3c2)cn1 ; "2 TFA"] | 6-(1-methyl-1H-pyrazol-4-yl)-4-(6-(4-(piperidine-2-carbonyl)piperazin-1-yl)pyridin-3-yl)pyrazolo[1,5-a]pyridine-3-carbonitrile bis(2,2,2-trifluoroacetate) | 496.2 (M + H) |
| 356 | 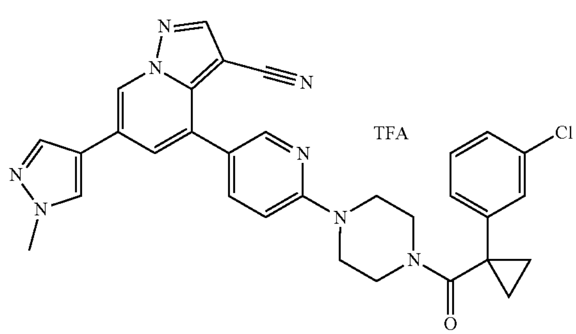 [SMILES: Cn1cc(-c2cc(-c3ccc(N4CCN(C(=O)C5(c6cccc(Cl)c6)CC5)CC4)nc3)c3c(C#N)cnn3c2)cn1 ; "TFA"] | 4-(6-(4-(1-(3-chlorophenyl)cyclopropane-1-carbonyl)piperazin-1-yl)pyridin-3-yl)-6-(1-methyl-1H-pyrazol-4-yl)pyrazolo[1,5-a]pyridine-3-carbonitrile 2,2,2-trifluoroacetate | 563.1 (M + H) |

TABLE GG-continued

| Ex # | Structure | Chemical Name | MS (apci) m/z |
|---|---|---|---|
| 357 | 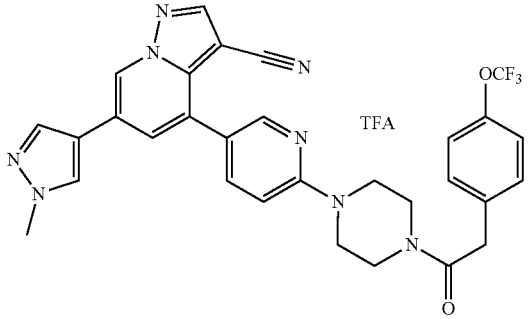 [SMILES: Cn1cc(-c2cc(-c3ccc(N4CCN(C(=O)Cc5ccc(OC(F)(F)F)cc5)CC4)nc3)c3c(C#N)cnn3c2)cn1 ; "TFA"] | 6-(1-methyl-1H-pyrazol-4-yl)-4-(6-(4-(2-(4-(trifluoromethoxy)phenyl)acetyl)piperazin-1-yl)pyridin-3-yl)pyrazolo[1,5-a]pyridine-3-carbonitrile 2,2,2-trifluoroacetate | 587.2 (M + H) |
| 358 | 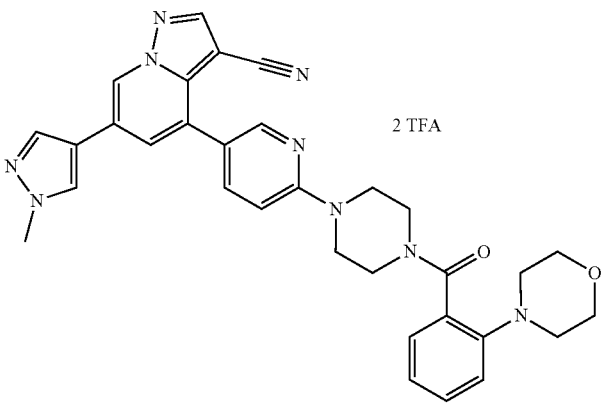 [SMILES: Cn1cc(-c2cc(-c3ccc(N4CCN(C(=O)c5ccccc5N5CCOCC5)CC4)nc3)c3c(C#N)cnn3c2)cn1 ; "2 TFA"] | 6-(1-methyl-1H-pyrazol-4-yl)-4-(6-(4-(2-morpholinobenzoyl)piperazin-1-yl)pyridin-3-yl)pyrazolo[1,5-a]pyridine-3-carbonitrile bis(2,2,2-trifluoroacetate) | 574.2 (M + H) |
| 359 | 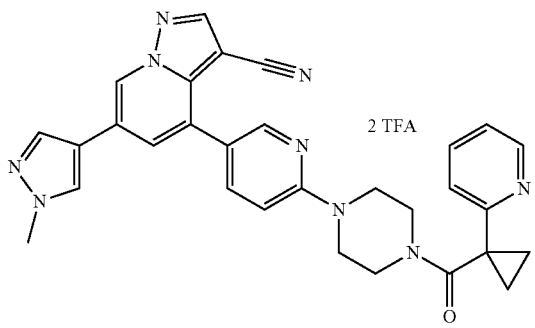 [SMILES: Cn1cc(-c2cc(-c3ccc(N4CCN(C(=O)C5(c6ccccn6)CC5)CC4)nc3)c3c(C#N)cnn3c2)cn1 ; "2 TFA"] | 6-(1-methyl-1H-pyrazol-4-yl)-4-(6-(4-(1-(pyridine-2-yl)cyclopropane-1-carbonyl)piperazin-1-yl)pyridin-3-yl)pyrazolo[1,5-a]pyridine-3-carbonitrile bis(2,2,2-trifluoroacetate) | 530.2 (M + H) |
| 360 | 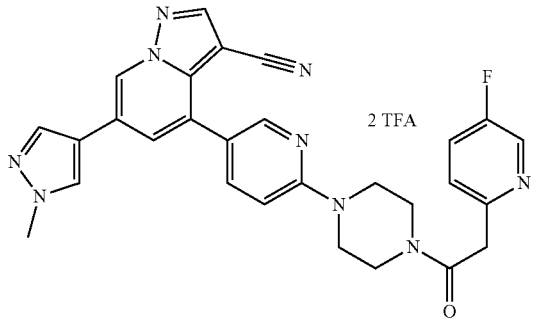 [SMILES: Cn1cc(-c2cc(-c3ccc(N4CCN(C(=O)Cc5ccc(F)cn5)CC4)nc3)c3c(C#N)cnn3c2)cn1 ; "2 TFA"] | 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate) | 522.2 (M + H) |

TABLE GG-continued

| Ex # | Structure | Chemical Name | MS (apci) m/z |
|---|---|---|---|
| 361 | 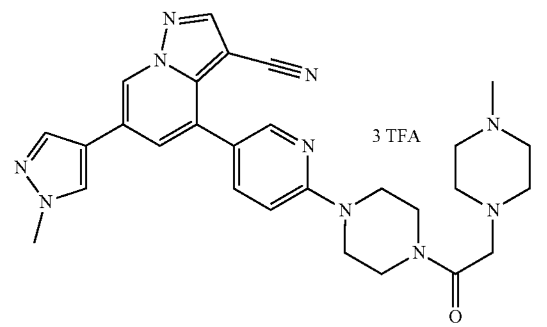 [SMILES: CN1CCN(CC(=O)N2CCN(c3ccc(-c4cc(-c5cnn(C)c5)cn5ncc(C#N)c45)cn3)CC2)CC1 ; "3 TFA"] | 6-(1-methyl-1H-pyrazol-4-yl)-4-(6-(4-(2-(4-methylpiperazin-1-yl)acetyl)piperazin-1-yl)pyridin-3-yl)pyrazolo[1,5-a]pyridine-3-carbonitrile tris(2,2,2-trifluoroacetate) | 525.2 (M + H) |
| 362 | 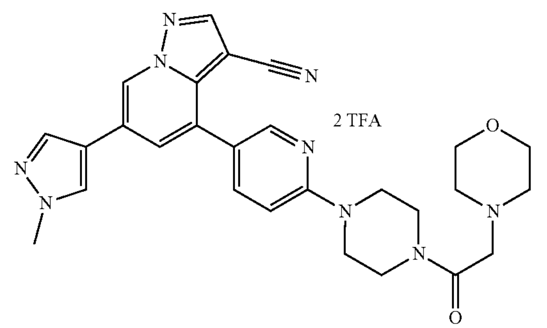 [SMILES: Cn1cc(-c2cc(-c3ccc(N4CCN(C(=O)CN5CCOCC5)CC4)nc3)c3c(C#N)cnn3c2)cn1 ; "2 TFA"] | 6-(1-methyl-1H-pyrazol-4-yl)-4-(6-(4-(2-morpholinoacetyl)piperazin-1-yl)pyridin-3-yl)pyrazolo[1,5-a]pyridine-3-carbonitrile bis(2,2,2-trifluoroacetate) | 512.2 (M + H) |
| 363 | 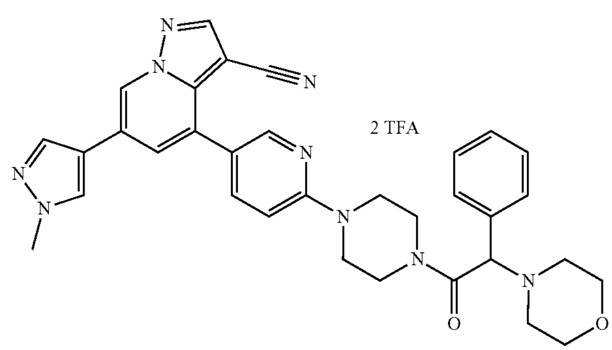 [SMILES: Cn1cc(-c2cc(-c3ccc(N4CCN(C(=O)C(c5ccccc5)N5CCOCC5)CC4)nc3)c3c(C#N)cnn3c2)cn1 ; "2 TFA"] | 6-(1-methyl-1H-pyrazol-4-yl)-4-(6-(4-(2-morpholino-2-phenylacetyl)piperazin-1-yl)pyridin-3-yl)pyrazolo[1,5-a]pyridine-3-carbonitrile bis(2,2,2-trifluoroacetate) | 588.2 (M + H) |
| 364 | 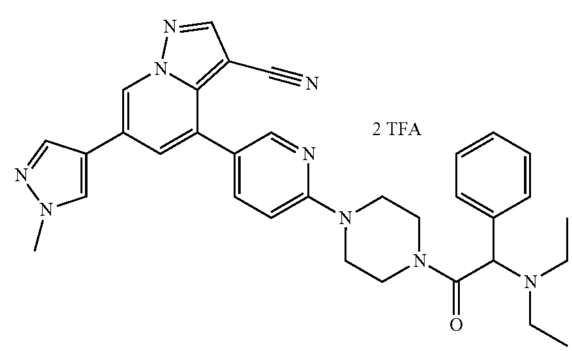 [SMILES: CCN(CC)C(C(=O)N1CCN(c2ccc(-c3cc(-c4cnn(C)c4)cn4ncc(C#N)c34)cn2)CC1)c1ccccc1 ; "2 TFA"] | 4-(6-(4-(2-(diethylamino)-2-phenylacetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate) | 574.3 (M + H) |

TABLE GG-continued

| Ex # | Structure | Chemical Name | MS (apci) m/z |
|---|---|---|---|
| 365 | 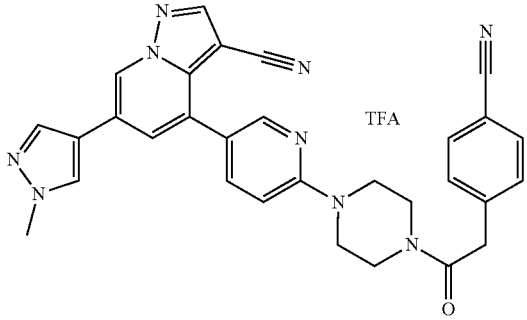 [SMILES: Cn1cc(-c2cc(-c3ccc(N4CCN(C(=O)Cc5ccc(C#N)cc5)CC4)nc3)c3c(C#N)cnn3c2)cn1 ; "TFA"] | 4-(6-(4-(2-(4-cyanophenyl)acetyl)piperazin-1-yl)pyridin-3-yl)-6-(1-methyl-1H-pyrazol-4-yl)pyrazolo[1,5-a]pyridine-3-carbonitrile 2,2,2-trifluoroacetate | 528.2 (M + H) |
| 366 | 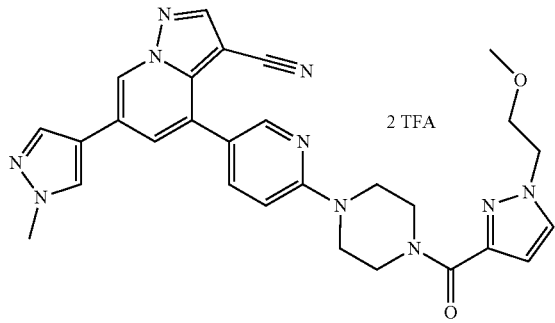 [SMILES: COCCn1ccc(C(=O)N2CCN(c3ccc(-c4cc(-c5cnn(C)c5)cn5ncc(C#N)c45)cn3)CC2)n1 ; "2 TFA"] | 4-(6-(4-(1-(2-methoxyethyl)-1H-pyrazole-3-carbonyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate) | 537.2 (M + H) |
| 367 | 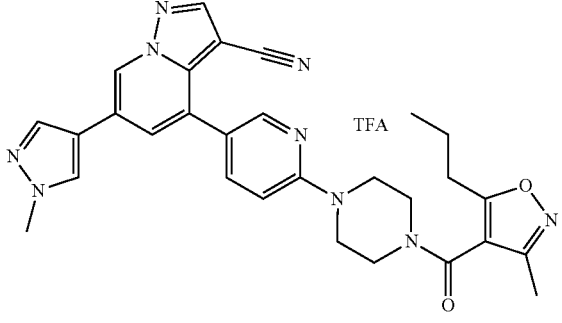 [SMILES: CCCc1onc(C)c1C(=O)N1CCN(c2ccc(-c3cc(-c4cnn(C)c4)cn4ncc(C#N)c34)cn2)CC1 ; "TFA"] | 6-(1-methyl-1H-pyrazol-4-yl)-4-(6-(4-(3-methyl-5-propylisoxazole-4-carbonyl)piperazin-1-yl)pyridin-3-yl)pyrazolo[1,5-a]pyridine-3-carbonitrile 2,2,2-trifluoroacetate | 536.2 (M + H) |
| 368 | 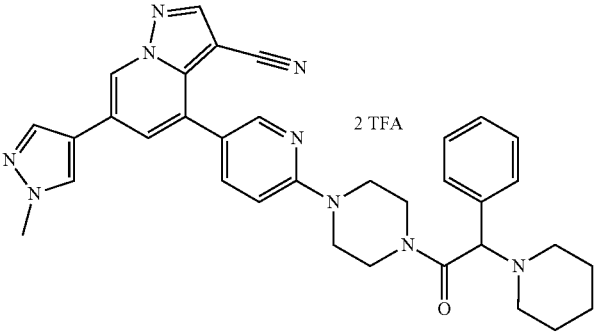 [SMILES: Cn1cc(-c2cc(-c3ccc(N4CCN(C(=O)C(c5ccccc5)N5CCCCC5)CC4)nc3)c3c(C#N)cnn3c2)cn1 ; "2 TFA"] | 6-(1-methyl-1H-pyrazol-4-yl)-4-(6-(4-(2-phenyl-2-(piperidin-1-yl)acetyl)piperazin-1-yl)pyridin-3-yl)pyrazolo[1,5-a]pyridine-3-carbonitrile bis(2,2,2-trifluoroacetate) | 586.3 (M + H) |

TABLE GG-continued

| Ex # | Structure | Chemical Name | MS (apci) m/z |
|---|---|---|---|
| 369 | 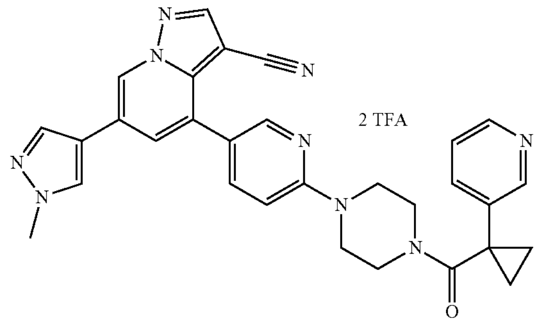 [SMILES: Cn1cc(-c2cc(-c3ccc(N4CCN(C(=O)C5(c6cccnc6)CC5)CC4)nc3)c3c(C#N)cnn3c2)cn1 ; "2 TFA"] | 6-(1-methyl-1H-pyrazol-4-yl)-4-(6-(4-(1-(pyridine-3-yl)cyclopropane-1-carbonyl)piperazin-1-yl)pyridin-3-yl)pyrazolo[1,5-a]pyridine-3-carbonitrile bis(2,2,2-trifluoroacetate) | 530.2 (M + H) |
| 370 | 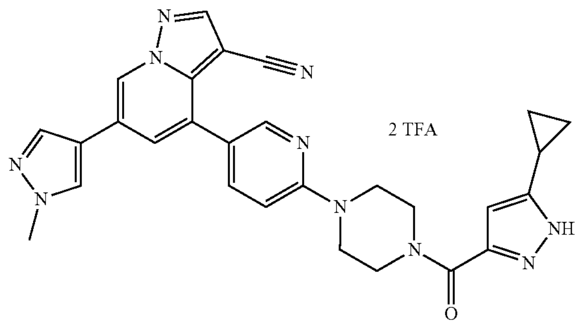 [SMILES: Cn1cc(-c2cc(-c3ccc(N4CCN(C(=O)c5cc(C6CC6)[nH]n5)CC4)nc3)c3c(C#N)cnn3c2)cn1 ; "2 TFA"] | 4-(6-(4-(5-cyclopropyl-1H-pyrazole-3-carbonyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate) | 519.2 (M + H) |

Example 371

(S)-6-(1-methyl-1H-pyrazol-4-yl)-4-(6-(4-(3,3,3-trifluoro-2-methoxy-2-phenylpropanoyl)piperazin-1-yl)pyridin-3-yl)pyrazolo[1,5-a]pyridine-3-carbonitrile A room temperature solution of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 15 mg 0.033 mmol) in DMF (0.2 mL) was treated with TEA (14 µL, 0.098 mmol) and (R)-3,3,3-trifluoro-2-methoxy-2-phenylpropanoyl chloride (12 mg, 0.049 mmol). The reaction mixture was stirred for 1 h at room temperature and then purified directly by C18 reverse phase chromatography (0-60% ACN/water as the gradient eluent) to afford the title compound (13 mg, 66% yield). MS (apci) m/z=601.1 (M+H).

Example 372

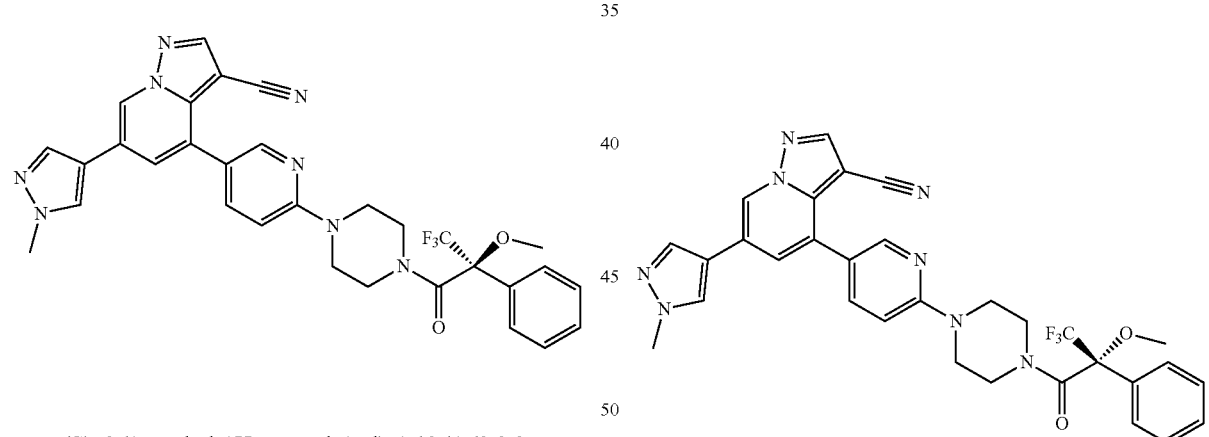

(R)-6-(1-methyl-1H-pyrazol-4-yl)-4-(6-(4-(3,3,3-trifluoro-2-methoxy-2-phenylpropanoyl)piperazin-1-yl)pyridin-3-yl)pyrazolo[1,5-a]pyridine-3-carbonitrile Using the procedure outlined for Example 371, replacing (R)-3,3,3-trifluoro-2-methoxy-2-phenylpropanoyl chloride with (S)-3,3,3-trifluoro-2-methoxy-2-phenylpropanoyl chloride, the title compound was cleanly isolated (16 mg, 61% yield) after purification by C18 reverse phase chromatography (0-60% ACN/water as the gradient eluent). MS (apci) m/z=601.2 (M+H).

Example 373

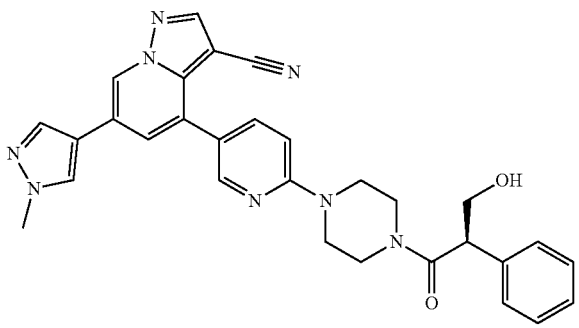 [SMILES: Cn1cc(-c2cc(-c3ccc(N4CCN(C(=O)[C@@H](CO)c5ccccc5)CC4)nc3)c3c(C#N)cnn3c2)cn1]

(R)-4-(6-(4-(3-hydroxy-2-phenylpropanol)piperazin-1-yl)pyridin-3-yl)-6-(1-methyl-1H-pyrazol-4-yl)pyrazolo[1,5-a]pyridine-3-carbonitrile A room temperature solution of 6-(1-methyl-1H-pyrazol-4-yl)-4-(6-(piperazin-1-yl)pyridine-3-yl)pyrazolo[1,5-a]pyridine-3-carbonitrile dihydrochloride (Example 2; 50.3 mg, 0.110 mmol) in DCM (1.10 mL) was treated with (R)-3-hydroxy-2-phenylpropanoic acid (Intermediate R12; 21.9 mg, 0.132 mmol), HATU (50.2 mg, 0.132 mmol) and DIEA (191.6 µL, 1.10 mmol). The reaction was stirred overnight at room temperature, and then directly purified by silica chromatography (10-90% DCM/Acetone) to afford the title compound (32.0 mg, 55% yield). MS (apci) m/z=533.2 (M+H).

Example 374

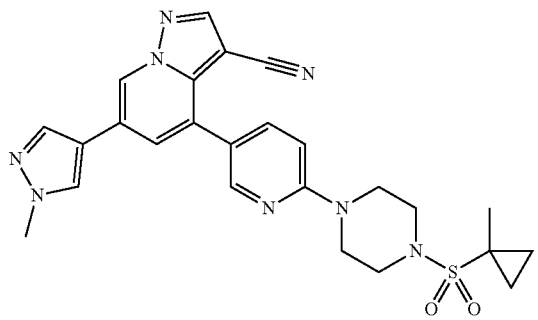 [SMILES: Cn1cc(-c2cc(-c3ccc(N4CCN(S(=O)(=O)C5(C)CC5)CC4)nc3)c3c(C#N)cnn3c2)cn1]

6-(1-methyl-1H-pyrazol-4-yl)-4-(6-(4-((1-methylcyclopropyl)sulfonyl)piperazin-1-yl)pyridin-3-yl)pyrazolo[1,5-a]pyridine-3-carbonitrile A mixture of 6-(1-methyl-1H-pyrazol-4-yl)-4-(6-(piperazin-1-yl)pyridine-3-yl)pyrazolo[1,5-a]pyridine-3-carbonitrile dihydrochloride (Example 2; 25 mg, 0.055 mmol), 1-methylcyclopropane-1-sulfonyl chloride (8.45 mg, 0.0547 mmol) and TEA (76 µL, 0.55 mmol) in DMA (500 µL) was stirred 20 h at 70° C. The crude reaction mixture was purified directly by silica chromatography (0.2% MeOH/0.2% NH4OH in DCM) to afford the title compound (8.5 mg, 31% yield). MS (apci) m/z=503.2 (M+H).

Example 375

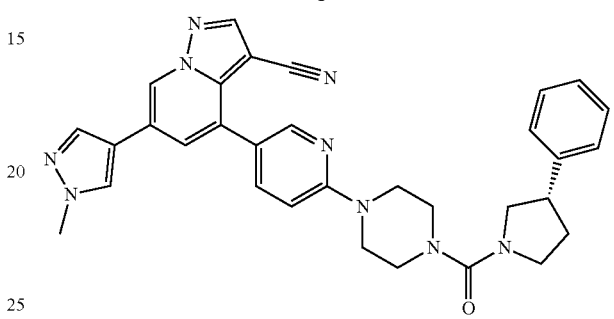

(S)-6-(1-methyl-1H-pyrazol-4-yl)-4-(6-(4-(3-phenylpyrrolidine-1-carbonyl)piperazin-1-yl)pyridin-3-yl)pyrazolo[1,5-a]pyridine-3-carbonitrile A suspension of 6-(1-methyl-1H-pyrazol-4-yl)-4-(6-(piperazin-1-yl)pyridine-3-yl)pyrazolo[1,5-a]pyridin-3-carbonitrile dihydrochloride (Example 2; 25 mg, 0.055 mmol) and DIEA (57 µL, 0.33) mmol) in DriSolv DCM (164 µL) was added dropwise to a 0° C. solution of triphosgene (8.1 mg, 0.027 mmol) in DriSolv® DCM (273 µL). After stirring for 90 min at 0° C., the reaction mixture was treated with (S)-3-phenylpyrrolidine hydrochloride (15 mg, 0.082 mmol), then stirred for 48 h at room temperature. The resulting mixture was purified directly by C18 reverse-phase chromatography (5-75% ACN/water as the gradient eluent) to provide the title compound (9.5 mg, 31% yield). MS (apci) m/z=558.2 (M+H).

The compounds in Table HH were prepared according to the method described for the synthesis of Example 375, replacing (S)-3-phenylpyrrolidine hydrochloride with the appropriate amine starting material. Reactions were monitored by LCMS and reaction times were adjusted as necessary. Products were purified by C18 reverse-phase chromatography utilizing an appropriate gradient eluent to cleanly afford the title compound.

TABLE HH

| Ex # | Structure | Chemical Name | MS (apci) m/z |
|---|---|---|---|
| 376 | 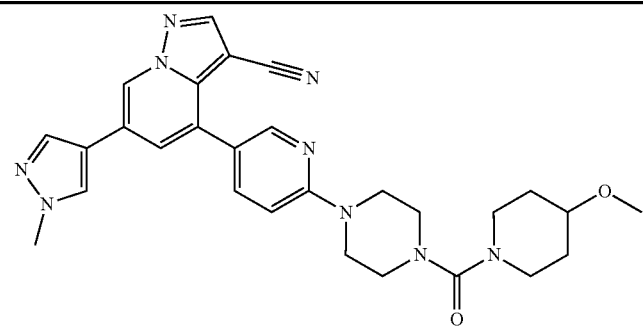 | 4-(6-(4-(4-methoxypiperidine-1-carbonyl)piperazin-1-yl)pyridin-3-yl)-6-(1-methyl-1H-pyrazol-4-yl)pyrazolo[1,5-a]pyridine-3-carbonitrile | 526.2 (M + H) |

TABLE HH-continued

| Ex # | Structure | Chemical Name | MS (apci) m/z |
|---|---|---|---|
| 377 | 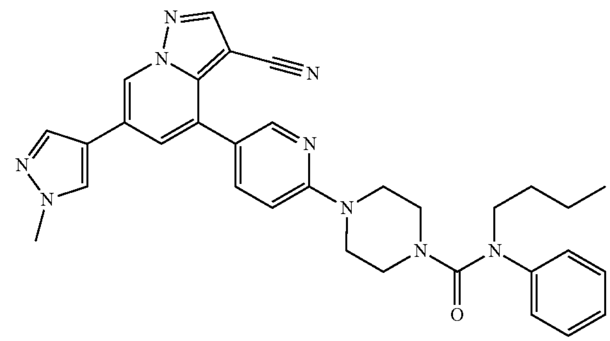 [SMILES: CCCCN(C(=O)N1CCN(c2ccc(-c3cc(-c4cnn(C)c4)cn4ncc(C#N)c34)cn2)CC1)c1ccccc1] | N-butyl-4-(5-(3-cyano-6-(1-methyl-1H-pyrazol-4-yl)pyrazolo[1,5-a]pyridin-4-yl)pyridine-2-yl)-N-phenylpiperazine-1-carboxamide | 560.1 (M + H) |
| 378 | 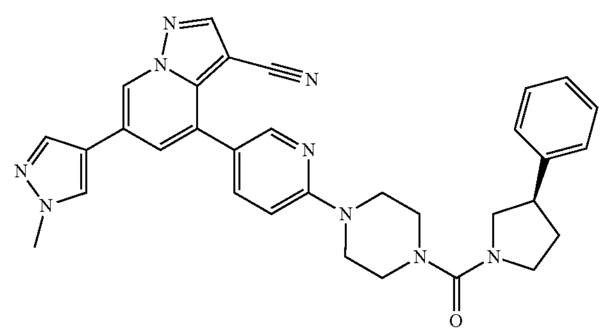 [SMILES: Cn1cc(-c2cc(-c3ccc(N4CCN(C(=O)N5CC[C@H](c6ccccc6)C5)CC4)nc3)c3c(C#N)cnn3c2)cn1] | (R)-6-(1-methyl-1H-pyrazol-4-yl)-4-(6-(4-(3-phenylpyrrolidine-1-carbonyl)piperazin-1-yl)pyridin-3-yl)pyrazolo[1,5-a]pyridine-3-carbonitrile | 558.2 (M + H) |
| 379 | 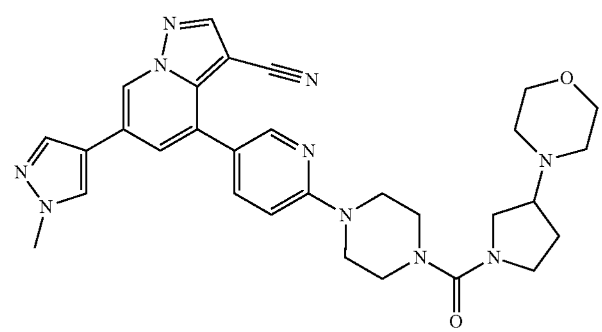 [SMILES: Cn1cc(-c2cc(-c3ccc(N4CCN(C(=O)N5CCC(N6CCOCC6)C5)CC4)nc3)c3c(C#N)cnn3c2)cn1] | 6-(1-methyl-1H-pyrazol-4-yl)-4-(6-(4-(3-morpholinopyrrolidine-1-carbonyl)piperazin-1-yl)pyridin-3-yl)pyrazolo[1,5-a]pyridine-3-carbonitrile | 567.2 (M + H) |
| 380 | 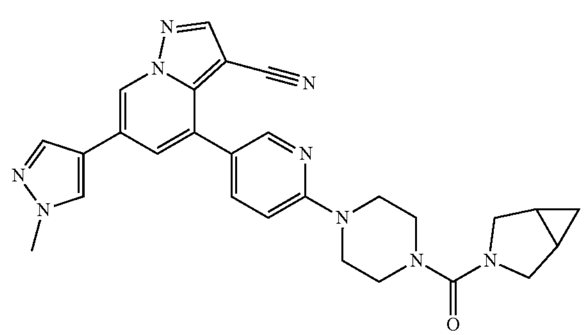 [SMILES: Cn1cc(-c2cc(-c3ccc(N4CCN(C(=O)N5CC6CC6C5)CC4)nc3)c3c(C#N)cnn3c2)cn1] | 4-(6-(4-(3-azabicyclo[3.1.0]hexane-3-carbonyl)piperazin-1-yl)pyridin-3-yl)-6-(1-methyl-1H-pyrazol-4-yl)pyrazolo[1,5-a]pyridine-3-carbonitrile | 494.1 (M + H) |

TABLE HH-continued

| Ex # | Structure | Chemical Name | MS (apci) m/z |
|---|---|---|---|
| 381 | 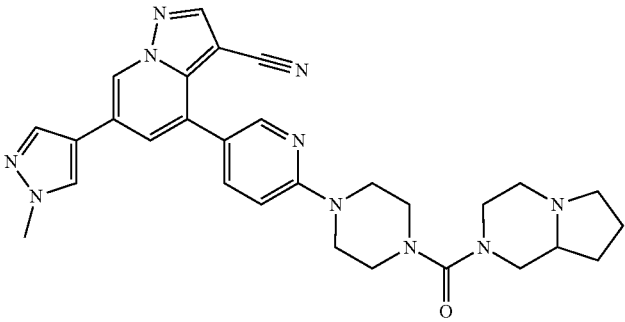 [SMILES: Cn1cc(-c2cc(-c3ccc(N4CCN(C(=O)N5CCN6CCCC6C5)CC4)nc3)c3c(C#N)cnn3c2)cn1] | 6-(1-methyl-1H-pyrazol-4-yl)-4-(6-(4-(octahydropyrrolo[1,2-a]pyrazine-2-carbonyl)piperazin-1-yl)pyridin-3-yl)pyrazolo[1,5-a]pyridine-3-carbonitrile | 537.3 (M + H) |
| 382 | 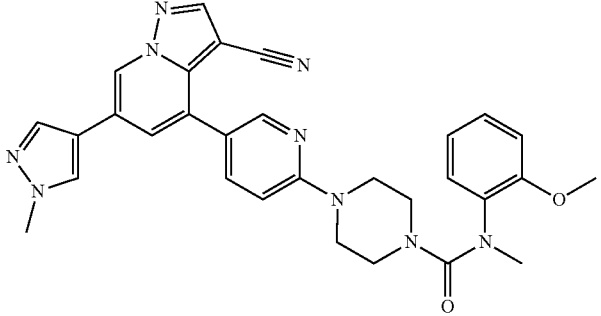 [SMILES: COc1ccccc1N(C)C(=O)N1CCN(c2ccc(-c3cc(-c4cnn(C)c4)cn4ncc(C#N)c34)cn2)CC1] | 4-(5-(3-cyano-6-(1-methyl-1H-pyrazol-4-yl)pyrazolo[1,5-a]pyridine-4-yl)pyridine-2-yl)-N-(2-methoxyphenyl)-N-methylpiperazine-1-carboxamide | 548.3 (M + H) |
| 383 | 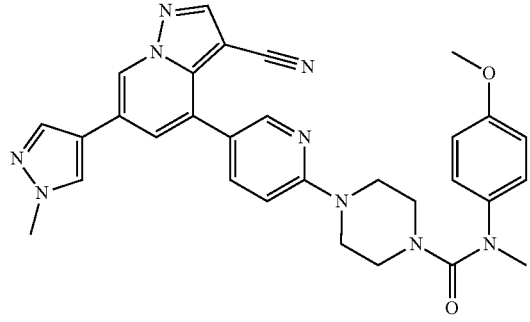 [SMILES: COc1ccc(N(C)C(=O)N2CCN(c3ccc(-c4cc(-c5cnn(C)c5)cn5ncc(C#N)c45)cn3)CC2)cc1] | 4-(5-(3-cyano-6-(1-methyl-1H-pyrazol-4-yl)pyrazolo[1,5-a]pyridine-4-yl)pyridin-2-yl)-N-(4-methoxyphenyl)-N-methylpiperazine-1-carboxamide | 548.3 (M + H) |
| 384 | 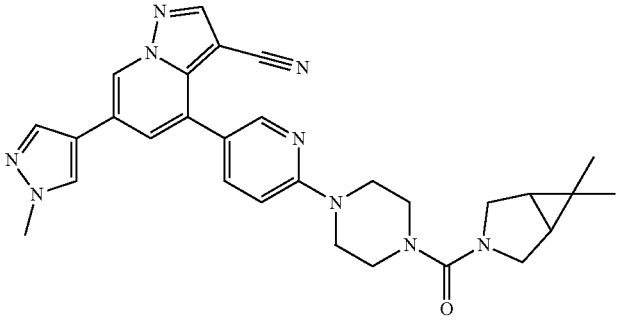 [SMILES: Cn1cc(-c2cc(-c3ccc(N4CCN(C(=O)N5CC6C(C5)C6(C)C)CC4)nc3)c3c(C#N)cnn3c2)cn1] | 4-(6-(4-(6,6-dimethyl-3-azabicyclo[3.1.0]hexane-3-carbonyl)piperazin-1-yl)pyridin-3-yl)-6-(1-methyl-1H-pyrazol-4-yl)pyrazolo[1,5-a]pyridine-3-carbonitrile | 522.4 (M + H) |

TABLE HH-continued

| Ex # | Structure | Chemical Name | MS (apci) m/z |
|---|---|---|---|
| 385 | 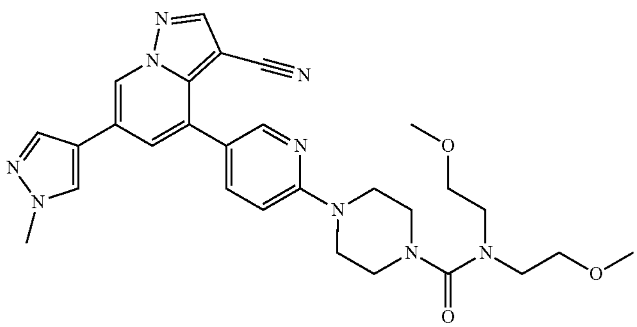 [SMILES: COCCN(CCOC)C(=O)N1CCN(c2ccc(-c3cc(-c4cnn(C)c4)cn4ncc(C#N)c34)cn2)CC1] | 4-(5-(3-cyano-6-(1-methyl-1H-pyrazol-4-yl)pyrazolo[1,5-a]pyridin-4-yl)pyridine-2-yl)-N,N-bis(2-methoxyethyl)piperazine-1-carboxamide | 544.2 (M + H) |

The compounds in Table II were prepared according the method described for the synthesis of Example 130, replacing 2-methoxy-N-methyl-ethanamine with the appropriate amine starting material. Reactions were monitored by LCMS, and reaction times were adjusted as necessary. Products were purified by reverse-phase preparative HPLC utilizing an appropriate gradient eluent to cleanly afford the title compounds.

TABLE II

| Ex # | Structure | Chemical Name | MS (apci) m/z |
|---|---|---|---|
| 386 | TFA | 4-(5-(3-cyano-6-(1-methyl-1H-pyrazol-4-yl)pyrazolo[1,5-a]pyridine-4-yl)pyridin-2-yl)-N-cycopropyl-N-methylpiperazine-1-carboxamide 2,2,2-trifluoroacetate | 482.2 (M + H) |
| 387 | 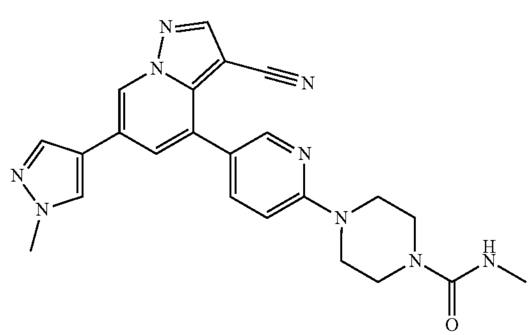 | 4-(5-(3-cyano-6-(1-methyl-1H-pyrazol-4-yl)pyrazolo[1,5-a]pyridin-4-yl)pyridin-2-yl)-N-methylpiperazine-1-carboxamide | 442.1 (M + H) |

Example 388

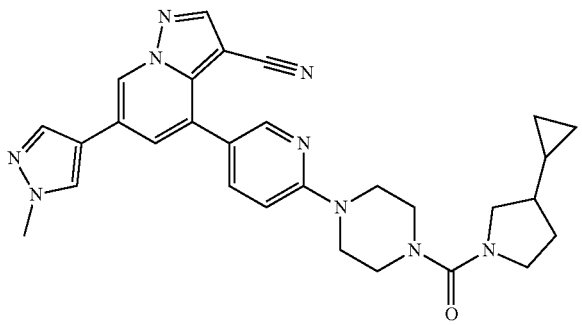 [SMILES: Cn1cc(-c2cc(-c3ccc(N4CCN(C(=O)N5CCC(C6CC6)C5)CC4)nc3)c3c(C#N)cnn3c2)cn1]

4-(6-(4-(3-cyclopropylpyrrolidine-1-carbnyl)piper-azin-1-yl)pyridin-3-yl)-6-(1-methyl-1H-pyrazol-4-yl)pyrazolo[1,5-a]pyridine-3-carbonitrile Step 1: Preparation of 4-nitrophenyl 4-(5-(3-cyano-6-(1-methyl-1H-pyrazol-4-yl)pyrazolo[1,5-a]pyridin-4-yl)pyridin-2-yl)piperazine-1-carboxylate A room temperature suspension of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 100 mg, 0.219 mmol) in DMA (2 mL) was treated sequentially with DIEA (114 µL, 0.656 mmol) and 4-nitrophenyl carbonochloridate (66.1 mg, 0.328 mmol). The mixture was stirred at room temperature for 4 h, at which point LCMS indicated that the title compound had formed as the major product, MS (apci) m/z=550 (M+H). The reaction mixture was divided into 6 equal fractions, and one fraction was used directly in Step 2. The remaining five parts were reserved, and used in the preparation of each of the compounds listed in Table JJ.

Step 2: Preparation of 4-(6-(4-(3-cyclopropylpyrrolidine-1-carbonyl)piperazin-1-yl)pyridin-3-yl)-6-(1-methyl-1H-pyrazol-4-yl)pyrazolo[1,5-a]pyridine-3-carbonitrile A room temperature solution of 3-cyclopropylpyrrolidine (6.1 mg, 0.055 mmol) in DMA (0.1 mL) and DIEA (19 µL, 0.11 mmol) was treated with a suspension of 4-nitrophenyl 4-(5-(3-cyano-6-(1-methyl-1H-pyrazol-4-yl)pyrazolo[1,5-a]pyridin-4-yl)pyridin-2-yl)piperazine-1-carboxylate (⅙th of the suspension from Step 1; about 20 mg, 0.036 mmol) in DIEA/DMA (about 0.35 mL, about 0.33 M). The resulting mixture was stirred for 16 h at 80° C. The reaction mixture was cooled to room temperature, diluted with water (1 mL), and then filtered. The solid filter cake was rinsed with water, then dissolved in ACN and purified by C18 reverse-phase chromatography (5-90% ACN/water as the gradient eluent) to cleanly afford the title compound (5.6 mg, 29% yield). MS (apci) m/z=522.2 (M+H).

The compounds in Table JJ were prepared according the method described in Step 2 in the synthesis of Example 388, replacing 3-cyclopropylpyrrolidine with the appropriate amine starting material. Reactions were monitored by LCMS, and reaction times were adjusted as necessary. Compounds were purified by C18 reverse-phase chromatography utilizing an appropriate gradient eluent to cleanly afford the title compound.

TABLE JJ

| Ex # | Structure | Chemical Name | MS (apci) m/z |
|---|---|---|---|
| 389 | 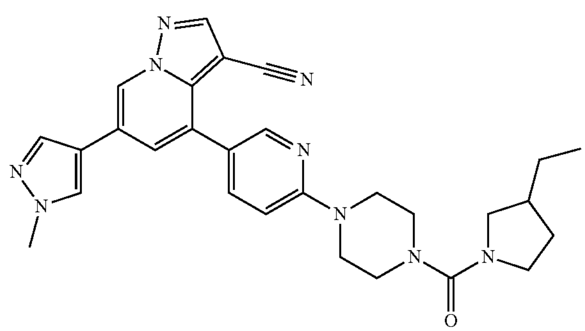 | 4-(6-(4-(3-ethylpyrrolidine-1-carbonyl)piperazin-1-yl)pyridin-3-yl)-6-(1-methyl-1H-pyrazol-4-yl)pyrazolo[1,5-a]pyridine-3-carbonitrile | 510.2 (M + H) |
| 390 | 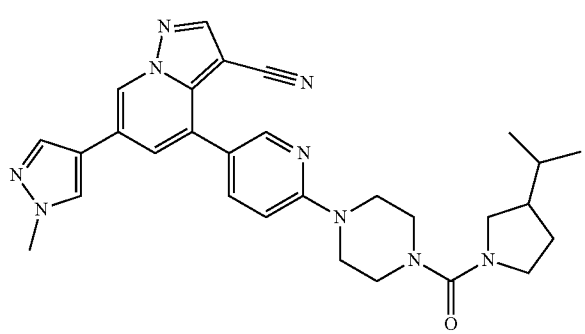 [SMILES: CC(C)C1CCN(C(=O)N2CCN(c3ccc(-c4cc(-c5cnn(C)c5)cn5ncc(C#N)c45)cn3)CC2)C1] | 4-(6-(4-(3-isopropylpyrrolidine-1-carbonyl)piperazin-1-yl)pyridin-3-yl)-6-(1-methyl-1H-pyrazol-4-yl)pyrazolo[1,5-a]pyridine-3-carbonitrile | 524.2 (M + H) |

TABLE JJ-continued

| Ex # | Structure | Chemical Name | MS (apci) m/z |
|---|---|---|---|
| 391 | 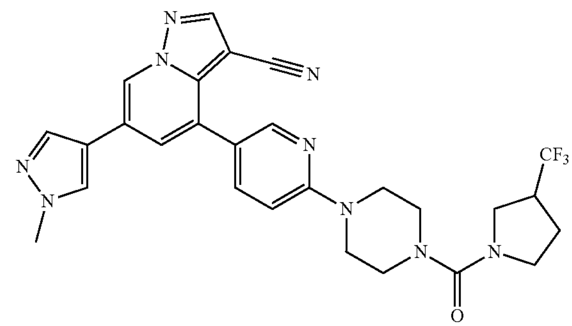 [SMILES: Cn1cc(-c2cc(-c3ccc(N4CCN(C(=O)N5CCC(C(F)(F)F)C5)CC4)nc3)c3c(C#N)cnn3c2)cn1] | 6-(1-methyl-1H-pyrazol-4-yl)-4-(6-(4-(3-(trifluoromethyl)pyrrolidine-1-carbonyl)piperazin-1-yl)pyridin-3-yl)pyrazolo[1,5-a]pyridine-3-carbonitrile | 550.2 (M + H) |

Example 392

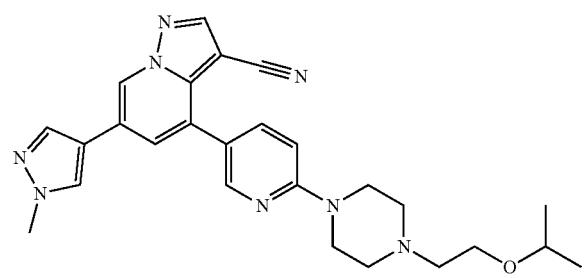 [SMILES: CC(C)OCCN1CCN(c2ccc(-c3cc(-c4cnn(C)c4)cn4ncc(C#N)c34)cn2)CC1]

4-(6-(4-(2-isopropoxyethyl)piperazin-1-yl)pyridin-3-yl)-6-(1-methyl-1H-pyrazol-4-yl)pyrazolo[1,5-a]pyridin-3-carbonitrile A room temperature solution of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 0.018 g, 0.0394 mmol) in dry DMF (0.3 mL) and TEA (54.9 µL, 0.394 mmol) was treated with 2-(2-bromoethoxy)propane (0.0197 g, 0.118 mmol). The reaction mixture was stirred overnight at 75° C., and then additional 2-(2-bromoethoxy)propane (1 eq) and TEA (1 eq) were added. The reaction mixture was allowed to stir 24 h at 75° C. After cooling to room temperature, the resulting reaction mixture was directly purified by C18 reverse phase chromatography (5-99% ACN/water as the gradient eluent) to afford the title compound (7.4 mg, 41% yield). MS (apci) m/z=471.2 (M+H).

The compounds in Table KK were prepared according to the method described for the synthesis of Example 392, using either DMF or DMA as the reaction solvent, and replacing 2-(2-bromoethoxy)propane with the appropriate alkyl halide starting materials. Reactions were monitored by LCMS, and reaction times/temperatures were adjusted accordingly. In some cases, the addition of extra equivalents of alkyl halide/TEA (1-5 eq) after 24 h at 75° C. was required. Title compounds were cleanly isolated following C18 reverse phase chromatography utilizing an appropriate gradient eluent.

TABLE KK

| Ex # | Structure | Chemical Name | MS (apci) m/z |
|---|---|---|---|
| 393 | 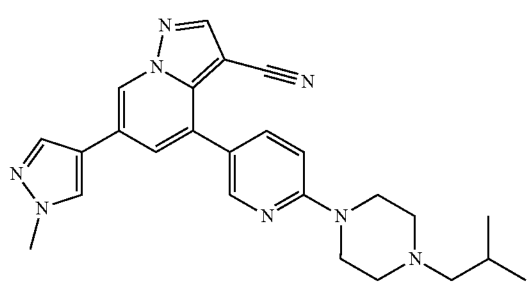 [SMILES: CC(C)CN1CCN(c2ccc(-c3cc(-c4cnn(C)c4)cn4ncc(C#N)c34)cn2)CC1] | 4-(6-(4-isobutylpiperazin-1-yl)pyridin-3-yl)-6-(1-methyl-1H-pyrazol-4-yl)pyrazolo[1,5-a]pyridine-3-carbonitrile | 441.1 (M + H) |

TABLE KK-continued

| Ex # | Structure | Chemical Name | MS (apci) m/z |
|---|---|---|---|
| 394 | 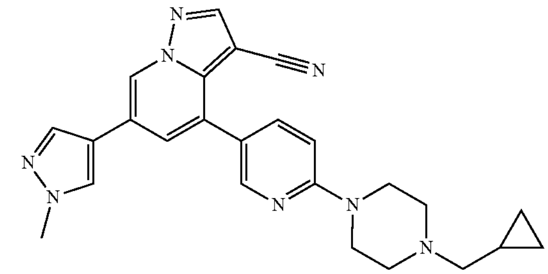 [SMILES: Cn1cc(-c2cc(-c3ccc(N4CCN(CC5CC5)CC4)nc3)c3c(C#N)cnn3c2)cn1] | 4-(6-(4-(cyclopropylmethyl)piperazin-1-yl)pyridin-3-yl)-6-(1-methyl-1H-pyrazol-4-yl)pyrazolo[1,5-a]pyridine-3-carbonitrile | 439.2 (M + H) |
| 395 | 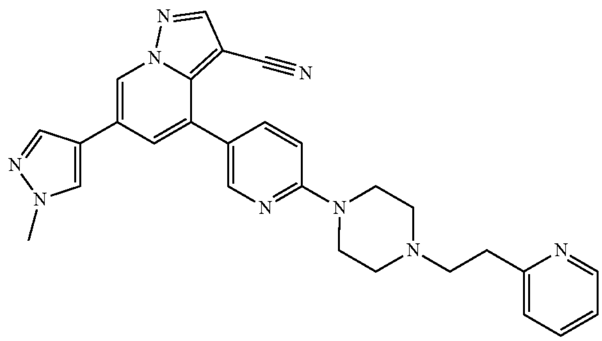 [SMILES: Cn1cc(-c2cc(-c3ccc(N4CCN(CCc5ccccn5)CC4)nc3)c3c(C#N)cnn3c2)cn1] | 6-(1-methyl-1H-pyrazol-4-yl)-4-(6-(4-(2-(pyridine-2-yl)ethyl)piperazin-1-yl)pyridin-3-yl)pyrazolo[1,5-a]pyridine-3-carbonitrile | 490.2 (M + H) |
| 396 | 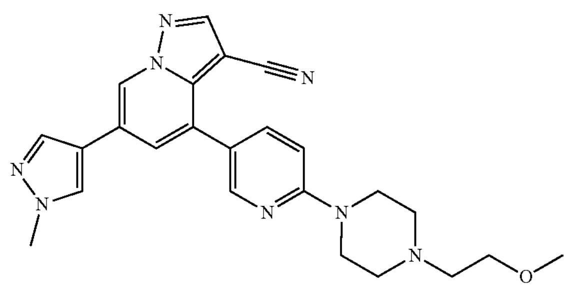 [SMILES: COCCN1CCN(c2ccc(-c3cc(-c4cnn(C)c4)cn4ncc(C#N)c34)cn2)CC1] | 4-(6-(4-(2-methoxyethyl)piperazin-1-yl)pyridin-3-yl)-6-(1-methyl-1H-pyrazol-4-yl)pyrazolo[1,5-a]pyridine-3-carbonitrile | 443.2 (M + H) |
| 397 | 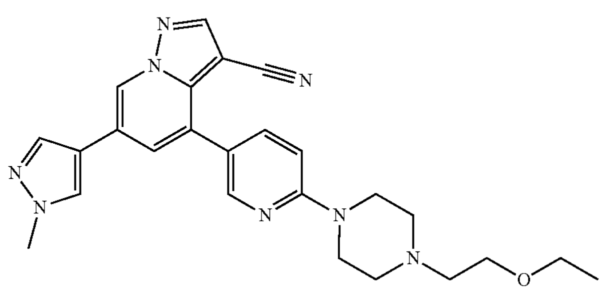 | 4-(6-(4-(2-ethoxyethyl)piperazin-1-yl)pyridin-3-yl)-6-(1-methyl-1H-pyrazol-4-yl)pyrazolo[1,5-a]pyridine-3-carbonitrile | 469.2 (M + H) |
| 398 | 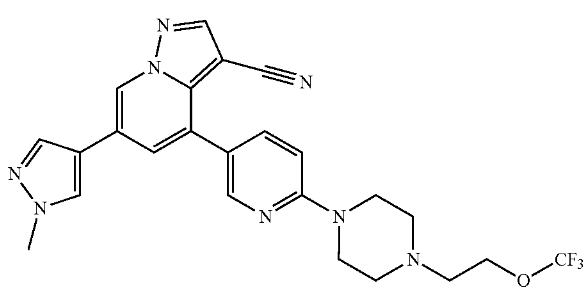 [SMILES: Cn1cc(-c2cc(-c3ccc(N4CCN(CCOC(F)(F)F)CC4)nc3)c3c(C#N)cnn3c2)cn1] | 6-(1-methyl-1H-pyrazol-4-yl)-4-(6-(4-(2-(trifluoromethoxy)ethyl)piperazin-1-yl)pyridin-3-yl)pyrazolo[1,5-a]pyridine-3-carbonitrile | 497.1 (M + H) |

TABLE KK-continued

| Ex # | Structure | Chemical Name | MS (apci) m/z |
|---|---|---|---|
| 399 | 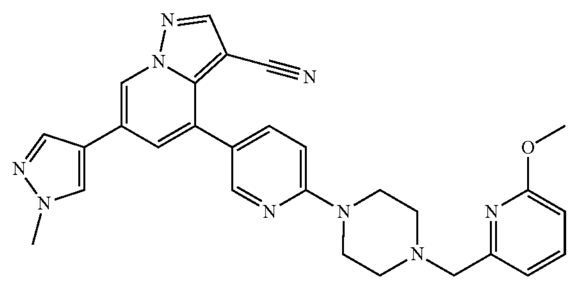 [SMILES: COc1cccc(CN2CCN(c3ccc(-c4cc(-c5cnn(C)c5)cn5ncc(C#N)c45)cn3)CC2)n1] | 4-(6-(4-((6-methoxypyridin-2-yl)methyl)piperazin-1-yl)pyridin-3-yl)-6-(1-methyl-1H-pyrazol-4-yl)pyrazolo[1,5-a]pyridine-3-carbonitrile | 506.2 (M + H) |
| 400 | 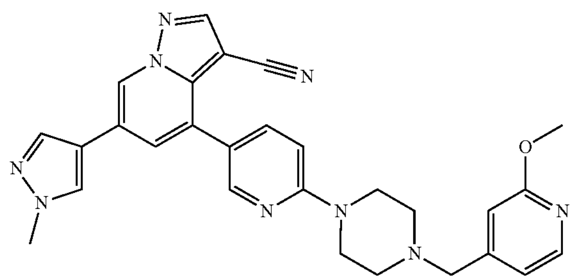 [SMILES: COc1cc(CN2CCN(c3ccc(-c4cc(-c5cnn(C)c5)cn5ncc(C#N)c45)cn3)CC2)ccn1] | 4-(6-(4-((2-methoxypyridin-4-yl)methyl)piperazin-1-yl)pyridin-3-yl)-6-(1-methyl-1H-pyrazol-4-yl)pyrazolo[1,5-a]pyridine-3-carbonitrile | 506.2 (M + H) |
| 401* | 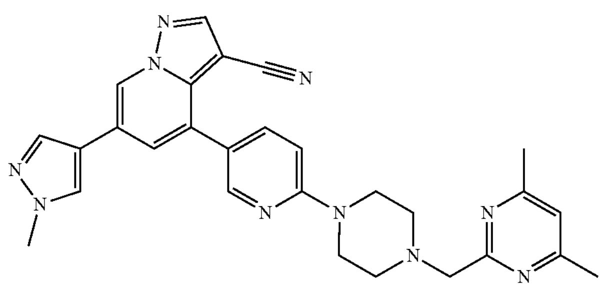 [SMILES: Cc1cc(C)nc(CN2CCN(c3ccc(-c4cc(-c5cnn(C)c5)cn5ncc(C#N)c45)cn3)CC2)n1] | 4-(6-(4-((4,6-dimethylpyrimidin-2-yl)methyl)piperazin-1-yl)pyridin-3-yl)-6-(1-methyl-1H-pyrazol-4-yl)pyrazolo[1,5-a]pyridine-3-carbonitrile | 505.2 (M + H) |

*Example 401: used only 1.5 eq of the alkyl halide (2-(chloromethyl)-4,6-dimethylpyrimidine), 10 eq of TEA, and was conducted at room temperature, but otherwise followed a similar procedure.

Example 402

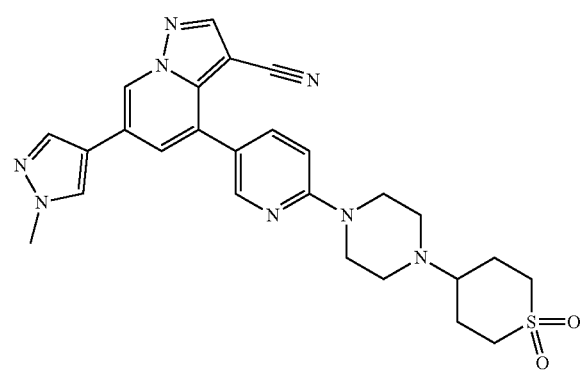 [SMILES: Cn1cc(-c2cc(-c3ccc(N4CCN(C5CCS(=O)(=O)CC5)CC4)nc3)c3c(C#N)cnn3c2)cn1]

4-(6-(4-(1,1-dioxidotetrahydro-2H-thiopyran-4-yl)piperazin-1-yl)pyridin-3-yl)-6-(1-methyl-1H-pyrazol-4-yl)pyrazolo[1,5-a]pyridine-3-carbonitrile A room temperature solution of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 0.0199 g, 0.0435 mmol) in dry DMF (1 mL) was treated with $Cs_2CO_3$ (0.0425 g, 0.131 mmol) and 4-bromotetrahydro-2H-thiopyran-1,1-dioxide (0.0185 g, 0.0870 mmol). The resulting mixture was stirred for 4 h at 60° C., then overnight at 75° C., and then additional 4-bromotetrahydro-2H-thiopyran 1,1-dioxide (20 mg, 0.939 mmol) and $Cs_2CO_3$ (40 mg, 0.301 mmol) were added. After 3 d at 75° C., this process was repeated, adding 4-bromotetrahydro-2H-thiopyran-1,1-dioxide (35 mg, 0.164 mmol) and $Cs_2CO_3$ (60 mg, 0.451 mmol), then stirring for an additional 24 h at 75° C. The reaction mixture was purified directly by C18 reverse phase chromatography (5-99% ACN/Water as the gradient eluent) to afford the title compound (4.2 mg, 19% yield). MS (apci) m/z=562.1 (M+2 Na).

Example 403

4-(6-(4-(2-(isopropylsulfonyl)ethyl)piperazin-1-yl)pyridin-3-yl)-6-(1-methyl-1H-pyrazol-4-yl)pyrazolo[1,5-a]pyridine-3-carbonitrile

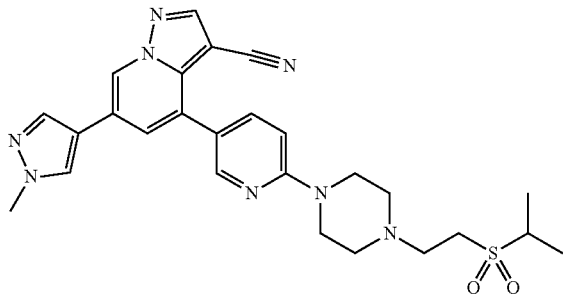 [SMILES: CC(C)S(=O)(=O)CCN1CCN(c2ccc(-c3cc(-c4cnn(C)c4)cn4ncc(C#N)c34)cn2)CC1]

A room temperature mixture of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 25 mg, 0.055 mmol), 2-((2-chloroethyl)sulfonyl)propane (18.7 mg, 0.109 mmol) and TEA (76 μL, 0.55 mmol) in dry DMA (500 μL) was stirred for 3 d at 70° C. The reaction mixture was purified directly by silica chromatography (2% MeOH/0.02% NH$_4$OH in DCM as the eluent) to afford the title compound (8.6 mg, 30% yield). MS (apci) m/z=519.2 (M+H).

The compounds in Table LL were prepared according to the method described for the synthesis of Example 403, replacing 2-((2-chloroethyl)sulfonyl)propane with the appropriate alkyl halide. Reactions were monitored for completion by LCMS, and reaction times were adjusted accordingly. Title compounds were cleanly isolated following silica chromatography (2% MeOH/0.02% NH$_4$OH in DCM as the eluent) unless otherwise noted.

TABLE LL

| Ex # | Structure | Chemical Name | MS (apci) m/z |
|---|---|---|---|
| 404* | 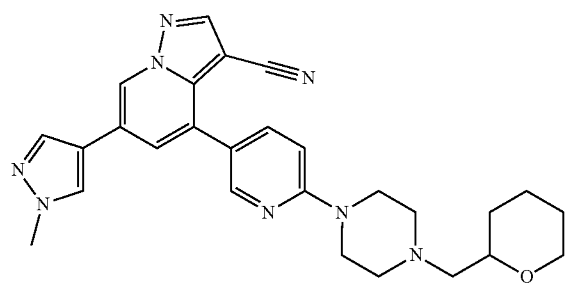 [SMILES: Cn1cc(-c2cc(-c3ccc(N4CCN(CC5CCCCO5)CC4)nc3)c3c(C#N)cnn3c2)cn1] | 6-(1-methyl-1H-pyrazol-4-yl)-4-(6-(4-((tetrahydro-2H-pyran-2-yl)methyl)piperazin-1-yl)pyridin-3-yl)pyrazolo[1,5-a]pyridine-3-carbonitrile | 483.3 (M + H) |
| 405** | 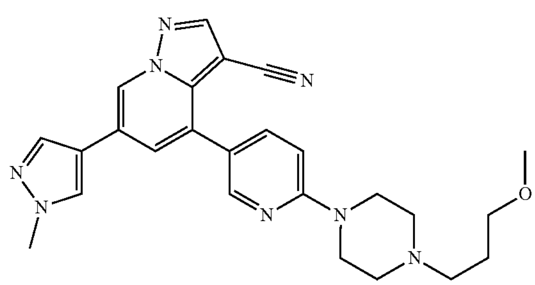 [SMILES: COCCCN1CCN(c2ccc(-c3cc(-c4cnn(C)c4)cn4ncc(C#N)c34)cn2)CC1] | 4-(6-(4-(3-methoxypropyl)piperazin-1-yl)pyridin-3-yl)-6-(1-methyl-1H-pyrazol-4-yl)pyrazolo[1,5-a]pyridine-3-carbonitrile | 457.2 (M + H) |
| 406 | 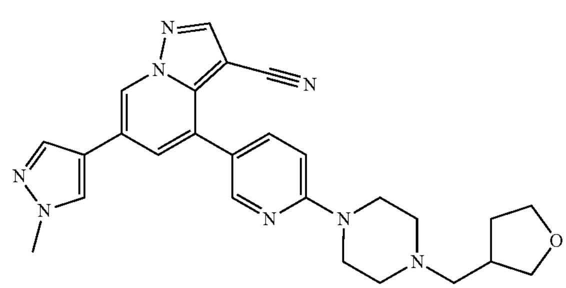 [SMILES: Cn1cc(-c2cc(-c3ccc(N4CCN(CC5CCOC5)CC4)nc3)c3c(C#N)cnn3c2)cn1] | 6-(1-methyl-1H-pyrazol-4-yl)-4-(6-(4-((tetrahydrofuran-3-yl)methyl)piperazin-1-yl)pyridin-3-yl)pyrazolo[1,5-a]pyridine-3-carbonitrile | 469.2 (M + H) |

*isolated following in vacuo removal of DMA followed by trituration with EtOAc and filtration
**4 eq of the alkyl halide was used

Example 407

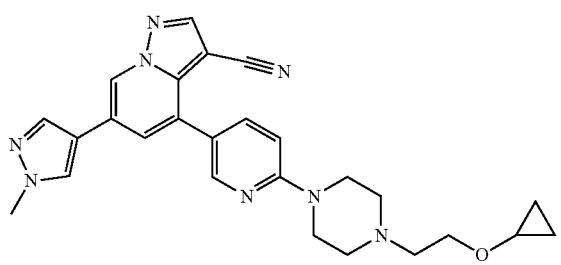 [SMILES: Cn1cc(-c2cc(-c3ccc(N4CCN(CCOC5CC5)CC4)nc3)c3c(C#N)cnn3c2)cn1]

4-(6-(4-(2-cyclopropoxyethyl)piperazin-1-yl)pyridin-3-yl)-6-(1-methyl-1H-pyrazol-4-yl)pyrazolo[1,5-a]pyridine-3-carbonitrile A room temperature solution of 6-(1-methyl-1H-pyrazol-4-yl)-4-(6-(piperazin-1-yl)pyridin-3-yl)pyrazolo[1,5-a]pyridin-3-carbonitrile dihydrochloride (Example 2; 0.0185 g, 0.0404 mmol) in dry DMF (0.3 mL) was treated with TEA (56.3 µL, 0.404 mmol) and (2-chloroethoxy)cyclopropane (0.0146 g, 0.121 mmol). The reaction mixture was stirred overnight at 75° C., and then additional (2-chloroethoxy)cyclopropane (1 eq) and DMF (0.2 mL) with KI (20.1 mg, 0.121 mmol) were added. The reaction was allowed stir for 48 h at 75° C., then cooled to room temperature. The reaction mixture was purified directly by C18 reverse phase chromatography (5-80% ACN/water as the gradient eluent) to afford the title compound (4.4 mg, 23% yield). MS (apci) m/z=469.2 (M+H).

Example 408

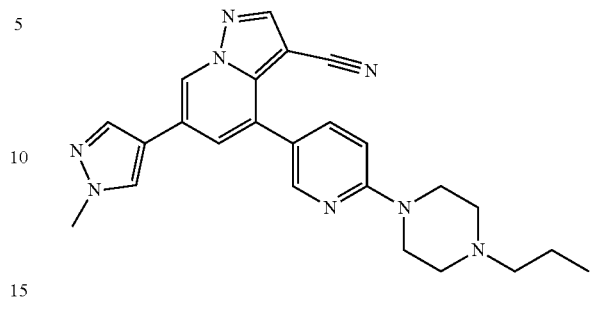

6-(1-methyl-1H-pyrazol-4-yl)-4-(6-(4-propylpiperazin-1-yl)pyridin-3-yl)pyrazolo[1,5-a]pyridine-3-carbonitrile A room temperature solution of 6-(1-methyl-1H-pyrazol-4-yl)-4-(6-(piperazin-1-yl)pyridine-3-yl)pyrazolo[1,5-a]pyridin-3-carbonitrile dihydrochloride (Example 2; 20 mg, 0.044 mmol) in DMF (300 µL) and TEA (61 µL, 0.44 mmol) was treated with 1-iodopropane (8.5 µL, 0.087 mmol). The reaction mixture was stirred overnight at room temperature, and then additional 1-iodopropane (8.5 µL, 0.087 mmol; 1 eq) was added. The reaction was allowed to stir at room temperature until complete by HPLC. The reaction mixture was directly purified by C18 reverse phase chromatography (10-99% ACN/Water as the gradient eluent) to afford the title compound (12 mg, 64% yield). MS (apci) m/z=427.2 (M+H).

The compounds in Table MM were prepared according to the method described for the synthesis of Example 408 (except where noted), replacing 1-iodopropane with the appropriate alkyl halide starting. Reactions were monitored by HPLC, and reaction times adjusted accordingly. In some cases, additional alkyl halide (1 eq)/TEA (1.2 eq) was required after stirring overnight. Title compounds were cleanly isolated following C18 reverse phase chromatography utilizing an appropriate gradient eluent.

TABLE MM

| Ex # | Structure | Chemical Name | MS (apci) m/z |
|---|---|---|---|
| 409 | 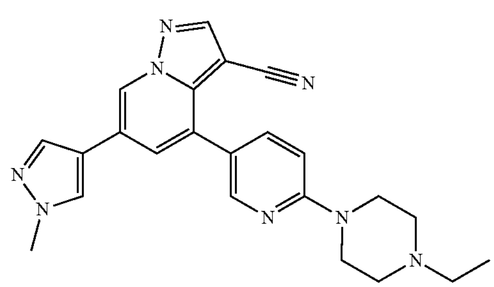 [SMILES: CCN1CCN(c2ccc(-c3cc(-c4cnn(C)c4)cn4ncc(C#N)c34)cn2)CC1] | 4-(6-(4-ethylpiperazin-1-yl)pyridin-3-yl)-6-(1-methyl-1H-pyrazol-4-yl)pyrazolo[1,5-a]pyridine-3-carbonitrile | 413.2 (M + H) |

TABLE MM-continued

| Ex # | Structure | Chemical Name | MS (apci) m/z |
|---|---|---|---|
| 410 | 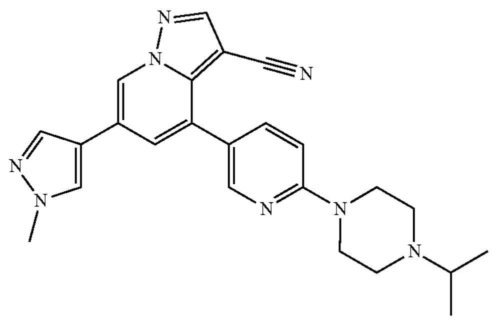 [SMILES: CC(C)N1CCN(c2ccc(-c3cc(-c4cnn(C)c4)cn4ncc(C#N)c34)cn2)CC1] | 4-(6-(4-isopropylpiperazin-1-yl)pyridin-3-yl)-6-(1-methyl-1H-pyrazol-4-yl)pyrazolo[1,5-a]pyridine-3-carbonitrile | 427.2 (M + H) |
| 411* | 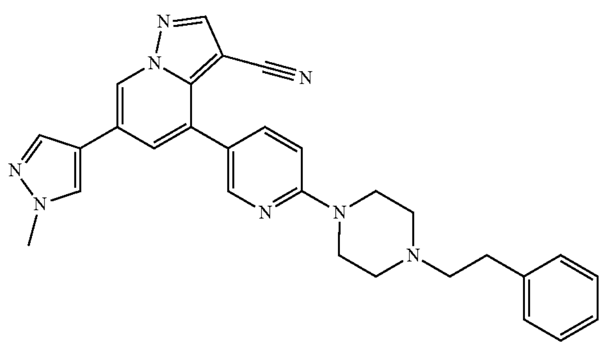 [SMILES: Cn1cc(-c2cc(-c3ccc(N4CCN(CCc5ccccc5)CC4)nc3)c3c(C#N)cnn3c2)cn1] | 6-(1-methyl-1H-pyrazol-4-yl)-4-(6-(4-phenethylpiperazin-1-yl)pyridin-3-yl)pyrazolo[1,5-a]pyridine-3-carbonitrile | 489.2 (M + H) |

*reaction was conducted at 75° C.

Example 412

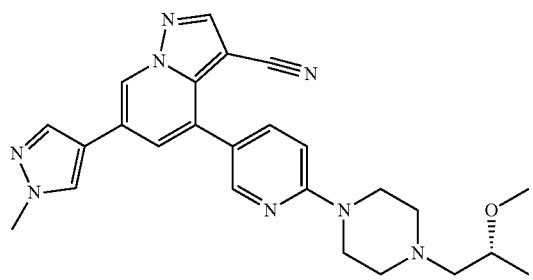

(R)-4-(6-(4-(2-methoxypropyl)piperazin-1-yl)pyridin-3-yl)-6-(1-methyl-1H-pyrazol-4-yl)pyrazolo[1,5-a]pyridine-3-carbonitrile NaH (60% w/w dispersion in mineral oil; 1.12 mg, 0.0280 mmol) was added to a cold (0° C.) solution of (R)-4-(6-(4-(2-hydroxypropyl)piperazin-1-yl)pyridin-3-yl)-6-(1-methyl-1H-pyrazol-4-yl)pyrazolo[1,5-a]pyridine-3-carbonitrile (Example 158; 6.2 mg, 0.0140 mmol) in dry THF (0.2 mL), and the reaction mixture was stirred for 10 min at 0° C. $CH_3I$ (1 M in THF; 1.74 μL, 0.0280 mmol) was added to the 0° C. mixture. The reaction mixture was stirred at room temperature at 0° C. overnight. The reaction was quenched with water and $CHCl_3$. The biphasic mixture was separated, the aqueous phase was extracted with $CHCl_3$, and the combined organic extracts were filtered through a PS frit. The filtrate was concentrated in vacuo, and the residue was purified by C18 reverse phase chromatography (25-90% ACN/water as the gradient eluent) to afford the title compound (2.8 mg, 44% yield). MS (apci) m/z=457.1 (M+H).

The compounds in Table NN were prepared according to the method described for the synthesis of Example 412, replacing (R)-4-(6-(4-(2-hydroxypropyl)piperazin-1-yl)pyridin-3-yl)-6-(1-methyl-1H-pyrazol-4-yl)pyrazolo[1,5-a]pyridine-3-carbonitrile (Example 158) with the appropriate alcohol. Reactions were monitored for completion by LCMS, and reaction times were adjusted accordingly. The title compounds were cleanly isolated following C18 reverse phase chromatography using an appropriate gradient.

TABLE NN

| Ex # | Structure | Chemical Name | MS (apci) m/z |
|---|---|---|---|
| 413* | 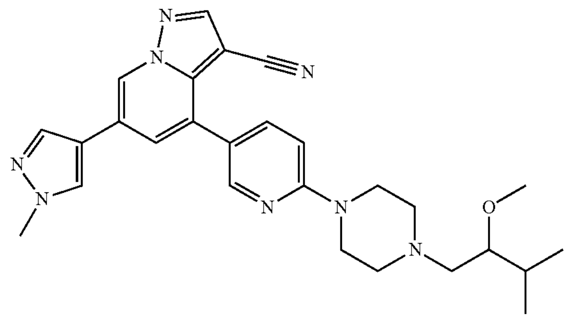 [SMILES: COC(CN1CCN(c2ccc(-c3cc(-c4cnn(C)c4)cn4ncc(C#N)c34)cn2)CC1)C(C)C] | 4-(6-(4-(2-methoxy-3-methylbutyl)piperazin-1-yl)pyridin-3-yl)-6-(1-methyl-1H-pyrazol-4-yl)pyrazolo[1,5-a]pyridine-3-carbonitrile | 485.2 (M + H) |
| 414 | 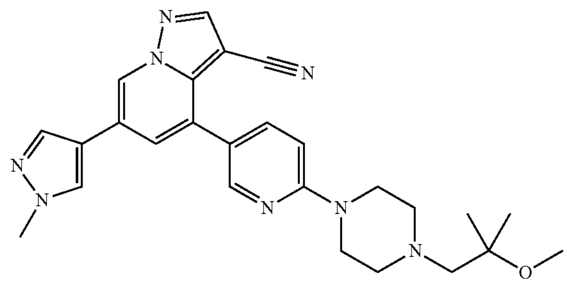 [SMILES: COC(C)(C)CN1CCN(c2ccc(-c3cc(-c4cnn(C)c4)cn4ncc(C#N)c34)cn2)CC1] | 4-(6-(4-(2-methoxy-2-methylpropyl)piperazin-1-yl)pyridin-3-yl)-6-(1-methyl-1H-pyrazol-4-yl)pyrazolo[1,5-a]pyridine-3-carbonitrile | 471.2 (M + H) |
| 415 | 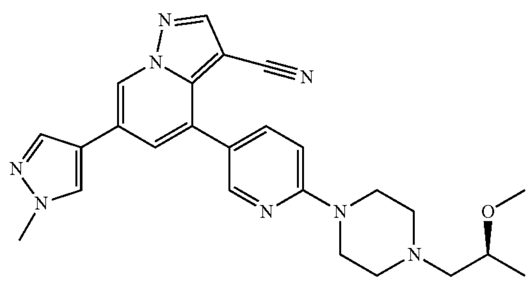 [SMILES: CO[C@@H](C)CN1CCN(c2ccc(-c3cc(-c4cnn(C)c4)cn4ncc(C#N)c34)cn2)CC1] | (S)-4-(6-(4-(2-methoxypropyl)piperazin-1-yl)pyridin-3-yl)-6-(1-methyl-1H-pyrazol-4-yl)pyrazolo[1,5-a]pyridine-3-carbonitrile | 457.1 (M + H) |
| 416 | 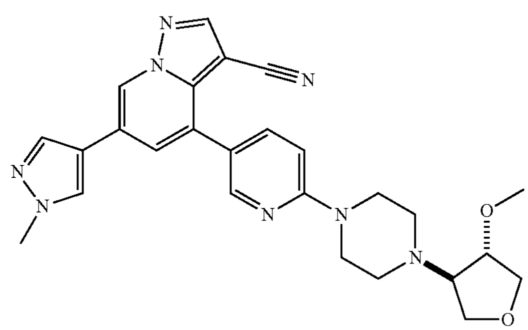 | 4-(6-(4-((3r,4s)-4-methoxytetrahydrofuran-3-yl)piperazin-1-yl)pyridin-3-yl)-6-(1-methyl-1H-pyrazol-4-yl)pyrazolo[1,5-a]pyridine-3-carbonitrile | 485.2 (M + H) |
| 417 | 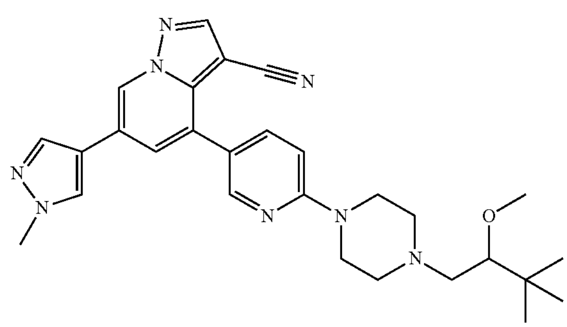 [SMILES: COC(CN1CCN(c2ccc(-c3cc(-c4cnn(C)c4)cn4ncc(C#N)c34)cn2)CC1)C(C)(C)C] | 4-(6-(4-(2-methoxy-3,3-dimethylbutyl)piperazin-1-yl)pyridin-3-yl)-6-(1-methyl-1H-pyrazol-4-yl)pyrazolo[1,5-a]pyridine-3-carbonitrile | 499.3 (M + H) |

*Example 413 utilized DCM in quench/work-up.

Example 418

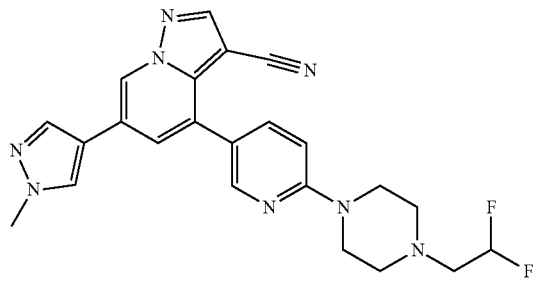 [SMILES: Cn1cc(-c2cc(-c3ccc(N4CCN(CC(F)F)CC4)nc3)c3c(C#N)cnn3c2)cn1]

4-(6-(4-(2,2-difluoroethyl)piperazin-1-yl)pyridin-3-yl)-6-(1-methyl-1H-pyrazol-4-yl)pyrazolo[1,5-a]pyridine-3-carbonitrile A room temperature solution of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 0.0199 g, 0.0435 mmol) in DMF (0.3 mL) was treated with TEA (60.6 µL, 0.435 mmol) and 2,2-difluoroethyl trifluoromethanesulfonate (0.0279 g, 0.131 mmol). The reaction mixture was stirred overnight at 65° C., and then purified directly by C18 reverse phase chromatography (5-99% ACN/water as the gradient eluent) to afford the title compound (10.6 mg, 54% yield). MS (apci) m/z=449.2 (M+H).

Example 419

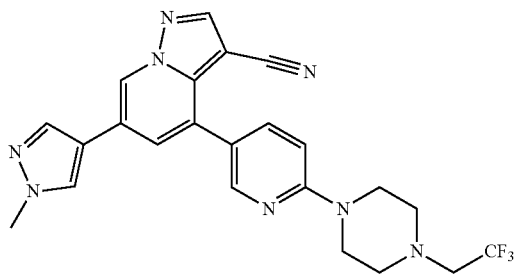 [SMILES: Cn1cc(-c2cc(-c3ccc(N4CCN(CC(F)(F)F)CC4)nc3)c3c(C#N)cnn3c2)cn1]

6-(1-methyl-1H-pyrazol-4-yl)-4-(6-(4-(2,2,2-trifluoroethyl)piperazin-1-yl)pyridin-3-yl)pyrazolo[1,5-a]pyridine-3-carbonitrile A room temperature solution of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 0.0203 g, 0.0444 mmol) in dry DMF (0.3 mL) was treated with TEA (61.9 µL, 0.444 mmol) and 1,1,1-trifluoro-2-iodoethane (0.0280 g, 0.133 mmol). The resulting suspension was stirred overnight at 70° C., and then additional dry DMF (0.2 mL), TEA (50 µL, 0.359 mmol) and 2,2,2-trifluoroethyl trifluoromethanesulfonate (19.8 µL, 0.133 mmol) were added. The resulting solution was stirred for 3 d at 70° C. After cooling to room temperature, the reaction mixture was purified directly by C18 reverse phase chromatography (5-99% ACN/water as the gradient eluent) to afford the title compound (12.8 mg, 62% yield). MS (apci) m/z=467.1 (M+H).

Example 420

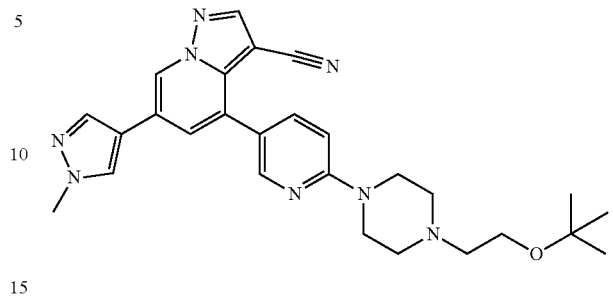

4-(6-(4-(2-(tert-butoxy)ethyl)piperazin-1-yl)pyridine-3-yl)-6-(1-methyl-1H-pyrazol-4-yl)pyrazolo[1,5-a]pyridine-3-carbonitrile A room temperature solution of 6-(1-methyl-1H-pyrazol-4-yl)-4-(6-(piperazin-1-yl)pyridine-3-yl)pyrazolo[1,5-a]pyridin-3-carbonitrile dihydrochloride (Example 2; 0.0175 g, 0.0383 mmol) in dry DMF (0.3 mL) was treated with TEA (53.3 µL, 0.383 mmol) and 2-(tert-butoxy)ethyl methanesulfonate (0.0150 g, 0.0765 mmol). The reaction mixture was stirred overnight at 75° C., and then additional 2-(tert-butoxy)ethyl methanesulfonate (7.5 mg, 0.0.0383 mmol) and dry DMF (0.2 mL) were added. The reaction was allowed to stir 48 h at 75° C., then for 24 h at 85° C. The reaction mixture was cooled to room temperature and purified directly by C18 reverse phase chromatography (20-90% ACN/water as the gradient eluent) to afford the title compound (8.7 mg, 47% yield). MS (apci) m/z=485.2 (M+H)

Example 421

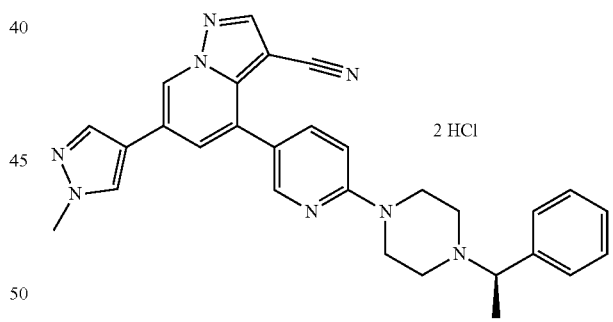

(R)-6-(1-methyl-1H-pyrazol-4-yl)-4-(6-(4-(1-phenylethyl)piperazin-1-yl)pyridin-3-yl)pyrazolo[1,5-a]pyridine-3-carbonitrile Dihydrochloride Step 1: Preparation of (S)-1-phenylethyl methanesulfonate A cold (0° C.) solution of (S)-1-phenylethanol (0.95 g, 7.78 mmol) and TEA (2.17 mL, 15.6 mmol) in DCM (10 mL) was treated over a 20 min period with methanesulfonyl chloride (1.07 g, 9.33 mmol). The resulting reaction mixture was allowed to warm to room temperature. The room temperature mixture was quenched with water (2 mL), and the combined organic extracts were separated using phase separation chromatography and concentrated in vacuo. The resultant oil was used directly in Step 2.

Step 2: Preparation of (R)-6-(1-methyl-1H-pyrazol-4-yl)-4-(6-(4-(1-phenylethyl)piperazin-1-yl)pyridin-3-yl)pyrazolo[1,5-a]pyridine-3-carbonitrile dihydrochloride A room temperature solution of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 0.05303 g, 0.1159 mmol) in dry DMF (0.9 mL) was treated with Cs$_2$CO$_3$ (0.3778 g, 1.159 mmol) and (S)-1-phenylethyl methanesulfonate (0.1393 g, 0.3478 mmol). The resulting mixture was stirred overnight at 70° C., and then additional (S)-1-phenylethyl methanesulfonate (50 µL) was added. The reaction temperature was raised to 80° C., and the reaction was allowed to stir for an additional 24 h. The reaction mixture was quenched with water/DCM. The combined organic extracts were separated, filtered through PS paper, and concentrated in vacuo. The residue was purified by C18 reverse phase chromatography (10-99%, ACN/Water with 0.01% HCl as the gradient eluent) to afford the title compound as the di-HCl salt (11.2 mg, 20% yield). MS (apci) m/z=489.2 (M+H).

Example 422

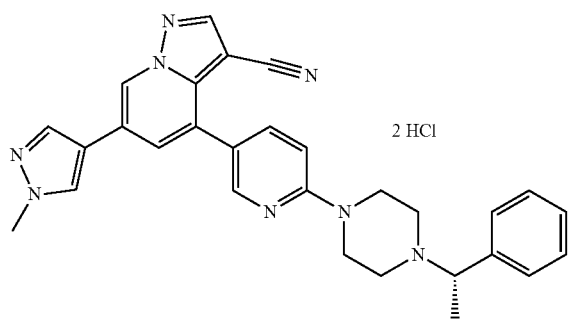 [SMILES: C[C@@H](c1ccccc1)N1CCN(c2ccc(-c3cc(-c4cnn(C)c4)cn4ncc(C#N)c34)cn2)CC1]

(S)-6-(1-methyl-1H-pyrazol-4-yl)-4-(6-(4-(1-phenylethyl)piperazin-1-yl)pyridine-3-yl)pyrazolo[1,5-a]pyridine-3-carbonitrile Dihydrochloride The title compound was prepared according to the method described for the synthesis of Example 421, replacing (S)-1-phenylethanol with (R)-1-phenylethanol in Step 1, and replacing (S)-1-phenylethyl methanesulfonate with (R)-1-phenylethyl methanesulfonate in Step 2, and increasing amounts of both the methanesulfonate reagent (6 eq) and Cs$_2$CO$_3$ (13 eq). Following C18 reverse phase chromatography (10-99%, ACN/Water with 0.01% HCl as the gradient eluent) the title compound was cleanly isolated as the di-HCl salt (13.7 mg, 25% yield). MS (apci) m/z=489.2 (M+H).

Example 423

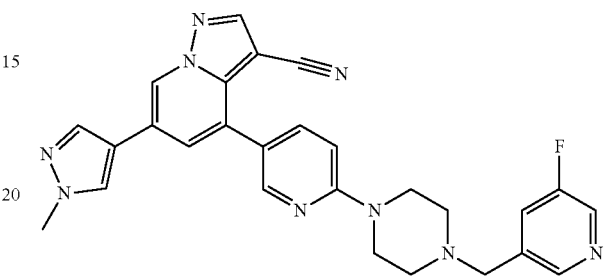

4-(6-(4-((5-fluoropyridin-3-yl)methyl)piperazin-1-yl)pyridin-3-yl)-6-(1-methyl-1H-pyrazol-4-yl)pyrazolo[1,5-a]pyridine-3-carbonitrile A room temperature mixture of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 30.00 mg, 78.04 mmol) and 5-fluoronicotinaldehyde (14.64 mg, 117.06 mmol) in DMF (1.00 mL) was treated with TEA (32.45 mL, 234.12 mmol). The mixture was acidified to pH 6 with acetic acid, and then stirred for 2 h at 25° C. NaBH$_3$CN (9.808 mg, 156.08 mmol) was added to the reaction mixture. The resulting mixture was stirred at 25° C. for 10 h. The reaction mixture was filtered to remove particulates, and the filtrate was purified by preparative HPLC (10 mM NH$_4$(HCO3)/ACN) to afford the title compound (14.8 mg, 38% yield). MS (apci) m/z=494.1 (M+H), 516.1 (M+Na).

The compounds in Table 00 were prepared according to the method described for the synthesis of Example 423, replacing 5-fluoronicotinaldehyde with the appropriate aldehyde. Reactions were monitored for completion by LCMS, and reaction times were adjusted accordingly. Title compounds were cleanly isolated following preparative HPLC using an appropriate gradient eluent.

TABLE OO

| Ex # | Structure | Chemical Name | MS (apci) m/z |
|---|---|---|---|
| 424 | 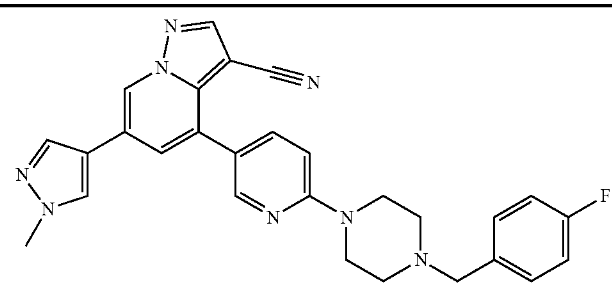 | 4-(6-(4-(4-fluorobenzyl)piperazin-1-yl)pyridin-3-yl)-6-(1-methyl-1H-pyrazol-4-yl)pyrazolo[1,5-a]pyridine-3-carbonitrile | 493.1 (M + H) |

TABLE OO-continued

| Ex # | Structure | Chemical Name | MS (apci) m/z |
|---|---|---|---|
| 425 | 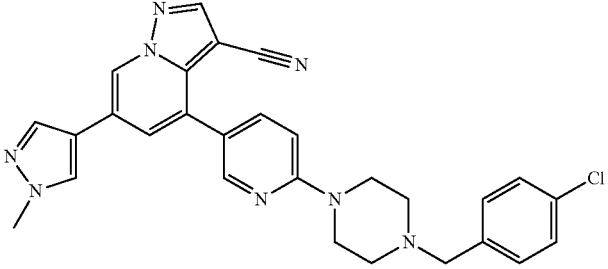 [SMILES: Cn1cc(-c2cc(-c3ccc(N4CCN(Cc5ccc(Cl)cc5)CC4)nc3)c3c(C#N)cnn3c2)cn1] | 4-(6-(4-(4-chlorobenzyl)piperazin-1-yl)pyridin-3-yl)-6-(1-methyl-1H-pyrazol-4-yl)pyrazolo[1,5-a]pyridine-3-carbonitrile | 509.1 (M + H) |
| 426 | 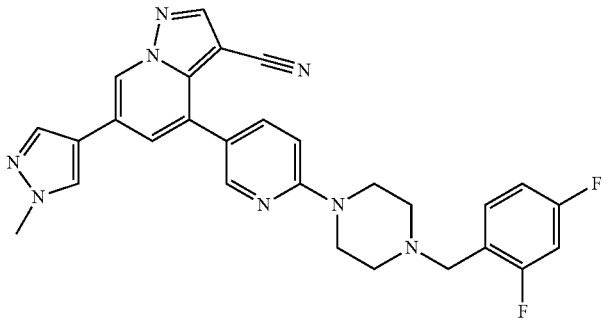 [SMILES: Cn1cc(-c2cc(-c3ccc(N4CCN(Cc5ccc(F)cc5F)CC4)nc3)c3c(C#N)cnn3c2)cn1] | 4-(6-(4-(2,4-difluorobenzyl)piperazin-1-yl)pyridin-3-yl)-6-(1-methyl-1H-pyrazol-4-yl)pyrazolo[1,5-a]pyridine-3-carbonitrile | 511.1 (M + H) |
| 427 | 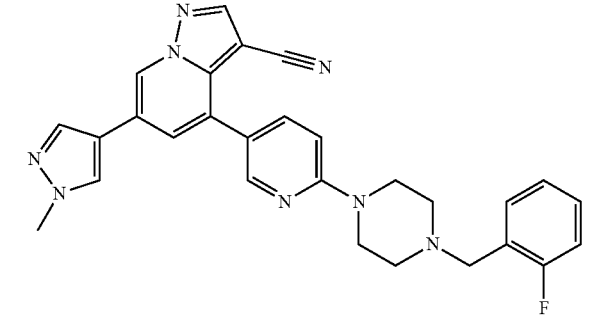 [SMILES: Cn1cc(-c2cc(-c3ccc(N4CCN(Cc5ccccc5F)CC4)nc3)c3c(C#N)cnn3c2)cn1] | 4-(6-(4-(2-fluorobenzyl)piperazin-1-yl)pyridin-3-yl)-6-(1-methyl-1H-pyrazol-4-yl)pyrazolo[1,5-a]pyridine-3-carbonitrile | 493.2 (M + H) |
| 428 | 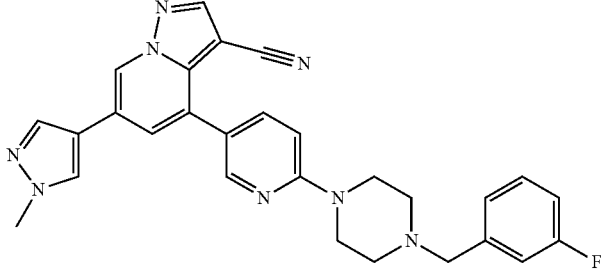 [SMILES: Cn1cc(-c2cc(-c3ccc(N4CCN(Cc5cccc(F)c5)CC4)nc3)c3c(C#N)cnn3c2)cn1] | 4-(6-(4-(3-fluorobenzyl)piperazin-1-yl)pyridin-3-yl)-6-(1-methyl-1H-pyrazol-4-yl)pyrazolo[1,5-a]pyridine-3-carbonitrile | 493.1 (M + H) |
| 429 | 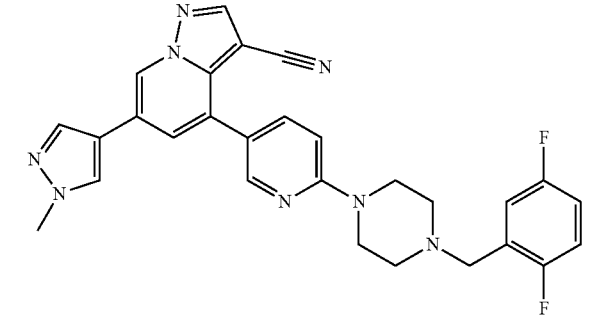 [SMILES: Cn1cc(-c2cc(-c3ccc(N4CCN(Cc5cc(F)ccc5F)CC4)nc3)c3c(C#N)cnn3c2)cn1] | 4-(6-(4-(2,5-difluorobenzyl)piperazin-1-yl)pyridin-3-yl)-6-(1-methyl-1H-pyrazol-4-yl)pyrazolo[1,5-a]pyridine-3-carbonitrile | 511.2 (M + H) |

TABLE OO-continued

| Ex # | Structure | Chemical Name | MS (apci) m/z |
|---|---|---|---|
| 430 | 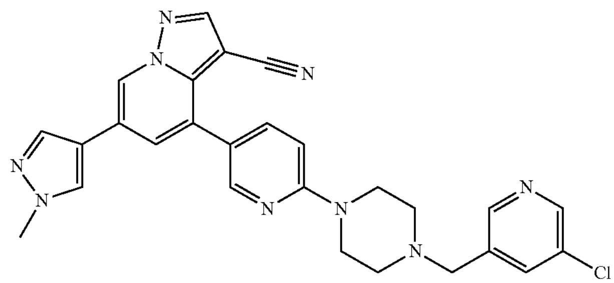 [SMILES: Cn1cc(-c2cc(-c3ccc(N4CCN(Cc5cncc(Cl)c5)CC4)nc3)c3c(C#N)cnn3c2)cn1] | 4-(6-(4-((5-chloropyridin-3-yl)methyl)piperazin-1-yl)pyridin-3-yl)-6-(1-methyl-1H-pyrazol-4-yl)pyrazolo[1,5-a]pyridine-3-carbonitrile | 510.1 (M + H) |
| 431 | 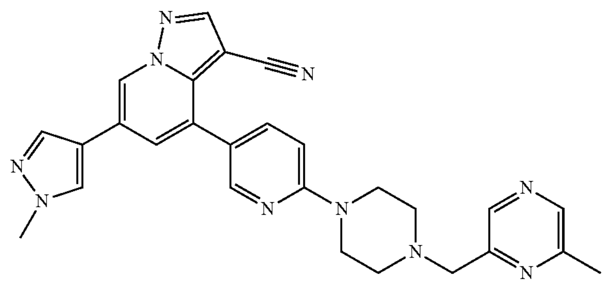 [SMILES: Cc1cncc(CN2CCN(c3ccc(-c4cc(-c5cnn(C)c5)cn5ncc(C#N)c45)cn3)CC2)n1] | 6-(1-methyl-1H-pyrazol-4-yl)-4-(6-(4-((6-methylpyrazin-2-yl)methyl)piperazin-1-yl)pyridin-3-yl)pyrazolo[1,5-a]pyridine-3-carbonitrile | 491.2 (M + H) |
| 432 | 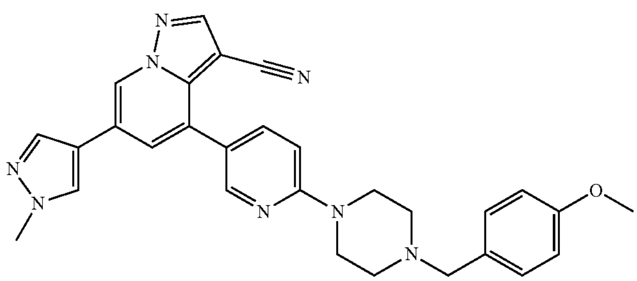 [SMILES: COc1ccc(CN2CCN(c3ccc(-c4cc(-c5cnn(C)c5)cn5ncc(C#N)c45)cn3)CC2)cc1] | 4-(6-(4-(4-methoxybenzyl)piperazin-1-yl)pyridin-3-yl)-6-(1-methyl-1H-pyrazol-4-yl)pyrazolo[1,5-a]pyridine-3-carbonitrile | 505.2 (M + H) |
| 433 | 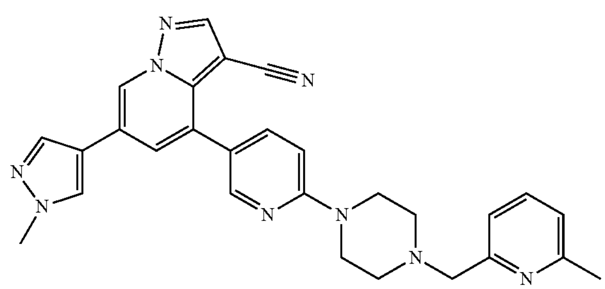 [SMILES: Cc1cccc(CN2CCN(c3ccc(-c4cc(-c5cnn(C)c5)cn5ncc(C#N)c45)cn3)CC2)n1] | 6-(1-methyl-1H-pyrazol-4-yl)-4-(6-(4-((6-methylpyridin-2-yl)methyl)piperazin-1-yl)pyridine-3-yl)pyrazolo[1,5-a]pyridine-3-carbonitrile | 490.2 (M + H) |
| 434 | 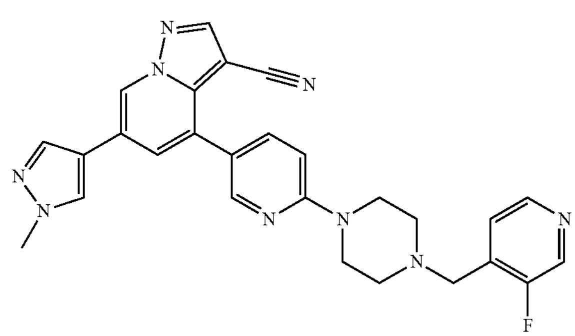 [SMILES: Cn1cc(-c2cc(-c3ccc(N4CCN(Cc5ccncc5F)CC4)nc3)c3c(C#N)cnn3c2)cn1] | 4-(6-(4-((3-fluoropyridin-4-yl)methyl)piperazin-1-yl)pyridin-3-yl)-6-(1-methyl-1H-pyrazol-4-yl)pyrazolo[1,5-a]pyridine-3-carbonitrile | 494.2 (M + H) |

TABLE OO-continued

| Ex # | Structure | Chemical Name | MS (apci) m/z |
|---|---|---|---|
| 435 | 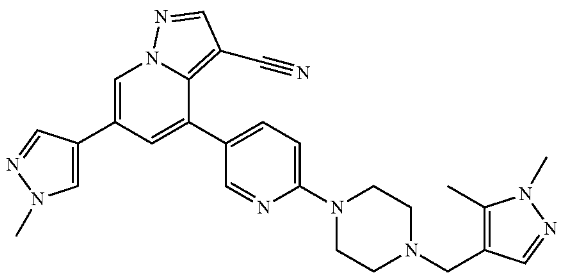 [SMILES: Cc1c(CN2CCN(c3ccc(-c4cc(-c5cnn(C)c5)cn5ncc(C#N)c45)cn3)CC2)cnn1C] | 4-(6-(4-((1,5-dimethyl-1H-pyrazol-4-yl)methyl)piperazin-1-yl)pyridin-3-yl)-6-(1-methyl-1H-pyrazol-4-yl)pyrazolo[1,5-a]pyridine-3-carbonitrile | 493.2 (M + H) |
| 436 | 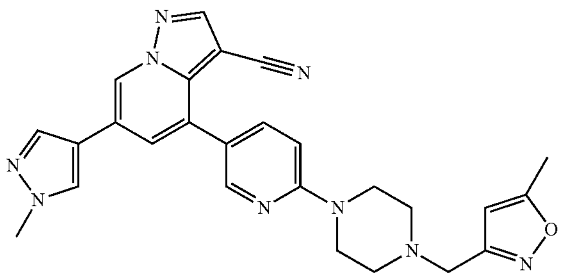 [SMILES: Cc1cc(CN2CCN(c3ccc(-c4cc(-c5cnn(C)c5)cn5ncc(C#N)c45)cn3)CC2)no1] | 6-(1-methyl-1H-pyrazol-4-yl)-4-(6-(4-((5-methylisoxazol-3-yl)methyl)piperazin-1-yl)pyridin-3-yl)pyrazolo[1,5-a]pyridine-3-carbonitrile | 480.1 (M + H) |
| 437 | 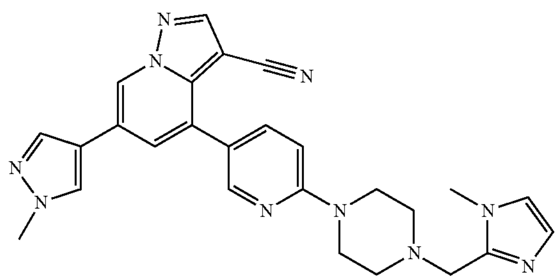 [SMILES: Cn1cc(-c2cc(-c3ccc(N4CCN(Cc5nccn5C)CC4)nc3)c3c(C#N)cnn3c2)cn1] | 4-(6-(4-((1-methyl-1H-imidazol-2-yl)methyl)piperazin-1-yl)pyridin-3-yl)-6-(1-methyl-1H-pyrazol-4-yl)pyrazolo[1,5-a]pyridine-3-carbonitrile | 479.2 (M + H) |
| 438 | 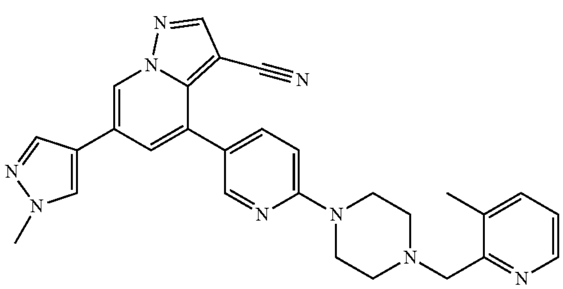 [SMILES: Cc1cccnc1CN1CCN(c2ccc(-c3cc(-c4cnn(C)c4)cn4ncc(C#N)c34)cn2)CC1] | 6-(1-methyl-1H-pyrazol-4-yl)-4-(6-(4-((3-methylpyridin-2-yl)methyl)piperazin-1-yl)pyridine-3-yl)pyrazolo[1,5-a]pyridine-3-carbonitrile | 490.2 (M + H) |
| 439 | 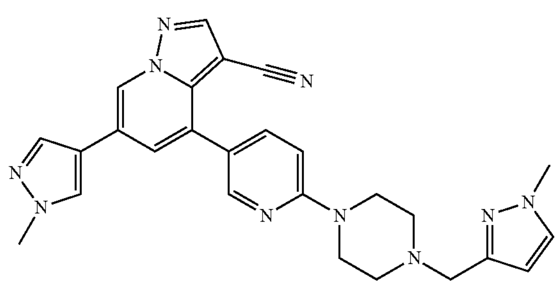 [SMILES: Cn1cc(-c2cc(-c3ccc(N4CCN(Cc5ccn(C)n5)CC4)nc3)c3c(C#N)cnn3c2)cn1] | 4-(6-(4-((1-methyl-1H-pyrazol-3-yl)methyl)piperazin-1-yl)pyridin-3-yl)-6-(1-methyl-1H-pyrazol-4-yl)pyrazolo[1,5-a]pyridine-3-carbonitrile | 479.2 (M + H) |

TABLE OO-continued

| Ex # | Structure | Chemical Name | MS (apci) m/z |
|---|---|---|---|
| 440 | 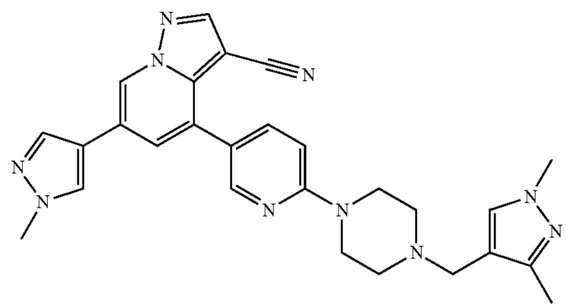 [SMILES: Cc1nn(C)cc1CN1CCN(c2ccc(-c3cc(-c4cnn(C)c4)cn4ncc(C#N)c34)cn2)CC1] | 4-(6-(4-((1,3-dimethyl-1H-pyrazol-4-yl)methyl)piperazin-1-yl)pyridine-3-yl)-6-(1-methyl-1H-pyrazol-4-yl)pyrazolo[1,5-a]pyridine-3-carbonitrile | 493.2 (M + H) |
| 441 | 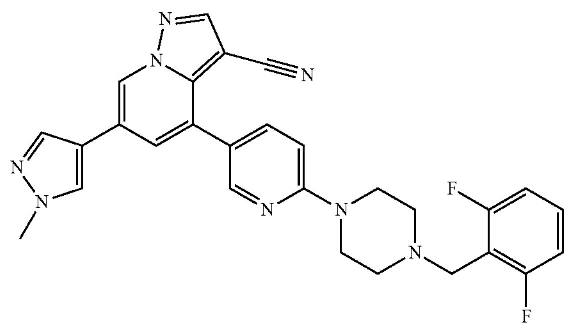 [SMILES: Cn1cc(-c2cc(-c3ccc(N4CCN(Cc5c(F)cccc5F)CC4)nc3)c3c(C#N)cnn3c2)cn1] | 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile | 511.1 (M + H) |
| 442 | 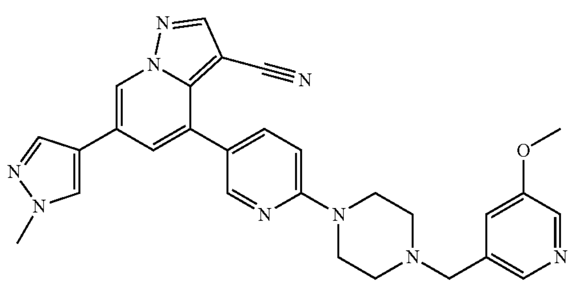 [SMILES: COc1cncc(CN2CCN(c3ccc(-c4cc(-c5cnn(C)c5)cn5ncc(C#N)c45)cn3)CC2)c1] | 4-(6-(4-((5-methoxypyridin-3-yl)methyl)piperazin-1-yl)pyridine-3-yl)-6-(1-methyl-1H-pyrazol-4-yl)pyrazolo[1,5-a]pyridine-3-carbonitrile | 506.2 (M + H) |
| 443 | 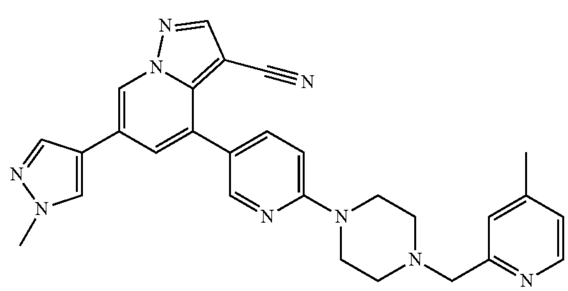 [SMILES: Cc1ccnc(CN2CCN(c3ccc(-c4cc(-c5cnn(C)c5)cn5ncc(C#N)c45)cn3)CC2)c1] | 6-(1-methyl-1H-pyrazol-4-yl)-4-(6-(4-((4-methylpyridin-2-yl)methyl)piperazin-1-yl)pyridine-3-yl)pyrazolo[1,5-a]pyridine-3-carbonitrile | 490.2 (M + H) |
| 444 | 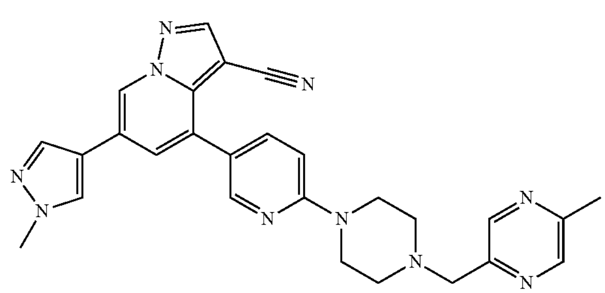 [SMILES: Cc1cnc(CN2CCN(c3ccc(-c4cc(-c5cnn(C)c5)cn5ncc(C#N)c45)cn3)CC2)cn1] | 6-(1-methyl-1H-pyrazol-4-yl)-4-(6-(4-((5-methylpyrazin-2-yl)methyl)piperazin-1-yl)pyridin-3-yl)pyrazolo[1,5-a]pyridine-3-carbonitrile | 491.1 (M + H) |

TABLE OO-continued

| Ex # | Structure | Chemical Name | MS (apci) m/z |
|---|---|---|---|
| 445 | 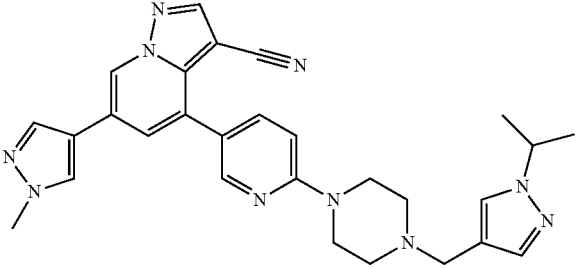 [SMILES: CC(C)n1cc(CN2CCN(c3ccc(-c4cc(-c5cnn(C)c5)cn5ncc(C#N)c45)cn3)CC2)cn1] | 4-(6-(4-((1-isopropyl-1H-pyrazol-4-yl)methyl)piperazin-1-yl)pyridin-3-yl)-6-(1-methyl-1H-pyrazol-4-yl)pyrazolo[1,5-a]pyridine-3-carbonitrile | 507.2 (M + H) |
| 446 | 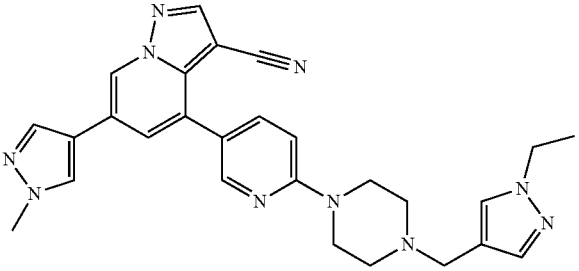 [SMILES: CCn1cc(CN2CCN(c3ccc(-c4cc(-c5cnn(C)c5)cn5ncc(C#N)c45)cn3)CC2)cn1] | 4-(6-(4-((1-ethyl-1H-pyrazol-4-yl)methyl)piperazin-1-yl)pyridin-3-yl)-6-(1-methyl-1H-pyrazol-4-yl)pyrazolo[1,5-a]pyridine-3-carbonitrile | 493.2 (M + H) |
| 447 | 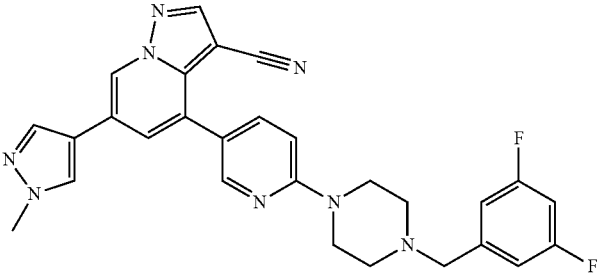 [SMILES: Cn1cc(-c2cc(-c3ccc(N4CCN(Cc5cc(F)cc(F)c5)CC4)nc3)c3c(C#N)cnn3c2)cn1] | 4-(6-(4-(3,5-difluorobenzyl)piperazin-1-yl)pyridin-3-yl)-6-(1-methyl-1H-pyrazol-4-yl)pyrazolo[1,5-a]pyridine-3-carbonitrile | 511.1 (M + H) |
| 448 | 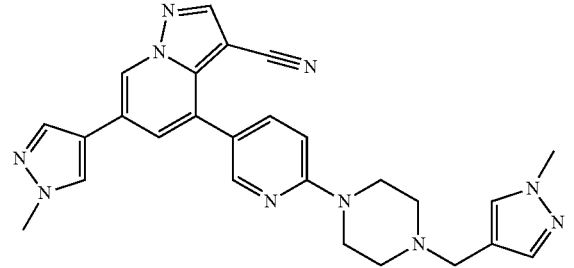 [SMILES: Cn1cc(CN2CCN(c3ccc(-c4cc(-c5cnn(C)c5)cn5ncc(C#N)c45)cn3)CC2)cn1] | 6-(1-methyl-1H-pyrazol-4-yl)-4-(6-(4-((1-methyl-1H-pyrazol-4-yl)methyl)piperazin-1-yl)pyridin-3-yl)pyrazolo[1,5-a]pyridine-3-carbonitrile | 479.2 (M + H) |
| 449 | 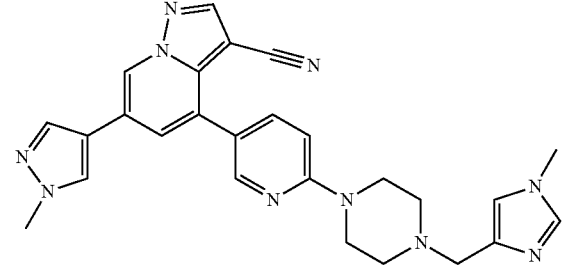 [SMILES: Cn1cnc(CN2CCN(c3ccc(-c4cc(-c5cnn(C)c5)cn5ncc(C#N)c45)cn3)CC2)c1] | 4-(6-(4-((1-methyl-1H-imidazol-4-yl)methyl)piperazin-1-yl)pyridin-3-yl)-6-(1-methyl-1H-pyrazol-4-yl)pyrazolo[1,5-a]pyridine-3-carbonitrile | 479.2 (M + H) |

TABLE OO-continued

| Ex # | Structure | Chemical Name | MS (apci) m/z |
|---|---|---|---|
| 450 | 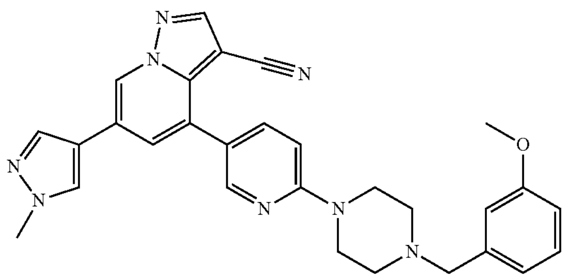 [SMILES: COc1cccc(CN2CCN(c3ccc(-c4cc(-c5cnn(C)c5)cn5ncc(C#N)c45)cn3)CC2)c1] | 4-(6-(4-(3-methoxybenzyl)piperazin-1-yl)pyridin-3-yl)-6-(1-methyl-1H-pyrazol-4-yl)pyrazolo[1,5-a]pyridine-3-carbonitrile | 505.2 (M + H) |
| 451 | 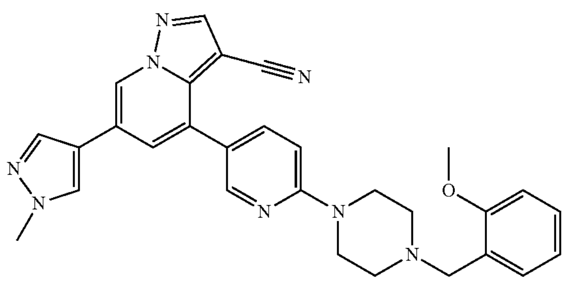 [SMILES: COc1ccccc1CN1CCN(c2ccc(-c3cc(-c4cnn(C)c4)cn4ncc(C#N)c34)cn2)CC1] | 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile | 505.2 (M + H) |
| 452 | 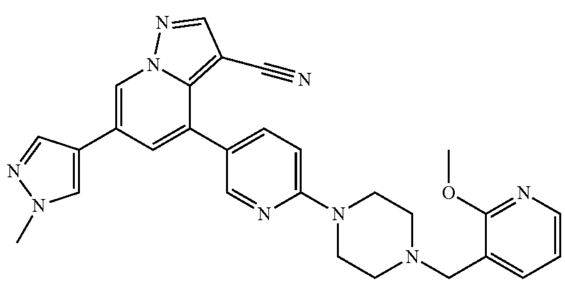 [SMILES: COc1ncccc1CN1CCN(c2ccc(-c3cc(-c4cnn(C)c4)cn4ncc(C#N)c34)cn2)CC1] | 4-(6-(4-((2-methoxypyridin-3-yl)methyl)piperazin-1-yl)pyridin-3-yl)-6-(1-methyl-1H-pyrazol-4-yl)pyrazolo[1,5-a]pyridine-3-carbonitrile | 506.2 (M + H) |
| 453 | 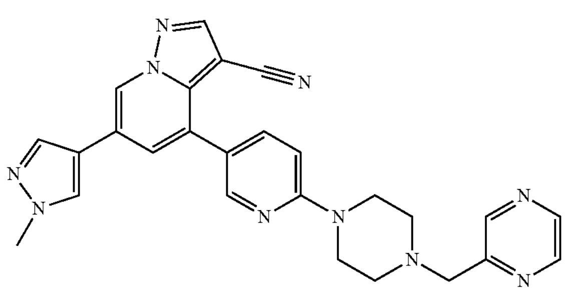 [SMILES: Cn1cc(-c2cc(-c3ccc(N4CCN(Cc5cnccn5)CC4)nc3)c3c(C#N)cnn3c2)cn1] | 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile | 477.1 (M + H) |
| 454 | 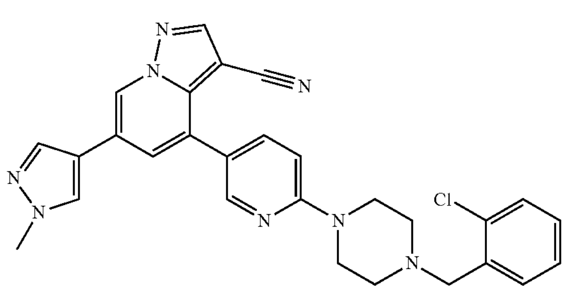 [SMILES: Cn1cc(-c2cc(-c3ccc(N4CCN(Cc5ccccc5Cl)CC4)nc3)c3c(C#N)cnn3c2)cn1] | 4-(6-(4-(2-chlorobenzyl)piperazin-1-yl)pyridin-3-yl)-6-(1-methyl-1H-pyrazol-4-yl)pyrazolo[1,5-a]pyridine-3-carbonitrile | 509.1 (M + H) |

TABLE OO-continued

| Ex # | Structure | Chemical Name | MS (apci) m/z |
|---|---|---|---|
| 455 | 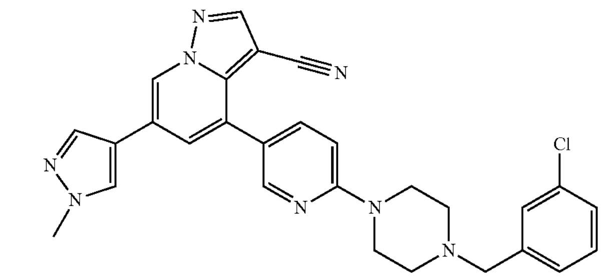 [SMILES: Cn1cc(-c2cc(-c3ccc(N4CCN(Cc5cccc(Cl)c5)CC4)nc3)c3c(C#N)cnn3c2)cn1] | 4-(6-(4-(3-chlorobenzyl)piperazin-1-yl)pyridin-3-yl)-6-(1-methyl-1H-pyrazol-4-yl)pyrazolo[1,5-a]pyridine-3-carbonitrile | 509.1 (M + H) |
| 456 | 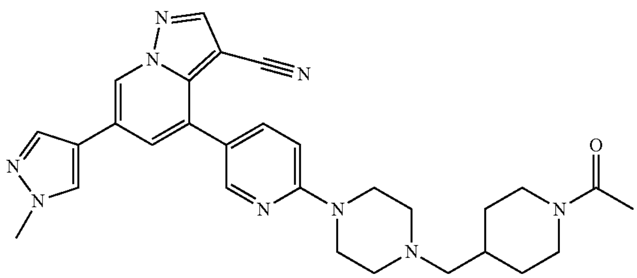 [SMILES: CC(=O)N1CCC(CN2CCN(c3ccc(-c4cc(-c5cnn(C)c5)cn5ncc(C#N)c45)cn3)CC2)CC1] | 4-(6-(4-((1-acetylpiperidin-4-yl)methyl)piperazin-1-yl)pyridin-3-yl)-6-(1-methyl-1H-pyrazol-4-yl)pyrazolo[1,5-a]pyridine-3-carbonitrile | 524.2 (M + H) |
| 457 | 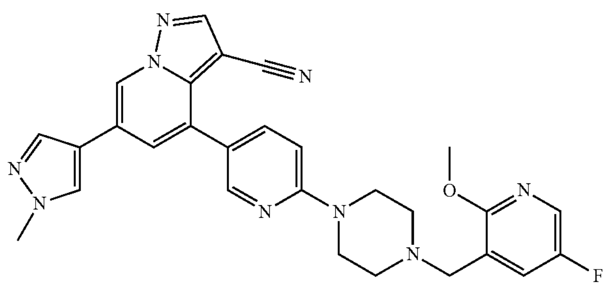 [SMILES: COc1ncc(F)cc1CN1CCN(c2ccc(-c3cc(-c4cnn(C)c4)cn4ncc(C#N)c34)cn2)CC1] | 4-(6-(4-((5-fluoro-2-methoxypyridin-3-yl)methyl)piperazin-1-yl)pyridin-3-yl)-6-(1-methyl-1H-pyrazol-4-yl)pyrazolo[1,5-a]pyridine-3-carbonitrile | 524.0 (M + H) |
| 458 | 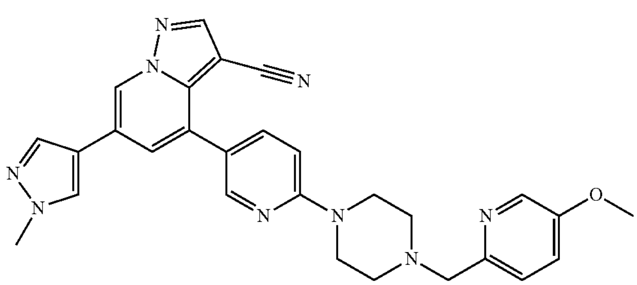 | 4-(6-(4-((5-methoxypyridin-2-yl)methyl)piperazin-1-yl)pyridin-3-yl)-6-(1-methyl-1H-pyrazol-4-yl)pyrazolo[1,5-a]pyridine-3-carbonitrile | 506.2 (M + H) |
| 459 | 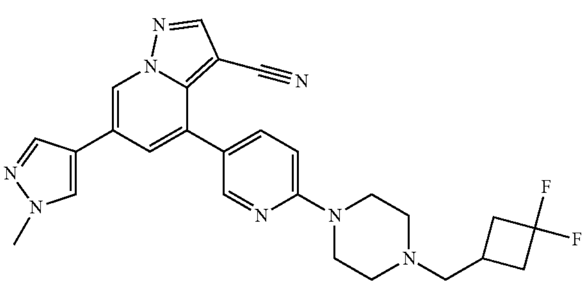 [SMILES: Cn1cc(-c2cc(-c3ccc(N4CCN(CC5CC(F)(F)C5)CC4)nc3)c3c(C#N)cnn3c2)cn1] | 4-(6-(4-((3,3-difluorocyclobutyl)methyl)piperazin-1-yl)pyridin-3-yl)-6-(1-methyl-1H-pyrazol-4-yl)pyrazolo[1,5-a]pyridine-3-carbonitrile | 489.0 (M + H) |

TABLE OO-continued

| Ex # | Structure | Chemical Name | MS (apci) m/z |
|---|---|---|---|
| 460 | 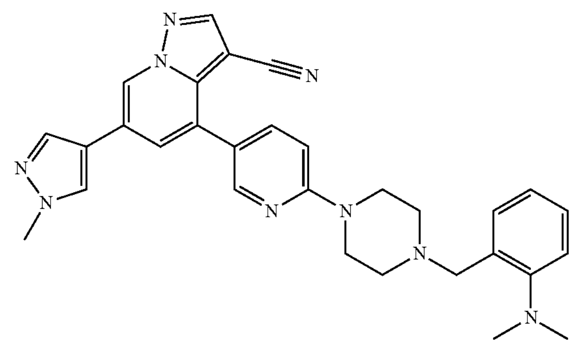 [SMILES: CN(C)c1ccccc1CN1CCN(c2ccc(-c3cc(-c4cnn(C)c4)cn4ncc(C#N)c34)cn2)CC1] | 4-(6-(4-(2-(dimethylamino)benzyl)piperazin-1-yl)pyridin-3-yl)-6-(1-methyl-1H-pyrazol-4-yl)pyrazolo[1,5-a]pyridine-3-carbonitrile | 518.0 (M + H) |
| 461 | 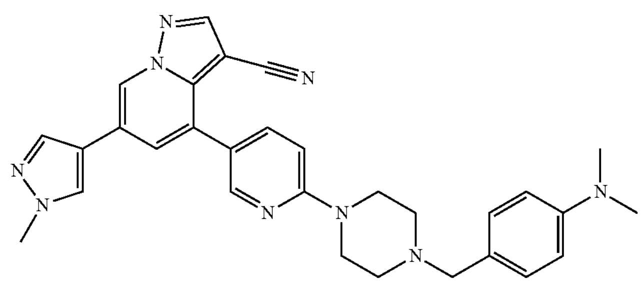 [SMILES: CN(C)c1ccc(CN2CCN(c3ccc(-c4cc(-c5cnn(C)c5)cn5ncc(C#N)c45)cn3)CC2)cc1] | 4-(6-(4-(4-(dimethylamino)benzyl)piperazin-1-yl)pyridin-3-yl)-6-(1-methyl-1H-pyrazol-4-yl)pyrazolo[1,5-a]pyridine-3-carbonitrile | 518.2 (M + H) |
| 462 | 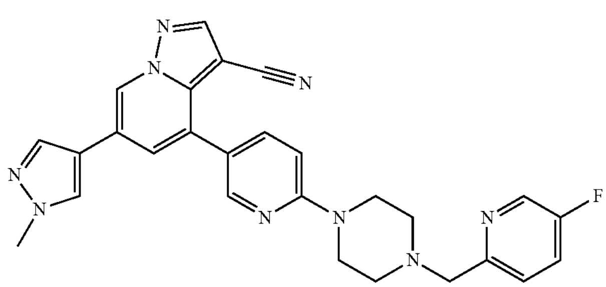 [SMILES: Cn1cc(-c2cc(-c3ccc(N4CCN(Cc5ccc(F)cn5)CC4)nc3)c3c(C#N)cnn3c2)cn1] | 4-(6-(4-((5-fluoropyridin-2-yl)methyl)piperazin-1-yl)pyridin-3-yl)-6-(1-methyl-1H-pyrazol-4-yl)pyrazolo[1,5-a]pyridine-3-carbonitrile | 494.1 (M + H) |
| 463 | 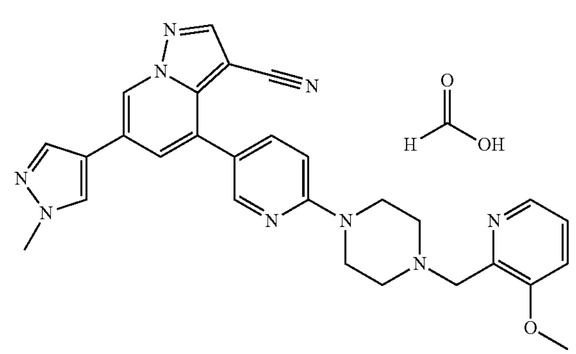 [SMILES: COc1cccnc1CN1CCN(c2ccc(-c3cc(-c4cnn(C)c4)cn4ncc(C#N)c34)cn2)CC1 ; O=CO] | 4-(6-(4-((3-methoxypyridin-2-yl)methyl)piperazin-1-yl)pyridin-3-yl)-6-(1-methyl-1H-pyrazol-4-yl)pyrazolo[1,5-a]pyridine-3-carbonitrile formate | 506.1 (M + H) |

Example 464

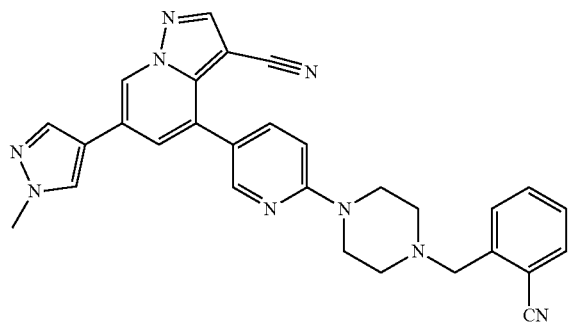 [SMILES: Cn1cc(-c2cc(-c3ccc(N4CCN(Cc5ccccc5C#N)CC4)nc3)c3c(C#N)cnn3c2)cn1]

4-(6-(4-(2-cyanobenzyl)piperazin-1-yl)pyridin-3-yl)-6-(1-methyl-1H-pyrazol-4-yl)pyrazolo[1,5-a]pyridine-3-carbonitrile A room temperature suspension of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 50 mg, 0.11 mmol) in DMF (1.1 mL) was treated with 2-formylbenzonitrile (22 mg, 0.16 mmol) and TEA (46 μL, 0.33 mmol). The mixture was acidified to pH 6 with acetic acid, and then stirred for 2 h at room temperature. NaBH$_3$CN (14 mg, 0.22 mmol) was added to the reaction mixture. The resulting mixture was stirred for 18 h at room temperature. The reaction mixture was warmed briefly, filtered to remove particulates, and the filtrate was purified by C18 reverse phase chromatography (5-50% ACN/water as the gradient eluent) to afford the title compound (24.8 mg, 44% yield). MS (apci) m/z=500.2 (M+H).

The compounds in Table PP were prepared according to the method described for the synthesis of Example 464, replacing 2-formylbenzonitrile with the appropriate aldehyde. Reactions were monitored for completion by LCMS, and reaction times were adjusted accordingly. The title compounds were cleanly isolated following C18 reverse phase chromatography using an appropriate gradient eluent, except where noted.

TABLE PP

| Ex. # | Structure | Chemical Name | MS (apci) m/z |
|---|---|---|---|
| 465* | 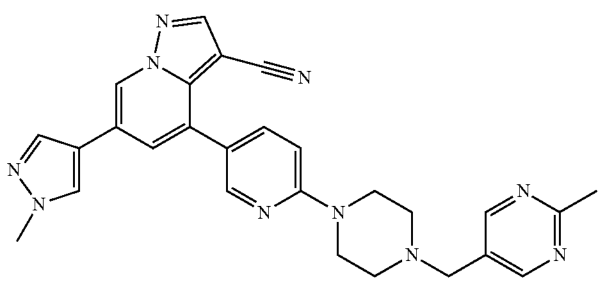 [SMILES: Cc1ncc(CN2CCN(c3ccc(-c4cc(-c5cnn(C)c5)cn5ncc(C#N)c45)cn3)CC2)cn1] | 6-(1-methyl-1H-pyrazol-4-yl)-4-(6-(4-((2-methylpyrimidin-5-yl)methyl)piperazin-1-yl)pyridin-3-yl)pyrazolo[1,5-a]pyridine-3-carbonitrile | 491.2 (M + H) |
| 466* | 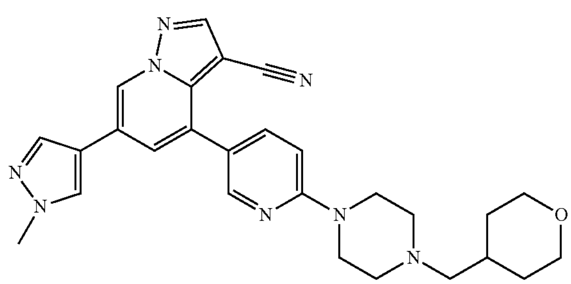 [SMILES: Cn1cc(-c2cc(-c3ccc(N4CCN(CC5CCOCC5)CC4)nc3)c3c(C#N)cnn3c2)cn1] | 6-(1-methyl-1H-pyrazol-4-yl)-4-(6-(4-((tetrahydro-2H-pyran-4-yl)methyl)piperazin-1-yl)pyridin-3-yl)pyrazolo[1,5-a]pyridine-3-carbonitrile | 483.2 (M + H) |
| 467 | 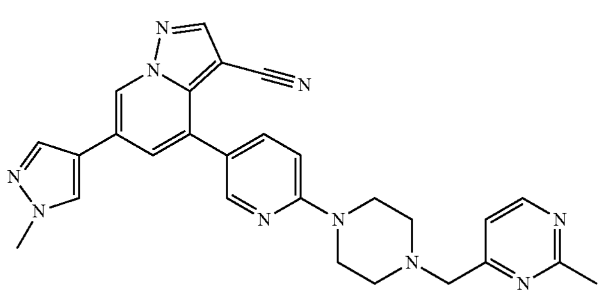 [SMILES: Cc1nccc(CN2CCN(c3ccc(-c4cc(-c5cnn(C)c5)cn5ncc(C#N)c45)cn3)CC2)n1] | 6-(1-methyl-1H-pyrazol-4-yl)-4-(6-(4-((2-methylpyrimidin-4-yl)methyl)piperazin-1-yl)pyridin-3-yl)pyrazolo[1,5-a]pyridine-3-carbonitrile | 491.2 (M + H) |

TABLE PP-continued

| Ex. # | Structure | Chemical Name | MS (apci) m/z |
|---|---|---|---|
| 468 | 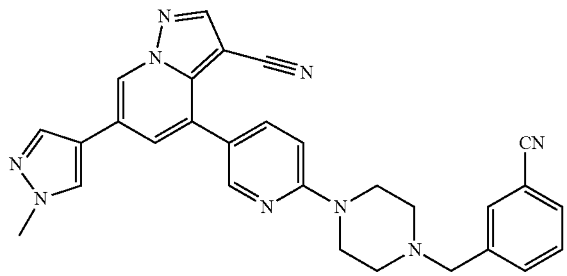 [SMILES: Cn1cc(-c2cc(-c3ccc(N4CCN(Cc5cccc(C#N)c5)CC4)nc3)c3c(C#N)cnn3c2)cn1] | 4-(6-(4-(3-cyanobenzyl)piperazin-1-yl)pyridin-3-yl)-6-(1-methyl-1H-pyrazol-4-yl)pyrazolo[1,5-a]pyridine-3-carbonitrile | 500.2 (M + H) |
| 469 | 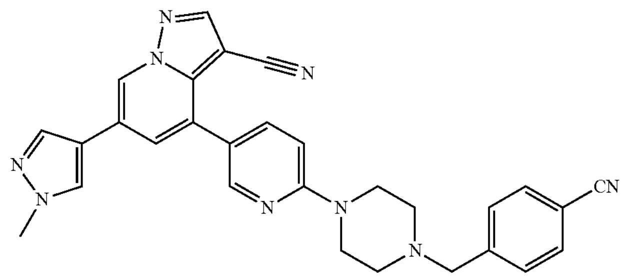 [SMILES: Cn1cc(-c2cc(-c3ccc(N4CCN(Cc5ccc(C#N)cc5)CC4)nc3)c3c(C#N)cnn3c2)cn1] | 4-(6-(4-(4-cyanobenzyl)piperazin-1-yl)pyridin-3-yl)-6-(1-methyl-1H-pyrazol-4-yl)pyrazolo[1,5-a]pyridine-3-carbonitrile | 500.2 (M + H) |
| 470 | 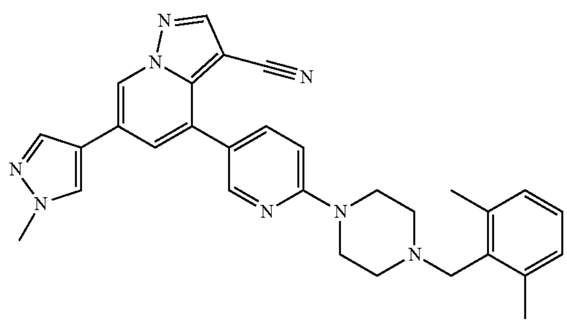 [SMILES: Cc1cccc(C)c1CN1CCN(c2ccc(-c3cc(-c4cnn(C)c4)cn4ncc(C#N)c34)cn2)CC1] | 4-(6-(4-(2,6-dimethylbenzyl)piperazin-1-yl)pyridin-3-yl)-6-(1-methyl-1H-pyrazol-4-yl)pyrazolo[1,5-a]pyridine-3-carbonitrile | 503.2 (M + H) |

*purified by an aqueous work up: partitioned between EtOAc and water; aqueous extract was neutralized (to pH 7) with saturated NaHCO₃, then extracted with EtOAc, and the combined organic extracts were dried over anhydrous Na₂SO₄, filtered, and concentrated in vacuo prior to chromatographic purification.

Example 471

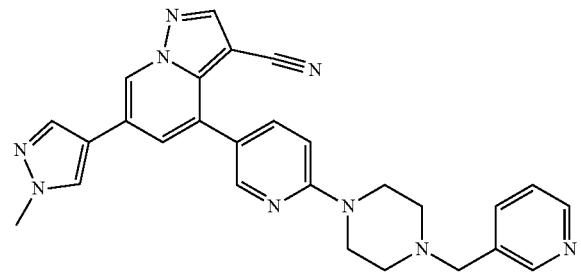 [SMILES: Cn1cc(-c2cc(-c3ccc(N4CCN(Cc5cccnc5)CC4)nc3)c3c(C#N)cnn3c2)cn1]

6-(1-methyl-1H-pyrazol-4-yl)-4-(6-(4-(pyridin-3-ylmethyl)piperazin-1-yl)pyridine-3-yl)pyrazolo[1,5-a]pyridine-3-carbonitrile A room temperature solution of 6-(1-methyl-1H-pyrazol-4-yl)-4-(6-(piperazin-1-yl)pyridine-3-yl)pyrazolo[1,5-a]pyridin-3-carbonitrile dihydrochloride (Example 2; 10 mg, 0.022 mmol) in DMF (0.2 mL) was treated with nicotinaldehyde (3.5 mg, 0.033 mmol), Me₄N(AcO)₃BH (14 mg, 0.22 mmol) and TEA (9.1 µL, 0.066 mmol). The resulting mixture was stirred for 18 h at room temperature, then purified directly by C18 reverse phase chromatography (5-60% ACN/water as the gradient eluent) to afford the title compound (6.5 mg, 63% yield). MS (apci) m/z=476.1 (M+H).

Example 472

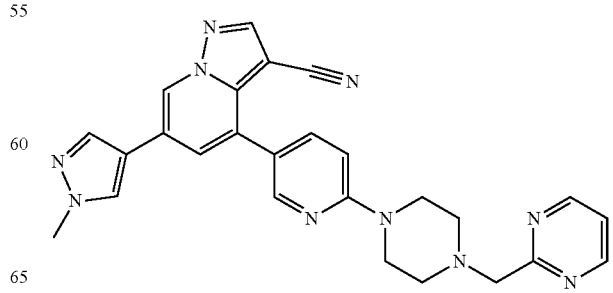

6-(1-methyl-1H-pyrazol-4-yl)-4-(6-(4-(pyrimidin-2-ylmethyl)piperazin-1-yl)pyridin-3-yl)pyrazolo[1,5-a]pyridine-3-carbonitrile A room temperature solution of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 0.128 g, 0.280 mmol) in dry DMA (3 mL) was treated with TEA (117 μL, 0.840 mmol), Me₄N(AcO)₃BH (147 mg, 0.560 mmol) and 2-pyrimidine carboxaldehyde (60.5 mg, 0.560 mmol). The resulting mixture was stirred for 3 d at room temperature, and then additional TEA (39 μL, 0.280 mmol), Me₄N(AcO)₃BH (73.5 mg, 0.187 mmol) and 2-pyrimidine carboxaldehyde (20.2 mg, 0.28 mmol) were added. After stirring an additional 24 h at room temperature, the reaction mixture was quenched with water and CHCl₃, and allowed to stir for 20 min. The resulting biphasic mixture was filtered through a PS frit, and the aqueous layer was washed with CHCl₃. The organic filtrate was concentrated in vacuo, and the residue was purified by C18 reverse phase chromatography (15-90% ACN/water as the gradient eluent) to afford the title compound (60 mg, 45% yield). MS (apci) m/z=477.1 (M+H).

Example 473

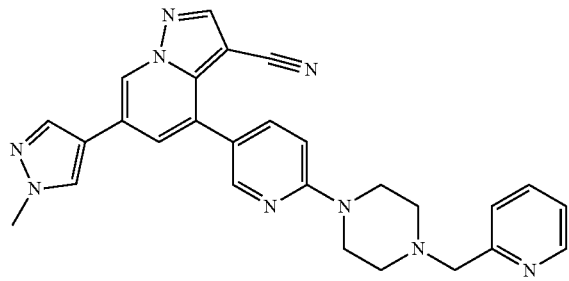 [SMILES: Cn1cc(-c2cc(-c3ccc(N4CCN(Cc5ccccn5)CC4)nc3)c3c(C#N)cnn3c2)cn1]

6-(1-methyl-1H-pyrazol-4-yl)-4-(6-(4-(pyridine-2-ylmethyl)piperazin-1-yl)pyridine-3-yl)pyrazolo[1,5-a]pyridine-3-carbonitrile A room temperature solution of 6-(1-methyl-1H-pyrazol-4-yl)-4-(6-(piperazin-1-yl)pyridine-3-yl)pyrazolo[1,5-a]pyridine-3-carbonitrile dihydrochloride (Example 2; 10 mg, 0.022 mmol) in DMF (0.2 mL) was treated with picolinaldehyde (3.5 mg, 0.033 mmol), Me₄N(AcO)₃BH (12 mg, 0.044 mmol) and TEA (9.1 μL, 0.066 mmol). The resulting mixture was stirred overnight at room temperature, then purified directly by C18 reverse phase chromatography (0-60% ACN/water as the gradient eluent) to afford the title compound (5.5 mg, 53% yield). MS (apci) m/z=476.2 (M+H).

Example 474

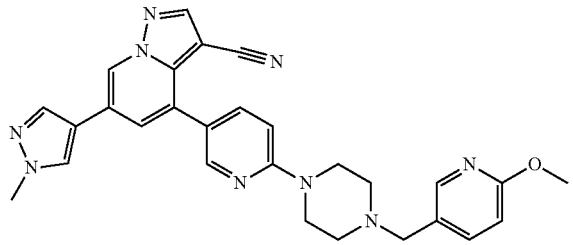

4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile A room temperature solution of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 0.125 g, 0.273 mmol) in dry DMA (2.5 mL) was treated with TEA (114 μL, 0.820 mmol), Me₄N(AcO)₃BH (144 mg, 0.547 mmol) and 6-methoxynicotinaldehyde (0.0750 g, 0.547 mmol). The resulting mixture was stirred overnight at room temperature, then quenched with water and CHCl₃ and allowed to stir for 30 min. The resulting biphasic mixture was filtered through a PS frit, and the aqueous layer was washed with CHCl₃. The organic filtrate was concentrated in vacuo, and the residue was purified by C18 reverse-phase chromatography (5-90% ACN/water as the gradient eluent) to afford the title compound (56 mg, 41% yield). MS (apci) m/z=506.0 (M+H).

Example 475

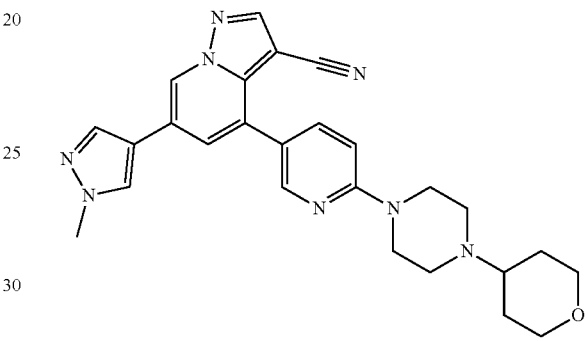

6-(1-methyl-1H-pyrazol-4-yl)-4-(6-(4-(tetrahydro-2H-pyran-4-yl)piperazin-1-yl)pyridin-3-yl)pyrazolo[1,5-a]pyridine-3-carbonitrile A room temperature solution of 6-(1-methyl-1H-pyrazol-4-yl)-4-(6-(piperazin-1-yl)pyridine-3-yl)pyrazolo[1,5-a]pyridin-3-carbonitrile dihydrochloride (Example 2; 0.0208 g, 0.0455 mmol) in dry DMF (0.4 mL) was treated with TEA (19.0 μL, 0.136 mmol), dihydro-2H-pyran-4(3H)-one (15.0 μL, 0.091 mmol) and Me₄N(AcO)₃BH (23.9 mg, 0.091 mmol). The resulting mixture was stirred overnight at 80° C., and then additional dihydro-2H-pyran-4(3H)-one (15.0 μL, 0.091 mmol) was added. The reaction mixture was allowed to stir at 80° C. until complete by LCMS, and then cooled to room temperature. The reaction mixture was purified directly by C18 reverse phase chromatography (10-99% ACN/Water as the gradient eluent) to afford the title compound (4.4 mg, 21% yield). MS (apci) m/z=469.1 (M+H).

Example 476

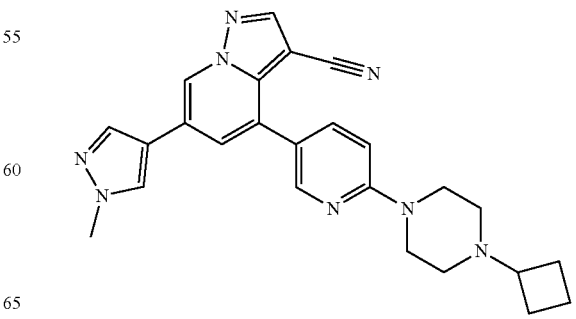

4-(6-(4-cyclobutylpiperazin-1-yl)pyridin-3-yl)-6-(1-methyl-1H-pyrazol-4-yl)pyrazolo[1,5-a]pyridine-3-carbonitrile A room temperature solution of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 0.018 g, 0.0394 mmol) in dry DMF (0.3 mL) was treated with TEA (16.5 µL, 0.118 mmol), cyclobutanone (10.0 µL, 0.0787 mmol) and Me$_4$N(AcO)$_3$BH (20.7 mg, 0.0787 mmol). The mixture was stirred overnight at 70° C., and then additional cyclobutanone (10.0 µL, 0.0787 mmol) and TEA (25 µL, 0.179 mmol) were added. The reaction mixture was allowed to stir at 80° C. overnight, then cooled to room temperature and purified directly by C18 reverse phase chromatography (10-99% ACN/Water as the gradient eluent) to afford the title compound (8 mg, 46% yield). MS (apci) m/z=439.2 (M+H).

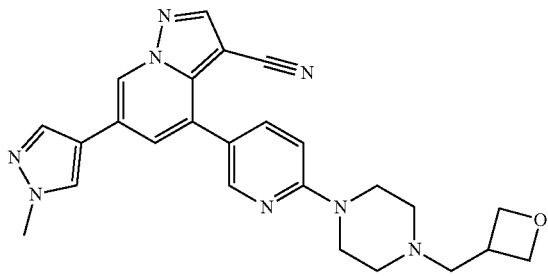 [SMILES: Cn1cc(-c2cc(-c3ccc(N4CCN(CC5COC5)CC4)nc3)c3c(C#N)cnn3c2)cn1]

Example 477

6-(1-methyl-1H-pyrazol-4-yl)-4-(6-(4-(oxetan-3-ylmethyl)piperazin-1-yl)pyridin-3-yl)pyrazolo[1,5-a]pyridine-3-carbonitrile A room temperature solution of 6-(1-methyl-1H-pyrazol-4-yl)-4-(6-(piperazin-1-yl)pyridin-3-yl)pyrazolo[1,5-a]pyridine-3-carbonitrile (Example 2a; 34.3 mg, 0.0892 mmol) in dry DCM (1.8 mL) was treated with oxetane-3-carbaldehyde (11.5 mg, 0.134 mmol), NaBH(AcO)$_3$ (28.4 mg, 0.134 mmol) and acetic acid (25.5 µL, 0.446 mmol). The resulting reaction mixture was allowed to stir 16 h at room temperature. The reaction mixture was diluted with DCM, and washed with saturated NaHCO$_3$. The combined organic extracts were dried over anhydrous Na$_2$SO$_4$, filtered, and concentrated in vacuo. The residue was purified by C18 reverse phase chromatography (5-95% water/ACN with 0.1% TFA as the gradient eluent) to afford the title compound as the TFA salt. The TFA salt was partitioned between 4:1 DCM/iPrOH and saturated NaHCO$_3$. The combined organic extracts were dried over anhydrous Na$_2$SO$_4$, filtered and concentrated in vacuo to afford the title compound (8 mg, 46% yield). MS (apci) m/z=455.2 (M+H).

The compounds in Table QQ were prepared according to the method described for the synthesis of Example 477, replacing oxetane-3-carbaldehyde with the appropriate aldehyde. Reactions were monitored for completion by LCMS, and reaction times were adjusted accordingly. The title compounds were cleanly isolated following C18 reverse phase chromatography using an appropriate gradient eluent.

TABLE QQ

| Ex # | Structure | Chemical Name | MS (apci) m/z |
|---|---|---|---|
| 478 | 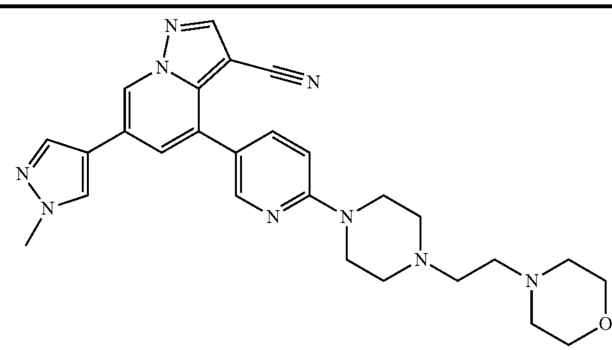 | 6-(1-methyl-1H-pyrazol-4-yl)-4-(6-(4-(2-morpholinoethyl)piperazin-1-yl)pyridin-3-yl)pyrazolo[1,5-a]pyridine-3-carbonitrile | 498.2 (M + H) |
| 479 | 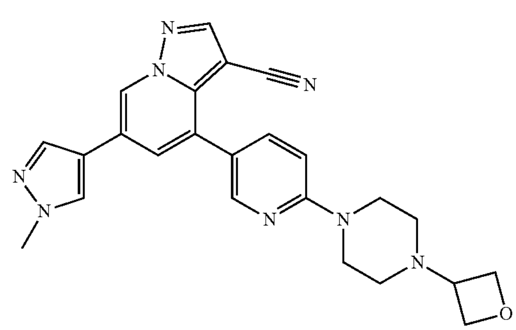 [SMILES: Cn1cc(-c2cc(-c3ccc(N4CCN(C5COC5)CC4)nc3)c3c(C#N)cnn3c2)cn1] | 6-(1-methyl-1H-pyrazol-4-yl)-4-(6-(4-(oxetan-3-yl)piperazin-1-yl)pyridin-3-yl)pyrazolo[1,5-a]pyridine-3-carbonitrile | 441.2 (M + H) |

Example 480

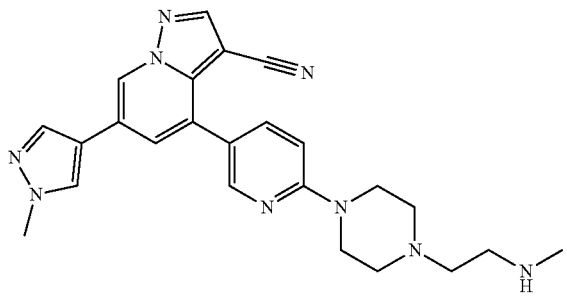 [SMILES: CNCCN1CCN(c2ccc(-c3cc(-c4cnn(C)c4)cn4ncc(C#N)c34)cn2)CC1]

6-(1-methyl-1H-pyrazol-4-yl)-4-(6-(4-(2-(methyl-amino)ethyl)piperazin-1-yl)pyridin-3-yl)pyrazolo[1,5-a]pyridine-3-carbonitrile A room temperature solution of 6-(1-methyl-1H-pyrazol-4-yl)-4-(6-(piperazin-1-yl)pyridin-3-yl)pyrazolo[1,5-a]pyridine-3-carbonitrile (Example 2a; 41.6 mg, 0.108 mmol) in dry DCM (1.1 mL) was treated with tert-butyl methyl(2-oxoethyl)carbamate (28.1 mg, 0.162 mmol), and then with NaBH(AcO)$_3$ (34.4 mg, 0.162 mmol). The reaction mixture was allowed to stir for 16 h at room temperature. The reaction mixture was diluted with DCM and washed with saturated NaHCO$_3$. The combined organic extracts were dried over anhydrous Na$_2$SO$_4$, filtered, and concentrated in vacuo. The residue was dissolved in 1:1 DCM/TFA (1.1 mL), stirred for 30 min at room temperature, and concentrated in vacuo. The residue was purified by C18 reverse phase chromatography (5-95% water/ACN with 0.1% TFA as the gradient eluent) to afford the title compound as the TFA salt. The TFA salt was partitioned between 4:1 DCM/iPrOH and saturated NaHCO$_3$. The combined organic extracts were dried over anhydrous Na$_2$SO$_4$, filtered and concentrated in vacuo to afford the title compound (24.5 mg, 51% yield). MS (apci) m/z=442.2 (M+H).

Example 481

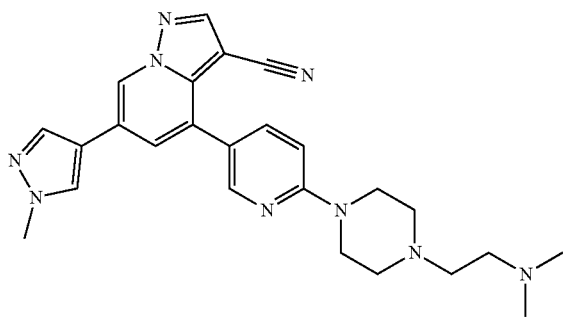 [SMILES: CN(C)CCN1CCN(c2ccc(-c3cc(-c4cnn(C)c4)cn4ncc(C#N)c34)cn2)CC1]

4-(6-(4-(2-(dimethylamino)ethyl)piperazin-1-yl)pyridin-3-yl)-6-(1-methyl-1H-pyrazol-4-yl)pyrazolo[1,5-a]pyridine-3-carbonitrile A room temperature solution of 6-(1-methyl-1H-pyrazol-4-yl)-4-(6-(4-(2-(methylamino)ethyl)piperazin-1-yl)pyridin-3-yl)pyrazolo[1,5-a]pyridine-3-carbonitrile (Example 480; 18.0 mg, 0.0408 mmol) in formic acid (308 µL) was treated with formaldehyde (91.9 µL, 1.22 mmol), and stirred at 80° C. for 16 h. The reaction mixture was cooled to room temperature, concentrated in vacuo, and purified by C18 reverse phase chromatography (5-95% water/ACN with 0.1% TFA) to afford the title compound as the TFA salt. The TFA salt was partitioned between 4:1 DCM/iPrOH and saturated NaHCO$_3$. The combined organic extracts were dried over anhydrous Na$_2$SO$_4$, filtered, and concentrated in vacuo to afford the title compound (9.8 mg, 53% yield). MS (apci) m/z=456.2 (M+H).

Example 482

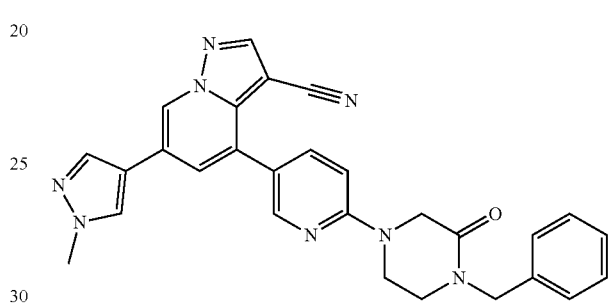

4-(6-(4-benzyl-3-oxopiperazin-1-yl)pyridin-3-yl)-6-(1-methyl-1H-pyrazol-4-yl)pyrazolo[1,5-a]pyridine-3-carbonitrile In a microwave vessel, a room temperature solution of 4-(6-fluoropyridin-3-yl)-6-(1-methyl-1H-pyrazol-4-yl)pyrazolo[1,5-a]pyridine-3-carbonitrile (Intermediate P6; 50 mg, 0.16 mmol) in DMSO (785 µL) was treated with 1-benzylpiperazin-2-one (59.8 mg, 0.314 mmol) and K$_2$CO$_3$ (65.1 mg, 0.471 mmol). The resulting mixture was subjected to microwave irradiation for 4 h at 150° C. The reaction mixture was cooled to room temperature and filtered. The filtrate was purified directly by C18 reverse phase chromatography (5-65% ACN/water) to afford the title compound (42.4 mg, 54% yield). MS (apci) m/z=489.2 (M+H).

Example 483

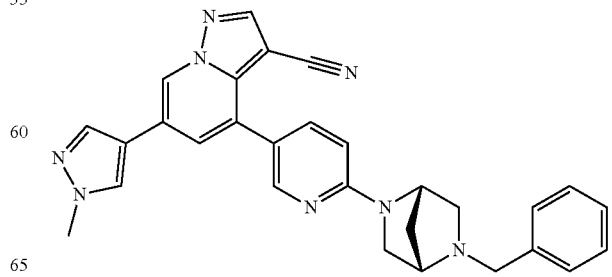

4-(6-((1S,4S)-5-benzyl-2,5-diazabicyclo[2.2.1]heptan-2-yl)pyridin-3-yl)-6-(1-methyl-1H-pyrazol-4-yl)pyrazolo[1,5-a]pyridine-3-carbonitrile Step 1: Preparation of 4-(6-((1S,4S)-2,5-diazabicyclo[2.2.1]heptan-2-yl)pyridin-3-yl)-6-(1-methyl-1H-pyrazol-4-yl)pyrazolo[1,5-a]pyridine-3-carbonitrile (1S,4S)-tert-butyl 5-(5-(3-cyano-6-(1-methyl-1H-pyrazol-4-yl)pyrazolo[1,5-a]pyridin-4-yl)pyridine-2-yl)-2,5-diazabicyclo[2.2.1]heptane-2-carboxylate (Example 170; 75 mg, 0.15 mmol) was dissolved in 1:1 DCM/TFA (2.0 mL) at room temperature. The reaction mixture was stirred for 1 h at room temperature, and then concentrated in vacuo. The residue was purified by silica chromatography (1-30% DCM/MeOH with 2% NH₄OH as the gradient eluent) to afford the title compound (59.8 mg, quantitative yield). MS (apci) m/z=397.2 (M+H).

Step 2: Preparation of 4-(6-((1S,4S)-5-benzyl-2,5-diazabicyclo[2.2.1]heptan-2-yl)pyridin-3-yl)-6-(1-methyl-1H-pyrazol-4-yl)pyrazolo[1,5-a]pyridine-3-carbonitrile A room temperature solution of 4-(6-((1S,4S)-2,5-diazabicyclo[2.2.1]heptan-2-yl)pyridin-3-yl)-6-(1-methyl-1H-pyrazol-4-yl)pyrazolo[1,5-a]pyridine-3-carbonitrile (59.8 mg, 0.151 mmol) in DCM (1.5 mL) was treated sequentially with TEA (102 μL, 0.754 mmol) and benzyl bromide (53.7 μL, 0.453 mmol). The reaction mixture was stirred for 16 h at room temperature, then concentrated in vacuo. The residue was purified by C18 reverse phase chromatography (5-95% water/ACN as the gradient eluent) to afford the title compound as the TFA salt. The TFA salt was suspended in 4:1 DCM/iPrOH and extracted with saturated NaHCO₃. The combined organic extracts were dried over anhydrous Na₂SO₄, filtered, and concentrated in vacuo to cleanly afford the title compound (35.3 mg, 48% yield). MS (apci) m/z=487.2 (M+H).

The compounds in Table RR were prepared according to the method described for the synthesis of Example 483, replacing (1S,4S)-tert-butyl 5-(5-(3-cyano-6-(1-methyl-1H-pyrazol-4-yl)pyrazolo[1,5-a]pyridin-4-yl)pyridine-2-yl)-2,5-diazabicyclo[2.2.1]heptane-2-carboxylate (Example 170) with the appropriate amino starting materials. Reactions were monitored by LCMS, and reaction times were adjusted accordingly to cleanly afford the title compounds.

TABLE RR

| Ex # | Structure | Chemical Name | MS (apci) m/z |
|---|---|---|---|
| 484 | 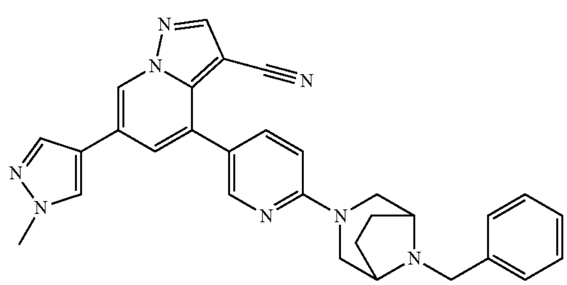 [SMILES: Cn1cc(-c2cc(-c3ccc(N4CC5CCC(C4)N5Cc4ccccc4)nc3)c3c(C#N)cnn3c2)cn1] | 4-(6-(8-benzyl-3,8-diazabicyclo[3.2.1]octan-3-yl)pyridin-3-yl)-6-(1-methyl-1H-pyrazol-4-yl)pyrazolo[1,5-a]pyridine-3-carbonitrile | 501.2 (M + H) |
| 485 | 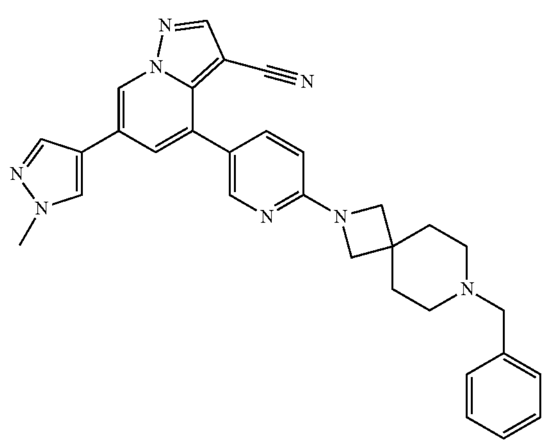 [SMILES: Cn1cc(-c2cc(-c3ccc(N4CC5(CCN(Cc6ccccc6)CC5)C4)nc3)c3c(C#N)cnn3c2)cn1] | 4-(6-(7-benzyl-2,7-diazaspiro[3.5]nonan-2-yl)pyridin-3-yl)-6-(1-methyl-1H-pyrazol-4-yl)pyrazolo[1,5-a]pyridine-3-carbonitrile | 515.2 (M + H) |

Example 486

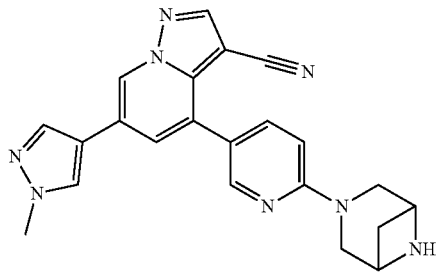 [SMILES: Cn1cc(-c2cc(-c3ccc(N4CC5CC(C4)N5)nc3)c3c(C#N)cnn3c2)cn1]

4-(6-(3,6-Diazabicyclo[3.1.1]heptan-3-yl)pyridin-3-yl)-6-(1-methyl-1H-pyrazol-4-yl)pyrazolo[1,5-a]pyridine-3-carbonitrile

Step 1: Preparation of Tert-Butyl 3-(5-(3-cyano-6-(1-methyl-1H-pyrazol-4-yl)pyrazolo[1,5-a]pyridine-4-yl)pyridin-2-yl)-3,6-diazabicyclo[3.1.1]heptane-6-carboxylate A room temperature mixture of 4-(6-fluoropyridin-3-yl)-6-(1-methyl-1H-pyrazol-4-yl)pyrazolo[1,5-a]pyridine-3-carbonitrile (Intermediate P6; 48.1 mg, 0.151 mmol) in s-BuOH (1.5 mL) was treated with 3,6-diaza-bicyclo[3.1.1]heptane-6-carboxylic acid tert-butyl ester (31.5 mg, 0.159 mmol) and DIEA (132 µL, 0.756 mmol). The reaction mixture was stirred for 16 h at 130° C., and then DMSO (1 mL) was added to alleviate solubility issues. The reaction mixture was stirred for an additional 24 h at 130° C., after which time additional 3,6-diaza-bicyclo[3.1.1]heptane-6-carboxylic acid tert-butyl ester (32 mg, 0.16 mmol) and DIEA (132 µL, 0.756 mmol) were added. The reaction mixture was stirred for an additional period of 60 h at 130° C., then cooled to room temperature, diluted with EtOAc, and washed successively with water and brine. The combined organic extracts were dried over anhydrous Na₂SO₄, filtered, and concentrated in vacuo to afford the title compound which was directly carried on to Step 2 without further purification. MS (apci) m/z=497.2 (M+H).

Step 2: Preparation of 4-(6-(3,6-diazabicyclo[3.1.1]heptan-3-yl)pyridin-3-yl)-6-(1-methyl-1H-pyrazol-4-yl)pyrazolo[1,5-a]pyridine-3-carbonitrile The tert-butyl 3-(5-(3-cyano-6-(1-methyl-1H-pyrazol-4-yl)pyrazolo[1,5-a]pyridin-4-yl)pyridin-2-yl)-3,6-diazabicyclo[3.1.1]heptane-6-carboxylate residue was dissolved in 1:1 DCM/TFA (2.0 mL), stirred for 1 h at room temperature, then concentrated in vacuo. The residue was purified by silica chromatography (1-30% DCM/MeOH with 2% NH₄OH as the gradient eluent) to cleanly afford the title compound (59.9 mg, quantitative yield). MS (apci) m/z=397.2 (M+H).

Example 487

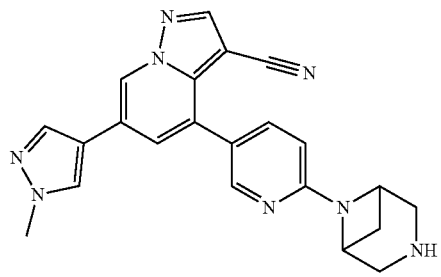 [SMILES: Cn1cc(-c2cc(-c3ccc(N4C5CNCC4C5)nc3)c3c(C#N)cnn3c2)cn1]

4-(6-(3,6-Diazabicyclo[3.1.1]heptan-6-yl)pyridine-3-yl)-6-(1-methyl-1H-pyrazol-4-yl)pyrazolo[1,5-a]pyridine-3-carbonitrile

Step 1: Preparation of Tert-Butyl 6-(5-(3-cyano-6-(1-methyl-1H-pyrazol-4-yl)pyrazolo[1,5-a]pyridine-4-yl)pyridine-2-yl)-3,6-diazabicyclo[3.1.1]heptane-3-carboxylate A room temperature mixture of 4-(6-fluoropyridin-3-yl)-6-(1-methyl-1H-pyrazol-4-yl)pyrazolo[1,5-a]pyridine-3-carbonitrile (Intermediate P6; (38.7 mg, 0.122 mmol) in DMSO (1.2 mL) was treated with 3,6-diaza-bicyclo[3.1.1]heptane-3-carboxylic acid tert-butyl ester (25.3 mg, 0.128 mmol) and DIEA (106 µL, 0.608 mmol). The reaction mixture was stirred for 16 h at 130° C., and then additional 3,6-diaza-bicyclo[3.1.1]heptane-3-carboxylic acid tert-butyl ester (25 mg, 0.13 mmol) and DIEA (106 µL, 0.608 mmol) were added. The reaction mixture was stirred for an additional 60 h at 130° C., then cooled to room temperature, diluted with EtOAc, and washed successively with water and brine. The combined organic extracts were dried over anhydrous Na₂SO₄, filtered, and concentrated in vacuo to afford the title compound which was directly carried on to Step 2 without further purification. MS (apci) m/z=497.2 (M+H).

Step 2: Preparation of 4-(6-(3,6-Diazabicyclo[3.1.1]heptan-6-yl)pyridin-3-yl)-6-(1-methyl-1H-pyrazol-4-yl)pyrazolo[1,5-a]pyridine-3-carbonitrile tert-butyl 6-(5-(3-cyano-6-(1-methyl-1H-pyrazol-4-yl)pyrazolo[1,5-a]pyridine-4-yl)pyridin-2-yl)-3,6-diazabicyclo[3.1.1]heptane-3-carboxylate was dissolved in 1:1 DCM/TFA (2.0 mL), stirred for 1 h at room temperature, and then concentrated in vacuo. The residue was purified by silica chromatography (1-30% DCM/MeOH with 2% NH₄OH as the gradient eluent) to cleanly afford the title compound (48.2 mg, quantitative yield). MS (apci) m/z=397.2 (M+H).

Example 488

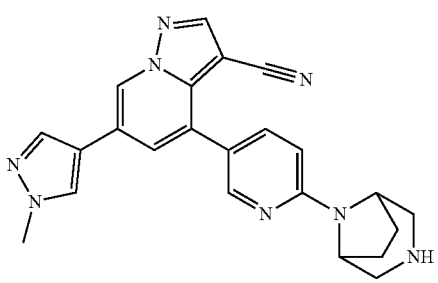 [SMILES: Cn1cc(-c2cc(-c3ccc(N4C5CCC4CNC5)nc3)c3c(C#N)cnn3c2)cn1]

4-(6-(3,8-Diazabicyclo[3.2.1]octan-8-yl)pyridine-3-yl)-6-(1-methyl-1H-pyrazol-4-yl)pyrazolo[1,5-a]pyridine-3-carbonitrile

Step 1: Preparation of Tert-Butyl 8-(5-(3-cyano-6-(1-methyl-1H-pyrazol-4-yl)pyrazolo[1,5-a]pyridine-4-yl)pyridin-2-yl)-3,8-diazabicyclo[3.2.1]octane-3-carboxylate A room temperature mixture of 4-(6-fluoropyridin-3-yl)-6-(1-methyl-1H-pyrazol-4-yl)pyrazolo[1,5-a]pyridine-3-carbonitrile (Intermediate P6; 48.1 mg, 0.151 mmol) in DMSO (1.2 mL) was treated with tert-Butyl 3,8-diazabicyclo[3.2.1]octane-3-carboxylate (49.9 mg, 0.235 mmol) and DIEA (102 µL, 0.587 mmol). The reaction mixture was stirred for 60 h at 130° C., then cooled to room temperature, diluted with EtOAc and washed successively with water and brine. The combined organic extracts were dried over anhydrous Na$_2$SO$_4$, filtered, and concentrated in vacuo. The residue was purified by silica chromatography (5-50% DCM/Acetone as the gradient eluent) to afford the title compound which was directly carried on to Step 2. MS (apci) m/z=511.2 (M+H).

Step 2: Preparation of 4-(6-(3,8-Diazabicyclo[3.2.1]octan-8-yl)pyridine-3-yl)-6-(1-methyl-1H-pyrazol-4-yl)pyrazolo[1,5-a]pyridine-3-carbonitrile tert-Butyl 8-(5-(3-cyano-6-(1-methyl-1H-pyrazol-4-yl)pyrazolo[1,5-a]pyridine-4-yl)pyridine-2-yl)-3,8-diazabicyclo[3.2.1]octane-3-carboxylate was dissolved in 1:1 DCM/TFA (2.0 mL), stirred for 30 min at room temperature and then concentrated in vacuo. The residue was purified by C18 reverse phase chromatography (5-95% water/ACN with 0.1% TFA as the gradient eluent) to afford the title compound as the TFA salt. The TFA salt was suspended in 4:1 DCM/iPrOH and extracted with saturated NaHCO$_3$. The combined organic extracts were dried over anhydrous Na$_2$SO$_4$, filtered, and concentrated in vacuo to cleanly afford the title compound (20.4 mg, 42% yield). MS (apci) m/z=411.1 (M+H).

Example 489

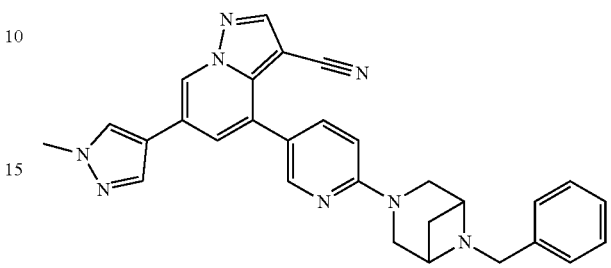

4-(6-(6-benzyl-3,6-diazabicyclo[3.1.1]heptan-3-yl)pyridin-3-yl)-6-(1-methyl-1H-pyrazol-4-yl)pyrazolo[1,5-a]pyridine-3-carbonitrile A room temperature solution of 4-(6-(3,6-diazabicyclo[3.1.1]heptan-3-yl)pyridin-3-yl)-6-(1-methyl-1H-pyrazol-4-yl)pyrazolo[1,5-a]pyridine-3-carbonitrile (Example 486; 59.9 mg, 0.151 mmol) in DCM (1.5 mL) was treated sequentially with TEA (102 µL, 0.755 mmol) and benzyl bromide (53.8 µL, 0.453 mmol). The reaction mixture was stirred 16 h at room temperature, then concentrated in vacuo. The residue was purified by C18 reverse phase chromatography (5-95% water/ACN with 0.1% TFA as the gradient eluent) to afford the title compound as the TFA salt. The TFA salt was suspended in 4:1 DCM/iPrOH and extracted with saturated NaHCO$_3$. The combined organic extracts were dried over anhydrous Na$_2$SO$_4$, filtered, and concentrated in vacuo. The residue was purified by silica chromatography (1-30% DCM/MeOH with 2% NH$_4$OH as the gradient eluent) to cleanly afford the title compound (9.3 mg, 13% yield). MS (apci) m/z=487.2 (M+H).

The compounds in Table SS were prepared according to the method described for the synthesis of Example 489, replacing 4-(6-(3,6-diazabicyclo[3.1.1]heptan-3-yl)pyridin-3-yl)-6-(1-methyl-1H-pyrazol-4-yl)pyrazolo[1,5-a]pyridine-3-carbonitrile with the appropriate amino starting materials. The title compounds were isolated cleanly following the free base work up (i.e. the final silica chromatographic purification was omitted).

TABLE SS

| Ex # | Structure | Chemical Name | MS (apci) m/z |
|---|---|---|---|
| 490 | 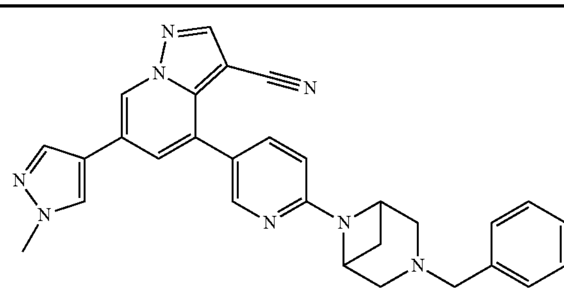 | 4-(6-(3-benzyl-3,6-diazabicyclo[3.1.1]heptan-6-yl)pyridin-3-yl)-6-(1-methyl-1H-pyrazol-4-yl)pyrazolo[1,5-a]pyridine-3-carbonitrile | 487.2 (M + H) |

TABLE SS-continued

| Ex # | Structure | Chemical Name | MS (apci) m/z |
|---|---|---|---|
| 491 | 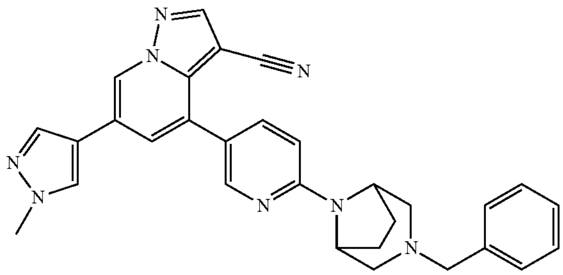 [SMILES: Cn1cc(-c2cc(-c3ccc(N4C5CCC4CN(Cc4ccccc4)C5)nc3)c3c(C#N)cnn3c2)cn1] | 4-(6-(3-benzyl-3,8-diazabicyclo[3.2.1]octan-8-yl)pyridin-3-yl)-6-(1-methyl-1H-pyrazol-4-yl)pyrazolo[1,5-a]pyridine-3-carbonitrile | 501.2 (M + H) |

Example 492

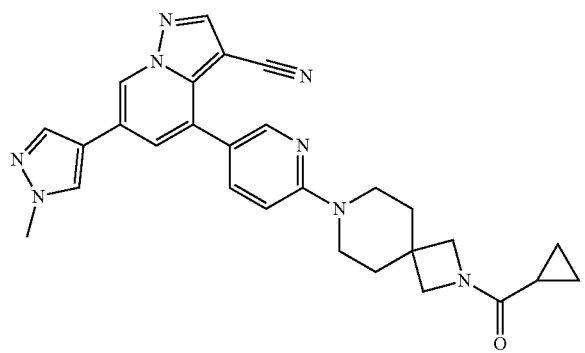 [SMILES: Cn1cc(-c2cc(-c3ccc(N4CCC5(CC4)CN(C(=O)C4CC4)C5)nc3)c3c(C#N)cnn3c2)cn1]

4-(6-(2-(cyclopropanecarbonyl)-2,7-diazaspiro[3.5]nonan-7-yl)pyridin-3-yl)-6-(1-methyl-1H-pyrazol-4-yl)pyrazolo[1,5-a]pyridine-3-carbonitrile A room temperature solution of 4-(6-(2,7-diazaspiro[3.5]nonan-7-yl)pyridin-3-yl)-6-(1-methyl-1H-pyrazol-4-yl)pyrazolo[1,5-a]pyridine-3-carbonitrile dihydrochloride (Example 215; 5.4 mg, 0.011 mmol) in DMA (0.2 mL) was treated sequentially with DIEA (11.4 µL, 0.065 mmol), then cyclopropanecarbonyl chloride (3.0 µL, 0.033 mmol). The reaction mixture was stirred for 1 h at room temperature, then diluted with water (2 mL) and stirred overnight. The reaction mixture was vacuum filtered. The isolated solids were rinsed with water and $Et_2O$, and dried in vacuo to afford the title compound (3.9 mg, 73% yield). MS (apci) m/z=493.1 (M+H).

The compounds in Table TT were prepared according to the method described for the synthesis of Example 492, replacing cyclopropanecarbonyl chloride with the appropriate acid chloride starting material, using either DMF or DMA as the reaction solvent and either DIEA or TEA as the base. Reactions were monitored by LCMS, and reaction times were adjusted accordingly. Title compounds were cleanly isolated by filtration after an aqueous quench, unless otherwise noted.

TABLE TT

| Ex # | Structure | Chemical Name | MS (apci) m/z |
|---|---|---|---|
| 493 | 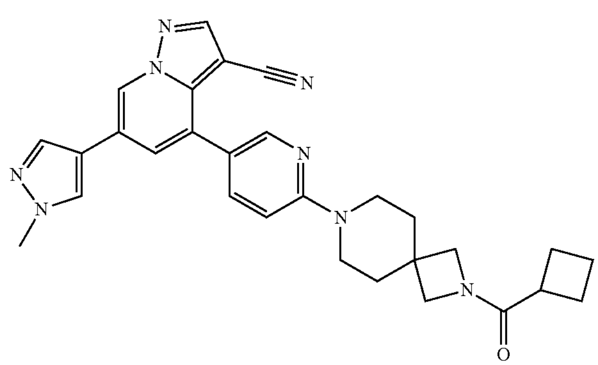 [SMILES: Cn1cc(-c2cc(-c3ccc(N4CCC5(CC4)CN(C(=O)C4CCC4)C5)nc3)c3c(C#N)cnn3c2)cn1] | 4-(6-(2-(cyclobutanecarbonyl)-2,7-diazaspiro[3.5]nonan-7-yl)pyridin-3-yl)-6-(1-methyl-1H-pyrazol-4-yl)pyrazolo[1,5-a]pyridine-3-carbonitrile | 507.1 (M + H) |

TABLE TT-continued

| Ex # | Structure | Chemical Name | MS (apci) m/z |
|---|---|---|---|
| 494* | 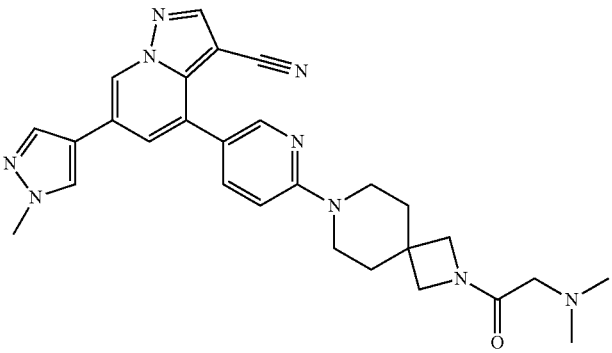 [SMILES: CN(C)CC(=O)N1CC2(CCN(c3ccc(-c4cc(-c5cnn(C)c5)cn5ncc(C#N)c45)cn3)CC2)C1] | 4-(6-(2-(2-(dimethylamino)acetyl)-2,7-diazaspiro[3.5]nonan-7-yl)pyridin-3-yl)-6-(1-methyl-1H-pyrazol-4-yl)pyrazolo[1,5-a]pyridine-3-carbonitrile | 510.2 (M + H) |
| 495 | 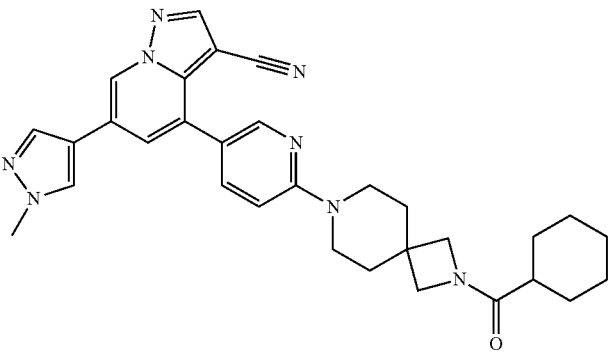 [SMILES: Cn1cc(-c2cc(-c3ccc(N4CCC5(CC4)CN(C(=O)C4CCCCC4)C5)nc3)c3c(C#N)cnn3c2)cn1] | 4-(6-(2-(cyclohexanecarbonyl)-2,7-diazaspiro[3.5]nonan-7-yl)pyridin-3-yl)-6-(1-methyl-1H-pyrazol-4-yl)pyrazolo[1,5-a]pyridine-3-carbonitrile | 535.2 (M + H) |
| 496 | 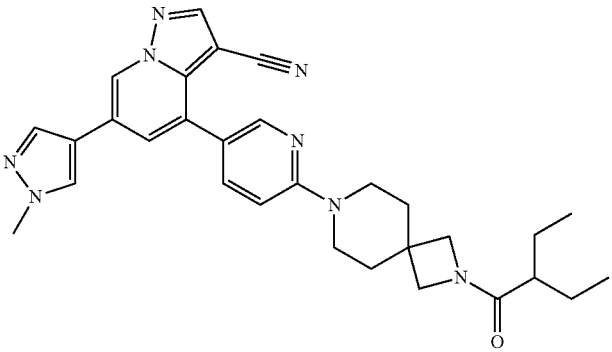 [SMILES: CCC(CC)C(=O)N1CC2(CCN(c3ccc(-c4cc(-c5cnn(C)c5)cn5ncc(C#N)c45)cn3)CC2)C1] | 4-(6-(2-(2-ethylbutanoyl)-2,7-diazaspiro[3.5]nonan-7-yl)pyridin-3-yl)-6-(1-methyl-1H-pyrazol-4-yl)pyrazolo[1,5-a]pyridine-3-carbonitrile | 523.2 (M + H) |
| 497 | 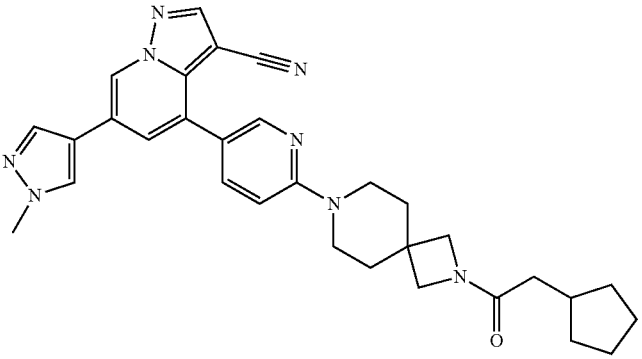 [SMILES: Cn1cc(-c2cc(-c3ccc(N4CCC5(CC4)CN(C(=O)CC4CCCC4)C5)nc3)c3c(C#N)cnn3c2)cn1] | 4-(6-(2-(2-cyclopentylacetyl)-2,7-diazaspiro[3.5]nonan-7-yl)pyridin-3-yl)-6-(1-methyl-1H-pyrazol-4-yl)pyrazolo[1,5-a]pyridine-3-carbonitrile | 535.2 (M + H) |

| Ex # | Structure | Chemical Name | MS (apci) m/z |
|---|---|---|---|
| 498 | 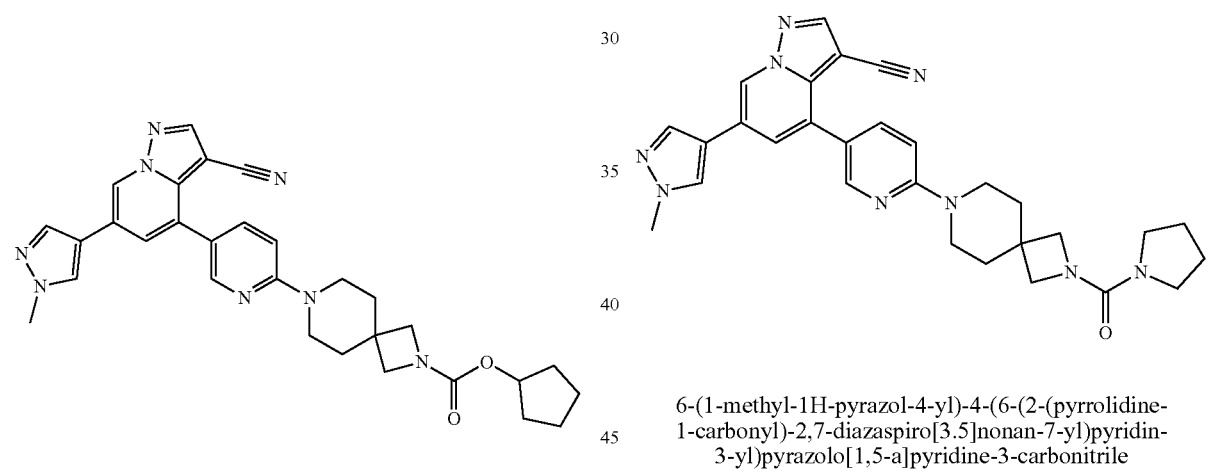 | 4-(6-(2-(2-cyclohexylacetyl)-2,7-diazaspiro[3.5]nonan-7-yl)pyridin-3-yl)-6-(1-methyl-1H-pyrazol-4-yl)pyrazolo[1,5-a]pyridine-3-carbonitrile | 549.2 (M + H) |

*Following aqueous quench, the reaction mixture was directly subjected to C18 reverse phase chromatographic purification utilizing an appropriate gradient eluent to cleanly afford the title compound.

Example 499

Cyclopentyl 7-(5-(3-cyano-6-(1-methyl-1H-pyrazol-4-yl)pyrazolo[1,5-a]pyridin-4-yl)pyridin-2-yl)-2,7-diazaspiro[3.5]nonane-2-carboxylate A room temperature solution of 4-(6-(2,7-diazaspiro[3.5]nonan-7-yl)pyridin-3-yl)-6-(1-methyl-1H-pyrazol-4-yl)pyrazolo[1,5-a]pyridine-3-carbonitrile dihydrochloride (Example 215; 8 mg, 0.016 mmol) in DMA (0.3 mL) was treated sequentially with DIEA (28 μL, 0.16 mmol), then cyclopentyl carbonochloridate (12 mg, 0.080 mmol). The reaction mixture was stirred 3 d at room temperature, and then diluted with water (2 mL). The resulting white suspension was filtered. The solid was collected, rinsed with water and Et₂O, and dried in vacuo. The crude solid was purified by silica chromatography (0-100% acetone/hexanes as the gradient eluent) to cleanly afford the title compound (2.1 mg, 24% yield). MS (apci) m/z=537.2 (M+H).

Example 500

6-(1-methyl-1H-pyrazol-4-yl)-4-(6-(2-(pyrrolidine-1-carbonyl)-2,7-diazaspiro[3.5]nonan-7-yl)pyridin-3-yl)pyrazolo[1,5-a]pyridine-3-carbonitrile A room temperature solution of 4-(6-(2,7-diazaspiro[3.5]nonan-7-yl)pyridin-3-yl)-6-(1-methyl-1H-pyrazol-4-yl)pyrazolo[1,5-a]pyridine-3-carbonitrile dihydrochloride (Example 215; 5.6 mg, 0.011 mmol) in DMA (0.2 mL) was treated sequentially with DIEA (12 μL, 0.068 mmol) and pyrrolidine-1-carbonyl chloride (3.0 mg, 0.023 mmol). The reaction mixture was stirred 1 h at room temperature before diluting with water (2 mL). The reaction mixture was stirred overnight, and then the suspension was filtered. The solids were collected and rinsed with water and Et₂O. The filtrate was filtered again, rinsing the solids rinsed with water and Et₂O. The collected solids were combined and dried in vacuo to afford the title compound (2.1 mg, 36% yield). MS (apci) m/z=522.2 (M+H).

The compounds in Table UU were according to the method described for the synthesis of Example 500, replacing pyrrolidine-1-carbonyl chloride with the appropriate acid halide starting material. Reactions were monitored by LCMS and reaction times/temperatures were adjusted accordingly. Title compounds were cleanly isolated following filtration except where noted.

TABLE UU

| Ex # | Structure | Chemical Name | MS (apci) m/z |
|---|---|---|---|
| 501* | 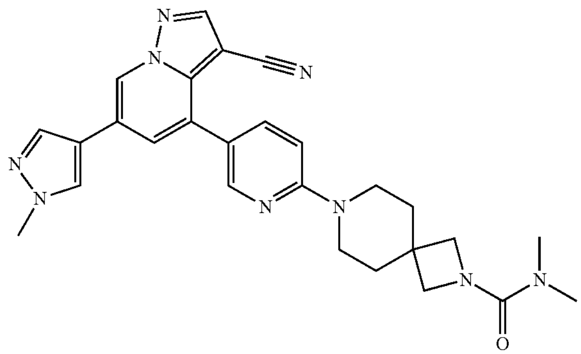 [SMILES: CN(C)C(=O)N1CC2(CCN(c3ccc(-c4cc(-c5cnn(C)c5)cn5ncc(C#N)c45)cn3)CC2)C1] | 7-(5-(3-cyano-6-(1-methyl-1H-pyrazol-4-yl)pyrazolo[1,5-a]pyridin-4-yl)pyridin-2-yl)-N,N-dimethyl-2,7-diazaspiro[3.5]nonane-2-carboxamide | 496.1 (M + H) |
| 502 | 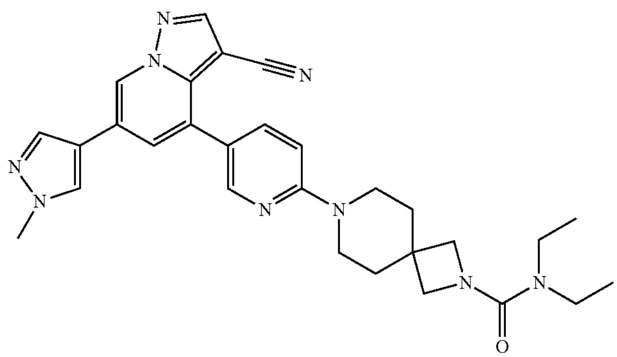 [SMILES: CCN(CC)C(=O)N1CC2(CCN(c3ccc(-c4cc(-c5cnn(C)c5)cn5ncc(C#N)c45)cn3)CC2)C1] | 7-(5-(3-cyano-6-(1-methyl-1H-pyrazol-4-yl)pyrazolo[1,5-a]pyridin-4-yl)pyridin-2-yl)-N,N-diethyl-2,7-diazaspiro[3.5]nonane-2-carboxamide | 524.2 (M + H) |

*purified by C18 reverse phase chromatography (5-90% ACN/water as the gradient eluent)

Example 503

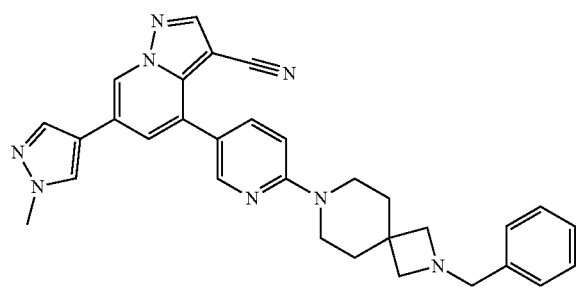 [SMILES: Cn1cc(-c2cc(-c3ccc(N4CCC5(CC4)CN(Cc4ccccc4)C5)nc3)c3c(C#N)cnn3c2)cn1]

4-(6-(2-benzyl-2,7-diazaspiro[3.5]nonan-7-yl)pyridin-3-yl)-6-(1-methyl-1H-pyrazol-4-yl)pyrazolo[1,5-a]pyridine-3-carbonitrile Step 1: Preparation of 4-(6-(2,7-diazaspiro[3.5]nonan-7-yl)pyridin-3-yl)-6-(1-methyl-1H-pyrazol-4-yl)pyrazolo[1,5-a]pyridine-3-carbonitrile 2,2,2-trifluoroacetate A room temperature solution of tert-butyl 7-(5-(3-cyano-6-(1-methyl-1H-pyrazol-4-yl)pyrazolo[1,5-a]pyridine-4-yl)pyridin-2-yl)-2,7-diazaspiro[3.5]nonane-2-carboxylate (Example 214; 56 mg, 0.11 mmol) in DCM (4.0 mL) was treated with TFA (2 mL, 26 mmol). The reaction mixture was stirred for 30 min at room temperature, then concentrated in vacuo to afford the title compound as the putative TFA salt (45 mg, quantitative yield). This material was carried on to Step 2 without further purification. MS (apci) m/z=425.2 (M+H)

Step 2: Preparation of 4-(6-(2-benzyl-2,7-diazaspiro[3.5]nonan-7-yl)pyridin-3-yl)-6-(1-methyl-1H-pyrazol-4-yl)pyrazolo[1,5-a]pyridine-3-carbonitrile A room temperature solution of 4-(6-(2,7-diazaspiro[3.5]nonan-7-yl)pyridin-3-yl)-6-(1-methyl-1H-pyrazol-4-yl)pyrazolo[1,5-a]pyridine-3-carbonitrile 2,2,2-trifluoroacetate (45 mg, 0.1 mmol) in DMF (2 mL) was treated sequentially with benzyl bromide (40.3 µL, 0.317 mmol) and TEA (102 µL, 0.754 mmol). The reaction mixture was stirred overnight at room temperature, and then additional benzyl bromide (37.7 µL, 0.339 mmol) and TEA (30.6 µL, 0.226 mmol) were added. The resulting mixture was stirred for another 5 h at room temperature. The reaction mixture was diluted with EtOAc, and washed with water. The combined organic extracts were dried over anhydrous $Na_2SO_4$, filtered, and concentrated in vacuo. The residue was purified by silica chromatography (eluting with a stepped gradient of DCM/MeOH (50:1) then DCM/MeOH (25:1)) to cleanly afford the title compound (10 mg, 18% yield). MS (apci) m/z=515.2 (M+H).

Example 504

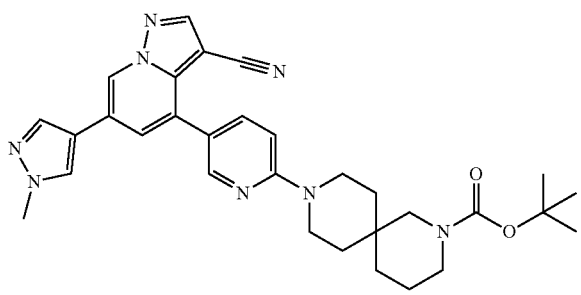 [SMILES: Cn1cc(-c2cc(-c3ccc(N4CCC5(CCCN(C(=O)OC(C)(C)C)C5)CC4)nc3)c3c(C#N)cnn3c2)cn1]

Tert-Butyl 9-(5-(3-cyano-6-(1-methyl-1H-pyrazol-4-yl)pyrazolo[1,5-a]pyridin-4-yl)pyridine-2-yl)-2,9-diazaspiro[5.5]undecane-2-carboxylate In a microwave vessel, a room temperature solution of tert-butyl 2,9-diazaspiro[5.5]undecane-2-carboxylate (95.89 mg, 0.3770 mmol) and DIEA (43.89 μL, 0.2513 mmol) in DMSO (1.00 mL) was treated with 4-(6-fluoropyridin-3-yl)-6-(1-methyl-1H-pyrazol-4-yl)pyrazolo[1,5-a]pyridine-3-carbonitrile (Intermediate P6; 40.00 mg, 0.1257 mmol) and subjected to microwave irradiation for 2 h at 125° C. After cooling to room temperature, the reaction mixture was directly purified by reverse-phase preparative HPLC (using 10 to 80% ACN/water as the gradient eluent) to afford the title compound (10 mg, 14% yield). MS (apci) m/z=553.3 (M+H).

The compounds in Table VV were prepared according the method described for the synthesis of Example 504, replacing tert-butyl 2,9-diazaspiro[5.5]undecane-2-carboxylate with the appropriate amine starting material. Reactions were monitored by LCMS, and reaction times were adjusted as necessary. Products were purified by reverse-phase preparative HPLC utilizing an appropriate gradient eluent to cleanly afford the title compounds.

TABLE VV

| Ex # | Structure | Chemical Name | MS (apci) m/z |
|---|---|---|---|
| 505 | 2 TFA | 6-(1-methyl-1H-pyrazol-4-yl)-4-(6-(4-(tetrahydrofuran-3-yl)piperazin-1-yl)pyridin-3-yl)pyrazolo[1,5-a]pyridine-3-carbonitrile bis(2,2,2-trifluoroacetate) | 455.2 (M + H) |
| 506 | 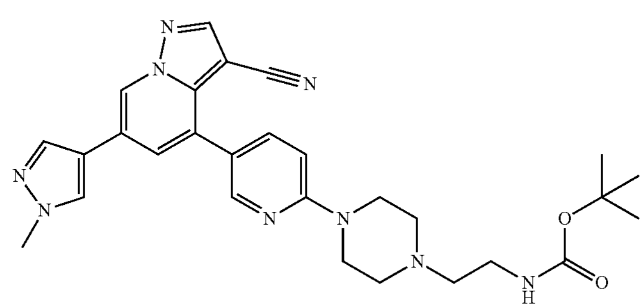 [SMILES: Cn1cc(-c2cc(-c3ccc(N4CCN(CCNC(=O)OC(C)(C)C)CC4)nc3)c3c(C#N)cnn3c2)cn1] | tert-butyl (2-(4-(5-(3-cyano-6-(1-methyl-1H-pyrazol-4-yl)pyrazolo[1,5-a]pyridin-4-yl)pyridin-2-yl)piperazin-1-yl)ethyl)carbamate | 528.2 (M + H) |
| 507 | 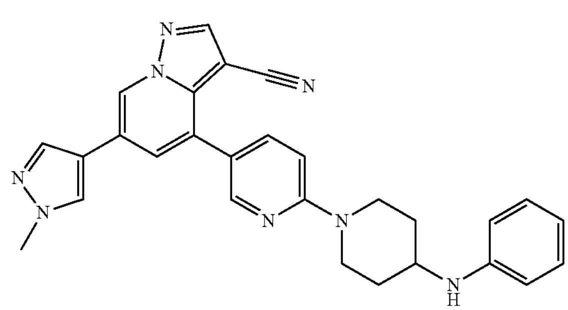 [SMILES: Cn1cc(-c2cc(-c3ccc(N4CCC(Nc5ccccc5)CC4)nc3)c3c(C#N)cnn3c2)cn1] | 6-(1-methyl-1H-pyrazol-4-yl)-4-(6-(4-(phenylamino)piperidin-1-yl)pyridin-3-yl)pyrazolo[1,5-a]pyridine-3-carbonitrile | 475.2 (M + H) |

TABLE VV-continued

| Ex # | Structure | Chemical Name | MS (apci) m/z |
|---|---|---|---|
| 508 | 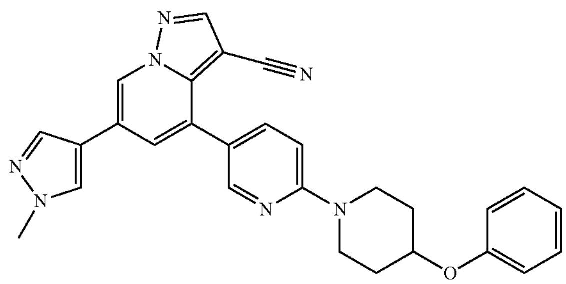 [SMILES: Cn1cc(-c2cc(-c3ccc(N4CCC(Oc5ccccc5)CC4)nc3)c3c(C#N)cnn3c2)cn1] | 6-(1-methyl-1H-pyrazol-4-yl)-4-(6-(4-phenoxypiperidin-1-yl)pyridin-3-yl)pyrazolo[1,5-a]pyridine-3-carbonitrile | 476.1 (M + H) |
| 509 | 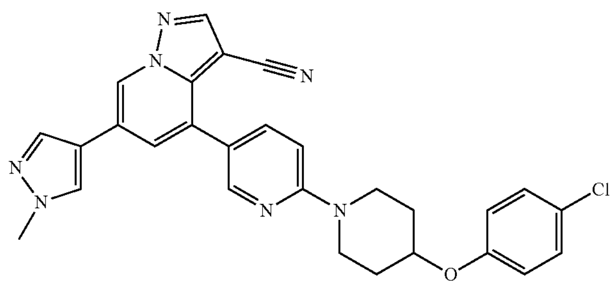 [SMILES: Cn1cc(-c2cc(-c3ccc(N4CCC(Oc5ccc(Cl)cc5)CC4)nc3)c3c(C#N)cnn3c2)cn1] | 4-(6-(4-(4-chlorophenoxy)piperidin-1-yl)pyridin-3-yl)-6-(1-methyl-1H-pyrazol-4-yl)pyrazolo[1,5-a]pyridine-3-carbonitrile | 509.9 (M + H) |
| 510 | 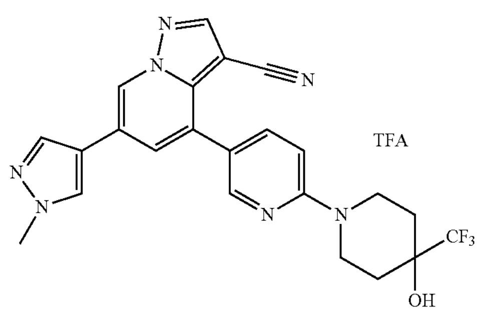 [SMILES: Cn1cc(-c2cc(-c3ccc(N4CCC(O)(C(F)(F)F)CC4)nc3)c3c(C#N)cnn3c2)cn1] | 4-(6-(4-hydroxy-4-(trifluoromethyl)piperidin-1-yl)pyridin-3-yl)-6-(1-methyl-1H-pyrazol-4-yl)pyrazolo[1,5-a]pyridine-3-carbonitrile 2,2,2-trifluoroacetate | 468.3 (M + H) |
| 511 | 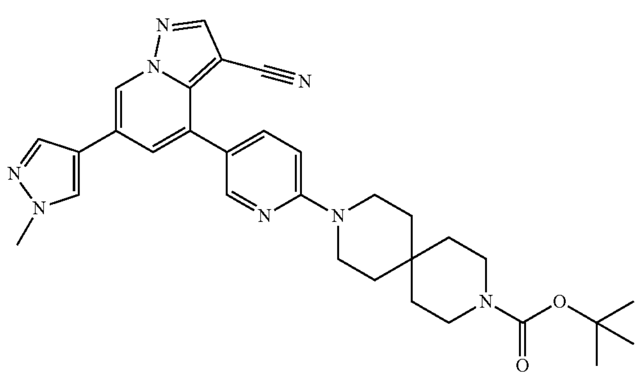 [SMILES: Cn1cc(-c2cc(-c3ccc(N4CCC5(CCN(C(=O)OC(C)(C)C)CC5)CC4)nc3)c3c(C#N)cnn3c2)cn1] | tert-butyl 9-(5-(3-cyano-6-(1-methyl-1H-pyrazol-4-yl)pyrazolo[1,5-a]pyridin-4-yl)pyridin-2-yl)-3,9-diazaspiro[5.5]undecane-3-carboxylate | 553.3 (M + H) |
| 512 | 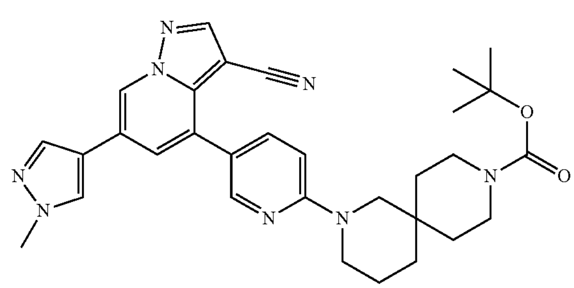 [SMILES: Cn1cc(-c2cc(-c3ccc(N4CCCC5(CCN(C(=O)OC(C)(C)C)CC5)C4)nc3)c3c(C#N)cnn3c2)cn1] | tert-butyl 2-(5-(3-cyano-6-(1-methyl-1H-pyrazol-4-yl)pyrazolo[1,5-a]pyridin-4-yl)pyridin-2-yl)-2,9-diazaspiro[5.5]undecane-9-carboxylate | 553.3 (M + H) |

TABLE VV-continued

| Ex # | Structure | Chemical Name | MS (apci) m/z |
|---|---|---|---|
| 513 | 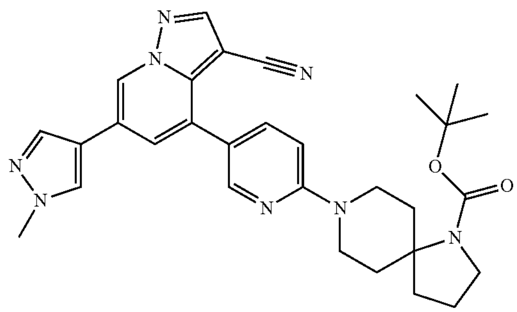 [SMILES: Cn1cc(-c2cc(-c3ccc(N4CCC5(CCCN5C(=O)OC(C)(C)C)CC4)nc3)c3c(C#N)cnn3c2)cn1] | tert-butyl 8-(5-(3-cyano-6-(1-methyl-1H-pyrazol-4-yl)pyrazolo[1,5-a]pyridin-4-yl)pyridin-2-yl)-1,8-diazaspiro[4.5]decane-1-carboxylate | 539.2 (M + H) |
| 514 | 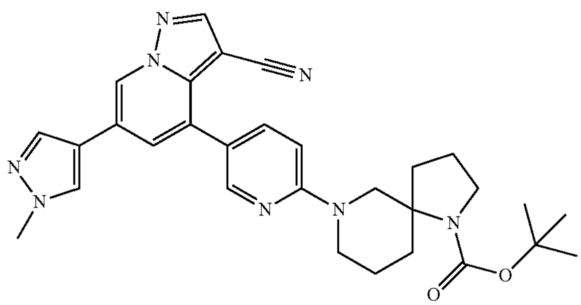 [SMILES: Cn1cc(-c2cc(-c3ccc(N4CCCC5(CCCN5C(=O)OC(C)(C)C)C4)nc3)c3c(C#N)cnn3c2)cn1] | tert-butyl 7-(5-(3-cyano-6-(1-methyl-1H-pyrazol-4-yl)pyrazolo[1,5-a]pyridin-4-yl)pyridin-2-yl)-1,7-diazaspiro[4.5]decane-1-carboxylate | 539.2 (M + H) |
| 515 | 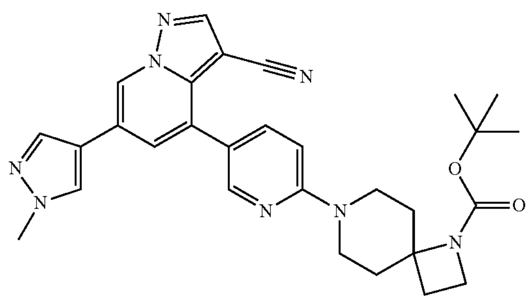 [SMILES: Cn1cc(-c2cc(-c3ccc(N4CCC5(CC4)CCN5C(=O)OC(C)(C)C)nc3)c3c(C#N)cnn3c2)cn1] | tert-butyl 7-(5-(3-cyano-6-(1-methyl-1H-pyrazol-4-yl)pyrazolo[1,5-a]pyridin-4-yl)pyridin-2-yl)-1,7-diazaspiro[3.5]nonane-1-carboxylate | 525.2 (M + H) |
| 516 | 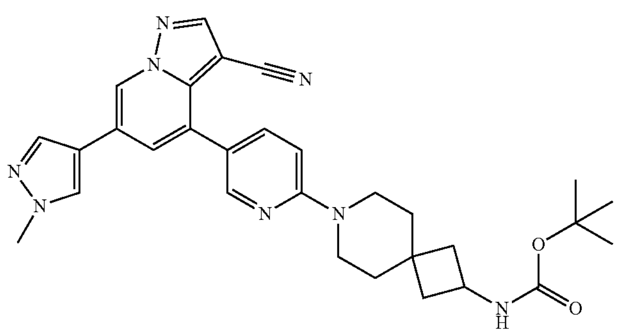 [SMILES: Cn1cc(-c2cc(-c3ccc(N4CCC5(CC4)CC(NC(=O)OC(C)(C)C)C5)nc3)c3c(C#N)cnn3c2)cn1] | tert-butyl (7-(5-(3-cyano-6-(1-methyl-1H-pyrazol-4-yl)pyrazolo[1,5-a]pyridin-4-yl)pyridin-2-yl)-7-azaspiro[3.5]nonan-2-yl)carbamate | 539.2 (M + H) |
| 517 | 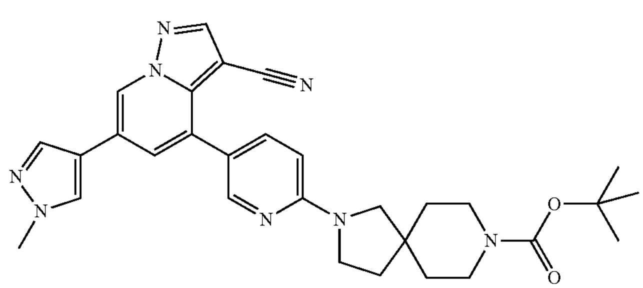 [SMILES: Cn1cc(-c2cc(-c3ccc(N4CCC5(CCN(C(=O)OC(C)(C)C)CC5)C4)nc3)c3c(C#N)cnn3c2)cn1] | tert-butyl 2-(5-(3-cyano-6-(1-methyl-1H-pyrazol-4-yl)pyrazolo[1,5-a]pyridin-4-yl)pyridin-2-yl)-2,8-diazaspiro[4.5]decane-8-carboxylate | 539.2 (M + H) |

TABLE VV-continued

| Ex # | Structure | Chemical Name | MS (apci) m/z |
|---|---|---|---|
| 518 | 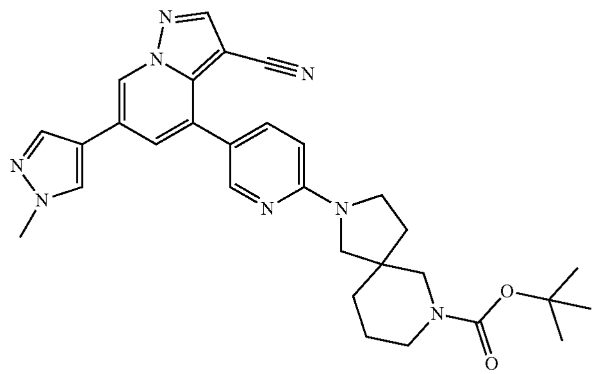 [SMILES: Cn1cc(-c2cc(-c3ccc(N4CCC5(CCCN(C(=O)OC(C)(C)C)C5)C4)nc3)c3c(C#N)cnn3c2)cn1] | tert-butyl 2-(5-(3-cyano-6-(1-methyl-1H-pyrazol-4-yl)pyrazolo[1,5-a]pyridin-4-yl)pyridin-2-yl)-2,7-diazaspiro[4.5]decane-7-carboxylate | 539.3 (M + H) |
| 519 | 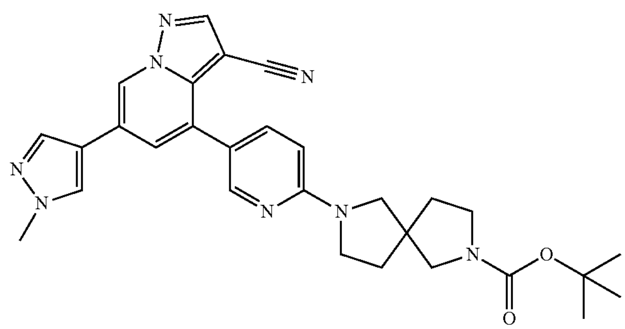 [SMILES: Cn1cc(-c2cc(-c3ccc(N4CCC5(CCN(C(=O)OC(C)(C)C)C5)C4)nc3)c3c(C#N)cnn3c2)cn1] | tert-butyl 7-(5-(3-cyano-6-(1-methyl-1H-pyrazol-4-yl)pyrazolo[1,5-a]pyridin-4-yl)pyridin-2-yl)-2,7-diazaspiro[4.4]nonane-2-carboxylate | 525.2 (M + H) |
| 520 | 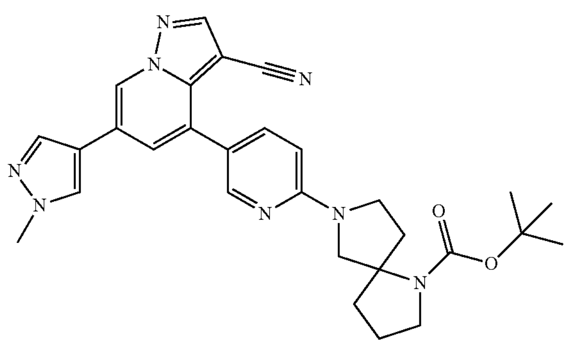 [SMILES: Cn1cc(-c2cc(-c3ccc(N4CCC5(CCCN5C(=O)OC(C)(C)C)C4)nc3)c3c(C#N)cnn3c2)cn1] | tert-butyl 7-(5-(3-cyano-6-(1-methyl-1H-pyrazol-4-yl)pyrazolo[1,5-a]pyridin-4-yl)pyridin-2-yl)-1,7-diazaspiro[4.4]nonane-1-carboxylate | 525.2 (M + H) |
| 521 | 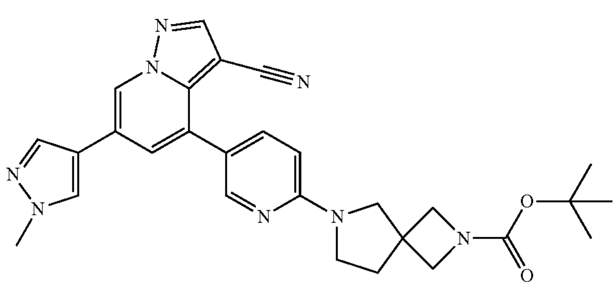 [SMILES: Cn1cc(-c2cc(-c3ccc(N4CCC5(CN(C(=O)OC(C)(C)C)C5)C4)nc3)c3c(C#N)cnn3c2)cn1] | tert-butyl 6-(5-(3-cyano-6-(1-methyl-1H-pyrazol-4-yl)pyrazolo[1,5-a]pyridin-4-yl)pyridin-2-yl)-2,6-diazaspiro[3.4]octane-2-carboxylate | 511.1 (M + H) |

TABLE VV-continued

| Ex # | Structure | Chemical Name | MS (apci) m/z |
|---|---|---|---|
| 522 | 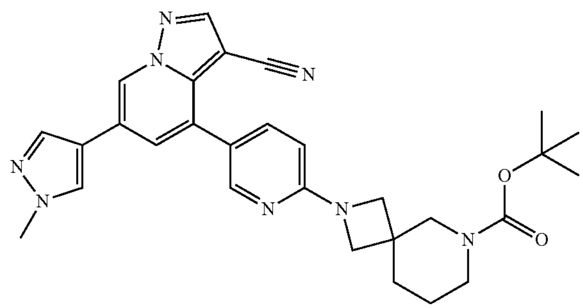 [SMILES: Cn1cc(-c2cc(-c3ccc(N4CC5(CCCN(C(=O)OC(C)(C)C)C5)C4)nc3)c3c(C#N)cnn3c2)cn1] | tert-butyl 2-(5-(3-cyano-6-(1-methyl-1H-pyrazol-4-yl)pyrazolo[1,5-a]pyridin-4-yl)pyridin-2-yl)-2,6-diazaspiro[3.5]nonane-6-carboxylate | 525.2 (M + H) |
| 523 | 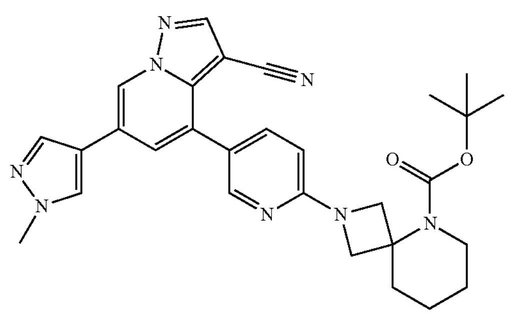 [SMILES: Cn1cc(-c2cc(-c3ccc(N4CC5(CCCCN5C(=O)OC(C)(C)C)C4)nc3)c3c(C#N)cnn3c2)cn1] | tert-butyl 2-(5-(3-cyano-6-(1-methyl-1H-pyrazol-4-yl)pyrazolo[1,5-a]pyridin-4-yl)pyridin-2-yl)-2,5-diazaspiro[3.5]nonane-5-carboxylate | 525.2 (M + H) |
| 524 | 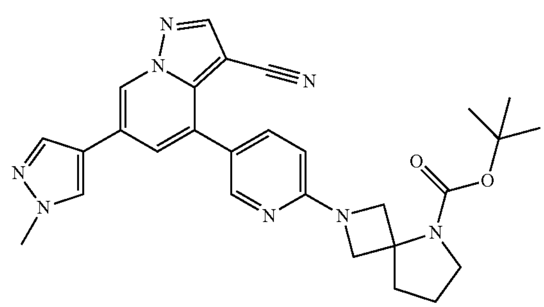 [SMILES: Cn1cc(-c2cc(-c3ccc(N4CC5(CCCN5C(=O)OC(C)(C)C)C4)nc3)c3c(C#N)cnn3c2)cn1] | tert-butyl 2-(5-(3-cyano-6-(1-methyl-1H-pyrazol-4-yl)pyrazolo[1,5-a]pyridin-4-yl)pyridin-2-yl)-2,5-diazaspiro[3.4]octane-5-carboxylate | 511.1 (M + H) |
| 525 | 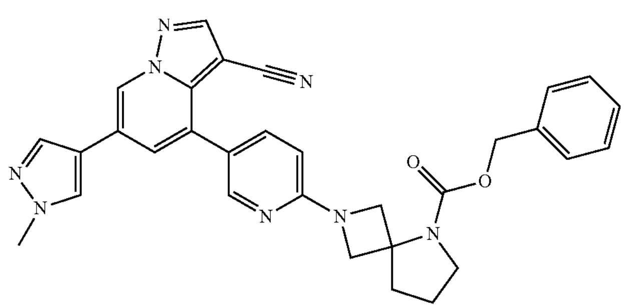 | benzyl 2-(5-(3-cyano-6-(1-methyl-1H-pyrazol-4-yl)pyrazolo[1,5-a]pyridin-4-yl)pyridin-2-yl)-2,5-diazaspiro[3.4]octane-5-carboxylate 2,2,2-trifluoroacetate | 545.3 (M + H) |

TABLE VV-continued

| Ex # | Structure | Chemical Name | MS (apci) m/z |
|---|---|---|---|
| 526 | 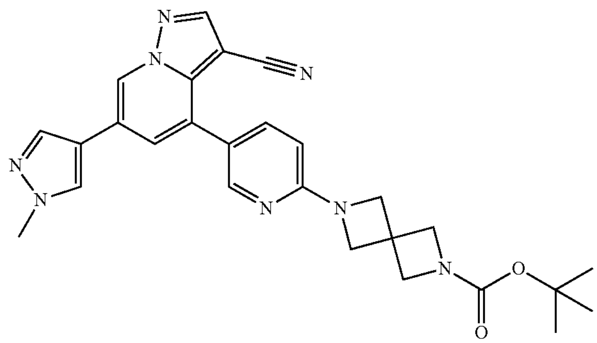 [SMILES: Cn1cc(-c2cc(-c3ccc(N4CC5(CN(C(=O)OC(C)(C)C)C5)C4)nc3)c3c(C#N)cnn3c2)cn1] | tert-butyl 6-(5-(3-cyano-6-(1-methyl-1H-pyrazol-4-yl)pyrazolo[1,5-a]pyridin-4-yl)pyridin-2-yl)-2,6-diazaspiro[3.3]heptane-2-carboxylate | 497.1 (M + H) |
| 527 | 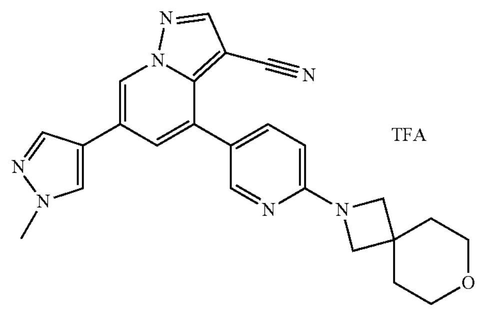 [SMILES: Cn1cc(-c2cc(-c3ccc(N4CC5(CCOCC5)C4)nc3)c3c(C#N)cnn3c2)cn1] | 4-(6-(7-oxa-2-azaspiro[3.5]nonan-2-yl)pyridin-3-yl)-6-(1-methyl-1H-pyrazol-4-yl)pyrazolo[1,5-a]pyridine-3-carbonitrile 2,2,2-trifluoroacetate | 426.1 (M + H) |
| 528 | 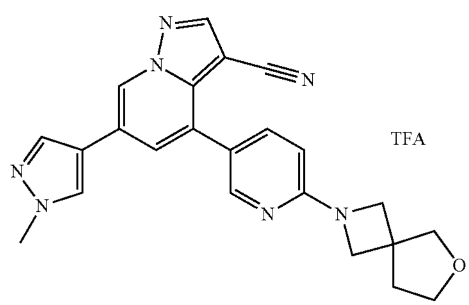 [SMILES: Cn1cc(-c2cc(-c3ccc(N4CC5(CCOC5)C4)nc3)c3c(C#N)cnn3c2)cn1] | 4-(6-(6-oxa-2-azaspiro[3.4]octan-2-yl)pyridin-3-yl)-6-(1-methyl-1H-pyrazol-4-yl)pyrazolo[1,5-a]pyridine-3-carbonitrile 2,2,2-trifluoroacetate | 412.1 (M + H) |
| 529 | 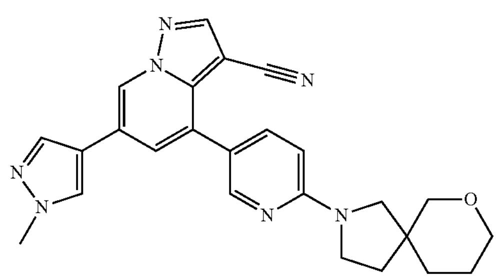 [SMILES: Cn1cc(-c2cc(-c3ccc(N4CCC5(CCCOC5)C4)nc3)c3c(C#N)cnn3c2)cn1] | 4-(6-(7-oxa-2-azaspiro[4.5]decan-2-yl)pyridin-3-yl)-6-(1-methyl-1H-pyrazol-4-yl)pyrazolo[1,5-a]pyridine-3-carbonitrile | 440.2 (M + H) |
| 530 | 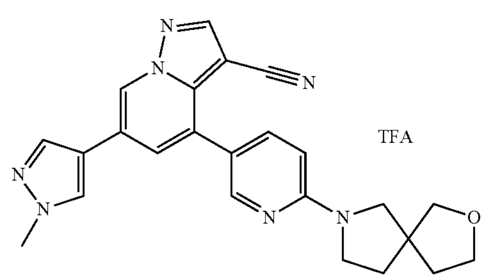 [SMILES: Cn1cc(-c2cc(-c3ccc(N4CCC5(CCOC5)C4)nc3)c3c(C#N)cnn3c2)cn1] | 4-(6-(2-oxa-7-azaspiro[4.4]nonan-7-yl)pyridin-3-yl)-6-(1-methyl-1H-pyrazol-4-yl)pyrazolo[1,5-a]pyridine-3-carbonitrile 2,2,2-trifluoroacetate | 426.2 (M + H) |

TABLE VV-continued

| Ex # | Structure | Chemical Name | MS (apci) m/z |
|---|---|---|---|
| 531 | 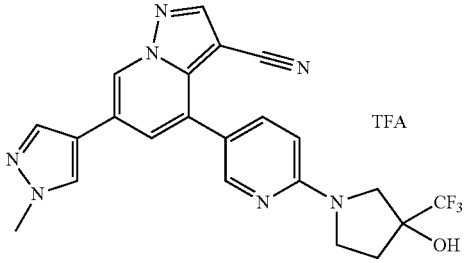 [SMILES: Cn1cc(-c2cc(-c3ccc(N4CCC(O)(C(F)(F)F)C4)nc3)c3c(C#N)cnn3c2)cn1] | 4-(6-(3-hydroxy-3-(trifluoromethyl)pyrrolidin-1-yl)pyridin-3-yl)-6-(1-methyl-1H-pyrazol-4-yl)pyrazolo[1,5-a]pyridine-3-carbonitrile 2,2,2-trifluoroacetate | 454.2 (M + H) |
| 532 | 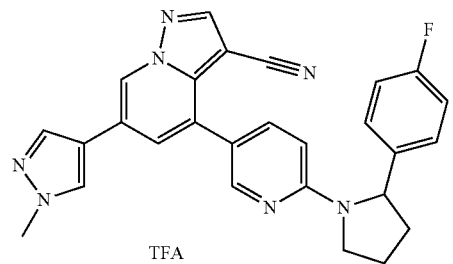 [SMILES: Cn1cc(-c2cc(-c3ccc(N4CCCC4c4ccc(F)cc4)nc3)c3c(C#N)cnn3c2)cn1] | 4-(6-(2-(4-fluorophenyl)pyrrolidin-1-yl)pyridin-3-yl)-6-(1-methyl-1H-pyrazol-4-yl)pyrazolo[1,5-a]pyridine-3-carbonitrile 2,2,2-trifluoroacetate | 464.2 (M + H) |
| 533 | 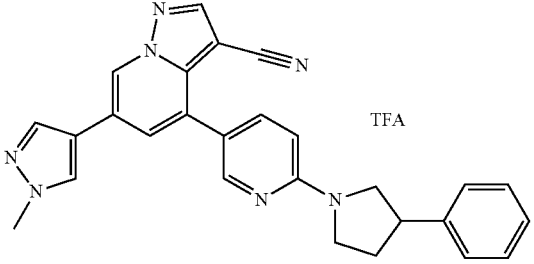 [SMILES: Cn1cc(-c2cc(-c3ccc(N4CCC(c5ccccc5)C4)nc3)c3c(C#N)cnn3c2)cn1] | 6-(1-methyl-1H-pyrazol-4-yl)-4-(6-(3-phenylpyrrolidin-1-yl)pyridin-3-yl)pyrazolo[1,5-a]pyridine-3-carbonitrile 2,2,2-trifluoroacetate | 446.2 (M + H) |
| 534 | 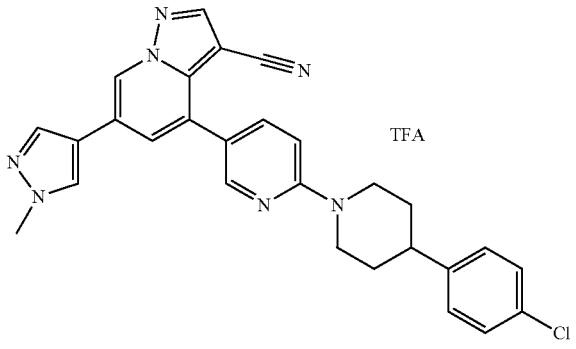 [SMILES: Cn1cc(-c2cc(-c3ccc(N4CCC(c5ccc(Cl)cc5)CC4)nc3)c3c(C#N)cnn3c2)cn1] | 4-(6-(4-(4-chlorophenyl)piperidin-1-yl)pyridin-3-yl)-6-(1-methyl-1H-pyrazol-4-yl)pyrazolo[1,5-a]pyridine-3-carbonitrile 2,2,2-trifluoroacetate | 494.3 (M + H) |
| 535 | 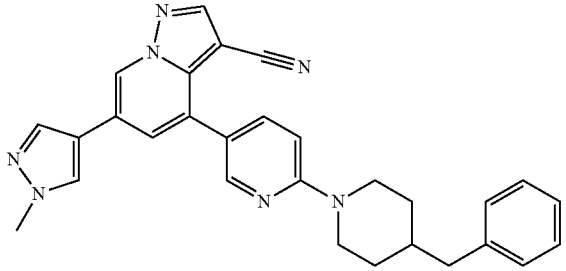 [SMILES: Cn1cc(-c2cc(-c3ccc(N4CCC(Cc5ccccc5)CC4)nc3)c3c(C#N)cnn3c2)cn1] | 4-(6-(4-benzylpiperidin-1-yl)pyridin-3-yl)-6-(1-methyl-1H-pyrazol-4-yl)pyrazolo[1,5-a]pyridine-3-carbonitrile | 474.1 (M + H) |

TABLE VV-continued

| Ex # | Structure | Chemical Name | MS (apci) m/z |
|---|---|---|---|
| 536 | 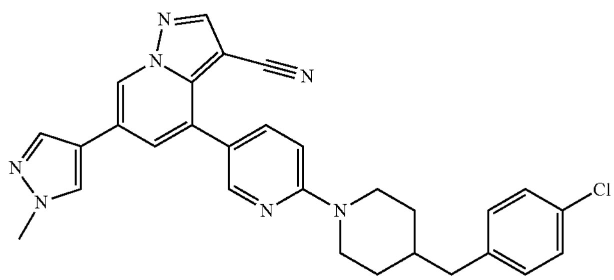 | 4-(6-(4-(4-chlorobenzyl)piperidin-1-yl)pyridin-3-yl)-6-(1-methyl-1H-pyrazol-4-yl)pyrazolo[1,5-a]pyridine-3-carbonitrile | 508.0 (M + H) |

Example 537

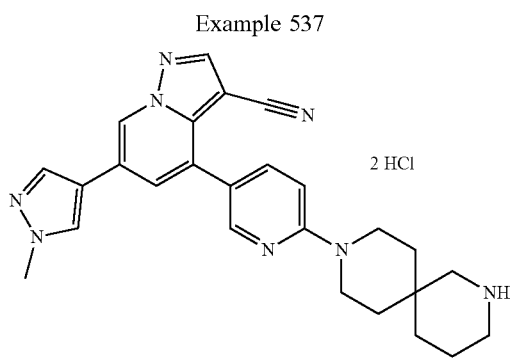

4-(6-(2,9-diazaspiro[5.5]undecan-9-yl)pyridin-3-yl)-6-(1-methyl-1H-pyrazol-4-yl)pyrazolo[1,5-a]pyridine-3-carbonitrile Dihydrochloride A room temperature mixture of tert-butyl 9-(5-(3-cyano-6-(1-methyl-1H-pyrazol-4-yl)pyrazolo[1,5-a]pyridin-4-yl)pyridin-2-yl)-2,9-diazaspiro[5.5]undecane-2-carboxylate (Example 504, 3 mg, 0.005 mmol) in DCM (133 µL) was treated with HCl in iPrOH [5 N, IPA](109 µL, 0.543 mmol). After stirring at room temperature for 2 h, the reaction mixture was concentrated in vacuo to afford the title compound (2.85 mg, 98% yield). MS (apci) m/z=453.2 (M+H).

The compounds in Table WW were prepared according to the method described for the synthesis of Example 537, replacing 9-(5-(3-cyano-6-(1-methyl-1H-pyrazol-4-yl)pyrazolo[1,5-a]pyridine-4-yl)pyridine-2-yl)-2,9-diazaspiro[5.5]undecane-2-carboxylate with the appropriate t-Butylcarboxylate from Table VV. Reactions were monitored by LCMS, and timing of additions, and reaction times were adjusted as necessary. Products were isolated by vacuum filtration,

TABLE WW

| Ex # | Structure | Chemical Name | MS (apci) m/z |
|---|---|---|---|
| 538 | 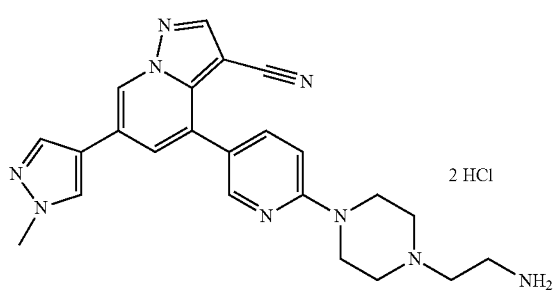 [SMILES: Cn1cc(-c2cc(-c3ccc(N4CCN(CCN)CC4)nc3)c3c(C#N)cnn3c2)cn1] | 4-(6-(4-(2-aminoethyl)piperazin-1-yl)pyridin-3-yl)-6-(1-methyl-1H-pyrazol-4-yl)pyrazolo[1,5-a]pyridine-3-carbonitrile dihydrochloride | 428.1 (M + H) |

TABLE WW-continued

| Ex # | Structure | Chemical Name | MS (apci) m/z |
|---|---|---|---|
| 539 | 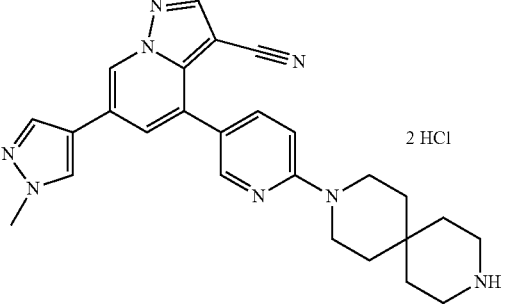 [SMILES: Cn1cc(-c2cc(-c3ccc(N4CCC5(CCNCC5)CC4)nc3)c3c(C#N)cnn3c2)cn1] 2 HCl | 4-(6-(3,9-diazaspiro[5.5]undecan-3-yl)pyridin-3-yl)-6-(1-methyl-1H-pyrazol-4-yl)pyrazolo[1,5-a]pyridine-3-carbonitrile dihydrochloride | 453.2 (M + H) |
| 540 | 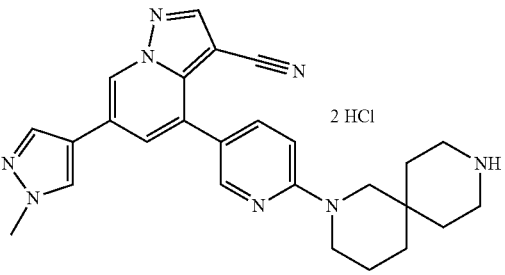 [SMILES: Cn1cc(-c2cc(-c3ccc(N4CCCC5(CCNCC5)C4)nc3)c3c(C#N)cnn3c2)cn1] 2 HCl | 4-(6-(2,9-diazaspiro[5.5]undecan-2-yl)pyridin-3-yl)-6-(1-methyl-1H-pyrazol-4-yl)pyrazolo[1,5-a]pyridine-3-carbonitrile dihydrochloride | 453.2 (M + H) |
| 541 | 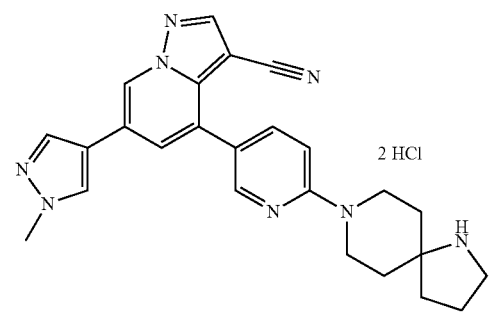 [SMILES: Cn1cc(-c2cc(-c3ccc(N4CCC5(CCCN5)CC4)nc3)c3c(C#N)cnn3c2)cn1] 2 HCl | 4-(6-(1,8-diazaspiro[4.5]decan-8-yl)pyridin-3-yl)-6-(1-methyl-1H-pyrazol-4-yl)pyrazolo[1,5-a]pyridine-3-carbonitrile dihydrochloride | 439.1 (M + H) |
| 542 | 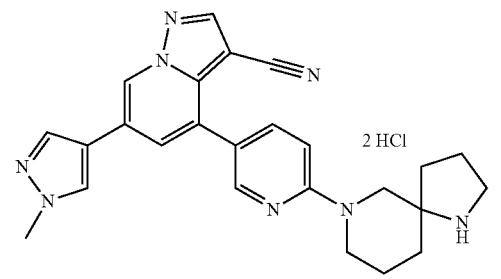 [SMILES: Cn1cc(-c2cc(-c3ccc(N4CCCC5(CCCN5)C4)nc3)c3c(C#N)cnn3c2)cn1] 2 HCl | 4-(6-(1,7-diazaspiro[4.5]decan-7-yl)pyridin-3-yl)-6-(1-methyl-1H-pyrazol-4-yl)pyrazolo[1,5-a]pyridine-3-carbonitrile dihydrochloride | 439.2 (M + H) |
| 543 | 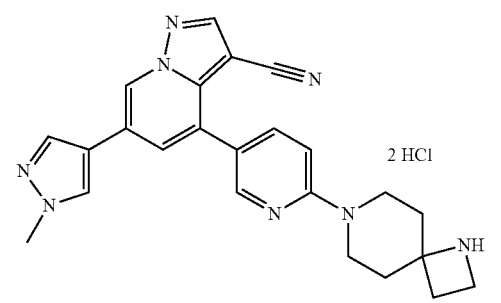 [SMILES: Cn1cc(-c2cc(-c3ccc(N4CCC5(CCN5)CC4)nc3)c3c(C#N)cnn3c2)cn1] 2 HCl | 4-(6-(1,7-diazaspiro[3.5]nonan-7-yl)pyridin-3-yl)-6-(1-methyl-1H-pyrazol-4-yl)pyrazolo[1,5-a]pyridine-3-carbonitrile dihydrochloride | 425.1 (M + H) |

TABLE WW-continued

| Ex # | Structure | Chemical Name | MS (apci) m/z |
|---|---|---|---|
| 544 | 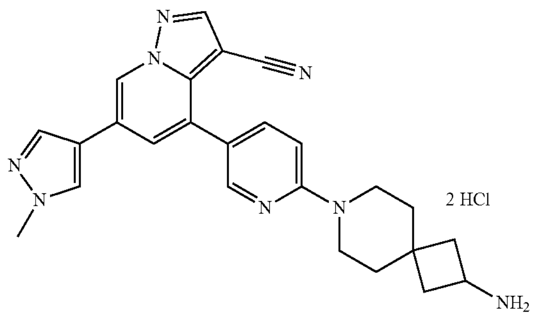 [SMILES: Cn1cc(-c2cc(-c3ccc(N4CCC5(CC4)CC(N)C5)nc3)c3c(C#N)cnn3c2)cn1] | 4-(6-(2-amino-7-azaspiro[3.5]nonan-7-yl)pyridin-3-yl)-6-(1-methyl-1H-pyrazol-4-yl)pyrazolo[1,5-a]pyridine-3-carbonitrile dihydrochloride | 439.2 (M + H) |
| 545 | 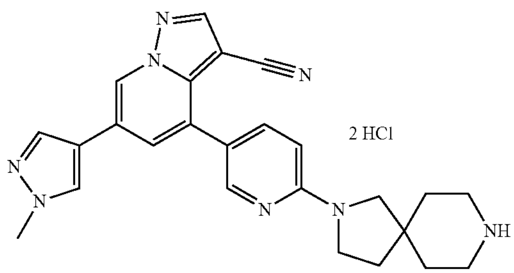 [SMILES: Cn1cc(-c2cc(-c3ccc(N4CCC5(CCNCC5)C4)nc3)c3c(C#N)cnn3c2)cn1] | 4-(6-(2,8-diazaspiro[4.5]decan-2-yl)pyridin-3-yl)-6-(1-methyl-1H-pyrazol-4-yl)pyrazolo[1,5-a]pyridine-3-carbonitrile dihydrochloride | 439.1 (M + H) |
| 546 | 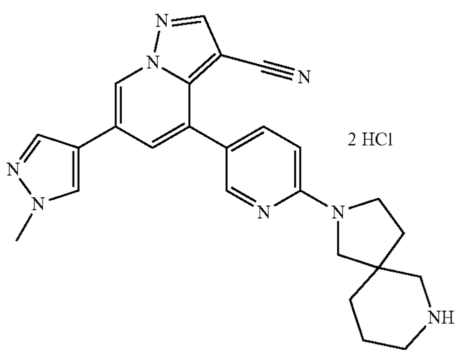 [SMILES: Cn1cc(-c2cc(-c3ccc(N4CCC5(CCCNC5)C4)nc3)c3c(C#N)cnn3c2)cn1] | 4-(6-(2,7-diazaspiro[4.5]decan-2-yl)pyridin-3-yl)-6-(1-methyl-1H-pyrazole-4-yl)pyrazolo[1,5-a]pyridine-3-carbonitrile dihydrochloride | 439.2 (M + H) |
| 547 | 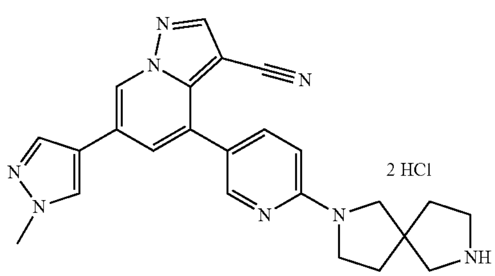 [SMILES: Cn1cc(-c2cc(-c3ccc(N4CCC5(CCNC5)C4)nc3)c3c(C#N)cnn3c2)cn1] | 4-(6-(2,7-diazaspiro[4.4]nonan-2-yl)pyridin-3-yl)-6-(1-methyl-1H-pyrazol-4-yl)pyrazolo[1,5-a]pyridine-3-carbonitrile dihydrochloride | 425.2 (M + H) |
| 548 | 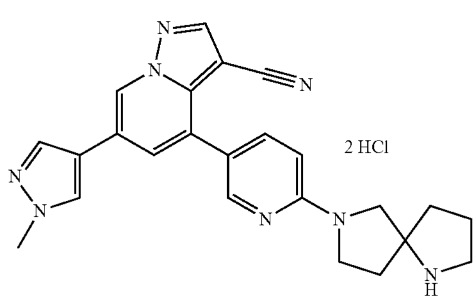 [SMILES: Cn1cc(-c2cc(-c3ccc(N4CCC5(CCCN5)C4)nc3)c3c(C#N)cnn3c2)cn1] | 4-(6-(1,7-diazaspiro[4.4]nonan-7-yl)pyridin-3-yl)-6-(1-methyl-1H-pyrazol-4-yl)pyrazolo[1,5-a]pyridine-3-carbonitrile dihydrochloride | 425.1 (M + H) |

TABLE WW-continued

| Ex # | Structure | Chemical Name | MS (apci) m/z |
|---|---|---|---|
| 549 | 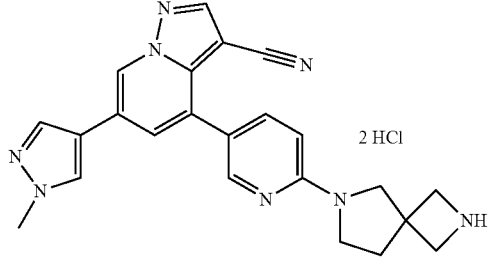 [SMILES: Cn1cc(-c2cc(-c3ccc(N4CCC5(CNC5)C4)nc3)c3c(C#N)cnn3c2)cn1] 2 HCl | 4-(6-(2,6-diazaspiro[3.4]octan-6-yl)pyridin-3-yl)-6-(1-methyl-1H-pyrazol-4-yl)pyrazolo[1,5-a]pyridine-3-carbonitrile dihydrochloride | 411.1 (M + H) |
| 550 | 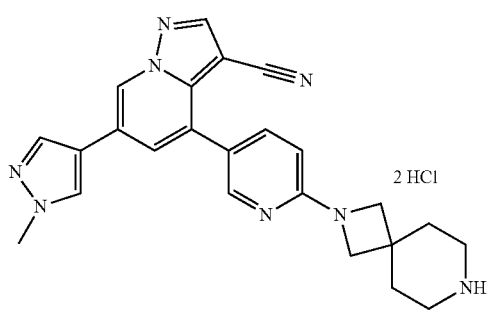 [SMILES: Cn1cc(-c2cc(-c3ccc(N4CC5(CCNCC5)C4)nc3)c3c(C#N)cnn3c2)cn1] 2 HCl | 4-(6-(2,7-diazaspiro[3.5]nonan-2-yl)pyridin-3-yl)-6-(1-methyl-1H-pyrazol-4-yl)pyrazolo[1,5-a]pyridine-3-carbonitrile dihydrochloride | 425.1 (M + H) |
| 551 | 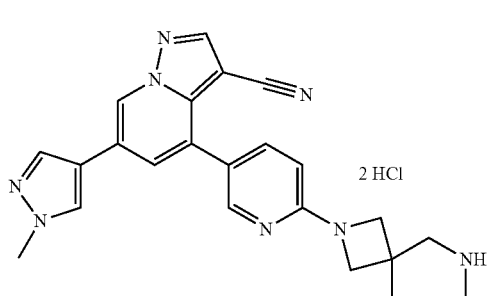 2 HCl | 4-(6-(2,6-diazaspiro[3.5]nonan-2-yl)pyridin-3-yl)-6-(1-methyl-1H-pyrazol-4-yl)pyrazolo[1,5-a]pyridine-3-carbonitrile dihydrochloride | 425.1 (M + H) |
| 552 | 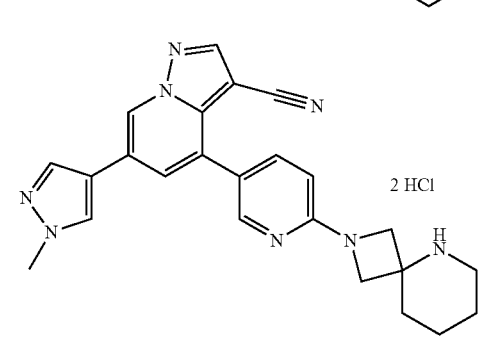 2 HCl | 4-(6-(2,5-diazaspiro[3.5]nonan-2-yl)pyridin-3-yl)-6-(1-methyl-1H-pyrazol-4-yl)pyrazolo[1,5-a]pyridine-3-carbonitrile dihydrochloride | 425.1 (M + H) |
| 553 | 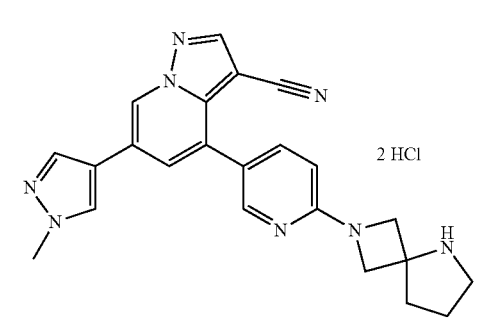 [SMILES: Cn1cc(-c2cc(-c3ccc(N4CC5(CCCN5)C4)nc3)c3c(C#N)cnn3c2)cn1] 2 HCl | 4-(6-(2,5-diazaspiro[3.4]octan-2-yl)pyridin-3-yl)-6-(1-methyl-1H-pyrazol-4-yl)pyrazolo[1,5-a]pyridine-3-carbonitrile dihydrochloride | 411.1 (M + H) |

Example 554

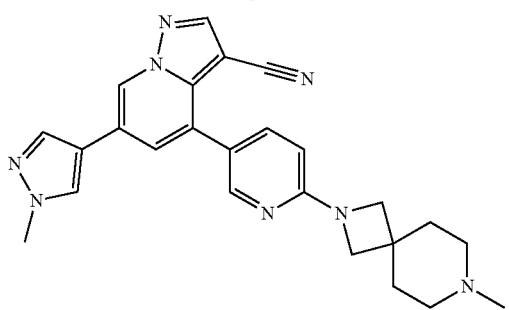 [SMILES: CN1CCC2(CC1)CN(c1ccc(-c3cc(-c4cnn(C)c4)cn4ncc(C#N)c34)cn1)C2]

6-(1-methyl-1H-pyrazol-4-yl)-4-(6-(7-methyl-2,7-diazaspiro[3.5]nonan-2-yl)pyridin-3-yl)pyrazolo[1,5-a]pyridine-3-carbonitrile A room temperature solution of 4-(6-(2,7-diazaspiro[3.5]nonan-2-yl)pyridin-3-yl)-6-(1-methyl-1H-pyrazol-4-yl)pyrazolo[1,5-a]pyridine-3-carbonitrile dihydrochloride (5 mg, 0.012 mmol) in dry DMF (200 μL) and TEA (16 μL, 0.12 mmol) was treated with 0.1 M iodomethane in MTBE (240 μL, 0.024 mmol). The reaction mixture was stirred overnight at room temperature, and then purified directly by C18 reverse phase chromatography (10-99% ACN/Water as the gradient eluent) to afford the title compound (1.7 mg, 33% yield). MS (apci) m/z=439.1 (M+H).

The compounds in Table XX were prepared according to the method described for the synthesis of 554 (except where noted), replacing 4-(6-(2,7-diazaspiro[3.5]nonan-2-yl)pyridin-3-yl)-6-(1-methyl-1H-pyrazol-4-yl)pyrazolo[1,5-a]pyridine-3-carbonitrile dihydrochloride with the appropriate amine dihydrochloride starting from Table WW. Reactions were monitored by LCMS, and reaction times and temperatures were adjusted accordingly. The title compounds were cleanly isolated following C18 reverse phase chromatography utilizing an appropriate gradient eluent.

TABLE XX

| Ex # | Structure | Chemical Name | MS (apci) m/z |
|---|---|---|---|
| 555 | 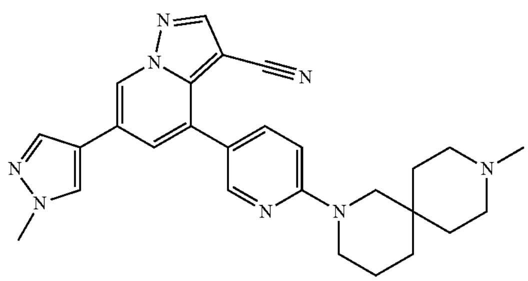 [SMILES: CN1CCC2(CCCN(c3ccc(-c4cc(-c5cnn(C)c5)cn5ncc(C#N)c45)cn3)C2)CC1] | 6-(1-methyl-1H-pyrazol-4-yl)-4-(6-(9-methyl-2,9-diazaspiro[5.5]undecan-2-yl)pyridin-3-yl)pyrazolo[1,5-a]pyridine-3-carbonitrile | 467.2 (M + H) |
| 556 | 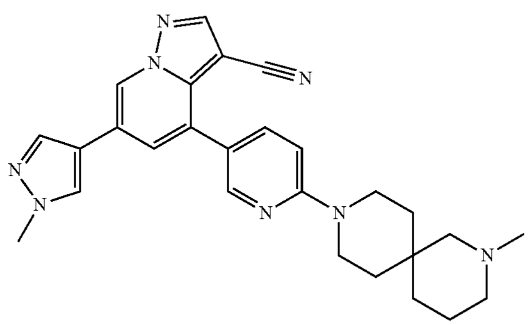 [SMILES: CN1CCCC2(CCN(c3ccc(-c4cc(-c5cnn(C)c5)cn5ncc(C#N)c45)cn3)CC2)C1] | 6-(1-methyl-1H-pyrazol-4-yl)-4-(6-(2-methyl-2,9-diazaspiro[5.5]undecan-9-yl)pyridin-3-yl)pyrazolo[1,5-a]pyridine-3-carbonitrile | 467.2 (M + H) |
| 557* | 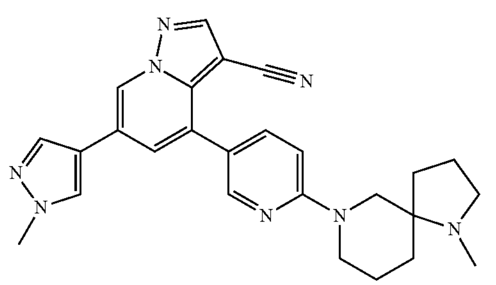 [SMILES: CN1CCCC12CCCN(c1ccc(-c3cc(-c4cnn(C)c4)cn4ncc(C#N)c34)cn1)C2] | 4-(6-(1-methyl-1,7-diazaspiro[4.5]decan-7-yl)pyridin-3-yl)-6-(1-methyl-1H-pyrazol-4-yl)pyrazolo[1,5-a]pyridine-3-carbonitrile | 453.2 (M + H) |

*Additional iodomethane (1 eq), TEA (1 eq) and DMF were added after 24 h, and after an additional 48 h reaction mixture was purified as noted in all other cases.

Example 558

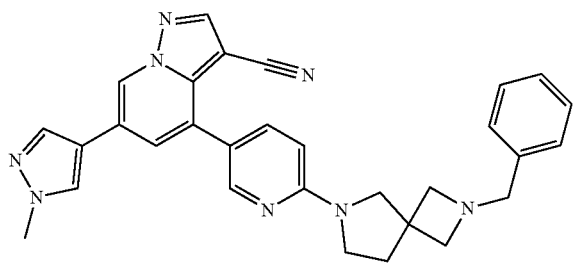 [SMILES: Cn1cc(-c2cc(-c3ccc(N4CCC5(CN(Cc6ccccc6)C5)C4)nc3)c3c(C#N)cnn3c2)cn1]

4-(6-(2-benzyl-2,6-diazaspiro[3.4]octan-6-yl)pyridin-3-yl)-6-(1-methyl-1H-pyrazol-4-yl)pyrazolo[1,5-a]pyridine-3-carbonitrile A room temperature solution of 4-(6-(2,6-diazaspiro[3.4]octan-6-yl)pyridin-3-yl)-6-(1-methyl-1H-pyrazol-4-yl)pyrazolo[1,5-a]pyridine-3-carbonitrile dihydrochloride (Example 549; 25 mg, 0.052 mmol) in DMF (2 mL) was treated sequentially with benzyl bromide (20 µL, 0.32 mmol) and TEA (721 µL, 0.517 mmol). The reaction mixture was stirred for 1 h at room temperature, then diluted with EtOAc and washed with water. The combined organic extracts were dried over anhydrous Na$_2$SO$_4$, filtered, and concentrated in vacuo. The residue was purified by silica chromatography (eluting with a stepped gradient of DCM/MeOH (50:1) then DCM/MeOH (25:1)) to cleanly afford the title compound (8 mg, 31% yield). MS (apci) m/z=501.2 (M+H).

Example 559

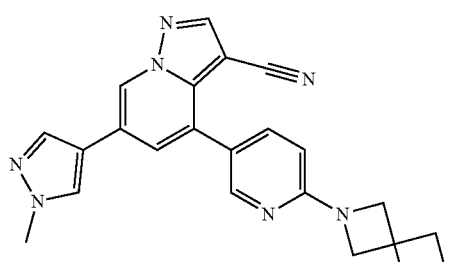

4-(6-(2,6-diazaspiro[3.3]heptan-2-yl)pyridin-3-yl)-6-(1-methyl-1H-pyrazol-4-yl)pyrazolo[1,5-a]pyridine-3-carbonitrile (1S,4S)-tert-butyl 5-(5-(3-cyano-6-(1-methyl-1H-pyrazol-4-yl)pyrazolo[1,5-a]pyridin-4-yl)pyridin-2-yl)-2,5-diazabicyclo[2.2.1]heptane-2-carboxylate (Example 526; 7.5 mg, 0.015 mmol) was dissolved in 1:1 DCM/TFA (0.3 mL). The reaction mixture was diluted with 4:1 DCM/iPrOH and extracted with saturated NaHCO$_3$. The combined organic extracts were dried over anhydrous Na$_2$SO$_4$, filtered, and concentrated in vacuo to cleanly afford the title compound (6 mg, quantitative yield). MS (apci) m/z=397.1 (M+H).

Example 560

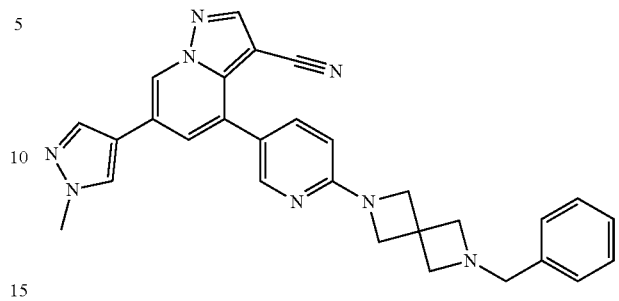

4-(6-(6-benzyl-2,6-diazaspiro[3.3]heptan-2-yl)pyridin-3-yl)-6-(1-methyl-1H-pyrazol-4-yl)pyrazolo[1,5-a]pyridine-3-carbonitrile A room temperature solution of 4-(6-(2,6-diazaspiro[3.3]heptan-2-yl)pyridin-3-yl)-6-(1-methyl-1H-pyrazol-4-yl)pyrazolo[1,5-a]pyridine-3-carbonitrile (Example 559; 6.0 mg, 0.0151 mmol) in DCM (0.3 mL) was treated sequentially with TEA (10.3 µL, 0.755 mmol) and benzyl bromide (5.39 µL, 0.0454 mmol). The reaction mixture was stirred for 16 h at room temperature and then concentrated in vacuo. The residue was purified by C18 reverse phase chromatography (5-95% water/ACN with 0.1% TFA as the gradient eluent) to afford the title compound as the TFA salt. The TFA salt was suspended in 4:1 DCM/iPrOH and extracted with saturated NaHCO$_3$. The combined organic extracts were dried over anhydrous Na$_2$SO$_4$, filtered, and concentrated in vacuo to cleanly afford the title compound (4.4 mg, 54% yield). MS (apci) m/z=487.2 (M+H).

Example 561

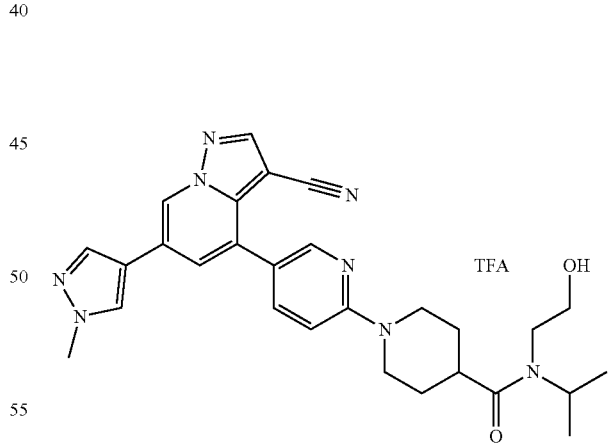

1-(5-(3-cyano-6-(1-methyl-1H-pyrazol-4-yl)pyrazolo[1,5-a]pyridin-4-yl)pyridin-2-yl)-N-(2-hydroxyethyl)-N-isopropylpiperidine-4-carboxamide 2,2,2-trifluoroacetate 2-(Isopropylamino)ethanol (0.014 mL, 0.12 mmol), DIEA (0.051 mL, 0.29 mmol), and HATU (45 mg, 0.12 mmol) were added sequentially to a room temperature solution of 1-(5-(3-cyano-6-(1-methyl-1H-pyrazol-4-yl)pyrazolo[1,5-a]pyridin-4-yl)pyridin-2-yl)piperidine-4-carboxylic acid (Example 231, Step 1; 25 mg, 0.058 mmol) in DMA (2 mL). After stirring at room temperature overnight, the reaction mixture was quenched with water and then extracted with EtOAc. The combined organic extracts were dried over anhydrous $Na_2SO_4$, filtered, concentrated in vacuo and purified by C18 reverse phase chromatography (5-95% water/ACN with 0.1% TFA as the gradient eluent) to afford the title compound as the TFA salt (4.7 mg, 15% yield). MS (apci) m/z=513.3 (M+H).

Example 562

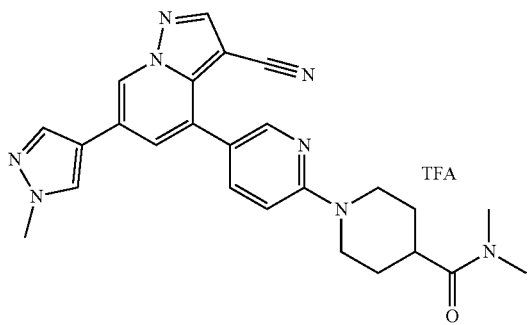 [SMILES: CN(C)C(=O)C1CCN(c2ccc(-c3cc(-c4cnn(C)c4)cn4ncc(C#N)c34)cn2)CC1]

1-(5-(3-cyano-6-(1-methyl-1H-pyrazol-4-yl)pyrazolo[1,5-a]pyridine-4-yl)pyridine-2-yl)-N,N-dimethylpiperidine-4-carboxamide 2,2,2-trifluoroacetate The title compound was isolated as a byproduct of the reaction of Example 561 (8.8 mg, 33% yield). MS (apci) m/z=455.2 (M+H).

Example 563

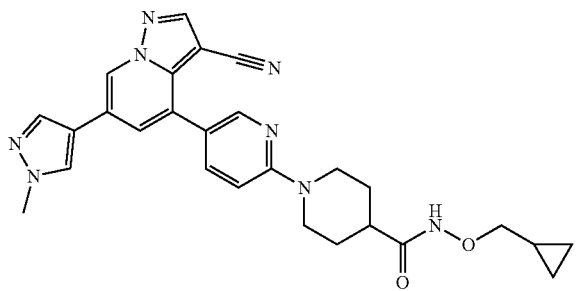 [SMILES: Cn1cc(-c2cc(-c3ccc(N4CCC(C(=O)NOCC5CC5)CC4)nc3)c3c(C#N)cnn3c2)cn1]

1-(5-(3-cyano-6-(1-methyl-1H-pyrazol-4-yl)pyrazolo[1,5-a]pyridin-4-yl)pyridin-2-yl)-N-(cyclopropylmethoxy)piperidine-4-carboxamide O-Cyclopropylmethyl-hydroxylamine hydrochloride (0.015 g, 0.12 mmol), DIEA (0.061 mL, 0.35 mmol), and HATU (45 mg, 0.12 mmol) were added sequentially to a solution 1-(5-(3-cyano-6-(1-methyl-1H-pyrazol-4-yl)pyrazolo[1,5-a]pyridin-4-yl)pyridin-2-yl)piperidine-4-carboxylic acid (Example 231, Step 1; 25 mg, 0.058 mmol) in DMA (2 mL). After stirring at ambient temperature overnight, the reaction mixture was quenched with water and extracted with EtOAc. The combined organic extracts were dried over anhydrous $Na_2SO_4$, filtered, concentrated in vacuo, and purified by silica chromatography (0-50% of 20% MeOH/DCM in EtOAc as the gradient eluent) to afford the title compound (8.5 mg, 28% yield). MS (apci) m/z=497.2 (M+H).

The compounds in Table YY were prepared according to the method described for the synthesis of Example 563, replacing O-Cyclopropylmethyl-hydroxylamine hydrochloride with the appropriate amines. Reactions were monitored by LCMS, and reaction times were adjusted accordingly. The title compounds were cleanly isolated following silica chromatography utilizing an appropriate gradient eluent.

TABLE YY

| Ex # | Structure | Chemical Name | MS (apci) m/z |
|---|---|---|---|
| 564 | 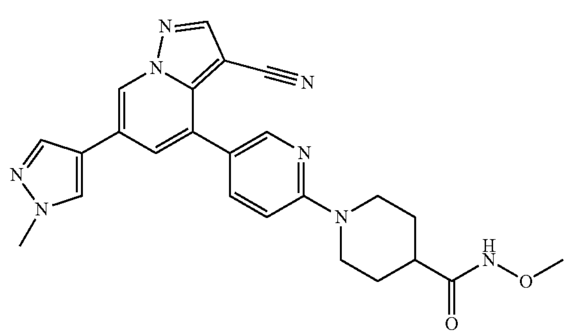 [SMILES: CONC(=O)C1CCN(c2ccc(-c3cc(-c4cnn(C)c4)cn4ncc(C#N)c34)cn2)CC1] | 1-(5-(3-cyano-6-(1-methyl-1H-pyrazol-4-yl)pyrazolo[1,5-a]pyridin-4-yl)pyridin-2-yl)-N-methoxypiperidine-4-carboxamide | 457.2 (M + H) |

TABLE YY-continued

| Ex # | Structure | Chemical Name | MS (apci) m/z |
|---|---|---|---|
| 565 | 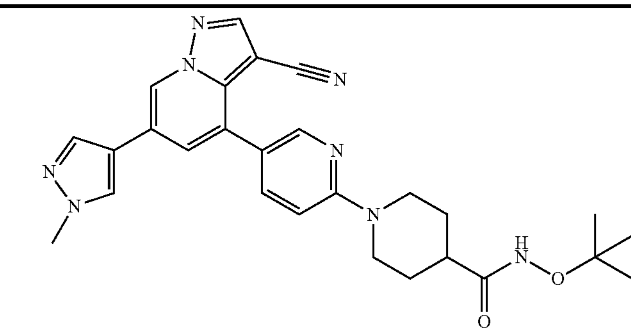 | N-(tert-butoxy)-1-(5-(3-cyano-6-(1-methyl-1H-pyrazol-4-yl)pyrazolo[1,5-a]pyridin-4-yl)pyridin-2-yl)piperidine-4-carboxamide | 499.3 (M + H) |
| 566 | 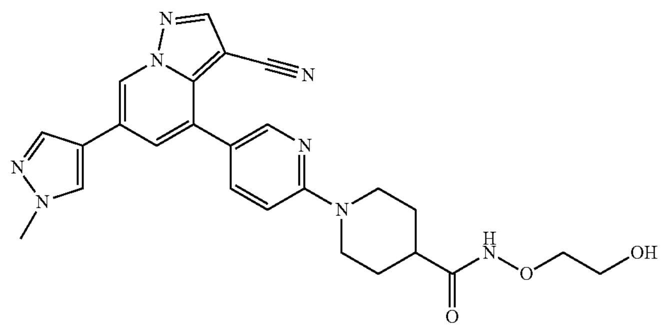 [SMILES: Cn1cc(-c2cc(-c3ccc(N4CCC(C(=O)NOCCO)CC4)nc3)c3c(C#N)cnn3c2)cn1] | 1-(5-(3-cyano-6-(1-methyl-1H-pyrazol-4-yl)pyrazolo[1,5-a]pyridin-4-yl)pyridin-2-yl)-N-(2-hydroxyethoxy)piperidine-4-carboxamide | 487.2 (M + H) |

Example 567

Example 568

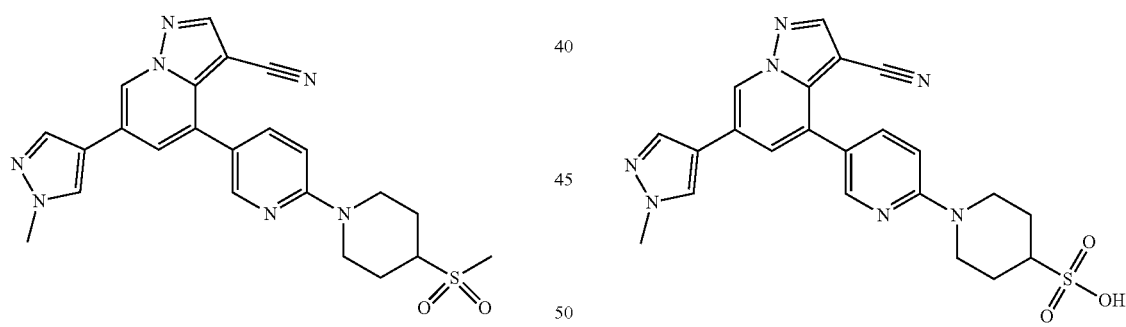

6-(1-methyl-1H-pyrazol-4-yl)-4-(6-(4-(methyl sulfonyl)piperidin-1-yl)pyridin-3-yl)pyrazolo[1,5-a]pyridine-3-carbonitrile A room temperature solution of 4-(6-fluoropyridin-3-yl)-6-(1-methyl-1H-pyrazol-4-yl)pyrazolo[1,5-a]pyridine-3-carbonitrile (Intermediate P6; 0.030 g, 0.094 mmol) in DMSO (6.28 mL) was treated with 4-(methylsulfonyl)piperidine (0.062 g, 0.38 mmol) and K$_2$CO$_3$ (0.10 g, 0.75 mmol) and stirred overnight at 80° C. The reaction mixture was adjusted to pH 7 with the addition of saturated NaHCO$_3$. The resulting suspension was vacuum filtered and rinsed with water to afford the title compound (26 mg, 57% yield). MS (apci) m/z=462.1 (M+H).

1-(5-(3-cyano-6-(1-methyl-1H-pyrazol-4-yl)pyrazolo[1,5-a]pyridin-4-yl)pyridin-2-yl)piperidine-4-sulfonic Acid A room temperature solution of 4-(6-fluoropyridin-3-yl)-6-(1-methyl-1H-pyrazol-4-yl)pyrazolo[1,5-a]pyridine-3-carbonitrile (Intermediate P6; 0.100 g, 0.314 mmol) in DMSO (2.4 mL) was treated with piperidine-4-sulfonic acid (0.16 g, 0.94 mmol) and K$_2$CO$_3$ (0.13 g, 0.94 mmol), then stirred overnight at 110° C. The reaction mixture was adjusted to pH 7 with 1 M HCl. The resulting suspension was vacuum filtered through a nylon membrane and rinsed with water to afford the title compound (85 mg, 78% yield). MS (apci) m/z=462.1 (M−H).

Example 569

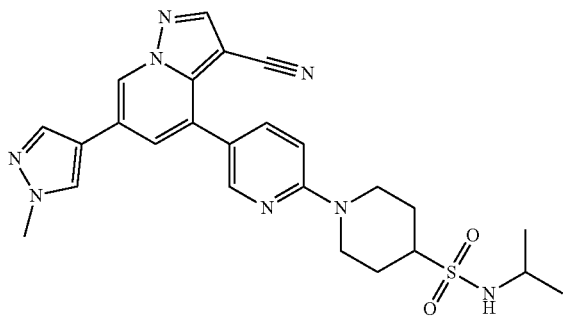 [SMILES: CC(C)NS(=O)(=O)C1CCN(c2ccc(-c3cc(-c4cnn(C)c4)cn4ncc(C#N)c34)cn2)CC1]

1-(5-(3-cyano-6-(1-methyl-1H-pyrazol-4-yl)pyrazolo[1,5-a]pyridin-4-yl)pyridin-2-yl)-N-isopropylpiperidine-4-sulfonamide Step 1: Preparation of 1-(5-(3-cyano-6-(1-methyl-1H-pyrazol-4-yl)pyrazolo[1,5-a]pyridin-4-yl)pyridin-2-yl)piperidine-4-sulfonyl Chloride A room temperature mixture of 1-(5-(3-cyano-6-(1-methyl-1H-pyrazol-4-yl)pyrazolo[1,5-a]pyridin-4-yl)pyridin-2-yl)piperidine-4-sulfonic acid (Example 568; 0.025 g, 0.054 mmol) in DCE (1.1 mL) was treated sequentially with SOCl₂ (0.020 mL, 0.27 mmol) and DMF (0.027 mL, 0.054 mmol). The resulting mixture was stirred for 3 h at reflux, and then cooled to room temperature. The reaction mixture was concentrated in vacuo to afford the crude title compound (25 mg, 96% yield), which was used directly in the next step without further purification.

Step 2: Preparation of 1-(5-(3-cyano-6-(1-methyl-1H-pyrazol-4-yl)pyrazolo[1,5-a]pyridin-4-yl)pyridin-2-yl)-N-isopropylpiperidine-4-sulfonamide A room temperature solution of 1-(5-(3-cyano-6-(1-methyl-1H-pyrazol-4-yl)pyrazolo[1,5-a]pyridine-4-yl)pyridine-2-yl)piperidine-4-sulfonyl chloride (from Step 1; 25 mg, 0.052 mmol) in DCM (2.6 mL) and DIEA (45 µL, 0.259 mmol) was treated with isopropyl amine (8.9 µL, 0.10 mmol). After stirring overnight at room temperature, the reaction mixture was quenched with water and extracted with DCM. The combined organic extracts were dried over anhydrous Na₂SO₄, filtered, and concentrated in vacuo. The residue was purified by silica gel (0-10% MeOH in DCM) to afford the title compound (12.2 mg, 45% yield). MS (apci) m/z=505.2 (M+H)

Example 570

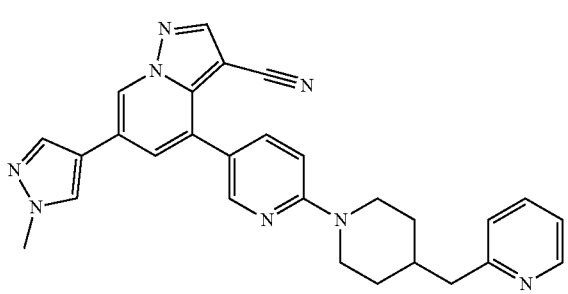 [SMILES: Cn1cc(-c2cc(-c3ccc(N4CCC(Cc5ccccn5)CC4)nc3)c3c(C#N)cnn3c2)cn1]

6-(1-methyl-1H-pyrazol-4-yl)-4-(6-(4-(pyridin-2-ylmethyl)piperidin-1-yl)pyridin-3-yl)pyrazolo[1,5-a]pyridine-3-carbonitrile In a microwave vessel, a room temperature solution of 4-(6-fluoropyridin-3-yl)-6-(1-methyl-1H-pyrazol-4-yl)pyrazolo[1,5-a]pyridine-3-carbonitrile (Intermediate P6; 30 mg, 0.094 mmol) in DMSO (471 µL) was treated with 2-(piperidin-4-ylmethyl)pyridine dihydrochloride (35 mg, 0.14 mmol) and K₂CO₃ (39 mg, 0.28 mmol). The resulting mixture was subjected to microwave irradiation for 1 h at 100° C., and then for 12 h at 150° C. The reaction mixture was cooled to room temperature, and filtered. The filtrate was purified directly by C18 reverse phase chromatography (5-40% ACN/water) to afford the title compound (15 mg, 33% yield). MS (apci) m/z=475.2 (M+H).

Example 571

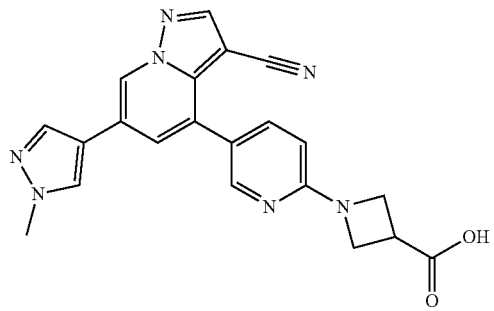 [SMILES: Cn1cc(-c2cc(-c3ccc(N4CC(C(=O)O)C4)nc3)c3c(C#N)cnn3c2)cn1]

1-(5-(3-cyano-6-(1-methyl-1H-pyrazol-4-yl)pyrazolo[1,5-a]pyridin-4-yl)pyridin-2-yl)azetidine-3-carboxylic Acid A room temperature solution of 4-(6-fluoropyridin-3-yl)-6-(1-methyl-1H-pyrazol-4-yl)pyrazolo[1,5-a]pyridine-3-carbonitrile (Intermediate P6; 0.300 g, 0.942 mmol) in DMSO (9.42 mL) was treated with azetidine-3-carboxylic acid (0.381 g, 3.77 mmol) and K₂CO₃₍ₛ₎ (0.521 g, 3.77 mmol), then stirred overnight at 110° C. The reaction mixture was acidified to pH 7 with 1 M HCl. The resulting suspension was vacuum filtered, and the solids were washed with water to cleanly afford the title compound (0.281 g, 74.6% yield). MS (apci) m/z=400.2 (M+H).

Example 572

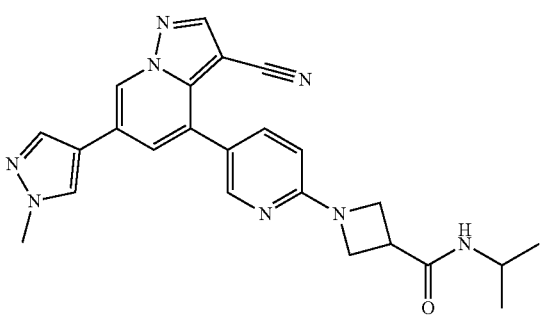 [SMILES: CC(C)NC(=O)C1CN(c2ccc(-c3cc(-c4cnn(C)c4)cn4ncc(C#N)c34)cn2)C1]

511

1-(5-(3-cyano-6-(1-methyl-1H-pyrazol-4-yl)pyrazolo[1,5-a]pyridin-4-yl)pyridin-2-yl)-N-isopropylazetidine-3-carboxamide A room temperature solution of 1-(5-(3-cyano-6-(1-methyl-1H-pyrazol-4-yl)pyrazolo[1,5-a]pyridin-2-yl)azetidine-3-carboxylic acid (Example 571; 25 mg, 0.0626 mmol) in DMA (2.09 mL) was added DIEA (54.5 µL, 0.313 mmol), propan-2-amine (7.4 mg, 0.125 mmol) and HATU (47.6 mg, 0.125 mmol). The reaction mixture was allowed to stir overnight at room temperature. The reaction mixture was quenched with water and extracted with EtOAc. The combined organic extracts were dried over anhydrous Na$_2$SO$_4$, filtered, and concentrated in vacuo. The residue was purified by silica chromatography (0-50% gradient of 20% MeOH/DCM in EtOAc as the eluent) to afford the title compound (8.7 mg, 31% yield). MS (apci) m/z=441.2 (M+H).

Example 573

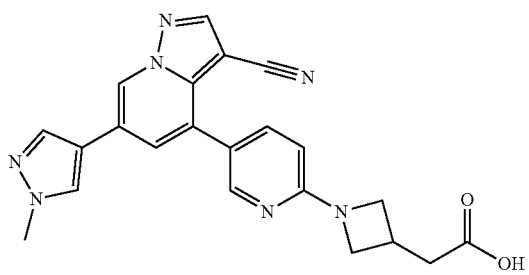 [SMILES: Cn1cc(-c2cc(-c3ccc(N4CC(CC(=O)O)C4)nc3)c3c(C#N)cnn3c2)cn1]

2-(1-(5-(3-cyano-6-(1-methyl-1H-pyrazol-4-yl)pyrazolo[1,5-a]pyridin-4-yl)pyridin-2-yl)azetidin-3-yl) acetic Acid A room temperature solution of 4-(6-fluoropyridin-3-yl)-6-(1-methyl-1H-pyrazol-4-yl)pyrazolo[1,5-a]pyridine-3-carbonitrile (Intermediate P6; 0.225 g, 0.707 mmol) in DMSO (7.07 mL) was treated with azetidin-3-yl-acetic acid hydrochloride (0.4296 g, 2.83 mmol) and K$_2$CO$_3$ (0.782 g, 5.66 mmol), then stirred overnight at 110° C. The reaction mixture was acidified to pH 7 with 1 M HCl. The resulting suspension was vacuum filtered, and the solids were washed with water to cleanly afford the title compound (0.393 g, quantitative yield). MS (apci) m/z=414.2 (M+H).

Example 574

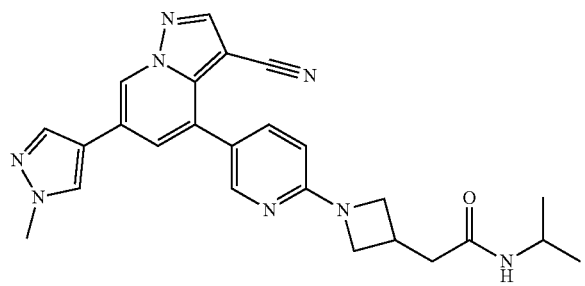 [SMILES: CC(C)NC(=O)CC1CN(c2ccc(-c3cc(-c4cnn(C)c4)cn4ncc(C#N)c34)cn2)C1]

512

2-(1-(5-(3-cyano-6-(1-methyl-1H-pyrazol-4-yl)pyrazolo[1,5-a]pyridin-4-yl)pyridin-2-yl)azetidin-3-yl)-N-isopropylacetamide A room temperature solution of 2-(1-(5-(3-cyano-6-(1-methyl-1H-pyrazol-4-yl)pyrazolo[1,5-a]pyridin-4-yl)pyridin-2-yl)azetidin-3-yl)acetic acid (Example 573; 50 mg, 0.121 mmol) in DMA (2.42 mL) was treated with DIEA (0.105 mL, 0.605 mmol), propan-2-amine (14.3 mg, 0.242 mmol) and HATU (92.0 mg, 0.242 mmol). The reaction mixture was allowed to stir overnight at room temperature. The reaction mixture was quenched with water and extracted with EtOAc. The combined organic extracts were dried over anhydrous Na$_2$SO$_4$, filtered, and concentrated in vacuo. The residue was purified by silica chromatography (0-50% gradient of 20% MeOH/DCM in EtOAc as the eluent) to afford the title compound (4.6 mg, 8% yield). MS (apci) m/z=455.2 (M+H).

Example 575

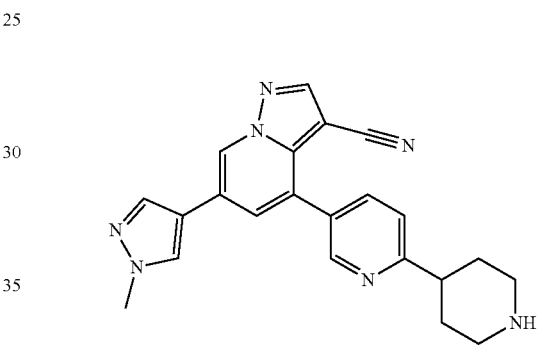

6-(1-methyl-1H-pyrazol-4-yl)-4-(6-(piperidin-4-yl)pyridin-3-yl)pyrazolo[1,5-a]pyridine-3-carbonitrile A room temperature solution of 3-cyano-6-(1-methyl-1H-pyrazol-4-yl)pyrazolo[1,5-a]pyridin-4-yl trifluoromethanesulfonate (Intermediate P5; 55.3 mg, 0.150 mmol) in 4:1 dioxane/water (1.5 mL) was treated with 2-(piperidin-4-yl)pyridine-5-boronic acid (61.4 mg, 0.298 mmol), Pd$_2$(dba)$_3$ (6.82 mg, 0.00745 mmol), XPhos (14.2 mg, 0.0298 mmol), and K$_2$CO$_3$ (61.8 mg, 0.447 mmol). The reaction mixture was sparged with Argon, sealed, and then stirred 16 h at 100° C. After cooling to room temperature, the reaction mixture was diluted with 4:1 DCM/iPrOH and washed with water. The combined organic extracts were dried over anhydrous Na$_2$SO$_4$, filtered, and concentrated in vacuo. The residue was purified by C18 reverse phase chromatography (5-95% water/ACN with 0.1% TFA as the gradient eluent) to afford the title compound as the TFA salt. The TFA salt was suspended in 4:1 DCM/iPrOH and extracted with saturated NaHCO$_3$. The combined organic extracts were dried over anhydrous Na$_2$SO$_4$, filtered, and concentrated in vacuo to cleanly afford the title compound (18.1 mg, 32% yield). MS (apci) m/z=384.1 (M+H).

Example 576

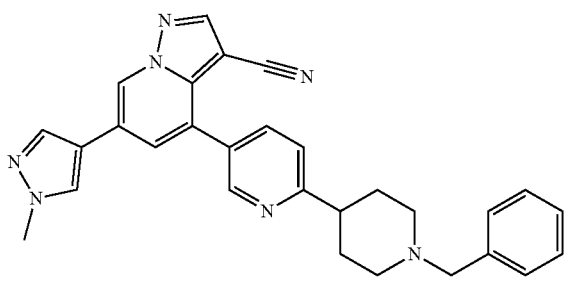 [SMILES: Cn1cc(-c2cc(-c3ccc(C4CCN(Cc5ccccc5)CC4)nc3)c3c(C#N)cnn3c2)cn1]

4-(6-(1-benzylpiperidin-4-yl)pyridin-3-yl)-6-(1-methyl-1H-pyrazol-4-yl)pyrazolo[1,5-a]pyridine-3-carbonitrile A room temperature solution of 6-(1-methyl-1H-pyrazol-4-yl)-4-(6-(piperidin-4-yl)pyridin-3-yl)pyrazolo[1,5-a]pyridine-3-carbonitrile (Example 575; 18.1 mg, 0.0472 mmol) in DCM (1.0 mL) was treated sequentially with TEA (32.0 µL, 0.236 mmol) and benzyl bromide (16.8 µL, 0.142 mmol). The reaction mixture was stirred for 16 h at room temperature and then concentrated in vacuo. The residue was purified by C18 reverse phase chromatography (5-95% water/ACN with 0.1% TFA as the gradient eluent) to afford the title compound as the TFA salt. The TFA salt was suspended in 4:1 DCM/iPrOH and extracted with saturated NaHCO$_3$. The combined organic extracts were dried over anhydrous Na$_2$SO$_4$, filtered, and concentrated in vacuo to cleanly afford the title compound (15.6 mg, 70% yield). MS (apci) m/z=474.2 (M+H).

Example 577

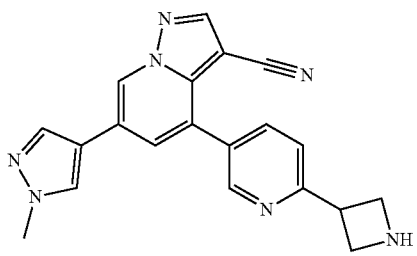 [SMILES: Cn1cc(-c2cc(-c3ccc(C4CNC4)nc3)c3c(C#N)cnn3c2)cn1]

4-(6-(azetidin-3-yl)pyridin-3-yl)-6-(1-methyl-1H-pyrazol-4-yl)pyrazolo[1,5-a]pyridine-3-carbonitrile Step 1: Preparation of Tert-Butyl 3-(5-(3-cyano-6-(1-methyl-1H-pyrazol-4-yl)pyrazolo[1,5-a]pyridin-4-yl)pyridin-2-yl)azetidine-1-carboxylate A room temperature solution of 3-cyano-6-(1-methyl-1H-pyrazol-4-yl)pyrazolo[1,5-a]pyridine-4-yl trifluoromethanesulfonate (Intermediate P5; 89.5 mg, 0.241 mmol) in 4:1 dioxane:water (2.5 mL) was treated with tert-butyl 3-(5-(4,4,5,5-tetramethyl-1,3,2-dioxaborolan-2-yl)pyridin-2-yl)azetidine-1-carboxylate (Intermediate R13; 174 mg, 0.482 mmol), Pd$_2$(dba)$_3$ (11.0 mg, 0.0120 mmol), XPhos (23 mg, 0.0482 mmol), and K$_2$CO$_3$ (100 mg, 0.723 mmol). The reaction mixture was sparged with Argon, sealed, and stirred 16 h at 100° C. After cooling to room temperature, the reaction mixture was diluted with 4:1 DCM/iPrOH and washed with water. The combined organic extracts were dried over anhydrous Na$_2$SO$_4$, filtered, and concentrated in vacuo. The residue was purified by C18 reverse phase chromatography (5-95% water/ACN with 0.1% TFA as the gradient eluent) to afford the title compound as the TFA salt. The TFA salt was suspended in 4:1 DCM/iPrOH and extracted with saturated NaHCO$_3$. The combined organic extracts were dried over anhydrous Na$_2$SO$_4$, filtered, and concentrated in vacuo to afford the title compound. MS (apci) m/z=356.1 ((M-Boc)+1).

Step 2: Preparation of 4-(6-(3,8-Diazabicyclo[3.2.1]octan-8-yl)pyridine-3-yl)-6-(1-methyl-1H-pyrazol-4-yl)pyrazolo[1,5-a]pyridine-3-carbonitrile The tert-butyl 3-(5-(3-cyano-6-(1-methyl-1H-pyrazol-4-yl)pyrazolo[1,5-a]pyridine-4-yl)pyridine-2-yl)azetidine-1-carboxylate was diluted with 1:1 DCM/TFA (2.0 mL), stirred for 30 min at room temperature, and then concentrated in vacuo. The residue was purified by C18 reverse phase chromatography (5-95% water/ACN with 0.1% TFA as the gradient eluent) to afford the title compound as the TFA salt. The TFA salt was suspended in 4:1 DCM/iPrOH and extracted with saturated NaHCO$_3$. The combined organic extracts were dried over anhydrous Na$_2$SO$_4$, filtered, and concentrated in vacuo to cleanly afford the title compound (12.7 mg, 15% yield). MS (apci) m/z=356.1 (M+H).

The compounds in the Table ZZ were prepared according to the method described for the synthesis of Example 577, replacing tert-butyl 3-(5-(4,4,5,5-tetramethyl-1,3,2-dioxaborolan-2-yl)pyridine-2-yl)azetidine-1-carboxylate in Step 1, with the appropriate boronate ester from Table DD. Reaction progression was followed by LCMS, and reaction times were adjusted as necessary. Products in each step were purified according to method described for the synthesis of Example 577, employing the appropriate stationary phase and gradient eluent.

TABLE ZZ

| Ex # | Structure | Chemical Name | MS (apci) m/z |
|------|-----------|---------------|---------------|
| 578 | 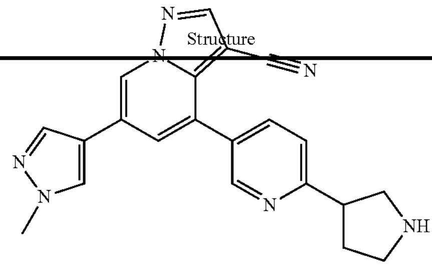 | 6-(1-methyl-1H-pyrazol-4-yl)-4-(6-(pyrrolidin-3-yl)pyridin-3-yl)pyrazolo[1,5-a]pyridine-3-carbonitrile | 370.1 (M + H) |
| 579 | 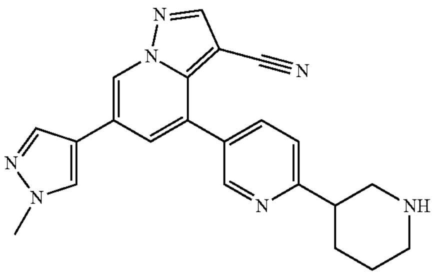 [SMILES: Cn1cc(-c2cc(-c3ccc(C4CCCNC4)nc3)c3c(C#N)cnn3c2)cn1] | 6-(1-methyl-1H-pyrazol-4-yl)-4-(6-(piperidin-3-yl)pyridin-3-yl)pyrazolo[1,5-a]pyridine-3-carbonitrile | 384.2 (M + H) |

Example 580

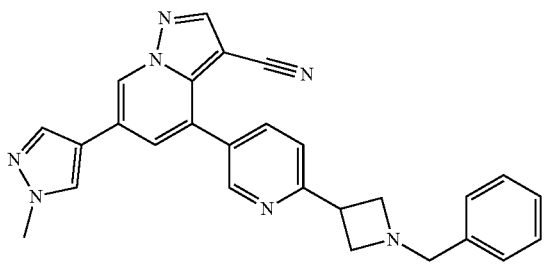 [SMILES: Cn1cc(-c2cc(-c3ccc(C4CN(Cc5ccccc5)C4)nc3)c3c(C#N)cnn3c2)cn1]

4-(6-(1-benzylazetidin-3-yl)pyridin-3-yl)-6-(1-methyl-1H-pyrazol-4-yl)pyrazolo[1,5-a]pyridine-3-carbonitrile A room temperature solution of 4-(6-(azetidin-3-yl)pyridin-3-yl)-6-(1-methyl-1H-pyrazol-4-yl)pyrazolo[1,5-a]pyridine-3-carbonitrile (Example 577; 12.7 mg, 0.0357 mmol) in DCM (0.7 mL) was treated sequentially with TEA (24.2 µL, 0.179 mmol) and benzyl bromide (12.7 µL, 0.107 mmol). The reaction mixture was stirred for 16 h at room temperature, and then concentrated in vacuo. The residue was purified by C18 reverse phase chromatography (5-95% water/ACN with 0.1% TFA as the gradient eluent) to afford the title compound as the TFA salt. The TFA salt was suspended in 4:1 DCM/iPrOH and extracted with saturated NaHCO$_3$. The combined organic extracts were dried over anhydrous Na$_2$SO$_4$, filtered, and concentrated in vacuo to cleanly afford the title compound (4.1 mg, 26% yield). MS (apci) m/z=446.2 (M+H).

The compounds in the Table AAA were prepared according to the method described for the synthesis of Example 580, replacing 4-(6-(azetidin-3-yl)pyridine-3-yl)-6-(1-methyl-1H-pyrazol-4-yl)pyrazolo[1,5-a]pyridine-3-carbonitrile with the appropriate amine from Table ZZ. Products were purified according to the method described for the synthesis of Example 580, employing the appropriate gradient eluent.

TABLE AAA

| Ex # | Structure | Chemical Name | MS (apci) m/z |
|------|-----------|---------------|---------------|
| 581 | 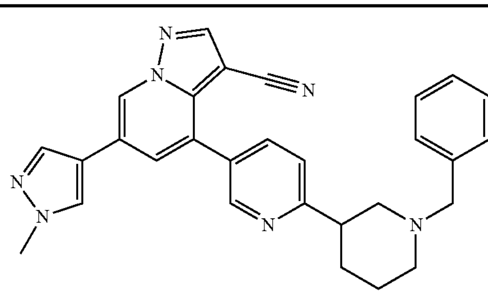 | 4-(6-(1-benzylpiperidin-3-yl)pyridine-3-yl)-6-(1-methyl-1H-pyrazol-4-yl)pyrazolo[1,5-a]pyridine-3-carbonitrile | 474.2 (M + H) |

| Ex # | Structure | Chemical Name | MS (apci) m/z |
|---|---|---|---|
| 582 | 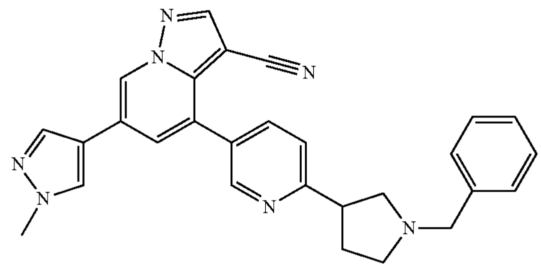 [SMILES: Cn1cc(-c2cc(-c3ccc(C4CCN(Cc5ccccc5)C4)nc3)c3c(C#N)cnn3c2)cn1] | 4-(6-(1-benzylpyrrolidin-3-yl)pyridine-3-yl)-6-(1-methyl-1H-pyrazol-4-yl)pyrazolo[1,5-a]pyridine-3-carbonitrile | 460.2 (M + H) |

Example 583

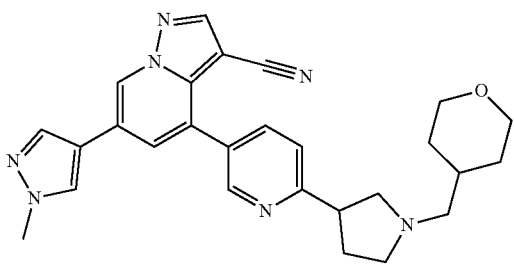 [SMILES: Cn1cc(-c2cc(-c3ccc(C4CCN(CC5CCOCC5)C4)nc3)c3c(C#N)cnn3c2)cn1]

6-(1-methyl-1H-pyrazol-4-yl)-4-(6-(1-((tetrahydro-2H-pyran-4-yl)methyl)pyrrolidin-3-yl)pyridin-3-yl)pyrazolo[1,5-a]pyridine-3-carbonitrile A room temperature solution of 6-(1-methyl-1H-pyrazol-4-yl)-4-(6-(pyrrolidin-3-yl)pyridin-3-yl)pyrazolo[1,5-a]pyridine-3-carbonitrile (Example 578; 31.3 mg, 0.0847 mmol) in 1:1 DCM/MeOH (1.7 mL) was treated with 4-formyltetrahydropyran (19.3 mg, 0.169 mmol), NaBH(AcO)$_3$ (35.9 mg, 0.169 mmol) and a drop of acetic acid. The reaction mixture was allowed to stir 16 h at room temperature. The reaction mixture was purified directly by C18 reverse phase chromatography (5->95% water/ACN with 0.1% TFA) to afford the title compound as the TFA salt. The TFA salt was suspended in 4:1 DCM/iPrOH and extracted with saturated NaHCO$_3$. The combined organic extracts were dried over anhydrous Na$_2$SO$_4$, filtered, and concentrated in vacuo to cleanly afford the title compound (29.0 mg, 73% yield). MS (apci) m/z=468.2 (M+H).

Example 584

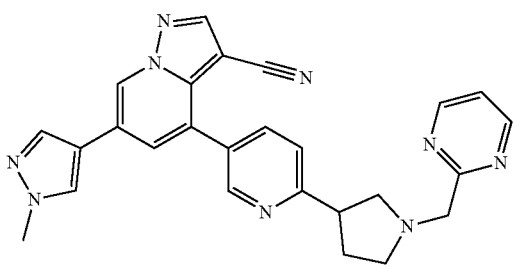 [SMILES: Cn1cc(-c2cc(-c3ccc(C4CCN(Cc5ncccn5)C4)nc3)c3c(C#N)cnn3c2)cn1]

6-(1-methyl-1H-pyrazol-4-yl)-4-(6-(1-(pyrimidin-2-ylmethyl)pyrrolidin-3-yl)pyridin-3-yl)pyrazolo[1,5-a]pyridine-3-carbonitrile Following a method similar to that used for Example 583, but replacing 4-formyltetrahydropyran with pyrimidine carboxaldehyde, the title compound was isolated cleanly (24.2 mg, 46% yield). MS (apci) m/z=462.2 (M+H).

Example 585

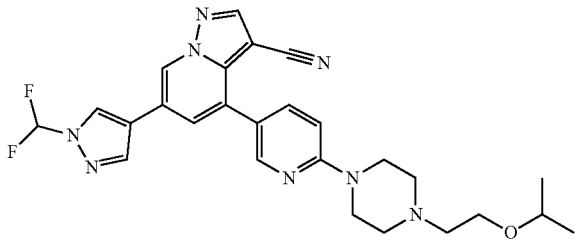 [SMILES: CC(C)OCCN1CCN(c2ccc(-c3cc(-c4cnn(C(F)F)c4)cn4ncc(C#N)c34)cn2)CC1]

6-(1-(difluoromethyl)-1H-pyrazol-4-yl)-4-(6-(4-(2-isopropoxyethyl)piperazin-1-yl)pyridin-3-yl)pyrazolo[1,5-a]pyridine-3-carbonitrile A room temperature solution of 6-(1-(difluoromethyl)-1H-pyrazol-4-yl)-4-(6-(piperazin-1-yl)pyridin-3-yl)pyrazolo[1,5-a]pyridine-3-carbonitrile dihydrochloride (Example 266; 20 mg, 0.041 mmol) in dry DMA (400 μL) was treated with TEA (76 μL, 0.55 mmol) and 2-(2-bromoethoxy)propane (0.0203 g, 0.122 mmol). The resulting reaction mixture was stirred overnight at 75° C. The reaction mixture was purified directly by C18 reverse phase chromatography (15-90% ACN/Water as the eluent) to afford the title compound (12.4 mg, 60% yield). MS (apci) m/z=507.2 (M+H).

Example 586

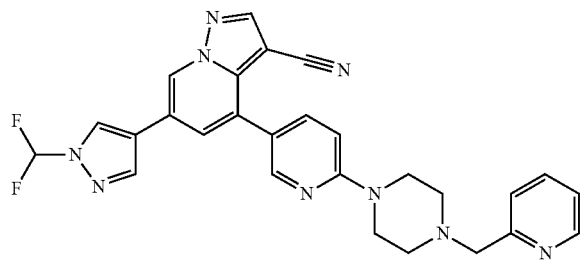 [SMILES: N#Cc1cnn2cc(-c3cnn(C(F)F)c3)cc(-c3ccc(N4CCN(Cc5ccccn5)CC4)nc3)c12]

6-(1-(difluoromethyl)-1H-pyrazol-4-yl)-4-(6-(4-(pyridine-2-ylmethyl)piperazin-1-yl)pyridin-3-yl)pyrazolo[1,5-a]pyridine-3-carbonitrile A room temperature solution of 6-(1-(difluoromethyl)-1H-pyrazol-4-yl)-4-(6-(piperazin-1-yl)pyridin-3-yl)pyrazolo[1,5-a]pyridine-3-carbonitrile dihydrochloride (Example 266; 10 mg, 0.020 mmol) and Me₄N(AcO)₃BH (16 mg, 0.061 mmol) in DMF (0.2 mL) was treated with picolinaldehyde (3.3 mg, 0.030 mmol) and TEA (8.5 µL, 0.061 mmol). The resulting mixture was stirred overnight at room temperature, and then purified directly by C18 reverse phase chromatography (0-60% ACN/water as the gradient eluent) to afford the title compound (2.4 mg, 23% yield). MS (apci) m/z=512.2 (M+H).

Example 587

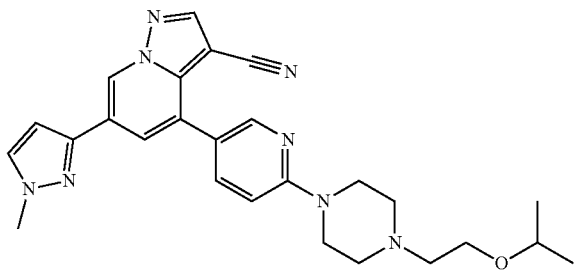 [SMILES: CC(C)OCCN1CCN(c2ccc(-c3cc(-c4ccn(C)n4)cn4ncc(C#N)c34)cn2)CC1]

4-(6-(4-(2-isopropoxyethyl)piperazin-1-yl)pyridin-3-yl)-6-(1-methyl-1H-pyrazol-3-yl)pyrazolo[1,5-a]pyridine-3-carbonitrile A room temperature solution of 6-(1-methyl-1H-pyrazol-3-yl)-4-(6-(piperazin-1-yl)pyridin-3-yl)pyrazolo[1,5-a]pyridine-3-carbonitrile dihydrochloride (Example 271; 21 mg, 0.046 mmol) in dry DMA (400 µL) was treated with TEA (64 µL, 0.46 mmol) and 2-(2-bromoethoxy)propane (23 mg, 0.138 mmol). The resulting reaction mixture was stirred overnight at 75° C. The reaction mixture was purified directly by C18 reverse phase chromatography (15-90% ACN/Water as the eluent) to afford the title compound (12.4 mg, 57% yield). MS (apci) m/z=471.2 (M+H).

Example 588

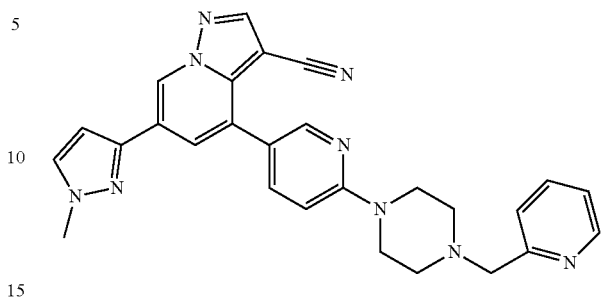

6-(1-methyl-1H-pyrazol-3-yl)-4-(6-(4-(pyridine-2-ylmethyl)piperazin-1-yl)pyridin-3-yl)pyrazolo[1,5-a]pyridine-3-carbonitrile A room temperature solution of 6-(1-methyl-1H-pyrazol-3-yl)-4-(6-(piperazin-1-yl)pyridin-3-yl)pyrazolo[1,5-a]pyridine-3-carbonitrile dihydrochloride (Example 271; 10 mg, 0.022 mmol) in DMF (0.2 mL) was treated with picolinaldehyde (3.5 mg, 0.033 mmol), Me₄N(AcO)₃BH (17 mg, 0.066 mmol) and TEA (9.1 µL, 0.066 mmol). The resulting mixture was stirred overnight at room temperature, and then purified directly by C18 reverse phase chromatography (0-60% ACN/water as the gradient eluent) to afford the title compound (2.3 mg, 22% yield). MS (apci) m/z=476.2 (M+H).

Example 589

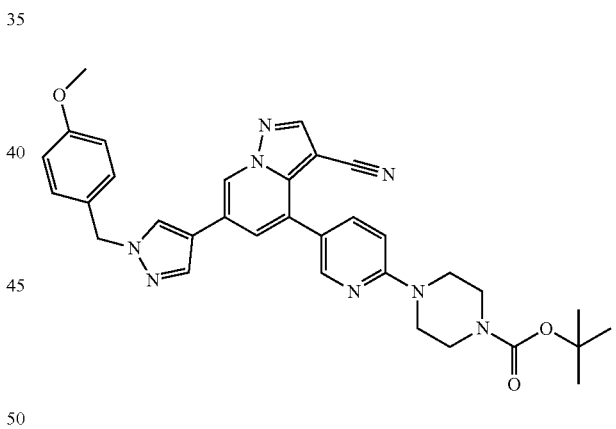

Tert-Butyl 4-(5-(3-cyano-6-(1-(4-methoxybenzyl)-1H-pyrazol-4-yl)pyrazolo[1,5-a]pyridin-4-yl)pyridin-2-yl)piperazine-1-carboxylate A room temperature solution of 3-cyano-6-(1-(4-methoxybenzyl)-1H-pyrazol-4-yl)pyrazolo[1,5-a]pyridin-4-yl trifluoromethanesulfonate (Intermediate P19; 0.538 g, 1.13 mmol) in dioxane (28.2 mL) was treated with tert-butyl 4-(5-(4,4,5,5-tetramethyl-1,3,2-dioxaborolan-2-yl)pyridine-2-yl)piperazine-1-carboxylate (0.658 g, 1.69 mmol) and 2 M K₂CO₃ (1.13 mL, 2.25 mmol), then sparged with N₂ for 5 min. The reaction mixture was treated with XPhos (0.107 g, 0.225 mmol) and Pd₂(dba)₃ (0.0516 g, 0.0563 mmol), then sparged with N₂ for 5 min, sealed, and stirred overnight at 80° C. After cooling to room temperature, the reaction mixture was diluted with water, and extracted with EtOAc.

The combined organic extracts were dried over anhydrous Na₂SO₄, filtered, and concentrated in vacuo. The residue was triturated with hexanes and vacuum filtered to afford the title compound (0.615 g, 92% yield). MS (apci) m/z=591.3 (M+H)

Example 590

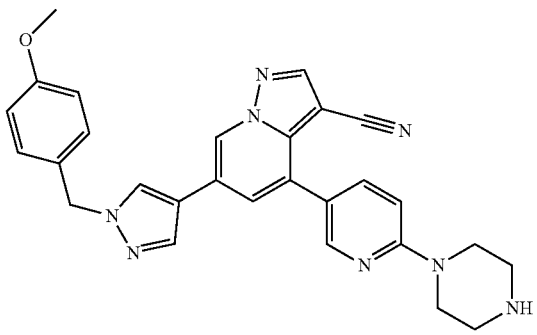 [SMILES: COc1ccc(Cn2cc(-c3cc(-c4ccc(N5CCNCC5)nc4)c4c(C#N)cnn4c3)cn2)cc1]

6-(1-(4-methoxybenzyl)-1H-pyrazol-4-yl)-4-(6-(piperazin-1-yl)pyridin-3-yl)pyrazolo[1,5-a]pyridine-3-carbonitrile A room temperature solution of tert-butyl 4-(5-(3-cyano-6-(1-(4-methoxybenzyl)-1H-pyrazol-4-yl)pyrazolo[1,5-a]pyridin-4-yl)pyridin-2-yl)piperazine-1-carboxylate (Example 589; 0.615 g, 1.04 mmol) in DCM (10.4 mL) was treated with TFA (5.21 mL, 1.04 mmol) and stirred for 30 min at room temperature. The reaction mixture was concentrated in vacuo. The residue was diluted with DCM and concentrated in vacuo to remove residual TFA. The residue was partitioned between 10% MeOH in DCM and saturated NaHCO₃, and the aqueous phase was extracted with 10% MeOH in DCM. The combined organic extracts were dried over anhydrous Na₂SO₄, filtered, and concentrated in vacuo to cleanly afford the title compound (0.489 g, 96% yield). MS (apci) m/z=491.2 (M+H).

Example 591

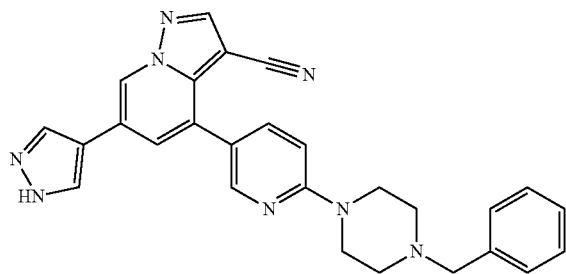 [SMILES: N#Cc1cnn2cc(-c3cn[nH]c3)cc(-c3ccc(N4CCN(Cc5ccccc5)CC4)nc3)c12]

4-(6-(4-benzylpiperazin-1-yl)pyridin-3-yl)-6-(1H-pyrazol-4-yl)pyrazolo[1,5-a]pyridine-3-carbonitrile Step 1: Preparation of 4-(6-(4-benzylpiperazin-1-yl)-6-(1-(4-methoxybenzyl)-1H-pyrazol-4-yl)pyrazolo[1,5-a]pyridine-3-carbonitrile A room temperature solution of 6-(1-(4-methoxybenzyl)-1H-pyrazol-4-yl)-4-(6-(piperazin-1-yl)pyridin-3-yl)pyrazolo[1,5-a]pyridine-3-carbonitrile (Example 590; 0.240 g, 0.489 mmol) in DMA (4.89 mL) was treated sequentially with TEA (0.341 mL, 2.45 mmol) and benzyl bromide (0.116 mL, 0.978 mmol). The reaction mixture was stirred overnight at room temperature and then quenched with water, and the biphasic mixture was extracted with EtOAc. The combined organic extracts were dried over anhydrous Na₂SO₄, filtered, and concentrated in vacuo to cleanly afford the title compound (0.284 g, quantitative yield). MS (apci) m/z=581.2 (M+H).

Step 2: Preparation of 4-(6-(4-benzylpiperazin-1-yl)pyridin-3-yl)-6-(1H-pyrazol-4-yl)pyrazolo[1,5-a]pyridine-3-carbonitrile 4-(6-(4-Benzylpiperazin-1-yl)pyridin-3-yl)-6-(1-(4-methoxybenzyl)-1H-pyrazol-4-yl)pyrazolo[1,5-a]pyridine-3-carbonitrile (0.284 g, 0.489 mmol) was treated with TFA (9.78 mL, 4.89 mmol). The reaction was stirred overnight at 70° C. and then concentrated in vacuo. The residue was diluted with DCM (15 mL) and treated with saturated NaHCO₃ (60 mL) and water (5 mL). The biphasic mixture was diluted with 20% MeOH/DCM (50 mL), and the resulting suspension was vacuum filtered. The biphasic filtrate was separated, and the organic phase was reserved. The aqueous extracts were washed with 20% MeOH/DCM. The combined organic extracts were dried over anhydrous Na₂SO₄, filtered, and concentrated in vacuo. The residue was purified by C18 reverse phase chromatography (0-60% ACN/H₂O as the gradient eluent) to afford the title compound (0.221 g, 98% yield). MS (apci) m/z=461.2 (M+H).

Example 592

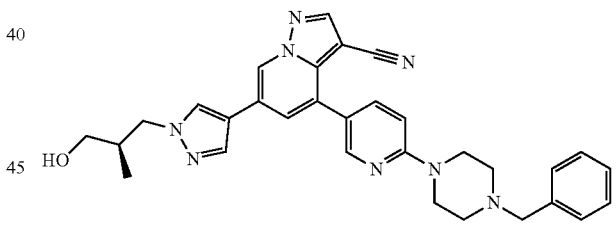

(R)-4-(6-(4-benzylpiperazin-1-yl)pyridin-3-yl)-6-(1-(3-hydroxy-2-methylpropyl)-1H-pyrazol-4-yl)pyrazolo[1,5-a]pyridine-3-carbonitrile A room temperature solution of 4-(6-(4-benzylpiperazin-1-yl)pyridin-3-yl)-6-(1H-pyrazol-4-yl)pyrazolo[1,5-a]pyridine-3-carbonitrile (Example 591; 0.014 g, 0.030 mmol) in dry DMF (1 mL) was treated with Cs₂CO₃ (0.050 g, 0.15 mmol) and (S)-3-bromo-2-methylpropan-1-ol (16 μL, 0.15 mmol). The resulting mixture was stirred for 6 hr at 70° C., and then quenched with water. The biphasic mixture was extracted with DCM and then filtered through a PS frit. The combined organic extracts then were concentrated in vacuo. The residue was purified by C18 reverse phase chromatography (10-80% ACN/Water with 0.1% Formic Acid as the gradient eluent) to afford the title compound (10.6 mg, 66% yield). MS (apci) m/z=533.2 (M+H).

Example 593

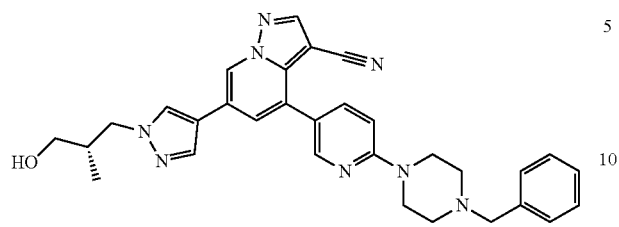

(S)-4-(6-(4-benzylpiperazin-1-yl)pyridine-3-yl)-6-(1-(3-hydroxy-2-methylpropyl)-1H-pyrazol-4-yl)pyrazolo[1,5-a]pyridine-3-carbonitrile The title compound was prepared according to the method described for the synthesis of (R)-4-(6-(4-benzylpiperazin-1-yl)pyridine-3-yl)-6-(1-(3-hydroxy-2-methylpropyl)-1H-pyrazol-4-yl)pyrazolo[1,5-a]pyridine-3-carbonitrile (Example 592), replacing (S)-3-bromo-2-methylpropan-1-ol with (R)-3-bromo-2-methylpropan-1-ol. The crude material was purified by C18 reverse phase chromatography (10-80% ACN/Water with 0.1% Formic Acid as the gradient eluent) to provide the title compound (17.4 mg, 56% yield). MS (apci) m/z=533.2 (M+H).

Example 594

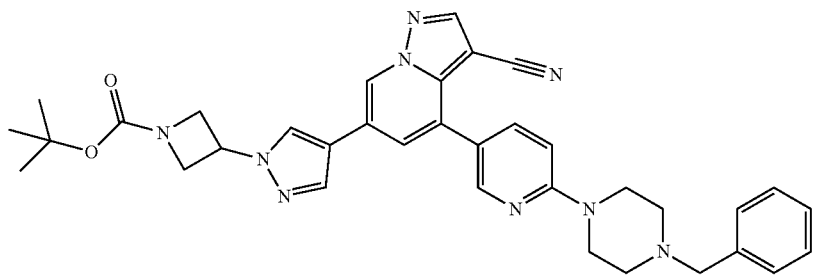 [SMILES: CC(C)(C)OC(=O)N1CC(n2cc(-c3cc(-c4ccc(N5CCN(Cc6ccccc6)CC5)nc4)c4c(C#N)cnn4c3)cn2)C1]

Tert-Butyl 3-(4-(4-(6-(4-benzylpiperazin-1-yl)pyridin-3-yl)-3-cyanopyrazolo[1,5-a]pyridine-6-yl)-1H-pyrazol-1-yl)azetidine-1-carboxylate A room temperature solution of 4-(6-(4-benzylpiperazin-1-yl)pyridin-3-yl)-6-(1H-pyrazol-4-yl)pyrazolo[1,5-a]pyridin-3-carbonitrile (Example 591; 0.1165, 0.2530 mmol) in dry DMF (0.5 mL) was treated with Cs$_2$CO$_3$ (0.3778 g, 1.159 mmol) and tert-butyl 3-((methyl sulfonyl)oxy)azetidine-1-carboxylate (0.1271 g, 0.5059 mmol). The resulting mixture was sealed in a pressure tube and stirred overnight at 70° C., and then quenched with water. The biphasic mixture was extracted with EtOAc and then with CHCl$_3$. The combined organic extracts were concentrated in vacuo, and the residue was purified by C18 reverse phase chromatography (5-99%, ACN/Water as the gradient eluent) to afford the title compound (26 mg, 17% yield). MS (apci) m/z=616.2 (M+H).

Example 595

6-(1-(azetidin-3-yl)-1H-pyrazol-4-yl)-4-(6-(4-benzylpiperazin-1-yl)pyridin-3-yl)pyrazolo[1,5-a]pyridine-3-carbonitrile Dihydrochloride A room temperature solution of tert-butyl 3-(4-(4-(6-(4-benzylpiperazin-1-yl)pyridin-3-yl)-3-cyanopyrazolo[1,5-a]pyridin-6-yl)-1H-pyrazol-1-yl)azetidine-1-carboxylate (Example 594; 0.024 g, 0.039 mmol) in dry DCM (0.2 mL) was treated with 5 M HCl in iPrOH (39 µL, 0.19 mmol). After stirring at room temperature for 2 d, additional 5 M HCl in iPrOH (7.8 µL, 0.038 mmol) was added. The reaction mixture was stirred overnight at room temperature and then concentrated in vacuo to afford the title compound as the dihydrochloride salt (25 mg, quantitative yield). MS (apci) m/z=516.2 (M+H).

Example 596

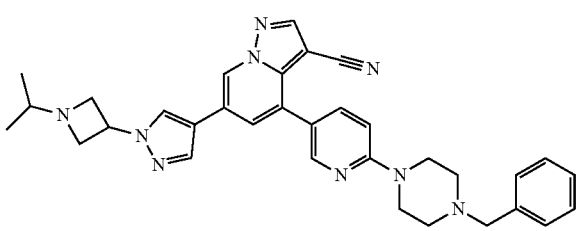 [SMILES: CC(C)N1CC(n2cc(-c3cc(-c4ccc(N5CCN(Cc6ccccc6)CC5)nc4)c4c(C#N)cnn4c3)cn2)C1]

4-(6-(4-benzylpiperazin-1-yl)pyridin-3-yl)-6-(1-(1-isopropylazetidin-3-yl)-1H-pyrazol-4-yl)pyrazolo[1,5-a]pyridine-3-carbonitrile A room temperature solution of 6-(1-(azetidin-3-yl)-1H-pyrazol-4-yl)-4-(6-(4-benzylpiperazin-1-yl)pyridin-3-yl)pyrazolo[1,5-a]pyridine-3-carbonitrile dihydrochloride (Example 595; 0.007 g, 0.012 mmol) in dry DMF (300 μL) was treated with TEA (17 μL, 0.12 mmol) and 2-iodopropane (3.6 μL, 0.036 mmol). The reaction mixture was stirred overnight at 70° C., then directly purified by C18 reverse phase chromatography using 5-85% ACN/Water as the gradient eluent and then further purified by C18 reverse phase chromatography using 70-99% ACN/Water with 0.1% Formic Acid as the gradient eluent to afford the title compound (1.6 mg, 24% yield). MS (apci) m/z=558.2 (M+H).

Example 597

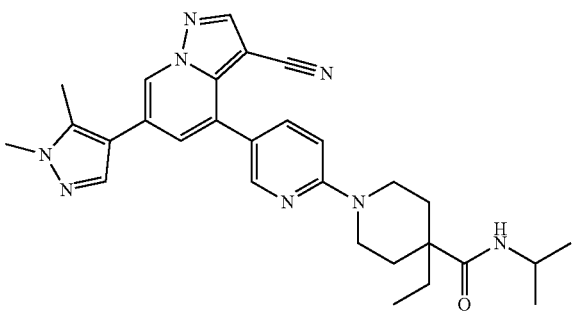 [SMILES: CCC1(C(=O)NC(C)C)CCN(c2ccc(-c3cc(-c4cnn(C)c4C)cn4ncc(C#N)c34)cn2)CC1]

1-(5-(3-cyano-6-(1,5-dimethyl-1H-pyrazol-4-yl)pyrazolo[1,5-a]pyridin-4-yl)pyridin-2-yl)-4-ethyl-N-isopropylpiperidine-4-carboxamide A room temperature solution of 3-cyano-6-(1,5-dimethyl-1H-pyrazol-4-yl)pyrazolo[1,5-a]pyridin-4-yl trifluoromethanesulfonate (Intermediate P21; 0.030 g, 0.078 mmol) in dioxane (1.95 mL) was treated with (6-(4-ethyl-4-(isopropylcarbamoyl)piperidin-1-yl)pyridin-3-yl)boronic acid (Intermediate R17; 0.037 g, 0.12 mmol) and 2 M $K_2CO_3$ (0.078 mL, 0.16 mmol), then sparged with $N_2$ for 5 min. The reaction mixture was treated with XPhos (0.0074 g, 0.016 mmol) and $Pd_2(dba)_3$ (0.0036 g, 0.0039 mmol), then sparged with $N_2$ for 5 min, sealed, and stirred overnight at 80° C. After cooling to room temperature, the reaction mixture was diluted with water and extracted with EtOAc. The combined organic extracts were dried over anhydrous $Na_2SO_4$, filtered, and concentrated in vacuo. The residue was purified by silica gel (0-10% MeOH in DCM) to afford the title compound (0.0187 g, 47% yield). MS (apci) m/z=511.3 (M+H).

Example 598

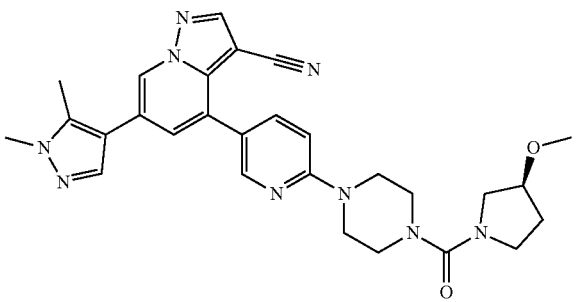

(S)-6-(1,5-dimethyl-1H-pyrazol-4-yl)-4-(6-(4-(3-methoxypyrrolidine-1-carbonyl)piperazin-1-yl)pyridin-3-yl)pyrazolo[1,5-a]pyridine-3-carbonitrile A room temperature solution of 3-cyano-6-(1,5-dimethyl-1H-pyrazol-4-yl)pyrazolo[1,5-a]pyridin-4-yl trifluoromethanesulfonate (Intermediate P21; 0.030 g, 0.078 mmol) in dioxane (1.95 mL) was treated with (S)-(6-(4-(3-methoxypyrrolidine-1-carbonyl)piperazin-1-yl)pyridin-3-yl)boronic acid (Intermediate R18; 0.039 g, 0.12 mmol) and 2 M $K_2CO_3$ (0.078 mL, 0.16 mmol), then sparged with $N_2$ for 5 min. The reaction mixture was treated with XPhos (0.0074 g, 0.016 mmol) and $Pd_2(dba)_3$ (0.0036 g, 0.0039 mmol), then sparged with $N_2$ for 5 min, sealed, and stirred overnight at 80° C. After cooling to room temperature, the reaction mixture was diluted with water, and extracted with EtOAc. The combined organic extracts were dried over anhydrous $Na_2SO_4$, filtered and concentrated in vacuo. The residue was purified by silica chromatography (0-50% gradient of 20% MeOH/DCM in EtOAc as the gradient eluent) to afford the title compound (24.2 mg, 57% yield). MS (apci) m/z=526.3 (M+H).

Example 599

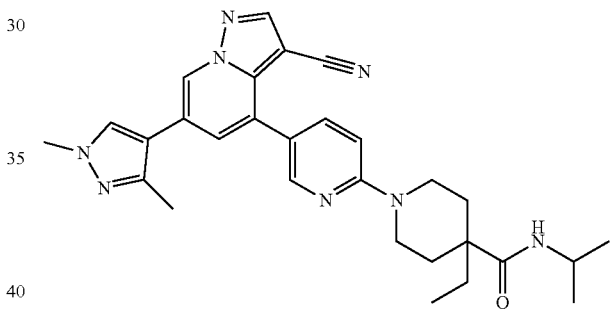

1-(5-(3-cyano-6-(1,3-dimethyl-1H-pyrazol-4-yl)pyrazolo[1,5-a]pyridin-4-yl)pyridin-2-yl)-4-ethyl-N-isopropylpiperidine-4-carboxamide A room temperature solution of 3-cyano-6-(1,3-dimethyl-1H-pyrazol-4-yl)pyrazolo[1,5-a]pyridin-4-yl trifluoromethanesulfonate (Intermediate P23; 0.030 g, 0.078 mmol) in dioxane (1.95 mL) was treated with (6-(4-ethyl-4-(isopropylcarbamoyl)piperidin-1-yl)pyridine-3-yl)boronic acid (Intermediate R17; 0.037 g, 0.12 mmol) and 2 M $K_2CO_3$ (0.078 mL, 0.16 mmol), then sparged with $N_2$ for 5 min. The reaction mixture was treated with XPhos (0.0074 g, 0.016 mmol) and $Pd_2(dba)_3$ (0.0036 g, 0.0039 mmol), then sparged with $N_2$ for 5 min, sealed, and stirred overnight at 80° C. After cooling to room temperature, the reaction mixture was diluted with water and extracted with EtOAc. The combined organic extracts were dried over anhydrous $Na_2SO_4$, filtered, and concentrated in vacuo. The residue was purified by silica chromatography (0-50% gradient of 20% MeOH/DCM in EtOAc as the eluent) to afford the title compound (0.0357 g, 89% yield). MS (apci) m/z=511.3 (M+H).

Example 600

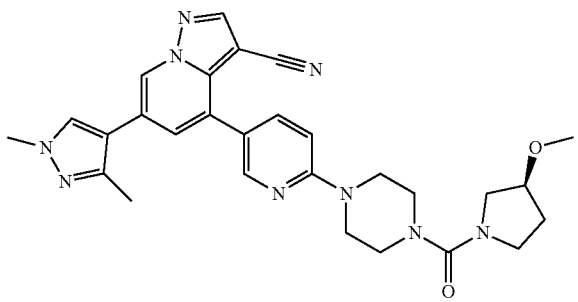

(S)-6-(1,3-dimethyl-1H-pyrazol-4-yl)-4-(6-(4-(3-methoxypyrrolidine-1-carbonyl)piperazin-1-yl)pyridin-3-yl)pyrazolo[1,5-a]pyridine-3-carbonitrile A room temperature solution of 3-cyano-6-(1,3-dimethyl-1H-pyrazol-4-yl)pyrazolo[1,5-a]pyridine-4-yl trifluoromethanesulfonate (Intermediate P23; 0.030 g, 0.078 mmol) in dioxane (1.9 mL) was treated with (S)-(6-(4-(3-methoxypyrrolidine-1-carbonyl)piperazin-1-yl)pyridine-3-yl)boronic acid (Intermediate R18; 0.039 g, 0.12 mmol) and 2 M $K_2CO_3$ (0.078 mL, 0.16 mmol) and sparged with $N_2$ for 5 min. The reaction mixture was treated with XPhos (0.0074 g, 0.016 mmol) and $Pd_2(dba)_3$ (0.0036 g, 0.0039 mmol), then sparged with $N_2$ for 5 min, sealed, and stirred overnight at 80° C. After cooling to room temperature, the reaction mixture was diluted with water and extracted with EtOAc. The combined organic extracts were dried over anhydrous $Na_2SO_4$, filtered, and concentrated in vacuo. The residue was purified by silica chromatography (0-50% gradient of 20% MeOH/DCM in EtOAc as the eluent) to afford the title compound (7.7 mg, 19% yield). MS (apci) m/z=526.3 (M+H).

Example 601

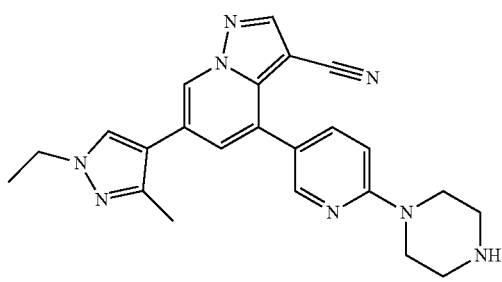 [SMILES: CCn1cc(-c2cc(-c3ccc(N4CCNCC4)nc3)c3c(C#N)cnn3c2)c(C)n1]

6-(1-ethyl-3-methyl-1H-pyrazol-4-yl)-4-(6-(piperazin-1-yl)pyridin-3-yl)pyrazolo[1,5-a]pyridine-3-carbonitrile Step 1: Preparation of Tert-Butyl 4-(5-(3-cyano-6-(1-ethyl-3-methyl-1H-pyrazol-4-yl)pyrazolo[1,5-a]pyridine-4-yl)pyridin-2-yl)piperazine-1-carboxylate A room temperature solution of tert-butyl 4-(5-(3-cyano-6-(((trifluoromethyl)sulfonyl)oxy)pyrazolo[1,5-a]pyridine-4-yl)pyridine-2-yl)piperazine-1-carboxylate (Intermediate P14; 98.6 mg, 0.178 mmol) in 4:1 dioxane/water (2.0 mL) was treated with 1-ethyl-3-methyl-4-(4,4,5,5-tetramethyl-1,3,2-dioxaborolan-2-yl)-1H-pyrazole (Intermediate R22; 46.3 mg, 0.196 mmol), $Pd_2(dba)_3$ (8.17 mg, 0.00892 mmol), XPhos (17.0 mg, 0.0357 mmol) and $K_2CO_{3(s)}$ (74.0 mg, 0.535 mmol). The reaction mixture was sparged with Argon, sealed, and stirred for 16 h at 100° C. After cooling to room temperature, the reaction mixture was diluted with 4:1 DCM/iPrOH and washed with water. The combined organic extracts were dried over anhydrous $Na_2SO_4$, filtered, and concentrated in vacuo. The residue was purified by silica chromatography (5-60% DCM-Acetone as the gradient eluent) to afford the title compound (44.6 mg, 61% yield). MS (apci) m/z=413.2 (M+H).

Step 2: Preparation of 6-(1-ethyl-3-methyl-1H-pyrazol-4-yl)-4-(6-(piperazin-1-yl)pyridine-3-yl)pyrazolo[1,5-a]pyridine-3-carbonitrile A room temperature solution of tert-butyl 4-(5-(3-cyano-6-(1-ethyl-3-methyl-1H-pyrazol-4-yl)pyrazolo[1,5-a]pyridine-4-yl)pyridine-2-yl)piperazine-1-carboxylate (Step 1; 44.6 mg, 0.108 mmol) in 1:1 DCM/TFA (3.0 mL) was stirred for 30 min at room temperature and then concentrated in vacuo. The residue was purified by silica chromatography (5-95% water/ACN with 0.1% TFA as the gradient eluent) to afford the title compound as the TFA salt. The TFA salt was suspended in 4:1 DCM/iPrOH and extracted with saturated $NaHCO_3$. The combined organic extracts were dried over anhydrous $Na_2SO_4$, filtered, and concentrated in vacuo to cleanly afford the title compound (44.6 mg, 61% yield). MS (apci) m/z=591.3 (M+H).

The compounds in Table BBB were prepared according to the method described for the synthesis of Example 601, replacing 1-ethyl-3-methyl-4-(4,4,5,5-tetramethyl-1,3,2-dioxaborolan-2-yl)-1H-pyrazole with the appropriate boronate ester starting materials from Table EE. Reactions were monitored by LCMS, and reaction times were adjusted accordingly.

TABLE BBB

| Ex # | Structure | Chemical Name | MS (apci) m/z |
|---|---|---|---|
| 602 | 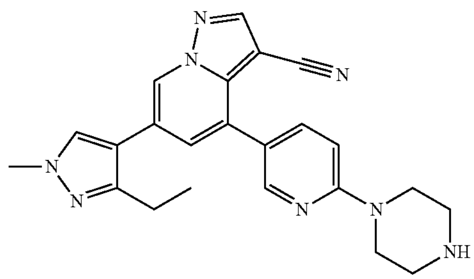 [SMILES: CCc1nn(C)cc1-c1cc(-c2ccc(N3CCNCC3)nc2)c2c(C#N)cnn2c1] | 6-(3-ethyl-1-methyl-1H-pyrazol-4-yl)-4-(6-(piperazin-1-yl)pyridin-3-yl)pyrazolo[1,5-a]pyridine-3-carbonitrile | 413.2 (M + H) |
| 603 | 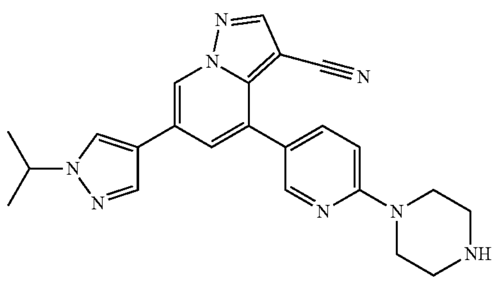 [SMILES: CC(C)n1cc(-c2cc(-c3ccc(N4CCNCC4)nc3)c3c(C#N)cnn3c2)cn1] | 6-(1-isopropyl-1H-pyrazol-4-yl)-4-(6-(piperazin-1-yl)pyridin-3-yl)pyrazolo[1,5-a]pyridine-3-carbonitrile | 413.2 (M + H) |
| 604 | 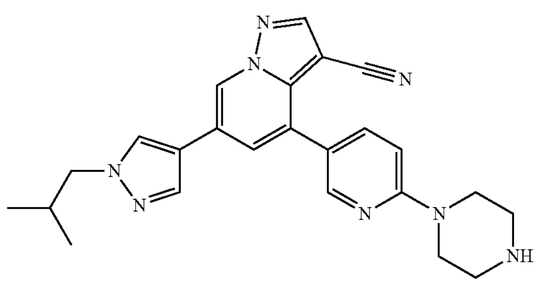 [SMILES: CC(C)Cn1cc(-c2cc(-c3ccc(N4CCNCC4)nc3)c3c(C#N)cnn3c2)cn1] | 6-(1-isobutyl-1H-pyrazol-4-yl)-4-(6-(piperazin-1-yl)pyridin-3-yl)pyrazolo[1,5-a]pyridine-3-carbonitrile | 427.2 (M + H) |
| 605 | 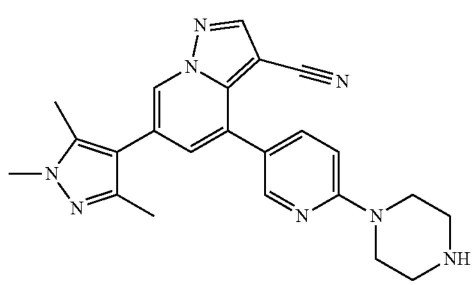 [SMILES: Cc1nn(C)c(C)c1-c1cc(-c2ccc(N3CCNCC3)nc2)c2c(C#N)cnn2c1] | 4-(6-(piperazin-1-yl)pyridin-3-yl)-6-(1,3,5-trimethyl-1H-pyrazol-4-yl)pyrazolo[1,5-a]pyridine-3-carbonitrile | 413.2 (M + H) |
| 606 | 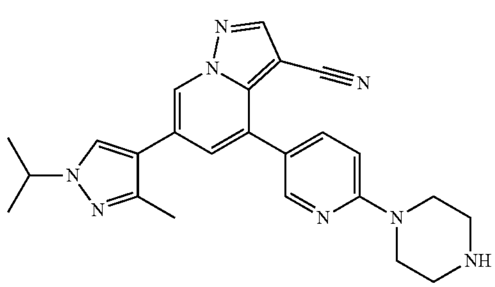 [SMILES: Cc1nn(C(C)C)cc1-c1cc(-c2ccc(N3CCNCC3)nc2)c2c(C#N)cnn2c1] | 6-(1-isopropyl-3-methyl-1H-pyrazol-4-yl)-4-(6-(piperazin-1-yl)pyridin-3-yl)pyrazolo[1,5-a]pyridine-3-carbonitrile | 427.2 (M + H) |

TABLE BBB-continued

| Ex # | Structure | Chemical Name | MS (apci) m/z |
|---|---|---|---|
| 607 | 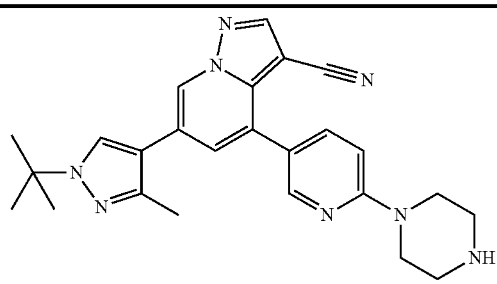 | 6-(1-(tert-butyl)-3-methyl-1H-pyrazol-4-yl)-4-(6-(piperazin-1-yl)pyridin-3-yl)pyrazolo[1,5-a]pyridine-3-carbonitrile | 441.2 (M + H) |
| 608 | 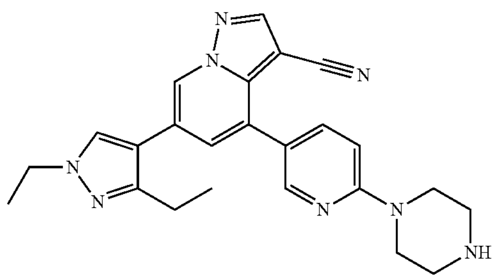 [SMILES: CCc1nn(CC)cc1-c1cc(-c2ccc(N3CCNCC3)nc2)c2c(C#N)cnn2c1] | 6-(1,3-diethyl-1H-pyrazol-4-yl)-4-(6-(piperazin-1-yl)pyridin-3-yl)pyrazolo[1,5-a]pyridine-3-carbonitrile | 427.2 (M + H) |

Example 609

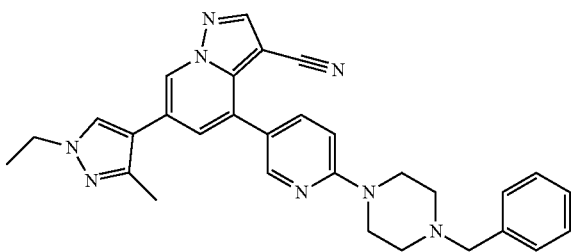 [SMILES: CCn1cc(-c2cc(-c3ccc(N4CCN(Cc5ccccc5)CC4)nc3)c3c(C#N)cnn3c2)c(C)n1]

4-(6-(4-benzylpiperazin-1-yl)pyridin-3-yl)-6-(1-ethyl-3-methyl-1H-pyrazol-4-yl)pyrazolo[1,5-a]pyridine-3-carbonitrile A room temperature solution of 6-(1-ethyl-3-methyl-1H-pyrazol-4-yl)-4-(6-(piperazin-1-yl)pyridin-3-yl)pyrazolo[1,5-a]pyridine-3-carbonitrile (Example 601; 28.8 mg, 0.0698 mmol) in DCM (1.4 mL) was treated sequentially with TEA (47.4 μL, 0.349 mmol) and benzyl bromide (24.9 μL, 0.209 mmol). The reaction mixture was stirred for 16 h at room temperature and then concentrated in vacuo. The residue was purified by C18 reverse phase chromatography (5-95% water/ACN with 0.1% TFA as the gradient eluent) to afford the title compound as the TFA salt. The TFA salt was suspended in 4:1 DCM/iPrOH and extracted with saturated NaHCO₃. The combined organic extracts were dried over anhydrous Na₂SO₄, filtered, and concentrated in vacuo to cleanly afford the title compound (17.9 mg, 51% yield). MS (apci) m/z=503.2 (M+H).

Except where noted, the compounds in Table CCC were prepared according to the method described for the synthesis of Example 609, replacing 6-(1-ethyl-3-methyl-1H-pyrazol-4-yl)-4-(6-(piperazin-1-yl)pyridin-3-yl)pyrazolo[1,5-a]pyridine-3-carbonitrile with the appropriate amino starting materials. Reactions were monitored by LCMS, and reaction times were adjusted accordingly to cleanly afford the title compounds.

TABLE CCC

| Ex # | Structure | Chemical Name | MS (apci) m/z |
|---|---|---|---|
| 610 | 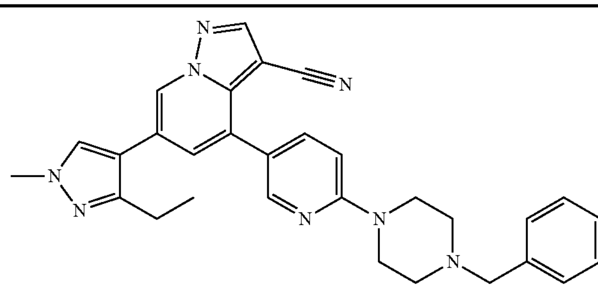 | 4-(6-(4-benzylpiperazin-1-yl)pyridin-3-yl)-6-(3-ethyl-1-methyl-1H-pyrazol-4-yl)pyrazolo[1,5-a]pyridine-3-carbonitrile | 503.2 (M + H) |

TABLE CCC-continued

| Ex # | Structure | Chemical Name | MS (apci) m/z |
|---|---|---|---|
| 611 | 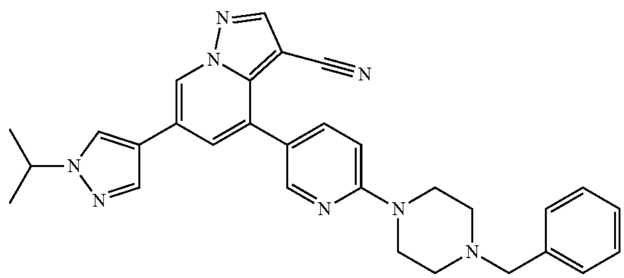 [SMILES: CC(C)n1cc(-c2cc(-c3ccc(N4CCN(Cc5ccccc5)CC4)nc3)c3c(C#N)cnn3c2)cn1] | 4-(6-(4-benzylpiperazin-1-yl)pyridin-3-yl)-6-(1-isopropyl-1H-pyrazol-4-yl)pyrazolo[1,5-a]pyridine-3-carbonitrile | 503.2 (M + H) |
| 612 | 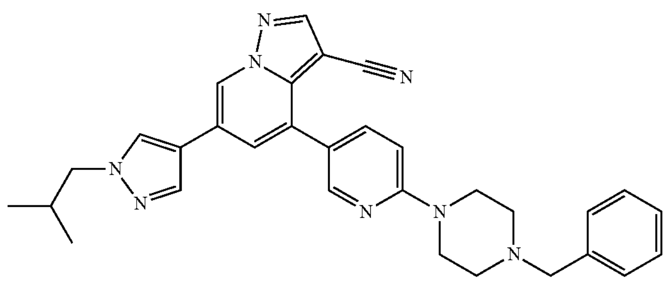 [SMILES: CC(C)Cn1cc(-c2cc(-c3ccc(N4CCN(Cc5ccccc5)CC4)nc3)c3c(C#N)cnn3c2)cn1] | 4-(6-(4-benzylpiperazin-1-yl)pyridin-3-yl)-6-(1-isobutyl-1H-pyrazol-4-yl)pyrazolo[1,5-a]pyridine-3-carbonitrile | 517.2 (M + H) |
| 613 | 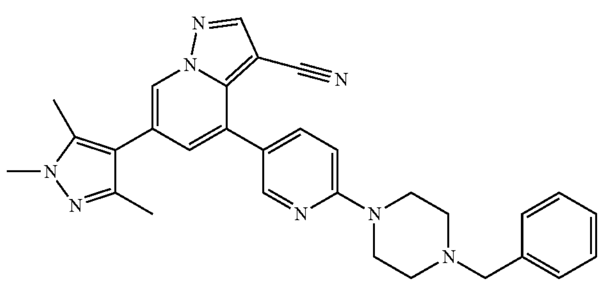 [SMILES: Cc1nn(C)c(C)c1-c1cc(-c2ccc(N3CCN(Cc4ccccc4)CC3)nc2)c2c(C#N)cnn2c1] | 4-(6-(4-benzylpiperazin-1-yl)pyridin-3-yl)-6-(1,3,5-trimethyl-1H-pyrazol-4-yl)pyrazolo[1,5-a]pyridine-3-carbonitrile | 503.2 (M + H) |
| 614* | 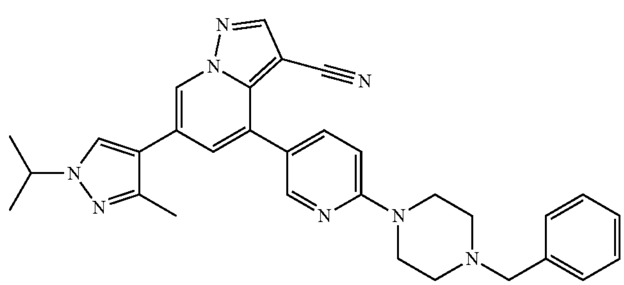 [SMILES: Cc1nn(C(C)C)cc1-c1cc(-c2ccc(N3CCN(Cc4ccccc4)CC3)nc2)c2c(C#N)cnn2c1] | 4-(6-(4-benzylpiperazin-1-yl)pyridin-3-yl)-6-(1-isopropyl-3-methyl-1H-pyrazol-4-yl)pyrazolo[1,5-a]pyridine-3-carbonitrile | 517.3 (M + H) |
| 615 | 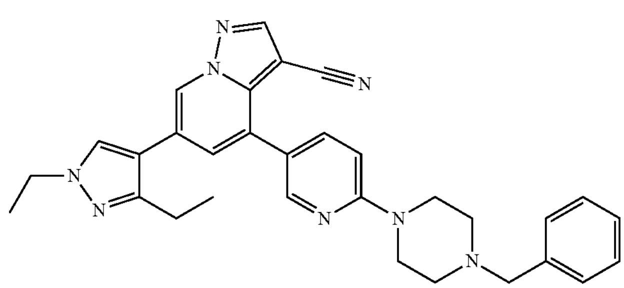 [SMILES: CCc1nn(CC)cc1-c1cc(-c2ccc(N3CCN(Cc4ccccc4)CC3)nc2)c2c(C#N)cnn2c1] | 4-(6-(4-benzylpiperazin-1-yl)pyridin-3-yl)-6-(1,3-diethyl-1H-pyrazol-4-yl)pyrazolo[1,5-a]pyridine-3-carbonitrile | 517.3 (M + H) |

| Ex # | Structure | Chemical Name | MS (apci) m/z |
|---|---|---|---|
| 616 | 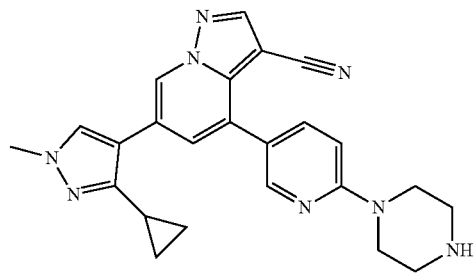 | 4-(6-(4-benzylpiperazin-1-yl)pyridin-3-yl)-6-(1-(tert-butyl)-3-methyl-1H-pyrazol-4-yl)pyrazolo[1,5-a]pyridine-3-carbonitrile | 531.2 (M + H) |

*Aqueous free-basing step was replaced with a silica chromatography using 1-30% DCM/MeOH with 2% NH₄OH as the gradient eluent for free-basing the TFA salt.

Example 617

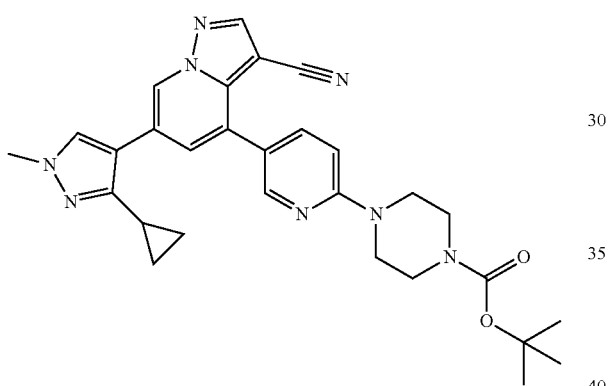

Tert-Butyl 4-(5-(3-cyano-6-(3-cyclopropyl-1-methyl-1H-pyrazol-4-yl)pyrazolo[1,5-a]pyridin-4-yl)pyridin-2-yl)piperazine-1-carboxylate A room temperature solution of tert-butyl 4-(5-(3-cyano-6-(((trifluoromethyl)sulfonyl)oxy)pyrazolo[1,5-a]pyridine-4-yl)pyridine-2-yl)piperazine-1-carboxylate (Intermediate P14; 60.0 mg, 0.11 mmol) in 4:1 dioxane/water (8 mL) was treated with 3-cyclopropyl-1-methyl-4-(4,4,5,5-tetramethyl-1,3,2-dioxaborolan-2-yl)-1H-pyrazole (40 mg, 0.16 mmol), K₂CO₃ (30 mg, 0.22 mmol), XPhos (10 mg, 0.022 mmol) and Pd₂(dba)₃ (5.0 mg, 0.0054 mmol). The mixture was sparged with Argon for 10 min, sealed, and stirred overnight at 90° C. After cooling to room temperature, the reaction mixture was diluted with water and extracted with EtOAc. The combined organic extracts were dried over anhydrous Na₂SO₄, filtered, and concentrated in vacuo. The residue was purified by silica chromatography (using 30-50% EtOAc in Hexanes as the eluent) to afford the title compound (0.032 g, 56% yield). MS (apci) m/z=525.3 (M+H).

Example 618

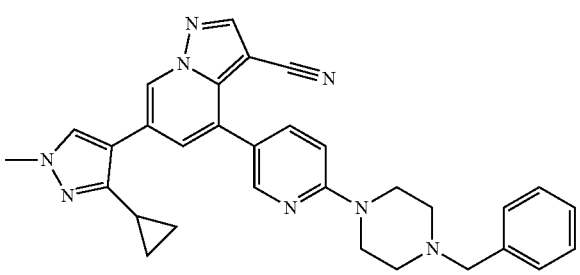 [SMILES: Cn1cc(-c2cc(-c3ccc(N4CCN(Cc5ccccc5)CC4)nc3)c3c(C#N)cnn3c2)c(C2CC2)n1]

6-(3-cyclopropyl-1-methyl-1H-pyrazol-4-yl)-4-(6-(piperazin-1-yl)pyridin-3-yl)pyrazolo[1,5-a]pyridine-3-carbonitrile A room temperature solution of tert-butyl 4-(5-(3-cyano-6-(3-cyclopropyl-1-methyl-1H-pyrazol-4-yl)pyrazolo[1,5-a]pyridin-4-yl)pyridin-2-yl)piperazine-1-carboxylate (Example 617; 32 mg, 0.061 mmol) in DCM (4 mL) was treated with TFA (2 mL, 0.40 mmol) and stirred for 30 min at room temperature. The reaction mixture was concentrated in vacuo. The residue was dissolved in 20% iPrOH in DCM and extracted with 10% NaHCO₃. The combined organic extracts were dried over anhydrous Na₂SO₄, filtered, and concentrated in vacuo to afford the title compound in sufficient purity (0.024 g, 92% yield). MS (apci) m/z=425.2 (M+H).

Example 619

4-(6-(4-benzylpiperazin-1-yl)pyridin-3-yl)-6-(3-cyclopropyl-1-methyl-1H-pyrazol-4-yl)pyrazolo[1,5-a]pyridine-3-carbonitrile A room temperature solution of 6-(3-cyclopropyl-1-methyl-1H-pyrazol-4-yl)-4-(6-(piperazin-1-yl)pyridin-3-yl)pyrazolo[1,5-a]pyridine-3-carbonitrile (Example 618; 12 mg, 0.028 mmol) in DMF (2 mL) was treated sequentially with benzyl bromide (10.7 µL, 0.0905 mmol) and TEA (19.7 µL, 0.141 mmol). The reaction mixture was stirred overnight at room temperature, then diluted with EtOAc and washed with water. The combined organic extracts were dried over anhydrous Na₂SO₄, filtered, and concentrated in vacuo. The residue was purified by silica chromatography (20% Hexanes in EtOAc as the gradient eluent) to cleanly afford the title compound (10 mg, 69% yield). MS (apci) m/z=515.2 (M+H).

Example 620

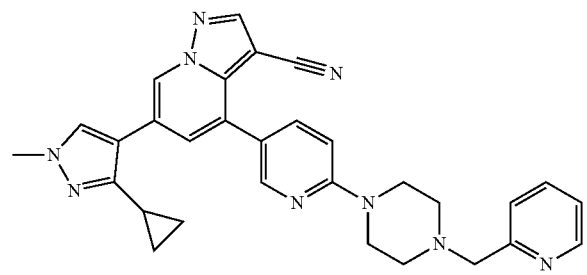 [SMILES: Cn1cc(-c2cc(-c3ccc(N4CCN(Cc5ccccn5)CC4)nc3)c3c(C#N)cnn3c2)c(C2CC2)n1]

6-(3-cyclopropyl-1-methyl-1H-pyrazol-4-yl)-4-(6-(4-(pyridin-2-ylmethyl)piperazin-1-yl)pyridin-3-yl)pyrazolo[1,5-a]pyridine-3-carbonitrile A room temperature solution of 6-(3-cyclopropyl-1-methyl-1H-pyrazol-4-yl)-4-(6-(piperazin-1-yl)pyridin-3-yl)pyrazolo[1,5-a]pyridine-3-carbonitrile (12 mg, 0.028 mmol) in DMF (2 mL) was treated successively with picolinaldehyde (11 mg, 0.099 mmol) and acetic acid (17 mg, 0.28 mmol). The resulting reaction mixture was stirred overnight at room temperature. The reaction mixture was diluted with EtOAc and washed with water. The combined organic extracts were dried over anhydrous Na₂SO₄, filtered, and concentrated in vacuo. The residue was purified by reverse phase HPLC (5-95% water/ACN with 0.1% TFA as the gradient eluent) to afford the title compound (10 mg, 69% yield). MS (apci) m/z=516.3 (M+H).

Example 621

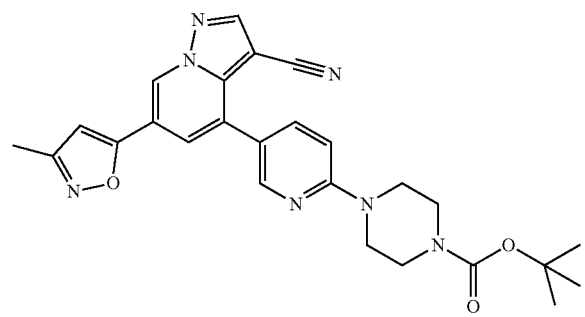 [SMILES: Cc1cc(-c2cc(-c3ccc(N4CCN(C(=O)OC(C)(C)C)CC4)nc3)c3c(C#N)cnn3c2)on1]

Tert-Butyl 4-(5-(3-cyano-6-(3-methylisoxazol-5-yl)pyrazolo[1,5-a]pyridin-4-yl)pyridin-2-yl)piperazine-1-carboxylate A mixture of tert-butyl 4-(5-(3-cyano-6-((((trifluoromethyl)sulfonyl)oxy)pyrazolo[1,5-a]pyridin-4-yl)pyridin-2-yl)piperazine-1-carboxylate (Intermediate P14; 150 mg, 0.271 mmol), 3-methyl-5-(4,4,5,5-tetramethyl-1,3,2-dioxaborolan-2-yl)isoxazole (85.1 mg, 0.407 mmol), Pd(PPh₃)₄ (31.4 mg, 0.0271 mmol) and 2 M Na₂CO₃ (679 µL, 1.36 mmol) in dioxane (20 mL) was sparged with N$_{2(g)}$, then sealed, and stirred 4 h at 100° C. The reaction mixture was cooled to room temperature, diluted with water (10 mL) and extracted with EtOAc. The combined organic extracts were filtered through PS paper, concentrated in vacuo, and purified by silica chromatography (0-100% EtOAc/hexanes as the eluent) to afford the title compound (124 mg, 94% yield). MS (apci) m/z=486.2 (M+H).

The compound in Table DDD was prepared according to the method described for the synthesis of Example 621, replacing 3-methyl-5-(4,4,5,5-tetramethyl-1,3,2-dioxaborolan-2-yl)isoxazole with the appropriate boronic ester.

TABLE DDD

| Ex # | Structure | Chemical Name | MS (apci) m/z |
|---|---|---|---|
| 622 | 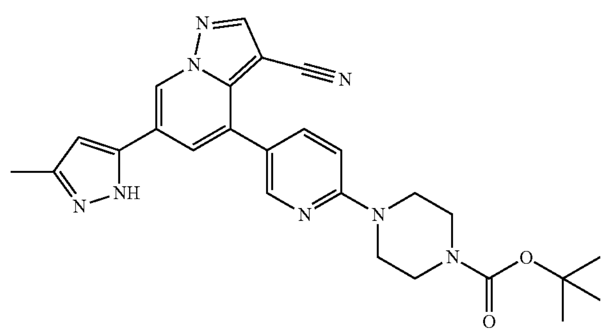 [SMILES: Cc1cc(-c2cc(-c3ccc(N4CCN(C(=O)OC(C)(C)C)CC4)nc3)c3c(C#N)cnn3c2)[nH]n1] | tert-butyl 4-(5-(3-cyano-6-(3-methyl-1H-pyrazol-5-yl)pyrazolo[1,5-a]pyridin-4-yl)pyridin-2-yl)piperazine-1-carboxylate | 485.2 (M + H) |

Example 623

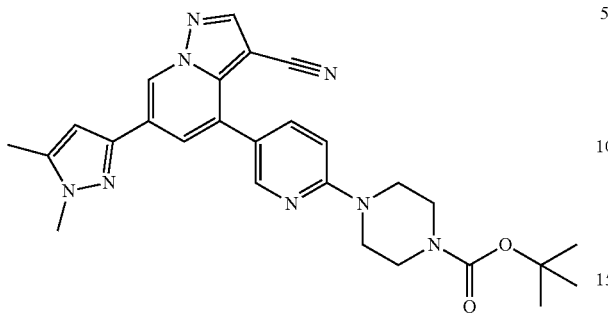

Tert-Butyl 4-(5-(3-cyano-6-(1,5-dimethyl-1H-pyrazol-3-yl)pyrazolo[1,5-a]pyridin-4-yl)pyridin-2-yl)piperazine-1-carboxylate A mixture of tert-butyl 4-(5-(3-cyano-6-(3-methyl-1H-pyrazol-5-yl)pyrazolo[1,5-a]pyridine-4-yl)pyridin-2-yl)piperazine-1-carboxylate (200 mg, 0.413 mmol), CH₃I (38.6 µL, 0.619 mmol) and Cs₂CO₃ (538 mg, 1.65 mmol) in DMF (2 mL) was stirred overnight at room temperature. The reaction was diluted with water (20 mL), and the resulting precipitate was vacuum filtered. The solids were washed with water and hexanes and then air-dried to cleanly afford the title compound (182 mg, 88% yield). MS (apci) m/z=499.2 (M+H).

Example 624

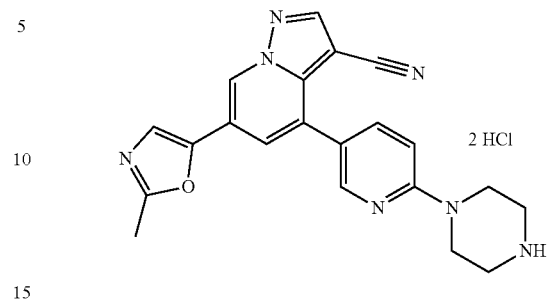

6-(2-methyloxazol-5-yl)-4-(6-(piperazin-1-yl)pyridin-3-yl)pyrazolo[1,5-a]pyridine-3-carbonitrile Dihydrochloride A room temperature solution of tert-butyl 4-(5-(3-cyano-6-(2-methyloxazol-5-yl)pyrazolo[1,5-a]pyridine-4-yl)pyridin-2-yl)piperazine-1-carboxylate (120 mg, 0.247 mmol) in DCM (2 mL) was treated with 5 M HCl in iPrOH (49.4 µL, 0.247 mmol). The reaction was stirred for 72 h at room temperature and then filtered. The solid was washed with Et₂O and air-dried to afford the title compound (50 mg, 53% yield). MS (apci) m/z=386.1 (M+H).

The compounds in Table EEE were prepared using a method similar to that used for Example 624, replacing tert-butyl 4-(5-(3-cyano-6-(2-methyloxazol-5-yl)pyrazolo[1,5-a]pyridine-4-yl)pyridin-2-yl)piperazine-1-carboxylate with the appropriate Boc-protected piperazine compound. Reactions were followed by LCMS, and reaction times were adjusted as necessary.

TABLE EEE

| Ex # | Structure | Chemical Name | MS (apci) m/z |
|---|---|---|---|
| 625* | 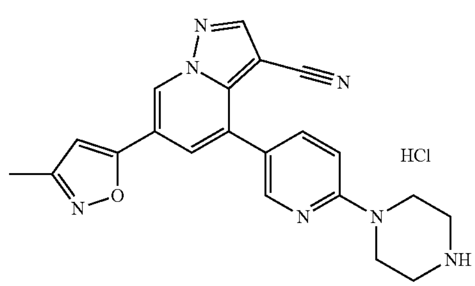 [SMILES: Cc1cc(-c2cc(-c3ccc(N4CCNCC4)nc3)c3c(C#N)cnn3c2)on1 ; Cl] | 6-(3-methylisoxazol-5-yl)-4-(6-(piperazin-1-yl)pyridin-3-yl)pyrazolo[1,5-a]pyridine-3-carbonitrile hydrochloride | 386.1 (M + H) |
| 626 | 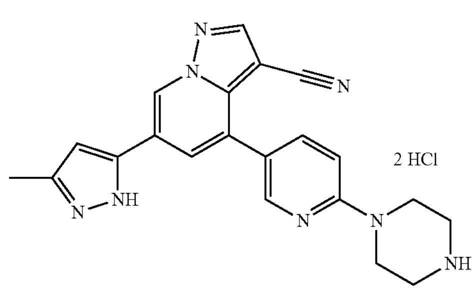 [SMILES: Cc1cc(-c2cc(-c3ccc(N4CCNCC4)nc3)c3c(C#N)cnn3c2)[nH]n1 ; "2 HCl"] | 6-(3-methyl-1H-pyrazol-5-yl)-4-(6-(piperazin-1-yl)pyridin-3-yl)pyrazolo[1,5-a]pyridine-3-carbonitrile dihydrochloride | 385.2 (M + H) |

TABLE EEE-continued

| Ex # | Structure | Chemical Name | MS (apci) m/z |
|---|---|---|---|
| 627 | 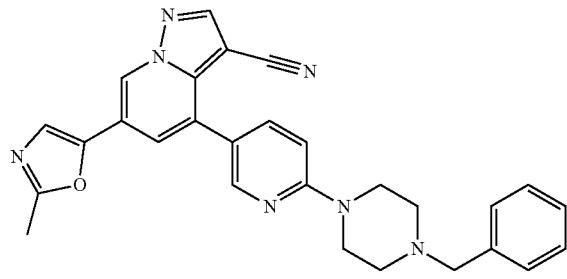 2 HCl | 6-(1,5-dimethyl-1H-pyrazol-3-yl)-4-(6-(piperazin-1-yl)pyridin-3-yl)pyrazolo[1,5-a]pyridine-3-carbonitrile dihydrochloride | 399.1 (M + H) |

*The starting material, tert-butyl 4-(5-(3-cyano-6-(2-methyloxazol-5-yl)pyrazolo[1,5-a]pyridin-4-yl)pyridin-2-yl)piperazine-1-carboxylate, was prepared according to example 621.

Example 628

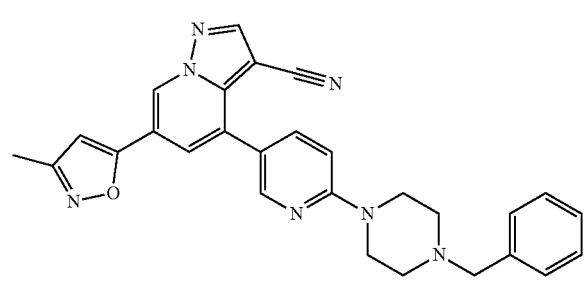 [SMILES: Cc1cc(-c2cc(-c3ccc(N4CCN(Cc5ccccc5)CC4)nc3)c3c(C#N)cnn3c2)on1]

4-(6-(4-benzylpiperazin-1-yl)pyridin-3-yl)-6-(2-methyloxazol-5-yl)pyrazolo[1,5-a]pyridine-3-carbonitrile A room temperature solution of 6-(2-methyloxazol-5-yl)-4-(6-(piperazin-1-yl)pyridin-3-yl)pyrazolo[1,5-a]pyridine-3-carbonitrile dihydrochloride (Example 624; 12 mg, 0.0262 mmol) in DMF (0.2 mL) was treated with TEA (10.9 µL, 0.0785 mmol) and (bromomethyl)benzene (4.04 µL, 0.0340 mmol). The resulting mixture was stirred for 1 h at room temperature and then directly purified by C18 reverse phase chromatography (0-60% ACN/water as the gradient eluent) to afford the title compound (6.8 mg, 55% yield). MS (apci) m/z=476.2 (M+H).

Example 629

4-(6-(4-benzylpiperazin-1-yl)pyridine-3-yl)-6-(3-methylisoxazol-5-yl)pyrazolo[1,5-a]pyridine-3-carbonitrile The title compound was prepared (3.3 mg, 32% yield) according to the method described for the synthesis of Example 628, replacing 6-(2-methyloxazol-5-yl)-4-(6-(piperazin-1-yl)pyridine-3-yl)pyrazolo[1,5-a]pyridine-3-carbonitrile dihydrochloride with 6-(3-methylisoxazol-5-yl)-4-(6-(piperazin-1-yl)pyridine-3-yl)pyrazolo[1,5-a]pyridine-3-carbonitrile dihydrochloride (Example 625). Following C18 reverse phase chromatography (0-60% ACN/water as the gradient eluent) the title compound was isolated cleanly (3.3 mg, 32% yield). MS (apci) m/z=476.2 (M+H).

Example 630

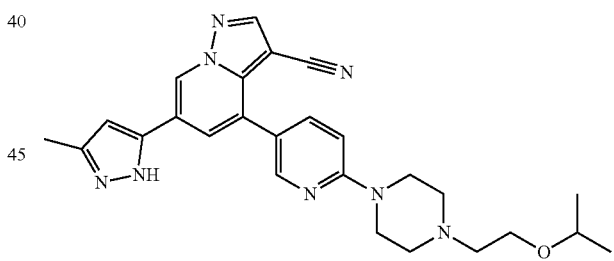

4-(6-(4-(2-isopropoxyethyl)piperazin-1-yl)pyridin-3-yl)-6-(3-methyl-1H-pyrazol-5-yl)pyrazolo[1,5-a]pyridine-3-carbonitrile A room temperature solution of 6-(3-methyl-1H-pyrazol-5-yl)-4-(6-(piperazin-1-yl)pyridin-3-yl)pyrazolo[1,5-a]pyridine-3-carbonitrile (Example 626; 10 mg, 0.026 mmol) in DMF (0.2 mL) was treated with TEA (18 µL, 0.13 mmol) and 2-(2-bromoethoxy)propane (8.7 mg, 0.052 mmol). The reaction mixture was stirred overnight at room temperature, then for 4 h at 60° C. After cooling to room temperature, the reaction mixture was purified directly by C18 reverse phase chromatography (0-60% ACN/water as the gradient eluent) to afford the title compound (3.4 mg, 28% yield). MS (apci) m/z=471.2 (M+H).

Example 631

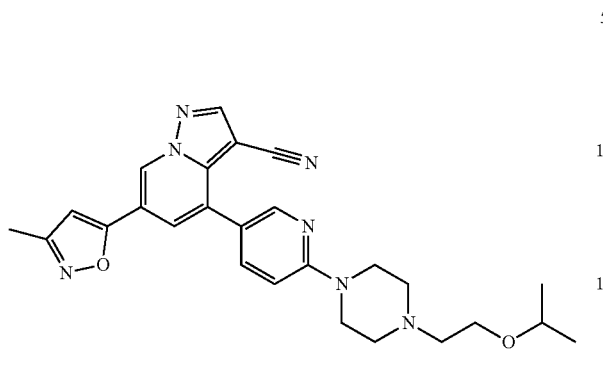

4-(6-(4-(2-isopropoxyethyl)piperazin-1-yl)pyridin-3-yl)-6-(3-methylisoxazol-5-yl)pyrazolo[1,5-a]pyridine-3-carbonitrile A room temperature solution of 6-(3-methylisoxazol-5-yl)-4-(6-(piperazin-1-yl)pyridin-3-yl)pyrazolo[1,5-a]pyridine-3-carbonitrile hydrochloride (Example 625; 5 mg, 0.012 mmol) in dry DMA (0.2 mL) was treated with TEA (16.5 µL, 0.12 mmol) and 2-(2-bromoethoxy)propane (6 mg, 0.036 mmol). The reaction mixture was stirred overnight at 75° C., and then additional TEA (7.2 µL, 0.052 mmol) and 2-(2-bromoethoxy)propane (6 mg, 0.036 mmol) were added. The resulting mixture was stirred at 75° C. for 36 hr until the reaction was complete by LCMS. After cooling to room temperature, the reaction mixture was purified directly by C18 reverse phase chromatography (20-80% ACN/water as the gradient eluent) to afford the title compound (2 mg, 36% yield). MS (apci) m/z=472.2 (M+H).

Example 632

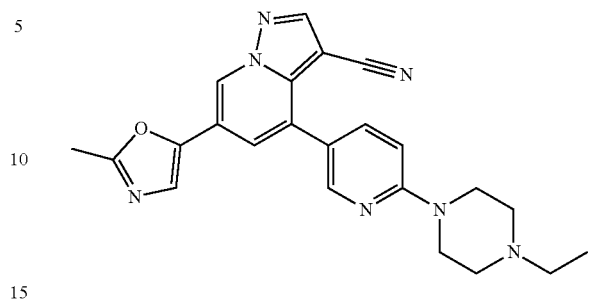

4-(6-(4-ethylpiperazin-1-yl)pyridine-3-yl)-6-(2-methyloxazol-5-yl)pyrazolo[1,5-a]pyridin-3-carbonitrile A room temperature solution of 6-(2-methyloxazol-5-yl)-4-(6-(piperazin-1-yl)pyridin-3-yl)pyrazolo[1,5-a]pyridine-3-carbonitrile dihydrochloride (Example 624; 8 mg, 0.02 mmol) in DMF (0.2 mL) was treated with DIEA (12.2 µL, 0.0698 mmol) and bromoethane (5 µL, 0.067 mmol). The reaction mixture was stirred for 15 h at 50° C., and then additional DIEA (20 µL, 0.114 mmol) and bromoethane (5 µL, 0.067 mmol) were added. The resulting mixture was stirred for 4 d at 75° C. After cooling to room temperature, the reaction mixture was purified directly by C18 reverse phase chromatography (5-70% ACN/water as the gradient eluent) to afford the title compound (3.2 mg, 44% yield). MS (apci) m/z=414.1 (M+H).

The compounds in Table FFF were prepared according to the method described for the synthesis of Example 632, replacing bromoethane with the appropriate alkyl halide. Reactions were followed by LCMS, and reaction times, as well as additions of supplemental DIEA and alkyl halide were adjusted as necessary. Purifications were accomplished by C18 reverse phase chromatography using an appropriate gradient eluent allowing the clean isolation of the title compounds.

TABLE FFF

| Ex # | Structure | Chemical Name | MS (apci) m/z |
|---|---|---|---|
| 633 | 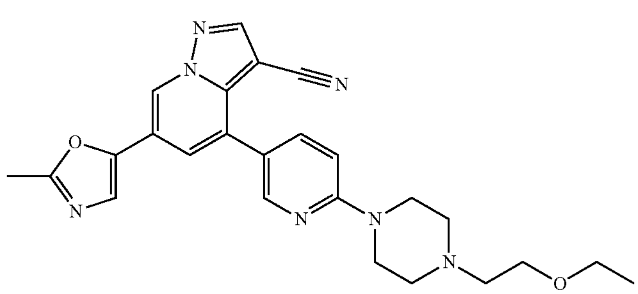 [SMILES: CCOCCN1CCN(c2ccc(-c3cc(-c4cnc(C)o4)cn4ncc(C#N)c34)cn2)CC1] | 4-(6-(4-(2-ethoxyethyl)piperazin-1-yl)pyridin-3-yl)-6-(2-methyloxazol-5-yl)pyrazolo[1,5-a]pyridine-3-carbonitrile | 458.2 (M + H) |

TABLE FFF-continued

| Ex # | Structure | Chemical Name | MS (apci) m/z |
|---|---|---|---|
| 634 | 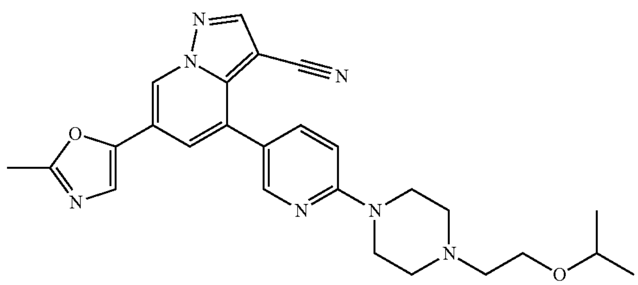 [SMILES: Cc1ncc(-c2cc(-c3ccc(N4CCN(CCOC(C)C)CC4)nc3)c3c(C#N)cnn3c2)o1] | 4-(6-(4-(2-isopropoxyethyl)piperazin-1-yl)pyridin-3-yl)-6-(2-methyloxazol-5-yl)pyrazolo[1,5-a]pyridine-3-carbonitrile | MS (apci) m/z = 472.2 (M + H) |

Example 635

4-(6-(4-((6-methoxypyridin-3-yl)methyl)piperazin-1-yl)pyridin-3-yl)-6-(3-methylisoxazol-5-yl)pyrazolo[1,5-a]pyridine-3-carbonitrile A room temperature solution of 6-(3-methylisoxazol-5-yl)-4-(6-(piperazin-1-yl)pyridin-3-yl)pyrazolo[1,5-a]pyridine-3-carbonitrile hydrochloride (Example 625; 6 mg, 0.014 mmol) in dry DMA (0.4 mL) was treated with TEA (6 µL, 0.043 mmol), Me₄N(AcO)₃BH (7.5 mg, 0.028 mmol) and 6-methoxynicotinaldehyde (4 mg, 0.0284 mmol). The resulting mixture was stirred overnight at room temperature, and then additional TEA (4 µL, 0.22 mmol), Me₄N(AcO)₃BH (7.5 mg, 0.028 mmol) and 6-methoxynicotinaldehyde (4 mg, 0.0284 mmol) were added. The reaction was stirred at room temperature for 84 hr, then quenched with water and CHCl₃, and allowed to stir for 30 min at room temperature. The resulting mixture was filtered through a PS frit, and the organics were extracted with EtOAc. The combined organic extracts were purified directly by C18 reverse phase chromatography (20-80% ACN/water as the gradient eluent) to afford the title compound (1.3 mg, 18% yield). MS (apci) m/z=507.1 (M+H).

Example 636

4-(6-(4-((6-methoxypyridin-3-yl)methyl)piperazin-1-yl)pyridin-3-yl)-6-(3-methyl-1H-pyrazol-5-yl)pyrazolo[1,5-a]pyridine-3-carbonitrile A room temperature solution of 6-(3-methyl-1H-pyrazol-5-yl)-4-(6-(piperazin-1-yl)pyridin-3-yl)pyrazolo[1,5-a]pyridine-3-carbonitrile dihydrochloride (Example 626; 40 mg, 0.087 mmol) in DMF (0.4 mL) was treated with TEA (61 µL, 0.44 mmol), 6-methoxynicotinaldehyde (36 mg, 0.26 mmol) and Me₄N(AcO)₃BH (23 mg, 0.087 mmol). The resulting mixture was stirred for 48 h at room temperature and then directly purified by C18 reverse phase chromatography (0-60% ACN/water as the gradient eluent) to afford the title compound (30 mg, 68% yield). MS (apci) m/z=506.2 (M+H).

The compounds in Table GGG were prepared according to the method described for the synthesis of Example 636, replacing 6-(3-methyl-1H-pyrazol-5-yl)-4-(6-(piperazin-1-yl)pyridine-3-yl)pyrazolo[1,5-a]pyridine-3-carbonitrile dihydrochloride and 6-methoxynicotinaldehyde with the appropriate piperazine from Table DDD, and the appropriate commercial aldehyde. Reactions were followed by LCMS, and reaction times were adjusted as necessary. In each example, title compounds were isolated cleanly following C18 reverse phase chromatography utilizing an appropriate gradient eluent.

TABLE GGG

| Ex # | Structure | Chemical Name | MS (apci) m/z |
|---|---|---|---|
| 637 | 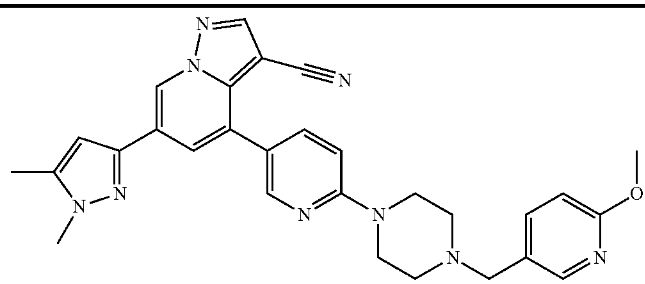 | 6-(1,5-dimethyl-1H-pyrazol-3-yl)-4-(6-(4-((6-methoxypyridin-3-yl)methyl)piperazin-1-yl)pyridin-3-yl)pyrazolo[1,5-a]pyridine-3-carbonitrile | 520.2 (M + H) |
| 638 | 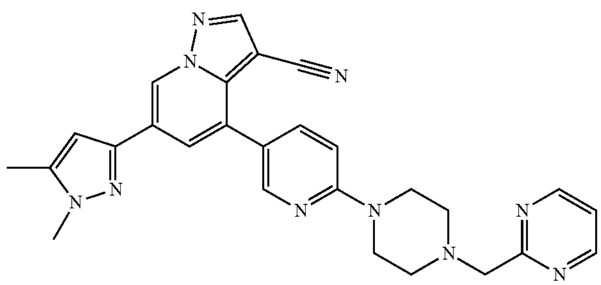 [SMILES: Cc1cc(-c2cc(-c3ccc(N4CCN(Cc5ncccn5)CC4)nc3)c3c(C#N)cnn3c2)nn1C] | 6-(1,5-dimethyl-1H-pyrazol-3-yl)-4-(6-(4-(pyrimidin-2-ylmethyl)piperazin-1-yl)pyridin-3-yl)pyrazolo[1,5-a]pyridine-3-carbonitrile | 491.2 (M + H) |

Example 639

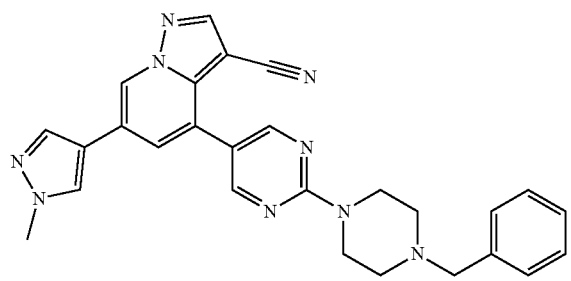 [SMILES: Cn1cc(-c2cc(-c3cnc(N4CCN(Cc5ccccc5)CC4)nc3)c3c(C#N)cnn3c2)cn1]

4-(2-(4-benzylpiperazin-1-yl)pyrimidin-5-yl)-6-(1-methyl-1H-pyrazol-4-yl)pyrazolo[1,5-a]pyridine-3-carbonitrile A room temperature solution of 6-(1-methyl-1H-pyrazol-4-yl)-4-(2-(piperazin-1-yl)pyrimidin-5-yl)pyrazolo[1,5-a]pyridine-3-carbonitrile dihydrochloride (Example 281; 15 mg, 0.033 mmol) in DMF (0.2 mL) was treated with (bromomethyl)benzene (8.4 mg, 0.049 mmol) and TEA (14 μL, 0.098 mmol). The resulting mixture was stirred for 1 h at room temperature, then directly purified by C18 reverse phase chromatography (using 0-60% ACN/water as the gradient eluent) to afford the title compound (9.5 mg, 61% yield). MS (apci) m/z=476.2 (M+H).

Example 640

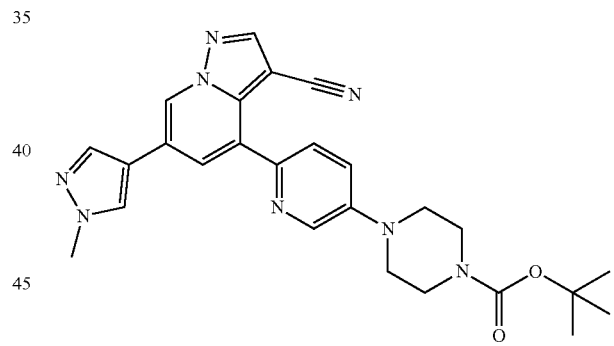

Tert-Butyl 4-(6-(3-cyano-6-(1-methyl-1H-pyrazol-4-yl)pyrazolo[1,5-a]pyridine-4-yl)pyridin-3-yl)piperazine-1-carboxylate A mixture of 3-cyano-6-(1-methyl-1H-pyrazol-4-yl)pyrazolo[1,5-a]pyridin-4-yl trifluoromethanesulfonate (Intermediate P5; 100 mg, 0.269 mmol), tert-butyl 4-(5-(4,4,5,5-tetramethyl-1,3,2-dioxaborolan-2-yl)pyridine-2-yl)piperazine-1-carboxylate (131 mg, 0.269 mmol), $Na_2CO_3$ (143 mg, 1.35 mmol), and $Pd(PPh_3)_4$ (15.6 mg, 0.0135 mmol) in 4:1 dioxane/water (4 mL) was sparged with Argon and then stirred overnight at 90° C. After cooling to room temperature, the reaction mixture was concentrated in vacuo, and the residue was partitioned between EtOAc and water. The aqueous extracts were washed with EtOAc, and the combined organic extracts were dried over anhydrous $Na_2SO_4$, filtered, and concentrated in vacuo. The residue was purified by silica chromatography (eluted with a stepped gradient of 50-50% Hexanes/EtOAc followed by 25-75%

Hexanes/EtOAc) to cleanly afford the title compound (13 mg, 10% yield). MS (apci) m/z=485.1 (M+H).

Example 641

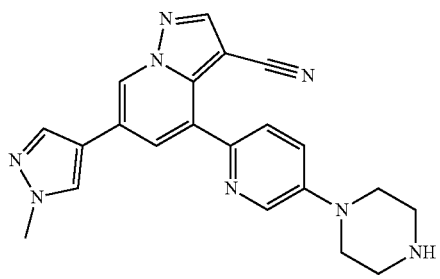 [SMILES: Cn1cc(-c2cc(-c3ccc(N4CCNCC4)cn3)c3c(C#N)cnn3c2)cn1]

6-(1-methyl-1H-pyrazol-4-yl)-4-(5-(piperazin-1-yl)pyridin-2-yl)pyrazolo[1,5-a]pyridine-3-carbonitrile A room temperature solution of tert-butyl 4-(6-(3-cyano-6-(1-methyl-1H-pyrazol-4-yl)pyrazolo[1,5-a]pyridine-4-yl)pyridin-3-yl)piperazine-1-carboxylate (Example 640; 13 mg, 0.027 mmol) in DCM (4 mL) was treated with TFA (2 mL, 0.4 mmol), and stirred for 4 h at room temperature. The reaction mixture was purified directly by reverse phase HPLC (5-95% water/ACN with 0.1% TFA as the gradient eluent) to afford the title compound as the TFA salt. The TFA salt was suspended in 4:1 DCM/iPrOH and washed with saturated NaHCO$_3$. The combined organic extracts were dried over anhydrous Na$_2$SO$_4$, filtered, and concentrated in vacuo to cleanly afford the title compound (9 mg, 87% yield). MS (apci) m/z=385.1 (M+H).

Example 642

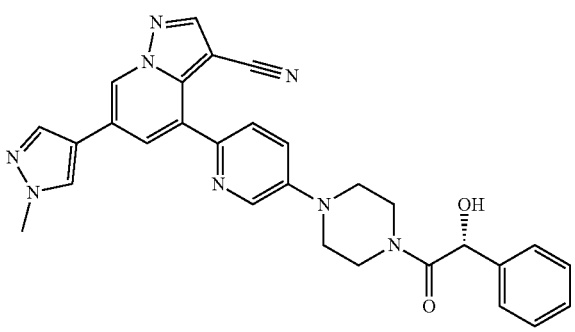

(R)-4-(5-(4-(2-hydroxy-2-phenylacetyl)piperazin-1-yl)pyridin-2-yl)-6-(1-methyl-1H-pyrazol-4-yl)pyrazolo[1,5-a]pyridine-3-carbonitrile A room temperature solution of 6-(1-methyl-1H-pyrazol-4-yl)-4-(5-(piperazin-1-yl)pyridine-2-yl)pyrazolo[1,5-a]pyridine-3-carbonitrile (Example 641; 9 mg, 0.023 mmol) in DMF (4 mL) was treated with D-(−)-mandelic acid (5.34 mg, 0.351 mmol), HATU (8.90 mg, 0.023 mmol) and DIEA (40.8 µL, 0.234 mmol). The reaction was stirred for 16 h at room temperature and then directly purified by silica chromatography (using a stepped gradient eluent of 100% EtOAc followed by 5% MeOH in EtOAc) to provide the title compound (3.2 mg, 26% yield). MS (apci) m/z=519.2 (M+H).

Example 643

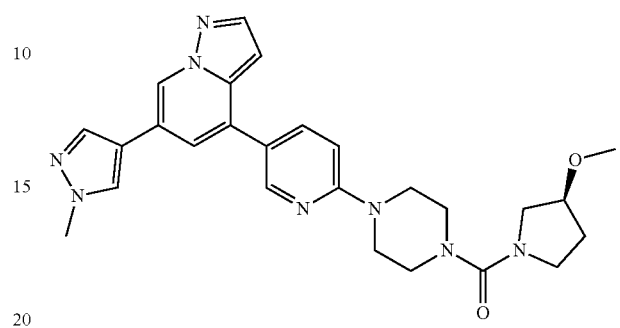

(S)-(3-methoxypyrrolidin-1-yl)(4-(5-(6-(1-methyl-1H-pyrazol-4-yl)pyrazolo[1,5-a]pyridin-4-yl)pyridin-2-yl)piperazin-1-yl)methanone A suspension of 6-(1-methyl-1H-pyrazol-4-yl)-4-(6-(piperazin-1-yl)pyridin-3-yl)pyrazolo[1,5-a]pyridine dihydrochloride (Example 312; 28.4 mg, 0.0657 mmol) and DIEA (114 µL, 0.657) mmol) in DCM (500 µL) was added dropwise to a 0° C. solution of triphosgene (7.80 mg, 0.0263 mmol) in DCM (273 µL). After stirring for 1 h at 0° C., the reaction mixture was treated with (S)-3-methoxypyrrolidine hydrochloride (9.94 mg, 0.0723 mmol) and then stirred for 16 h at room temperature. The resulting mixture was purified directly by silica chromatography (40-100% DCM/acetone as the gradient eluent) to provide the title compound (13.5 mg, 42% yield). MS (apci) m/z=487.1 (M+H).

Example 644

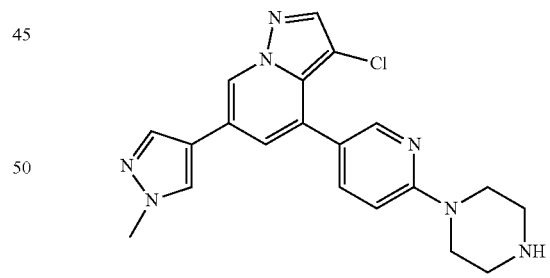

3-chloro-6-(1-methyl-1H-pyrazol-4-yl)-4-(6-(piperazin-1-yl)pyridin-3-yl)pyrazolo[1,5-a]pyridine A room temperature solution of tert-butyl 4-(5-(3-chloro-6-(1-methyl-1H-pyrazol-4-yl)pyrazolo[1,5-a]pyridin-4-yl)pyridin-2-yl)piperazine-1-carboxylate (Example 325; 1.55 g, 3.13 mmol) in 1:1 DCM/TFA (15.0 mL) was stirred for 30 min at room temperature, then concentrated in vacuo to afford the title compound as the TFA salt. The TFA salt was suspended in 4:1 DCM/iPrOH and extracted with saturated NaHCO$_3$. The combined organic extracts were dried over anhydrous Na$_2$SO$_4$, filtered, and concentrated in vacuo. The residue was purified by silica chromatography (1-30% DCM/MeOH with 2% NH$_4$OH as the gradient eluent) to afford the title compound (716 mg, 58% yield). MS (apci) m/z=494.2 (M+H), 495.2 (M+2), with Cl pattern.

Example 645

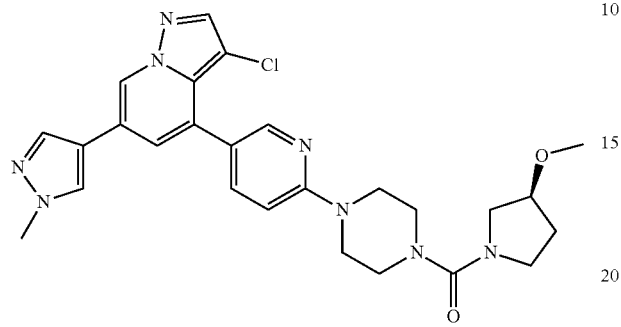

(S)-(4-(5-(3-chloro-6-(1-methyl-1H-pyrazol-4-yl)pyrazolo[1,5-a]pyridin-4-yl)pyridin-2-yl)piperazin-1-yl)(3-methoxypyrrolidin-1-yl)methanone A suspension of 3-chloro-6-(1-methyl-1H-pyrazol-4-yl)-4-(6-(piperazin-1-yl)pyridine-3-yl)pyrazolo[1,5-a]pyridine dihydrochloride (Example 326; 14.1 mg, 0.0302 mmol) and DIEA (52.6 µL, 0.302) mmol) in DCM (500 µL) was added dropwise to a 0° C. solution of triphosgene (3.59 mg, 0.0121 mmol) in DCM (500 µL). After stirring for 1 h at 0° C., the reaction mixture was treated with (S)-3-methoxypyrrolidine hydrochloride (4.57 mg, 0.0332 mmol) and then stirred for 16 h at room temperature. The resulting mixture was diluted with DCM and washed with saturated NaHCO$_3$. The combined organic extracts were dried over anhydrous Na$_2$SO$_4$, filtered, and concentrated in vacuo. The residue was purified by silica chromatography (40-100% DCM/acetone as the gradient eluent) to provide the title compound (7.2 mg, 46% yield). MS (apci) m/z=521.1 (M+H), 522.1 (M+2H).

Example 646

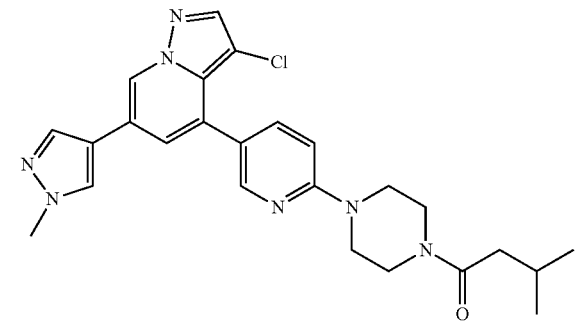 [SMILES: CC(C)CC(=O)N1CCN(c2ccc(-c3cc(-c4cnn(C)c4)cn4ncc(Cl)c34)cn2)CC1]

1-(4-(5-(3-chloro-6-(1-methyl-1H-pyrazol-4-yl)pyrazolo[1,5-a]pyridin-4-yl)pyridin-2-yl)piperazin-1-yl)-3-methylbutan-1-one A room temperature solution of 3-chloro-6-(1-methyl-1H-pyrazol-4-yl)-4-(6-(piperazin-1-yl)pyridin-3-yl)pyrazolo[1,5-a]pyridine (Example 644; 51.7 mg, 0.131 mmol) in DCM (1.3 mL) was treated sequentially with DIEA (45.7 µL, 0.263 mmol) and isovaleryl chloride (19.2 µL, 0.158 mmol). The reaction mixture was stirred for 16 h at room temperature and then directly purified by C18 reverse phase chromatography (5-95% water/ACN with 0.1% TFA as the gradient eluent) to afford the title compound as the TFA salt. The TFA salt was suspended in 4:1 DCM/iPrOH and extracted with saturated NaHCO$_3$. The combined organic extracts were dried over anhydrous Na$_2$SO$_4$, filtered, and concentrated in vacuo to cleanly afford the title compound (48.9 mg, 78% yield). MS (apci) m/z=478.1 (M+H), 479.1 (M+2H).

Example 647

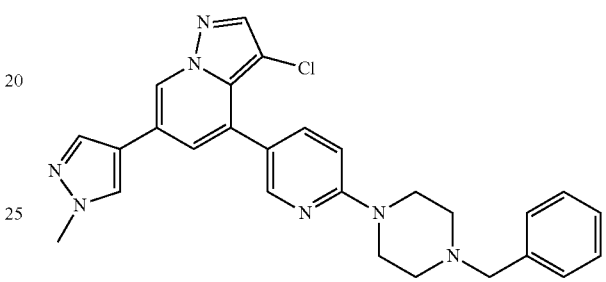

4-(6-(4-benzylpiperazin-1-yl)pyridine-3-yl)-3-chloro-6-(1-methyl-1H-pyrazol-4-yl)pyrazolo[1,5-a]pyridine A room temperature solution of 3-chloro-6-(1-methyl-1H-pyrazol-4-yl)-4-(6-(piperazin-1-yl)pyridine-3-yl)pyrazolo[1,5-a]pyridine (Example 644; 52.3 mg, 0.133 mmol) in DCM (1.3 mL) was treated sequentially with TEA (90.1 µL, 0.664 mmol) and benzyl bromide (47.3 µL, 0.398 mmol). The resulting mixture was stirred for 16 h at room temperature and then directly purified by silica chromatography (1-25% DCM/MeOH with 2% NH$_4$OH as the gradient eluent) to afford the title compound (43.5 mg, 68% yield). MS (apci) m/z=484.1 (M+H), 485.1 (M+2H).

Example 648

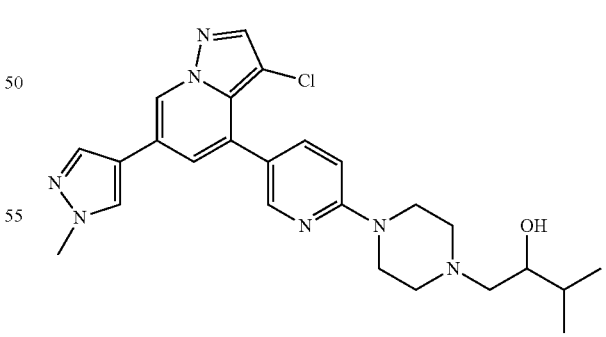

1-(4-(5-(3-chloro-6-(1-methyl-1H-pyrazol-4-yl)pyrazolo[1,5-a]pyridin-4-yl)pyridine-2-yl)piperazin-1-yl)-3-methylbutan-2-ol A room temperature solution of 3-chloro-6-(1-methyl-1H-pyrazol-4-yl)-4-(6-(piperazin-1-yl)pyridin-3-yl)pyrazolo[1, 5-a]pyridine (Example 644; 52.6 mg, 0.134 mmol) in MeOH (1.3 mL) was treated with 1,2-epoxy-3-methylbutane (13.8 mg, 0.160 mmol). The resulting mixture was sealed and stirred for 16 h at 80° C. After cooling to room temperature, the reaction mixture was concentrated in vacuo, and the residue was purified by silica chromatography (1-25% DCM/MeOH with 2% NH₄OH as the gradient eluent) to afford the title compound (46.2 mg, 72% yield). MS (apci) m/z=480.2 (M+H), 481.2 (M+2), with Cl pattern.

Example 649

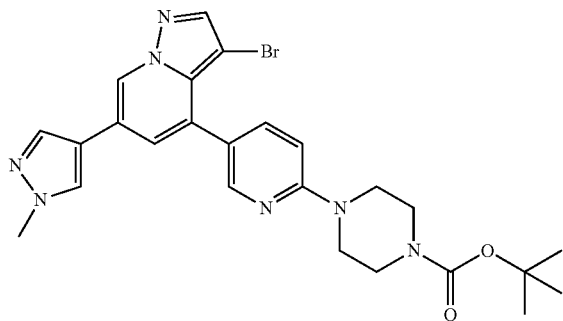 [SMILES: Cn1cc(-c2cc(-c3ccc(N4CCN(C(=O)OC(C)(C)C)CC4)nc3)c3c(Br)cnn3c2)cn1]

Tert-Butyl 4-(5-(3-bromo-6-(1-methyl-1H-pyrazol-4-yl)pyrazolo[1,5-a]pyridin-4-yl)pyridin-2-yl)piperazine-1-carboxylate A cold (0° C.) solution of tert-butyl 4-(5-(6-(1-methyl-1H-pyrazol-4-yl)pyrazolo[1,5-a]pyridine-4-yl)pyridine-2-yl)piperazine-1l-carboxylate (Example 311; 0.203 g, 0.442 mmol) in DMF (4 mL) was treated with NBS (0.0865 g, 0.486 mmol). After stirring for 1 h at room temperature, the reaction mixture was diluted with EtOAc and washed with brine. The combined organic extracts were dried over anhydrous Na₂SO₄, filtered, and concentrated in vacuo. The residue was purified by silica chromatography (0-50% EtOAc in Hexanes as the gradient eluent) to afford the title compound (0.157 g, 66% yield). MS (apci) m/z=538.0 (M+H).

Example 650

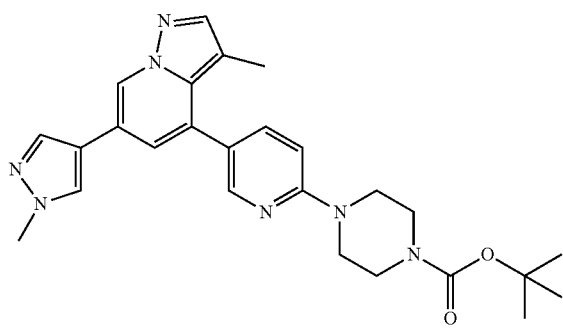 [SMILES: Cc1cnn2cc(-c3cnn(C)c3)cc(-c3ccc(N4CCN(C(=O)OC(C)(C)C)CC4)nc3)c12]

Tert-Butyl 4-(5-(3-methyl-6-(1-methyl-1H-pyrazol-4-yl)pyrazolo[1,5-a]pyridin-4-yl)pyridin-2-yl)piperazine-1-carboxylate A mixture of 3-methyl-6-(1-methyl-1H-pyrazol-4-yl)pyrazolo[1,5-a]pyridine-4-yl trifluoromethanesulfonate (Intermediate 27; 250 mg, 0.694 mmol), tert-butyl 4-(5-(4,4,5,5-tetramethyl-1,3,2-dioxaborolan-2-yl)pyrazin-2-yl)piperazine-1-carboxylate (297 mg, 0.763 mmol), Na₂CO₃ (368 mg, 3.47 mmol), and Pd(PPh₃)₄ (40.1 mg, 0.0347 mmol) in 4:1 dioxane/water (4 mL) was sparged with Argon for 10 min, then stirred overnight at 90° C. under an Argon atmosphere. After cooling to room temperature, the reaction mixture was concentrated in vacuo, and the residue was partitioned between EtOAc and water. The combined organic extracts were dried over anhydrous Na₂SO₄, filtered, and concentrated in vacuo. The residue was purified by silica chromatography (using 50-100% EtOAc in Hexanes as the gradient eluent) to cleanly afford the title compound (225 mg, 69% yield). MS (apci) m/z=485.1 (M+H). MS (apci) m/z=474.2 (M+H).

Example 651

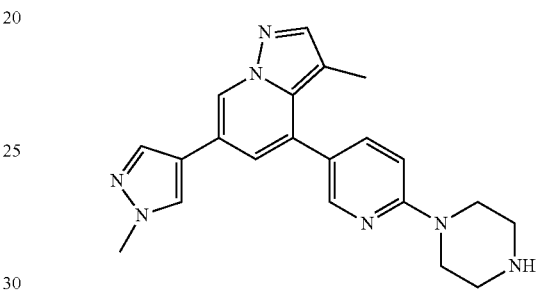

3-methyl-6-(1-methyl-1H-pyrazol-4-yl)-4-(6-(piperazin-1-yl)pyridin-3-yl)pyrazolo[1,5-a]pyridine A room temperature solution of tert-butyl 4-(5-(3-chloro-6-(1-methyl-1H-pyrazol-4-yl)pyrazolo[1,5-a]pyridin-4-yl)pyridin-2-yl)piperazine-1-carboxylate (Example 650; 1.55 g, 3.13 mmol) in DCM (4.0 mL) was treated with TFA, then stirred overnight at room temperature. The reaction mixture was concentrated in vacuo and the residue was purified by reverse phase HPLC (5-95% water/ACN with 0.1% TFA as the gradient eluent) to afford the title compound as the TFA salt. The TFA salt was suspended in 4:1 DCM/iPrOH and washed with saturated NaHCO₃. The combined organic extracts were dried over anhydrous Na₂SO₄, filtered, and concentrated in vacuo to afford the title compound (151 mg, 79% yield). MS (apci) m/z=374.2 (M+H).

Example 652

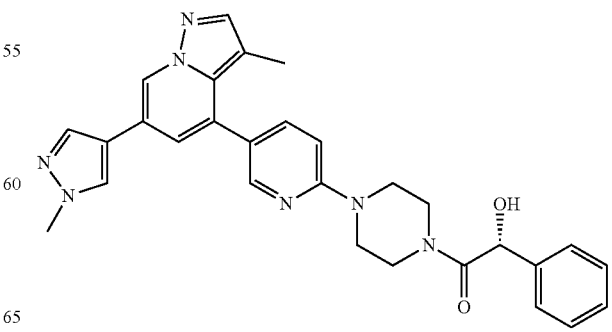

(R)-2-hydroxy-1-(4-(5-(3-methyl-6-(1-methyl-1H-pyrazol-4-yl)pyrazolo[1,5-a]pyridin-4-yl)pyridin-2-yl)piperazin-1-yl)-2-phenylethan-1-one A room temperature solution of 3-methyl-6-(1-methyl-1H-pyrazol-4-yl)-4-(6-(piperazin-1-yl)pyridin-3-yl)pyrazolo[1,5-a]pyridine (Example 651; 20 mg, 0.054 mmol) in DMF (4 mL) was treated with D-(−)-mandelic acid (12 mg, 0.080 mmol), HATU (20 mg, 0.054 mmol) and DIEA (93 µL, 0.54 mmol). The reaction was stirred for 16 h at room temperature, and then diluted with EtOAc and washed with water. The combined organic extracts were dried over anhydrous Na$_2$SO$_4$, filtered, and concentrated in vacuo. The residue was purified by silica chromatography (using a stepped gradient of 25% Hexanes in EtOAc followed by 100% EtOAc) to provide the title compound (20 mg, 74% yield). MS (apci) m/z=508.2 (M+H).

Example 653

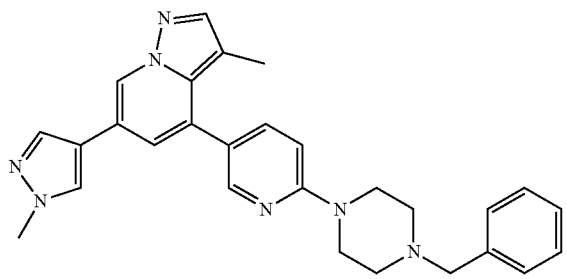 [SMILES: Cc1cnn2cc(-c3cnn(C)c3)cc(-c3ccc(N4CCN(Cc5ccccc5)CC4)nc3)c12]

4-(6-(4-benzylpiperazin-1-yl)pyridin-3-yl)-3-methyl-6-(1-methyl-1H-pyrazol-4-yl)pyrazolo[1,5-a]pyridine A room temperature solution of 3-methyl-6-(1-methyl-1H-pyrazol-4-yl)-4-(6-(piperazin-1-yl)pyridin-3-yl)pyrazolo[1,5-a]pyridine (Example 651; 17 mg, 0.0455 mmol) in DMF (2 mL) was treated sequentially with benzyl bromide (17.3 µL, 0.0905 mmol) and TEA (31.7 µL, 0.146 mmol). The reaction mixture was stirred overnight at room temperature, then diluted with EtOAc and washed with water. The combined organic extracts were dried over anhydrous Na$_2$SO$_4$, filtered, and concentrated in vacuo. The residue was purified by silica chromatography (using a stepped gradient eluent of 25% Hexanes in EtOAc followed by 100% EtOAc) to cleanly afford the title compound (16 mg, 76% yield). MS (apci) m/z=464.2 (M+H).

Example 654

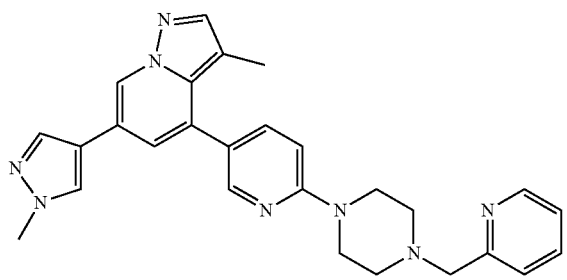 [SMILES: Cc1cnn2cc(-c3cnn(C)c3)cc(-c3ccc(N4CCN(Cc5ccccn5)CC4)nc3)c12]

3-methyl-6-(1-methyl-1H-pyrazol-4-yl)-4-(6-(4-(pyridine-2-ylmethyl)piperazin-1-yl)pyridin-3-yl)pyrazolo[1,5-a]pyridine A room temperature solution of 3-methyl-6-(1-methyl-1H-pyrazol-4-yl)-4-(6-(piperazin-1-yl)pyridin-3-yl)pyrazolo[1,5-a]pyridine (Example 651; 21 mg, 0.56 mmol) in DMF (2 mL) was treated sequentially with picolinaldehyde (0.021 g, 0.20 mmol), TEA (39 µL, 0.28 mmol) and NaBH(AcO)$_3$ (28.4 mg, 0.134 mmol). The resulting reaction mixture was allowed to stir for 1 h at room temperature and then acetic acid (10 eq) was added. The reaction mixture was stirred overnight at room temperature. The reaction mixture was diluted with EtOAc and washed with water. The combined organic extracts were dried over anhydrous Na$_2$SO$_4$, filtered, and concentrated in vacuo. The residue was purified by reverse phase HPLC (5-95% water/ACN with 0.1% TFA as the gradient eluent) to afford the title compound as the TFA salt. The TFA salt was suspended in 4:1 DCM/iPrOH and washed with saturated NaHCO$_3$. The combined organic extracts were dried over anhydrous Na$_2$SO$_4$, filtered, and concentrated in vacuo to afford the title compound (20 mg, 77% yield) MS (apci) m/z=465.2 (M+H).

Example 655

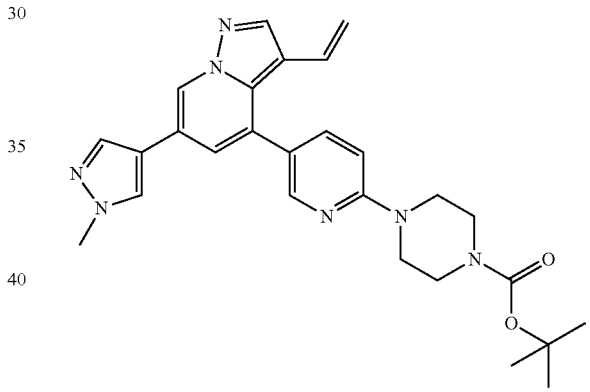

Tert-Butyl 4-(5-(6-(1-methyl-1H-pyrazol-4-yl)-3-vinylpyrazolo[1,5-a]pyridin-4-yl)pyridin-2-yl)piperazine-1-carboxylate A room temperature suspension of tert-butyl 4-(5-(3-bromo-6-(1-methyl-1H-pyrazol-4-yl)pyrazolo[1,5-a]pyridin-4-yl)pyridin-2-yl)piperazine-1-carboxylate (Example 649; 0.220 g, 0.409 mmol), potassium vinyltrifluoroborate (350 mg, 1.23 mmol), Pd$_2$(dba)$_3$ (59.9 mg, 0.0654 mmol), XPhos (62.3 mg, 0.131 mmol) and K$_2$CO$_3$ (169 mg, 1.23 mmol) in 4:1 dioxane/water (8 mL) was sparged with Argon and then stirred for 4 h at 90° C. under an atmosphere of Argon. After cooling to room temperature, the reaction mixture was concentrated in vacuo, then diluted with EtOAc and extracted with water. The combined organic extracts were dried over anhydrous Na$_2$SO$_4$, filtered and concentrated in vacuo. The residue was purified by silica chromatography (30-75% EtOAc in Hexanes as the gradient eluent) to afford the title compound (120 mg, 61% yield). MS (apci) m/z=486.1 (M+H).

Example 656

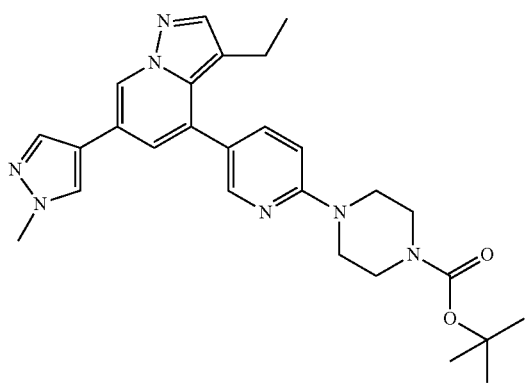 [SMILES: CCc1cnn2cc(-c3cnn(C)c3)cc(-c3ccc(N4CCN(C(=O)OC(C)(C)C)CC4)nc3)c12]

Tert-Butyl 4-(5-(3-ethyl-6-(1-methyl-1H-pyrazol-4-yl)pyrazolo[1,5-a]pyridin-4-yl)pyridin-2-yl)piperazine-1-carboxylate A room temperature solution of tert-butyl 4-(5-(6-(1-methyl-1H-pyrazol-4-yl)-3-vinylpyrazolo[1,5-a]pyridin-4-yl)pyridin-2-yl)piperazine-1-carboxylate (Example 655; 0.120 g, 0.247 mmol) in EtOAc (6 mL) was treated with 10% Pd/C (0.0263 g, 0.0247 mmol), then sparged with $H_2$ for 10 min and stirred under an atmosphere of $H_2$ overnight at room temperature. The reaction mixture was filtered through GF/F paper and the filtrate was concentrated in vacuo to afford the title compound (120 mg, quantitative yield) in sufficient purity. MS (apci) m/z=488.1 (M+H).

Example 657

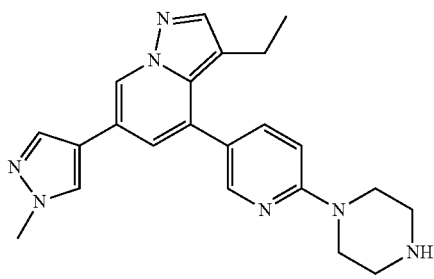 [SMILES: CCc1cnn2cc(-c3cnn(C)c3)cc(-c3ccc(N4CCNCC4)nc3)c12]

3-ethyl-6-(1-methyl-1H-pyrazol-4-yl)-4-(6-(piperazin-1-yl)pyridin-3-yl)pyrazolo[1,5-a]pyridine A room temperature solution of tert-butyl 4-(5-(3-ethyl-6-(1-methyl-1H-pyrazol-4-yl)pyrazolo[1,5-a]pyridin-4-yl)pyridin-2-yl)piperazine-1-carboxylate (Example 656; 0.120 g, 0.246 mmol) in DCM (4.0 mL) was treated with TFA (2 mL), then stirred for 4 h at room temperature. The reaction mixture was concentrated in vacuo, and the residue was purified by reverse phase HPLC (5-95% water/ACN with 0.1% TFA as the gradient eluent) to afford the title compound as the TFA salt. The TFA salt was suspended in 4:1 DCM/iPrOH and washed with saturated $NaHCO_3$. The combined organic extracts were dried over anhydrous $Na_2SO_4$, filtered, and concentrated in vacuo to afford the title compound (70 mg, 73% yield). MS (apci) m/z=388.2 (M+H).

Example 658

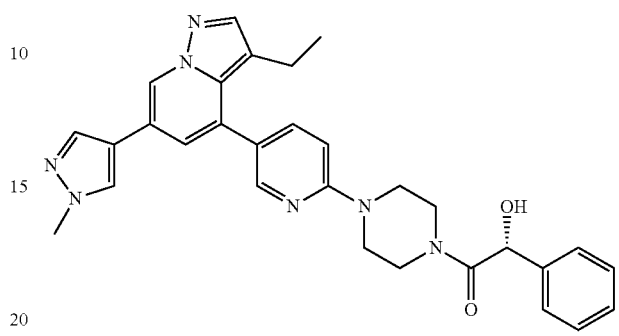

(R)-1-(4-(5-(3-ethyl-6-(1-methyl-1H-pyrazol-4-yl)pyrazolo[1,5-a]pyridin-4-yl)pyridin-2-yl)piperazin-1-yl)-2-hydroxy-2-phenylethanone A room temperature solution of 3-ethyl-6-(1-methyl-1H-pyrazol-4-yl)-4-(6-(piperazin-1-yl)pyridin-3-yl)pyrazolo[1,5-a]pyridine (Example 657; 27 mg, 0.070 mmol) in DMF (4 mL) was treated with D-(−)-mandelic acid (16 mg, 0.10 mmol), HATU (26 mg, 0.070 mmol) and DIEA (121 µL, 0.70 mmol). The reaction was stirred 16 h at room temperature, and then diluted with EtOAc and washed with water. The combined organic extracts were dried over anhydrous $Na_2SO_4$, filtered, and concentrated in vacuo. The residue was purified by silica chromatography (using a stepped gradient of 1:2 Hexanes in EtOAc followed by 1:4 Hexanes in EtOAc) to provide the title compound (20 mg, 55% yield). MS (apci) m/z=522.2 (M+H).

Example 659

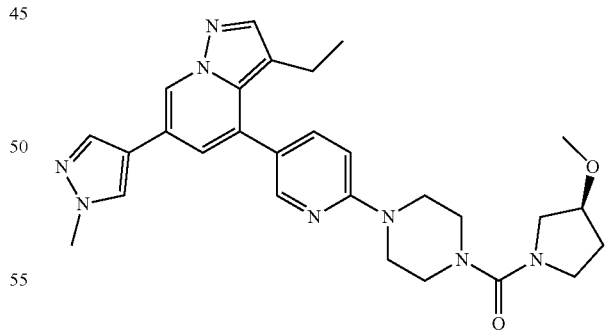

(S)-(4-(5-(3-ethyl-6-(1-methyl-1H-pyrazol-4-yl)pyrazolo[1,5-a]pyridin-4-yl)pyridin-2-yl)piperazin-1-yl)(3-methoxypyrrolidin-1-yl)methanone A suspension of 3-ethyl-6-(1-methyl-1H-pyrazol-4-yl)-4-(6-(piperazin-1-yl)pyridin-3-yl)pyrazolo[1,5-a]pyridine (Example 657; 38 mg, 0.098 mmol) and DIEA (102 µL, 0.59) mmol) in DriSolv® DCM (490 µL) was added dropwise to a 0° C. solution of triphosgene (13 mg, 0.044 mmol) in DriSolv® DCM (490 µL). After stirring for 30 min at 0° C., the reaction mixture was treated with (S)-3-methoxypyrrolidine hydrochloride (13 mg, 0.098 mmol), then stirred for 48 h at room temperature. The resulting mixture was diluted with EtOAc and washed with water. The combined organic extracts were dried over anhydrous Na$_2$SO$_4$, filtered, and concentrated in vacuo. The residue was purified by reverse-phase HPLC (5-95% water/ACN with 0.1% TFA as the gradient eluent) to afford the title compound as the TFA salt. The TFA salt was suspended in 4:1 DCM/iPrOH and washed with saturated NaHCO$_3$. The combined organic extracts were dried over anhydrous Na$_2$SO$_4$, filtered, and concentrated in vacuo to provide the title compound (30 mg, 59% yield). MS (apci) m/z=515.2 (M+H).

Example 660

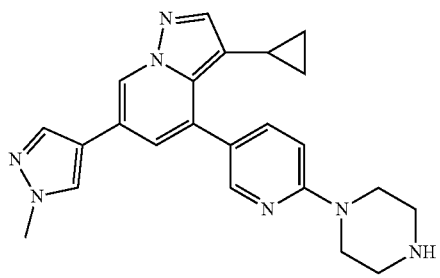 [SMILES: Cn1cc(-c2cc(-c3ccc(N4CCNCC4)nc3)c3c(C4CC4)cnn3c2)cn1]

3-cyclopropyl-6-(1-methyl-1H-pyrazol-4-yl)-4-(6-(piperazin-1-yl)pyridin-3-yl)pyrazolo[1,5-a]pyridine In a sealed vessel, a −35° C. solution of tert-butyl 4-(5-(6-(1-methyl-1H-pyrazol-4-yl)-3-vinylpyrazolo[1,5-a]pyridin-4-yl)pyridin-2-yl)piperazine-1-carboxylate (Example 655; 0.100 g, 0.206 mmol) in DCE (2 mL) was treated sequentially with 1.0 M diethylzinc in Hexanes (4.12 mL, 4.12 mmol) and diiodomethane (0.332 mL, 4.12 mmol). The resulting mixture was brought to room temperature, and then stirred overnight at 75° C. The reaction mixture was diluted with DCM and washed with water. The combined organic extracts were dried over anhydrous Na$_2$SO$_4$, filtered, and concentrated in vacuo to afford tert-butyl 4-(5-(3-cyclopropyl-6-(1-methyl-1H-pyrazol-4-yl)pyrazolo[1,5-a]pyridin-4-yl)pyridin-2-yl)piperazine-1-carboxylate. The crude material was immediately suspended in 1:2 TFA/DCM (3 mL), and stirred for 30 min at room temperature. The reaction mixture was concentrated in vacuo and the residue was purified by reverse phase HPLC (5-95% water/ACN with 0.1% TFA as the gradient eluent) to afford the title compound as the TFA salt. The TFA salt was suspended in 4:1 DCM/iPrOH and extracted with saturated NaHCO$_3$. The combined organic extracts were dried over anhydrous Na$_2$SO$_4$, filtered, and concentrated in vacuo to afford the title compound (1.1 mg, 1.3% yield). MS (apci) m/z=400.2 (M+H).

Example 661

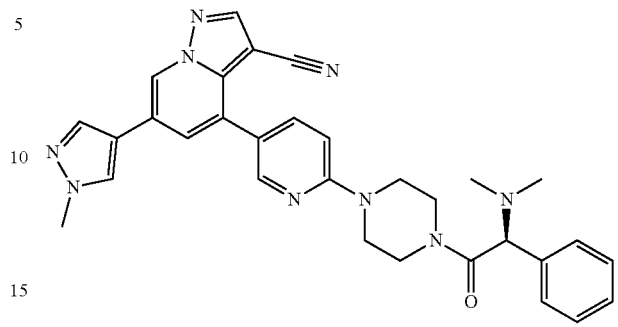

(S)-4-(6-(4-(2-(dimethylamino)-2-phenylacetyl)piperazin-1-yl)pyridin-3-yl)-6-(1-methyl-1H-pyrazol-4-yl)pyrazolo[1,5-a]pyridine-3-carbonitrile A suspension of (S)-4-(6-(4-(2-amino-2-phenylacetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate) (Example 50; 7 mg, 0.014 mmol) in anhydrous MeOH (0.4 mL) was treated sequentially with formaldehyde (20.3 µL, 0.27 mmol) and Me$_4$N(AcO)$_3$BH (21.3 mg, 0.0811 mmol). The reaction mixture was allowed to stir overnight at ambient temperature, before introducing additional formaldehyde (5 µL, 0.066 mmol), and Me$_4$N(AcO)$_3$BH (5 mg, 0.019 mmol). After stirring an additional period of 3 d at ambient temperature, the mixture was quenched with water and CHCl$_3$, and then extracted with CHCl$_3$ in a PS frit. The combined organic extracts were concentrated in vacuo, and the resulting residue was purified by C18 reverse-phase chromatography (25-80% ACN in water as the gradient eluent) to afford the title compound (3 mg, 41% yield). MS (apci) m/z=546.3 (M+H).

Example 662

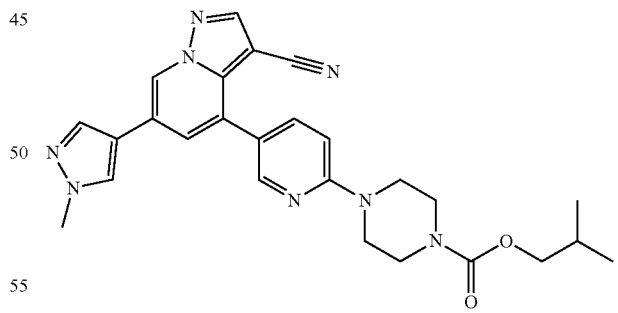

Isobutyl 4-(5-(3-cyano-6-(1-methyl-1H-pyrazol-4-yl)pyrazolo[1,5-a]pyridin-4-yl)pyridin-2-yl)piperazine-1-carboxylate A solution of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 50 mg, 0.11 mmol), isobutyl carbonochloridate (28 µL, 0.22 mmol), DMAP (1.3 mg, 0.011 mmol) and DIEA (98 OL, 0.55 mmol) in DCM (1.0 mL) was stirred overnight at ambient temperature. The reaction mixture was washed with water, and the organic extracts were dried over anhydrous Na₂SO₄, filtered, concentrated in vacuo. The resulting residue was purified by silica chromatography (0-20% acetone in DCM as the gradient eluent) to afford the title compound (4.2 mg, 8% yield). MS (apci) m/z=484.9 (M+H).

Example 663

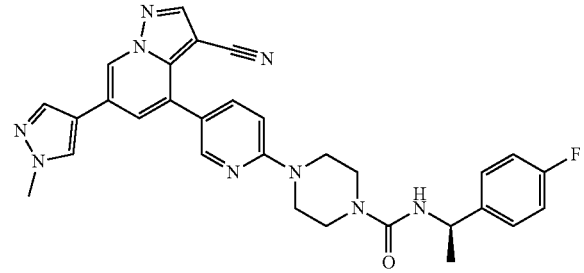 [SMILES: C[C@@H](NC(=O)N1CCN(c2ccc(-c3cc(-c4cnn(C)c4)cn4ncc(C#N)c34)cn2)CC1)c1ccc(F)cc1]

(R)-4-(5-(3-cyano-6-(1-methyl-1H-pyrazol-4-yl) pyrazolo[1,5-a]pyridin-4-yl)pyridin-2-yl)-N-(1-(4-fluorophenyl)ethyl)piperazine-1-carboxamide A suspension of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 34 mg 0.074 mmol) in anhydrous DMA (0.9 mL) was treated with (R)-1-fluoro-4-(1-isocyanatoethyl)benzene (14.7 mg, 0.089 mmol) and TEA (52 µL, 0.37 mmol). While monitoring by LCMS, the resulting reaction mixture was stirred at ambient temperature until complete. The mixture was directly purified by C18 reverse-phase chromatography (20-80% ACN/water with 0.1% formic acid) to afford the title compound (29.2 mg, 72% yield). MS (apci) m/z=550.3 (M+H).

Example 664

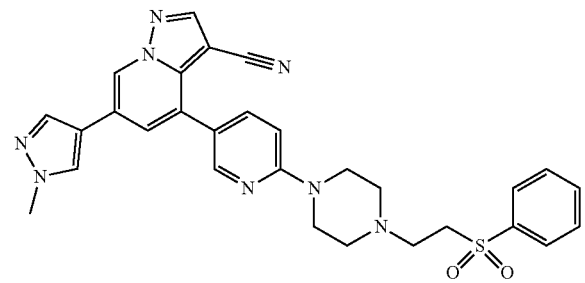 [SMILES: Cn1cc(-c2cc(-c3ccc(N4CCN(CCS(=O)(=O)c5ccccc5)CC4)nc3)c3c(C#N)cnn3c2)cn1]

6-(1-methyl-1H-pyrazol-4-yl)-4-(6-(4-(2-(phenylsulfonyl)ethyl)piperazin-1-yl)pyridin-3-yl)pyrazolo[1, 5-a]pyridine-3-carbonitrile A mixture of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 19.6 mg, 0.0429 mmol), ((2-chloroethyl)sulfonyl)benzene (26.3 mg, 0.129 mmol) and TEA (59.7 µL, 0.429 mmol) in dry DMA (500 µL) was stirred overnight at 75° C. The reaction mixture was purified directly by C18 reverse-phase chromatography (20-80% ACN/Water as the gradient eluent) to afford the title compound (10.2 mg, 43% yield). MS (apci) m/z=553.2 (M+H).

Example 665

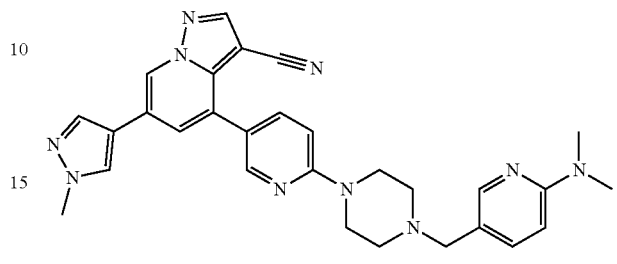

4-(6-(4-((6-(dimethylamino)pyridin-3-yl)methyl) piperazin-1-yl)pyridin-3-yl)-6-(1-methyl-1H-pyrazol-4-yl)pyrazolo[1,5-a]pyridine-3-carbonitrile A suspension of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 0.125 g, 0.273 mmol) in dry DMA (500 µL) was treated sequentially with TEA (40.7 µL, 0.292 mmol), Me₄N(AcO)₃BH (23.0 mg, 0.0876 mmol), 6-(dimethylamino)nicotinaldehyde (13.2 mg, 0.0876 mmol) and 1 drop of glacial acetic acid. After stirring overnight at ambient temperature, the mixture was quenched with water/CHCl₃ and extracted with CHCl₃ in a PS frit. The combined organic extracts were concentrated in vacuo, and the residue was purified by C18 reverse-phase chromatography (20-80% ACN in water as the gradient eluent) to afford the title compound (15 mg, 50% yield). MS (apci) m/z=519.2 (M+H).

Example 666

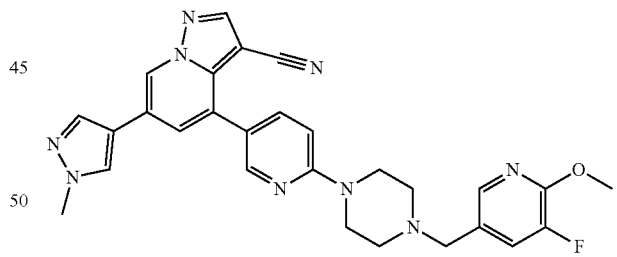

4-(6-(4-((5-fluoro-6-methoxypyridin-3-yl)methyl) piperazin-1-yl)pyridin-3-yl)-6-(1-methyl-1H-pyrazol-4-yl)pyrazolo[1,5-a]pyridine-3-carbonitrile A suspension of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 100 mg, 0.219 mmol) in DCM (3 mL) was treated with DIEA (95.5 µL, 0.547 mmol). After stirring for 5 min at ambient temperature, the mixture was treated sequentially with 5-fluoro-6-methoxynicotinaldehyde (37.3 mg, 0.241 mmol) and NaBH(AcO)₃ (92.7 mg, 0.437 mmol). After stirring for 12 h at room temperature, the reaction mixture was diluted with DCM and washed with 10% Na$_2$CO$_{3(aq)}$. The organic extracts were dried over anhydrous MgSO$_4$, filtered, and concentrated in vacuo. The crude residue was purified by silica chromatography (10% MeOH/DCM with 1% NH$_4$OH as the eluent) to afford the title compound (85 mg, 74% yield). MS (apci) m/z=524.2 (M+H).

Example 667

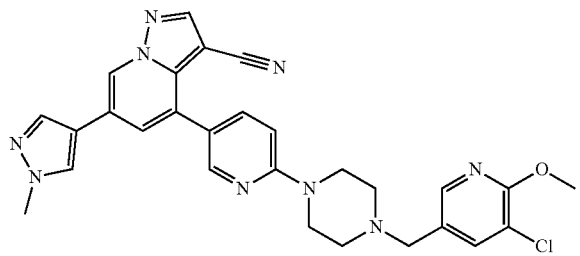 [SMILES: COc1ncc(CN2CCN(c3ccc(-c4cc(-c5cnn(C)c5)cn5ncc(C#N)c45)cn3)CC2)cc1F]

4-(6-(4-((5-chloro-6-methoxypyridin-3-yl)methyl) piperazin-1-yl)pyridin-3-yl)-6-(1-methyl-1H-pyrazol-4-yl)pyrazolo[1,5-a]pyridine-3-carbonitrile A suspension of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 30 mg, 0.066 mmol) in DCM (1 mL) was treated with DIEA (29 µL, 0.16 mmol). After stirring for 5 min at ambient temperature, the mixture was treated sequentially with 3-chloro-5-formyl-2-methoxypyridine (17 mg, 0.098 mmol) and NaBH(AcO)$_3$ (28 mg, 0.13 mmol). The resulting mixture was stirred for 12 h at room temperature, and then concentrated in vacuo. The residue was purified by C18 reverse-phase chromatography (5-95% ACN/water with 0.1% TFA as the gradient eluent) to afford the title compound as the TFA salt. The salt was diluted with EtOAc, treated with saturated NaHCO$_{3(aq)}$, and stirred for 10 min at ambient temperature. The organic extracts were separated, dried over anhydrous MgSO$_4$, filtered, and concentrated in vacuo to cleanly afford the title compound (29 mg, 82% yield). MS (apci) m/z=540.2 (M+H).

The compounds in Table HHH were prepared and purified according the method described for the synthesis of Example 667, replacing 3-chloro-5-formyl-2-methoxypyridine with the appropriate aldehyde starting material.

TABLE HHH

| Ex # | Structure | Chemical Name | MS apci (m/z) |
|---|---|---|---|
| 668 | 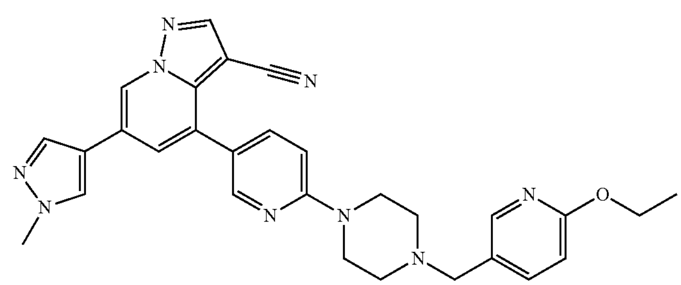 [SMILES: CCOc1ccc(CN2CCN(c3ccc(-c4cc(-c5cnn(C)c5)cn5ncc(C#N)c45)cn3)CC2)cn1] | 4-(6-(4-((6-ethoxypyridin-3-yl)methyl)piperazin-1-yl)pyridin-3-yl)-6-(1-methyl-1H-pyrazol-4-yl)pyrazolo[1,5-a]pyridine-3-carbonitrile | 520.3 (M + H) |
| 669 | 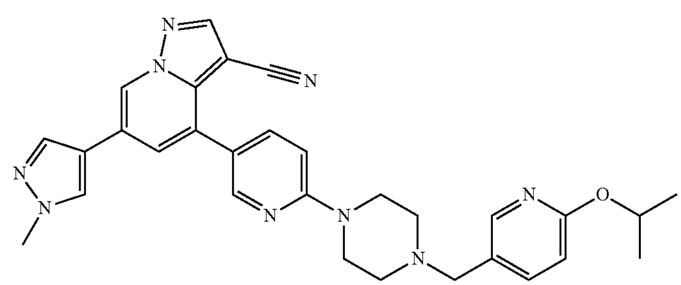 [SMILES: CC(C)Oc1ccc(CN2CCN(c3ccc(-c4cc(-c5cnn(C)c5)cn5ncc(C#N)c45)cn3)CC2)cn1] | 4-(6-(4-((6-isopropoxypyridin-3-yl)methyl)piperazin-1-yl)pyridin-3-yl)-6-(1-methyl-1H-pyrazol-4-yl)pyrazolo[1,5-a]pyridine-3-carbonitrile | 534.3 (M + H) |
| 670 | 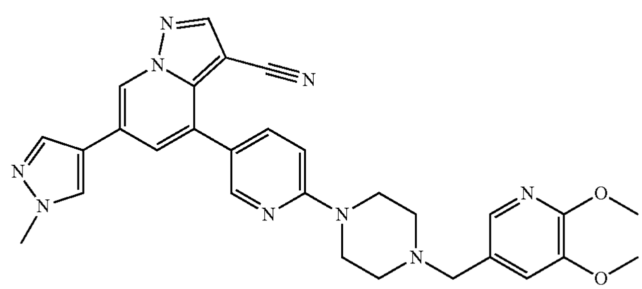 [SMILES: COc1cc(CN2CCN(c3ccc(-c4cc(-c5cnn(C)c5)cn5ncc(C#N)c45)cn3)CC2)cnc1OC] | 4-(6-(4-((5,6-dimethoxypyridin-3-yl)methyl)piperazin-1-yl)pyridin-3-yl)-6-(1-methyl-1H-pyrazol-4-yl)pyrazolo[1,5-a]pyridine-3-carbonitrile | 536.2 (M + H) |

TABLE HHH-continued

| Ex # | Structure | Chemical Name | MS apci (m/z) |
|---|---|---|---|
| 671 | 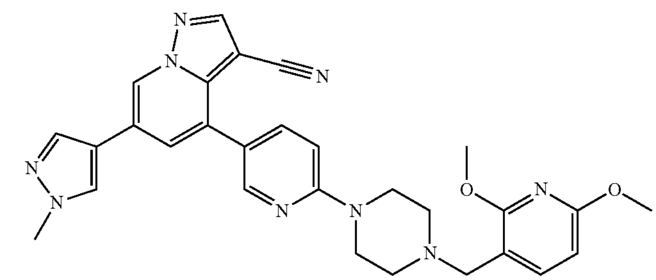 [SMILES: COc1ccc(CN2CCN(c3ccc(-c4cc(-c5cnn(C)c5)cn5ncc(C#N)c45)cn3)CC2)c(OC)n1] | 4-(6-(4-((2,6-dimethoxypyridin-3-yl)methyl)piperazin-1-yl)pyridin-3-yl)-6-(1-methyl-1H-pyrazol-4-yl)pyrazolo[1,5-a]pyridine-3-carbonitrile | 536.3 (M + H) |
| 672 | 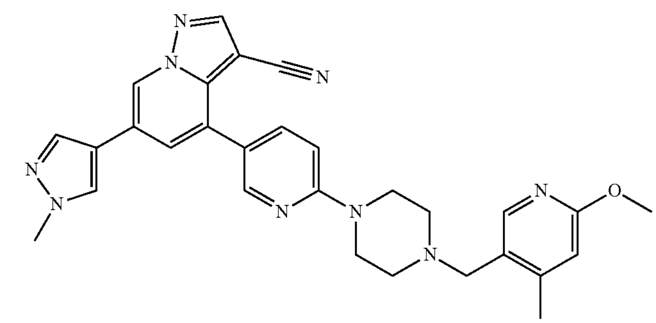 [SMILES: COc1cc(C)c(CN2CCN(c3ccc(-c4cc(-c5cnn(C)c5)cn5ncc(C#N)c45)cn3)CC2)cn1] | 4-(6-(4-((6-methoxy-4-methylpyridin-3-yl)methyl)piperazin-1-yl)pyridin-3-yl)-6-(1-methyl-1H-pyrazol-4-yl)pyrazolo[1,5-a]pyridine-3-carbonitrile | 520.2 (M + H) |
| 673 | 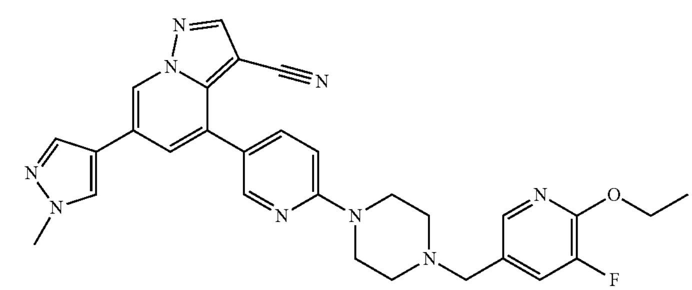 [SMILES: CCOc1ncc(CN2CCN(c3ccc(-c4cc(-c5cnn(C)c5)cn5ncc(C#N)c45)cn3)CC2)cc1F] | 4-(6-(4-((6-ethoxy-5-fluoropyridin-3-yl)methyl)piperazin-1-yl)pyridin-3-yl)-6-(1-methyl-1H-pyrazol-4-yl)pyrazolo[1,5-a]pyridine-3-carbonitrile | 538.3 (M + H) |
| 674 | 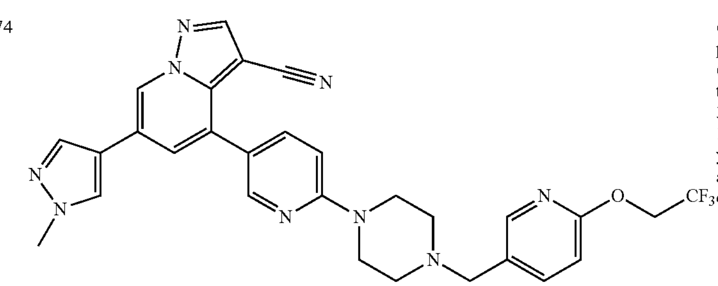 | 6-(1-methyl-1H-pyrazol-4-yl)-4-(6-(4-((6-(2,2,2-trifluoroethoxy)pyridin-3-yl)methyl)piperazin-1-yl)pyridin-3-yl)pyrazolo[1,5-a]pyridine-3-carbonitrile | 574.2 (M + H) |
| 675 | 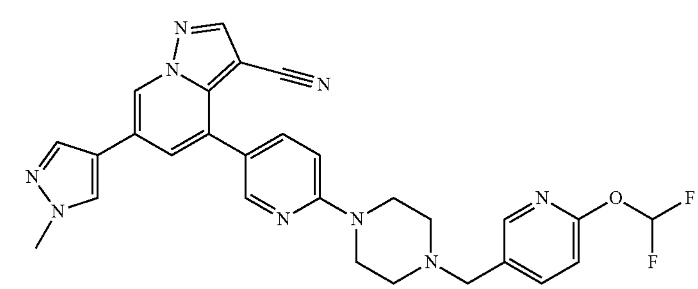 [SMILES: Cn1cc(-c2cc(-c3ccc(N4CCN(Cc5ccc(OC(F)F)nc5)CC4)nc3)c3c(C#N)cnn3c2)cn1] | 4-(6-(4-((6-(difluoromethoxy)pyridin-3-yl)methyl)piperazin-1-yl)pyridin-3-yl)-6-(1-methyl-1H-pyrazol-4-yl)pyrazolo[1,5-a]pyridine-3-carbonitrile | 542.2 (M + H) |

TABLE HHH-continued

| Ex # | Structure | Chemical Name | MS apci (m/z) |
|---|---|---|---|
| 676 | 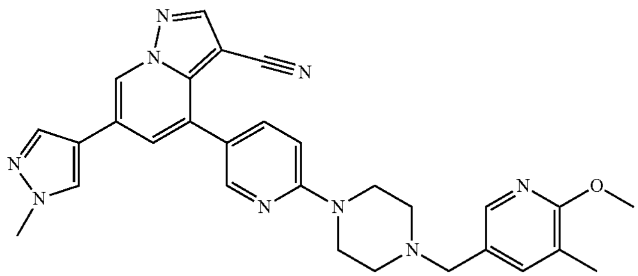 [SMILES: COc1ncc(CN2CCN(c3ccc(-c4cc(-c5cnn(C)c5)cn5ncc(C#N)c45)cn3)CC2)cc1C] | 4-(6-(4-((6-methoxy-5-methylpyridin-3-yl)methyl)piperazin-1-yl)pyridin-3-yl)-6-(1-methyl-1H-pyrazol-4-yl)pyrazolo[1,5-a]pyridine-3-carbonitrile | 520.2 (M + H) |
| 677 | 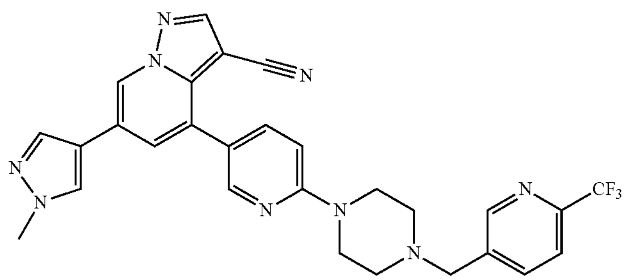 [SMILES: Cn1cc(-c2cc(-c3ccc(N4CCN(Cc5ccc(C(F)(F)F)nc5)CC4)nc3)c3c(C#N)cnn3c2)cn1] | 6-(1-methyl-1H-pyrazol-4-yl)-4-(6-(4-((6-(trifluoromethyl)pyridin-3-yl)methyl)piperazin-1-yl)pyridin-3-yl)pyrazolo[1,5-a]pyridine-3-carbonitrile | 544.2 (M + H) |
| 678 | 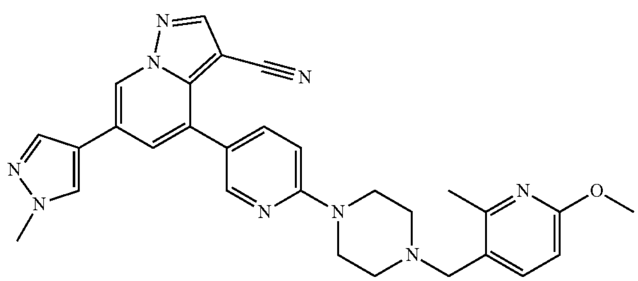 [SMILES: COc1ccc(CN2CCN(c3ccc(-c4cc(-c5cnn(C)c5)cn5ncc(C#N)c45)cn3)CC2)c(C)n1] | 4-(6-(4-((6-methoxy-2-methylpyridin-3-yl)methyl)piperazin-1-yl)pyridin-3-yl)-6-(1-methyl-1H-pyrazol-4-yl)pyrazolo[1,5-a]pyridine-3-carbonitrile | 520.3 (M + H) |
| 679 | 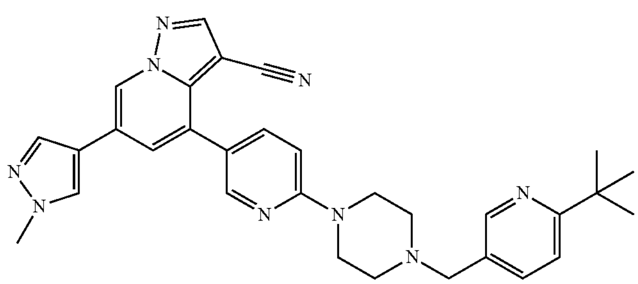 [SMILES: Cn1cc(-c2cc(-c3ccc(N4CCN(Cc5ccc(C(C)(C)C)nc5)CC4)nc3)c3c(C#N)cnn3c2)cn1] | 4-(6-(4-((6-(tert-butyl)pyridin-3-yl)methyl)piperazin-1-yl)pyridin-3-yl)-6-(1-methyl-1H-pyrazol-4-yl)pyrazolo[1,5-a]pyridine-3-carbonitrile | 532.3 (M + H) |
| 680 | 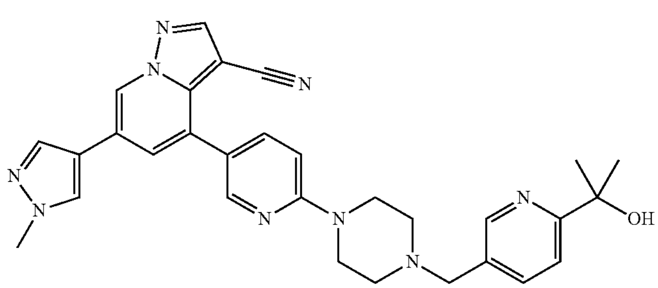 [SMILES: Cn1cc(-c2cc(-c3ccc(N4CCN(Cc5ccc(C(C)(C)O)nc5)CC4)nc3)c3c(C#N)cnn3c2)cn1] | 4-(6-(4-((6-(2-hydroxypropan-2-yl)pyridin-3-yl)methyl)piperazin-1-yl)pyridin-3-yl)-6-(1-methyl-1H-pyrazol-4-yl)pyrazolo[1,5-a]pyridine-3-carbonitrile | 534.3 (M + H) |

TABLE HHH-continued

| Ex # | Structure | Chemical Name | MS apci (m/z) |
|---|---|---|---|
| 681 | 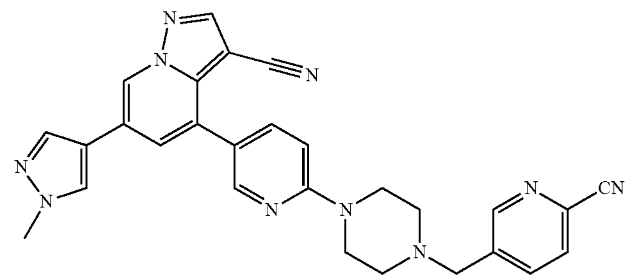 [SMILES: Cn1cc(-c2cc(-c3ccc(N4CCN(Cc5ccc(C#N)nc5)CC4)nc3)c3c(C#N)cnn3c2)cn1] | 4-(6-(4-((6-cyanopyridin-3-yl)methyl)piperazin-1-yl)pyridin-3-yl)-6-(1-methyl-1H-pyrazol-4-yl)pyrazolo[1,5-a]pyridine-3-carbonitrile | 501.2 (M + H) |

Example 682

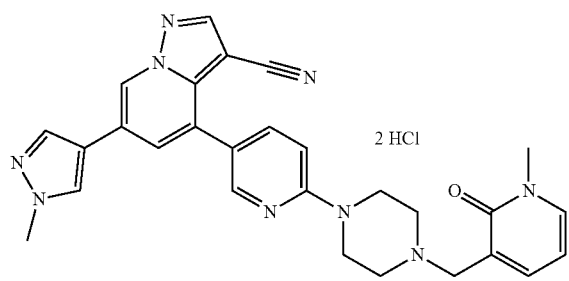 [SMILES: Cn1cc(-c2cc(-c3ccc(N4CCN(Cc5cccn(C)c5=O)CC4)nc3)c3c(C#N)cnn3c2)cn1]

6-(1-methyl-1H-pyrazol-4-yl)-4-(6-(4-((1-methyl-2-oxo-1,2-dihydropyridin-3-yl)methyl)piperazin-1-yl)pyridin-3-yl)pyrazolo[1,5-a]pyridine-3-carbonitrile Dihydrochloride A suspension of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 50 mg, 0.109 mmol) in DMF (1093 μL) was treated with 1-methyl-2-oxo-1,2-dihydropyridine-3-carbaldehyde (22.5 mg, 0.164 mmol) and TEA (45.7 μL, 0.328 mmol). The mixture was acidified to about pH 6 with AcOH, and then stirred for 1 h at ambient temperature. The reaction mixture was treated with NaBH$_3$CN (10.3 mg, 0.164 mmol), and stirred for 2 d at ambient temperature. The resulting suspension was warmed to dissolve particulates, and directly purified by C18 reverse-phase chromatography (5-60% ACN/water as the gradient eluent) to afford the title compound together with impurities. Additional purification by C18 reverse-phase chromatography (5-45% ACN/water with 0.1% HCl$_{(aq)}$ as the gradient eluent) cleanly afforded the title compound as the dihydrochloride salt (11.2 mg, 19% yield). MS (apci) m/z=506.2 (M+H).

Example 683

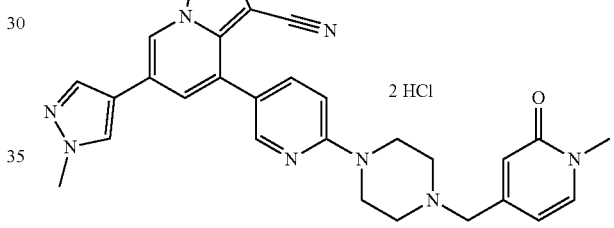

6-(1-methyl-1H-pyrazol-4-yl)-4-(6-(4-((1-methyl-2-oxo-1,2-dihydropyridin-4-yl)methyl)piperazin-1-yl)pyridin-3-yl)pyrazolo[1,5-a]pyridine-3-carbonitrile Dihydrochloride A suspension of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 50 mg, 0.109 mmol) in DMF (1093 μL) was treated with 1-methyl-2-oxo-1,2-dihydropyridine-4-carbaldehyde (22.5 mg, 0.164 mmol) and TEA (45.7 μL, 0.328 mmol). The mixture was acidified to about pH 6 with AcOH, and then stirred for 2 h at ambient temperature. The reaction mixture was treated with NaBH$_3$CN (10.3 mg, 0.164 mmol), and stirred for 2 d at ambient temperature. The resulting suspension was warmed to dissolve particulates, and directly purified by C18 reverse-phase chromatography (5-50% ACN/water as the gradient eluent) to afford semi pure title compound. Additional purification, of this semi pure material, by C18 reverse-phase chromatography (5-50% ACN/water with 0.1% HCl$_{(aq)}$ as the gradient eluent) cleanly afforded the title compound as the dihydrochloride salt (20.2 mg, 32% yield). MS (apci) m/z=506.2 (M+H).

Example 684

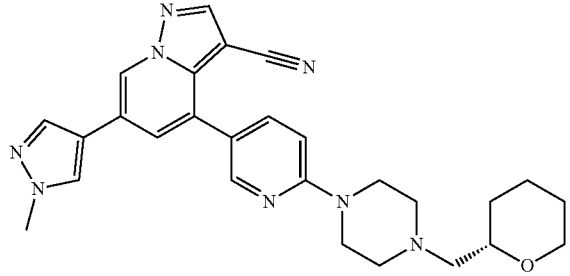 [SMILES: Cn1cc(-c2cc(-c3ccc(N4CCN(C[C@@H]5CCCCO5)CC4)nc3)c3c(C#N)cnn3c2)cn1]

(S)-6-(1-methyl-1H-pyrazol-4-yl)-4-(6-(4-((tetra-hydro-2H-pyran-2-yl)methyl)piperazin-1-yl)pyridin-3-yl)pyrazolo[1,5-a]pyridine-3-carbonitrile

Step 1: Preparation of (S)-(tetrahydro-2H-pyran-2-yl)methyl 4-methylbenzenesulfonate A mixture of (S)-(tetrahydro-2H-pyran-2-yl)methanol (1 g, 8.61 mmol), sulfur (0.276 g, 8.61 mmol), TsCl (1.81 g, 9.47 mmol), and KOH(s) (0.725 g, 12.9 mmol) in THF (10 mL) was stirred overnight at ambient temperature. The resulting suspension was filtered through a glass frit, rinsing with THF. The filtrate was concentrated in vacuo, and the resulting residue was purified by silica chromatography (100% DCM as eluent) to afford the title compound (1.33 g, 57% yield). $^1$H NMR (CDCl$_3$) δ 7.79 (d, 2H), 7.33 (d, 2H), 3.95 (d, 2H), 3.91-3.96 (m, 1H), 3.50-3.56 (m, 1H), 3.34-3.40 (m, 1H), 2.44 (s, 3H), 1.82-1.86 (m, 1H), 1.41-1.59 (m, 4H), 1.22-1.31 (m, 1H).

Step 2: Preparation of (S)-6-(1-methyl-1H-pyrazol-4-yl)-4-(6-(4-((tetrahydro-2H-pyran-2-yl)methyl)piperazin-1-yl)pyridin-3-yl)pyrazolo[1,5-a]pyridine-3-carbonitrile A mixture of 6-(1-methyl-1H-pyrazol-4-yl)-4-(6-(piperazin-1-yl)pyridin-3-yl)pyrazolo[1,5-a]pyridine-3-carbonitrile dihydrochloride (Example 2; 50 mg, 0.109 mmol), (S)-(tetrahydro-2H-pyran-2-yl)methyl 4-methylbenzenesulfonate (Step 1; 35.5 mg, 0.131 mmol) and TEA (76.2 μL, 0.547 mmol) was dissolved in 1:1 DCM:DMA (2 mL). After stirring overnight at 90° C., additional (S)-(tetrahydro-2H-pyran-2-yl)methyl 4-methylbenzenesulfonate (Step 1; 35.5 mg, 0.131 mmol) and a drop of TEA were added and reaction was stirred for another day to reach completion. The crude mixture was directly purified by reverse-phase chromatography (5-50% ACN/water) to afford the title compound (26.5 mg, 50% yield). MS (apci) m/z=483.2 (M+H).

Example 685

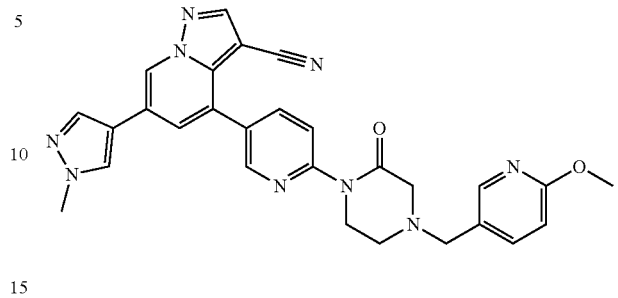

4-(6-(4-((6-methoxypyridin-3-yl)methyl)-2-oxopiperazin-1-yl)pyridin-3-yl)-6-(1-methyl-1H-pyrazol-4-yl)pyrazolo[1,5-a]pyridine-3-carbonitrile

Step 1: Preparation of Tert-Butyl 4-(5-bromopyridin-2-yl)-3-oxopiperazine-1-carboxylate A mixture of 5-bromo-2-fluoropyridine (0.175 mL, 1.70 mmol), tert-butyl 3-oxopiperazine-1-carboxylate (0.512 g, 2.56 mmol) and potassium t-butoxide (0.287 g, 2.56 mmol) in toluene (17.0 mL) was refluxed overnight. After cooling to ambient temperature, the mixture was extracted with EtOAc and water. The organic extracts were washed with brine, then dried over anhydrous Na$_2$SO$_4$, filtered and concentrated in vacuo. The crude residue (607 mg, quantitative yield) was carried forward without further purification.

Step 2: Preparation of 1-(5-bromopyridin-2-yl)piperazin-2-one

A mixture of tert-butyl 4-(5-bromopyridin-2-yl)-3-oxopiperazine-1-carboxylate (607 mg, 1.70 mmol) in TFA (8 mL, 1.70 mmol) and DCM (8.52 mL) was stirred for 30 min at ambient temperature. The reaction mixture was concentrated in vacuo. The resulting residue was purified by silica chromatography (5-95% Hexanes:EtOAc as the gradient eluent) to afford the title compound (208 mg, 48% yield). MS (apci) m/z=258.0 (M+2), with bromine isotopic ratio.

Step 3: Preparation of 1-(5-bromopyridin-2-yl)-4-((6-methoxypyridin-3-yl)methyl)piperazin-2-one A mixture of 1-(5-bromopyridin-2-yl)piperazin-2-one (208 mg, 0.812 mmol) and 6-methoxynicotinaldehyde (0.134 g, 0.975 mmol) in DCE (8.12 mL) was stirred for 10 min at ambient temperature, and then NaBH(AcO)$_3$ (0.344 g, 1.62 mmol) was added. The resulting mixture was stirred for an additional 2 h at ambient temperature before extracting with DCM and water. The aqueous extracts were back-extracted with additional DCM. The combined DCM extracts were washed with brine, dried over anhydrous Na$_2$SO$_4$, filtered and concentrated in vacuo. The crude residue was purified by silica chromatography (5-95% EtOAc:Hexanes as the gradient eluent) to afford the title compound (274 mg, 89% yield). MS (apci) m/z=377.0 (M+), 379.1 (M+2), with bromine isotopic ratio.

Step 4: Preparation of 4-((6-methoxypyridin-3-yl)methyl)-1-(5-(4,4,5,5-tetramethyl-1,3,2-dioxaborolan-2-yl)pyridin-2-yl)piperazin-2-one A mixture of 1-(5-bromopyridin-2-yl)-4-((6-methoxypyridin-3-yl)methyl)piperazin-2-one (274 mg, 0.726 mmol), 4,4,4',4',5,5,5',5'-octamethyl-2,2'-bi(1,3,2-dioxaborolane) (738 mg, 2.91 mmol), KOAc (143 mg, 1.45 mmol) and PdCl₂(dppf).CH₂Cl2 (59.3 mg, 0.0726 mmol) in dioxane (7.26 mL) was stirred overnight at 90° C. After cooling to ambient temperature, the reaction mixture was filtered through GF/F paper. The filtrate was concentrated in vacuo, and the resulting residue was purified by silica chromatography (5-95% Hexanes:EtOAc as the gradient eluent) to afford the title compound (60 mg, 20% yield). MS (apci) m/z=425.2 (M+H).

Step 5: Preparation of 4-(6-(4-((6-methoxypyridin-3-yl)methyl)-2-oxopiperazin-1-yl)pyridin-3-yl)-6-(1-methyl-1H-pyrazol-4-yl)pyrazolo[1,5-a]pyridine-3-carbonitrile A mixture of 3-cyano-6-(1-methyl-1H-pyrazol-4-yl)pyrazolo[1,5-a]pyridin-4-yl trifluoromethanesulfonate (Intermediate P5; 45 mg, 0.12 mmol) 4-((6-methoxypyridin-3-yl)methyl)-1-(5-(4,4,5,5-tetramethyl-1,3,2-dioxaborolan-2-yl)pyridin-2-yl)piperazin-2-one (62 mg, 0.15 mmol), Pd₂(dba)₃ (5.6 mg, 0.0061 mmol), X-Phos (12 mg, 0.024 mmol) and 2 M Na₂CO₃(aq) (0.15 mL, 0.303 mmol) in dioxane (0.61 mL) was degassed with Ar for 5 min. The mixture was stirred for 3 h at 90° C. After cooling to ambient temperature, the reaction mixture was filtered through GF/F paper and then concentrated in vacuo. The residue was purified by C18 reverse-phase chromatography (5-95% ACN/water containing 0.1% TFA) to afford the title compound as a TFA salt (27 mg). The TFA salt was partitioned between DCM and saturated Na₂CO₃(aq). The organic extracts were washed with brine, dried over anhydrous Na₂SO₄, filtered and concentrated in vacuo to cleanly afford the title compound (20.4 mg, 32% yield). MS (apci) m/z=520.2 (M+H).

Example 686

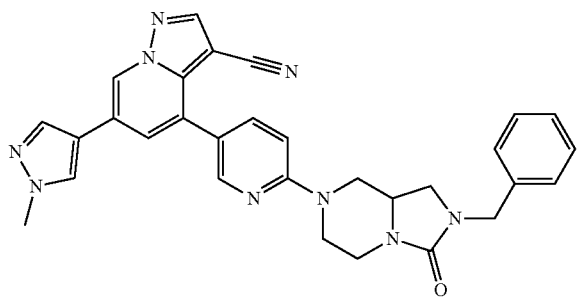 [SMILES: Cn1cc(-c2cc(-c3ccc(N4CCN5C(=O)N(Cc6ccccc6)CC5C4)nc3)c3c(C#N)cnn3c2)cn1]

4-(6-(2-benzyl-3-oxohexahydroimidazo[1,5-a]pyrazin-7(1H)-yl)pyridin-3-yl)-6-(1-methyl-1H-pyrazol-4-yl)pyrazolo[1,5-a]pyridine-3-carbonitrile In a microwave vessel, a room temperature mixture of 4-(6-Fluoropyridin-3-yl)-6-(1-methyl-1H-pyrazol-4-yl)pyrazolo[1,5-a]pyridine-3-carbonitrile (Intermediate P6; 30 mg, 0.094 mmol) and 2-benzylhexahydroimidazo[1,5-a]pyrazin-3(2H)-one (44 mg, 0.19 mmol) in DMSO (471 µL) was subjected to microwave irradiation for 28 h at 150° C. The reaction mixture was cooled to room temperature, and then purified directly by C18 reverse-phase chromatography (5-60% ACN/water as the gradient eluent) to afford the title compound (8.1 mg, 15% yield). MS (apci) m/z=530.2 (M+H).

Example 687

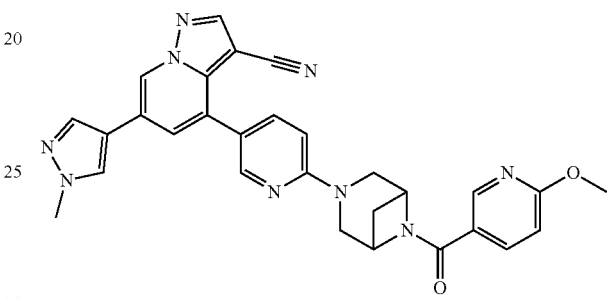

4-(6-(6-(6-methoxynicotinoyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile At ambient temperature, a mixture of 4-(6-(3,6-diazabicyclo[3.1.1]heptan-3-yl)pyridin-3-yl)-6-(1-methyl-1H-pyrazol-4-yl)pyrazolo[1,5-a]pyridine-3-carbonitrile (Example 486; 21 mg, 0.053 mmol), 2-methoxy-5-pyridinecarboxylic acid (12.2 mg, 0.0795 mmol) and HATU (22.2 mg, 0.0583 mmol) in DCM (530 µL) was treated with DIEA (46.3 µL, 0.265 mmol). The resulting mixture was stirred for 1 h at ambient temperature before concentrating in vacuo. The crude residue was purified by C18 reverse-phase chromatography (5-95% ACN/water containing 0.1% TFA as the gradient eluent) to afford the title compound as the TFA salt. The TFA salt was partitioned between DCM and saturated NaHCO₃(aq). The DCM extracts were reserved and the aqueous extracts were back-extracted with DCM. The DCM extracts were combined, washed with brine, dried over anhydrous Na₂SO₄, filtered and concentrated in vacuo to cleanly afford the title compound (19.1 mg, 68% yield). MS (apci) m/z=532.2 (M+H).

The compounds in the Table III were prepared, purified and free-based in a similar fashion as described for the synthesis of Example 687, replacing 2-methoxy-5-pyridinecarboxylic acid with the appropriate carboxylic acid starting material. Reaction progression in each example was followed by LCMS, and reaction times were adjusted as necessary.

TABLE III

| Ex # | Structure | Chemical Name | MS apci (m/z) |
|---|---|---|---|
| 688 | 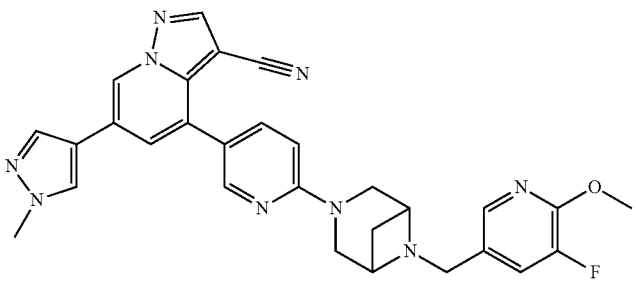 | 4-(6-(6-(5-fluoro-6-methoxynicotinoyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile | 550.2 (M + H) |
| 689 | 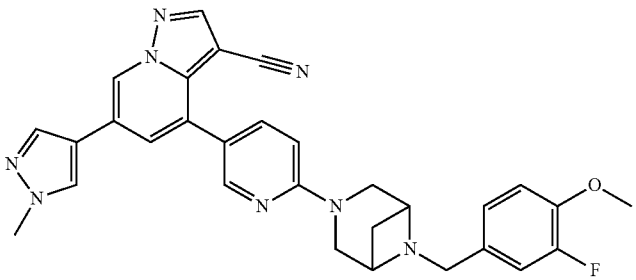 | 4-(6-(6-(3-fluoro-4-methoxybenzoyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile | 549.2 (M + H) |
| 690 | 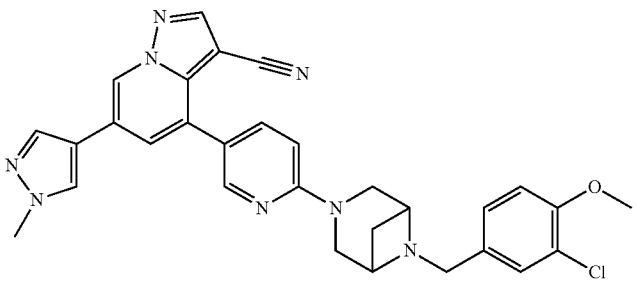 | 4-(6-(6-(3-chloro-4-methoxybenzoyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile | 565.2 (M + H) |
| 691 | 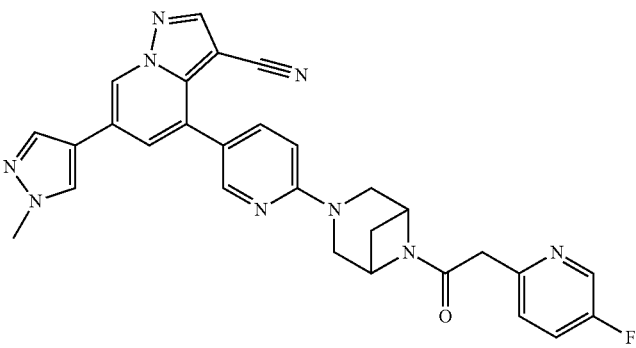 [SMILES: Cn1cc(-c2cc(-c3ccc(N4CC5CC(C4)N5C(=O)Cc4ccc(F)cn4)nc3)c3c(C#N)cnn3c2)cn1] | 4-(6-(6-(2-(5-fluoropyridin-2-yl)acetyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile | 534.2 (M + H) |

Example 692

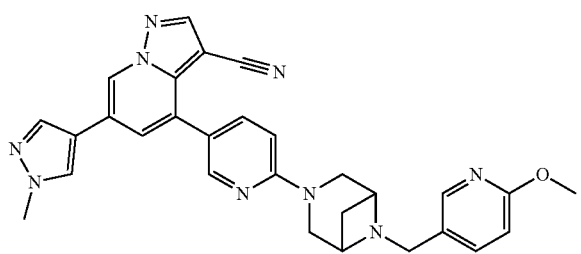 [SMILES: COc1ccc(CN2C3CC2CN(c2ccc(-c4cc(-c5cnn(C)c5)cn5ncc(C#N)c45)cn2)C3)cn1]

4-(6-(6-(((6-methoxypyridin-3-yl)methyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile Step 1: Preparation of 4-(6-(3,6-diazabicyclo[3.1.1]heptan-3-yl)pyridin-3-yl)-6-(1-methyl-1H-pyrazol-4-yl)pyrazolo[1,5-a]pyridine-3-carbonitrile dihydrochloride A solution of 4-(6-Fluoropyridin-3-yl)-6-(1-methyl-1H-pyrazol-4-yl)pyrazolo[1,5-a]pyridine-3-carbonitrile (Intermediate P6; 0.10 g, 0.31 mmol) in DMSO (5 mL) was treated with tert-butyl 3,6-diazabicyclo[3.1.1]heptane-6-carboxylate (69 mg, 0.35 mmol) and $K_2CO_3$ (0.22 g, 1.6 mmol). The resulting mixture was stirred overnight at 90° C. before introducing additional tert-butyl 3,6-diazabicyclo[3.1.1]heptane-6-carboxylate (70 mg, 0.36 mmol) and $K_2CO_3$ (0.1 g, 0.73 mmol). The reaction mixture was stirred for an additional 24 h at 90° C. After cooling to ambient temperature, the reaction mixture was diluted with EtOAc (10 mL), and washed with water. The combined organic extracts were dried over anhydrous $Na_2SO_4$, then filtered and concentrated in vacuo. The isolated solids were dissolved in DCM (2.5 mL), treated with 5M HCl in iPrOH, (0.3 mL) and stirred overnight at ambient temperature. Concentration of the reaction mixture in vacuo afforded the title compound as the dihydrochloride salt, which was used directly in the next step without further purification (133.7 mg, 89% yield). MS (apci) m/z=397.2 (M+H).

Step 2: Preparation of 4-(6-(6-(((6-methoxypyridin-3-yl)methyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile A solution of 4-(6-(3,6-diazabicyclo[3.1.1]heptan-3-yl)pyridin-3-yl)-6-(1-methyl-1H-pyrazol-4-yl)pyrazolo[1,5-a]pyridine-3-carbonitrile dihydrochloride (Step 1; 26 mg, 0.055 mmol) in DMA (1 mL) was treated with TEA (23.2 μL, 0.166 mmol), NaBH(AcO)$_3$ (17.6 mg, 0.0831 mmol) and 6-methoxynicotinaldehyde (11.4 mg, 0.0831 mmol). The resulting mixture was stirred for 2 d at room temperature, before quenching with water. The mixture was extracted with DCM, and the combined organic extracts were dried over anhydrous $Na_2SO_4$, filtered, and concentrated in vacuo. The crude residue was purified by C18 reverse-phase chromatography (20-80% ACN/water as the gradient) to afford the title compound (5.3 mg, 19% yield). MS (apci) m/z=518.2 (M+H).

Example 693

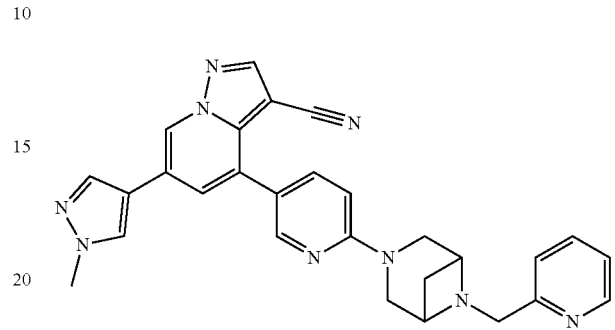

6-(1-methyl-1H-pyrazol-4-yl)-4-(6-(6-(pyridin-2-ylmethyl)-3,6-diazabicyclo[3.1.1]heptan-3-yl)pyridin-3-yl)pyrazolo[1,5-a]pyridine-3-carbonitrile Following a similar method to that used in Step 2 for the preparation and purification of Example 692, replacing 6-methoxynicotinaldehyde with picolinaldehyde, the title compound was isolated cleanly (7.4 mg, 26% yield). MS (apci) m/z=488.2 (M+H).

Example 694

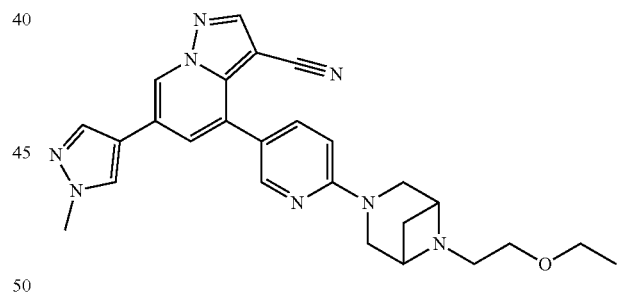

4-(6-(6-(2-ethoxyethyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile A solution of 4-(6-(3,6-diazabicyclo[3.1.1]heptan-3-yl)pyridin-3-yl)-6-(1-methyl-1H-pyrazol-4-yl)pyrazolo[1,5-a]pyridine-3-carbonitrile dihydrochloride (Example 692, Step 1; 20 mg, 0.0426 mmol) in DMA (500 μL) was treated with TEA (59.4 μL, 0.426 mmol), and 1-bromo-2-ethoxyethane (16.1 μL, 0.128 mmol). The resulting mixture was stirred overnight at 75° C., then cooled to ambient temperature and directly purified by C18 reverse-phase chromatography (20-80% ACN/water as the gradient eluent) to afford the title compound (2 mg, 10% yield). MS (apci) m/z=469.2 (M+H).

Example 695

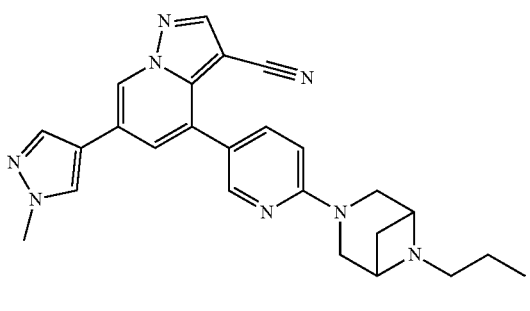 [SMILES: CCCN1C2CC1CN(c1ccc(-c3cc(-c4cnn(C)c4)cn4ncc(C#N)c34)cn1)C2]

6-(1-methyl-1H-pyrazol-4-yl)-4-(6-(6-propyl-3,6-diazabicyclo[3.1.1]heptan-3-yl)pyridin-3-yl)pyrazolo[1,5-a]pyridine-3-carbonitrile A solution of 4-(6-(3,6-diazabicyclo[3.1.1]heptan-3-yl)pyridin-3-yl)-6-(1-methyl-1H-pyrazol-4-yl)pyrazolo[1,5-a]pyridine-3-carbonitrile dihydrochloride (Example 692, Step 1; 20 mg, 0.0426 mmol) in DMA (500 µL) was treated with TEA (5.94 µL, 0.0426 mmol), and 1-iodopropane (7.24 mg, 0.0426 mmol). The resulting mixture was stirred overnight at ambient temperature, and then directly purified by C18 reverse-phase chromatography (20-80% ACN/water as the gradient eluent) to afford the title compound (2 mg, 10% yield). MS (apci) m/z=439.2 (M+H).

Example 696

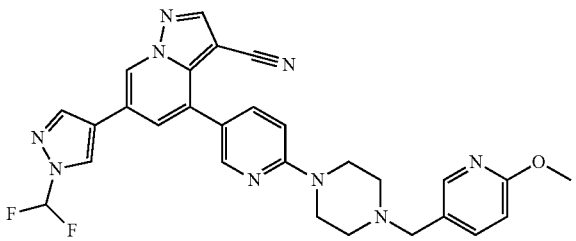 [SMILES: COc1ccc(CN2CCN(c3ccc(-c4cc(-c5cnn(C(F)F)c5)cn5ncc(C#N)c45)cn3)CC2)cn1]

6-(1-(difluoromethyl)-1H-pyrazol-4-yl)-4-(6-(4-((6-methoxypyridin-3-yl)methyl)piperazin-1-yl)pyridin-3-yl)pyrazolo[1,5-a]pyridine-3-carbonitrile A solution of 6-(1-(difluoromethyl)-1H-pyrazol-4-yl)-4-(6-(piperazin-1-yl)pyridin-3-yl)pyrazolo[1,5-a]pyridine-3-carbonitrile dihydrochloride (Example 266; 21 mg, 0.043 mmol) in DMA (0.5 mL) was treated with TEA (17.8 µL, 0.128 mmol), Me₄N(AcO)₃BH (16.8 mg, 0.0638 mmol) and 6-methoxynicotinaldehyde (7 mg, 0.05 mmol). The resulting mixture was stirred overnight at room temperature before introducing additional TEA (20 µL, 0.144 mmol), Me₄N(AcO)₃BH (10 mg, 0.038 mmol) and 6-methoxynicotinaldehyde (7.01 mg, 0.0511 mmol). The reaction mixture was stirred for an additional period of 3 d prior and then quenched with water/CHCl₃. The quenched mixture was extracted with CHCl₃ in a PS Frit, and the combined organic extracts were concentrated in vacuo. The crude residue was purified by C18 reverse-phase chromatography (20-80% ACN/water as the gradient eluent) to afford the title compound (6.9 mg, 30% yield). MS (apci) m/z=519.2 (M+H).

Example 697

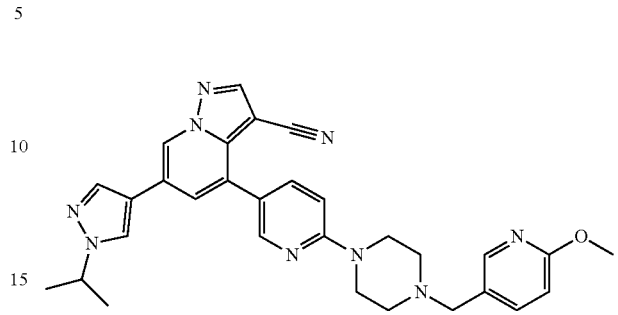

6-(1-isopropyl-1H-pyrazol-4-yl)-4-(6-(4-((6-methoxypyridin-3-yl)methyl)piperazin-1-yl)pyridin-3-yl)pyrazolo[1,5-a]pyridine-3-carbonitrile

Step 1: Preparation of 1-amino-3,5-dibromopyridin-1-ium 2,4,6-trimethylbenzenesulfonate To a solution of O-(mesitylsulfonyl)hydroxylamine (Intermediate R1; 409 g, 1.90 mol) in DCM (2 L) was added a solution of 3,5-dibromopyridine (320 g, 1.35 mol) in DCM (2.5 L) at 0-5° C. The reaction was stirred for 16 h at this temperature before ether (5 L) was added at 0-5° C. The suspension was filtered and the filter cake was washed with Et₂O (4 L) to give the title product (500 g, 82% yield), which was directly used for the next step without further purifications. ¹H NMR (d⁶-DMSO) δ 9.11 (s, 2H), 8.92 (s, 1H), 8.73 (s, 2H), 6.75 (s, 2H), 2.50 (s, 3H), 2.17 (s, 3H).

Step 2: Preparation of 4,6-dibromopyrazolo[1,5-a]pyridine-3-carbonitrile

To a mixture of 1-amino-3,5-dibromopyridin-1-ium 2,4,6-trimethylbenzenesulfonate (40 g, 88.5 mmol) in dioxane (400 mL) was added acrylonitrile (10.72 g, 202 mmol) and DIEA (14.8 g, 11.5 mmol), then stirred at ambient temperature for 3 h. 2,3-Dichloro-5,6-dicyano-1,4-benzoquinone (41.8 g, 184 mmol) was added to the reaction mixture and stirred at ambient temperature for 3 hrs. The reaction mixture was poured into water (1.6 L), filtered, and the resulting solid was purified by silica chromatography (eluent=EtOAc/Petroleum ether 1:2) to afford the title product as white solid (13.8 g, 52% yield). ¹H NMR (CDCl₃) δ 8.69 (d, J=1.4 Hz, 1H), 8.28 (s, 1H), 7.73 (d, J=1.4 Hz, 1H).

Step 3: Preparation of 1-((6-methoxypyridin-3-yl)methyl)-4-(5-(4,4,5,5-tetramethyl-1,3,2-dioxaborolan-2-yl)pyridin-2-yl)piperazine A cold (0° C.) solution of 1-(5-(4,4,5,5-tetramethyl-1,3,2-dioxaborolan-2-yl)pyridin-2-yl)piperazine (20.00 g, 69.16 mmol), 6-methoxynicotinaldehyde (10.43 g, 76.08 mmol), and acetic acid (0.40 mL, 6.916 mmol) in anhydrous DCM (350 mL) was treated with NaBH(OAc)₃ (21.99 g, 103.7 mmol), added in 2 portions approximately 1 min apart. The resulting mixture was stirred overnight at ambient temperature. The reaction mixture was quenched with the addition of silica gel (40 g) and Celite® (40 g). The quenched mixture was stirred for 5 min at ambient temperature before activated charcoal (20 g) was introduced. After stirring for 10 min at ambient temperature, the mixture was filtered through a silica gel plug (100 g) topped with Celite® and the plug was rinsed with a solution of 70% acetone in DCM (5×250 mL). The resultant filtrate was concentrated in vacuo. The crude residue was diluted with heptane (80 mL), and the solution was slowly treated with saturated NaHCO$_{3(aq)}$ (300 mL). The biphasic suspension was cooled in an ice bath to an internal temperature of 10° C., and subsequently vacuum filtered, rinsing the filter cake with minimal cool water and cool heptane. The filter cake was dissolved in MTBE, concentrated in vacuo, and dried in a vacuum oven to cleanly afford the title compound (20.66 g, 73% yield). MS (apci) m/z=411.2 (M+H).

Step 4: Preparation of 6-bromo-4-(6-(4-((6-methoxypyridin-3-yl)methyl)piperazin-1-yl)pyridin-3-yl)pyrazolo[1,5-a]pyridine-3-carbonitrile A mixture of 4,6-dibromopyrazolo[1,5-a]pyridine-3-carbonitrile (55 mg, 0.18 mmol), 1-((6-methoxypyridin-3-yl)methyl)-4-(5-(4,4,5,5-tetramethyl-1,3,2-dioxaborolan-2-yl)pyridin-2-yl)piperazine (67 mg, 0.16 mmol), Pd(PPh$_3$)$_4$ (5.3 mg, 0.0046 mmol) and 2 M Na$_2$CO$_{3(aq)}$ (15 µL, 135 mmol) in DMF (1.8 mL) was stirred overnight at 60° C. After cooling to ambient temperature, the reaction mixture was directly purified by silica chromatography (1-10% DCM: MeOH as the eluent) to afford the title compound (79 mg, 86% yield). MS (apci) m/z=505.1 (M+1). $^1$H NMR showed 7:1 selectivity. $^1$H NMR (400 MHz, CDCl3-d) δ 8.68 (d, 1H), 8.32 (d, 1H), 8.25 (s, 1H), 8.08 (d, 1H), 7.68 (dd, 1H), 7.62 (dd, 1H), 7.37 (d, 1H), 6.74 (d, 2H), 3.94 (s, 3H), 3.65 (t, 4H), 3.49 (s, 2H), 2.55 (t, 4H).

Step 5: Preparation of 6-(1-isopropyl-1H-pyrazol-4-yl)-4-(6-(4-((6-methoxypyridin-3-yl)methyl)piperazin-1-yl)pyridin-3-yl)pyrazolo[1,5-a]pyridine-3-carbonitrile A mixture of 6-bromo-4-(6-(4-((6-methoxypyridin-3-yl)methyl)piperazin-1-yl)pyridin-3-yl)pyrazolo[1,5-a]pyridine-3-carbonitrile (24 mg, 0.0476 mmol), 1-isopropyl-4-(4,4,5,5-tetramethyl-1,3,2-dioxaborolan-2-yl)-1H-pyrazole (13.5 mg, 0.0571 mmol), Pd(PPh$_3$)$_4$ (1.37 mg, 0.00119 mmol) and 2 M Na$_2$CO$_{3(aq)}$ (59.5 µL, 0.119 mmol) in dioxane (476 µL) was stirred overnight at 90° C. After cooling to ambient temperature, the reaction mixture was directly purified by C18 reverse-phase chromatography (5-95% water/ACN with 1% TFA as the gradient eluent) to afford the title compound as the TFA salt. The TFA salt was partitioned between DCM and saturated NaHCO$_{3(aq)}$. After back-extracting the aqueous layer with DCM, the combined organic extracts were washed with brine, dried over anhydrous Na$_2$SO$_4$, filtered, and concentrated in vacuo to cleanly afford the title compound (15.7 mg, 62% yield). MS (apci) m/z=534.4 (M+H).

Example 698

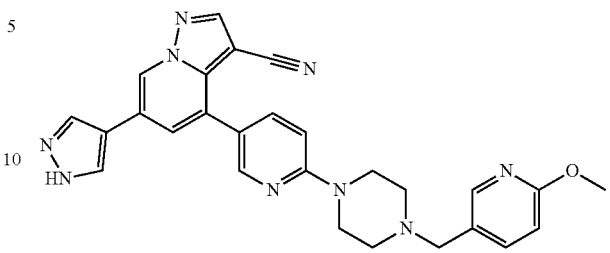

4-(6-(4-((6-methoxypyridin-3-yl)methyl)piperazin-1-yl)pyridin-3-yl)-6-(1H-pyrazol-4-yl)pyrazolo[1,5-a]pyridine-3-carbonitrile Step 1: Preparation of 4-(6-(piperazin-1-yl)pyridin-3-yl)-6-(1H-pyrazol-4-yl)pyrazolo[1,5-a]pyridine-3-carbonitrile bis(2,2,2-trifluoroacetate)

A solution of 6-(1-(4-methoxybenzyl)-1H-pyrazol-4-yl)-4-(6-(piperazin-1-yl)pyridin-3-yl)pyrazolo[1,5-a]pyridine-3-carbonitrile (Example 590; 250 mg, 0.510 mmol) in TFA (10.2 mL, 5.10 mmol) was stirred overnight at 65° C. After cooling to ambient temperature, the mixture was concentrated in vacuo to afford the title compound (288 mg, 94% yield), which was used in the next step without further purification or analysis.

Step 2: Preparation of 4-(6-(4-((6-methoxypyridin-3-yl)methyl)piperazin-1-yl)pyridin-3-yl)-6-(1H-pyrazol-4-yl)pyrazolo[1,5-a]pyridine-3-carbonitrile A solution of 4-(6-(piperazin-1-yl)pyridin-3-yl)-6-(1H-pyrazol-4-yl)pyrazolo[1,5-a]pyridine-3-carbonitrile bis(2,2,2-trifluoroacetate) (288 mg, 0.481 mmol) in dry DMA (3 mL) was treated with TEA (213 µL, 1.53 mmol), Me$_4$N(AcO)$_3$BH (201 mg, 0.765 mmol) and 6-methoxynicotinaldehyde (84.0 mg, 0.612 mmol). The mixture was stirred overnight at room temperature and then quenched with water and CHCl$_3$. The mixture was extracted with CHCl$_3$, and the combined organic extracts were dried over anhydrous Na$_2$SO$_4$, filtered, and concentrated in vacuo. The crude residue was first purified by C18 reverse-phase chromatography using 15-50% ACN/water with 1% HCl as the gradient eluent and then purified by C18 reverse-phase chromatography using 5-50 ACN/water with 0.1% formic acid as the gradient eluent to afford the title compound (40 mg, 16% yield). MS (apci) m/z=492.2 (M+H).

Example 699

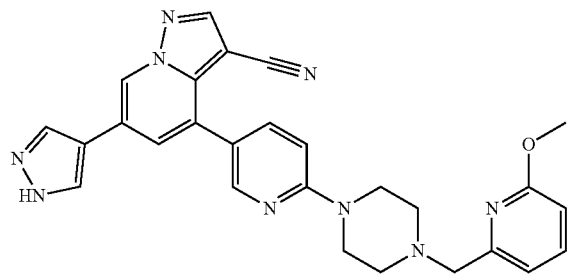 [SMILES: COc1cccc(CN2CCN(c3ccc(-c4cc(-c5cn[nH]c5)cn5ncc(C#N)c45)cn3)CC2)n1]

4-(6-(4-((6-methoxypyridin-2-yl)methyl)piperazin-1-yl)pyridin-3-yl)-6-(1H-pyrazol-4-yl)pyrazolo[1,5-a]pyridine-3-carbonitrile A room temperature solution of 4-(6-(piperazin-1-yl)pyridin-3-yl)-6-(1H-pyrazol-4-yl)pyrazolo[1,5-a]pyridine-3-carbonitrile bis(2,2,2-trifluoroacetate) (Example 698, Step 1; 6 mg, 0.0162 mmol) in dry DMA (900 µL) was treated sequentially with TEA (22.6 µL, 0.162 mmol) and 2-(bromomethyl)-6-methoxypyridine (9.82 mg, 0.0486 mmol). The reaction mixture was stirred overnight at room temperature before introducing additional TEA (1 µL, 0.01 mmol) and 2-(bromomethyl)-6-methoxypyridine (2 mg, 0.01 mmol). The reaction mixture was stirred at room temperature until LCMS indicated the reaction was complete. The reaction mixture was directly purified by C18 reverse-phase chromatography (15-80% ACN/water with 0.1% formic acid as the gradient eluent) to cleanly afford the title compound (2.5 mg, 51% yield). MS (apci) m/z=492.2 (M+H).

Example 700

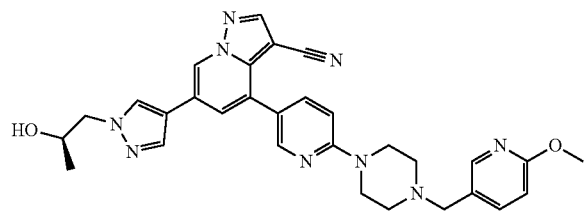 [SMILES: COc1ccc(CN2CCN(c3ccc(-c4cc(-c5cnn(C[C@@H](C)O)c5)cn5ncc(C#N)c45)cn3)CC2)cn1]

(R)-6-(1-(2-hydroxypropyl)-1H-pyrazol-4-yl)-4-(6-(4-((6-methoxypyridin-3-yl)methyl)piperazin-1-yl)pyridin-3-yl)pyrazolo[1,5-a]pyridine-3-carbonitrile A solution of 4-(6-(4-((6-methoxypyridin-3-yl)methyl)piperazin-1-yl)pyridin-3-yl)-6-(1H-pyrazol-4-yl)pyrazolo[1,5-a]pyridine-3-carbonitrile (Example 698; Step 2; 18 mg, 0.0366 mmol) in 2-methoxyethanol (1 mL) was treated sequentially with Cs₂CO₃ (40 mg, 0.123 mmol) and (R)-2-methyloxirane (7.7 µL, 0.110 mmol). The mixture was stirred for 40 h at 75° C. After cooling to ambient temperature, the mixture was filtered to remove the inorganic material (Cs₂CO₃), and the filtrate was directly purified by C18 reverse-phase chromatography (10-80% ACN/water with 0.1% formic acid as the gradient eluent) to afford the title compound (13 mg, 65% yield). MS (apci) m/z=550.3 (M+H).

Example 701

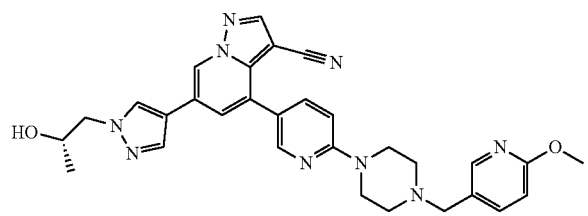 [SMILES: COc1ccc(CN2CCN(c3ccc(-c4cc(-c5cnn(C[C@H](C)O)c5)cn5ncc(C#N)c45)cn3)CC2)cn1]

(S)-6-(1-(2-hydroxypropyl)-1H-pyrazol-4-yl)-4-(6-(4-((6-methoxypyridin-3-yl)methyl)piperazin-1-yl)pyridin-3-yl)pyrazolo[1,5-a]pyridine-3-carbonitrile A solution of 4-(6-(4-((6-methoxypyridin-3-yl)methyl)piperazin-1-yl)pyridin-3-yl)-6-(1H-pyrazol-4-yl)pyrazolo[1,5-a]pyridine-3-carbonitrile (Example 698; Step 2; 23 mg, 0.0468 mmol) in 2-methoxyethanol (500 µL) was treated sequentially with Cs₂CO₃ (45.7 mg, 0.140 mmol) and (S)-2-methyloxirane (8.2 mg, 0.140 mmol). The resulting mixture was stirred at 75° C. and monitored for completion by LCMS. Upon completion the reaction mixture was cooled to ambient temperature, then diluted with DCM and quenched with saturated NH₄Cl$_{(aq)}$. The biphasic mixture was extracted with DCM, and the combined organic extracts were dried over anhydrous Na₂SO₄, filtered and concentrated in vacuo. The crude residue was purified by C18 reverse-phase chromatography (10-70% ACN/water with 0.1% formic acid as the gradient eluent) to afford the title compound (14.6 mg, 57% yield). MS (apci) m/z=550.3 (M+H).

Example 702

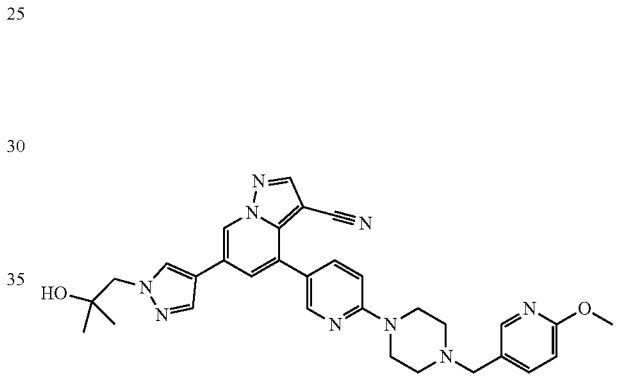

6-(1-(2-hydroxy-2-methylpropyl)-1H-pyrazol-4-yl)-4-(6-(4-((6-methoxypyridin-3-yl)methyl)piperazin-1-yl)pyridin-3-yl)pyrazolo[1,5-a]pyridine-3-carbonitrile A solution of 4-(6-(4-((6-methoxypyridin-3-yl)methyl)piperazin-1-yl)pyridin-3-yl)-6-(1H-pyrazol-4-yl)pyrazolo[1,5-a]pyridine-3-carbonitrile (Example 698; Step 2; 11.8 mg, 0.02401 mmol) in dry DMA (500 µL) was treated sequentially with Cs₂CO₃ (78.2 mg, 0.240 mmol) and 1-chloro-2-methylpropan-2-ol (12.3 µL, 0.110 mmol). The resulting mixture was stirred overnight at ambient temperature before introducing additional 1-chloro-2-methylpropan-2-ol (12 µL, 0.110 mmol). After stirring for 24 h at ambient temperature, additional 1-chloro-2-methylpropan-2-ol (12.3 µL, 0.110 mmol) was introduced, and the reaction was monitored for completion by LCMS. Upon completion, the reaction mixture was quenched with water/CHCl₃, and the biphasic mixture was extracted with CHCl₃ in a PS Frit. The combined organic extracts were concentrated in vacuo, and the crude residue was purified by C18 reverse-phase chromatography (15-80% ACN/water with 0.1% formic acid as the gradient eluent) to afford the title compound (1.9 mg, 14% yield). MS (apci) m/z=564.3 (M+H).

Example 703

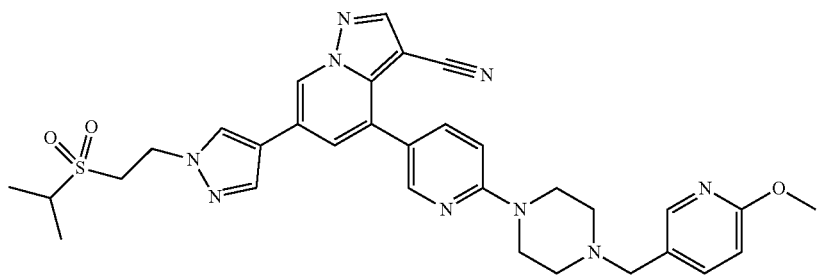 [SMILES: COc1ccc(CN2CCN(c3ccc(-c4cc(-c5cnn(CCS(=O)(=O)C(C)C)c5)cn5ncc(C#N)c45)cn3)CC2)cn1]

6-(1-(2-(isopropylsulfonyl)ethyl)-1H-pyrazol-4-yl)-4-(6-(4-((6-methoxypyridin-3-yl)methyl)piperazin-1-yl)pyridin-3-yl)pyrazolo[1,5-a]pyridine-3-carbonitrile A solution of 4-(6-(4-((6-methoxypyridin-3-yl)methyl)piperazin-1-yl)pyridin-3-yl)-6-(1H-pyrazol-4-yl)pyrazolo[1,5-a]pyridine-3-carbonitrile (Example 698; Step 2; 23 mg, 0.047 mmol) in dry DMA (500 µL) was treated sequentially with $Cs_2CO_3$ (91 mg, 0.28 mmol) and 2-((2-chloroethyl)sulfonyl)propane (24 mg, 0.14 mmol). The resulting mixture was stirred overnight at 60° C. After cooling to ambient temperature, the reaction mixture was diluted with $CHCl_3$ and quenched with saturated $NH_4Cl_{(aq)}$. The resulting biphasic mixture was extracted with $CHCl_3$ in a PS Frit. The combined organic extracts then were concentrated in vacuo, and the crude residue was purified by C18 reverse-phase chromatography (10-70% ACN/water with 0.1% formic acid as the gradient eluent) to afford the title compound (14 mg, 48% yield). MS (apci) m/z=626.3 (M+H).

The compounds in Table JJJ were prepared using a similar method to that described for the synthesis of Example 703, replacing 2-((2-chloroethyl)sulfonyl)propane with the appropriate alkyl halide starting material and using temperatures ranging from 60° C.-75° C. Reaction progression in each example was monitored by LCMS, and reaction times were adjusted as necessary. Upon completion, reactions were quenched using $CHCl_3$ and either water or saturated $NH_4Cl_{(aq)}$, then worked up and purified using a method similar to that described in Example 703 using the appropriate gradient eluent in C18 reverse-phase chromatographic purification.

TABLE JJJ

| Ex # | Structure | Chemical Name | MS apci (m/z) |
|---|---|---|---|
| 704 | 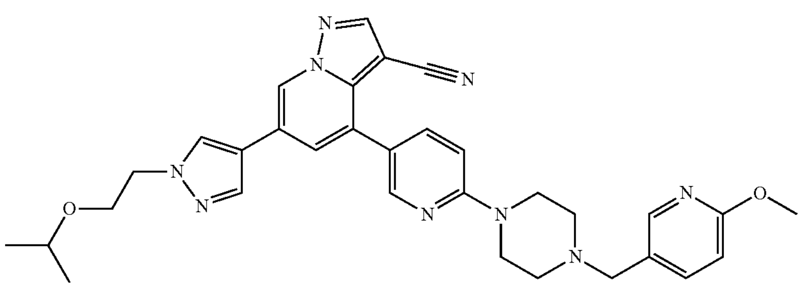 [SMILES: COc1ccc(CN2CCN(c3ccc(-c4cc(-c5cnn(CCOC(C)C)c5)cn5ncc(C#N)c45)cn3)CC2)cn1] | 6-(1-(2-isopropoxyethyl)-1H-pyrazol-4-yl)-4-(6-(4-((6-methoxypyridin-3-yl)methyl)piperazin-1-yl)pyridin-3-yl)pyrazolo[1,5-a]pyridine-3-carbonitrile | 578.4 (M + H) |
| 705 | 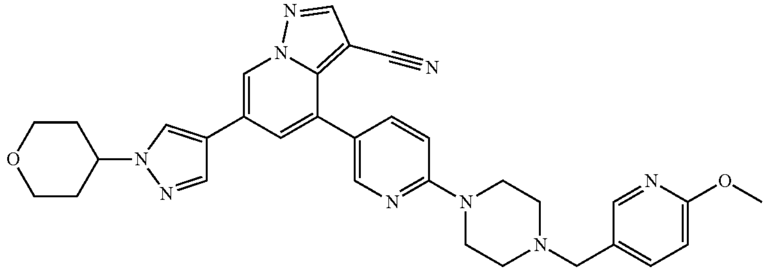 [SMILES: COc1ccc(CN2CCN(c3ccc(-c4cc(-c5cnn(C6CCOCC6)c5)cn5ncc(C#N)c45)cn3)CC2)cn1] | 4-(6-(4-((6-methoxypyridin-3-yl)methyl)piperazin-1-yl)pyridin-3-yl)-6-(1-(tetrahydro-2H-pyran-4-yl)-1H-pyrazol-4-yl)pyrazolo[1,5-a]pyridine-3-carbonitrile | 576.4 (M + H) |

TABLE JJJ-continued

| Ex # | Structure | Chemical Name | MS apci (m/z) |
|---|---|---|---|
| 706 | 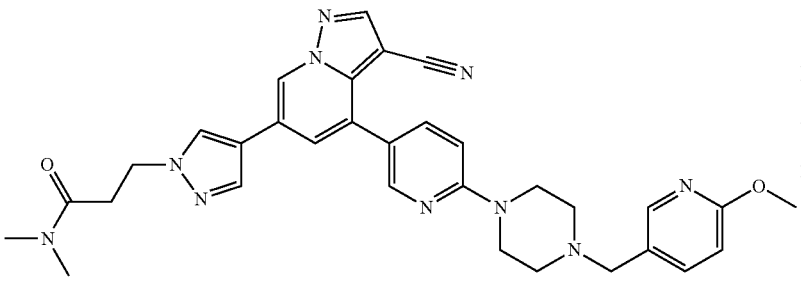 | 3-(4-(3-cyano-4-(6-(4-((6-methoxypyridin-3-yl)methyl)piperazin-1-yl)pyridin-3-yl)pyrazolo[1,5-a]pyridin-6-yl)-1H-pyrazol-1-yl)-N,N-dimethylpropanamide | 591.3 (M + H) |
| 707 | 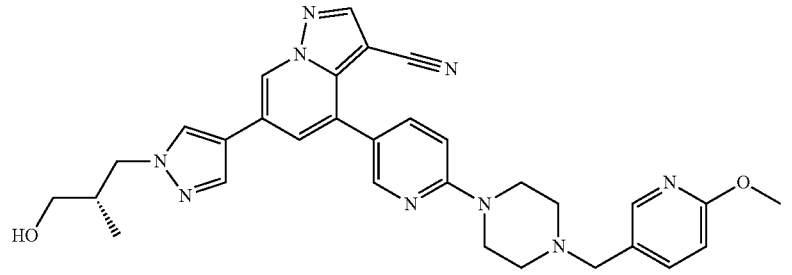 [SMILES: COc1ccc(CN2CCN(c3ccc(-c4cc(-c5cnn(C[C@H](C)CO)c5)cn5ncc(C#N)c45)cn3)CC2)cn1] | (R)-6-(1-(3-hydroxy-2-methylpropyl)-1H-pyrazol-4-yl)-4-(6-(4-((6-methoxypyridin-3-yl)methyl)piperazin-1-yl)pyridin-3-yl)pyrazolo[1,5-a]pyridine-3-carbonitrile | 564.3 (M + H) |
| 708 | 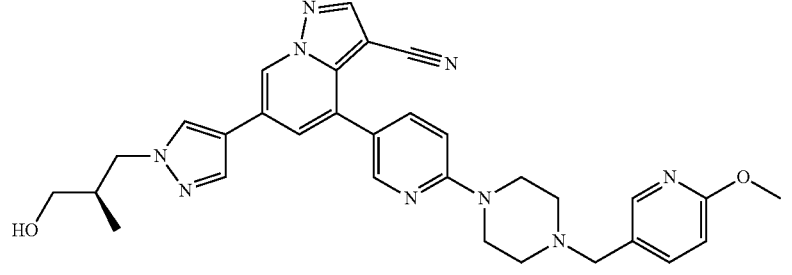 [SMILES: COc1ccc(CN2CCN(c3ccc(-c4cc(-c5cnn(C[C@@H](C)CO)c5)cn5ncc(C#N)c45)cn3)CC2)cn1] | (S)-6-(1-(3-hydroxy-2-methylpropyl)-1H-pyrazol-4-yl)-4-(6-(4-((6-methoxypyridin-3-yl)methyl)piperazin-1-yl)pyridin-3-yl)pyrazolo[1,5-a]pyridine-3-carbonitrile | 564.3 (M + H) |
| 709 | 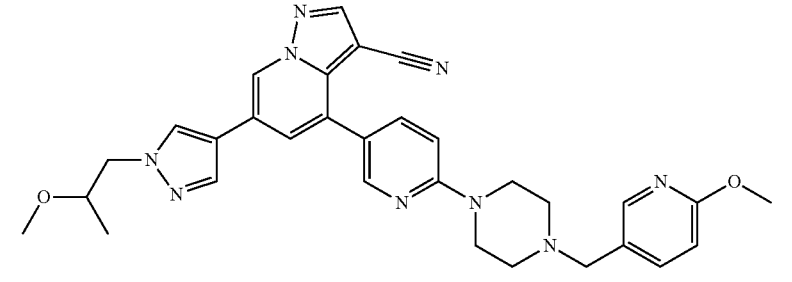 | 6-(1-(2-methoxypropyl)-1H-pyrazol-4-yl)-4-(6-(4-((6-methoxypyridin-3-yl)methyl)piperazin-1-yl)pyridin-3-yl)pyrazolo[1,5-a]pyridine-3-carbonitrile | 564.3 (M + H) |
| 710 | 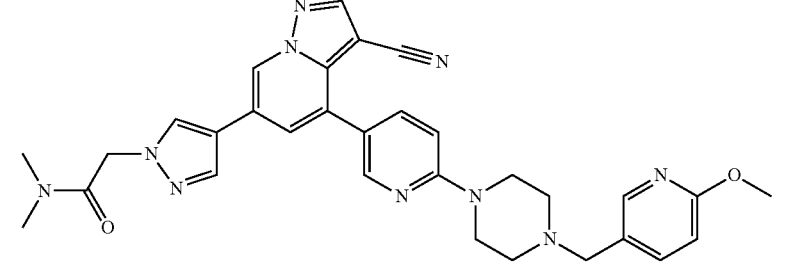 | 2-(4-(3-cyano-4-(6-(4-((6-methoxypyridin-3-yl)methyl)piperazin-1-yl)pyridin-3-yl)pyrazolo[1,5-a]pyridin-6-yl)-1H-pyrazol-1-yl)-N,N-dimethylacetamide | 577.3 (M + H) |

Example 711

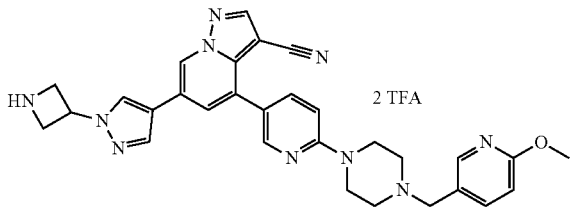 [SMILES: COc1ccc(CN2CCN(c3ccc(-c4cc(-c5cnn(C6CNC6)c5)cn5ncc(C#N)c45)cn3)CC2)cn1]

6-(1-(azetidin-3-yl)-1H-pyrazol-4-yl)-4-(6-(4-((6-methoxypyridin-3-yl)methyl)-piperazin-1-yl)pyridin-3-yl)pyrazolo[1,5-a]pyridine-3-carbonitrile bis(2,2,2-trifluoroacetate)

Step 1: Preparation of Tert-Butyl 3-(4-(3-cyano-4-(6-(4-((6-methoxypyridin-3-yl)methyl)piperazin-1-yl)pyridin-3-yl)pyrazolo[1,5-a]pyridin-6-yl)-1H-pyrazol-1-yl)azetidine-1-carboxylate A solution of 4-(6-(4-((6-methoxypyridin-3-yl)methyl)piperazin-1-yl)pyridin-3-yl)-6-(1H-pyrazol-4-yl)pyrazolo[1,5-a]pyridine-3-carbonitrile (Example 698; Step 2; 60 mg, 0.12 mmol) in DMA (1 mL) was treated sequentially with $Cs_2CO_3$ (240 mg, 0.73 mmol) and tert-butyl 3-iodoazetidine-1-carboxylate (100 mg, 0.370 mmol). The resulting mixture was stirred for 4 h at 60° C. After cooling to ambient temperature, the reaction mixture was quenched with saturated $NH_4Cl_{(aq)}$. The resulting biphasic mixture was extracted with $CHCl_3$. The combined organic extracts were dried over anhydrous $Na_2SO_4$, filtered and concentrated in vacuo. The crude residue was purified by silica chromatography (0-15% MeOH/EtOAc as the gradient eluent) to afford the title compound (70 mg, 89% yield). MS (apci) m/z=647.3 (M+H).

Step 2: Preparation of 6-(1-(azetidin-3-yl)-1H-pyrazol-4-yl)-4-(6-(4-((6-methoxypyridin-3-yl)methyl)piperazin-1-yl)pyridin-3-yl)pyrazolo[1,5-a]pyridine-3-carbonitrile bis(2,2,2-trifluoroacetate)

A suspension of tert-butyl 3-(4-(3-cyano-4-(6-(4-((6-methoxypyridin-3-yl)methyl)piperazin-1-yl)pyridin-3-yl)pyrazolo[1,5-a]pyridin-6-yl)-1H-pyrazol-1-yl)azetidine-1-carboxylate (Step 1; 70 mg, 0.11 mmol) in DCM (1 mL) was treated with 5 M HCl in iPrOH (110 μL, 0.54 mmol). The resulting suspension was stirred overnight at ambient temperature. The mixture was solubilized using 1 M $HCl_{(aq)}$ and adjusted to pH 7 using 1 M $NaOH_{(aq)}$. The biphasic mixture was extracted with DCM, and the combined organic extracts were dried over anhydrous $Na_2SO_4$, filtered and concentrated in vacuo. The crude residue was purified by C18 reverse-phase chromatography (5-95% ACN/water with 0.1% TFA as the gradient eluent) to cleanly afford the title compound (4.4 mg, 7% yield). MS (apci) m/z=547.3 (M+H).

Example 712

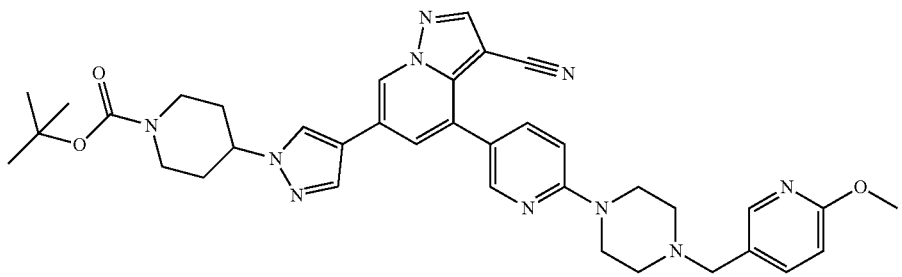 [SMILES: COc1ccc(CN2CCN(c3ccc(-c4cc(-c5cnn(C6CCN(C(=O)OC(C)(C)C)CC6)c5)cn5ncc(C#N)c45)cn3)CC2)cn1]

Tert-Butyl 4-(4-(3-cyano-4-(6-(4-((6-methoxypyridin-3-yl)methyl)piperazin-1-yl)pyridin-3-yl)pyrazolo[1,5-a]pyridin-6-yl)-1H-pyrazol-1-yl)piperidine-1-carboxylate A mixture of 4-(6-(4-((6-methoxypyridin-3-yl)methyl)piperazin-1-yl)pyridin-3-yl)-6-(1H-pyrazol-4-yl)pyrazolo[1,5-a]pyridine-3-carbonitrile (Example 698; Step 2; 0.070 g, 0.142 mmol) and $Cs_2CO_3$ (0.199 g, 0.610 mmol) in DMA (1 mL) was treated sequentially with tert-butyl 4-bromopiperidine-1-carboxylate (113 mg, 0.427 mmol). The resulting mixture was stirred overnight at 75° C. before introducing additional $Cs_2CO_3$ (278 mg, 0.142 mmol) and tert-butyl 4-bromopiperidine-1-carboxylate (38 mg, 0.142 mmol). The resulting mixture was stirred for 3 h at 75° C. After cooling to ambient temperature, the reaction mixture was diluted with DCM, and quenched with saturated $NH_4Cl_{(aq)}$. The resulting biphasic mixture was extracted with DCM. The combined organic extracts were dried over anhydrous $Na_2SO_4$, filtered and concentrated in vacuo. The crude residue was purified by silica chromatography (0-10% MeOH/EtOAc as the gradient eluent) to afford the title compound (113 mg, quantitative yield). MS (apci) m/z=675.3 (M+H).

Example 713

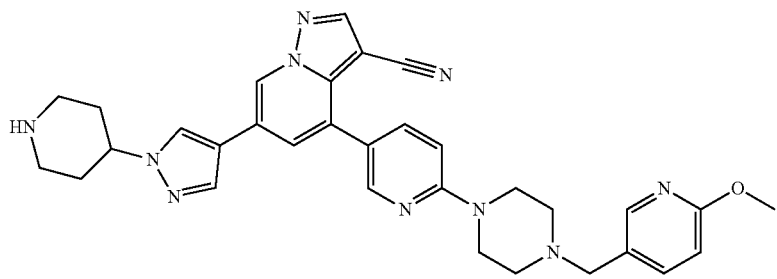 [SMILES: COc1ccc(CN2CCN(c3ccc(-c4cc(-c5cnn(C6CCNCC6)c5)cn5ncc(C#N)c45)cn3)CC2)cn1]

4-(6-(4-((6-methoxypyridin-3-yl)methyl)piperazin-1-yl)pyridin-3-yl)-6-(1-(piperidin-4-yl)-1H-pyrazol-4-yl)pyrazolo[1,5-a]pyridine-3-carbonitrile A solution of tert-butyl 4-(4-(3-cyano-4-(6-(4-((6-methoxypyridin-3-yl)methyl)piperazin-1-yl)pyridin-3-yl)pyrazolo[1,5-a]pyridin-6-yl)-1H-pyrazol-1-yl)piperidine-1-carboxylate (Example 712; 113 mg, 0.167 mmol) in DCM (1 mL) was treated with 5 M HCl in iPrOH (200 µL, 0.837 mmol). The resulting mixture was stirred for 2 h at ambient temperature, before concentrating in vacuo. The residue was solubilized using 1 M HCl$_{(aq)}$, and then treated with 1 M NaOH$_{(aq)}$. The resulting suspension was concentrated in vacuo, and the crude residue was purified by C18 reverse-phase chromatography (10-70% ACN/water with 0.1% formic acid as the gradient eluent) to cleanly afford the title compound (42.3 mg, 52% yield). MS (apci) m/z=575.3 (M+H).

Example 714

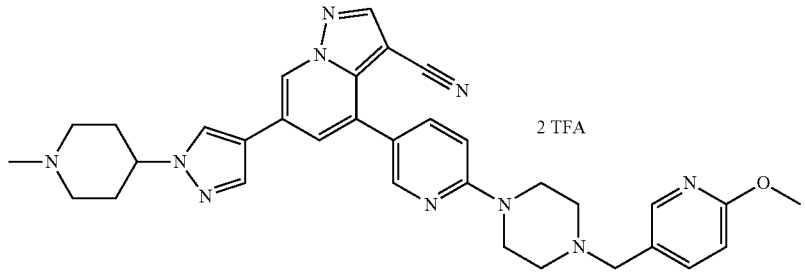

4-(6-(4-((6-methoxypyridin-3-yl)methyl)piperazin-1-yl)pyridin-3-yl)-6-(1-(1-methylpiperidin-4-yl)-1H-pyrazol-4-yl)pyrazolo[1,5-a]pyridine-3-carbonitrile bis(2,2,2-trifluoroacetate)

A solution of tert-butyl 4-(4-(3-cyano-4-(6-(4-((6-methoxypyridin-3-yl)methyl)piperazin-1-yl)pyridin-3-yl)pyrazolo[1,5-a]pyridin-6-yl)-1H-pyrazol-1-yl)piperidine-1-carboxylate (Example 712; 8 mg, 0.01 mmol) in Formic acid (89.4 µL, 2.37 mmol) and formaldehyde (35.6 µL, 0.474 mmol) was sealed and stirred for 4 h at 90° C. After cooling to ambient temperature, the reaction mixture was concentrated in vacuo then purified by C18 reverse-phase chromatography (5-95% ACN/water with 0.1% TFA as the gradient eluent) to cleanly afford the title compound as the bis-TFA salt (3.8 mg, 54% yield). MS (apci) m/z=589.3 (M+H).

Example 715

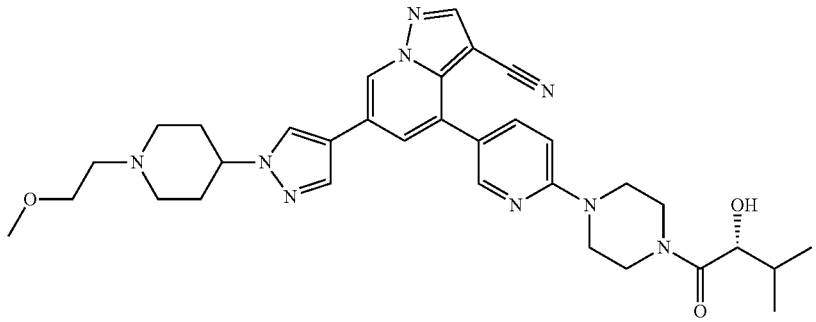 [SMILES: COCCN1CCC(n2cc(-c3cc(-c4ccc(N5CCN(C(=O)[C@H](O)C(C)C)CC5)nc4)c4c(C#N)cnn4c3)cn2)CC1]

(R)-4-(6-(4-(2-hydroxy-3-methylbutanoyl)piperazin-1-yl)pyridin-3-yl)-6-(1-(1-(2-methoxyethyl)piperidin-4-yl)-1H-pyrazol-4-yl)pyrazolo[1,5-a]pyridine-3-carbonitrile Step 1: Preparation of 4-(4-(4,4,5,5-tetramethyl-1,3,2-dioxaborolan-2-yl)-1H-pyrazol-1-yl)piperidine hydrochloride Cold (0° C.) TFA (2 mL) was added to tert-butyl 4-(4-(4,4,5,5-tetramethyl-1,3,2-dioxaborolan-2-yl)-1H-pyrazol-1-yl)piperidine-1-carboxylate (1.5 g, 4.0 mmol), and the mixture was stirred for 10 min at ambient temperature. The mixture was concentrated in vacuo, and the resulting residue was treated with 4N HCl in dioxane (5 mL). The reaction mixture was concentrated in vacuo, azeotroping with ACN, and then dried under high vacuum to cleanly afford the title compound (1.7 g, quantitative yield). MS (apci) m/z=278.2 (M+H).

Step 2: Preparation of 1-(2-methoxyethyl)-4-(4-(4,4,5,5-tetramethyl-1,3,2-dioxaborolan-2-yl)-1H-pyrazol-1-yl)piperidine At ambient temperature, a solution 4-(4-(4,4,5,5-tetramethyl-1,3,2-dioxaborolan-2-yl)-1H-pyrazol-1-yl)piperidine hydrochloride (Step 1; 1.5 g, 4.8 mmol) in DMF (19 mL) was treated sequentially with $K_2CO_3$ (2.3 g, 17 mmol) and 1-bromo-2-methoxyethane (1.1 mL, 12 mmol). The resulting mixture was stirred for 3 h at 70° C., then overnight at ambient temperature. The reaction mixture was filtered, and the filtrate was concentrated in vacuo. The resulting residue was suspended in 5% iPrOH/DCM (100 mL), and stirred for 5-10 min at ambient temperature. The mixture was filtered through GF/F paper, and the filtrate was concentrated and dried in vacuo. The resulting residue was triturated with hexanes (5 mL) to afford the title compound (2.43 g, quantitative yield). MS (apci) m/z=336.2 (M+H).

Step 3: Preparation of Tert-Butyl 4-(5-(3-cyano-6-(1-(1-(2-methoxyethyl)piperidin-4-yl)-1H-pyrazol-4-yl)pyrazolo[1,5-a]pyridin-4-yl)pyridin-2-yl)piperazine-1-carboxylate In a pressure tube, a mixture of tert-butyl 4-(5-(3-cyano-6-(((trifluoromethyl)sulfonyl)oxy)pyrazolo[1,5-a]pyridin-4-yl)pyridin-2-yl)piperazine-1-carboxylate (Intermediate P14; 100 mg, 0.181 mmol), 1-(2-methoxyethyl)-4-(4-(4,4,5,5-tetramethyl-1,3,2-dioxaborolan-2-yl)-1H-pyrazol-1-yl)piperidine (60.7 mg, 0.181 mmol), Pd$_2$(dba)$_3$.CHCl$_3$ (9.37 mg, 0.00905 mmol), XPhos (17.3 mg, 0.0362 mmol) and K$_2$CO$_{3(s)}$ (75.0 mg, 0.543 mmol) in 4:1 dioxane/water (1.81 mL) was sparged for 5 min with N$_{2(g)}$, and the pressure tube was sealed. The reaction mixture was stirred overnight at 100° C. After cooling to room temperature, the reaction mixture was diluted with a solution of 5% iPrOH/DCM (20 mL) and washed with water (5 mL). The organic extracts were dried over anhydrous MgSO$_4$, filtered, and concentrated in vacuo to afford the title compound which was carried forward without further purification. MS (apci) m/z=611.9, 612.8 (M+H).

Step 4: Preparation of 6-(1-(1-(2-methoxyethyl)piperidin-4-yl)-1H-pyrazol-4-yl)-4-(6-(piperazin-1-yl)pyridin-3-yl)pyrazolo[1,5-a]pyridine-3-carbonitrile Dihydrochloride A room temperature solution of tert-butyl 4-(5-(3-cyano-6-(1-(1-(2-methoxyethyl)piperidin-4-yl)-1H-pyrazol-4-yl)pyrazolo[1,5-a]pyridin-4-yl)pyridin-2-yl)piperazine-1-carboxylate in TFA (2 mL) was stirred for 1 h at room temperature, and then concentrated in vacuo. The crude residue was purified by C18 reverse-phase chromatography (5-80% ACN/water with 0.1% TFA as the gradient eluent) to cleanly afford the title compound as the TFA salt. The TFA salt was suspended in DCM (1 mL) containing a few drops of MeOH, then treated with 4 N HCl in dioxane (2 mL). The resulting mixture was concentrated and dried in vacuo to cleanly afford the title compound as the dihydrochloride salt (45 mg, 43% yield). MS (apci) m/z=511.9 (M+H).

Step 5: Preparation of (R)-4-(6-(4-(2-hydroxy-3-methylbutanoyl)piperazin-1-yl)pyridin-3-yl)-6-(1-(1-(2-methoxyethyl)piperidin-4-yl)-1H-pyrazol-4-yl)pyrazolo[1,5-a]pyridine-3-carbonitrile A solution of 6-(1-(1-(2-methoxyethyl)piperidin-4-yl)-1H-pyrazol-4-yl)-4-(6-(piperazin-1-yl)pyridin-3-yl)pyrazolo[1,5-a]pyridine-3-carbonitrile dihydrochloride (31 mg, 0.053 mmol) in DMF (1.1 mL) was treated with D-alpha-Hydroxyisovaleric acid (7.5 mg, 0.064 mmol), HATU (24.2 mg, 0.0636 mmol) and DIEA (46.2 µL, 0.265 mmol). The resulting solution was stirred overnight at ambient temperature. The reaction mixture was diluted with 5% MeOH/DCM (20 mL) and washed with water (5 mL). The combined organic extracts were dried over anhydrous MgSO$_4$, then filtered and concentrated in vacuo. The crude residue was purified by silica chromatography (8% MeOH/DCM with 2% NH$_4$OH$_{(aq)}$ as the eluent) to cleanly afford the title compound (20 mg, 62% yield). MS (apci) m/z=611.9, 612.9 (M+1).

Example 716

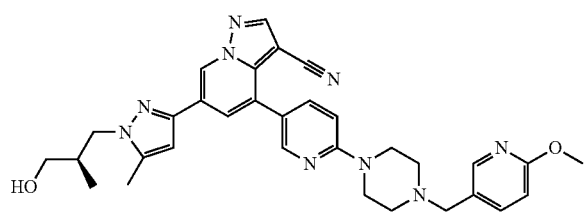 [SMILES: COc1ccc(CN2CCN(c3ccc(-c4cc(-c5cc(C)n(C[C@@H](C)CO)n5)cn5ncc(C#N)c45)cn3)CC2)cn1]

(R)-6-(1-(3-hydroxy-2-methylpropyl)-5-methyl-1H-pyrazol-3-yl)-4-(6-(4-((6-methoxypyridin-3-yl)methyl)piperazin-1-yl)pyridin-3-yl)pyrazolo[1,5-a]pyridine-3-carbonitrile A mixture of 4-(6-(4-((6-methoxypyridin-3-yl)methyl)piperazin-1-yl)pyridin-3-yl)-6-(3-methyl-1H-pyrazol-5-yl)pyrazolo[1,5-a]pyridine-3-carbonitrile (Example 636; 8 mg, 0.0158 mmol), (S)-3-bromo-2-methylpropan-1-ol (2.91 mg, 0.0190 mmol) and Cs$_2$CO$_3$ (25.8 mg, 0.0791 mmol) in DMA (200 µL) was stirred overnight at ambient temperature, then purified directly by C18 reverse-phase chromatography (0-60% ACN/water as the gradient eluent) to afford the title compound (3.3 mg, 36% yield). MS (apci) m/z=578.3 (M+H).

Example 717

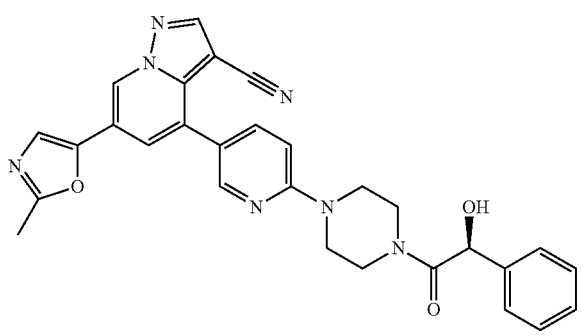 [SMILES: Cc1ncc(-c2cc(-c3ccc(N4CCN(C(=O)[C@@H](O)c5ccccc5)CC4)nc3)c3c(C#N)cnn3c2)o1]

(S)-4-(6-(4-(2-hydroxy-2-phenylacetyl)piperazin-1-yl)pyridin-3-yl)-6-(2-methyloxazol-5-yl)pyrazolo[1,5-a]pyridine-3-carbonitrile A solution of 6-(2-methyloxazol-5-yl)-4-(6-(piperazin-1-yl)pyridin-3-yl)pyrazolo[1,5-a]pyridine-3-carbonitrile dihydrochloride (Example 624; 21.3 mg, 0.0465 mmol) in dry DMF (500 μL) was treated sequentially with DIEA (24.3 μL, 0.139 mmol), HATU (26.5 mg, 0.0697 mmol) and (S)-2-hydroxy-2-phenylacetic acid (10.6 mg, 0.0697 mmol). The resulting solution was stirred 4 d at ambient temperature, during which time additional amounts of DIEA, HATU and (R)-2-hydroxy-2-phenylacetic acid were added (1 equivalent/day of each, total of 3 additional equivalents of each reagent) in an effort to drive the reaction to completion. The reaction mixture was quenched with water/CHCl$_3$, and the resulting biphasic mixture was extracted with CHCl$_3$ in a PS Frit. The combined organic extracts were concentrated in vacuo and purified by C18 reverse-phase chromatography (25-80% ACN in water with 0.1% formic acid as the gradient eluent) to afford the title compound (2.3 mg, 10% yield). MS (apci) m/z=520.2 (M+H).

Example 718

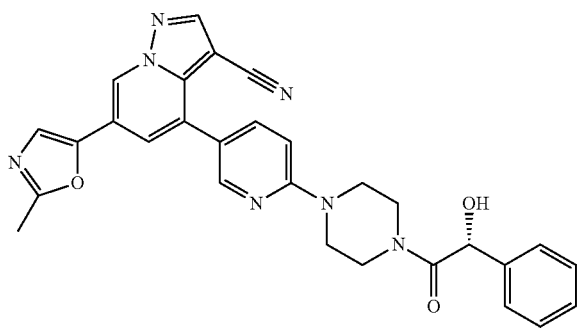 [SMILES: Cc1ncc(-c2cc(-c3ccc(N4CCN(C(=O)[C@H](O)c5ccccc5)CC4)nc3)c3c(C#N)cnn3c2)o1]

(R)-4-(6-(4-(2-hydroxy-2-phenylacetyl)piperazin-1-yl)pyridin-3-yl)-6-(2-methyloxazol-5-yl)pyrazolo[1,5-a]pyridine-3-carbonitrile Following a similar method to that used in Step 2 for the preparation and purification of Example 717, replacing (S)-2-hydroxy-2-phenylacetic acid with (R)-2-hydroxy-2-phenylacetic acid, the title compound was isolated cleanly (2.6 mg, 11% yield). MS (apci) m/z=520.2 (M+H).

Example 719

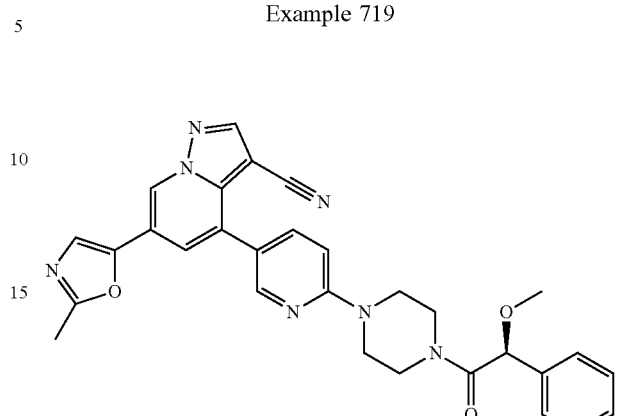

(S)-4-(6-(4-(2-methoxy-2-phenylacetyl)piperazin-1-yl)pyridin-3-yl)-6-(2-methyloxazol-5-yl)pyrazolo[1,5-a]pyridine-3-carbonitrile Following a similar method to that used in Step 2 for the preparation and purification of Example 717, replacing (S)-2-hydroxy-2-phenylacetic acid with (S)-2-methoxy-2-phenylacetic acid, omitting the addition of extra reagents and using anhydrous Na$_2$SO$_4$ rather than the PS Frit as the drying agent, the title compound was isolated cleanly (6.3 mg, 32% yield). MS (apci) m/z=534.2 (M+H).

Example 720

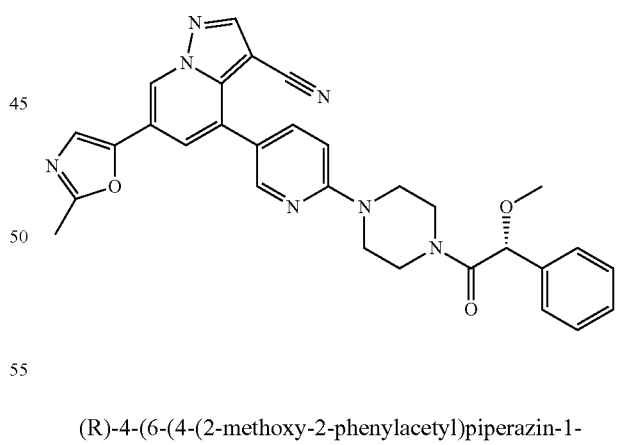

(R)-4-(6-(4-(2-methoxy-2-phenylacetyl)piperazin-1-yl)pyridin-3-yl)-6-(2-methyloxazol-5-yl)pyrazolo[1,5-a]pyridine-3-carbonitrile Following a similar method to that used in Step 2 for the preparation and purification of Example 717, replacing (S)-2-hydroxy-2-phenylacetic acid with (R)-2-methoxy-2-phenylacetic acid, and omitting the addition of extra reagents, the title compound was isolated cleanly (4.3 mg, 18% yield). MS (apci) m/z=534.2 (M+H).

Example 721

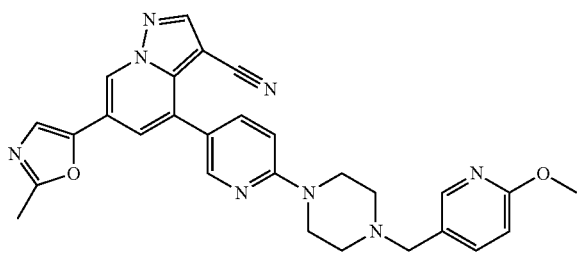 [SMILES: COc1ccc(CN2CCN(c3ccc(-c4cc(-c5cnc(C)o5)cn5ncc(C#N)c45)cn3)CC2)cn1]

4-(6-(4-((6-methoxypyridin-3-yl)methyl)piperazin-1-yl)pyridin-3-yl)-6-(2-methyloxazol-5-yl)pyrazolo[1,5-a]pyridine-3-carbonitrile A solution of 6-(2-methyloxazol-5-yl)-4-(6-(piperazin-1-yl)pyridin-3-yl)pyrazolo[1,5-a]pyridine-3-carbonitrile dihydrochloride (Example 624; 20.1 mg, 0.0439 mmol) in dry DMA (500 μL) was treated with TEA (18.3 μL, 0.132 mmol), Me$_4$N(AcO)$_3$BH (17.3 mg, 0.0658 mmol) and 6-methoxynicotinaldehyde (9.02 mg, 0.0658 mmol). The resulting mixture was stirred at ambient temperature for 5 hours, before introducing additional TEA (6.1 μL, 0.044 mmol), Me$_4$N(AcO)$_3$BH (11.5 mg, 0.044 mmol) and 6-methoxynicotinaldehyde (6.01 mg, 0.044 mmol). The reaction mixture was stirred overnight at ambient temperature, then treated with additional TEA and 6-methoxynicotinaldehyde (20 μL of each). The reaction mixture was stirred for an additional 3 d before quenching with water/CHCl$_3$. The quenched mixture was extracted with CHCl$_3$ in a PS Frit, and the combined organic extracts were concentrated in vacuo. The crude residue was purified by C18 reverse-phase chromatography (15-80% ACN/water as the gradient eluent) to afford the title compound (2.7 mg, 12% yield). MS (apci) m/z=506.8 (M+H).

Example 722

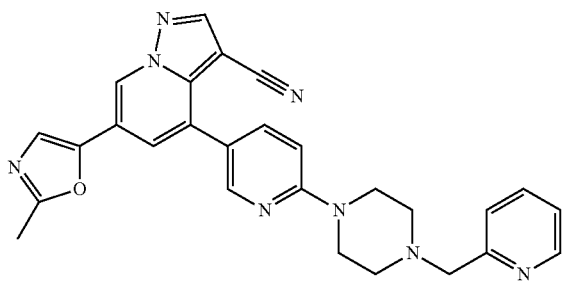 [SMILES: Cc1ncc(-c2cc(-c3ccc(N4CCN(Cc5ccccn5)CC4)nc3)c3c(C#N)cnn3c2)o1]

6-(2-methyloxazol-5-yl)-4-(6-(4-(pyridin-2-ylmethyl)piperazin-1-yl)pyridin-3-yl)pyrazolo[1,5-a]pyridine-3-carbonitrile A solution of 6-(2-methyloxazol-5-yl)-4-(6-(piperazin-1-yl)pyridin-3-yl)pyrazolo[1,5-a]pyridine-3-carbonitrile dihydrochloride (Example 624; 21.7 mg, 0.0473 mmol) in dry DMA (500 μL) was treated sequentially with TEA (19.8 μL, 0.142 mmol), Me$_4$N(AcO)$_3$BH (18.7 mg, 0.071 mmol) and picolinaldehyde (6.8 μL, 0.071 mmol). The resulting mixture was stirred at ambient temperature for 5 hours before introducing additional TEA (6.6 μL, 0.048 mmol), Me$_4$N(AcO)$_3$BH (12.5 mg, 0.047 mmol) and picolinaldehyde (4.5 μL, 0.047 mmol). The reaction mixture was stirred overnight at ambient temperature, then quenched with water/CHCl$_3$. The quenched mixture was extracted with CHCl$_3$ in a PS Frit, and the combined organic extracts were concentrated in vacuo. The crude residue was purified by C18 reverse-phase chromatography (15-90% ACN/water as the gradient eluent) to afford the title compound (4.4 mg, 20% yield). MS (apci) m/z=477.2 (M+H).

Example 723

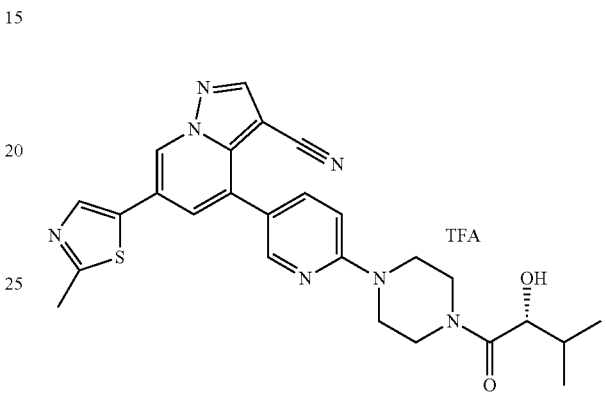

(R)-4-(6-(4-(2-hydroxy-3-methylbutanoyl)piperazin-1-yl)pyridin-3-yl)-6-(2-methylthiazol-5-yl)pyrazolo[1,5-a]pyridine-3-carbonitrile 2,2,2-trifluoroacetate Step 1: Preparation of Tert-Butyl 4-(5-(3-cyano-6-(2-methylthiazol-5-yl)pyrazolo[1,5-a]pyridin-4-yl)pyridin-2-yl)piperazine-1-carboxylate In a pressure tube, a mixture of tert-butyl 4-(5-(3-cyano-6-(((trifluoromethyl)sulfonyl)oxy)pyrazolo[1,5-a]pyridin-4-yl)pyridin-2-yl)piperazine-1-carboxylate (Intermediate P14; 100 mg, 0.181 mmol), 2-methyl-5-(4,4,5,5-tetramethyl-1,3,2-dioxaborolan-2-yl)thiazole (48.9 mg, 0.217 mmol), Pd$_2$(dba)$_3$.CHCl$_3$ (9.37 mg, 0.00905 mmol), XPhos (17.3 mg, 0.0362 mmol) and K$_2$CO$_{3(s)}$ (75.0 mg, 0.543 mmol) in 4:1 dioxane/water (1.81 mL) was sparged for 5 min with N$_{2(g)}$. The vessel was sealed and the reaction mixture was stirred overnight at 100° C. After cooling to room temperature, the reaction mixture was diluted with EtOAc (20 mL) and washed with water (5 mL). The organic extracts were dried over anhydrous MgSO$_4$, filtered, and concentrated in vacuo. The crude residue was purified by silica chromatography (2-40% acetone/DCM as the gradient eluent) to afford the title compound (80 mg, 88% yield). MS (apci) m/z=502.2 (M+H).

Step 2: Preparation of 6-(2-methylthiazol-5-yl)-4-(6-(piperazin-1-yl)pyridin-3-yl)pyrazolo[1,5-a]pyridine-3-carbonitrile Dihydrochloride A solution of tert-butyl 4-(5-(3-cyano-6-(2-methylthiazol 5-yl)pyrazolo[1,5-a]pyridin-4-yl)pyridin-2-yl)piperazine-1-carboxylate (78 g, 156 mmol) in TFA (2 mL) was stirred for 30 min at ambient temperature, and then concentrated in vacuo. The residue was dissolve in DCM (1 mL) and treated with 4 N HCl (2 mL) in dioxane. The resulting suspension was stirred for 10 min at ambient temperature. The mixture was concentrated in vacuo, azeotroping with ACN to cleanly afford the title compound as the dihydrochloride salt which was carried on without further purification. MS (apci) m/z=402.1 (M+H).

Step 3: Preparation of (R)-4-(6-(4-(2-hydroxy-3-methylbutanoyl)piperazin-1-yl)pyridin-3-yl)-6-(2-methylthiazol-5-yl)pyrazolo[1,5-a]pyridine-3-carbonitrile 2,2,2-trifluoroacetate A solution of 6-(2-methylthiazol-5-yl)-4-(6-(piperazin-1-yl)pyridin-3-yl)pyrazolo[1,5-a]pyridine-3-carbonitrile dihydrochloride (42 mg, 0.0885 mmol) in DCM (3 mL) was treated with DIEA (61.7 µL, 0.354 mmol), D-alpha-Hydroxyisovaleric acid (12.5 mg, 0.106 mmol) and HATU (40.4 mg, 0.106 mmol). The resulting solution was stirred overnight at ambient temperature. The reaction mixture was concentrated in vacuo, and the crude residue was purified by C18 reverse-phase chromatography (5-95% ACN/water with 0.1% TFA as the gradient eluent) to cleanly afford the title compound as the bistrifluoroacetate salt (15 mg, 28% yield). MS (apci) m/z=502.2 (M+H).

Example 724

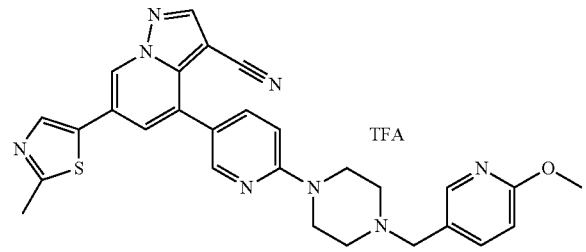 [SMILES: COc1ccc(CN2CCN(c3ccc(-c4cc(-c5cnc(C)s5)cn5ncc(C#N)c45)cn3)CC2)cn1]

4-(6-(4-((6-methoxypyridin-3-yl)methyl)piperazin-1-yl)pyridin-3-yl)-6-(2-methylthiazol-5-yl)pyrazolo[1,5-a]pyridine-3-carbonitrile 2,2,2-trifluoroacetate Step 1: Preparation of 6-(2-methylthiazol-5-yl)-4-(6-(piperazin-1-yl)pyridin-3-yl)pyrazolo[1,5-a]pyridine-3-carbonitrile A solution of 6-(2-methylthiazol-5-yl)-4-(6-(piperazin-1-yl)pyridin-3-yl)pyrazolo[1,5-a]pyridine-3-carbonitrile dihydrochloride (Example 723, Step 2; 37 mg, 0.0780 mmol) in MeOH (7.8 mL) and water (2 mL) containing several drops of AcOH was extracted with 5% iPrOH/DCM (30 mL). The organic extracts were washed with saturated NaHCO$_{3(aq)}$ and brine. The neutralized organic phase was then dried over anhydrous MgSO$_4$, filtered, and concentrated in vacuo to afford the title compound as the free base (28 mg, 90% recovery). MS (apci) m/z=502.2 (M+H).

Step 2: Preparation of 4-(6-(4-((6-methoxypyridin-3-yl)methyl)piperazin-1-yl)pyridin-3-yl)-6-(2-methylthiazol-5-yl)pyrazolo[1,5-a]pyridine-3-carbonitrile 2,2,2-trifluoroacetate A solution of 6-(2-methylthiazol-5-yl)-4-(6-(piperazin-1-yl)pyridin-3-yl)pyrazolo[1,5-a]pyridine-3-carbonitrile (28.0 mg, 0.0697 mmol) in MeOH (2.0 mL) was treated sequentially with 6-methoxynicotinaldehyde (19.1 mg, 0.139 mmol), NaBH(AcO)$_3$ (41 mg, 0.209 mmol) and 2-3 drops of AcOH. The resulting mixture was stirred at ambient temperature overnight. About 60% of unreacted starting material remained in the mixture. Therefore, additional acetic acid (0.5 mL) was added and the reaction mixture was stirred for another 24 h, but this failed to drive the reaction to completion. Therefore the mixture was concentrated in vacuo. The residue obtained was re-suspended in DCM (10 mL) and re-treated with 6-methoxynicotinaldehyde (30.7 mg, 0.224 mmol), NaBH(AcO)$_3$ (65.8 mg, 0.336 mmol) and AcOH (1 mL). The resulting mixture was stirred for 36 h at ambient temperature and then quenched with water. The quenched mixture was extracted with DCM. The combined organic extracts were dried over anhydrous MgSO$_4$, filtered, and concentrated in vacuo. The crude residue was purified by C18 reverse-phase chromatography (5-95% ACN/water with 0.1% TFA as the gradient eluent) to afford the title compound as the mono trifluoroacetate salt (12.7 mg, 12% yield). MS (apci) m/z=523.2 (M+H).

Example 725

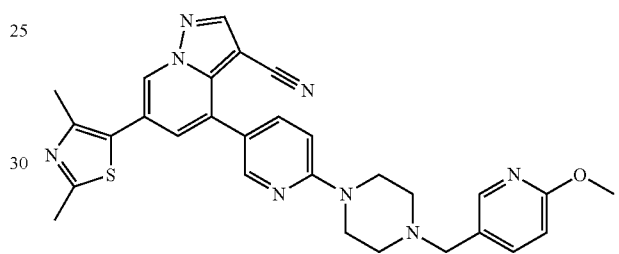

6-(2,4-dimethylthiazol-5-yl)-4-(6-(4-((6-methoxy-pyridin-3-yl)methyl)piperazin-1-yl)pyridin-3-yl)pyrazolo[1,5-a]pyridine-3-carbonitrile Step 1: Preparation of Tert-Butyl 4-(5-(3-cyano-6-(2,4-dimethylthiazol-5-yl)pyrazolo[1,5-a]pyridin-4-yl)pyridin-2-yl)piperazine-1-carboxylate In a pressure tube, a mixture of tert-butyl 4-(5-(3-cyano-6-(((trifluoromethyl)sulfonyl)oxy)pyrazolo[1,5-a]pyridin-4-yl)pyridin-2-yl)piperazine-1-carboxylate (Intermediate P14; 50 mg, 0.0905 mmol), 2,4-dimethyl-5-(4,4,5,5-tetramethyl-1,3,2-dioxaborolan-2-yl)thiazole (26.0 mg, 0.109 mmol), Pd$_2$(dba)$_3$·CHCl$_3$ (4.68 mg, 0.00452 mmol), XPhos (8.63 mg, 0.0181 mmol) and K$_2$CO$_{3(s)}$ (37.5 mg, 0.271 mmol) in 4:1 dioxane/water (0.91 mL) was sparged for 5 min with N$_{2(g)}$. The pressure tube was sealed and the reaction mixture was stirred overnight at 100° C. After cooling to room temperature, the reaction mixture was diluted with EtOAc (20 mL) and washed with water (5 mL). The organic layer was dried over anhydrous MgSO$_4$, filtered, and concentrated in vacuo. The crude residue was purified by silica chromatography (30% acetone/DCM as the eluent) to afford the title compound (58.2 mg, quantitative yield). MS (apci) m/z=516.2 (M+H).

Step 2: Preparation of 6-(2,4-dimethylthiazol-5-yl)-4-(6-(piperazin-1-yl)pyridin-3-yl)pyrazolo[1,5-a]pyridine-3-carbonitrile Dihydrochloride A solution of tert-butyl 4-(5-(3-cyano-6-(2,4-dimethylthiazol-5-yl)pyrazolo[1,5-a]pyridin-4-yl)pyridin-2-yl)piperazine-1-carboxylate (45 mg, 0.087 mmol) in TFA (2 mL) was stirred for 20 min at ambient temperature, and then concentrated in vacuo. The residue was dissolved in DCM (2 mL) and treated with a solution of 4 N HCl in dioxane (2 mL). After stirring for 10 min at ambient temperature, the suspension was concentrated in vacuo to afford the title compound as the dihydrochloride salt which was used in the next step without further purification (41 mg, 96% yield). MS (apci) m/z=416.2 (M+H).

Step 3: Preparation of 4-(6-(4-((6-methoxypyridin-3-yl)methyl)piperazin-1-yl)pyridin-3-yl)-6-(2-methylthiazol-5-yl)pyrazolo[1,5-a]pyridine-3-carbonitrile 2,2,2-trifluoroacetate A mixture of 6-(2,4-dimethylthiazol-5-yl)-4-(6-(piperazin-1-yl)pyridin-3-yl)pyrazolo[1,5-a]pyridine-3-carbonitrile (45 mg, 0.108 mmol) in methanol (1083 μL, 0.108 mmol) was sequentially treated with 6-methoxynicotinaldehyde (29.7 mg, 0.217 mmol), Na(OAc)$_3$BH (63.7 mg, 0.325 mmol) and 2-3 drops of acetic acid. The resulting mixture was stirred at ambient temperature overnight to reach about 50% conversion by LCMS. The mixture was re-treated with additional 6-methoxynicotinaldehyde (29.7 mg, 0.217 mmol), Na(OAc)$_3$BH (63.7 mg, 0.325 mmol) and a few drops of acetic acid and allowed to stir at ambient temperature over 48 h. The reaction still did not go to completion (LCMS). Additional acetic acid (0.5 mL) was added and the mixture was allowed to stir at ambient temperature for another 24 h. This failed to drive the reaction to completion. The mixture was retreated with additional acetic acid (0.5 mL) and stirred at 45° C. for 4 hours before it was concentrated in vacuo. The resulting residue was taken up in DCE (5 mL), then re-treated with 6-methoxynicotinaldehyde (29.7 mg, 0.217 mmol), Na(OAc)$_3$BH (63.7 mg, 0.325 mmol) and few drops of acetic acid. The resulting mixture was stirred at ambient temperature. After 24 h the mixture was diluted with DCM (15 mL) and washed with brine (5 mL). The organic layer was separated, dried over MgSO$_4$ and concentrated in vacuo. The residue was purified by silica chromatography (5-75% acetone/hexanes) to provide the title product as a solid (10.1 mg, 17.4% yield). MS (apci) m/z=537.2 (M+H).

Example 726

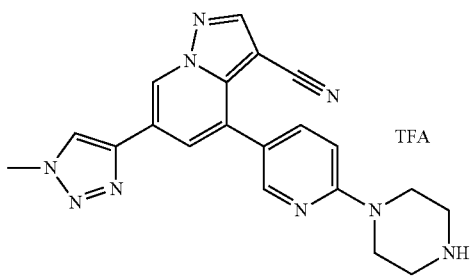 [SMILES: Cn1cc(-c2cc(-c3ccc(N4CCNCC4)nc3)c3c(C#N)cnn3c2)nn1]

6-(1-methyl-1H-1,2,3-triazol-4-yl)-4-(6-(piperazin-1-yl)pyridin-3-yl)pyrazolo[1,5-a]pyridine-3-carbonitrile 2,2,2-trifluoroacetate Step 1: Preparation of Tert-Butyl 4-(5-(3-cyano-6-((trimethylsilyl)ethynyl)pyrazolo[1,5-a]pyridin-4-yl)pyridin-2-yl)piperazine-1-carboxylate In a pressure tube, a mixture of tert-butyl 4-(5-(3-cyano-6-(((trifluoromethyl)sulfonyl)oxy)pyrazolo[1,5-a]pyridin-4-yl)pyridin-2-yl)piperazine-1-carboxylate (Intermediate P14; 200 mg, 0.362 mmol), Cu(I)I (13.8 mg, 0.0724 mmol), PdCl$_2$(PPh$_3$)$_2$ (25.4 mg, 0.0362 mmol), TEA (151 μL, 1.09 mmol), and PPh$_3$ (4.75 mg, 0.0181 mmol) in DMF (1.45 mL) was sparged for 5 min with N$_{2(g)}$. The sparged mixture was treated with ethynyltrimethylsilane (60.2 μL, 0.434 mmol), and sparged again for 5 min with N$_{2(g)}$, before sealing the vessel. The reaction mixture was stirred for 6 h at 65° C., then overnight at ambient temperature. The reaction mixture was poured into water (10 mL), and extracted with EtOAc. The combined organic extracts were washed with brine, then dried over anhydrous MgSO$_4$, filtered, and concentrated in vacuo. The crude product residue was purified by silica chromatography (2-40% EtOAc/hexanes as the gradient eluent) to afford the title compound (142 mg, 78% yield). MS (apci) m/z=501.2 (M+H).

Step 2: Preparation of Tert-Butyl 4-(5-(3-cyano-6-ethynylpyrazolo[1,5-a]pyridin-4-yl)pyridin-2-yl)piperazine-1-carboxylate A solution of tert-butyl 4-(5-(3-cyano-6-((trimethyl silyl)ethynyl)pyrazolo[1,5-a]pyridin-4-yl)pyridin-2-yl)piperazine-1-carboxylate (140 mg, 0.280 mmol) in MeOH (2.8 mL) was treated with powdered K$_2$CO$_3$ (11.6 mg, 0.0839 mmol). The resulting mixture was stirred for 3 h at ambient temperature, before concentrating the mixture in vacuo. The resulting residue was partitioned between EtOAc (50 mL) and water (10 mL). The organic extracts were dried over anhydrous MgSO$_4$, filtered, and concentrated in vacuo. The crude product residue was purified by silica chromatography (10-70% acetone/DCM as the gradient eluent) to afford the title compound (121.3 mg, quantitative yield). MS (apci) m/z=492.2 (M+H).

Step 3: Preparation of Tert-Butyl 4-(5-(3-cyano-6-(1-methyl-1H-1,2,3-triazol-4-yl)pyrazolo[1,5-a]pyridin-4-yl)pyridin-2-yl)piperazine-1-carboxylate A slurry of tert-butyl 4-(5-(3-cyano-6-ethynylpyrazolo[1,5-a]pyridin-4-yl)pyridin-2-yl)piperazine-1-carboxylate (55 mg, 0.13 mmol) in 1:1 t-BuOH:H$_2$O (2 mL) was treated with CuSO$_4$ (4.1 mg, 0.026 mmol), sodium (R)-5-((S)-1,2-dihydroxyethyl)-4-hydroxy-2-oxo-2,5-dihydrofuran-3-olate (13 mg, 0.064 mmol) and (azidomethyl)trimethylsilane (17 mg, 0.13 mmol). The resulting reaction mixture was stirred for 15 h at ambient temperature before introducing additional (azidomethyl)trimethylsilane (10 mg, 0.076 mmol), and sodium (R)-5-((S)-1,2-dihydroxyethyl)-4-hydroxy-2-oxo-2,5-dihydrofuran-3-olate (13 mg, 0.064 mmol), CuSO$_4$ (4.1 mg, 0.026 mmol). The mixture then was stirred for an additional 3 d at ambient temperature before diluting the mixture with water (20 mL). The aqueous mixture was extracted with EtOAc (3×30 mL). The combined organic extracts were dried over anhydrous MgSO$_4$, filtered, and concentrated in vacuo to afford the intermediate tert-butyl 4-(5-(3-cyano-6-(1-((trimethylsilyl)methyl)-1H-1,2,3-triazol-4-yl)pyrazolo[1,5-a]pyridin-4-yl)pyridin-2-yl)piperazine-1-carboxylate (MS apci (m/z)=558.3 (M+H)) and unreacted alkyne. The crude mixture was dissolved in THF (2 mL), and treated with 1 M TBAF in THF (128 μL, 0.13 mmol). The resulting reaction mixture was stirred for 2 h at ambient temperature, then diluted with EtOAc (30 mL) and washed with water (10 mL). The organic extracts were washed with brine (10 mL), dried over anhydrous MgSO$_4$, filtered, and concentrated in vacuo to afford a 2:1 mixture of the title compound (about 41 mg, 66% yield, based on LCMS % and total mass; MS (apci) m/z=486.2 (M+H)) and some unreacted alkyne. The crude mixture was used in the next step without purification.

Step 4: Preparation of 6-(1-methyl-1H-1,2,3-triazol-4-yl)-4-(6-(piperazin-1-yl)pyridin-3-yl)pyrazolo[1,5-a]pyridine-3-carbonitrile 2,2,2-trifluoroacetate A solution of the impure tert-butyl 4-(5-(3-cyano-6-(1-methyl-1H-1,2,3-triazol-4-yl)pyrazolo[1,5-a]pyridin-4-yl)pyridin-2-yl)piperazine-1-carboxylate (41 mg, 0.084 mmol) in TFA (2 mL) was stirred for 1 h at ambient temperature, and then concentrated in vacuo to afford the title compound in a 2:1 ratio with the unreacted alkyne carried over from Step 3. The TFA salt of the pure title compound (27 mg, 42% overall yield from Step 2) was isolated by purification of the impure mixture by C18 reverse-phase chromatography (5-95% ACN/water with 0.1% TFA as the gradient eluent). MS (apci) m/z=385.9, 386.9 (M+H).

Example 727

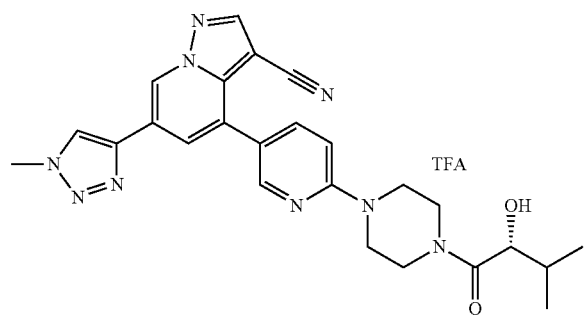 [SMILES: CC(C)[C@@H](O)C(=O)N1CCN(c2ccc(-c3cc(-c4cn(C)nn4)cn4ncc(C#N)c34)cn2)CC1 ; "TFA"]

(R)-4-(6-(4-(2-hydroxy-3-methylbutanoyl)piperazin-1-yl)pyridin-3-yl)-6-(1-methyl-1H-1,2,3-triazol-4-yl)pyrazolo[1,5-a]pyridine-3-carbonitrile 2,2,2-trifluoroacetate Step 1: Preparation of 6-(1-methyl-1H-1,2,3-triazol-4-yl)-4-(6-(piperazin-1-yl)pyridin-3-yl)pyrazolo[1,5-a]pyridine-3-carbonitrile hydrochloride A solution of 6-(1-methyl-1H-1,2,3-triazol-4-yl)-4-(6-(piperazin-1-yl)pyridin-3-yl)pyrazolo[1,5-a]pyridine-3-carbonitrile 2,2,2-trifluoroacetate (Example 726, Step 4; 27 mg, 0.0541 mmol) in 4 N HCl in dioxane (2 mL) was stirred for 5 min at ambient temperature. The mixture was concentrated in vacuo, azeotroping with MeOH, to afford the title compound (22 mg, 96% yield). This material was used directly in Step 2 without further purification or analysis.

Step 2: Preparation of (R)-4-(6-(4-(2-hydroxy-3-methylbutanoyl)piperazin-1-yl)pyridin-3-yl)-6-(1-methyl-1H-1,2,3-triazol-4-yl)pyrazolo[1,5-a]pyridine-3-carbonitrile 2,2,2-trifluoroacetate A suspension of 6-(1-methyl-1H-1,2,3-triazol-4-yl)-4-(6-(piperazin-1-yl)pyridin-3-yl)pyrazolo[1,5-a]pyridine-3-carbonitrile hydrochloride (22 mg, 0.0521 mmol) in DMF (1.5 mL) was treated with DIEA (45.4 µL, 0.261 mmol), D-alpha-Hydroxyisovaleric acid (7.39 mg, 0.0626 mmol) and HATU (23.8 mg, 0.0626 mmol). The resulting solution was stirred overnight at ambient temperature. The reaction mixture was diluted with 5% MeOH/DCM (20 mL) and washed with water (5 mL). The organic extracts were dried over anhydrous MgSO4, filtered, and concentrated in vacuo. The crude residue was triturated with 2:1 MeOH:TFA (2.25 mL). The precipitate that formed was collected by filtration, then rinsed with ACN (0.5 mL) and dried in vacuo to cleanly afford the title compound as the trifluoroacetate salt (12 mg, 38% yield). MS (apci) m/z=485.8, 486.9 (M+H).

Example 728

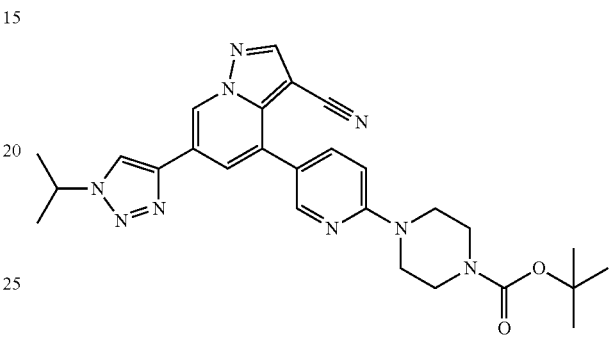

Tert-Butyl 4-(5-(3-cyano-6-(1-isopropyl-1H-1,2,3-triazol-4-yl)pyrazolo[1,5-a]pyridin-4-yl)pyridin-2-yl)piperazine-1-carboxylate Step 1: Preparation of 4-methoxy-6-((trimethylsilyl)ethynyl)pyrazolo[1,5-a]pyridine-3-carbonitrile In a pressure tube, a mixture of 6-bromo-4-methoxypyrazolo[1,5-a]pyridine-3-carbonitrile (Intermediate P4; 1.0 g, 3.97 mmol), Cu(I)I (0.151 g, 0.793 mmol), PdCl2(PPh3)2 (0.278 g, 0.397 mmol), TEA (1.66 mL, 11.9 mmol), and PPh3 (52 mg, 0.198 mmol) in DMF (16 mL) was sparged for 5 min with N2(g). The sparged mixture was treated with ethynyltrimethylsilane (659 µL, 4.76 mmol) and flushed with N2(g), before sealing the vessel. The reaction mixture was stirred for 6 h at 65° C., then overnight at ambient temperature. At room temperature, the reaction mixture was poured into water (20 mL), and extracted with EtOAc (2×50 mL). The combined organic extracts were washed with brine (10 mL), then dried over anhydrous MgSO4, filtered, and concentrated in vacuo. The crude product residue was purified by silica chromatography (2-40% EtOAc/hexanes as the gradient eluent) to afford the title compound (700 mg, 66% yield). $^1$H NMR (400 MHz, CDCl3) δ 8.30 (d, J=0.78 Hz, 1H), 8.16 (s, 1H), 6.64 (d, J=0.78 Hz, 1H), 4.02 (s, 3H), 0.26 (s, 9H)

Step 2: Preparation of 6-ethynyl-4-methoxypyrazolo[1,5-a]pyridine-3-carbonitrile A solution of 4-methoxy-6-((trimethylsilyl)ethynyl)pyrazolo[1,5-a]pyridine-3-carbonitrile (Step 1; 0.7 g, 2.60 mmol) in MeOH (26 mL) was treated with powdered K2CO3 (0.108 g, 0.780 mmol). The resulting mixture was stirred for 3 h at ambient temperature before concentrating the mixture in vacuo. The resulting residue was partitioned between EtOAc (100 mL) and water (30 mL). The organic extracts were dried over anhydrous MgSO4, filtered, and concentrated in vacuo to afford the title compound (530 mg, quantitative yield), which was carried on without further purification. $^1$H NMR (400 MHz, CDCl$_3$) δ 8.331 (d, J=1.17 Hz, 1H), 8.17 (s, 1H), 6.66 (d, J=0.78 Hz, 1H), 4.04 (s, 3H), 3.16 (s, 1H).

Step 3: Preparation of 6-(1-isopropyl-1H-1,2,3-triazol-4-yl)-4-methoxypyrazolo[1,5-a]pyridine-3-carbonitrile A mixture of isopropyl bromide (1.43 mL, 15.2 mmol) and sodium azide (989 mg, 15.2 mmol) in 1:2 t-BuOH:H$_2$O (3 mL) was stirred for 2 h at 80° C. After cooling to ambient temperature, the reaction mixture was treated with 6-ethynyl-4-methoxypyrazolo[1,5-a]pyridine-3-carbonitrile (300 mg, 1.52 mmol) and Cu(I)I (29.0 mg, 0.152 mmol). The resulting reaction mixture was stirred for 16 h at 80° C. The mixture was cooled to ambient temperature, diluted with EtOAc (100 mL) and washed with water (30 mL). The organic extracts were dried over anhydrous MgSO$_4$, filtered, and concentrated in vacuo. The crude residue was triturated with ACN. The precipitate that formed was collected by filtration, then rinsed with ACN and dried in vacuo to cleanly afford the title compound (294 mg, 69% yield). MS (apci) m/z=283.0 (M+H).

Step 4: Preparation of 4-hydroxy-6-(1-isopropyl-1H-1,2,3-triazol-4-yl)pyrazolo[1,5-a]pyridine-3-carbonitrile Two batches of 6-(1-Isopropyl-1H-1,2,3-triazol-4-yl)-4-methoxypyrazolo[1,5-a]pyridine-3-carbonitrile (total 290 mg) were processed as described below to provide the title compound.

Batch 1: 6-(1-Isopropyl-1H-1,2,3-triazol-4-yl)-4-methoxypyrazolo[1,5-a]pyridine-3-carbonitrile (150 mg, 0.531 mmol) was suspended in 1,2-dichloroethane (5.3 mL, 0.531 mmol) and heated to 80° C. At 50° C. the mixture became a clear solution. The resulting solution was cooled to 50° C. and treated with AlCl$_3$ (283 mg, 2.13 mmol) and heated at reflux for 4 h with vigorous stirring. The mixture was then allowed to stir at ambient temperature overnight and 80° C. for 3 h. The mixture was cooled to 0° C. and poured into a mixture of Na$_2$SO$_4$-10H$_2$O (3355 mg, 10.4 mmol) in THF (20 mL).

Batch 2: A second batch of 6-(1-Isopropyl-1H-1,2,3-triazol-4-yl)-4-methoxypyrazolo[1,5-a]pyridine-3-carbonitrile (140 mg) was also processed as described above to obtain a second crude batch of the title compound. The crude products obtained from the two reactions were combined and purified by silica chromatography (1-10% MeOH/DCM) to provide the title compound (200 mg, 71.6% yield, from 290 mg of starting material). MS (APCI+) m/z 269.1 (M+1).

Step 5: Preparation of 3-cyano-6-(1-isopropyl-1H-1,2,3-triazol-4-yl)pyrazolo[1,5-a]pyridin-4-yl Trifluoromethanesulfonate An ambient temperature solution of 4-hydroxy-6-(1-isopropyl-1H-1,2,3-triazol-4-yl)pyrazolo[1,5-a]pyridine-3-carbonitrile (200 mg, 0.746 mmol) and DIEA (649 µL, 3.73 mmol) in THF (7.46 µL) was treated with 1,1,1-trifluoro-N-phenyl-N—((trifluoromethyl)sulfonyl)methanesulfonamide (533 mg, 1.49 mmol). The resulting mixture was stirred for 6 h at ambient temperature, and then stored in the freezer 3 d. The mixture was poured into water (20 mL), and extracted with DCM (100 mL). The organic extracts were dried over anhydrous MgSO$_4$, filtered, and concentrated in vacuo. The residue obtained was purified by silica chromatography (10-90% EtOAc/hexane as the gradient eluent) to afford the title compound (220 mg, 74% yield). $^1$H NMR (400 MHz, CDCl$_3$) δ 9.08 (d, J=0.74 Hz, 1H), 8.31 (s, 1H), 7.91 (d, J=0.78, 1H), 7.86 (s, 1H), 4.95-4.88 (m, 1H), 1.65 (d, 6H).

Step 6: Preparation tert-butyl 4-(5-(3-cyano-6-(1-isopropyl-1H-1,2,3-triazol-4-yl)pyrazolo[1,5-a]pyridin-4-yl)pyridin-2-yl)piperazine-1-carboxylate In a pressure tube, a mixture of 3-cyano-6-(1-isopropyl-1H-1,2,3-triazol-4-yl)pyrazolo[1,5-a]pyridin-4-yl trifluoromethanesulfonate (50 mg, 0.12 mmol), tert-butyl 4-(5-(4,4,5,5-tetramethyl-1,3,2-dioxaborolan-2-yl)pyridin-2-yl)piperazine-1-carboxylate (49 mg, 0.12 mmol), Pd$_2$(dba)$_3$.CHCl$_3$ (6.5 mg, 0.0062 mmol), XPhos (12 mg, 0.025 mmol), K$_2$CO$_{3(s)}$ (52 mg, 0.37 mmol) in 4:1 dioxane/water (1.25 mL) was sparged for 5 min with N$_{2(g)}$, and subsequently the vessel was sealed. The reaction mixture was stirred overnight at 100° C. After cooling to room temperature, the reaction mixture was diluted with DCM (20 mL) and washed with water (5 mL). The organic extracts were dried over anhydrous MgSO$_4$, filtered, and concentrated in vacuo. The residue obtained was purified by silica chromatography (1-40% acetone/DCM as the gradient eluent) to afford the title compound (60 mg, 94% yield). MS (apci) m/z=513.8 (M+H).

Example 729

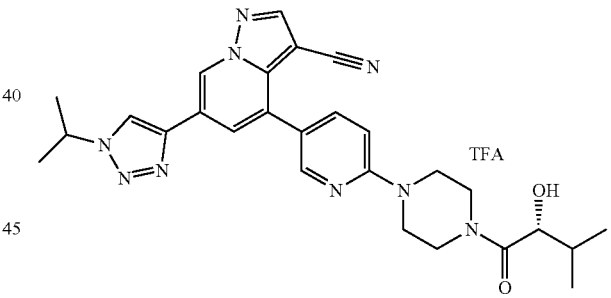

(R)-4-(6-(4-(2-hydroxy-3-methylbutanoyl)piperazin-1-yl)pyridin-3-yl)-6-(1-isopropyl-1H-1,2,3-triazol-4-yl)pyrazolo[1,5-a]pyridine-3-carbonitrile 2,2,2-trifluoroacetate Step 1: Preparation of 6-(1-isopropyl-1H-1,2,3-triazol-4-yl)-4-(6-(piperazin-1-yl)pyridin-3-yl)pyrazolo[1,5-a]pyridine-3-carbonitrile Hydrochloride A solution of tert-butyl 4-(5-(3-cyano-6-(1-isopropyl-1H-1,2,3-triazol-4-yl)pyrazolo[1,5-a]pyridin-4-yl)pyridin-2-yl)piperazine-1-carboxylate (Example 728, Step 6; 59 mg, 0.11 mmol) in TFA (2 mL) was stirred for 1 h at ambient temperature. The resulting mixture was concentrated in vacuo. The residue was dissolved in DCM (1 mL) and treated with 4 N HCl in dioxane (2 mL). The resulting suspension was stirred for 10 min at ambient temperature and then concentrated in vacuo to afford the title compound (55 mg, quantitative yield). MS (apci) m/z=413.9 (M+H).

Step 2: Preparation of (R)-4-(6-(4-(2-hydroxy-3-methylbutanoyl)piperazin-1-yl)pyridin-3-yl)-6-(1-isopropyl-1H-1,2,3-triazol-4-yl)pyrazolo[1,5-a]pyridine-3-carbonitrile 2,2,2-trifluoroacetate A suspension of 6-(1-isopropyl-1H-1,2,3-triazol-4-yl)-4-(6-(piperazin-1-yl)pyridin-3-yl)pyrazolo[1,5-a]pyridine-3-carbonitrile hydrochloride (50 mg, 0.111 mmol) in DMF (1.5 mL) was treated with DIEA (96.8 µL, 0.556 mmol), D-alpha-Hydroxyisovaleric acid (15.8 mg, 0.133 mmol) and HATU (50.7 mg, 0.133 mmol). The resulting solution was stirred overnight at ambient temperature. The reaction mixture was diluted with 5% MeOH/DCM (20 mL), and washed with water (5 mL). The organic extracts were dried over anhydrous MgSO$_4$, filtered, and concentrated in vacuo. The crude residue was purified by C18 reverse-phase chromatography (5-95% ACN/water with 0.1% TFA as the gradient eluent) to cleanly afford the title compound as the trifluoroacetate salt (12 mg, 17% yield). MS (apci) m/z=513.9 (M+H).

Example 730

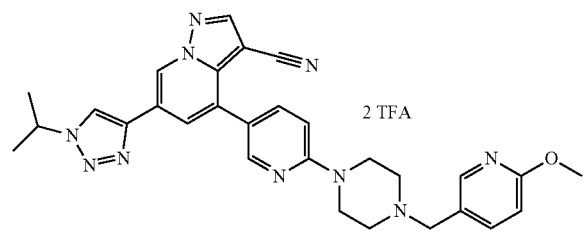 [SMILES: COc1ccc(CN2CCN(c3ccc(-c4cc(-c5cn(C(C)C)nn5)cn5ncc(C#N)c45)cn3)CC2)cn1]

6-(1-isopropyl-1H-1,2,3-triazol-4-yl)-4-(6-(4-((6-methoxypyridin-3-yl)methyl)piperazin-1-yl)pyridin-3-yl)pyrazolo[1,5-a]pyridine-3-carbonitrile bis(2,2,2-trifluoroacetate)

In a pressure tube, a mixture of 3-cyano-6-(1-isopropyl-1H-1,2,3-triazol-4-yl)pyrazolo[1,5-a]pyridin-4-yl trifluoromethanesulfonate (Example 728, Step 5; 50 mg, 0.12 mmol), 1-((6-methoxypyridin-3-yl)methyl)-4-(5-(4,4,5,5-tetramethyl-1,3,2-dioxaborolan-2-yl)pyridin-2-yl)piperazine (Example 697, Step 3; 61 mg, 0.15 mmol), Pd$_2$(dba)$_3$.CHCl$_3$ (6.5 mg, 0.0062 mmol), XPhos (12 mg, 0.025 mmol), K$_2$CO$_{3(s)}$ (52 mg, 0.37 mmol) in 4:1 dioxane/water (1.25 mL) was sparged for 5 min with N$_{2(g)}$, and subsequently the vessel was sealed. The reaction mixture was stirred overnight at 100° C. After cooling to room temperature, the reaction mixture was diluted with 5% MeOH/DCM (20 mL), and washed with water (5 mL). The organic extracts were dried over anhydrous MgSO$_4$, filtered, and concentrated in vacuo. The residue obtained was purified by silica chromatography (5-70% acetone/DCM as the gradient eluent), and then again by C18 reverse-phase chromatography (5-95% ACN/water with 0.1% TFA as the gradient eluent) to afford the title compound as the bistrifluoroacetate salt (55 mg, 58% yield). MS (apci) m/z=534.8, 535.8 (M+H).

Example 731

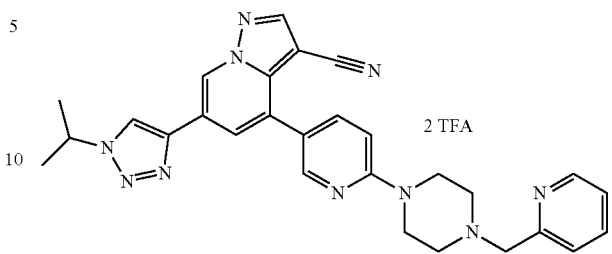

6-(1-isopropyl-1H-1,2,3-triazol-4-yl)-4-(6-(4-(pyridin-2-ylmethyl)piperazin-1-yl)pyridin-3-yl)pyrazolo[1,5-a]pyridine-3-carbonitrile bis(2,2,2-trifluoroacetate)

Step 1: Preparation of 1-(pyridin-2-ylmethyl)-4-(5-(4,4,5,5-tetramethyl-1,3,2-dioxaborolan-2-yl)pyridin-2-yl)piperazine A solution of 1-(5-(4,4,5,5-tetramethyl-1,3,2-dioxaborolan-2-yl)pyridin-2-yl)piperazine (3 g, 10.4 mmol), in DCM (85 mL) was treated with picolinaldehyde (1.22 g, 11.4 mmol). The resulting mixture was stirred for 1 h at ambient temperature before introducing NaBH(OAc)$_3$ (4.40 g, 20.7 mmol). The resulting mixture was stirred overnight at ambient temperature, and then concentrated in vacuo. The residue was dissolved in EtOAc, and washed sequentially with saturated NaHCO$_{3(aq)}$ and brine. The organic extracts were dried over anhydrous Na$_2$SO$_4$, filtered, and concentrated in vacuo. The resulting thick oil was dissolved in minimal boiling EtOAc, and the resulting solution was allowed to cool. The crystals that formed were collected by vacuum filtration, washed with hexanes and dried under high vacuum to cleanly afford the title compound (2.88 g, 73% yield). $^1$H NMR (CDCl$_3$) δ 8.58-8.59 (m, 1H), 8.53 (m, 1H), 7.79-7.82 (m, 1H), 7.65-7.69 (m, 1H), 7.43-7.45 (m, 1H), 7.16-7.20 (m, 1H), 6.56-6.59 (m, 1H), 3.71 (s, 2H), 3.65 (t, 4H), 2.61 (t, 4H), 1.31 (s, 12H).

Step 2: Preparation of 6-(1-isopropyl-1H-1,2,3-triazol-4-yl)-4-(6-(4-(pyridin-2-ylmethyl)piperazin-1-yl)pyridin-3-yl)pyrazolo[1,5-a]pyridine-3-carbonitrile bis(2,2,2-trifluoroacetate)

In a pressure tube, a mixture of 3-cyano-6-(1-isopropyl-1H-1,2,3-triazol-4-yl)pyrazolo[1,5-a]pyridin-4-yl trifluoromethanesulfonate (Example 728, Step 5; 50 mg, 0.12 mmol), 1-(pyridin-2-ylmethyl)-4-(5-(4,4,5,5-tetramethyl-1,3,2-dioxaborolan-2-yl)pyridin-2-yl)piperazine (Step 1; 57 mg, 0.15 mmol), Pd$_2$(dba)$_3$.CHCl$_3$ (6.5 mg, 0.0062 mmol), XPhos (12 mg, 0.025 mmol), K$_2$CO$_{3(s)}$ (52 mg, 0.37 mmol) in 4:1 dioxane/water (1.25 mL) was sparged for 5 min with N$_{2(g)}$, and subsequently the vessel was sealed. The reaction mixture was stirred overnight at 90° C. After cooling to room temperature, the reaction mixture was diluted with 5% MeOH/DCM (20 mL), and washed with water (5 mL). The organic layer was dried over anhydrous MgSO$_4$, filtered, and concentrated in vacuo. The residue obtained was purified by C18 reverse-phase chromatography (5-80% ACN/water with 0.1% TFA as the gradient eluent) to afford the title

Example 732

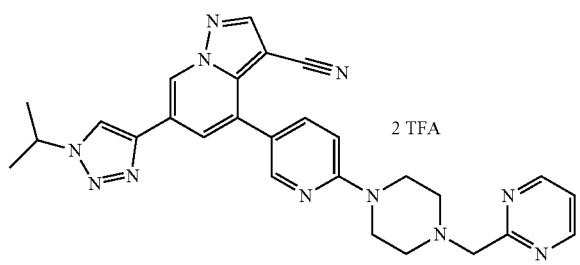 [SMILES: CC(C)n1cc(-c2cc(-c3ccc(N4CCN(Cc5ncccn5)CC4)nc3)c3c(C#N)cnn3c2)nn1]

6-(1-isopropyl-1H-1,2,3-triazol-4-yl)-4-(6-(4-(pyrimidin-2-ylmethyl)piperazin-1-yl)pyridin-3-yl)pyrazolo[1,5-a]pyridine-3-carbonitrile bis(2,2,2-trifluoroacetate)

Step 1: Preparation of 2-((4-(5-(4,4,5,5-tetramethyl-1,3,2-dioxaborolan-2-yl)pyridin-2-yl)piperazin-1-yl)methyl)pyrimidine A solution of 1-(5-(4,4,5,5-tetramethyl-1,3,2-dioxaborolan-2-yl)pyridin-2-yl)piperazine (1.0 g, 3.5 mmol), 2-(chloromethyl)pyrimidine hydrochloride (0.68 g, 4.1 mmol), and $Cs_2CO_3$ (2.8 g, 8.6 mmol) in DMF (6 mL) was stirred overnight at ambient temperature, and then at 50° C. until LCMS indicated reaction completion. After cooling to ambient temperature, the reaction mixture was diluted with MTBE (20 mL), and extracted sequentially with 1:1 water: saturated $NaHCO_{3(aq)}$ (5 mL) and brine (3×5 mL). The organic extracts were dried over anhydrous $MgSO_4$, filtered, and concentrated in vacuo. The residue obtained was purified by silica chromatography (1-25% DCM-MeOH as the gradient eluent) to afford the title compound (500 mg, 38% yield). $^1$H NMR (400 MHz, $CDCl_3$) δ 8.76-8.75 (d, 2H), 8.54-8.53 (d, 1H), 7.82-7.79 (dd, 1H), 7.22-7.20 (t, 1H), 6.59-6.57 (d, 1H), 3.88 (s, 2H), 3.71-3.68 (m, 4H), 2.70-2.68 (m, 4H), 1.31 (s, 12H).

Step 2: Preparation of 6-(1-isopropyl-1H-1,2,3-triazol-4-yl)-4-(6-(4-(pyrimidin-2-ylmethyl)piperazin-1-yl)pyridin-3-yl)pyrazolo[1,5-a]pyridine-3-carbonitrile bis(2,2,2-trifluoroacetate)

In a pressure tube, a mixture of 3-cyano-6-(1-isopropyl-1H-1,2,3-triazol-4-yl)pyrazolo[1,5-a]pyridin-4-yl trifluoromethanesulfonate (Example 728, Step 5; 50 mg, 0.12 mmol), 2-((4-(5-(4,4,5,5-tetramethyl-1,3,2-dioxaborolan-2-yl)pyridin-2-yl)piperazin-1-yl)methyl)pyrimidine (Step 1; 57 mg, 0.15 mmol), $Pd_2(dba)_3 \cdot CHCl_3$ (6.5 mg, 0.0062 mmol), XPhos (12 mg, 0.025 mmol), and $K_2CO_{3(s)}$ (52 mg, 0.37 mmol) in 4:1 dioxane/water (1.25 mL) was sparged for 5 min with $N_{2(g)}$, and the vessel was sealed. The reaction mixture was stirred overnight at 100° C. After cooling to room temperature, the reaction mixture was diluted with 5% MeOH/DCM (20 mL), and washed with water (5 mL). The organic extracts were dried over anhydrous $MgSO_4$, filtered, and concentrated in vacuo. The residue obtained was purified by C18 reverse-phase chromatography (5-80% ACN/water with 0.1% TFA as the gradient eluent) to afford the title compound as the bistrifluoroacetate salt (42 mg, 46% yield). MS (apci) m/z=505.8, 506.8 (M+H).

Example 733

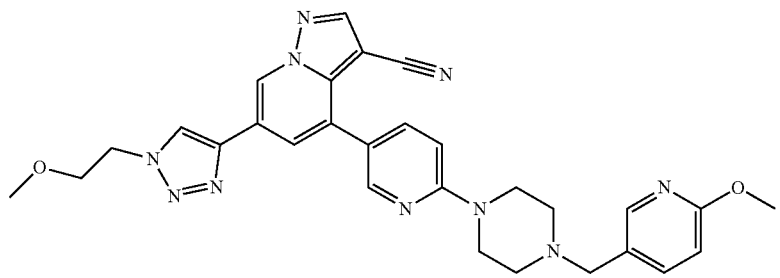

6-(1-(2-methoxyethyl)-1H-1,2,3-triazol-4-yl)-4-(6-(4-((6-methoxypyridin-3-yl)methyl)piperazin-1-yl)pyridin-3-yl)pyrazolo[1,5-a]pyridine-3-carbonitrile

Step 1: Preparation of 6-bromo-4-(methoxymethoxy)pyrazolo[1,5-a]pyridine-3-carbonitrile A solution of 6-bromo-4-hydroxypyrazolo[1,5-a]pyridine-3-carbonitrile (Intermediate P17; 2.0 g, 8.40 mmol) in DMA (33.6 mL) was treated with $K_2CO_{3(s)}$ (3.48 g, 25.2 mmol), and stirred for 10 min at ambient temperature before reducing the temperature to 0° C. The 0° C. mixture then was treated dropwise with chloro(methoxy)methane (0.766 mL, 10.1 mmol). After stirring the resultant mixture for 10 min at 0° C., the mixture was stirred overnight at ambient temperature. The reaction mixture was poured into ice water (300 mL) and stirred for 1 h at ambient temperature. The resulting suspension was filtered, and the isolated solids were rinse with water and reserved. The filtrate was extracted with DCM (4×50 mL). The combined organic extracts were dried over anhydrous $MgSO_4$, filtered, and concentrated in vacuo. The crude product residue was triturated with ACN/Hexanes. The solid from the trituration was combined with the reserved solids to afford the title compound (2.34 mg, 99% yield). $^1$H NMR (400 MHz, $CDCl_3$) δ 8.36 (d, J=1.17 Hz, 1H), 8.137 (s, 1H), 7.09 (d, J=1.17 Hz, 1H), 5.38 (s, 2H), 3.56 (s, 3H).

Step 2: Preparation of 4-(methoxymethoxy)-6-((trimethylsilyl)ethynyl)pyrazolo[1,5-a]pyridine-3-carbonitrile A solution of 6-bromo-4-(methoxymethoxy)pyrazolo[1,5-a]pyridine-3-carbonitrile (1.22 g, 4.32 mmol), Cu(I)I (0.165 g, 0.865 mmol), PdCl$_2$(PPh$_3$)$_2$ (0.304 g, 0.432 mmol), TEA (1.81 mL, 13.0 mmol), and PPh$_3$ (56.7 mg, 0.216 mmol) in DMF (17 mL) was sparged for 5 min with N$_{2(g)}$. The sparged mixture was treated with ethynyltrimethylsilane (659 µL, 4.76 mmol), and sparged again for 5 min with N$_{2(g)}$. The reaction mixture was stirred under a N$_{2(g)}$ atmosphere for 5 h at ambient temperature. The resulting mixture was poured into water (50 mL) and extracted with EtOAc (3×70 mL). The combined organic extracts were washed with brine (20 mL), then dried over anhydrous MgSO$_4$, filtered, and concentrated in vacuo. The crude product residue was purified by silica chromatography (1-25% EtOAc/hexanes as the gradient eluent) to afford the title compound (1.1 g, 85% yield). $^1$H NMR (400 MHz, CDCl$_3$) δ 8.34 (d, J=1.17 Hz, 1H), 8.17 (s, 1H), 6.96 (d, J=1.17 Hz, 1H), 5.38 (s, 2H), 3.56 (s, 3H), 0.253 (s, 9H).

Step 3: Preparation of 6-ethynyl-4-(methoxymethoxy)pyrazolo[1,5-a]pyridine-3-carbonitrile A solution of 4-(methoxymethoxy)-6-((trimethylsilyl)ethynyl)pyrazolo[1,5-a]pyridine-3-carbonitrile (1.1 g, 3.67 mmol) in MeOH (37 mL) was treated with powdered K$_2$CO$_3$ (0.152 g, 1.10 mmol). The resulting mixture was stirred overnight at ambient temperature, before concentrating the mixture in vacuo. The resulting residue was partitioned between EtOAc (150 mL) and water (30 mL). The organic extracts were dried over anhydrous MgSO$_4$, filtered, and concentrated in vacuo. The crude product residue was purified by silica chromatography (1-40% EtOAc/Hexanes as the gradient eluent) to afford the title compound (760 mg, 91% yield). $^1$H NMR (400 MHz, CDCl$_3$) δ 8.37 (d, J=0.78 Hz, 1H), 8.19 (s, 1H), 7.00 (d, J=1.17 Hz, 1H), 5.38 (s, 2H), 3.56 (s, 3H), 3.16 (s, 1H).

Step 4: Preparation of 6-(1-(2-methoxyethyl)-1H-1,2,3-triazol-4-yl)-4-(methoxymethoxy)pyrazolo[1,5-a]pyridine-3-carbonitrile A mixture of 1-bromo-2-methoxyethane (901.6 µL, 9.59 mmol) and sodium azide (623.7 mg, 9.59 mmol) in 1:2 t-BuOH:H$_2$O (1.92 mL) was stirred for 2 h at 80° C. After cooling to ambient temperature, the reaction mixture was treated with 6-ethynyl-4-(methoxymethoxy)pyrazolo[1,5-a]pyridine-3-carbonitrile (218 mg, 0.96 mmol) and Cu(I)I (18.27 mg, 0.096 mmol). The resulting reaction mixture was stirred for 1 h at 80° C. The mixture was cooled to ambient temperature and diluted with water (50 mL). The resulting suspension was stirred for 30 min at ambient temperature. The precipitate that formed was collected by filtration, then rinsed with water (2×10 mL), and dried in vacuo to cleanly afford the title compound (316 mg, 100% yield). MS (apci) m/z=328.9, 329.9 (M+H).

Step 5: Preparation of 4-hydroxy-6-(1-(2-methoxyethyl)-1H-1,2,3-triazol-4-yl)pyrazolo[1,5-a]pyridine-3-carbonitrile Hydrochloride A suspension of 6-(1-(2-methoxyethyl)-1H-1,2,3-triazol-4-yl)-4-(methoxymethoxy)pyrazolo[1,5-a]pyridine-3-carbonitrile (315 mg, 0.959 mmol) in THF (4 mL) was treated with 4 N HCl$_{(aq)}$ and stirred overnight at ambient temperature. The mixture was concentrated in vacuo and the residue was dried under high vacuum to afford the title compound as the hydrochloride salt (257 mg, 84% yield). MS (apci) m/z=284.9 (M+H).

Step 6: Preparation of 3-cyano-6-(1-(2-methoxyethyl)-1H-1,2,3-triazol-4-yl)pyrazolo[1,5-a]pyridin-4-yl Trifluoromethanesulfonate An ambient temperature solution of 4-hydroxy-6-(1-(2-methoxyethyl)-1H-1,2,3-triazol-4-yl)pyrazolo[1,5-a]pyridine-3-carbonitrile hydrochloride (Step 5; 255 mg, 0.795 mmol) in THF (7.46 µL) was treated sequentially with DIEA (831 µL, 4.77 mmol) and 1,1,1-trifluoro-N-phenyl-N-((trifluoromethyl)sulfonyl)-methanesulfonamide (568 mg, 1.59 mmol). The resulting mixture was stirred for 2 h at ambient temperature. The mixture was poured into water (20 mL), and extracted with EtOAc (100 mL). The organic extracts were dried over anhydrous MgSO$_4$, filtered, and concentrated in vacuo. The residue obtained was purified by silica chromatography (1-55% acetone/DCM as the gradient eluent) to afford the title compound (380 mg, quantitative yield). $^1$H NMR (400 MHz, CDCl$_3$) δ 9.07 (d, J=1.17 Hz, 1H), 8.31 (s, 1H), 7.94 (d, J=1.17 Hz, 1H), 4.62 (m, 2H), 3.79 (m, 2H), 3.39 (s, 3H).

Step 7: Preparation 6-(1-(2-methoxyethyl)-1H-1,2,3-triazol-4-yl)-4-(6-(4-((6-methoxypyridin-3-yl)methyl)piperazin-1-yl)pyridin-3-yl)pyrazolo[1,5-a]pyridine-3-carbonitrile In a pressure tube, a mixture of 3-cyano-6-(1-(2-methoxyethyl)-1H-1,2,3-triazol-4-yl)pyrazolo[1,5-a]pyridin-4-yl trifluoromethanesulfonate (50 mg, 0.12 mmol), 1-((6-methoxypyridin-3-yl)methyl)-4-(5-(4,4,5,5-tetramethyl-1,3,2-dioxaborolan-2-yl)pyridin-2-yl)piperazine (Example 697, Step 3; 59 mg, 0.14 mmol), Pd$_2$(dba)$_3$ (6.2 mg, 0.0060 mmol), XPhos (11 mg, 0.024 mmol), K$_2$CO$_{3(s)}$ (50 mg, 0.36 mmol) in 4:1 dioxane/water (1.20 mL) was sparged for 5 min with N$_{2(g)}$, and subsequently the vessel was sealed. The reaction mixture was stirred overnight at 100° C. After cooling to room temperature, the reaction mixture was diluted with 5% MeOH/DCM (20 mL), and washed with water (5 mL). The organic extracts were dried over anhydrous MgSO$_4$, filtered, and concentrated in vacuo. The residue was purified by silica chromatography (5-70% acetone/DCM as the gradient eluent), and the isolated solids were triturated with MeOH to cleanly afford the title compound (4.5 mg, 7% yield). MS (apci) m/z=551.2 (M+H).

Example 734

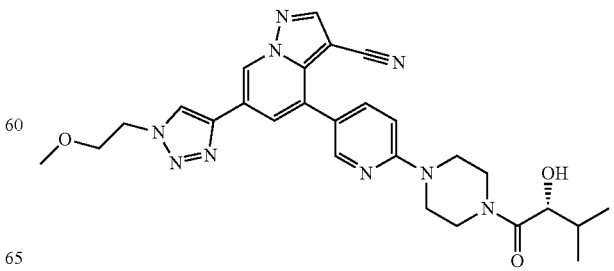

(R)-4-(6-(4-(2-hydroxy-3-methylbutanoyl)piperazin-1-yl)pyridin-3-yl)-6-(1-(2-methoxyethyl)-1H-1,2,3-triazol-4-yl)pyrazolo[1,5-a]pyridine-3-carbonitrile Step 1: Preparation of Tert-Butyl 4-(5-(3-cyano-6-(1-(2-methoxyethyl)-1H-1,2,3-triazol-4-yl)pyrazolo[1,5-a]pyridin-4-yl)pyridin-2-yl)piperazine-1-carboxylate In a pressure tube, a mixture of 3-cyano-6-(1-(2-methoxyethyl)-1H-1,2,3-triazol-4-yl)pyrazolo[1,5-a]pyridin-4-yl trifluoromethanesulfonate (Example 733, Step 6; 150 mg, 0.360 mmol), tert-butyl 4-(5-(4,4,5,5-tetramethyl-1,3,2-dioxaborolan-2-yl)pyridin-2-yl)piperazine-1-carboxylate (154 mg, 0.396 mmol), Pd$_2$(dba)$_3$·CHCl$_3$ (18.6 mg, 0.0180 mmol), XPhos (34.4 mg, 0.0721 mmol), and K$_2$CO$_{3(s)}$ (149 mg, 1.08 mmol) were combined in 4:1 dioxane/water (3.60 mL). The mixture was sparged for 5 min with N$_{2(g)}$, and the vessel was sealed. The reaction mixture was stirred overnight at 100° C. After cooling to room temperature, the reaction mixture was diluted with DCM (20 mL), and washed with water (5 mL). The organic extracts were dried over anhydrous MgSO$_4$, filtered, and concentrated in vacuo. The residue obtained was purified by silica chromatography (1-40% acetone/DCM as the gradient eluent), and subsequently the isolated solids were triturated with MeOH to cleanly afford the title compound (130 mg, 68% yield). MS (apci) m/z=530.2 (M+H).

Step 2: Preparation of 6-(1-(2-methoxyethyl)-1H-1,2,3-triazol-4-yl)-4-(6-(piperazin-1-yl)pyridin-3-yl)pyrazolo[1,5-a]pyridine-3-carbonitrile Dihydrochloride A solution of tert-butyl 4-(5-(3-cyano-6-(1-(2-methoxyethyl)-1H-1,2,3-triazol-4-yl)pyrazolo[1,5-a]pyridin-4-yl)pyridin-2-yl)piperazine-1-carboxylate (128 mg, 0.242 mmol) in TFA (3 mL) was stirred for 1 h at ambient temperature. The resulting mixture was concentrated in vacuo. The residue obtained was dissolved in DCM (1 mL) and treated with 4 N HCl in dioxane (3 mL). The resulting suspension was stirred for 5 min at ambient temperature before concentrating the mixture in vacuo to afford the title compound (130 mg, quantitative yield). MS (apci) m/z=430.2 (M+H).

Step 3: Preparation of (R)-4-(6-(4-(2-hydroxy-3-methylbutanoyl)piperazin-1-yl)pyridin-3-yl)-6-(1-(2-methoxyethyl)-1H-1,2,3-triazol-4-yl)pyrazolo[1,5-a]pyridine-3-carbonitrile A solution of 6-(1-(2-methoxyethyl)-1H-1,2,3-triazol-4-yl)-4-(6-(piperazin-1-yl)pyridin-3-yl)pyrazolo[1,5-a]pyridine-3-carbonitrile dihydrochloride (40 mg, 0.0796 mmol) in DMF (1.6 mL) was treated with D-alpha-Hydroxyisovaleric acid (11.3 mg, 0.0955 mmol), HATU (36.3 mg, 0.0955 mmol) and DIEA (69.3 µl, 0.398 mmol). The resulting solution was stirred overnight at ambient temperature. The reaction mixture was diluted with 5% MeOH/DCM (20 mL) and washed with water (5 mL). The organic extracts were dried over anhydrous MgSO$_4$, filtered, and concentrated in vacuo. The crude residue was purified by silica chromatography (1-55% acetone/DCM as the gradient eluent) to cleanly afford the title compound (2 mg, 5% yield). MS (apci) m/z=530.2 (M+H).

Example 735

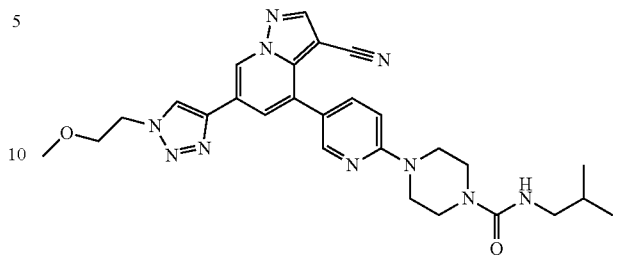

4-(5-(3-cyano-6-(1-(2-methoxyethyl)-1H-1,2,3-triazol-4-yl)pyrazolo[1,5-a]pyridin-4-yl)pyridin-2-yl)-N-isobutylpiperazine-1-carboxamide A solution of 6-(1-(2-methoxyethyl)-1H-1,2,3-triazol-4-yl)-4-(6-(piperazin-1-yl)pyridin-3-yl)pyrazolo[1,5-a]pyridine-3-carbonitrile dihydrochloride (Example 734, Step 2; 40 mg, 0.0796 mmol) in DCM (2.65 mL) was treated with TEA (66.6 µL, 0.478 mmol), and stirred for 15 min at ambient temperature. The reaction mixture was treated with 1-isocyanato-2-methylpropane (9.87 µL, 0.0876 mmol). The resulting mixture was stirred for 3 h at ambient temperature, before quenching with water (1 mL). The quenched reaction mixture was extracted with DCM (3×10 mL), and the combined organic extracts were dried over anhydrous MgSO$_4$, filtered, and concentrated in vacuo. The residue was triturated with MeOH (2 mL). The resulting solids were filtered, washed with additional MeOH (1 mL) and dried in vacuo to cleanly afford the title compound (2 mg, 5% yield). MS (apci) m/z=529.2 (M+H).

Example 736

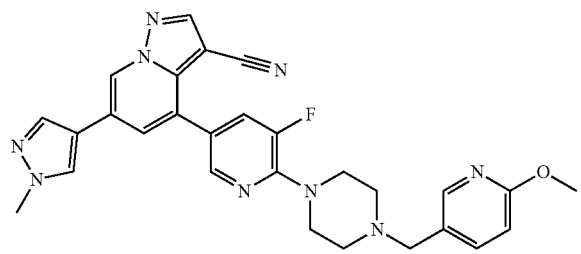 [SMILES: COc1ccc(CN2CCN(c3ncc(-c4cc(-c5cnn(C)c5)cn5ncc(C#N)c45)cc3F)CC2)cn1]

4-(5-fluoro-6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile Step 1: Preparation of 4-(5,6-difluoropyridin-3-yl)-6-(1-methyl-1H-pyrazol-4-yl)pyrazolo[1,5-a]pyridine-3-carbonitrile A mixture of 3-cyano-6-(1-methyl-1H-pyrazol-4-yl)pyrazolo[1,5-a]pyridin-4-yl trifluoromethanesulfonate (Intermediate P5; 150 mg, 0.404 mmol), (5,6-difluoropyridin-3-yl)boronic acid (89.9 mg, 0.566 mmol), Pd$_2$(dba)$_3$ (18.5 mg, 0.0202 mmol), XPhos (38.5 mg, 0.0808 mmol), and 2 M Na$_2$CO$_{3(aq)}$ (0.505 mL, 1.01 mmol) in dioxane (2.0 mL) was sparged for 5 min with argon. The vessel was sealed and the reaction mixture was stirred overnight at 90° C. After cooling to room temperature, the reaction mixture was purified directly by silica chromatography (1-10% DCM:MeOH as the gradient eluent) to cleanly afford the title compound (36 mg, 27% yield).

Step 2: Preparation of 4-(5-fluoro-6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile A mixture of 4-(5,6-difluoropyridin-3-yl)-6-(1-methyl-1H-pyrazol-4-yl)pyrazolo[1,5-a]pyridine-3-carbonitrile (0.036 g, 0.107 mmol), 1-((6-methoxypyridin-3-yl)methyl)piperazine (26.6 mg, 0.128 mmol) and K$_2$CO$_3$ (29.6 mg, 0.214 mmol) in DMSO (1.07 mL) was stirred overnight at 80° C. After cooling to ambient temperature, the reaction mixture was partitioned between DCM and water. The organic extracts were washed sequentially with water and brine, then dried over anhydrous Na$_2$SO$_4$, filtered, and concentrated in vacuo. The crude product residue was purified by C18 reverse-phase chromatography (5-95% ACN/water with 0.1% TFA as the gradient eluent) to afford the title compound as the TFA salt. The TFA salt was dissolved in DCM and extracted with saturated Na$_2$CO$_{3(aq)}$. The organic extracts were washed with brine, then dried over anhydrous Na$_2$SO$_4$, filtered, and concentrated in vacuo to afford the title compound (29.2 mg, 52% yield). MS (apci) m/z=524.2 (M+H).

Example 737

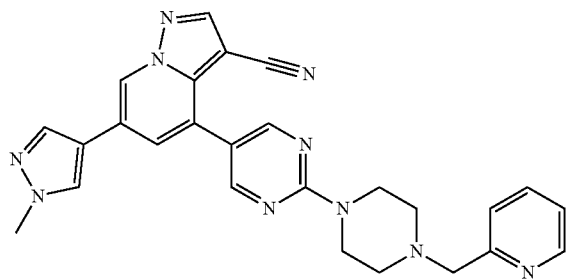 [SMILES: Cn1cc(-c2cc(-c3cnc(N4CCN(Cc5ccccn5)CC4)nc3)c3c(C#N)cnn3c2)cn1]

6-(1-methyl-1H-pyrazol-4-yl)-4-(2-(4-(pyridin-2-ylmethyl)piperazin-1-yl)pyrimidin-5-yl)pyrazolo[1,5-a]pyridine-3-carbonitrile A solution of 6-(1-methyl-1H-pyrazol-4-yl)-4-(2-(piperazin-1-yl)pyrimidin-5-yl)pyrazolo[1,5-a]pyridine-3-carbonitrile dihydrochloride (Example 281; 10 mg, 0.022 mmol) in DMA (0.1 mL) was treated sequentially with picolinaldehyde (3.0 mg, 0.028 mmol), Me$_4$N(AcO)$_3$BH (8.6 mg, 0.033 mmol) and TEA (9.1 μL, 0.065 mmol). The reaction mixture was stirred for 20 h at ambient temperature, and then directly purified by C18 reverse-phase chromatography (0-70% ACN/water as the gradient eluent) followed by C18 reverse-phase chromatography (0-70% ACN/water with 0.1% formic acid as the gradient eluent) to cleanly afford the title compound (1.2 mg, 12% yield). MS (apci) m/z=477.2 (M+H).

Example 738

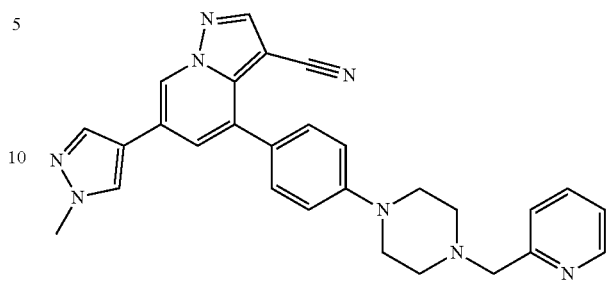

6-(1-methyl-1H-pyrazol-4-yl)-4-(4-(4-(pyridin-2-ylmethyl)piperazin-1-yl)phenyl)pyrazolo[1,5-a]pyridine-3-carbonitrile A solution of 6-(1-methyl-1H-pyrazol-4-yl)-4-(4-(piperazin-1-yl)phenyl)pyrazolo[1,5-a]pyridine-3-carbonitrile dihydrochloride (Example 291; 25 mg, 0.055 mmol) in DMA (0.1 mL) was treated sequentially with picolinaldehyde (7.6 mg, 0.071 mmol), Me$_4$N(AcO)$_3$BH (22 mg, 0.082 mmol) and TEA (23 μL, 0.16 mmol). The reaction mixture was stirred for 20 h at ambient temperature, and then directly purified by C18 reverse-phase chromatography (0-70% ACN/water as the gradient eluent) to afford the title compound (23 mg, 88% yield). MS (apci) m/z=475.2 (M+H).

Example 739

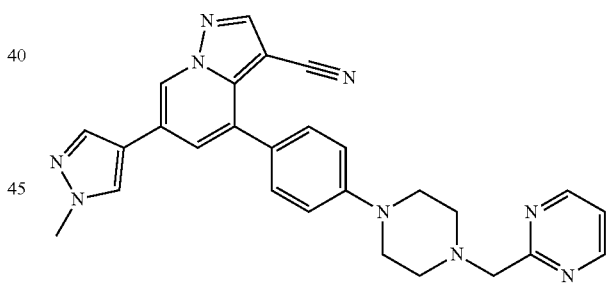

6-(1-methyl-1H-pyrazol-4-yl)-4-(4-(4-(pyrimidin-2-ylmethyl)piperazin-1-yl)phenyl)pyrazolo[1,5-a]pyridine-3-carbonitrile A solution of 6-(1-methyl-1H-pyrazol-4-yl)-4-(4-(piperazin-1-yl)phenyl)pyrazolo[1,5-a]pyridine-3-carbonitrile dihydrochloride (Example 291; 10 mg, 0.022 mmol) in DMA (0.1 mL) was treated sequentially with pyrimidine-2-carbaldehyde (3.1 mg, 0.028 mmol), Me$_4$N(AcO)$_3$BH (8.6 mg, 0.033 mmol) and TEA (9.2 μL, 0.066 mmol). The reaction mixture was stirred for 20 h at ambient temperature, and then directly purified by C18 reverse-phase chromatography (0-70% ACN/water as the gradient eluent) to afford the title compound (6.5 mg, 62% yield). MS (apci) m/z=476.2 (M+H).

Example 740

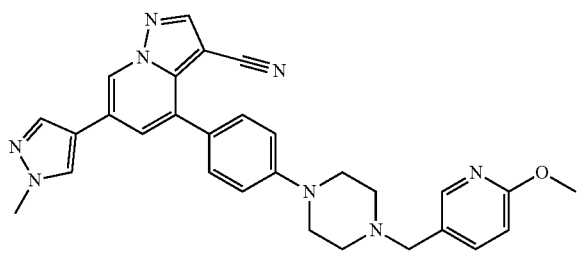 [SMILES: COc1ccc(CN2CCN(c3ccc(-c4cc(-c5cnn(C)c5)cn5ncc(C#N)c45)cc3)CC2)cn1]

4-(4-(4-((6-methoxypyridin-3-yl)methyl)piperazin-1-yl)phenyl)-6-(1-methyl-1H-pyrazol-4-yl)pyrazolo[1,5-a]pyridine-3-carbonitrile A solution of 6-(1-methyl-1H-pyrazol-4-yl)-4-(4-(piperazin-1-yl)phenyl)pyrazolo[1,5-a]pyridine-3-carbonitrile dihydrochloride (Example 291; 25 mg, 0.055 mmol) in DMA (0.1 mL) was treated sequentially with 6-methoxynicotinaldehyde (3.9 mg, 0.028 mmol), Me$_4$N(AcO)$_3$BH (8.6 mg, 0.033 mmol) and TEA (9.2 µL, 0.066 mmol). The reaction mixture was stirred for 20 h at ambient temperature, and then directly purified by C18 reverse-phase chromatography (0-65% ACN/water as the gradient eluent) to afford the title compound (2.3 mg, 21% yield). MS (apci) m/z=505.2 (M+H).

Example 741

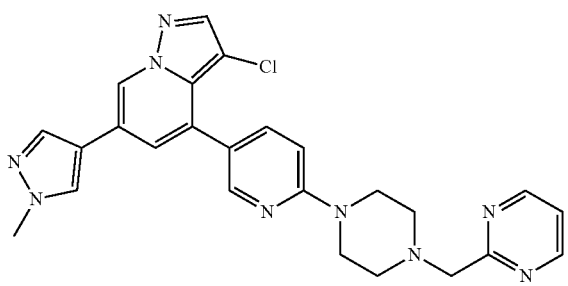 [SMILES: Cn1cc(-c2cc(-c3ccc(N4CCN(Cc5ncccn5)CC4)nc3)c3c(Cl)cnn3c2)cn1]

3-chloro-6-(1-methyl-1H-pyrazol-4-yl)-4-(6-(4-(pyrimidin-2-ylmethyl)piperazin-1-yl)pyridin-3-yl)pyrazolo[1,5-a]pyridine A mixture of 3-chloro-6-(1-methyl-1H-pyrazol-4-yl)-4-(6-(piperazin-1-yl)pyridin-3-yl)pyrazolo[1,5-a]pyridine (Example 644; 49.9 mg, 0.127 mmol) in 1:1 DCM:MeOH (1.2 mL) was treated with DIEA (29 µL, 0.16 mmol). After stirring for 5 min, the mixture was treated sequentially with 2-pyrimidinecarboxaldehyde (27.4 mg, 0.253 mmol), NaBH(AcO)$_3$ (53.7 mg, 0.253 mmol) and a couple of drops of AcOH. The resulting mixture was stirred at ambient temperature for 5 d, introducing additional reagents, 2-pyrimidinecarboxaldehyde (27 mg), NaBH(AcO)$_3$ (54 mg) and AcOH (2 drops), 3 times at 24 h intervals during the first 3 days of the time course. Upon completion, as determined by LCMS, the reaction mixture was diluted with DCM, and washed with saturated NaHCO$_{3(aq)}$. The organic extracts were dried over anhydrous Na$_2$SO$_4$, filtered, and concentrated in vacuo. The residue was purified by C18 reverse-phase chromatography (5-95% ACN/water with 0.1% TFA as the gradient eluent) to afford the title compound as the TFA salt. The salt was dissolved in 4:1 DCM:iPrOH, and extracted with saturated NaHCO$_{3(aq)}$. The organic extracts were dried over anhydrous Na$_2$SO$_4$, filtered, and concentrated in vacuo to cleanly afford the title compound (41.9 mg, 68% yield). MS (apci) m/z=486.2, 487.2 (M+H).

Example 742

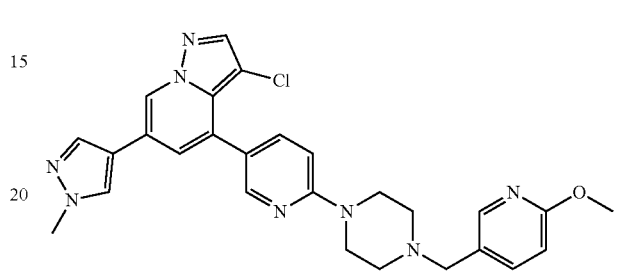

3-chloro-4-(6-(4-((6-methoxypyridin-3-yl)methyl)piperazin-1-yl)pyridin-3-yl)-6-(1-methyl-1H-pyrazol-4-yl)pyrazolo[1,5-a]pyridine In a pressure vessel, a solution of 3-chloro-6-(1-methyl-1H-pyrazol-4-yl)pyrazolo[1,5-a]pyridin-4-yl trifluoromethanesulfonate (52.7 mg, 0.138 mmol) (Intermediate P8; 52.7 mg, 0.138 mmol) in 4:1 dioxane:water (1.4 mL) was treated with 1-((6-methoxypyridin-3-yl)methyl)-4-(5-(4,4,5,5-tetramethyl-1,3,2-dioxaborolan-2-yl)pyridin-2-yl)piperazine (Example 697, Step 3; 62.5 mg, 0.152 mmol), Pd$_2$(dba)$_3$ (6.3 mg, 0.0069 mmol), XPhos (13.2 mg, 0.028 mmol), and K$_2$CO$_{3(aq)}$ (57.4 mg, 0.415 mmol). After sparging the mixture with Ar$_{(g)}$, the vessel was sealed. The reaction mixture was stirred for 16 h at 90° C. After cooling to ambient temperature, the mixture was diluted 4:1 DCM:iPrOH, and washed with water. The organic extracts were dried over anhydrous Na$_2$SO$_4$, filtered, and concentrated in vacuo. The residue was purified by C18 reverse-phase chromatography (5-95% ACN/water with 0.1% TFA as the gradient eluent) to afford the title compound as the TFA salt. The salt was diluted with 4:1 DCM:iPrOH, and treated with saturated NaHCO$_{3(aq)}$. The organic extracts were dried over anhydrous Na$_2$SO$_4$, filtered, and concentrated in vacuo to cleanly afford the title compound (49 mg, 69% yield). MS (apci) m/z=515.2, 516.2 (M+H).

Example 743

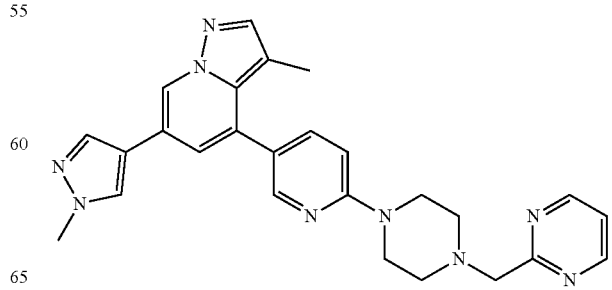

3-methyl-6-(1-methyl-1H-pyrazol-4-yl)-4-(6-(4-(pyrimidin-2-ylmethyl)piperazin-1-yl)pyridin-3-yl)pyrazolo[1,5-a]pyridine A solution of 3-methyl-6-(1-methyl-1H-pyrazol-4-yl)pyrazolo[1,5-a]pyridin-4-yl trifluoromethanesulfonate (Intermediate P27; 52.0 mg, 0.144 mmol) in 4:1 dioxane:water (1.4 mL) was treated with 2-((4-(5-(4,4,5,5-tetramethyl-1,3,2-dioxaborolan-2-yl)pyridin-2-yl)piperazin-1-yl)methyl)pyrimidine (Example 732, Step 1; 60.5 mg, 0.159 mmol), Pd$_2$(dba)$_3$ (6.6 mg, 0.0069 mmol), XPhos (13.8 mg, 0.029 mmol), and Na$_2$CO$_{3(s)}$ (45.9 mg, 0.433 mmol). After sparging the mixture with Ar$_{(g)}$, the reaction vessel was sealed. The reaction mixture was stirred for 16 h at 100° C. After cooling to ambient temperature, the mixture was diluted 4:1 DCM:iPrOH, and washed with water. The organic extracts were dried over anhydrous Na$_2$SO$_4$, filtered, and concentrated in vacuo. The residue was purified by C18 reverse-phase chromatography (5-95% ACN/water with 0.1% TFA as the gradient eluent) to afford the title compound as the TFA salt. The salt was dissolved in 4:1 DCM:iPrOH, and extracted with saturated NaHCO$_{3(aq)}$. The organic extracts were dried over anhydrous Na$_2$SO$_4$, filtered, and concentrated in vacuo to cleanly afford the title compound (36.9 mg, 59% yield). MS (apci) m/z=466.2 (M+H).

Example 744

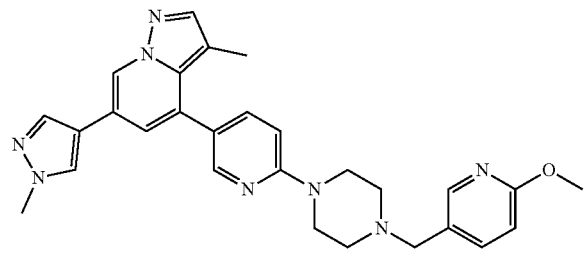 [SMILES: COc1ccc(CN2CCN(c3ccc(-c4cc(-c5cnn(C)c5)cn5ncc(C)c45)cn3)CC2)cn1]

4-(6-(4-((6-methoxypyridin-3-yl)methyl)piperazin-1-yl)pyridin-3-yl)-3-methyl-6-(1-methyl-1H-pyrazol-4-yl)pyrazolo[1,5-a]pyridine A solution of 3-methyl-6-(1-methyl-1H-pyrazol-4-yl)pyrazolo[1,5-a]pyridin-4-yl trifluoromethanesulfonate (Intermediate P27; 50.1 mg, 0.139 mmol) in 4:1 dioxane:water (1.4 mL) was treated with 1-((6-methoxypyridin-3-yl)methyl)-4-(5-(4,4,5,5-tetramethyl-1,3,2-dioxaborolan-2-yl)pyridin-2-yl)piperazine (Example 697, Step 3; 62.8 mg, 0.153 mmol), Pd$_2$(dba)$_3$ (6.4 mg, 0.0070 mmol), XPhos (13.3 mg, 0.028 mmol), and Na$_2$CO$_{3(s)}$ (44.2 mg, 0.417 mmol). After sparging the mixture with Ar$_{(g)}$, the reaction vessel was sealed. The reaction mixture was stirred for 16 h at 100° C. After cooling to ambient temperature, the mixture was diluted with 4:1 DCM:iPrOH, and washed with water The organic extracts were dried over anhydrous Na$_2$SO$_4$, filtered, and concentrated in vacuo. The residue was purified by C18 reverse-phase chromatography (5-95% ACN/water with 0.1% TFA as the gradient eluent) to afford the title compound as the TFA salt. The salt then was diluted with 4:1 DCM:iPrOH, and treated with saturated NaHCO$_{3(aq)}$. The organic extracts were dried over anhydrous Na$_2$SO$_4$, filtered, and concentrated in vacuo to cleanly afford the title compound (43.6 mg, 63% yield). MS (apci) m/z=495.2 (M+H).

ABBREVIATIONS

| | |
|---|---|
| ACN | Acetonitrile |
| AcOH | Acetic Acid |
| Boc-anhydride | di-tert-butyl dicarbonate |
| n-BuLi | n-butyllithium or 1-butyllithium |
| s-BuOH | Sec-Butanol or 2-Butanol |
| t-BuOH | tert-Butanol or 2-Methylpropan-2-ol |
| CuI | Copper (I) Iodide |
| d | day, days |
| DCE | 1,2-Dichloroethane |
| DCM | Dichloromethane |
| DIEA | N,N-Diisopropylethylamine |
| DMA | N,N-Dimethylacetamide |
| DMAP | 4-Dimethylaminopyridine |
| DME | 1,2-Dimethoxyethane |
| DMF | N,N-Dimethylformamide |
| DMSO | Dimethylsulfoxide |
| EDC-HCl | 1-Ethyl-3-(3-dimethylaminopropyl)carbodiimide hydrochloride |
| eq | equivalent |
| Et$_2$O | Diethyl Ether |
| EtOAc | Ethyl Acetate |
| EtOH | Ethanol |
| GF/F paper | GF/F glass microfiber filter paper |
| h | hour, hours |
| HATU | 1-[Bis(dimethylamino)methylene]-1H-1,2,3-triazolo[4,5-b]pyridinium 3-oxide hexafluorophosphate or 2-(7-Aza-1H-benzotriazole-1-yl)-1,1,3,3-tetramethyluronium hexafluorophosphate |
| HBTU | 3-[Bis(dimethylamino)methyliumyl]-3H-benzotriazol-1-oxide hexafluorophosphate or 2-(1H-benzotriazole-1-yl)-1,1,3,3-tetramethyluronium hexafluorophosphate |
| iPrOH | Isopropanol |
| KOAc | Potassium Acetate |
| K$_2$HPO$_4$ | Potassium Phosphate, Dibasic |
| LCMS | Liquid chromatography-mass spectrometry |
| Me$_4$N(AcO)$_3$BH | Tetramethylammonium Triacetoxyborohydride |

| | |
|---|---|
| NaBH(AcO)₃ | Sodium Triacetoxyborohydride |
| MeOH | Methanol |
| min | minute, minutes |
| MSH | o-(mesitylsulfonyl)hydroxylamine |
| MTBE | Methyl tert-Butyl Ether |
| NBS | N-Bromosuccinimide |
| NCS | N-Chlorosuccinimide |
| NIS | N-Iodosuccinimide |
| 10% Pd/C | Palladium 10 wt. % (dry basis), active carbon, wet, Degussa |
| Pd(PPh₃)₄ | Tetrakis(triphenylphosphine)palladium (0) |
| Pd₂(dba)₃ | tris(dibenzylideneacetone)dipalladium (0) |
| PdCl₂(dppf)•CH₂Cl₂ | 1,1'-Bis(diphenylphosphino)ferrocene-palladium(II)dichloride dichloromethane complex |
| PdCl₂(PPh₃)₂ | Palladium(II)bis(triphenylphosphine) dichloride, |
| PPTS | Pyridinium p-toluenesulfonate |
| PS frit | Biotage ® "Isolute Phase Separators" |
| PS paper | Whatman ® silicone treated Phase Separators filter paper |
| PVDF (0.45 μm) disc | polyvinylidene difluoride membrane with a 0.45-micron pore size |
| rt | Room temperature |
| TBAF | Tetra-n-butylammonium fluoride |
| TEA | Triethylamine |
| TFA | Trifluoroacetic acid |
| THF | tetrahydrofuran |
| TsCl | 4-Toluenesulfonyl chloride |
| Triphosgene | (bis(trichloromethyl) carbonate |
| X-phos | dicyclohexyl(2',4',6'-triisopropyl-[1,1'-biphenyl]-2-yl)phosphine |

What is claimed is:

1. A method for treating a cancer that exhibits a dysregulation of a RET gene, a RET protein, or expression or activity or level of any of the same, the method comprising: administering a therapeutically effective amount of a compound having Formula I or a

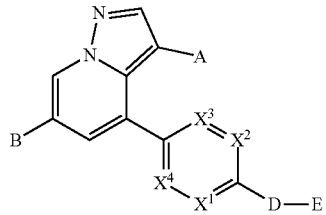

pharmaceutically acceptable salt or solvate thereof:

I wherein:
$X^1$ is CH or N;
$X^2$ is CH or N;
$X^3$ is CH or N;
$X^4$ is CH or N;
wherein one or two of $X^1$, $X^2$, $X^3$ and $X^4$ is N;
A is CN;
B is hetAr$^1$;
hetAr$^1$ is a 5-membered heteroaryl ring having 1-3 ring nitrogen atoms, wherein said heteroaryl ring is optionally substituted with one or more substituents independently selected from the group consisting of halogen, C1-C6 alkyl, hydroxyC1-C6 alkyl, fluoroC1-C6 alkyl, difluoroC1-C6 alkyl, trifluoroC1-C6 alkyl, cyanoC1-C6 alkyl, (C1-C6 alkoxy)C1-C6 alkyl, (C1-C4 alkoxy)CH$_2$C(=O)—, (C1-C4 alkoxy)C(=O)C1-C3 alkyl, C3-C6 cycloalkyl, (R$^a$R$^b$N)C1-C6 alkyl, (R$^a$R$^b$N)C(=O)C1-C6 alkyl, (C1-C6 alkylSO$_2$)C1-C6 alkyl, and 4-methoxybenzyl;
R$^a$ and R$^b$ are independently H or C1-C6 alkyl;
D is hetCyc$^1$;
hetCyc$^1$ is a 4-6 membered heterocyclic ring having 1-2 ring nitrogen atoms, wherein said heterocyclic ring is optionally substituted with one or more substituents independently selected from the group consisting of C1-C3 alkyl, fluoroC1-C3 alkyl, difluoroC1-C3 alkyl, trifluoroC1-C3 alkyl and OH, or said heterocyclic ring is substituted with a C3-C6 cycloalkylidene ring, or said heterocyclic ring is substituted with an oxo group;

E is
(w) Ar$^2$C(=O)—,
(x) Ar$^2$C1-C6 alkyl-,
(z) Ar$^2$(C1-C3 alkyl)C(=O)— wherein said alkyl portion is optionally substituted with one or two groups independently selected from the group consisting of OH, C1-C6 alkyl (optionally substituted with 1-3 fluoros), hydroxyC1-C6 alkyl, C1-C6 alkoxy and R$^e$R$^f$N—, where R$^e$ and R$^f$ are independently H or C1-C6 alkyl, or R$^e$ and R$^f$ together with the nitrogen to which they are attached form a 5-6 membered azacyclic ring optionally having an additional ring heteroatom selected from N and O,
(cc) hetAr$^2$(C1-C3 alkyl)C(=O)—, wherein said alkyl portion is optionally substituted with one or two groups independently selected from the group consisting of OH, C1-C6 alkyl, hydroxyC1-C6 alkyl, C1-C6 alkoxy and R$^e$R$^f$N—, wherein R$^e$ and R$^f$ are independently H or C1-C6 alkyl or R$^e$ and R$^f$ together with the nitrogen to which they are attached form a 5-6 membered azacyclic ring optionally having an additional ring heteroatom selected from N and O,
(dd) R$^1$R$^2$NC(=O)—, or
(oo) hetAr$^2$C1-C6 alkyl-;
Ar$^2$ is phenyl optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, CN, a 5-6 membered heterocyclic ring having 1-2 ring heteroatoms independently selected from N and O, and R$^i$R$^j$N— wherein R$^i$ and R$^j$ are independently H or C1-C6 alkyl;
hetAr$^2$ is a 5-6 membered heteroaryl ring having 1-3 ring heteroatoms independently selected from N, O and S and optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, hydroxyC1-C6 alkyl, (C3-C6)cycloalkyl, (C1-C6 alkoxy)C1-C6 alkyl, CN, OH, and R'R"N—, wherein R' and R" are independently H or C1-C3 alkyl;
R$^1$ is H, C1-C6 alkyl or (C1-C6 alkoxy)C1-C6 alkyl; and
R$^2$ is H, C1-C6 alkyl (optionally substituted with 1-3 fluoros), (C1-C6 alkoxy)C1-C6 alkyl (optionally substituted with 1-3 fluoros), hydroxyC1-C6 alkyl (optionally substituted with 1-3 fluoros), C1-C6 alkoxy (optionally substituted with 1-3 fluoros), (C1-C6 alkoxy)C(=O), hydroxyC1-C6 alkoxy or (3-6C cycloalkyl)CH$_2$O.

2. The method of claim 1, wherein ring D is

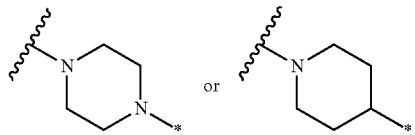

or wherein the wavy line indicates the point of attachment of Ring D to the ring comprising $X^1$, $X^2$, $X^3$, and $X^4$, and the asterisk indicates the point of attachment of Ring D to the E group.

3. The method of claim 2, wherein ring D is

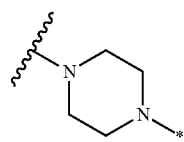

wherein the wavy line indicates the point of attachment of Ring D to the ring comprising X1, X2, X3, and X4, and the asterisk indicates the point of attachment of Ring D to the E group.

4. The method of claim 3, wherein E is (w) $Ar^2C(=O)—$, (x) $Ar^2$C1-C6 alkyl, (cc) $hetAr^2$(C1-C3 alkyl)C(=O)— wherein the alkyl portion is optionally substituted with one or two groups independently selected from the group consisting of OH, C1-C6 alkyl, hydroxyC1-C6 alkyl, C1-C6 alkoxy and $R^eR^fN—$, wherein $R^e$ and $R^f$ are independently H or C1-C6 alkyl, (dd) $R^1R^2NC(=O)—$, or (oo) $hetAr^2$C1-C6 alkyl.

5. The method of claim 2, wherein Ring D is

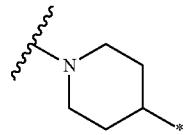

wherein the wavy line indicates the point of attachment of Ring D to the ring comprising X1, X2, X3, and X4, and the asterisk indicates the point of attachment of Ring D to the E group.

6. The method of claim 5, wherein E is (dd) $R^1R^2NC(=O)—$.

7. The method of claim 1, wherein $X^1$ is N, and $X^2$, $X^3$, and $X^4$ are CH.

8. The method of claim 1, wherein $X^1$ is CH, $X^2$ is N, and $X^3$ and $X^4$ are CH.

9. The method of claim 1, wherein the compound of Formula I is selected from the group consisting of:

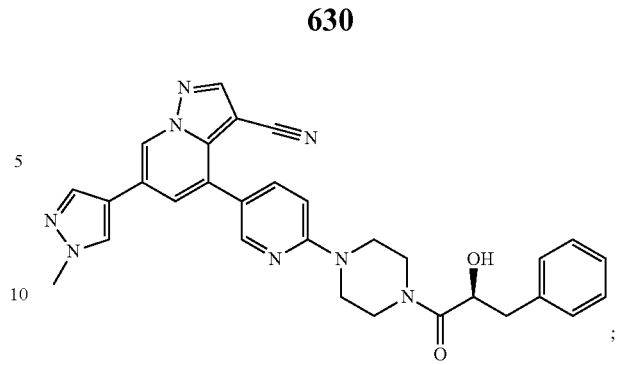

;

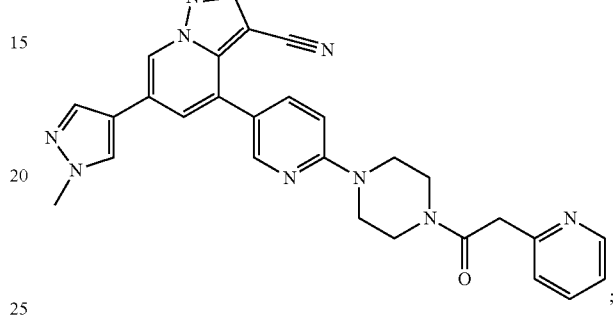

;

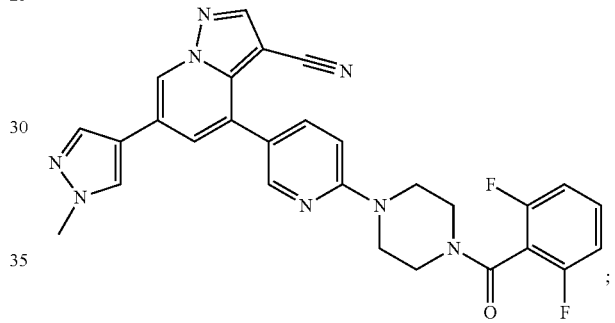

;

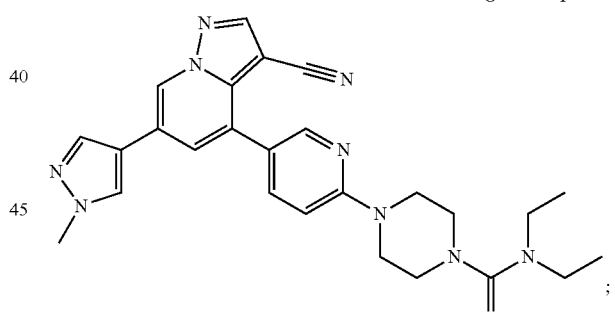

;

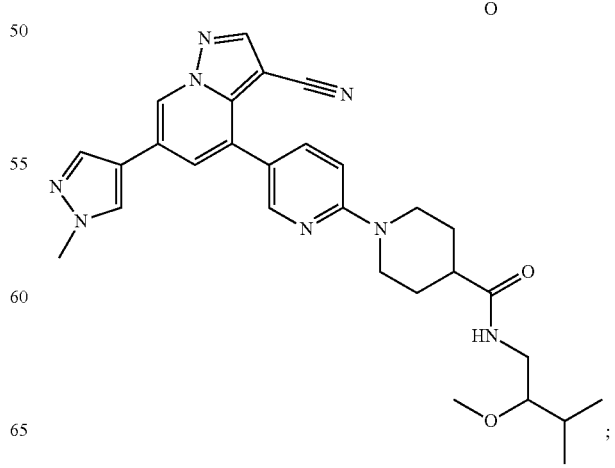

;

-continued

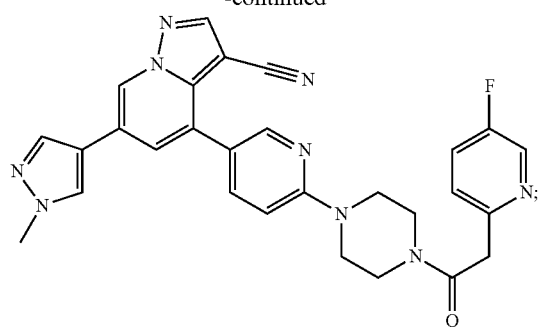

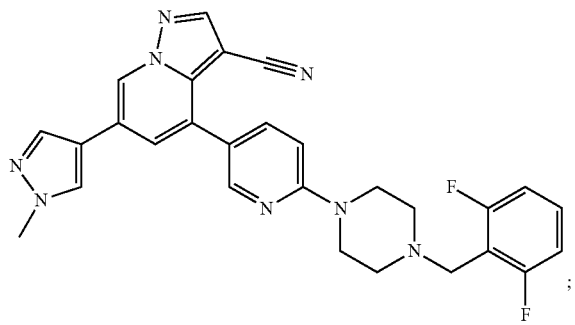

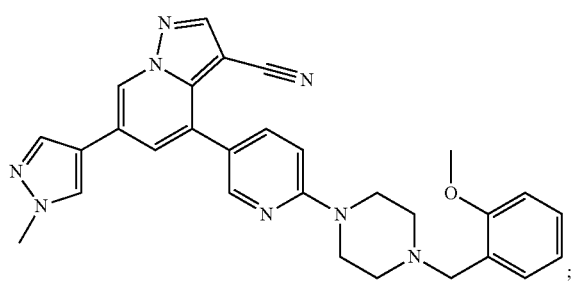

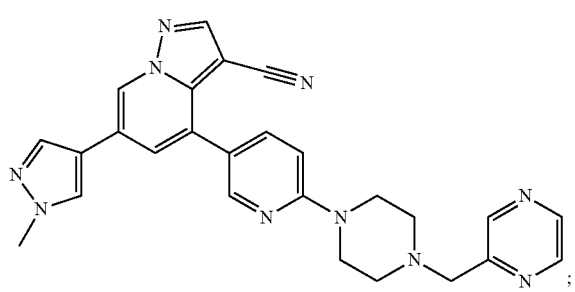

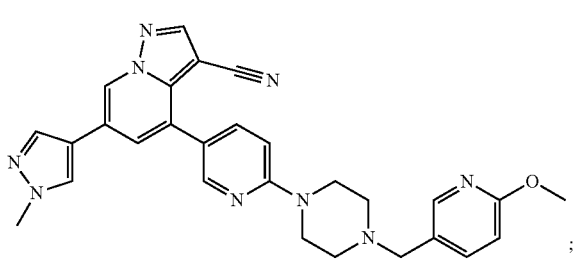 [SMILES: COc1ccc(CN2CCN(c3ccc(-c4cc(-c5cnn(C)c5)cn5ncc(C#N)c45)cn3)CC2)cn1]

or a pharmaceutically acceptable salt or solvate thereof.

10. The method of claim 1, wherein the compound of Formula I is

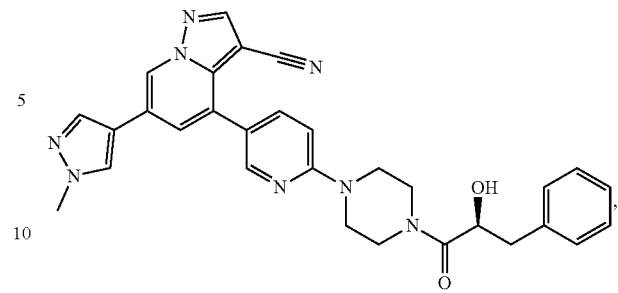

or a pharmaceutically acceptable salt or solvate thereof.

11. The method of claim 1, wherein the compound of Formula I is

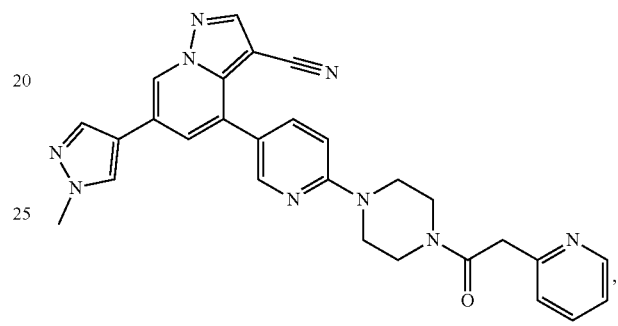

or a pharmaceutically acceptable salt or solvate thereof.

12. The method of claim 1, wherein the compound of Formula I is

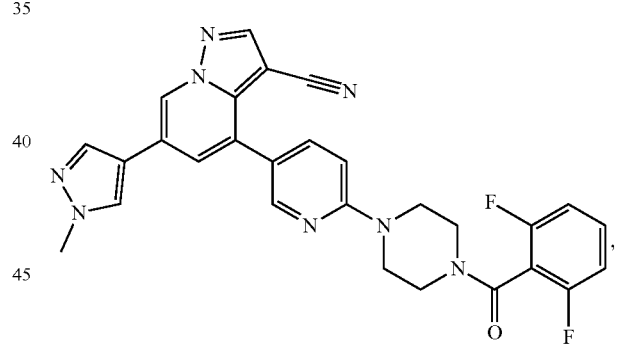

or a pharmaceutically acceptable salt or solvate thereof.

13. The method of claim 1, wherein the compound of Formula I is

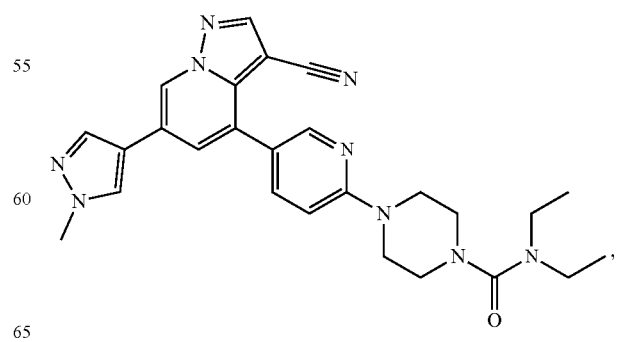

or a pharmaceutically acceptable salt or solvate thereof.

14. The method of claim 1, wherein the compound of Formula I is

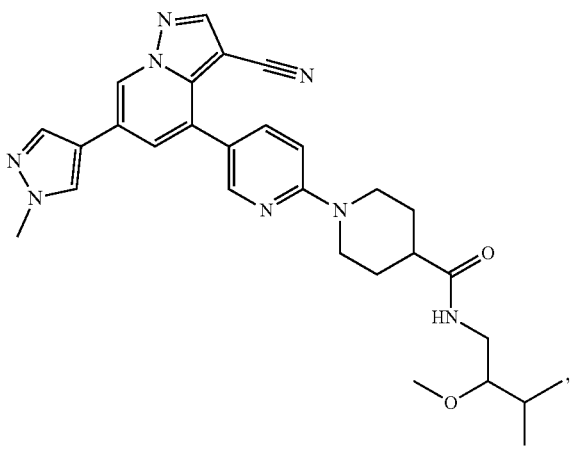 [SMILES: COC(CNC(=O)C1CCN(c2ccc(-c3cc(-c4cnn(C)c4)cn4ncc(C#N)c34)cn2)CC1)C(C)C]

or a pharmaceutically acceptable salt or solvate thereof.

15. The method of claim 1, wherein the compound of Formula I is

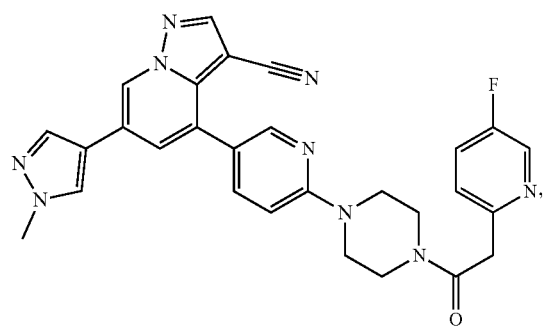 [SMILES: Cn1cc(-c2cc(-c3ccc(N4CCN(C(=O)Cc5ccc(F)cn5)CC4)nc3)c3c(C#N)cnn3c2)cn1]

or a pharmaceutically acceptable salt or solvate thereof.

16. The method of claim 1, wherein the compound of Formula I is

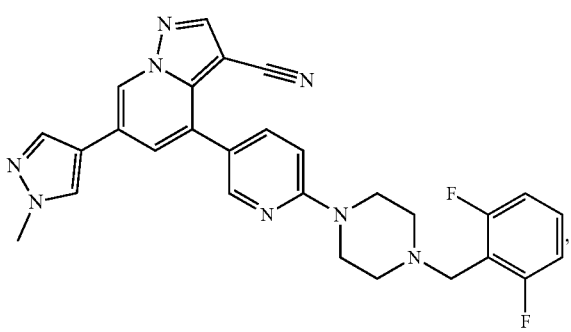 [SMILES: Cn1cc(-c2cc(-c3ccc(N4CCN(Cc5c(F)cccc5F)CC4)nc3)c3c(C#N)cnn3c2)cn1]

or a pharmaceutically acceptable salt or solvate thereof.

17. The method of claim 1, wherein the compound of Formula I is

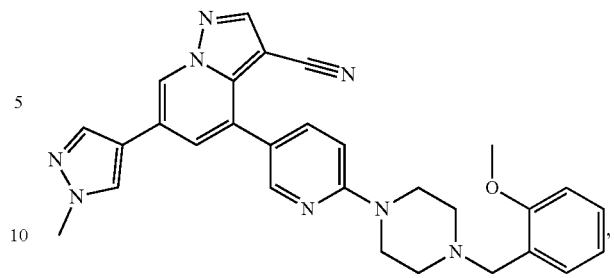

or a pharmaceutically acceptable salt or solvate thereof.

18. The method of claim 1, wherein the compound of Formula I is

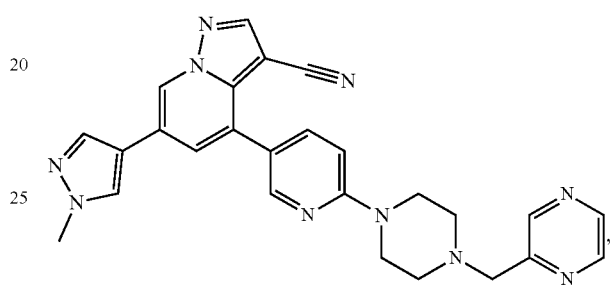

or a pharmaceutically acceptable salt or solvate thereof.

19. The method of claim 1, wherein the compound of Formula I is

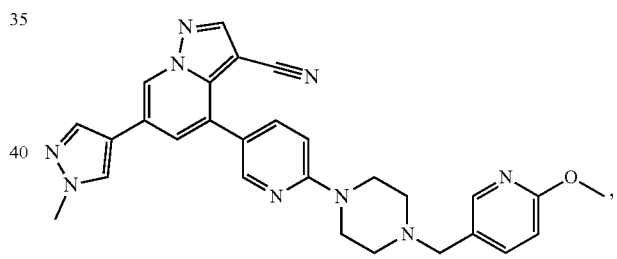

or a pharmaceutically acceptable salt or solvate thereof.

20. The method of claim 1, wherein the cancer is selected from the group consisting of acute lymphoblastic leukemia (ALL), acute myeloid leukemia (AML), breast cancer, cervical cancer, colorectal cancer, ganglioneuromatosis of the gastroenteric mucosa, gastric cancer, gastrointestinal stromal tumors, glioma, leukemia, lung cancer, lymphoma, multiple endocrine neoplasia type 2A or 2B (MEN2A or MEN2B, respectively), multiple myeloma, non-Hodgkin's lymphoma, non-small cell lung cancer, ovarian cancer, papillary renal cell carcinoma, paraganglioma, parathyroid hyperplasia, pheochromocytoma, and thyroid cancer.

21. The method of claim 20, wherein the cancer is leukemia.

22. The method of claim 1, wherein the dysregulation of a RET gene, a RET kinase, or the expression or activity or level of any of the same results in the translation of a RET fusion protein or a mutation of a RET kinase.

23. The method of claim 22, wherein the RET fusion protein is selected from the group consisting of BCR-RET, CLIP1-RET, KIF5B-RET, CCDC6-RET, NCOA4-RET, TRIM33-RET, ERC1-RET, FGFR1OP-RET, RET-MBD1, RET-RAB61P2, RET-PRKAR1A, RET-TRIM24, RET-GOLGA5, HOOK3-RET, KTN1-RET, TRIM27-RET, AKAP13-RET, FKBP 15-RET, SPECC1L-RET, TBL1XR1/RET, CEP55-RET, CUX1-RET, KIAA1468-RET, RFG8/RET, ACBD5-RET, PTClex9-RET, MYH13-RET, PIBF1-RET, KIAA1217-RET, and MPRIP-RET.

24. The method of claim 22, wherein the mutation is one or more point mutations in a RET gene.

25. The method of claim 24, wherein the one or more point mutation results in the translation of a RET protein comprising an amino acid substitution at an amino acid position selected from the group consisting of 32, 34, 40, 64, 67, 114, 145, 292, 321, 330, 338, 360, 393, 510, 511, 513, 515, 525, 531, 532, 533, 550, 591, 593, 600, 602, 603, 606, 609, 611, 618, 619, 620, 623, 624, 630, 631, 632, 634, 635, 636, 640, 641, 648, 649, 664, 665, 666, 686, 691, 694, 700, 706, 713, 736, 748, 750, 765, 766, 768, 769, 770, 771, 777, 778, 781, 788, 790, 791, 804, 805, 806, 810, 818, 819, 823, 826, 833, 841, 843, 844, 848, 852, 865, 866, 873, 876, 881, 883, 884, 886, 891, 897, 898, 900, 901, 904, 905, 907, 908, 911, 912, 918, 919, 921, 922, 930, 961, 972, 981, 982, 1009, 1015, 1017, 1041, 1064, and 1096.

26. The method of claim 24, wherein the one or more point mutations results in the translation of a RET protein comprising an amino acid substitution selected from the group consisting of S32L, D34S, L40P, P64L, R67H, R114H, V145G, V292M, G321R, R330Q, T338I, R360W, F393L, A510V, E511K, C515S, C515W, R525W, C531R, G533C, G533S, G550E, V591I, G593E, R600Q, I602V, K603Q, K603E, Y606C, C609Y, C609S, C609G, C609R, C609F, C609W, C611R, C611S, C611G, C611Y, C611F, C611W, C618S, C618Y, C618R, C618G, C618F, C618W, F619F, C620S, C620W, C620R, C620G, C620L, C620Y, C620F, E623K, D624N, C630A, C630R, C630S, C630Y, C630F, D631N, D631Y, D631A, D631G, D631V, D631E, E632K, E632G, C634W, C634Y, C634S, C634R, C634F, C634G, C634L, C634A, C634T, R635G, T636P, T636M, A640G, A641S, A641T, V648I, S649L, A664D, H665Q, K666E, K666M, K666N, S686N, G691S, R694Q, M700L, V706M, V706A, E713K, G736R, G748C, A750P, S765P, P766S, P766M, E768Q, E768D, L769L, R770Q, D771N, N777S, V778I, Q781R, L790F, Y791F, V804L, V804M, V804E, E805K, Y806E, Y806F, Y806S, Y806G, Y806C, E818K, S819I, G823E, Y826M, R833C, P841L, P841P, E843D, R844W, R844Q, R844L, M848T, I852M, R873W, A876V, L881V, A883F, A883S, A883T, E884K, R886W, S891A, R897Q, D898V, E901K, S904F, S904C, K907E, K907M, R908K, G911D, R912P, R912Q, M918T, M918V, M918L, A919V, E921K, S922P, S922Y, T930M, F961L, R972G, R982C, M1009V, D1017N, V1041G, and M1064T.

27. The method of claim 1, further comprising administering an additional therapy or therapeutic agent to the patient.

28. The method of claim 27, wherein the additional therapy or therapeutic agent is selected from the group consisting of radiotherapy, cytotoxic chemotherapeutics, kinase targeted therapeutics, apoptosis modulators, signal transduction inhibitors, immune-targeted therapies, and angiogenesis-targeted therapies.

29. The method of claim 27, wherein the additional therapy is a second RET inhibitor, an immunotherapy, or a combination thereof.

* * * * *

SEQUENCE LISTING

<160> NUMBER OF SEQ ID NOS: 1

<210> SEQ ID NO 1
<211> LENGTH: 1114
<212> TYPE: PRT
<213> ORGANISM: Homo sapiens

<400> SEQUENCE: 1

```
Met Ala Lys Ala Thr Ser Gly Ala Ala Gly Leu Arg Leu Leu Leu
1               5                   10                  15

Leu Leu Leu Pro Leu Leu Gly Lys Val Ala Leu Gly Leu Tyr Phe Ser
                20                  25                  30

Arg Asp Ala Tyr Trp Glu Lys Leu Tyr Val Asp Gln Ala Ala Gly Thr
            35                  40                  45

Pro Leu Leu Tyr Val His Ala Leu Arg Asp Ala Pro Glu Glu Val Pro
        50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
```

-continued

```
            195                 200                 205
Gly Glu Gly Leu Pro Phe Arg Cys Ala Pro Asp Ser Leu Glu Val Ser
210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Val Val Met Val
                245                 250                 255

Pro Phe Pro Val Thr Val Tyr Asp Glu Asp Ser Ala Pro Thr Phe
            260                 265                 270

Pro Ala Gly Val Asp Thr Ala Ser Ala Val Val Glu Phe Lys Arg Lys
            275                 280                 285

Glu Asp Thr Val Val Ala Thr Leu Arg Val Phe Asp Ala Asp Val Val
290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
                340                 345                 350

Asp Tyr Arg Leu Val Leu Asn Arg Asn Leu Ser Ile Ser Glu Asn Arg
                355                 360                 365

Thr Met Gln Leu Ala Val Leu Val Asn Asp Ser Asp Phe Gln Gly Pro
370                 375                 380

Gly Ala Gly Val Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
                420                 425                 430

Phe Ser Gly Ile Asn Val Gln Tyr Lys Leu His Ser Ser Gly Ala Asn
                435                 440                 445

Cys Ser Thr Leu Gly Val Val Thr Ser Ala Glu Asp Thr Ser Gly Ile
                450                 455                 460

Leu Phe Val Asn Asp Thr Lys Ala Leu Arg Arg Pro Lys Cys Ala Glu
465                 470                 475                 480

Leu His Tyr Met Val Ala Thr Asp Gln Gln Thr Ser Arg Gln Ala
                485                 490                 495

Gln Ala Gln Leu Leu Val Thr Val Glu Gly Ser Tyr Val Ala Glu Glu
                500                 505                 510

Ala Gly Cys Pro Leu Ser Cys Ala Val Ser Lys Arg Arg Leu Glu Cys
                515                 520                 525

Glu Glu Cys Gly Gly Leu Gly Ser Pro Thr Gly Arg Cys Glu Trp Arg
                530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
                580                 585                 590

Gly His Glu Pro Gly Glu Pro Arg Gly Ile Lys Ala Gly Tyr Gly Thr
                595                 600                 605

Cys Asn Cys Phe Pro Glu Glu Glu Lys Cys Phe Cys Glu Pro Glu Asp
610                 615                 620
```

```
Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Ser Ala Phe Cys
            645                 650                 655

Ile His Cys Tyr His Lys Phe Ala His Lys Pro Pro Ile Ser Ser Ala
                660                 665                 670

Glu Met Thr Phe Arg Arg Pro Ala Gln Ala Phe Pro Val Ser Tyr Ser
            675                 680                 685

Ser Ser Gly Ala Arg Arg Pro Ser Leu Asp Ser Met Glu Asn Gln Val
        690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
            740                 745                 750

Thr Thr Val Ala Val Lys Met Leu Lys Glu Asn Ala Ser Pro Ser Glu
        755                 760                 765

Leu Arg Asp Leu Leu Ser Glu Phe Asn Val Leu Lys Gln Val Asn His
770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
                805                 810                 815

Arg Glu Ser Arg Lys Val Gly Pro Gly Tyr Leu Gly Ser Gly Gly Ser
            820                 825                 830

Arg Asn Ser Ser Ser Leu Asp His Pro Asp Glu Arg Ala Leu Thr Met
        835                 840                 845

Gly Asp Leu Ile Ser Phe Ala Trp Gln Ile Ser Gln Gly Met Gln Tyr
850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
            900                 905                 910

Ile Pro Val Lys Trp Met Ala Ile Glu Ser Leu Phe Asp His Ile Tyr
        915                 920                 925

Thr Thr Gln Ser Asp Val Trp Ser Phe Gly Val Leu Leu Trp Glu Ile
930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp Ile Ser Lys Asp Leu Glu Lys Met
        995                 1000                1005

Met Val Lys Arg Arg Asp Tyr Leu Asp Leu Ala Ala Ser Thr Pro
    1010                1015                1020

Ser Asp Ser Leu Ile Tyr Asp Asp Gly Leu Ser Glu Glu Thr
    1025                1030                1035
```

-continued

```
Pro  Leu  Val  Asp  Cys  Asn  Asn  Ala  Pro  Leu  Pro  Arg  Ala  Leu  Pro
     1040                universal1045               1050

Ser  Thr  Trp  Ile  Glu  Asn  Lys  Leu  Tyr  Gly  Met  Ser  Asp  Pro  Asn
     1055                universal1060               1065

Trp  Pro  Gly  Glu  Ser  Pro  Val  Pro  Leu  Thr  Arg  Ala  Asp  Gly  Thr
     1070                universal1075               1080

Asn  Thr  Gly  Phe  Pro  Arg  Tyr  Pro  Asn  Asp  Ser  Val  Tyr  Ala  Asn
     1085                universal1090               1095

Trp  Met  Leu  Ser  Pro  Ser  Ala  Ala  Lys  Leu  Met  Asp  Thr  Phe  Asp
     1100                universal1105               1110

Ser
```